US011091546B2

(12) United States Patent
Young et al.

(10) Patent No.: US 11,091,546 B2
(45) Date of Patent: Aug. 17, 2021

(54) OPTIMIZED PNE-BASED CHIMERIC RECEPTOR T CELL SWITCHES AND USES THEREOF

(71) Applicant: The Scripps Research Institute, La Jolla, CA (US)

(72) Inventors: Travis Young, La Jolla, CA (US); David T. Rodgers, San Diego, CA (US); Ian Hardy, San Diego, CA (US); Chanhyuk Kim, San Diego, CA (US); Peter G. Schultz, La Jolla, CA (US); Eric Hampton, San Marcos, CA (US); Eduardo Laborda, San Diego, CA (US); Leonard Presta, San Francisco, CA (US)

(73) Assignee: The Scripps Research Institute, La Jolla, CA (US)

(*) Notice: Subject to any disclaimer, the term of this patent is extended or adjusted under 35 U.S.C. 154(b) by 94 days.

(21) Appl. No.: 15/566,680

(22) PCT Filed: Apr. 15, 2016

(86) PCT No.: PCT/US2016/027997
§ 371 (c)(1),
(2) Date: Oct. 13, 2017

(87) PCT Pub. No.: WO2016/168773
PCT Pub. Date: Oct. 20, 2016

(65) Prior Publication Data

US 2019/0169289 A1 Jun. 6, 2019

Related U.S. Application Data

(60) Provisional application No. 62/253,467, filed on Nov. 10, 2015, provisional application No. 62/148,063, filed on Apr. 15, 2015.

(51) Int. Cl.

| | |
|---|---|
| ***C07K 16/28*** | (2006.01) |
| ***A61K 35/17*** | (2015.01) |
| ***C07K 16/18*** | (2006.01) |
| ***C07K 16/32*** | (2006.01) |
| ***A61P 35/00*** | (2006.01) |
| ***C07K 14/39*** | (2006.01) |
| *A61K 39/00* | (2006.01) |

(52) U.S. Cl.
CPC .......... *C07K 16/2803* (2013.01); *A61K 35/17* (2013.01); *A61P 35/00* (2018.01); *C07K 14/39* (2013.01); *C07K 16/18* (2013.01); *C07K 16/2851* (2013.01); *C07K 16/2866* (2013.01); *C07K 16/2878* (2013.01); *C07K 16/32* (2013.01); *A61K 2039/505* (2013.01); *A61K 2039/507* (2013.01); *A61K 2039/5156* (2013.01); *A61K 2039/585* (2013.01); *C07K 2317/24* (2013.01); *C07K 2317/34* (2013.01); *C07K 2317/53* (2013.01); *C07K 2317/55* (2013.01); *C07K 2317/622* (2013.01); *C07K 2317/73* (2013.01); *C07K 2317/92* (2013.01); *C07K 2319/00* (2013.01); *C07K 2319/02* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 3,773,919 | A | 11/1973 | Boswell |
| 3,854,480 | A | 12/1974 | Zaffaroni |
| 3,887,699 | A | 6/1975 | Yolles |
| 4,452,775 | A | 6/1984 | Kent |
| 4,485,045 | A | 11/1984 | Regen |
| 4,544,545 | A | 10/1985 | Ryan et al. |
| 4,619,794 | A | 10/1986 | Hauser |
| 4,675,189 | A | 6/1987 | Kent et al. |
| 5,133,974 | A | 7/1992 | Paradissis et al. |
| 5,372,930 | A | 12/1994 | Colton et al. |
| 5,407,686 | A | 4/1995 | Patel et al. |
| 5,654,010 | A | 8/1997 | Johnson et al. |
| 5,686,072 | A | 11/1997 | Uhr |
| 5,736,152 | A | 4/1998 | Dunn |
| 5,861,156 | A | 1/1999 | George et al. |
| 5,906,936 | A | 5/1999 | Eshhar et al. |

(Continued)

FOREIGN PATENT DOCUMENTS

| | | |
|---|---|---|
| CA | 1176565 | 10/1984 |
| DE | 3218121 | 11/1983 |

(Continued)

OTHER PUBLICATIONS

Genbank Accession No: BAF90733.1, two copies of the FLAG epitope and hexahistidine [Schizosaccharomyces pombe expression vector pDUAL-FFH1], Genebank database, published on Oct. 1, 2007, 1 page.
Gianpietro Dotti et al., "Design and development of therapies using chimeric antigen receptor-expressing T cells", Immunological Reviews 257(1):107-126 (2013).
Michael C Jensen et al, "Design and implementation of adoptive therapy with chimeric antigen receptor-modified T cells Authors' addresses", Immunological Reviews., 257(1):127-144 (2013).
David T. Rodgers et al: "Switch-medicated activation and retargeting of CAR-T cells for β-cell malignancies," Proceedings National Academy of Sciences PNAS 113(4):E459- E468 (2016).

(Continued)

*Primary Examiner* — Nelson B Moseley, II
(74) *Attorney, Agent, or Firm* — Hugh Wang; Thomas Fitting

(57) ABSTRACT

Disclosed herein are chimeric antigen receptor effector cells (CAR-ECs) and CAR-EC switches. The switchable CAR-ECs are generally T cells. The one or more chimeric antigen receptors may recognize a peptidic antigen on the CAR-EC switch. The CAR-ECs and switches may be used for the treatment of a condition in a subject in need thereof.

12 Claims, 113 Drawing Sheets

Specification includes a Sequence Listing.

(56) References Cited

U.S. PATENT DOCUMENTS

| | | | |
|---|---|---|---|
| 5,912,172 A | 6/1999 | Eshhar et al. | |
| 6,083,751 A | 7/2000 | Feldhaus et al. | |
| 6,372,716 B1 | 4/2002 | Bush et al. | |
| 6,566,329 B1 | 5/2003 | Meyn et al. | |
| 6,686,940 B2 | 2/2004 | Matsuura et al. | |
| 7,258,986 B2 | 8/2007 | Maur et al. | |
| 7,446,190 B2 | 11/2008 | Sadelain et al. | |
| 7,514,537 B2 | 4/2009 | Jensen | |
| 8,802,374 B2 | 8/2014 | Jensen | |
| 8,916,381 B1 | 12/2014 | June et al. | |
| 9,624,276 B2 | 4/2017 | Young et al. | |
| 2003/0180714 A1 | 9/2003 | Sidhu et al. | |
| 2004/0044177 A1 | 3/2004 | Macke et al. | |
| 2004/0072299 A1 | 4/2004 | Gillies | |
| 2005/0113564 A1 | 5/2005 | Campana et al. | |
| 2005/0129671 A1 | 6/2005 | Cooper et al. | |
| 2006/0083683 A1 | 4/2006 | Hsei | |
| 2007/0172504 A1 | 7/2007 | Shirwan et al. | |
| 2008/0260731 A1 | 10/2008 | Bernett | |
| 2009/0117108 A1 | 5/2009 | Wang et al. | |
| 2010/0178276 A1 | 7/2010 | Sadelain et al. | |
| 2010/0278830 A1 | 11/2010 | Shoemaker et al. | |
| 2010/0297076 A1 | 11/2010 | Morrison | |
| 2010/0324008 A1 | 12/2010 | Low et al. | |
| 2012/0034223 A1 | 2/2012 | Hall et al. | |
| 2012/0213783 A1 | 8/2012 | Rosenberg et al. | |
| 2013/0287752 A1* | 10/2013 | Davila | A61K 47/6859 424/93.71 |
| 2014/0065171 A1 | 3/2014 | Geierstanger et al. | |
| 2014/0234348 A1 | 8/2014 | Scholler et al. | |
| 2015/0238631 A1 | 8/2015 | Kim et al. | |
| 2017/0246270 A1 | 8/2017 | Young et al. | |

FOREIGN PATENT DOCUMENTS

| | | | |
|---|---|---|---|
| EP | 0036676 | 9/1981 | |
| EP | 0058481 | 1/1982 | |
| EP | 0052322 | 5/1982 | |
| EP | 0088046 | 2/1983 | |
| EP | 0102324 | 3/1984 | |
| EP | 0133988 | 3/1985 | |
| EP | 0142641 | 5/1985 | |
| EP | 0143949 | 6/1985 | |
| EP | 0158277 | 10/1985 | |
| EP | 0517565 | 12/1992 | |
| EP | 3 115 373 * | 1/2017 | C07K 14/70 |
| WO | WO-1993/15722 | 8/1993 | |
| WO | WO-1994/20069 | 9/1994 | |
| WO | WO-96/07399 | 3/1996 | |
| WO | WO-96/29998 | 10/1996 | |
| WO | WO 96/40072 | 12/1996 | |
| WO | WO-97/03692 | 2/1997 | |
| WO | WO-1997/015669 A1 | 5/1997 | |
| WO | WO-04/009664 | 1/2004 | |
| WO | WO-2004/106380 A2 | 12/2004 | |
| WO | WO-05/087201 | 9/2005 | |
| WO | WO-2007/059312 A2 | 5/2007 | |
| WO | WO-2007/070659 A2 | 6/2007 | |
| WO | WO-2007/079130 A2 | 7/2007 | |
| WO | WO-2007/094916 A2 | 8/2007 | |
| WO | WO-2008/025558 A2 | 3/2008 | |
| WO | WO 2008/045437 * | 4/2008 | C12N 15/09 |
| WO | WO-2008//077079 A1 | 6/2008 | |
| WO | WO-2008/083346 A1 | 7/2008 | |
| WO | WO-2009/026177 A1 | 2/2009 | |
| WO | WO-2010/037062 A1 | 4/2010 | |
| WO | WO 2010/104749 | 9/2010 | |
| WO | WO-2011/028195 A2 | 3/2011 | |
| WO | WO-2012/031744 A1 | 3/2012 | |
| WO | WO-2012/055961 A1 | 5/2012 | |
| WO | WO-2012/079000 A1 | 6/2012 | |
| WO | WO 2012/082841 * | 6/2012 | A61K 39/395 |
| WO | WO-2012/082841 | 6/2012 | |
| WO | WO-2012//082841 A2 | 6/2012 | |
| WO | WO-2012/166559 A1 | 12/2012 | |
| WO | WO-2012/166560 A1 | 12/2012 | |
| WO | WO-2013/019615 A2 | 2/2013 | |
| WO | WO-2013/044225 A1 | 3/2013 | |
| WO | WO-2013/093809 A1 | 6/2013 | |
| WO | WO-2013/123061 A1 | 8/2013 | |
| WO | WO-2014/100615 A1 | 6/2014 | |
| WO | WO-2014/153002 A1 | 9/2014 | |
| WO | WO-2014/153164 A1 | 9/2014 | |

OTHER PUBLICATIONS

Ang et al., "Generating a Chimeric Antigen Receptor to Redirect T-cell Specificity after Infusion," Molecular Therapy 19( Suppl 1): No. 353, p. S137 (2011).

Arcondéguy et al., "Survey and Summary. VEGF-A mRNA processing, stability and translation: a paradigm for intricate regulation of gene expression at the post-transcriptional level," Nucleic Acids Research 41(17): 7997-8010 (2013).

Axup, J. et al., "Synthesis of site-specific antibody-drug conjugates using unnatural amino acids," PNAS 109(40):16101-16106 (2012).

Backer et al., "Self-assembled "dock and lock" system for linking payloads to targeting proteins," Bioconjug Chem. Jul. Aug.;I7(4):912-919 (2006).

Baeuerle et al., "BiTE: Teaching antibodies to engage T-cells for cancer therapy," Curr Opin Mol Ther 11(1):22-30 (2009).

Beers, S.A. et al., "Antigenic modulation limits the efficacy of anti-CD20 antibodies: implications for antibody selection," Blood 115(25):5191-5201 (2010).

Bibl et al., "Stability of amyloid-beta peptides in plasma and serum," Electrophoresis 33(3):445-450 (2012).

Bluemel et al., "Epitope distance to the target cell membrane and antigen size determine the potency of T cell-mediated lysis by BiTE antibodies specific for a large melanoma surface antigen," Cancer Immunol Immunother 59(8):1197-1209 (2010).

Boder et al., "Directed evolution of antibody fragments with monovalent femtomolar antigen-binding affinity," Proc Natl Acad Sci U S A 97(20):10701-10705 (2000).

Bonini et al., "The suicide gene therapy challenge: how to improve a successful gene therapy approach," Mol Ther 15(7):1248-1252 (2007).

Boulassel and Galal, "Immunotherapy for B-Cell Neoplasms using T Cells expressing Chimeric Antigen Receptors: From antigen choice to clinical implementation," Sultan Qaboos Univ Med J 12(3):273-285 (2012).

Brentjens et al., "Eradication of systemic B-cell tumors by genetically targeted human T lymphocytes co-stimulated by CD80 and interleukin-15," Nature Medicine 9(3): 279-286 (2003).

Brentjens et al., "Genetically Targeted T Cells Eradicate Systemic Acute Lymphoblastic Leukemia Xenografts," Clinical Cancer Research 13(18): 5426-5435, Sep. 15 (2007).

Brentjens et al., "Treatment of chronic lymphocytic leukemia with genetically targeted autologous T cells: case report of an unforeseen adverse event in a phase I clinical trialm," Mol Ther 18(4):666-668 (2010).

Bridgeman et al., "Structural and biophysical determinants of alphabeta T-cell antigen recognition," Immunology 135(1):9-18 (2011).

Cairoet al., "NCI first International Workshop on the biology, prevention, and treatment of relapse after allogeneic hematopoietic stem cell transplantation: report from the committee on the biological considerations of hematological relapse following allogeneic stem cell transplantation unrelated to graft-versus-tumor effects: state of the science," Biol Blood Marrow Transplant 16(6):709-728 (2010).

Cameron et al., "Identification of a Titin-Derived HLA-AI-Presented Peptide as a Cross-Reactive Target for Engineered MAGE A3-Directed T Cells," Sci Transl Med 197(5):197ra103; 1-11 (2013).

Carpenito et al., "Control of large, established tumor xenografts with genetically retargeted human T cells containing CD28 and CD137 domains," Proc Natl Acad Sci U S A 106(9):3360-3365 (2009).

(56) References Cited

OTHER PUBLICATIONS

Carpenter et al., "B-cell maturation antigen is a promising target for adoptive T-cell therapy of multiple myeloma," Clinical Cancer Research 19(8):2048-2060 (2013).
Chatterjee et al., "A Versatile Platform for Single- and Multiple-Unnatural Amino Acid Mutagenesis in *Escherichia coli*," Biochemistry 52(10):1-23 (2013).
Chiarella et al., "Antigenic features of protein carriers commonly used in immunisation trials," Biotechnol Lett 32(9):1215-1221 (2010).
Chlewicki et al., "High-affinity, peptide-specific T cell receptors can be generated by mutations in CDR1, CDR2 or CDR3," J Mol Biol 346(1):223-239 (2005).
Chung et al., "CD19 is a major B cell receptor-independent activator of MYC-driven B-lymphomagenesis," J Clin Invest 122(6):2257-2266 (2012).
Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462.
Cole et al., "The molecular determinants of CD8 co-receptor function," Immunology 137(2):139-148 (2012).
Connor et al., "Enzymatic N-terminal Addition of Noncanonical Amino Adds to Peptides and Proteins," ChemBioChem 9:366-369 (2008).
Cui et al., "Chemically programmed bispecific antibodies that recruit and activate T cells," Journal of Biological Chemistry 287(34):28206-28214 (2012).
Davila et al., "CD19 CAR-targeted T cells induce long-term remission and B Cell Aplasia in an immunocompetent mouse model of B cell acute lymphoblastic leukemia," PLoS One 8(4) e61338 (2013), 14 pages.
Davis et al., "Therapy of B-Cell Lymphoma with Anti-CD20 Antibodies Can Result in the Loss of CD20 Antigen Expression," Clinical Cancer Research 5: 611-615, (1999).
Dengl et al., "Engineered hapten-binding antibody derivatives for modulation of pharmacokinetic properties of small molecules and targeted payload delivery," Immunological Reviews 270:165-177 (2016).
Dubrovska et al., "A chemically induced vaccine strategy for prostate cancer," ACS Chem Biol 6(11):1223-1231 (2011).
Eppstein et al., "Biological activity of liposome-encapsulated murine interferon γ is mediated by a cell membrane receptor," Proc. Natl. Acad. Sci. USA, 82: 3688-92 (1985).
Ertl et al., "Considerations for the Clinical Application of Chimeric Antigen Receptor T Cells: Observations from a Recombinant DNA Advisory Committee Symposium Held Jun. 15, 2010," Cancer Research 71(9): 3175-3181 (2011).
Eshhar and Gross, "Chimeric T cell receptor which incorporates the anti-tumour specificity of a monoclonal antibody with the cytolytic activity of T cells: a model system for immunotherapeutical approach," Br. J. Cancer 62: 27-29 (1990).
Eshhar et al., "Specific activation and targeting of cytotoxic lymphocytes through chimeric single chains consisting of antibody-binding domains and the Y or subunits of the immunoglobulin and T-cell receptors," Proc. Natl. Acad. Sci. USA 90:720-724 (1993).
Eshhar, "The T-Body Approach: Redirecting T Cells with Antibody Specificity," Y. Chernajovsky, A. Nissim (eds.), Therapeutic Antibodies. Handbook of Experimental Pharmacology 181. Springer-Verlag Berlin Heidelberg, pp. 329-342 (2008).
Fernando et al., "Targeted Therapy of Colorectal Cancer: Clinical Experience with Bevacizumab," The Oncologist 9(suppl 1):11-18 (2004).
Fitzer-Attas et al., "Harnessing Syk Family Tyrosine Kinases as Signaling Domains for Chimeric Single Chain of the Variable Domain Receptors: Optimal Design for T Cell Activation," The Journal of Immunology 160: 145-154 (1998).
Friedmann-Morvinski et al., "Redirected primary T cells harboring a chimeric receptor require costimulation for their antigen-specific activation," Blood 105: 3087-3093 (2005).
Frost et al., "In Vitro Evaluation of Avidin Antibody Pretargeting Using 211At-Labeled and Biotinylated Poly-L-Lysine as Effector Molecule," Cancer 116(4 suppl): 1101-1110 (2010).
Gamzatova et al., "Human leucocyte antigen (HLA) A2 as a negative clinical prognostic factor in patients with advanced ovarian cancer," Gynecologic Oncology 103: 145-150 (2006).
Gavrilyuk et al., "β-Lactam-based Approach for the Chemical Programming of Aldolase Antibody 38C2," Bioorg Med Chem Lett. 19(5):1421-1424 (2009).
GenBank Accession No. AB064051: Homo sapiens IGK mRNA for immunoglobulin kappa light chain VLJ region, partial cds, clone: K10. Jul. 2, 2002, 2 pages.
Gilham et al., "CAR-T cells and solid tumors: tuning T cells to challenge an inveterate foe," Trends in Molecular Medicine 18(7):377-384 (2012).
Gillies et al., "Targeting Human Cytotoxic T Lymphocytes to Kill Heterologous Epidermal Growth Factor Receptor-Bearing Tumor Cells. Tumor-Infiltrating Lymphocyte/Hormone Receptor/ Recombinant Antibody," J. Immu. 146(3):1067-1071 (1991).
Grada et al., 'TanCAR: A Novel Bispecific Chimeric Antigen Receptor for Cancer Immunotherapy, Molecular Therapy-Nucleic Acids 2(7):1-11 (2013).
Griffioen, M., et al., "Retroviral transfer of human CD20 as a suicide gene for adoptive T-cell therapy," Haematologica 94(9):1316-1320 (2009).
Gross and Eshhar, "Endowing T cells with antibody specificity using chimeric T cell receptors," FASEB J. 6: 3370-3378 (1992).
Gross et al., "Expression of immunoglobulin-T-cell receptor chimeric molecules as functional receptors with antibody-type specificity," Proc Natl Acad Sci U S A 86(24):10024-10028 (1989).
Grupp et al., "Chimeric antigen receptor-modified T cells for acute lymphoid leukemia," N Engl J Med 68(16):1509-1518 (2013).
Guest et al., "The Role of Extracellular Spacer Regions in the Optimal Design of Chimeric Immune Receptors. Evaluation of Four Different scFvs and Antigens," J. Immunother 28(3): 203-211 (2005).
Hanes et al., "Ribosome display efficiently selects and evolves high-affinity antibodies in vitro from immune libraries," Proc Natl Acad Sci U S A 95(24): 14130-1435 (1998).
Herron et al., "High resolution structures of the 4-4-20 Fab-fluorescein complex in two solvent systems: effects of solvent on structure and antigen-binding affinity," Biophys J 67(6):2167-2183 (1994).
Heslop, "Safer CARS," Mol Ther 18(4):661-662 (2010).
Hollatz, G., et al., "T cells for suicide gene therapy: activation, functionality and clinical relevance," J Immunol Methods, 2008, pp. 69-81, vol. 331(1-2).
Hombach et al., "T cell activation by recombinant FcεRI γ-chain immune receptors: an extracellular spacer domain impairs antigen-dependent T cell activation but not antigen recognition," Gene Therapy 7: 1067-1075 (2000).
Hotfilder et al., "Leukemic stem cells in childhood high-risk ALL/ t(9;22) and t(4;11) are present in primitive lymphoid-restricted CD34+CD19-cells," Cancer Res 65(4):1442-1449 (2005).
Hudecek et al., "Receptor affinity and extracellular domain modifications affect tumor recognition by ROR1-specific chimeric antigen receptor T cells," Clin Cancer Res 19(12):3153-3164 (2013).
Hutchins et al., "Site-Specific Coupling and Sterically Controlled Formation of Multimeric Antibody Fab Fragments with Unnatural Amino Acids, Journal of Molecular Biology," J Mol Biol 406(4):595-603 (2011).
Hutchins et al., "Selective formation of covalent protein heterodimers with an unnatural amino acid," Chemistry & Biology 18(3):299-303 (2011).
Hwang et al., "Hepatic uptake and degradation of unilamellar sphingomyelin/cholesterol liposomes: a kinetic study," Proc. Natl. Acad. Sci. USA, 77: 4030-4034 (1980).
Hwu et al., "Lysis of Ovarian Cancer Cells by Human Lymphocytes Redirected with a Chimeric Gene Composed of an Antibody Variable Region and the Fc Receptor γ Chain," J. Exp. Med. 178: 361-366 (1993).

(56) References Cited

OTHER PUBLICATIONS

Johnson et al., "RF1 Knockout Allows Ribosomal Incorporation of Unnatural Amino Acids at Multiple Sites," Nat Chem Biol, 7(11):779-86 (2011).
Johnson et al., "Gene therapy with human and mouse T-cell receptors mediates cancer regression and targets normal tissues expressing cognate antigen," Blood 114: 535-546 (2009).
Jung et al., "Improving in vivo folding and stability of a single-chain Fv antibody fragment by loop grafting," Protein Engineering 10(8):959-966 (1997).
Kalos et al., "T cells with chimeric antigen receptors have potent antitumor effects and can establish memory in patients with advanced leukemia," Science Translational Medicine 3(95):95ra73 (2011), 37 pages.
Kammerer et al., "A conserved trimerization motif controls the topology of short coiled coils," Proc Natl Acad Sci USA 102:13891-13896 (2005).
Kazane et al., "Self-assembled antibody multimers through peptide nucleic acid conjugation," Journal Am Chem Soc 135(1):340-346 (2013).
Kershaw et al., "A Phase I Study on Adoptive Immunotherapy Using Gene-Modified T Cells for Ovarian Cancer," Clinical Cancer Research 12(20 Pt 1):6106-6115 (2006).
Kershaw et al., "Gene-Engineered T Cells as a Superior Adjuvant Therapy for Metastatic Cancer," The Journal of Immunology 173(3): 2143-2150 (2004).
Kim et al., "Protein conjugation with genetically encoded unnatural amino acids," Current Opinion in Chemical Biology 17(3):412-419 (2013).
Kim et al., "Synthesis of Bispecific Antibodies using Genetically Encoded Unnatural Amino Acids," Journal of the American Chemical Society 134(24):9918-9921 (2012).
Kochenderfer et al., "Construction and pre-clinical evaluation of an anti-CD19 chimeric antigen receptor," Journal of Immunotherapy 32(7):689-702 (2009).
Kochenderfer et al., "Adoptive transfer of syngeneic T cells transduced with a chimeric antigen receptor that recognizes murine CD19 can eradicate lymphoma and normal B cells," Blood 116(19):3875-3886 (2010).
Kochenderfer et al., "B-cell depletion and remissions of malignancy along with cytokine-associated toxicity in a clinical trial of anti-CD19 chimeric-antigen receptor-transduced T cells," Blood 119(12):2709-2720 (2012).
Kontermann, "Dual targeting strategies with bispecific antibodies," Mar. 1, 2012 4(2):182-197 (2012).
Kranz et al., "Conjugates of folate and anti-T-cell-receptor antibodies specifically target folate-receptor-positive tumor cells for lysis," Proc. Natl. Acad. Sci. USA 92: 9057-9061 (1995).
Krause et al., "Antigen-dependent CD28 Signaling Selectively Enhances Survival and Proliferation in Genetically Modified Activated Human Primary T Lymphocytes," J. Exp. Med. 188(4):619-626 (1998).
Kudoet al, "T Lymphocytes expressing a CD16 signaling receptor exert antibody-dependent cancer cell killing," Cancer Research 74(1):93-103 (2014), e-pub Nov. 6, 2013.
Kularatne et al., "Prostate-specific membrane antigen targeted imaging and therapy of prostate cancer using a PSMA inhibitor as a homing ligand," Molecular Pharmaceutics 6(3):780-789 (2009).
Kuroki et al., "Strategies to Endow Cytotoxic T Lymphocytes or Natural Killer Cells with Antibody Activity against Carcinoembryonic Antigen," Tumor Biol. 25: 208-216 (2004).
Lamers et al., "Treatment of Metastatic Renal Cell Carcinoma With Autologous T-Lymphocytes Genetically Retargeted Against Carbonic Anhydrase IX: First Clinical Experience," Journal of Clinical Oncology 24(13): e20-e22 (2006).
Lamers et al., "Immune responses to transgene and retroviral vector in patients treated with ex vivo-engineered T cells," Blood 117(1):72-82 (2011), e-pub Oct. 1, 2010.
Lang et al., "Genetic encoding of bicyclononynes and trans-cyclooctenes for site-specific protein labeling in vitro and in live mammalian cells via rapid fluorgenic Diels-Alder reactions," Journal of the American Chemical Society, 2012, pp. 10317-10320, vol. 134, No. 25.
le Viseur, C. et al., "In childhood acute lymphoblastic leukemia, blasts at different stages of immunophenotypic maturation have stem cell properties," Cancer Cell, 14(1):47-58 (2008).
Lee and Brentjens, "Retroviral transduction of murine primary T lymphocytes," Methods in Molecular Biology 506:83-96 (2009).
Lin et al., "Transglutaminase-Catalyzed Site-Specific Conjugation of Small-Molecules to Proteins in Vitro and on the Surface of Living Cells," J. Am. Chem. Soc. 128:4542-4543 (2006).
Linette et al., "Cardiovascular toxicity and titin cross-reactivity of affinity-enhanced T cells in myeloma and melanoma," Blood 122(6):863-871 (2013).
Litowski et al., "Designing heterodimeric two-stranded alpha-helical coiled-coils. Effects of hydrophobicity and alpha-helical propensity on protein folding, stability, and specificity," J Biol Chem, 277:37272-37279 (2002).
Liu et al., "Adding new chemistries to the genetic code," Annual Review of Biochemistry 79:413-444 (2010).
Lobbestael et al., "Immunohistochemical detection of transgene expression in the brain using small epitope tags," BMC Biotechnology 10, six pages, 2010.
Lu et al., "Site-Specific Antibody-Polymer Conjugates for siRNA Delivery," Journal of American Chemical Society 135(37):13885-13891 (2013).
Lu et al., "Strategy to prevent drug-related hypersensitivity in folate-targeted hapten immunotherapy of cancer," AAPS J 11(3):628-638 (2009).
Ma et al., "Carcinoembryonic antigen-immunoglobulin Fc fusion protein (CEA-Fc) for identification and activation of anti-CEA immunoglobulin-T-cell receptor-modified T cells, representative of a new class of Ig fusion proteins," C. Gene Therapy 11: 297-306 (2004).
Ma et al., "Genetically engineered T cells as adoptive immunotherapy of cancer," Cancer Chemother Biol Response Modif 20:315-341 (2002).
Ma et al., "Targeting of antigens to B lymphocytes via CD19 as a means for tumor vaccine development," Journal of Immunology 190(11):5588-5599 (2013).
Maher et al., "Human T-lymphocyte cytotoxicity and proliferation directed by a single chimeric TCRζ/CD28 receptor," Nature Biotechnology 20: 70-75 ( 2002).
Maher, J., "Immunotherapy of malignant disease using chimeric antigen receptor engrafted T cells," International Scholarly Research Notices Oncology, 2012:278093 (2012).
Masir et al., "Loss of CD19 expression in B-cell neoplasms," Histopathology 48(3):239-246 (2006).
Milone et al., "Chimeric receptors containing CD137 signal transduction domains mediate enhanced survival of T cells and increased antileukemic efficacy in vivo," Molecular Therapy 17(8):1453-1464 (2009).
Moore et al., "Application of dual affinity retargeting molecules to achieve optimal redirected T-cell killing of B-cell lymphoma," Blood 117(17):4542-4551 (2011).
Morgan et al., "Case report of a serious adverse event following the administration of T cells transduced with a chimeric antigen receptor recognizing ERBB2," Molecular Therapy 18(4):843-851 (2010).
Mossner et al., "Fast selection of antibodies without antigen purification: adaptation of the protein fragment complementation assay to select antigen-antibody pairs," Journal of Molecular Biology 308(2):115-122 (2001).
Murphy et al., "Elevated expression of il-8 and il-8 receptors in prostate cancer cells correlates with disease progression and resistance to oxaliplatin," Proc. Amer. Assoc. Cancer Res., 2005, 46, abstract No. 1495, 2 pages.
Nauerth et al., "TCR-ligand koff rate correlates with the protective capacity of antigen-specific CD8+ T cells for adoptive transfer," Science Translational Medicine 5(192):192ra87; pp. 1-10 (2013).
Ogg et al., "Sensitization of tumour cells to lysis by virus-specific CTL using antibody-targeted MHC class I/peptide complexes," British Journal of Cancer 82(5):1058-1062 (2000).

(56) References Cited

OTHER PUBLICATIONS

Olejniczak et al., "A quantitative exploration of surface antigen expression in common B-cell malignancies using flow cytometry," Immunol Invest 35(1):93-114 (2006).
Oshimi et al., "Increased Lysis of Patient CD10-Positive Leukemic Cells by T Cells Coated With Anti-CD3 Fab' Antibody Cross-Linked to Anti-CD10 Fab' Antibody," Blood 77(5): 1044-1049, (1991).
Park et al., "Adoptive Transfer of Chimeric Antigen Receptor Re-directed Cytolytic T Lymphocyte Clones in Patients with Neuroblastoma," Molecular Therapy 15(4): 825-833 (2007).
Perez et al., "Specific targeting of cytotoxic T cells by anti-T3 linked to anti-target cell antibody," Nature 316: 354-356, Jul. 25 (1985).
Popkov, et al., "Instant immunity through chemically programmable vaccination and covalent self-assembly," Proceedings of the National Academy of Sciences of the United States of America. Early Edition. Jan. 7, 2009, pp. 1-6.
Porter et al., "Chimeric antigen receptor-modified T cells in chronic lymphoid leukemia," New England Journal of Medicine 355(8):725-733 (2011).
Pule et al., "Virus-specific T cells engineered to coexpress tumor-specific receptors: persistence and antitumor activity in individuals with neuroblastoma," Nature Medicine 14(11): 1264-1270 (Nov. 2008).
Rabuka et al., "Site-specific chemical protein conjugation using genetically encoded aldehyde tags," Nature Protocols 7(6):1052-1067 (2012).
Rader, et al., "A Humanized Aldolase Antibody for Selective Chemotherapy and Adaptor Immunotherapy," Journal of Molecular Biology332:889-899 (2003).
Rader, et al., "Chemically programmed antibodies," Trends in Biotechnology 32(4):186-197 (2014).
Rader, et al., "Chemically programmed monoclonal antibodies for cancer therapy: Adaptor immunotherapy based on a covalent antibody catalyst," PNAS 100(9):5396-5400 (2003).
Reichert, "Biospecific antibodies: A global overview of development as innovative therapeutics," AAPS 2013 National Biotechnology Conference, May 21, 2013, 14 pages.
Reid et al., "Extrinsic Cotton Effects in Hapten-Carrier and Hapten-Antibody Interactions," Proc. Nat. Acad. Sci. USA 68(6): 1184-1187 (1971).
Restifo et al., "Adoptive immunotherapy for cancer: harnessing the T cell response," Nature Reviews Immunology 12(4):269-281 (2012).
Rezvani and Maloneym, "Rituximab resistance," Best Pract Res Clin Haematol 24(2):203-216 (2011).
Riddell and Protzer, "Carving the CAR," Gene Therapy 17: 1191-1192 (2010).
Riviere et al., "Effects of retroviral vector design on expression of human adenosine deaminase in murine bone marrow transplant recipients engrafted with genetically modified cells," Proc Natl Acad Sci USA 92(15):6733-6737 (1995).
Roberts et al., "Chemistry for peptide and protein PEGylation," Advanced Drug Delivery Reviews 54:459-476 (2002).
Romer et al., "Preculture of PBMCs at high cell density increases sensitivity of T-cell responses, revealing cytokine release by CD28 superagonist TGN1412," Blood 118(26):6772-6782 (2011).
Rossi et.al., "Stably tethered multifunctional structures of defined composition made by the dock and lock method for use in cancer targeting," Proc Natl Acad Sci US A. May 2;103(18):6841-6846 (2006).
Sadelain et al., "The promise and potential pitfalls of chimeric antigen receptors," Current Opinion in Immunology 21: 215-223 (2009).
Savage et al., "Induction of viral and tumor specific CTL responses using antibody targeted HLA class I peptide complexes," British Journal of Cancer 86: 1336-1342 (2002).
Schmitt-Verhulst et al., "H-2-Restricted Cytotoxic Effectors Generated In Vitro by the Addition of Trinitrophenyl-Conjugated Soluble Proteins," The Journal of Experimental Medicine 147: 352-368 (1978).
Scholler et al., "Decade-long safety and function of retroviral-modified chimeric antigen receptor T cells," Science Translational Medicine 4(132) pp. 132ra53 (2012), 16 pages.
Scott et al., "Immunogenicity of biotinylated hapten-avidin complexes," Mol Immunol 21(11):1055-1060 (1984).
Shirasu et al., "Construction and Molecular Characterization of Human Chimeric T-Cell Antigen Receptors Specific for Carcinoembryonic Antigen," Anticancer Research 30: 2731-2738 (2010).
Sigma-Aldrich Co. LLC, Product Information Monoclanal Anti-CD3, clone UCHT-1 produced in mouse, purified immunoglobulin. Catalog No. C7048, 2012, 2 pages.
Siliciano et al., "The Interaction of Nominal Antigen With T Cell Antigen Receptors. I. Specific Binding of Multivalent Nominal Antigen to Cytolytic T Cell Clone," The Journal of Immunology 135(2):906-914 (1985).
Sinha et al., "Preparation of integrin $\alpha(v)\beta(3)$-targeting Ab 38C2 constructs," Nature Protocols 2:449-456 (2007).
Stone et al., "A sensitivity scale for targeting T cells with chimeric antigen receptors (CARs) and bispecific T-cell Engagers (BiTEs)," Oncoimmunology 1(6): 863-873 (2012).
Straathof et al., "An inducible caspase 9 safety switch for T-cell therapy," Blood, 105(11):4247-4254 (2005).
Suhoski et al., "Engineering artificial antigen-presenting cells to express a diverse array of co-stimulatory molecules," Molecular Therapy 15(5):981-988 (2007).
Tai et al., "Development of a Peptide-Drug Conjugate for Prostate Cancer Therapy," Molecular Pharmaceutics 8:901-912 (2011).
Tamada et al., "Redirecting Gene-Modified T Cells toward Various Cancer Types Using Tagged Antibodies," Clinical Cancer Research, 18(23):6436-6445 (2012).
Terakuraet al., "Generation of CD19-chimeric antigen receptor modified CD8+ T cells derived from virus-specific central memory T cells," Blood 119(1):72-82 (2012) e-pub Oct. 26, 2011.
Themeli et al., "Generation of tumor-targeted human T lymphocytes from induced pluripotent stem cells for cancer therapy," Nature Biotechnology 31:928-933 (2013).
Thomas et al., "Application of strain-promoted azide-alkyne cycloaddition and tetrazine ligation to targeted Fc-drug conjugates," Bioconjugate Chemistry 23(10): 2007-2013 (2012).
Till et al., "Adoptive immunotherapy for indolent non-Hodgkin lymphoma and mantle cell lymphoma using genetically modified autologous CD20-specific T cells," Blood 112(6): 2261-2271 (2008).
Traversari et al., "The potential immunogenicity of the TK suicide gene does not prevent full clinical benefit associated with the use of TK-transduced donor lymphocytes in HSCT for hematologic malignancies," Blood 109(11):4708-4715 (2007).
Turatti et al., "Redirected activity of human antitumor chimeric immune receptors is governed by antigen and receptor expression levels and affinity of interaction," Journal of Immunotherapy 30(7):684-693 (2007).
Urbanska, et al, "Targeted cancer immunotherapy via combination of designer bispecific antibody and novel gene-engineered T cells," Journal of Translational Medicine 12:347-359 (2014).
Urbanska and Powell, "Development of a novel universal immune receptor for antigen targeting: To Infinity and beyond," Oncoimmunology 1(5):777-779 (2012).
Urbanska, K., et al., "A universal strategy for adoptive immunotherapy of cancer through use of a novel T-cell antigen receptor," Cancer Research 72(7):1844-1852 (2012).
Uttenthal et al., "Challenges in T cell receptor gene therapy," Journal of Gene Med 14(6):386-399 (2012).
van Dam et al., "Intraoperative tumor-specific fluorescence imaging in ovarian cancer by folate receptor-alpha targeting: first in-human results," Nature Medicine 17(10):1315-1319 (2011).
Vaughan et al., "Human antibodies with sub-nanomolar affinities isolated from a large non-immunized phage display library," Nat Biotechnol 14(3):309-314 (1996).
Wang et al. Expanding the genetic code. Angew Chem Int Ed44:34-66 (2005).
Weiden and Breitz, "Pretargeted radioimmunotherapy (PRIT™) for treatment of non-Hodgkin's lymphoma (NHL)," Critical Reviews in Oncology/Hematology 40:37-51 (2001).

(56) References Cited

OTHER PUBLICATIONS

Woolfson, "The design of coiled-coil structures and assemblies," Adv Protein Chem, 70: 79-112 (2005).
Xiang et al., "Production of hybrid bispecific antibody recognizing human colorectal carcinoma and CD3 antigen," Mol. Biother. 4: 5-23 (1992).
Xu et al., "Efficacy and safety of adoptive immunotherapy using anti-CD19 chimeric antigen receptor transduced T-cells: a systematic review of phase I clinical trials," Leuk Lymphoma 54(2):255-260 (2013).
Young et al, "Beyond the canonical 20 amino acids: expanding the genetic lexicon," Journal of Biological Chemistry 285(15):11039-11044 (2010).
Young et al., "An enhanced system for unnatural amino acid mutagenesis in *E. coli*," Journal Molecular Biology 395(2):361-374 (2010), e-pub Oct. 21, 2009.
Yu et al., "A non-transgenic mouse model for B-cell lymphoma: in vivo infection of p53-null bone marrow progenitors by a Myc retrovirus is sufficient for tumorigenesis," Oncogene 21(12):1922-1927 (2002).
Yu et al., "Oscillation between B-lymphoid and myeloid lineages in Myc-induced hematopoietic tumors following spontaneous silencing/reactivation of the EBF/Pax5 pathway," Blood 101(5):1950-1955 (2003), e-pub Oct. 24, 2002.
Zahndet al., "Directed in vitro evolution and crystallographic analysis of a peptide-binding single chain antibody fragment (scFv) with low picomolar affinity," Journal of Biological Chemistry 279(18):18870-18877 (2004).
Zeidler et al., "Simultaneous Activation of T Cells and Accessory Cells by a New Class of Intact Bispecific Antibody Results in Efficient Tumor Cell Killing," The Journal of Immunology 163: 1246-1252 (1999).
Zhang et al., "Identification and characterization of a new cross-reactive human immunodeficiency virus type 1-neutralizing human monoclonal antibody," Journal of Virology 78(17):9233-9242 (2004).
Zhang et al., "Identification of a novel CD4i human monoclonal antibody Fab that neutralizes HIV-1 primary isolates from different clades," Antiviral Research 61(3):161-164 (2004).

* cited by examiner

++ or +++ anti-peptide CAR-T cells (long hinge) vs U937 ($CLL1^+$)

anti-peptide CAR-T cells (short, dimeric hinge) vs U937 ($CLL1^+$)

Anti-CD33 hP67.6 Fab SEQ ID

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | |
|---|---|---|---|---|---|---|---|---|---|---|---|---|---|---|---|---|---|---|---|---|---|---|---|---|
| LC | 231 | 231 | 231 | 217 | 222 | 217 | 222 | 231 | 231 | 231 | 231 | 231 | 230 | 223 | 224 | 218 | 219 | 231 | 222 | 223 | 224 | 218 | 219 | SEQ ID |
| HC | 232 | 220 | 225 | 232 | 232 | 220 | 225 | 228 | 229 | 226 | 227 | 221 | 232 | 232 | 232 | 232 | 232 | 232 | 228 | 226 | 227 | 221 | 221 | |

Cytotoxicity, E:T = 10:1, 24 h, FACS 7-AAD

Cytotoxicity, E:T = 10:1, 24 h, FACS 7-AAD 5.0e$^6$ Her2$^+$ cells SC; 3e$^7$ sCAR-T (50% transd) day 10; *q.a.d.* switch Peptide fusion sites:
P1: LCNT
P2: LCCT
P3: HCNT
P4: HCCT

| | EC50 (nM) |
|---|---|
| αHer2 Fab | N.D. |
| LCNT | 2.0±0.2 |
| LCCT | 2.3±0.4 |
| HCNT | 1.5±0.2 |
| HCCT | 2.5±0.2 |
| NTBV | 1.6±0.2 |
| CTBV | 1.8±0.2 |

| | EC50 (nM) |
|---|---|
| αHer2 Fab | N.D. |
| LCNT | 1.7±0.1 |
| LCCT | 3.8±0.3 |
| HCNT | 1.7±0.4 |
| HCCT | 2.2±0.3 |
| NTBV | 1.4±0.2 |
| CTBV | 1.6±0.2 |

A

| | $EC_{50}$ (nM) |
|---|---|
| CTBV | 0.22±0.03 |
| αHer2 Fab | N.D. |

SEQUENCE LISTING

```
<160> NUMBER OF SEQ ID NOS: 276

<210> SEQ ID NO 1
<211> LENGTH: 8835
<212> TYPE: DNA
<213> ORGANISM: Artificial Sequence
<220> FEATURE:
<223> OTHER INFORMATION: Chimeric antigen receptor - LV-EF1a-
      GCN4(52SR4)-BBZ

<400> SEQUENCE: 1

caggtggcac ttttcgggga aatgtgcgcg gaacccctat ttgtttattt ttctaaatac     60

attcaaatat gtatccgctc atgagacaat aaccctgata aatgcttcaa taatattgaa    120

aaaggaagag tatgagtatt caacatttcc gtgtcgccct tattcccttt tttgcggcat    180

tttgccttcc tgtttttgct cacccagaaa cgctggtgaa agtaaaagat gctgaagatc    240

agttgggtgc acgagtgggt tacatcgaac tggatctcaa cagcggtaag atccttgaga    300

gttttcgccc cgaagaacgt tttccaatga tgagcacttt taaagttctg ctatgtggcg    360

cggtattatc ccgtattgac gccgggcaag agcaactcgg tcgccgcata cactattctc    420

agaatgactt ggttgagtac tcaccagtca cagaaaagca tcttacggat ggcatgacag    480

taagagaatt atgcagtgct gccataacca tgagtgataa cactgcggcc aacttacttc    540

tgacaacgat cggaggaccg aaggagctaa ccgctttttt gcacaacatg ggggatcatg    600

taactcgcct tgatcgttgg gaaccggagc tgaatgaagc cataccaaac gacgagcgtg    660

acaccacgat gcctgtagca atggcaacaa cgttgcgcaa actattaact ggcgaactac    720

ttactctagc ttcccggcaa caattaatag actggatgga ggcggataaa gttgcaggac    780

cacttctgcg ctcggccctt ccggctggct ggtttattgc tgataaatct ggagccggtg    840

agcgtgggtc tcgcggtatc attgcagcac tggggccaga tggtaagccc tcccgtatcg    900

tagttatcta cacgacgggg agtcaggcaa ctatggatga acgaaataga cagatcgctg    960

agataggtgc ctcactgatt aagcattggt aactgtcaga ccaagtttac tcatatatac   1020

tttagattga tttaaaactt catttttaat ttaaaaggat ctaggtgaag atcctttttg   1080

ataatctcat gaccaaaatc ccttaacgtg agttttcgtt ccactgagcg tcagaccccg   1140

tagaaaagat caaaggatct tcttgagatc ctttttttct gcgcgtaatc tgctgcttgc   1200

aaacaaaaaa accaccgcta ccagcggtgg tttgtttgcc ggatcaagag ctaccaactc   1260

tttttccgaa ggtaactggc ttcagcagag cgcagatacc aaatactgtc cttctagtgt   1320

agccgtagtt aggccaccac ttcaagaact ctgtagcacc gcctacatac ctcgctctgc   1380

taatcctgtt accagtggct gctgccagtg gcgataagtc gtgtcttacc gggttggact   1440

caagacgata gttaccggat aaggcgcagc ggtcgggctg aacggggggt tcgtgcacac   1500

agcccagctt ggagcgaacg acctacaccg aactgagata cctacagcgt gagctatgag   1560
```

-continued

```
aaagcgccac gcttcccgaa gggagaaagg cggacaggta tccggtaagc ggcagggtcg   1620
gaacaggaga gcgcacgagg gagcttccag ggggaaacgc ctggtatctt tatagtcctg   1680
tcgggtttcg ccacctctga cttgagcgtc gatttttgtg atgctcgtca ggggggcgga   1740
gcctatggaa aaacgccagc aacgcggcct ttttacggtt cctggccttt tgctggcctt   1800
ttgctcacat gttctttcct gcgttatccc ctgattctgt ggataaccgt attaccgcct   1860
ttgagtgagc tgataccgct cgccgcagcc gaacgaccga gcgcagcgag tcagtgagcg   1920
aggaagcgga agagcgccca atacgcaaac cgcctctccc cgcgcgttgg ccgattcatt   1980
aatgcagctg gcacgacagg tttcccgact ggaaagcggg cagtgagcgc aacgcaatta   2040
atgtgagtta gctcactcat taggcacccc aggctttaca ctttatgctt ccggctcgta   2100
tgttgtgtgg aattgtgagc ggataacaat ttcacacagg aaacagctat gaccatgatt   2160
acgccaagcg cgcaattaac cctcactaaa gggaacaaaa gctggagctg caagcttaat   2220
gtagtcttat gcaatactct tgtagtcttg caacatggta acgatgagtt agcaacatgc   2280
cttacaagga gagaaaaagc accgtgcatg ccgattggtg gaagtaaggt ggtacgatcg   2340
tgccttatta ggaaggcaac agacgggtct gacatggatt ggacgaacca ctgaattgcc   2400
gcattgcaga gatattgtat ttaagtgcct agctcgatac aataaacggg tctctctggt   2460
tagaccagat ctgagcctgg gagctctctg gctaactagg gaacccactg cttaagcctc   2520
aataaagctt gccttgagtg cttcaagtag tgtgtgcccg tctgttgtgt gactctggta   2580
actagagatc cctcagaccc ttttagtcag tgtggaaaat ctctagcagt ggcgcccgaa   2640
cagggacctg aaagcgaaag ggaaaccaga gctctctcga cgcaggactc ggcttgctga   2700
agcgcgcacg gcaagaggcg aggggcggcg actggtgagt acgccaaaaa ttttgactag   2760
cggaggctag aaggagagag atgggtgcga gagcgtcagt attaagcggg ggagaattag   2820
atcgcgatgg gaaaaaattc ggttaaggcc agggggaaag aaaaaatata aattaaaaca   2880
tatagtatgg gcaagcaggg agctagaacg attcgcagtt aatcctggcc tgttagaaac   2940
atcagaaggc tgtagacaaa tactgggaca gctacaacca tcccttcaga caggatcaga   3000
agaacttaga tcattatata atacagtagc aaccctctat tgtgtgcatc aaaggataga   3060
gataaaagac accaaggaag ctttagacaa gatagaggaa gagcaaaaca aaagtaagac   3120
caccgcacag caagcggccg ctgatcttca gacctggagg aggagatatg agggacaatt   3180
ggagaagtga attatataaa tataaagtag taaaaattga accattagga gtagcaccca   3240
ccaaggcaaa gagaagagtg gtgcagagag aaaaaaagagc agtgggaata ggagctttgt  3300
tccttgggtt cttgggagca gcaggaagca ctatgggcgc agcctcaatg acgctgacgg   3360
tacaggccag acaattattg tctggtatag tgcagcagca gaacaatttg ctgagggcta   3420
ttgaggcgca acagcatctg ttgcaactca cagtctgggg catcaagcag ctccaggcaa   3480
gaatcctggc tgtggaaaga tacctaaagg atcaacagct cctggggatt tggggttgct   3540
ctggaaaact catttgcacc actgctgtgc cttggaatgc tagttggagt aataaatctc   3600
tggaacagat tggaatcaca cgacctggat ggagtgggac agagaaatta acaattacac   3660
aagcttaata cactccttaa ttgaagaatc gcaaaaccag caagaaaaga atgaacaaga   3720
attattggaa ttagataaat gggcaagttt gtggaattgg tttaacataa caaattggct   3780
gtggtatata aaattattca taatgatagt aggaggcttg gtaggtttaa gaatagtttt   3840
tgctgtactt tctatagtga atagagttag gcagggatat tcaccattat cgtttcagac   3900
ccacctccca accccgaggg gacccgacag gcccgaagga atagaagaag aaggtggaga   3960
```

```
gagagacaga gacagatcca ttcgattagt gaacggatct cgacggttaa cttttaaaag   4020
aaaagggggg attgggggt acagtgcagg ggaaagaata gtagacataa tagcaacaga   4080
catacaaact aaagaattac aaaaacaaat tacaaaaatt caaaatttta tcgagctttg   4140
caaagatgga taaagtttta aacagagagg aatctttgca gctaatggac cttctaggtc   4200
ttgaaaggag tgcctcgtga ggctccggtg cccgtcagtg ggcagagcgc acatcgccca   4260
cagtccccga gaagttgggg ggaggggtcg gcaattgaac cggtgcctag agaaggtggc   4320
gcggggtaaa ctgggaaagt gatgtcgtgt actggctccg cctttttccc gagggtgggg   4380
gagaaccgta tataagtgca gtagtcgccg tgaacgttct ttttcgcaac gggtttgccg   4440
ccagaacaca ggtaagtgcc gtgtgtggtt cccgcgggcc tggcctcttt acgggttatg   4500
gcccttgcgt gccttgaatt acttccacct ggctgcagta cgtgattctt gatcccgagc   4560
ttcgggttgg aagtgggtgg gagagttcga ggccttgcgc ttaaggagcc ccttcgcctc   4620
gtgcttgagt tgaggcctgg cctgggcgct ggggccgccg cgtgcgaatc tggtggcacc   4680
ttcgcgcctg tctcgctgct ttcgataagt ctctagccat ttaaaatttt tgatgacctg   4740
ctgcgacgct ttttttctgg caagatagtc ttgtaaatgc gggccaagat ctgcacactg   4800
gtatttcggt ttttggggcc gcgggcggcg acggggcccg tgcgtcccag cgcacatgtt   4860
cggcgaggcg gggcctgcga gcgcggccac cgagaatcgg acgggggtag tctcaagctg   4920
gccggcctgc tctggtgcct ggcctcgcgc cgccgtgtat cgccccgccc tgggcggcaa   4980
ggctggcccg gtcggcacca gttgcgtgag cggaaagatg gccgcttccc ggccctgctg   5040
cagggagctc aaaatggagg acgcggcgct cgggagagcg ggcgggtgag tcacccacac   5100
aaaggaaaag ggcctttccg tcctcagccg tcgcttcatg tgactccacg gagtaccggg   5160
cgccgtccag gcacctcgat tagttctcga gcttttggag tacgtcgtct ttaggttggg   5220
gggaggggtt ttatgcgatg gagtttcccc acactgagtg ggtggagact gaagttaggc   5280
cagcttggca cttgatgtaa ttctccttgg aatttgccct ttttgagttt ggatcttggt   5340
tcattctcaa gcctcagaca gtggttcaaa gtttttttct tccatttcag gtgtcgtgag   5400
gaattcggta ccgcggccgc ccggggatcc atggccttac cagtgaccgc cttgctcctg   5460
ccgctggcct tgctgctcca cgccgccagg ccggacgccg ttgtgaccca ggaatccgct   5520
ctgacctctt ctccaggcga aaccgtgact ctgacttgcc gtagtagcac cggggctgtg   5580
accacatcta actatgccag ttgggtccag gaaaaaccgg atcacctgtt tactggcctg   5640
attggcggca ccaacaatcg cgcaccgggt gtgcccgctc gtttcagcgg ttccctgatt   5700
ggggacaagg cagcactgac tatcaccggc gcccagaccg aagatgaggc gatctatttt   5760
tgcgtcctgt ggtacagcga ccattgggtg ttcgggggag gcaccaaact gacagtgctg   5820
ggcggaggag gaggttcagg aggaggaggt agcgggggag gcggttccgg gggaggcggt   5880
tctgatgtgc agctgcaaga atccgggcca ggactggttg cgccttctca gagtctgtca   5940
attacatgta ctgttagtgg ctttctgctg accgactatg gtgtgaactg ggttcgtcag   6000
agcccaggca agggtctgga gtggctggga gtgatttggg gggatggaat cacagactac   6060
aatagcgcac tgaaatctcg gctgagtgtt accaaagata acagcaagtc ccaggtcttc   6120
ctgaagatga acagcctgca aagcggcgac tccgctcgct attactgcgt taccggactg   6180
tttgattatt gggggcaggg gacaactctg actgtttcct ccaccacgac gccagcgccg   6240
cgaccaccaa caccggcgcc caccatcgcg tcgcagcccc tgtccctgcg cccagaggcg   6300
```

-continued

```
tgccggccag cggcgggggg cgcagtgcac acgagggggc tggacttcgc ctgtgatatc   6360
tacatctggg cgcccttggc cgggacttgt ggggtccttc tcctgtcact ggttatcacc   6420
ctttactgca aacggggcag aaagaaactc ctgtatatat tcaaacaacc atttatgaga   6480
ccagtacaaa ctactcaaga ggaagatggc tgtagctgcc gatttccaga agaagaagaa   6540
ggaggatgtg aactgagagt gaagttcagc aggagcgcag acgcccccgc gtacaagcag   6600
ggccagaacc agctctataa cgagctcaat ctaggacgaa gagaggagta cgatgttttg   6660
gacaagagac gtggccggga ccctgagatg gggggaaagc cgagaaggaa gaaccctcag   6720
gaaggcctgt acaatgaact gcagaaagat aagatggcgg aggcctacag tgagattggg   6780
atgaaaggcg agcgccggag gggcaagggg cacgatggcc tttaccaggg tctcagtaca   6840
gccaccaagg acacctacga cgcccttcac atgcaggccc tgccccctcg ctaagtcgac   6900
aatcaacctc tggattacaa aatttgtgaa agattgactg gtattcttaa ctatgttgct   6960
ccttttacgc tatgtggata cgctgcttta atgcctttgt atcatgctat tgcttcccgt   7020
atggctttca ttttctcctc cttgtataaa tcctggttgc tgtctcttta tgaggagttg   7080
tggcccgttg tcaggcaacg tggcgtggtg tgcactgtgt ttgctgacgc aacccccact   7140
ggttggggca ttgccaccac ctgtcagctc ctttccggga ctttcgcttt ccccctccct   7200
attgccacgg cggaactcat cgccgcctgc cttgcccgct gctggacagg ggctcggctg   7260
ttgggcactg acaattccgt ggtgttgtcg gggaagctga cgtcctttcc atggctgctc   7320
gcctgtgttg ccacctggat tctgcgcggg acgtccttct gctacgtccc ttcggccctc   7380
aatccagcgg accttccttc ccgcggcctg ctgccggctc tgcggcctct tccgcgtctt   7440
cgccttcgcc ctcagacgag tcggatctcc ctttgggccg cctccccgcc tggaattcga   7500
gctcggtacc tttaagacca atgacttaca aggcagctgt agatcttagc cactttttaa   7560
aagaaaaggg gggactggaa gggctaattc actcccaacg aagacaagat ctgctttttg   7620
cttgtactgg gtctctctgg ttagaccaga tctgagcctg ggagctctct ggctaactag   7680
ggaacccact gcttaagcct caataaagct tgccttgagt gcttcaagta gtgtgtgccc   7740
gtctgttgtg tgactctggt aactagagat ccctcagacc cttttagtca gtgtggaaaa   7800
tctctagcag tagtagttca tgtcatctta ttattcagta tttataactt gcaaagaaat   7860
gaatatcaga gagtgagagg aacttgttta ttgcagctta taatggttac aaataaagca   7920
atagcatcac aaatttcaca aataaagcat ttttttcact gcattctagt tgtggtttgt   7980
ccaaactcat caatgtatct tatcatgtct ggctctagct atcccgcccc taactccgcc   8040
cagttccgcc cattctccgc cccatggctg actaattttt tttatttatg cagaggccga   8100
ggccgcctcg gcctctgagc tattccagaa gtagtgagga ggcttttttg gaggcctagg   8160
cttttgcgtc gagacgtacc caattcgccc tatagtgagt cgtattacgc gcgctcactg   8220
gccgtcgttt tacaacgtcg tgactgggaa aaccctggcg ttacccaact taatcgcctt   8280
gcagcacatc cccctttcgc cagctggcgt aatagcgaag aggcccgcac cgatcgccct   8340
tcccaacagt tgcgcagcct gaatggcgaa tggcgcgacg cgccctgtag cggcgcatta   8400
agcgcggcgg gtgtggtggt tacgcgcagc gtgaccgcta cacttgccag cgccctagcg   8460
cccgctcctt tcgctttctt cccttccttt ctcgccacgt tcgccggctt tccccgtcaa   8520
gctctaaatc gggggctccc tttagggttc cgatttagtg ctttacggca cctcgacccc   8580
aaaaaacttg attagggtga tggttcacgt agtgggccat cgccctgata gacggttttt   8640
cgccctttga cgttggagtc cacgttcttt aatagtggac tcttgttcca aactggaaca   8700
```

```
acactcaacc ctatctcggt ctattctttt gatttataag ggattttgcc gatttcggcc   8760

tattggttaa aaaatgagct gatttaacaa aaatttaacg cgaattttaa caaaatatta   8820

acgtttacaa tttcc                                                     8835


<210> SEQ ID NO 2
<211> LENGTH: 33
<212> TYPE: PRT
<213> ORGANISM: Artificial Sequence
<220> FEATURE:
<223> OTHER INFORMATION: CAR binding region - modified yeast
      transcription factor GCN4

<400> SEQUENCE: 2

Arg Met Lys Gln Leu Glu Pro Lys Val Glu Glu Leu Leu Pro Lys Asn
1               5                   10                  15

Tyr His Leu Glu Asn Glu Val Ala Arg Leu Lys Lys Leu Val Gly Glu
            20                  25                  30

Arg


<210> SEQ ID NO 3
<211> LENGTH: 14
<212> TYPE: PRT
<213> ORGANISM: Artificial Sequence
<220> FEATURE:
<223> OTHER INFORMATION: CAR binding region - yeast transcription factor
      GCN4

<400> SEQUENCE: 3

Asn Tyr His Leu Glu Asn Glu Val Ala Arg Leu Lys Lys Leu
1               5                   10


<210> SEQ ID NO 4
<211> LENGTH: 24
<212> TYPE: PRT
<213> ORGANISM: Artificial Sequence
<220> FEATURE:
<223> OTHER INFORMATION: CAR binding region -  yeast transcription
      factor GCN4 with linkers

<400> SEQUENCE: 4

Gly Gly Gly Gly Ser Asn Tyr His Leu Glu Asn Glu Val Ala Arg Leu
1               5                   10                  15

Lys Lys Leu Gly Gly Gly Gly Ser
            20


<210> SEQ ID NO 5
<211> LENGTH: 13
<212> TYPE: PRT
<213> ORGANISM: Artificial Sequence
<220> FEATURE:
<223> OTHER INFORMATION: Hydrophobic target peptide

<400> SEQUENCE: 5

Gly Gly Gly Gly Ser Asp Tyr Lys Asp Asp Asp Asp Lys
1               5                   10


<210> SEQ ID NO 6
<211> LENGTH: 14
<212> TYPE: PRT
<213> ORGANISM: Artificial Sequence
<220> FEATURE:
<223> OTHER INFORMATION: Hydrophobic target peptide

<400> SEQUENCE: 6
```

```
Gly Gly Gly Gly Ser Asp Tyr Lys Asp Asp Asp Asp Lys Pro
1               5                   10


<210> SEQ ID NO 7
<211> LENGTH: 8
<212> TYPE: PRT
<213> ORGANISM: Artificial Sequence
<220> FEATURE:
<223> OTHER INFORMATION: FLAG tag peptide

<400> SEQUENCE: 7

Asp Tyr Lys Asp Asp Asp Asp Lys
1               5


<210> SEQ ID NO 8
<211> LENGTH: 642
<212> TYPE: DNA
<213> ORGANISM: Artificial Sequence
<220> FEATURE:
<223> OTHER INFORMATION: Made in Lab - polynucleotide light chain anti-
      CD19 antibody

<400> SEQUENCE: 8

gacatccaga tgacacagac tacatcctcc ctgtctgcct ctctgggaga cagagtcacc     60

atcagttgca gggcaagtca ggacattagt aaatatttaa attggtatca gcagaaacca    120

gatggaactg ttaaactcct gatctaccat acatcaagat tacactcagg agtcccatca    180

aggttcagtg gcagtgggtc tggaacagat tattctctca ccattagcaa cctggagcaa    240

gaagatattg ccacttactt ttgccaacag ggtaatacgc ttccgtacac gttcggaggg    300

gggaccaagc ttgagatcaa acgaactgtg gctgcaccat ctgtcttcat cttcccgcca    360

tctgatgagc agttgaaatc tggaactgcc tctgtcgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgtcctcgc ccgtcacaaa gagcttcaac aggggagagt gt                       642


<210> SEQ ID NO 9
<211> LENGTH: 669
<212> TYPE: DNA
<213> ORGANISM: Artificial Sequence
<220> FEATURE:
<223> OTHER INFORMATION: Made in Lab - polynucleotide light chain anti-
      CD19 antibody Fab

<400> SEQUENCE: 9

gaggtgaaac tgcaggagtc aggacctggc ctggtggcgc cctcacagag cctgtccgtc     60

acatgcactg tctcaggggt ctcattaccc gactatggtg taagctggat tcgccagcct    120

ccacgaaagg gtctggagtg gctgggagta atatggggta gtgaaaccac atactataat    180

tcagctctca aatccagact gaccatcatc aaggacaact ccaagagcca agttttctta    240

aaaatgaaca gtctgcaaac tgatgacaca gccatttact actgtgccaa acattattac    300

tacggtggta gctatgctat ggactactgg ggccaaggaa cctcagtcac cgtctcctca    360

gcctccacca agggcccatc ggtcttcccc ctggcaccct cctccaagag cacctctggg    420

ggcacagcgg ccctgggctg cctggtcaag gactacttcc ccgaaccggt gacggtgtcg    480

tggaactcag gcgccctgac cagcggcgtg cacaccttcc cggctgtcct acagtcctca    540
```

```
ggactctact ccctcagcag cgtggtgact gtgccctcta gcagcttggg cacccagacc    600

tacatctgca acgtgaatca caagcccagc aacaccaagg tggacaagaa agttgagccc    660

aaatcttgt                                                            669
```

<210> SEQ ID NO 10
<211> LENGTH: 1347
<212> TYPE: DNA
<213> ORGANISM: Artificial Sequence
<220> FEATURE:
<223> OTHER INFORMATION: Made in Lab - polynucleotide light chain anti-CD19 IgG

<400> SEQUENCE: 10

```
gaggtgaaac tgcaggagtc aggacctggc ctggtggcgc cctcacagag cctgtccgtc     60

acatgcactg tctcaggggt ctcattaccc gactatggtg taagctggat tcgccagcct    120

ccacgaaagg gtctggagtg gctgggagta atatggggta gtgaaaccac atactataat    180

tcagctctca aatccagact gaccatcatc aaggacaact ccaagagcca agttttctta    240

aaaatgaaca gtctgcaaac tgatgacaca gccatttact actgtgccaa acattattac    300

tacggtggta gctatgctat ggactactgg ggccaaggaa cctcagtcac cgtctcctca    360

gcctccacca agggcccatc ggtcttcccc ctggcaccct cctccaagag cacctctggg    420

ggcacagcgg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgact gtgccctcta gcagcttggg cacccagacc    600

tacatctgca acgtgaatca caagcccagc aacaccaagg tggacaagaa agttgagccc    660

aaatcttgtg acaaaactca cacatgccca ccgtgcccag cacctccagt cgccggaccg    720

tcagtcttcc tcttccctcc aaaacccaag gacaccctca tgatctcccg gacccctgag    780

gtcacatgcg tggtggtgga cgtgagccac gaagaccctg aggtcaagtt caactggtac    840

gtggacggcg tggaggtgca taatgccaag acaaagccgc gggaggagca gtacaacagc    900

acgtaccgtg tggtcagcgt cctcaccgtc ctgcaccagg actggctgaa tggcaaggag    960

tacaagtgca aggtctccaa caaaggcctc ccaagctcca tcgagaaaac catctccaaa   1020

gccaaagggc agccccgaga accacaggtg tacaccctgc ctccatcccg ggatgagctg   1080

accaagaacc aggtcagcct gacctgcctg gtcaaaggct tctatcccag cgacatcgcc   1140

gtggagtggg agagcaatgg gcagccggag aacaactaca agaccacgcc tcccgtgctg   1200

gactccgacg gctccttctt cctctacagc aagctcaccg tggacaagag caggtggcag   1260

caggggaacg tcttctcatg ctccgtgatg catgaggctc tgcacaacca ctacacgcag   1320

aagagcctct ccctgtctcc gggtaaa                                       1347
```

<210> SEQ ID NO 11
<211> LENGTH: 711
<212> TYPE: DNA
<213> ORGANISM: Artificial Sequence
<220> FEATURE:
<223> OTHER INFORMATION: Made in lab polynucleotide light chain of trastuzumab (anti-Her2)

<400> SEQUENCE: 11

```
atgaaaaaga atatcgcatt tcttcttgct agcatgttcg tttttctat tgctacaaac     60

gcatacgctg acatccagat gacccagtct ccatcctccc tgtctgcatc tgtaggagac    120

agagtcacca tcacttgccg ggcaagtcag gatgtgaata ccgcggtcgc atggtatcag    180
```

```
cagaaaccag ggaaagcccc taagctcctg atctattctg catccttctt gtatagtggg    240

gtcccatcaa ggttcagtgg cagtagatct gggacagatt tcactctcac catcagcagt    300

ctgcaacctg aagattttgc aacttactac tgtcaacagc attacactac ccctccgacg    360

ttcggccaag gtaccaagct tgagatcaaa cgaactgtgg ctgcaccatc tgtcttcatc    420

ttcccgccat ctgatgagca gttgaaatct ggaactgcct ctgtcgtgtg cctgctgaat    480

aacttctatc ccagagaggc caaagtacag tggaaggtgg ataacgccct ccaatcgggt    540

aactcccagg agagtgtcac agagcaggac agcaaggaca gcacctacag cctcagcagc    600

accctgacgc tgagcaaagc agactacgag aaacacaaag tctacgcctg cgaagtcacc    660

catcagggcc tgtcctcgcc cgtcacaaag agcttcaaca ggggagagtg t             711
```

```
<210> SEQ ID NO 12
<211> LENGTH: 753
<212> TYPE: DNA
<213> ORGANISM: Artificial Sequence
<220> FEATURE:
<223> OTHER INFORMATION: Made in lab polynucleotide heavy chain of
      trastuzumab (anti-Her2)

<400> SEQUENCE: 12

atgaaaaaga atatcgcatt tcttcttgca tctatgttcg tttttctat tgctacaaac      60

gcgtacgctg aggtgcagct ggtggagtct ggaggaggct tggtccagcc tggggggtcc    120

ctgagactct cctgtgcagc ctctgggttc aatattaagg acacttacat ccactgggtc    180

cgccaggctc cagggaaggg gctggagtgg gtcgcacgta tttatcctac caatggttac    240

acacgctacg cagactccgt gaagggccga ttcaccatct ccgcagacac ttccaagaac    300

acggcgtatc ttcaaatgaa cagcctgaga gccgaggaca cggccgtgta ttactgttcg    360

agatggggcg gtgacggctt ctatgccatg gactactggg gccaaggaac cctggtcacc    420

gtctcctcag cctccaccaa gggcccatcg gtcttccccc tggcaccctc ctccaagagc    480

acctctgggg gcacagcggc cctgggctgc ctggtcaagg actacttccc cgaaccggtg    540

acggtgtcgt ggaactcagg cgccctgacc agcggcgtgc acaccttccc ggctgtccta    600

cagtcctcag gactctactc cctcagcagc gtggtgactg tgccctctag cagcttgggc    660

acccagacct acatctgcaa cgtgaatcac aagcccagca acaccaaggt ggacaagaaa    720

gttgagccca aatcttgtga caaaactcac aca                                 753
```

```
<210> SEQ ID NO 13
<211> LENGTH: 708
<212> TYPE: DNA
<213> ORGANISM: Artificial Sequence
<220> FEATURE:
<223> OTHER INFORMATION: Made in lab polynucleotide light chain of
      Rituximab (anti-CD20)

<400> SEQUENCE: 13

atgaaaaaga atatcgcatt tcttcttgct agcatgttcg tttttctat tgctacaaac      60

gcatacgctc agattgtgct gagccagagc ccggcgattc tgagcgcgag cccgggcgaa    120

aaagtgacca tgacctgccg cgcgagcagc agcgtgagct atattcattg gtttcagcag    180

aaaccgggca gcagcccgaa accgtggatt tatgcgacca gcaacctggc gagcggcgtg    240

ccggtgcgct ttagcggcag cggcagcggc accagctata gcctgaccat tagccgcgtg    300

gaagcggaag atgcggcgac ctattattgc cagcagtgga ccagcaaccc gccgaccttt    360
```

```
ggcggcggca ccaagcttga gatcaaacga actgtggctg caccatctgt cttcatcttc    420

ccgccatctg atgagcagtt gaaatctgga actgcctctg tcgtgtgcct gctgaataac    480

ttctatccca gagaggccaa agtacagtgg aaggtggata acgccctcca atcgggtaac    540

tcccaggaga gtgtcacaga gcaggacagc aaggacagca cctacagcct cagcagcacc    600

ctgacgctga gcaaagcaga ctacgagaaa cacaaagtct acgcctgcga agtcacccat    660

cagggcctgt cctcgcccgt cacaaagagc ttcaacaggg gagagtgt                708


<210> SEQ ID NO 14
<211> LENGTH: 756
<212> TYPE: DNA
<213> ORGANISM: Artificial Sequence
<220> FEATURE:
<223> OTHER INFORMATION: Made in lab polynucleotide heavy chain of
      Rituximab (anti-CD20)

<400> SEQUENCE: 14

atgaaaaaga atatcgcatt tcttcttgca tctatgttcg tttttttctat tgctacaaac     60

gcgtacgctc aggtgcagct gcagcagccg ggcgcggaac tggtgaaacc gggcgcgagc    120

gtgaaaatga gctgcaaagc gagcggctat acctttacca gctataacat gcattgggtg    180

aaacagaccc cgggccgcgg cctggaatgg attggcgcga tttatccggg caacggcgat    240

accagctata accagaaatt taaaggcaaa gcgaccctga ccgcggataa aagcagcagc    300

accgcgtata tgcagctgag cagcctgacc agcgaagata gcgcggtgta ttattgcgcg    360

cgcagcacct attatggcgg cgattggtat tttaacgtgt ggggcgcggg caccaccgtg    420

accgtgagcg cggcgagcac caagggccca tcggtcttcc ccctggcacc ctcctccaag    480

agcacctctg ggggcacagc ggccctgggc tgcctggtca aggactactt ccccgaaccg    540

gtgacggtgt cgtggaactc aggcgccctg accagcggcg tgcacacctt cccggctgtc    600

ctacagtcct caggactcta ctccctcagc agcgtggtga ctgtgccctc tagcagcttg    660

ggcacccaga cctacatctg caacgtgaat cacaagccca gcaacaccaa ggtggacaag    720

aaagttgagc ccaaatcttg tgacaaaact cacaca                              756


<210> SEQ ID NO 15
<211> LENGTH: 708
<212> TYPE: DNA
<213> ORGANISM: Artificial sequence
<220> FEATURE:
<223> OTHER INFORMATION: Made in lab polynucleotide light chain of clone
      C225 (anti-EGFR)

<400> SEQUENCE: 15

atgagggtcc ccgctcagct cctggggctc ctgctgctct ggctcccagg tgcacgatgt     60

gacatcctgc tgacccagtc ccccgtgatc ctgtccgtgt cccctggcga gcgggtgtcc    120

ttctcctgcc gggcctccca gtccatcggc accaacatcc actggtatca gcagcggacc    180

aacggctccc ctcggctgct gatcaagtac gcctccgagt ctatctccgg catcccttcc    240

cggttctccg gctccggctc tggcaccgac ttcaccctgt ccatcaactc cgtggagtcc    300

gaggatatcg ccgactacta ctgccagcag aacaacaact ggcctaccac cttcggcgct    360

ggaaccaagc tggagctgaa gcgtacggtg gctgcaccat ctgtcttcat cttcccgcca    420

tctgatgagc agttgaaatc tggaactgcc tctgttgtgt gcctgctgaa taacttctat    480

cccagagagg ccaaagtaca gtggaaggtg gataacgccc tccaatcggg taactcccag    540

gagagtgtca cagagcagga cagcaaggac agcacctaca gcctcagcag caccctgacg    600
```

ctgagcaaag cagactacga gaaacacaaa gtctacgcct gcgaagtcac ccatcagggc 660
ctgagctcgc ccgtcacaaa gagcttcaac aggggagagt gttgatga 708

<210> SEQ ID NO 16
<211> LENGTH: 753
<212> TYPE: DNA
<213> ORGANISM: Artificial Sequence
<220> FEATURE:
<223> OTHER INFORMATION: Made in lab polynucleotide heavy chain of clone C225 (anti-EGFR)

<400> SEQUENCE: 16
atgggttgga gcctcatctt gctcttcctt gtcgctgttg ctacgcgtgt ccactcccag 60
gtgcagctga agcagtccgg ccctggcctg gtgcagcctt cccagtccct gtccatcacc 120
tgcaccgtgt ccggcttctc cctgaccaac tacggcgtgc actgggtgcg ccagtccccc 180
ggcaagggcc tggagtggct gggcgtgatc tggtccggcg gcaacaccga ctacaacacc 240
cctttcacct cccggctgtc catcaacaag gacaactcca agtcccaggt gttcttcaag 300
atgaactccc tgcagtccaa cgacaccgcc atctactact gcgccagagc cctgacctac 360
tatgactacg agttcgccta ctggggccag ggcaccctgg tgaccgtgtc cgccgctagc 420
accaagggcc catcggtctt ccccctggca ccctcctcca agagcacctc tgggggcaca 480
gcggccctgg gctgcctggt caaggactac ttccccgaac cggtgacggt gtcgtggaac 540
tcaggcgccc tgaccagcgg cgtgcacacc ttcccggctg tcctacagtc ctcaggactc 600
tactccctca gcagcgtggt gaccgtgccc tccagcagct tgggcaccca gacctacatc 660
tgcaacgtga atcacaagcc cagcaacacc aaggtggaca agaaagttga gcccaaatct 720
tgtgacaaaa ctcacacatg cccaccgtgc cca 753

<210> SEQ ID NO 17
<211> LENGTH: 645
<212> TYPE: DNA
<213> ORGANISM: Artificial Sequence
<220> FEATURE:
<223> OTHER INFORMATION: Made in lab polynucleotide light chain of anti-CLL1 antibody

<400> SEQUENCE: 17
gagaacgtgc tcacccaatc ccccgccatt atgtccgcct ccccaggcga aaaggtgaca 60
atgacctgca gggccagctc caacgtgatc agctcttacg tgcactggta ccagcaacgg 120
tccggcgcct cccctaagct gtggatctat agcacaagca acctggcttc cggcgtgcct 180
gcacggttca gcggaagcgg aagcggaaca agttactccc tcaccatttc tagcgttgaa 240
gccgaggatg ccgctacata ctattgtcaa cagtacagcg gataccccct gaccttcgga 300
gccggcacaa aactggagct caagagagca gctgcagctc ccagcgtgtt catttttcct 360
ccctccgacg aacaactgaa aagcggaaca gcctctgtcg tttgcctgtt gaacaatttc 420
taccctaggg aggccaaggt ccagtggaaa gtggataacg ctctgcaaag cggaaattct 480
caggaaagcg ttaccgaaca ggattctaag gactctacat actctctgtc tagcacactc 540
acgctgagca aagcagacta cgagaaacac aaagtctacg cctgcgaagt cacccatcag 600
ggcctgtcct cgcccgtcac aaagagcttc aacaggggag agtgt 645

<210> SEQ ID NO 18
<211> LENGTH: 678
<212> TYPE: DNA

<213> ORGANISM: Artificial Sequence
<220> FEATURE:
<223> OTHER INFORMATION: Made in lab polynucleotide heavy chain of anti-
CLL1 antibody

<400> SEQUENCE: 18
gacatccagc tgcaggagag cggccccggc ctggtgaagc ccagccagag cctgagcctg 60
acctgcagcg tgaccggcta cagcatcacc agcgcctatt actggaactg gatccggcag 120
ttccccggca acaagctgga gtggatgggc tacatcagct acgacggccg gaacaactac 180
aacccaagcc tgaagaaccg gatcagcatc acccgggaca ccagcaagaa ccagtttttc 240
ctgaagctga acagcgtgac cacagaggac accgccacct attactgcgc caaggaggga 300
gactacgacg tgggcaacta ctacgccatg gactactggg gccagggcac cagcgtgacc 360
gtgtctagcg cccggaccaa gggccccagc gtgttccccc tggcccccag ctctaagagc 420
accagcggcg gaaccgccgc tctgggctgc ctggtgaagg actacttccc cgagcccgtg 480
accgtgagct ggaacagcgg cgccctgacc agcggcgtgc acaccttccc cgccgtgctg 540
cagagctctg gcctgtacag cctgagcagc gtggttaccg tgcccagttc ttccctgggc 600
acccagacct acatctgcaa cgtgaaccac aagcccagca acaccaaggt ggacaagaaa 660
gtggagccca agagctgc 678

<210> SEQ ID NO 19
<211> LENGTH: 654
<212> TYPE: DNA
<213> ORGANISM: Artificial Sequence
<220> FEATURE:
<223> OTHER INFORMATION: Made in lab polynucleotide light chain of anti-
CD33 antibody

<400> SEQUENCE: 19
gatattcaga tgacccagag cccgagcagc ctgagcgcga gcgtgggcga tcgcgtgacc 60
attacctgcc gcgcgagcga aagcgtggat aactatggca ttagctttat gaactggttt 120
cagcagaaac cgggcaaagc gccgaaactg ctgatttatg cggcgagcaa ccagggcagc 180
ggcgtgccga gccgctttag cggcagcggc agcggcaccg attttaccct gaacattagc 240
agcctgcagc cggatgattt tgcgacctat tattgccagc agagcaaaga agtgccgtgg 300
acctttggcc agggcaccaa agtggaaatt aaacgaactg tggctgcacc atctgtcttc 360
atcttcccgc catctgatga gcagttgaaa tctggaactg cctctgttgt gtgcctgctg 420
aataacttct atcccagaga ggccaaagta cagtggaagg tggataacgc cctccaatcg 480
ggtaactccc aggagagtgt cacagagcag gacagcaagg acagcaccta cagcctcagc 540
agcaccctga cgctgagcaa agcagactac gagaaacaca aagtctacgc ctgcgaagtc 600
acccatcagg gcctgagctc gcccgtcaca aagagcttca acaggggaga gtgt 654

<210> SEQ ID NO 20
<211> LENGTH: 690
<212> TYPE: DNA
<213> ORGANISM: Artificial Sequence
<220> FEATURE:
<223> OTHER INFORMATION: Made in lab polynucleotide heavy chain of anti-
CD33 antibody

<400> SEQUENCE: 20
caggtgcagc tggtgcagag cggcgcggaa gtgaaaaaac cgggcagcag cgtgaaagtg 60
agctgcaaag cgagcggcta tacctttacc gattataaca tgcattgggt gcgccaggcg 120

-continued

```
ccgggccagg gcctggaatg gattggctat atttatccgt ataacggcgg caccggctat    180

aaccagaaat ttaaaagcaa agcgaccatt accgcggatg aaagcaccaa caccgcgtat    240

atggaactga gcagcctgcg cagcgaagat accgcggtgt attattgcgc gcgcggccgc    300

ccggcgatgg attattgggg ccagggcacc ctggtgaccg tgagcagcgc ctccaccaag    360

ggcccatcgg tcttcccct ggcaccctcc tcctagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cccagaccta catctgcaac    600

gtgaatcaca agcccagcaa caccaaggtc gacaagaaag ttgagcccaa atcttgtggt    660

ggcggtcacc atcaccatca tcaccaccac                                     690
```

```
<210> SEQ ID NO 21
<211> LENGTH: 107
<212> TYPE: PRT
<213> ORGANISM: Artificial Sequence
<220> FEATURE:
<223> OTHER INFORMATION: Made in lab - CAR-T switch targeting
      polypeptide light chain anti-CS1 antibody

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Tyr Pro Tyr
                85                  90                  95

Thr Phe Gly Gln Gly Thr Lys Leu Glu Ile Lys
            100                 105


<210> SEQ ID NO 22
<211> LENGTH: 222
<212> TYPE: PRT
<213> ORGANISM: Artificial Sequence
<220> FEATURE:
<223> OTHER INFORMATION: Made in lab - CAR-T switch targeting
      polypeptide heavy chain anti-CS1 antibody Fab

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
```

-continued

```
                85                  90                  95

Ala Arg Pro Asp Gly Asn Tyr Trp Tyr Phe Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220


<210> SEQ ID NO 23
<211> LENGTH: 214
<212> TYPE: PRT
<213> ORGANISM: Artificial Sequence
<220> FEATURE:
<223> OTHER INFORMATION: Made in lab - CAR-T switch targeting
      polypeptide light chain anti-EGFRvIII antibody (Hu806) Fab

<400> SEQUENCE: 23

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Asn Ser Asn
            20                  25                  30

Ile Gly Trp Leu Gln Gln Lys Pro Gly Lys Ser Phe Lys Gly Leu Ile
        35                  40                  45

Tyr His Gly Thr Asn Leu Asp Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 24
<211> LENGTH: 217
<212> TYPE: PRT
<213> ORGANISM: Artificial Sequence
<220> FEATURE:
<223> OTHER INFORMATION: Made in lab - CAR-T switch targeting
polypeptide heavy chain anti-EGFRvIII antibody (Hu806) Fab

<400> SEQUENCE: 24

```
Gln Leu Gln Glu Ser Gly Pro Gly Leu Val Lys Pro Ser Gln Thr Leu
1               5                   10                  15

Ser Leu Thr Cys Thr Val Ser Gly Tyr Ser Ile Ser Ser Asp Phe Ala
            20                  25                  30

Trp Asn Trp Ile Arg Gln Pro Pro Gly Lys Gly Leu Glu Trp Met Gly
        35                  40                  45

Tyr Ile Ser Tyr Ser Gly Asn Thr Arg Tyr Gln Pro Ser Leu Lys Ser
    50                  55                  60

Arg Ile Thr Ile Ser Arg Asp Thr Ser Lys Asn Gln Phe Phe Leu Lys
65                  70                  75                  80

Leu Asn Ser Val Thr Ala Ala Asp Thr Ala Thr Tyr Tyr Cys Val Thr
                85                  90                  95

Ala Gly Arg Gly Phe Pro Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys
    210                 215
```

<210> SEQ ID NO 25
<211> LENGTH: 214
<212> TYPE: PRT
<213> ORGANISM: Artificial Sequence
<220> FEATURE:
<223> OTHER INFORMATION: Made in lab - CAR-T switch targeting
polypeptide light chain anti-BCMA antibody (BCMA98) Fab

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Arg Ala Asn Gln Gly Ile Ser Asn Asn
            20                  25                  30

Leu Asn Trp Tyr Gln Gln Lys Pro Gly Lys Ala Pro Lys Pro Leu Ile
        35                  40                  45

Tyr Tyr Thr Ser Asn Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80
```

```
Glu Asp Phe Ala Thr Tyr Tyr Cys Gln Gln Phe Thr Ser Leu Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 26
<211> LENGTH: 224
<212> TYPE: PRT
<213> ORGANISM: Artificial Sequence
<220> FEATURE:
<223> OTHER INFORMATION: Made in lab - CAR-T switch targeting
      polypeptide heavy chain anti-BCMA antibody (BCMA98) Fab

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Asp Met Ala Trp Val Arg Gln Ala Pro Gly Lys Gly Leu Val Trp Val
        35                  40                  45

Ser Ser Ile Thr Thr Gly Gly Gly Asp Thr Tyr Tyr Ala Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Val Tyr Tyr Cys
                85                  90                  95

Val Arg His Gly Tyr Tyr Asp Gly Tyr His Leu Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

<210> SEQ ID NO 27
<211> LENGTH: 214
<212> TYPE: PRT
<213> ORGANISM: Artificial Sequence
<220> FEATURE:
<223> OTHER INFORMATION: Made in lab - CAR-T switch targeting polypeptide light chain anti-CD19 antibody

<400> SEQUENCE: 27

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 28
<211> LENGTH: 449
<212> TYPE: PRT
<213> ORGANISM: Artificial Sequence
<220> FEATURE:
<223> OTHER INFORMATION: Made in lab - CAR-T switch targeting polypeptide heavy chain anti-CD19 antibody IgG

<400> SEQUENCE: 28

```
Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80
```

```
Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 29
<211> LENGTH: 223
<212> TYPE: PRT
<213> ORGANISM: Artificial Sequence
<220> FEATURE:
<223> OTHER INFORMATION: Made in lab - CAR-T switch targeting polypeptide heavy chain anti-CD19 antibody Fab

<400> SEQUENCE: 29

Glu Val Lys Leu Gln Glu Ser Gly Pro Gly Leu Val Ala Pro Ser Gln
1 5 10 15

Ser Leu Ser Val Thr Cys Thr Val Ser Gly Val Ser Leu Pro Asp Tyr
20 25 30

Gly Val Ser Trp Ile Arg Gln Pro Pro Arg Lys Gly Leu Glu Trp Leu
35 40 45

Gly Val Ile Trp Gly Ser Glu Thr Thr Tyr Tyr Asn Ser Ala Leu Lys
50 55 60

Ser Arg Leu Thr Ile Ile Lys Asp Asn Ser Lys Ser Gln Val Phe Leu
65 70 75 80

Lys Met Asn Ser Leu Gln Thr Asp Asp Thr Ala Ile Tyr Tyr Cys Ala
85 90 95

Lys His Tyr Tyr Tyr Gly Gly Ser Tyr Ala Met Asp Tyr Trp Gly Gln
100 105 110

Gly Thr Ser Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys
210 215 220

<210> SEQ ID NO 30
<211> LENGTH: 237
<212> TYPE: PRT
<213> ORGANISM: Artificial Sequence
<220> FEATURE:
<223> OTHER INFORMATION: Made in lab - CAR-T switch anti-CD19 Fab CL1-
GCN4 switch Light Chain

<400> SEQUENCE: 30

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Lys Arg Thr Val Ala Ala
100 105 110

Pro Ser Val Phe Ile Phe Pro Pro Ser Asp Glu Gln Leu Lys Ser Gly

```
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Gly Gly Gly Gly Ser Asn Tyr His
                165                 170                 175

Leu Glu Asn Glu Val Ala Arg Leu Lys Lys Leu Gly Gly Gly Gly Ser
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235


<210> SEQ ID NO 31
<211> LENGTH: 237
<212> TYPE: PRT
<213> ORGANISM: Artificial Sequence
<220> FEATURE:
<223> OTHER INFORMATION: Made in lab - CAR-T switch anti-CD19 IgG CL1-
      GCN4 switch Light Chain

<400> SEQUENCE: 31

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Gly Gly Gly Gly Ser Asn Tyr His
                165                 170                 175

Leu Glu Asn Glu Val Ala Arg Leu Lys Lys Leu Gly Gly Gly Gly Ser
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 32
<211> LENGTH: 234
<212> TYPE: PRT
<213> ORGANISM: Artificial Sequence
<220> FEATURE:
<223> OTHER INFORMATION: Made in lab - CAR-T switch anti-CD19 Fab HC1-
GCN4 switch Heavy Chain

<400> SEQUENCE: 32

```
Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Asn Tyr His Leu Glu Asn Glu Val Ala
    130                 135                 140

Arg Leu Lys Lys Leu Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys
225                 230
```

<210> SEQ ID NO 33
<211> LENGTH: 460
<212> TYPE: PRT
<213> ORGANISM: Artificial Sequence
<220> FEATURE:
<223> OTHER INFORMATION: Made in Lab - CAR-T switch anti-CD19 IgG HC1-
GCN4 switch Heavy Chain

<400> SEQUENCE: 33

```
Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60
```

```
Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Asn Tyr His Leu Glu Asn Glu Val Ala
    130                 135                 140

Arg Leu Lys Lys Leu Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Gly Leu Pro Ser Ser Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460
```

<210> SEQ ID NO 34
<211> LENGTH: 242
<212> TYPE: PRT

<213> ORGANISM: Artificial Sequence
<220> FEATURE:
<223> OTHER INFORMATION: Made in Lab - CAR-T switch anti-CD19 Fab C term-GCN4 switch Heavy Chain

<400> SEQUENCE: 34

Glu Val Lys Leu Gln Glu Ser Gly Pro Gly Leu Val Ala Pro Ser Gln
1 5 10 15

Ser Leu Ser Val Thr Cys Thr Val Ser Gly Val Ser Leu Pro Asp Tyr
20 25 30

Gly Val Ser Trp Ile Arg Gln Pro Pro Arg Lys Gly Leu Glu Trp Leu
35 40 45

Gly Val Ile Trp Gly Ser Glu Thr Thr Tyr Tyr Asn Ser Ala Leu Lys
50 55 60

Ser Arg Leu Thr Ile Ile Lys Asp Asn Ser Lys Ser Gln Val Phe Leu
65 70 75 80

Lys Met Asn Ser Leu Gln Thr Asp Asp Thr Ala Ile Tyr Tyr Cys Ala
85 90 95

Lys His Tyr Tyr Tyr Gly Gly Ser Tyr Ala Met Asp Tyr Trp Gly Gln
100 105 110

Gly Thr Ser Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Gly
210 215 220

Gly Gly Gly Ser Asn Tyr His Leu Glu Asn Glu Val Ala Arg Leu Lys
225 230 235 240

Lys Leu

<210> SEQ ID NO 35
<211> LENGTH: 471
<212> TYPE: PRT
<213> ORGANISM: Artificial Sequence
<220> FEATURE:
<223> OTHER INFORMATION: Made in Lab - CAR-T switch anti-CD19 IgG hinge-GCN4 switch Heavy Chain

<400> SEQUENCE: 35

Glu Val Lys Leu Gln Glu Ser Gly Pro Gly Leu Val Ala Pro Ser Gln
1 5 10 15

Ser Leu Ser Val Thr Cys Thr Val Ser Gly Val Ser Leu Pro Asp Tyr
20 25 30

Gly Val Ser Trp Ile Arg Gln Pro Pro Arg Lys Gly Leu Glu Trp Leu
35 40 45

Gly Val Ile Trp Gly Ser Glu Thr Thr Tyr Tyr Asn Ser Ala Leu Lys
50 55 60

Ser Arg Leu Thr Ile Ile Lys Asp Asn Ser Lys Ser Gln Val Phe Leu
65 70 75 80

```
Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Gly
    210                 215                 220

Gly Gly Gly Ser Asn Tyr His Leu Glu Asn Glu Val Ala Arg Leu Lys
225                 230                 235                 240

Lys Leu Gly Gly Ser Asp Lys Thr His Thr Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470
```

<210> SEQ ID NO 36
<211> LENGTH: 233

```
<212> TYPE: PRT
<213> ORGANISM: Artificial Sequence
<220> FEATURE:
<223> OTHER INFORMATION: Made in lab - CAR-T switch anti-CD19 Fab Light
      Chain NT1

<400> SEQUENCE: 36

Asn Tyr His Leu Glu Asn Glu Val Ala Arg Leu Lys Lys Leu Gly Gly
1               5                   10                  15

Gly Gly Ser Asp Ile Gln Met Thr Gln Thr Thr Ser Ser Leu Ser Ala
            20                  25                  30

Ser Leu Gly Asp Arg Val Thr Ile Ser Cys Arg Ala Ser Gln Asp Ile
        35                  40                  45

Ser Lys Tyr Leu Asn Trp Tyr Gln Gln Lys Pro Asp Gly Thr Val Lys
    50                  55                  60

Leu Leu Ile Tyr His Thr Ser Arg Leu His Ser Gly Val Pro Ser Arg
65                  70                  75                  80

Phe Ser Gly Ser Gly Ser Gly Thr Asp Tyr Ser Leu Thr Ile Ser Asn
                85                  90                  95

Leu Glu Gln Glu Asp Ile Ala Thr Tyr Phe Cys Gln Gln Gly Asn Thr
            100                 105                 110

Leu Pro Tyr Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230


<210> SEQ ID NO 37
<211> LENGTH: 237
<212> TYPE: PRT
<213> ORGANISM: Artificial Sequence
<220> FEATURE:
<223> OTHER INFORMATION: Made in lab - CAR-T switch anti-BCMA GCN4 CL1
      light chain

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Asn Gln Gly Ile Ser Asn Asn
            20                  25                  30

Leu Asn Trp Tyr Gln Gln Lys Pro Gly Lys Ala Pro Lys Pro Leu Ile
        35                  40                  45

Tyr Tyr Thr Ser Asn Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80
```

```
Glu Asp Phe Ala Thr Tyr Tyr Cys Gln Gln Phe Thr Ser Leu Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Gly Gly Gly Gly Ser Asn Tyr His
                165                 170                 175

Leu Glu Asn Glu Val Ala Arg Leu Lys Lys Leu Gly Gly Gly Gly Ser
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235


<210> SEQ ID NO 38
<211> LENGTH: 450
<212> TYPE: PRT
<213> ORGANISM: Artificial Sequence
<220> FEATURE:
<223> OTHER INFORMATION: Made in lab - CAR-T switch anti-BCMA heavy
      chain WT IgG

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Asp Met Ala Trp Val Arg Gln Ala Pro Gly Lys Gly Leu Val Trp Val
        35                  40                  45

Ser Ser Ile Thr Thr Gly Gly Gly Asp Thr Tyr Tyr Ala Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Val Tyr Tyr Cys
                85                  90                  95

Val Arg His Gly Tyr Tyr Asp Gly Tyr His Leu Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

```
Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 39
<211> LENGTH: 5574
<212> TYPE: DNA
<213> ORGANISM: Artificial Sequence
<220> FEATURE:
<223> OTHER INFORMATION: Made in lab - pBAD vector with CAR-T targeting moiety

<400> SEQUENCE: 39

```
aagaaaccaa ttgtccatat tgcatcagac attgccgtca ctgcgtcttt tactggctct      60

tctcgctaac caaaccggta accctgatta tttgcacgga gtcacacttt gctatgccat     120

agcattttta tccataagat tagcggatcc tacctgacgc tttttatcgc aactctctac     180

tgtttctcca tacccgtttt tttgggctag aaataatttt gtttaacttt aagaaggaga     240

atacatcaac tagtacgcaa gttcacgtaa aaagggtatc tagaggttga ggtgatttta     300

tgaaaaagaa tatcgcattt cttcttgcta gcatgttcgt tttttctatt gctacaaacg     360

catacgctga catccagatg acacagacta catcctccct gtctgcctct ctgggagaca     420

gagtcaccat cagttgcagg gcaagtcagg acattagtaa atatttaaat tggtatcagc     480

agaaaccaga tggaactgtt aaactcctga tctaccatac atcaagatta cactcaggag     540

tcccatcaag gttcagtggc agtgggtctg gaacagatta ttctctcacc attagcaacc     600
```

```
tggagcaaga agatattgcc acttactttt gccaacaggg taatacgctt ccgtacacgt    660
tcggaggggg gaccaagctt gagatcaaac gaactgtggc tgcaccatct gtcttcatct    720
tcccgccatc tgatgagcag ttgaaatctg gaactgcctc tgtcgtgtgc ctgctgaata    780
acttctatcc cagagaggcc aaagtacagt ggaaggtgga taacgccctc caatcgggta    840
actcccagga gagtgtcaca gagcaggaca gcaaggacag cacctacagc ctcagcagca    900
ccctgacgct gagcaaagca gactacgaga aacacaaagt ctacgcctgc gaagtcaccc    960
atcagggcct gtcctcgccc gtcacaaaga gcttcaacag gggagagtgt taagctgggg   1020
atcctctaga ggttgaggtg attttatgaa aaagaatatc gcatttcttc ttgcatctat   1080
gttcgttttt tctattgcta caaacgcgta cgctgaggtg aaactgcagg agtcaggacc   1140
tggcctggtg gcgccctcac agagcctgtc cgtcacatgc actgtctcag ggtctcatt    1200
acccgactat ggtgtaagct ggattcgcca gcctccacga aagggtctgg agtggctggg   1260
agtaatatgg ggtagtgaaa ccacatacta taattcagct ctcaaatcca gactgaccat   1320
catcaaggac aactccaaga gccaagtttt cttaaaaatg aacagtctgc aaactgatga   1380
cacagccatt tactactgtg ccaaacatta ttactacggt ggtagctatg ctatggacta   1440
ctggggccaa ggaacctcag tcaccgtctc ctcagcctcc accaagggcc catcggtctt   1500
ccccctggca ccctcctcca agagcacctc tgggggcaca gcggccctgg gctgcctggt   1560
caaggactac ttccccgaac cggtgacggt gtcgtggaac tcaggcgccc tgaccagcgg   1620
cgtgcacacc ttcccggctg tcctacagtc ctcaggactc tactccctca gcagcgtggt   1680
gactgtgccc tctagcagct tgggcaccca gacctacatc tgcaacgtga atcacaagcc   1740
cagcaacacc aaggtggaca agaaagttga gcccaaatct tgtgacaaaa ctcacacata   1800
ataagtcgac cgatgccctt gagagccttc aacccagtca gctccttccg gtgggcgcgg   1860
ggcatgacta tcgtcgccgc acttatgact gtcttcttta tcatgcaact cgtaggacag   1920
gtgccaaacg gtctccagct tggctgtttt ggcggatgag agaagatttt cagcctgata   1980
cagattaaat cagaacgcag aagcggtctg ataaaacaga atttgcctgg cggcagtagc   2040
gcggtggtcc cacctgaccc catgccgaac tcagaagtga aacgccgtag cgccgatggt   2100
agtgtggggt ctccccatgc gagagtaggg aactgccagg catcaaataa aacgaaaggc   2160
tcagtcgaaa gactgggcct ttcgttttat ctgttgtttg tcggtgaacg ctctcctgag   2220
taggacaaat ccgccgggag cggatttgaa cgttgcgaag caacggcccg gagggtggcg   2280
ggcaggacgc ccgccataaa ctgccaggca tcaaattaag cagaaggcca tcctgacgga   2340
tggccttttt gcgtttctac aaactctttt tgtttatttt tctaaataca ttcaaatatg   2400
tatccgctca tgagacaata accctgataa atgcttcaat aatattgaaa aaggaagagt   2460
atgagtattc aacatttccg tgtcgccctt attccctttt ttgcggcatt ttgccttcct   2520
gtttttgctc acccagaaac gctggtgaaa gtaaaagatg ctgaagatca gttgggtgca   2580
cgagtgggtt acatcgaact ggatctcaac agcggtaaga tccttgagag ttttcgcccc   2640
gaagaacgtt ttccaatgat gagcactttt aaagttctgc tatgtggcgc ggtattatcc   2700
cgtgttgacg ccgggcaaga gcaactcggt cgccgcatac actattctca gaatgacttg   2760
gttgagtact caccagtcac agaaaagcat cttacggatg gcatgacagt aagagaatta   2820
tgcagtgctg ccataaccat gagtgataac actgcggcca acttacttct gacaacgatc   2880
ggaggaccga aggagctaac cgcttttttg cacaacatgg gggatcatgt aactcgcctt   2940
```

```
gatcgttggg aaccggagct gaatgaagcc ataccaaacg acgagcgtga caccacgatg   3000
cctgtagcaa tggcaacaac gttgcgcaaa ctattaactg gcgaactact tactctagct   3060
tcccggcaac aattaataga ctggatggag gcggataaag ttgcaggacc acttctgcgc   3120
tcggcccttc cggctggctg gtttattgct gataaatctg gagccggtga gcgtgggtct   3180
cgcggtatca ttgcagcact ggggccagat ggtaagccct cccgtatcgt agttatctac   3240
acgacgggga gtcaggcaac tatggatgaa cgaaatagac agatcgctga gataggtgcc   3300
tcactgatta agcattggta actgtcagac caagtttact catatatact ttagattgat   3360
ttaaaacttc atttttaatt taaaaggatc taggtgaaga tcctttttga taatctcatg   3420
accaaaatcc cttaacgtga gttttcgttc cactgagcgt cagaccccgt agaaaagatc   3480
aaaggatctt cttgagatcc tttttttctg cgcgtaatct gctgcttgca aacaaaaaaa   3540
ccaccgctac cagcggtggt ttgtttgccg gatcaagagc taccaactct ttttccgaag   3600
gtaactggct tcagcagagc gcagatacca aatactgtcc ttctagtgta gccgtagtta   3660
ggccaccact tcaagaactc tgtagcaccg cctacatacc tcgctctgct aatcctgtta   3720
ccagtggctg ctgccagtgg cgataagtcg tgtcttaccg ggttggactc aagacgatag   3780
ttaccggata aggcgcagcg gtcgggctga acggggggtt cgtgcacaca gcccagcttg   3840
gagcgaacga cctacaccga actgagatac ctacagcgtg agctatgaga aagcgccacg   3900
cttcccgaag ggagaaaggc ggacaggtat ccggtaagcg gcagggtcgg aacaggagag   3960
cgcacgaggg agcttccagg gggaaacgcc tggtatcttt atagtcctgt cgggtttcgc   4020
cacctctgac ttgagcgtcg atttttgtga tgctcgtcag gggggcggag cctatggaaa   4080
aacgccagca acgcggcctt tttacggttc ctggcctttt gctggccttt tgctcacatg   4140
ttctttcctg cgttatcccc tgattctgtg gataaccgta ttaccgcctt tgagtgagct   4200
gataccgctc gccgcagccg aacgaccgag cgcagcgagt cagtgagcga ggaagcggaa   4260
gagcgcctga tgcggtattt tctccttacg catctgtgcg gtatttcaca ccgcatatgg   4320
tgcactctca gtacaatctg ctctgatgcc gcatagttaa gccagtatac actccgctat   4380
cgctacgtga ctgggtcatg gctgcgcccc gacacccgcc aacacccgct gacgcgccct   4440
gacgggcttg tctgctcccg gcatccgctt acagacaagc tgtgaccgtc tccgggagct   4500
gcatgtgtca gaggttttca ccgtcatcac cgaaacgcgc gaggcagcag atcaattcgc   4560
gcgcgaaggc gaagcggcat gcataatgtg cctgtcaaat ggacgaagca gggattctgc   4620
aaaccctatg ctactccgtc aagccgtcaa ttgtctgatt cgttaccaat tatgacaact   4680
tgacggctac atcattcact ttttcttcac aaccggcacg gaactcgctc gggctggccc   4740
cggtgcattt tttaaatacc cgcgagaaat agagttgatc gtcaaaacca acattgcgac   4800
cgacggtggc gataggcatc cgggtggtgc tcaaaagcag cttcgcctgg ctgatacgtt   4860
ggtcctcgcg ccagcttaag acgctaatcc ctaactgctg gcggaaaaga tgtgacagac   4920
gcgacggcga caagcaaaca tgctgtgcga cgctggcgat atcaaaattg ctgtctgcca   4980
ggtgatcgct gatgtactga caagcctcgc gtacccgatt atccatcggt ggatggagcg   5040
actcgttaat cgcttccatg cgccgcagta acaattgctc aagcagattt atcgccagca   5100
gctccgaata gcgcccttcc ccttgcccgg cgttaatgat ttgcccaaac aggtcgctga   5160
aatgcggctg gtgcgcttca tccgggcgaa agaaccccgt attggcaaat attgacggcc   5220
agttaagcca ttcatgccag taggcgcgcg gacgaaagta aacccactgg tgataccatt   5280
cgcgagcctc cggatgacga ccgtagtgat gaatctctcc tggcgggaac agcaaaatat   5340
```

cacccggtcg gcaaacaaat tctcgtccct gatttttcac cacccccctga ccgcgaatgg 5400 tgagattgag aatataacct ttcattccca gcggtcggtc gataaaaaaa tcgagataac 5460
cgttggcctc aatcggcgtt aaacccgcca ccagatgggc attaaacgag tatcccggca 5520
gcaggggatc attttgcgct tcagccatac ttttcatact cccgccattc agag 5574

<210> SEQ ID NO 40
<211> LENGTH: 5
<212> TYPE: PRT
<213> ORGANISM: Artificial Sequence
<220> FEATURE:
<223> OTHER INFORMATION: Linker peptide

<400> SEQUENCE: 40

Gly Gly Gly Gly Ser
1 5

<210> SEQ ID NO 41
<211> LENGTH: 4
<212> TYPE: PRT
<213> ORGANISM: Artificial Sequence
<220> FEATURE:
<223> OTHER INFORMATION: Linker peptide

<400> SEQUENCE: 41

Gly Gly Gly Ser
1

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45
<211> LENGTH: 14
<212> TYPE: PRT
<213> ORGANISM: Artificial Sequence
<220> FEATURE:
<223> OTHER INFORMATION: Linker peptide - rigid switch fusion/grafting
linker 3

<400> SEQUENCE: 45

Leu Val Gly Glu Ala Ala Ala Lys Glu Ala Ala Ala Lys Ala
1 5 10

<210> SEQ ID NO 46
<211> LENGTH: 12
<212> TYPE: PRT
<213> ORGANISM: Artificial Sequence
<220> FEATURE:
<223> OTHER INFORMATION: Linker peptide - rigid switch fusion/grafting
linker 4

<400> SEQUENCE: 46

Ala Glu Ala Ala Ala Lys Glu Ala Ala Ala Lys Ala
1 5 10

<210> SEQ ID NO 47
<211> LENGTH: 16
<212> TYPE: PRT
<213> ORGANISM: Artificial Sequence
<220> FEATURE:
<223> OTHER INFORMATION: Linker peptide - rigid switch fusion/grafting linker 4a

<400> SEQUENCE: 47

Glu Ala Ala Ala Lys Glu Ala Ala Ala Lys Glu Ala Ala Ala Lys Ala
1 5 10 15

<210> SEQ ID NO 48
<211> LENGTH: 14
<212> TYPE: PRT
<213> ORGANISM: Artificial Sequence
<220> FEATURE:
<223> OTHER INFORMATION: Linker peptide - flexible switch fusion/grafting linker - prophetic

<400> SEQUENCE: 48

Glu Gly Lys Ser Ser Gly Ser Gly Ser Glu Ser Lys Ser Thr
1 5 10

<210> SEQ ID NO 49
<211> LENGTH: 12
<212> TYPE: PRT
<213> ORGANISM: Artificial Sequence
<220> FEATURE:
<223> OTHER INFORMATION: Linker peptide - rigid switch fusion/grafting linker 5

<400> SEQUENCE: 49

Gly Ser Ala Gly Ser Ala Ala Gly Ser Gly Glu Phe
1 5 10

<210> SEQ ID NO 50
<211> LENGTH: 14
<212> TYPE: PRT
<213> ORGANISM: Artificial Sequence
<220> FEATURE:
<223> OTHER INFORMATION: Linker peptide - prolyl switch fusion/grafting linker - prophetic

<400> SEQUENCE: 50

Ala Pro Ala Pro Ala Pro Ala Pro Ala Pro Ala Pro Ala Pro
1 5 10

<210> SEQ ID NO 51
<211> LENGTH: 7028
<212> TYPE: DNA
<213> ORGANISM: Artificial Sequence
<220> FEATURE:
<223> OTHER INFORMATION: Made in lab - GCN4-CD28-CD3z(1-3) chimeric antigen receptor polynucleotide

<400> SEQUENCE: 51
tcgagaagct tgccaccatg ggtgtcccta cccagctcct gggactgctc ctgctgtgga 60
tcaccgacgc catctgcgac gccgttgtga cccaggaatc cgctctgacc tcttctccag 120
gcgaaaccgt gactctgact tgccgtagta gcaccggggc tgtgaccaca tctaactatg 180
ccagttgggt ccaggaaaaa ccggatcacc tgtttactgg cctgattggc ggcaccaaca 240

```
atcgcgcacc gggtgtgccc gctcgtttca gcggttccct gattggggac aaggcagcac    300
tgactatcac cggcgcccag accgaagatg aggcgatcta tttttgcgtc ctgtggtaca    360
gcgaccattg ggtgttcggg ggaggcacca aactgacagt gctgggcgga ggaggaggtt    420
caggaggagg aggtagcggg ggaggcggtt ccgggggagg cggttctgat gtgcagctgc    480
aagaatccgg gccaggactg gttgcgcctt ctcagagtct gtcaattaca tgtactgtta    540
gtggctttct gctgaccgac tatggtgtga actgggttcg tcagagccca ggcaagggtc    600
tggagtggct gggagtgatt tgggggggatg gaatcacaga ctacaatagc gcactgaaat    660
ctcggctgag tgttaccaaa gataacagca agtcccaggt cttcctgaag atgaacagcc    720
tgcaaagcgg cgactccgct cgctattact gcgttaccgg actgtttgat tattgggggc    780
aggggacaac tctgactgtt tcctccatcg agttcatgta ccccccctccc tacctggaca    840
acgagagaag caacggcacc atcatccaca tcaaagaaaa gcacctgtgc cacacccaga    900
gcagccccaa gctgttctgg gccctggtgg tggtggccgg cgtgctgttc tgttacggcc    960
tgctggtcac agtggccctg tgcgtgatct ggaccaacag cagaagaaac agaggcggcc   1020
agagcgacta catgaacatg acccccagaa ggccaggcct gaccagaaag ccctaccagc   1080
cctacgcccc tgccagagac ttcgccgcct acagacccag agccaagttc agcagatccg   1140
ccgagacagc cgccaacctg caggatccca accagctgtt caacgagctg aacctgggca   1200
gacgggagga attcgacgtg ctggaaaaga agagagccag ggaccccgag atgggcggca   1260
agcagcagag aagaagaaac cctcaggaag gcgtctacaa cgccctgcag aaagacaaga   1320
tggccgaggc ctacagcgag atcggcacca agggcgagag aagaaggggc aagggccacg   1380
atggcctgtt ccagggcctg tccaccgcca ccaaggacac cttcgacgcc ctgcacatgc   1440
agaccctggc cccccagatga gtcgacggta ccgcgggccc gggatccgat aaaataaaag   1500
attttattta gtctccagaa aaagggggga atgaaagacc ccacctgtag gtttggcaag   1560
ctagcttaag taacgccatt ttgcaaggca tggaaaatac ataactgaga atagagaagt   1620
tcagatcaag gttaggaaca gagagacagc agaatatggg ccaaacagga tatctgtggt   1680
aagcagttcc tgccccggct cagggccaag aacagatggt ccccagatgc ggtcccgccc   1740
tcagcagttt ctagagaacc atcagatgtt tccagggtgc cccaaggacc tgaaaatgac   1800
cctgtgcctt atttgaacta accaatcagt tcgcttctcg cttctgttcg cgcgcttctg   1860
ctccccgagc tcaataaaag agcccacaac ccctcactcg gcgcgccagt cctccgatag   1920
actgcgtcgc ccgggtaccc gtgtatccaa taaaccctct tgcagttgca tccgacttgt   1980
ggtctcgctg ttccttggga gggtctcctc tgagtgattg actacccgtc agcgggggtc   2040
tttcatgggt aacagtttct tgaagttgga gaacaacatt ctgagggtag gagtcgaata   2100
ttaagtaatc ctgactcaat tagccactgt tttgaatcca catactccaa tactcctgaa   2160
atccatcgat ggagttcatt atggacagcg cagaaagagc tggggagaat tgtgaaattg   2220
ttatccgctc acaattccac acaacatacg agccggaagc ataaagtgta aagcctgggg   2280
tgcctaatga gtgagctaac tcacattaat tgcgttgcgc tcactgcccg ctttccagtc   2340
gggaaacctg tcgtgccagc tgcattaatg aatcggccaa cgcgcgggga gaggcggttt   2400
gcgtattggg cgctcttccg cttcctcgct cactgactcg ctgcgctcgg tcgttcggct   2460
gcggcgagcg gtatcagctc actcaaaggc ggtaatacgg ttatccacag aatcagggga   2520
taacgcagga aagaacatgt gagcaaaagg ccagcaaaag gccaggaacc gtaaaaaggc   2580
```

-continued

```
cgcgttgctg gcgtttttcc ataggctccg cccccctgac gagcatcaca aaaatcgacg   2640
ctcaagtcag aggtggcgaa acccgacagg actataaaga taccaggcgt ttccccctgg   2700
aagctccctc gtgcgctctc ctgttccgac cctgccgctt accggatacc tgtccgcctt   2760
tctcccttcg ggaagcgtgg cgctttctca tagctcacgc tgtaggtatc tcagttcggt   2820
gtaggtcgtt cgctccaagc tgggctgtgt gcacgaaccc cccgttcagc ccgaccgctg   2880
cgccttatcc ggtaactatc gtcttgagtc caacccggta agacacgact tatcgccact   2940
ggcagcagcc actggtaaca ggattagcag agcgaggtat gtaggcggtg ctacagagtt   3000
cttgaagtgg tggcctaact acggctacac tagaaggaca gtatttggta tctgcgctct   3060
gctgaagcca gttaccttcg gaaaaagagt tggtagctct tgatccggca aacaaaccac   3120
cgctggtagc ggtggttttt ttgtttgcaa gcagcagatt acgcgcagaa aaaaaggatc   3180
tcaagaagat cctttgatct tttctacggg gtctgacgct cagtggaacg aaaactcacg   3240
ttaagggatt ttggtcatga gattatcaaa aaggatcttc acctagatcc ttttaaatta   3300
aaaatgaagt tttaaatcaa tctaaagtat atatgagtaa acttggtctg acagttacca   3360
atgcttaatc agtgaggcac ctatctcagc gatctgtcta tttcgttcat ccatagttgc   3420
ctgactcccc gtcgtgtaga taactacgat acgggagggc ttaccatctg gccccagtgc   3480
tgcaatgata ccgcgagacc cacgctcacc ggctccagat ttatcagcaa taaaccagcc   3540
agccggaagg gccgagcgca gaagtggtcc tgcaacttta tccgcctcca tccagtctat   3600
taattgttgc cgggaagcta gagtaagtag ttcgccagtt aatagtttgc gcaacgttgt   3660
tgccattgct acaggcatcg tggtgtcacg ctcgtcgttt ggtatggctt cattcagctc   3720
cggttcccaa cgatcaaggc gagttacatg atcccccatg ttgtgcaaaa aagcggttag   3780
ctccttcggt cctccgatcg ttgtcagaag taagttggcc gcagtgttat cactcatggt   3840
tatggcagca ctgcataatt ctcttactgt catgccatcc gtaagatgct tttctgtgac   3900
tggtgagtac tcaaccaagt cattctgaga atagtgtatg cggcgaccga gttgctcttg   3960
cccggcgtca atacgggata ataccgcgcc acatagcaga actttaaaag tgctcatcat   4020
tggaaaacgt tcttcggggc gaaaactctc aaggatctta ccgctgttga gatccagttc   4080
gatgtaaccc actcgtgcac ccaactgatc ttcagcatct tttactttca ccagcgtttc   4140
tgggtgagca aaaacaggaa ggcaaaatgc cgcaaaaaag ggaataaggg cgacacggaa   4200
atgttgaata ctcatactct tcctttttca atattattga agcatttatc agggttattg   4260
tctcatgagc ggatacatat ttgaatgtat ttagaaaaat aaacaaatag gggttccgcg   4320
cacatttccc cgaaaagtgc cacctgacgt ctaagaaacc attattatca tgacattaac   4380
ctataaaaat aggcgtatca cgaggccctt tcgtctcgcg cgtttcggtg atgacggtga   4440
aaacctctga cacatgcagc tcccggagac ggtcacagct tgtctgtaag cggatgccgg   4500
gagcagacaa gcccgtcagg gcgcgtcagc gggtgttggc gggtgtcggg gctggcttaa   4560
ctatgcggca tcagagcaga ttgtactgag agtgcaccat atgcggtgtg aaataccgca   4620
cagatgcgta aggagaaaat accgcatcag gcgccattcg ccattcaggc tgcgcaactg   4680
ttgggaaggg cgatcggtgc gggcctcttc gctattacgc cagctggcga aaggggggatg  4740
tgctgcaagg cgattaagtt gggtaacgcc agggttttcc cagtcacgac gttgtaaaac   4800
gacggccagt gccacgctct cccttatgcg actcctgcat taggaagcag cccagtagta   4860
ggttgaggcc gttgagcacc gccgccgcaa ggaatggtgc atgcaaggag atggcgccca   4920
acagtccccc ggccacgggg cctgccacca tacccacgcc gaaacaagcg ctcatgagcc   4980
```

```
cgaagtggcg agcccgatct tccccatcgg tgatgtcggc gatataggcg ccagcaaccg   5040

cacctgtggc gccggtgatg ccggccacga tgcgtccggc gtagaggcga tttaaagaca   5100

ggatatcagt ggtccaggct ctagttttga ctcaacaata tcaccagctg aagcctatag   5160

agtacgagcc atagataaaa taaaagattt tatttagtct ccagaaaaag gggggaatga   5220

aagaccccac ctgtaggttt ggcaagctag cttaagtaac gccattttgc aaggcatgga   5280

aaatacataa ctgagaatag agaagttcag atcaaggtta ggaacagaga gacagcagaa   5340

tatgggccaa acaggatatc tgtggtaagc agttcctgcc ccggctcagg gccaagaaca   5400

gatggtcccc agatgcggtc ccgccctcag cagtttctag agaaccatca gatgtttcca   5460

gggtgcccca aggacctgaa aatgaccctg tgccttattt gaactaacca atcagttcgc   5520

ttctcgcttc tgttcgcgcg cttctgctcc ccgagctcaa taaaagagcc cacaacccct   5580

cactcggcgc gccagtcctc cgatagactg cgtcgcccgg gtacccgtat tcccaataaa   5640

gcctcttgct gtttgcatcc gaatcgtgga ctcgctgatc cttgggaggg tctcctcaga   5700

ttgattgact gcccacctcg gggtctttc atttggaggt tccaccgaga tttggagacc   5760

cctgcctagg gaccaccgac ccccccgccg ggaggtaagc tggccagcgg tcgtttcgtg   5820

tctgtctctg tctttgtgcg tgtttgtgcc ggcatctaat gtttgcgcct gcgtctgtac   5880

tagttagcta actagctctg tatctggcgg acccgtggtg gaactgacga gttcggaaca   5940

cccggccgca accctgggag acgtcccagg gacttcgggg gccgtttttg tggcccgacc   6000

tgagtccaaa aatcccgatc gttttggact ctttggtgca cccccttag aggagggata   6060

tgtggttctg gtaggagacg agaacctaaa acagttcccg cctccgtctg aatttttgct   6120

ttcggtttgg gaccgaagcc gcgccgcgcg tcttgtctgc tgcagcatcg ttctgtgttg   6180

tctctgtctg actgtgtttc tgtatttgtc tgagaatatg ggcccgggct agcctgttac   6240

cactccctta agtttgacct taggtcactg gaaagatgtc gagcggatcg ctcacaacca   6300

gtcggtagat gtcaagaaga gacgttgggt taccttctgc tctgcagaat ggccaacctt   6360

taacgtcgga tggccgcgag acggcacctt taaccgagac ctcatcaccc aggttaagat   6420

caaggtcttt tcacctggcc cgcatggaca cccagaccag gtcccctaca tcgtgacctg   6480

ggaagccttg gcttttgacc cccctccctg ggtcaagccc tttgtacacc ctaagcctcc   6540

gcctcctctt cctccatccg ccccgtctct ccccccttgaa cctcctcgtt cgaccccgcc   6600

tcgatcctcc ctttatccag ccctcactcc ttctctaggc gcccccatat ggccatatga   6660

gatcttatat ggggcacccc cgccccttgt aaacttccct gaccctgaca tgacaagagt   6720

tactaacagc ccctctctcc aagctcactt acaggctctc tacttagtcc agcacgaagt   6780

ctggagacct ctggcggcag cctaccaaga acaactggac cgaccggtgg tacctcaccc   6840

ttaccgagtc ggcgacacag tgtgggtccg ccgacaccag actaagaacc tagaacctcg   6900

ctggaaagga ccttacacag tcctgctgac cacccccacc gccctcaaag tagacggcat   6960

cgcagcttgg atacacgccg cccacgtgaa ggctgccgac cccgggggtg gaccatcctc   7020

tagactgc                                                            7028
```

<210> SEQ ID NO 52
<211> LENGTH: 4206
<212> TYPE: DNA
<213> ORGANISM: Artificial Sequence
<220> FEATURE:
<223> OTHER INFORMATION: Made in lab - mCD19(1D3)-LC-CL1 anti-mouse CD19 switch antibody polynucleotide

<400> SEQUENCE: 52

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cggacattca gctgacccag tctccagctt     660
ccctgtctac atctctggga gaaactgtca ccatccaatg tcaagcaagt gaggacattt     720
acagtggttt agcgtggtat cagcagaagc cagggaaatc tcctcagctc ctgatctatg     780
gtgcaagtga cttacaagac ggcgtcccat cacgattcag tggcagtgga tctggcacac     840
agtattctct caagatcacc agcatgcaaa ctgaagatga aggggtttat ttctgtcaac     900
agggtttaac gtatcctcgg acgttcggtg gcggcaccaa gctggaaatc aaacgaactg     960
tggctgcacc atctgtcttc atcttcccgc catctgatga gcagttgaaa tctggaactg    1020
cctctgtcgt gtgcctgctg aataacttct atcccagaga ggccaaagta cagtggaagg    1080
tggataacgc cctccaatcg ggtaactccc aggagagtgt cacagagcag gacagcggcg    1140
gaggcgggag caattatcat cttgaaaatg aggtcgctcg tctcaagaaa ctcggtggcg    1200
gaggcagcga cagcacctac agcctcagca gcaccctgac gcttagcaaa gcagactacg    1260
agaaacacaa agtctacgcc tgcgaagtca cccatcaggg cctgtcctcg cccgtcacaa    1320
agagcttcaa caggggagag tgttgataag tgctagctgg ccagacatga taagatacat    1380
tgatgagttt ggacaaacca caactagaat gcagtgaaaa aaatgcttta tttgtgaaat    1440
ttgtgatgct attgctttat ttgtaaccat tataagctgc aataaacaag ttaacaacaa    1500
caattgcatt cattttatgt ttcaggttca gggggaggtg tgggaggttt tttaaagcaa    1560
gtaaaacctc tacaaatgtg gtatggaatt aattctaaaa tacagcatag caaaacttta    1620
acctccaaat caagcctcta cttgaatcct tttctgaggg atgaataagg cataggcatc    1680
aggggctgtt gccaatgtgc attagctgtt tgcagcctca ccttctttca tggagtttaa    1740
gatatagtgt attttcccaa ggtttgaact agctcttcat ttctttatgt tttaaatgca    1800
ctgacctccc acattccctt tttagtaaaa tattcagaaa taatttaaat acatcattgc    1860
aatgaaaata aatgtttttt attaggcaga atccagatgc tcaaggccct tcataatatc    1920
ccccagttta gtagttggac ttagggaaca aaggaacctt taatagaaat tggacagcaa    1980
gaaagcgagc ttctagctta tcctcagtcc tgctcctctg ccacaaagtg cacgcagttg    2040
ccggccgggt cgcgcagggc gaactcccgc ccccacggct gctcgccgat ctcggtcatg    2100
gccggcccgg aggcgtcccg gaagttcgtg gacacgacct ccgaccactc ggcgtacagc    2160
tcgtccaggc cgcgcaccca cacccaggcc agggtgttgt ccggcaccac ctggtcctgg    2220
accgcgctga tgaacagggt cacgtcgtcc cggaccacac cggcgaagtc gtcctccacg    2280
```

aagtcccggg agaacccgag ccggtcggtc cagaactcga ccgctccggc gacgtcgcgc 2340
gcggtgagca ccggaacggc actggtcaac ttggccatga tggctcctcc tgtcaggaga 2400
ggaaagagaa gaaggttagt acaattgcta tagtgagttg tattatacta tgcagatata 2460
ctatgccaat gattaattgt caaactaggg ctgcagggtt catagtgcca cttttcctgc 2520
actgccccat ctcctgccca ccctttccca ggcatagaca gtcagtgact taccaaactc 2580
acaggaggga gaaggcagaa gcttgagaca gacccgcggg accgccgaac tgcgagggga 2640
cgtggctagg gcggcttctt ttatggtgcg ccggccctcg gaggcagggc gctcggggag 2700
gcctagcggc caatctgcgg tggcaggagg cggggccgaa ggccgtgcct gaccaatccg 2760
gagcacatag gagtctcagc cccccgcccc aaagcaaggg gaagtcacgc gcctgtagcg 2820
ccagcgtgtt gtgaaatggg ggcttggggg ggttggggcc ctgactagtc aaaacaaact 2880
cccattgacg tcaatggggt ggagacttgg aaatccccgt gagtcaaacc gctatccacg 2940
cccattgatg tactgccaaa accgcatcat catggtaata gcgatgacta atacgtagat 3000
gtactgccaa gtaggaaagt cccataaggt catgtactgg gcataatgcc aggcgggcca 3060
tttaccgtca ttgacgtcaa tagggggcgt acttggcata tgatacactt gatgtactgc 3120
caagtgggca gtttaccgta aatactccac ccattgacgt caatggaaag tccctattgg 3180
cgttactatg ggaacatacg tcattattga cgtcaatggg cgggggtcgt tgggcggtca 3240
gccaggcggg ccatttaccg taagttatgt aacgcctgca ggttaattaa gaacatgtga 3300
gcaaaaggcc agcaaaaggc caggaaccgt aaaaaggccg cgttgctggc gtttttccat 3360
aggctccgcc cccctgacga gcatcacaaa aatcgacgct caagtcagag gtggcgaaac 3420
ccgacaggac tataaagata ccaggcgttt ccccctggaa gctccctcgt gcgctctcct 3480
gttccgaccc tgccgcttac cggatacctg tccgcctttc tcccttcggg aagcgtggcg 3540
ctttctcata gctcacgctg taggtatctc agttcggtgt aggtcgttcg ctccaagctg 3600
ggctgtgtgc acgaaccccc cgttcagccc gaccgctgcg ccttatccgg taactatcgt 3660
cttgagtcca acccggtaag acacgactta tcgccactgg cagcagccac tggtaacagg 3720
attagcagag cgaggtatgt aggcggtgct acagagttct tgaagtggtg gcctaactac 3780
ggctacacta gaagaacagt atttggtatc tgcgctctgc tgaagccagt taccttcgga 3840
aaaagagttg gtagctcttg atccggcaaa caaaccaccg ctggtagcgg tggttttttt 3900
gtttgcaagc agcagattac gcgcagaaaa aaaggatctc aagaagatcc tttgatcttt 3960
tctacggggt ctgacgctca gtggaacgaa aactcacgtt aagggatttt ggtcatggct 4020
agttaattaa catttaaatc agcggccgca ataaaatatc tttattttca ttacatctgt 4080
gtgttggttt tttgtgtgaa tcgtaactaa catacgctct ccatcaaaac aaaacgaaac 4140
aaaacaaact agcaaaatag gctgtcccca gtgcaagtgc aggtgccaga acatttctct 4200
atcgaa 4206

<210> SEQ ID NO 53
<211> LENGTH: 4137
<212> TYPE: DNA
<213> ORGANISM: Artificial Sequence
<220> FEATURE:
<223> OTHER INFORMATION: Made in lab - mCD19(1D3)-LC-WT anti-mouse CD19
switch antibody polynucleotide

<400> SEQUENCE: 53
ggatctgcga tcgctccggt gcccgtcagt gggcagagcg cacatcgccc acagtccccg 60

-continued

```
agaagttggg gggaggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cggacattca gctgacccag tctccagctt    660
ccctgtctac atctctggga gaaactgtca ccatccaatg tcaagcaagt gaggacattt    720
acagtggttt agcgtggtat cagcagaagc cagggaaatc tcctcagctc ctgatctatg    780
gtgcaagtga cttacaagac ggcgtcccat cacgattcag tggcagtgga tctggcacac    840
agtattctct caagatcacc agcatgcaaa ctgaagatga aggggtttat ttctgtcaac    900
agggtttaac gtatcctcgg acgttcggtg gcggcaccaa gctggaaatc aaacgaactg    960
tggctgcacc atctgtcttc atcttcccgc catctgatga gcagttgaaa tctggaactg   1020
cctctgtcgt gtgcctgctg aataacttct atcccagaga ggccaaagta cagtggaagg   1080
tggataacgc cctccaatcg ggtaactccc aggagagtgt cacagagcag gacagcaagg   1140
acagcaccta cagcctcagc agcaccctga cgctgagcaa agcagactac gagaaacaca   1200
aagtctacgc ctgcgaagtc acccatcagg gcctgtcctc gcccgtcaca aagagcttca   1260
acaggggaga gtgttgataa gtgctagctg gccagacatg ataagataca ttgatgagtt   1320
tggacaaacc acaactagaa tgcagtgaaa aaaatgcttt atttgtgaaa tttgtgatgc   1380
tattgcttta tttgtaacca ttataagctg caataaacaa gttaacaaca acaattgcat   1440
tcattttatg tttcaggttc agggggaggt gtgggaggtt ttttaaagca agtaaaacct   1500
ctacaaatgt ggtatggaat taattctaaa atacagcata gcaaaacttt aacctccaaa   1560
tcaagcctct acttgaatcc ttttctgagg gatgaataag gcataggcat caggggctgt   1620
tgccaatgtg cattagctgt ttgcagcctc accttctttc atggagttta agatatagtg   1680
tattttccca aggtttgaac tagctcttca tttctttatg ttttaaatgc actgacctcc   1740
cacattccct ttttagtaaa atattcagaa ataatttaaa tacatcattg caatgaaaat   1800
aaatgttttt tattaggcag aatccagatg ctcaaggccc ttcataatat cccccagttt   1860
agtagttgga cttagggaac aaaggaacct ttaatagaaa ttggacagca agaaagcgag   1920
cttctagctt atcctcagtc ctgctcctct gccacaaagt gcacgcagtt gccggccggg   1980
tcgcgcaggg cgaactcccg cccccacggc tgctcgccga tctcggtcat ggccggcccg   2040
gaggcgtccc ggaagttcgt ggacacgacc tccgaccact cggcgtacag ctcgtccagg   2100
ccgcgcaccc acacccaggc cagggtgttg tccggcacca cctggtcctg gaccgcgctg   2160
atgaacaggg tcacgtcgtc ccggaccaca ccggcgaagt cgtcctccac gaagtcccgg   2220
gagaacccga gccggtcggt ccagaactcg accgctccgg cgacgtcgcg cgcggtgagc   2280
accggaacgg cactggtcaa cttggccatg atggctcctc ctgtcaggag aggaaagaga   2340
agaaggttag tacaattgct atagtgagtt gtattatact atgcagatat actatgccaa   2400
tgattaattg tcaaactagg gctgcagggt tcatagtgcc acttttcctg cactgcccca   2460
```

tctcctgccc accctttccc aggcatagac agtcagtgac ttaccaaact cacaggaggg 2520
agaaggcaga agcttgagac agacccgcgg gaccgccgaa ctgcgagggg acgtggctag 2580
ggcggcttct tttatggtgc gccggccctc ggaggcaggg cgctcgggga ggcctagcgg 2640
ccaatctgcg gtggcaggag gcggggccga aggccgtgcc tgaccaatcc ggagcacata 2700
ggagtctcag ccccccgccc caaagcaagg ggaagtcacg cgcctgtagc gccagcgtgt 2760
tgtgaaatgg gggcttgggg gggttggggc cctgactagt caaaacaaac tcccattgac 2820
gtcaatgggg tggagacttg gaaatccccg tgagtcaaac cgctatccac gcccattgat 2880
gtactgccaa aaccgcatca tcatggtaat agcgatgact aatacgtaga tgtactgcca 2940
agtaggaaag tcccataagg tcatgtactg ggcataatgc caggcgggcc atttaccgtc 3000
attgacgtca atagggggcg tacttggcat atgatacact tgatgtactg ccaagtgggc 3060
agtttaccgt aaatactcca cccattgacg tcaatggaaa gtccctattg gcgttactat 3120
gggaacatac gtcattattg acgtcaatgg gcgggggtcg ttgggcggtc agccaggcgg 3180
gccatttacc gtaagttatg taacgcctgc aggttaatta agaacatgtg agcaaaaggc 3240
cagcaaaagg ccaggaaccg taaaaaggcc gcgttgctgg cgtttttcca taggctccgc 3300
ccccctgacg agcatcacaa aaatcgacgc tcaagtcaga ggtggcgaaa cccgacagga 3360
ctataaagat accaggcgtt tccccctgga agctccctcg tgcgctctcc tgttccgacc 3420
ctgccgctta ccggatacct gtccgccttt ctcccttcgg gaagcgtggc gctttctcat 3480
agctcacgct gtaggtatct cagttcggtg taggtcgttc gctccaagct gggctgtgtg 3540
cacgaacccc ccgttcagcc cgaccgctgc gccttatccg gtaactatcg tcttgagtcc 3600
aacccggtaa gacacgactt atcgccactg gcagcagcca ctggtaacag gattagcaga 3660
gcgaggtatg taggcggtgc tacagagttc ttgaagtggt ggcctaacta cggctacact 3720
agaagaacag tatttggtat ctgcgctctg ctgaagccag ttaccttcgg aaaaagagtt 3780
ggtagctctt gatccggcaa acaaaccacc gctggtagcg gtggtttttt tgtttgcaag 3840
cagcagatta cgcgcagaaa aaaaggatct caagaagatc ctttgatctt ttctacgggg 3900
tctgacgctc agtggaacga aaactcacgt taagggattt tggtcatggc tagttaatta 3960
acatttaaat cagcggccgc aataaaatat ctttattttc attacatctg tgtgttggtt 4020
ttttgtgtga atcgtaacta acatacgctc tccatcaaaa caaaacgaaa caaaacaaac 4080
tagcaaaata ggctgtcccc agtgcaagtg caggtgccag aacatttctc tatcgaa 4137

<210> SEQ ID NO 54
<211> LENGTH: 4152
<212> TYPE: DNA
<213> ORGANISM: Artificial sequence
<220> FEATURE:
<223> OTHER INFORMATION: Made in lab - mCD19(1D3)-HC-WT Fab anti-mouse
CD19 switch antibody polynucleotide

<400> SEQUENCE: 54
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360

```
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cgcaagtgca gctggtgcag tctggggctg    660
agcttgtgag acctgggacc tctgtgaagt tatcttgcaa agtttctggc gataccatta    720
cattttacta catgcacttt gtgaagcaaa ggcctggaca gggtctggaa tggataggaa    780
ggattgatcc tgaggatgaa agtactaaat attctgagaa gttcaaaaac aaggcgacac    840
tcactgcaga tacatcttcc aacacagcct acctgaagct cagcagcctg acctctgagg    900
acactgcaac ctatttttgt atctacggag gatactactt tgattactgg ggcccaggaa    960
ccatggtcac cgtgtcctca gcctccacca agggcccatc ggtcttcccc ctggcaccct   1020
cctccaagag cacctctggg ggcacagcgg ccctgggctg cctggtcaag gactacttcc   1080
ccgaaccggt gacggtgtcg tggaactcag gcgccctgac cagcggcgtg cacaccttcc   1140
cggctgtcct acagtcctca ggactctact ccctcagcag cgtggtgact gtgccctcta   1200
gcagcttggg cacccagacc tacatctgca acgtgaatca caagcccagc aacaccaagg   1260
tggacaagaa agttgagccc aaatcttgtt gataagtgct agctggccag acatgataag   1320
atacattgat gagtttggac aaaccacaac tagaatgcag tgaaaaaaat gctttatttg   1380
tgaaatttgt gatgctattg ctttatttgt aaccattata agctgcaata aacaagttaa   1440
caacaacaat tgcattcatt ttatgtttca ggttcagggg gaggtgtggg aggtttttta   1500
aagcaagtaa aacctctaca aatgtggtat ggaattaatt ctaaaataca gcatagcaaa   1560
actttaacct ccaaatcaag cctctacttg aatccttttc tgagggatga ataaggcata   1620
ggcatcaggg gctgttgcca atgtgcatta gctgtttgca gcctcacctt ctttcatgga   1680
gtttaagata tagtgtattt tcccaaggtt tgaactagct cttcatttct ttatgtttta   1740
aatgcactga cctcccacat tcccttttta gtaaaatatt cagaaataat ttaaatacat   1800
cattgcaatg aaaataaatg ttttttatta ggcagaatcc agatgctcaa ggcccttcat   1860
aatatccccc agtttagtag ttggacttag ggaacaaagg aacctttaat agaaattgga   1920
cagcaagaaa gcgagcttct agcttatcct cagtcctgct cctctgccac aaagtgcacg   1980
cagttgccgg ccgggtcgcg cagggcgaac tcccgccccc acggctgctc gccgatctcg   2040
gtcatggccg gcccggaggc gtcccggaag ttcgtggaca cgacctccga ccactcggcg   2100
tacagctcgt ccaggccgcg cacccacacc caggccaggg tgttgtccgg caccacctgg   2160
tcctggaccg cgctgatgaa cagggtcacg tcgtcccgga ccacaccggc gaagtcgtcc   2220
tccacgaagt cccgggagaa cccgagccgg tcggtccaga actcgaccgc tccggcgacg   2280
tcgcgcgcgg tgagcaccgg aacggcactg gtcaacttgg ccatgatggc tcctcctgtc   2340
aggagaggaa agagaagaag gttagtacaa ttgctatagt gagttgtatt atactatgca   2400
gatatactat gccaatgatt aattgtcaaa ctagggctgc agggttcata gtgccacttt   2460
tcctgcactg ccccatctcc tgcccaccct ttcccaggca tagacagtca gtgacttacc   2520
aaactcacag gagggagaag gcagaagctt gagacagacc cgcgggaccg ccgaactgcg   2580
aggggacgtg gctagggcgg cttcttttat ggtgcgccgg ccctcggagg cagggcgctc   2640
ggggaggcct agcggccaat ctgcggtggc aggaggcggg gccgaaggcc gtgcctgacc   2700
```

aatccggagc acataggagt ctcagccccc cgccccaaag caaggggaag tcacgcgcct 2760
gtagcgccag cgtgttgtga aatgggggct tggggggggtt ggggccctga ctagtcaaaa 2820
caaactccca ttgacgtcaa tggggtggag acttggaaat ccccgtgagt caaaccgcta 2880
tccacgccca ttgatgtact gccaaaaccg catcatcatg gtaatagcga tgactaatac 2940
gtagatgtac tgccaagtag gaaagtccca taaggtcatg tactgggcat aatgccaggc 3000
gggccattta ccgtcattga cgtcaatagg gggcgtactt ggcatatgat acacttgatg 3060
tactgccaag tgggcagttt accgtaaata ctccacccat tgacgtcaat ggaaagtccc 3120
tattggcgtt actatgggaa catacgtcat tattgacgtc aatgggcggg ggtcgttggg 3180
cggtcagcca ggcgggccat ttaccgtaag ttatgtaacg cctgcaggtt aattaagaac 3240
atgtgagcaa aaggccagca aaaggccagg aaccgtaaaa aggccgcgtt gctggcgttt 3300
ttccataggc tccgcccccc tgacgagcat cacaaaaatc gacgctcaag tcagaggtgg 3360
cgaaacccga caggactata aagataccag gcgtttcccc ctggaagctc cctcgtgcgc 3420
tctcctgttc cgaccctgcc gcttaccgga tacctgtccg cctttctccc ttcgggaagc 3480
gtggcgcttt ctcatagctc acgctgtagg tatctcagtt cggtgtaggt cgttcgctcc 3540
aagctgggct gtgtgcacga accccccgtt cagcccgacc gctgcgcctt atccggtaac 3600
tatcgtcttg agtccaaccc ggtaagacac gacttatcgc cactggcagc agccactggt 3660
aacaggatta gcagagcgag gtatgtaggc ggtgctacag agttcttgaa gtggtggcct 3720
aactacggct acactagaag aacagtattt ggtatctgcg ctctgctgaa gccagttacc 3780
ttcggaaaaa gagttggtag ctcttgatcc ggcaaacaaa ccaccgctgg tagcggtggt 3840 tttttgttt gcaagcagca gattacgcgc agaaaaaaag gatctcaaga agatcctttg 3900
atcttttcta cggggtctga cgctcagtgg aacgaaaact cacgttaagg gattttggtc 3960
atggctagtt aattaacatt taaatcagcg gccgcaataa aatatcttta ttttcattac 4020
atctgtgtgt tggtttttg tgtgaatcgt aactaacata cgctctccat caaaacaaaa 4080
cgaaacaaaa caaactagca aaataggctg tccccagtgc aagtgcaggt gccagaacat 4140
ttctctatcg aa 4152

<210> SEQ ID NO 55
<211> LENGTH: 4236
<212> TYPE: DNA
<213> ORGANISM: Artificial Sequence
<220> FEATURE:
<223> OTHER INFORMATION: Made in lab - mCD19(1D3)-HC_NT3 anti-mouse CD19 switch antibody polynucleotide

<400> SEQUENCE: 55
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540

```
ctacctgaga tcaccggcga aggagggcca ccatgtacag gatgcaactc ctgtcttgca    600
ttgcactaag tcttgcactt gtcacgaatt cgaactacca cctggagaat gaagtcgcca    660
gactgaagaa actgctggtt ggcgaggccg cagctaagga agccgcagct aaagcccaag    720
tgcagctggt gcagtctggg gctgagcttg tgagacctgg gacctctgtg aagttatctt    780
gcaaagtttc tggcgatacc attacatttt actacatgca ctttgtgaag caaaggcctg    840
gacagggtct ggaatggata ggaaggattg atcctgagga tgaaagtact aaatattctg    900
agaagttcaa aaacaaggcg acactcactg cagatacatc ttccaacaca gcctacctga    960
agctcagcag cctgacctct gaggacactg caacctattt ttgtatctac ggaggatact   1020
actttgatta ctggggccca ggaaccatgg tcaccgtgtc ctcagcctcc accaagggcc   1080
catcggtctt ccccctggca ccctcctcca agagcacctc tgggggcaca gcggccctgg   1140
gctgcctggt caaggactac ttccccgaac cggtgacggt gtcgtggaac tcaggcgccc   1200
tgaccagcgg cgtgcacacc ttcccggctg tcctacagtc ctcaggactc tactccctca   1260
gcagcgtggt gactgtgccc tctagcagct tgggcaccca gacctacatc tgcaacgtga   1320
atcacaagcc cagcaacacc aaggtggaca agaaagttga gcccaaatct tgttgataag   1380
tgctagctgg ccagacatga taagatacat tgatgagttt ggacaaacca caactagaat   1440
gcagtgaaaa aaatgcttta tttgtgaaat ttgtgatgct attgctttat ttgtaaccat   1500
tataagctgc aataaacaag ttaacaacaa caattgcatt cattttatgt ttcaggttca   1560
gggggaggtg tgggaggttt tttaaagcaa gtaaaacctc tacaaatgtg gtatggaatt   1620
aattctaaaa tacagcatag caaaacttta acctccaaat caagcctcta cttgaatcct   1680
tttctgaggg atgaataagg cataggcatc aggggctgtt gccaatgtgc attagctgtt   1740
tgcagcctca ccttctttca tggagtttaa gatatagtgt attttcccaa ggtttgaact   1800
agctcttcat ttctttatgt tttaaatgca ctgacctccc acattccctt tttagtaaaa   1860
tattcagaaa taatttaaat acatcattgc aatgaaaata aatgtttttt attaggcaga   1920
atccagatgc tcaaggccct tcataatatc cccagttta gtagttggac ttagggaaca   1980
aaggaacctt taatagaaat tggacagcaa gaaagcgagc ttctagctta tcctcagtcc   2040
tgctcctctg ccacaaagtg cacgcagttg ccggccgggt cgcgcagggc gaactcccgc   2100
ccccacggct gctcgccgat ctcggtcatg gccggcccgg aggcgtcccg gaagttcgtg   2160
gacacgacct ccgaccactc ggcgtacagc tcgtccaggc cgcgcaccca cacccaggcc   2220
agggtgttgt ccggcaccac ctggtcctgg accgcgctga tgaacagggt cacgtcgtcc   2280
cggaccacac cggcgaagtc gtcctccacg aagtcccggg agaacccgag ccggtcggtc   2340
cagaactcga ccgctccggc gacgtcgcgc gcggtgagca ccggaacggc actggtcaac   2400
ttggccatga tggctcctcc tgtcaggaga ggaaagagaa gaaggttagt acaattgcta   2460
tagtgagttg tattatacta tgcagatata ctatgccaat gattaattgt caaactaggg   2520
ctgcagggtt catagtgcca cttttcctgc actgccccat ctcctgccca ccctttccca   2580
ggcatagaca gtcagtgact taccaaactc acaggaggga gaaggcagaa gcttgagaca   2640
gacccgcggg accgccgaac tgcgagggga cgtggctagg gcggcttctt ttatggtgcg   2700
ccggccctcg gaggcagggc gctcggggag gcctagcggc caatctgcgg tggcaggagg   2760
cggggccgaa ggccgtgcct gaccaatccg gagcacatag gagtctcagc cccccgcccc   2820
aaagcaaggg gaagtcacgc gcctgtagcg ccagcgtgtt gtgaaatggg ggcttggggg   2880
ggttggggcc ctgactagtc aaaacaaact cccattgacg tcaatggggt ggagacttgg   2940
```

aaatccccgt gagtcaaacc gctatccacg cccattgatg tactgccaaa accgcatcat 3000
catggtaata gcgatgacta atacgtagat gtactgccaa gtaggaaagt cccataaggt 3060
catgtactgg gcataatgcc aggcgggcca tttaccgtca ttgacgtcaa tagggggcgt 3120
acttggcata tgatacactt gatgtactgc caagtgggca gtttaccgta aatactccac 3180
ccattgacgt caatggaaag tccctattgg cgttactatg ggaacatacg tcattattga 3240
cgtcaatggg cgggggtcgt tgggcggtca gccaggcggg ccatttaccg taagttatgt 3300
aacgcctgca ggttaattaa gaacatgtga gcaaaaggcc agcaaaaggc caggaaccgt 3360
aaaaaggccg cgttgctggc gtttttccat aggctccgcc cccctgacga gcatcacaaa 3420
aatcgacgct caagtcagag gtggcgaaac ccgacaggac tataaagata ccaggcgttt 3480
ccccctggaa gctccctcgt gcgctctcct gttccgaccc tgccgcttac cggatacctg 3540
tccgcctttc tcccttcggg aagcgtggcg ctttctcata gctcacgctg taggtatctc 3600
agttcggtgt aggtcgttcg ctccaagctg ggctgtgtgc acgaaccccc cgttcagccc 3660
gaccgctgcg ccttatccgg taactatcgt cttgagtcca acccggtaag acacgactta 3720
tcgccactgg cagcagccac tggtaacagg attagcagag cgaggtatgt aggcggtgct 3780
acagagttct tgaagtggtg gcctaactac ggctacacta gaagaacagt atttggtatc 3840
tgcgctctgc tgaagccagt taccttcgga aaaagagttg gtagctcttg atccggcaaa 3900
caaaccaccg ctggtagcgg tggttttttt gtttgcaagc agcagattac gcgcagaaaa 3960
aaaggatctc aagaagatcc tttgatcttt tctacggggt ctgacgctca gtggaacgaa 4020
aactcacgtt aagggatttt ggtcatggct agttaattaa catttaaatc agcggccgca 4080
ataaaatatc tttattttca ttacatctgt gtgttggttt tttgtgtgaa tcgtaactaa 4140
catacgctct ccatcaaaac aaaacgaaac aaaacaaact agcaaaatag gctgtcccca 4200
gtgcaagtgc aggtgccaga acatttctct atcgaa 4236

<210> SEQ ID NO 56
<211> LENGTH: 4209
<212> TYPE: DNA
<213> ORGANISM: Artificial Sequence
<220> FEATURE:
<223> OTHER INFORMATION: Made in lab - mCD19(1D3)-HC-Cterm anti-mouse CD19 switch antibody polynucleotide

<400> SEQUENCE: 56
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacctgaga tcaccggcga aggagggcca ccatgtacag gatgcaactc ctgtcttgca 600
ttgcactaag tcttgcactt gtcacgaatt cgcaagtgca gctggtgcag tctggggctg 660
agcttgtgag acctgggacc tctgtgaagt tatcttgcaa agtttctggc gataccatta 720

```
cattttacta catgcacttt gtgaagcaaa ggcctggaca gggtctggaa tggataggaa    780
ggattgatcc tgaggatgaa agtactaaat attctgagaa gttcaaaaac aaggcgacac    840
tcactgcaga tacatcttcc aacacagcct acctgaagct cagcagcctg acctctgagg    900
acactgcaac ctatttttgt atctacggag gatactactt tgattactgg ggcccaggaa    960
ccatggtcac cgtgtcctca gcctccacca agggcccatc ggtcttcccc ctggcaccct   1020
cctccaagag cacctctggg ggcacagcgg ccctgggctg cctggtcaag gactacttcc   1080
ccgaaccggt gacggtgtcg tggaactcag gcgccctgac cagcggcgtg cacaccttcc   1140
cggctgtcct acagtcctca ggactctact ccctcagcag cgtggtgact gtgccctcta   1200
gcagcttggg cacccagacc tacatctgca acgtgaatca caagcccagc aacaccaagg   1260
tggacaagaa agttgagccc aaatcttgtg gcgggggagg ctcaaactac cacctggaga   1320
atgaagtcgc cagactgaag aaactgtgat aagtgctagc tggccagaca tgataagata   1380
cattgatgag tttggacaaa ccacaactag aatgcagtga aaaaaatgct ttatttgtga   1440
aatttgtgat gctattgctt tatttgtaac cattataagc tgcaataaac aagttaacaa   1500
caacaattgc attcatttta tgtttcaggt tcagggggag gtgtgggagg ttttttaaag   1560
caagtaaaac ctctacaaat gtggtatgga attaattcta aaatacagca tagcaaaact   1620
ttaacctcca aatcaagcct ctacttgaat ccttttctga gggatgaata aggcataggc   1680
atcaggggct gttgccaatg tgcattagct gtttgcagcc tcaccttctt tcatggagtt   1740
taagatatag tgtattttcc caaggtttga actagctctt catttcttta tgttttaaat   1800
gcactgacct cccacattcc ctttttagta aaatattcag aaataattta aatacatcat   1860
tgcaatgaaa ataaatgttt tttattaggc agaatccaga tgctcaaggc ccttcataat   1920
atcccccagt ttagtagttg gacttaggga acaaaggaac ctttaataga aattggacag   1980
caagaaagcg agcttctagc ttatcctcag tcctgctcct ctgccacaaa gtgcacgcag   2040
ttgccggccg ggtcgcgcag ggcgaactcc cgcccccacg gctgctcgcc gatctcggtc   2100
atggccggcc cggaggcgtc ccggaagttc gtggacacga cctccgacca ctcggcgtac   2160
agctcgtcca ggccgcgcac ccacacccag gccagggtgt tgtccggcac cacctggtcc   2220
tggaccgcgc tgatgaacag ggtcacgtcg tcccggacca caccggcgaa gtcgtcctcc   2280
acgaagtccc gggagaaccc gagccggtcg gtccagaact cgaccgctcc ggcgacgtcg   2340
cgcgcggtga gcaccggaac ggcactggtc aacttggcca tgatggctcc tcctgtcagg   2400
agaggaaaga gaagaaggtt agtacaattg ctatagtgag ttgtattata ctatgcagat   2460
atactatgcc aatgattaat tgtcaaacta gggctgcagg gttcatagtg ccacttttcc   2520
tgcactgccc catctcctgc ccaccctttc ccaggcatag acagtcagtg acttaccaaa   2580
ctcacaggag ggagaaggca gaagcttgag acagacccgc gggaccgccg aactgcgagg   2640
ggacgtggct agggcggctt cttttatggt gcgccggccc tcggaggcag ggcgctcggg   2700
gaggcctagc ggccaatctg cggtggcagg aggcggggcc gaaggccgtg cctgaccaat   2760
ccggagcaca taggagtctc agccccccgc cccaaagcaa ggggaagtca cgcgcctgta   2820
gcgccagcgt gttgtgaaat gggggcttgg gggggttggg gccctgacta gtcaaaacaa   2880
actcccattg acgtcaatgg ggtggagact tggaaatccc cgtgagtcaa accgctatcc   2940
acgcccattg atgtactgcc aaaaccgcat catcatggta atagcgatga ctaatacgta   3000
gatgtactgc caagtaggaa agtcccataa ggtcatgtac tgggcataat gccaggcggg   3060
```

ccatttaccg tcattgacgt caataggggg cgtacttggc atatgataca cttgatgtac 3120
tgccaagtgg gcagtttacc gtaaatactc cacccattga cgtcaatgga aagtccctat 3180
tggcgttact atgggaacat acgtcattat tgacgtcaat gggcgggggt cgttgggcgg 3240
tcagccaggc gggccattta ccgtaagtta tgtaacgcct gcaggttaat taagaacatg 3300
tgagcaaaag gccagcaaaa ggccaggaac cgtaaaaagg ccgcgttgct ggcgtttttc 3360
cataggctcc gcccccctga cgagcatcac aaaaatcgac gctcaagtca gaggtggcga 3420
aacccgacag gactataaag ataccaggcg tttccccctg gaagctccct cgtgcgctct 3480
cctgttccga ccctgccgct taccggatac ctgtccgcct ttctcccttc gggaagcgtg 3540
gcgctttctc atagctcacg ctgtaggtat ctcagttcgg tgtaggtcgt tcgctccaag 3600
ctgggctgtg tgcacgaacc ccccgttcag cccgaccgct gcgccttatc cggtaactat 3660
cgtcttgagt ccaacccggt aagacacgac ttatcgccac tggcagcagc cactggtaac 3720
aggattagca gagcgaggta tgtaggcggt gctacagagt tcttgaagtg gtggcctaac 3780
tacggctaca ctagaagaac agtatttggt atctgcgctc tgctgaagcc agttaccttc 3840
ggaaaaagag ttggtagctc ttgatccggc aaacaaacca ccgctggtag cggtggtttt 3900
tttgtttgca agcagcagat tacgcgcaga aaaaaaggat ctcaagaaga tcctttgatc 3960
ttttctacgg ggtctgacgc tcagtggaac gaaaactcac gttaagggat tttggtcatg 4020
gctagttaat taacatttaa atcagcggcc gcaataaaat atctttattt tcattacatc 4080
tgtgtgttgg ttttttgtgt gaatcgtaac taacatacgc tctccatcaa aacaaaacga 4140
aacaaaacaa actagcaaaa taggctgtcc ccagtgcaag tgcaggtgcc agaacatttc 4200
tctatcgaa 4209

<210> SEQ ID NO 57
<211> LENGTH: 4194
<212> TYPE: DNA
<213> ORGANISM: Artificial Sequence
<220> FEATURE:
<223> OTHER INFORMATION: Made in lab - mCD19(1D3)-LC-Cterm anti-mouse CD19 switch antibody polynucleotide

<400> SEQUENCE: 57
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacctgaga tcaccggcga aggagggcca ccatgtacag gatgcaactc ctgtcttgca 600
ttgcactaag tcttgcactt gtcacgaatt cggacattca gctgacccag tctccagctt 660
ccctgtctac atctctggga gaaactgtca ccatccaatg tcaagcaagt gaggacattt 720
acagtggttt agcgtggtat cagcagaagc cagggaaatc tcctcagctc ctgatctatg 780
gtgcaagtga cttacaagac ggcgtcccat cacgattcag tggcagtgga tctggcacac 840

```
agtattctct caagatcacc agcatgcaaa ctgaagatga aggggtttat ttctgtcaac    900
agggtttaac gtatcctcgg acgttcggtg gcggcaccaa gctggaaatc aaacgaactg    960
tggctgcacc atctgtcttc atcttcccgc catctgatga gcagttgaaa tctggaactg   1020
cctctgtcgt gtgcctgctg aataacttct atcccagaga ggccaaagta cagtggaagg   1080
tggataacgc cctccaatcg ggtaactccc aggagagtgt cacagagcag gacagcaagg   1140
acagcaccta cagcctcagc agcaccctga cgctgagcaa agcagactac gagaaacaca   1200
aagtctacgc ctgcgaagtc acccatcagg gcctgtcctc gcccgtcaca aagagcttca   1260
acaggggaga gtgtggcggg ggaggctcaa actaccacct ggagaatgaa gtcgccagac   1320
tgaagaaact gtgataagtg ctagctggcc agacatgata agatacattg atgagtttgg   1380
acaaaccaca actagaatgc agtgaaaaaa atgctttatt tgtgaaattt gtgatgctat   1440
tgctttattt gtaaccatta taagctgcaa taaacaagtt aacaacaaca attgcattca   1500
ttttatgttt caggttcagg gggaggtgtg ggaggttttt taaagcaagt aaaacctcta   1560
caaatgtggt atggaattaa ttctaaaata cagcatagca aaactttaac ctccaaatca   1620
agcctctact tgaatccttt tctgagggat gaataaggca taggcatcag gggctgttgc   1680
caatgtgcat tagctgtttg cagcctcacc ttctttcatg gagtttaaga tatagtgtat   1740
tttcccaagg tttgaactag ctcttcattt ctttatgttt taaatgcact gacctcccac   1800
attccctttt tagtaaaata ttcagaaata atttaaatac atcattgcaa tgaaaataaa   1860
tgttttttat taggcagaat ccagatgctc aaggcccttc ataatatccc ccagtttagt   1920
agttggactt agggaacaaa ggaaccttta atagaaattg gacagcaaga aagcgagctt   1980
ctagcttatc ctcagtcctg ctcctctgcc acaaagtgca cgcagttgcc ggccgggtcg   2040
cgcagggcga actcccgccc ccacggctgc tcgccgatct cggtcatggc cggcccggag   2100
gcgtcccgga agttcgtgga cacgacctcc gaccactcgg cgtacagctc gtccaggccg   2160
cgcacccaca cccaggccag ggtgttgtcc ggcaccacct ggtcctggac cgcgctgatg   2220
aacagggtca cgtcgtcccg gaccacaccg gcgaagtcgt cctccacgaa gtcccgggag   2280
aacccgagcc ggtcggtcca gaactcgacc gctccggcga cgtcgcgcgc ggtgagcacc   2340
ggaacggcac tggtcaactt ggccatgatg gctcctcctg tcaggagagg aaagagaaga   2400
aggttagtac aattgctata gtgagttgta ttatactatg cagatatact atgccaatga   2460
ttaattgtca aactagggct gcagggttca tagtgccact tttcctgcac tgccccatct   2520
cctgcccacc ctttcccagg catagacagt cagtgactta ccaaactcac aggagggaga   2580
aggcagaagc ttgagacaga cccgcgggac cgccgaactg cgaggggacg tggctagggc   2640
ggcttctttt atggtgcgcc ggccctcgga ggcagggcgc tcggggaggc ctagcggcca   2700
atctgcggtg gcaggaggcg gggccgaagg ccgtgcctga ccaatccgga gcacatagga   2760
gtctcagccc cccgccccaa agcaagggga agtcacgcgc ctgtagcgcc agcgtgttgt   2820
gaaatggggg cttgggggggg ttggggccct gactagtcaa aacaaactcc cattgacgtc   2880
aatggggtgg agacttggaa atccccgtga gtcaaaccgc tatccacgcc cattgatgta   2940
ctgccaaaac cgcatcatca tggtaatagc gatgactaat acgtagatgt actgccaagt   3000
aggaaagtcc cataaggtca tgtactgggc ataatgccag gcgggccatt taccgtcatt   3060
gacgtcaata gggggcgtac ttggcatatg atacacttga tgtactgcca agtgggcagt   3120
ttaccgtaaa tactccaccc attgacgtca atggaaagtc cctattggcg ttactatggg   3180
aacatacgtc attattgacg tcaatgggcg ggggtcgttg ggcggtcagc caggcgggcc   3240
```

atttaccgta agttatgtaa cgcctgcagg ttaattaaga acatgtgagc aaaaggccag 3300
caaaaggcca ggaaccgtaa aaaggccgcg ttgctggcgt ttttccatag gctccgcccc 3360
cctgacgagc atcacaaaaa tcgacgctca agtcagaggt ggcgaaaccc gacaggacta 3420
taaagatacc aggcgtttcc ccctggaagc tccctcgtgc gctctcctgt tccgaccctg 3480
ccgcttaccg gatacctgtc cgcctttctc ccttcgggaa gcgtggcgct ttctcatagc 3540
tcacgctgta ggtatctcag ttcggtgtag gtcgttcgct ccaagctggg ctgtgtgcac 3600
gaaccccccg ttcagcccga ccgctgcgcc ttatccggta actatcgtct tgagtccaac 3660
ccggtaagac acgacttatc gccactggca gcagccactg gtaacaggat tagcagagcg 3720
aggtatgtag gcggtgctac agagttcttg aagtggtggc ctaactacgg ctacactaga 3780
agaacagtat ttggtatctg cgctctgctg aagccagtta ccttcggaaa aagagttggt 3840
agctcttgat ccggcaaaca aaccaccgct ggtagcggtg gtttttttgt ttgcaagcag 3900
cagattacgc gcagaaaaaa aggatctcaa gaagatcctt tgatcttttc tacggggtct 3960
gacgctcagt ggaacgaaaa ctcacgttaa gggattttgg tcatggctag ttaattaaca 4020
tttaaatcag cggccgcaat aaaatatctt tattttcatt acatctgtgt gttggttttt 4080
tgtgtgaatc gtaactaaca tacgctctcc atcaaaacaa aacgaaacaa aacaaactag 4140
caaaataggc tgtccccagt gcaagtgcag gtgccagaac atttctctat cgaa 4194

<210> SEQ ID NO 58
<211> LENGTH: 4194
<212> TYPE: DNA
<213> ORGANISM: Artificial sequence
<220> FEATURE:
<223> OTHER INFORMATION: Made in lab - mCD19(1D3)-LC_NT1 anti-mouse CD19 switch antibody polynucleotide

<400> SEQUENCE: 58
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacctgaga tcaccggcga aggagggcca ccatgtacag gatgcaactc ctgtcttgca 600
ttgcactaag tcttgcactt gtcacgaatt cgaactacca cctggagaat gaagtcgcca 660
gactgaagaa actgggcggg ggaggctcag acattcagct gacccagtct ccagcttccc 720
tgtctacatc tctgggagaa actgtcacca tccaatgtca agcaagtgag gacatttaca 780
gtggtttagc gtggtatcag cagaagccag ggaaatctcc tcagctcctg atctatggtg 840
caagtgactt acaagacggc gtcccatcac gattcagtgg cagtggatct ggcacacagt 900
attctctcaa gatcaccagc atgcaaactg aagatgaagg ggtttatttc tgtcaacagg 960
gtttaacgta tcctcggacg ttcggtggcg gcaccaagct tgagatcaaa cgaactgtgg 1020
ctgcaccatc tgtcttcatc ttcccgccat ctgatgagca gttgaaatct ggaactgcct 1080

-continued

```
ctgtcgtgtg cctgctgaat aacttctatc ccagagaggc caaagtacag tggaaggtgg   1140
ataacgccct ccaatcgggt aactcccagg agagtgtcac agagcaggac agcaaggaca   1200
gcacctacag cctcagcagc accctgacgc tgagcaaagc agactacgag aaacacaaag   1260
tctacgcctg cgaagtcacc catcagggcc tgtcctcgcc cgtcacaaag agcttcaaca   1320
ggggagagtg ttgataagtg ctagctggcc agacatgata agatacattg atgagtttgg   1380
acaaaccaca actagaatgc agtgaaaaaa atgctttatt tgtgaaattt gtgatgctat   1440
tgctttattt gtaaccatta taagctgcaa taaacaagtt aacaacaaca attgcattca   1500
ttttatgttt caggttcagg gggaggtgtg ggaggttttt taaagcaagt aaaacctcta   1560
caaatgtggt atggaattaa ttctaaaata cagcatagca aaactttaac ctccaaatca   1620
agcctctact tgaatccttt tctgagggat gaataaggca taggcatcag gggctgttgc   1680
caatgtgcat tagctgtttg cagcctcacc ttctttcatg gagtttaaga tatagtgtat   1740
tttcccaagg tttgaactag ctcttcattt ctttatgttt taaatgcact gacctcccac   1800
attccctttt tagtaaaata ttcagaaata atttaaatac atcattgcaa tgaaaataaa   1860
tgttttttat taggcagaat ccagatgctc aaggcccttc ataatatccc ccagtttagt   1920
agttggactt agggaacaaa ggaaccttta atagaaattg gacagcaaga aagcgagctt   1980
ctagcttatc ctcagtcctg ctcctctgcc acaaagtgca cgcagttgcc ggccgggtcg   2040
cgcagggcga actcccgccc ccacggctgc tcgccgatct cggtcatggc cggcccggag   2100
gcgtcccgga agttcgtgga cacgacctcc gaccactcgg cgtacagctc gtccaggccg   2160
cgcacccaca cccaggccag ggtgttgtcc ggcaccacct ggtcctggac cgcgctgatg   2220
aacagggtca cgtcgtcccg gaccacaccg gcgaagtcgt cctccacgaa gtcccgggag   2280
aacccgagcc ggtcggtcca gaactcgacc gctccggcga cgtcgcgcgc ggtgagcacc   2340
ggaacggcac tggtcaactt ggccatgatg gctcctcctg tcaggagagg aaagagaaga   2400
aggttagtac aattgctata gtgagttgta ttatactatg cagatatact atgccaatga   2460
ttaattgtca aactagggct gcagggttca tagtgccact tttcctgcac tgccccatct   2520
cctgcccacc ctttcccagg catagacagt cagtgactta ccaaactcac aggagggaga   2580
aggcagaagc ttgagacaga cccgcgggac cgccgaactg cgaggggacg tggctagggc   2640
ggcttctttt atggtgcgcc ggccctcgga ggcagggcgc tcggggaggc ctagcggcca   2700
atctgcggtg gcaggaggcg ggccgaaggc ccgtgcctga ccaatccgga gcacatagga   2760
gtctcagccc cccgccccaa agcaagggga agtcacgcgc ctgtagcgcc agcgtgttgt   2820
gaaatggggg cttggggggg ttggggccct gactagtcaa aacaaactcc cattgacgtc   2880
aatggggtgg agacttggaa atccccgtga gtcaaaccgc tatccacgcc cattgatgta   2940
ctgccaaaac cgcatcatca tggtaatagc gatgactaat acgtagatgt actgccaagt   3000
aggaaagtcc cataaggtca tgtactgggc ataatgccag gcgggccatt taccgtcatt   3060
gacgtcaata gggggcgtac ttggcatatg atacacttga tgtactgcca agtgggcagt   3120
ttaccgtaaa tactccaccc attgacgtca atggaaagtc cctattggcg ttactatggg   3180
aacatacgtc attattgacg tcaatgggcg ggggtcgttg ggcggtcagc caggcgggcc   3240
atttaccgta agttatgtaa cgcctgcagg ttaattaaga acatgtgagc aaaaggccag   3300
caaaaggcca ggaaccgtaa aaaggccgcg ttgctggcgt ttttccatag gctccgcccc   3360
cctgacgagc atcacaaaaa tcgacgctca agtcagaggt ggcgaaaccc gacaggacta   3420
```

taaagatacc aggcgtttcc ccctggaagc tccctcgtgc gctctcctgt tccgaccctg 3480
ccgcttaccg gatacctgtc cgcctttctc ccttcgggaa gcgtggcgct ttctcatagc 3540
tcacgctgta ggtatctcag ttcggtgtag gtcgttcgct ccaagctggg ctgtgtgcac 3600
gaaccccccg ttcagcccga ccgctgcgcc ttatccggta actatcgtct tgagtccaac 3660
ccggtaagac acgacttatc gccactggca gcagccactg gtaacaggat tagcagagcg 3720
aggtatgtag gcggtgctac agagttcttg aagtggtggc ctaactacgg ctacactaga 3780
agaacagtat ttggtatctg cgctctgctg aagccagtta ccttcggaaa aagagttggt 3840
agctcttgat ccggcaaaca aaccaccgct ggtagcggtg gtttttttgt ttgcaagcag 3900
cagattacgc gcagaaaaaa aggatctcaa gaagatcctt tgatcttttc tacggggtct 3960
gacgctcagt ggaacgaaaa ctcacgttaa gggattttgg tcatggctag ttaattaaca 4020
tttaaatcag cggccgcaat aaaatatctt tattttcatt acatctgtgt gttggttttt 4080
tgtgtgaatc gtaactaaca tacgctctcc atcaaaacaa aacgaaacaa aacaaactag 4140
caaaataggc tgtccccagt gcaagtgcag gtgccagaac atttctctat cgaa 4194

<210> SEQ ID NO 59
<211> LENGTH: 4209
<212> TYPE: DNA
<213> ORGANISM: Artificial Sequence
<220> FEATURE:
<223> OTHER INFORMATION: Made in lab - mCD19(1D3)-LC_NT2 anti-mouse CD19 switch antibody polynucleotide

<400> SEQUENCE: 59
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atataagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctacctgaga tcaccggcga aggagggcca ccatgtacag gatgcaactc ctgtcttgca 600
ttgcactaag tcttgcactt gtcacgaatt cgaactacca cctggagaat gaagtcgcca 660
gactgaagaa actgggcggg ggaggctcag ggggaggcgg gtcagacatt cagctgaccc 720
agtctccagc ttccctgtct acatctctgg gagaaactgt caccatccaa tgtcaagcaa 780
gtgaggacat ttacagtggt ttagcgtggt atcagcagaa gccagggaaa tctcctcagc 840
tcctgatcta tggtgcaagt gacttacaag acggcgtccc atcacgattc agtggcagtg 900
gatctggcac acagtattct ctcaagatca ccagcatgca aactgaagat gaaggggttt 960
atttctgtca acagggttta acgtatcctc ggacgttcgg tggcggcacc aagcttgaga 1020
tcaaacgaac tgtggctgca ccatctgtct tcatcttccc gccatctgat gagcagttga 1080
aatctggaac tgcctctgtc gtgtgcctgc tgaataactt ctatcccaga gaggccaaag 1140
tacagtggaa ggtggataac gccctccaat cgggtaactc ccaggagagt gtcacagagc 1200
aggacagcaa ggacagcacc tacagcctca gcagcaccct gacgctgagc aaagcagact 1260

-continued

```
acgagaaaca caaagtctac gcctgcgaag tcacccatca gggcctgtcc tcgcccgtca   1320
caaagagctt caacagggga gagtgttgat aagtgctagc tggccagaca tgataagata   1380
cattgatgag tttggacaaa ccacaactag aatgcagtga aaaaaatgct ttatttgtga   1440
aatttgtgat gctattgctt tatttgtaac cattataagc tgcaataaac aagttaacaa   1500
caacaattgc attcatttta tgtttcaggt tcagggggag gtgtgggagg ttttttaaag   1560
caagtaaaac ctctacaaat gtggtatgga attaattcta aaatacagca tagcaaaact   1620
ttaacctcca aatcaagcct ctacttgaat ccttttctga gggatgaata aggcataggc   1680
atcaggggct gttgccaatg tgcattagct gtttgcagcc tcaccttctt tcatggagtt   1740
taagatatag tgtattttcc caaggtttga actagctctt catttcttta tgttttaaat   1800
gcactgacct cccacattcc ctttttagta aaatattcag aaataattta aatacatcat   1860
tgcaatgaaa ataaatgttt tttattaggc agaatccaga tgctcaaggc ccttcataat   1920
atcccccagt ttagtagttg gacttaggga acaaaggaac ctttaataga aattggacag   1980
caagaaagcg agcttctagc ttatcctcag tcctgctcct ctgccacaaa gtgcacgcag   2040
ttgccggccg ggtcgcgcag ggcgaactcc cgcccccacg gctgctcgcc gatctcggtc   2100
atggccggcc cggaggcgtc ccggaagttc gtggacacga cctccgacca ctcggcgtac   2160
agctcgtcca ggccgcgcac ccacacccag gccagggtgt tgtccggcac cacctggtcc   2220
tggaccgcgc tgatgaacag ggtcacgtcg tcccggacca caccggcgaa gtcgtcctcc   2280
acgaagtccc gggagaaccc gagccggtcg gtccagaact cgaccgctcc ggcgacgtcg   2340
cgcgcggtga gcaccggaac ggcactggtc aacttggcca tgatggctcc tcctgtcagg   2400
agaggaaaga gaagaaggtt agtacaattg ctatagtgag ttgtattata ctatgcagat   2460
atactatgcc aatgattaat tgtcaaacta gggctgcagg gttcatagtg ccacttttcc   2520
tgcactgccc catctcctgc ccaccctttc ccaggcatag acagtcagtg acttaccaaa   2580
ctcacaggag ggagaaggca gaagcttgag acagacccgc gggaccgccg aactgcgagg   2640
ggacgtggct agggcggctt cttttatggt gcgccggccc tcggaggcag ggcgctcggg   2700
gaggcctagc ggccaatctg cggtggcagg aggcggggcc gaaggccgtg cctgaccaat   2760
ccggagcaca taggagtctc agccccccgc cccaaagcaa ggggaagtca cgcgcctgta   2820
gcgccagcgt gttgtgaaat gggggcttgg gggggttggg gccctgacta gtcaaaacaa   2880
actcccattg acgtcaatgg ggtggagact tggaaatccc cgtgagtcaa accgctatcc   2940
acgcccattg atgtactgcc aaaaccgcat catcatggta atagcgatga ctaatacgta   3000
gatgtactgc caagtaggaa agtcccataa ggtcatgtac tgggcataat gccaggcggg   3060
ccatttaccg tcattgacgt caataggggg cgtacttggc atatgataca cttgatgtac   3120
tgccaagtgg gcagtttacc gtaaatactc cacccattga cgtcaatgga aagtccctat   3180
tggcgttact atgggaacat acgtcattat tgacgtcaat gggcgggggt cgttgggcgg   3240
tcagccaggc gggccattta ccgtaagtta tgtaacgcct gcaggttaat taagaacatg   3300
tgagcaaaag gccagcaaaa ggccaggaac cgtaaaaagg ccgcgttgct ggcgtttttc   3360
cataggctcc gcccccctga cgagcatcac aaaaatcgac gctcaagtca gaggtggcga   3420
aacccgacag gactataaag ataccaggcg tttccccctg gaagctccct cgtgcgctct   3480
cctgttccga ccctgccgct taccggatac ctgtccgcct ttctcccttc gggaagcgtg   3540
gcgctttctc atagctcacg ctgtaggtat ctcagttcgg tgtaggtcgt tcgctccaag   3600
ctgggctgtg tgcacgaacc ccccgttcag cccgaccgct gcgccttatc cggtaactat   3660
```

```
cgtcttgagt ccaacccggt aagacacgac ttatcgccac tggcagcagc cactggtaac   3720

aggattagca gagcgaggta tgtaggcggt gctacagagt tcttgaagtg gtggcctaac   3780

tacggctaca ctagaagaac agtatttggt atctgcgctc tgctgaagcc agttaccttc   3840

ggaaaaagag ttggtagctc ttgatccggc aaacaaacca ccgctggtag cggtggtttt   3900

tttgtttgca agcagcagat tacgcgcaga aaaaaaggat ctcaagaaga tcctttgatc   3960

ttttctacgg ggtctgacgc tcagtggaac gaaaactcac gttaagggat tttggtcatg   4020

gctagttaat taacatttaa atcagcggcc gcaataaaat atctttattt tcattacatc   4080

tgtgtgttgg ttttttgtgt gaatcgtaac taacatacgc tctccatcaa aacaaaacga   4140

aacaaaacaa actagcaaaa taggctgtcc ccagtgcaag tgcaggtgcc agaacatttc   4200

tctatcgaa                                                           4209
```

```
<210> SEQ ID NO 60
<211> LENGTH: 4209
<212> TYPE: DNA
<213> ORGANISM: Artificial Sequence
<220> FEATURE:
<223> OTHER INFORMATION: Made in lab - mCD19(1D3)-HC_NT1 anti-mouse CD19
      switch antibody polynucleotide

<400> SEQUENCE: 60
```

```
ggatctgcga tcgctccggt gcccgtcagt gggcagagcg cacatcgccc acagtccccg     60

agaagttggg gggaggggtc ggcaattgaa cgggtgccta gagaaggtgg cgcggggtaa    120

actgggaaag tgatgtcgtg tactggctcc gcctttttcc cgagggtggg ggagaaccgt    180

atataagtgc agtagtcgcc gtgaacgttc tttttcgcaa cgggtttgcc gccagaacac    240

agctgaagct tcgaggggct cgcatctctc cttcacgcgc ccgccgccct acctgaggcc    300

gccatccacg ccggttgagt cgcgttctgc cgcctcccgc ctgtggtgcc tcctgaactg    360

cgtccgccgt ctaggtaagt ttaaagctca ggtcgagacc gggcctttgt ccggcgctcc    420

cttggagcct acctagactc agccggctct ccacgctttg cctgaccctg cttgctcaac    480

tctacgtctt tgtttcgttt tctgttctgc gccgttacag atccaagctg tgaccggcgc    540

ctacctgaga tcaccggcga aggagggcca ccatgtacag gatgcaactc ctgtcttgca    600

ttgcactaag tcttgcactt gtcacgaatt cgaactacca cctggagaat gaagtcgcca    660

gactgaagaa actgggcggg ggaggctcag gggaggcgg gtcagacatt cagctgaccc    720

agtctccagc ttccctgtct acatctctgg gagaaactgt caccatccaa tgtcaagcaa    780

gtgaggacat ttacagtggt ttagcgtggt atcagcagaa gccagggaaa tctcctcagc    840

tcctgatcta tggtgcaagt gacttacaag acggcgtccc atcacgattc agtggcagtg    900

gatctggcac acagtattct ctcaagatca ccagcatgca aactgaagat gaaggggttt    960

atttctgtca acagggttta acgtatcctc ggacgttcgg tggcggcacc aagcttgaga   1020

tcaaacgaac tgtggctgca ccatctgtct tcatcttccc gccatctgat gagcagttga   1080

aatctggaac tgcctctgtc gtgtgcctgc tgaataactt ctatcccaga gaggccaaag   1140

tacagtggaa ggtggataac gccctccaat cgggtaactc ccaggagagt gtcacagagc   1200

aggacagcaa ggacagcacc tacagcctca gcagcaccct gacgctgagc aaagcagact   1260

acgagaaaca caaagtctac gcctgcgaag tcacccatca gggcctgtcc tcgcccgtca   1320

caaagagctt caacagggga gagtgttgat aagtgctagc tggccagaca tgataagata   1380

cattgatgag tttggacaaa ccacaactag aatgcagtga aaaaaatgct ttatttgtga   1440
```

-continued

```
aatttgtgat gctattgctt tatttgtaac cattataagc tgcaataaac aagttaacaa   1500
caacaattgc attcatttta tgtttcaggt tcagggggag gtgtgggagg tttttaaag    1560
caagtaaaac ctctacaaat gtggtatgga attaattcta aaatacagca tagcaaaact   1620
ttaacctcca aatcaagcct ctacttgaat ccttttctga gggatgaata aggcataggc   1680
atcaggggct gttgccaatg tgcattagct gtttgcagcc tcaccttctt tcatggagtt   1740
taagatatag tgtattttcc caaggtttga actagctctt catttcttta tgttttaaat   1800
gcactgacct cccacattcc ctttttagta aaatattcag aaataattta aatacatcat   1860
tgcaatgaaa ataaatgttt tttattaggc agaatccaga tgctcaaggc ccttcataat   1920
atcccccagt ttagtagttg gacttaggga acaaaggaac ctttaataga aattggacag   1980
caagaaagcg agcttctagc ttatcctcag tcctgctcct ctgccacaaa gtgcacgcag   2040
ttgccggccg ggtcgcgcag ggcgaactcc cgcccccacg gctgctcgcc gatctcggtc   2100
atggccggcc cggaggcgtc ccggaagttc gtggacacga cctccgacca ctcggcgtac   2160
agctcgtcca ggccgcgcac ccacacccag gccagggtgt tgtccggcac cacctggtcc   2220
tggaccgcgc tgatgaacag ggtcacgtcg tcccggacca caccggcgaa gtcgtcctcc   2280
acgaagtccc gggagaaccc gagccggtcg gtccagaact cgaccgctcc ggcgacgtcg   2340
cgcgcggtga gcaccggaac ggcactggtc aacttggcca tgatggctcc tcctgtcagg   2400
agaggaaaga gaagaaggtt agtacaattg ctatagtgag ttgtattata ctatgcagat   2460
atactatgcc aatgattaat tgtcaaacta gggctgcagg gttcatagtg ccacttttcc   2520
tgcactgccc catctcctgc ccaccctttc ccaggcatag acagtcagtg acttaccaaa   2580
ctcacaggag ggagaaggca gaagcttgag acagacccgc gggaccgccg aactgcgagg   2640
ggacgtggct agggcggctt cttttatggt gcgccggccc tcggaggcag ggcgctcggg   2700
gaggcctagc ggccaatctg cggtggcagg aggcggggcc gaaggccgtg cctgaccaat   2760
ccggagcaca taggagtctc agccccccgc cccaaagcaa ggggaagtca cgcgcctgta   2820
gcgccagcgt gttgtgaaat gggggcttgg gggggttggg gccctgacta gtcaaaacaa   2880
actcccattg acgtcaatgg ggtggagact tggaaatccc cgtgagtcaa accgctatcc   2940
acgcccattg atgtactgcc aaaaccgcat catcatggta atagcgatga ctaatacgta   3000
gatgtactgc caagtaggaa agtcccataa ggtcatgtac tgggcataat gccaggcggg   3060
ccatttaccg tcattgacgt caatagggggg cgtacttggc atatgataca cttgatgtac  3120
tgccaagtgg gcagtttacc gtaaatactc cacccattga cgtcaatgga aagtccctat   3180
tggcgttact atgggaacat acgtcattat tgacgtcaat gggcgggggt cgttgggcgg   3240
tcagccaggc gggccattta ccgtaagtta tgtaacgcct gcaggttaat taagaacatg   3300
tgagcaaaag gccagcaaaa ggccaggaac cgtaaaaagg ccgcgttgct ggcgtttttc   3360
cataggctcc gcccccctga cgagcatcac aaaaatcgac gctcaagtca gaggtggcga   3420
aacccgacag gactataaag ataccaggcg tttccccctg gaagctccct cgtgcgctct   3480
cctgttccga ccctgccgct taccggatac ctgtccgcct ttctcccttc gggaagcgtg   3540
gcgctttctc atagctcacg ctgtaggtat ctcagttcgg tgtaggtcgt tcgctccaag   3600
ctgggctgtg tgcacgaacc ccccgttcag cccgaccgct gcgccttatc cggtaactat   3660
cgtcttgagt ccaacccggt aagacacgac ttatcgccac tggcagcagc cactggtaac   3720
aggattagca gagcgaggta tgtaggcggt gctacagagt tcttgaagtg gtggcctaac   3780
```

-continued

```
tacggctaca ctagaagaac agtatttggt atctgcgctc tgctgaagcc agttaccttc   3840

ggaaaaagag ttggtagctc ttgatccggc aaacaaacca ccgctggtag cggtggtttt   3900

tttgtttgca agcagcagat tacgcgcaga aaaaaaggat ctcaagaaga tcctttgatc   3960

ttttctacgg ggtctgacgc tcagtggaac gaaaactcac gttaagggat tttggtcatg   4020

gctagttaat taacatttaa atcagcggcc gcaataaaat atctttattt tcattacatc   4080

tgtgtgttgg ttttttgtgt gaatcgtaac taacatacgc tctccatcaa aacaaaacga   4140

aacaaaacaa actagcaaaa taggctgtcc ccagtgcaag tgcaggtgcc agaacatttc   4200

tctatcgaa                                                            4209


<210> SEQ ID NO 61
<211> LENGTH: 4224
<212> TYPE: DNA
<213> ORGANISM: Artificial Sequence
<220> FEATURE:
<223> OTHER INFORMATION: Made in lab - mCD19(1D3)-HC_NT2 anti-mouse CD19
      switch antibody polynucleotide

<400> SEQUENCE: 61

ggatctgcga tcgctccggt gcccgtcagt gggcagagcg cacatcgccc acagtccccg     60

agaagttggg gggaggggtc ggcaattgaa cgggtgccta gagaaggtgg cgcggggtaa    120

actgggaaag tgatgtcgtg tactggctcc gcctttttcc cgagggtggg ggagaaccgt    180

atataagtgc agtagtcgcc gtgaacgttc tttttcgcaa cgggtttgcc gccagaacac    240

agctgaagct tcgaggggct cgcatctctc cttcacgcgc ccgccgccct acctgaggcc    300

gccatccacg ccggttgagt cgcgttctgc cgcctcccgc ctgtggtgcc tcctgaactg    360

cgtccgccgt ctaggtaagt ttaaagctca ggtcgagacc gggcctttgt ccggcgctcc    420

cttggagcct acctagactc agccggctct ccacgctttg cctgaccctg cttgctcaac    480

tctacgtctt tgtttcgttt tctgttctgc gccgttacag atccaagctg tgaccggcgc    540

ctacctgaga tcaccggcga aggagggcca ccatgtacag gatgcaactc ctgtcttgca    600

ttgcactaag tcttgcactt gtcacgaatt cgaactacca cctggagaat gaagtcgcca    660

gactgaagaa actgggcggg ggaggctcag ggggaggcgg gtcacaagtg cagctggtgc    720

agtctggggc tgagcttgtg agacctggga cctctgtgaa gttatcttgc aaagtttctg    780

gcgataccat tacattttac tacatgcact ttgtgaagca aaggcctgga cagggtctgg    840

aatggatagg aaggattgat cctgaggatg aaagtactaa atattctgag aagttcaaaa    900

acaaggcgac actcactgca gatacatctt ccaacacagc ctacctgaag ctcagcagcc    960

tgacctctga ggacactgca acctattttt gtatctacgg aggatactac tttgattact   1020

ggggaccagg aaccatggtc accgtgtcct cagcctccac caagggccca tcggtcttcc   1080

ccctggcacc ctcctccaag agcacctctg ggggcacagc ggccctgggc tgcctggtca   1140

aggactactt ccccgaaccg gtgacggtgt cgtggaactc aggcgccctg accagcggcg   1200

tgcacacctt cccggctgtc ctacagtcct caggactcta ctccctcagc agcgtggtga   1260

ctgtgccctc tagcagcttg ggcacccaga cctacatctg caacgtgaat cacaagccca   1320

gcaacaccaa ggtggacaag aaagttgagc ccaaatcttg ttgataagtg ctagctggcc   1380

agacatgata agatacattg atgagtttgg acaaaccaca actagaatgc agtgaaaaaa   1440

atgctttatt tgtgaaattt gtgatgctat tgctttattt gtaaccatta taagctgcaa   1500

taaacaagtt aacaacaaca attgcattca ttttatgttt caggttcagg gggaggtgtg   1560
```

-continued

```
ggaggttttt taaagcaagt aaaacctcta caaatgtggt atggaattaa ttctaaaata   1620
cagcatagca aaactttaac ctccaaatca agcctctact tgaatccttt tctgagggat   1680
gaataaggca taggcatcag ggctgttgc caatgtgcat tagctgtttg cagcctcacc   1740
ttctttcatg gagtttaaga tatagtgtat tttcccaagg tttgaactag ctcttcattt   1800
ctttatgttt taaatgcact gacctcccac attccctttt tagtaaaata ttcagaaata   1860
atttaaatac atcattgcaa tgaaaataaa tgttttttat taggcagaat ccagatgctc   1920
aaggcccttc ataatatccc ccagtttagt agttggactt agggaacaaa ggaaccttta   1980
atagaaattg gacagcaaga aagcgagctt ctagcttatc ctcagtcctg ctcctctgcc   2040
acaaagtgca cgcagttgcc ggccgggtcg cgcagggcga actcccgccc ccacggctgc   2100
tcgccgatct cggtcatggc cggcccggag gcgtcccgga agttcgtgga cacgacctcc   2160
gaccactcgg cgtacagctc gtccaggccg cgcacccaca cccaggccag ggtgttgtcc   2220
ggcaccacct ggtcctggac cgcgctgatg aacagggtca cgtcgtcccg gaccacaccg   2280
gcgaagtcgt cctccacgaa gtcccgggag aacccgagcc ggtcggtcca gaactcgacc   2340
gctccggcga cgtcgcgcgc ggtgagcacc ggaacggcac tggtcaactt ggccatgatg   2400
gctcctcctg tcaggagagg aaagagaaga aggttagtac aattgctata gtgagttgta   2460
ttatactatg cagatatact atgccaatga ttaattgtca aactagggct gcagggttca   2520
tagtgccact tttcctgcac tgccccatct cctgcccacc ctttcccagg catagacagt   2580
cagtgactta ccaaactcac aggagggaga aggcagaagc ttgagacaga cccgcgggac   2640
cgccgaactg cgaggggacg tggctagggc ggcttctttt atggtgcgcc ggccctcgga   2700
ggcagggcgc tcggggaggc ctagcggcca atctgcggtg gcaggaggcg gggccgaagg   2760
ccgtgcctga ccaatccgga gcacatagga gtctcagccc cccgccccaa agcaaggga    2820
agtcacgcgc ctgtagcgcc agcgtgttgt gaaatggggg cttgggggg ttggggccct    2880
gactagtcaa aacaaactcc cattgacgtc aatggggtgg agacttggaa atccccgtga   2940
gtcaaaccgc tatccacgcc cattgatgta ctgccaaaac cgcatcatca tggtaatagc   3000
gatgactaat acgtagatgt actgccaagt aggaaagtcc cataaggtca tgtactgggc   3060
ataatgccag gcgggccatt taccgtcatt gacgtcaata gggggcgtac ttggcatatg   3120
atacacttga tgtactgcca agtgggcagt ttaccgtaaa tactccaccc attgacgtca   3180
atggaaagtc cctattggcg ttactatggg aacatacgtc attattgacg tcaatgggcg   3240
ggggtcgttg ggcggtcagc caggcgggcc atttaccgta agttatgtaa cgcctgcagg   3300
ttaattaaga acatgtgagc aaaaggccag caaaaggcca ggaaccgtaa aaaggccgcg   3360
ttgctggcgt ttttccatag gctccgcccc cctgacgagc atcacaaaaa tcgacgctca   3420
agtcagaggt ggcgaaaccc gacaggacta taaagatacc aggcgtttcc ccctggaagc   3480
tccctcgtgc gctctcctgt tccgaccctg ccgcttaccg gatacctgtc cgcctttctc   3540
ccttcgggaa gcgtggcgct ttctcatagc tcacgctgta ggtatctcag ttcggtgtag   3600
gtcgttcgct ccaagctggg ctgtgtgcac gaaccccccg ttcagcccga ccgctgcgcc   3660
ttatccggta actatcgtct tgagtccaac ccggtaagac acgacttatc gccactggca   3720
gcagccactg gtaacaggat tagcagagcg aggtatgtag gcggtgctac agagttcttg   3780
aagtggtggc ctaactacgg ctacactaga agaacagtat ttggtatctg cgctctgctg   3840
aagccagtta ccttcggaaa aagagttggt agctcttgat ccggcaaaca aaccaccgct   3900
ggtagcggtg gtttttttgt ttgcaagcag cagattacgc gcagaaaaaa aggatctcaa   3960
```

gaagatcctt tgatcttttc tacggggtct gacgctcagt ggaacgaaaa ctcacgttaa 4020
gggattttgg tcatggctag ttaattaaca tttaaatcag cggccgcaat aaaatatctt 4080
tattttcatt acatctgtgt gttggttttt tgtgtgaatc gtaactaaca tacgctctcc 4140
atcaaaacaa aacgaaacaa aacaaactag caaaataggc tgtccccagt gcaagtgcag 4200
gtgccagaac atttctctat cgaa 4224

<210> SEQ ID NO 62
<211> LENGTH: 6102
<212> TYPE: DNA
<213> ORGANISM: Artificial Sequence
<220> FEATURE:
<223> OTHER INFORMATION: Made in lab - NYESO1(1G4-113)-TCRb-WT soluble T cell receptor polynucleotide

<400> SEQUENCE: 62
atccggatat agttcctcct ttcagcaaaa aacccctcaa gacccgttta gaggccccaa 60
ggggttatgc tagttattgc tcagcggtgg cagcagccaa ctcagcttcc tttcgggctt 120
tgttagcagc cggatctcag tggtggtggt ggtggtgctc gagttagtca gcacgacccc 180
acgcttctgc actgacaatt tgcgtaaccg gttttgcacg gtcctgggtc cattcatcat 240
tttcgctcag gccgtagaat tgaacctgac agcgaaaatg gttacgcggg tcctgccaga 300
aggtggcaga cacgcgcaga cgggaactca gggcataacg gctgtcattc agcgccggtt 360
gttctttcag cggctgcgga tcggtacaca cacccgagtg gacttctttg ccgttcaccc 420
accatgacag ttcgacatgg tccggataaa agccggtggc caggcacacc agcgtcgctt 480
tctgggtatg ggagatttca gcttcactcg gttcgaaaac tgccacttcc ggcggaaaga 540
catttttcag atcttccaga accgtcagac gagaaccttc gccgaaaaac agttcaccgg 600
tgttgcccag gtaagagctt gcgcagaaat aaacagacgt ttggctcggt gctgcgctca 660
gcagacgcag cggaaagtct tcaatggtcg aacgtgaaac attgtaaccg ttcggcactt 720
cgccttgatc cgtggtctgg atggcgaccg aatagtgaat cagacgcaga cccatacccg 780
ggtcctgacg gtaccatgac atatattcat ggttcatatc ttgggcacat tgcagcgtca 840
tggattggcc cgttttcagg acttggaatt tcggcgtttg ggtcacacca gcgttcatat 900
gtatatctcc ttcttaaagt taaacaaaat tatttctaga ggggaattgt tatccgctca 960
caattcccct atagtgagtc gtattaattt cgcgggatcg agatctcgat cctctacgcc 1020
ggacgcatcg tggccggcat caccggcgcc acaggtgcgg ttgctggcgc ctatatcgcc 1080
gacatcaccg atggggaaga tcgggctcgc cacttcgggc tcatgagcgc ttgtttcggc 1140
gtgggtatgg tggcaggccc cgtggccggg ggactgttgg gcgccatctc cttgcatgca 1200
ccattccttg cggcggcggt gctcaacggc ctcaacctac tactgggctg cttcctaatg 1260
caggagtcgc ataagggaga gcgtcgagat cccggacacc atcgaatggc gcaaaacctt 1320
tcgcggtatg gcatgatagc gcccggaaga gagtcaattc agggtggtga atgtgaaacc 1380
agtaacgtta tacgatgtcg cagagtatgc cggtgtctct tatcagaccg tttcccgcgt 1440
ggtgaaccag gccagccacg tttctgcgaa aacgcgggaa aaagtggaag cggcgatggc 1500
ggagctgaat tacattccca accgcgtggc acaacaactg gcgggcaaac agtcgttgct 1560
gattggcgtt gccacctcca gtctggccct gcacgcgccg tcgcaaattg tcgcggcgat 1620
taaatctcgc gccgatcaac tgggtgccag cgtggtggtg tcgatggtag aacgaagcgg 1680
cgtcgaagcc tgtaaagcgg cggtgcacaa tcttctcgcg caacgcgtca gtggctgat 1740

```
cattaactat ccgctggatg accaggatgc cattgctgtg gaagctgcct gcactaatgt   1800
tccggcgtta tttcttgatg tctctgacca gacacccatc aacagtatta ttttctccca   1860
tgaagacggt acgcgactgg gcgtggagca tctggtcgca ttgggtcacc agcaaatcgc   1920
gctgttagcg ggcccattaa gttctgtctc ggcgcgtctg cgtctggctg gctggcataa   1980
atatctcact cgcaatcaaa ttcagccgat agcggaacgg gaaggcgact ggagtgccat   2040
gtccggtttt caacaaacca tgcaaatgct gaatgagggc atcgttccca ctgcgatgct   2100
ggttgccaac gatcagatgg cgctgggcgc aatgcgcgcc attaccgagt ccgggctgcg   2160
cgttggtgcg gatatctcgg tagtgggata cgacgatacc gaagacagct catgttatat   2220
cccgccgtta accaccatca aacaggattt tcgcctgctg gggcaaacca gcgtggaccg   2280
cttgctgcaa ctctctcagg gccaggcggt gaagggcaat cagctgttgc ccgtctcact   2340
ggtgaaaaga aaaaccaccc tggcgcccaa tacgcaaacc gcctctcccc gcgcgttggc   2400
cgattcatta atgcagctgg cacgacaggt ttcccgactg gaaagcgggc agtgagcgca   2460
acgcaattaa tgtaagttag ctcactcatt aggcaccggg atctcgaccg atgcccttga   2520
gagccttcaa cccagtcagc tccttccggt gggcgcgggg catgactatc gtcgccgcac   2580
ttatgactgt cttctttatc atgcaactcg taggacaggt gccggcagcg ctctgggtca   2640
ttttcggcga ggaccgcttt cgctggagcg cgacgatgat cggcctgtcg cttgcggtat   2700
tcggaatctt gcacgccctc gctcaagcct tcgtcactgg tcccgccacc aaacgtttcg   2760
gcgagaagca ggccattatc gccggcatgg cggccccacg ggtgcgcatg atcgtgctcc   2820
tgtcgttgag gacccggcta ggctggcggg gttgccttac tggttagcag aatgaatcac   2880
cgatacgcga gcgaacgtga agcgactgct gctgcaaaac gtctgcgacc tgagcaacaa   2940
catgaatggt cttcggtttc cgtgtttcgt aaagtctgga aacgcggaag tcagcgccct   3000
gcaccattat gttccggatc tgcatcgcag gatgctgctg gctaccctgt ggaacaccta   3060
catctgtatt aacgaagcgc tggcattgac cctgagtgat ttttctctgg tcccgccgca   3120
tccataccgc cagttgttta ccctcacaac gttccagtaa ccgggcatgt tcatcatcag   3180
taacccgtat cgtgagcatc ctctctcgtt tcatcggtat cattaccccc atgaacagaa   3240
atcccccctta cacggaggca tcagtgacca aacaggaaaa aaccgccctt aacatggccc   3300
gctttatcag aagccagaca ttaacgcttc tggagaaact caacgagctg gacgcggatg   3360
aacaggcaga catctgtgaa tcgcttcacg accacgctga tgagctttac cgcagctgcc   3420
tcgcgcgttt cggtgatgac ggtgaaaacc tctgacacat gcagctcccg gagacggtca   3480
cagcttgtct gtaagcggat gccgggagca gacaagcccg tcagggcgcg tcagcgggtg   3540
ttggcgggtg tcggggcgca gccatgaccc agtcacgtag cgatagcgga gtgtatactg   3600
gcttaactat gcggcatcag agcagattgt actgagagtg caccatatat gcggtgtgaa   3660
ataccgcaca gatgcgtaag gagaaaatac cgcatcaggc gctcttccgc ttcctcgctc   3720
actgactcgc tgcgctcggt cgttcggctg cggcgagcgg tatcagctca ctcaaaggcg   3780
gtaatacggt tatccacaga atcaggggat aacgcaggaa agaacatgtg agcaaaaggc   3840
cagcaaaagg ccaggaaccg taaaaaggcc gcgttgctgg cgtttttcca taggctccgc   3900
cccccctgacg agcatcacaa aaatcgacgc tcaagtcaga ggtggcgaaa cccgacagga   3960
ctataaagat accaggcgtt tccccctgga agctccctcg tgcgctctcc tgttccgacc   4020
ctgccgctta ccggatacct gtccgccttt ctcccttcgg gaagcgtggc gctttctcat   4080
```

agctcacgct gtaggtatct cagttcggtg taggtcgttc gctccaagct gggctgtgtg 4140
cacgaacccc ccgttcagcc cgaccgctgc gccttatccg gtaactatcg tcttgagtcc 4200
aacccggtaa gacacgactt atcgccactg gcagcagcca ctggtaacag gattagcaga 4260
gcgaggtatg taggcggtgc tacagagttc ttgaagtggt ggcctaacta cggctacact 4320
agaaggacag tatttggtat ctgcgctctg ctgaagccag ttaccttcgg aaaaagagtt 4380
ggtagctctt gatccggcaa acaaaccacc gctggtagcg gtggtttttt tgtttgcaag 4440
cagcagatta cgcgcagaaa aaaaggatct caagaagatc ctttgatctt ttctacgggg 4500
tctgacgctc agtggaacga aaactcacgt taagggattt tggtcatgag attatcaaaa 4560
aggatcttca cctagatcct tttaaattaa aaatgaagtt ttaaatcaat ctaaagtata 4620
tatgagtaaa cttggtctga cagttaccaa tgcttaatca gtgaggcacc tatctcagcg 4680
atctgtctat ttcgttcatc catagttgcc tgactccccg tcgtgtagat aactacgata 4740
cgggagggct taccatctgg ccccagtgct gcaatgatac cgcgagaccc acgctcaccg 4800
gctccagatt tatcagcaat aaaccagcca gccggaaggg ccgagcgcag aagtggtcct 4860
gcaactttat ccgcctccat ccagtctatt aattgttgcc gggaagctag agtaagtagt 4920
tcgccagtta atagtttgcg caacgttgtt gccattgctg caggcatcgt ggtgtcacgc 4980
tcgtcgtttg gtatggcttc attcagctcc ggttcccaac gatcaaggcg agttacatga 5040
tcccccatgt tgtgcaaaaa agcggttagc tccttcggtc ctccgatcgt tgtcagaagt 5100
aagttggccg cagtgttatc actcatggtt atggcagcac tgcataattc tcttactgtc 5160
atgccatccg taagatgctt ttctgtgact ggtgagtact caaccaagtc attctgagaa 5220
tagtgtatgc ggcgaccgag ttgctcttgc ccggcgtcaa tacgggataa taccgcgcca 5280
catagcagaa ctttaaaagt gctcatcatt ggaaaacgtt cttcggggcg aaaactctca 5340
aggatcttac cgctgttgag atccagttcg atgtaaccca ctcgtgcacc caactgatct 5400
tcagcatctt ttactttcac cagcgtttct gggtgagcaa aaacaggaag gcaaaatgcc 5460
gcaaaaaagg gaataagggc gacacggaaa tgttgaatac tcatactctt cctttttcaa 5520
tattattgaa gcatttatca gggttattgt ctcatgagcg gatacatatt tgaatgtatt 5580
tagaaaaata aacaaatagg ggttccgcgc acatttcccc gaaaagtgcc acctgaaatt 5640
gtaaacgtta atattttgtt aaaattcgcg ttaaattttt gttaaatcag ctcatttttt 5700
aaccaatagg ccgaaatcgg caaaatccct tataaatcaa aagaatagac cgagataggg 5760
ttgagtgttg ttccagtttg gaacaagagt ccactattaa agaacgtgga ctccaacgtc 5820
aaagggcgaa aaaccgtcta tcagggcgat ggcccactac gtgaaccatc accctaatca 5880
agttttttgg ggtcgaggtg ccgtaaagca ctaaatcgga accctaaagg gagcccccga 5940
tttagagctt gacggggaaa gccggcgaac gtggcgagaa aggaagggaa gaaagcgaaa 6000
ggagcgggcg ctagggcgct ggcaagtgta gcggtcacgc tgcgcgtaac caccacaccc 6060
gccgcgctta atgcgccgct acagggcgcg tcccattcgc ca 6102

<210> SEQ ID NO 63
<211> LENGTH: 6159
<212> TYPE: DNA
<213> ORGANISM: Artificial Sequence
<220> FEATURE:
<223> OTHER INFORMATION: Made in lab -NYESO1(1G4-113)-TCRb-GCN4-NT1
soluble T cell receptor polynucleotide

<400> SEQUENCE: 63

```
atccggatat agttcctcct ttcagcaaaa aacccctcaa gacccgttta gaggccccaa     60
ggggttatgc tagttattgc tcagcggtgg cagcagccaa ctcagcttcc tttcgggctt    120
tgttagcagc cggatctcag tggtggtggt ggtggtgctc gagttagtca gcacgacccc    180
acgcttctgc actgacaatt tgcgtaaccg gttttgcacg gtcctgggtc cattcatcat    240
tttcgctcag gccgtagaat tgaacctgac agcgaaaatg gttacgcggg tcctgccaga    300
aggtggcaga cacgcgcaga cgggaactca gggcataacg gctgtcattc agcgccggtt    360
gttctttcag cggctgcgga tcggtacaca cacccgagtg gacttctttg ccgttcaccc    420
accatgacag ttcgacatgg tccggataaa agccggtggc caggcacacc agcgtcgctt    480
tctgggtatg ggagatttca gcttcactcg gttcgaaaac tgccacttcc ggcggaaaga    540
catttttcag atcttccaga accgtcagac gagaaccttc gccgaaaaac agttcaccgg    600
tgttgcccag gtaagagctt gcgcagaaat aaacagacgt ttggctcggt gctgcgctca    660
gcagacgcag cggaaagtct tcaatggtcg aacgtgaaac attgtaaccg ttcggcactt    720
cgccttgatc cgtggtctgg atggcgaccg aatagtgaat cagacgcaga cccatacccg    780
ggtcctgacg gtaccatgac atatattcat ggttcatatc ttgggcacat tgcagcgtca    840
tggattggcc cgttttcagg acttggaatt tcggcgtttg ggtcacacca gcgttgctac    900
cgccaccgcc cagtttttc aggcgcgcaa cttcattttc caggtggtag ttcatatgta    960
tatctccttc ttaaagttaa acaaaattat ttctagaggg gaattgttat ccgctcacaa   1020
ttcccctata gtgagtcgta ttaatttcgc gggatcgaga tctcgatcct ctacgccgga   1080
cgcatcgtgg ccggcatcac cggcgccaca ggtgcggttg ctggcgccta tatcgccgac   1140
atcaccgatg gggaagatcg ggctcgccac ttcgggctca tgagcgcttg tttcggcgtg   1200
ggtatggtgg caggccccgt ggccggggga ctgttgggcg ccatctcctt gcatgcacca   1260
ttccttgcgg cggcggtgct caacggcctc aacctactac tgggctgctt cctaatgcag   1320
gagtcgcata agggagagcg tcgagatccc ggacaccatc gaatggcgca aaacctttcg   1380
cggtatggca tgatagcgcc cggaagagag tcaattcagg gtggtgaatg tgaaaccagt   1440
aacgttatac gatgtcgcag agtatgccgg tgtctcttat cagaccgttt cccgcgtggt   1500
gaaccaggcc agccacgttt ctgcgaaaac gcgggaaaaa gtggaagcgg cgatggcgga   1560
gctgaattac attcccaacc gcgtggcaca acaactggcg ggcaaacagt cgttgctgat   1620
tggcgttgcc acctccagtc tggccctgca cgcgccgtcg caaattgtcg cggcgattaa   1680
atctcgcgcc gatcaactgg gtgccagcgt ggtggtgtcg atggtagaac gaagcggcgt   1740
cgaagcctgt aaagcggcgg tgcacaatct tctcgcgcaa cgcgtcagtg ggctgatcat   1800
taactatccg ctggatgacc aggatgccat tgctgtggaa gctgcctgca ctaatgttcc   1860
ggcgttattt cttgatgtct ctgaccagac acccatcaac agtattattt tctcccatga   1920
agacggtacg cgactgggcg tggagcatct ggtcgcattg ggtcaccagc aaatcgcgct   1980
gttagcgggc ccattaagtt ctgtctcggc gcgtctgcgt ctggctggct ggcataaata   2040
tctcactcgc aatcaaattc agccgatagc ggaacgggaa ggcgactgga gtgccatgtc   2100
cggttttcaa caaaccatgc aaatgctgaa tgagggcatc gttcccactg cgatgctggt   2160
tgccaacgat cagatggcgc tgggcgcaat gcgcgccatt accgagtccg ggctgcgcgt   2220
tggtgcggat atctcggtag tgggatacga cgataccgaa gacagctcat gttatatccc   2280
gccgttaacc accatcaaac aggattttcg cctgctgggg caaaccagcg tggaccgctt   2340
gctgcaactc tctcagggcc aggcggtgaa gggcaatcag ctgttgcccg tctcactggt   2400
```

```
gaaaagaaaa accaccctgg cgcccaatac gcaaaccgcc tctccccgcg cgttggccga   2460
ttcattaatg cagctggcac gacaggtttc ccgactggaa agcgggcagt gagcgcaacg   2520
caattaatgt aagttagctc actcattagg caccgggatc tcgaccgatg cccttgagag   2580
ccttcaaccc agtcagctcc ttccggtggg cgcggggcat gactatcgtc gccgcactta   2640
tgactgtctt ctttatcatg caactcgtag gacaggtgcc ggcagcgctc tgggtcattt   2700
tcggcgagga ccgctttcgc tggagcgcga cgatgatcgg cctgtcgctt gcggtattcg   2760
gaatcttgca cgccctcgct caagccttcg tcactggtcc cgccaccaaa cgtttcggcg   2820
agaagcaggc cattatcgcc ggcatggcgg ccccacgggt gcgcatgatc gtgctcctgt   2880
cgttgaggac ccggctaggc tggcggggtt gccttactgg ttagcagaat gaatcaccga   2940
tacgcgagcg aacgtgaagc gactgctgct gcaaaacgtc tgcgacctga gcaacaacat   3000
gaatggtctt cggtttccgt gtttcgtaaa gtctggaaac gcggaagtca gcgccctgca   3060
ccattatgtt ccggatctgc atcgcaggat gctgctggct accctgtgga acacctacat   3120
ctgtattaac gaagcgctgg cattgaccct gagtgatttt tctctggtcc cgccgcatcc   3180
ataccgccag ttgtttaccc tcacaacgtt ccagtaaccg ggcatgttca tcatcagtaa   3240
cccgtatcgt gagcatcctc tctcgtttca tcggtatcat tacccccatg aacagaaatc   3300
ccccttacac ggaggcatca gtgaccaaac aggaaaaaac cgcccttaac atggcccgct   3360
ttatcagaag ccagacatta acgcttctgg agaaactcaa cgagctggac gcggatgaac   3420
aggcagacat ctgtgaatcg cttcacgacc acgctgatga gctttaccgc agctgcctcg   3480
cgcgtttcgg tgatgacggt gaaaacctct gacacatgca gctcccggag acggtcacag   3540
cttgtctgta agcggatgcc gggagcagac aagcccgtca gggcgcgtca gcgggtgttg   3600
gcgggtgtcg gggcgcagcc atgacccagt cacgtagcga tagcggagtg tatactggct   3660
taactatgcg gcatcagagc agattgtact gagagtgcac catatatgcg gtgtgaaata   3720
ccgcacagat gcgtaaggag aaaataccgc atcaggcgct cttccgcttc ctcgctcact   3780
gactcgctgc gctcggtcgt tcggctgcgg cgagcggtat cagctcactc aaaggcggta   3840
atacggttat ccacagaatc aggggataac gcaggaaaga acatgtgagc aaaaggccag   3900
caaaaggcca ggaaccgtaa aaaggccgcg ttgctggcgt ttttccatag gctccgcccc   3960
cctgacgagc atcacaaaaa tcgacgctca agtcagaggt ggcgaaaccc gacaggacta   4020
taaagatacc aggcgtttcc ccctggaagc tccctcgtgc gctctcctgt tccgaccctg   4080
ccgcttaccg gatacctgtc cgcctttctc ccttcgggaa gcgtggcgct ttctcatagc   4140
tcacgctgta ggtatctcag ttcggtgtag gtcgttcgct ccaagctggg ctgtgtgcac   4200
gaaccccccg ttcagcccga ccgctgcgcc ttatccggta actatcgtct tgagtccaac   4260
ccggtaagac acgacttatc gccactggca gcagccactg gtaacaggat tagcagagcg   4320
aggtatgtag gcggtgctac agagttcttg aagtggtggc ctaactacgg ctacactaga   4380
aggacagtat ttggtatctg cgctctgctg aagccagtta ccttcggaaa aagagttggt   4440
agctcttgat ccggcaaaca aaccaccgct ggtagcggtg gtttttttgt ttgcaagcag   4500
cagattacgc gcagaaaaaa aggatctcaa gaagatcctt tgatcttttc tacggggtct   4560
gacgctcagt ggaacgaaaa ctcacgttaa gggattttgg tcatgagatt atcaaaaagg   4620
atcttcacct agatcctttt aaattaaaaa tgaagtttta aatcaatcta aagtatatat   4680
gagtaaactt ggtctgacag ttaccaatgc ttaatcagtg aggcacctat ctcagcgatc   4740
```

```
tgtctatttc gttcatccat agttgcctga ctccccgtcg tgtagataac tacgatacgg   4800
gagggcttac catctggccc cagtgctgca atgataccgc gagacccacg ctcaccggct   4860
ccagatttat cagcaataaa ccagccagcc ggaagggccg agcgcagaag tggtcctgca   4920
actttatccg cctccatcca gtctattaat tgttgccggg aagctagagt aagtagttcg   4980
ccagttaata gtttgcgcaa cgttgttgcc attgctgcag gcatcgtggt gtcacgctcg   5040
tcgtttggta tggcttcatt cagctccggt tcccaacgat caaggcgagt tacatgatcc   5100
cccatgttgt gcaaaaaagc ggttagctcc ttcggtcctc cgatcgttgt cagaagtaag   5160
ttggccgcag tgttatcact catggttatg gcagcactgc ataattctct tactgtcatg   5220
ccatccgtaa gatgcttttc tgtgactggt gagtactcaa ccaagtcatt ctgagaatag   5280
tgtatgcggc gaccgagttg ctcttgcccg gcgtcaatac gggataatac cgcgccacat   5340
agcagaactt taaaagtgct catcattgga aaacgttctt cggggcgaaa actctcaagg   5400
atcttaccgc tgttgagatc cagttcgatg taacccactc gtgcacccaa ctgatcttca   5460
gcatctttta ctttcaccag cgtttctggg tgagcaaaaa caggaaggca aaatgccgca   5520
aaaaagggaa taagggcgac acggaaatgt tgaatactca tactcttcct ttttcaatat   5580
tattgaagca tttatcaggg ttattgtctc atgagcggat acatatttga atgtatttag   5640
aaaaataaac aaataggggt tccgcgcaca tttccccgaa aagtgccacc tgaaattgta   5700
aacgttaata ttttgttaaa attcgcgtta aatttttgtt aaatcagctc attttttaac   5760
caataggccg aaatcggcaa aatcccttat aaatcaaaag aatagaccga gatagggttg   5820
agtgttgttc cagtttggaa caagagtcca ctattaaaga acgtggactc caacgtcaaa   5880
gggcgaaaaa ccgtctatca gggcgatggc ccactacgtg aaccatcacc ctaatcaagt   5940
tttttggggt cgaggtgccg taaagcacta aatcggaacc ctaaagggag cccccgattt   6000
agagcttgac ggggaaagcc ggcgaacgtg gcgagaaagg aagggaagaa agcgaaagga   6060
gcgggcgcta gggcgctggc aagtgtagcg gtcacgctgc gcgtaaccac cacacccgcc   6120
gcgcttaatg cgccgctaca gggcgcgtcc cattcgcca                          6159
```

<210> SEQ ID NO 64
<211> LENGTH: 6054
<212> TYPE: DNA
<213> ORGANISM: Artificial Sequence
<220> FEATURE:
<223> OTHER INFORMATION: Made in lab - NYESO1(1G4-113)-TCRa-GCN4-NT1 soluble T cell receptor polynucleotide

<400> SEQUENCE: 64

```
atccggatat agttcctcct ttcagcaaaa aacccctcaa gacccgttta gaggccccaa     60
ggggttatgc tagttattgc tcagcggtgg cagcagccaa ctcagcttcc tttcgggctt    120
tgttagcagc cggatctcag tggtggtggt ggtggtgctc gagttaagag ctttccgggc    180
tcgggaaaaa cgtatcttcc gggataatac tattgttgaa tgcgttggcg cacgcaaagt    240
cagatttatt gctccaagca actgccgagt ttgatttgaa atccatagag cgcatgtcca    300
gaacacattt atcggtaata tacacgtcgg aatctttgga ttgactgaca ttcgtctgac    360
tgtcgaaatc ggtaaacagg cacacgcttt tgtccgatga tttgctatca cgcagttggt    420
acaccgccgg gtccgggttc tggatatacg gatggacaat caggctggta ccgcggccaa    480
acgtcgggat ataggtacca tccagcagcg gacgcaccgc acacaggtac gtagcggagt    540
cacccggctg acttgctgca atatacaggg tggaactacc agagctttta tccagcgatg    600
```

-continued

```
cattcaggcg gcctgaggtt tgttcacgct gccacggcgt gatcagcagc aggctggtca    660
gacctttgcc cggatcttga cgaaaccact gcaggttgta aatggcgcta tccgtaaagg    720
agcaattcag caccagattt tcaccttccg ggaccgacag agcagccggg atttgggtaa    780
cttcttgttt gctaccgcca ccgcccagtt ttttcaggcg cgcaacttca ttttccaggt    840
ggtagttcat atgtatatct ccttcttaaa gttaaacaaa attatttcta gaggggaatt    900
gttatccgct cacaattccc ctatagtgag tcgtattaat ttcgcgggat cgagatctcg    960
atcctctacg ccggacgcat cgtggccggc atcaccggcg ccacaggtgc ggttgctggc   1020
gcctatatcg ccgacatcac cgatggggaa gatcgggctc gccacttcgg gctcatgagc   1080
gcttgtttcg gcgtgggtat ggtggcaggc cccgtggccg ggggactgtt gggcgccatc   1140
tccttgcatg caccattcct tgcggcggcg gtgctcaacg gcctcaacct actactgggc   1200
tgcttcctaa tgcaggagtc gcataaggga gagcgtcgag atcccggaca ccatcgaatg   1260
gcgcaaaacc tttcgcggta tggcatgata gcgcccggaa gagagtcaat tcagggtggt   1320
gaatgtgaaa ccagtaacgt tatacgatgt cgcagagtat gccggtgtct cttatcagac   1380
cgtttcccgc gtggtgaacc aggccagcca cgtttctgcg aaaacgcggg aaaaagtgga   1440
agcggcgatg gcggagctga attacattcc caaccgcgtg gcacaacaac tggcgggcaa   1500
acagtcgttg ctgattggcg ttgccacctc cagtctggcc ctgcacgcgc cgtcgcaaat   1560
tgtcgcggcg attaaatctc gcgccgatca actgggtgcc agcgtggtgg tgtcgatggt   1620
agaacgaagc ggcgtcgaag cctgtaaagc ggcggtgcac aatcttctcg cgcaacgcgt   1680
cagtgggctg atcattaact atccgctgga tgaccaggat gccattgctg tggaagctgc   1740
ctgcactaat gttccggcgt tatttcttga tgtctctgac cagacaccca tcaacagtat   1800
tattttctcc catgaagacg gtacgcgact gggcgtggag catctggtcg cattgggtca   1860
ccagcaaatc gcgctgttag cgggcccatt aagttctgtc tcggcgcgtc tgcgtctggc   1920
tggctggcat aaatatctca ctcgcaatca aattcagccg atagcggaac gggaaggcga   1980
ctggagtgcc atgtccggtt ttcaacaaac catgcaaatg ctgaatgagg gcatcgttcc   2040
cactgcgatg ctggttgcca acgatcagat ggcgctgggc gcaatgcgcg ccattaccga   2100
gtccgggctg cgcgttggtg cggatatctc ggtagtggga tacgacgata ccgaagacag   2160
ctcatgttat atcccgccgt taaccaccat caaacaggat tttcgcctgc tggggcaaac   2220
cagcgtggac cgcttgctgc aactctctca gggccaggcg gtgaagggca atcagctgtt   2280
gcccgtctca ctggtgaaaa gaaaaaccac cctggcgccc aatacgcaaa ccgcctctcc   2340
ccgcgcgttg gccgattcat taatgcagct ggcacgacag gtttcccgac tggaaagcgg   2400
gcagtgagcg caacgcaatt aatgtaagtt agctcactca ttaggcaccg ggatctcgac   2460
cgatgccctt gagagccttc aacccagtca gctccttccg gtgggcgcgg ggcatgacta   2520
tcgtcgccgc acttatgact gtcttcttta tcatgcaact cgtaggacag gtgccggcag   2580
cgctctgggt cattttcggc gaggaccgct ttcgctggag cgcgacgatg atcggcctgt   2640
cgcttgcggt attcggaatc ttgcacgccc tcgctcaagc cttcgtcact ggtcccgcca   2700
ccaaacgttt cggcgagaag caggccatta tcgccggcat ggcggcccca cgggtgcgca   2760
tgatcgtgct cctgtcgttg aggacccggc taggctggcg gggttgcctt actggttagc   2820
agaatgaatc accgatacgc gagcgaacgt gaagcgactg ctgctgcaaa acgtctgcga   2880
cctgagcaac aacatgaatg gtcttcggtt tccgtgtttc gtaaagtctg gaaacgcgga   2940
agtcagcgcc ctgcaccatt atgttccgga tctgcatcgc aggatgctgc tggctaccct   3000
```

-continued

```
gtggaacacc tacatctgta ttaacgaagc gctggcattg accctgagtg atttttctct   3060
ggtcccgccg catccatacc gccagttgtt taccctcaca acgttccagt aaccgggcat   3120
gttcatcatc agtaacccgt atcgtgagca tcctctctcg tttcatcggt atcattaccc   3180
ccatgaacag aaatccccct tacacggagg catcagtgac caaacaggaa aaaaccgccc   3240
ttaacatggc ccgctttatc agaagccaga cattaacgct tctggagaaa ctcaacgagc   3300
tggacgcgga tgaacaggca gacatctgtg aatcgcttca cgaccacgct gatgagcttt   3360
accgcagctg cctcgcgcgt ttcggtgatg acggtgaaaa cctctgacac atgcagctcc   3420
cggagacggt cacagcttgt ctgtaagcgg atgccgggag cagacaagcc cgtcagggcg   3480
cgtcagcggg tgttggcggg tgtcggggcg cagccatgac ccagtcacgt agcgatagcg   3540
gagtgtatac tggcttaact atgcggcatc agagcagatt gtactgagag tgcaccatat   3600
atgcggtgtg aaataccgca cagatgcgta aggagaaaat accgcatcag gcgctcttcc   3660
gcttcctcgc tcactgactc gctgcgctcg gtcgttcggc tgcggcgagc ggtatcagct   3720
cactcaaagg cggtaatacg gttatccaca gaatcagggg ataacgcagg aaagaacatg   3780
tgagcaaaag gccagcaaaa ggccaggaac cgtaaaaagg ccgcgttgct ggcgtttttc   3840
cataggctcc gcccccctga cgagcatcac aaaaatcgac gctcaagtca gaggtggcga   3900
aacccgacag gactataaag ataccaggcg tttccccctg gaagctccct cgtgcgctct   3960
cctgttccga ccctgccgct taccggatac ctgtccgcct ttctcccttc gggaagcgtg   4020
gcgctttctc atagctcacg ctgtaggtat ctcagttcgg tgtaggtcgt tcgctccaag   4080
ctgggctgtg tgcacgaacc ccccgttcag cccgaccgct gcgccttatc cggtaactat   4140
cgtcttgagt ccaacccggt aagacacgac ttatcgccac tggcagcagc cactggtaac   4200
aggattagca gagcgaggta tgtaggcggt gctacagagt tcttgaagtg gtggcctaac   4260
tacggctaca ctagaaggac agtatttggt atctgcgctc tgctgaagcc agttaccttc   4320
ggaaaaagag ttggtagctc ttgatccggc aaacaaacca ccgctggtag cggtggtttt   4380
tttgtttgca agcagcagat tacgcgcaga aaaaaaggat ctcaagaaga tcctttgatc   4440
ttttctacgg ggtctgacgc tcagtggaac gaaaactcac gttaagggat tttggtcatg   4500
agattatcaa aaaggatctt cacctagatc cttttaaatt aaaaatgaag ttttaaatca   4560
atctaaagta tatatgagta aacttggtct gacagttacc aatgcttaat cagtgaggca   4620
cctatctcag cgatctgtct atttcgttca tccatagttg cctgactccc cgtcgtgtag   4680
ataactacga tacgggaggg cttaccatct ggccccagtg ctgcaatgat accgcgagac   4740
ccacgctcac cggctccaga tttatcagca ataaaccagc cagccggaag ggccgagcgc   4800
agaagtggtc ctgcaacttt atccgcctcc atccagtcta ttaattgttg ccgggaagct   4860
agagtaagta gttcgccagt taatagtttg cgcaacgttg ttgccattgc tgcaggcatc   4920
gtggtgtcac gctcgtcgtt tggtatggct tcattcagct ccggttccca acgatcaagg   4980
cgagttacat gatcccccat gttgtgcaaa aaagcggtta gctccttcgg tcctccgatc   5040
gttgtcagaa gtaagttggc cgcagtgtta tcactcatgg ttatggcagc actgcataat   5100
tctcttactg tcatgccatc cgtaagatgc ttttctgtga ctggtgagta ctcaaccaag   5160
tcattctgag aatagtgtat gcggcgaccg agttgctctt gcccggcgtc aatacgggat   5220
aataccgcgc cacatagcag aactttaaaa gtgctcatca ttggaaaacg ttcttcgggg   5280
cgaaaactct caaggatctt accgctgttg agatccagtt cgatgtaacc cactcgtgca   5340
```

```
cccaactgat cttcagcatc ttttactttc accagcgttt ctgggtgagc aaaaacagga   5400

aggcaaaatg ccgcaaaaaa gggaataagg gcgacacgga aatgttgaat actcatactc   5460

ttcctttttc aatattattg aagcatttat cagggttatt gtctcatgag cggatacata   5520

tttgaatgta tttagaaaaa taaacaaata ggggttccgc gcacatttcc ccgaaaagtg   5580

ccacctgaaa ttgtaaacgt taatattttg ttaaaattcg cgttaaattt ttgttaaatc   5640

agctcatttt ttaaccaata ggccgaaatc ggcaaaatcc cttataaatc aaaagaatag   5700

accgagatag ggttgagtgt tgttccagtt tggaacaaga gtccactatt aaagaacgtg   5760

gactccaacg tcaaagggcg aaaaaccgtc tatcagggcg atggcccact acgtgaacca   5820

tcaccctaat caagtttttt ggggtcgagg tgccgtaaag cactaaatcg gaaccctaaa   5880

gggagccccc gatttagagc ttgacgggga aagccggcga acgtggcgag aaaggaaggg   5940

aagaaagcga aaggagcggg cgctagggcg ctggcaagtg tagcggtcac gctgcgcgta   6000

accaccacac ccgccgcgct taatgcgccg ctacagggcg cgtcccattc gcca         6054
```

```
<210> SEQ ID NO 65
<211> LENGTH: 5997
<212> TYPE: DNA
<213> ORGANISM: Artificial Sequence
<220> FEATURE:
<223> OTHER INFORMATION: Made in lab - NYESO1(1G4-113)-TCRa-WT soluble T
      cell receptor polynucleotide

<400> SEQUENCE: 65
```

```
atccggatat agttcctcct ttcagcaaaa aacccctcaa gacccgttta gaggccccaa     60

ggggttatgc tagttattgc tcagcggtgg cagcagccaa ctcagcttcc tttcgggctt    120

tgttagcagc cggatctcag tggtggtggt ggtggtgctc gagttaagag ctttccgggc    180

tcgggaaaaa cgtatcttcc gggataatac tattgttgaa tgcgttggcg cacgcaaagt    240

cagatttatt gctccaagca actgccgagt ttgatttgaa atccatagag cgcatgtcca    300

gaacacattt atcggtaata tacacgtcgg aatctttgga ttgactgaca ttcgtctgac    360

tgtcgaaatc ggtaaacagg cacacgcttt tgtccgatga tttgctatca cgcagttggt    420

acaccgccgg gtccgggttc tggatatacg gatggacaat caggctggta ccgcggccaa    480

acgtcgggat ataggtacca tccagcagcg gacgcaccgc acacaggtac gtagcggagt    540

cacccggctg acttgctgca atatacaggg tggaactacc agagctttta tccagcgatg    600

cattcaggcg gcctgaggtt tgttcacgct gccacggcgt gatcagcagc aggctggtca    660

gacctttgcc cggatcttga cgaaaccact gcaggttgta aatggcgcta tccgtaaagg    720

agcaattcag caccagattt tcaccttccg ggaccgacag agcagccggg atttgggtaa    780

cttcttgttt catatgtata tctccttctt aaagttaaac aaaattattt ctagagggga    840

attgttatcc gctcacaatt cccctatagt gagtcgtatt aatttcgcgg gatcgagatc    900

tcgatcctct acgccggacg catcgtggcc ggcatcaccg gcgccacagg tgcggttgct    960

ggcgcctata tcgccgacat caccgatggg gaagatcggg ctcgccactt cgggctcatg   1020

agcgcttgtt tcggcgtggg tatggtggca ggccccgtgg ccgggggact gttgggcgcc   1080

atctccttgc atgcaccatt ccttgcggcg gcggtgctca acggcctcaa cctactactg   1140

ggctgcttcc taatgcagga gtcgcataag ggagagcgtc gagatcccgg acaccatcga   1200

atggcgcaaa acctttcgcg gtatggcatg atagcgcccg gaagagagtc aattcagggt   1260

ggtgaatgtg aaaccagtaa cgttatacga tgtcgcagag tatgccggtg tctcttatca   1320
```

-continued

```
gaccgtttcc cgcgtggtga accaggccag ccacgtttct gcgaaaacgc gggaaaaagt   1380
ggaagcggcg atggcggagc tgaattacat tcccaaccgc gtggcacaac aactggcggg   1440
caaacagtcg ttgctgattg gcgttgccac ctccagtctg gccctgcacg cgccgtcgca   1500
aattgtcgcg gcgattaaat ctcgcgccga tcaactgggt gccagcgtgg tggtgtcgat   1560
ggtagaacga agcggcgtcg aagcctgtaa agcggcggtg cacaatcttc tcgcgcaacg   1620
cgtcagtggg ctgatcatta actatccgct ggatgaccag gatgccattg ctgtggaagc   1680
tgcctgcact aatgttccgg cgttatttct tgatgtctct gaccagacac ccatcaacag   1740
tattattttc tcccatgaag acggtacgcg actgggcgtg gagcatctgg tcgcattggg   1800
tcaccagcaa atcgcgctgt tagcgggccc attaagttct gtctcggcgc gtctgcgtct   1860
ggctggctgg cataaatatc tcactcgcaa tcaaattcag ccgatagcgg aacgggaagg   1920
cgactggagt gccatgtccg gttttcaaca aaccatgcaa atgctgaatg agggcatcgt   1980
tcccactgcg atgctggttg ccaacgatca gatggcgctg ggcgcaatgc gcgccattac   2040
cgagtccggg ctgcgcgttg gtgcggatat ctcggtagtg ggatacgacg ataccgaaga   2100
cagctcatgt tatatcccgc cgttaaccac catcaaacag gattttcgcc tgctggggca   2160
aaccagcgtg gaccgcttgc tgcaactctc tcagggccag gcggtgaagg gcaatcagct   2220
gttgcccgtc tcactggtga aaagaaaaac caccctggcg cccaatacgc aaaccgcctc   2280
tccccgcgcg ttggccgatt cattaatgca gctggcacga caggtttccc gactggaaag   2340
cgggcagtga gcgcaacgca attaatgtaa gttagctcac tcattaggca ccgggatctc   2400
gaccgatgcc cttgagagcc ttcaacccag tcagctcctt ccggtgggcg cggggcatga   2460
ctatcgtcgc cgcacttatg actgtcttct ttatcatgca actcgtagga caggtgccgg   2520
cagcgctctg ggtcattttc ggcgaggacc gctttcgctg gagcgcgacg atgatcggcc   2580
tgtcgcttgc ggtattcgga atcttgcacg ccctcgctca agccttcgtc actggtcccg   2640
ccaccaaacg tttcggcgag aagcaggcca ttatcgccgg catggcggcc ccacgggtgc   2700
gcatgatcgt gctcctgtcg ttgaggaccc ggctaggctg gcggggttgc cttactggtt   2760
agcagaatga atcaccgata cgcgagcgaa cgtgaagcga ctgctgctgc aaaacgtctg   2820
cgacctgagc aacaacatga atggtcttcg gtttccgtgt ttcgtaaagt ctggaaacgc   2880
ggaagtcagc gccctgcacc attatgttcc ggatctgcat cgcaggatgc tgctggctac   2940
cctgtggaac acctacatct gtattaacga agcgctggca ttgaccctga gtgatttttc   3000
tctggtcccg ccgcatccat accgccagtt gtttaccctc acaacgttcc agtaaccggg   3060
catgttcatc atcagtaacc cgtatcgtga gcatcctctc tcgtttcatc ggtatcatta   3120
cccccatgaa cagaaatccc ccttacacgg aggcatcagt gaccaaacag gaaaaaaccg   3180
cccttaacat ggcccgcttt atcagaagcc agacattaac gcttctggag aaactcaacg   3240
agctggacgc ggatgaacag gcagacatct gtgaatcgct tcacgaccac gctgatgagc   3300
tttaccgcag ctgcctcgcg cgtttcggtg atgacggtga aaacctctga cacatgcagc   3360
tcccggagac ggtcacagct tgtctgtaag cggatgccgg gagcagacaa gcccgtcagg   3420
gcgcgtcagc gggtgttggc gggtgtcggg gcgcagccat gacccagtca cgtagcgata   3480
gcggagtgta tactggctta actatgcggc atcagagcag attgtactga gagtgcacca   3540
tatatgcggt gtgaaatacc gcacagatgc gtaaggagaa aataccgcat caggcgctct   3600
tccgcttcct cgctcactga ctcgctgcgc tcggtcgttc ggctgcggcg agcggtatca   3660
gctcactcaa aggcggtaat acggttatcc acagaatcag gggataacgc aggaaagaac   3720
```

```
atgtgagcaa aaggccagca aaaggccagg aaccgtaaaa aggccgcgtt gctggcgttt   3780
ttccataggc tccgcccccc tgacgagcat cacaaaaatc gacgctcaag tcagaggtgg   3840
cgaaacccga caggactata aagataccag gcgtttcccc ctggaagctc cctcgtgcgc   3900
tctcctgttc cgaccctgcc gcttaccgga tacctgtccg cctttctccc ttcgggaagc   3960
gtggcgcttt ctcatagctc acgctgtagg tatctcagtt cggtgtaggt cgttcgctcc   4020
aagctgggct gtgtgcacga accccccgtt cagcccgacc gctgcgcctt atccggtaac   4080
tatcgtcttg agtccaaccc ggtaagacac gacttatcgc cactggcagc agccactggt   4140
aacaggatta gcagagcgag gtatgtaggc ggtgctacag agttcttgaa gtggtggcct   4200
aactacggct acactagaag gacagtattt ggtatctgcg ctctgctgaa gccagttacc   4260
ttcggaaaaa gagttggtag ctcttgatcc ggcaaacaaa ccaccgctgg tagcggtggt   4320
tttttgttt gcaagcagca gattacgcgc agaaaaaaag gatctcaaga agatcctttg   4380
atcttttcta cggggtctga cgctcagtgg aacgaaaact cacgttaagg gattttggtc   4440
atgagattat caaaaaggat cttcacctag atccttttaa attaaaaatg aagttttaaa   4500
tcaatctaaa gtatatatga gtaaacttgg tctgacagtt accaatgctt aatcagtgag   4560
gcacctatct cagcgatctg tctatttcgt tcatccatag ttgcctgact ccccgtcgtg   4620
tagataacta cgatacggga gggcttacca tctggcccca gtgctgcaat gataccgcga   4680
gacccacgct caccggctcc agatttatca gcaataaacc agccagccgg aagggccgag   4740
cgcagaagtg gtcctgcaac tttatccgcc tccatccagt ctattaattg ttgccgggaa   4800
gctagagtaa gtagttcgcc agttaatagt ttgcgcaacg ttgttgccat tgctgcaggc   4860
atcgtggtgt cacgctcgtc gtttggtatg gcttcattca gctccggttc ccaacgatca   4920
aggcgagtta catgatcccc catgttgtgc aaaaaagcgg ttagctcctt cggtcctccg   4980
atcgttgtca gaagtaagtt ggccgcagtg ttatcactca tggttatggc agcactgcat   5040
aattctctta ctgtcatgcc atccgtaaga tgcttttctg tgactggtga gtactcaacc   5100
aagtcattct gagaatagtg tatgcggcga ccgagttgct cttgcccggc gtcaatacgg   5160
gataataccg cgccacatag cagaacttta aaagtgctca tcattggaaa acgttcttcg   5220
gggcgaaaac tctcaaggat cttaccgctg ttgagatcca gttcgatgta acccactcgt   5280
gcacccaact gatcttcagc atcttttact ttcaccagcg tttctgggtg agcaaaaaca   5340
ggaaggcaaa atgccgcaaa aaagggaata agggcgacac ggaaatgttg aatactcata   5400
ctcttccttt ttcaatatta ttgaagcatt tatcagggtt attgtctcat gagcggatac   5460
atatttgaat gtatttagaa aaataaacaa ataggggttc cgcgcacatt tccccgaaaa   5520
gtgccacctg aaattgtaaa cgttaatatt ttgttaaaat tcgcgttaaa tttttgttaa   5580
atcagctcat tttttaacca ataggccgaa atcggcaaaa tcccttataa atcaaaagaa   5640
tagaccgaga tagggttgag tgttgttcca gtttggaaca agagtccact attaaagaac   5700
gtggactcca acgtcaaagg gcgaaaaacc gtctatcagg gcgatggccc actacgtgaa   5760
ccatcaccct aatcaagttt tttggggtcg aggtgccgta aagcactaaa tcggaaccct   5820
aaagggagcc cccgatttag agcttgacgg ggaaagccgg cgaacgtggc gagaaaggaa   5880
gggaagaaag cgaaaggagc gggcgctagg gcgctggcaa gtgtagcggt cacgctgcgc   5940
gtaaccacca cacccgccgc gcttaatgcg ccgctacagg gcgcgtccca ttcgcca      5997
```

<210> SEQ ID NO 66

<211> LENGTH: 6192
<212> TYPE: DNA
<213> ORGANISM: Artificial Sequence
<220> FEATURE:
<223> OTHER INFORMATION: Made in lab - NYESO1(1G4-113)-TCRb-GCN4-Cterm
soluble T cell receptor polynucleotide

<400> SEQUENCE: 66
atccggatat agttcctcct ttcagcaaaa aacccctcaa gacccgttta gaggccccaa 60
ggggttatgc tagttattgc tcagcggtgg cagcagccaa ctcagcttcc tttcgggctt 120
tgttagcagc cggatctcag tggtggtggt ggtggtgctc gagttagtga tggtgatggt 180
gatggctacc gccaccgccc agtttttca ggcgcgcaac ttcattttcc aggtggtagt 240
tggaaccgcc accgccgtca gcacgacccc acgcttctgc actgacaatt tgcgtaaccg 300
gttttgcacg gtcctgggtc cattcatcat tttcgctcag gccgtagaat tgaacctgac 360
agcgaaaatg gttacgcggg tcctgccaga aggtggcaga cacgcgcaga cgggaactca 420
gggcataacg gctgtcattc agcgccggtt gttctttcag cggctgcgga tcggtacaca 480
cacccgagtg gacttctttg ccgttcaccc accatgacag ttcgacatgg tccggataaa 540
agccggtggc caggcacacc agcgtcgctt tctgggtatg ggagatttca gcttcactcg 600
gttcgaaaac tgccacttcc ggcggaaaga catttttcag atcttccaga accgtcagac 660
gagaaccttc gccgaaaaac agttcaccgg tgttgcccag gtaagagctt gcgcagaaat 720
aaacagacgt ttggctcggt gctgcgctca gcagacgcag cggaaagtct tcaatggtcg 780
aacgtgaaac attgtaaccg ttcggcactt cgccttgatc cgtggtctgg atggcgaccg 840
aatagtgaat cagacgcaga cccatacccg ggtcctgacg gtaccatgac atatattcat 900
ggttcatatc ttgggcacat tgcagcgtca tggattggcc cgttttcagg acttggaatt 960
tcggcgtttg ggtcacacca gcgttcatat gtatatctcc ttcttaaagt taaacaaaat 1020
tatttctaga ggggaattgt tatccgctca caattcccct atagtgagtc gtattaattt 1080
cgcgggatcg agatctcgat cctctacgcc ggacgcatcg tggccggcat caccggcgcc 1140
acaggtgcgg ttgctggcgc ctatatcgcc gacatcaccg atggggaaga tcgggctcgc 1200
cacttcgggc tcatgagcgc ttgtttcggc gtgggtatgg tggcaggccc cgtggccggg 1260
ggactgttgg gcgccatctc cttgcatgca ccattccttg cggcggcggt gctcaacggc 1320
ctcaacctac tactgggctg cttcctaatg caggagtcgc ataagggaga gcgtcgagat 1380
cccggacacc atcgaatggc gcaaaacctt tcgcggtatg gcatgatagc gcccggaaga 1440
gagtcaattc agggtggtga atgtgaaacc agtaacgtta tacgatgtcg cagagtatgc 1500
cggtgtctct tatcagaccg tttcccgcgt ggtgaaccag gccagccacg tttctgcgaa 1560
aacgcgggaa aaagtggaag cggcgatggc ggagctgaat tacattccca accgcgtggc 1620
acaacaactg gcgggcaaac agtcgttgct gattggcgtt gccacctcca gtctggccct 1680
gcacgcgccg tcgcaaattg tcgcggcgat taaatctcgc gccgatcaac tgggtgccag 1740
cgtggtggtg tcgatggtag aacgaagcgg cgtcgaagcc tgtaaagcgg cggtgcacaa 1800
tcttctcgcg caacgcgtca gtgggctgat cattaactat ccgctggatg accaggatgc 1860
cattgctgtg gaagctgcct gcactaatgt tccggcgtta tttcttgatg tctctgacca 1920
gacacccatc aacagtatta ttttctccca tgaagacggt acgcgactgg gcgtggagca 1980
tctggtcgca ttgggtcacc agcaaatcgc gctgttagcg ggcccattaa gttctgtctc 2040
ggcgcgtctg cgtctggctg gctggcataa atatctcact cgcaatcaaa ttcagccgat 2100
agcggaacgg gaaggcgact ggagtgccat gtccggtttt caacaaacca tgcaaatgct 2160
gaatgagggc atcgttccca ctgcgatgct ggttgccaac gatcagatgg cgctgggcgc 2220
aatgcgcgcc attaccgagt ccgggctgcg cgttggtgcg gatatctcgg tagtgggata 2280
cgacgatacc gaagacagct catgttatat cccgccgtta accaccatca aacaggattt 2340
tcgcctgctg gggcaaacca gcgtggaccg cttgctgcaa ctctctcagg gccaggcggt 2400
gaagggcaat cagctgttgc ccgtctcact ggtgaaaaga aaaaccaccc tggcgcccaa 2460
tacgcaaacc gcctctcccc gcgcgttggc cgattcatta atgcagctgg cacgacaggt 2520
ttcccgactg gaaagcgggc agtgagcgca acgcaattaa tgtaagttag ctcactcatt 2580
aggcaccggg atctcgaccg atgcccttga gagccttcaa cccagtcagc tccttccggt 2640
gggcgcgggg catgactatc gtcgccgcac ttatgactgt cttctttatc atgcaactcg 2700
taggacaggt gccggcagcg ctctgggtca ttttcggcga ggaccgcttt cgctggagcg 2760
cgacgatgat cggcctgtcg cttgcggtat tcggaatctt gcacgccctc gctcaagcct 2820
tcgtcactgg tcccgccacc aaacgtttcg gcgagaagca ggccattatc gccggcatgg 2880
cggccccacg ggtgcgcatg atcgtgctcc tgtcgttgag gacccggcta ggctggcggg 2940
gttgccttac tggttagcag aatgaatcac cgatacgcga gcgaacgtga agcgactgct 3000
gctgcaaaac gtctgcgacc tgagcaacaa catgaatggt cttcggtttc cgtgtttcgt 3060
aaagtctgga aacgcggaag tcagcgccct gcaccattat gttccggatc tgcatcgcag 3120
gatgctgctg gctaccctgt ggaacaccta catctgtatt aacgaagcgc tggcattgac 3180
cctgagtgat ttttctctgg tcccgccgca tccataccgc cagttgttta ccctcacaac 3240
gttccagtaa ccgggcatgt tcatcatcag taacccgtat cgtgagcatc ctctctcgtt 3300
tcatcggtat cattaccccc atgaacagaa atccccctta cacggaggca tcagtgacca 3360
aacaggaaaa aaccgccctt aacatggccc gctttatcag aagccagaca ttaacgcttc 3420
tggagaaact caacgagctg gacgcggatg aacaggcaga catctgtgaa tcgcttcacg 3480
accacgctga tgagctttac cgcagctgcc tcgcgcgttt cggtgatgac ggtgaaaacc 3540
tctgacacat gcagctcccg gagacggtca cagcttgtct gtaagcggat gccgggagca 3600
gacaagcccg tcagggcgcg tcagcgggtg ttggcgggtg tcggggcgca gccatgaccc 3660
agtcacgtag cgatagcgga gtgtatactg gcttaactat gcggcatcag agcagattgt 3720
actgagagtg caccatatat gcggtgtgaa ataccgcaca gatgcgtaag gagaaaatac 3780
cgcatcaggc gctcttccgc ttcctcgctc actgactcgc tgcgctcggt cgttcggctg 3840
cggcgagcgg tatcagctca ctcaaaggcg gtaatacggt tatccacaga atcaggggat 3900
aacgcaggaa agaacatgtg agcaaaaggc cagcaaaagg ccaggaaccg taaaaaggcc 3960
gcgttgctgg cgtttttcca taggctccgc ccccctgacg agcatcacaa aaatcgacgc 4020
tcaagtcaga ggtggcgaaa cccgacagga ctataaagat accaggcgtt tccccctgga 4080
agctccctcg tgcgctctcc tgttccgacc ctgccgctta ccggatacct gtccgccttt 4140
ctcccttcgg gaagcgtggc gctttctcat agctcacgct gtaggtatct cagttcggtg 4200
taggtcgttc gctccaagct gggctgtgtg cacgaacccc ccgttcagcc cgaccgctgc 4260
gccttatccg gtaactatcg tcttgagtcc aacccggtaa gacacgactt atcgccactg 4320
gcagcagcca ctggtaacag gattagcaga gcgaggtatg taggcggtgc tacagagttc 4380
ttgaagtggt ggcctaacta cggctacact agaaggacag tatttggtat ctgcgctctg 4440
ctgaagccag ttaccttcgg aaaaagagtt ggtagctctt gatccggcaa acaaaccacc 4500

```
gctggtagcg gtggtttttt tgtttgcaag cagcagatta cgcgcagaaa aaaaggatct   4560

caagaagatc ctttgatctt ttctacgggg tctgacgctc agtggaacga aaactcacgt   4620

taagggattt tggtcatgag attatcaaaa aggatcttca cctagatcct tttaaattaa   4680

aaatgaagtt ttaaatcaat ctaaagtata tatgagtaaa cttggtctga cagttaccaa   4740

tgcttaatca gtgaggcacc tatctcagcg atctgtctat ttcgttcatc catagttgcc   4800

tgactccccg tcgtgtagat aactacgata cgggagggct taccatctgg ccccagtgct   4860

gcaatgatac cgcgagaccc acgctcaccg gctccagatt tatcagcaat aaaccagcca   4920

gccggaaggg ccgagcgcag aagtggtcct gcaactttat ccgcctccat ccagtctatt   4980

aattgttgcc gggaagctag agtaagtagt tcgccagtta atagtttgcg caacgttgtt   5040

gccattgctg caggcatcgt ggtgtcacgc tcgtcgtttg gtatggcttc attcagctcc   5100

ggttcccaac gatcaaggcg agttacatga tcccccatgt tgtgcaaaaa agcggttagc   5160

tccttcggtc ctccgatcgt tgtcagaagt aagttggccg cagtgttatc actcatggtt   5220

atggcagcac tgcataattc tcttactgtc atgccatccg taagatgctt ttctgtgact   5280

ggtgagtact caaccaagtc attctgagaa tagtgtatgc ggcgaccgag ttgctcttgc   5340

ccggcgtcaa tacgggataa taccgcgcca catagcagaa ctttaaaagt gctcatcatt   5400

ggaaaacgtt cttcggggcg aaaactctca aggatcttac cgctgttgag atccagttcg   5460

atgtaaccca ctcgtgcacc caactgatct tcagcatctt ttactttcac cagcgtttct   5520

gggtgagcaa aaacaggaag gcaaaatgcc gcaaaaaagg gaataagggc gacacggaaa   5580

tgttgaatac tcatactctt cctttttcaa tattattgaa gcatttatca gggttattgt   5640

ctcatgagcg gatacatatt tgaatgtatt tagaaaaata aacaaatagg ggttccgcgc   5700

acatttcccc gaaaagtgcc acctgaaatt gtaaacgtta atattttgtt aaaattcgcg   5760

ttaaattttt gttaaatcag ctcatttttt aaccaatagg ccgaaatcgg caaaatccct   5820

tataaatcaa aagaatagac cgagataggg ttgagtgttg ttccagtttg gaacaagagt   5880

ccactattaa agaacgtgga ctccaacgtc aaagggcgaa aaaccgtcta tcagggcgat   5940

ggcccactac gtgaaccatc accctaatca agttttttgg ggtcgaggtg ccgtaaagca   6000

ctaaatcgga accctaaagg gagcccccga tttagagctt gacggggaaa gccggcgaac   6060

gtggcgagaa aggaagggaa gaaagcgaaa ggagcgggcg ctagggcgct ggcaagtgta   6120

gcggtcacgc tgcgcgtaac caccacaccc gccgcgctta atgcgccgct acagggcgcg   6180

tcccattcgc ca                                                       6192
```

<210> SEQ ID NO 67
<211> LENGTH: 6054
<212> TYPE: DNA
<213> ORGANISM: Artificial Sequence
<220> FEATURE:
<223> OTHER INFORMATION: Made in lab - NYESO1(1G4-113)-TCRa-GCN4-Cterm soluble T cell receptor polynucleotide

<400> SEQUENCE: 67

```
atccggatat agttcctcct ttcagcaaaa aacccctcaa gacccgttta gaggccccaa     60

ggggttatgc tagttattgc tcagcggtgg cagcagccaa ctcagcttcc tttcgggctt    120

tgttagcagc cggatctcag tggtggtggt ggtggtgctc gagttacagt tttttcaggc    180

gcgcaacttc attttccagg tggtagttgg aaccgccacc gccagagctt tccgggctcg    240

ggaaaaacgt atcttccggg ataatactat tgttgaatgc gttggcgcac gcaaagtcag    300
```

-continued

```
atttattgct ccaagcaact gccgagtttg atttgaaatc catagagcgc atgtccagaa    360
cacatttatc ggtaatatac acgtcggaat ctttggattg actgacattc gtctgactgt    420
cgaaatcggt aaacaggcac acgcttttgt ccgatgattt gctatcacgc agttggtaca    480
ccgccgggtc cgggttctgg atatacggat ggacaatcag gctggtaccg cggccaaacg    540
tcgggatata ggtaccatcc agcagcggac gcaccgcaca caggtacgta gcggagtcac    600
ccggctgact tgctgcaata tacagggtgg aactaccaga gcttttatcc agcgatgcat    660
tcaggcggcc tgaggtttgt tcacgctgcc acggcgtgat cagcagcagg ctggtcagac    720
ctttgcccgg atcttgacga aaccactgca ggttgtaaat ggcgctatcc gtaaaggagc    780
aattcagcac cagattttca ccttccggga ccgacagagc agccgggatt tgggtaactt    840
cttgtttcat atgtatatct ccttcttaaa gttaaacaaa attatttcta gaggggaatt    900
gttatccgct cacaattccc ctatagtgag tcgtattaat ttcgcgggat cgagatctcg    960
atcctctacg ccggacgcat cgtggccggc atcaccggcg ccacaggtgc ggttgctggc   1020
gcctatatcg ccgacatcac cgatggggaa gatcgggctc gccacttcgg gctcatgagc   1080
gcttgtttcg gcgtgggtat ggtggcaggc cccgtggccg ggggactgtt gggcgccatc   1140
tccttgcatg caccattcct tgcggcggcg gtgctcaacg gcctcaacct actactgggc   1200
tgcttcctaa tgcaggagtc gcataaggga gagcgtcgag atcccggaca ccatcgaatg   1260
gcgcaaaacc tttcgcggta tggcatgata gcgcccggaa gagagtcaat tcagggtggt   1320
gaatgtgaaa ccagtaacgt tatacgatgt cgcagagtat gccggtgtct cttatcagac   1380
cgtttcccgc gtggtgaacc aggccagcca cgtttctgcg aaaacgcggg aaaaagtgga   1440
agcggcgatg gcggagctga attacattcc caaccgcgtg gcacaacaac tggcgggcaa   1500
acagtcgttg ctgattggcg ttgccacctc cagtctggcc ctgcacgcgc cgtcgcaaat   1560
tgtcgcggcg attaaatctc gcgccgatca actgggtgcc agcgtggtgg tgtcgatggt   1620
agaacgaagc ggcgtcgaag cctgtaaagc ggcggtgcac aatcttctcg cgcaacgcgt   1680
cagtgggctg atcattaact atccgctgga tgaccaggat gccattgctg tggaagctgc   1740
ctgcactaat gttccggcgt tatttcttga tgtctctgac cagacaccca tcaacagtat   1800
tattttctcc catgaagacg gtacgcgact gggcgtggag catctggtcg cattgggtca   1860
ccagcaaatc gcgctgttag cgggcccatt aagttctgtc tcggcgcgtc tgcgtctggc   1920
tggctggcat aaatatctca ctcgcaatca aattcagccg atagcggaac gggaaggcga   1980
ctggagtgcc atgtccggtt ttcaacaaac catgcaaatg ctgaatgagg gcatcgttcc   2040
cactgcgatg ctggttgcca acgatcagat ggcgctgggc gcaatgcgcg ccattaccga   2100
gtccgggctg cgcgttggtg cggatatctc ggtagtggga tacgacgata ccgaagacag   2160
ctcatgttat atcccgccgt taaccaccat caaacaggat tttcgcctgc tggggcaaac   2220
cagcgtggac cgcttgctgc aactctctca gggccaggcg gtgaagggca atcagctgtt   2280
gcccgtctca ctggtgaaaa gaaaaaccac cctggcgccc aatacgcaaa ccgcctctcc   2340
ccgcgcgttg gccgattcat taatgcagct ggcacgacag gtttcccgac tggaaagcgg   2400
gcagtgagcg caacgcaatt aatgtaagtt agctcactca ttaggcaccg ggatctcgac   2460
cgatgccctt gagagccttc aacccagtca gctccttccg gtgggcgcgg ggcatgacta   2520
tcgtcgccgc acttatgact gtcttcttta tcatgcaact cgtaggacag gtgccggcag   2580
cgctctgggt cattttcggc gaggaccgct ttcgctggag cgcgacgatg atcggcctgt   2640
```

-continued

```
cgcttgcggt attcggaatc ttgcacgccc tcgctcaagc cttcgtcact ggtcccgcca   2700

ccaaacgttt cggcgagaag caggccatta tcgccggcat ggcggcccca cgggtgcgca   2760

tgatcgtgct cctgtcgttg aggacccggc taggctggcg gggttgcctt actggttagc   2820

agaatgaatc accgatacgc gagcgaacgt gaagcgactg ctgctgcaaa acgtctgcga   2880

cctgagcaac aacatgaatg gtcttcggtt tccgtgtttc gtaaagtctg gaaacgcgga   2940

agtcagcgcc ctgcaccatt atgttccgga tctgcatcgc aggatgctgc tggctaccct   3000

gtggaacacc tacatctgta ttaacgaagc gctggcattg accctgagtg atttttctct   3060

ggtcccgccg catccatacc gccagttgtt taccctcaca acgttccagt aaccgggcat   3120

gttcatcatc agtaacccgt atcgtgagca tcctctctcg tttcatcggt atcattaccc   3180

ccatgaacag aaatccccct tacacggagg catcagtgac caaacaggaa aaaaccgccc   3240

ttaacatggc ccgctttatc agaagccaga cattaacgct tctggagaaa ctcaacgagc   3300

tggacgcgga tgaacaggca gacatctgtg aatcgcttca cgaccacgct gatgagcttt   3360

accgcagctg cctcgcgcgt ttcggtgatg acggtgaaaa cctctgacac atgcagctcc   3420

cggagacggt cacagcttgt ctgtaagcgg atgccgggag cagacaagcc cgtcagggcg   3480

cgtcagcggg tgttggcggg tgtcggggcg cagccatgac ccagtcacgt agcgatagcg   3540

gagtgtatac tggcttaact atgcggcatc agagcagatt gtactgagag tgcaccatat   3600

atgcggtgtg aaataccgca cagatgcgta aggagaaaat accgcatcag gcgctcttcc   3660

gcttcctcgc tcactgactc gctgcgctcg gtcgttcggc tgcggcgagc ggtatcagct   3720

cactcaaagg cggtaatacg gttatccaca gaatcagggg ataacgcagg aaagaacatg   3780

tgagcaaaag gccagcaaaa ggccaggaac cgtaaaaagg ccgcgttgct ggcgtttttc   3840

cataggctcc gcccccctga cgagcatcac aaaaatcgac gctcaagtca gaggtggcga   3900

aacccgacag gactataaag ataccaggcg tttccccctg gaagctccct cgtgcgctct   3960

cctgttccga ccctgccgct taccggatac ctgtccgcct ttctcccttc gggaagcgtg   4020

gcgctttctc atagctcacg ctgtaggtat ctcagttcgg tgtaggtcgt tcgctccaag   4080

ctgggctgtg tgcacgaacc ccccgttcag cccgaccgct gcgccttatc cggtaactat   4140

cgtcttgagt ccaacccggt aagacacgac ttatcgccac tggcagcagc cactggtaac   4200

aggattagca gagcgaggta tgtaggcggt gctacagagt tcttgaagtg gtggcctaac   4260

tacggctaca ctagaaggac agtatttggt atctgcgctc tgctgaagcc agttaccttc   4320

ggaaaaagag ttggtagctc ttgatccggc aaacaaacca ccgctggtag cggtggtttt   4380

tttgtttgca agcagcagat tacgcgcaga aaaaaaggat ctcaagaaga tcctttgatc   4440

ttttctacgg ggtctgacgc tcagtggaac gaaaactcac gttaagggat tttggtcatg   4500

agattatcaa aaaggatctt cacctagatc cttttaaatt aaaaatgaag ttttaaatca   4560

atctaaagta tatatgagta aacttggtct gacagttacc aatgcttaat cagtgaggca   4620

cctatctcag cgatctgtct atttcgttca tccatagttg cctgactccc cgtcgtgtag   4680

ataactacga tacgggaggg cttaccatct ggccccagtg ctgcaatgat accgcgagac   4740

ccacgctcac cggctccaga tttatcagca ataaaccagc cagccggaag ggccgagcgc   4800

agaagtggtc ctgcaacttt atccgcctcc atccagtcta ttaattgttg ccgggaagct   4860

agagtaagta gttcgccagt taatagtttg cgcaacgttg ttgccattgc tgcaggcatc   4920

gtggtgtcac gctcgtcgtt tggtatggct tcattcagct ccggttccca acgatcaagg   4980

cgagttacat gatcccccat gttgtgcaaa aaagcggtta gctccttcgg tcctccgatc   5040
```

gttgtcagaa gtaagttggc cgcagtgtta tcactcatgg ttatggcagc actgcataat 5100
tctcttactg tcatgccatc cgtaagatgc ttttctgtga ctggtgagta ctcaaccaag 5160
tcattctgag aatagtgtat gcggcgaccg agttgctctt gcccggcgtc aatacgggat 5220
aataccgcgc cacatagcag aactttaaaa gtgctcatca ttggaaaacg ttcttcgggg 5280
cgaaaactct caaggatctt accgctgttg agatccagtt cgatgtaacc cactcgtgca 5340
cccaactgat cttcagcatc ttttactttc accagcgttt ctgggtgagc aaaaacagga 5400
aggcaaaatg ccgcaaaaaa gggaataagg gcgacacgga aatgttgaat actcatactc 5460
ttcctttttc aatattattg aagcatttat cagggttatt gtctcatgag cggatacata 5520
tttgaatgta tttagaaaaa taaacaaata ggggttccgc gcacatttcc ccgaaaagtg 5580
ccacctgaaa ttgtaaacgt taatattttg ttaaaattcg cgttaaattt ttgttaaatc 5640
agctcatttt ttaaccaata ggccgaaatc ggcaaaatcc cttataaatc aaaagaatag 5700
accgagatag ggttgagtgt tgttccagtt tggaacaaga gtccactatt aaagaacgtg 5760
gactccaacg tcaaagggcg aaaaaccgtc tatcagggcg atggcccact acgtgaacca 5820
tcaccctaat caagtttttt ggggtcgagg tgccgtaaag cactaaatcg gaaccctaaa 5880
gggagccccc gatttagagc ttgacgggga aagccggcga acgtggcgag aaaggaaggg 5940
aagaaagcga aaggagcggg cgctagggcg ctggcaagtg tagcggtcac gctgcgcgta 6000
accaccacac ccgccgcgct taatgcgccg ctacagggcg cgtcccattc gcca 6054

<210> SEQ ID NO 68
<211> LENGTH: 45
<212> TYPE: PRT
<213> ORGANISM: Artificial Sequence
<220> FEATURE:
<223> OTHER INFORMATION: Made in lab - CD8 hinge peptide sequence

<400> SEQUENCE: 68

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp
35 40 45

<210> SEQ ID NO 69

<400> SEQUENCE: 69

000

<210> SEQ ID NO 70
<211> LENGTH: 12
<212> TYPE: PRT
<213> ORGANISM: Artificial Sequence
<220> FEATURE:
<223> OTHER INFORMATION: Made in lab - IgG4 hinge peptide sequence

<400> SEQUENCE: 70

Glu Ser Lys Tyr Gly Pro Pro Cys Pro Ser Cys Pro
1 5 10

<210> SEQ ID NO 71
<211> LENGTH: 12
<212> TYPE: PRT
<213> ORGANISM: Artificial Sequence

```
<220> FEATURE:
<223> OTHER INFORMATION: Made in lab - IgG4 m hinge peptide sequence

<400> SEQUENCE: 71

Glu Ser Lys Tyr Gly Pro Pro Cys Pro Pro Cys Pro
1               5                   10


<210> SEQ ID NO 72
<211> LENGTH: 1329
<212> TYPE: DNA
<213> ORGANISM: Artificial Sequence
<220> FEATURE:
<223> OTHER INFORMATION: Made in lab - LV-EF1a-GCN4(52SR4)-BBZ_no hinge
      chimeric antigen receptor polynucleotide

<400> SEQUENCE: 72

atggccttac cagtgaccgc cttgctcctg ccgctggcct tgctgctcca cgccgccagg     60

ccggacgccg ttgtgaccca ggaatccgct ctgacctctt ctccaggcga aaccgtgact    120

ctgacttgcc gtagtagcac cggggctgtg accacatcta actatgccag ttgggtccag    180

gaaaaaccgg atcacctgtt tactggcctg attggcggca ccaacaatcg cgcaccgggt    240

gtgcccgctc gtttcagcgg ttccctgatt ggggacaagg cagcactgac tatcaccggc    300

gcccagaccg aagatgaggc gatctatttt tgcgtcctgt ggtacagcga ccattgggtg    360

ttcgggggag gcaccaaact gacagtgctg ggcggaggag gaggttcagg aggaggaggt    420

agcgggggag gcggttccgg gggaggcggt tctgatgtgc agctgcaaga atccgggcca    480

ggactggttg cgccttctca gagtctgtca attacatgta ctgttagtgg ctttctgctg    540

accgactatg gtgtgaactg ggttcgtcag agcccaggca agggtctgga gtggctggga    600

gtgatttggg gggatggaat cacagactac aatagcgcac tgaaatctcg gctgagtgtt    660

accaaagata acagcaagtc ccaggtcttc ctgaagatga acagcctgca aagcggcgac    720

tccgctcgct attactgcgt taccggactg tttgattatt gggggcaggg gacaactctg    780

actgtttcct ccgatatcta catctgggcg ccccttggcg ggacttgtgg ggtccttctc    840

ctgtcactgg ttatcaccct ttactgcaaa cggggcagaa agaaactcct gtatatattc    900

aaacaaccat ttatgagacc agtacaaact actcaagagg aagatggctg tagctgccga    960

tttccagaag aagaagaagg aggatgtgaa ctgagagtga agttcagcag gagcgcagac   1020

gcccccgcgt acaagcaggg ccagaaccag ctctataacg agctcaatct aggacgaaga   1080

gaggagtacg atgttttgga caagagacgt ggccgggacc ctgagatggg gggaaagccg   1140

agaaggaaga accctcagga aggcctgtac aatgaactgc agaaagataa gatggcggag   1200

gcctacagtg agattgggat gaaaggcgag cgccggaggg gcaaggggca cgatggcctt   1260

taccagggtc tcagtacagc caccaaggac acctacgacg cccttcacat gcaggccctg   1320

ccccctcgc                                                           1329


<210> SEQ ID NO 73
<211> LENGTH: 1365
<212> TYPE: DNA
<213> ORGANISM: Artificial Sequence
<220> FEATURE:
<223> OTHER INFORMATION: Made in lab - LV-EF1a-GCN4(52SR4)-BBZ_IgG4(Pro)
      (CAR containing hinge) chimeric antigen receptor polynucleotide

<400> SEQUENCE: 73

atggccttac cagtgaccgc cttgctcctg ccgctggcct tgctgctcca cgccgccagg     60

ccggacgccg ttgtgaccca ggaatccgct ctgacctctt ctccaggcga aaccgtgact    120
```

```
ctgacttgcc gtagtagcac cggggctgtg accacatcta actatgccag ttgggtccag    180

gaaaaaccgg atcacctgtt tactggcctg attggcggca ccaacaatcg cgcaccgggt    240

gtgcccgctc gtttcagcgg ttccctgatt ggggacaagg cagcactgac tatcaccggc    300

gcccagaccg aagatgaggc gatctatttt tgcgtcctgt ggtacagcga ccattgggtg    360

ttcgggggag gcaccaaact gacagtgctg ggcggaggag gaggttcagg aggaggaggt    420

agcgggggag gcggttccgg gggaggcggt tctgatgtgc agctgcaaga atccgggcca    480

ggactggttg cgccttctca gagtctgtca attacatgta ctgttagtgg ctttctgctg    540

accgactatg gtgtgaactg ggttcgtcag agcccaggca agggtctgga gtggctggga    600

gtgatttggg gggatggaat cacagactac aatagcgcac tgaaatctcg gctgagtgtt    660

accaaagata acagcaagtc ccaggtcttc ctgaagatga acagcctgca aagcggcgac    720

tccgctcgct attactgcgt taccggactg tttgattatt gggggcaggg gacaactctg    780

actgtttcct ccgaaagcaa gtatggccca ccttgtccaa gctgtcccga tatctacatc    840

tgggcgccct tggccgggac ttgtggggtc cttctcctgt cactggttat caccctttac    900

tgcaaacggg gcagaaagaa actcctgtat atattcaaac aaccatttat gagaccagta    960

caaactactc aagaggaaga tggctgtagc tgccgatttc cagaagaaga agaaggagga   1020

tgtgaactga gagtgaagtt cagcaggagc gcagacgccc ccgcgtacaa gcagggccag   1080

aaccagctct ataacgagct caatctagga cgaagagagg agtacgatgt tttggacaag   1140

agacgtggcc gggaccctga gatgggggga aagccgagaa ggaagaaccc tcaggaaggc   1200

ctgtacaatg aactgcagaa agataagatg gcggaggcct acagtgagat tgggatgaaa   1260

ggcgagcgcc ggaggggcaa ggggcacgat ggcctttacc agggtctcag tacagccacc   1320

aaggacacct acgacgccct tcacatgcag gccctgcccc ctcgc                   1365
```

<210> SEQ ID NO 74
<211> LENGTH: 1365
<212> TYPE: DNA
<213> ORGANISM: Artificial Sequence
<220> FEATURE:
<223> OTHER INFORMATION: Made in lab - LV-EF1a-GCN4(52SR4)-BBZ_IgG4(Ser) (CAR containing hinge) chimeric antigen receptor polynucleotide

<400> SEQUENCE: 74

```
atggccttac cagtgaccgc cttgctcctg ccgctggcct tgctgctcca cgccgccagg     60

ccggacgccg ttgtgaccca ggaatccgct ctgacctctt ctccaggcga aaccgtgact    120

ctgacttgcc gtagtagcac cggggctgtg accacatcta actatgccag ttgggtccag    180

gaaaaaccgg atcacctgtt tactggcctg attggcggca ccaacaatcg cgcaccgggt    240

gtgcccgctc gtttcagcgg ttccctgatt ggggacaagg cagcactgac tatcaccggc    300

gcccagaccg aagatgaggc gatctatttt tgcgtcctgt ggtacagcga ccattgggtg    360

ttcgggggag gcaccaaact gacagtgctg ggcggaggag gaggttcagg aggaggaggt    420

agcgggggag gcggttccgg gggaggcggt tctgatgtgc agctgcaaga atccgggcca    480

ggactggttg cgccttctca gagtctgtca attacatgta ctgttagtgg ctttctgctg    540

accgactatg gtgtgaactg ggttcgtcag agcccaggca agggtctgga gtggctggga    600

gtgatttggg gggatggaat cacagactac aatagcgcac tgaaatctcg gctgagtgtt    660

accaaagata acagcaagtc ccaggtcttc ctgaagatga acagcctgca aagcggcgac    720

tccgctcgct attactgcgt taccggactg tttgattatt gggggcaggg gacaactctg    780
```

actgtttcct ccgaaagcaa gtatggccca ccttgtccac cttgtcccga tatctacatc 840
tgggcgccct tggccgggac ttgtggggtc cttctcctgt cactggttat caccctttac 900
tgcaaacggg gcagaaagaa actcctgtat atattcaaac aaccatttat gagaccagta 960
caaactactc aagaggaaga tggctgtagc tgccgatttc cagaagaaga agaaggagga 1020
tgtgaactga gagtgaagtt cagcaggagc gcagacgccc ccgcgtacaa gcagggccag 1080
aaccagctct ataacgagct caatctagga cgaagagagg agtacgatgt tttggacaag 1140
agacgtggcc gggaccctga gatgggggga aagccgagaa ggaagaaccc tcaggaaggc 1200
ctgtacaatg aactgcagaa agataagatg gcggaggcct acagtgagat tgggatgaaa 1260
ggcgagcgcc ggaggggcaa ggggcacgat ggcctttacc agggtctcag tacagccacc 1320
aaggacacct acgacgccct tcacatgcag gccctgcccc ctcgc 1365

<210> SEQ ID NO 75
<211> LENGTH: 14
<212> TYPE: PRT
<213> ORGANISM: Artificial Sequence
<220> FEATURE:
<223> OTHER INFORMATION: Synthesized GCN4 epitope

<400> SEQUENCE: 75

Ala Tyr His Leu Glu Asn Glu Val Ala Arg Leu Lys Lys Leu
1 5 10

<210> SEQ ID NO 76
<211> LENGTH: 14
<212> TYPE: PRT
<213> ORGANISM: Artificial Sequence
<220> FEATURE:
<223> OTHER INFORMATION: Synthesized GCN4 epitope

<400> SEQUENCE: 76

Ala Ala His Leu Glu Asn Glu Val Ala Arg Leu Lys Lys Leu
1 5 10

<210> SEQ ID NO 77
<211> LENGTH: 14
<212> TYPE: PRT
<213> ORGANISM: Artificial Sequence
<220> FEATURE:
<223> OTHER INFORMATION: Synthesized GCN4 epitope

<400> SEQUENCE: 77

Ala Ala Ala Leu Glu Asn Glu Val Ala Arg Leu Lys Lys Leu
1 5 10

<210> SEQ ID NO 78
<211> LENGTH: 14
<212> TYPE: PRT
<213> ORGANISM: Artificial Sequence
<220> FEATURE:
<223> OTHER INFORMATION: Synthesized GCN4 epitope

<400> SEQUENCE: 78

Ala Ala Ala Ala Glu Asn Glu Val Ala Arg Leu Lys Lys Leu
1 5 10

<210> SEQ ID NO 79
<211> LENGTH: 14
<212> TYPE: PRT
<213> ORGANISM: Artificial Sequence
<220> FEATURE:

<223> OTHER INFORMATION: Synthesized GCN4 epitope

<400> SEQUENCE: 79

Asn Tyr His Leu Glu Asn Glu Val Ala Arg Leu Lys Lys Ala
1 5 10

<210> SEQ ID NO 80
<211> LENGTH: 14
<212> TYPE: PRT
<213> ORGANISM: Artificial Sequence
<220> FEATURE:
<223> OTHER INFORMATION: Synthesized GCN4 epitope

<400> SEQUENCE: 80

Asn Tyr His Leu Glu Asn Glu Val Ala Arg Leu Lys Ala Ala
1 5 10

<210> SEQ ID NO 81
<211> LENGTH: 14
<212> TYPE: PRT
<213> ORGANISM: Artificial Sequence
<220> FEATURE:
<223> OTHER INFORMATION: Synthesized GCN4 epitope

<400> SEQUENCE: 81

Asn Tyr His Leu Glu Asn Glu Val Ala Arg Leu Ala Ala Ala
1 5 10

<210> SEQ ID NO 82
<211> LENGTH: 14
<212> TYPE: PRT
<213> ORGANISM: Artificial Sequence
<220> FEATURE:
<223> OTHER INFORMATION: Synthesized GCN4 epitope

<400> SEQUENCE: 82

Asn Tyr His Leu Glu Asn Glu Val Ala Arg Ala Ala Ala Ala
1 5 10

<210> SEQ ID NO 83
<211> LENGTH: 18
<212> TYPE: PRT
<213> ORGANISM: Artificial Sequence
<220> FEATURE:
<223> OTHER INFORMATION: Synthesized GCN4 epitope

<400> SEQUENCE: 83

Leu Leu Pro Lys Asn Tyr His Leu Glu Asn Glu Val Ala Arg Leu Lys
1 5 10 15

Lys Leu

<210> SEQ ID NO 84
<211> LENGTH: 18
<212> TYPE: PRT
<213> ORGANISM: Artificial Sequence
<220> FEATURE:
<223> OTHER INFORMATION: Synthesized GCN4 epitope

<400> SEQUENCE: 84

Asp Leu Pro Gln Lys Tyr His Leu Glu Asn Glu Val Ala Arg Leu Lys
1 5 10 15

Lys Leu

<210> SEQ ID NO 85
<211> LENGTH: 714

```
<212> TYPE: DNA
<213> ORGANISM: Artificial Sequence
<220> FEATURE:
<223> OTHER INFORMATION: Made in lab - CD19(FMC63)-LC-NT2 switch
      antibody polynucleotide

<400> SEQUENCE: 85

aattatcatc ttgaaaatga ggtcgctcgt ctcaagaaac tcggcggagg cgggagcggc     60

ggaggcggga gcgacatcca gatgacacag actacatcct ccctgtctgc ctctctggga    120

gacagagtca ccatcagttg cagggcaagt caggacatta gtaaatattt aaattggtat    180

cagcagaaac cagatggaac tgttaaactc ctgatctacc atacatcaag attacactca    240

ggagtcccat caaggttcag tggcagtggg tctggaacag attattctct caccattagc    300

aacctggagc aagaagatat tgccacttac ttttgccaac agggtaatac gcttccgtac    360

acgttcggag gggggaccaa gcttgagatc aaacgaactg tggctgcacc atctgtcttc    420

atcttcccgc catctgatga gcagttgaaa tctggaactg cctctgtcgt gtgcctgctg    480

aataacttct atcccagaga ggccaaagta cagtggaagg tggataacgc cctccaatcg    540

ggtaactccc aggagagtgt cacagagcag gacagcaagg acagcaccta cagcctcagc    600

agcaccctga cgctgagcaa agcagactac gagaaacaca aagtctacgc ctgcgaagtc    660

acccatcagg gcctgtcctc gcccgtcaca aagagcttca acaggggaga gtgt          714


<210> SEQ ID NO 86
<211> LENGTH: 726
<212> TYPE: DNA
<213> ORGANISM: Artificial Sequence
<220> FEATURE:
<223> OTHER INFORMATION: Made in lab - CD19(FMC63)-HC-NT1 switch
      antibody polynucleotide

<400> SEQUENCE: 86

aattatcatc ttgaaaatga ggtcgctcgt ctcaagaaac tcggcggagg cgggagcgag     60

gtgaaactgc aggagtcagg acctggcctg gtggcgccct cacagagcct gtccgtcaca    120

tgcactgtct caggggtctc attacccgac tatggtgtaa gctggattcg ccagcctcca    180

cgaaagggtc tggagtggct gggagtaata tggggtagtg aaaccacata ctataattca    240

gctctcaaat ccagactgac catcatcaag gacaactcca agagccaagt tttcttaaaa    300

atgaacagtc tgcaaactga tgacacagcc atttactact gtgccaaaca ttattactac    360

ggtggtagct atgctatgga ctactggggc caaggaacct cagtcaccgt ctcctcagcc    420

tccaccaagg gcccatcggt cttccccctg gcaccctcct ccaagagcac ctctgggggc    480

acagcggccc tgggctgcct ggtcaaggac tacttccccg aaccggtgac ggtgtcgtgg    540

aactcaggcg ccctgaccag cggcgtgcac accttcccgg ctgtcctaca gtcctcagga    600

ctctactccc tcagcagcgt ggtgactgtg ccctctagca gcttgggcac ccagacctac    660

atctgcaacg tgaatcacaa gcccagcaac accaaggtgg acaagaaagt tgagcccaaa    720

tcttgt                                                               726


<210> SEQ ID NO 87
<211> LENGTH: 741
<212> TYPE: DNA
<213> ORGANISM: Artificial Sequence
<220> FEATURE:
<223> OTHER INFORMATION: Made in lab - CD19(FMC63)-HC-NT2 switch
      antibody polynucleotide

<400> SEQUENCE: 87
```

```
aattatcatc ttgaaaatga ggtcgctcgt ctcaagaaac tcggcggagg cgggagcggc     60
ggaggcggga gcgaggtgaa actgcaggag tcaggacctg gcctggtggc gccctcacag    120
agcctgtccg tcacatgcac tgtctcaggg gtctcattac ccgactatgg tgtaagctgg    180
attcgccagc ctccacgaaa gggtctggag tggctgggag taatatgggg tagtgaaacc    240
acatactata attcagctct caaatccaga ctgaccatca tcaaggacaa ctccaagagc    300
caagttttct taaaaatgaa cagtctgcaa actgatgaca cagccattta ctactgtgcc    360
aaacattatt actacggtgg tagctatgct atggactact ggggccaagg aacctcagtc    420
accgtctcct cagcctccac caagggccca tcggtcttcc ccctggcacc ctcctccaag    480
agcacctctg ggggcacagc ggccctgggc tgcctggtca aggactactt ccccgaaccg    540
gtgacggtgt cgtggaactc aggcgccctg accagcggcg tgcacacctt cccggctgtc    600
ctacagtcct caggactcta ctccctcagc agcgtggtga ctgtgccctc tagcagcttg    660
ggcacccaga cctacatctg caacgtgaat cacaagccca gcaacaccaa ggtggacaag    720
aaagttgagc ccaaatcttg t                                              741
```

<210> SEQ ID NO 88
<211> LENGTH: 753
<212> TYPE: DNA
<213> ORGANISM: Artificial Sequence
<220> FEATURE:
<223> OTHER INFORMATION: Made in lab - CD19(FMC63)-HC-NT3 switch antibody polynucleotide

<400> SEQUENCE: 88

```
aattatcatc ttgaaaatga ggtcgctcgt ctcaagaaac tcctggttgg cgaggccgca     60
gctaaggaag ccgcagctaa agccgaggtg aaactgcagg agtcaggacc tggcctggtg    120
gcgccctcac agagcctgtc cgtcacatgc actgtctcag gggtctcatt acccgactat    180
ggtgtaagct ggattcgcca gcctccacga aagggtctgg agtggctggg agtaatatgg    240
ggtagtgaaa ccacatacta taattcagct ctcaaatcca gactgaccat catcaaggac    300
aactccaaga gccaagtttt cttaaaaatg aacagtctgc aaactgatga cacagccatt    360
tactactgtg ccaaacatta ttactacggt ggtagctatg ctatggacta ctggggccaa    420
ggaacctcag tcaccgtctc ctcagcctcc accaagggcc catcggtctt ccccctggca    480
ccctcctcca agagcacctc tgggggcaca gcggccctgg gctgcctggt caaggactac    540
ttccccgaac cggtgacggt gtcgtggaac tcaggcgccc tgaccagcgg cgtgcacacc    600
ttcccggctg tcctacagtc ctcaggactc tactccctca gcagcgtggt gactgtgccc    660
tctagcagct tgggcaccca gacctacatc tgcaacgtga atcacaagcc cagcaacacc    720
aaggtggaca agaaagttga gcccaaatct tgt                                 753
```

<210> SEQ ID NO 89
<211> LENGTH: 747
<212> TYPE: DNA
<213> ORGANISM: Artificial Sequence
<220> FEATURE:
<223> OTHER INFORMATION: Made in lab - CD19(FMC63)-HC-NT4 switch antibody polynucleotide

<400> SEQUENCE: 89

```
aattatcatc ttgaaaatga ggtcgctcgt ctcaagaaac tcgccgaggc cgccgcaaag     60
gaagctgctg ccaaggctga ggtgaaactg caggagtcag gacctggcct ggtggcgccc    120
```

```
tcacagagcc tgtccgtcac atgcactgtc tcaggggtct cattacccga ctatggtgta    180

agctggattc gccagcctcc acgaaagggt ctggagtggc tgggagtaat atggggtagt    240

gaaaccacat actataattc agctctcaaa tccagactga ccatcatcaa ggacaactcc    300

aagagccaag ttttcttaaa aatgaacagt ctgcaaactg atgacacagc catttactac    360

tgtgccaaac attattacta cggtggtagc tatgctatgg actactgggg ccaaggaacc    420

tcagtcaccg tctcctcagc ctccaccaag ggcccatcgg tcttcccct ggcaccctcc    480

tccaagagca cctctggggg cacagcggcc ctgggctgcc tggtcaagga ctacttcccc    540

gaaccggtga cggtgtcgtg gaactcaggc gccctgacca gcggcgtgca caccttcccg    600

gctgtcctac agtcctcagg actctactcc ctcagcagcg tggtgactgt gccctctagc    660

agcttgggca cccagaccta catctgcaac gtgaatcaca agcccagcaa caccaaggtg    720

gacaagaaag ttgagcccaa atcttgt                                        747
```

<210> SEQ ID NO 90
<211> LENGTH: 735
<212> TYPE: DNA
<213> ORGANISM: Artificial Sequence
<220> FEATURE:
<223> OTHER INFORMATION: Made in lab - CD19(FMC63)-HC2 switch antibody polynucleotide

<400> SEQUENCE: 90

```
gaggtgaaac tgcaggagtc aggacctggc ctggtggcgc cctcacagag cctgtccgtc     60

acatgcactg tctcaggggt ctcattaccc gactatggtg taagctggat tcgccagcct    120

ccacgaaagg gtctggagtg gctgggagta atatggggta gtgaaaccac atactataat    180

tcagctctca aatccagact gaccatcatc aaggacaact ccaagagcca agttttctta    240

aaaatgaaca gtctgcaaac tgatgacaca gccatttact actgtgccaa acattattac    300

tacggtggta gctatgctat ggactactgg ggccaaggaa cctcagtcac cgtctcctca    360

gcctccacca agggcccatc ggtcttcccc ctggcaccct cctccaagag cacctctggg    420

ggcacagcgg ccctgggctg cctggtcaag gactacttcc ccgaaccggt gacggtgtcg    480

tggaactcag gcgccctgac cagcggcgtg cacaccttcc cggctgtcct acagtccggc    540

gggggaggct caaactacca cctggagaat gaagtcgcca gactgaagaa actgggggga    600

ggcgggtcac tctactccct cagcagcgtg gtgactgtgc cctctagcag cttgggcacc    660

cagacctaca tctgcaacgt gaatcacaag cccagcaaca ccaaggtgga caagaaagtt    720

gagcccaaat cttgt                                                     735
```

<210> SEQ ID NO 91
<211> LENGTH: 735
<212> TYPE: DNA
<213> ORGANISM: Artificial Sequence
<220> FEATURE:
<223> OTHER INFORMATION: Made in lab - CD19(FMC63)-S74_1 switch antibody polynucleotide

<400> SEQUENCE: 91

```
gaggtgaaac tgcaggagtc aggacctggc ctggtggcgc cctcacagag cctgtccgtc     60

acatgcactg tctcaggggt ctcattaccc gactatggtg taagctggat tcgccagcct    120

ccacgaaagg gtctggagtg gctgggagta atatggggta gtgaaaccac atactataat    180

tcagctctca aatccagact gaccatcatc aaggacaacg gcggaggcgg gagcaactat    240

cacctggaaa acgaagtggc aaggctgaaa aaactgggcg gggcggaag tagccaagtt    300
```

```
ttcttaaaaa tgaacagtct gcaaactgat gacacagcca tttactactg tgccaaacat    360

tattactacg gtggtagcta tgctatggac tactggggcc aaggaacctc agtcaccgtc    420

tcctcagcct ccaccaaggg cccatcggtc ttccccctgg caccctcctc caagagcacc    480

tctgggggca cagcggccct gggctgcctg gtcaaggact acttccccga accggtgacg    540

gtgtcgtgga actcaggcgc cctgaccagc ggcgtgcaca ccttcccggc tgtcctacag    600

tcctcaggac tctactccct cagcagcgtg gtgactgtgc cctctagcag cttgggcacc    660

cagacctaca tctgcaacgt gaatcacaag cccagcaaca ccaaggtgga caagaaagtt    720

gagcccaaat cttgt                                                     735
```

```
<210> SEQ ID NO 92
<211> LENGTH: 735
<212> TYPE: DNA
<213> ORGANISM: Artificial Sequence
<220> FEATURE:
<223> OTHER INFORMATION: Made in lab - CD19(FMC63)-S74_2 switch antibody
      polynucleotide

<400> SEQUENCE: 92

gaggtgaaac tgcaggagtc aggacctggc ctggtggcgc cctcacagag cctgtccgtc     60

acatgcactg tctcaggggt ctcattaccc gactatggtg taagctggat tcgccagcct    120

ccacgaaagg gtctggagtg gctgggagta atatggggta gtgaaaccac atactataat    180

tcagctctca aatccagact gaccatcatc aaggacaacg gcggaggcgg gagcaactat    240

cacctggaaa acgaagtggc aaggctgaaa aaactgggcg ggggcggaag tagccaagtt    300

ttcttaaaaa tgaacagtct gcaaactgat gacacagcca tttactactg tgccaaacat    360

tattactacg gtggtagcta tgctatggac tactggggcc aaggaacctc agtcaccgtc    420

tcctcagcct ccaccaaggg cccatcggtc ttccccctgg caccctcctc caagagcacc    480

tctgggggca cagcggccct gggctgcctg gtcaaggact acttccccga accggtgacg    540

gtgtcgtgga actcaggcgc cctgaccagc ggcgtgcaca ccttcccggc tgtcctacag    600

tcctcaggac tctactccct cagcagcgtg gtgactgtgc cctctagcag cttgggcacc    660

cagacctaca tctgcaacgt gaatcacaag cccagcaaca ccaaggtgga caagaaagtt    720

gagcccaaat cttgt                                                     735
```

```
<210> SEQ ID NO 93
<211> LENGTH: 732
<212> TYPE: DNA
<213> ORGANISM: Artificial Sequence
<220> FEATURE:
<223> OTHER INFORMATION: Made in lab - CD19(FMC63)-LC-NT4a switch
      antibody polynucleotide

<400> SEQUENCE: 93

aactatcacc tggaaaacga agtggcaagg ctgaaaaaac tggaggccgc cgcaaaggaa     60

gcagccgcca aagaggctgc cgcgaaagcg gacatccaga tgacacagac tacatcctcc    120

ctgtctgcct ctctgggaga cagagtcacc atcagttgca gggcaagtca ggacattagt    180

aaatatttaa attggtatca gcagaaacca gatggaactg ttaaactcct gatctaccat    240

acatcaagat tacactcagg agtcccatca aggttcagtg gcagtgggtc tggaacagat    300

tattctctca ccattagcaa cctggagcaa gaagatattg ccacttactt ttgccaacag    360

ggtaatacgc ttccgtacac gttcggaggg gggaccaagc ttgagatcaa acgaactgtg    420
```

```
gctgcaccat ctgtcttcat cttcccgcca tctgatgagc agttgaaatc tggaactgcc    480

tctgtcgtgt gcctgctgaa taacttctat cccagagagg ccaaagtaca gtggaaggtg    540

gataacgccc tccaatcggg taactcccag gagagtgtca cagagcagga cagcaaggac    600

agcacctaca gcctcagcag caccctgacg ctgagcaaag cagactacga gaaacacaaa    660

gtctacgcct gcgaagtcac ccatcagggc ctgtcctcgc ccgtcacaaa gagcttcaac    720

aggggagagt gt                                                        732


<210> SEQ ID NO 94
<211> LENGTH: 720
<212> TYPE: DNA
<213> ORGANISM: Artificial Sequence
<220> FEATURE:
<223> OTHER INFORMATION: Made in lab - CD19(FMC63)-LC-NT5 switch
      antibody polynucleotide

<400> SEQUENCE: 94

aactatcacc tggaaaacga agtggcaagg ctgaaaaaac tgggttccgc cggttccgca     60

gccggctccg gagaattcga catccagatg acacagacta catcctccct gtctgcctct    120

ctgggagaca gagtcaccat cagttgcagg gcaagtcagg acattagtaa atatttaaat    180

tggtatcagc agaaaccaga tggaactgtt aaactcctga tctaccatac atcaagatta    240

cactcaggag tcccatcaag gttcagtggc agtgggtctg gaacagatta ttctctcacc    300

attagcaacc tggagcaaga agatattgcc acttactttt gccaacaggg taatacgctt    360

ccgtacacgt tcggaggggg gaccaagctt gagatcaaac gaactgtggc tgcaccatct    420

gtcttcatct tcccgccatc tgatgagcag ttgaaatctg gaactgcctc tgtcgtgtgc    480

ctgctgaata acttctatcc cagagaggcc aaagtacagt ggaaggtgga taacgccctc    540

caatcgggta actcccagga gagtgtcaca gagcaggaca gcaaggacag cacctacagc    600

ctcagcagca ccctgacgct gagcaaagca gactacgaga aacacaaagt ctacgcctgc    660

gaagtcaccc atcagggcct gtcctcgccc gtcacaaaga gcttcaacag gggagagtgt    720


<210> SEQ ID NO 95
<211> LENGTH: 759
<212> TYPE: DNA
<213> ORGANISM: Artificial Sequence
<220> FEATURE:
<223> OTHER INFORMATION: Made in lab - CD19(FMC63)-HC-NT4a switch
      antibody polynucleotide

<400> SEQUENCE: 95

aattatcatc ttgaaaatga ggtcgctcgt ctcaagaaac tcgaggccgc cgcaaaggaa     60

gcagccgcca aagaggctgc cgcgaaagcg gaggtgaaac tgcaggagtc aggacctggc    120

ctggtggcgc cctcacagag cctgtccgtc acatgcactg tctcaggggt ctcattaccc    180

gactatggtg taagctggat tcgccagcct ccacgaaagg gtctggagtg gctgggagta    240

atatggggta gtgaaaccac atactataat tcagctctca aatccagact gaccatcatc    300

aaggacaact ccaagagcca agttttctta aaaatgaaca gtctgcaaac tgatgacaca    360

gccatttact actgtgccaa acattattac tacggtggta gctatgctat ggactactgg    420

ggccaaggaa cctcagtcac cgtctcctca gcctccacca agggcccatc ggtcttcccc    480

ctggcaccct cctccaagag cacctctggg ggcacagcgg ccctgggctg cctggtcaag    540

gactacttcc ccgaaccggt gacggtgtcg tggaactcag gcgccctgac cagcggcgtg    600

cacaccttcc cggctgtcct acagtcctca ggactctact ccctcagcag cgtggtgact    660
```

```
gtgccctcta gcagcttggg cacccagacc tacatctgca acgtgaatca caagcccagc    720

aacaccaagg tggacaagaa agttgagccc aaatcttgt                           759


<210> SEQ ID NO 96
<211> LENGTH: 747
<212> TYPE: DNA
<213> ORGANISM: Artificial Sequence
<220> FEATURE:
<223> OTHER INFORMATION: Made in lab - CD19(FMC63)-HC-NT5 switch
      antibody polynucleotide

<400> SEQUENCE: 96

aattatcatc ttgaaaatga ggtcgctcgt ctcaagaaac tcggttccgc cggttccgca     60

gccggctccg gagaattcga ggtgaaactg caggagtcag gacctggcct ggtggcgccc    120

tcacagagcc tgtccgtcac atgcactgtc tcaggggtct cattacccga ctatggtgta    180

agctggattc gccagcctcc acgaaagggt ctggagtggc tgggagtaat atggggtagt    240

gaaaccacat actataattc agctctcaaa tccagactga ccatcatcaa ggacaactcc    300

aagagccaag ttttcttaaa aatgaacagt ctgcaaactg atgacacagc catttactac    360

tgtgccaaac attattacta cggtggtagc tatgctatgg actactgggg ccaaggaacc    420

tcagtcaccg tctcctcagc ctccaccaag ggcccatcgg tcttccccct ggcaccctcc    480

tccaagagca cctctggggg cacagcggcc ctgggctgcc tggtcaagga ctacttcccc    540

gaaccggtga cggtgtcgtg gaactcaggc gccctgacca gcggcgtgca caccttcccg    600

gctgtcctac agtcctcagg actctactcc ctcagcagcg tggtgactgt gccctctagc    660

agcttgggca cccagaccta catctgcaac gtgaatcaca agcccagcaa caccaaggtg    720

gacaagaaag ttgagcccaa atcttgt                                        747


<210> SEQ ID NO 97
<211> LENGTH: 699
<212> TYPE: DNA
<213> ORGANISM: Artificial Sequence
<220> FEATURE:
<223> OTHER INFORMATION: Made in lab - CD19(FMC63)-LC-Cterm switch
      antibody polynucleotide

<400> SEQUENCE: 97

gacatccaga tgacacagac tacatcctcc ctgtctgcct ctctgggaga cagagtcacc     60

atcagttgca gggcaagtca ggacattagt aaatatttaa attggtatca gcagaaacca    120

gatggaactg ttaaactcct gatctaccat acatcaagat tacactcagg agtcccatca    180

aggttcagtg gcagtgggtc tggaacagat tattctctca ccattagcaa cctggagcaa    240

gaagatattg ccacttactt ttgccaacag ggtaatacgc ttccgtacac gttcggaggg    300

gggaccaagc ttgagatcaa acgaactgtg gctgcaccat ctgtcttcat cttcccgcca    360

tctgatgagc agttgaaatc tggaactgcc tctgtcgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgtcctcgc ccgtcacaaa gagcttcaac aggggagagt gtggcggagg cgggagcaat    660

tatcatcttg aaaatgaggt cgctcgtctc aagaaactc                           699


<210> SEQ ID NO 98
```

<211> LENGTH: 711
<212> TYPE: DNA
<213> ORGANISM: Artificial Sequence
<220> FEATURE:
<223> OTHER INFORMATION: Made in lab - CD19(FMC63)-LC-NT1_LLPKN switch antibody polynucleotide

<400> SEQUENCE: 98

```
ctgctgccga aaaattatca tcttgaaaat gaggtcgctc gtctcaagaa actcggcgga     60

ggcgggagcg acatccagat gacacagact acatcctccc tgtctgcctc tctgggagac    120

agagtcacca tcagttgcag ggcaagtcag gacattagta aatatttaaa ttggtatcag    180

cagaaaccag atggaactgt taaactcctg atctaccata catcaagatt acactcagga    240

gtcccatcaa ggttcagtgg cagtgggtct ggaacagatt attctctcac cattagcaac    300

ctggagcaag aagatattgc cacttacttt tgccaacagg gtaatacgct tccgtacacg    360

ttcggagggg ggaccaagct tgagatcaaa cgaactgtgg ctgcaccatc tgtcttcatc    420

ttcccgccat ctgatgagca gttgaaatct ggaactgcct ctgtcgtgtg cctgctgaat    480

aacttctatc ccagagaggc caaagtacag tggaaggtgg ataacgccct ccaatcgggt    540

aactcccagg agagtgtcac agagcaggac agcaaggaca gcacctacag cctcagcagc    600

accctgacgc tgagcaaagc agactacgag aaacacaaag tctacgcctg cgaagtcacc    660

catcagggcc tgtcctcgcc cgtcacaaag agcttcaaca ggggagagtg t             711
```

<210> SEQ ID NO 99
<211> LENGTH: 711
<212> TYPE: DNA
<213> ORGANISM: Artificial Sequence
<220> FEATURE:
<223> OTHER INFORMATION: Made in lab - CD19(FMC63)-LC-NT1_DLPKQ switch antibody polynucleotide

<400> SEQUENCE: 99

```
gacctcccca agcagtatca tcttgaaaat gaggtcgctc gtctcaagaa actcggcgga     60

ggcgggagcg acatccagat gacacagact acatcctccc tgtctgcctc tctgggagac    120

agagtcacca tcagttgcag ggcaagtcag gacattagta aatatttaaa ttggtatcag    180

cagaaaccag atggaactgt taaactcctg atctaccata catcaagatt acactcagga    240

gtcccatcaa ggttcagtgg cagtgggtct ggaacagatt attctctcac cattagcaac    300

ctggagcaag aagatattgc cacttacttt tgccaacagg gtaatacgct tccgtacacg    360

ttcggagggg ggaccaagct tgagatcaaa cgaactgtgg ctgcaccatc tgtcttcatc    420

ttcccgccat ctgatgagca gttgaaatct ggaactgcct ctgtcgtgtg cctgctgaat    480

aacttctatc ccagagaggc caaagtacag tggaaggtgg ataacgccct ccaatcgggt    540

aactcccagg agagtgtcac agagcaggac agcaaggaca gcacctacag cctcagcagc    600

accctgacgc tgagcaaagc agactacgag aaacacaaag tctacgcctg cgaagtcacc    660

catcagggcc tgtcctcgcc cgtcacaaag agcttcaaca ggggagagtg t             711
```

<210> SEQ ID NO 100
<211> LENGTH: 5631
<212> TYPE: DNA
<213> ORGANISM: Artificial Sequence
<220> FEATURE:
<223> OTHER INFORMATION: Made in lab - CD19(FMC63)-HC-WT/LC-NT1 switch antibody polynucleotide

<400> SEQUENCE: 100

-continued

```
aagaaaccaa ttgtccatat tgcatcagac attgccgtca ctgcgtcttt tactggctct     60
tctcgctaac caaaccggta accctgatta tttgcacgga gtcacacttt gctatgccat    120
agcattttta tccataagat tagcggatcc tacctgacgc tttttatcgc aactctctac    180
tgtttctcca tacccgtttt tttgggctag aaataatttt gtttaacttt aagaaggaga    240
atacatcaac tagtacgcaa gttcacgtaa aaagggtatc tagaggttga ggtgatttta    300
tgaaaaagaa tatcgcattt cttcttgcta gcatgttcgt tttttctatt gctacaaacg    360
catacgctaa ctaccatctg gaaaacgaag ttgcgcgcct gaaaaaactg ggtggcggtg    420
gcagcgacat ccagatgaca cagactacat cctccctgtc tgcctctctg ggagacagag    480
tcaccatcag ttgcagggca agtcaggaca ttagtaaata tttaaattgg tatcagcaga    540
aaccagatgg aactgttaaa ctcctgatct accatacatc aagattacac tcaggagtcc    600
catcaaggtt cagtggcagt gggtctggaa cagattattc tctcaccatt agcaacctgg    660
agcaagaaga tattgccact tacttttgcc aacagggtaa tacgcttccg tacacgttcg    720
gaggggggac caagctggag atcaaacgaa ctgtggctgc accatctgtc ttcatcttcc    780
cgccatctga tgagcagttg aaatctggaa ctgcctctgt cgtgtgcctg ctgaataact    840
tctatcccag agaggccaaa gtacagtgga aggtggataa cgccctccaa tcgggtaact    900
cccaggagag tgtcacagag caggacagca aggacagcac ctacagcctc agcagcaccc    960
tgacgctgag caaagcagac tacgagaaac acaaagtcta cgcctgcgaa gtcacccatc   1020
agggcctgtc ctcgcccgtc acaaagagct tcaacagggg agagtgttaa gctggggatc   1080
ctctagaggt tgaggtgatt ttatgaaaaa gaatatcgca tttcttcttg catctatgtt   1140
cgtttttttct attgctacaa acgcgtacgc tgaggtgaaa ctgcaggagt caggacctgg   1200
cctggtggcg ccctcacaga gcctgtccgt cacatgcact gtctcagggg tatcattacc   1260
cgactatggt gtaagctgga ttcgccagcc tccacgaaag ggtctggagt ggctgggagt   1320
aatatggggt agtgaaacca catactataa ttcagctctc aaatccagac tgaccatcat   1380
caaggacaac tccaagagcc aagttttctt aaaaatgaac agtctgcaaa ctgatgacac   1440
agccatttac tactgtgcca aacattatta ctacggtggt agctatgcta tggactactg   1500
gggccaagga acctcagtca ccgtctcctc agcctccacc aagggcccat cggtcttccc   1560
cctggcaccc tcctccaaga gcacctctgg gggcacagcg gccctgggct gcctggtcaa   1620
ggactacttc cccgaaccgg tgacggtgtc gtggaactca ggcgccctga ccagcggcgt   1680
gcacaccttc ccggctgtcc tacagtcctc aggactctac tccctcagca gcgtggtgac   1740
tgtgccctct agcagcttgg gcacccagac ctacatctgc aacgtgaatc acaagcccag   1800
caacaccaag gtggacaaga aagttgagcc caaatcttgt gacaaaactc acacataata   1860
agtcgaccga tgcccttgag agccttcaac ccagtcagct ccttccggtg ggcgcggggc   1920
atgactatcg tcgccgcact tatgactgtc ttctttatca tgcaactcgt aggacaggtg   1980
ccaaacggtc tccagcttgg ctgttttggc ggatgagaga agattttcag cctgatacag   2040
attaaatcag aacgcagaag cggtctgata aaacagaatt tgcctggcgg cagtagcgcg   2100
gtggtcccac ctgaccccat gccgaactca gaagtgaaac gccgtagcgc cgatggtagt   2160
gtggggtctc cccatgcgag agtagggaac tgccaggcat caaataaaac gaaaggctca   2220
gtcgaaagac tgggcctttc gttttatctg ttgtttgtcg gtgaacgctc tcctgagtag   2280
gacaaatccg ccgggagcgg atttgaacgt tgcgaagcaa cggcccggag ggtggcgggc   2340
aggacgcccg ccataaactg ccaggcatca aattaagcag aaggccatcc tgacggatgg   2400
```

```
cctttttgcg tttctacaaa ctctttttgt ttatttttct aaatacattc aaatatgtat   2460
ccgctcatga gacaataacc ctgataaatg cttcaataat attgaaaaag gaagagtatg   2520
agtattcaac atttccgtgt cgcccttatt ccctttttg cggcattttg ccttcctgtt   2580
tttgctcacc cagaaacgct ggtgaaagta aaagatgctg aagatcagtt gggtgcacga   2640
gtgggttaca tcgaactgga tctcaacagc ggtaagatcc ttgagagttt tcgccccgaa   2700
gaacgttttc caatgatgag cacttttaaa gttctgctat gtggcgcggt attatcccgt   2760
gttgacgccg ggcaagagca actcggtcgc cgcatacact attctcagaa tgacttggtt   2820
gagtactcac cagtcacaga aaagcatctt acggatggca tgacagtaag agaattatgc   2880
agtgctgcca taaccatgag tgataacact gcggccaact tacttctgac aacgatcgga   2940
ggaccgaagg agctaaccgc ttttttgcac aacatggggg atcatgtaac tcgccttgat   3000
cgttgggaac cggagctgaa tgaagccata ccaaacgacg agcgtgacac cacgatgcct   3060
gtagcaatgg caacaacgtt gcgcaaacta ttaactggcg aactacttac tctagcttcc   3120
cggcaacaat taatagactg gatggaggcg gataaagttg caggaccact tctgcgctcg   3180
gcccttccgg ctggctggtt tattgctgat aaatctggag ccggtgagcg tgggtctcgc   3240
ggtatcattg cagcactggg gccagatggt aagccctccc gtatcgtagt tatctacacg   3300
acggggagtc aggcaactat ggatgaacga aatagacaga tcgctgagat aggtgcctca   3360
ctgattaagc attggtaact gtcagaccaa gtttactcat atatacttta gattgattta   3420
aaacttcatt tttaatttaa aaggatctag gtgaagatcc tttttgataa tctcatgacc   3480
aaaatccctt aacgtgagtt ttcgttccac tgagcgtcag accccgtaga aaagatcaaa   3540
ggatcttctt gagatccttt ttttctgcgc gtaatctgct gcttgcaaac aaaaaaacca   3600
ccgctaccag cggtggtttg tttgccggat caagagctac caactctttt tccgaaggta   3660
actggcttca gcagagcgca gataccaaat actgtccttc tagtgtagcc gtagttaggc   3720
caccacttca agaactctgt agcaccgcct acatacctcg ctctgctaat cctgttacca   3780
gtggctgctg ccagtggcga taagtcgtgt cttaccgggt tggactcaag acgatagtta   3840
ccggataagg cgcagcggtc gggctgaacg gggggttcgt gcacacagcc cagcttggag   3900
cgaacgacct acaccgaact gagataccta cagcgtgagc tatgagaaag cgccacgctt   3960
cccgaaggga gaaaggcgga caggtatccg gtaagcggca gggtcggaac aggagagcgc   4020
acgagggagc ttccaggggg aaacgcctgg tatctttata gtcctgtcgg gtttcgccac   4080
ctctgacttg agcgtcgatt tttgtgatgc tcgtcagggg ggcggagcct atggaaaaac   4140
gccagcaacg cggccttttt acggttcctg gccttttgct ggccttttgc tcacatgttc   4200
tttcctgcgt tatcccctga ttctgtggat aaccgtatta ccgcctttga gtgagctgat   4260
accgctcgcc gcagccgaac gaccgagcgc agcgagtcag tgagcgagga agcggaagag   4320
cgcctgatgc ggtattttct ccttacgcat ctgtgcggta tttcacaccg catatggtgc   4380
actctcagta caatctgctc tgatgccgca tagttaagcc agtatacact ccgctatcgc   4440
tacgtgactg ggtcatggct gcgccccgac acccgccaac acccgctgac gcgccctgac   4500
gggcttgtct gctcccggca tccgcttaca gacaagctgt gaccgtctcc gggagctgca   4560
tgtgtcagag gttttcaccg tcatcaccga aacgcgcgag gcagcagatc aattcgcgcg   4620
cgaaggcgaa gcggcatgca taatgtgcct gtcaaatgga cgaagcaggg attctgcaaa   4680
ccctatgcta ctccgtcaag ccgtcaattg tctgattcgt taccaattat gacaacttga   4740
```

cggctacatc attcactttt tcttcacaac cggcacggaa ctcgctcggg ctggccccgg 4800
tgcatttttt aaatacccgc gagaaataga gttgatcgtc aaaaccaaca ttgcgaccga 4860
cggtggcgat aggcatccgg gtggtgctca aaagcagctt cgcctggctg atacgttggt 4920
cctcgcgcca gcttaagacg ctaatcccta actgctggcg gaaaagatgt gacagacgcg 4980
acggcgacaa gcaaacatgc tgtgcgacgc tggcgatatc aaaattgctg tctgccaggt 5040
gatcgctgat gtactgacaa gcctcgcgta cccgattatc catcggtgga tggagcgact 5100
cgttaatcgc ttccatgcgc cgcagtaaca attgctcaag cagatttatc gccagcagct 5160
ccgaatagcg cccttcccct tgcccggcgt taatgatttg cccaaacagg tcgctgaaat 5220
gcggctggtg cgcttcatcc gggcgaaaga accccgtatt ggcaaatatt gacggccagt 5280
taagccattc atgccagtag gcgcgcggac gaaagtaaac ccactggtga taccattcgc 5340
gagcctccgg atgacgaccg tagtgatgaa tctctcctgg cgggaacagc aaaatatcac 5400
ccggtcggca aacaaattct cgtccctgat tttcaccac cccctgaccg cgaatggtga 5460
gattgagaat ataacctttc attcccagcg gtcggtcgat aaaaaaatcg agataaccgt 5520
tggcctcaat cggcgttaaa cccgccacca gatgggcatt aaacgagtat cccggcagca 5580
ggggatcatt ttgcgcttca gccatacttt tcatactccc gccattcaga g 5631

<210> SEQ ID NO 101
<211> LENGTH: 5631
<212> TYPE: DNA
<213> ORGANISM: Artificial Sequence
<220> FEATURE:
<223> OTHER INFORMATION: Made in lab - CD19(FMC63)-HC-WT/LC-NT1 switch antibody polynucleotide

<400> SEQUENCE: 101
aagaaaccaa ttgtccatat tgcatcagac attgccgtca ctgcgtcttt tactggctct 60
tctcgctaac caaaccggta accctgatta tttgcacgga gtcacacttt gctatgccat 120
agcattttta tccataagat tagcggatcc tacctgacgc tttttatcgc aactctctac 180
tgtttctcca tacccgtttt tttgggctag aaataatttt gtttaacttt aagaaggaga 240
atacatcaac tagtacgcaa gttcacgtaa aaagggtatc tagaggttga ggtgatttta 300
tgaaaaagaa tatcgcattt cttcttgcta gcatgttcgt tttttctatt gctacaaacg 360
catacgctaa ctaccatctg gaaaacgaag ttgcgcgcct gaaaaaactg ggtggcggtg 420
gcagcgatat tcagatgacg cagaccacct catctctcag cgcgtcctta ggtgatcgcg 480
taacaatttc ctgtcgtgcc tctcaggata ttagcaagta cctgaattgg tatcagcaga 540
agcctgatgg gaccgttaaa cttctcattt atcacactag tcgtctgcat tcgggcgttc 600
catcccggtt ctccggttct ggttcgggca ctgactactc gttaaccatc tcgaatctgg 660
aacaggagga tattgcaacc tatttttgtc agcaaggtaa tacgctgccg tacacgttcg 720
gcggaggtac gaagcttgaa atcaaacgca ccgtcgcggc gccgagcgtg tttatcttcc 780
cgccgagtga tgaacagctc aaaagcggta ctgccagcgt tgtttgctta ctcaacaatt 840
tttatccacg ggaggccaaa gttcaatgga aagttgacaa cgcactgcag agcggtaaca 900
gtcaagaatc tgtcacggag caagactcga aagacagcac ctacagctta tccagcaccc 960
tgacgctttc gaaagcggac tacgaaaagc acaaagttta tgcatgtgaa gtgacccatc 1020
agggcctttc ctcaccggtg accaaatcat ttaaccgtgg cgagtgctaa gctggggatc 1080
ctctagaggt tgaggtgatt ttatgaaaaa gaatatcgca tttcttcttg catctatgtt 1140

```
cgtttttttct attgctacaa acgcgtacgc tgaggttaag ttgcaggagt caggcccggg   1200
tttagtggca ccttctcagt ccttgtcagt gacatgcacg gttagcggcg tgagcttgcc   1260
ggactatggc gtgagctgga tccgccagcc cccgcgcaaa ggtctggagt ggttgggcgt   1320
tatttggggc tccgaaacca cctactacaa cagcgcgttg aaaagtcgtc tgacgatcat   1380
taaagataac tcgaaatcgc aggtttttct gaagatgaac tccctgcaga ccgatgatac   1440
agcgatctat tattgcgcga aacattacta ttatggcggt agttacgcga tggactactg   1500
gggtcaggga acgagcgtaa ccgtgtcatc ggccagcact aagggcccga gcgtattccc   1560
gttggctcca tcttctaaaa gtaccagcgg gggtaccgcg gcgctgggct gtttagtgaa   1620
agactatttt cctgagcccg tgacggtttc gtggaacagc ggtgcgctga cctctggtgt   1680
tcatactttt ccggccgtct tgcagagctc tggtttatac agcctctcaa gtgtggtgac   1740
ggtaccttct agctcactgg gtactcagac atatatttgt aacgttaacc acaagccgag   1800
caacaccaaa gtcgataaaa aagtggaacc taaaagctgc gataaaaccc atacgtaata   1860
agtcgaccga tgcccttgag agccttcaac ccagtcagct ccttccggtg ggcgcggggc   1920
atgactatcg tcgccgcact tatgactgtc ttctttatca tgcaactcgt aggacaggtg   1980
ccaaacggtc tccagcttgg ctgttttggc ggatgagaga agattttcag cctgatacag   2040
attaaatcag aacgcagaag cggtctgata aaacagaatt tgcctggcgg cagtagcgcg   2100
gtggtcccac ctgaccccat gccgaactca gaagtgaaac gccgtagcgc cgatggtagt   2160
gtggggtctc cccatgcgag agtagggaac tgccaggcat caaataaaac gaaaggctca   2220
gtcgaaagac tgggcctttc gttttatctg ttgtttgtcg gtgaacgctc tcctgagtag   2280
gacaaatccg ccgggagcgg atttgaacgt tgcgaagcaa cggcccggag ggtggcgggc   2340
aggacgcccg ccataaactg ccaggcatca aattaagcag aaggccatcc tgacggatgg   2400
cctttttgcg tttctacaaa ctctttttgt ttatttttct aaatacattc aaatatgtat   2460
ccgctcatga gacaataacc ctgataaatg cttcaataat attgaaaaag gaagagtatg   2520
agtattcaac atttccgtgt cgcccttatt cccttttttg cggcattttg ccttcctgtt   2580
tttgctcacc cagaaacgct ggtgaaagta aaagatgctg aagatcagtt gggtgcacga   2640
gtgggttaca tcgaactgga tctcaacagc ggtaagatcc ttgagagttt tcgccccgaa   2700
gaacgttttc caatgatgag cacttttaaa gttctgctat gtggcgcggt attatcccgt   2760
gttgacgccg ggcaagagca actcggtcgc cgcatacact attctcagaa tgacttggtt   2820
gagtactcac cagtcacaga aaagcatctt acggatggca tgacagtaag agaattatgc   2880
agtgctgcca taaccatgag tgataacact gcggccaact tacttctgac aacgatcgga   2940
ggaccgaagg agctaaccgc ttttttgcac aacatggggg atcatgtaac tcgccttgat   3000
cgttgggaac cggagctgaa tgaagccata ccaaacgacg agcgtgacac cacgatgcct   3060
gtagcaatgg caacaacgtt gcgcaaacta ttaactggcg aactacttac tctagcttcc   3120
cggcaacaat taatagactg gatggaggcg gataaagttg caggaccact tctgcgctcg   3180
gcccttccgg ctggctggtt tattgctgat aaatctggag ccggtgagcg tgggtctcgc   3240
ggtatcattg cagcactggg gccagatggt aagccctccc gtatcgtagt tatctacacg   3300
acggggagtc aggcaactat ggatgaacga aatagacaga tcgctgagat aggtgcctca   3360
ctgattaagc attggtaact gtcagaccaa gtttactcat atatacttta gattgattta   3420
aaacttcatt tttaatttaa aaggatctag gtgaagatcc tttttgataa tctcatgacc   3480
aaaatccctt aacgtgagtt ttcgttccac tgagcgtcag accccgtaga aaagatcaaa   3540
```

ggatcttctt gagatccttt ttttctgcgc gtaatctgct gcttgcaaac aaaaaaacca 3600
ccgctaccag cggtggtttg tttgccggat caagagctac caactctttt tccgaaggta 3660
actggcttca gcagagcgca gataccaaat actgtccttc tagtgtagcc gtagttaggc 3720
caccacttca agaactctgt agcaccgcct acatacctcg ctctgctaat cctgttacca 3780
gtggctgctg ccagtggcga taagtcgtgt cttaccgggt tggactcaag acgatagtta 3840
ccggataagg cgcagcggtc gggctgaacg gggggttcgt gcacacagcc cagcttggag 3900
cgaacgacct acaccgaact gagataccta cagcgtgagc tatgagaaag cgccacgctt 3960
cccgaaggga gaaaggcgga caggtatccg gtaagcggca gggtcggaac aggagagcgc 4020
acgagggagc ttccaggggg aaacgcctgg tatctttata gtcctgtcgg gtttcgccac 4080
ctctgacttg agcgtcgatt tttgtgatgc tcgtcagggg ggcggagcct atggaaaaac 4140
gccagcaacg cggccttttt acggttcctg gccttttgct ggccttttgc tcacatgttc 4200
tttcctgcgt tatcccctga ttctgtggat aaccgtatta ccgcctttga gtgagctgat 4260
accgctcgcc gcagccgaac gaccgagcgc agcgagtcag tgagcgagga agcggaagag 4320
cgcctgatgc ggtattttct ccttacgcat ctgtgcggta tttcacaccg catatggtgc 4380
actctcagta caatctgctc tgatgccgca tagttaagcc agtatacact ccgctatcgc 4440
tacgtgactg ggtcatggct gcgccccgac acccgccaac acccgctgac gcgccctgac 4500
gggcttgtct gctcccggca tccgcttaca gacaagctgt gaccgtctcc gggagctgca 4560
tgtgtcagag gttttcaccg tcatcaccga aacgcgcgag gcagcagatc aattcgcgcg 4620
cgaaggcgaa gcggcatgca taatgtgcct gtcaaatgga cgaagcaggg attctgcaaa 4680
ccctatgcta ctccgtcaag ccgtcaattg tctgattcgt taccaattat gacaacttga 4740
cggctacatc attcactttt tcttcacaac cggcacggaa ctcgctcggg ctggccccgg 4800
tgcatttttt aaatacccgc gagaaataga gttgatcgtc aaaaccaaca ttgcgaccga 4860
cggtggcgat aggcatccgg gtggtgctca aaagcagctt cgcctggctg atacgttggt 4920
cctcgcgcca gcttaagacg ctaatcccta actgctggcg gaaaagatgt gacagacgcg 4980
acggcgacaa gcaaacatgc tgtgcgacgc tggcgatatc aaaattgctg tctgccaggt 5040
gatcgctgat gtactgacaa gcctcgcgta cccgattatc catcggtgga tggagcgact 5100
cgttaatcgc ttccatgcgc cgcagtaaca attgctcaag cagatttatc gccagcagct 5160
ccgaatagcg cccttcccct tgcccggcgt taatgatttg cccaaacagg tcgctgaaat 5220
gcggctggtg cgcttcatcc gggcgaaaga accccgtatt ggcaaatatt gacggccagt 5280
taagccattc atgccagtag gcgcgcggac gaaagtaaac ccactggtga taccattcgc 5340
gagcctccgg atgacgaccg tagtgatgaa tctctcctgg cgggaacagc aaaatatcac 5400
ccggtcggca aacaaattct cgtccctgat tttcaccac ccccctgaccg cgaatggtga 5460 gattgagaat ataacctttc attcccagcg gtcggtcgat aaaaaaatcg agataaccgt 5520
tggcctcaat cggcgttaaa cccgccacca gatgggcatt aaacgagtat cccggcagca 5580
ggggatcatt ttgcgcttca gccatacttt tcatactccc gccattcaga g 5631

<210> SEQ ID NO 102
<211> LENGTH: 762
<212> TYPE: DNA
<213> ORGANISM: Artificial Sequence
<220> FEATURE:
<223> OTHER INFORMATION: Made in lab - CLL1(1075.7)-HC_NT3 switch
      antibody polynucleotide

<400> SEQUENCE: 102
aattatcatc ttgaaaatga ggtcgctcgt ctcaagaaac tcctggttgg cgaggccgca 60
gctaaggaag ccgcagctaa agccgatatc cagctgcagg agtccggacc aggtctggtg 120
aagcccagcc agtccctgtc tctgacctgc agcgtcactg gctattccat caccagtgca 180
tactattgga actggatcag acagttccct ggaaacaaac tggagtggat ggggtacatc 240
tcttacgacg gtagaaacaa ctacaacccc agcctcaaaa acaggattag cattacccgc 300
gacactagta agaaccagtt tttcctgaag ctcaacagtg tgacaactga ggacactgct 360
acttattatt gtgccaagga gggcgactat gatgtcggca attattacgc tatggactat 420
tggggtcagg ggactagcgt gaccgtcagt tctgccagga ccaaaggacc gtccgtcttt 480
cctctggccc cttcctctaa gtccacaagc ggtgggaccg cagcactggg atgcctggtg 540
aaggattact tccctgagcc ggtgaccgtg tcctggaact ccggagctct cacctccggt 600
gtccatacct ttcctgccgt cctgcagtcc tccggcctgt acagcctctc tagcgtcgtg 660
actgtgccct ccagctccct gggcacccaa acttatatct gcaatgttaa ccacaagcct 720
tctaatacca aggtcgacaa gaaagtggag ccgaagagct gt 762

<210> SEQ ID NO 103
<211> LENGTH: 702
<212> TYPE: DNA
<213> ORGANISM: Artificial Sequence
<220> FEATURE:
<223> OTHER INFORMATION: Made in lab - CLL1(1075.7)-LC_NT1 switch
antibody polynucleotide

<400> SEQUENCE: 103
aactatcacc tggaaaacga agtggcaagg ctgaaaaaac tgggcggggg cggaagtgaa 60
aacgtgctca cccagagtcc cgccatcatg agcgccagtc ccggcgagaa ggtgaccatg 120
acctgtaggg cctcttccaa tgtgatctct agctacgtgc attggtacca gcagcgtagt 180
ggggccagcc ctaagctctg gatttactcc acctccaacc tggcctccgg ggtccccgcc 240
cgtttctctg gcagtggctc tggtacctct tactccctga ctatcagcag cgtcgaggcc 300
gaggatgccg ctacatacta ctgtcagcag tacagtggat accctctgac cttcggggct 360
ggcaccaagc tggagctgaa gcgcgctgcc gccgccccca gtgtcttcat tttccccccct 420 tccgatgagc agctgaagag cggtacagcc tctgttgttt gtctgctgaa caacttctat 480
ccacgcgagg ccaaggtgca gtggaaagtt gataacgcgc tgcagagtgg caactcccag 540
gagtctgtga cagagcagga cagtaaagac agcacatatt ccctgtctag cacactgact 600
ctgtccaagg ctgactatga gaagcacaag gtgtacgctt gcgaggtcac ccaccaggga 660
ctgagttctc ctgtgaccaa gtccttcaat cgcggcgagt gt 702

<210> SEQ ID NO 104
<211> LENGTH: 735
<212> TYPE: DNA
<213> ORGANISM: Artificial Sequence
<220> FEATURE:
<223> OTHER INFORMATION: Made in lab - CLL1(1075.7)-HC_Cterm switch
antibody polynucleotide

<400> SEQUENCE: 104
gatatccagc tgcaggagtc cggaccaggt ctggtgaagc ccagccagtc cctgtctctg 60
acctgcagcg tcactggcta ttccatcacc agtgcatact attggaactg gatcagacag 120

```
ttccctggaa acaaactgga gtggatgggg tacatctctt acgacggtag aaacaactac    180

aaccccagcc tcaaaaacag gattagcatt acccgcgaca ctagtaagaa ccagtttttc    240

ctgaagctca acagtgtgac aactgaggac actgctactt attattgtgc caaggagggc    300

gactatgatg tcggcaatta ttacgctatg gactattggg gtcaggggac tagcgtgacc    360

gtcagttctg ccaggaccaa aggaccgtcc gtctttcctc tggccccttc ctctaagtcc    420

acaagcggtg ggaccgcagc actgggatgc ctggtgaagg attacttccc tgagccggtg    480

accgtgtcct ggaactccgg agctctcacc tccggtgtcc atacctttcc tgccgtcctg    540

cagtcctccg gcctgtacag cctctctagc gtcgtgactg tgccctccag ctccctgggc    600

acccaaactt atatctgcaa tgttaaccac aagccttcta ataccaaggt cgacaagaaa    660

gtggagccga agagctgtgg cggaggcggg agcaattatc atcttgaaaa tgaggtcgct    720

cgtctcaaga aactc                                                     735
```

<210> SEQ ID NO 105
<211> LENGTH: 702
<212> TYPE: DNA
<213> ORGANISM: Artificial Sequence
<220> FEATURE:
<223> OTHER INFORMATION: Made in lab - CLL1(1075.7)-LC_Cterm switch
      antibody polynucleotide

<400> SEQUENCE: 105

```
gaaaacgtgc tcacccagag tcccgccatc atgagcgcca gtcccggcga gaaggtgacc     60

atgacctgta gggcctcttc caatgtgatc tctagctacg tgcattggta ccagcagcgt    120

agtggggcca gccctaagct ctggatttac tccacctcca acctggcctc cggggtcccc    180

gcccgtttct ctggcagtgg ctctggtacc tcttactccc tgactatcag cagcgtcgag    240

gccgaggatg ccgctacata ctactgtcag cagtacagtg gataccctct gaccttcggg    300

gctggcacca agctggagct gaagcgcgct gccgccgccc ccagtgtctt catttttccc    360

ccttccgatg agcagctgaa gagcggtaca gcctctgttg tttgtctgct gaacaacttc    420

tatccacgcg aggccaaggt gcagtggaaa gttgataacg cgctgcagag tggcaactcc    480

caggagtctg tgacagagca ggacagtaaa gacagcacat attccctgtc tagcacactg    540

actctgtcca aggctgacta tgagaagcac aaggtgtacg cttgcgaggt cacccaccag    600

ggactgagtt ctcctgtgac caagtccttc aatcgcggcg agtgtggcgg aggcgggagc    660

aattatcatc ttgaaaatga ggtcgctcgt ctcaagaaac tc                       702
```

<210> SEQ ID NO 106
<211> LENGTH: 681
<212> TYPE: DNA
<213> ORGANISM: Artificial Sequence
<220> FEATURE:
<223> OTHER INFORMATION: Made in lab - CD22(m971)-HC-WT Fab switch
      antibody polynucleotide

<400> SEQUENCE: 106

```
caggtacagc tgcagcagtc aggtccagga ctggtgaagc cctcgcagac cctctcactc     60

acctgtgcca tctccgggga cagtgtctct agcaacagtg ctgcttggaa ctggatcagg    120

cagtccccat cgagaggcct tgagtggctg ggaaggacat actacaggtc caagtggtat    180

aatgattatg cagtatctgt gaaaagtcga ataaccatca acccagacac atccaagaac    240

cagttctccc tgcagctgaa ctctgtgact cccgaggaca cggctgtgta ttactgtgca    300

agagaagtga ctggggatct cgaggatgct tttgatatct ggggccaagg gacaatggtc    360
```

accgtctcct cagcctccac caagggccca tcggtcttcc ccctggcacc ctcctccaag 420
agcacctctg gggcacagc ggccctgggc tgcctggtca aggactactt ccccgaaccg 480
gtgacggtgt cgtggaactc aggcgccctg accagcggcg tgcacacctt cccggctgtc 540
ctacagtcct caggactcta ctccctcagc agcgtggtga ctgtgccctc tagcagcttg 600
ggcacccaga cctacatctg caacgtgaat cacaagccca gcaacaccaa ggtggacaag 660
aaagttgagc ccaaatcttg t 681

<210> SEQ ID NO 107
<211> LENGTH: 642
<212> TYPE: DNA
<213> ORGANISM: Artificial Sequence
<220> FEATURE:
<223> OTHER INFORMATION: Made in lab - CD22(m971)-LC-WT switch antibody polynucleotide

<400> SEQUENCE: 107
gacatccaga tgacccagtc tccatcgtcc ctgtctgcat ctgtaggaga cagagtcacc 60
atcacttgcc gggcaagcca gaccatttgg agctacttaa attggtatca gcagagacca 120
gggaaagccc ctaacctcct gatctatgct gcatccagtt tgcaaagtgg ggtcccatca 180
aggttcagtg gcaggggatc tgggacagat ttcactctca ccatcagcag tctgcaagct 240
gaagattttg caacttacta ctgtcaacag agttacagta tccctcagac ttttggccag 300
gggaccaagc tggagatcaa acgaactgtg gctgcaccat ctgtcttcat cttcccgcca 360
tctgatgagc agttgaaatc tggaactgcc tctgtcgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgtcctcgc ccgtcacaaa gagcttcaac aggggagagt gt 642

<210> SEQ ID NO 108
<211> LENGTH: 765
<212> TYPE: DNA
<213> ORGANISM: Artificial Sequence
<220> FEATURE:
<223> OTHER INFORMATION: Made in lab - CD22(m971)-HC_NT3 switch antibody polynucleotide

<400> SEQUENCE: 108
aattatcatc ttgaaaatga ggtcgctcgt ctcaagaaac tcctggttgg cgaggccgca 60
gctaaggaag ccgcagctaa agcccaggta cagctgcagc agtcaggtcc aggactggtg 120
aagccctcgc agaccctctc actcacctgt gccatctccg gggacagtgt ctctagcaac 180
agtgctgctt ggaactggat caggcagtcc ccatcgagag gccttgagtg gctgggaagg 240
acatactaca ggtccaagtg gtataatgat tatgcagtat ctgtgaaaag tcgaataacc 300
atcaacccag acacatccaa gaaccagttc tccctgcagc tgaactctgt gactcccgag 360
gacacggctg tgtattactg tgcaagagaa gtgactgggg atctcgagga tgcttttgat 420
atctggggcc aagggacaat ggtcaccgtc tcctcagcct ccaccaaggg cccatcggtc 480 ttcccccctgg caccctcctc caagagcacc tctgggggca cagcggccct gggctgcctg 540
gtcaaggact acttccccga accggtgacg gtgtcgtgga actcaggcgc cctgaccagc 600
ggcgtgcaca ccttcccggc tgtcctacag tcctcaggac tctactccct cagcagcgtg 660
gtgactgtgc cctctagcag cttgggcacc cagacctaca tctgcaacgt gaatcacaag 720
cccagcaaca ccaaggtgga caagaaagtt gagcccaaat cttgt 765

<210> SEQ ID NO 109
<211> LENGTH: 699
<212> TYPE: DNA
<213> ORGANISM: Artificial Sequence
<220> FEATURE:
<223> OTHER INFORMATION: Made in lab - CD22(m971)-LC_NT1 switch antibody polynucleotide

<400> SEQUENCE: 109
aactatcacc tggaaaacga agtggcaagg ctgaaaaaac tgggcggggg cggaagtgac 60
atccagatga cccagtctcc atcgtccctg tctgcatctg taggagacag agtcaccatc 120
acttgccggg caagccagac catttggagc tacttaaatt ggtatcagca gagaccaggg 180
aaagccccta acctcctgat ctatgctgca tccagtttgc aaagtggggt cccatcaagg 240
ttcagtggca ggggatctgg gacagatttc actctcacca tcagcagtct gcaagctgaa 300
gattttgcaa cttactactg tcaacagagt tacagtatcc ctcagacttt tggccagggg 360
accaagctgg agatcaaacg aactgtggct gcaccatctg tcttcatctt cccgccatct 420
gatgagcagt tgaaatctgg aactgcctct gtcgtgtgcc tgctgaataa cttctatccc 480
agagaggcca aagtacagtg gaaggtggat aacgccctcc aatcgggtaa ctcccaggag 540
agtgtcacag agcaggacag caaggacagc acctacagcc tcagcagcac cctgacgctg 600
agcaaagcag actacgagaa acacaaagtc tacgcctgcg aagtcaccca tcagggcctg 660
tcctcgcccg tcacaaagag cttcaacagg ggagagtgt 699

<210> SEQ ID NO 110
<211> LENGTH: 738
<212> TYPE: DNA
<213> ORGANISM: Artificial Sequence
<220> FEATURE:
<223> OTHER INFORMATION: Made in lab - CD22(m971)-HC_Cterm switch antibody polynucleotide

<400> SEQUENCE: 110
caggtacagc tgcagcagtc aggtccagga ctggtgaagc cctcgcagac cctctcactc 60
acctgtgcca tctccgggga cagtgtctct agcaacagtg ctgcttggaa ctggatcagg 120
cagtccccat cgagaggcct tgagtggctg ggaaggacat actacaggtc caagtggtat 180
aatgattatg cagtatctgt gaaaagtcga ataaccatca acccagacac atccaagaac 240
cagttctccc tgcagctgaa ctctgtgact cccgaggaca cggctgtgta ttactgtgca 300
agagaagtga ctggggatct cgaggatgct tttgatatct ggggccaagg gacaatggtc 360
accgtctcct cagcctccac caagggccca tcggtcttcc ccctggcacc ctcctccaag 420
agcacctctg ggggcacagc ggccctgggc tgcctggtca aggactactt ccccgaaccg 480
gtgacggtgt cgtggaactc aggcgccctg accagcggcg tgcacacctt cccggctgtc 540
ctacagtcct caggactcta ctccctcagc agcgtggtga ctgtgccctc tagcagcttg 600
ggcacccaga cctacatctg caacgtgaat cacaagccca gcaacaccaa ggtggacaag 660
aaagttgagc ccaaatcttg tggcggaggc gggagcaatt atcatcttga aaatgaggtc 720
gctcgtctca agaaactc 738

<210> SEQ ID NO 111
<211> LENGTH: 699

<212> TYPE: DNA
<213> ORGANISM: Artificial Sequence
<220> FEATURE:
<223> OTHER INFORMATION: Made in lab - CD22(m971)-LC_Cterm switch antibody polynucleotide

<400> SEQUENCE: 111
gacatccaga tgacccagtc tccatcgtcc ctgtctgcat ctgtaggaga cagagtcacc 60
atcacttgcc gggcaagcca gaccatttgg agctacttaa attggtatca gcagagacca 120
gggaaagccc ctaacctcct gatctatgct gcatccagtt tgcaaagtgg ggtcccatca 180
aggttcagtg gcaggggatc tgggacagat ttcactctca ccatcagcag tctgcaagct 240
gaagattttg caacttacta ctgtcaacag agttacagta tccctcagac ttttggccag 300
gggaccaagc tggagatcaa acgaactgtg gctgcaccat ctgtcttcat cttcccgcca 360
tctgatgagc agttgaaatc tggaactgcc tctgtcgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgtcctcgc ccgtcacaaa gagcttcaac aggggagagt gtggcggagg cgggagcaat 660
tatcatcttg aaaatgaggt cgctcgtctc aagaaactc 699

<210> SEQ ID NO 112
<211> LENGTH: 660
<212> TYPE: DNA
<213> ORGANISM: Artificial Sequence
<220> FEATURE:
<223> OTHER INFORMATION: Made in lab - CD22(m972)-HC-WT Fab switch antibody polynucleotide

<400> SEQUENCE: 112
gaggtgcaac tcgttcagag cgggggcggc gtcgtcaggc ctggcggctc cctccgtctg 60
ccttgtgctg cctccggctt taccttcgac gattacggaa tgtcctgggt tcgccaggct 120
cctggcaagg gtctggagtg ggtctctggc atcaactgga atggcggcag caccggttat 180
gctgacagtg tgaaggggag gttcacaatt agccgggaca atgccaagaa cagcctgtac 240
ctgcagatga actccctgcg tgctgaggac accgctctgt atcactgcgc gagaggcggt 300
gacgacgcct ttgacatttg gggccagggt accatggtta cagtgagctc tgctagcacc 360
aagggcccga gcgtcttccc tctggccccc agctctaaat ctacttccgg gggcaccgcc 420
gccctcgggt gcctggtgaa ggactatttc cctgagcctg tgacagtgag ctggaactcc 480
ggagcattga cttctggtgt gcacactttc cccgctgtgc tgcagtcctc tggactgtat 540
tccctgtcct ccgtggtgac tgtcccaagc tcctctctgg ggacacagac atacatctgt 600
aatgtgaacc acaaaccgtc caacactaag gtggacaaga aagtggaacc aaagtcttgt 660

<210> SEQ ID NO 113
<211> LENGTH: 645
<212> TYPE: DNA
<213> ORGANISM: Artificial Sequence
<220> FEATURE:
<223> OTHER INFORMATION: Made in lab - CD22(m972)-LC-WT switch antibody polynucleotide

<400> SEQUENCE: 113
cggatcgtta tgacacagtc cccgggcacc ctgagcgtca gccccggaga gaccgctaca 60
ctctcctgca gggcctccca gtcttttagc aacatgctcg cgtggtacca acagaagagc 120
ggacaaccac ctcgcctgct catttatggc gtttctaccc gggcagctgg ggtgcctgcg 180
cggttctctg gctccgggtc cggaactgag tttactctga caattagcaa cctccaatcc 240
gaggactttg ctgtctacta ctgtcaacaa tacggagact ggccgcgcta cacctttggc 300
caagggacta aagtggaaag aaagcgtaca gttgccgctc ctagcgtctt catcttcccc 360
ccctctgatg agcagttgaa gtccggaacc gcctccgtgg tgtgtctgct gaacaacttc 420 taccccccgcg aggctaaggt gcagtggaag gtcgataacg ccttgcaatc tgggaactct 480
caggaaagcg tgacagagca ggactccaaa gacagcacct atagcctgag ctctactctg 540
accctgagca aggctgacta cgagaaacat aaggtttacg catgcgaggt gacccaccag 600
ggactgagta gtcctgtcac caagagtttc aatcgtggcg aatgt 645

<210> SEQ ID NO 114
<211> LENGTH: 744
<212> TYPE: DNA
<213> ORGANISM: Artificial Sequence
<220> FEATURE:
<223> OTHER INFORMATION: Made in lab - CD22(m972)-HC_NT3 switch antibody polynucleotide

<400> SEQUENCE: 114
aattatcatc ttgaaaatga ggtcgctcgt ctcaagaaac tcctggttgg cgaggccgca 60
gctaaggaag ccgcagctaa agccgaggtg caactcgttc agagcggggg cggcgtcgtc 120
aggcctggcg gctccctccg tctgccttgt gctgcctccg gctttacctt cgacgattac 180
ggaatgtcct gggttcgcca ggctcctggc aagggtctgg agtgggtctc tggcatcaac 240
tggaatggcg gcagcaccgg ttatgctgac agtgtgaagg ggaggttcac aattagccgg 300
gacaatgcca agaacagcct gtacctgcag atgaactccc tgcgtgctga ggacaccgct 360
ctgtatcact gcgcgagagg cggtgacgac gcctttgaca tttggggcca gggtaccatg 420
gttacagtga gctctgctag caccaagggc ccgagcgtct tccctctggc ccccagctct 480
aaatctactt ccgggggcac cgccgccctc gggtgcctgg tgaaggacta tttccctgag 540
cctgtgacag tgagctggaa ctccggagca ttgacttctg gtgtgcacac tttccccgct 600
gtgctgcagt cctctggact gtattccctg tcctccgtgg tgactgtccc aagctcctct 660
ctggggacac agacatacat ctgtaatgtg aaccacaaac cgtccaacac taaggtggac 720
aagaaagtgg aaccaaagtc ttgt 744

<210> SEQ ID NO 115
<211> LENGTH: 702
<212> TYPE: DNA
<213> ORGANISM: Artificial Sequence
<220> FEATURE:
<223> OTHER INFORMATION: Made in lab - CD22(m972)-LC_NT1 switch antibody polynucleotide

<400> SEQUENCE: 115
aactatcacc tggaaaacga agtggcaagg ctgaaaaaac tgggcggggg cggaagtcgg 60
atcgttatga cacagtcccc gggcaccctg agcgtcagcc ccggagagac cgctacactc 120
tcctgcaggg cctcccagtc ttttagcaac atgctcgcgt ggtaccaaca gaagagcgga 180
caaccacctc gcctgctcat ttatggcgtt tctacccggg cagctggggt gcctgcgcgg 240
ttctctggct ccgggtccgg aactgagttt actctgacaa ttagcaacct ccaatccgag 300
gactttgctg tctactactg tcaacaatac ggagactggc cgcgctacac ctttggccaa 360
gggactaaag tggaaagaaa gcgtacagtt gccgctccta gcgtcttcat cttccccccc 420
tctgatgagc agttgaagtc cggaaccgcc tccgtggtgt gtctgctgaa caacttctac 480
ccccgcgagg ctaaggtgca gtggaaggtc gataacgcct tgcaatctgg gaactctcag 540
gaaagcgtga cagagcagga ctccaaagac agcacctata gcctgagctc tactctgacc 600
ctgagcaagg ctgactacga gaaacataag gtttacgcat gcgaggtgac ccaccaggga 660
ctgagtagtc ctgtcaccaa gagtttcaat cgtggcgaat gt 702

<210> SEQ ID NO 116
<211> LENGTH: 660
<212> TYPE: DNA
<213> ORGANISM: Artificial Sequence
<220> FEATURE:
<223> OTHER INFORMATION: Made in lab - CD22(m972)-HC_Cterm switch antibody polynucleotide

<400> SEQUENCE: 116
gaggtgcaac tcgttcagag cgggggcggc gtcgtcaggc ctggcggctc cctccgtctg 60
ccttgtgctg cctccggctt taccttcgac gattacggaa tgtcctgggt tcgccaggct 120
cctggcaagg gtctggagtg ggtctctggc atcaactgga atggcggcag caccggttat 180
gctgacagtg tgaaggggag gttcacaatt agccgggaca atgccaagaa cagcctgtac 240
ctgcagatga actccctgcg tgctgaggac accgctctgt atcactgcgc gagaggcggt 300
gacgacgcct ttgacatttg gggccagggt accatggtta cagtgagctc tgctagcacc 360
aagggcccga gcgtcttccc tctggccccc agctctaaat ctacttccgg gggcaccgcc 420
gccctcgggt gcctggtgaa ggactatttc cctgagcctg tgacagtgag ctggaactcc 480
ggagcattga cttctggtgt gcacactttc cccgctgtgc tgcagtcctc tggactgtat 540
tccctgtcct ccgtggtgac tgtcccaagc tcctctctgg ggacacagac atacatctgt 600
aatgtgaacc acaaaccgtc caacactaag gtggacaaga aagtggaacc aaagtcttgt 660

<210> SEQ ID NO 117
<211> LENGTH: 702
<212> TYPE: DNA
<213> ORGANISM: Artificial Sequence
<220> FEATURE:
<223> OTHER INFORMATION: Made in lab - CD22(m972)-LC_Cterm switch antibody polynucleotide

<400> SEQUENCE: 117
cggatcgtta tgacacagtc cccgggcacc ctgagcgtca gccccggaga gaccgctaca 60
ctctcctgca gggcctccca gtcttttagc aacatgctcg cgtggtacca acagaagagc 120
ggacaaccac ctcgcctgct catttatggc gtttctaccc gggcagctgg ggtgcctgcg 180
cggttctctg gctccgggtc cggaactgag tttactctga caattagcaa cctccaatcc 240
gaggactttg ctgtctacta ctgtcaacaa tacggagact ggccgcgcta cacctttggc 300
caagggacta aagtggaaag aaagcgtaca gttgccgctc ctagcgtctt catcttcccc 360
ccctctgatg agcagttgaa gtccggaacc gcctccgtgg tgtgtctgct gaacaacttc 420
tacccccgcg aggctaaggt gcagtggaag gtcgataacg ccttgcaatc tgggaactct 480
caggaaagcg tgacagagca ggactccaaa gacagcacct atagcctgag ctctactctg 540
accctgagca aggctgacta cgagaaacat aaggtttacg catgcgaggt gacccaccag 600
ggactgagta gtcctgtcac caagagtttc aatcgtggcg aatgtggcgg aggcgggagc 660
aattatcatc ttgaaaatga ggtcgctcgt ctcaagaaac tc 702

<210> SEQ ID NO 118
<211> LENGTH: 672
<212> TYPE: DNA
<213> ORGANISM: Artificial Sequence
<220> FEATURE:
<223> OTHER INFORMATION: Made in lab - CD22(CMC544)-HC-WT Fab switch
antibody polynucleotide

<400> SEQUENCE: 118
gaagtgcaac tgcagcagtc cgggactgtg ctggcccgtc ccggagcaag cgtcaagatg 60
agctgtaagg cgtctgggta caggttcacc aattactgga tccactgggt gaaacaaagg 120
ccaggtcagg gtctggaatg gattggtggc atcaacccag gaaataacta taccacttac 180
aaacgtaacc tgaaaggcaa ggccaccctg actgccgtta caagcgccag cactgcttat 240
atggatctga gcagtctcac ctccgaggat tccgctgtgt actactgcac acgcgaaggc 300
tacggtaact atggcgcctg gttcgcctac tggggccagg gcaccttggt taccgtgtcc 360
tctgcgtcca ccaagggacc aagcgtgttt cccctcgccc caagcagcaa gagcacttct 420
ggcggcactg cggctttggg ctgcctggtc aaagattact ttcccgagcc cgttaccgtg 480
agctggaact ccggagctct gacctccggc gttcatacct ttccggcggt gctgcagtcc 540
tctggcctgt attctctgtc ctctgtcgtc accgttcctt cctcctccct cggaacccaa 600
acctacatct gtaacgtgaa ccacaaaccc tctaacacaa aggttgacaa gaaggttgag 660
ccaaaatcct gt 672

<210> SEQ ID NO 119
<211> LENGTH: 657
<212> TYPE: DNA
<213> ORGANISM: Artificial Sequence
<220> FEATURE:
<223> OTHER INFORMATION: Made in lab - CD22(CMC544)-LC-WT switch
antibody polynucleotide

<400> SEQUENCE: 119
gatgtggtcg tgacccagac tccactgtct ctgcctgtga gtttcggtga ccaagtcagc 60
atttcttgca gaagttctca atccctggct aactcttacg gtaacacctt tctgtcttgg 120
tatctggaca aacctggcga gagccctcag ctgctgatct acggcatcag caaccggttc 180
agcggtgtcc ccgaccgctt caccggttct ggctccggca ctgacttcac actgaagatc 240
tctactatca aaccagaaga cttgggcatg tactattgtt tggaaggcac ccaccagcca 300
tatactttcg gtggcggcac aaagctggag atcaaacgca ccgtcgccgc cccttccgtg 360
ttcatctttc ctccttccga cgaacagctg aagagtggca cagcatctgt ggtctgcctg 420
ctgaacaatt tctaccctag agaggccaag gtccagtgga aggtggacaa tgcactccag 480
tccgggaact ctcaggagag tgtgacagag caggattcta aggattccac ttactccctg 540
agctctacat tgactctgtc caaagccgac tacgaaaagc ataaggttta cgcgtgtgaa 600
gtgacccacc agggcctgtc cagccctgtg accaagagtt ttaaccgggg ggagtgc 657

<210> SEQ ID NO 120
<211> LENGTH: 756
<212> TYPE: DNA
<213> ORGANISM: Artificial Sequence
<220> FEATURE:
<223> OTHER INFORMATION: Made in lab - CD22(CMC544)-HC_NT3 switch
antibody polynucleotide

<400> SEQUENCE: 120

```
aattatcatc ttgaaaatga ggtcgctcgt ctcaagaaac tcctggttgg cgaggccgca     60

gctaaggaag ccgcagctaa agccgaagtg caactgcagc agtccgggac tgtgctggcc    120

cgtcccggag caagcgtcaa gatgagctgt aaggcgtctg ggtacaggtt caccaattac    180

tggatccact gggtgaaaca aaggccaggt cagggtctgg aatggattgg tggcatcaac    240

ccaggaaata actataccac ttacaaacgt aacctgaaag gcaaggccac cctgactgcc    300

gttacaagcg ccagcactgc ttatatggat ctgagcagtc tcacctccga ggattccgct    360

gtgtactact gcacacgcga aggctacggt aactatggcg cctggttcgc ctactggggc    420

cagggcacct tggttaccgt gtcctctgcg tccaccaagg gaccaagcgt gtttcccctc    480

gccccaagca gcaagagcac ttctggcggc actgcggctt tgggctgcct ggtcaaagat    540

tactttcccg agcccgttac cgtgagctgg aactccggag ctctgacctc cggcgttcat    600

acctttccgg cggtgctgca gtcctctggc ctgtattctc tgtcctctgt cgtcaccgtt    660

ccttcctcct ccctcggaac ccaaacctac atctgtaacg tgaaccacaa accctctaac    720

acaaaggttg acaagaaggt tgagccaaaa tcctgt                              756
```

<210> SEQ ID NO 121
<211> LENGTH: 714
<212> TYPE: DNA
<213> ORGANISM: Artificial Sequence
<220> FEATURE:
<223> OTHER INFORMATION: Made in lab - CD22(CMC544)-LC_NT1 switch antibody polynucleotide

<400> SEQUENCE: 121

```
aactatcacc tggaaaacga agtggcaagg ctgaaaaaac tgggcggggg cggaagtgat     60

gtggtcgtga cccagactcc actgtctctg cctgtgagtt tcggtgacca agtcagcatt    120

tcttgcagaa gttctcaatc cctggctaac tcttacggta acacctttct gtcttggtat    180

ctggacaaac ctggcgagag ccctcagctg ctgatctacg gcatcagcaa ccggttcagc    240

ggtgtccccg accgcttcac cggttctggc tccggcactg acttcacact gaagatctct    300

actatcaaac cagaagactt gggcatgtac tattgtttgg aaggcaccca ccagccatat    360

actttcggtg gcggcacaaa gctggagatc aaacgcaccg tcgccgcccc ttccgtgttc    420

atctttcctc cttccgacga acagctgaag agtggcacag catctgtggt ctgcctgctg    480

aacaatttct accctagaga ggccaaggtc cagtggaagg tggacaatgc actccagtcc    540

gggaactctc aggagagtgt gacagagcag gattctaagg attccactta ctccctgagc    600

tctacattga ctctgtccaa agccgactac gaaaagcata aggtttacgc gtgtgaagtg    660

acccaccagg gcctgtccag ccctgtgacc aagagtttta accgggggga gtgc          714
```

<210> SEQ ID NO 122
<211> LENGTH: 732
<212> TYPE: DNA
<213> ORGANISM: Artificial Sequence
<220> FEATURE:
<223> OTHER INFORMATION: Made in lab - CD22(CMC544)-HC_Cterm switch antibody polynucleotide

<400> SEQUENCE: 122

```
gaagtgcaac tgcagcagtc cgggactgtg ctggcccgtc ccggagcaag cgtcaagatg     60

agctgtaagg cgtctgggta caggttcacc aattactgga tccactgggt gaaacaaagg    120

ccaggtcagg gtctggaatg gattggtggc atcaacccag gaaataacta taccacttac    180
```

aaacgtaacc tgaaaggcaa ggccaccctg actgccgtta caagcgccag cactgcttat 240
atggatctga gcagtctcac ctccgaggat tccgctgtgt actactgcac acgcgaaggc 300
tacggtaact atggcgcctg gttcgcctac tggggccagg gcaccttggt taccgtgtcc 360
tctgcgtcca ccaagggacc aagcgtgttt cccctcgccc caagcagcaa gagcacttct 420
ggcggcactg cggctttggg ctgcctggtc aaagattact ttcccgagcc cgttaccgtg 480
agctggaact ccggagctct gacctccggc gttcatacct ttccggcggt gctgcagtcc 540
tctggcctgt attctctgtc ctctgtcgtc accgttcctt cctcctccct cggaacccaa 600
acctacatct gtaacgtgaa ccacaaaccc tctaacacaa aggttgacaa gaaggttgag 660
ccaaaatcct gtggcggagg cgggagcaat tatcatcttg aaaatgaggt cgctcgtctc 720
aagaaactct aa 732

<210> SEQ ID NO 123
<211> LENGTH: 714
<212> TYPE: DNA
<213> ORGANISM: Artificial Sequence
<220> FEATURE:
<223> OTHER INFORMATION: Made in lab - CD22(CMC544)-LC_Cterm switch
antibody polynucleotide

<400> SEQUENCE: 123
gatgtggtcg tgacccagac tccactgtct ctgcctgtga gtttcggtga ccaagtcagc 60
atttcttgca gaagttctca atccctggct aactcttacg gtaacacctt tctgtcttgg 120
tatctggaca aacctggcga gagccctcag ctgctgatct acggcatcag caaccggttc 180
agcggtgtcc ccgaccgctt caccggttct ggctccggca ctgacttcac actgaagatc 240
tctactatca aaccagaaga cttgggcatg tactattgtt tggaaggcac ccaccagcca 300
tatactttcg gtggcggcac aaagctggag atcaaacgca ccgtcgccgc cccttccgtg 360
ttcatctttc ctccttccga cgaacagctg aagagtggca cagcatctgt ggtctgcctg 420
ctgaacaatt tctaccctag agaggccaag gtccagtgga aggtggacaa tgcactccag 480
tccgggaact ctcaggagag tgtgacagag caggattcta aggattccac ttactccctg 540
agctctacat tgactctgtc caaagccgac tacgaaaagc ataaggttta cgcgtgtgaa 600
gtgacccacc agggcctgtc cagccctgtg accaagagtt ttaaccgggg ggagtgcggc 660
ggaggcggga gcaattatca tcttgaaaat gaggtcgctc gtctcaagaa actc 714

<210> SEQ ID NO 124
<211> LENGTH: 756
<212> TYPE: DNA
<213> ORGANISM: Artificial Sequence
<220> FEATURE:
<223> OTHER INFORMATION: Made in lab - CD20(RTX)-HC_NT3 switch antibody
polynucleotide

<400> SEQUENCE: 124
aattatcatc ttgaaaatga ggtcgctcgt ctcaagaaac tcctggttgg cgaggccgca 60
gctaaggaag ccgcagctaa agcccaggtg cagctgcagc agccgggcgc ggaactggtg 120
aaaccgggcg cgagcgtgaa aatgagctgc aaagcgagcg gctatacctt taccagctat 180
aacatgcatt gggtgaaaca gacccccggc cgcggcctgg aatggattgg cgcgatttat 240
ccgggcaacg gcgataccag ctataaccag aaatttaaag gcaaagcgac cctgaccgcg 300
gataaaagca gcagcaccgc gtatatgcag ctgagcagcc tgaccagcga agatagcgcg 360
gtgtattatt gcgcgcgcag cacctattat ggcggcgatt ggtattttaa cgtgtggggc 420

```
gcgggcacca ccgtgaccgt gagcgcggcg agcaccaagg gcccatcggt cttccccctg    480

gcaccctcct ccaagagcac ctctgggggc acagcggccc tgggctgcct ggtcaaggac    540

tacttccccg aaccggtgac ggtgtcgtgg aactcaggcg ccctgaccag cggcgtgcac    600

accttcccgg ctgtcctaca gtcctcagga ctctactccc tcagcagcgt ggtgactgtg    660

ccctctagca gcttgggcac ccagacctac atctgcaacg tgaatcacaa gcccagcaac    720

accaaggtgg acaagaaagt tgagcccaaa tcttgt                              756
```

<210> SEQ ID NO 125
<211> LENGTH: 696
<212> TYPE: DNA
<213> ORGANISM: Artificial Sequence
<220> FEATURE:
<223> OTHER INFORMATION: Made in lab - CD20(RTX)-LC_NT1 switch antibody polynucleotide

<400> SEQUENCE: 125

```
aactatcacc tggaaaacga agtggcaagg ctgaaaaaac tgggcggggg cggaagtcag     60

attgtgctga gccagagccc ggcgattctg agcgcgagcc cgggcgaaaa agtgaccatg    120

acctgccgcg cgagcagcag cgtgagctat attcattggt ttcagcagaa accgggcagc    180

agcccgaaac cgtggattta tgcgaccagc aacctggcga gcggcgtgcc ggtgcgcttt    240

agcggcagcg gcagcggcac cagctatagc ctgaccatta gccgcgtgga agcggaagat    300

gcggcgacct attattgcca gcagtggacc agcaacccgc cgacctttgg cggcggcacc    360

aagcttgaga tcaaacgaac tgtggctgca ccatctgtct tcatcttccc gccatctgat    420

gagcagttga aatctggaac tgcctctgtc gtgtgcctgc tgaataactt ctatcccaga    480

gaggccaaag tacagtggaa ggtggataac gccctccaat cgggtaactc ccaggagagt    540

gtcacagagc aggacagcaa ggacagcacc tacagcctca gcagcaccct gacgctgagc    600

aaagcagact acgagaaaca caaagtctac gcctgcgaag tcacccatca gggcctgtcc    660

tcgcccgtca caaagagctt caacagggga gagtgt                              696
```

<210> SEQ ID NO 126
<211> LENGTH: 729
<212> TYPE: DNA
<213> ORGANISM: Artificial Sequence
<220> FEATURE:
<223> OTHER INFORMATION: Made in lab - CD20(RTX)-HC_Cterm switch antibody polynucleotide

<400> SEQUENCE: 126

```
caggtgcagc tgcagcagcc gggcgcggaa ctggtgaaac cgggcgcgag cgtgaaaatg     60

agctgcaaag cgagcggcta tacctttacc agctataaca tgcattgggt gaaacagacc    120

ccgggccgcg gcctggaatg gattggcgcg atttatccgg gcaacggcga taccagctat    180

aaccagaaat ttaaaggcaa agcgaccctg accgcggata aaagcagcag caccgcgtat    240

atgcagctga gcagcctgac cagcgaagat agcgcggtgt attattgcgc gcgcagcacc    300

tattatggcg gcgattggta ttttaacgtg tggggcgcgg gcaccaccgt gaccgtgagc    360

gcggcgagca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg actgtgccct ctagcagctt gggcacccag    600
```

```
acctacatct gcaacgtgaa tcacaagccc agcaacacca aggtggacaa gaaagttgag    660

cccaaatctt gtggcggagg cgggagcaat tatcatcttg aaaatgaggt cgctcgtctc    720

aagaaactc                                                            729


<210> SEQ ID NO 127
<211> LENGTH: 696
<212> TYPE: DNA
<213> ORGANISM: Artificial Sequence
<220> FEATURE:
<223> OTHER INFORMATION: Made in lab - CD20(RTX)-LC_Cterm switch
      antibody polynucleotide

<400> SEQUENCE: 127

cagattgtgc tgagccagag cccggcgatt ctgagcgcga gcccgggcga aaaagtgacc     60

atgacctgcc gcgcgagcag cagcgtgagc tatattcatt ggtttcagca gaaaccgggc    120

agcagcccga aaccgtggat ttatgcgacc agcaacctgg cgagcggcgt gccggtgcgc    180

tttagcggca gcggcagcgg caccagctat agcctgacca ttagccgcgt ggaagcggaa    240

gatgcggcga cctattattg ccagcagtgg accagcaacc cgccgacctt tggcggcggc    300

accaagcttg agatcaaacg aactgtggct gcaccatctg tcttcatctt cccgccatct    360

gatgagcagt tgaaatctgg aactgcctct gtcgtgtgcc tgctgaataa cttctatccc    420

agagaggcca aagtacagtg gaaggtggat aacgccctcc aatcgggtaa ctcccaggag    480

agtgtcacag agcaggacag caaggacagc acctacagcc tcagcagcac cctgacgctg    540

agcaaagcag actacgagaa acacaaagtc tacgcctgcg aagtcaccca tcagggcctg    600

tcctcgcccg tcacaaagag cttcaacagg ggagagtgtg gcggaggcgg gagcaattat    660

catcttgaaa atgaggtcgc tcgtctcaag aaactc                              696


<210> SEQ ID NO 128
<211> LENGTH: 666
<212> TYPE: DNA
<213> ORGANISM: Artificial Sequence
<220> FEATURE:
<223> OTHER INFORMATION: Made in lab - CD20(GA101[34I])-HC-WT Fab switch
      antibody polynucleotide

<400> SEQUENCE: 128

caagtgcagc tcgtgcagag tggcgcagag gtgaagaaac ctggctcaag tgttaaggtg     60

tcctgtaagg ctagtggcta cgctttttct tacagttgga tcaactgggt tcgccaagcc    120

cccgggcagg gattggaatg gatgggcagg atctttccag gcgatggaga cactgactat    180

aacggcaagt ttaagggcag ggtgacaatc acggcggaca aaagcacaag cactgcctac    240

atggagctga gctcactgcg gtcagaggac acggctgtat attactgcgc caggaacgtg    300

ttcgatggct actggctggt gtattggggg cagggcacgc ttgtgactgt tagcagcgca    360

agtactaagg gtccatcagt gttcccactg gctccatcct ctaagtcaac gtctggcggt    420

acagcagctc ttggctgtct cgttaaggac tattttccgg agcctgtgac cgtcagttgg    480

aattctggcg cactgacgtc aggagtgcat acttttcctg ccgtcctgca gagttccgga    540

ctgtacagcc tttcctccgt cgtgactgtt ccatccagca gcctgggaac ccagacctat    600

atttgtaacg tgaaccacaa gccctcaaac accaaggttg acaagaaggt ggagcctaag    660

agttgt                                                               666


<210> SEQ ID NO 129
<211> LENGTH: 666
```

<212> TYPE: DNA
<213> ORGANISM: Artificial Sequence
<220> FEATURE:
<223> OTHER INFORMATION: Made in lab - CD20(GA101[34I])-LC-WT switch
      antibody polynucleotide

<400> SEQUENCE: 129

```
gatatagtaa tgacacaaac gcctctgtct cttcctgtca cgcccggcga accagcctcc     60

atatcctgca gatcatctaa aagtcttctc cactccaacg gaattacgta tttgtactgg    120

tatttgcaga agcctgggca gtctccccaa ctgctgattt atcagatgtc taacttggta    180

agcggggtgc ccgataggtt ttcagggtcc ggaagcggca cagatttcac gctgaagatc    240

agcagagtgg aagccgagga cgtgggcgtg tattattgcg cgcagaattt ggagctccca    300

tataccttcg gaggtgggac caaggtagaa atcaagcgaa ctgtcaggac tgtcgctgcc    360

ccgagcgttt tcatcttccc cccgtctgac gaacagctta aaagcggcac tgcaagcgtg    420

gtgtgcctgc ttaacaattt ctatcccaga gaagcgaagg ttcagtggaa ggtggataac    480

gccctgcaat ctggcaatag ccaggagtcc gttacagaac aagattcaaa agactcaacg    540

tactctctgt cctccacact gaccctgagc aaagctgatt acgaaaaaca taaggtttac    600

gcctgcgagg tcacacacca ggggctttct agtccggtga ctaaatcttt taaccgcggg    660

gaatgt                                                               666
```

<210> SEQ ID NO 130
<211> LENGTH: 750
<212> TYPE: DNA
<213> ORGANISM: Artificial Sequence
<220> FEATURE:
<223> OTHER INFORMATION: Made in lab - CD20(GA101[34I])-HC_NT3 switch
      antibody polynucleotide

<400> SEQUENCE: 130

```
aattatcatc ttgaaaatga ggtcgctcgt ctcaagaaac tcctggttgg cgaggccgca     60

gctaaggaag ccgcagctaa agcccaagtg cagctcgtgc agagtggcgc agaggtgaag    120

aaacctggct caagtgttaa ggtgtcctgt aaggctagtg gctacgcttt ttcttacagt    180

tggatcaact gggttcgcca agcccccggg cagggattgg aatggatggg caggatcttt    240

ccaggcgatg gagacactga ctataacggc aagtttaagg gcagggtgac aatcacggcg    300

gacaaaagca caagcactgc ctacatggag ctgagctcac tgcggtcaga ggacacggct    360

gtatattact gcgccaggaa cgtgttcgat ggctactggc tggtgtattg gggcagggc    420

acgcttgtga ctgttagcag cgcaagtact aagggtccat cagtgttccc actggctcca    480

tcctctaagt caacgtctgg cggtacagca gctcttggct gtctcgttaa ggactatttt    540

ccggagcctg tgaccgtcag ttggaattct ggcgcactga cgtcaggagt gcatactttt    600

cctgccgtcc tgcagagttc cggactgtac agcctttcct ccgtcgtgac tgttccatcc    660

agcagcctgg gaacccagac ctatatttgt aacgtgaacc acaagccctc aaacaccaag    720

gttgacaaga aggtggagcc taagagttgt                                     750
```

<210> SEQ ID NO 131
<211> LENGTH: 723
<212> TYPE: DNA
<213> ORGANISM: Artificial Sequence
<220> FEATURE:
<223> OTHER INFORMATION: Made in lab - CD20(GA101[34I])-LC_NT1 switch
      antibody polynucleotide

<400> SEQUENCE: 131
aactatcacc tggaaaacga agtggcaagg ctgaaaaaac tgggcggggg cggaagtgat 60
atagtaatga cacaaacgcc tctgtctctt cctgtcacgc ccggcgaacc agcctccata 120
tcctgcagat catctaaaag tcttctccac tccaacggaa ttacgtattt gtactggtat 180
ttgcagaagc ctgggcagtc tccccaactg ctgatttatc agatgtctaa cttggtaagc 240
ggggtgcccg ataggttttc agggtccgga agcggcacag atttcacgct gaagatcagc 300
agagtggaag ccgaggacgt gggcgtgtat tattgcgcgc agaatttgga gctcccatat 360
accttcggag gtgggaccaa ggtagaaatc aagcgaactg tcaggactgt cgctgccccg 420
agcgttttca tcttcccccc gtctgacgaa cagcttaaaa gcggcactgc aagcgtggtg 480
tgcctgctta acaatttcta tcccagagaa gcgaaggttc agtggaaggt ggataacgcc 540
ctgcaatctg gcaatagcca ggagtccgtt acagaacaag attcaaaaga ctcaacgtac 600
tctctgtcct ccacactgac cctgagcaaa gctgattacg aaaaacataa ggtttacgcc 660
tgcgaggtca cacaccaggg gctttctagt ccggtgacta aatcttttaa ccgcggggaa 720
tgt 723

<210> SEQ ID NO 132
<211> LENGTH: 723
<212> TYPE: DNA
<213> ORGANISM: Artificial Sequence
<220> FEATURE:
<223> OTHER INFORMATION: Made in lab - CD20(GA101[34I])-HC_Cterm switch antibody polynucleotide

<400> SEQUENCE: 132
caagtgcagc tcgtgcagag tggcgcagag gtgaagaaac ctggctcaag tgttaaggtg 60
tcctgtaagg ctagtggcta cgctttttct tacagttgga tcaactgggt tcgccaagcc 120
cccgggcagg gattggaatg gatgggcagg atctttccag gcgatggaga cactgactat 180
aacggcaagt ttaagggcag ggtgacaatc acggcggaca aaagcacaag cactgcctac 240
atggagctga gctcactgcg gtcagaggac acggctgtat attactgcgc caggaacgtg 300
ttcgatggct actggctggt gtattggggg cagggcacgc ttgtgactgt tagcagcgca 360
agtactaagg gtccatcagt gttcccactg gctccatcct ctaagtcaac gtctggcggt 420
acagcagctc ttggctgtct cgttaaggac tattttccgg agcctgtgac cgtcagttgg 480
aattctggcg cactgacgtc aggagtgcat acttttcctg ccgtcctgca gagttccgga 540
ctgtacagcc tttcctccgt cgtgactgtt ccatccagca gcctgggaac ccagacctat 600
atttgtaacg tgaaccacaa gccctcaaac accaaggttg acaagaaggt ggagcctaag 660
agttgtggcg gaggcgggag caattatcat cttgaaaatg aggtcgctcg tctcaagaaa 720
ctc 723

<210> SEQ ID NO 133
<211> LENGTH: 723
<212> TYPE: DNA
<213> ORGANISM: Artificial Sequence
<220> FEATURE:
<223> OTHER INFORMATION: Made in lab - CD20(GA101[34I])-LC_Cterm switch antibody polynucleotide

<400> SEQUENCE: 133
gatatagtaa tgacacaaac gcctctgtct cttcctgtca cgcccggcga accagcctcc 60
atatcctgca gatcatctaa aagtcttctc cactccaacg gaattacgta tttgtactgg 120

```
tatttgcaga agcctgggca gtctccccaa ctgctgattt atcagatgtc taacttggta    180

agcggggtgc ccgataggtt ttcagggtcc ggaagcggca cagatttcac gctgaagatc    240

agcagagtgg aagccgagga cgtgggcgtg tattattgcg cgcagaattt ggagctccca    300

tataccttcg gaggtgggac caaggtagaa atcaagcgaa ctgtcaggac tgtcgctgcc    360

ccgagcgttt tcatcttccc cccgtctgac gaacagctta aaagcggcac tgcaagcgtg    420

gtgtgcctgc ttaacaattt ctatcccaga gaagcgaagg ttcagtggaa ggtggataac    480

gccctgcaat ctggcaatag ccaggagtcc gttacagaac aagattcaaa agactcaacg    540

tactctctgt cctccacact gaccctgagc aaagctgatt acgaaaaaca taaggtttac    600

gcctgcgagg tcacacacca ggggctttct agtccggtga ctaaatcttt taaccgcggg    660

gaatgtggcg gaggcgggag caattatcat cttgaaaatg aggtcgctcg tctcaagaaa    720

ctc                                                                  723
```

<210> SEQ ID NO 134
<211> LENGTH: 675
<212> TYPE: DNA
<213> ORGANISM: Artificial Sequence
<220> FEATURE:
<223> OTHER INFORMATION: Made in lab - CD20(OFA)-HC-WT Fab switch antibody polynucleotide

<400> SEQUENCE: 134

```
gaggtgcagc tggtcgagtc aggcggaggc ctggttcagc cagggagatc cctcaggctt     60

tcctgcgccg cctccggttt taccttcaac gactacgcta tgcactgggt tcgccaggct    120

cccggaaagg gacttgaatg ggtgagcact atcagctgga attctggaag cattgggtat    180

gccgactccg tcaagggccg ctttactatt tctcgggata atgcgaagaa gtctctgtac    240

ctgcagatga acagtcttcg ggcagaagac acggctcttt actattgcgc aaaagacatc    300

cagtacggaa actattatta cggaatggat gtgtggggtc agggcaccac tgtgacagta    360

agcagtgcta gtacaaaggg accttctgtg tttccacttg ctcctagctc caaatccacg    420

tccgggggca ctgccgctct gggctgcctc gttaaagatt acttcccaga gcctgtcact    480

gtgtcctgga attccggcgc ccttacgtca ggggtacaca catttcccgc ggtactccag    540

tcaagcggct tgtacagcct gtcctccgta gtgacagtgc cttcctcttc tctcggcact    600

caaacttaca tctgcaatgt caatcacaaa ccgagtaaca ctaaggttga caagaaagtt    660

gaacctaaga gctgt                                                     675
```

<210> SEQ ID NO 135
<211> LENGTH: 642
<212> TYPE: DNA
<213> ORGANISM: Artificial Sequence
<220> FEATURE:
<223> OTHER INFORMATION: Made in lab - CD20(OFA)-LC-WT switch antibody polynucleotide

<400> SEQUENCE: 135

```
gaaatcgtcc tgacgcagtc acctgcaacc ctgagtctca gccctggtga gcgggccacc     60

ctgagctgca gggccagcca gagtgtatct tcttacctgg cttggtatca gcagaaacca    120

ggacaggccc caagactgct gatctacgac gcttccaata gagccacggg catccctgcc    180

cgattttccg gatcagggtc cggtacagat ttcacgctga ccatcagctc cctcgagccc    240

gaagattttg ctgtgtatta ttgccagcag cggtccaatt ggcccattac cttcggtcag    300

gggaccaggc tggagattaa acggaccgtg gctgctccct cagttttcat ctttccccca    360
```

```
tctgatgagc agctgaagtc cgggaccgca agcgtcgtgt gcctccttaa caatttttac    420

ccacgagaag ctaaggttca gtggaaggtg gataatgctc tccagtccgg taattctcag    480

gaatcagtga ccgaacagga tagcaaagat tctacctata gcttgtcatc aactctgacc    540

ctctccaaag ccgactacga gaaacacaaa gtctacgcat gcgaggtgac tcaccaaggt    600

ctgagttcac ccgttactaa aagctttaac agaggagaat gt                       642


<210> SEQ ID NO 136
<211> LENGTH: 759
<212> TYPE: DNA
<213> ORGANISM: Artificial Sequence
<220> FEATURE:
<223> OTHER INFORMATION: Made in lab - CD20(OFA)-HC_NT3 switch antibody
      polynucleotide

<400> SEQUENCE: 136

aattatcatc ttgaaaatga ggtcgctcgt ctcaagaaac tcctggttgg cgaggccgca     60

gctaaggaag ccgcagctaa agccgaggtg cagctggtcg agtcaggcgg aggcctggtt    120

cagccaggga gatccctcag gctttcctgc gccgcctccg gttttacctt caacgactac    180

gctatgcact gggttcgcca ggctcccgga aagggacttg aatgggtgag cactatcagc    240

tggaattctg gaagcattgg gtatgccgac tccgtcaagg gccgctttac tatttctcgg    300

gataatgcga agaagtctct gtacctgcag atgaacagtc ttcgggcaga agacacggct    360

ctttactatt gcgcaaaaga catccagtac ggaaactatt attacggaat ggatgtgtgg    420

ggtcagggca ccactgtgac agtaagcagt gctagtacaa agggaccttc tgtgtttcca    480

cttgctccta gctccaaatc cacgtccggg ggcactgccg ctctgggctg cctcgttaaa    540

gattacttcc cagagcctgt cactgtgtcc tggaattccg gcgcccttac gtcaggggta    600

cacacatttc ccgcggtact ccagtcaagc ggcttgtaca gcctgtcctc cgtagtgaca    660

gtgccttcct cttctctcgg cactcaaact tacatctgca atgtcaatca caaaccgagt    720

aacactaagg ttgacaagaa agttgaacct aagagctgt                           759


<210> SEQ ID NO 137
<211> LENGTH: 699
<212> TYPE: DNA
<213> ORGANISM: Artificial Sequence
<220> FEATURE:
<223> OTHER INFORMATION: Made in lab - CD20(OFA)-LC_NT1 switch antibody
      polynucleotide

<400> SEQUENCE: 137

aactatcacc tggaaaacga agtggcaagg ctgaaaaaac tgggcggggg cggaagtgaa     60

atcgtcctga cgcagtcacc tgcaaccctg agtctcagcc ctggtgagcg ggccaccctg    120

agctgcaggg ccagccagag tgtatcttct tacctggctt ggtatcagca gaaaccagga    180

caggccccaa gactgctgat ctacgacgct tccaatagag ccacgggcat ccctgcccga    240

ttttccggat cagggtccgg tacagatttc acgctgacca tcagctccct cgagcccgaa    300

gattttgctg tgtattattg ccagcagcgg tccaattggc ccattacctt cggtcagggg    360

accaggctgg agattaaacg gaccgtggct gctccctcag ttttcatctt tcccccatct    420

gatgagcagc tgaagtccgg gaccgcaagc gtcgtgtgcc tccttaacaa tttttaccca    480

cgagaagcta aggttcagtg gaaggtggat aatgctctcc agtccggtaa ttctcaggaa    540

tcagtgaccg aacaggatag caaagattct acctatagct tgtcatcaac tctgaccctc    600
```

tccaaagccg actacgagaa acacaaagtc tacgcatgcg aggtgactca ccaaggtctg 660
agttcacccg ttactaaaag ctttaacaga ggagaatgt 699

<210> SEQ ID NO 138
<211> LENGTH: 732
<212> TYPE: DNA
<213> ORGANISM: Artificial Sequence
<220> FEATURE:
<223> OTHER INFORMATION: Made in lab - CD20(OFA)-HC_Cterm switch antibody polynucleotide

<400> SEQUENCE: 138
gaggtgcagc tggtcgagtc aggcggaggc ctggttcagc cagggagatc cctcaggctt 60
tcctgcgccg cctccggttt taccttcaac gactacgcta tgcactgggt tcgccaggct 120
cccggaaagg gacttgaatg ggtgagcact atcagctgga attctggaag cattgggtat 180
gccgactccg tcaagggccg ctttactatt tctcgggata atgcgaagaa gtctctgtac 240
ctgcagatga acagtcttcg ggcagaagac acggctcttt actattgcgc aaaagacatc 300
cagtacggaa actattatta cggaatggat gtgtggggtc agggcaccac tgtgacagta 360
agcagtgcta gtacaaaggg accttctgtg tttccacttg ctcctagctc caaatccacg 420
tccgggggca ctgccgctct gggctgcctc gttaaagatt acttcccaga gcctgtcact 480
gtgtcctgga attccggcgc ccttacgtca ggggtacaca catttcccgc ggtactccag 540
tcaagcggct tgtacagcct gtcctccgta gtgacagtgc cttcctcttc tctcggcact 600
caaacttaca tctgcaatgt caatcacaaa ccgagtaaca ctaaggttga caagaaagtt 660
gaacctaaga gctgtggcgg aggcgggagc aattatcatc ttgaaaatga ggtcgctcgt 720
ctcaagaaac tc 732

<210> SEQ ID NO 139
<211> LENGTH: 699
<212> TYPE: DNA
<213> ORGANISM: Artificial Sequence
<220> FEATURE:
<223> OTHER INFORMATION: Made in lab - CD20(OFA)-LC_Cterm switch antibody polynucleotide

<400> SEQUENCE: 139
gaaatcgtcc tgacgcagtc acctgcaacc ctgagtctca gccctggtga gcgggccacc 60
ctgagctgca gggccagcca gagtgtatct tcttacctgg cttggtatca gcagaaacca 120
ggacaggccc caagactgct gatctacgac gcttccaata gagccacggg catccctgcc 180
cgattttccg gatcagggtc cggtacagat ttcacgctga ccatcagctc cctcgagccc 240
gaagattttg ctgtgtatta ttgccagcag cggtccaatt ggcccattac cttcggtcag 300
gggaccaggc tggagattaa acggaccgtg gctgctccct cagttttcat ctttccccca 360
tctgatgagc agctgaagtc cgggaccgca agcgtcgtgt gcctccttaa caatttttac 420
ccacgagaag ctaaggttca gtggaaggtg gataatgctc tccagtccgg taattctcag 480
gaatcagtga ccgaacagga tagcaaagat tctacctata gcttgtcatc aactctgacc 540
ctctccaaag ccgactacga gaaacacaaa gtctacgcat gcgaggtgac tcaccaaggt 600
ctgagttcac ccgttactaa aagctttaac agaggagaat gtggcggagg cgggagcaat 660
tatcatcttg aaaatgaggt cgctcgtctc aagaaactc 699

<210> SEQ ID NO 140
<211> LENGTH: 753

```
<212> TYPE: DNA
<213> ORGANISM: Artificial Sequence
<220> FEATURE:
<223> OTHER INFORMATION: Made in lab - Her2(trastuzumab)-HC_NT3 switch
      antibody polynucleotide

<400> SEQUENCE: 140

aattatcatc ttgaaaatga ggtcgctcgt ctcaagaaac tcctggttgg cgaggccgca     60

gctaaggaag ccgcagctaa agccgaagtg cagctggtgg agtctggcgg aggactggtg    120

cagccagggg gcagcctgag actgtcttgc gccgcctccg gcttcaacat caaggacacc    180

tacatccact gggtccgcca ggcaccaggc aagggactgg aatgggtggc ccggatctac    240

cctaccaacg gctacaccag atacgccgac tccgtgaagg gccggttcac catctccgcc    300

gacacctcca agaacaccgc ctacctgcag atgaattccc tgagggccga ggacaccgcc    360

gtgtactact gctccagatg gggaggcgac ggcttctacg ccatggacta ctggggccag    420

ggcaccctgg tcacagtgtc ctctgctagc accaagggcc catcggtctt ccccctggca    480

ccctcctcca agagcacctc tgggggcaca gcggccctgg gctgcctggt caaggactac    540

ttccccgaac cggtgacggt gtcgtggaac tcaggcgccc tgaccagcgg cgtgcacacc    600

ttcccggctg tcctacagtc ctcaggactc tactccctca gcagcgtggt gaccgtgccc    660

tccagcagct tgggcaccca gacctacatc tgcaacgtga atcacaagcc cagcaacacc    720

aaggtggaca agaaagttga gcccaaatct tgt                                 753


<210> SEQ ID NO 141
<211> LENGTH: 699
<212> TYPE: DNA
<213> ORGANISM: Artificial Sequence
<220> FEATURE:
<223> OTHER INFORMATION: Made in lab - Her2(trastuzumab)-LC_NT1 switch
      antibody polynucleotide

<400> SEQUENCE: 141

aactatcacc tggaaaacga agtggcaagg ctgaaaaaac tgggcggggg cggaagtgac     60

atccagatga cccagtcccc ctcctccctg tctgcctccg tgggcgacag agtgaccatc    120

acctgtcggg cctcccagga tgtgaacacc gccgtggcct ggtatcagca gaagcctggc    180

aaggccccta agctgctgat ctactccgcc tccttcctgt actccggcgt gccctcccgg    240

ttctccggct ccagatccgg caccgacttc accctgacca tctccagcct gcagcctgag    300

gacttcgcca cctactactg ccagcagcac tacaccaccc ctccaacctt cggccagggc    360

accaaggtgg agatcaagcg tacggtggct gcaccatctg tcttcatctt cccgccatct    420

gatgagcagt tgaaatctgg aactgcctct gttgtgtgcc tgctgaataa cttctatccc    480

agagaggcca aagtacagtg gaaggtggat aacgccctcc aatcgggtaa ctcccaggag    540

agtgtcacag agcaggacag caaggacagc acctacagcc tcagcagcac cctgacgctg    600

agcaaagcag actacgagaa acacaaagtc tacgcctgcg aagtcaccca tcagggcctg    660

agctcgcccg tcacaaagag cttcaacagg ggagagtgt                           699


<210> SEQ ID NO 142
<211> LENGTH: 726
<212> TYPE: DNA
<213> ORGANISM: Artificial Sequence
<220> FEATURE:
<223> OTHER INFORMATION: Made in lab - Her2(trastuzumab)-HC_Cterm switch
      antibody polynucleotide

<400> SEQUENCE: 142
```

gaagtgcagc tggtggagtc tggcggagga ctggtgcagc caggggggcag cctgagactg 60 tcttgcgccg cctccggctt caacatcaag gacacctaca tccactgggt ccgccaggca 120
ccaggcaagg gactggaatg ggtggcccgg atctacccta ccaacggcta caccagatac 180
gccgactccg tgaagggccg gttcaccatc tccgccgaca cctccaagaa caccgcctac 240
ctgcagatga attccctgag ggccgaggac accgccgtgt actactgctc cagatgggga 300
ggcgacggct tctacgccat ggactactgg ggccagggca ccctggtcac agtgtcctct 360
gctagcacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagaa agttgagccc 660
aaatcttgtg gcggaggcgg gagcaattat catcttgaaa atgaggtcgc tcgtctcaag 720
aaactc 726

<210> SEQ ID NO 143
<211> LENGTH: 699
<212> TYPE: DNA
<213> ORGANISM: Artificial Sequence
<220> FEATURE:
<223> OTHER INFORMATION: Made in lab - Her2(trastuzumab)-LC_Cterm switch antibody polynucleotide

<400> SEQUENCE: 143
gacatccaga tgacccagtc cccctcctcc ctgtctgcct ccgtgggcga cagagtgacc 60
atcacctgtc gggcctccca ggatgtgaac accgccgtgg cctggtatca gcagaagcct 120
ggcaaggccc ctaagctgct gatctactcc gcctccttcc tgtactccgg cgtgccctcc 180
cggttctccg gctccagatc cggcaccgac ttcaccctga ccatctccag cctgcagcct 240
gaggacttcg ccacctacta ctgccagcag cactacacca cccctccaac cttcggccag 300
ggcaccaagg tggagatcaa gcgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gtggcggagg cgggagcaat 660
tatcatcttg aaaatgaggt cgctcgtctc aagaaactc 699

<210> SEQ ID NO 144
<211> LENGTH: 672
<212> TYPE: DNA
<213> ORGANISM: Artificial Sequence
<220> FEATURE:
<223> OTHER INFORMATION: Made in lab - BCMA(BCMA-98)-HC-WT Fab switch antibody polynucleotide

<400> SEQUENCE: 144
gaagttcagc tggttgaatc tggtggtggt ctggttcagc cgggtggttc tctgcgtctg 60
tcttgcgctg cttctggttt caccttctct aacttcgaca tggcttgggt tcgtcaggct 120
ccgggtaaag gtctggtttg ggtttcttct atcaccaccg gtggtggtga cacctactac 180
gctgactctg ttaaaggtcg tttcaccatc tctcgtgaca acgctaaatc taccctgtac 240
ctgcagatgg actctctgcg ttctgaagac accgctgttt actactgcgt tcgtcacggt 300
tactacgacg gttaccacct gttcgactac tggggtcagg gtaccctggt taccgtttct 360
tctgcctcca ccaagggccc atcggtcttc cccctggcac cctcctccaa gagcacctct 420
gggggcacag cggccctggg ctgcctggtc aaggactact tccccgaacc ggtgacggtg 480
tcgtggaact caggcgccct gaccagcggc gtgcacacct tcccggctgt cctacagtcc 540
tcaggactct actccctcag cagcgtggtg actgtgccct ctagcagctt gggcacccag 600
acctacatct gcaacgtgaa tcacaagccc agcaacacca aggtggacaa gaaagttgag 660
cccaaatctt gt 672

<210> SEQ ID NO 145
<211> LENGTH: 699
<212> TYPE: DNA
<213> ORGANISM: Artificial Sequence
<220> FEATURE:
<223> OTHER INFORMATION: Made in lab - BCMA(BCMA-98)-LC-NT1 switch
antibody polynucleotide

<400> SEQUENCE: 145
aactaccacc tggagaatga agtcgccaga ctgaagaaac tgggcggggg aggctcagac 60
atccagatga cccagtctcc gtcttctctg tctgcttctg ttggtgaccg tgttaccatc 120
acctgccgtg ctaaccaggg tatctctaac aacctgaact ggtaccagca gaaaccgggt 180
aaagctccga aaccgctgat ctactacacc tctaacctgc agtctggtgt tccgtctcgt 240
ttctctggtt ctggttctgg taccgactac accctgacca tctcttctct gcagccggaa 300
gacttcgcta cctactactg ccagcagttc acctctctgc cgtacacctt cggtcagggt 360
accaaactgg aaatcaaacg aactgtggct gcaccatctg tcttcatctt cccgccatct 420
gatgagcagt tgaaatctgg aactgcctct gtcgtgtgcc tgctgaataa cttctatccc 480
agagaggcca aagtacagtg gaaggtggat aacgccctcc aatcgggtaa ctcccaggag 540
agtgtcacag agcaggacag caaagacagc acctacagcc tcagcagcac cctgacgctg 600
agcaaagcag actacgagaa acacaaagtc tacgcctgcg aagtcaccca tcagggcctg 660
tcctcgcccg tcacaaagag cttcaacagg ggagagtgt 699

<210> SEQ ID NO 146
<211> LENGTH: 714
<212> TYPE: DNA
<213> ORGANISM: Artificial Sequence
<220> FEATURE:
<223> OTHER INFORMATION: Made in lab - BCMA(BCMA-98)-LC-NT2 switch
antibody polynucleotide

<400> SEQUENCE: 146
aactaccacc tggagaatga agtcgccaga ctgaagaaac tgggcggggg aggctcaggg 60
ggaggcgggt cagacatcca gatgacccag tctccgtctt ctctgtctgc ttctgttggt 120
gaccgtgtta ccatcacctg ccgtgctaac cagggtatct ctaacaacct gaactggtac 180
cagcagaaac cgggtaaagc tccgaaaccg ctgatctact acacctctaa cctgcagtct 240
ggtgttccgt ctcgtttctc tggttctggt tctggtaccg actacaccct gaccatctct 300
tctctgcagc cggaagactt cgctacctac tactgccagc agttcacctc tctgccgtac 360
accttcggtc agggtaccaa actggaaatc aaacgaactg tggctgcacc atctgtcttc 420
atcttcccgc catctgatga gcagttgaaa tctggaactg cctctgtcgt gtgcctgctg 480
aataacttct atcccagaga ggccaaagta cagtggaagg tggataacgc cctccaatcg 540
ggtaactccc aggagagtgt cacagagcag gacagcaaag acagcaccta cagcctcagc 600
agcaccctga cgctgagcaa agcagactac gagaaacaca aagtctacgc ctgcgaagtc 660
acccatcagg gcctgtcctc gcccgtcaca aagagcttca acaggggaga gtgt 714

<210> SEQ ID NO 147
<211> LENGTH: 729
<212> TYPE: DNA
<213> ORGANISM: Artificial Sequence
<220> FEATURE:
<223> OTHER INFORMATION: Made in lab - BCMA(BCMA-98)-HC-NT1 switch antibody polynucleotide

<400> SEQUENCE: 147
aactaccacc tggagaatga agtcgccaga ctgaagaaac tgggcggggg aggctcagaa 60
gttcagctgg ttgaatctgg tggtggtctg gttcagccgg gtggttctct gcgtctgtct 120
tgcgctgctt ctggtttcac cttctctaac ttcgacatgg cttgggttcg tcaggctccg 180
ggtaaaggtc tggtttgggt ttcttctatc accaccggtg gtggtgacac ctactacgct 240
gactctgtta aaggtcgttt caccatctct cgtgacaacg ctaaatctac cctgtacctg 300
cagatggact ctctgcgttc tgaagacacc gctgtttact actgcgttcg tcacggttac 360
tacgacggtt accacctgtt cgactactgg ggtcagggta ccctggttac cgtttcttct 420
gcctccacca agggcccatc ggtcttcccc ctggcaccct cctccaagag cacctctggg 480
ggcacagcgg ccctgggctg cctggtcaag gactacttcc ccgaaccggt gacggtgtcg 540
tggaactcag gcgccctgac cagcggcgtg cacaccttcc cggctgtcct acagtcctca 600
ggactctact ccctcagcag cgtggtgact gtgccctcta gcagcttggg cacccagacc 660
tacatctgca acgtgaatca caagcccagc aacaccaagg tggacaagaa agttgagccc 720
aaatcttgt 729

<210> SEQ ID NO 148
<211> LENGTH: 744
<212> TYPE: DNA
<213> ORGANISM: Artificial Sequence
<220> FEATURE:
<223> OTHER INFORMATION: Made in lab - BCMA(BCMA-98)-HC-NT2 switch antibody polynucleotide

<400> SEQUENCE: 148
aactaccacc tggagaatga agtcgccaga ctgaagaaac tgggcggggg aggctcaggg 60
ggaggcgggt cagaagttca gctggttgaa tctggtggtg gtctggttca gccgggtggt 120
tctctgcgtc tgtcttgcgc tgcttctggt ttcaccttct ctaacttcga catggcttgg 180
gttcgtcagg ctccgggtaa aggtctggtt tgggtttctt ctatcaccac cggtggtggt 240
gacacctact acgctgactc tgttaaaggt cgtttcacca tctctcgtga caacgctaaa 300
tctaccctgt acctgcagat ggactctctg cgttctgaag acaccgctgt ttactactgc 360
gttcgtcacg gttactacga cggttaccac ctgttcgact actggggtca gggtaccctg 420
gttaccgttt cttctgcctc caccaagggc ccatcggtct tccccctggc accctcctcc 480
aagagcacct ctgggggcac agcggccctg ggctgcctgg tcaaggacta cttccccgaa 540
ccggtgacgg tgtcgtggaa ctcaggcgcc ctgaccagcg gcgtgcacac cttcccggct 600
gtcctacagt cctcaggact ctactccctc agcagcgtgg tgactgtgcc ctctagcagc 660
ttgggcaccc agacctacat ctgcaacgtg aatcacaagc ccagcaacac caaggtggac 720
aagaaagttg agcccaaatc ttgt 744

<210> SEQ ID NO 149
<211> LENGTH: 633
<212> TYPE: DNA
<213> ORGANISM: Artificial Sequence
<220> FEATURE:
<223> OTHER INFORMATION: Made in lab - CD19(huB4)-LC-WT switch antibody polynucleotide

<400> SEQUENCE: 149
gagattgtcc tgacccagtc ccctgctatt atgtctgctt cccccggcga aagagtgacc 60
atgacctgta gtgcctccag cggcgtcaac tacatgcact ggtatcagca gaagccaggg 120
acctctcccc ggagatggat ctacgacaca tcaaagctgg ccagcggagt gcctgcacgg 180
ttctccggat ctggcagtgg gactgactat agcctgacca tcagcagcat ggagccagaa 240
gatgccgcta cctactattg ccatcagagg ggctcctaca catttggcgg gggaactaag 300
ctggagatca aacgcacagt ggcagccccc agcgtcttca tttttccccc ttccgatgaa 360
cagctgaagt ccggcactgc ttctgtggtc tgtctgctga acaatttcta tcccagagag 420
gccaaggtgc agtggaaagt ggacaacgct ctgcagtccg gcaacagcca ggagagtgtg 480
accgaacagg atagtaagga cagcacatat tctctgtcta gtaccctgac actgagtaag 540
gcagattacg agaagcacaa agtgtatgcc tgcgaagtca ctcatcaggg actgtcaagc 600
cccgtgacca agagcttcaa ccggggcgag tgt 633

<210> SEQ ID NO 150
<211> LENGTH: 669
<212> TYPE: DNA
<213> ORGANISM: Artificial Sequence
<220> FEATURE:
<223> OTHER INFORMATION: Made in lab - CD19(huB4)-HC-WT Fab switch antibody polynucleotide

<400> SEQUENCE: 150
caggtgcagc tggtccagcc aggggcagag gtcgtcaagc caggagcatc cgtcaaactg 60
tcatgtaaaa caagcgggta tactttcacc agcaattgga tgcactgggt gaagcaggcc 120
cccggacagg gcctggagtg gatcggggaa attgacccta gtgattcata cactaactac 180
aaccagaact tccagggaaa ggccaaactg accgtggaca aaagcacctc cacagcttat 240
atggaggtga gcagcctgcg gtccgacgat actgcagtct actattgcgc cagaggctct 300
aacccttact attacgctat ggattactgg gggcagggaa caagcgtgac tgtctctagt 360
gcatcaacaa agggaccaag cgtgtttcca ctggcccccct caagcaagag cacctccgga 420
gggacagccg ctctgggatg tctggtgaaa gactacttcc ccgagcctgt gactgtctct 480
tggaatagtg gcgctctgac ctccggggtg cacacatttc cagcagtcct gcagtcctct 540
ggactgtatt ctctgagttc agtggtcacc gtgcccagct cctctctggg cactcagacc 600
tacatctgca atgtcaacca taagcctagt aacacaaaag tggataagaa agtcgaacca 660
aagagctgt 669

<210> SEQ ID NO 151
<211> LENGTH: 702
<212> TYPE: DNA
<213> ORGANISM: Artificial Sequence
<220> FEATURE:
<223> OTHER INFORMATION: Made in lab - CD19(huB4)-LC1 switch antibody polynucleotide

<400> SEQUENCE: 151
gagattgtcc tgacccagtc ccctgctatt atgtctgctt cccccggcga aagagtgacc 60
atgacctgta gtgcctccag cggcgtcaac tacatgcact ggtatcagca gaagccaggg 120
acctctcccc ggagatggat ctacgacaca tcaaagctgg ccagcggagt gcctgcacgg 180
ttctccggat ctggcagtgg gactgactat agcctgacca tcagcagcat ggagccagaa 240
gatgccgcta cctactattg ccatcagagg ggctcctaca catttggcgg gggaactaag 300
ctggagatca aacgcacagt ggcagccccc agcgtcttca tttttccccc ttccgatgaa 360
cagctgaagt ccggcactgc ttctgtggtc tgtctgctga acaatttcta tcccagagag 420
gccaaggtgc agtggaaagt ggacaacgct ctgcagtccg gcaacagcca ggagagtgtg 480
accgaacagg atagtggcgg gggaggctca aactaccacc tggagaatga agtcgccaga 540
ctgaagaaac tgggggaggg cgggtcagac agcacatatt ctctgtctag taccctgaca 600
ctgagtaagg cagattacga gaagcacaaa gtgtatgcct gcgaagtcac tcatcaggga 660
ctgtcaagcc ccgtgaccaa gagcttcaac cggggcgagt gt 702

<210> SEQ ID NO 152
<211> LENGTH: 702
<212> TYPE: DNA
<213> ORGANISM: Artificial Sequence
<220> FEATURE:
<223> OTHER INFORMATION: Made in lab - CD19(huB4)-HC1 switch antibody
polynucleotide

<400> SEQUENCE: 152
caggtgcagc tggtccagcc aggggcagag gtcgtcaagc caggagcatc cgtcaaactg 60
tcatgtaaaa caagcgggta tactttcacc agcaattgga tgcactgggt gaagcaggcc 120
cccggacagg gcctggagtg gatcggggaa attgacccta gtgattcata cactaactac 180
aaccagaact tccagggaaa ggccaaactg accgtggaca aaagcacctc cacagcttat 240
atggaggtga gcagcctgcg gtccgacgat actgcagtct actattgcgc cagaggctct 300
aacccttact attacgctat ggattactgg gggcagggaa caagcgtgac tgtctctagt 360
gcatcaacaa agggaccaag cgtgtttcca ctggccccct caagcaatta tcatctggag 420
aacgaagtgg ccaggctgaa gaaactgtcc ggagggacag ccgctctggg atgtctggtg 480
aaagactact tccccgagcc tgtgactgtc tcttggaata gtggcgctct gacctccggg 540
gtgcacacat ttccagcagt cctgcagtcc tctggactgt attctctgag ttcagtggtc 600
accgtgccca gctcctctct gggcactcag acctacatct gcaatgtcaa ccataagcct 660
agtaacacaa aagtggataa gaaagtcgaa ccaaagagct gt 702

<210> SEQ ID NO 153
<211> LENGTH: 690
<212> TYPE: DNA
<213> ORGANISM: Artificial Sequence
<220> FEATURE:
<223> OTHER INFORMATION: Made in lab - CD19(huB4)-LC-NT1 switch antibody
polynucleotide

<400> SEQUENCE: 153
aactaccacc tggagaatga agtcgccaga ctgaagaaac tgggcggggg aggctcagag 60
attgtcctga cccagtcccc tgctattatg tctgcttccc ccggcgaaag agtgaccatg 120
acctgtagtg cctccagcgg cgtcaactac atgcactggt atcagcagaa gccagggacc 180
tctccccgga gatggatcta cgacacatca aagctggcca gcggagtgcc tgcacggttc 240
tccggatctg gcagtgggac tgactatagc ctgaccatca gcagcatgga gccagaagat 300
gccgctacct actattgcca tcagaggggc tcctacacat ttggcggggg aactaagctg 360
gagatcaaac gcacagtggc agcccccagc gtcttcattt ttcccccttc cgatgaacag 420
ctgaagtccg gcactgcttc tgtggtctgt ctgctgaaca atttctatcc cagagaggcc 480
aaggtgcagt ggaaagtgga caacgctctg cagtccggca acagccagga gagtgtgacc 540
gaacaggata gtaaggacag cacatattct ctgtctagta ccctgacact gagtaaggca 600
gattacgaga agcacaaagt gtatgcctgc gaagtcactc atcagggact gtcaagcccc 660
gtgaccaaga gcttcaaccg gggcgagtgt 690

<210> SEQ ID NO 154
<211> LENGTH: 705
<212> TYPE: DNA
<213> ORGANISM: Artificial Sequence
<220> FEATURE:
<223> OTHER INFORMATION: Made in lab - CD19(huB4)-LC-NT2 switch antibody polynucleotide

<400> SEQUENCE: 154
aactaccacc tggagaatga agtcgccaga ctgaagaaac tgggcggggg aggctcaggg 60
ggaggcgggt cagagattgt cctgacccag tcccctgcta ttatgtctgc ttcccccggc 120
gaaagagtga ccatgacctg tagtgcctcc agcggcgtca actacatgca ctggtatcag 180
cagaagccag ggacctctcc ccggagatgg atctacgaca catcaaagct ggccagcgga 240
gtgcctgcac ggttctccgg atctggcagt gggactgact atagcctgac catcagcagc 300
atggagccag aagatgccgc tacctactat tgccatcaga ggggctccta cacatttggc 360
gggggaacta agctggagat caaacgcaca gtggcagccc ccagcgtctt catttttccc 420
ccttccgatg aacagctgaa gtccggcact gcttctgtgg tctgtctgct gaacaatttc 480
tatcccagag aggccaaggt gcagtggaaa gtggacaacg ctctgcagtc cggcaacagc 540
caggagagtg tgaccgaaca ggatagtaag gacagcacat attctctgtc tagtaccctg 600
acactgagta aggcagatta cgagaagcac aaagtgtatg cctgcgaagt cactcatcag 660
ggactgtcaa gccccgtgac caagagcttc aaccggggcg agtgt 705

<210> SEQ ID NO 155
<211> LENGTH: 726
<212> TYPE: DNA
<213> ORGANISM: Artificial Sequence
<220> FEATURE:
<223> OTHER INFORMATION: Made in lab - CD19(huB4)-HC-NT1 switch antibody polynucleotide

<400> SEQUENCE: 155
aactaccacc tggagaatga agtcgccaga ctgaagaaac tgggcggggg aggctcacag 60
gtgcagctgg tccagccagg ggcagaggtc gtcaagccag gagcatccgt caaactgtca 120
tgtaaaacaa gcgggtatac tttcaccagc aattggatgc actgggtgaa gcaggccccc 180
ggacagggcc tggagtggat cggggaaatt gaccctagtg attcatacac taactacaac 240
cagaacttcc agggaaaggc caaactgacc gtggacaaaa gcacctccac agcttatatg 300
gaggtgagca gcctgcggtc cgacgatact gcagtctact attgcgccag aggctctaac 360
ccttactatt acgctatgga ttactggggg cagggaacaa gcgtgactgt ctctagtgca 420

```
tcaacaaagg gaccaagcgt gtttccactg gccccctcaa gcaagagcac ctccggaggg    480

acagccgctc tgggatgtct ggtgaaagac tacttccccg agcctgtgac tgtctcttgg    540

aatagtggcg ctctgacctc cggggtgcac acatttccag cagtcctgca gtcctctgga    600

ctgtattctc tgagttcagt ggtcaccgtg cccagctcct ctctgggcac tcagacctac    660

atctgcaatg tcaaccataa gcctagtaac acaaaagtgg ataagaaagt cgaaccaaag    720

agctgt                                                               726
```

<210> SEQ ID NO 156
<211> LENGTH: 741
<212> TYPE: DNA
<213> ORGANISM: Artificial Sequence
<220> FEATURE:
<223> OTHER INFORMATION: Made in lab - CD19(huB4)-HC-NT2 switch antibody polynucleotide

<400> SEQUENCE: 156

```
aactaccacc tggagaatga agtcgccaga ctgaagaaac tgggcggggg aggctcaggg     60

ggaggcgggt cacaggtgca gctggtccag ccaggggcag aggtcgtcaa gccaggagca    120

tccgtcaaac tgtcatgtaa aacaagcggg tatactttca ccagcaattg gatgcactgg    180

gtgaagcagg cccccggaca gggcctggag tggatcgggg aaattgaccc tagtgattca    240

tacactaact acaaccagaa cttccaggga aaggccaaac tgaccgtgga caaaagcacc    300

tccacagctt atatggaggt gagcagcctg cggtccgacg atactgcagt ctactattgc    360

gccagaggct ctaaccctta ctattacgct atggattact gggggcaggg aacaagcgtg    420

actgtctcta gtgcatcaac aaagggacca agcgtgtttc cactggcccc ctcaagcaag    480

agcacctccg gagggacagc cgctctggga tgtctggtga aagactactt ccccgagcct    540

gtgactgtct cttggaatag tggcgctctg acctccgggg tgcacacatt tccagcagtc    600

ctgcagtcct ctggactgta ttctctgagt tcagtggtca ccgtgcccag ctcctctctg    660

ggcactcaga cctacatctg caatgtcaac cataagccta gtaacacaaa agtggataag    720

aaagtcgaac caaagagctg t                                              741
```

<210> SEQ ID NO 157
<211> LENGTH: 672
<212> TYPE: DNA
<213> ORGANISM: Artificial Sequence
<220> FEATURE:
<223> OTHER INFORMATION: Made in lab - CEA(A5B7)-HC-WT Fab switch antibody polynucleotide

<400> SEQUENCE: 157

```
caggtccaac tgcaggagtc aggaggaggc ttggtacagc ctgggggttc tctgagactc     60

tcctgtgcaa cttctgggtt caccttcact gattactaca tgaactgggt ccgccagcct    120

ccaggaaagg cacttgagtg gttgggtttt attggaaaca aagctaatgg ttacacaaca    180

gagtacagtg catctgtgaa gggtcggttc accatctcca gagataaatc ccaaagcatc    240

ctctatcttc aaatgaacac cctgagagct gaggacagtg ccacttatta ctgtaccaga    300

gatagggggc tacggttcta ctttgactac tggggccaag ggaccacggt caccgtctcc    360

tcagcctcca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg actgtgccct ctagcagctt gggcacccag    600
```

acctacatct gcaacgtgaa tcacaagccc agcaacacca aggtggacaa gaaagttgag 660
cccaaatctt gt 672

<210> SEQ ID NO 158
<211> LENGTH: 711
<212> TYPE: DNA
<213> ORGANISM: Artificial Sequence
<220> FEATURE:
<223> OTHER INFORMATION: Made in lab - CEA(A5B7)-CL1 switch antibody polynucleotide

<400> SEQUENCE: 158
gacattgagc tcacccagtc tccagcaatc ctgtctgcat ctccagggga gaaggtcaca 60
atgacttgca gggccagctc aagtgtaact tacattcact ggtaccagca gaagccagga 120
tcctccccca aatcctggat ttatgccaca tccaacctgg cttctggagt ccctgctcgc 180
ttcagtggca gtgggtctgg gacctcttac tctctcacaa tcagcagagt ggaggctgaa 240
gatgctgcca cttattactg ccaacattgg agtagtaaac caccgacgtt cggtggaggg 300
accaagctcg agatcaaaaa acgaactgtg gctgcaccat ctgtcttcat cttcccgcca 360
tctgatgagc agttgaaatc tggaactgcc tctgtcgtgt gcctgctgaa taacttctat 420
cccagagagg ccaaagtaca gtggaaggtg gataacgccc tccaatcggg taactcccag 480
gagagtgtca cagagcagga cagcggcgga ggcgggagca attatcatct tgaaaatgag 540
gtcgctcgtc tcaagaaact cggtggcgga ggcagcgaca gcacctacag cctcagcagc 600
accctgacgc tgagcaaagc agactacgag aaacacaaag tctacgcctg cgaagtcacc 660
catcagggcc tgtcctcgcc cgtcacaaag agcttcaaca ggggagagtg t 711

<210> SEQ ID NO 159
<211> LENGTH: 642
<212> TYPE: DNA
<213> ORGANISM: Artificial Sequence
<220> FEATURE:
<223> OTHER INFORMATION: Made in lab - CEA(A5B7)-LC-WT switch antibody polynucleotide

<400> SEQUENCE: 159
gacattgagc tcacccagtc tccagcaatc ctgtctgcat ctccagggga gaaggtcaca 60
atgacttgca gggccagctc aagtgtaact tacattcact ggtaccagca gaagccagga 120
tcctccccca aatcctggat ttatgccaca tccaacctgg cttctggagt ccctgctcgc 180
ttcagtggca gtgggtctgg gacctcttac tctctcacaa tcagcagagt ggaggctgaa 240
gatgctgcca cttattactg ccaacattgg agtagtaaac caccgacgtt cggtggaggg 300
accaagctcg agatcaaaaa acgaactgtg gctgcaccat ctgtcttcat cttcccgcca 360
tctgatgagc agttgaaatc tggaactgcc tctgtcgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgtcctcgc ccgtcacaaa gagcttcaac aggggagagt gt 642

<210> SEQ ID NO 160
<211> LENGTH: 729
<212> TYPE: DNA
<213> ORGANISM: Artificial Sequence
<220> FEATURE:

<223> OTHER INFORMATION: Made in lab - CEA(A5B7)-HC-Cterm switch
antibody polynucleotide

<400> SEQUENCE: 160
caggtccaac tgcaggagtc aggaggaggc ttggtacagc ctgggggttc tctgagactc 60
tcctgtgcaa cttctgggtt caccttcact gattactaca tgaactgggt ccgccagcct 120
ccaggaaagg cacttgagtg gttgggtttt attggaaaca aagctaatgg ttacacaaca 180
gagtacagtg catctgtgaa gggtcggttc accatctcca gagataaatc ccaaagcatc 240
ctctatcttc aaatgaacac cctgagagct gaggacagtg ccacttatta ctgtaccaga 300 gataggggc tacggttcta ctttgactac tggggccaag ggaccacggt caccgtctcc 360
tcagcctcca ccaagggccc atcggtcttc cccctggcac cctcctccaa gagcacctct 420
gggggcacag cggccctggg ctgcctggtc aaggactact tccccgaacc ggtgacggtg 480
tcgtggaact caggcgccct gaccagcggc gtgcacacct tcccggctgt cctacagtcc 540
tcaggactct actccctcag cagcgtggtg actgtgccct ctagcagctt gggcacccag 600
acctacatct gcaacgtgaa tcacaagccc agcaacacca aggtggacaa gaaagttgag 660
cccaaatctt gtggcggagg cgggagcaat tatcatcttg aaaatgaggt cgctcgtctc 720
aagaaactc 729

<210> SEQ ID NO 161
<211> LENGTH: 756
<212> TYPE: DNA
<213> ORGANISM: Artificial Sequence
<220> FEATURE:
<223> OTHER INFORMATION: Made in lab - CD33(hM195)-HC_NT3 switch
antibody polynucleotide

<400> SEQUENCE: 161
aattatcatc ttgaaaatga ggtcgctcgt ctcaagaaac tcctggttgg cgaggccgca 60
gctaaggaag ccgcagctaa agcccaggtg cagctggtgc agagcggcgc ggaagtgaaa 120
aaaccgggca gcagcgtgaa agtgagctgc aaagcgagcg gctatacctt taccgattat 180
aacatgcatt gggtgcgcca ggcgccgggc cagggcctgg aatggattgg ctatatttat 240
ccgtataacg gcggcaccgg ctataaccag aaatttaaaa gcaaagcgac cattaccgcg 300
gatgaaagca ccaacaccgc gtatatggaa ctgagcagcc tgcgcagcga agataccgcg 360
gtgtattatt gcgcgcgcgg ccgcccggcg atggattatt ggggccaggg caccctggtg 420
accgtgagca gcgcctccac caagggccca tcggtcttcc ccctggcacc ctcctccaag 480
agcacctctg ggggcacagc ggccctgggc tgcctggtca aggactactt ccccgaaccg 540
gtgacggtgt cgtggaactc aggcgccctg accagcggcg tgcacacctt cccggctgtc 600
ctacagtcct caggactcta ctccctcagc agcgtggtga ctgtgccctc tagcagcttg 660
ggcacccaga cctacatctg caacgtgaat cacaagccca gcaacaccaa ggtggacaag 720
aaagttgagc ccaaatcttg tgacaaaact cacaca 756

<210> SEQ ID NO 162
<211> LENGTH: 711
<212> TYPE: DNA
<213> ORGANISM: Artificial Sequence
<220> FEATURE:
<223> OTHER INFORMATION: Made in lab - CD33(hM195)-LC_NT1 switch
antibody polynucleotide

<400> SEQUENCE: 162
aactatcacc tggaaaacga agtggcaagg ctgaaaaaac tgggcggggg cggaagtgat 60
attcagatga cccagagccc gagcagcctg agcgcgagcg tgggcgatcg cgtgaccatt 120
acctgccgcg cgagcgaaag cgtggataac tatggcatta gctttatgaa ctggtttcag 180
cagaaaccgg gcaaagcgcc gaaactgctg atttatgcgg cgagcaacca gggcagcggc 240
gtgccgagcc gctttagcgg cagcggcagc ggcaccgatt ttaccctgaa cattagcagc 300
ctgcagccgg atgattttgc gacctattat tgccagcaga gcaaagaagt gccgtggacc 360
tttggccagg gcaccaaagt ggaaattaaa cgaactgtgg ctgcaccatc tgtcttcatc 420
ttcccgccat ctgatgagca gttgaaatct ggaactgcct ctgttgtgtg cctgctgaat 480
aacttctatc ccagagaggc caaagtacag tggaaggtgg ataacgccct ccaatcgggt 540
aactcccagg agagtgtcac agagcaggac agcaaggaca gcacctacag cctcagcagc 600
accctgacgc tgagcaaagc agactacgag aaacacaaag tctacgcctg cgaagtcacc 660
catcagggcc tgagctcgcc cgtcacaaag agcttcaaca ggggagagtg t 711

<210> SEQ ID NO 163
<211> LENGTH: 729
<212> TYPE: DNA
<213> ORGANISM: Artificial Sequence
<220> FEATURE:
<223> OTHER INFORMATION: Made in lab - CD33(hM195)-HC_Cterm switch antibody polynucleotide

<400> SEQUENCE: 163
caggtgcagc tggtgcagag cggcgcggaa gtgaaaaaac cgggcagcag cgtgaaagtg 60
agctgcaaag cgagcggcta tacctttacc gattataaca tgcattgggt gcgccaggcg 120
ccgggccagg gcctggaatg gattggctat atttatccgt ataacggcgg caccggctat 180
aaccagaaat ttaaaagcaa agcgaccatt accgcggatg aaagcaccaa caccgcgtat 240
atggaactga gcagcctgcg cagcgaagat accgcggtgt attattgcgc gcgcggccgc 300
ccggcgatgg attattgggg ccagggcacc ctggtgaccg tgagcagcgc ctccaccaag 360
ggcccatcgg tcttccccct ggcaccctcc tccaagagca cctctggggg cacagcggcc 420
ctgggctgcc tggtcaagga ctacttcccc gaaccggtga cggtgtcgtg gaactcaggc 480
gccctgacca gcggcgtgca caccttcccg gctgtcctac agtcctcagg actctactcc 540
ctcagcagcg tggtgactgt gccctctagc agcttgggca cccagaccta catctgcaac 600
gtgaatcaca agcccagcaa caccaaggtg gacaagaaag ttgagcccaa atcttgtgac 660
aaaactcaca caggcggagg cgggagcaat tatcatcttg aaaatgaggt cgctcgtctc 720
aagaaactc 729

<210> SEQ ID NO 164
<211> LENGTH: 711
<212> TYPE: DNA
<213> ORGANISM: Artificial Sequence
<220> FEATURE:
<223> OTHER INFORMATION: Made in lab - CD33(hM195)-LC_Cterm switch antibody polynucleotide

<400> SEQUENCE: 164
gatattcaga tgacccagag cccgagcagc ctgagcgcga gcgtgggcga tcgcgtgacc 60
attacctgcc gcgcgagcga aagcgtggat aactatggca ttagctttat gaactggttt 120
cagcagaaac cgggcaaagc gccgaaactg ctgatttatg cggcgagcaa ccagggcagc 180
ggcgtgccga gccgctttag cggcagcggc agcggcaccg attttaccct gaacattagc 240

```
agcctgcagc cggatgattt tgcgacctat tattgccagc agagcaaaga agtgccgtgg    300

acctttggcc agggcaccaa agtggaaatt aaacgaactg tggctgcacc atctgtcttc    360

atcttcccgc catctgatga gcagttgaaa tctggaactg cctctgttgt gtgcctgctg    420

aataacttct atcccagaga ggccaaagta cagtggaagg tggataacgc cctccaatcg    480

ggtaactccc aggagagtgt cacagagcag gacagcaagg acagcaccta cagcctcagc    540

agcaccctga cgctgagcaa agcagactac gagaaacaca aagtctacgc ctgcgaagtc    600

acccatcagg gcctgagctc gcccgtcaca aagagcttca acaggggaga gtgtggcgga    660

ggcgggagca attatcatct tgaaaatgag gtcgctcgtc tcaagaaact c             711
```

```
<210> SEQ ID NO 165
<211> LENGTH: 237
<212> TYPE: PRT
<213> ORGANISM: Artificial Sequence
<220> FEATURE:
<223> OTHER INFORMATION: Made in lab - h52SR4L2_h52SR4H2 humanized GCN4
      scFv

<400> SEQUENCE: 165

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Ser Trp Val Gln Gln Lys Pro Gly Gln Ala Pro Arg Gly
        35                  40                  45

Leu Ile Gly Gly Thr Asn Asn Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Glu Tyr Tyr Cys Val Leu Trp Tyr Ser Asp
                85                  90                  95

His Trp Val Phe Gly Gly Gly Thr Lys Leu Thr Val Leu Gly Gly Gly
            100                 105                 110

Gly Ser Gly Gly Gly Gly Ser Gly Gly Gly Gly Ser Gln Val Gln Leu
        115                 120                 125

Gln Glu Ser Gly Pro Gly Leu Val Lys Pro Ser Glu Thr Leu Ser Leu
    130                 135                 140

Thr Cys Thr Val Ser Gly Phe Leu Leu Thr Asp Tyr Gly Val Asn Trp
145                 150                 155                 160

Ile Arg Gln Pro Pro Gly Lys Gly Leu Glu Trp Ile Gly Val Ile Trp
                165                 170                 175

Gly Asp Gly Ile Thr Asp Tyr Asn Pro Ser Leu Lys Ser Arg Val Thr
            180                 185                 190

Ile Ser Lys Asp Thr Ser Lys Asn Gln Phe Ser Leu Lys Leu Ser Ser
        195                 200                 205

Val Thr Ala Ala Asp Thr Ala Val Tyr Tyr Cys Val Thr Gly Leu Phe
    210                 215                 220

Asp Tyr Trp Gly Gln Gly Thr Leu Val Thr Val Ser Ser
225                 230                 235


<210> SEQ ID NO 166
<211> LENGTH: 237
<212> TYPE: PRT
<213> ORGANISM: Artificial Sequence
<220> FEATURE:
```

<223> OTHER INFORMATION: Made in lab - h52SR4L2_h52SR4H3 humanized GCN4
scFv

<400> SEQUENCE: 166

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Ser Trp Val Gln Gln Lys Pro Gly Gln Ala Pro Arg Gly
        35                  40                  45

Leu Ile Gly Gly Thr Asn Asn Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Glu Tyr Tyr Cys Val Leu Trp Tyr Ser Asp
                85                  90                  95

His Trp Val Phe Gly Gly Gly Thr Lys Leu Thr Val Leu Gly Gly Gly
            100                 105                 110

Gly Ser Gly Gly Gly Gly Ser Gly Gly Gly Gly Ser Gln Val Gln Leu
        115                 120                 125

Gln Glu Ser Gly Pro Gly Leu Val Lys Pro Ser Glu Thr Leu Ser Ile
    130                 135                 140

Thr Cys Thr Val Ser Gly Phe Leu Leu Thr Asp Tyr Gly Val Asn Trp
145                 150                 155                 160

Val Arg Gln Pro Pro Gly Lys Gly Leu Glu Trp Leu Gly Val Ile Trp
                165                 170                 175

Gly Asp Gly Ile Thr Asp Tyr Asn Pro Ser Leu Lys Ser Arg Leu Thr
            180                 185                 190

Val Ser Lys Asp Thr Ser Lys Asn Gln Val Ser Leu Lys Met Ser Ser
        195                 200                 205

Leu Thr Ala Ala Asp Thr Ala Val Tyr Tyr Cys Val Thr Gly Leu Phe
    210                 215                 220

Asp Tyr Trp Gly Gln Gly Thr Leu Leu Thr Val Ser Ser
225                 230                 235
```

<210> SEQ ID NO 167
<211> LENGTH: 237
<212> TYPE: PRT
<213> ORGANISM: Artificial Sequence
<220> FEATURE:
<223> OTHER INFORMATION: Made in lab - h52SR4L3_h52SR4H2 humanized GCN4
scFv

<400> SEQUENCE: 167

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Ser Trp Val Gln Gln Lys Pro Gly Gln Ala Phe Arg Gly
        35                  40                  45

Leu Ile Gly Gly Thr Asn Asn Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Glu Tyr Tyr Cys Val Leu Trp Tyr Ser Asp
                85                  90                  95
```

```
His Trp Val Phe Gly Gly Gly Thr Lys Leu Thr Val Leu Gly Gly Gly
            100                 105                 110

Gly Ser Gly Gly Gly Gly Ser Gly Gly Gly Gly Ser Gln Val Gln Leu
        115                 120                 125

Gln Glu Ser Gly Pro Gly Leu Val Lys Pro Ser Glu Thr Leu Ser Leu
    130                 135                 140

Thr Cys Thr Val Ser Gly Phe Leu Leu Thr Asp Tyr Gly Val Asn Trp
145                 150                 155                 160

Ile Arg Gln Pro Pro Gly Lys Gly Leu Glu Trp Ile Gly Val Ile Trp
                165                 170                 175

Gly Asp Gly Ile Thr Asp Tyr Asn Pro Ser Leu Lys Ser Arg Val Thr
            180                 185                 190

Ile Ser Lys Asp Thr Ser Lys Asn Gln Phe Ser Leu Lys Leu Ser Ser
        195                 200                 205

Val Thr Ala Ala Asp Thr Ala Val Tyr Tyr Cys Val Thr Gly Leu Phe
    210                 215                 220

Asp Tyr Trp Gly Gln Gly Thr Leu Val Thr Val Ser Ser
225                 230                 235


<210> SEQ ID NO 168
<211> LENGTH: 237
<212> TYPE: PRT
<213> ORGANISM: Artificial Sequence
<220> FEATURE:
<223> OTHER INFORMATION: Made in lab - h52SR4L3_h52SR4H3 humanized GCN4
      scFv

<400> SEQUENCE: 168

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Ser Trp Val Gln Gln Lys Pro Gly Gln Ala Phe Arg Gly
        35                  40                  45

Leu Ile Gly Gly Thr Asn Asn Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Glu Tyr Tyr Cys Val Leu Trp Tyr Ser Asp
                85                  90                  95

His Trp Val Phe Gly Gly Gly Thr Lys Leu Thr Val Leu Gly Gly Gly
            100                 105                 110

Gly Ser Gly Gly Gly Gly Ser Gly Gly Gly Gly Ser Gln Val Gln Leu
        115                 120                 125

Gln Glu Ser Gly Pro Gly Leu Val Lys Pro Ser Glu Thr Leu Ser Ile
    130                 135                 140

Thr Cys Thr Val Ser Gly Phe Leu Leu Thr Asp Tyr Gly Val Asn Trp
145                 150                 155                 160

Val Arg Gln Pro Pro Gly Lys Gly Leu Glu Trp Leu Gly Val Ile Trp
                165                 170                 175

Gly Asp Gly Ile Thr Asp Tyr Asn Pro Ser Leu Lys Ser Arg Leu Thr
            180                 185                 190

Val Ser Lys Asp Thr Ser Lys Asn Gln Val Ser Leu Lys Met Ser Ser
        195                 200                 205

Leu Thr Ala Ala Asp Thr Ala Val Tyr Tyr Cys Val Thr Gly Leu Phe
    210                 215                 220
```

```
Asp Tyr Trp Gly Gln Gly Thr Leu Leu Thr Val Ser Ser
225                 230                 235


<210> SEQ ID NO 169
<211> LENGTH: 237
<212> TYPE: PRT
<213> ORGANISM: Artificial Sequence
<220> FEATURE:
<223> OTHER INFORMATION: Made in lab - h52SR4L4_h52SR4H2 humanized GCN4
      scFv

<400> SEQUENCE: 169

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Ser Trp Val Gln Gln Lys Pro Asp His Leu Phe Arg Gly
        35                  40                  45

Leu Ile Gly Gly Thr Asn Asn Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Glu Tyr Tyr Cys Val Leu Trp Tyr Ser Asp
                85                  90                  95

His Trp Val Phe Gly Gly Gly Thr Lys Leu Thr Val Leu Gly Gly Gly
            100                 105                 110

Gly Ser Gly Gly Gly Gly Ser Gly Gly Gly Gly Ser Gln Val Gln Leu
        115                 120                 125

Gln Glu Ser Gly Pro Gly Leu Val Lys Pro Ser Glu Thr Leu Ser Leu
    130                 135                 140

Thr Cys Thr Val Ser Gly Phe Leu Leu Thr Asp Tyr Gly Val Asn Trp
145                 150                 155                 160

Ile Arg Gln Pro Pro Gly Lys Gly Leu Glu Trp Ile Gly Val Ile Trp
                165                 170                 175

Gly Asp Gly Ile Thr Asp Tyr Asn Pro Ser Leu Lys Ser Arg Val Thr
            180                 185                 190

Ile Ser Lys Asp Thr Ser Lys Asn Gln Phe Ser Leu Lys Leu Ser Ser
        195                 200                 205

Val Thr Ala Ala Asp Thr Ala Val Tyr Tyr Cys Val Thr Gly Leu Phe
    210                 215                 220

Asp Tyr Trp Gly Gln Gly Thr Leu Val Thr Val Ser Ser
225                 230                 235


<210> SEQ ID NO 170
<211> LENGTH: 237
<212> TYPE: PRT
<213> ORGANISM: Artificial Sequence
<220> FEATURE:
<223> OTHER INFORMATION: Made in lab - h52SR4L4_h52SR4H3 humanized GCN4
      scFv

<400> SEQUENCE: 170

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Ser Trp Val Gln Gln Lys Pro Asp His Leu Phe Arg Gly
        35                  40                  45
```

```
Leu Ile Gly Gly Thr Asn Asn Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Glu Tyr Tyr Cys Val Leu Trp Tyr Ser Asp
                85                  90                  95

His Trp Val Phe Gly Gly Gly Thr Lys Leu Thr Val Leu Gly Gly Gly
            100                 105                 110

Gly Ser Gly Gly Gly Gly Ser Gly Gly Gly Gly Ser Gln Val Gln Leu
        115                 120                 125

Gln Glu Ser Gly Pro Gly Leu Val Lys Pro Ser Glu Thr Leu Ser Ile
    130                 135                 140

Thr Cys Thr Val Ser Gly Phe Leu Leu Thr Asp Tyr Gly Val Asn Trp
145                 150                 155                 160

Val Arg Gln Pro Pro Gly Lys Gly Leu Glu Trp Leu Gly Val Ile Trp
                165                 170                 175

Gly Asp Gly Ile Thr Asp Tyr Asn Pro Ser Leu Lys Ser Arg Leu Thr
            180                 185                 190

Val Ser Lys Asp Thr Ser Lys Asn Gln Val Ser Leu Lys Met Ser Ser
        195                 200                 205

Leu Thr Ala Ala Asp Thr Ala Val Tyr Tyr Cys Val Thr Gly Leu Phe
    210                 215                 220

Asp Tyr Trp Gly Gln Gly Thr Leu Leu Thr Val Ser Ser
225                 230                 235


<210> SEQ ID NO 171
<211> LENGTH: 1443
<212> TYPE: DNA
<213> ORGANISM: Artificial Sequence
<220> FEATURE:
<223> OTHER INFORMATION: Made in lab - LV-EF1a-huGCN4-BBZ_L2,H2
      humanized GCN4 scFv in CAR polynucleotide

<400> SEQUENCE: 171

atggccttac cagtgaccgc cttgctcctg ccgctggcct tgctgctcca cgccgccagg      60

ccgcaggcgg tagtcaccca ggagccaagt ctcacggtga gccccggcgg taccgtcaca     120

cttacatgcg gaagctctac cggggctgtg accacaagca actacgcatc ctgggtccag     180

cagaaacccg gtcaggctcc tcggggcctc attggtggga caaataacag agccccgggt     240

gttcccgccc gattttctgg cagtcttctg ggaggaaagg ccgctctgac aatatctggc     300

gcacagcccg aagacgaggc cgagtactat tgcgtgttgt ggtatagcga ccactgggta     360

ttcggtggag gaacaaagct gacagtgctc ggcggtggag ggagtggtgg cggtggcagc     420

ggagggggcg gatcacaagt gcaattgcag gagagtggac ctggactcgt gaaaccatct     480

gaaacactct ccctgacttg tacggtttca gggttcctgc tgacagacta tggagtaaac     540

tggatcaggc agccacccgg caagggcttg gagtggattg gcgtcatttg gggcgacgga     600

atcaccgact ataacccatc actcaaatct cgggtgacca tttccaagga taccagtaag     660

aatcagttca gcctgaaact ttcatccgtg acagctgcgg acaccgccgt gtactactgt     720

gtgacaggac tttttgacta ctggggccag ggaccctgg tgacagttag ctccaccacg      780

acgccagcgc cgcgaccacc aacaccggcg cccaccatcg cgtcgcagcc cctgtccctg     840

cgcccagagg cgtgccggcc agcggcgggg ggcgcagtgc acacgagggg gctggacttc     900

gcctgtgata tctacatctg ggcgcccttg gccgggactt gtggggtcct tctcctgtca     960
```

```
ctggttatca ccctttactg caaacggggc agaaagaaac tcctgtatat attcaaacaa   1020

ccatttatga gaccagtaca aactactcaa gaggaagatg gctgtagctg ccgatttcca   1080

gaagaagaag aaggaggatg tgaactgaga gtgaagttca gcaggagcgc agacgccccc   1140

gcgtacaagc agggccagaa ccagctctat aacgagctca atctaggacg aagagaggag   1200

tacgatgttt tggacaagag acgtggccgg gaccctgaga tggggggaaa gccgagaagg   1260

aagaaccctc aggaaggcct gtacaatgaa ctgcagaaag ataagatggc ggaggcctac   1320

agtgagattg ggatgaaagg cgagcgccgg aggggcaagg ggcacgatgg cctttaccag   1380

ggtctcagta cagccaccaa ggacacctac gacgcccttc acatgcaggc cctgccccct   1440

cgc                                                                 1443
```

<210> SEQ ID NO 172
<211> LENGTH: 1443
<212> TYPE: DNA
<213> ORGANISM: Artificial Sequence
<220> FEATURE:
<223> OTHER INFORMATION: Made in lab - LV-EF1a-huGCN4-BBZ_L2,H3
humanized GCN4 scFv in CAR polynucleotide

<400> SEQUENCE: 172

```
atggccttac cagtgaccgc cttgctcctg ccgctggcct tgctgctcca cgccgccagg     60

ccgcaggcgg tagtcaccca ggagccaagt ctcacggtga gccccggcgg taccgtcaca    120

cttacatgcg gaagctctac cggggctgtg accacaagca actacgcatc ctgggtccag    180

cagaaacccg gtcaggcgcc ccggggcctc attggtggga caaataacag agccccgggt    240

gttcccgccc gatttctgg cagtcttctg ggaggaaagg ccgctctgac aatatctggc    300

gcacagcccg aagacgaggc cgagtactat tgcgtgttgt ggtatagcga ccactgggta    360

ttcggtggag gaacaaagct gacagtgctc ggcggtggag ggagtggtgg cggtggcagc    420

ggagggggcg gatcacaagt gcaattgcag gagagtggac ctggactcgt gaaaccatct    480

gaaacactct ccataacttg tacggtttca gggttcctgc tgacagacta tggagtaaac    540

tgggttaggc agccacccgg caagggcttg gagtggctgg gcgtcatttg gggcgacgga    600

atcaccgact ataacccatc actcaaatct cggcttaccg tctccaagga tacgagtaag    660

aatcaggtca gcctgaaaat gtcatccctc acagctgcgg acaccgccgt gtactactgt    720

gtgacaggac tttttgacta ctggggccag gggaccctgc tcacagttag ctccaccacg    780

acgccagcgc cgcgaccacc aacaccggcg cccaccatcg cgtcgcagcc cctgtccctg    840

cgcccagagg cgtgccggcc agcggcgggg ggcgcagtgc acacgagggg gctggacttc    900

gcctgtgata tctacatctg ggcgcccttg gccgggactt gtggggtcct tctcctgtca    960

ctggttatca ccctttactg caaacggggc agaaagaaac tcctgtatat attcaaacaa   1020

ccatttatga gaccagtaca aactactcaa gaggaagatg gctgtagctg ccgatttcca   1080

gaagaagaag aaggaggatg tgaactgaga gtgaagttca gcaggagcgc agacgccccc   1140

gcgtacaagc agggccagaa ccagctctat aacgagctca atctaggacg aagagaggag   1200

tacgatgttt tggacaagag acgtggccgg gaccctgaga tggggggaaa gccgagaagg   1260

aagaaccctc aggaaggcct gtacaatgaa ctgcagaaag ataagatggc ggaggcctac   1320

agtgagattg ggatgaaagg cgagcgccgg aggggcaagg ggcacgatgg cctttaccag   1380

ggtctcagta cagccaccaa ggacacctac gacgcccttc acatgcaggc cctgccccct   1440

cgc                                                                 1443
```

<210> SEQ ID NO 173
<211> LENGTH: 1443
<212> TYPE: DNA
<213> ORGANISM: Artificial Sequence
<220> FEATURE:
<223> OTHER INFORMATION: Made in lab - LV-EF1a-huGCN4-BBZ_L3,H2
humanized GCN4 scFv in CAR polynucleotide

<400> SEQUENCE: 173
atggccttac cagtgaccgc cttgctcctg ccgctggcct tgctgctcca cgccgccagg 60
ccgcaggcgg tagtcaccca ggagccaagt ctcacggtga gccccggcgg taccgtcaca 120
cttacatgcg gaagctctac cggggctgtg accacaagca actacgcatc ctgggtccag 180
cagaaacccg gacaagcgtt ccggggcctc attggtggga caaataacag agccccgggt 240
gttcccgccc gattttctgg cagtcttctg ggaggaaagg ccgctctgac aatatctggc 300
gcacagcccg aagacgaggc cgagtactat tgcgtgttgt ggtatagcga ccactgggta 360
ttcggtggag gaacaaagct gacagtgctc ggcggtggag ggagtggtgg cggtggcagc 420
ggagggggcg gatcacaagt gcaattgcag gagagtggac ctggactcgt gaaaccatct 480
gaaacactct ccctcacttg tacggtttca gggttcctgc tgacagacta tggagtaaac 540
tggattaggc agccacccgg caagggcttg gagtggatcg gcgtcatttg gggcgacgga 600
atcaccgact ataacccatc actcaaatct cgggtcacca tctccaagga taccagtaag 660
aatcagttca gcctgaaact gtcatccgtc acagctgcgg acaccgccgt gtactactgt 720
gtgacaggac tttttgacta ctggggccag gggaccctgg taacagttag ctccaccacg 780
acgccagcgc cgcgaccacc aacaccggcg cccaccatcg cgtcgcagcc cctgtccctg 840
cgcccagagg cgtgccggcc agcggcgggg ggcgcagtgc acacgagggg gctggacttc 900
gcctgtgata tctacatctg ggcgcccttg gccgggactt gtggggtcct tctcctgtca 960
ctggttatca ccctttactg caaacggggc agaaagaaac tcctgtatat attcaaacaa 1020
ccatttatga gaccagtaca aactactcaa gaggaagatg gctgtagctg ccgatttcca 1080
gaagaagaag aaggaggatg tgaactgaga gtgaagttca gcaggagcgc agacgccccc 1140
gcgtacaagc agggccagaa ccagctctat aacgagctca atctaggacg aagagaggag 1200
tacgatgttt tggacaagag acgtggccgg gaccctgaga tgggggggaaa gccgagaagg 1260 aagaaccctc aggaaggcct gtacaatgaa ctgcagaaag ataagatggc ggaggcctac 1320
agtgagattg ggatgaaagg cgagcgccgg aggggcaagg ggcacgatgg cctttaccag 1380
ggtctcagta cagccaccaa ggacacctac gacgcccttc acatgcaggc cctgccccct 1440
cgc 1443

<210> SEQ ID NO 174
<211> LENGTH: 1443
<212> TYPE: DNA
<213> ORGANISM: Artificial Sequence
<220> FEATURE:
<223> OTHER INFORMATION: Made in lab - LV-EF1a-huGCN4-BBZ_L3,H3
humanized GCN4 scFv in CAR polynucleotide

<400> SEQUENCE: 174
atggccttac cagtgaccgc cttgctcctg ccgctggcct tgctgctcca cgccgccagg 60
ccgcaggcgg tagtcaccca ggagccaagt ctcacggtga gccccggcgg taccgtcaca 120
cttacatgcg gaagctctac cggggctgtg accacaagca actacgcatc ctgggtccag 180
cagaaacccg gtcaggcatt ccggggcctc attggtggga caaataacag agccccgggt 240
gttcccgccc gattttctgg cagtcttctg ggaggaaagg ccgctctgac aatatctggc 300
gcacagcccg aagacgaggc cgagtactat tgcgtgttgt ggtatagcga ccactgggta 360
ttcggtggag gaacaaagct gacagtgctc ggcggtggag ggagtggtgg cggtggcagc 420
ggagggggcg gatcacaagt gcaattgcag gagagtggac ctggactcgt gaaaccatct 480
gaaacactct ccataacttg tacggtttca gggttcctgc tgacagacta tggagtaaac 540
tgggtcaggc agccacccgg caagggcttg gagtggctcg gcgtcatttg gggcgacgga 600
atcaccgact ataacccatc actcaaatct cggttgaccg tgtccaagga taccagtaag 660
aatcaggtca gcctgaaaat gtcatccctg acagctgcgg acaccgccgt gtactactgt 720
gtgacaggac tttttgacta ctggggccag gggaccctgt tgacagttag ctccaccacg 780
acgccagcgc cgcgaccacc aacaccggcg cccaccatcg cgtcgcagcc cctgtccctg 840
cgcccagagg cgtgccggcc agcggcgggg ggcgcagtgc acacgagggg gctggacttc 900
gcctgtgata tctacatctg ggcgcccttg gccgggactt gtggggtcct tctcctgtca 960
ctggttatca ccctttactg caaacggggc agaaagaaac tcctgtatat attcaaacaa 1020
ccatttatga gaccagtaca aactactcaa gaggaagatg gctgtagctg ccgatttcca 1080
gaagaagaag aaggaggatg tgaactgaga gtgaagttca gcaggagcgc agacgccccc 1140
gcgtacaagc agggccagaa ccagctctat aacgagctca atctaggacg aagagaggag 1200
tacgatgttt tggacaagag acgtggccgg gaccctgaga tggggggaaa gccgagaagg 1260
aagaaccctc aggaaggcct gtacaatgaa ctgcagaaag ataagatggc ggaggcctac 1320
agtgagattg ggatgaaagg cgagcgccgg aggggcaagg ggcacgatgg cctttaccag 1380
ggtctcagta cagccaccaa ggacacctac gacgcccttc acatgcaggc cctgccccct 1440
cgc 1443

<210> SEQ ID NO 175
<211> LENGTH: 1443
<212> TYPE: DNA
<213> ORGANISM: Artificial Sequence
<220> FEATURE:
<223> OTHER INFORMATION: Made in lab - LV-EF1a-huGCN4-BBZ_L4,H2
humanized GCN4 scFv in CAR polynucleotide

<400> SEQUENCE: 175
atggccttac cagtgaccgc cttgctcctg ccgctggcct tgctgctcca cgccgccagg 60
ccgcaggcgg tagtcaccca ggagccaagt ctcacggtga gccccggcgg taccgtcaca 120
cttacatgcg gaagctctac cggggctgtg accacaagca actacgcatc ctgggtccag 180
cagaaacccg atcacctgtt ccggggcctc attggtggga caaataacag agccccgggt 240
gttcccgccc gattttctgg cagtcttctg ggaggaaagg ccgctctgac aatatctggc 300
gcacagcccg aagacgaggc cgagtactat tgcgtgttgt ggtatagcga ccactgggta 360
ttcggtggag gaacaaagct gacagtgctc ggcggtggag ggagtggtgg cggtggcagc 420
ggagggggcg gatcacaagt gcaattgcag gagagtggac ctggactcgt gaaaccatct 480
gaaacactct cccttacttg tacggtttca gggttcctgc tgacagacta tggagtaaac 540
tggatcaggc agccacccgg caagggcttg gagtggatcg gcgtcatttg gggcgacgga 600
atcaccgact ataacccatc actcaaatct cgggtcacca tctccaagga tacgagtaag 660
aatcagttca gcctgaaact ctcatccgtt acagctgcgg acaccgccgt gtactactgt 720
gtgacaggac tttttgacta ctggggccag ggaccctgg taacagttag ctccaccacg 780
acgccagcgc cgcgaccacc aacaccggcg cccaccatcg cgtcgcagcc cctgtccctg 840
cgcccagagg cgtgccggcc agcggcgggg ggcgcagtgc acacgagggg gctggacttc 900
gcctgtgata tctacatctg ggcgcccttg gccgggactt gtggggtcct tctcctgtca 960
ctggttatca ccctttactg caaacggggc agaaagaaac tcctgtatat attcaaacaa 1020
ccatttatga gaccagtaca aactactcaa gaggaagatg gctgtagctg ccgatttcca 1080
gaagaagaag aaggaggatg tgaactgaga gtgaagttca gcaggagcgc agacgccccc 1140
gcgtacaagc agggccagaa ccagctctat aacgagctca atctaggacg aagagaggag 1200
tacgatgttt tggacaagag acgtggccgg gaccctgaga tgggggggaaa gccgagaagg 1260 aagaaccctc aggaaggcct gtacaatgaa ctgcagaaag ataagatggc ggaggcctac 1320
agtgagattg ggatgaaagg cgagcgccgg aggggcaagg ggcacgatgg cctttaccag 1380
ggtctcagta cagccaccaa ggacacctac gacgcccttc acatgcaggc cctgcccccct 1440 cgc 1443

<210> SEQ ID NO 176
<211> LENGTH: 1443
<212> TYPE: DNA
<213> ORGANISM: Artificial Sequence
<220> FEATURE:
<223> OTHER INFORMATION: Made in lab - LV-EF1a-huGCN4-BBZ_L4,H3
humanized GCN4 scFv in CAR polynucleotide

<400> SEQUENCE: 176
atggccttac cagtgaccgc cttgctcctg ccgctggcct tgctgctcca cgccgccagg 60
ccgcaggcgg tagtcaccca ggagccaagt ctcacggtga gccccggcgg taccgtcaca 120
cttacatgcg gaagctctac cggggctgtg accacaagca actacgcatc ctgggtccag 180
cagaaacccg accatctgtt tcggggcctc attggtggga caaataacag agccccgggt 240
gttcccgccc gattttctgg cagtcttctg ggaggaaagg ccgctctgac aatatctggc 300
gcacagcccg aagacgaggc cgagtactat tgcgtgttgt ggtatagcga ccactgggta 360
ttcggtggag gaacaaagct gacagtgctc ggcggtggag ggagtggtgg cggtggcagc 420
ggagggggcg gatcacaagt gcaattgcag gagagtggac ctggactcgt gaaaccatct 480
gaaacactct ccattacttg tacggtttca gggttcctgc tgacagacta tggagtaaac 540
tgggtgaggc agccacccgg caagggcttg gagtggctcg gcgtcatttg gggcgacgga 600
atcaccgact ataacccatc actcaaatct cggttgaccg tgtccaagga taccagtaag 660
aatcaggtga gcctgaaaat gtcatccctg acagctgcgg acaccgccgt gtactactgt 720
gtgacaggac tttttgacta ctggggccag ggaccctgc tgacagttag ctccaccacg 780
acgccagcgc cgcgaccacc aacaccggcg cccaccatcg cgtcgcagcc cctgtccctg 840
cgcccagagg cgtgccggcc agcggcgggg ggcgcagtgc acacgagggg gctggacttc 900
gcctgtgata tctacatctg ggcgcccttg gccgggactt gtggggtcct tctcctgtca 960
ctggttatca ccctttactg caaacggggc agaaagaaac tcctgtatat attcaaacaa 1020
ccatttatga gaccagtaca aactactcaa gaggaagatg gctgtagctg ccgatttcca 1080
gaagaagaag aaggaggatg tgaactgaga gtgaagttca gcaggagcgc agacgccccc 1140
gcgtacaagc agggccagaa ccagctctat aacgagctca atctaggacg aagagaggag 1200
tacgatgttt tggacaagag acgtggccgg gaccctgaga tgggggggaaa gccgagaagg 1260

```
aagaaccctc aggaaggcct gtacaatgaa ctgcagaaag ataagatggc ggaggcctac   1320

agtgagattg ggatgaaagg cgagcgccgg aggggcaagg ggcacgatgg cctttaccag   1380

ggtctcagta cagccaccaa ggacacctac gacgcccttc acatgcaggc cctgccccct   1440

cgc                                                                 1443


<210> SEQ ID NO 177
<211> LENGTH: 214
<212> TYPE: PRT
<213> ORGANISM: Artificial Sequence
<220> FEATURE:
<223> OTHER INFORMATION: Made in lab - Anti-CD20 OFA Light chain WT

<400> SEQUENCE: 177

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 178
<211> LENGTH: 225
<212> TYPE: PRT
<213> ORGANISM: Artificial Sequence
<220> FEATURE:
<223> OTHER INFORMATION: Made in lab - Anti-CD20 OFA Heavy chain (Fab)
      WT

<400> SEQUENCE: 178

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45
```

```
Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225
```

<210> SEQ ID NO 179
<211> LENGTH: 226
<212> TYPE: PRT
<213> ORGANISM: Artificial Sequence
<220> FEATURE:
<223> OTHER INFORMATION: Made in lab - IgG1 Fc region
(E233P/L234V/L235A/?G236 + A327G/A330S/P331S)

<400> SEQUENCE: 179

```
Asp Lys Thr His Thr Cys Pro Pro Cys Pro Ala Pro Pro Val Ala Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Gly Leu Pro Ser Ser Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Asp Glu Leu Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
```

-continued

```
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
225


<210> SEQ ID NO 180
<211> LENGTH: 487
<212> TYPE: PRT
<213> ORGANISM: Artificial Sequence
<220> FEATURE:
<223> OTHER INFORMATION: Made in lab - sCAR

<400> SEQUENCE: 180

Met Ala Leu Pro Val Thr Ala Leu Leu Leu Pro Leu Ala Leu Leu Leu
1               5                   10                  15

His Ala Ala Arg Pro Asp Ala Val Val Thr Gln Glu Ser Ala Leu Thr
            20                  25                  30

Ser Ser Pro Gly Glu Thr Val Thr Leu Thr Cys Arg Ser Ser Thr Gly
        35                  40                  45

Ala Val Thr Thr Ser Asn Tyr Ala Ser Trp Val Gln Glu Lys Pro Asp
    50                  55                  60

His Leu Phe Thr Gly Leu Ile Gly Gly Thr Asn Asn Arg Ala Pro Gly
65                  70                  75                  80

Val Pro Ala Arg Phe Ser Gly Ser Leu Ile Gly Asp Lys Ala Ala Leu
                85                  90                  95

Thr Ile Thr Gly Ala Gln Thr Glu Asp Glu Ala Ile Tyr Phe Cys Val
            100                 105                 110

Leu Trp Tyr Ser Asp His Trp Val Phe Gly Gly Gly Thr Lys Leu Thr
        115                 120                 125

Val Leu Gly Gly Gly Gly Gly Ser Gly Gly Gly Gly Ser Gly Gly Gly
    130                 135                 140

Gly Ser Gly Gly Gly Gly Ser Asp Val Gln Leu Gln Glu Ser Gly Pro
145                 150                 155                 160

Gly Leu Val Ala Pro Ser Gln Ser Leu Ser Ile Thr Cys Thr Val Ser
                165                 170                 175

Gly Phe Leu Leu Thr Asp Tyr Gly Val Asn Trp Val Arg Gln Ser Pro
            180                 185                 190

Gly Lys Gly Leu Glu Trp Leu Gly Val Ile Trp Gly Asp Gly Ile Thr
        195                 200                 205

Asp Tyr Asn Ser Ala Leu Lys Ser Arg Leu Ser Val Thr Lys Asp Asn
    210                 215                 220

Ser Lys Ser Gln Val Phe Leu Lys Met Asn Ser Leu Gln Ser Gly Asp
225                 230                 235                 240

Ser Ala Arg Tyr Tyr Cys Val Thr Gly Leu Phe Asp Tyr Trp Gly Gln
                245                 250                 255

Gly Thr Thr Leu Thr Val Ser Ser Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
```

```
    290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
            325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
    370                 375                 380

Ala Pro Ala Tyr Lys Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
            405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
            485


<210> SEQ ID NO 181
<211> LENGTH: 486
<212> TYPE: PRT
<213> ORGANISM: Artificial Sequence
<220> FEATURE:
<223> OTHER INFORMATION: Made in lab - CART-19

<400> SEQUENCE: 181

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
            85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
```

```
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485


<210> SEQ ID NO 182
<211> LENGTH: 1419
<212> TYPE: DNA
<213> ORGANISM: Artificial Sequence
<220> FEATURE:
<223> OTHER INFORMATION: Made in Lab - CART20 BBZ

<400> SEQUENCE: 182

gaggtgcagc tggtcgagtc aggcggaggc ctggttcagc cagggagatc cctcaggctt      60

tcctgcgccg cctccggttt taccttcaac gactacgcta tgcactgggt tcgccaggct     120

cccggaaagg gacttgaatg ggtgagcact atcagctgga attctggaag cattgggtat     180

gccgactccg tcaagggccg ctttactatt tctcgggata atgcgaagaa gtctctgtac     240
```

-continued

```
ctgcagatga acagtcttcg ggcagaagac acggctcttt actattgcgc aaaagacatc    300

cagtacggaa actattatta cggaatggat gtgtggggtc agggcaccac tgtgacagta    360

agcagtggcg gaggaggagg ttcaggagga ggaggtagcg gggggaggcgg ttccgggggga    420

ggcggttctg aaatcgtcct gacgcagtca cctgcaaccc tgagtctcag ccctggtgag    480

cgggccaccc tgagctgcag ggccagccag agtgtatctt cttacctggc ttggtatcag    540

cagaaaccag gacaggcccc aagactgctg atctacgacg cttccaatag agccacgggc    600

atccctgccc gattttccgg atcagggtcc ggtacagatt tcacgctgac catcagctcc    660

ctcgagcccg aagattttgc tgtgtattat tgccagcagc ggtccaattg gcccattacc    720

ttcggtcagg ggaccaggct ggagattaaa accacgacgc cagcgccgcg accaccaaca    780

ccggcgccca ccatcgcgtc gcagcccctg tccctgcgcc cagaggcgtg ccggccagcg    840

gcgggggggcg cagtgcacac gagggggctg gacttcgcct gtgatatcta catctgggcg    900

cccttggccg ggacttgtgg ggtccttctc ctgtcactgg ttatcaccct ttactgcaaa    960

cggggcagaa agaaactcct gtatatattc aaacaaccat ttatgagacc agtacaaact   1020

actcaagagg aagatggctg tagctgccga tttccagaag aagaagaagg aggatgtgaa   1080

ctgagagtga agttcagcag gagcgcagac gcccccgcgt acaagcaggg ccagaaccag   1140

ctctataacg agctcaatct aggacgaaga gaggagtacg atgttttgga caagagacgt   1200

ggccgggacc ctgagatggg gggaaagccg agaaggaaga accctcagga aggcctgtac   1260

aatgaactgc agaaagataa gatggcggag gcctacagtg agattgggat gaaaggcgag   1320

cgccggaggg gcaaggggca cgatggcctt taccagggtc tcagtacagc caccaaggac   1380

acctacgacg cccttcacat gcaggccctg ccccctcgc                          1419
```

<210> SEQ ID NO 183
<211> LENGTH: 729
<212> TYPE: DNA
<213> ORGANISM: Artificial Sequence
<220> FEATURE:
<223> OTHER INFORMATION: Made in Lab - hu 52SR4 L5 H6

<400> SEQUENCE: 183

```
caggctgtgg tgactcagga gccctcactg actgtgtccc caggagggac agtcactctc     60

acctgtggct ccagcactgg agctgtcacc acttccaact atgcctcatg ggtgcaggag    120

aagcctgacc acctcttcag gggctgatt ggtggcacaa acaacagggc tcctggggtg    180

cctgcccggt tctcaggctc cctccttggg ggcaaagctg ccctgaccat ttcgggtgcg    240

cagcctgagg atgaggctat ttatttctgc gtgctctggt atagtgacca ttgggtgttc    300

ggcggaggga ccaagctgac cgtcctaggc ggaggaggag gttcaggagg aggaggtagc    360

gggggaggcg gttccggggg aggcggttct caggtgcagc tgcagcagtc gggcccagga    420

ctggtgaagc cttcggagac cctgtccatc acctgcactg tctctggttt ctccctgacc    480

gactacggcg taaactgggt gcggcagccc ccagggaagg gactggagtg gctgggggtg    540

atctggggtg acgggagcac cgactacaac ccctccctca agagtcgact gaccgtgtcc    600

aaggacaact ccaagaacca ggtgtccctg aagatgagct ctctgaccgc cgcagacacg    660

gccgtgtatt actgtgtcac cggcctgttc gactactggg gccagggcac cctgctgacc    720

gtctcctca                                                            729
```

<210> SEQ ID NO 184

<211> LENGTH: 1302
<212> TYPE: DNA
<213> ORGANISM: Artificial Sequence
<220> FEATURE:
<223> OTHER INFORMATION: Made in Lab - hu 52SR4 L5 H4b

<400> SEQUENCE: 184
caggctgtgg tgactcagga gccctcactg actgtgtccc caggagggac agtcactctc 60
acctgtggct ccagcactgg agctgtcacc acttccaact atgcctcatg ggtgcaggag 120
aagcctgacc acctcttcag gggctgatt ggtggcacaa acaacagggc tcctggggtg 180
cctgcccggt tctcaggctc cctccttggg ggcaaagctg ccctgaccat ttcgggtgcg 240
cagcctgagg atgaggctat ttatttctgc gtgctctggt atagtgacca ttgggtgttc 300
ggcggaggga ccaagctgac cgtcctaggc ggaggaggag gttcaggagg cggaggtagc 360
gggggaggcg gttccggggg aggcggttct caggtgcagc tgcagcagtc gggcccagga 420
ctggtgaagc cttcggagac cctgtccatc acctgcactg tctctggttt cctgctgacc 480
gactacggcg taaactgggt gcggcagccc ccagggaagg gactggagtg gctgggggtg 540
atctggggtg acgggatcac cgactacaac ccctccctca agagtcgact gaccgtgtcc 600
aaggacacat ccaagaacca ggtgtccctg aagatgagct ctctgaccgc cgcagacacg 660
gcccggtatt actgtgtcac cggcctgttc gactactggg gccagggcac caccctgacc 720
gtctcctcag aaagcaagta tggcccacct tgtccacctt gtcccgatat ctacatctgg 780
gcgcccttgg ccgggacttg tggggtcctt ctcctgtcac tggttatcac cctttactgc 840
aaacggggca gaaagaaact cctgtatata ttcaaacaac catttatgag accagtacaa 900
actactcaag aggaagatgg ctgtagctgc cgatttccag aagaagaaga aggaggatgt 960
gaactgagag tgaagttcag caggagcgca gacgcccccg cgtacaagca gggccagaac 1020
cagctctata acgagctcaa tctaggacga agagaggagt acgatgtttt ggacaagaga 1080
cgtggccggg accctgagat gggggaaag ccgagaagga agaaccctca ggaaggcctg 1140
tacaatgaac tgcagaaaga taagatggcg gaggcctaca gtgagattgg gatgaaaggc 1200
gagcgccgga ggggcaaggg gcacgatggc ctttaccagg gtctcagtac agccaccaag 1260
gacacctacg acgcccttca catgcaggcc ctgccccctc gc 1302

<210> SEQ ID NO 185
<211> LENGTH: 1302
<212> TYPE: DNA
<213> ORGANISM: Artificial Sequence
<220> FEATURE:
<223> OTHER INFORMATION: Made in Lab - hu 52SR4 L5 H6b

<400> SEQUENCE: 185
caggctgtgg tgactcagga gccctcactg actgtgtccc caggagggac agtcactctc 60
acctgtggct ccagcactgg agctgtcacc acttccaact atgcctcatg ggtgcaggag 120
aagcctgacc acctcttcag gggctgatt ggtggcacaa acaacagggc tcctggggtg 180
cctgcccggt tctcaggctc cctccttggg ggcaaagctg ccctgaccat ttcgggtgcg 240
cagcctgagg atgaggctat ttatttctgc gtgctctggt atagtgacca ttgggtgttc 300
ggcggaggga ccaagctgac cgtcctaggc ggaggaggag gttcaggagg cggaggtagc 360
gggggaggcg gttccggggg aggcggttct caggtgcagc tgcagcagtc gggcccagga 420
ctggtgaagc cttcggagac cctgtccatc acctgcactg tctctggttt ctccctgacc 480
gactacggcg taaactgggt gcggcagccc ccagggaagg gactggagtg gctgggggtg 540
atctggggtg acgggagcac cgactacaac ccctccctca agagtcgact gaccgtgtcc 600
aaggacacct ccaagaacca ggtgtccctg aagatgagct ctctgaccgc cgcagacacg 660
gccgtgtatt actgtgtcac cggcctgttc gactactggg gccagggcac cctgctgacc 720
gtctcctcag aaagcaagta tggcccacct tgtccacctt gtcccgatat ctacatctgg 780
gcgcccttgg ccgggacttg tggggtcctt ctcctgtcac tggttatcac cctttactgc 840
aaacggggca gaaagaaact cctgtatata ttcaaacaac catttatgag accagtacaa 900
actactcaag aggaagatgg ctgtagctgc cgatttccag aagaagaaga aggaggatgt 960
gaactgagag tgaagttcag caggagcgca gacgcccccg cgtacaagca gggccagaac 1020
cagctctata acgagctcaa tctaggacga agagaggagt acgatgtttt ggacaagaga 1080
cgtggccggg accctgagat ggggggaaag ccgagaagga agaaccctca ggaaggcctg 1140
tacaatgaac tgcagaaaga taagatggcg gaggcctaca gtgagattgg gatgaaaggc 1200
gagcgccgga ggggcaaggg gcacgatggc ctttaccagg gtctcagtac agccaccaag 1260
gacacctacg acgcccttca catgcaggcc ctgccccctc gc 1302

<210> SEQ ID NO 186
<211> LENGTH: 660
<212> TYPE: DNA
<213> ORGANISM: Artificial Sequence
<220> FEATURE:
<223> OTHER INFORMATION: Made in Lab - hLL2 LC WT FAB

<400> SEQUENCE: 186
gacatccagc tgacccagtc cccctcctcc ctgtccgcct ccgtgggcga ccgggtgacc 60
atgagctgca agtcctccca gtccgtgctg tactccgcca accacaagaa ctacctggcc 120
tggtaccagc agaagcccgg caaggccccc aagctgctga tctactgggc cagcacccgc 180
gagagcggcg tgccctcccg gttctccggc tccggctccg gcaccgactt caccttcacc 240
atctcctccc tgcagcccga ggacatcgcc acctactact gccaccagta cctgtcctcc 300
tggaccttcg gcggcggcac caagctggag atcaagcgca cggtggccgc ccccagtgtc 360
ttcattttcc ccccttccga tgagcagctg aagagcggta cagcctctgt tgtttgtctg 420
ctgaacaact tctatccacg cgaggccaag gtgcagtgga aagttgataa cgcgctgcag 480
agtggcaact cccaggagtc tgtgacagag caggacagta aagacagcac atattccctg 540
tctagcacac tgactctgtc caaggctgac tatgagaagc acaaggtgta cgcttgcgag 600
gtcacccacc agggactgag ttctcctgtg accaagtcct tcaatcgcgg cgagtgttaa 660

<210> SEQ ID NO 187
<211> LENGTH: 660
<212> TYPE: DNA
<213> ORGANISM: Artificial Sequence
<220> FEATURE:
<223> OTHER INFORMATION: Made in Lab - hLL2 HC WT FAB

<400> SEQUENCE: 187
caggtgcagc tggtgcagtc cggcgccgag gtgaagaagc ccggctcctc cgtgaaggtg 60
tcctgcaagg cctccggcta caccttcacc tcctactggc tgcactgggt gcggcaggcc 120
cccggccagg gcctggagtg gatcggctac atcaaccccc ggaacgacta caccgagtac 180
aaccagaact tcaaggacaa ggccaccatc accgccgacg agtccaccaa caccgcctac 240
atggagctgt cctccctgcg gtccgaggac accgccttct acttctgcgc ccggcgggac 300
atcaccacct tctactgggg ccagggcacc actgtgaccg tgtcctccgc caggaccaaa 360
ggaccgtccg tctttcctct ggccccttcc tctaagtcca caagcggtgg gaccgcagca 420
ctgggatgcc tggtgaagga ttacttccct gagccggtga ccgtgtcctg gaactccgga 480
gctctcacct ccggtgtcca tacctttcct gccgtcctgc agtcctccgg cctgtacagc 540
ctctctagcg tcgtgactgt gccctccagc tccctgggca cccaaactta tatctgcaat 600
gttaaccaca agccttctaa taccaaggtc gacaagaaag tggagccgaa gagctgttaa 660

<210> SEQ ID NO 188
<211> LENGTH: 717
<212> TYPE: DNA
<213> ORGANISM: Artificial Sequence
<220> FEATURE:
<223> OTHER INFORMATION: Made in Lab - hLL2 LCNT FAB

<400> SEQUENCE: 188
aactatcacc tggaaaacga agtggcaagg ctgaaaaaac tgggcggggg cggaagtgac 60
atccagctga cccagtcccc ctcctccctg tccgcctccg tgggcgaccg ggtgaccatg 120
agctgcaagt cctcccagtc cgtgctgtac tccgccaacc acaagaacta cctggcctgg 180
taccagcaga agcccggcaa ggcccccaag ctgctgatct actgggccag cacccgcgag 240
agcggcgtgc cctcccggtt ctccggctcc ggctccggca ccgacttcac cttcaccatc 300
tcctccctgc agcccgagga catcgccacc tactactgcc accagtacct gtcctcctgg 360
accttcggcg gcggcaccaa gctggagatc aagcgcacgg tggccgcccc cagtgtcttc 420 atttccccc cttccgatga gcagctgaag agcggtacag cctctgttgt ttgtctgctg 480
aacaacttct atccacgcga ggccaaggtg cagtggaaag ttgataacgc gctgcagagt 540
ggcaactccc aggagtctgt gacagagcag gacagtaaag acagcacata ttccctgtct 600
agcacactga ctctgtccaa ggctgactat gagaagcaca aggtgtacgc ttgcgaggtc 660
acccaccagg gactgagttc tcctgtgacc aagtccttca atcgcggcga gtgttaa 717

<210> SEQ ID NO 189
<211> LENGTH: 717
<212> TYPE: DNA
<213> ORGANISM: Artificial Sequence
<220> FEATURE:
<223> OTHER INFORMATION: Made in Lab - hLL2 LCCT FAB

<400> SEQUENCE: 189
gacatccagc tgacccagtc cccctcctcc ctgtccgcct ccgtgggcga ccgggtgacc 60
atgagctgca agtcctccca gtccgtgctg tactccgcca accacaagaa ctacctggcc 120
tggtaccagc agaagcccgg caaggccccc aagctgctga tctactgggc cagcacccgc 180
gagagcggcg tgccctcccg gttctccggc tccggctccg gcaccgactt caccttcacc 240
atctcctccc tgcagcccga ggacatcgcc acctactact gccaccagta cctgtcctcc 300
tggaccttcg gcggcggcac caagctggag atcaagcgca cggtggccgc ccccagtgtc 360
ttcattttcc ccccttccga tgagcagctg aagagcggta cagcctctgt tgtttgtctg 420
ctgaacaact tctatccacg cgaggccaag gtgcagtgga aagttgataa cgcgctgcag 480
agtggcaact cccaggagtc tgtgacagag caggacagta aagacagcac atattccctg 540
tctagcacac tgactctgtc caaggctgac tatgagaagc acaaggtgta cgcttgcgag 600
gtcacccacc agggactgag ttctcctgtg accaagtcct tcaatcgcgg cgagtgtggc 660
ggaggcggga gcaattatca tcttgaaaat gaggtcgctc gtctcaagaa actctaa 717

<210> SEQ ID NO 190
<211> LENGTH: 744
<212> TYPE: DNA
<213> ORGANISM: Artificial Sequence
<220> FEATURE:
<223> OTHER INFORMATION: Made in Lab - hLL2 HCNT FAB

<400> SEQUENCE: 190
aattatcatc ttgaaaatga ggtcgctcgt ctcaagaaac tcctggttgg cgaggccgca 60
gctaaggaag ccgcagctaa agcccaggtg cagctggtgc agtccggcgc cgaggtgaag 120
aagcccggct cctccgtgaa ggtgtcctgc aaggcctccg gctacacctt cacctcctac 180
tggctgcact gggtgcggca ggcccccggc cagggcctgg agtggatcgg ctacatcaac 240
ccccggaacg actacaccga gtacaaccag aacttcaagg acaaggccac catcaccgcc 300
gacgagtcca ccaacaccgc ctacatggag ctgtcctccc tgcggtccga ggacaccgcc 360
ttctacttct gcgcccggcg ggacatcacc accttctact ggggccaggg caccactgtg 420
accgtgtcct ccgccaggac caaaggaccg tccgtctttc ctctggcccc ttcctctaag 480
tccacaagcg gtgggaccgc agcactggga tgcctggtga aggattactt ccctgagccg 540
gtgaccgtgt cctggaactc cggagctctc acctccggtg tccatacctt tcctgccgtc 600
ctgcagtcct ccggcctgta cagcctctct agcgtcgtga ctgtgccctc cagctccctg 660
ggcacccaaa cttatatctg caatgttaac cacaagcctt ctaataccaa ggtcgacaag 720
aaagtggagc cgaagagctg ttaa 744

<210> SEQ ID NO 191
<211> LENGTH: 717
<212> TYPE: DNA
<213> ORGANISM: Artificial Sequence
<220> FEATURE:
<223> OTHER INFORMATION: Made in lab - hLL2 HCCT FAB

<400> SEQUENCE: 191
caggtgcagc tggtgcagtc cggcgccgag gtgaagaagc ccggctcctc cgtgaaggtg 60
tcctgcaagg cctccggcta caccttcacc tcctactggc tgcactgggt gcggcaggcc 120
cccggccagg gcctggagtg gatcggctac atcaaccccc ggaacgacta caccgagtac 180
aaccagaact tcaaggacaa ggccaccatc accgccgacg agtccaccaa caccgcctac 240
atggagctgt cctccctgcg gtccgaggac accgccttct acttctgcgc ccggcgggac 300
atcaccacct tctactgggg ccagggcacc actgtgaccg tgtcctccgc caggaccaaa 360
ggaccgtccg tctttcctct ggccccttcc tctaagtcca caagcggtgg gaccgcagca 420
ctgggatgcc tggtgaagga ttacttccct gagccggtga ccgtgtcctg gaactccgga 480
gctctcacct ccggtgtcca tacctttcct gccgtcctgc agtcctccgg cctgtacagc 540
ctctctagcg tcgtgactgt gccctccagc tccctgggca cccaaactta tatctgcaat 600
gttaaccaca agccttctaa taccaaggtc gacaagaaag tggagccgaa gagctgtggc 660
ggaggcggga gcaattatca tcttgaaaat gaggtcgctc gtctcaagaa actctaa 717

<210> SEQ ID NO 192
<211> LENGTH: 732
<212> TYPE: DNA
<213> ORGANISM: Artificial Sequence
<220> FEATURE:
<223> OTHER INFORMATION: Made in Lab - hLL2 LCCT2 FAB

<400> SEQUENCE: 192
gacatccagc tgacccagtc cccctcctcc ctgtccgcct ccgtgggcga ccgggtgacc 60
atgagctgca agtcctccca gtccgtgctg tactccgcca accacaagaa ctacctggcc 120
tggtaccagc agaagcccgg caaggccccc aagctgctga tctactgggc cagcacccgc 180
gagagcggcg tgccctcccg gttctccggc tccggctccg gcaccgactt caccttcacc 240
atctcctccc tgcagcccga ggacatcgcc acctactact gccaccagta cctgtcctcc 300
tggaccttcg gcggcggcac caagctggag atcaagcgca cggtggccgc ccccagtgtc 360
ttcattttcc ccccttccga tgagcagctg aagagcggta cagcctctgt tgtttgtctg 420
ctgaacaact tctatccacg cgaggccaag gtgcagtgga aagttgataa cgcgctgcag 480
agtggcaact cccaggagtc tgtgacagag caggacagta aagacagcac atattccctg 540
tctagcacac tgactctgtc caaggctgac tatgagaagc acaaggtgta cgcttgcgag 600
gtcacccacc agggactgag ttctcctgtg accaagtcct tcaatcgcgg cgagtgtggc 660
ggaggcggga gcggcggagg cgggagcaat tatcatcttg aaaatgaggt cgctcgtctc 720
aagaaactct aa 732

<210> SEQ ID NO 193
<211> LENGTH: 747
<212> TYPE: DNA
<213> ORGANISM: Artificial Sequence
<220> FEATURE:
<223> OTHER INFORMATION: Made in Lab - hLL2 LCCT3 FAB

<400> SEQUENCE: 193
gacatccagc tgacccagtc cccctcctcc ctgtccgcct ccgtgggcga ccgggtgacc 60
atgagctgca agtcctccca gtccgtgctg tactccgcca accacaagaa ctacctggcc 120
tggtaccagc agaagcccgg caaggccccc aagctgctga tctactgggc cagcacccgc 180
gagagcggcg tgccctcccg gttctccggc tccggctccg gcaccgactt caccttcacc 240
atctcctccc tgcagcccga ggacatcgcc acctactact gccaccagta cctgtcctcc 300
tggaccttcg gcggcggcac caagctggag atcaagcgca cggtggccgc ccccagtgtc 360
ttcattttcc ccccttccga tgagcagctg aagagcggta cagcctctgt tgtttgtctg 420
ctgaacaact tctatccacg cgaggccaag gtgcagtgga aagttgataa cgcgctgcag 480
agtggcaact cccaggagtc tgtgacagag caggacagta aagacagcac atattccctg 540
tctagcacac tgactctgtc caaggctgac tatgagaagc acaaggtgta cgcttgcgag 600
gtcacccacc agggactgag ttctcctgtg accaagtcct tcaatcgcgg cgagtgtggc 660
ggaggcggga gcggcggagg cgggagcggc ggaggcggga gcaattatca tcttgaaaat 720
gaggtcgctc gtctcaagaa actctaa 747

<210> SEQ ID NO 194
<211> LENGTH: 732
<212> TYPE: DNA
<213> ORGANISM: Artificial Sequence
<220> FEATURE:
<223> OTHER INFORMATION: Made in Lab - hLL2 HCCT2 FAB

<400> SEQUENCE: 194
caggtgcagc tggtgcagtc cggcgccgag gtgaagaagc ccggctcctc cgtgaaggtg 60
tcctgcaagg cctccggcta caccttcacc tcctactggc tgcactgggt gcggcaggcc 120
cccggccagg gcctggagtg gatcggctac atcaaccccc ggaacgacta caccgagtac 180
aaccagaact tcaaggacaa ggccaccatc accgccgacg agtccaccaa caccgcctac 240
atggagctgt cctccctgcg gtccgaggac accgccttct acttctgcgc ccggcgggac 300
atcaccacct tctactgggg ccagggcacc actgtgaccg tgtcctccgc caggaccaaa 360
ggaccgtccg tctttcctct ggccccttcc tctaagtcca caagcggtgg gaccgcagca 420
ctgggatgcc tggtgaagga ttacttccct gagccggtga ccgtgtcctg gaactccgga 480
gctctcacct ccggtgtcca tacctttcct gccgtcctgc agtcctccgg cctgtacagc 540
ctctctagcg tcgtgactgt gccctccagc tccctgggca cccaaactta tatctgcaat 600
gttaaccaca agccttctaa taccaaggtc gacaagaaag tggagccgaa gagctgtggc 660
ggaggcggga gcggcggagg cgggagcaat tatcatcttg aaaatgaggt cgctcgtctc 720
aagaaactct aa 732

<210> SEQ ID NO 195
<211> LENGTH: 747
<212> TYPE: DNA
<213> ORGANISM: Artificial Sequence
<220> FEATURE:
<223> OTHER INFORMATION: Made in lab - hLL2 HCCT3 FAB

<400> SEQUENCE: 195
caggtgcagc tggtgcagtc cggcgccgag gtgaagaagc ccggctcctc cgtgaaggtg 60
tcctgcaagg cctccggcta caccttcacc tcctactggc tgcactgggt gcggcaggcc 120
cccggccagg gcctggagtg gatcggctac atcaaccccc ggaacgacta caccgagtac 180
aaccagaact tcaaggacaa ggccaccatc accgccgacg agtccaccaa caccgcctac 240
atggagctgt cctccctgcg gtccgaggac accgccttct acttctgcgc ccggcgggac 300
atcaccacct tctactgggg ccagggcacc actgtgaccg tgtcctccgc caggaccaaa 360
ggaccgtccg tctttcctct ggccccttcc tctaagtcca caagcggtgg gaccgcagca 420
ctgggatgcc tggtgaagga ttacttccct gagccggtga ccgtgtcctg gaactccgga 480
gctctcacct ccggtgtcca tacctttcct gccgtcctgc agtcctccgg cctgtacagc 540
ctctctagcg tcgtgactgt gccctccagc tccctgggca cccaaactta tatctgcaat 600
gttaaccaca agccttctaa taccaaggtc gacaagaaag tggagccgaa gagctgtggc 660
ggaggcggga gcggcggagg cgggagcggc ggaggcggga gcaattatca tcttgaaaat 720
gaggtcgctc gtctcaagaa actctaa 747

<210> SEQ ID NO 196
<211> LENGTH: 1338
<212> TYPE: DNA
<213> ORGANISM: Artificial Sequence
<220> FEATURE:
<223> OTHER INFORMATION: Made in Lab - hLL2 HC WT IgG

<400> SEQUENCE: 196
caggtgcagc tggtgcagtc cggcgccgag gtgaagaagc ccggctcctc cgtgaaggtg 60
tcctgcaagg cctccggcta caccttcacc tcctactggc tgcactgggt gcggcaggcc 120
cccggccagg gcctggagtg gatcggctac atcaaccccc ggaacgacta caccgagtac 180
aaccagaact tcaaggacaa ggccaccatc accgccgacg agtccaccaa caccgcctac 240
atggagctgt cctccctgcg gtccgaggac accgccttct acttctgcgc ccggcgggac 300
atcaccacct tctactgggg ccagggcacc actgtgaccg tgtcctccgc caggaccaaa 360

-continued

```
ggaccgtccg tctttcctct ggccccttcc tctaagtcca caagcggtgg gaccgcagca    420

ctgggatgcc tggtgaagga ttacttccct gagccggtga ccgtgtcctg gaactccgga    480

gctctcacct ccggtgtcca tacctttcct gccgtcctgc agtcctccgg cctgtacagc    540

ctctctagcg tcgtgactgt gccctccagc tccctgggca cccaaactta tatctgcaat    600

gttaaccaca agccttctaa taccaaggtc gacaagaaag tggagccgaa gagctgtgac    660

aaaactcaca catgcccacc gtgcccagca cctccagtcg ccggaccgtc agtcttcctc    720

ttccctccaa aacccaagga caccctcatg atctcccgga cccctgaggt cacatgcgtg    780

gtggtggacg tgagccacga agaccctgag gtcaagttca actggtacgt ggacggcgtg    840

gaggtgcata atgccaagac aaagccgcgg gaggagcagt acaacagcac gtaccgtgtg    900

gtcagcgtcc tcaccgtcct gcaccaggac tggctgaatg gcaaggagta caagtgcaag    960

gtctccaaca aaggcctccc aagctccatc gagaaaacca tctccaaagc caaagggcag   1020

ccccgagaac cacaggtgta caccctgcct ccatcccggg atgagctgac caagaaccag   1080

gtcagcctga cctgcctggt caaaggcttc tatcccagcg acatcgccgt ggagtgggag   1140

agcaatgggc agccggagaa caactacaag accacgcctc ccgtgctgga ctccgacggc   1200

tccttcttcc tctacagcaa gctcaccgtg gacaagagca ggtggcagca ggggaacgtc   1260

ttctcatgct ccgtgatgca tgaggctctg cacaaccact acacgcagaa gagcctctcc   1320

ctgtctccgg gtaaataa                                                 1338
```

```
<210> SEQ ID NO 197
<211> LENGTH: 1395
<212> TYPE: DNA
<213> ORGANISM: Artificial Sequence
<220> FEATURE:
<223> OTHER INFORMATION: Made in Lab - hLL2 HCCT IgG

<400> SEQUENCE: 197
```

```
caggtgcagc tggtgcagtc cggcgccgag gtgaagaagc ccggctcctc cgtgaaggtg     60

tcctgcaagg cctccggcta caccttcacc tcctactggc tgcactgggt gcggcaggcc    120

cccggccagg gcctggagtg gatcggctac atcaaccccc ggaacgacta caccgagtac    180

aaccagaact tcaaggacaa ggccaccatc accgccgacg agtccaccaa caccgcctac    240

atggagctgt cctccctgcg gtccgaggac accgccttct acttctgcgc ccggcgggac    300

atcaccacct tctactgggg ccagggcacc actgtgaccg tgtcctccgc caggaccaaa    360

ggaccgtccg tctttcctct ggccccttcc tctaagtcca caagcggtgg gaccgcagca    420

ctgggatgcc tggtgaagga ttacttccct gagccggtga ccgtgtcctg gaactccgga    480

gctctcacct ccggtgtcca tacctttcct gccgtcctgc agtcctccgg cctgtacagc    540

ctctctagcg tcgtgactgt gccctccagc tccctgggca cccaaactta tatctgcaat    600

gttaaccaca agccttctaa taccaaggtc gacaagaaag tggagccgaa gagctgtgac    660

aaaactcaca catgcccacc gtgcccagca cctccagtcg ccggaccgtc agtcttcctc    720

ttccctccaa aacccaagga caccctcatg atctcccgga cccctgaggt cacatgcgtg    780

gtggtggacg tgagccacga agaccctgag gtcaagttca actggtacgt ggacggcgtg    840

gaggtgcata atgccaagac aaagccgcgg gaggagcagt acaacagcac gtaccgtgtg    900

gtcagcgtcc tcaccgtcct gcaccaggac tggctgaatg gcaaggagta caagtgcaag    960

gtctccaaca aaggcctccc aagctccatc gagaaaacca tctccaaagc caaagggcag   1020

ccccgagaac cacaggtgta caccctgcct ccatcccggg atgagctgac caagaaccag   1080
```

gtcagcctga cctgcctggt caaaggcttc tatcccagcg acatcgccgt ggagtgggag 1140
agcaatgggc agccggagaa caactacaag accacgcctc ccgtgctgga ctccgacggc 1200
tccttcttcc tctacagcaa gctcaccgtg gacaagagca ggtggcagca ggggaacgtc 1260
ttctcatgct ccgtgatgca tgaggctctg cacaaccact acacgcagaa gagcctctcc 1320
ctgtctccgg gtaaaggcgg aggcgggagc aattatcatc ttgaaaatga ggtcgctcgt 1380
ctcaagaaac tctaa 1395

<210> SEQ ID NO 198
<211> LENGTH: 1362
<212> TYPE: DNA
<213> ORGANISM: Artificial Sequence
<220> FEATURE:
<223> OTHER INFORMATION: Made in Lab - m971 HC WT IgG

<400> SEQUENCE: 198
caggtacagc tgcagcagtc aggtccagga ctggtgaagc cctcgcagac cctctcactc 60
acctgtgcca tctccgggga cagtgtctct agcaacagtg ctgcttggaa ctggatcagg 120
cagtccccat cgagaggcct tgagtggctg ggaaggacat actacaggtc caagtggtat 180
aatgattatg cagtatctgt gaaaagtcga ataaccatca acccagacac atccaagaac 240
cagttctccc tgcagctgaa ctctgtgact cccgaggaca cggctgtgta ttactgtgca 300
agagaagtga ctggggatct cgaggatgct tttgatatct ggggccaagg gacaatggtc 360
accgtctcct cagcctccac caagggccca tcggtcttcc ccctggcacc ctcctccaag 420
agcacctctg ggggcacagc ggccctgggc tgcctggtca aggactactt ccccgaaccg 480
gtgacggtgt cgtggaactc aggcgccctg accagcggcg tgcacacctt cccggctgtc 540
ctacagtcct caggactcta ctccctcagc agcgtggtga ctgtgccctc tagcagcttg 600
ggcacccaga cctacatctg caacgtgaat cacaagccca gcaacaccaa ggtggacaag 660
aaagttgagc ccaaatcttg tgacaaaact cacacatgcc caccgtgccc agcacctcca 720
gtcgccggac cgtcagtctt cctcttccct ccaaaaccca aggacaccct catgatctcc 780
cggacccctg aggtcacatg cgtggtggtg gacgtgagcc acgaagaccc tgaggtcaag 840
ttcaactggt acgtggacgg cgtggaggtg cataatgcca agacaaagcc gcgggaggag 900
cagtacaaca gcacgtaccg tgtggtcagc gtcctcaccg tcctgcacca ggactggctg 960
aatggcaagg agtacaagtg caaggtctcc aacaaaggcc tcccaagctc catcgagaaa 1020
accatctcca aagccaaagg gcagccccga gaaccacagg tgtacaccct gcctccatcc 1080
cgggatgagc tgaccaagaa ccaggtcagc ctgacctgcc tggtcaaagg cttctatccc 1140
agcgacatcg ccgtggagtg ggagagcaat gggcagccgg agaacaacta caagaccacg 1200
cctcccgtgc tggactccga cggctccttc ttcctctaca gcaagctcac cgtggacaag 1260
agcaggtggc agcaggggaa cgtcttctca tgctccgtga tgcatgaggc tctgcacaac 1320
cactacacgc agaagagcct ctccctgtct ccgggtaaat aa 1362

<210> SEQ ID NO 199
<211> LENGTH: 1419
<212> TYPE: DNA
<213> ORGANISM: Artificial Sequence
<220> FEATURE:
<223> OTHER INFORMATION: Made in Lab - m971 HCCT IgG

<400> SEQUENCE: 199

```
caggtacagc tgcagcagtc aggtccagga ctggtgaagc cctcgcagac cctctcactc     60

acctgtgcca tctccgggga cagtgtctct agcaacagtg ctgcttggaa ctggatcagg    120

cagtccccat cgagaggcct tgagtggctg ggaaggacat actacaggtc caagtggtat    180

aatgattatg cagtatctgt gaaaagtcga ataaccatca acccagacac atccaagaac    240

cagttctccc tgcagctgaa ctctgtgact cccgaggaca cggctgtgta ttactgtgca    300

agagaagtga ctggggatct cgaggatgct tttgatatct ggggccaagg gacaatggtc    360

accgtctcct cagcctccac caagggccca tcggtcttcc ccctggcacc ctcctccaag    420

agcacctctg gggcacagc ggccctgggc tgcctggtca aggactactt ccccgaaccg    480

gtgacggtgt cgtggaactc aggcgccctg accagcggcg tgcacacctt cccggctgtc    540

ctacagtcct caggactcta ctccctcagc agcgtggtga ctgtgccctc tagcagcttg    600

ggcacccaga cctacatctg caacgtgaat cacaagccca gcaacaccaa ggtggacaag    660

aaagttgagc ccaaatcttg tgacaaaact cacacatgcc caccgtgccc agcacctcca    720

gtcgccggac cgtcagtctt cctcttccct ccaaaaccca aggacaccct catgatctcc    780

cggacccctg aggtcacatg cgtggtggtg gacgtgagcc acgaagaccc tgaggtcaag    840

ttcaactggt acgtggacgg cgtggaggtg cataatgcca agacaaagcc gcgggaggag    900

cagtacaaca gcacgtaccg tgtggtcagc gtcctcaccg tcctgcacca ggactggctg    960

aatggcaagg agtacaagtg caaggtctcc aacaaaggcc tcccaagctc catcgagaaa   1020

accatctcca aagccaaagg gcagccccga gaaccacagg tgtacaccct gcctccatcc   1080

cgggatgagc tgaccaagaa ccaggtcagc ctgacctgcc tggtcaaagg cttctatccc   1140

agcgacatcg ccgtggagtg ggagagcaat gggcagccgg agaacaacta caagaccacg   1200

cctcccgtgc tggactccga cggctccttc ttcctctaca gcaagctcac cgtggacaag   1260

agcaggtggc agcaggggaa cgtcttctca tgctccgtga tgcatgaggc tctgcacaac   1320

cactacacgc agaagagcct ctccctgtct ccgggtaaag gcggaggcgg gagcaattat   1380

catcttgaaa atgaggtcgc tcgtctcaag aaactctaa                          1419
```

<210> SEQ ID NO 200
<211> LENGTH: 1428
<212> TYPE: DNA
<213> ORGANISM: Artificial Sequence
<220> FEATURE:
<223> OTHER INFORMATION: Made in lab - 1D3 CART19

<400> SEQUENCE: 200

```
atgggtgtcc ctacccagct cctgggactg ctcctgctgt ggatcaccga cgccatctgc     60

gacatccaga tgacccagag ccctgccagc ctgtctacca gcctgggcga gacagtgacc    120

atccagtgtc aggccagcga ggacatctac tctggcctgg cttggtatca gcagaagccc    180

ggcaagagcc ctcagctgct gatctacggc gccagcgacc tgcaggacgg cgtgcctagc    240

agattcagcg gcagcggctc cggaacccag tacagcctga agatcaccag catgcagacc    300

gaggacgagg gcgtgtactt ctgccagcaa ggcctgacct accctagaac cttcggagga    360

ggcaccaagc tggaactgaa gggcggaggc ggaagtggag gcggaggatc tggcggcgga    420

ggctctgaag tgcagctgca gcagtctggc gctgaactgg tccggcctgg cactagcgtg    480

aagctgtcct gcaaggtgtc cggcgacacc atcaccttct actacatgca cttcgtgaag    540

cagaggccag gacagggcct ggaatggatc ggcagaatcg accctgagga cgagagcacc    600

aagtacagcg agaagttcaa gaacaaggcc accctgaccg ccgacaccag cagcaacacc    660
```

gcctacctga agctgtctag cctgacctcc gaggacaccg ccacctactt ttgcatctac 720
ggcggctact acttcgacta ctggggccag ggcgtgatgg tcaccgtgtc cagcatcgag 780
ttcatgtacc cccctcccta cctggacaac gagagaagca acggcaccat catccacatc 840
aaagaaaagc acctgtgcca cacccagagc agccccaagc tgttctgggc cctggtggtg 900
gtggccggcg tgctgttctg ttacggcctg ctggtcacag tggccctgtg cgtgatctgg 960
accaacagca gaagaaacag aggcggccag agcgactaca tgaacatgac ccccagaagg 1020
ccaggcctga ccagaaagcc ctaccagccc tacgcccctg ccagagactt cgccgcctac 1080
agacccagag ccaagttcag cagatccgcc gagacagccg ccaacctgca ggatcccaac 1140
cagctgttca acgagctgaa cctgggcaga cgggaggaat tcgacgtgct ggaaaagaag 1200
agagccaggg accccgagat gggcggcaag cagcagagaa gaagaaaccc tcaggaaggc 1260
gtctacaacg ccctgcagaa agacaagatg gccgaggcct acagcgagat cggcaccaag 1320
ggcgagagaa gaaggggcaa gggccacgat ggcctgttcc agggcctgtc caccgccacc 1380
aaggacacct tcgacgccct gcacatgcag accctggccc ccagatga 1428

<210> SEQ ID NO 201
<211> LENGTH: 1443
<212> TYPE: DNA
<213> ORGANISM: Artificial Sequence
<220> FEATURE:
<223> OTHER INFORMATION: Made in Lab - murine sCAR 28Z

<400> SEQUENCE: 201
atgggtgtcc ctacccagct cctgggactg ctcctgctgt ggatcaccga cgccatctgc 60
gacgccgttg tgacccagga atccgctctg acctcttctc caggcgaaac cgtgactctg 120
acttgccgta gtagcaccgg ggctgtgacc acatctaact atgccagttg ggtccaggaa 180
aaaccggatc acctgtttac tggcctgatt ggcggcacca acaatcgcgc accgggtgtg 240
cccgctcgtt tcagcggttc cctgattggg gacaaggcag cactgactat caccggcgcc 300
cagaccgaag atgaggcgat ctatttttgc gtcctgtggt acagcgacca ttgggtgttc 360
gggggaggca ccaaactgac agtgctgggc ggaggaggag gttcaggagg aggaggtagc 420
gggggaggcg gttccggggg aggcggttct gatgtgcagc tgcaagaatc cgggccagga 480
ctggttgcgc cttctcagag tctgtcaatt acatgtactg ttagtggctt tctgctgacc 540
gactatggtg tgaactgggt tcgtcagagc ccaggcaagg gtctggagtg gctgggagtg 600
atttgggggg atggaatcac agactacaat agcgcactga aatctcggct gagtgttacc 660
aaagataaca gcaagtccca ggtcttcctg aagatgaaca gcctgcaaag cggcgactcc 720
gctcgctatt actgcgttac cggactgttt gattattggg ggcaggggac aactctgact 780
gtttcctcca tcgagttcat gtaccccccct ccctacctgg acaacgagag aagcaacggc 840
accatcatcc acatcaaaga aaagcacctg tgccacaccc agagcagccc caagctgttc 900
tgggccctgg tggtggtggc cggcgtgctg ttctgttacg gcctgctggt cacagtggcc 960
ctgtgcgtga tctggaccaa cagcagaaga aacagaggcg gccagagcga ctacatgaac 1020
atgaccccca gaaggccagg cctgaccaga aagccctacc agccctacgc ccctgccaga 1080
gacttcgccg cctacagacc cagagccaag ttcagcagat ccgccgagac agccgccaac 1140
ctgcaggatc ccaaccagct gttcaacgag ctgaacctgg gcagacggga ggaattcgac 1200
gtgctggaaa agaagagagc cagggacccc gagatgggcg gcaagcagca gagaagaaga 1260
aaccctcagg aaggcgtcta caacgccctg cagaaagaca agatggccga ggcctacagc 1320
gagatcggca ccaagggcga gagaagaagg ggcaagggcc acgatggcct gttccagggc 1380
ctgtccaccg ccaccaagga caccttcgac gccctgcaca tgcagaccct ggcccccaga 1440
tga 1443

<210> SEQ ID NO 202
<211> LENGTH: 1374
<212> TYPE: DNA
<213> ORGANISM: Artificial Sequence
<220> FEATURE:
<223> OTHER INFORMATION: Made in Lab - 52SR4, co-stim chimera 1

<400> SEQUENCE: 202
atgggtgtcc ctacccagct cctgggactg ctcctgctgt ggatcaccga cgccatctgc 60
gacgccgttg tgacccagga atccgctctg acctcttctc caggcgaaac cgtgactctg 120
acttgccgta gtagcaccgg ggctgtgacc acatctaact atgccagttg ggtccaggaa 180
aaaccggatc acctgtttac tggcctgatt ggcggcacca acaatcgcgc accgggtgtg 240
cccgctcgtt tcagcggttc cctgattggg gacaaggcag cactgactat caccggcgcc 300
cagaccgaag atgaggcgat ctatttttgc gtcctgtggt acagcgacca ttgggtgttc 360
gggggaggca ccaaactgac agtgctgggc ggaggaggag gttcaggagg aggaggtagc 420
gggggaggcg gttccggggg aggcggttct gatgtgcagc tgcaagaatc cgggccagga 480
ctggttgcgc cttctcagag tctgtcaatt acatgtactg ttagtggctt tctgctgacc 540
gactatggtg tgaactgggt tcgtcagagc ccaggcaagg gtctggagtg gctgggagtg 600
atttgggggg atggaatcac agactacaat agcgcactga aatctcggct gagtgttacc 660
aaagataaca gcaagtccca ggtcttcctg aagatgaatt ccctgcaaag cggcgactcc 720
gctcgctatt actgcgttac cggactgttt gattattggg ggcaggggac aactctgact 780
gtttcctccg aaagcaagta tggcccacct tgtccacctt gtcccattta catctgggca 840
cccttggccg gaatctgcgt ggcccttctg ctgtccttga tcatcactct catctgcaaa 900
tggatcagga aaaaattccc ccacatattc aagcaaccat ttaagaagac cactggagca 960
gctcaagagg aagatgcttg tagctgccga tgtccacagg aagaagaagg aggaggagga 1020
ggctatgagc tgagagccaa gttcagcaga tccgccgaga cagccgccaa cctgcaggat 1080
cccaaccagc tgttcaacga gctgaacctg ggcagacggg aggaattcga cgtgctggaa 1140
aagaagagag ccagggaccc cgagatgggc ggcaagcagc agagaagaag aaaccctcag 1200
gaaggcgtct acaacgccct gcagaaagac aagatggccg aggcctacag cgagatcggc 1260
accaagggcg agagaagaag gggcaagggc cacgatggcc tgttccaggg cctgtccacc 1320
gccaccaagg acaccttcga cgccctgcac atgcagaccc tggcccccag atga 1374

<210> SEQ ID NO 203
<211> LENGTH: 1374
<212> TYPE: DNA
<213> ORGANISM: Artificial Sequence
<220> FEATURE:
<223> OTHER INFORMATION: Made in Lab - 52SR4, co-stim chimera 2

<400> SEQUENCE: 203
atgggtgtcc ctacccagct cctgggactg ctcctgctgt ggatcaccga cgccatctgc 60
gacgccgttg tgacccagga atccgctctg acctcttctc caggcgaaac cgtgactctg 120
acttgccgta gtagcaccgg ggctgtgacc acatctaact atgccagttg ggtccaggaa 180

```
aaaccggatc acctgtttac tggcctgatt ggcggcacca acaatcgcgc accgggtgtg    240

cccgctcgtt tcagcggttc cctgattggg gacaaggcag cactgactat caccggcgcc    300

cagaccgaag atgaggcgat ctatttttgc gtcctgtggt acagcgacca ttgggtgttc    360

gggggaggca ccaaactgac agtgctgggc ggaggaggag gttcaggagg aggaggtagc    420

gggggaggcg gttccggggg aggcggttct gatgtgcagc tgcaagaatc cgggccagga    480

ctggttgcgc cttctcagag tctgtcaatt acatgtactg ttagtggctt tctgctgacc    540

gactatggtg tgaactgggt tcgtcagagc ccaggcaagg gtctggagtg gctgggagtg    600

atttgggggg atggaatcac agactacaat agcgcactga aatctcggct gagtgttacc    660

aaagataaca gcaagtccca ggtcttcctg aagatgaatt ccctgcaaag cggcgactcc    720

gctcgctatt actgcgttac cggactgttt gattattggg ggcaggggac aactctgact    780

gtttcctccg aaagcaagta tggcccacct tgtccacctt gtcccattta catctgggca    840

cccttggccg gaatctgcgt ggcccttctg ctgtccttga tcatcactct catctgcaaa    900

tggatcagga aaaaattccc ccacatattc aagcaaccat ttaagaagac cactggagca    960

gctcaagagg aagatgcttg tagctgccga tgtccacagg aagaagaagg aggaggagga   1020

ggctatgagc tgagagcaaa attcagcagg agtgcagaga ctgctgccaa cctgcaggac   1080

cccaaccagc tctacaatga gctcaatcta gggcgaagag aggaatatga cgtcttggag   1140

aagaagcggg ctcgggatcc agagatggga ggcaaacagc agaggaggag gaacccccag   1200

gaaggcgtat acaatgcact gcagaaagac aagatggcag aagcctacag tgagatcggc   1260

acaaaaggcg agaggcggag aggcaagggg cacgatggcc tttaccaggg tctcagcact   1320

gccaccaagg acacctatga tgccctgcat atgcagaccc tggcccctcg ctaa         1374
```

<210> SEQ ID NO 204
<211> LENGTH: 1467
<212> TYPE: DNA
<213> ORGANISM: Artificial Sequence
<220> FEATURE:
<223> OTHER INFORMATION: Made in lab - 52SR4, co-stim chimera 3

<400> SEQUENCE: 204

```
atgggtgtcc ctacccagct cctgggactg ctcctgctgt ggatcaccga cgccatctgc     60

gacgccgttg tgacccagga atccgctctg acctcttctc caggcgaaac cgtgactctg    120

acttgccgta gtagcaccgg ggctgtgacc acatctaact atgccagttg ggtccaggaa    180

aaaccggatc acctgtttac tggcctgatt ggcggcacca acaatcgcgc accgggtgtg    240

cccgctcgtt tcagcggttc cctgattggg gacaaggcag cactgactat caccggcgcc    300

cagaccgaag atgaggcgat ctatttttgc gtcctgtggt acagcgacca ttgggtgttc    360

gggggaggca ccaaactgac agtgctgggc ggaggaggag gttcaggagg aggaggtagc    420

gggggaggcg gttccggggg aggcggttct gatgtgcagc tgcaagaatc cgggccagga    480

ctggttgcgc cttctcagag tctgtcaatt acatgtactg ttagtggctt tctgctgacc    540

gactatggtg tgaactgggt tcgtcagagc ccaggcaagg gtctggagtg gctgggagtg    600

atttgggggg atggaatcac agactacaat agcgcactga aatctcggct gagtgttacc    660

aaagataaca gcaagtccca ggtcttcctg aagatgaatt ccctgcaaag cggcgactcc    720

gctcgctatt actgcgttac cggactgttt gattattggg ggcaggggac aactctgact    780

gtttcctcca ctactaccaa gccagtgctg cgaactccct cacctgtgca ccctaccggg    840
```

-continued

```
acatctcagc cccagagacc agaagattgt cggccccgtg gctcagtgaa ggggaccgga    900

ttggacttcg cctgtgatat ttacatctgg gcacccttgg ccggaatctg cgtggccctt    960

ctgctgtcct tgatcatcac tctcatctgc aaatggatca ggaaaaaatt cccccacata   1020

ttcaagcaac catttaagaa gaccactgga gcagctcaag aggaagatgc ttgtagctgc   1080

cgatgtccac aggaagaaga aggaggagga ggaggctatg agctgagagc caagttcagc   1140

agatccgccg agacagccgc caacctgcag gatcccaacc agctgttcaa cgagctgaac   1200

ctgggcagac gggaggaatt cgacgtgctg gaaaagaaga gagccaggga ccccgagatg   1260

ggcggcaagc agcagagaag aagaaaccct caggaaggcg tctacaacgc cctgcagaaa   1320

gacaagatgg ccgaggccta cagcgagatc ggcaccaagg gcgagagaag aaggggcaag   1380

ggccacgatg gcctgttcca gggcctgtcc accgccacca aggacacctt cgacgccctg   1440

cacatgcaga ccctggcccc cagatga                                       1467
```

<210> SEQ ID NO 205
<211> LENGTH: 1467
<212> TYPE: DNA
<213> ORGANISM: Artificial Sequence
<220> FEATURE:
<223> OTHER INFORMATION: Made in lab - 52SR4, co-stim chimera 4

<400> SEQUENCE: 205

```
atgggtgtcc ctacccagct cctgggactg ctcctgctgt ggatcaccga cgccatctgc     60

gacgccgttg tgacccagga atccgctctg acctcttctc caggcgaaac cgtgactctg    120

acttgccgta gtagcaccgg ggctgtgacc acatctaact atgccagttg ggtccaggaa    180

aaaccggatc acctgtttac tggcctgatt ggcggcacca acaatcgcgc accgggtgtg    240

cccgctcgtt tcagcggttc cctgattggg gacaaggcag cactgactat caccggcgcc    300

cagaccgaag atgaggcgat ctatttttgc gtcctgtggt acagcgacca ttgggtgttc    360

gggggaggca ccaaactgac agtgctgggc ggaggaggag gttcaggagg aggaggtagc    420

gggggaggcg gttccggggg aggcggttct gatgtgcagc tgcaagaatc cgggccagga    480

ctggttgcgc cttctcagag tctgtcaatt acatgtactg ttagtggctt tctgctgacc    540

gactatggtg tgaactgggt tcgtcagagc ccaggcaagg gtctggagtg gctgggagtg    600

atttgggggg atggaatcac agactacaat agcgcactga aatctcggct gagtgttacc    660

aaagataaca gcaagtccca ggtcttcctg aagatgaatt ccctgcaaag cggcgactcc    720

gctcgctatt actgcgttac cggactgttt gattattggg gcaggggac aactctgact     780

gtttcctcca ctactaccaa gccagtgctg cgaactccct cacctgtgca ccctaccggg    840

acatctcagc cccagagacc agaagattgt cggccccgtg gctcagtgaa ggggaccgga    900

ttggacttcg cctgtgatat ttacatctgg gcacccttgg ccggaatctg cgtggccctt    960

ctgctgtcct tgatcatcac tctcatctgc aaatggatca ggaaaaaatt cccccacata   1020

ttcaagcaac catttaagaa gaccactgga gcagctcaag aggaagatgc ttgtagctgc   1080

cgatgtccac aggaagaaga aggaggagga ggaggctatg agctgagagc aaaattcagc   1140

aggagtgcag agactgctgc caacctgcag gaccccaacc agctctacaa tgagctcaat   1200

ctagggcgaa gagaggaata tgacgtcttg gagaagaagc gggctcggga tccagagatg   1260

ggaggcaaac agcagaggag gaggaacccc caggaaggcg tatacaatgc actgcagaaa   1320

gacaagatgg cagaagccta cagtgagatc ggcacaaaag gcgagaggcg gagaggcaag   1380

gggcacgatg gcctttacca gggtctcagc actgccacca aggacaccta tgatgccctg   1440
```

catatgcaga ccctggcccc tcgctaa 1467

<210> SEQ ID NO 206
<211> LENGTH: 1359
<212> TYPE: DNA
<213> ORGANISM: Artificial Sequence
<220> FEATURE:
<223> OTHER INFORMATION: Made in Lab - 1D3, co-stim chimera 1

<400> SEQUENCE: 206
atgggtgtcc ctacccagct cctgggactg ctcctgctgt ggatcaccga cgccatctgc 60
gacatccaga tgacccagag ccctgccagc ctgtctacca gcctgggcga gacagtgacc 120
atccagtgtc aggccagcga ggacatctac tctggcctgg cttggtatca gcagaagccc 180
ggcaagagcc ctcagctgct gatctacggc gccagcgacc tgcaggacgg cgtgcctagc 240
agattcagcg gcagcggctc cggaacccag tacagcctga agatcaccag catgcagacc 300
gaggacgagg gcgtgtactt ctgccagcaa ggcctgacct accctagaac cttcggagga 360
ggcaccaagc tggaactgaa gggcggaggc ggaagtggag gcggaggatc tggcggcgga 420
ggctctgaag tgcagctgca gcagtctggc gctgaactgg tccggcctgg cactagcgtg 480
aagctgtcct gcaaggtgtc cggcgacacc atcaccttct actacatgca cttcgtgaag 540
cagaggccag gacagggcct ggaatggatc ggcagaatcg accctgagga cgagagcacc 600
aagtacagcg agaagttcaa gaacaaggcc accctgaccg ccgacaccag cagcaacacc 660
gcctacctga agctgtctag cctgacctcc gaggacaccg ccacctactt ttgcatctac 720
ggcggctact acttcgacta ctggggccag ggcgtgatgg tcaccgtgtc cagcgaaagc 780
aagtatggcc caccttgtcc accttgtccc atttacatct gggcaccctt ggccggaatc 840
tgcgtggccc ttctgctgtc cttgatcatc actctcatct gcaaatggat caggaaaaaa 900
ttcccccaca tattcaagca accatttaag aagaccactg gagcagctca agaggaagat 960
gcttgtagct gccgatgtcc acaggaagaa gaaggaggag gaggaggcta tgagctgaga 1020
gccaagttca gcagatccgc cgagacagcc gccaacctgc aggatcccaa ccagctgttc 1080
aacgagctga acctgggcag acgggaggaa ttcgacgtgc tggaaaagaa gagagccagg 1140
gaccccgaga tgggcggcaa gcagcagaga agaagaaacc ctcaggaagg cgtctacaac 1200
gccctgcaga aagacaagat ggccgaggcc tacagcgaga tcggcaccaa gggcgagaga 1260
agaaggggca agggccacga tggcctgttc cagggcctgt ccaccgccac caaggacacc 1320
ttcgacgccc tgcacatgca gaccctggcc cccagatga 1359

<210> SEQ ID NO 207
<211> LENGTH: 1359
<212> TYPE: DNA
<213> ORGANISM: Artificial Sequence
<220> FEATURE:
<223> OTHER INFORMATION: Made in Lab - 1D3, co-stim chimera 2

<400> SEQUENCE: 207
atgggtgtcc ctacccagct cctgggactg ctcctgctgt ggatcaccga cgccatctgc 60
gacatccaga tgacccagag ccctgccagc ctgtctacca gcctgggcga gacagtgacc 120
atccagtgtc aggccagcga ggacatctac tctggcctgg cttggtatca gcagaagccc 180
ggcaagagcc ctcagctgct gatctacggc gccagcgacc tgcaggacgg cgtgcctagc 240
agattcagcg gcagcggctc cggaacccag tacagcctga agatcaccag catgcagacc 300

```
gaggacgagg gcgtgtactt ctgccagcaa ggcctgacct accctagaac cttcggagga    360

ggcaccaagc tggaactgaa gggcggaggc ggaagtggag gcggaggatc tggcggcgga    420

ggctctgaag tgcagctgca gcagtctggc gctgaactgg tccggcctgg cactagcgtg    480

aagctgtcct gcaaggtgtc cggcgacacc atcaccttct actacatgca cttcgtgaag    540

cagaggccag gacagggcct ggaatggatc ggcagaatcg accctgagga cgagagcacc    600

aagtacagcg agaagttcaa gaacaaggcc accctgaccg ccgacaccag cagcaacacc    660

gcctacctga agctgtctag cctgacctcc gaggacaccg ccacctactt ttgcatctac    720

ggcggctact acttcgacta ctggggccag ggcgtgatgg tcaccgtgtc cagcgaaagc    780

aagtatggcc caccttgtcc accttgtccc atttacatct gggcaccctt ggccggaatc    840

tgcgtggccc ttctgctgtc cttgatcatc actctcatct gcaaatggat caggaaaaaa    900

ttcccccaca tattcaagca accatttaag aagaccactg gagcagctca agaggaagat    960

gcttgtagct gccgatgtcc acaggaagaa gaaggaggag gaggaggcta tgagctgaga   1020

gcaaaattca gcaggagtgc agagactgct gccaacctgc aggaccccaa ccagctctac   1080

aatgagctca atctagggcg aagagaggaa tatgacgtct tggagaagaa gcgggctcgg   1140

gatccagaga tgggaggcaa acagcagagg aggaggaacc cccaggaagg cgtatacaat   1200

gcactgcaga aagacaagat ggcagaagcc tacagtgaga tcggcacaaa aggcgagagg   1260

cggagaggca aggggcacga tggcctttac cagggtctca gcactgccac caaggacacc   1320

tatgatgccc tgcatatgca gaccctggcc cctcgctaa                          1359


<210> SEQ ID NO 208
<211> LENGTH: 1452
<212> TYPE: DNA
<213> ORGANISM: Artificial Sequence
<220> FEATURE:
<223> OTHER INFORMATION: Made in Lab - 1D3,  co-stim chimera 3

<400> SEQUENCE: 208

atgggtgtcc ctacccagct cctgggactg ctcctgctgt ggatcaccga cgccatctgc     60

gacatccaga tgacccagag ccctgccagc ctgtctacca gcctgggcga gacagtgacc    120

atccagtgtc aggccagcga ggacatctac tctggcctgg cttggtatca gcagaagccc    180

ggcaagagcc ctcagctgct gatctacggc gccagcgacc tgcaggacgg cgtgcctagc    240

agattcagcg gcagcggctc cggaacccag tacagcctga agatcaccag catgcagacc    300

gaggacgagg gcgtgtactt ctgccagcaa ggcctgacct accctagaac cttcggagga    360

ggcaccaagc tggaactgaa gggcggaggc ggaagtggag gcggaggatc tggcggcgga    420

ggctctgaag tgcagctgca gcagtctggc gctgaactgg tccggcctgg cactagcgtg    480

aagctgtcct gcaaggtgtc cggcgacacc atcaccttct actacatgca cttcgtgaag    540

cagaggccag gacagggcct ggaatggatc ggcagaatcg accctgagga cgagagcacc    600

aagtacagcg agaagttcaa gaacaaggcc accctgaccg ccgacaccag cagcaacacc    660

gcctacctga agctgtctag cctgacctcc gaggacaccg ccacctactt ttgcatctac    720

ggcggctact acttcgacta ctggggccag ggcgtgatgg tcaccgtgtc cagcactact    780

accaagccag tgctgcgaac tccctcacct gtgcacccta ccgggacatc tcagccccag    840

agaccagaag attgtcggcc ccgtggctca gtgaagggga ccggattgga cttcgcctgt    900

gatatttaca tctgggcacc cttggccgga atctgcgtgg cccttctgct gtccttgatc    960

atcactctca tctgcaaatg gatcaggaaa aaattccccc acatattcaa gcaaccattt   1020
```

```
aagaagacca ctggagcagc tcaagaggaa gatgcttgta gctgccgatg tccacaggaa   1080

gaagaaggag gaggaggagg ctatgagctg agagccaagt tcagcagatc cgccgagaca   1140

gccgccaacc tgcaggatcc caaccagctg ttcaacgagc tgaacctggg cagacgggag   1200

gaattcgacg tgctggaaaa gaagagagcc agggaccccg agatgggcgg caagcagcag   1260

agaagaagaa accctcagga aggcgtctac aacgccctgc agaaagacaa gatggccgag   1320

gcctacagcg agatcggcac caagggcgag agaagaaggg gcaagggcca cgatggcctg   1380

ttccagggcc tgtccaccgc caccaaggac accttcgacg ccctgcacat gcagaccctg   1440

gcccccagat ga                                                        1452
```

<210> SEQ ID NO 209
<211> LENGTH: 1452
<212> TYPE: DNA
<213> ORGANISM: Artificial Sequence
<220> FEATURE:
<223> OTHER INFORMATION: Made in Lab - 1D3, co-stim chimera 4

<400> SEQUENCE: 209

```
atgggtgtcc ctacccagct cctgggactg ctcctgctgt ggatcaccga cgccatctgc     60

gacatccaga tgacccagag ccctgccagc ctgtctacca gcctgggcga gacagtgacc    120

atccagtgtc aggccagcga ggacatctac tctggcctgg cttggtatca gcagaagccc    180

ggcaagagcc ctcagctgct gatctacggc gccagcgacc tgcaggacgg cgtgcctagc    240

agattcagcg gcagcggctc cggaacccag tacagcctga agatcaccag catgcagacc    300

gaggacgagg gcgtgtactt ctgccagcaa ggcctgacct accctagaac cttcggagga    360

ggcaccaagc tggaactgaa gggcggaggc ggaagtggag gcggaggatc tggcggcgga    420

ggctctgaag tgcagctgca gcagtctggc gctgaactgg tccggcctgg cactagcgtg    480

aagctgtcct gcaaggtgtc cggcgacacc atcaccttct actacatgca cttcgtgaag    540

cagaggccag gacagggcct ggaatggatc ggcagaatcg accctgagga cgagagcacc    600

aagtacagcg agaagttcaa gaacaaggcc accctgaccg ccgacaccag cagcaacacc    660

gcctacctga agctgtctag cctgacctcc gaggacaccg ccacctactt ttgcatctac    720

ggcggctact acttcgacta ctggggccag ggcgtgatgg tcaccgtgtc cagcactact    780

accaagccag tgctgcgaac tccctcacct gtgcacccta ccgggacatc tcagccccag    840

agaccagaag attgtcggcc ccgtggctca gtgaagggga ccggattgga cttcgcctgt    900

gatatttaca tctgggcacc cttggccgga atctgcgtgg cccttctgct gtccttgatc    960

atcactctca tctgcaaatg gatcaggaaa aaattccccc acatattcaa gcaaccattt   1020

aagaagacca ctggagcagc tcaagaggaa gatgcttgta gctgccgatg tccacaggaa   1080

gaagaaggag gaggaggagg ctatgagctg agagcaaaat tcagcaggag tgcagagact   1140

gctgccaacc tgcaggaccc caaccagctc tacaatgagc tcaatctagg gcgaagagag   1200

gaatatgacg tcttggagaa gaagcgggct cgggatccag agatgggagg caaacagcag   1260

aggaggagga acccccagga aggcgtatac aatgcactgc agaaagacaa gatggcagaa   1320

gcctacagtg agatcggcac aaaaggcgag aggcggagag gcaaggggca cgatggcctt   1380

taccagggtc tcagcactgc caccaaggac acctatgatg ccctgcatat gcagaccctg   1440

gcccctcgct aa                                                        1452
```

<210> SEQ ID NO 210

<211> LENGTH: 1371
<212> TYPE: DNA
<213> ORGANISM: Artificial Sequence
<220> FEATURE:
<223> OTHER INFORMATION: Made in lab - 52SR4, co-stim chimera 5

<400> SEQUENCE: 210
atgggtgtcc ctacccagct cctgggactg ctcctgctgt ggatcaccga cgccatctgc 60
gacgccgttg tgacccagga atccgctctg acctcttctc caggcgaaac cgtgactctg 120
acttgccgta gtagcaccgg ggctgtgacc acatctaact atgccagttg ggtccaggaa 180
aaaccggatc acctgtttac tggcctgatt ggcggcacca acaatcgcgc accgggtgtg 240
cccgctcgtt tcagcggttc cctgattggg gacaaggcag cactgactat caccggcgcc 300
cagaccgaag atgaggcgat ctatttttgc gtcctgtggt acagcgacca ttgggtgttc 360
gggggaggca ccaaactgac agtgctgggc ggaggaggag gttcaggagg aggaggtagc 420
gggggaggcg gttccggggg aggcggttct gatgtgcagc tgcaagaatc cgggccagga 480
ctggttgcgc cttctcagag tctgtcaatt acatgtactg ttagtggctt tctgctgacc 540
gactatggtg tgaactgggt tcgtcagagc ccaggcaagg gtctggagtg gctgggagtg 600
atttgggggg atggaatcac agactacaat agcgcactga aatctcggct gagtgttacc 660
aaagataaca gcaagtccca ggtcttcctg aagatgaaca gcctgcaaag cggcgactcc 720
gctcgctatt actgcgttac cggactgttt gattattggg ggcaggggac aactctgact 780
gtttcctccg aaagcaagta tggcccacct tgtccacctt gtcccttctg ggccctggtg 840
gtggtggccg gcgtgctgtt ctgttacggc ctgctggtca cagtggccct gtgcgtgatc 900
tggaccaaca gcagaagaaa cagaggcggc cagagcgact acatgaacat gacccccaga 960
aggccaggcc tgaccagaaa gccctaccag ccctacgccc ctgccagaga cttcgccgcc 1020
tacagaccca gagccaagtt cagcagatcc gccgagacag ccgccaacct gcaggatccc 1080
aaccagctgt tcaacgagct gaacctgggc agacgggagg aattcgacgt gctggaaaag 1140
aagagagcca gggaccccga gatgggcggc aagcagcaga gaagaagaaa ccctcaggaa 1200
ggcgtctaca acgccctgca gaaagacaag atggccgagg cctacagcga gatcggcacc 1260
aagggcgaga gaagaagggg caagggccac gatggcctgt tccagggcct gtccaccgcc 1320
accaaggaca ccttcgacgc cctgcacatg cagaccctgg cccccagatg a 1371

<210> SEQ ID NO 211
<211> LENGTH: 1371
<212> TYPE: DNA
<213> ORGANISM: Artificial Sequence
<220> FEATURE:
<223> OTHER INFORMATION: Made in Lab - 52SR4, co-stim chimera 6

<400> SEQUENCE: 211
atgggtgtcc ctacccagct cctgggactg ctcctgctgt ggatcaccga cgccatctgc 60
gatgtgcagc tgcaagaatc cgggccagga ctggttgcgc cttctcagag tctgtcaatt 120
acatgtactg ttagtggctt tctgctgacc gactatggtg tgaactgggt tcgtcagagc 180
ccaggcaagg gtctggagtg gctgggagtg atttgggggg atggaatcac agactacaat 240
agcgcactga aatctcggct gagtgttacc aaagataaca gcaagtccca ggtcttcctg 300
aagatgaaca gcctgcaaag cggcgactcc gctcgctatt actgcgttac cggactgttt 360
gattattggg ggcaggggac aactctgact gtttcctccg gaggaggagg ttcaggagga 420
ggaggtagcg gggaggcgg ttccggggga ggcggttctg acgccgttgt gacccaggaa 480
tccgctctga cctcttctcc aggcgaaacc gtgactctga cttgccgtag tagcaccggg 540
gctgtgacca catctaacta tgccagttgg gtccaggaaa aaccggatca cctgtttact 600
ggcctgattg gcggcaccaa caatcgcgca ccgggtgtgc ccgctcgttt cagcggttcc 660
ctgattgggg acaaggcagc actgactatc accggcgccc agaccgaaga tgaggcgatc 720
tatttttgcg tcctgtggta cagcgaccat tgggtgttcg ggggaggcac caaactgaca 780
gtgctgggcg aaagcaagta tggcccacct tgtccacctt gtcccttctg ggccctggtg 840
gtggtggccg gcgtgctgtt ctgttacggc ctgctggtca cagtggccct gtgcgtgatc 900
tggaccaaca gcagaagaaa cagaggcggc cagagcgact acatgaacat gacccccaga 960
aggccaggcc tgaccagaaa gccctaccag ccctacgccc ctgccagaga cttcgccgcc 1020
tacagaccca gagccaagtt cagcagatcc gccgagacag ccgccaacct gcaggatccc 1080
aaccagctgt tcaacgagct gaacctgggc agacgggagg aattcgacgt gctggaaaag 1140
aagagagcca gggaccccga gatgggcggc aagcagcaga gaagaagaaa ccctcaggaa 1200
ggcgtctaca acgccctgca gaaagacaag atggccgagg cctacagcga gatcggcacc 1260
aagggcgaga gaagaagggg caagggccac gatggcctgt tccagggcct gtccaccgcc 1320
accaaggaca ccttcgacgc cctgcacatg cagaccctgg cccccagatg a 1371

<210> SEQ ID NO 212
<211> LENGTH: 1365
<212> TYPE: DNA
<213> ORGANISM: Artificial Sequence
<220> FEATURE:
<223> OTHER INFORMATION: Made in Lab - 52SR4, co-stim chimera 7

<400> SEQUENCE: 212
atgggtgtcc ctacccagct cctgggactg ctcctgctgt ggatcaccga cgccatctgc 60
gacgccgttg tgacccagga atccgctctg acctcttctc caggcgaaac cgtgactctg 120
acttgccgta gtagcaccgg ggctgtgacc acatctaact atgccagttg ggtccaggaa 180
aaaccggatc acctgtttac tggcctgatt ggcggcacca acaatcgcgc accgggtgtg 240
cccgctcgtt tcagcggttc cctgattggg gacaaggcag cactgactat caccggcgcc 300
cagaccgaag atgaggcgat ctatttttgc gtcctgtggt acagcgacca ttgggtgttc 360
gggggaggca ccaaactgac agtgctgggc ggaggaggag gttcaggagg aggaggtagc 420
gggggaggcg gttccggggg aggcggttct gatgtgcagc tgcaagaatc cgggccagga 480
ctggttgcgc cttctcagag tctgtcaatt acatgtactg ttagtggctt tctgctgacc 540
gactatggtg tgaactgggt tcgtcagagc ccaggcaagg gtctggagtg gctgggagtg 600
atttgggggg atggaatcac agactacaat agcgcactga aatctcggct gagtgttacc 660
aaagataaca gcaagtccca ggtcttcctg aagatgaaca gcctgcaaag cggcgactcc 720
gctcgctatt actgcgttac cggactgttt gattattggg ggcaggggac aactctgact 780
gtttcctccg aaagcaagta tggcccacct tgtccacctt gtcccgatat ctacatctgg 840
gcgcccttgg ccgggacttg tggggtcctt ctcctgtcac tggttatcac cctttactgc 900
aaacggggca gaaagaaact cctgtatata ttcaaacaac catttatgag accagtacaa 960
actactcaag aggaagatgg ctgtagctgc cgatttccag aagaagaaga aggaggatgt 1020
gaactgagag tgaagttcag caggagcgca gacgcccccg cgtacaagca gggccagaac 1080
cagctctata acgagctcaa tctaggacga agagaggagt acgatgtttt ggacaagaga 1140
cgtggccggg accctgagat gggggggaaag ccgagaagga agaaccctca ggaaggcctg 1200
tacaatgaac tgcagaaaga taagatggcg gaggcctaca gtgagattgg gatgaaaggc 1260
gagcgccgga ggggcaaggg gcacgatggc ctttaccagg gtctcagtac agccaccaag 1320
gacacctacg acgcccttca catgcaggcc ctgccccctc gctaa 1365

<210> SEQ ID NO 213
<211> LENGTH: 1446
<212> TYPE: DNA
<213> ORGANISM: Artificial Sequence
<220> FEATURE:
<223> OTHER INFORMATION: Made in lab - 1D3, co-stim chimera 5

<400> SEQUENCE: 213
atgggtgtcc ctacccagct cctgggactg ctcctgctgt ggatcaccga cgccatctgc 60
gacatccaga tgacccagag ccctgccagc ctgtctacca gcctgggcga gacagtgacc 120
atccagtgtc aggccagcga ggacatctac tctggcctgg cttggtatca gcagaagccc 180
ggcaagagcc ctcagctgct gatctacggc gccagcgacc tgcaggacgg cgtgcctagc 240
agattcagcg gcagcggctc cggaacccag tacagcctga agatcaccag catgcagacc 300
gaggacgagg gcgtgtactt ctgccagcaa ggcctgacct accctagaac cttcggagga 360
ggcaccaagc tggaactgaa gggcggaggc ggaagtggag gcggaggatc tggcggcgga 420
ggctctgaag tgcagctgca gcagtctggc gctgaactgg tccggcctgg cactagcgtg 480
aagctgtcct gcaaggtgtc cggcgacacc atcaccttct actacatgca cttcgtgaag 540
cagaggccag gacagggcct ggaatggatc ggcagaatcg accctgagga cgagagcacc 600
aagtacagcg agaagttcaa gaacaaggcc accctgaccg ccgacaccag cagcaacacc 660
gcctacctga agctgtctag cctgacctcc gaggacaccg ccacctactt ttgcatctac 720
ggcggctact acttcgacta ctggggccag ggcgtgatgg tcaccgtgtc cagcaccacg 780
acgccagcgc cgcgaccacc aacaccggcg cccaccatcg cgtcgcagcc cctgtccctg 840
cgcccagagg cgtgccggcc agcggcgggg ggcgcagtgc acacgagggg gctggacttc 900
gcctgtgata tctacatctg ggcgcccttg gccgggactt gtggggtcct tctcctgtca 960
ctggttatca ccctttactg caaacggggc agaaagaaac tcctgtatat attcaaacaa 1020
ccatttatga gaccagtaca aactactcaa gaggaagatg gctgtagctg ccgatttcca 1080
gaagaagaag aaggaggatg tgaactgaga gtgaagttca gcaggagcgc agacgccccc 1140
gcgtacaagc agggccagaa ccagctctat aacgagctca atctaggacg aagagaggag 1200
tacgatgttt tggacaagag acgtggccgg gaccctgaga tgggggggaaa gccgagaagg 1260 aagaaccctc aggaaggcct gtacaatgaa ctgcagaaag ataagatggc ggaggcctac 1320
agtgagattg ggatgaaagg cgagcgccgg aggggcaagg ggcacgatgg cctttaccag 1380
ggtctcagta cagccaccaa ggacacctac gacgcccttc acatgcaggc cctgccccct 1440
cgctaa 1446

<210> SEQ ID NO 214

<400> SEQUENCE: 214

000

<210> SEQ ID NO 215
<211> LENGTH: 250
<212> TYPE: PRT

<213> ORGANISM: Artificial Sequence
<220> FEATURE:
<223> OTHER INFORMATION: Made in Lab - 1D3 LCNT short linker

<400> SEQUENCE: 215

```
Met Tyr Arg Met Gln Leu Leu Ser Cys Ile Ala Leu Ser Leu Ala Leu
1               5                   10                  15

Val Thr Asn Ser Asn Tyr His Leu Glu Asn Glu Val Ala Arg Leu Lys
            20                  25                  30

Lys Leu Gly Gly Asp Ile Gln Leu Thr Gln Ser Pro Ala Ser Leu Ser
        35                  40                  45

Thr Ser Leu Gly Glu Thr Val Thr Ile Gln Cys Gln Ala Ser Glu Asp
    50                  55                  60

Ile Tyr Ser Gly Leu Ala Trp Tyr Gln Gln Lys Pro Gly Lys Ser Pro
65                  70                  75                  80

Gln Leu Leu Ile Tyr Gly Ala Ser Asp Leu Gln Asp Gly Val Pro Ser
                85                  90                  95

Arg Phe Ser Gly Ser Gly Ser Gly Thr Gln Tyr Ser Leu Lys Ile Thr
            100                 105                 110

Ser Met Gln Thr Glu Asp Glu Gly Val Tyr Phe Cys Gln Gln Gly Leu
        115                 120                 125

Thr Tyr Pro Arg Thr Phe Gly Gly Gly Thr Lys Leu Glu Ile Lys Arg
    130                 135                 140

Thr Val Ala Ala Pro Ser Val Phe Ile Phe Pro Pro Ser Asp Glu Gln
145                 150                 155                 160

Leu Lys Ser Gly Thr Ala Ser Val Val Cys Leu Leu Asn Asn Phe Tyr
                165                 170                 175

Pro Arg Glu Ala Lys Val Gln Trp Lys Val Asp Asn Ala Leu Gln Ser
            180                 185                 190

Gly Asn Ser Gln Glu Ser Val Thr Glu Gln Asp Ser Lys Asp Ser Thr
        195                 200                 205

Tyr Ser Leu Ser Ser Thr Leu Thr Leu Ser Lys Ala Asp Tyr Glu Lys
    210                 215                 220

His Lys Val Tyr Ala Cys Glu Val Thr His Gln Gly Leu Ser Ser Pro
225                 230                 235                 240

Val Thr Lys Ser Phe Asn Arg Gly Glu Cys
                245                 250
```

<210> SEQ ID NO 216
<211> LENGTH: 255
<212> TYPE: PRT
<213> ORGANISM: Artificial Sequence
<220> FEATURE:
<223> OTHER INFORMATION: Made in Lab - 1D3 HCNT short linker

<400> SEQUENCE: 216

```
Met Tyr Arg Met Gln Leu Leu Ser Cys Ile Ala Leu Ser Leu Ala Leu
1               5                   10                  15

Val Thr Asn Ser Asn Tyr His Leu Glu Asn Glu Val Ala Arg Leu Lys
            20                  25                  30

Lys Leu Gly Gly Gln Val Gln Leu Val Gln Ser Gly Ala Glu Leu Val
        35                  40                  45

Arg Pro Gly Thr Ser Val Lys Leu Ser Cys Lys Val Ser Gly Asp Thr
    50                  55                  60

Ile Thr Phe Tyr Tyr Met His Phe Val Lys Gln Arg Pro Gly Gln Gly
65                  70                  75                  80
```

```
Leu Glu Trp Ile Gly Arg Ile Asp Pro Glu Asp Glu Ser Thr Lys Tyr
                85                  90                  95

Ser Glu Lys Phe Lys Asn Lys Ala Thr Leu Thr Ala Asp Thr Ser Ser
            100                 105                 110

Asn Thr Ala Tyr Leu Lys Leu Ser Ser Leu Thr Ser Glu Asp Thr Ala
        115                 120                 125

Thr Tyr Phe Cys Ile Tyr Gly Gly Tyr Tyr Phe Asp Tyr Trp Gly Pro
    130                 135                 140

Gly Thr Met Val Thr Val Ser Ser Ala Ser Thr Lys Gly Pro Ser Val
145                 150                 155                 160

Phe Pro Leu Ala Pro Ser Ser Lys Ser Thr Ser Gly Gly Thr Ala Ala
                165                 170                 175

Leu Gly Cys Leu Val Lys Asp Tyr Phe Pro Glu Pro Val Thr Val Ser
            180                 185                 190

Trp Asn Ser Gly Ala Leu Thr Ser Gly Val His Thr Phe Pro Ala Val
        195                 200                 205

Leu Gln Ser Ser Gly Leu Tyr Ser Leu Ser Ser Val Val Thr Val Pro
    210                 215                 220

Ser Ser Ser Leu Gly Thr Gln Thr Tyr Ile Cys Asn Val Asn His Lys
225                 230                 235                 240

Pro Ser Asn Thr Lys Val Asp Lys Lys Val Glu Pro Lys Ser Cys
                245                 250                 255


<210> SEQ ID NO 217
<211> LENGTH: 236
<212> TYPE: PRT
<213> ORGANISM: Artificial Sequence
<220> FEATURE:
<223> OTHER INFORMATION: Made in Lab - CD33 (hP67.6) LCNT1

<400> SEQUENCE: 217

Asn Tyr His Leu Glu Asn Glu Val Ala Arg Leu Lys Lys Leu Gly Gly
1               5                   10                  15

Gly Gly Ser Asp Ile Gln Leu Thr Gln Ser Pro Ser Thr Leu Ser Ala
            20                  25                  30

Ser Val Gly Asp Arg Val Thr Ile Thr Cys Arg Ala Ser Glu Ser Leu
        35                  40                  45

Asp Asn Tyr Gly Ile Arg Phe Leu Thr Trp Phe Gln Gln Lys Pro Gly
    50                  55                  60

Lys Ala Pro Lys Leu Leu Met Tyr Ala Ala Ser Asn Gln Gly Ser Gly
65                  70                  75                  80

Val Pro Ser Arg Phe Ser Gly Ser Gly Ser Gly Thr Glu Phe Thr Leu
                85                  90                  95

Thr Ile Ser Ser Leu Gln Pro Asp Asp Phe Ala Thr Tyr Tyr Cys Gln
            100                 105                 110

Gln Thr Lys Glu Val Pro Trp Ser Phe Gly Gln Gly Thr Lys Val Glu
        115                 120                 125

Val Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190
```

-continued

Ser Thr Tyr Ser Leu Ser Ser Thr Leu Thr Leu Ser Lys Ala Asp Tyr
195 200 205

Glu Lys His Lys Val Tyr Ala Cys Glu Val Thr His Gln Gly Leu Ser
210 215 220

Ser Pro Val Thr Lys Ser Phe Asn Arg Gly Glu Cys
225 230 235

<210> SEQ ID NO 218
<211> LENGTH: 241
<212> TYPE: PRT
<213> ORGANISM: Artificial Sequence
<220> FEATURE:
<223> OTHER INFORMATION: Made in Lab - CD33 (hP67.6) LCNT2

<400> SEQUENCE: 218

Asn Tyr His Leu Glu Asn Glu Val Ala Arg Leu Lys Lys Leu Gly Gly
1 5 10 15

Gly Gly Ser Gly Gly Gly Gly Ser Asp Ile Gln Leu Thr Gln Ser Pro
20 25 30

Ser Thr Leu Ser Ala Ser Val Gly Asp Arg Val Thr Ile Thr Cys Arg
35 40 45

Ala Ser Glu Ser Leu Asp Asn Tyr Gly Ile Arg Phe Leu Thr Trp Phe
50 55 60

Gln Gln Lys Pro Gly Lys Ala Pro Lys Leu Leu Met Tyr Ala Ala Ser
65 70 75 80

Asn Gln Gly Ser Gly Val Pro Ser Arg Phe Ser Gly Ser Gly Ser Gly
85 90 95

Thr Glu Phe Thr Leu Thr Ile Ser Ser Leu Gln Pro Asp Asp Phe Ala
100 105 110

Thr Tyr Tyr Cys Gln Gln Thr Lys Glu Val Pro Trp Ser Phe Gly Gln
115 120 125

Gly Thr Lys Val Glu Val Arg Thr Val Ala Ala Pro Ser Val Phe Ile
130 135 140

Phe Pro Pro Ser Asp Glu Gln Leu Lys Ser Gly Thr Ala Ser Val Val
145 150 155 160

Cys Leu Leu Asn Asn Phe Tyr Pro Arg Glu Ala Lys Val Gln Trp Lys
165 170 175

Val Asp Asn Ala Leu Gln Ser Gly Asn Ser Gln Glu Ser Val Thr Glu
180 185 190

Gln Asp Ser Lys Asp Ser Thr Tyr Ser Leu Ser Ser Thr Leu Thr Leu
195 200 205

Ser Lys Ala Asp Tyr Glu Lys His Lys Val Tyr Ala Cys Glu Val Thr
210 215 220

His Gln Gly Leu Ser Ser Pro Val Thr Lys Ser Phe Asn Arg Gly Glu
225 230 235 240

Cys

<210> SEQ ID NO 219
<211> LENGTH: 246
<212> TYPE: PRT
<213> ORGANISM: Artificial Sequence
<220> FEATURE:
<223> OTHER INFORMATION: Made in Lab - CD33 (hP67.6) LCNT3

<400> SEQUENCE: 219

Asn Tyr His Leu Glu Asn Glu Val Ala Arg Leu Lys Lys Leu Gly Gly
1 5 10 15

-continued

```
Gly Gly Ser Gly Gly Gly Gly Ser Gly Gly Gly Gly Ser Asp Ile Gln
            20                  25                  30

Leu Thr Gln Ser Pro Ser Thr Leu Ser Ala Ser Val Gly Asp Arg Val
        35                  40                  45

Thr Ile Thr Cys Arg Ala Ser Glu Ser Leu Asp Asn Tyr Gly Ile Arg
    50                  55                  60

Phe Leu Thr Trp Phe Gln Gln Lys Pro Gly Lys Ala Pro Lys Leu Leu
65                  70                  75                  80

Met Tyr Ala Ala Ser Asn Gln Gly Ser Gly Val Pro Ser Arg Phe Ser
                85                  90                  95

Gly Ser Gly Ser Gly Thr Glu Phe Thr Leu Thr Ile Ser Ser Leu Gln
            100                 105                 110

Pro Asp Asp Phe Ala Thr Tyr Tyr Cys Gln Gln Thr Lys Glu Val Pro
        115                 120                 125

Trp Ser Phe Gly Gln Gly Thr Lys Val Glu Val Arg Thr Val Ala Ala
    130                 135                 140

Pro Ser Val Phe Ile Phe Pro Pro Ser Asp Glu Gln Leu Lys Ser Gly
145                 150                 155                 160

Thr Ala Ser Val Val Cys Leu Leu Asn Asn Phe Tyr Pro Arg Glu Ala
                165                 170                 175

Lys Val Gln Trp Lys Val Asp Asn Ala Leu Gln Ser Gly Asn Ser Gln
            180                 185                 190

Glu Ser Val Thr Glu Gln Asp Ser Lys Asp Ser Thr Tyr Ser Leu Ser
        195                 200                 205

Ser Thr Leu Thr Leu Ser Lys Ala Asp Tyr Glu Lys His Lys Val Tyr
    210                 215                 220

Ala Cys Glu Val Thr His Gln Gly Leu Ser Ser Pro Val Thr Lys Ser
225                 230                 235                 240

Phe Asn Arg Gly Glu Cys
                245


<210> SEQ ID NO 220
<211> LENGTH: 247
<212> TYPE: PRT
<213> ORGANISM: Artificial Sequence
<220> FEATURE:
<223> OTHER INFORMATION: Made in Lab - CD33 (hP67.6) HCNT1

<400> SEQUENCE: 220

Asn Tyr His Leu Glu Asn Glu Val Ala Arg Leu Lys Lys Leu Leu Val
1               5                   10                  15

Gly Glu Ala Ala Ala Lys Glu Ala Ala Ala Lys Ala Glu Val Gln Leu
            20                  25                  30

Val Gln Ser Gly Ala Glu Val Lys Lys Pro Gly Ser Ser Val Lys Val
        35                  40                  45

Ser Cys Lys Ala Ser Gly Tyr Thr Ile Thr Asp Ser Asn Ile His Trp
    50                  55                  60

Val Arg Gln Ala Pro Gly Gln Ser Leu Glu Trp Ile Gly Tyr Ile Tyr
65                  70                  75                  80

Pro Tyr Asn Gly Gly Thr Asp Tyr Asn Gln Lys Phe Lys Asn Arg Ala
                85                  90                  95

Thr Leu Thr Val Asp Asn Pro Thr Asn Thr Ala Tyr Met Glu Leu Ser
            100                 105                 110

Ser Leu Arg Ser Glu Asp Thr Ala Phe Tyr Tyr Cys Val Asn Gly Asn
        115                 120                 125
```

```
Pro Trp Leu Ala Tyr Trp Gly Gln Gly Thr Leu Val Thr Val Ser Ser
    130                 135                 140

Ala Arg Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys
                245


<210> SEQ ID NO 221
<211> LENGTH: 249
<212> TYPE: PRT
<213> ORGANISM: Artificial Sequence
<220> FEATURE:
<223> OTHER INFORMATION: Made in Lab - CD33 (hP67.6) HCNT2

<400> SEQUENCE: 221

Asn Tyr His Leu Glu Asn Glu Val Ala Arg Leu Lys Lys Leu Glu Ala
1               5                   10                  15

Ala Ala Lys Glu Ala Ala Ala Lys Glu Ala Ala Ala Lys Ala Glu Val
            20                  25                  30

Gln Leu Val Gln Ser Gly Ala Glu Val Lys Lys Pro Gly Ser Ser Val
        35                  40                  45

Lys Val Ser Cys Lys Ala Ser Gly Tyr Thr Ile Thr Asp Ser Asn Ile
    50                  55                  60

His Trp Val Arg Gln Ala Pro Gly Gln Ser Leu Glu Trp Ile Gly Tyr
65                  70                  75                  80

Ile Tyr Pro Tyr Asn Gly Gly Thr Asp Tyr Asn Gln Lys Phe Lys Asn
                85                  90                  95

Arg Ala Thr Leu Thr Val Asp Asn Pro Thr Asn Thr Ala Tyr Met Glu
            100                 105                 110

Leu Ser Ser Leu Arg Ser Glu Asp Thr Ala Phe Tyr Tyr Cys Val Asn
        115                 120                 125

Gly Asn Pro Trp Leu Ala Tyr Trp Gly Gln Gly Thr Leu Val Thr Val
    130                 135                 140

Ser Ser Ala Arg Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240
```

```
Asp Lys Lys Val Glu Pro Lys Ser Cys
                245


<210> SEQ ID NO 222
<211> LENGTH: 236
<212> TYPE: PRT
<213> ORGANISM: Artificial Sequence
<220> FEATURE:
<223> OTHER INFORMATION: Made in lab - CD33 (hP67.6) LCCT1

<400> SEQUENCE: 222

Asp Ile Gln Leu Thr Gln Ser Pro Ser Thr Leu Ser Ala Ser Val Gly
1               5                   10                  15

Asp Arg Val Thr Ile Thr Cys Arg Ala Ser Glu Ser Leu Asp Asn Tyr
            20                  25                  30

Gly Ile Arg Phe Leu Thr Trp Phe Gln Gln Lys Pro Gly Lys Ala Pro
        35                  40                  45

Lys Leu Leu Met Tyr Ala Ala Ser Asn Gln Gly Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln Gln Thr Lys
                85                  90                  95

Glu Val Pro Trp Ser Phe Gly Gln Gly Thr Lys Val Glu Val Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Gly Gly Gly Gly Ser Asn Tyr
    210                 215                 220

His Leu Glu Asn Glu Val Ala Arg Leu Lys Lys Leu
225                 230                 235


<210> SEQ ID NO 223
<211> LENGTH: 241
<212> TYPE: PRT
<213> ORGANISM: Artificial Sequence
<220> FEATURE:
<223> OTHER INFORMATION: Made in lab - CD33 (hP67.6) LCCT2

<400> SEQUENCE: 223

Asp Ile Gln Leu Thr Gln Ser Pro Ser Thr Leu Ser Ala Ser Val Gly
1               5                   10                  15

Asp Arg Val Thr Ile Thr Cys Arg Ala Ser Glu Ser Leu Asp Asn Tyr
            20                  25                  30

Gly Ile Arg Phe Leu Thr Trp Phe Gln Gln Lys Pro Gly Lys Ala Pro
        35                  40                  45

Lys Leu Leu Met Tyr Ala Ala Ser Asn Gln Gly Ser Gly Val Pro Ser
    50                  55                  60
```

```
Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln Gln Thr Lys
                85                  90                  95

Glu Val Pro Trp Ser Phe Gly Gln Gly Thr Lys Val Glu Val Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Gly Gly Gly Gly Ser Gly Gly
    210                 215                 220

Gly Gly Ser Asn Tyr His Leu Glu Asn Glu Val Ala Arg Leu Lys Lys
225                 230                 235                 240

Leu


<210> SEQ ID NO 224
<211> LENGTH: 246
<212> TYPE: PRT
<213> ORGANISM: Artificial Sequence
<220> FEATURE:
<223> OTHER INFORMATION: Made in lab - CD33 (hP67.6) LCCT3

<400> SEQUENCE: 224

Asp Ile Gln Leu Thr Gln Ser Pro Ser Thr Leu Ser Ala Ser Val Gly
1               5                   10                  15

Asp Arg Val Thr Ile Thr Cys Arg Ala Ser Glu Ser Leu Asp Asn Tyr
            20                  25                  30

Gly Ile Arg Phe Leu Thr Trp Phe Gln Gln Lys Pro Gly Lys Ala Pro
        35                  40                  45

Lys Leu Leu Met Tyr Ala Ala Ser Asn Gln Gly Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln Gln Thr Lys
                85                  90                  95

Glu Val Pro Trp Ser Phe Gly Gln Gly Thr Lys Val Glu Val Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175
```

```
Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Gly Gly Gly Gly Ser Gly Gly
    210                 215                 220

Gly Gly Ser Gly Gly Gly Gly Ser Asn Tyr His Leu Glu Asn Glu Val
225                 230                 235                 240

Ala Arg Leu Lys Lys Leu
                245
```

<210> SEQ ID NO 225
<211> LENGTH: 238
<212> TYPE: PRT
<213> ORGANISM: Artificial Sequence
<220> FEATURE:
<223> OTHER INFORMATION: Made in lab - CD33 (hP67.6) HCCT1

<400> SEQUENCE: 225

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Ile Thr Asp Ser
            20                  25                  30

Asn Ile His Trp Val Arg Gln Ala Pro Gly Gln Ser Leu Glu Trp Ile
        35                  40                  45

Gly Tyr Ile Tyr Pro Tyr Asn Gly Gly Thr Asp Tyr Asn Gln Lys Phe
    50                  55                  60

Lys Asn Arg Ala Thr Leu Thr Val Asp Asn Pro Thr Asn Thr Ala Tyr
65                  70                  75                  80

Met Glu Leu Ser Ser Leu Arg Ser Glu Asp Thr Ala Phe Tyr Tyr Cys
                85                  90                  95

Val Asn Gly Asn Pro Trp Leu Ala Tyr Trp Gly Gln Gly Thr Leu Val
            100                 105                 110

Thr Val Ser Ser Ala Arg Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Gly Gly Gly Gly Ser
    210                 215                 220

Asn Tyr His Leu Glu Asn Glu Val Ala Arg Leu Lys Lys Leu
225                 230                 235
```

<210> SEQ ID NO 226
<211> LENGTH: 243
<212> TYPE: PRT
<213> ORGANISM: Artificial Sequence
<220> FEATURE:
<223> OTHER INFORMATION: Made in lab - CD33 (hP67.6) HCCT2

<400> SEQUENCE: 226

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Ile Thr Asp Ser
            20                  25                  30

Asn Ile His Trp Val Arg Gln Ala Pro Gly Gln Ser Leu Glu Trp Ile
        35                  40                  45

Gly Tyr Ile Tyr Pro Tyr Asn Gly Gly Thr Asp Tyr Asn Gln Lys Phe
    50                  55                  60

Lys Asn Arg Ala Thr Leu Thr Val Asp Asn Pro Thr Asn Thr Ala Tyr
65                  70                  75                  80

Met Glu Leu Ser Ser Leu Arg Ser Glu Asp Thr Ala Phe Tyr Tyr Cys
                85                  90                  95

Val Asn Gly Asn Pro Trp Leu Ala Tyr Trp Gly Gln Gly Thr Leu Val
            100                 105                 110

Thr Val Ser Ser Ala Arg Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Gly Gly Gly Gly Ser
    210                 215                 220

Gly Gly Gly Gly Ser Asn Tyr His Leu Glu Asn Glu Val Ala Arg Leu
225                 230                 235                 240

Lys Lys Leu


<210> SEQ ID NO 227
<211> LENGTH: 248
<212> TYPE: PRT
<213> ORGANISM: Artificial Sequence
<220> FEATURE:
<223> OTHER INFORMATION: Made in lab - CD33 (hP67.6) HCCT3

<400> SEQUENCE: 227

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Ile Thr Asp Ser
            20                  25                  30

Asn Ile His Trp Val Arg Gln Ala Pro Gly Gln Ser Leu Glu Trp Ile
        35                  40                  45

Gly Tyr Ile Tyr Pro Tyr Asn Gly Gly Thr Asp Tyr Asn Gln Lys Phe
    50                  55                  60

Lys Asn Arg Ala Thr Leu Thr Val Asp Asn Pro Thr Asn Thr Ala Tyr
65                  70                  75                  80

Met Glu Leu Ser Ser Leu Arg Ser Glu Asp Thr Ala Phe Tyr Tyr Cys
                85                  90                  95

Val Asn Gly Asn Pro Trp Leu Ala Tyr Trp Gly Gln Gly Thr Leu Val
            100                 105                 110
```

```
Thr Val Ser Ser Ala Arg Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Gly Gly Gly Gly Ser
    210                 215                 220

Gly Gly Gly Gly Ser Gly Gly Gly Gly Ser Asn Tyr His Leu Glu Asn
225                 230                 235                 240

Glu Val Ala Arg Leu Lys Lys Leu
                245
```

<210> SEQ ID NO 228
<211> LENGTH: 230
<212> TYPE: PRT
<213> ORGANISM: Artificial Sequence
<220> FEATURE:
<223> OTHER INFORMATION: Made in lab - CD33 (hP67.6) HCC1

<400> SEQUENCE: 228

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Ile Thr Asp Ser
            20                  25                  30

Asn Ile His Trp Val Arg Gln Ala Pro Gly Gln Ser Leu Glu Trp Ile
        35                  40                  45

Gly Tyr Ile Tyr Pro Tyr Asn Gly Gly Thr Asp Tyr Asn Gln Lys Phe
    50                  55                  60

Lys Asn Arg Ala Thr Leu Thr Val Asp Asn Pro Thr Asn Thr Ala Tyr
65                  70                  75                  80

Met Glu Leu Ser Ser Leu Arg Ser Glu Asp Thr Ala Phe Tyr Tyr Cys
                85                  90                  95

Val Asn Gly Asn Pro Trp Leu Ala Tyr Trp Gly Gln Gly Thr Leu Val
            100                 105                 110

Thr Val Ser Ser Ala Arg Thr Lys Gly Pro Ser Val Phe Pro Leu Ala
        115                 120                 125

Pro Ser Ser Asn Tyr His Leu Glu Asn Glu Val Ala Arg Leu Lys Lys
    130                 135                 140

Leu Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220
```

Val Glu Pro Lys Ser Cys
225 230

<210> SEQ ID NO 229
<211> LENGTH: 241
<212> TYPE: PRT
<213> ORGANISM: Artificial Sequence
<220> FEATURE:
<223> OTHER INFORMATION: Made in lab - CD33 (hP67.6) HCC1 G4S

<400> SEQUENCE: 229

Glu Val Gln Leu Val Gln Ser Gly Ala Glu Val Lys Lys Pro Gly Ser
1 5 10 15

Ser Val Lys Val Ser Cys Lys Ala Ser Gly Tyr Thr Ile Thr Asp Ser
20 25 30

Asn Ile His Trp Val Arg Gln Ala Pro Gly Gln Ser Leu Glu Trp Ile
35 40 45

Gly Tyr Ile Tyr Pro Tyr Asn Gly Gly Thr Asp Tyr Asn Gln Lys Phe
50 55 60

Lys Asn Arg Ala Thr Leu Thr Val Asp Asn Pro Thr Asn Thr Ala Tyr
65 70 75 80

Met Glu Leu Ser Ser Leu Arg Ser Glu Asp Thr Ala Phe Tyr Tyr Cys
85 90 95

Val Asn Gly Asn Pro Trp Leu Ala Tyr Trp Gly Gln Gly Thr Leu Val
100 105 110

Thr Val Ser Ser Ala Arg Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Gly
165 170 175

Gly Gly Gly Ser Asn Tyr His Leu Glu Asn Glu Val Ala Arg Leu Lys
180 185 190

Lys Leu Gly Gly Gly Gly Ser Leu Tyr Ser Leu Ser Ser Val Val Thr
195 200 205

Val Pro Ser Ser Ser Leu Gly Thr Gln Thr Tyr Ile Cys Asn Val Asn
210 215 220

His Lys Pro Ser Asn Thr Lys Val Asp Lys Lys Val Glu Pro Lys Ser
225 230 235 240

Cys

<210> SEQ ID NO 230
<211> LENGTH: 240
<212> TYPE: PRT
<213> ORGANISM: Artificial Sequence
<220> FEATURE:
<223> OTHER INFORMATION: Made in Lab - CD33 (hP67.6) LCC1 G4S

<400> SEQUENCE: 230

Asp Ile Gln Leu Thr Gln Ser Pro Ser Thr Leu Ser Ala Ser Val Gly
1 5 10 15

Asp Arg Val Thr Ile Thr Cys Arg Ala Ser Glu Ser Leu Asp Asn Tyr
20 25 30

Gly Ile Arg Phe Leu Thr Trp Phe Gln Gln Lys Pro Gly Lys Ala Pro
35 40 45

-continued

```
Lys Leu Leu Met Tyr Ala Ala Ser Asn Gln Gly Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln Gln Thr Lys
                85                  90                  95

Glu Val Pro Trp Ser Phe Gly Gln Gly Thr Lys Val Glu Val Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Gly Gly Gly Gly Ser
                165                 170                 175

Asn Tyr His Leu Glu Asn Glu Val Ala Arg Leu Lys Lys Leu Gly Gly
            180                 185                 190

Gly Gly Ser Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240


<210> SEQ ID NO 231
<211> LENGTH: 218
<212> TYPE: PRT
<213> ORGANISM: Artificial Sequence
<220> FEATURE:
<223> OTHER INFORMATION: Made in lab - CD33 (hP67.6) LCWT

<400> SEQUENCE: 231

Asp Ile Gln Leu Thr Gln Ser Pro Ser Thr Leu Ser Ala Ser Val Gly
1               5                   10                  15

Asp Arg Val Thr Ile Thr Cys Arg Ala Ser Glu Ser Leu Asp Asn Tyr
            20                  25                  30

Gly Ile Arg Phe Leu Thr Trp Phe Gln Gln Lys Pro Gly Lys Ala Pro
        35                  40                  45

Lys Leu Leu Met Tyr Ala Ala Ser Asn Gln Gly Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln Gln Thr Lys
                85                  90                  95

Glu Val Pro Trp Ser Phe Gly Gln Gly Thr Lys Val Glu Val Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175
```

```
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 232
<211> LENGTH: 224
<212> TYPE: PRT
<213> ORGANISM: Artificial Sequence
<220> FEATURE:
<223> OTHER INFORMATION: Made in Lab - CD33 (hP67.6) HCWT

<400> SEQUENCE: 232

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Ile Thr Asp Ser
            20                  25                  30

Asn Ile His Trp Val Arg Gln Ala Pro Gly Gln Ser Leu Glu Trp Ile
        35                  40                  45

Gly Tyr Ile Tyr Pro Tyr Asn Gly Gly Thr Asp Tyr Asn Gln Lys Phe
    50                  55                  60

Lys Asn Arg Ala Thr Leu Thr Val Asp Asn Pro Thr Asn Thr Ala Tyr
65                  70                  75                  80

Met Glu Leu Ser Ser Leu Arg Ser Glu Asp Thr Ala Phe Tyr Tyr Cys
                85                  90                  95

Val Asn Gly Asn Pro Trp Leu Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220
```

<210> SEQ ID NO 233
<211> LENGTH: 217
<212> TYPE: PRT
<213> ORGANISM: Artificial Sequence
<220> FEATURE:
<223> OTHER INFORMATION: Made in Lab - CD123 32716 LCWT

<400> SEQUENCE: 233

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45
```

```
Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Pro Thr Phe Gly Ala Gly Thr Lys Leu Glu Leu Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 234
<211> LENGTH: 221
<212> TYPE: PRT
<213> ORGANISM: Artificial Sequence
<220> FEATURE:
<223> OTHER INFORMATION: Made in Lab - CD123 32716  HCWT

<400> SEQUENCE: 234

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asn Tyr
            20                  25                  30

Gly Met Asn Trp Val Lys Gln Ala Pro Gly Lys Ser Phe Lys Trp Met
        35                  40                  45

Gly Trp Ile Asn Thr Tyr Thr Gly Glu Ser Thr Tyr Ser Ala Asp Phe
    50                  55                  60

Lys Gly Arg Phe Ala Phe Ser Leu Glu Thr Ser Ala Ser Thr Ala Tyr
65                  70                  75                  80

Leu His Ile Asn Asp Leu Lys Asn Glu Asp Thr Ala Thr Tyr Phe Cys
                85                  90                  95

Ala Arg Ser Gly Gly Tyr Asp Pro Met Asp Tyr Trp Gly Gln Gly Thr
            100                 105                 110

Ser Val Thr Val Ser Ser Ala Arg Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

```
Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220
```

<210> SEQ ID NO 235
<211> LENGTH: 213
<212> TYPE: PRT
<213> ORGANISM: Artificial Sequence
<220> FEATURE:
<223> OTHER INFORMATION: Made in Lab - CD123 26292 LCWT

<400> SEQUENCE: 235

```
Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Asp
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Lys Tyr Pro Tyr
                85                  90                  95

Thr Phe Gly Gly Gly Thr Lys Leu Glu Ile Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 236
<211> LENGTH: 218
<212> TYPE: PRT
<213> ORGANISM: Artificial Sequence
<220> FEATURE:
<223> OTHER INFORMATION: Made in Lab - CD123 26292 HCWT

<400> SEQUENCE: 236

```
Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Asp Gln Gly Leu Glu Trp Ile
        35                  40                  45

Gly Arg Ile Asp Pro Tyr Asp Ser Glu Thr His Tyr Asn Gln Lys Phe
```

-continued

```
    50                  55                  60

Lys Asp Lys Ala Ile Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Asn Trp Asp Asp Tyr Trp Gly Gln Gly Thr Thr Leu Thr
            100                 105                 110

Val Ser Ser Ala Arg Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys
    210                 215


<210> SEQ ID NO 237
<211> LENGTH: 232
<212> TYPE: PRT
<213> ORGANISM: Artificial Sequence
<220> FEATURE:
<223> OTHER INFORMATION: Made in Lab - CD123 26292   LCNT1

<400> SEQUENCE: 237

Asn Tyr His Leu Glu Asn Glu Val Ala Arg Leu Lys Lys Leu Gly Gly
1               5                   10                  15

Gly Gly Ser Asp Val Gln Ile Thr Gln Ser Pro Ser Tyr Leu Ala Ala
            20                  25                  30

Ser Pro Gly Glu Thr Ile Thr Ile Asn Cys Arg Ala Ser Lys Ser Ile
        35                  40                  45

Ser Lys Asp Leu Ala Trp Tyr Gln Glu Lys Pro Gly Lys Thr Asn Lys
    50                  55                  60

Leu Leu Ile Tyr Ser Gly Ser Thr Leu Gln Ser Gly Ile Pro Ser Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Met Tyr Tyr Cys Gln Gln His Asn Lys
            100                 105                 110

Tyr Pro Tyr Thr Phe Gly Gly Gly Thr Lys Leu Glu Ile Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
```

```
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230


<210> SEQ ID NO 238
<211> LENGTH: 236
<212> TYPE: PRT
<213> ORGANISM: Artificial Sequence
<220> FEATURE:
<223> OTHER INFORMATION: Made in Lab - CD123 32716  LCNT1

<400> SEQUENCE: 238

Asn Tyr His Leu Glu Asn Glu Val Ala Arg Leu Lys Lys Leu Gly Gly
1               5                   10                  15

Gly Gly Ser Asp Ile Val Leu Thr Gln Ser Pro Ala Ser Leu Ala Val
            20                  25                  30

Ser Leu Gly Gln Arg Ala Thr Ile Ser Cys Arg Ala Ser Glu Ser Val
        35                  40                  45

Asp Asn Tyr Gly Asn Thr Phe Met His Trp Tyr Gln Gln Lys Pro Gly
    50                  55                  60

Gln Pro Pro Lys Leu Leu Ile Tyr Arg Ala Ser Asn Leu Glu Ser Gly
65                  70                  75                  80

Ile Pro Ala Arg Phe Ser Gly Ser Gly Ser Arg Thr Asp Phe Thr Leu
                85                  90                  95

Thr Ile Asn Pro Val Glu Ala Asp Asp Val Ala Thr Tyr Tyr Cys Gln
            100                 105                 110

Gln Ser Asn Glu Asp Pro Pro Thr Phe Gly Ala Gly Thr Lys Leu Glu
        115                 120                 125

Leu Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235


<210> SEQ ID NO 239
<211> LENGTH: 246
<212> TYPE: PRT
<213> ORGANISM: Artificial Sequence
<220> FEATURE:
<223> OTHER INFORMATION: Made in Lab - CD123 32716  LCNT3

<400> SEQUENCE: 239

Asn Tyr His Leu Glu Asn Glu Val Ala Arg Leu Lys Lys Leu Gly Gly
1               5                   10                  15

Gly Gly Ser Gly Gly Gly Gly Ser Gly Gly Gly Gly Ser Asp Ile Val
            20                  25                  30
```

-continued

```
Leu Thr Gln Ser Pro Ala Ser Leu Ala Val Ser Leu Gly Gln Arg Ala
        35                  40                  45

Thr Ile Ser Cys Arg Ala Ser Glu Ser Val Asp Asn Tyr Gly Asn Thr
    50                  55                  60

Phe Met His Trp Tyr Gln Gln Lys Pro Gly Gln Pro Pro Lys Leu Leu
65                  70                  75                  80

Ile Tyr Arg Ala Ser Asn Leu Glu Ser Gly Ile Pro Ala Arg Phe Ser
                85                  90                  95

Gly Ser Gly Ser Arg Thr Asp Phe Thr Leu Thr Ile Asn Pro Val Glu
            100                 105                 110

Ala Asp Asp Val Ala Thr Tyr Tyr Cys Gln Gln Ser Asn Glu Asp Pro
        115                 120                 125

Pro Thr Phe Gly Ala Gly Thr Lys Leu Glu Leu Arg Thr Val Ala Ala
    130                 135                 140

Pro Ser Val Phe Ile Phe Pro Pro Ser Asp Glu Gln Leu Lys Ser Gly
145                 150                 155                 160

Thr Ala Ser Val Val Cys Leu Leu Asn Asn Phe Tyr Pro Arg Glu Ala
                165                 170                 175

Lys Val Gln Trp Lys Val Asp Asn Ala Leu Gln Ser Gly Asn Ser Gln
            180                 185                 190

Glu Ser Val Thr Glu Gln Asp Ser Lys Asp Ser Thr Tyr Ser Leu Ser
        195                 200                 205

Ser Thr Leu Thr Leu Ser Lys Ala Asp Tyr Glu Lys His Lys Val Tyr
    210                 215                 220

Ala Cys Glu Val Thr His Gln Gly Leu Ser Ser Pro Val Thr Lys Ser
225                 230                 235                 240

Phe Asn Arg Gly Glu Cys
                245
```

<210> SEQ ID NO 240
<211> LENGTH: 241
<212> TYPE: PRT
<213> ORGANISM: Artificial Sequence
<220> FEATURE:
<223> OTHER INFORMATION: Made in Lab - CD123 32716 LCNT2

<400> SEQUENCE: 240

```
Asn Tyr His Leu Glu Asn Glu Val Ala Arg Leu Lys Lys Leu Gly Gly
1               5                   10                  15

Gly Gly Ser Gly Gly Gly Gly Ser Asp Ile Val Leu Thr Gln Ser Pro
            20                  25                  30

Ala Ser Leu Ala Val Ser Leu Gly Gln Arg Ala Thr Ile Ser Cys Arg
        35                  40                  45

Ala Ser Glu Ser Val Asp Asn Tyr Gly Asn Thr Phe Met His Trp Tyr
    50                  55                  60

Gln Gln Lys Pro Gly Gln Pro Pro Lys Leu Leu Ile Tyr Arg Ala Ser
65                  70                  75                  80

Asn Leu Glu Ser Gly Ile Pro Ala Arg Phe Ser Gly Ser Gly Ser Arg
                85                  90                  95

Thr Asp Phe Thr Leu Thr Ile Asn Pro Val Glu Ala Asp Asp Val Ala
            100                 105                 110

Thr Tyr Tyr Cys Gln Gln Ser Asn Glu Asp Pro Pro Thr Phe Gly Ala
        115                 120                 125

Gly Thr Lys Leu Glu Leu Arg Thr Val Ala Ala Pro Ser Val Phe Ile
    130                 135                 140
```

```
Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys


<210> SEQ ID NO 241
<211> LENGTH: 246
<212> TYPE: PRT
<213> ORGANISM: Artificial Sequence
<220> FEATURE:
<223> OTHER INFORMATION: Made in Lab - CD123 26292  HCNT1

<400> SEQUENCE: 241

Asn Tyr His Leu Glu Asn Glu Val Ala Arg Leu Lys Lys Leu Leu Val
1               5                   10                  15

Gly Glu Ala Ala Ala Lys Glu Ala Ala Ala Lys Ala Gln Val Gln Leu
            20                  25                  30

Gln Gln Pro Gly Ala Glu Leu Val Arg Pro Gly Ala Ser Val Lys Leu
        35                  40                  45

Ser Cys Lys Ala Ser Gly Tyr Thr Phe Thr Ser Tyr Trp Met Asn Trp
    50                  55                  60

Val Lys Gln Arg Pro Asp Gln Gly Leu Glu Trp Ile Gly Arg Ile Asp
65                  70                  75                  80

Pro Tyr Asp Ser Glu Thr His Tyr Asn Gln Lys Phe Lys Asp Lys Ala
                85                  90                  95

Ile Leu Thr Val Asp Lys Ser Ser Ser Thr Ala Tyr Met Gln Leu Ser
            100                 105                 110

Ser Leu Thr Ser Glu Asp Ser Ala Val Tyr Tyr Cys Ala Arg Gly Asn
        115                 120                 125

Trp Asp Asp Tyr Trp Gly Gln Gly Thr Thr Leu Thr Val Ser Ser Ala
    130                 135                 140

Arg Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys
                245
```

<210> SEQ ID NO 242
<211> LENGTH: 249
<212> TYPE: PRT
<213> ORGANISM: Artificial Sequence
<220> FEATURE:
<223> OTHER INFORMATION: Made in lab - CD123 32716 HCNT1

<400> SEQUENCE: 242

```
Asn Tyr His Leu Glu Asn Glu Val Ala Arg Leu Lys Lys Leu Leu Val
1               5                   10                  15

Gly Glu Ala Ala Ala Lys Glu Ala Ala Ala Lys Ala Gln Ile Gln Leu
            20                  25                  30

Val Gln Ser Gly Pro Glu Leu Lys Lys Pro Gly Glu Thr Val Lys Ile
        35                  40                  45

Ser Cys Lys Ala Ser Gly Tyr Ile Phe Thr Asn Tyr Gly Met Asn Trp
    50                  55                  60

Val Lys Gln Ala Pro Gly Lys Ser Phe Lys Trp Met Gly Trp Ile Asn
65                  70                  75                  80

Thr Tyr Thr Gly Glu Ser Thr Tyr Ser Ala Asp Phe Lys Gly Arg Phe
                85                  90                  95

Ala Phe Ser Leu Glu Thr Ser Ala Ser Thr Ala Tyr Leu His Ile Asn
            100                 105                 110

Asp Leu Lys Asn Glu Asp Thr Ala Thr Tyr Phe Cys Ala Arg Ser Gly
        115                 120                 125

Gly Tyr Asp Pro Met Asp Tyr Trp Gly Gln Gly Thr Ser Val Thr Val
    130                 135                 140

Ser Ser Ala Arg Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys
                245
```

<210> SEQ ID NO 243
<211> LENGTH: 251
<212> TYPE: PRT
<213> ORGANISM: Artificial Sequence
<220> FEATURE:
<223> OTHER INFORMATION: Made in lab - CD123 32716 HCNT2

<400> SEQUENCE: 243

```
Asn Tyr His Leu Glu Asn Glu Val Ala Arg Leu Lys Lys Leu Glu Ala
1               5                   10                  15

Ala Ala Lys Glu Ala Ala Ala Lys Glu Ala Ala Ala Lys Ala Gln Ile
            20                  25                  30

Gln Leu Val Gln Ser Gly Pro Glu Leu Lys Lys Pro Gly Glu Thr Val
        35                  40                  45

Lys Ile Ser Cys Lys Ala Ser Gly Tyr Ile Phe Thr Asn Tyr Gly Met
    50                  55                  60
```

```
Asn Trp Val Lys Gln Ala Pro Gly Lys Ser Phe Lys Trp Met Gly Trp
65                  70                  75                  80

Ile Asn Thr Tyr Thr Gly Glu Ser Thr Tyr Ser Ala Asp Phe Lys Gly
                85                  90                  95

Arg Phe Ala Phe Ser Leu Glu Thr Ser Ala Ser Thr Ala Tyr Leu His
            100                 105                 110

Ile Asn Asp Leu Lys Asn Glu Asp Thr Ala Thr Tyr Phe Cys Ala Arg
        115                 120                 125

Ser Gly Gly Tyr Asp Pro Met Asp Tyr Trp Gly Gln Gly Thr Ser Val
    130                 135                 140

Thr Val Ser Ser Ala Arg Thr Lys Gly Pro Ser Val Phe Pro Leu Ala
145                 150                 155                 160

Pro Ser Ser Lys Ser Thr Ser Gly Gly Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
        195                 200                 205

Gly Leu Tyr Ser Leu Ser Ser Val Val Thr Val Pro Ser Ser Ser Leu
    210                 215                 220

Gly Thr Gln Thr Tyr Ile Cys Asn Val Asn His Lys Pro Ser Asn Thr
225                 230                 235                 240

Lys Val Asp Lys Lys Val Glu Pro Lys Ser Cys
                245                 250


<210> SEQ ID NO 244
<211> LENGTH: 232
<212> TYPE: PRT
<213> ORGANISM: Artificial Sequence
<220> FEATURE:
<223> OTHER INFORMATION: Made in Lab - CD123 26292   LCCT1

<400> SEQUENCE: 244

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Asp
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Lys Tyr Pro Tyr
                85                  90                  95

Thr Phe Gly Gly Gly Thr Lys Leu Glu Ile Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175
```

```
Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Gly Gly Gly Ser Asn Tyr His Leu Glu Asn
    210                 215                 220

Glu Val Ala Arg Leu Lys Lys Leu
225                 230


<210> SEQ ID NO 245
<211> LENGTH: 236
<212> TYPE: PRT
<213> ORGANISM: Artificial Sequence
<220> FEATURE:
<223> OTHER INFORMATION: Made in Lab - CD123 32716   LCCT1

<400> SEQUENCE: 245

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Pro Thr Phe Gly Ala Gly Thr Lys Leu Glu Leu Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Gly Gly Gly Gly Ser Asn Tyr
    210                 215                 220

His Leu Glu Asn Glu Val Ala Arg Leu Lys Lys Leu
225                 230                 235


<210> SEQ ID NO 246
<211> LENGTH: 241
<212> TYPE: PRT
<213> ORGANISM: Artificial Sequence
<220> FEATURE:
<223> OTHER INFORMATION: Made in lab - CD123 32716   LCCT2

<400> SEQUENCE: 246

Asp Ile Val Leu Thr Gln Ser Pro Ala Ser Leu Ala Val Ser Leu Gly
1               5                   10                  15
```

```
Gln Arg Ala Thr Ile Ser Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Pro Thr Phe Gly Ala Gly Thr Lys Leu Glu Leu Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Gly Gly Gly Gly Ser Gly Gly
    210                 215                 220

Gly Gly Ser Asn Tyr His Leu Glu Asn Glu Val Ala Arg Leu Lys Lys
225                 230                 235                 240

Leu


<210> SEQ ID NO 247
<211> LENGTH: 246
<212> TYPE: PRT
<213> ORGANISM: Artificial Sequence
<220> FEATURE:
<223> OTHER INFORMATION: Made in Lab - CD123 32716   LCCT3

<400> SEQUENCE: 247

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Pro Thr Phe Gly Ala Gly Thr Lys Leu Glu Leu Arg Thr
            100                 105                 110

Val Ala Ala Pro Ser Val Phe Ile Phe Pro Pro Ser Asp Glu Gln Leu
        115                 120                 125
```

```
Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Gly Gly Gly Gly Ser Gly Gly
    210                 215                 220

Gly Gly Ser Gly Gly Gly Gly Ser Asn Tyr His Leu Glu Asn Glu Val
225                 230                 235                 240

Ala Arg Leu Lys Lys Leu
                245


<210> SEQ ID NO 248
<211> LENGTH: 237
<212> TYPE: PRT
<213> ORGANISM: Artificial Sequence
<220> FEATURE:
<223> OTHER INFORMATION: Made in Lab - CD123 26292 HCCT1

<400> SEQUENCE: 248

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Asp Gln Gly Leu Glu Trp Ile
        35                  40                  45

Gly Arg Ile Asp Pro Tyr Asp Ser Glu Thr His Tyr Asn Gln Lys Phe
    50                  55                  60

Lys Asp Lys Ala Ile Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Asn Trp Asp Asp Tyr Trp Gly Gln Gly Thr Thr Leu Thr
            100                 105                 110

Val Ser Ser Ala Arg Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Gly Gly Gly Gly Ser Asn
    210                 215                 220

Tyr His Leu Glu Asn Glu Val Ala Arg Leu Lys Lys Leu
225                 230                 235
```

<210> SEQ ID NO 249
<211> LENGTH: 240
<212> TYPE: PRT
<213> ORGANISM: Artificial Sequence
<220> FEATURE:
<223> OTHER INFORMATION: Made in Lab - CD123 32716 HCCT1

<400> SEQUENCE: 249

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asn Tyr
            20                  25                  30

Gly Met Asn Trp Val Lys Gln Ala Pro Gly Lys Ser Phe Lys Trp Met
        35                  40                  45

Gly Trp Ile Asn Thr Tyr Thr Gly Glu Ser Thr Tyr Ser Ala Asp Phe
    50                  55                  60

Lys Gly Arg Phe Ala Phe Ser Leu Glu Thr Ser Ala Ser Thr Ala Tyr
65                  70                  75                  80

Leu His Ile Asn Asp Leu Lys Asn Glu Asp Thr Ala Thr Tyr Phe Cys
                85                  90                  95

Ala Arg Ser Gly Gly Tyr Asp Pro Met Asp Tyr Trp Gly Gln Gly Thr
            100                 105                 110

Ser Val Thr Val Ser Ser Ala Arg Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Gly Gly Gly
    210                 215                 220

Gly Ser Asn Tyr His Leu Glu Asn Glu Val Ala Arg Leu Lys Lys Leu
225                 230                 235                 240
```

<210> SEQ ID NO 250
<211> LENGTH: 245
<212> TYPE: PRT
<213> ORGANISM: Artificial Sequence
<220> FEATURE:
<223> OTHER INFORMATION: Made in Lab - CD123 32716 HCCT2

<400> SEQUENCE: 250

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asn Tyr
            20                  25                  30

Gly Met Asn Trp Val Lys Gln Ala Pro Gly Lys Ser Phe Lys Trp Met
        35                  40                  45

Gly Trp Ile Asn Thr Tyr Thr Gly Glu Ser Thr Tyr Ser Ala Asp Phe
    50                  55                  60

Lys Gly Arg Phe Ala Phe Ser Leu Glu Thr Ser Ala Ser Thr Ala Tyr
65                  70                  75                  80
```

```
Leu His Ile Asn Asp Leu Lys Asn Glu Asp Thr Ala Thr Tyr Phe Cys
                85                  90                  95

Ala Arg Ser Gly Gly Tyr Asp Pro Met Asp Tyr Trp Gly Gln Gly Thr
            100                 105                 110

Ser Val Thr Val Ser Ser Ala Arg Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Gly Gly Gly
    210                 215                 220

Gly Ser Gly Gly Gly Gly Ser Asn Tyr His Leu Glu Asn Glu Val Ala
225                 230                 235                 240

Arg Leu Lys Lys Leu
                245


<210> SEQ ID NO 251
<211> LENGTH: 250
<212> TYPE: PRT
<213> ORGANISM: Artificial Sequence
<220> FEATURE:
<223> OTHER INFORMATION: Made in lab - CD123 32716   HCCT3

<400> SEQUENCE: 251

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asn Tyr
            20                  25                  30

Gly Met Asn Trp Val Lys Gln Ala Pro Gly Lys Ser Phe Lys Trp Met
        35                  40                  45

Gly Trp Ile Asn Thr Tyr Thr Gly Glu Ser Thr Tyr Ser Ala Asp Phe
    50                  55                  60

Lys Gly Arg Phe Ala Phe Ser Leu Glu Thr Ser Ala Ser Thr Ala Tyr
65                  70                  75                  80

Leu His Ile Asn Asp Leu Lys Asn Glu Asp Thr Ala Thr Tyr Phe Cys
                85                  90                  95

Ala Arg Ser Gly Gly Tyr Asp Pro Met Asp Tyr Trp Gly Gln Gly Thr
            100                 105                 110

Ser Val Thr Val Ser Ser Ala Arg Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

```
Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Gly Gly Gly
    210                 215                 220

Gly Ser Gly Gly Gly Gly Ser Gly Gly Gly Gly Ser Asn Tyr His Leu
225                 230                 235                 240

Glu Asn Glu Val Ala Arg Leu Lys Lys Leu
                245                 250


<210> SEQ ID NO 252
<211> LENGTH: 232
<212> TYPE: PRT
<213> ORGANISM: Artificial Sequence
<220> FEATURE:
<223> OTHER INFORMATION: Made in lab - CD123 32716   HCC1

<400> SEQUENCE: 252

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asn Tyr
            20                  25                  30

Gly Met Asn Trp Val Lys Gln Ala Pro Gly Lys Ser Phe Lys Trp Met
        35                  40                  45

Gly Trp Ile Asn Thr Tyr Thr Gly Glu Ser Thr Tyr Ser Ala Asp Phe
    50                  55                  60

Lys Gly Arg Phe Ala Phe Ser Leu Glu Thr Ser Ala Ser Thr Ala Tyr
65                  70                  75                  80

Leu His Ile Asn Asp Leu Lys Asn Glu Asp Thr Ala Thr Tyr Phe Cys
                85                  90                  95

Ala Arg Ser Gly Gly Tyr Asp Pro Met Asp Tyr Trp Gly Gln Gly Thr
            100                 105                 110

Ser Val Thr Val Ser Ser Ala Arg Thr Lys Gly Pro Ser Val Phe Pro
        115                 120                 125

Leu Ala Pro Ser Ser Asn Tyr His Leu Glu Asn Glu Val Ala Arg Leu
    130                 135                 140

Lys Lys Leu Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys
225                 230


<210> SEQ ID NO 253
<211> LENGTH: 243
<212> TYPE: PRT
<213> ORGANISM: Artificial Sequence
<220> FEATURE:
<223> OTHER INFORMATION: Made in Lab - CD123 32716   HCC1 G4S

<400> SEQUENCE: 253

Gln Ile Gln Leu Val Gln Ser Gly Pro Glu Leu Lys Lys Pro Gly Glu
```

```
1               5                   10                  15

Thr Val Lys Ile Ser Cys Lys Ala Ser Gly Tyr Ile Phe Thr Asn Tyr
            20                  25                  30

Gly Met Asn Trp Val Lys Gln Ala Pro Gly Lys Ser Phe Lys Trp Met
        35                  40                  45

Gly Trp Ile Asn Thr Tyr Thr Gly Glu Ser Thr Tyr Ser Ala Asp Phe
    50                  55                  60

Lys Gly Arg Phe Ala Phe Ser Leu Glu Thr Ser Ala Ser Thr Ala Tyr
65                  70                  75                  80

Leu His Ile Asn Asp Leu Lys Asn Glu Asp Thr Ala Thr Tyr Phe Cys
                85                  90                  95

Ala Arg Ser Gly Gly Tyr Asp Pro Met Asp Tyr Trp Gly Gln Gly Thr
            100                 105                 110

Ser Val Thr Val Ser Ser Ala Arg Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Gly Gly Gly Gly Ser Asn Tyr His Leu Glu Asn Glu Val Ala Arg
            180                 185                 190

Leu Lys Lys Leu Gly Gly Gly Gly Ser Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys


<210> SEQ ID NO 254
<211> LENGTH: 240
<212> TYPE: PRT
<213> ORGANISM: Artificial Sequence
<220> FEATURE:
<223> OTHER INFORMATION: Made in Lab - CD123 32716   LCC1 G4S

<400> SEQUENCE: 254

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Pro Thr Phe Gly Ala Gly Thr Lys Leu Glu Leu Arg Thr
            100                 105                 110

Val Ala Ala Pro Ser Val Phe Ile Phe Pro Pro Ser Asp Glu Gln Leu
        115                 120                 125
```

```
Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Gly Gly Gly Gly Ser
                165                 170                 175

Asn Tyr His Leu Glu Asn Glu Val Ala Arg Leu Lys Lys Leu Gly Gly
            180                 185                 190

Gly Gly Ser Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 255
<211> LENGTH: 1302
<212> TYPE: DNA
<213> ORGANISM: Artificial Sequence
<220> FEATURE:
<223> OTHER INFORMATION: Made in Lab - hu 52SR4 L6b H4

<400> SEQUENCE: 255

```
caggctgtgg tgactcagga gccctcactg actgtgtccc caggagggac agtcactctc      60

acctgtggct ccagcactgg agctgtcacc acttccaact atgcctcatg ggtgcaggag     120

aagcctggcc aagccttcag gggctgatt ggtggcacaa acaacagggc tcctggggtg     180

cctgcccggt tctcaggctc cctccttggg ggcaaagctg ccctgaccat ttcgggtgcg     240

cagcctgagg atgaggctat ttatttctgc gtgctctggt atagtgacca ttgggtgttc     300

ggcggaggga ccaagctgac cgtcctaggc ggaggaggag gttcaggagg cggaggtagc     360

gggggaggcg gttccggggg aggcggttct caggtgcagc tgcaggagtc gggcccagga     420

ctggtgaagc cttcggagac cctgtccatc acctgcactg tctctggttt cctgctgacc     480

gactacggcg taaactgggt gcggcagccc ccagggaagg gactggagtg gctgggggtg     540

atctggggtg acgggatcac cgactacaac ccctccctca agagtcgact gaccgtgtcc     600

aaggacacat ccaagaacca ggtgtccctg aagatgagct ctctgaccgc cgcagacacg     660

gcccggtatt actgtgtcac cggcctgttc gactactggg gccagggcac caccctgacc     720

gtctcctcag aaagcaagta tggcccacct tgtccacctt gtcccgatat ctacatctgg     780

gcgcccttgg ccgggacttg tggggtcctt ctcctgtcac tggttatcac cctttactgc     840

aaacggggca gaaagaaact cctgtatata ttcaaacaac catttatgag accagtacaa     900

actactcaag aggaagatgg ctgtagctgc cgatttccag aagaagaaga aggaggatgt     960

gaactgagag tgaagttcag caggagcgca gacgcccccg cgtacaagca gggccagaac    1020

cagctctata acgagctcaa tctaggacga agagaggagt acgatgtttt ggacaagaga    1080

cgtggccggg accctgagat gggggaaag ccgagaagga agaaccctca ggaaggcctg    1140

tacaatgaac tgcagaaaga taagatggcg gaggcctaca gtgagattgg gatgaaaggc    1200

gagcgccgga ggggcaaggg gcacgatggc ctttaccagg gtctcagtac agccaccaag    1260

gacacctacg acgcccttca catgcaggcc ctgccccctc gc                       1302
```

<210> SEQ ID NO 256
<211> LENGTH: 1302

<212> TYPE: DNA
<213> ORGANISM: Artificial Sequence
<220> FEATURE:
<223> OTHER INFORMATION: Made in Lab - hu 52SR4 L5b H4b

<400> SEQUENCE: 256
caggctgtgg tgactcagga gccctcactg actagctccc caggagggac agtcactctc 60
acctgtggct ccagcactgg agctgtcacc acttccaact atgcctcatg ggtgcaggag 120
aagcctgacc acctcttcag gggctgatt ggtggcacaa acaacagggc tcctggggtg 180
cctgcccggt tctcaggctc cctccttggg ggcaaagctg ccctgaccat ttcgggtgcg 240
cagcctgagg atgaggctat ttatttctgc gtgctctggt atagtgacca ttgggtgttc 300
ggcggaggga ccaagctgac cgtcctaggc ggaggaggag gttcaggagg cggaggtagc 360
gggggaggcg gttccggggg aggcggttct caggtgcagc tgcagcagtc gggcccagga 420
ctggtgaagc cttcggagac cctgtccatc acctgcactg tctctggttt cctgctgacc 480
gactacggcg taaactgggt gcggcagccc ccagggaagg gactggagtg gctgggggtg 540
atctggggtg acgggatcac cgactacaac ccctccctca agagtcgact gaccgtgtcc 600
aaggacacat ccaagaacca ggtgtccctg aagatgagct ctctgaccgc cgcagacacg 660
gcccggtatt actgtgtcac cggcctgttc gactactggg gccagggcac caccctgacc 720
gtctcctcag aaagcaagta tggcccacct tgtccacctt gtcccgatat ctacatctgg 780
gcgcccttgg ccgggacttg tggggtcctt ctcctgtcac tggttatcac cctttactgc 840
aaacggggca gaaagaaact cctgtatata ttcaaacaac catttatgag accagtacaa 900
actactcaag aggaagatgg ctgtagctgc cgatttccag aagaagaaga aggaggatgt 960
gaactgagag tgaagttcag caggagcgca gacgcccccg cgtacaagca gggccagaac 1020
cagctctata acgagctcaa tctaggacga agagaggagt acgatgtttt ggacaagaga 1080
cgtggccggg accctgagat ggggggaaag ccgagaagga agaaccctca ggaaggcctg 1140
tacaatgaac tgcagaaaga taagatggcg gaggcctaca gtgagattgg gatgaaaggc 1200
gagcgccgga ggggcaaggg gcacgatggc ctttaccagg gtctcagtac agccaccaag 1260
gacacctacg acgcccttca catgcaggcc ctgccccctc gc 1302

<210> SEQ ID NO 257
<211> LENGTH: 1302
<212> TYPE: DNA
<213> ORGANISM: Artificial Sequence
<220> FEATURE:
<223> OTHER INFORMATION: Made in Lab - hu 52SR4 L6 H6

<400> SEQUENCE: 257
caggctgtgg tgactcagga gccctcactg actgtgtccc caggagggac agtcactctc 60
acctgtggct ccagcactgg agctgtcacc acttccaact atgcctcatg ggtgcaggag 120
aagcctggcc aagcccccag gggctgatt ggtggcacaa acaacagggc tcctggggtg 180
cctgcccggt tctcaggctc cctccttggg ggcaaagctg ccctgaccat ttcgggtgcg 240
cagcctgagg atgaggctat ttatttctgc gtgctctggt atagtgacca ttgggtgttc 300
ggcggaggga ccaagctgac cgtcctaggc ggaggaggag gttcaggagg aggaggtagc 360
gggggaggcg gttccggggg aggcggttct caggtgcagc tgcagcagtc gggcccagga 420
ctggtgaagc cttcggagac cctgtccatc acctgcactg tctctggttt ctccctgacc 480
gactacggcg taaactgggt gcggcagccc ccagggaagg gactggagtg gctgggggtg 540
atctggggtg acgggagcac cgactacaac ccctccctca agagtcgact gaccgtgtcc 600
aaggacaact ccaagaacca ggtgtccctg aagatgagct ctctgaccgc cgcagacacg 660
gccgtgtatt actgtgtcac cggcctgttc gactactggg gccagggcac cctgctgacc 720
gtctcctcag aaagcaagta tggcccacct tgtccacctt gtcccgatat ctacatctgg 780
gcgcccttgg ccgggacttg tggggtcctt ctcctgtcac tggttatcac cctttactgc 840
aaacggggca gaaagaaact cctgtatata ttcaaacaac catttatgag accagtacaa 900
actactcaag aggaagatgg ctgtagctgc cgatttccag aagaagaaga aggaggatgt 960
gaactgagag tgaagttcag caggagcgca gacgcccccg cgtacaagca gggccagaac 1020
cagctctata acgagctcaa tctaggacga agagaggagt acgatgtttt ggacaagaga 1080
cgtggccggg accctgagat ggggggaaag ccgagaagga agaaccctca ggaaggcctg 1140
tacaatgaac tgcagaaaga taagatggcg gaggcctaca gtgagattgg gatgaaaggc 1200
gagcgccgga ggggcaaggg gcacgatggc ctttaccagg gtctcagtac agccaccaag 1260
gacacctacg acgcccttca catgcaggcc ctgccccctc gc 1302

<210> SEQ ID NO 258
<211> LENGTH: 8
<212> TYPE: PRT
<213> ORGANISM: Artificial Sequence
<220> FEATURE:
<223> OTHER INFORMATION: FLAG tag peptide

<400> SEQUENCE: 258

Ser Asp Tyr Lys Asp Asp Asp Lys
1 5

<210> SEQ ID NO 259
<211> LENGTH: 1431
<212> TYPE: DNA
<213> ORGANISM: Artificial Sequence
<220> FEATURE:
<223> OTHER INFORMATION: Made in Lab - anti-CD19 (FMC63) IgG HCNT

<400> SEQUENCE: 259
aattatcatc ttgaaaatga ggtcgctcgt ctcaagaaac tcctggttgg cgaggccgca 60
gctaaggaag ccgcagctaa agccgaggtg aaactgcagg agtcaggacc tggcctggtg 120
gcgccctcac agagcctgtc cgtcacatgc actgtctcag ggtctcatt acccgactat 180 ggtgtaagct ggattcgcca gcctccacga aagggtctgg agtggctggg agtaatatgg 240
ggtagtgaaa ccacatacta taattcagct ctcaaatcca gactgaccat catcaaggac 300
aactccaaga gccaagtttt cttaaaaatg aacagtctgc aaactgatga cacagccatt 360
tactactgtg ccaaacatta ttactacggt ggtagctatg ctatggacta ctggggccaa 420
ggaacctcag tcaccgtctc ctcagcctcc accaagggcc catcggtctt ccccctggca 480
ccctcctcca agagcacctc tgggggcaca gcggccctgg gctgcctggt caaggactac 540
ttccccgaac cggtgacggt gtcgtggaac tcaggcgccc tgaccagcgg cgtgcacacc 600
ttcccggctg tcctacagtc ctcaggactc tactccctca gcagcgtggt gactgtgccc 660
tctagcagct tgggcaccca gacctacatc tgcaacgtga atcacaagcc cagcaacacc 720
aaggtggaca agaaagttga gcccaaatct tgtgacaaaa ctcacacatg cccaccgtgc 780
ccagcacctc cagtcgccgg accgtcagtc ttcctcttcc ctccaaaacc caaggacacc 840
ctcatgatct cccggacccc tgaggtcaca tgcgtggtgg tggacgtgag ccacgaagac 900

-continued

```
cctgaggtca agttcaactg gtacgtggac ggcgtggagg tgcataatgc caagacaaag    960

ccgcgggagg agcagtacaa cagcacgtac cgtgtggtca gcgtcctcac cgtcctgcac   1020

caggactggc tgaatggcaa ggagtacaag tgcaaggtct ccaacaaagg cctcccaagc   1080

tccatcgaga aaaccatctc caaagccaaa gggcagcccc gagaaccaca ggtgtacacc   1140

ctgcctccat cccgggatga gctgaccaag aaccaggtca gcctgacctg cctggtcaaa   1200

ggcttctatc ccagcgacat cgccgtggag tgggagagca atgggcagcc ggagaacaac   1260

tacaagacca cgcctcccgt gctggactcc gacggctcct tcttcctcta cagcaagctc   1320

accgtggaca agagcaggtg gcagcagggg aacgtcttct catgctccgt gatgcatgag   1380

gctctgcaca accactacac gcagaagagc ctctccctgt ctccgggtaa a            1431
```

<210> SEQ ID NO 260
<211> LENGTH: 1398
<212> TYPE: DNA
<213> ORGANISM: Artificial Sequence
<220> FEATURE:
<223> OTHER INFORMATION: Made in Lab - 52SR4 CAR

<400> SEQUENCE: 260

```
gacgccgttg tgacccagga atccgctctg acctcttctc caggcgaaac cgtgactctg     60

acttgccgta gtagcaccgg ggctgtgacc acatctaact atgccagttg ggtccaggaa    120

aaaccggatc acctgtttac tggcctgatt ggcggcacca acaatcgcgc accgggtgtg    180

cccgctcgtt tcagcggttc cctgattggg gacaaggcag cactgactat caccggcgcc    240

cagaccgaag atgaggcgat ctatttttgc gtcctgtggt acagcgacca ttgggtgttc    300

gggggaggca ccaaactgac agtgctgggc ggaggaggag gttcaggagg aggaggtagc    360

gggggaggcg gttccggggg aggcggttct gatgtgcagc tgcaagaatc cgggccagga    420

ctggttgcgc cttctcagag tctgtcaatt acatgtactg ttagtggctt tctgctgacc    480

gactatggtg tgaactgggt tcgtcagagc ccaggcaagg gtctggagtg gctgggagtg    540

atttgggggg atggaatcac agactacaat agcgcactga aatctcggct gagtgttacc    600

aaagataaca gcaagtccca ggtcttcctg aagatgaaca gcctgcaaag cggcgactcc    660

gctcgctatt actgcgttac cggactgttt gattattggg ggcaggggac aactctgact    720

gtttcctcca ccacgacgcc agcgccgcga ccaccaacac cggcgcccac catcgcgtcg    780

cagcccctgt ccctgcgccc agaggcgtgc cggccagcgg cggggggcgc agtgcacacg    840

agggggctgg acttcgcctg tgatatctac atctgggcgc ccttggccgg gacttgtggg    900

gtccttctcc tgtcactggt tatcaccctt tactgcaaac ggggcagaaa gaaactcctg    960

tatatattca aacaaccatt tatgagacca gtacaaacta ctcaagagga agatggctgt   1020

agctgccgat ttccagaaga agaagaagga ggatgtgaac tgagagtgaa gttcagcagg   1080

agcgcagacg cccccgcgta caagcagggc cagaaccagc tctataacga gctcaatcta   1140

ggacgaagag aggagtacga tgttttggac aagagacgtg gccgggaccc tgagatgggg   1200

ggaaagccga gaaggaagaa ccctcaggaa ggcctgtaca atgaactgca gaaagataag   1260

atggcggagg cctacagtga gattgggatg aaaggcgagc gccggagggg caaggggcac   1320

gatggccttt accagggtct cagtacagcc accaaggaca cctacgacgc ccttcacatg   1380

caggccctgc cccctcgc                                                 1398
```

<210> SEQ ID NO 261
<211> LENGTH: 214

<212> TYPE: PRT
<213> ORGANISM: Artificial Sequence
<220> FEATURE:
<223> OTHER INFORMATION: Made in Lab - anti-Her2 Fab wild type light
      chain

<400> SEQUENCE: 261

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 262
<211> LENGTH: 228
<212> TYPE: PRT
<213> ORGANISM: Artificial Sequence
<220> FEATURE:
<223> OTHER INFORMATION: Made in Lab - anti-Her2 Fab wild type heavy
      chain

<400> SEQUENCE: 262

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

-continued

```
Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr
225


<210> SEQ ID NO 263
<211> LENGTH: 233
<212> TYPE: PRT
<213> ORGANISM: Artificial Sequence
<220> FEATURE:
<223> OTHER INFORMATION: Made in Lab - anti-Her2 Fab wild type light
      chain with GCN4 transcription factor peptide

<400> SEQUENCE: 263

Asn Tyr His Leu Glu Asn Glu Val Ala Arg Leu Lys Lys Leu Gly Gly
1               5                   10                  15

Gly Gly Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Val
        35                  40                  45

Asn Thr Ala Val Ala Trp Tyr Gln Gln Lys Pro Gly Lys Ala Pro Lys
    50                  55                  60

Leu Leu Ile Tyr Ser Ala Ser Phe Leu Tyr Ser Gly Val Pro Ser Arg
65                  70                  75                  80

Phe Ser Gly Ser Arg Ser Gly Thr Asp Phe Thr Leu Thr Ile Ser Ser
                85                  90                  95

Leu Gln Pro Glu Asp Phe Ala Thr Tyr Tyr Cys Gln Gln His Tyr Thr
            100                 105                 110

Thr Pro Pro Thr Phe Gly Gln Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220
```

```
Thr Lys Ser Phe Asn Arg Gly Glu Cys
225                 230


<210> SEQ ID NO 264
<211> LENGTH: 233
<212> TYPE: PRT
<213> ORGANISM: Artificial Sequence
<220> FEATURE:
<223> OTHER INFORMATION: Made in Lab - anti-Her2 Fab wild type light
      chain with GCN4 transcription factor peptide

<400> SEQUENCE: 264

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Asn Tyr His Leu Glu
    210                 215                 220

Asn Glu Val Ala Arg Leu Lys Lys Leu
225                 230


<210> SEQ ID NO 265
<211> LENGTH: 242
<212> TYPE: PRT
<213> ORGANISM: Artificial Sequence
<220> FEATURE:
<223> OTHER INFORMATION: Made in Lab - anti-Her2 Fab wild type heavy
      chain with GCN4 transcription factor peptide

<400> SEQUENCE: 265

Asn Tyr His Leu Glu Asn Glu Val Ala Arg Leu Lys Lys Leu Gly Gly
1               5                   10                  15

Gly Gly Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45
```

```
Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys


<210> SEQ ID NO 266
<211> LENGTH: 247
<212> TYPE: PRT
<213> ORGANISM: Artificial Sequence
<220> FEATURE:
<223> OTHER INFORMATION: Made in Lab - anti-Her2 Fab wild type heavy
      chain with GCN4 transcription factor peptide

<400> SEQUENCE: 266

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Gly Gly Gly Gly Ser Asn Tyr His Leu Glu Asn Glu
225                 230                 235                 240

Val Ala Arg Leu Lys Lys Leu
                245
```

<210> SEQ ID NO 267
<211> LENGTH: 232
<212> TYPE: PRT
<213> ORGANISM: Artificial Sequence
<220> FEATURE:
<223> OTHER INFORMATION: Made in Lab - anti-Her2 Fab wild type light chain with FLAG tag

<400> SEQUENCE: 267

```
Asp Tyr Lys Asp Asp Asp Asp Lys Gly Gly Gly Gly Ser Gly Gly Gly
1               5                   10                  15

Gly Ser Asp Ile Gln Met Thr Gln Ser Pro Ser Ser Leu Ser Ala Ser
            20                  25                  30

Val Gly Asp Arg Val Thr Ile Thr Cys Arg Ala Ser Gln Asp Val Asn
        35                  40                  45

Thr Ala Val Ala Trp Tyr Gln Gln Lys Pro Gly Lys Ala Pro Lys Leu
    50                  55                  60

Leu Ile Tyr Ser Ala Ser Phe Leu Tyr Ser Gly Val Pro Ser Arg Phe
65                  70                  75                  80

Ser Gly Ser Arg Ser Gly Thr Asp Phe Thr Leu Thr Ile Ser Ser Leu
                85                  90                  95

Gln Pro Glu Asp Phe Ala Thr Tyr Tyr Cys Gln Gln His Tyr Thr Thr
            100                 105                 110

Pro Pro Thr Phe Gly Gln Gly Thr Lys Leu Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230
```

<210> SEQ ID NO 268
<211> LENGTH: 232
<212> TYPE: PRT

-continued

<213> ORGANISM: Artificial Sequence
<220> FEATURE:
<223> OTHER INFORMATION: Made in Lab - anti-Her2 Fab wild type light chain with FLAG tag

<400> SEQUENCE: 268

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gly Gly Gly Gly Ser Gly Gly Gly Gly Ser
210 215 220

Asp Tyr Lys Asp Asp Asp Asp Lys
225 230

<210> SEQ ID NO 269
<211> LENGTH: 246
<212> TYPE: PRT
<213> ORGANISM: Artificial Sequence
<220> FEATURE:
<223> OTHER INFORMATION: Made in Lab - anti-Her2 Fab wild type heavy chain with FLAG tag

<400> SEQUENCE: 269

Asp Tyr Lys Asp Asp Asp Asp Lys Gly Gly Gly Gly Ser Gly Gly Gly
1 5 10 15

Gly Ser Glu Val Gln Leu Val Glu Ser Gly Gly Gly Leu Val Gln Pro
20 25 30

Gly Gly Ser Leu Arg Leu Ser Cys Ala Ala Ser Gly Phe Asn Ile Lys
35 40 45

Asp Thr Tyr Ile His Trp Val Arg Gln Ala Pro Gly Lys Gly Leu Glu
50 55 60

Trp Val Ala Arg Ile Tyr Pro Thr Asn Gly Tyr Thr Arg Tyr Ala Asp
65 70 75 80

Ser Val Lys Gly Arg Phe Thr Ile Ser Ala Asp Thr Ser Lys Asn Thr

-continued

```
                85                  90                  95

Ala Tyr Leu Gln Met Asn Ser Leu Arg Ala Glu Asp Thr Ala Val Tyr
            100                 105                 110

Tyr Cys Ser Arg Trp Gly Gly Asp Gly Phe Tyr Ala Met Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr
                245


<210> SEQ ID NO 270
<211> LENGTH: 246
<212> TYPE: PRT
<213> ORGANISM: Artificial Sequence
<220> FEATURE:
<223> OTHER INFORMATION: Made in Lab - anti-Her2 Fab wild type heavy
      chain with FLAG tag

<400> SEQUENCE: 270

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Gly Gly Gly Gly Ser Gly Gly Gly Gly Ser Asp Tyr
225                 230                 235                 240

Lys Asp Asp Asp Asp Lys
                245


<210> SEQ ID NO 271
<211> LENGTH: 470
<212> TYPE: PRT
<213> ORGANISM: Artificial Sequence
<220> FEATURE:
<223> OTHER INFORMATION: Made in Lab - CAR-Her2 (CD8 hinge)

<400> SEQUENCE: 271

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Gly Gly Gly
            100                 105                 110

Gly Ser Gly Gly Gly Gly Ser Gly Gly Gly Gly Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Asn Ile Lys Asp Thr Tyr Ile His Trp
145                 150                 155                 160

Val Arg Gln Ala Pro Gly Lys Gly Leu Glu Trp Val Ala Arg Ile Tyr
                165                 170                 175

Pro Thr Asn Gly Tyr Thr Arg Tyr Ala Asp Ser Val Lys Gly Arg Phe
            180                 185                 190

Thr Ile Ser Ala Asp Thr Ser Lys Asn Thr Ala Tyr Leu Gln Met Asn
        195                 200                 205

Ser Leu Arg Ala Glu Asp Thr Ala Val Tyr Tyr Cys Ser Arg Trp Gly
    210                 215                 220

Gly Asp Gly Phe Tyr Ala Met Asp Tyr Trp Gly Gln Gly Thr Leu Val
225                 230                 235                 240

Thr Val Ser Ser Ala Ala Ala Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Ile Tyr Ile Trp Ala Pro Leu Ala Gly Thr Cys Gly
    290                 295                 300
```

-continued

```
Val Leu Leu Leu Ser Leu Val Ile Thr Leu Tyr Cys Lys Arg Gly Arg
305                 310                 315                 320

Lys Lys Leu Leu Tyr Ile Phe Lys Gln Pro Phe Met Arg Pro Val Gln
                325                 330                 335

Thr Thr Gln Glu Glu Asp Gly Cys Ser Cys Arg Phe Pro Glu Glu Glu
            340                 345                 350

Glu Gly Gly Cys Glu Leu Arg Val Lys Phe Ser Arg Ser Ala Asp Ala
        355                 360                 365

Pro Ala Tyr Lys Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465                 470


<210> SEQ ID NO 272
<211> LENGTH: 438
<212> TYPE: PRT
<213> ORGANISM: Artificial Sequence
<220> FEATURE:
<223> OTHER INFORMATION: Made in Lab - CAR-Her2 (IgG4m hinge)

<400> SEQUENCE: 272

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Gly Gly Gly
            100                 105                 110

Gly Ser Gly Gly Gly Gly Ser Gly Gly Gly Gly Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Asn Ile Lys Asp Thr Tyr Ile His Trp
145                 150                 155                 160

Val Arg Gln Ala Pro Gly Lys Gly Leu Glu Trp Val Ala Arg Ile Tyr
                165                 170                 175

Pro Thr Asn Gly Tyr Thr Arg Tyr Ala Asp Ser Val Lys Gly Arg Phe
            180                 185                 190
```

```
Thr Ile Ser Ala Asp Thr Ser Lys Asn Thr Ala Tyr Leu Gln Met Asn
        195                 200                 205

Ser Leu Arg Ala Glu Asp Thr Ala Val Tyr Tyr Cys Ser Arg Trp Gly
    210                 215                 220

Gly Asp Gly Phe Tyr Ala Met Asp Tyr Trp Gly Gln Gly Thr Leu Val
225                 230                 235                 240

Thr Val Ser Ser Ala Ala Ala Glu Ser Lys Tyr Gly Pro Pro Cys Pro
                245                 250                 255

Pro Cys Pro Asp Ile Tyr Ile Trp Ala Pro Leu Ala Gly Thr Cys Gly
            260                 265                 270

Val Leu Leu Leu Ser Leu Val Ile Thr Leu Tyr Cys Lys Arg Gly Arg
        275                 280                 285

Lys Lys Leu Leu Tyr Ile Phe Lys Gln Pro Phe Met Arg Pro Val Gln
    290                 295                 300

Thr Thr Gln Glu Glu Asp Gly Cys Ser Cys Arg Phe Pro Glu Glu Glu
305                 310                 315                 320

Glu Gly Gly Cys Glu Leu Arg Val Lys Phe Ser Arg Ser Ala Asp Ala
                325                 330                 335

Pro Ala Tyr Lys Gln Gly Gln Asn Gln Leu Tyr Asn Glu Leu Asn Leu
            340                 345                 350

Gly Arg Arg Glu Glu Tyr Asp Val Leu Asp Lys Arg Arg Gly Arg Asp
        355                 360                 365

Pro Glu Met Gly Gly Lys Pro Arg Arg Lys Asn Pro Gln Glu Gly Leu
    370                 375                 380

Tyr Asn Glu Leu Gln Lys Asp Lys Met Ala Glu Ala Tyr Ser Glu Ile
385                 390                 395                 400

Gly Met Lys Gly Glu Arg Arg Arg Gly Lys Gly His Asp Gly Leu Tyr
                405                 410                 415

Gln Gly Leu Ser Thr Ala Thr Lys Asp Thr Tyr Asp Ala Leu His Met
            420                 425                 430

Gln Ala Leu Pro Pro Arg
        435
```

<210> SEQ ID NO 273
<211> LENGTH: 466
<212> TYPE: PRT
<213> ORGANISM: Artificial Sequence
<220> FEATURE:
<223> OTHER INFORMATION: Made in Lab - CAR-GCN4 (CD8 hinge)

<400> SEQUENCE: 273

```
Asp Ala Val Val Thr Gln Glu Ser Ala Leu Thr Ser Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp Tyr Ser Asp
                85                  90                  95

His Trp Val Phe Gly Gly Gly Thr Lys Leu Thr Val Leu Gly Gly Gly
            100                 105                 110
```

```
Gly Gly Ser Gly Gly Gly Gly Ser Gly Gly Gly Gly Ser Gly Gly Gly
        115                 120                 125

Gly Ser Asp Val Gln Leu Gln Glu Ser Gly Pro Gly Leu Val Ala Pro
    130                 135                 140

Ser Gln Ser Leu Ser Ile Thr Cys Thr Val Ser Gly Phe Leu Leu Thr
145                 150                 155                 160

Asp Tyr Gly Val Asn Trp Val Arg Gln Ser Pro Gly Lys Gly Leu Glu
                165                 170                 175

Trp Leu Gly Val Ile Trp Gly Asp Gly Ile Thr Asp Tyr Asn Ser Ala
            180                 185                 190

Leu Lys Ser Arg Leu Ser Val Thr Lys Asp Asn Ser Lys Ser Gln Val
        195                 200                 205

Phe Leu Lys Met Asn Ser Leu Gln Ser Gly Asp Ser Ala Arg Tyr Tyr
    210                 215                 220

Cys Val Thr Gly Leu Phe Asp Tyr Trp Gly Gln Gly Thr Thr Leu Thr
225                 230                 235                 240

Val Ser Ser Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
        275                 280                 285

Ile Tyr Ile Trp Ala Pro Leu Ala Gly Thr Cys Gly Val Leu Leu Leu
    290                 295                 300

Ser Leu Val Ile Thr Leu Tyr Cys Lys Arg Gly Arg Lys Lys Leu Leu
305                 310                 315                 320

Tyr Ile Phe Lys Gln Pro Phe Met Arg Pro Val Gln Thr Thr Gln Glu
                325                 330                 335

Glu Asp Gly Cys Ser Cys Arg Phe Pro Glu Glu Glu Glu Gly Gly Cys
            340                 345                 350

Glu Leu Arg Val Lys Phe Ser Arg Ser Ala Asp Ala Pro Ala Tyr Lys
        355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
        435                 440                 445

Thr Ala Thr Lys Asp Thr Tyr Asp Ala Leu His Met Gln Ala Leu Pro
    450                 455                 460

Pro Arg
465
```

<210> SEQ ID NO 274
<211> LENGTH: 434
<212> TYPE: PRT
<213> ORGANISM: Artificial Sequence
<220> FEATURE:
<223> OTHER INFORMATION: Made in lab - CAR-GCN4 (IgG4m hinge)

<400> SEQUENCE: 274

-continued

```
Asp Ala Val Val Thr Gln Glu Ser Ala Leu Thr Ser Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp Tyr Ser Asp
                85                  90                  95

His Trp Val Phe Gly Gly Gly Thr Lys Leu Thr Val Leu Gly Gly Gly
            100                 105                 110

Gly Gly Ser Gly Gly Gly Gly Ser Gly Gly Gly Gly Ser Gly Gly Gly
        115                 120                 125

Gly Ser Asp Val Gln Leu Gln Glu Ser Gly Pro Gly Leu Val Ala Pro
    130                 135                 140

Ser Gln Ser Leu Ser Ile Thr Cys Thr Val Ser Gly Phe Leu Leu Thr
145                 150                 155                 160

Asp Tyr Gly Val Asn Trp Val Arg Gln Ser Pro Gly Lys Gly Leu Glu
                165                 170                 175

Trp Leu Gly Val Ile Trp Gly Asp Gly Ile Thr Asp Tyr Asn Ser Ala
            180                 185                 190

Leu Lys Ser Arg Leu Ser Val Thr Lys Asp Asn Ser Lys Ser Gln Val
        195                 200                 205

Phe Leu Lys Met Asn Ser Leu Gln Ser Gly Asp Ser Ala Arg Tyr Tyr
    210                 215                 220

Cys Val Thr Gly Leu Phe Asp Tyr Trp Gly Gln Gly Thr Thr Leu Thr
225                 230                 235                 240

Val Ser Ser Glu Ser Lys Tyr Gly Pro Pro Cys Pro Pro Cys Pro Asp
                245                 250                 255

Ile Tyr Ile Trp Ala Pro Leu Ala Gly Thr Cys Gly Val Leu Leu Leu
            260                 265                 270

Ser Leu Val Ile Thr Leu Tyr Cys Lys Arg Gly Arg Lys Lys Leu Leu
        275                 280                 285

Tyr Ile Phe Lys Gln Pro Phe Met Arg Pro Val Gln Thr Thr Gln Glu
    290                 295                 300

Glu Asp Gly Cys Ser Cys Arg Phe Pro Glu Glu Glu Glu Gly Gly Cys
305                 310                 315                 320

Glu Leu Arg Val Lys Phe Ser Arg Ser Ala Asp Ala Pro Ala Tyr Lys
                325                 330                 335

Gln Gly Gln Asn Gln Leu Tyr Asn Glu Leu Asn Leu Gly Arg Arg Glu
            340                 345                 350

Glu Tyr Asp Val Leu Asp Lys Arg Arg Gly Arg Asp Pro Glu Met Gly
        355                 360                 365

Gly Lys Pro Arg Arg Lys Asn Pro Gln Glu Gly Leu Tyr Asn Glu Leu
    370                 375                 380

Gln Lys Asp Lys Met Ala Glu Ala Tyr Ser Glu Ile Gly Met Lys Gly
385                 390                 395                 400

Glu Arg Arg Arg Gly Lys Gly His Asp Gly Leu Tyr Gln Gly Leu Ser
                405                 410                 415

Thr Ala Thr Lys Asp Thr Tyr Asp Ala Leu His Met Gln Ala Leu Pro
```

```
        420                 425                 430

Pro Arg


<210> SEQ ID NO 275
<211> LENGTH: 464
<212> TYPE: PRT
<213> ORGANISM: Artificial Sequence
<220> FEATURE:
<223> OTHER INFORMATION: Made in Lab - CAR-FLAG (CD8 hinge)

<400> SEQUENCE: 275

Asp Ile Val Met Thr Gln Thr Pro Leu Thr Leu Ser Val Thr Phe Gly
1               5                   10                  15

Gln Pro Ala Ser Ile Ser Cys Lys Ser Ser Gln Ser Leu Leu Asp Ser
            20                  25                  30

Asp Gly Gln Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110

Gly Gly Gly Gly Ser Gly Gly Gly Gly Ser Gly Gly Gly Gly Ser Glu
        115                 120                 125

Val Gln Leu Gln Gln Ser Gly Ala Glu Leu Val Lys Pro Gly Ala Ser
    130                 135                 140

Val Lys Leu Ser Cys Thr Ala Ser Gly Phe Asn Ile Lys Asp Tyr Tyr
145                 150                 155                 160

Met His Trp Val Lys Gln Arg Thr Glu Gln Gly Leu Glu Trp Ile Gly
                165                 170                 175

Arg Ile Asp Pro Glu Asp Gly Glu Thr Lys Tyr Ala Pro Lys Phe Gln
            180                 185                 190

Gly Lys Ala Thr Ile Thr Ala Asp Thr Ser Ser Lys Thr Ala Tyr Leu
        195                 200                 205

Gln Leu Ser Ser Leu Thr Ser Glu Asp Thr Ala Val Tyr Tyr Cys Ala
    210                 215                 220

Arg Leu Lys Gly Gly Tyr Trp Gly Gln Gly Thr Thr Leu Thr Val Ser
225                 230                 235                 240

Ser Thr Thr Thr Pro Ala Pro Arg Pro Pro Thr Pro Ala Pro Thr Ile
                245                 250                 255

Ala Ser Gln Pro Leu Ser Leu Arg Pro Glu Ala Cys Arg Pro Ala Ala
            260                 265                 270

Gly Gly Ala Val His Thr Arg Gly Leu Asp Phe Ala Cys Asp Ile Tyr
        275                 280                 285

Ile Trp Ala Pro Leu Ala Gly Thr Cys Gly Val Leu Leu Leu Ser Leu
    290                 295                 300

Val Ile Thr Leu Tyr Cys Lys Arg Gly Arg Lys Lys Leu Leu Tyr Ile
305                 310                 315                 320

Phe Lys Gln Pro Phe Met Arg Pro Val Gln Thr Thr Gln Glu Glu Asp
                325                 330                 335

Gly Cys Ser Cys Arg Phe Pro Glu Glu Glu Glu Gly Gly Cys Glu Leu
            340                 345                 350
```

```
Arg Val Lys Phe Ser Arg Ser Ala Asp Ala Pro Ala Tyr Lys Gln Gly
        355                 360                 365

Gln Asn Gln Leu Tyr Asn Glu Leu Asn Leu Gly Arg Arg Glu Glu Tyr
    370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
        435                 440                 445

Thr Lys Asp Thr Tyr Asp Ala Leu His Met Gln Ala Leu Pro Pro Arg
    450                 455                 460


<210> SEQ ID NO 276
<211> LENGTH: 432
<212> TYPE: PRT
<213> ORGANISM: Artificial Sequence
<220> FEATURE:
<223> OTHER INFORMATION: Made in lab - CAR-FLAG (IgG4m hinge)

<400> SEQUENCE: 276

Asp Ile Val Met Thr Gln Thr Pro Leu Thr Leu Ser Val Thr Phe Gly
1               5                   10                  15

Gln Pro Ala Ser Ile Ser Cys Lys Ser Ser Gln Ser Leu Leu Asp Ser
            20                  25                  30

Asp Gly Gln Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110

Gly Gly Gly Gly Ser Gly Gly Gly Gly Ser Gly Gly Gly Gly Ser Glu
        115                 120                 125

Val Gln Leu Gln Gln Ser Gly Ala Glu Leu Val Lys Pro Gly Ala Ser
    130                 135                 140

Val Lys Leu Ser Cys Thr Ala Ser Gly Phe Asn Ile Lys Asp Tyr Tyr
145                 150                 155                 160

Met His Trp Val Lys Gln Arg Thr Glu Gln Gly Leu Glu Trp Ile Gly
                165                 170                 175

Arg Ile Asp Pro Glu Asp Gly Glu Thr Lys Tyr Ala Pro Lys Phe Gln
            180                 185                 190

Gly Lys Ala Thr Ile Thr Ala Asp Thr Ser Ser Lys Thr Ala Tyr Leu
        195                 200                 205

Gln Leu Ser Ser Leu Thr Ser Glu Asp Thr Ala Val Tyr Tyr Cys Ala
    210                 215                 220

Arg Leu Lys Gly Gly Tyr Trp Gly Gln Gly Thr Thr Leu Thr Val Ser
225                 230                 235                 240

Ser Glu Ser Lys Tyr Gly Pro Pro Cys Pro Pro Cys Pro Asp Ile Tyr
                245                 250                 255
```

-continued

```
Ile Trp Ala Pro Leu Ala Gly Thr Cys Gly Val Leu Leu Leu Ser Leu
            260                 265                 270

Val Ile Thr Leu Tyr Cys Lys Arg Gly Arg Lys Lys Leu Leu Tyr Ile
        275                 280                 285

Phe Lys Gln Pro Phe Met Arg Pro Val Gln Thr Thr Gln Glu Glu Asp
    290                 295                 300

Gly Cys Ser Cys Arg Phe Pro Glu Glu Glu Glu Gly Gly Cys Glu Leu
305                 310                 315                 320

Arg Val Lys Phe Ser Arg Ser Ala Asp Ala Pro Ala Tyr Lys Gln Gly
                325                 330                 335

Gln Asn Gln Leu Tyr Asn Glu Leu Asn Leu Gly Arg Arg Glu Glu Tyr
            340                 345                 350

Asp Val Leu Asp Lys Arg Arg Gly Arg Asp Pro Glu Met Gly Gly Lys
        355                 360                 365

Pro Arg Arg Lys Asn Pro Gln Glu Gly Leu Tyr Asn Glu Leu Gln Lys
    370                 375                 380

Asp Lys Met Ala Glu Ala Tyr Ser Glu Ile Gly Met Lys Gly Glu Arg
385                 390                 395                 400

Arg Arg Gly Lys Gly His Asp Gly Leu Tyr Gln Gly Leu Ser Thr Ala
                405                 410                 415

Thr Lys Asp Thr Tyr Asp Ala Leu His Met Gln Ala Leu Pro Pro Arg
            420                 425                 430
```

OPTIMIZED PNE-BASED CHIMERIC RECEPTOR T CELL SWITCHES AND USES THEREOF

CROSS-REFERENCE

This application is a 371 of international application no. PCT/US2016/027997, filed Apr. 15, 2016, which application claims priority to U.S. Provisional Application No. 62/148,063, filed, Apr. 15, 2015, and U.S. Provisional Application No. 62/253,467, filed Nov. 10, 2015, each of which applications are incorporated by reference herein in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is CIBR_008_01WO_ST25.txt. The text file is 534 KB, was created on Apr. 15, 2016, and is being submitted electronically via EFS-Web.

BACKGROUND OF THE INVENTION

Immunotherapies are becoming attractive alternatives to chemotherapies, including immunotherapies that use adoptive transfer of genetically modified T cells to "reteach" the immune system to recognize and eliminate malignant tumor cells. Genetically modified T cells express chimeric antigen receptors, which generally consist of a signaling endodomain, a CD3-zeta transmembrane domain and an extracellular single-chain variable fragment (scFv) derived from a monoclonal antibody which gives the receptor specificity for a tumor-associated antigen on a target malignant cell. Upon binding the tumor-associated antigen via the chimeric antigen receptor, the chimeric antigen receptor expressing T cell (CAR T-cell) mounts an immune response that is cytotoxic to the malignant cell. Such therapies can circumvent chemotherapy resistance and have been shown to be active against relapsed/refractory disease, resulting in sustained remissions for some chronic lymphocytic leukemia (CLL) and acute lymphoblastic leukemia (ALL) patients. However, these therapies require further investigation and optimization, as they caused undesirable effects such as toxic lymphophenia, chronic hypogammaglobulinemia for hematological targets, fatal off-target cytolysis for solid tumor targets, persistent B cell aplasia with the use of anti-CD19 antibody expressing CAR T-cells, and, in some cases, death.

SUMMARY OF THE INVENTION

Disclosed herein are chimeric antigen receptors ("CAR") comprising an extracellular domain, a transmembrane domain an intracellular signaling domain, wherein the extracellular domain comprises: a region that interacts with a chimeric antigen receptor switch; and a hinge domain. The hinge domain may be about one to about twenty amino acids long. The hinge domain may be greater than about 20 amino acids long. The hinge domain may be flexible. The hinge domain may be rigid. A first cysteine of a first chimeric antigen receptor and a second cysteine of a second chimeric antigen receptor may form a disulfide bond, resulting in multimerization of the first chimeric antigen receptor and the second chimeric antigen receptor. The hinge domain may have a sequence selected from SEQ ID NOS: 68-71. The hinge domain may have a sequence that is at least 50% homologous to a sequence selected from SEQ ID NOS: 68-71. The extracellular domain may comprise a humanized anti-GCN4 scFv. The humanized anti-GCN4 scFv may have a sequence selected from SEQ ID NOS: 165-170. The humanized anti-GCN4 scFv may have a sequence that is at least 50% homologous to a sequence selected from SEQ ID NOS: 165-170. The hinge domain may comprise a peptide derived from a protein selected from a CD8, an IgG, portions thereof, and combinations thereof. The region that interacts with a chimeric antigen receptor switch may interact with a chimeric antigen receptor binding peptide of the chimeric antigen receptor switch. The chimeric antigen receptor may have a sequence selected from SEQ ID NOS: 51, 73, 74, and 171-176. The chimeric antigen receptor may have a sequence that is at least 50% homologous to a sequence selected from SEQ ID NOS: 51, 73, 74, and 171-176.

Further disclosed herein are soluble T cell receptor switches comprising: a chimeric antigen receptor binding peptide; and a soluble T cell receptor or portion thereof. The chimeric antigen receptor binding peptide may be fused to a terminus of a domain of the soluble T cell receptor. The chimeric antigen receptor binding peptide may be grafted into an internal site of a domain of the soluble T cell receptor. The domain of the soluble T cell receptor may be selected from an alpha chain and a beta chain. The soluble T cell receptor switch may have a sequence selected from SEQ ID NOS: 62-67. The soluble T cell receptor switch may have a sequence at least 50% homologous to a sequence selected from SEQ ID NOS: 62-67. The soluble T cell receptor switch may further comprise a linker, wherein the linker links the chimeric antigen receptor binding peptide to the soluble T cell receptor or portion thereof. The linker may be flexible. The linker may be rigid. The linker may be selected from SEQ ID NOS: 45-50 and $(GGGGS)_n$, $(GGGS)_n$, $(GGS)_n$, $(G_mS)_n$, and $(X_mS)_n$, wherein n is at least 1, m is at least 1, and X is any amino acid.

Disclosed herein are chimeric antigen receptor switches comprising: a chimeric antigen receptor binding peptide; a targeting moiety; and a linker, wherein the linker links the chimeric antigen receptor binding peptide to the targeting moiety. The linker may be rigid. The linker may comprise an alpha helix. The linker may be flexible.

Further disclosed herein are chimeric antigen receptor switches comprising: a fusion antibody comprising: a chimeric antigen receptor binding peptide; and a light chain of an antibody or antibody fragment, wherein the chimeric antigen receptor binding peptide is connected to the light chain of the targeting antibody or antibody fragment; and a heavy chain of the targeting antibody or antibody fragment. The fusion antibody may be encoded by a nucleotide sequence selected from SEQ ID NOS: 85, 93, 94, 97, 97-99, 151, 153 and 154 and the heavy chain of the targeting antibody or antibody fragment may be encoded by a nucleotide sequence selected from SEQ ID NOS. 9, 10 and 150. The fusion antibody may be encoded by a nucleotide sequence that is at least about 50% homologous to a sequence selected from SEQ ID NOS: 85, 93, 94, 97, 97-99, 151, 153 and 154, and the heavy chain of the targeting antibody or antibody fragment may be encoded by a nucleotide sequence that is at least about 50% homologous to a sequence selected from SEQ ID NOS. 9, 10 and 150. The fusion antibody may be encoded by a nucleotide sequence selected from SEQ ID NOS: 103 and 105, and the heavy chain of the targeting antibody or antibody fragment may be encoded by a nucleotide sequence of SEQ ID NO. 18. The fusion antibody may be encoded by a nucleotide sequence that is at least about 50% homologous to a sequence selected from SEQ ID NOS: 103 and 105, and the heavy chain of the targeting antibody or antibody fragment may be encoded by a nucleotide sequence that is at least about 50% homologous to SEQ ID NO. 18. The fusion antibody may be encoded by a nucleotide sequence selected from SEQ ID NOS: 109, 111, 115, 117, 121 and 123, and the heavy chain of the targeting antibody or antibody fragment may be encoded by a nucleotide sequence selected from SEQ ID NOS: 106, 112 and 118. The fusion antibody may be encoded by a nucleotide sequence that is at least about 50% homologous to a sequence selected from SEQ ID NOS: 109, 111, 115, 117, 121 and 123, and the heavy chain of the targeting antibody or antibody fragment may be encoded by a nucleotide sequence that is at least about 50% homologous to a sequence selected from SEQ ID NOS: 106, 112 and 118. The fusion antibody may be encoded by a nucleotide sequence selected from SEQ ID NOS: 125, 127, 131, 133, 137 and 139, and the heavy chain of the targeting antibody or antibody fragment may be encoded by a nucleotide sequence selected from SEQ ID NOS: 14, 128 and 134. The fusion antibody may be encoded by a nucleotide sequence that is at least about 50% homologous to a sequence selected from SEQ ID NOS: 125, 127, 131, 133, 137 and 139, and the heavy chain of the targeting antibody or antibody fragment may be encoded by a nucleotide sequence that is at least about 50% homologous to a sequence selected from SEQ ID NOS: 14, 128 and 134. The fusion antibody may be encoded by a nucleotide sequence selected from SEQ ID NOS: 141 and 143, and the heavy chain of the targeting antibody or antibody fragment may be encoded by a nucleotide sequence of SEQ ID NO: 12. The fusion antibody may be encoded by a nucleotide sequence that is at least about 50% homologous to a sequence selected from SEQ ID NOS: 141 and 143, and the heavy chain of the targeting antibody or antibody fragment may be encoded by a nucleotide sequence that is at least about 50% homologous to SEQ ID NO: 12. The fusion antibody may be encoded by a nucleotide sequence selected from SEQ ID NOS: 145 and 146, and the heavy chain of the targeting antibody or antibody fragment may be encoded by a nucleotide sequence of SEQ ID NO: 144. The fusion antibody may be encoded by a nucleotide sequence that is at least about 50% homologous to a sequence selected from SEQ ID NOS: 145 and 146, and the heavy chain of the targeting antibody or antibody fragment may be encoded by a nucleotide sequence that is at least about 50% homologous to SEQ ID NO: 144. The fusion antibody may be encoded by a nucleotide sequence of SEQ ID NO: 158, and the heavy chain of the targeting antibody or antibody fragment may be encoded by a nucleotide sequence of SEQ ID NO: 157. The fusion antibody may be encoded by a nucleotide sequence that is at least about 50% homologous to SEQ ID NO: 158, and the heavy chain of the targeting antibody or antibody fragment may be encoded by a nucleotide sequence that is at least about 50% homologous to SEQ ID NO: 157. The fusion antibody may be encoded by a nucleotide sequence selected from SEQ ID NOS: 162 and 164, and the heavy chain of the targeting antibody or antibody fragment may be encoded by a nucleotide sequence of SEQ ID NO: 20. The fusion antibody may be encoded by a nucleotide sequence that is at least about 50% homologous to a sequence selected from SEQ ID NOS: 162 and 164, and the heavy chain of the targeting antibody or antibody fragment may be encoded by a nucleotide sequence that is at least about 50% homologous to SEQ ID NO: 20. The fusion antibody and the heavy chain of the targeting antibody or antibody fragment may be encoded by one or more nucleotide sequences in a polynucleotide vector, wherein the polynucleotide vector has a sequence selected from SEQ ID NOS: 100 and 101. The fusion antibody and the heavy chain of the targeting antibody or antibody fragment may be encoded by one or more nucleotide sequences in a vector, wherein the vector has a sequence that is at least 50% homologous to a sequence selected from SEQ ID NOS: 100 and 101. The fusion antibody may have a sequence selected from SEQ ID NOS: 30 and 31, and the heavy chain of the targeting antibody or antibody fragment has a sequence selected from SEQ ID NOS: 28 and 29. The fusion antibody may have a sequence that is at least about 50% homologous to a sequence selected from SEQ ID NOS: 30 and 31, and the heavy chain of the targeting antibody or antibody fragment has a sequence that is at least about 50% homologous to a sequence selected from SEQ ID NOS: 28 and 29.

Disclosed herein are chimeric antigen receptor switches comprising: a fusion antibody comprising: a chimeric antigen receptor binding peptide; and a heavy chain of an antibody or antibody fragment, wherein the chimeric antigen receptor binding peptide is connected to the heavy chain of the targeting antibody or antibody fragment; and a light chain of the targeting antibody or antibody fragment. The fusion antibody may be encoded by a nucleotide sequence selected from SEQ ID NOS: 86-92, 95, 96, 152, 155 and 156, and the light chain of the targeting antibody or antibody fragment may be encoded by a nucleotide sequence selected from SEQ ID NOS: 8 and 149. The fusion antibody may be encoded by a nucleotide sequence that is at least about 50% homologous to a sequence selected from SEQ ID NOS: 86-92, 95, 96, 152, 155 and 156, and the light chain of the targeting antibody or antibody fragment may be encoded by a nucleotide sequence that is at least about 50% homologous to a sequence selected from SEQ ID NOS: 8 and 149. The fusion antibody may be encoded by a nucleotide sequence selected from SEQ ID NOS: 102 and 104, and the light chain of the targeting antibody or antibody fragment may be encoded by a nucleotide sequence of SEQ ID NO. 17. The fusion antibody may be encoded by a nucleotide sequence that is at least about 50% homologous to a sequence selected from SEQ ID NOS: 102 and 104, and the light chain of the targeting antibody or antibody fragment may be encoded by a nucleotide sequence that is at least about 50% homologous to SEQ ID NO. 17. The fusion antibody may be encoded by a nucleotide sequence selected from SEQ ID NOS: 108, 110, 116, 120 and 122, and the light chain of the targeting antibody or antibody fragment may be encoded by a nucleotide sequence selected from SEQ ID NOS: 113 and 119. The fusion antibody may be encoded by a nucleotide sequence that is at least about 50% homologous to a sequence selected from SEQ ID NOS: 108, 110, 116, 120 and 122 and 104, and the light chain of the targeting antibody or antibody fragment may be encoded by a nucleotide sequence that is at least about 50% homologous to a sequence selected from SEQ ID NOS: 113 and 119. The fusion antibody may be encoded by a nucleotide sequence selected from SEQ ID NOS: 124, 126, 130, 132, 136 and 138, and the light chain of the targeting antibody or antibody fragment may be encoded by a nucleotide sequence selected from SEQ ID NOS: 129 and 135. The fusion antibody may be encoded by a nucleotide sequence that is at least about 50% homologous to a sequence selected from SEQ ID NOS: 124, 126, 130, 132, 136 and 138, and the light chain of the targeting antibody or antibody fragment may be encoded by a nucleotide sequence that is at least about 50% homologous to a sequence selected from SEQ ID NOS: 129 and 135. The fusion antibody may be encoded by a nucleotide sequence selected from SEQ ID NOS: 140 and 142, and the light chain of the targeting antibody or antibody fragment may be encoded by a nucleotide sequence of SEQ ID NO: 11. The fusion antibody may be encoded by a nucleotide sequence that is at least about 50% homologous to a sequence selected from SEQ ID NOS: 140 and 142, and the light chain of the targeting antibody or antibody fragment may be encoded by a nucleotide sequence that is at least about 50% homologous to SEQ ID NO: 11. The fusion antibody may be encoded by a nucleotide sequence selected from SEQ ID NOS: 147 and 148. The fusion antibody may be encoded by a nucleotide sequence that is at least about 50% homologous to a sequence selected from SEQ ID NOS: 147 and 148. The fusion antibody may be encoded by a nucleotide sequence of SEQ ID NO: 160, and the light chain of the targeting antibody or antibody fragment may be encoded by a nucleotide sequence of SEQ ID NO: 159. The fusion antibody may be encoded by a nucleotide sequence that is at least about 50% homologous to SEQ ID NO: 160, and the light chain of the targeting antibody or antibody fragment may be encoded by a nucleotide sequence that is at least about 50% homologous to SEQ ID NO: 159. The fusion antibody may be encoded by a nucleotide sequence selected from SEQ ID NOS: 161 and 163, and the light chain of the targeting antibody or antibody fragment may be encoded by a nucleotide sequence of SEQ ID NO: 19. The fusion antibody may be encoded by a nucleotide sequence that is at least about 50% homologous to a nucleotide sequence selected from SEQ ID NOS: 161 and 163, and the light chain of the targeting antibody or antibody fragment may be encoded by a sequence that is at least about 50% homologous to SEQ ID NO: 19. The fusion antibody may have a sequence selected from SEQ ID NOS: 32-25 and the light chain of the targeting antibody or antibody fragment may have a sequence of SEQ ID NO. 27. The fusion antibody may have a sequence at least about 50% homologous to a sequence selected from SEQ ID NOS: 32-25 and the light chain of the targeting antibody or antibody fragment may have a sequence at least about 50% homologous to SEQ ID NO. 27.

Further disclosed herein are pharmaceutical compositions comprising any one of the chimeric antibody antigen receptor switches disclosed herein. Disclosed herein are methods of administering the chimeric antigen receptor switch and the chimeric antigen receptor effector cell disclosed herein to a subject in need thereof, wherein the chimeric antigen receptor switch and/or chimeric antigen receptor effector cell is administered by a method selected from intraperitoneal injection and intravenous injection. The method may comprise administering the chimeric antigen receptor switch and/or the chimeric antigen receptor effector cell multiple times.

Disclosed herein are methods of producing an optimal switchable chimeric antigen receptor platform, comprising: incorporating a first chimeric antigen receptor binding peptide to a first site of a targeting moiety that binds a first cell surface molecule on a first target cell to produce a first switch; incorporating a second chimeric antigen receptor binding peptide to a second site of a second targeting moiety that binds a second cell surface molecule on a second target cell to produce a second switch; contacting the first target cell with the first switch and a first chimeric antigen receptor effector cell expressing a first chimeric antigen receptor; contacting the second target cell with the second switch and a second chimeric antigen receptor effector cell expressing a second chimeric antigen receptor; and comparing a first cytotoxic effect of the first switch and the first chimeric antigen receptor effector cell on the first target cell to a second cytotoxic effect of the second switch and the second chimeric antigen receptor effector cell on the second target cell; and selecting the first switch and first chimeric antigen receptor effector cell or the second switch and the second chimeric antigen receptor effector cell as the optimal switchable chimeric antigen receptor platform based on comparing the first cytotoxic effect to the second cytotoxic effect. The first chimeric antigen receptor binding peptide and the second chimeric antigen receptor binding peptide may be the same. The first targeting moiety and the second targeting moiety may be the same. The first site and the second site may be the same. The first site and the second site may be different. The first and/or second targeting moiety may comprise a peptide or protein. The first site and/or second site may be selected from an N terminus of the peptide or protein, a C terminus of the peptide or protein, and an internal site of the peptide or protein. The first and/or second targeting moiety comprises an antibody or antibody fragment. The first site and/or second site may be selected from an N terminus of the antibody or antibody fragment, a C terminus of the antibody or antibody fragment, and an internal site of the antibody or antibody fragment. The first site and/or second site may be selected from a light chain of the antibody or antibody fragment and a heavy chain of the antibody or antibody fragment. The first site and/or second site may be selected from a variable region of the antibody or antibody fragment and a constant region of the antibody or antibody fragment. The first site and/or second site may be selected from a VL domain, a CL domain, a VH domain, a CH1 domain, a CH2 domain, a CH3 domain, and a hinge domain of the antibody or antibody fragment. Incorporating the first/second chimeric antigen receptor binding peptide may comprise a method selected from fusing, grafting, conjugating, linking, and combinations thereof. The method may further comprise incorporating a first linker to the first site, wherein the first linker links the first chimeric antigen receptor binding peptide to the first targeting moiety. The method may further comprise incorporating a second linker to the second site wherein the second linker links the second chimeric antigen receptor binding peptide to the second targeting moiety. The first linker and the second linker may be the same. The first linker and the second linker may be different. The first linker and the second linker may differ by a feature selected from flexibility, length, amino acid sequence, and combinations thereof. The first and/or second linker may have a sequence selected from SEQ ID NOS: 45-50 and $(GGGGS)_n$, $(GGGS)_n$, $(GGS)_n$, $(G_mS)_n$, and $(X_mS)_n$, wherein n is at least 1, m is at least 1, and X is any amino acid. The first chimeric antigen receptor and the second chimeric antigen receptor may be the same. The first chimeric antigen receptor and the second chimeric antigen receptor may be different. The first chimeric antigen receptor and the second chimeric antigen receptor may differ by a domain selected from an extracellular domain, a transmembrane domain, an intracellular domain, and a hinge domain (also known as a spacer domain). A first hinge domain of the first chimeric antigen receptor and a second hinge domain of the second chimeric antigen receptor may differ by a feature selected from flexibility, length, amino acid sequence and combinations thereof. The method may further comprise incorporating one or more additional chimeric antigen receptor binding peptides to the first and/or second targeting moiety to produce a first multivalent switch and/or a second multivalent switch. The method may further comprise incorporating a cysteine residue into the first chimeric antigen receptor and/or the second chimeric antigen receptor in order to multimerize the first chimeric antigen receptor and/or the second chimeric antigen receptor through a disulfide bond. Contacting the first target cell and/or contacting the second target cell may occur in vitro. Contacting the first target cell and/or contacting the second target cell may occur in vivo. Comparing the first cytotoxic effect to the second cytotoxic effect may comprise comparing a feature selected from viability of target cells, viability of off-target cells, tumor burden, and health of an in vivo model.

Disclosed herein are optimized chimeric antigen receptor-effector cell platforms, comprising: a chimeric antigen receptor-effector cell switch comprising a chimeric antigen receptor binding peptide and a targeting moiety; and a chimeric antigen receptor-effector cell that expresses a chimeric antigen receptor, wherein the chimeric antigen receptor-effector cell platform is derived by a method comprising: incorporating a first chimeric antigen receptor binding peptide to a first site of a targeting moiety that binds a first cell surface molecule on a first target cell to produce a first switch; incorporating a second chimeric antigen receptor binding peptide to a second site of a second targeting moiety that binds a second cell surface molecule on a second target cell to produce a second switch; contacting the first target cell with the first switch and a first chimeric antigen receptor effector cell expressing a first chimeric antigen receptor; contacting the second target cell with the second switch and a second chimeric antigen receptor effector cell expressing a second chimeric antigen receptor; and comparing a first cytotoxic effect of the first switch and the first chimeric antigen receptor effector cell on the first target cell to a second cytotoxic effect of the second switch and the second chimeric antigen receptor effector cell on the second target cell; and selecting the first switch and first chimeric antigen receptor effector cell or the second switch and the second chimeric antigen receptor effector cell as the optimal switchable chimeric antigen receptor platform based on comparing the first cytotoxic effect to the second cytotoxic effect. The chimeric antigen receptor effector cell may be derived from a T cell. The chimeric antigen receptor-binding peptide may comprise a peptide selected from a non-human peptide, a non-mammalian peptide, a synthetic non-naturally occurring peptide, and a peptide that has low immunogenicity in a human subject. The chimeric antigen receptor-binding peptide may comprise a sequence selected from SEQ ID NOS: 2-6. The targeting moiety may be selected from a protein, a peptide, an antibody, an antibody fragment, a small molecule, and a soluble T cell receptor or portion thereof. The targeting moiety may comprise an antibody or antibody fragment that binds a cell surface molecule. The targeting moiety may comprise an antibody or antibody fragment that binds a cell surface molecule selected from CD19, CD20, CD22, CD33, CD123, CEA, CLL1, BCMA, EGFRvIII, EGFR, CS1 and Her2. The targeting moiety may comprise a sequence selected from SEQ ID NOS: 21-38, or a portion thereof, or a homolog thereof. The targeting moiety may be encoded by a sequence selected from SEQ ID NOS: 8-20, or a portion thereof, or a homolog thereof.

In embodiments, a switch may be constructed by combining any of the heavy or light chain sequences disclosed herein.

Further disclosed herein are methods of enriching a population of chimeric antigen receptor effector cells comprising contacting the chimeric antigen receptor effector cells with an antigen that binds the chimeric antigen receptor of the chimeric antigen receptor effector cells. The antigen may be located on a chimeric antigen receptor effector cell switch. The contacting may occur multiple times. The antigen may be removed between the multiple times.

Disclosed herein are model systems for testing a CAR-EC platform, comprising: a chimeric antigen receptor-effector cell switch comprising a chimeric antigen receptor binding peptide and a targeting moiety, wherein the targeting moiety binds a non-human cell surface molecule on a non-human target cell; and a chimeric antigen receptor-effector cell that expresses a chimeric antigen receptor, wherein the chimeric antigen receptor-effector cell is a non-human cell. The non-human target cell may be produced by a cell line. The model system may be an in vitro model system. The non-human target cell may be in vivo. The model system may be selected from a rat, a mouse, and a monkey. The targeting moiety may comprise an anti-mouse antibody or antibody fragment. The targeting moiety may have a sequence selected from SEQ ID NOS: 52-61. The targeting moiety may have a sequence at least 50% homologous to a sequence selected from SEQ ID NOS: 52-61. The chimeric antigen receptor may be encoded by SEQ ID NO. 51. The chimeric antigen receptor may be encoded by a sequence at least 50% homologous to SEQ ID NO. 51.

Further disclosed herein are methods of treating cancer in a subject comprising administering a chimeric antigen receptor effector cell and a chimeric antigen receptor switch to the subject. The chimeric antigen receptor effector cell may be administered to the subject prior to administration of the chimeric antigen receptor switch. The chimeric antigen receptor switch may comprise a soluble T cell receptor switch described herein or a chimeric antigen receptor switch described herein. The chimeric antigen receptor switch may be administered in an amount titrated in the subject to optimize the treatment of the cancer. The chimeric antigen receptor switch may be administered at an initial dose, wherein the initial dose is the smallest dose necessary to treat the cancer. The chimeric antigen receptor switch may be administered at a second dose after about 1, 2, 3, 4, 5, 6, 7, 8, or more weeks of treatment at the initial dose, wherein the second dose is larger than the initial dose. Administration of the chimeric antigen receptor switch may be terminated after one or more of a) adverse effects or b) elimination of the cancer. The adverse effects may comprise one or more of tumor lysis syndrome or cytokine release syndrome. Administration of the chimeric antigen receptor switch may be continued after recurrence of the cancer.

BRIEF DESCRIPTION OF THE DRAWINGS

FIG. 4A shows an example of switchable CAR-T cell and formation of a monovalent immunological synapse from a monovalent switch and a monovalent CAR. FIG. 4B shows an example of switchable CAR-T cell and formation of a bivalent immunological synapse from a bivalent switch and a monovalent CAR.

FIG. 4C shows an example of switchable CAR-T cell and formation of a bivalent immunological synapse from a monovalent switch and a bivalent CAR. FIG. 4D shows an example of switchable CAR-T cell and formation of a bivalent immunological synapse from a bivalent switch and a bivalent CAR. Relative activity of switchable CAR-T cells is shown by (+) signs below each of FIGS. 4A-D.

FIG. 7A shows data from sCAR-T cells containing the short (IgG4; SEQ ID: 70) or short-dimeric (IgG4m; SEQ ID: 71) hinges, which were stained with the APC-conjugated goat-anti mouse IgG (H&L) (top) or the HiLyte 488-conjugated PNE (bottom) for 30 minutes at 4° C. and then analyzed by flow cytometry: the reduced binding of the goat-anti mouse IgG (H&L) polyclonal antibody to the IgG4 and IgG4m sCAR-T cells compared with the long sCAR and CART19 is likely due to there being less binding epitopes with the shortened sCAR and indeed binding of the HiLyte 488-PNE is normal. FIG. 7B shows a Western blot showing the dimerization of the chimeric antigen receptors of the sCAR-T cells and CART19 cultured with RS4;11 (R) or K562 (K) cells, anti-human CD3ζ (green) was used to detect endogenous CD3ζ (~20 KDal) and the CD3 present in the CAR signaling domain (monomers=50-60 KDal; dimers (white arrow)=100-125KDal): non-reduced samples are shown on the left and reduced samples on the right. GAPDH (band labeled at ~37 KDa) was used as an endogenous control.

FIG. 8A depicts a PDB 1P4B crystal structure of an affinity matured scFv (light and medium gray represent light chain and heavy chain) bound to a peptide derived from the yeast transcription factor GCN4 (7P-14P) (dark grey represents the GCN4 peptide; SEQ ID: 2). FIG. 8B shows mass spectrometry of a CAR-EC switch comprising an anti-CD19-Fab with a GCN4 graft in the CL1 loop (SEQ ID: 30 & 29). Calculated: 49533, found: 49537.09.

FIG. 10A shows that potency increases when CAR-T cells with shorter hinges are incubated with the anti-CD19 Fab LCNT switch (SEQ ID: 29 & 36) and RS4;11 (CD19-positive) cells. sCAR-T effector cells were cultured with RS4;11 (CD19+) target cells at a ratio of 10:1 for 24 hours with the anti-CD19 Fab LCNT switch (SEQ ID: 29 & 36) before cytotoxicity was determined by the amount of LDH released into the assay supernatant. FIG. 10B shows that the increased activity associated with shortening the hinge design does not result in an increase in non-specific lysis of K562 (CD19-negative) cells.

FIG. 11 A-C shows activity of sCAR-T cells with anti-CD19 switch.

FIG. 12A shows distance and orientations by dashed lines of target cell binding and CAR-T binding to the switch. FIG. 12B shows the target cell binding region domains of the switch. Arrow points to VH beta turn on the VH N term.

FIG. 13A shows a denaturing SDS-page gel depicting the anti-CD19 IgG, anti-CD19 Fab switches derived from the FMC63 clone under non-reducing (top) and reducing (bottom) conditions. In some grafting positions the heavy and light chains resolve into two bands on the reduced gel, while in other cases they overlap and appear as one band. FIG. 13B shows an SDS-page gel showing the anti-CD20 Fab switches derived from the Ofatumumab clone under non-reducing (top) and reducing (bottom) conditions.

FIG. 20A shows conventional CAR-T cells (left) utilize an scFv that directly targets tumor associated cell surface antigens. Upon binding, signaling through the CAR drives an effector response that leads to the killing of target cells and propagation of the anti-tumor immune response. The same response is achieved with switchable CAR-T cells (right), however, antigen recognition is uncoupled from T cell signaling by the introduction of an antibody based "switch" that targets tumor associated antigens. The switch is then recognized by the switchable CAR-T cell (sCAR-T) through an scFv that binds to, with high affinity, a peptide neo-epitope (PNE) that is engrafted onto the switch. Thus sCAR-T cells only target antigens in the presence of a switch and offer controlled activation, deactivation and re-targeting of CAR-T cell therapy. The LCCT switch is shown as an example.

FIG. 20B shows the relative immunogenicity of PNE engrafted Herceptin heavy or light chains (HCNT and LCNT respectively), which was measured in silico by EpiVax and showed minimal increases compared with the wild type heavy and light chains (HCWT and LCWT respectively). Using this analysis, scores of >20 are considered to be potentially immunogenic.

FIG. 21A shows representative thermal stability analysis for the anti-CD19 Fab and IgG switches with accompanying table showing the melt temperatures of the WT, LCNT, HCNT, NTBV, LCC1, HCC1, C1BV, LCCT, HCCT and CTBV switches, in both IgG and Fab formats, using the Protein Thermal Shift™ kit (Thermo). The first melt temperature indicates the Fab melt where all PNE grafting resided. The second melt temperature indicates the Fc region and is only present for full length IgG constructs. FIG. 21B shows the indicated switches binding to $CD19^+$ RS4;11 cells and FIG. 21C shows the lack of switch binding to $CD19^-$ K562 cells with both Fab and IgG based switches. Data for FIGS. 21B-C was acquired by incubating the cells with each switch for 30 minutes at 4° C. in FACS buffer (PBS, 1% FCS, 1 mM EDTA) followed by incubating with a PE-conjugated goat-anti-human-kappa chain antibody for 30 minutes at 4° C. and analyzing by flow cytometry. The $EC_{50}$ of binding for each switch is indicated in the legend in FIG. 21B.

FIG. 22A shows an AF647-conjugated goat-anti-mouse IgG (H&L) antibody (Thermo) was used to show surface expression of CART19 and the sCAR by flow cytometry; alternatively, a AF488-conjugated PNE (Anaspec) was used to detect surface expression of the sCAR by flow cytometry. FIG. 22B shows switch binding to sCAR-T cells. The $EC_{50}$ of binding for each switch is indicated in the legend. FIG. 22C shows lack of switch binding in mock transduced PBMC (sCAR negative). Data for FIGS. 22A-C were acquired for each switch using the method described in FIG. 21B.

FIG. 23A shows cytotoxicity of sCAR-T cells with CD8, IgG4, or IgG4m hinges, or non-transduced T cells (mock) against RS4;11 cells with titration of the anti-CD19 LCNT Fab switch (SEQ ID: 29 & 36). FIG. 23B shows cytotoxicity as described in (A) against K562 cells. FIG. 23C shows activation of sCAR-T cells with short-dimeric hinge or mock cells in the presence of RS4;11 cells with or without 1 nM LCNT anti-CD19 Fab switch (SEQ ID: 29 & 36) was measured by flow cytometry with staining for CD25 and CD69. FIG. 23D shows IL-2 released from sCAR-T cells cultured with RS4;11 cells and 1 nM of the indicated anti-CD19 Fab switches. FIG. 23E top panel shows quantification of the flow cytometry assay shown in (C) in the presence of 1 nM of the indicated anti-CD19 Fab switch design. FIG. 23E bottom panel shows the IL-2 release from sCAR-T cells when cultured with the different switches and K562 cells. In (D) and (E) gray asterisks denote significance between CART-19 and sCAR-T cells and black asterisks denote significance between sCAR-T cell hinges. Mean values for CART-19 is indicated by dotted horizontal line. Values listed next to switch show $EC_{50}$ of cytotoxicity. All cytotoxicity and cytokine assays were performed with E:T=10:1 and 24 h incubation. Cytotoxicity was assessed by LDH release. Data are represented as mean±SD, and statistical significance was calculated using the 1-way ANOVA with Tukey's post-test (B & D) where *=$p<0.05$, =$p<0.01$ and *=$p<0.001$.

FIG. 24A shows data for the Fab switches and FIG. 24B shows data for the CD8 hinge, IgG4m hinge, and the IgG4 hinge sCAR-T cells when cultured with K562 and the switches denoted in the figure key. $EC_{50}$ values, where calculatable, for each switch are denoted within parentheses. Unless otherwise stated, all in vitro cytotoxicity assays were conducted at a ratio of 10 effector cells to 1 target cell.

FIG. 25A shows cytotoxicity of CD8 hinge sCAR-T cells against $CD20^+$ Raji cells with titrations of anti-CD20 Fab switch designs. FIG. 25B shows IL-2 released from sCAR-T cells cultured with Raji cells and 1 nM anti-CD20 Fab switches against. All assays were performed with E:T=10:1 and 24 h incubation. Cytotoxicity was assessed by LDH release. Data are represented as mean±SD. Values listed next to switches show $EC_{50}$ of cytotoxicity. Significance was calculated using the student's t-test where =$p<0.01$ and *=$p<0.001$.

FIG. 26A-F shows that switch-induced activity of short-dimeric sCAR-T cells can be controlled by the addition of free PNE. FIG. 26A shows LDH cytotoxicity assay, which utilized a dose titration of the LCNT Fab switch in the presence of various concentrations of free PNE or a non-binding alanine mutant of the PNE (PNE-X; grey line) as a control. FIG. 26B shows cytokine release induced by 1 nM LCNT switch in the presence of various concentrations of free PNE or the PNE-X control mentioned above, as measured by CBA. FIG. 26C shows upregulation of T cell activation markers induced by 1 nM LCNT switch in the presence of various concentrations of free PNE or the PNE-X control mentioned above. The non-binding mutated version of the PNE (PNE-X; bar farthest to the right) was, again, used as a control. FIG. 26D shows that a peptide based CAR is highly specific.

Alanine mutated free peptide (PepX) has no effect. Only the cognate free peptide epitope inhibits cytotoxicity (see FIGS. 26D-F). FIG. 26E-F show live cell imaging (Incucyte, Essen). FIG. 26E shows quantification of the killing of RS4;11 cells in the presences of the Cell Tox Green® cell viability dye. FIG. 26F shows clustering of Nalm6$^{GFP/Luc}$ (green) cells±LCNT switch or mock transduced cells with the LCNT switch (the reduction of GFP$^+$ cluster size indicates target cell lysis).

FIG. 27A shows cytotoxicity assay whereby IgG4 sCAR-T cells were cultured with RS4;11 cells and a panel of anti-CD19 Fab switches. FIG. 27B shows cytotoxicity assay whereby IgG4m sCAR-T cells were cultured with RS4;11 cells and a panel of anti-CD19 Fab switches. $EC_{50}$ values are denoted within parentheses.

FIG. 28A shows cytotoxicity of IgG4m sCAR-T cells against Raji cells with titration of anti-CD20 Fab switch designs. Values listed next to switch show $EC_{50}$ of cytotoxicity. All cytotoxicity and cytokine assays were performed with E:T=10:1 and 24 h incubation. Cytotoxicity was assessed by LDH release. Data are represented as mean±SD. FIG. 28B shows flow cytometry based cytotoxicity assay whereby sCAR-T cells were cultured with Raji cells (CD22+) and the anti-CD22 (clone hLL2) WT or GCN4-based Fab switches. FIG. 28C shows flow cytometry based cytotoxicity assay whereby sCAR-T cells were cultured with Raji cells (CD22+) and the anti-CD22 (clone m971) WT or GCN4-based Fab switches. FIG. 28D shows SDS gel images of anti-CD22 (clone hLL2)-Fab CTBV1 (SEQ ID NO: 189 & 191), CTBV2 (SEQ ID NO: 192 & 194) or CTBV3 (SEQ ID NO: 193 & 195). M represents protein marker. FIG. 28E shows mass spectrometry of anti-CD22 (clone hLL2)-Fab-CTBVs. FIG. 28F shows flow cytometry based cytotoxicity assay whereby sCAR-T cells (SEQ ID NO: 74) were cultured with Raji cells (CD22+) and the anti-CD22 CTBV1, CTBV2 and CTBV3 switches. FIG. 28G shows position of GCN4 tag in IgG format switches. FIG. 28H shows SDS gel images of anti-CD22 IgG (clone M971 and clone hLL2)-LCCT, HCCT, and CTBV switches. Samples were treated with 10 mM DTT before running the gel to reduce the protein. FIG. 28I shows Mass spectrometry of anti-CD22-IgG (clone m971)-LCCT, HCCT, and CTBV. Samples were treated with PNGase F for deglycosylation and 10 mM DTT for reduction. FIG. 28J shows flow cytometry based cytotoxicity assay whereby sCAR-T cells (SEQ ID NO: 74) were cultured with Raji cells (CD22+) and the switch concentrations indicated on the x axis of the figure. FIG. 28K shows mass spectrometry of anti-CD22-IgG (clone hLL2)-LCCT, HCCT, and CTBV. Samples were treated with PNGase F for deglycosylation and 10 mM DTT for reduction. FIG. 28L shows cytotoxicity of sCAR-T cells (determined using the Flow cytometry-based cytotoxicity assay) with short-dimeric hinge against Raji cells (CD22+) with anti-CD22 IgG (clone hLL2) IgG switches: Switch concentrations indicated on the x axis of the figure.

FIG. 29A shows representative IVIS images depicting long, short, or short-dimeric sCAR-T cells dosed with the LCNT Fab switch.

FIG. 29B shows quantified tumor burden (as average radiance from luciferase activity from each mouse) from (A) during switch dosing period (n=5). FIG. 29C shows enumeration of T cells in peripheral blood from (A) at day 17 by flow cytometry. FIG. 29D shows representative IVIS images depicting short-dimeric sCAR-T cells dosed with anti-CD19 Fab switch designs. FIG. 29E shows quantified tumor burden from (D) during switch dosing period (n=5). FIG. 29F shows enumeration of T cells in peripheral blood from (A) at day 17 by flow cytometry. Asterisks indicate significance from LCNT Fab group. Data are represented as means±SEM, and statistical significance was calculated using the 2-way ANOVA with Bonferroni's post-test (B & E; shown for final time-point only) or by one-tailed student's t-test (C & F) where *=p<0.05, =p<0.01 and *=p<0.001.

FIG. 30A shows results after six days, 5 cohorts (n=3) of mice were randomized into 3 groups and injected I.V. with 40×10$^6$ CART-19, SCAR-T cells with (+) LCNT Fab switch, or no T cells (PBS group). A fourth group consisted of two cohorts (n=3) of mice injected I.V. with sCAR-T cells without (–) LCNT Fab switch. LCNT Fab dosing in the indicated group was carried out daily at 0.5 mg/kg after the initial T cell infusion. Luminescence was measured at 6 h and subsequently every 24 h as indicated. Cohorts were sacrificed for analysis immediately following IVIS imaging. FIG. 30B shows quantified tumor burden (radiance, left axis) and quantified human IL-2 (pg/mL, right axis) in peripheral blood from each cohort shown in (A) at time indicated. Gray lines indicate tumor burden in PBS and sCAR-T cell—LCNT Fab controls. FIG. 30C shows the proportion of leukocytes that were human CD3$^+$CD4/8$^+$ in the blood, spleen, lungs and liver at 96 h in the + LCNT Fab and – LCNT Fab groups quantified by flow cytometry FIG. 30D shows relative proliferation of T cells in the spleen, lung, and liver at 96 h in + and – LCNT Fab groups, determined by dye dilution. Data are represented as means±SEM, and statistical significance was calculated using the one-tailed student's t-test (C & D) where *=p<0.05, =p<0.01 and *=p<0.001.

FIG. 31A shows representative IVIS images from FIG. 33A. FIG. 31B shows CD3$^+$CD4/8$^+$ T cells were enumerated in the blood of NSG mice treated with sCAR-T cells over 70 days using count bright absolute counting beads (BD); switch was dosed from day 6-21 using either the q.d., q.a.d., or q.5.d. strategies as described in FIG. 33A. FIG. 31C shows a flow cytometry gating strategy to identify CD3$^+$ T cells that expressed CD4, CD8, CD45RA or CD62-L as presented in FIG. 33D.

FIG. 32A shows the spleen, lungs, liver and blood of NGS mice that were engrafted with Nalm6$^{GFP/Luc}$ cells were homogenized to produce a single cell suspension (lungs were digested using 1 mg/ml Liberase LT (Roche) and 50 μg/ml DNaseI (Sigma) for 45 min at 37° C. prior to homogenization) and analyzed by flow cytometry: by day 5 Nalm6$^{Luc/GFP}$ cells were detected in the lung and liver but not in the spleens or blood. FIG. 32B shows the proportion of lymphocytes that are Nalm6$^{GFP/Luc}$ over the first 96 hours of the NSG model, these data were generated using the gating strategy presented in FIG. 32A. FIG. 32C shows CART19 or sCAR-T cells were infused into Nalm6$^{GFP/Luc}$ engrafted NSG mice at day 6 and dosed q.d. with the LCNT switch (0.5 mg/kg). Prior to infusion, the T cells were labelled with the E450 proliferation tracker dye (eBiosciences; 0.5 μM per 10^6 cells) which enabled cell proliferation to be analyzed by flow cytometry ex vivo as shown in this representative histogram. FIG. 32D shows an E450 dilution in CART19 and IgG4m sCAR-T cells+LCNT switch over 5 days in the spleen, lung and liver as measured by flow cytometry; data are presented as mean fluorescence intensity (MFI) of the proliferation dye.

FIG. 33A shows quantified tumor burden from groups dosed every day (q.d.) every other day (q.a.d.) or every fifth day (q.5.d) with 0.5 mg/kg LNCT Fab. Dosing was carried out for 15 d starting at day 6 (corresponding with sCAR-T cell infusion) as indicated by gray shading. Control groups CART-19 and PBS received no switch. The NS group received sCAR-T cells but no switch. Open circles denote the death of individual mice without evidence of tumor burden and may reflect GVHD. Triangles in PBS, NS and q.a.d. group indicate death due to increasing tumor burden. (n=3) FIG. 33B shows quantified IL-2, INFγ, and TNFα at 24 h after first dose of switch, from groups dosed every day with 0, 0.05, 0.5, or 2.5 mg/kg of LNCT Fab. (19) indicates CART-19. FIG. 33C shows quantified tumor burden by IVIS from groups in (B) after 10 d. (19) indicates CART-19. FIG. 33D shows quantified tumor burden from mice dosed with 0.05 mg/kg LCNT Fab for 10 d indicated by gray box. Dosing was resumed at 0.5 mg/kg when the average tumor burden in group became significantly higher than CART-19 control at day 33, indicated by asterisk and second gray box. Triangles indicate the death of individual mice with significant tumor burden. The single mouse death in the 0.05 mg/kg group occurred while tumor burden was decreasing. (n=5) FIG. 33E shows the phenotype of T cells in the peripheral blood from (B) after 21 days as the proportion of $CD3^{+}CD4/CD8^{+}$by flow cytometry with staining for CD62-L and CD45RA using the gating strategy presented in FIG. 31C. Statistical significance was calculated using the one-tailed student's t-test (B, C & E) where *=p<0.05, =p<0.01 and *=p<0.001.

FIG. 34A shows data from a dual targeting experiment. Mice with CD19+/CD20+ Raji xenograft tumors are cleared initially using a CD19 switch, rechallenged with the same CD19+/CD20+ Raji, and cleared using a CD20 switch.

FIG. 34B shows data from a dual targeting experiment that is similar to FIG. 34A, except the rechallenge group was CD19 negative: mice with CD19+/CD20+ Raji xenograft tumors are cleared initially using a CD19 switch, rechallenged with $CD19^{-}$/CD20+ Raji, and cleared using a CD20 switch.

FIG. 36A shows murine anti-peptide CAR-T cell cytokine production. FIG. 36B shows cytokine production from co-culture of MYC5-GFP-CD19 target cells with CAR-T cells and $10^{-1}$ nM switch.

FIG. 38A illustrates multiple fusion/grafting locations: A=LCNT1 (light chain N terminus version 1), B=HCNT3 (heavy chain N terminus version 3), C=heavy chain C terminus, and D=light chain C terminus). FIG. 38B shows cytotoxic activity against U9347 (CLL1+) cells of the CLL1 switch with a long (CD8) hinge CAR. FIG. 38C shows cytotoxic activity against U9347 (CLL1+) cells of the CLL1 switch with a short, dimeric (IgG4m) hinge CAR. FIG. 38D shows cytokine production by the various anti-CLL1 switches.

FIG. 40A shows non-reduced peaks correlating to the non-reduced 1G4c113-TCR with GCN4-Cterm peptide graft. FIG. 40B shows reduced 1G4c113 TCR beta chain with grafted GCN4-Cterm. FIG. 40C shows reduced 1G4c113 TCR alpha chain.

FIG. 41A shows a schematic depiction of the soluble based TCR (sTCR) interacting with a peptide presenting HLA molecule. FIG. 41B shows a sTCR specific for HLA molecules bound to the cancer associated NY-ESO-1 peptide. The sTCR was expressed with a C-terminal GCN4 and a 6×HIS tag on the beta chain and was used to stain T2 cells expressing HLA molecules loaded with the NY-ESO-1 peptide as determined by flow cytometry. FIG. 41C shows results from $10^5$ T2 cells loaded with $10^{\circ}$-$10^{-8}$ nM of the NY-ESO-1 of a HIV peptide for 2 hours at 37° C. in 200 μl of DMEM medium with no serum protein added. The cells were then labelled with the NY-ESO-1 specific sTCR as described in FIG. 41B. The data are presented as MFI of the switch binding against the concentration of the peptide used to load the cells. These data indicated that 1 nM of peptide loaded onto the T2 HLA molecules was sufficient for the sTCR to bind to the T2 cells and therefore was used for subsequent experiments. FIG. 41D shows that short-dimeric (IgG4m: SEQ ID: 71) sCAR-T cells can kill T2 cells pulsed with NY-ESO-1 peptide but not HIV peptide. FIG. 41E shows that sTCR switches activate T cells in in vitro cytotoxicity assays. FIG. 41F shows elicited cytokines from the activated T cells in FIG. 41D.

FIG. 42A shows cytotoxicity of sCAR-T cells against Her2 3+ SKBR3 cells with titrations of anti-HER2 Fab switch designs. FIG. 42B shows cytotoxicity of sCAR-T cells against Her2 2+ MDA MB453 cells with titrations of anti-HER2 Fab switch designs. FIG. 42C shows cytotoxicity of sCAR-T cells against Her2 1+MB435 cells with titrations of anti-HER2 Fab switch designs. FIG. 42D shows cytotoxicity of sCAR-T cells against $Her2^{-}$ MB468 cells with titrations of anti-HER2 Fab switch designs. FIG. 42E shows in vivo cytotoxicity of sCAR-T cells against Her2 2+ MDA MB453 cells with the CTBV anti-HER2 Fab switch. FIG. 42F shows in vivo cytotoxicity of sCAR-T cells against Her2 3+ HCC1954 cells with the CTBV anti-HER2 Fab switch.

FIG. 43A shows SDS-PAGE analysis of switches before and after anti-Her2 Fab fusion with GCN4 (B) under non-reducing and reducing conditions. FIG. 43B shows mass spectrometric analysis of anti-Her2-GCN4 fusions obtained on an Agilent Quadruple Time-of-Flight (QTOF) mass spectrometer. Deconvoluted masses were obtained using Agilent Qualitative Analysis software.

FIG. 44A shows the crystal structure of the anti-Her2 Fab 4D5 bound to Her2. The location of the two N-terminal and two C-terminal positions that were grafted with the PNE (GCN4) are indicated by P1, P3 (N-terminal) and P2, P4 (C-terminal). FIG. 44B shows a schematic representation of anti-GCN4 sCARs containing the CD8 signaling sequence, corresponding scFv, extracellular hinge region (CD8 or IgG4m), CD8 transmembrane domain, 4-1BB costimulatory domain and CD3 signaling domain. FIG. 44C show the relative distances between bivalent sites on the CTBV switch, as modeled over the 4D5 Fab structure (Protein Data Bank ID 1N8Z). Distance were calculated with UCSF Chimera 1.10.2. The LCCT and HCCT grafting positions for the PNE are only 11.6 Å apart. FIG. 44D shows Binding of different GCN4 switches to GCN4 specific CAR-T cells (both CD8 and IgG4m). Cells were incubated with indicated switches and detected with Alexa Fluor647 conjugated anti-human kappa chain antibody. The EC50 value was calculated with Graphpad Prism software.

FIG. 46A shows switch binding to GCN4 specific CAR-T cells with CD8 hinge. FIG. 46B shows switch binding to GCN4 specific CAR-T cells with IgG4m hinge. FIG. 46C shows validation of binding specificity of GCN4 specific CAR-T cells with irrelevant tag-based antibody switches. Cells were incubated with indicated switches and detected with Alexa Fluor647 conjugated anti-human kappa chain antibody. No cross binding was observed to occur between GCN4-based sCAR-T cells and irrelevant tag-based switches.

FIG. 48A shows ELISA detection of IL-2. FIG. 48B shows ELISA detection of IFN-γ. FIG. 48C shows ELISA detection of TNF-α. *=$p<0.005$, =$p<0.05$ and NS=$p>0.05$ were calculated using the Student's t-test, and a p value <0.05 was considered significant.

FIG. 50A shows in vitro cytotoxicity of sCAR-T cells with different hinge lengths on Her2 1+BT20 and MDA MB231 cancer cells. Different concentrations of GCN4 CTBV switch was used to induce the corresponding CAR-T activity on target cells. FIG. 50B shows in vitro cytotoxicity comparison of different GCN4 switches redirected anti-GCN4 CAR-T (IgG4m hinge) cells against different Her2 1+ cancer cells. Cytotoxicity was determined by measuring the amount of LDH released into cultured medium.

FIG. 52A shows The FLAG specific sCAR-T cells containing different hinges were incubated with SKBR3, MDA MB453, MDA MB435 and MDA MB468 cancer cells at an E: T=10:1 ratio with serial dilution of FLAG switch CTBV. FIG. 52B shows ELISA measurement of T cell activation, which was evaluated by CD69/CD25 staining and cytokine release (IL-2, IFN-γ and TNF-α) in media.

FIG. 55A shows HCC1954 xenograft model. FIG. 55B shows MDA MB453 xenograft model. FIG. 55C shows MDA MB231 xenograft model. Ten days after cancer cell implantation in NSG mice, mice were i.v. injected with $30\times10^6$ CAR-T cells, followed by a dose of switch or wild type 4D5 Fab at 0.5 mg/kg every other day for 14 days. The control group received saline instead of switch and did not receive any T cells. Tumor volume was calculated by W×L×H. Each data point represents tumor volume of five mice in each group. Error bars represent SD. Arrows indicate time of CAR-T cell injection or of treatment with specific antibodies.

DETAILED DESCRIPTION OF THE INVENTION

Figure 1:
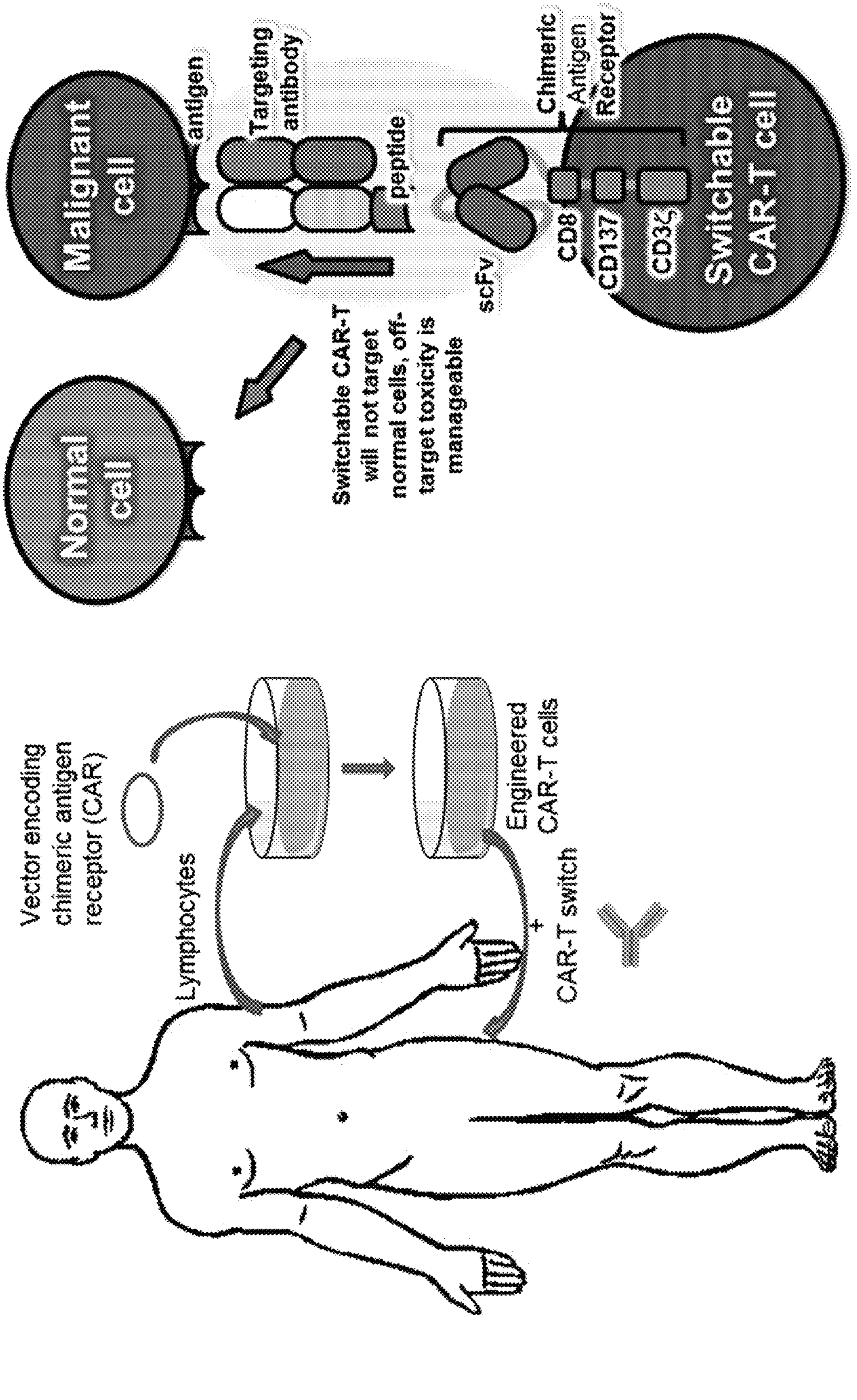
FIG. 1 illustrates a general overview of chimeric antigen receptor-T cell (CAR T-cell) and CAR T-cell switch therapy with switches disclosed herein. Lymphocytes are isolated from a subject and an expression vector encoding a chimeric antigen receptor is subsequently introduced to the lymphocytes to produce chimeric antigen receptor expressing cells. Resulting engineered lymphocytes are administered to the subject, along with a CAR T-cell switch. The CAR T-cell switch comprises a peptide that is bound by the chimeric antigen receptor of the CAR T-cell and a targeting antibody that is selective for a target cell. Binding of the CAR T-cell switch to the CAR T-cell induces an immune response that would be cytotoxic to the malignant cell also bound to the CAR T-cell switch.

Current chimeric antigen receptor T cell (CAR T-cell) therapies can be unreliable due to lack of means to control CAR T-cell activity. Disclosed herein are compositions and methods for selectively activating and deactivating chimeric antigen receptor T cells, which may provide for safer and more versatile immunotherapies than those currently being tested and administered. Disclosed herein are switchable chimeric antigen receptor effector cells (CAR-ECs) and chimeric antigen receptor effector cell (CAR-EC) switches ("switch," or "CAR EC switch," interchangeably), wherein the switch is a polypeptide fusion comprising a first region that is bound by a CAR-EC and a second region that binds a cell surface molecule on target cell. The switches may comprise a peptide neo-eptiope (PNE) that is bound by a chimeric antigen receptor on the CAR-EC and an antibody or antibody fragment that binds a cell surface molecule on a target cell, bringing the target cell in proximity of the CAR-EC and thereby stimulating an immune response from the CAR-EC that is cytotoxic to the bound target cell. In general, the CAR-EC is a T cell, and the CAR-EC is referred to as a switchable CAR-T cell (sCAR-T cell). In this way, the CAR-EC switch may act as an "on-switch" for CAR-EC activity. Activity may be "turned off" or reduced by reducing or ceasing administration of the switch or adding a switch component that competes with the switch. These CAR-EC switches may be used with CAR-ECs disclosed herein, as well as existing CAR T-cells for the treatment of a disease or condition, such as cancer, wherein the target cell is a malignant cell. Such treatment may be referred to herein as switchable immunotherapy, for which an exemplary schematic overview is depicted in FIG. 1.

Major advantages of the switchable CAR platforms disclosed herein include control, safety, titratability, and universality. Switchable CARs can be turned on and off with addition and cessation or competition of the switch. In addition, CAR-EC switches can be titrated to a desired response. For example, solid tumors may be targeted by titration of therapy to achieve suitable therapeutic index. The response may be titrated "on" to avoid CRS (cytokine release syndrome) and TLS (tumor lysis syndrome) events, providing for personalized therapy. Furthermore, administration of a switch can be terminated or reduced in case of an adverse event. The switchable CAR-T cell can be designed to target a non-endogenous antigen with a switch that can be reduced at any time. In contrast, a canonical CAR-T cell is always "on" as long as a target exists. This always "on" can lead to T cell anergy. A switchable CAR-T cell can be stimulated and rested. This is more analogous to the natural stimulation of a T cell responding to an infection. Iterative stimulations in this nature, if timed correctly, may be able to better recapitulate the natural stimulation and resting cycles of T cells that would be encountered, for example, with an acute infection. This type of natural life expansion and contraction of T cells may off-set anergy (or T cell dysfunction) and promote the formation of long-lived memory cells. Long-lived memory cells are known to be advantageous in CAR-T cells. Therefore, a switchable approach to CAR-T cells may be advantageous in that it can promote more favorable T cell responses and phenotypes/lineage commitments than canonical CAR-T cells.

Another advantage of the sCAR-EC system is that it is easier and faster to design multiple switches for each CAR-EC rather than empirically building and testing CAR hinge designs. This is because the switches are biologics which may be easier, less expensive, and faster to build multiple variants than the CAR which requires cell engineering and cell handling. Further, previously approved monoclonal antibody biologics with known safety profiles can be adapted into switches. Thus a universal CAR has a significant advantage in design of the optimal immunological synapse. In addition, CAR-EC switches make it possible for a single CAR-T cell to be redirected to multiple therapeutic targets. Redirection during therapy, by variation of switches, can combat antigen-loss escape mutants with a single CAR. Treatment of heterologous tumors with multiple switches is more straightforward than with multiple CARs. Switches also enable standardized treatment protocols which may provide safety and lower up front treatment costs.

Each target antigen and epitope requires empirical design of a canonical CAR in order to find the optimal CAR-T cell activation, but a switch enables more geometric options than a canonical CAR, allowing for optimal geometry and/or distance of the immunological synapse. An advantage to switchable CAR-ECs is the additional flexibility in geometric orientations that can be provided by a switch that cannot be provided by modifying the CAR-EC hinge. The additional geometric orientations may be useful in forming optimal immunological synapses. Switch designs that provide maximal ternary complex formation may correlate with increased sCAR-T cell activity. On the other hand, improper balancing of kinetics, as a result of sub-optimal design, can result in auto-inhibition of the ternary complex formation, translating to a decrease in the number of immunological synapses that can form between the CAR-EC and target cell, which may be detrimental to activity. States of auto-inhibition may result in increased activation induced cell death (AICD) through sub-optimal signaling. Recursive CAR signaling can also result in AICD. Other sCAR-T cell platforms with non-specific labeling of antibodies or constrained site labeling are unable to comprehensively explore these design considerations.

Mathematical models related to binary binding equilibria and concentration (which is related to antigen density) of each component to the formation of the ternary complex as a function of switch concentration are considered in optimizing the sCAR-T immunological synapse. These models take into account auto-inhibition of the ternary complex by high concentrations of the switch or disproportionately high affinities of the binary interactions, which may reduce the cytotoxic capacity of the sCAR-EC cells. In order to apply these models, sCARs and switches with varied affinities are produced by specific mutations, grafting/fusion sites, and quantitative flow cytometry is used to establish sCAR density. The increased avidity of the IgG based switch, relative to a Fab switch, enables a larger range of off-rates to study. Target cells with a range of cell surface antigen density are also employed. Candidate designs are tested for cytotoxicity, cytokine release, AICD and up-regulation of activation markers on sCAR-EC cells. Optimal ternary complex and immunological synapse formation may be achieved when the affinity of the sCAR is far lower than the concentration of sCAR on the surface of the T cell. Alternatively, optimal ternary complex and immunological synapse formation may be achieved when the affinity of the sCAR is relatively high and the concentration of sCAR on the surface of the T cell is relatively low.

The examples disclosed herein demonstrate that changes in the length of the hinge region of the sCAR could be matched with compensatory switch modifications (e.g., geometry) to yields switch-sCAR pairs that exhibit robust cytotoxicity, upregulation of activation markers, and production of cytokines. For example, optimal configurations of switches and sCAR hinges afforded high potency on breast cancer cells expressing high (3+) mid (2+) and low (1+) levels of Her2 expression with no activity on Her2 negative (0) cell lines. We have shown this with at least two switches that differ by their CAR binding region. These platforms eliminated established Her2 3+, 2+ and 1+ solid and orthotopic tumor xenografts with comparable efficacy to the conventional anti-Her2 CAR-T cells. This controllable nature of sCAR-T cells is expected to provide increased safety in the translation of CAR-T cell strategies for solid tumors, especially in the treatment of patients with Her2-low malignancies for which trastuzumab is not approved.

The CAR-EC switches disclosed herein comprise a first region that binds a cell surface molecule on a target cell, and a second region that is bound by a chimeric antigen receptor. In general the first region is a targeting polypeptide. The targeting polypeptide may be a targeting antibody or antibody fragment that binds an antigen on the target cell. Alternatively or additionally, the first region may comprise a non-peptide small molecule (e.g., vitamin, metabolite). The second region, referred to herein as a chimeric antigen binding peptidic antigen (CAR-BP) or peptide neo-epitope (PNE), comprises a peptide. For simplicity, the term chimeric antigen binding peptidic antigen may simply be referred to herein as a peptidic antigen. In general, the CAR-BP is fused to a terminus of the targeting polypeptide or grafted within the targeting polypeptide. Fusing or grafting the CAR-BP to the targeting polypeptide may be carried out by cloning one or more polynucleotides encoding the first region and the second region into a polynucleotide expression vector, in a desired order or combination.

Methods of treating a disease or condition comprising administering the CAR-EC switches, disclosed herein, may provide for a titratable response, improved safety and/or cessation of CAR-EC activity by reducing or ceasing administration of the CAR-EC switch. In contrast to other approaches of controlling CAR-EC activity, which "turn off" CAR-EC activity by competing with the target cell surface molecule for binding the CAR, the CAR-EC switches disclosed herein, generally function as CAR-EC activators or "on" switches.

Further disclosed herein are CAR-EC platforms including CAR-EC switches and effector cells comprising universal chimeric antigen receptors (CAR) that can bind multiple CAR-EC switches, providing for sequential targeting of one or more types of target cells (e.g., treatment of heterogeneous tumors). The CAR may comprise an ultra-high affinity antibody or antibody fragment (e.g., scFv) to the switch. Methods of producing the CAR-EC switches disclosed herein may advantageously provide for control of CAR-EC cell activity, titration of off-target reactivity, abrogation of tumor lysis syndrome (TLS), attenuation of cytokine release syndrome (CRS), and/or optimization of CAR-EC switch binding by affinity, valency, geometry, length and/or chemistry through site-specific grafting/fusing of CAR-EC switch peptides/antibodies. Methods also may advantageously provide for titrating the dose of the switch over the course of treatment of the subject in order to maximize targeting of the target cells while minimizing adverse effects such as TLS and CRS.

Unless otherwise specified, the terms "switch" and "CAR-EC switch", as used herein, are used interchangeably and may refer to a peptide switch. The antibody portion of the peptide antibody switch may comprise at least a portion of an antibody or an entire antibody. For example, the antibody portion of the peptide antibody switch may comprise at least a portion of a heavy chain, a portion of a light chain, a portion of a variable region, a portion of a constant region, a portion of a complementarity determining region (CDR), or a combination thereof. The antibody portion of the peptide antibody switch and/or hapten antibody switch may comprise at least a portion of the Fc (fragment, crystallizable) region. The antibody portion of the peptide antibody switch may comprise at least a portion of the complementarity determining region (e.g., CDR1, CDR2, CDR3). The antibody portion of the peptide antibody switch may comprise at least a portion of the Fab (fragment, antigen-binding) region. The peptide switch may be a peptide-Fab switch.

Before the present methods, kits and compositions are described in greater detail, it is to be understood that this invention is not limited to particular method, kit or composition described, as such may, of course, vary. It is also to be understood that the terminology used herein is for the purpose of describing particular embodiments only, and is not intended to be limiting, since the scope of the present invention will be limited only by the appended claims. Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms “a”, “an”, and “the” include plural referents unless the context clearly dictates otherwise. Thus, for example, reference to “a cell” includes a plurality of such cells and reference to “the peptide” includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods, kits and compositions are provided for producing CAR-EC platforms and CAR-EC switches used to bring an effector cell together with a target in a subject. These methods, kits and compositions find therapeutic use in a number of diseases. For example, heterogeneous tumors and blood cell malignancies (e.g., acute lymphoblastic leukemia and chronic lymphocytic leukemia) may be more effectively treated with a CAR-EC platform when the length, valency and orientation of the CAR-EC switch linkage as well as the CAR-EC switch cell targeting moiety is optimized. Heterogeneous tumors may be more effectively treated with multiple CAR-EC switches that target more than one tumor antigens. Advantages, and features of the invention will become apparent to those persons skilled in the art upon reading the details of the compositions and methods as more fully described below.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

IA. Peptide Switch

Disclosed herein are chimeric antigen receptor-effector cell switches comprising: a peptidic antigen or peptide neo-epitope (PNE) that binds a chimeric antigen receptor on an effector cell; and a targeting moiety that binds a cell surface molecule on a target. The targeting moiety may be a targeting polypeptide, comprising a targeting peptide that binds the cell surface molecule. The targeting moiety may be a targeting antibody or antibody fragment comprising the targeting peptide, wherein the targeting peptide is an antigen binding site of the targeting antibody or antibody fragment. The targeting peptide may be at least a portion of an antibody fragment and the cell surface molecule may be an antigen. The targeting moiety may comprise one or more peptides that recognize and/or bind one or more antigens. The targeting moiety may comprise one or more peptides that recognize and/or bind only one antigen. The peptidic antigen may not comprise an antibody or antibody fragment that recognizes and/or binds an antigen.

Figure 2:
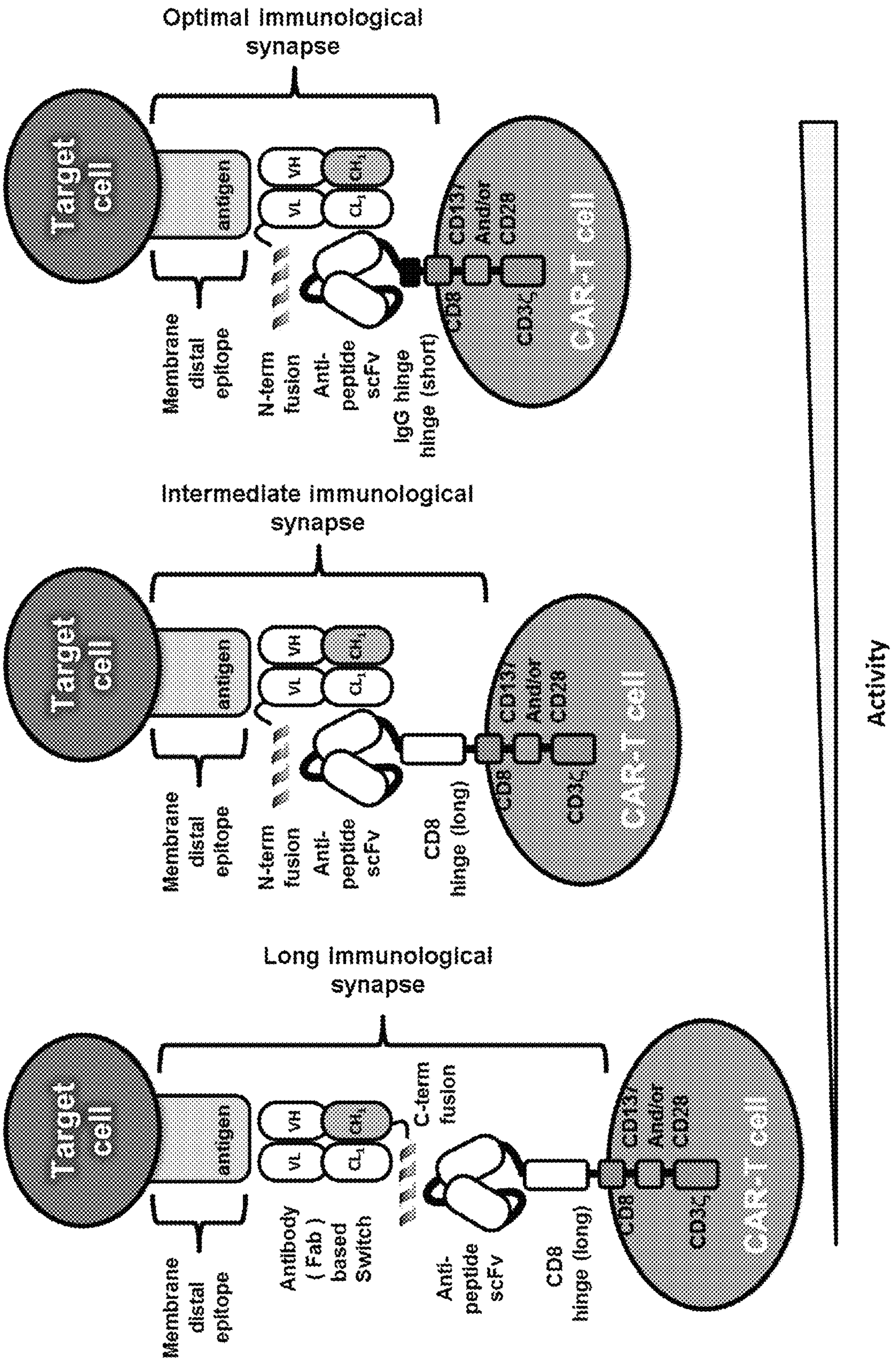
FIG. 2 exemplifies switch optimization for switchable CAR-T cells by varying the length of the immunological synapse from long (left) to intermediate (middle) to short (right), activity increasing from left to right.
Figure 3:
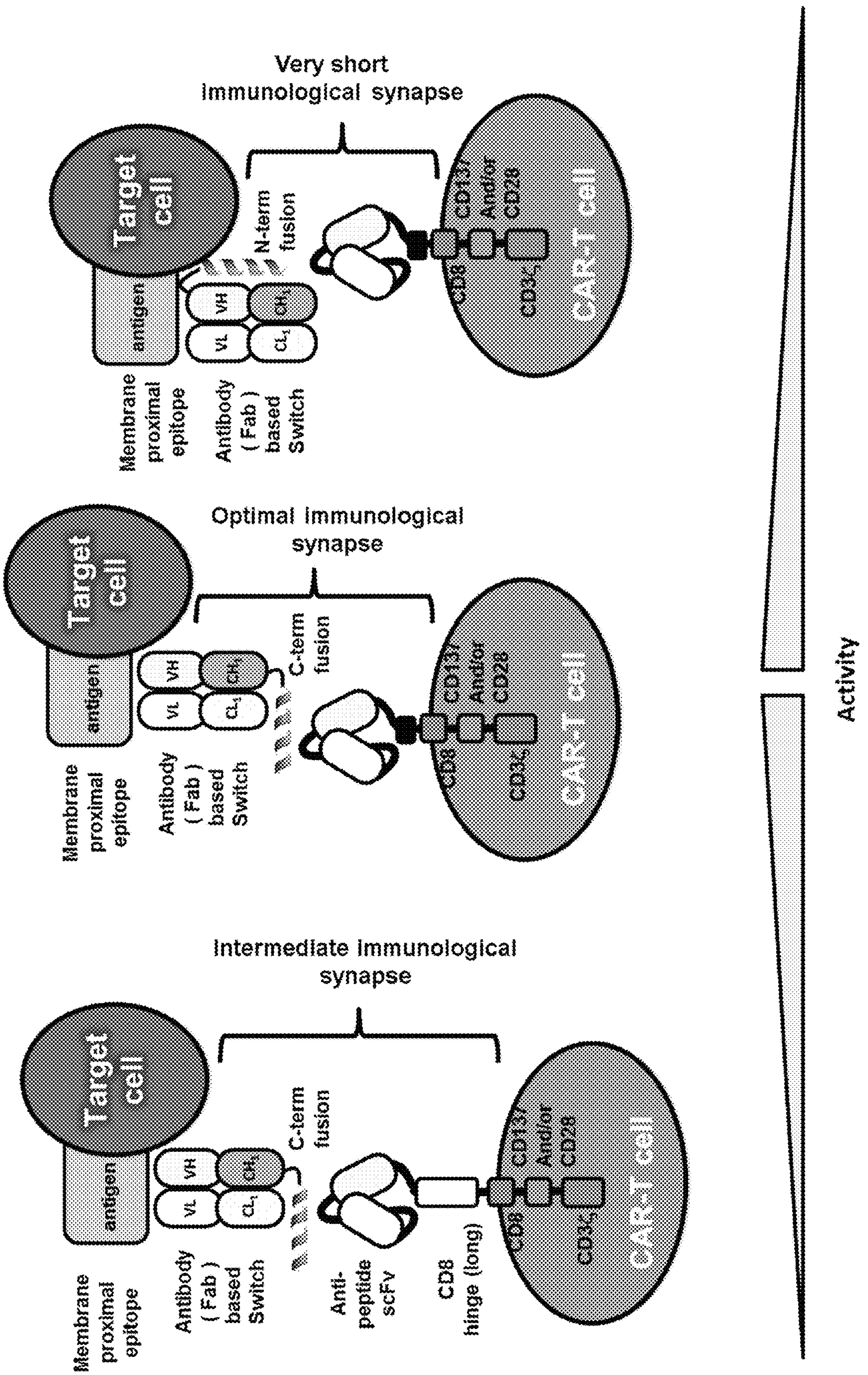
FIG. 3 exemplifies switch optimization for switchable CAR-T cells by varying the length of the immunological from intermediate (left) to short (middle) to very short (right), switch activity optimal with a short synapse, relative to switch activity produced with the intermediate synapse or very short synapse.

The design of the switch (e.g., grafting position, linker length) is critical to the cytotoxicity, activation, and cytokine release of the peptide switchable CAR-EC cells. The switch grafting position may be empirically designed for each unique target based on the epitope location of each antibody on each antigen in order to find an optimal distance and geometry (immunological synapse) between the CAR-EC and the target cell. For example, for antibodies that bind to epitopes of an antigen that are far from the membrane (membrane distal), switch designs that provide an overall short immunological synapse through the use of an N-terminal fusion improve the activity (FIG. 2 (middle)). Designs which provide too much distance between the CAR-EC and target cell through the use of a C-terminal fusion result in suboptimal activity (FIG. 2 (left)). The CAR can also be modified to shorten the hinge region. This can bring the CAR-T cell and target cell closer together (FIG. 2 (right)) which is further advantageous. Also, by way of a non-limiting example, for antibodies that bind to epitopes of an antigen that are close the membrane (membrane proximal), switch designs that provides sufficient distance (through the use of a C-terminal fusion) for the immunological synapse to form are optimal (FIG. 3 (middle)). Designs which do not provide enough distance between the CAR-EC and the target cell through the use of N-terminal fusions result in suboptimal or no activity due to steric hindrance (FIG. 3 (right)). Designs which provide too much distance between the CAR-EC and target cell (through a longer hinge region) result in suboptimal activity (FIG. 3 (left)).

Further disclosed herein are CAR-EC switches comprising: a peptidic antigen that binds a CAR (CAR-BP) on an effector cell, wherein the CAR-BP; and a targeting polypeptide that binds a cell surface molecule on a target cell. The peptidic antigen may be fused to a terminus of the targeting polypeptide. The peptidic antigen may be grafted into the targeting polypeptide (e.g., between chosen amino acids of the targeting polypeptide). The targeting polypeptide may be fused to a terminus of the peptidic antigen. The targeting polypeptide may be grafted into the peptidic antigen (e.g., between chosen amino acids of the peptidic antigen).

Disclosed herein are CAR-EC switches comprising: a peptidic antigen that binds a CAR (CAR-BP) on an effector cell; and a targeting antibody or antibody fragment that binds an antigen on a target. The targeting antibody or antibody fragment may be selected from an immunoglobulin, a Fab, a Fab', a $F(ab')_2$ and an scFv. The targeting antibody or antibody fragment may comprise a light chain. The targeting antibody or antibody fragment may comprise a heavy chain.

The peptidic antigen may be fused to an N terminus of the light chain of the targeting antibody or antibody fragment. The peptidic antigen may be fused to a C terminus of the light chain of the targeting antibody or antibody fragment. The peptidic antigen may be fused to an N terminus of the heavy chain of the targeting antibody or antibody fragment. The peptidic antigen may be fused to a C terminus of the heavy chain of the targeting antibody or antibody fragment. The peptidic antigen may be fused to an N terminus of a VL domain of the targeting antibody or antibody fragment. The peptidic antigen may be fused to an N terminus of a VH domain of the targeting antibody or antibody fragment. The peptidic antigen may be fused to a C terminus of a CL domain of the targeting antibody or antibody fragment. The peptidic antigen may be fused to a C terminus of an Fc domain of the targeting antibody or antibody fragment. The peptidic antigen may be fused to an N terminus of a VL domain of an IgG. The peptidic antigen may be fused to an N terminus of a VH domain of an IgG. The peptidic antigen may be fused to a C terminus of a CL domain of an IgG. The peptidic antigen may be fused to a C terminus of an Fc domain of an IgG. The peptidic antigen may be fused to an N terminus of a VL domain of a Fab. The peptidic antigen may be fused to an N terminus of a VH domain of a Fab. The peptidic antigen may be fused to a C terminus of a CL domain of a Fab. The peptidic antigen may be fused to a C terminus of a $CH_1$ domain of the Fab.

The peptidic antigen may be grafted into an internal site of a targeting antibody or antibody fragment (e.g., between chosen amino acids of the targeting antibody or antibody fragment). The peptidic antigen may be grafted into a heavy chain of a targeting antibody or antibody fragment. The peptidic antigen may be grafted into a light chain of a targeting antibody or antibody fragment. The peptidic antigen may be grafted into a constant domain/region of a targeting antibody or antibody fragment. The peptidic antigen may be grafted into a variable domain/region of a targeting antibody or antibody fragment. The peptidic antigen may be grafted into an internal site of a Fab. The peptidic antigen may be grafted into an internal site of an immunoglobulin (e.g., IgG). The peptidic antigen may be grafted into a domain of the targeting antibody or fragment thereof selected from a CL domain, a $CH_1$ domain, a $CH_2$ domain, a $CH_3$ domain, a VL domain, a VH domain and a hinge domain. The peptidic antigen may be grafted between two domains of the antibody or fragment thereof selected from a CL domain, a $CH_1$ domain, a $CH_2$ domain, a $CH_3$ domain, a VL domain, a VH domain and a hinge domain, wherein the two domains are adjacent. The peptidic antigen may be grafted into a CL domain of the antibody or fragment thereof. The peptidic antigen may be grafted into a $CH_1$ domain of the antibody or fragment thereof. The peptidic antigen may be grafted into a hinge domain of the antibody or fragment thereof. The peptidic antigen may be grafted into a loop of the antibody or fragment thereof. The peptidic antigen may be grafted into a CL domain loop of the antibody or fragment thereof.

The CAR-BP may be grafted into the C terminus of the antibody or antibody fragment and therefore the distance between the chimeric antigen receptor and the target may differ substantially depending on the size of CAR-EC switch (approximately 40 Å for scFv, 70 Å for Fab, and 120 Å for IgG). While a larger distance may negatively impact efficacy in vitro, the increased residence time of the full length antibody may be superior in vivo.

The CAR-EC switch may further comprise a linker, wherein the linker links the CAR-BP and the targeting moiety. The linker may be flexible. The linker may be rigid. Flexible and rigid linkers are understood by a person of skill in the art and are described in Chen et al. (Adv Drug Deliv Rev. 2013 65: 1357-1369). Switch linker design may be critical to the expression yields and the potency of the switch. The linker may connect the CAR-BP to the targeting antibody sequence by fusion and grafting. Design of the linker may directly impact the stability (e.g., thermal stability, proteolytic stability) of the switch. The linker may further dictate how the peptide is presented to the CAR, especially in the distance and relative orientation to the switch. For example a flexible linker may present many different orientations, while a rigid linker may form an alpha helix and present only one orientation of the peptide epitope relative to the antibody. The linker may be flexible such as GGGGS (SEQ ID NO. 40, n=1), or the linker may be rigid such as EAAAKEAAAKEAAAKA (SEQ ID NO. 47). The linker may provide the CAR-EC switch flexibility, length or geometry optimal for facilitating an interaction or effect of the CAR-EC on the target cell. The CAR-BP may further comprise one or more linkers. The CAR-BP may comprise two linkers. The linker may comprise a peptide. The linker may be at least about 1, at least about 2, at least about 3, at least about 4, at least about 5, at least about 6, at least about 7, at least about 8, at least about 9 or at least about 10 amino acids in length. The one or more linkers may comprise about 5, about 10, about 15, about 20, about 25, about 30, about 35, about 40, about 45, about 50, about 55, about 60, about 70, about 80, about 90 or about 100 amino acids. The linker may be located at the N terminus or the C terminus of the CAR-BP to graft the CAR-BP to the targeting polypeptide. A first linker may be fused to the N terminus of the CAR-BP and a second linker may be fused to the C terminus of the CAR-BP. The linker may be comprised of the sequence $(GGGGS)_n$, (SEQ ID NO.40), wherein n may be 1, 2, 3, 4, 5 or more. The linker may be comprised of the sequence $(GGS)_n$, (SEQ ID NO.40), wherein n may be 1, 2, 3, 4, 5 or more. The CAR-BP may be grafted into an internal site of the targeting polypeptide with a linker on either end of the CAR-BP. The linker may comprise a sequence selected from SEQ ID NOS: 45-50 and $(GGGGS)_n$, $(GGGS)_n$, $(GGS)_n$, $(G_mS)_n$, and $(X_mS)_n$, wherein n is at least 1, m is at least 1, and X is any amino acid.

The Peptidic Antigen

Unless otherwise specified, the terms “peptidic antigen,” “peptide neo-epitope (PNE),” and “chimeric antigen binding peptidic antigen (CAR-BP),” as used herein, are used interchangeably. The peptidic antigen may be a peptide that is bound by a chimeric antigen receptor (CAR). The peptidic antigen may have high proteolytic stability and low immunogenicity in humans relative to peptides in general. The CAR-BP may be selected from a hormone, a cytokine, a chemokine, a growth factor, a cell adhesion molecule, a signaling peptide, a receptor, a cell surface peptide and fragments thereof. The CAR-BP may be a peptoid. The CAR-BP may be a peptide nucleic acid (PNA). The CAR-BP may be a ligand or a fragment thereof. The ligand may be a hormonal ligand. The ligand may be a peptide ligand. The CAR-BP may be a cyclic peptide. The CAR-BP may be a linear peptide. The CAR-BP may have a length of between about 2 and about 10, about 10 and about 20, about 20 and about 30, about 30 and about 40, about 40 and about 50, about 50 and about 60, about 60 and about 70, about 70 and about 80, and about 80 and about 90 amino acids. The CAR-BP may be an antigen. The CAR-BP may be an epitope. The CAR-BP may be a nonlinear epitope. The CAR-BP may further comprise a second peptide.

The peptidic antigen may not comprise an antibody or antibody fragment. The peptidic antigen may comprise less than 10 amino acids of an antibody or antibody fragment. The peptidic antigen may comprise less than 12 amino acids of an antibody or antibody fragment. The peptidic antigen may comprise less than 15 amino acids of an antibody or antibody fragment. The peptidic antigen may comprise less than 20 amino acids of an antibody or antibody fragment. The peptidic antigen may comprise less than 22 amino acids of an antibody or antibody fragment. The peptidic antigen may comprise less than 30 amino acids of an antibody or antibody fragment. The peptidic antigen may not comprise a paratope of an antibody or antibody fragment.

Disclosed herein are chimeric antigen receptor effector cell switches comprising a targeting moiety and a peptidic antigen, wherein the targeting moiety is a targeting polypeptide. The targeting polypeptide may comprise a targeting antibody or antibody fragment. The targeting antibody or antibody fragment may comprise a variable domain. The variable domain may be selected from a VH domain and a VL domain. The peptidic antigen may be located at or near the N terminus of the VH domain. The peptidic antigen may be located at or near the N terminus of the VL domain.

The peptidic antigen may comprise a non-naturally occurring peptide. The peptidic antigen may comprise a synthetic peptide. The peptidic antigen may comprise a non-animal peptide (e.g., a peptide not expressed in an animal). The peptidic antigen may comprise a non-mammalian peptide. The peptidic antigen may comprise a non-human peptide. The peptide may comprise a peptide derived from a plant, a yeast, a bacteria, a reptile, a bird or an insect.

The peptidic antigen may comprise a myc-tag. The peptidic antigen may comprise His-tag. The peptidic antigen may comprise an HA-tag. The peptidic antigen may comprise peridinin chlorophyll protein complex. The peptidic antigen may comprise green fluorescent protein (GFP). The peptidic antigen may comprise red fluorescent protein (RFP). The peptidic antigen may comprise phycoerythrin (PE). The peptidic antigen may comprise streptavidin. The peptidic antigen may comprise avidin. The peptidic antigen may comprise horseradish peroxidase (HRP). The peptidic antigen may comprise alkaline phosphatase. The peptidic antigen may comprise glucose oxidase. The peptidic antigen may comprise glutathione-S-transferase (GST). The peptidic antigen may comprise maltose binding protein. The peptidic antigen, by non-limiting example, may be a c-myc tag, polyhistidine tag, V5, VSVG, softag 1, softag 3, express tag, S tag, palmitoylation, nitrosylation, SUMO tag, thioredoxin, poly(NANP), poly-Arg, calmodulin binding protein, PurF fragment, ketosteroid isomerase, PaP3.30, TAF12 histone fold domain, FKBP-tag, SNAP tag, Halo-tag, peptides from RNAse I. The peptidic antigen may comprise a protease cleavage site. The protease cleavage site may be recognized by thrombin, factor Xa, TEV protease or enterokinase.

The peptidic antigen may be a small linear hydrophilic peptide. The small linear hydrophilic peptide may comprise a linker. The small linear hydrophilic peptide may be a hydrophilic target peptide (HTP). The small linear hydrophilic peptide may comprise the sequence GGGGSDYKDDDDK (SEQ ID NO: 5). The small linear hydrophilic peptide may comprise the sequence GGGGSDYKDDDDKP (SEQ ID NO: 6). The small linear hydrophilic peptide may consist essentially of the sequence GGGGSDYKDDDDK (SEQ ID NO: 5). The small linear hydrophilic peptide may consist essentially of the sequence GGGGSDYKDDDDKP (SEQ ID NO: 6). The small linear hydrophilic peptide may be at least about 50% homologous to SEQ ID NOs: 5 or 6. The small linear hydrophilic peptide may be at least about 60% homologous to SEQ ID NOs: 5 or 6. The small linear hydrophilic peptide may be at least about 70% homologous to SEQ ID NOs: 5 or 6. The small linear hydrophilic peptide may be at least about 80% homologous to SEQ ID NOs: 5 or 6. The small linear hydrophilic peptide may be at least about 85% homologous to SEQ ID NOs: 5 or 6. The small linear hydrophilic peptide may be at least about 90% homologous to SEQ ID NOs: 5 or 6. The small linear hydrophilic peptide may have reduced non-specific binding relative to other peptides known in the art. The small linear hydrophilic peptide may have reduced non-specific binding and reduced fusion protein instability relative to other peptides disclosed herein. The peptidic antigen may comprise a FLAG® tag (SEQ ID NO: 7) or a derivative or a homolog thereof.

The peptidic antigen may be based on or derived from a naturally occurring peptide. The peptide may be based on or derived from a human peptide. The peptidic antigen may be a non-endogenous peptide or a non-native peptide, as opposed to an endogenous peptide or native peptide. An endogenous peptide may be something that is naturally or normally present in the human body (e.g., biotin, Fc of monoclonal antibody) or that the human body typically encounters. Thus, a non-endogenous peptide would be something foreign or not naturally present in the human body. For example, switches disclosed herein may employ GCN4 peptides as CAR-BPs, which are not normally encountered in vivo. In some embodiments, such non-natural peptides maintain orthogonality of the sCAR-switch interaction. The peptidic antigen may be a non-immunogenic peptide (e.g., a peptide known to cause no immune response or a negligible immune response in the human body).

The peptidic antigen may be based on or derived from a peptide expressed in animal selected from a chimpanzee, a monkey, a rat, a mouse, a bird, a fish, a pig, a horse, a cow, a goat, a chicken, a rabbit and a guinea pig. The peptidic antigen may be based on or derived from a mammalian peptide. The peptidic antigen may be based on or derived from a non-mammalian peptide. The peptidic antigen may be based on or derived from a peptide expressed in a plant. The peptidic antigen may be based on or derived from a peptide expressed in a bacterium. The peptidic antigen may be based on or derived from a prokaryotic peptide. The peptidic antigen may be based on or derived from a eukaryotic peptide. The peptidic antigen may be based on or derived from a peptide expressed by a yeast. The peptidic antigen may comprise a yeast transcription factor GCN4 peptide or a derivative or a homolog thereof. The yeast transcription factor GCN4 peptide may comprise the sequence RMKQLEPKVEELLPKNYHLENEVARLKKLVGER (SEQ ID NO: 2). The yeast transcription factor GCN4 peptide may comprise the sequence NYHLENEVARLKKL (SEQ ID NO: 3). The yeast transcription factor GCN4 peptide may consist essentially of the sequence RMKQLEPKVEELLPKNYHLENEVARLKKLVGER (SEQ ID NO: 2). The yeast transcription factor GCN4 peptide may consist essentially of the sequence NYHLENEVARLKKL (SEQ ID NO: 3). The yeast transcription factor GCN4 peptide may comprise a portion of SEQ ID NO. 2. The portion of SEQ ID NO. 2 may be at least 4 amino acids long. The portion of SEQ ID NO. 2 may be about 4, about 5, about 6, about 7, about 8, about 9, about 10, about 11, about 12 or about 13 amino acids long. The yeast transcription factor GCN4 peptide may be at least about 50% homologous to SEQ ID NOs: 2 or 3. The yeast transcription factor GCN4 peptide may be at least about 60% homologous to SEQ ID NOs: 2 or 3. The yeast transcription factor GCN4 peptide may be at least about 70% homologous to SEQ ID NOs: 2 or 3. The yeast transcription factor GCN4 peptide may be at least about 80% homologous to SEQ ID NOs: 2 or 3. The yeast transcription factor GCN4 peptide may be at least about 85% homologous to SEQ ID NOs: 2 or 3. The yeast transcription factor GCN4 peptide may be at least about 90% homologous to SEQ ID NOs: 2 or 3. The CAR-EC switch may comprise a yeast GCN4 peptide and one or more linkers. The CAR-EC switch may comprise SEQ ID NO. 4.

The Targeting Moiety

The targeting moiety may bind to a cell surface molecule on a target. The cell surface molecule may comprise an antigen. The cell surface molecule may be selected from a protein, a lipid moiety, a glycoprotein, a glycolipid, a carbohydrate, a polysaccharide, a nucleic acid, an MHC-bound peptide, or a combination thereof. The cell surface molecule may comprise parts (e.g., coats, capsules, cell walls, flagella, fimbrae, and toxins) of bacteria, viruses, and other microorganisms. The cell surface molecule may be expressed by the target cell. The cell surface molecule may not be expressed by the target cell. By way of non-limiting example, the cell surface molecule may be a ligand expressed by a cell that is not the target cell and that is bound to the target cell or a cell surface molecule of the target cell. Also, by non-limiting example, the cell surface molecule may be a toxin, exogenous molecule or viral protein that is bound to a cell surface or cell surface receptor of the target cell.

The targeting polypeptide may be a targeting antibody or antibody fragment. The targeting antibody or antibody fragment may be an immunoglobulin (Ig). The immunoglobulin may selected from an IgG, an IgA, an IgD, an IgE, an IgM, a fragment thereof or a modification thereof. The immunoglobulin may be IgG. The IgG may be IgG1. The IgG may be IgG2. The IgG may have one or more Fc mutations for modulating endogenous T cell FcR binding to the CAR-EC switch. The IgG may have one or more Fc mutations for removing the Fc binding capacity to the FcR of FcR-positive cells. Removal of the Fc binding capacity may reduce the opportunity for crosslinking of the CAR-EC to FcR positive cells, wherein crosslinking of the CAR-EC to FcR positive cells would activate the CAR-EC in the absence of the target cell. As such, modulating the endogenous T cell FcR binding to the CAR-EC switch may reduce an ineffective or undesirable immune response. The one or more Fc mutations may remove a glycosylation site. The one or more Fc mutations may be selected from E233P, L234V, L235A, delG236, A327G, A330S, P331S, N297Q and any combination thereof. The one or more Fc mutations may be in IgG1. The one or more Fc mutations in the IgG1 may be L234A, L235A, or both. Alternatively, or additionally, the one or more Fc mutations in the IgG1 may be L234A, L235E, or both. Alternatively, or additionally, the one or more Fc mutations in the IgG1 may be N297A. Alternatively, or additionally, the one or more mutations may be in IgG2. The one or more Fc mutations in the IgG2 may be V234A, V237A, or both.

The targeting antibody or antibody fragment may be an Fc null immunoglobulin or a fragment thereof.

As used herein, the term "antibody fragment" refers to any form of an antibody other than the full-length form. Antibody fragments herein include antibodies that are smaller components that exist within full-length antibodies, and antibodies that have been engineered. Antibody fragments include, but are not limited to, Fv, Fc, Fab, and (Fab')2, single chain Fv (scFv), diabodies, triabodies, tetrabodies, bifunctional hybrid antibodies, a CDR1, a CDR2, a CDR3, combinations of CDRs, variable regions, framework regions, constant regions, heavy chains, light chains, alternative scaffold non-antibody molecules, and bispecific antibodies. Unless specifically noted otherwise, statements and claims that use the term "antibody" or "antibodies" may specifically include "antibody fragment" and "antibody fragments."

The targeting antibody or antibody fragment may be a Fab. A central tenant of the sCAR-T cells described herein is the orthogonality of PNE-grafted switches in that they only interact with the target cell and sCAR and no other immune receptors or cell types. Lack of orthogonality has the potential to cause off-target effects. For example, while IgG-based switches described herein were potent in in vitro cytotoxicity assays, they could fail to have significant impact on disease burden in the xenograft model. However, the Fc of IgG may also bind to other cell types in mouse and human. Thus, in some embodiments, Fabs may be desirable because their lack of an Fc domain removes the possibility of an Fc receptor-mediated off target binding. In some embodiments, their smaller size and shorter half-life (approximately 1-5 h for Fab vs 10-20 d for IgG provides better tumor penetration and greater temporal control over sCAR-T cell activation, in clinical translation. In addition, the Fab may differ from the IgG in valency, off-rate, or tissue distribution.

The targeting antibody fragment may be human, fully human, humanized, human engineered, non-human, and/or chimeric antibody. The non-human antibody may be humanized to reduce immunogenicity to humans, while retaining the specificity and affinity of the parental non-human antibody. Chimeric antibodies may refer to antibodies created through the joining of two or more antibody genes which originally encoded for separate antibodies. A chimeric antibody may comprise at least one amino acid from a first antibody and at least one amino acid from a second antibody, wherein the first and second antibodies are different. At least a portion of the antibody or antibody fragment may be from a bovine species, a human species, or a murine species. At least a portion of the antibody or antibody fragment may be from a rat, a goat, a guinea pig or a rabbit. At least a portion of the antibody or antibody fragment may be from a human. At least a portion of the antibody or antibody fragment antibody may be from cynomolgus monkey.

The targeting antibody or antibody fragment may be based on or derived from an antibody or antibody fragment from a mammal, bird, fish, amphibian, or reptile. Mammals include, but are not limited to, carnivores, rodents, elephants, marsupials, rabbits, bats, primates, seals, anteaters, cetaceans, odd-toed ungulates and even-toed ungulates. The mammal may be a human, non-human primate, mouse, sheep, cat, dog, cow, horse, goat, or pig.

The targeting antibody or an antibody fragment may target an antigen selected from, by non-limiting example, CD19, Her2, CLL1, CD33, CD123, EGFT, EGFRvIII, CD20, CD22, CS1, BCMA, CEA or a fragment thereof. The antigen may comprise a wildtype antigen. The antigen may comprise one or more mutations. The targeting antibody or antibody fragment may be a B cell targeting moiety. The targeting antibody or antibody fragment may be an anti-CD19 antibody or antibody fragment. The anti-CD19 antibody or antibody fragment may be selected from antibody clone huB4 (see, e.g., SEQ ID NOS: 150-157) and FMC63 (see, e.g., SEQ ID NOS.: 85-102). The targeting antibody or antibody fragment may be an anti-CLL1 antibody or antibody fragment. The anti-CLL1 antibody or antibody fragment may be antibody clone 1075.7 (see, e.g., SEQ ID NOS: 103-106). The targeting antibody or antibody fragment may be an anti-CD22 antibody or antibody fragment. The anti-CD22 antibody or antibody fragment may be selected from antibody clone m972 (see, e.g., SEQ ID NOS: 113-118) and m971 (see, e.g., SEQ ID NOS: 107-112). The targeting antibody or antibody fragment may be an anti-CD20 antibody or antibody fragment. The anti-CD20 antibody or antibody fragment may be selected from antibody clone OFA (see, e.g., SEQ ID NOS: 135-140), RTX (see, e.g., SEQ ID NOS: 125-128), and GA101 (see, e.g., SEQ ID NOS: 129-134). The targeting antibody or antibody fragment may be an anti-BCMA antibody or antibody fragment. The anti-BCMA antibody or antibody fragment may be antibody clone BCMA-98 (see, e.g., SEQ ID NOS: 145-149). The targeting antibody or antibody fragment may be an anti-Her2 antibody or antibody fragment. The anti-Her2 antibody or antibody fragment may be selected from antibody clone trastuzumab (see, e.g., SEQ ID NOS: 11, 12, 141-144). The targeting antibody or antibody fragment may be an anti-CS1 antibody or antibody fragment. The anti-CS1 antibody or antibody fragment may be antibody clone elotuzumab (see, e.g., SEQ ID NOS: 21-22). The targeting antibody or antibody fragment may be an anti-CD33 antibody or antibody fragment. The anti-CD33 antibody or antibody fragment may be antibody clone hM195 (see, e.g., SEQ ID NOS: 53-56, 162-165). The targeting antibody or antibody fragment may be an anti-CEA antibody or antibody fragment. The anti-CEA antibody or antibody fragment may be antibody clone A5B7 (see, e.g., SEQ ID NOS: 158-161). The expression of each switch requires a heavy chain and light chain gene to be co-transfected into one or more expression cells (e.g., HEK). The CAR-BP may be located in only the heavy chain to provide a monovalent switch. The CAR-BP may be located in only the light chain to provide a monovalent switch. The CAR-BP may be located in both the heavy chain and the light chain to provide a bivalent switch. The CAR-BP may be located in both the heavy chain and the light chain to provide a multivalent switch.

The targeting antibody or antibody fragment may be an anti-CD19 antibody or a fragment thereof. The targeting polypeptide may be an anti-CD22 antibody. The targeting polypeptide may be an anti-BCMA antibody or a fragment thereof. The targeting polypeptide may be an anti-CS1 antibody or a fragment thereof. The targeting polypeptide may be an anti-EGFRvIII antibody or a fragment thereof. The targeting polypeptide may be an anti-Her2 antibody or a fragment thereof. The targeting polypeptide may comprise an anti-CD20 antibody or antibody fragment. The targeting polypeptide may comprise rituximab. The targeting polypeptide may comprise an anti-EGFR antibody or antibody fragment. The targeting polypeptide may comprise an anti-CEA antibody or antibody fragment. The targeting polypeptide may comprise an anti-CLL1 antibody or antibody fragment. The targeting polypeptide may comprise an anti-CD33 antibody or antibody fragment. The targeting polypeptide may not comprise an anti-EpCAM antibody or fragment thereof.

The targeting antibody or antibody fragment may be selected any commercially available antibody. The targeting antibody or antibody fragment may be selected from ado-trastuzumab emtansine, alemtuzumab, bevacizumab, brentuximab, vedotin, gemtuzumab, ozogamicin, ipilimumab, ibritumomab, tiuxetan, panitumumab, cetuximab, erbitux, rituximab, trastuzumab and fragments thereof.

The targeting antibody or antibody fragment may comprise an anti-CD19 antibody or fragment thereof. The targeting antibody or fragment thereof may comprise a light chain of the anti-CD19 antibody or fragment thereof. The light chain of the anti-CD19 antibody or fragment thereof may be encoded by a nucleotide sequence based on or derived from SEQ ID NO. 8. The nucleotide sequence may be about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 8. The targeting antibody or fragment thereof may comprise a heavy chain of the anti-CD19 antibody or fragment thereof. The heavy chain of the anti-CD19 antibody or fragment thereof may be encoded by a sequence based on or derived from SEQ ID NO. 9. The nucleotide sequence may be about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 9.

The targeting antibody or antibody fragment may comprise an anti-CD19 antibody or fragment thereof. The targeting antibody or fragment thereof may comprise a light chain of the anti-CD19 antibody or fragment thereof. The light chain of the anti-CD19 antibody or fragment may comprise an amino acid sequence based on or derived from SEQ ID NO. 27. The amino acid sequence may be about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 27. The targeting antibody or fragment thereof may comprise a heavy chain of the anti-CD19 or fragment thereof. The targeting antibody or fragment thereof may comprise a heavy chain of an anti-CD19 IgG. The heavy chain of the anti-CD19 IgG may comprise a sequence based on or derived from SEQ ID NO. 28. The amino acid sequence may be about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 28. The targeting antibody or fragment thereof may comprise a heavy chain of an anti-CD19 Fab. The heavy chain of the anti-CD19 Fab may comprise a sequence based on or derived from SEQ ID NO. 29. The amino acid sequence may be about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 29.

The targeting antibody or fragment thereof may comprise a light chain of the anti-CLL1 antibody or fragment thereof. The light chain of the anti-CLL1 antibody or fragment thereof may be encoded by SEQ ID NO. 17. The light chain of the anti-CLL1 antibody or fragment thereof may be encoded by a sequence at least about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 17. The targeting antibody or fragment thereof may comprise a heavy chain of the anti-CLL1 antibody or fragment thereof. The heavy chain of the anti-CLL1 antibody or fragment thereof may be encoded by SEQ ID NO. 18. The heavy chain of the anti-CLL1 antibody or fragment thereof may be encoded by a sequence at least about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 18.

The targeting antibody or fragment thereof may comprise a light chain of the anti-CD22 antibody or fragment thereof. The light chain of the anti-CD22 antibody or fragment thereof may be encoded by a sequence selected from SEQ ID NOS: 108, 114 and 120. The light chain of the anti-CD22 antibody or fragment thereof may be encoded by a sequence at least about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to a sequence selected from SEQ ID NOS: 108, 114 and 120. The targeting antibody or fragment thereof may comprise a heavy chain of the anti-CD22 antibody or fragment thereof. The heavy chain of the anti-CD22 antibody or fragment thereof may be a sequence selected from SEQ ID NOS:107, 113 and 119. The heavy chain of the anti-CD22 antibody or fragment thereof may be encoded by a sequence at least about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to a sequence selected from SEQ ID NOS: 107, 113 and 119.

The targeting antibody or fragment thereof may comprise a light chain of the anti-CD20 antibody or fragment thereof. The light chain of the anti-CD20 antibody or fragment thereof may be encoded by a sequence selected from SEQ ID NOS: 13, 130 and 136. The light chain of the anti-CD20 antibody or fragment thereof may be encoded by a sequence at least about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to a sequence selected from SEQ ID NOS: 13, 130 and 136. The targeting antibody or fragment thereof may comprise a heavy chain of the anti-CD20 antibody or fragment thereof. The heavy chain of the anti-CD20 antibody or fragment thereof may be a sequence selected from SEQ ID NOS: 14, 129 and 135. The heavy chain of the anti-CD20 antibody or fragment thereof may be encoded by a sequence at least about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to a sequence selected from SEQ ID NOS: 14, 129 and 135. The chimeric antigen receptor-effector cell switch may comprise a heavy chain of SEQ ID NOS: 13, 129 or 135 and a light chain of SEQ ID NOS: 13, 130 or 136, or homologs thereof or fragments thereof.

The targeting antibody or fragment thereof may comprise a light chain of the anti-Her2 antibody or fragment thereof. The light chain of the anti-Her2 antibody or fragment thereof may be encoded by SEQ ID NO. 11. The light chain of the anti-Her2 antibody or fragment thereof may be encoded by a sequence at least about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 11. The targeting antibody or fragment thereof may comprise a heavy chain of the anti-Her2 antibody or fragment thereof. The heavy chain of the anti-Her2 antibody or fragment thereof may be encoded by SEQ ID NO. 12. The heavy chain of the anti-Her2 antibody or fragment thereof may be encoded by a sequence at least about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 12. The chimeric antigen receptor-effector cell switch may comprise a heavy chain of SEQ ID NO. 12 and a light chain of SEQ ID NO. 11, or homologs thereof, or fragments thereof.

The targeting antibody or fragment thereof may comprise a light chain of the anti-BCMA antibody or fragment thereof. The light chain of the anti-BCMA antibody or fragment thereof may be encoded by SEQ ID NO. 25. The light chain of the anti-BCMA antibody or fragment thereof may be encoded by a sequence at least about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 25. The targeting antibody or fragment thereof may comprise a heavy chain of the anti-BCMA antibody or fragment thereof. The heavy chain of the anti-BCMA antibody or fragment thereof may be encoded by a sequence selected from SEQ ID NOS: 26 and 38. The heavy chain of the anti-BCMA antibody or fragment thereof may be encoded by a sequence at least about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to a sequence selected from SEQ ID NOS: 26 and 38. The chimeric antigen receptor-effector cell switch may comprise a heavy chain of SEQ ID NOS: 26 or 38 and a light chain of SEQ ID NO. 25, or homologs thereof, or fragments thereof.

The targeting antibody or fragment thereof may comprise a light chain of the anti-CEA antibody or fragment thereof. The light chain of the anti-CEA antibody or fragment thereof may be encoded by SEQ ID NO. 160. The light chain of the anti-CEA antibody or fragment thereof may be encoded by a sequence at least about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 160. The targeting antibody or fragment thereof may comprise a heavy chain of the anti-CEA antibody or fragment thereof. The heavy chain of the anti-CEA antibody or fragment thereof may be encoded by SEQ ID NO. 158. The heavy chain of the anti-CEA antibody or fragment thereof may be encoded by a sequence at least about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 158. The chimeric antigen receptor-effector cell switch may comprise a heavy chain of SEQ ID NO. 158 and a light chain of SEQ ID NO. 160, or homologs thereof, or fragments thereof.

The targeting antibody or fragment thereof may comprise a light chain of the anti-CS1 antibody or fragment thereof. The light chain of the anti-CS1 antibody or fragment thereof may be encoded by SEQ ID NO. 21. The light chain of the anti-CS1 antibody or fragment thereof may be encoded by a sequence at least about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 21. The targeting antibody or fragment thereof may comprise a heavy chain of the anti-CS1 antibody or fragment thereof. The heavy chain of the anti-CS1 antibody or fragment thereof may be encoded by SEQ ID NO. 22. The heavy chain of the anti-CS1 antibody or fragment thereof may be encoded by a sequence at least about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 22. The chimeric antigen receptor-effector cell switch may comprise a heavy chain of SEQ ID NO. 22 and a light chain of SEQ ID NO. 21, or homologs thereof, or fragments thereof.

The targeting antibody or fragment thereof may comprise a light chain of the anti-CD33 antibody or fragment thereof. The light chain of the anti-CD33 antibody or fragment thereof may be encoded by SEQ ID NO. 19. The light chain of the anti-CD33 antibody or fragment thereof may be encoded by a sequence at least about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 19. The targeting antibody or fragment thereof may comprise a heavy chain of the anti-CD33 antibody or fragment thereof. The heavy chain of the anti-CD33 antibody or fragment thereof may be encoded by SEQ ID NO. 20. The heavy chain of the anti-CD33 antibody or fragment thereof may be encoded by a sequence at least about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO. 20. The chimeric antigen receptor-effector cell switch may comprise a heavy chain of SEQ ID NO. 20 and a light chain of SEQ ID NO. 19, or homologs thereof, or fragments thereof.

The targeting antibody or antibody fragment may comprise a nucleotide sequence selected from SEQ ID NOs: 8-20. The targeting polypeptide may be based on or derived from a nucleotide selected from SEQ ID NOs: 8-20. The targeting antibody or antibody fragment may comprise an amino acid sequence selected from SEQ ID NOs: 21-29. The targeting polypeptide may be based on or derived from an amino acid sequence selected from SEQ ID NOs: 21-29.

Disclosed herein are chimeric antigen receptor effector cell (CAR-EC) switches comprising a peptidic antigen and a targeting moiety that binds a cell surface molecule on a target cell. Generally, binding of the effector cell and the target cell to the CAR-EC switch construct brings the target cell into proximity with the effector cell sufficiently close for an activity of the effector cell to have an effect on the target cell. For example, when the T cell and the target cell are bound to the CAR-EC switch, the T cell may produce an immune response that has a cytotoxic effect on the target cell.

The CAR-EC switches may interact with a plurality of target cells. The target cell may be an infected cell. The target cell may be a pathogenically infected cell. The target cell may be a diseased cell. The target cell may be a genetically-modified cell. The target cell may not be a host cell. The target cell may come from an invading organism (e.g., yeast, worm, bacteria, fungus). Further disclosed herein are CAR-EC switches that interact with a molecule on a non-cell target. The non-cell target may be a virus or a portion thereof. The non-cell target may be a fragment of a cell. The non-cell target may be an extracellular matrix component or protein.

The target cell may be derived from a tissue. The tissue may be selected from brain, esophagus, breast, colon, lung, glia, ovary, uterus, testes, prostate, gastrointestinal tract, bladder, liver, thymus, bone and skin. The target cell may be derived from one or more endocrine glands. Alternatively, or additionally, the target cell may be derived from one or more endocrine glands. The endocrine gland may be a lymph gland, pituitary gland, thyroid gland, parathyroid gland, pancreas, gonad or pineal gland.

The target cell may be selected from a stem cell, a pluripotent cell, a hematopoietic stem cell or a progenitor cell. The target cell may a circulating cell. The target cell may be an immune cell.

The target cell may be a cancer stem cell. The target cell may be a cancer cell. The cancer cell may be derived from a tissue. The tissue may be selected from, by way of non-limiting example, a brain, an esophagus, a breast, a colon, a lung, a glia, an ovary, a uterus, a testicle, a prostate, a gastrointestinal tract, a bladder, a liver, a thyroid and skin. The cancer cell may be derived from bone. The cancer cell may be derived from blood. The cancer cell may be derived from a B cell, a T cell, a monocyte, a thrombocyte, a leukocyte, a neutrophil, an eosinophil, a basophil, a lymphocyte, a hematopoietic stem cell or an endothelial cell progenitor. The cancer cell may be derived from a CD19-positive B lymphocyte. The cancer cell may be derived from a stem cell. The cancer cell may be derived from a pluripotent cell. The cancer cell may be derived from one or more endocrine glands. The endocrine gland may be a lymph gland, pituitary gland, thyroid gland, parathyroid gland, pancreas, gonad or pineal gland.

The cancer cell may be a CD19-positive cell. The cancer cell may be a CD19-positive B lymphocyte. The cancer cell may be a Her2-positive cell. The Her2-positive cell may be a Her2-positive breast cancer cell. The target cell may be a BCMA-positive cell. The cancer cell may be a BCMA-positive multiple myeloma cell. The cancer cell may be a CS1-positive cell. The CS1-positive cell may be a multiple myeloma cell. The cancer cell may be a EGFRvIII-positive cell. The cancer cell may be a EGFRvIII-positive glioblastoma cell. The cancer cell may be a CD20-positive cell. The cancer cell may be a CD22-positive cell.

The cell surface molecule may be an antigen. The antigen may be at least a portion of a surface antigen or a cell surface marker on a cell. The antigen may be a receptor or a co-receptor on a cell. The antigen may refer to a molecule or molecular fragment that may be bound by a major histocompatibility complex (MHC) and presented to a T-cell receptor. The term "antigen" may also refer to an immunogen. The immunogen may provoke an adaptive immune response if injected on its own into a subject. The immunogen may induce an immune response by itself. The antigen may be a superantigen, T-dependent antigen or a T-independent antigen. The antigen may be an exogenous antigen. Exogenous antigens are typically antigens that have entered the body from the outside, for example by inhalation, ingestion, or injection. Some antigens may start out as exogenous antigens, and later become endogenous (for example, intracellular viruses). The antigen may be an endogenous antigen. The endogenous antigen may be an antigen that has been generated within cells as a result of normal cell metabolism, or because of pathogenic infections (e.g., viral, bacterial, fungal, parasitic). The antigen may be an autoantigen. The autoantigen may be a normal protein or complex of proteins (and sometimes DNA or RNA) that is recognized by the immune system of patients suffering from a specific autoimmune disease. These antigens should, under normal conditions, not be the target of the immune system, but, due to genetic and/or environmental factors, the normal immunological tolerance for such an antigen is not present in these patients. The antigen may be present or over-expressed due to a condition or disease. The condition or disease may be a cancer or a leukemia. The condition may be an inflammatory disease or condition. The condition or disease may be a metabolic disease. The condition may be a genetic disorder.

The cell surface molecule may be an antigen that has been designated as a tumor antigen. Tumor antigens or neoantigens may be antigens that are presented by MHC I or MHC II molecules on the surface of tumor cells. These antigens may sometimes be presented by tumor cells and never by the normal ones. In this case, they are called tumor-specific antigens (TSAs) and, in general, result from a tumor-specific mutation. More common are antigens that are presented by tumor cells and normal cells, and they are called tumor-associated antigens (TAAs). Cytotoxic T lymphocytes that recognize these antigens may be able to destroy the tumor cells before they proliferate or metastasize. Tumor antigens may also be on the surface of the tumor in the form of, for example, a mutated receptor, in which case they may be recognized by B cells. Unless otherwise specified, the terms "tumor antigen," "tumor specific antigen" and "tumor associated antigen," are used interchangeably herein.

The cell surface molecule may be a receptor. The receptor may be an extracellular receptor. The receptor may be a cell surface receptor. By way of non-limiting example, the receptor may bind a hormone, a neurotransmitter, a cytokine, a growth factor or a cell recognition molecule. The receptor may be a transmembrane receptor. The receptor may be an enzyme-linked receptor. The receptor may be a G-protein couple receptor (GPCR). The receptor may be a growth factor receptor. By way of non-limiting example, the growth factor receptor may be selected from an epidermal growth factor receptor, a fibroblast growth factor receptor, a platelet derived growth factor receptor, a nerve growth factor receptor, a transforming growth factor receptor, a bone morphogenic protein growth factor receptor, a hepatocyte growth factor receptor, a vascular endothelial growth factor receptor, a stem cell factor receptor, an insulin growth factor receptor, a somatomedin receptor, an erythropoietin receptor and homologs and fragments thereof. The receptor may be a hormone receptor. The receptor may be an insulin receptor. By way of non-limiting example, the receptor may selected from an eicosanoid receptor, a prostaglandin receptor, an estrogen receptor, a follicle stimulating hormone receptor, a progesterone receptor, a growth hormone receptor, a gonadotropin-releasing hormone receptor, homologs thereof and fragments thereof. The receptor may be an adrenergic receptor. The receptor may be an integrin. The receptor may be an Eph receptor. The receptor may be a luteinizing hormone receptor. The cell surface molecule may be at least about 50% homologous to a luteinizing hormone receptor. The receptor may be an immune receptor. By way of non-limiting example, the immune receptor may be selected from a pattern recognition receptor, a toll-like receptor, a NOD like receptor, a killer activated receptor, a killer inhibitor receptor, an Fc receptor, a B cell receptor, a complement receptor, a chemokines receptor and a cytokine receptor. By way of non-limiting example, the cytokine receptor may be selected from an interleukin receptor, an interferon receptor, a transforming growth factor receptor, a tumor necrosis factor receptor, a colony stimulating factor receptor, homologs thereof and fragments thereof. The receptor may be a receptor kinase. The receptor kinase may be a tyrosine kinase receptor. The receptor kinase may be a serine kinase receptor. The receptor kinase may be a threonine kinase receptor. By way of non-limiting example, the receptor kinase may activate a signaling protein selected from a Ras, a Raf, a PI3K, a protein kinase A, a protein kinase B, a protein kinase C, an AKT, an AMPK, a phospholipase, homologs thereof and fragments thereof. The receptor kinase may activate a MAPK/ERK signaling pathway. The receptor kinase may activate Jak, Stat or Smad.

The cell surface molecule may be a non-receptor cell surface protein. The cell surface molecule may be a cluster of differentiation proteins. By way of non-limiting example, the cell surface molecule may be selected from CD34, CD31, CD117, CD45, CD11b, CD15, CD24, CD114, CD182, CD14, CD11a, CD91, CD16, CD3, CD4, CD25, CD8, CD38, CD22, CD61, CD56, CD30, CD13, CD33, CD123, CD19, CD20, fragments thereof, and homologs thereof.

The cell surface molecule may be a molecule that does not comprise a peptide. The cell surface molecule may comprise a lipid. The cell surface molecule may comprise a lipid moiety or a lipid group. The lipid moiety may comprise a sterol. The lipid moiety may comprise a fatty acid. The antigen may comprise a glycolipid. The cell surface molecule may comprise a carbohydrate.

Disclosed herein are CAR-EC switches comprising (a) a chimeric antigen receptor binding peptidic antigen comprising a peptide from a yeast transcription factor peptide; and (b) a targeting polypeptide. The yeast transcription factor peptide may be a GCN4 peptide. The targeting polypeptide may comprise a targeting antibody or antibody fragment. The targeting antibody or antibody fragment may comprise a heavy chain of an antibody. The targeting antibody or antibody fragment may comprise a light chain of an antibody. The targeting antibody or antibody fragment may comprise a Fab of an antibody. The targeting antibody or antibody fragment may comprise an anti-CD19 antibody or a fragment thereof. The targeting antibody or antibody fragment may comprise an anti-Her2 antibody or a fragment thereof. The targeting antibody or antibody fragment may be selected from an anti-CS1 antibody, an anti-BCMA antibody, an anti-EGFRvIII antibody, an anti-CD20 antibody, an anti-EGFR antibody, an anti-CEA antibody, an anti-CLL1 antibody, an anti-CD33 antibody and fragments thereof.

Further disclosed herein are CAR-EC switches comprising (a) a CAR binding region comprising a hydrophilic target peptide (HTP) tag; and (b) a targeting polypeptide. The targeting polypeptide may comprise a targeting antibody or antibody fragment. The targeting antibody or antibody fragment may comprise a heavy chain of an antibody. The targeting antibody or antibody fragment may comprise a light chain of an antibody. The targeting antibody or antibody fragment may comprise a Fab of an antibody. The targeting antibody or antibody fragment may comprise an anti-CD19 antibody or a fragment thereof. The targeting antibody or antibody fragment may comprise an anti-Her2 antibody or a fragment thereof. The targeting antibody or antibody fragment may be selected from an anti-CS1 antibody, an anti-BCMA antibody, an anti-EGFRvIII antibody, an anti-CD20 antibody, an anti-EGFR antibody, an anti-CEA antibody, an anti-CLL1 antibody, an anti-CD33 antibody and fragments thereof.

The chimeric antigen receptor-effector cell switch may comprise a heavy chain selected from SEQ ID NO. 32, SEQ ID NO. 33, SEQ ID NO. 34, SEQ ID NO. 35 and SEQ ID NO. 38. The chimeric antigen receptor-effector cell switch may comprise a heavy chain that is at least 50% homologous to a sequence selected from SEQ ID NO. 32, SEQ ID NO. 33, SEQ ID NO. 34, SEQ ID NO. 35 and SEQ ID NO. 38. The chimeric antigen receptor-effector cell switch may comprise a heavy chain that is at least 60% homologous to a sequence selected from SEQ ID NO. 32, SEQ ID NO. 33, SEQ ID NO. 34, SEQ ID NO. 35 and SEQ ID NO. 38. The chimeric antigen receptor-effector cell switch may comprise a heavy chain that is at least 70% homologous to a sequence selected from SEQ ID NO. 32, SEQ ID NO. 33, SEQ ID NO. 34, SEQ ID NO. 35 and SEQ ID NO. 38. The chimeric antigen receptor-effector cell switch may comprise a heavy chain that is at least 80% homologous to a sequence selected from SEQ ID NO. 32, SEQ ID NO. 33, SEQ ID NO. 34, SEQ ID NO. 35 and SEQ ID NO. 38. The chimeric antigen receptor-effector cell switch may comprise a heavy chain that is at least 90% homologous to a sequence selected from SEQ ID NO. 32, SEQ ID NO. 33, SEQ ID NO. 34, SEQ ID NO. 35 and SEQ ID NO. 38.

The chimeric antigen receptor-effector cell switch may comprise a light chain selected from SEQ ID NO. 30, SEQ ID NO. 31, SEQ ID NO. 36 and SEQ ID NO. 37. The chimeric antigen receptor-effector cell switch may comprise a light chain that is at least 50% homologous to a sequence selected from SEQ ID NO. 30, SEQ ID NO. 31, SEQ ID NO. 36 and SEQ ID NO. 37. The chimeric antigen receptor-effector cell switch may comprise a light chain that is at least 60% homologous to a sequence selected from SEQ ID NO. 30, SEQ ID NO. 31, SEQ ID NO. 36 and SEQ ID NO. 37. The chimeric antigen receptor-effector cell switch may comprise a light chain that is at least 70% homologous to a sequence selected from SEQ ID NO. 30, SEQ ID NO. 31, SEQ ID NO. 36 and SEQ ID NO. 37. The chimeric antigen receptor-effector cell switch may comprise a light chain that is at least 80% homologous to a sequence selected from SEQ ID NO. 30, SEQ ID NO. 31, SEQ ID NO. 36 and SEQ ID NO. 37. The chimeric antigen receptor-effector cell switch may comprise a light chain that is at least 90% homologous to a sequence selected from SEQ ID NO. 30, SEQ ID NO. 31, SEQ ID NO. 36 and SEQ ID NO. 37.

The chimeric antigen receptor-effector cell switch may comprise a heavy chain of SEQ ID NO. 29 and a light chain of SEQ ID NO. 30. The chimeric antigen receptor-effector cell switch may comprise a heavy chain of SEQ ID NO. 29 and a light chain of SEQ ID NO. 36. The chimeric antigen receptor-effector cell switch may comprise a heavy chain of SEQ ID NO. 28 and a light chain of SEQ ID NO. 31. The chimeric antigen receptor-effector cell switch may comprise a heavy chain of SEQ ID NO. 32 and a light chain of SEQ ID NO. 27. The chimeric antigen receptor-effector cell switch may comprise a heavy chain of SEQ ID NO. 33 and a light chain of SEQ ID NO. 27. The chimeric antigen receptor-effector cell switch may comprise a heavy chain of SEQ ID NO. 34 and a light chain of SEQ ID NO. 27. The chimeric antigen receptor-effector cell switch may comprise a heavy chain of SEQ ID NO. 35 and a light chain of SEQ ID NO. 27. The chimeric antigen receptor-effector cell switch may comprise a heavy chain of SEQ ID NO. 38 and a light chain of SEQ ID NO. 37.

Multivalent CAR-EC Switches

Exemplified herein are CAR-EC switches comprising a chimeric antigen receptor binding peptidic antigen (CAR-BP) and a targeting polypeptide. However, one skilled in the art would understand that these switches could further comprise additional targeting polypeptides and/or additional CAR-BPs. One or more CAR-BPs may be grafted into one or more grafting sites of the targeting polypeptide. One or more CAR-BPs may be fused to one or more termini of the targeting polypeptide. Such switches are referred to herein as a "multivalent switch."

Figure 4A:
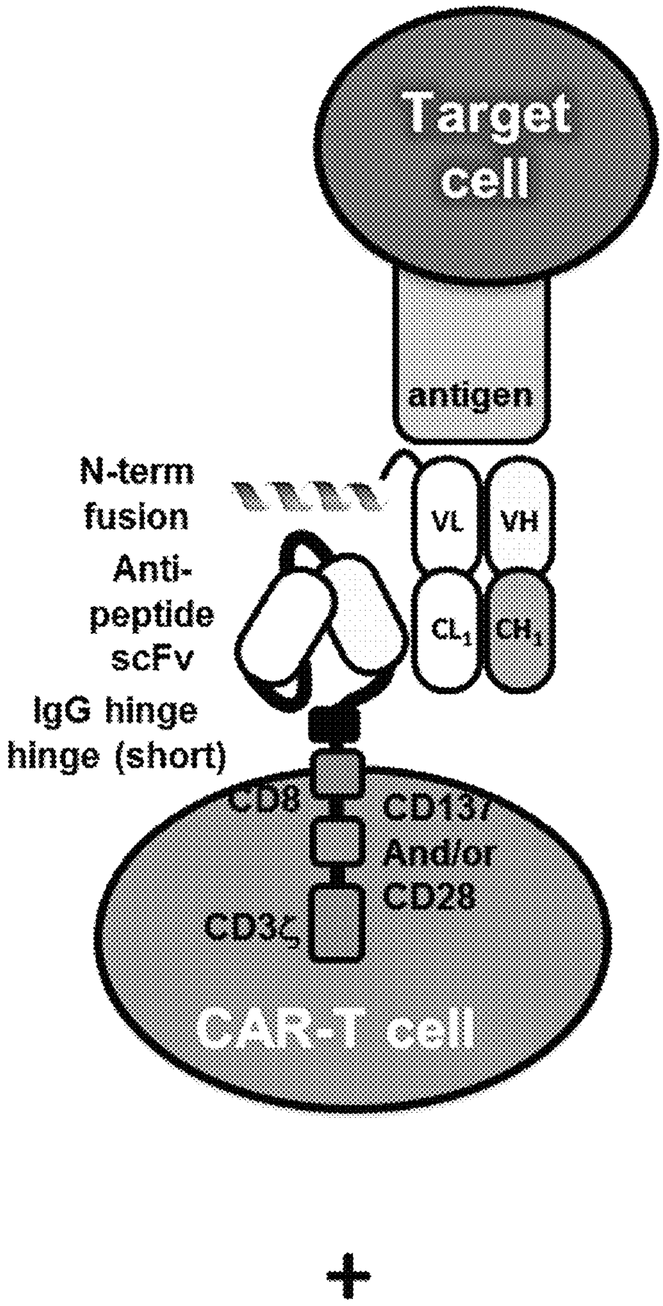
FIG. 4A-D exemplifies CAR hinge and CAR switch optimization.
Figure 4B:
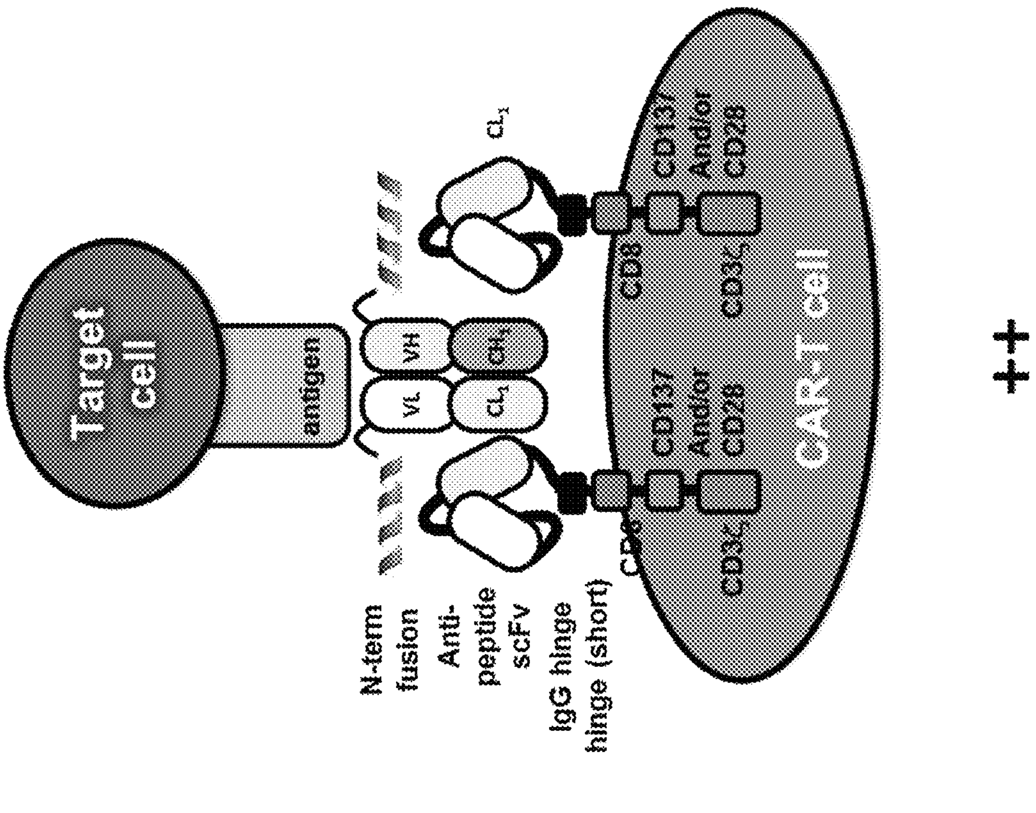

Multivalent switches are advantageous in CAR-T cell activation for at least the reason that multiple CARs are recruited for every one switch (and correspondingly one antigen) (FIG. 4B). This is expected to increase the signal transduction, CAR-T cell activation, and target cell lysis. The multivalent switch may bind to a CAR with a longer hinge region than that of canonical CARs in order for the CAR to access multiple peptides of the switch. However, the multivalent switch may, alternatively or additionally, have an optimal geometry and/or length for efficient activity with the CAR, including a canonical CARs or CARs with short hinges.

A first CAR-BP may be grafted into a first domain of the targeting polypeptide and a second CAR-BP may be grafted into a second domain of the targeting polypeptide. The first domain and the second domain may be the same. The first domain and the second domain may be different. By way of non-limiting example, the first CAR-BP may be grafted into a light chain of a targeting antibody or antibody fragment and a second CAR-BP may be grafted into heavy chain of the targeting antibody or antibody fragment. The first CAR-BP may be fused to a first terminus of the targeting polypeptide and a second CAR-BP may be fused to a second terminus of the targeting polypeptide. By way of non-limiting example, the first CAR-BP may be fused to a C terminus of a light chain of a targeting antibody or antibody fragment and a second CAR-BP may be fused to an N terminus of a heavy chain of the targeting antibody or antibody fragment. The first CAR-BP may be fused to a terminus of the targeting polypeptide and a second CAR-BP may be grafted within a domain of the targeting polypeptide. The first CAR-BP and the second CAR-BP may be the same or similar, such that the CAR-EC switch may be used with a CAR-EC cell that expresses one CAR. The first CAR-BP and the second CAR-BP may be different, such that the CAR-EC switch may be used with a CAR-EC cell that expresses one or more CARs or multiple CAR-EC cells that express different CARs.

The peptide switches disclosed herein may comprise one or more CAR-BPs. The peptide switches disclosed herein may comprise two or more CAR-BPs. The peptide switches disclosed herein may comprise three or more CAR-BPs. The peptide switches disclosed herein may comprise 1, 2, 3, 4, 5, 6, 7 or more CAR-BPs. The one or more CAR-BPs may be fused or grafted to the targeting polypeptide via one or more linkers. Thus, the peptide switches disclosed herein may comprise one or more linkers (e.g., L1, L2). The peptide switches disclosed herein may comprise two or more linkers. The peptide switches disclosed herein may comprise three or more linkers. The peptide switches disclosed herein may comprise 1, 2, 3, 4, 5, 6, 7 or more linkers. The linker may comprise a sequence selected from SEQ ID NOS: 45-50 and $(GGGGS)_n$, $(GGGS)_n$, $(GGS)_n$, $(G_mS)_n$, and $(X_mS)_n$, wherein n is at least 1, m is at least 1, and X is any amino acid. The linker may comprise a sequence that is at least about 50% homologous to a sequence selected from SEQ ID NOS: 45-50 and $(GGGGS)_n$, $(GGGS)_n$, $(GGS)_n$, $(G_mS)_n$, and $(X_mS)_n$, wherein n is at least 1, m is at least 1, and X is any amino acid. The linker may comprise a sequence selected from SEQ ID NOS: 68-71. The linker may comprise a sequence that is at least about 50% homologous to a sequence selected from SEQ ID NOS: 68-71.

The distance between the first CAR-BP and the second CAR-BP may be any suitable distance such that the CAR-BPs are able to bind to their target CAR-EC domains. For example, the distance may be between about 0 Å and about 200 Å or between about 0 Å and about 150 Å, or about 0 Å and about 100 Å, including all integers (e.g., 121 Å, 122 Å, 123 Å, 124 Å) and ranges (e.g., about 25 Å to about 125 Å, about 50 Å to about 125 Å, about 70 Å to about 115 Å) in between. The distance between the first CAR-BP and the second CAR-BP may be about 12 Å. The distance between the first CAR-BP and the second CAR-BP may be about 24 Å.

IB. Peptide-Small Molecule Switch

Further disclosed herein are CAR-EC switches comprising a CAR binding region and a targeting moiety, wherein the CAR binding region is a CAR-binding peptidic antigen and the targeting moiety is a non-peptidic small molecule. The non-peptidic small molecule may be a cell-targeting molecule, a chemical ligand, a nucleic acid, a vitamin, a substrate or a substrate analog. The non-peptidic small molecule may not comprise two amino acids, wherein the two amino acids are connected by an amide bond. The CAR-EC switch may further comprise a linker. The CAR-binding peptidic antigen (CAR-BP) and the small molecule may be site-specifically linked. The CAR-binding peptidic antigen may comprise an unnatural amino acid. The CAR-binding peptidic antigen and the small molecule may be site-specifically linked by the unnatural amino acid. The small molecule may bind a cell surface molecule on a target cell. The cell surface molecule may be selected from an antigen, a protein, a peptide, a lipid, a sterol, a glycolipid and a cell surface marker. The CAR-binding peptidic antigen may be selected from FLAG® tag, yeast transcription factor GCN4 and a hydrophilic target peptide (HTP). The small molecule may be 2-[3-(1,3-dicarboxypropyl)ureido]pentanedioic acid. The small molecule may be folate. The CAR-EC switch may further comprise a linker.

Disclosed herein are methods of producing CAR-EC switches comprising conjugating the CAR binding region to the targeting moiety, wherein the CAR-EC switches comprise a CAR binding region and a targeting moiety, wherein the CAR binding region is a CAR-binding peptidic antigen and the targeting moiety is a small molecule. The method may further comprise conjugating the small molecule to the linker to create a small molecule-linker intermediate. The small molecule or the small molecule-linker intermediate may comprise one or more reactive functional groups that may react with a complementary reactive functional group on the CAR-BP, previous to incorporation into the CAR-EC switch. The linker or the small molecule-linker intermediate may be bifunctional. The linker or the small molecule-linker intermediate may be heterobifunctional.

The small molecule-linker intermediate or the CAR-EC switch may be the product of a bioorthogonal reaction, non-limiting examples of which are reviewed in Kim et al., Curr Opin Chem Bio 17:412-419 (2013). The small molecule-linker intermediate, linker or the CAR-EC switch may comprise an oxime, a tetrazole, a Diels Alder adduct, a hetero Diels Alder adduct, an aromatic substitution reaction product, a nucleophilic substitution reaction product, an ester, an amide, a carbamate, an ether, a thioether, or a Michael reaction product. The small molecule-linker intermediate, linker or the CAR-EC switch be a cycloaddition product, a metathesis reaction product, a metal-mediated cross-coupling reaction product, a radical polymerization product, an oxidative coupling product, an acyl-transfer reaction product, or a photo click reaction product. The cycloaddition may be a Huisgen-cycloaddition. The cycloaddition may be a copper-free [3+2] Huisgen-cycloaddition. The cycloaddition may be a Diels-Alder reaction. The cycloaddition may be a hetero Diels-Alder reaction. The small molecule-linker intermediate may be the product of an enzyme-mediated reaction. The small molecule-linker intermediate may be a product of a transglutaminase-mediated reaction, non-limiting examples of which are described in Lin et al., J. Am. Chem. Soc. 128:4542-4543 (2006) and WO 2013/093809. The small molecule-linker intermediate, linker or the CAR-EC switch may comprise a disulfide bridge that connects two cysteine residues, such as ThioBridge™ technology by PolyTherics. The small molecule-linker intermediate, linker or the CAR-EC switch may comprise a maleimide bridge that connects two amino acid residues. The small molecule-linker intermediate, linker or the CAR-EC switch may comprise a maleimide bridge that connects two cysteine residues.

The small molecule-linker intermediate or linker may comprise an alkoxy-amine (or aminooxy) group, azide group and/or cyclooctyne group at one or more termini. The small molecule-linker intermediate or linker may comprise an alkoxy-amine at one terminus and an azide group at the other terminus. The small molecule-linker intermediate or linker may comprise an alkoxy-amine at one terminus and a cyclooctyne group at the other terminus. The alkoxy-amine may form a stable oxime with a ketone group on an amino acid. The alkoxy-amine may form a stable oxime with a ketone group on an unnatural amino acid. The ketone group may be on a p-acetyl phenylalanine (pAcF).

IC. Soluble T Cell Receptors Switches

TCR and biologics derived from TCRs, such as affinity matured soluble TCR (sTCR) and single chain TCR (scTCR) can also be used as a moiety for peptide-switch targeting. These reagents allow detection of intracellular proteins displayed on the cell surface in the context of MHC. An example of this targeting strategy is the affinity matured sTCR 1G4c113 which recognizes a peptide derived from the cancer/testes antigen NYESO-1 in the context of HLA-A201. Grafting peptides onto TCR-derived products like 1G4c113 enables the expansion of CAR-EC targeting to intracellular antigens not normally accessible by conventional antibody-derived switches. An example of grafting strategies for TCR-derived switches can be seen in (SEQ ID NOS: 62-67).

A major limitation of antibody-based targeting is the restriction to cell surface targets; however many tumor associated antigens are intracellular, non-membrane bound proteins. One way to target intracellular proteins is by immunologic targeting using T cell receptors (TCRs). This exploits the mechanism in which a T cell naturally surveys the intracellular proteome, represented as peptides displayed by human leukocyte antigen (HLA, MHC). Affinity matured, tumor-specific TCRs transduced into adoptively transferred T cells have the potential to lose specificity and have caused serious adverse effects in the clinic due to off-target reactivity. For example, adoptive transfer of engineered T cells harboring a high avidity TCR against MAGE-A3 for melanoma and myeloma resulted in two deaths in the clinic due to off-target reactivity with the protein Titin in cardiac tissue. On-target, off-tumor toxicity has also been reported. An affinity matured TCR against CEA caused severe inflammatory colitis even at doses of T cells 100 fold lower than those typically given with autologous tumor infiltrating lymphocyte (TIL) therapy. Surprisingly, these serious safety concerns have not stopped researchers from initiating clinical trials for more than a dozen targets. Therefore, using a soluble TCR as a CAR-EC switch may be highly advantageous.

The use of soluble mTCRs as switches for sCAR-T will allow dose titratable sCAR-T cell targeting of intracellular tumor associated antigens that may be turned off in the case of an adverse event.

The heterologous expression of mTCRs and their use as soluble therapeutics is well established. Because natural TCRs have weak affinity (1-100 uM) for their targets (naturally tuned for cooperative binding of CD8), directed evolution strategies have used phage display to produce mTCRs with affinities strong as 1 pM. Soluble TCRs have additional advantages over mAbs including the ability to target intracellular proteins, small size and improved tumor penetration, detection of very low cell surface antigen densities, are fully human, and are inexpensively expressed in *E. coli.*

The soluble TCR switch may comprise a fusion of the CAR-BP to the soluble TCR. The soluble TCR switch may comprise the CAR-BP, wherein the CAR-BP is grafted within the soluble TCR. Soluble TCR switches may comprise a fusion of the CAR-BP to the N-terminus of the TCR alpha chain, the N-terminus of the TCR beta-chain, the C-terminus of the TCR alpha chain or the C-terminus of the TCR beta chain. Alternatively, additional structure based design may be employed to fuse the CAR-BP to additional chains/regions of the TCR that are permissive to mutation. The CAR-BP may be grafted within a chain/region of the soluble TCR. The soluble TCR switch may recognize and bind to a target cell antigen bound to MHC.

The potential to target intracellular antigens opens the door to sCAR-T cells that can remodel the tumor microenvironment. For example, naturally occurring CD8 T cells have been recently identified that recognize FoxP3 or indoleamine-pyrrole 2,3-dioxygenase (IDO) expressing regulatory T cells (Treg) and myeloid-derived suppressor cells (MDSC), respectively. The cloning and heterologous expression of mTCRs from these cells as switches may enable a sCAR-T cell to deplete immunosuppressive cells within the tumor microenvironment. This may be a novel route to overcoming disease-mediated immunosuppression.

II. Chimeric Antigen Receptor (CAR)

Disclosed herein are CAR-EC switches that regulate the activities of a cell expressing a chimeric antigen receptor (CAR). The chimeric antigen receptor may comprise an extracellular domain, transmembrane domain and intracellular domain. The extracellular domain may bind to the peptidic antigen (e.g., CAR-BP) of the CAR-EC switch. The extracellular domain may comprise an antibody or antibody fragment that binds to the CAR-BP of the CAR-EC switch (a CAR-antibody). The CAR-antibody may comprise at least a portion of an antibody. In some instances, the CAR-antibody is not a full-length antibody. The CAR-antibody may comprise at least a portion of an immunoglobulin or fragment thereof. The immunoglobulin or fragment thereof may be selected from the group consisting of an scFv, a di-scFv, a bi-scFv, a Fab, an Fc, an $F(ab')_2$, a pFc', a nanobody, an affibody, a DARPin, a diabody, a camelid, an engineered T cell receptor and a monobody. The immunoglobulin may be selected from the group consisting of an IgA1, an IgA2, an IgD, an IgM, an IgE, an IgG1, an IgG2, an IgG3, and an IgG4. The CAR-antibody may comprise at least a portion of a single chain variable fragment (scFv). The CAR-antibody may be human, fully human, humanized, human engineered, non-human, and/or chimeric antibody. The extracellular domain may comprise a humanized anti-GCN4 scFv (e.g., clone 52SR4). The humanized anti-GCN4 scFV may be encoded by a sequence selected from SEQ ID NOS: 165-170.

The CAR-antibody may have a binding affinity for the CAR-BP of less than about 0.01 pM, about 0.02 pM, about 0.03 pM, about 0.04 pM, 0.05 pM, about 0.06 pM, about 0.07 pM, about 0.08 pM, about 0.09 pM, about 0.1 pM, about 0.2 pM, 0.3 pM, about 0.4 pM, about 0.5 pM, about 0.6 pM, about 0.7 pM, about 0.8 pM, about 0.9 pM or about 1 pM, about 2 pM, about 3 pM, about 4 pM, about 5 pM, about 6 pM, about 7 pM, about 8 pM, about 9 pM, about 10 pM, about 0.01 nM, about 0.02 nM, about 0.03 nM, about 0.04 nM, about 0.05 nM, about 0.06 nM, about 0.07 nM, about 0.08 nM, about 0.09 nM, about 0.1 nM, about 0.2 nM, about 0.3 nM, about 0.4 nM, about 0.5 nM, about 0.6 nM, about 0.7 nM, about 0.8 nM, about 0.9 nM, about 1 nM, about 2 nM, about 2.5 nM, about 3 nM, about 4 nM, about 5 nM, about 6 nM, about 7 nM, about 8 nM, about 9 nM, about 10 nM, about 12 nM, about 14 nM, about 16 nM, about 18 nM, about 20 nM, about 22 nM, about 24 nM, about 26 nM, about 28 nM or about 30 nM.

The CAR-antibody may recognize a synthetic (non-naturally-occurring) peptide. The CAR-antibody may comprise an antibody or antibody fragment that recognizes a FLAG® tag or a fragment thereof. The CAR-antibody may comprise an antibody or antibody fragment that recognizes a yeast transcription factor GCN4 or a fragment thereof. The CAR-antibody may comprise an anti-HTP antibody or a fragment thereof.

The transmembrane domain and/or the intracellular domain of the CAR may comprise at least a portion of a cytoplasmic signaling domain. The intracellular domain may comprise at least a portion of a signaling molecule selected from the group comprising CD3zeta, CD28, and 4-1BB. The intracellular domain may comprise an Fc receptor or a portion thereof. The Fc receptor or portion thereof may be CD16 or a portion thereof. The signaling molecule may comprise CD3zeta. The signaling molecule may comprise CD28. The signaling molecule may comprise 4-1BB. The intracellular domain may comprise at least a portion of CD3zeta. The intracellular domain may comprise at least a portion of CD28, The intracellular domain may comprise at least a portion of 4-1BB, The intracellular domain may comprise at least a portion of OX-40, The intracellular domain may comprise at least a portion of CD30, The intracellular domain may comprise at least a portion of CD40, The intracellular domain may comprise at least a portion of CD2. The intracellular domain may comprise at least a portion of CD27. The intracellular domain may comprise at least a portion of PD-1. The intracellular domain may comprise at least a portion of ICOS. The intracellular domain may comprise at least a portion of lymphocyte function-associated antigen-1 (LFA-1). The intracellular domain may comprise at least a portion of CD7. The intracellular domain may comprise at least a portion of LIGHT. The intracellular domain may comprise at least a portion of NKG2C. The intracellular domain may comprise at least a portion of B7-H3. The intracellular domain may comprise at least a portion of a cytoplasmic signaling domain from one or more signaling molecules. The intracellular domain may comprise at least a portion of two or more cytoplasmic signaling domains. The two or more cytoplasmic signaling domains may be from two or more different signaling molecules. The intracellular domain may comprise at least a portion of three or more cytoplasmic signaling domains. The intracellular domain may comprise at least a portion of four or more cytoplasmic signaling domains. The intracellular domain may comprise at least a portion of a ligand that binds to one or more signaling molecules. The intracellular domain may comprise at least a portion of a ligand that binds to CD83.

The CAR may comprise a hinge. The hinge may be located between the transmembrane domain and the extracellular domain. The hinge may comprise a portion of the transmembrane domain. The hinge may comprise a portion of the extracellular domain. The hinge may provide a length, orientation, geometry or flexibility to the CAR that is necessary for an optimal immunological synapse. The optimal immunological synapse may provide for an optimal distance and/or orientation between the CAR-EC and the target cell. The optimal immunological synapse may provide for optimal and/or maximal cytotoxicity against the target cell. The hinge may be derived from the extracellular domain of an endogenous transmembrane protein specific to T cell such as CD28 or 4-1BB, or components of CD3. The hinge may be derived from a synthetically derived sequence (such as the ones listed for linkers relevant to switch design). The hinge may be derived from a human protein. The hinge may be contiguous with the transmembrane domain. This hinge may comprise part of the heavy chain constant region 1 of the scFv). This hinge may comprise part of the light chain constant region 1 of the scFv).

The hinge length may be between about 1 amino acid and about 10 amino acids. The hinge length may be between 1 amino acid and about 20 amino acids. The hinge length may be between about 1 amino acid and about 50 amino acids. The hinge length may be between about 1 amino acid and about 100 amino acids. The hinge length may be between 10 amino acids and about 50 amino acids. The hinge length may be about 12 amino acids. The hinge may length may be about 45 amino acids.

The hinge may be a long hinge. The long hinge may have a length of about 20 to about 200 amino acids, about 20 to about 100 amino acids, about 30 to about 100 amino acids, about 40 to about 100 amino acids, or about 45 to about 100 amino acids.

The hinge may be a short hinge. The short hinge may have a length of about 1 to about 20 amino acids, about 5 to about 20 amino acids, or about 10 to about 20 amino acids.

The hinge may comprise a portion of a CD8 protein. The portion of the CD8 protein may be between about 4 amino acids and about 100 amino acids. The portion of the CD8 protein may be about 45 amino acids. The hinge may comprise a portion of an immunoglobulin. The immunoglobulin may be an IgG. The immunoglobulin may be an IgG4. The IgG4 may be mutated (referred to herein as IgG4m). The portion of the immunoglobulin may be between about 1 amino acid and about 20 amino acids. The portion of the immunoglobulin may be about 12 amino acids.

The hinge may be flexible. The hinge may be structured.

As used herein in reference to a peptide sequence (e.g. a hinge or linker disclosed herein), the term "flexible" means a peptide sequence that comprises a linear sequence of amino acids with little or no known secondary structure. Such flexible sequences may comprise linear sequences of amino acids in which the torsion angles or rotation around the bonds of the polypeptide backbone have freedom to occupy many different orientations. In some embodiments, reference to a "flexible hinge" means that a hinge comprises a flexible peptide sequence that allows a CAR to bind CAR-BPs via various binging orientations, thus, alleviating steric hindrance that would otherwise have been detrimental to the CAR-BP binding the CAR extracellular domain.

As used herein in reference to a peptide sequence (e.g. a hinge or linker disclosed herein), the term "structured" means a peptide sequence that comprises a linear sequence of amino acids that forms a defined secondary structure. Such structured sequences may comprise a linear sequence of amino acids in which the torsion angles or rotation around the bonds of the polypeptide backbone have defined preferences to occupy a limited number of orientations. In some embodiments, a structured hinge may comprise a peptide sequence that defines the immunological synapse and reduces entropic costs of finding more productice orientation. Said another way, a structured hinge is, in some embodiments, a hinge that is not flexible. In various embodiments, the terms "rigid" and "structured," are used interchangeably in reference to a peptide sequence (e.g., a hinge or linker disclosed herein).

The hinge may comprise a sequence selected from SEQ ID NOS: 45-50 and $(GGGGS)_n$, $(GGGS)_n$, $(GGS)_n$, $(G_mS)_n$, and $(X_mS)_n$, wherein n is at least 1, m is at least 1, and X is any amino acid. The hinge may comprise a sequence that is at least about 50% homologous to a sequence selected from SEQ ID NOS: 45-50 and $(GGGGS)_n$, $(GGGS)_n$, $(GGS)_n$, $(G_mS)_n$, and $(X_mS)_n$, wherein n is at least 1, m is at least 1, and X is any amino acid. The hinge may comprise a sequence selected from SEQ ID NOS: 68-71. The hinge may comprise a sequence that is at least about 50% homologous to a sequence selected from 68-71. The CAR having a hinge region may be encoded by a sequence selected from SEQ ID NOS: 72-74. The CAR having a hinge region may be encoded by a sequence that is at least about 50% homologous to a sequence selected from SEQ ID NOS: 72-74.

The CAR may be expressed at relatively low levels on the CAR-EC. The CAR may be expressed at relatively high levels on the CAR-EC. The CAR may be expressed at a cell density of less than about $2\times10^6$ receptors per cell. The CAR may be expressed at a cell density of about $0.5\times10^6$ receptors per cell. The CAR may be expressed at a cell density of more than about $0.05\times10^6$ per cell The CAR may be expressed under the control of a promoter selected from EF1a, IL-2, CMV, and synthetic promoters designed to increase or decrease CAR expression. The promoter may be constitutive. The promoter may be inducible.

Multivalent CARS

Figure 4C:
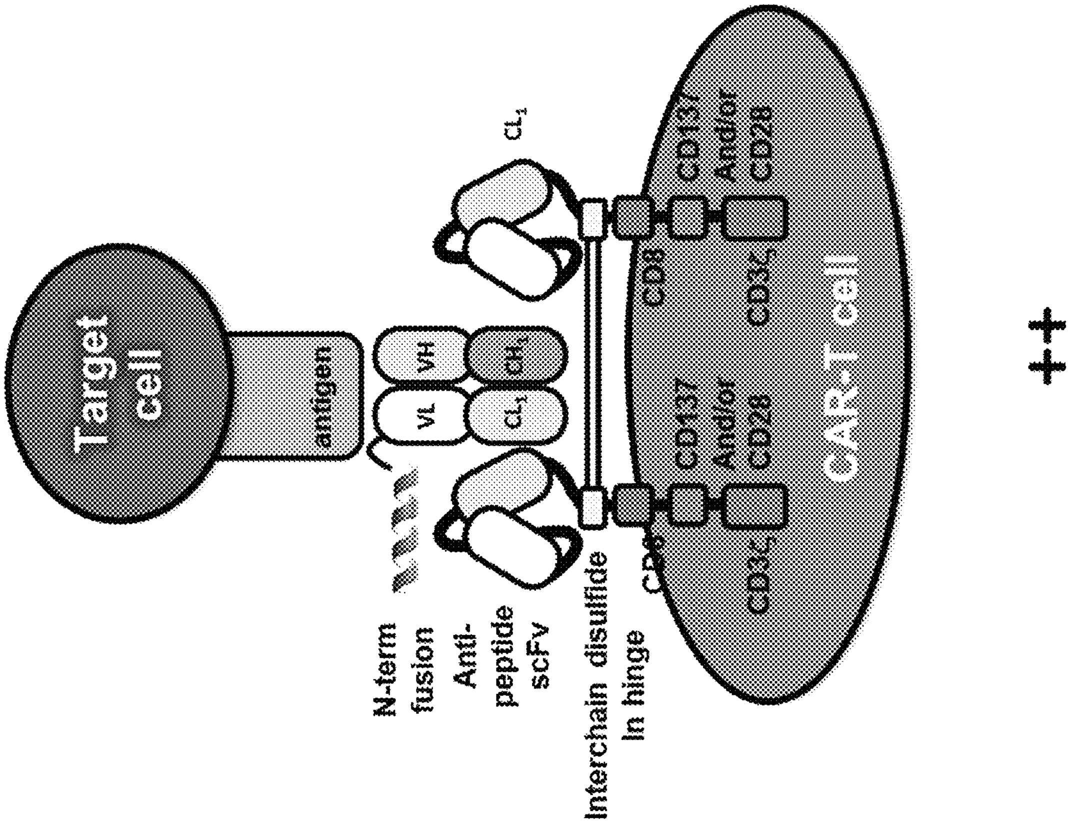
Figure 4D:
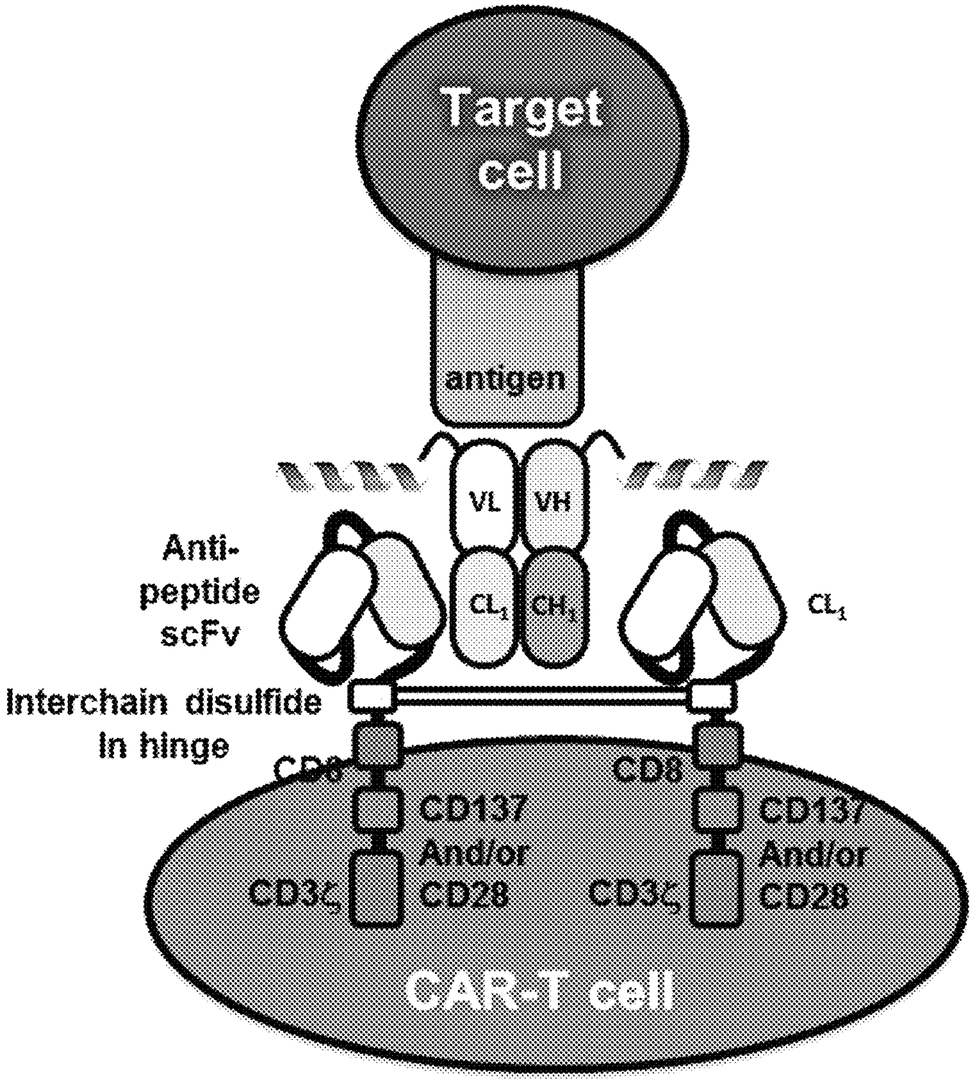

Valency can also be engineered into a CAR hinge (FIG. 4C). By way of non-limiting example, a monovalent switches may recruit two CARs through a disulfide that forms in the hinge region of the CAR. The hinge may be a CD8-derived hinge (SEQ ID NO. 68) which is expected to be monovalent. The hinge may be derived from the hinge region of an IgG molecule. The IgG molecule may be selected from IgG1, IgG4 or IgG4m (mutated). The IgG4 hinge (SEQ ID NO. 70) may not participate in interchain disulfides but instead has intrachain disulfide bonds which do not dimerize the CAR. The hinge may be considered functionally monovalent. The IgG1 and IgG4m hinge (SEQ ID NO. 71) may contain a serine to proline mutation which enables it to participate in interchain disulfide bonds which covalently dimerizes the hinge region (FIG. 4). These hinges may be used to study both the distance constraints of an immunological synapse (by testing the long CD8-derived hinge vs the short IgG4 derived hinge) and the valency effect (by testing the short IgG4 derived hinge vs an IgG4m derived CAR) of the CAR and/or switch. Other hinges may comprise $CH_2$ and/or $CH_3$ of IgG1, IgG2, IgG3, or IgG4 molecules, or portions thereof, or combinations thereof. The hinge may be derived from CD28. The hinge may dimerize.

coCARS/iCARs

The switchable CARs and switches disclosed herein may encompass inhibitory chimeric antigen receptor (iCAR)-T cell switches and switchable iCAR-T cells for targeting an immune response to specific cells (e.g., diseased cells) and minimizing an immune attack on healthy cells. The switchable CARs and switches disclosed herein may also encompass co-stimulatory chimeric antigen receptor (coCAR)-T cell switches for use with switchable coCAR-T cells for targeting an immune response to target cells (e.g., diseased cells) and maximizing an immune attack on these cells. iCAR-T cell switches and coCAR-T cell switches comprise a CAR-binding domain and a target binding domain. Compositions disclosed herein may comprise a plurality of switches for modulating a chimeric antigen receptor-effector cell (CAR-EC), wherein a first switch that interacts with a first antigen on a first target cell and a first chimeric antigen receptor (CAR) on the CAR-EC; and a second switch that interacts with a second antigen on a second target cell and a second chimeric antigen receptor (CAR) on the CAR-EC. The plurality of switches may be used with existing CAR-T cells and with CAR-ECs that express a canonical CAR and/or an inhibitory CAR (iCAR). The plurality of switches may be used with existing CAR-T cells and with CAR-ECs that express a canonical CAR and/or a co-stimulatory CAR (coCAR).

The switchable CAR-EC cells disclosed herein may comprise a first switchable CAR and a second switchable CAR. The first switchable CAR may be a canonical CAR and the second switchable CAR may be an iCAR. The first switchable CAR may be a canonical CAR and the second switchable CAR may be a co-CAR.

The iCAR may comprise a chimeric receptor which provides an inhibitory signal to CAR-T cells. The iCAR may comprise a cytoplasmic domain selected from PD-1 or CTLA-4. The iCAR may be expressed by the same cell as a canonical (activating) CAR. Activation of the iCAR may tune down a canonical CAR signal and/or activity. The specificity of the iCAR can be used to protect tissues in which CAR-T cell activity is not desirable. iCAR activity may be controlled by a switch, referred to as an "iCAR switch" herein. Similarly, canonical CAR activity may be controlled by the first and/or second switch, referred to as an "aCAR switch" herein. A switchable iCAR-T cell enables targeting of antigens that may be unsafe to target with a canonical or CAR-T cell.

To mount an immune response, the aCAR switch binds a positive, or "A" antigen on a target cell that is to be attacked (e.g. cancer cell) and the canonical CAR, stimulating cytotoxic activity towards the target cell through activation of the canonical CAR. To protect normal tissue, the iCAR switch binds a negative, or "B", antigen on a cell that is to be avoided by T cells (e.g., a healthy cell) and the iCAR, inhibiting immune activity through signaling of the iCAR. The "B" antigen may be ubiquitously expressed on normal tissue but down-regulated in most malignant cells. The "A" antigen may be over-expressed in malignant cells relative to normal tissue. The B antigen may be opioid binding protein/cell adhesion molecule-like gene (OPCML). The B antigen may be selected from hyaluronidase 2 (HYAL2), deleted in colorectal cancer (DCC), and SMAR1.

The coCAR may comprise a chimeric receptor which provides a co-stimulatory signal to CAR-T cells. The coCAR may comprise a cytoplasmic domain selected from CD137 and/or CD28. The coCAR may be expressed by the same cell as a canonical (activating) CAR. Activation of the coCAR may enhance and/or synergize a canonical CAR signal and/or activity. The coCAR may increase cytotoxicity towards a target cell relative to the cytotoxicity towards a target cell generated by a CAR-T cell that only expresses a canonical CAR-T cell. coCAR activity may be controlled by a switch, referred to as an "coCAR switch" herein. Similarly, canonical CAR activity may be controlled by the first and/or second switch, referred to as an "aCAR switch" herein.

Non-Antibody CARS

In contrast to conventional CARS, the chimeric antigen receptors disclosed herein may comprise a non-antibody extracellular domain that interacts with the CAR-BP. That is, the extracellular domain may comprise a non-antibody protein or a non-antibody peptide that interacts with the CAR-BP. Thus, the chimeric antigen receptor may not actually recognize an antigen on a target in the traditional sense of an antibody or antibody fragment recognizing an antigen, but interact with the target in ways that a non-antibody protein or peptide would. In these cases, the chimeric antigen receptor may be referred to more accurately as a "chimeric receptor." A person of skill in the art would understand that in many examples and descriptions throughout this disclosure, the chimeric antigen receptor may be a chimeric receptor. The chimeric receptor binding partner of the switch may be non-antibody protein or peptide. Thus, the chimeric receptor and the switch may have a protein-protein interaction or a protein-peptide interaction.

Epsilon CAR

Further disclosed herein are chimeric antigen receptors comprising: an extracellular domain that interacts with an anti-CD3 antibody or fragment thereof on the switch; a transmembrane domain; and an intracellular domain, wherein at least a portion of the transmembrane domain or at least a portion of the intracellular domain is not based on or derived from a CD3 protein. The extracellular domain may comprise a CD3 extracellular domain or portion thereof. The extracellular domain may comprise a CD3 epsilon extracellular domain or portion thereof. The extracellular domain may comprise a CD3 delta extracellular domain or portion thereof. The extracellular domain may comprise a CD3 gamma extracellular domain or portion thereof. The extracellular domain may comprise a CD3 zeta extracellular domain or portion thereof. The extracellular domain may comprise an alpha chain of TCR extracellular domain or portion thereof. The extracellular domain may comprise a pre-alpha chain of TCR extracellular domain or portion thereof. The extracellular domain may comprise a beta chain of TCR extracellular domain or portion thereof.

III. Chimeric Antigen Receptor Effector Cells (CAR-EC)

The methods, platforms and kits disclosed herein may comprise one or more chimeric antigen receptor effector cells (CAR-EC) or uses thereof. The chimeric antigen receptor effector cells disclosed herein express a chimeric antigen receptor. The chimeric antigen receptor (CAR) may be any CAR disclosed herein. Wherein the methods, platforms or kits comprise two or more effector cells, the two or more effector cells may be of the same cell type. The two or more effector cells may be of a different cell type. The two or more effector cells may be of the same cell lineage. The two or more effector cells may be of different cell lineages. The two or more effector cells may comprise two or more identical CARs. The two or more effector cells may comprise two or more different CARs. The two or more effector cells may comprise two or more similar CARs.

The effector cell may be a T cell. The effector cell may be a cell of a T cell lineage. The effector cell may be a mature T cell. The effector cell may be a precursor T cell. The effector cell may be a cytotoxic T cell. The effector cell may be a naive T cell. The effector cell may be a memory stem cell T cell ($T_{MSC}$). The effector cell may be a central memory T cell ($T_{CM}$). The effector cell may be an effector T cell (TE). The effector cell may be a CD4+ T cell. The T cell may be a CD8+ T cell. The effector cell may be a CD4+ and CD8+ cell. The effector cell may be an alpha-beta T cell. The effector cell may be a gamma-beta T cell. The effector cell may be a natural killer T cell. The effector cell may be a helper T cell.

While preferred embodiments of the present disclosure describe methods, kits and platforms comprising T cells, one skilled in the art may also understand that other cell types may be used in place of a T cell. The effector cell may be an effector cell that has an effect on a target or target cell when brought into proximity of the target or target cell. The effector cell may be a cell that has a cytotoxic effect on a target or target cell when brought into proximity of the target or target cell. The effector cell may be an immune cell. The effector cell may be selected from a B cell, a monocyte, a thrombocyte, a leukocyte, a neutrophil, an eosinophil, a basophil, or a lymphocyte. The effector cell may be a lymphocyte. The effector cell may be a macrophage. The effector cell may be a phagocytic cell. The effector cell may be an effector B cell. The effector cell may be a natural killer cell. The effector cell may isolated or derived from a subject suffering from a disease or condition. The effector cell may be a cell derived from a subject to be treated with a CAR-EC switch or CAR-EC platform disclosed herein.

The T cell may express a chimeric antigen receptor encoded by one or more polynucleotides based on or derived from SEQ ID NO: 1. The polynucleotide may be at least about 5%, 10%, 15%, 20%, 25%, 30%, 35%, 40%, 45%, 50%, 55%, 60%, 65%, 70%, 75%, 80%, 85%, 90% or 95% identical to one or more polynucleotides based on or derived from SEQ ID NO: 1. The polynucleotide may be at least about 70% identical to one or more polynucleotides based on or derived from SEQ ID NO: 1. The polypeptide encoded by one or more polynucleotides may be based on or derived from SEQ ID NO: 1. The polypeptide may be encoded by a polynucleotide that is at least about 5%, 10%, 15%, 20%, 25%, 30%, 35%, 40%, 45%, 50%, 55%, 60%, 65%, 70%, 75%, 80%, 85%, 90% or 95% identical to one or more polynucleotides based on or derived from SEQ ID NO: 1. The polynucleotide may be constitutively expressed. The polynucleotide may be conditionally expressed.

Disclosed herein are methods of producing a chimeric antigen receptor effector cell (CAR-EC), the methods comprising introducing one or more polynucleotides encoding a chimeric antigen receptor or a chimeric antigen receptor complex into an effector cell. The effector cell may be a T cell. Introducing one or more polynucleotides encoding a chimeric antigen receptor or a chimeric antigen receptor complex into an effector cell may comprise transfecting the effector cell with the one or more polynucleotides. Introducing one or more polynucleotides encoding a chimeric antigen receptor or a chimeric antigen receptor complex into an effector cell may comprise virally infecting the effector cell with one or more viruses comprising the one or more polynucleotides encoding a chimeric antigen receptor disclosed herein. The virus may be a lentivirus. The virus may be an adenovirus. The virus may be a retrovirus. The virus may be an adeno-associated virus. The virus may be a self-complementary adeno-associated virus (scAAV). The virus may be a modified human immunodeficiency (HIV) virus. The virus may be a modified herpes simplex virus (HSV) virus. Other methods of producing the CAR-EC may comprise a method of transferring one or more polynucleotides encoding a chimeric antigen receptor into a cell, wherein the methods comprise adding a transposon, a zinc finger nuclease, a TALEN or a CRISPR to the cell. The transposon may be a sleeping beauty transposon. The one or more polynucleotides may be based on or derived from SEQ ID NO: 1.

Tumor Infiltrating Lymphocytes (TILs)

The effector cell may be a tumor-infiltrating lymphocyte (TIL). TILs are a type of white blood cell found in tumors. TILs are implicated in killing tumor cells, and the presence of lymphocytes in tumors is often associated with better clinical outcomes. To obtain TILs, autologous lymphocytes may be isolated from patients' tumors and grown to very large numbers of cells in vitro. Prior to TIL treatment, the subject may be given nonmyeloablative chemotherapy to deplete native lymphocytes ("lymphodepletion") that can suppress tumor killing. Once lymphodepletion is complete, the subject may be infused with the TILs. TILs may be administered in combination with interleukin 2 (IL-2).

The present application provides for TILs that are modified to express a CAR and applications thereof (e.g., CAR-TIL therapy). Disclosed herein are T cells (e.g., TILs) modified to express a chimeric antigen receptor. Further disclosed herein are methods for treating a condition in a subject in need thereof, comprising administering a TIL, wherein the TIL expresses a CAR. The CAR may be a co-receptor of a T cell receptor (TCR) expressed by the TIL. The CAR may associate with a TCR of the TIL. The CAR may enhance TCR activation. The CAR may have intracellular signaling domains that are activated upon association and/or interaction with a TCR, wherein the TCR is bound to an antigen on a target cell. These methods may be referred to as chimeric antigen receptor tumor infiltrating lymphocyte therapy (CAR-TIL therapy). An advantage of this application is to utilize the specificity of endogenous T cell receptors (TCRs) of the engineered T cells (e.g., antigen specific MHC), circumventing the need to introduce artificial tumor targeting moieties (e.g., antibody-based switches) used in conventional CAR-T approaches, for the recognition of the target tumor cells. The endogenous TCRs expressed on tumor specific T cells are heterogeneous, but may be pre-selected for specifically targeting tumor-associated peptide antigens bound to major histocompatibility complexes (MHCs) on tumor cells. Moreover, the diverse repertoire of the endogenous, tumor specific TCRs are suitable to target heterogeneous tumors.

IV. CAR-EC Platform

Disclosed herein are chimeric antigen receptor effector cell (CAR-EC) platforms comprising (i) an effector cell, wherein the effector cell comprises a polynucleotide encoding a chimeric antigen receptor (CAR); and (ii) a chimeric antigen receptor effector cell (CAR-EC) switch, wherein the CAR-EC switch comprises a CAR binding peptidic antigen and a targeting polypeptide and wherein the CAR-EC switch binds a cell surface molecule on a target cell. The CAR-EC switch may be selected from any CAR-EC switches disclosed herein. As used herein, the terms "switchable CAR platform", "CAR-EC platform", "sCAR-T platform", "sCAR-T cell platform", "switchable chimeric antigen receptor platform", "chimeric antigen receptor-effector cell platform", "CAR-T switch platform", "sCAR platform", "switch platform", and "switchable platform" are used interchangeably.

The CAR-EC platforms may comprise two or more CAR-EC switches. The CAR-EC platforms may comprise 3, 4, 5, 6, 7, 8, 9, 10, 11, 12, 13, 14, 15, 16, 17, 18, 19, 20 or more CAR-EC switches. The CAR-EC platforms may comprise may comprise more than 20, more than 25, more than 30, more than 35, more than 40, more than 45 or more than 50 CAR-EC switches. The two or more switches may be selected from one or more CAR-EC switches disclosed herein or a combination thereof.

The CAR-EC platforms disclosed herein may further comprise a first CAR-EC switch and a second CAR-EC switch, wherein the first CAR-EC switch comprises a first CAR-BP and a first targeting polypeptide and the second CAR-EC switch comprises a second CAR-BP and a second targeting polypeptide. The first CAR-BP and the second CAR-BP may be the same. The first CAR-BP and the second CAR-BP may be different. The first CAR-BP and the second CAR-BP may be about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous. The first targeting polypeptide and the second targeting polypeptide may be the same. The first targeting polypeptide and the second targeting polypeptide may be different. The first targeting polypeptide and the second targeting polypeptide may be about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous.

V. Kits, Vectors and Polynucleotides

Disclosed herein are kits comprising one or more CAR-EC switches disclosed herein. The kit may further comprise two or more CAR-EC switches. The kit may comprise three CAR-EC switches. The kit may comprise about 3, 4, 5, 6, 7, 8, 9, 10, 12, 15, 20, 24, 30, 35, 48, 50, 55, 60, 65, 70, 75, 80, 85, 90, 96, 100, 120, 150, 200, 300, 384, 400, 500, 600, 700, 800, 900 or 1000 CAR-EC switches. The kit may be employed for biological research. The kit may be used for diagnosing a disease or a condition. The kit may be used for treating a disease or condition. The CAR-EC switches of the kit may be used with CAR-EC cells disclosed herein or existing CAR T-cells clinically used or tested. The kit may further comprise one or more effector cells. The kit may further comprise one or more CAR-EC cells. The CAR-EC cell may be a T cell. The T cell may express one or more CARs. The kit may further comprise a polynucleotide encoding one or more CARs. The kit may further comprise a vector comprising a polynucleotide encoding one or more CARs. The CAR may be selected from any of the CARs disclosed herein. The kit may comprise one or more polynucleotide encoding a CAR-EC switch disclosed herein or a portion thereof (e.g., antibody, antibody fragment, peptide).

Further disclosed herein are and vectors and polynucleotides encoding CAR-EC switches or portions thereof, wherein the CAR-EC switch comprises a chimeric antigen receptor binding peptidic antigen and a targeting polypeptide, wherein the targeting peptide binds a cell surface molecule on a target cell. The polynucleotides may be DNA. The polynucleotides may be RNA. Unless otherwise specified, the terms "polynucleotide" and "vector," as used herein, are used interchangeably. The targeting polypeptide may be an antibody or antibody fragment. The vector may comprise a sequence encoding a heavy chain of the antibody or antibody fragment. The vectors may comprise a sequence encoding a light chain of the antibody or antibody fragment. The vectors may comprise the sequence encoding the light chain of the antibody or antibody fragment and the sequence encoding the heavy chain of the antibody or antibody fragment. The light chain and the heavy chain may be expressed from the same vector. The light chain and the heavy chain may be expressed from two separate vectors.

Disclosed herein are vectors and polynucleotides encoding chimeric antigen receptors, wherein the chimeric antigen receptors comprise an extracellular domain that binds to a peptide of a chimeric antigen receptor effector cell switch. The extracellular domain may comprise an antibody or antibody fragment. The antibody or antibody fragment may bind a peptidic antigen of a chimeric antigen receptor effector cell switch. The peptidic antigen may be a yeast peptide. The yeast peptide may be GCN4. f a or portions thereof may be encoded by one or more polynucleotides based on or derived from SEQ ID NO: 1. CARs or portions thereof may be encoded by a polynucleotide at least about 5%, 10%, 15%, 20%, 25%, 30%, 35%, 40%, 45%, 50%, 55%, 60%, 65%, 70%, 75%, 80%, 85%, 90% or 95% identical to one or more polynucleotides based on or derived from SEQ ID NO: 1. CARs or portions thereof encoded by a polynucleotide may be at least about 70% identical to one or more polynucleotides based on or derived from SEQ ID NO: 1. Disclosed herein are vectors comprising one or more polynucleotides based on or derived from SEQ ID NO: 1.

Vectors comprising sequences encoding chimeric antigen receptors and/or chimeric antigen receptor effector cell switches and portions thereof, disclosed herein, may be selected from any commercially available expression vector. The expression vector may be a prokaryotic expression vector. The expression vector may be a eukaryotic expression vector. The expression vector may be a mammalian expression vector. The expression vector may be a viral expression vector. The expression vector may have a constitutive promoter for constitutive expression of the CAR and/or CAR-EC switch encoding sequences. The expression vector may have an inducible promoter for conditional expression of the CAR and/or CAR-EC switch encoding sequences.

VI. Therapeutic Use

Disclosed herein are methods, platforms and kits for treating a disease or condition in a subject in need thereof, the method comprising administering a chimeric antigen receptor effector cell (CAR-EC) switch to the subject, wherein the CAR-EC switch comprises: a CAR-binding peptidic antigen; and a targeting moiety. Disclosed herein are methods of treating a disease or condition in a subject in need thereof, the method comprising administering any one of the CAR-EC switches disclosed herein. The disease or condition may be cancer.

The methods may comprise administering a CAR-EC cell and one or more CAR-EC switches. The methods may comprise administering about 1, 2, 3, 4, 5, 6, 7, 8, 9, 10, 12, 15, 20, 24, 30, 35, 48, 50, 55, 60, 65, 70, 75, 80, 85, 90, 96, 100, 120, 150, 200, 300, 384, 400, 500, 600, 700, 800, 900, 1000 or more CAR-EC switches. The methods may comprise administering two or more CAR-EC switches. The two or more CAR-EC switches may comprise the same CAR-binding peptidic antigen. The two more CAR-EC switches may comprise the same cell targeting polypeptide. The two or more CAR-EC switches may comprise one or more different CAR-binding peptidic antigens. The two more CAR-EC switches may comprise one or more different cell targeting polypeptides. The methods may comprising a plurality of CAR-EC cells and one or more CAR-EC switches. Administering the CAR-EC cell may comprise intravenous CAR-EC delivery. Administering the CAR-EC cell may comprise intraperitoneal CAR-EC delivery. Administering the CAR-EC cell may comprise intravenous CAR-EC delivery and intraperitoneal CAR-EC delivery. Administering the CAR-EC cell may occur once. Administering the CAR-EC cell may occur more than once (e.g., repeat injection). The CAR-ECs may be sorted to enrich a memory population of CAR-ECs before administering the CAR-ECs. The CAR-ECs may be subjected to iterative stimulation to enrich the memory population, as opposed to recursive stimulation which promotes exhaustion, provide for a long-lived, persistent phenotype. This rationale is based on natural acute infections with enrich long-lived memory cells through a 1-2 week long contraction phase that occurs after the challenge has been cleared. Similarly, the sCAR-T cell system in which adoptively transferred cells are rested following stimulation may more closely recapitulate a physiological duration of T cell activation.

Disclosed herein are methods of treating a disease or condition in a subject in need thereof, the method comprising administering a chimeric antigen receptor effector cell (CAR-EC) switch to the subject, wherein the CAR-EC switch comprises: a chimeric antigen receptor binding peptidic antigen (CAR-BP); and a targeting moiety that binds an antigen on a target. The CAR-BP, by non-limiting example, may be selected from a FLAG® tag, a yeast transcription factor GCN4 and a hydrophilic target peptide (HTP). The targeting moiety, by non-limiting example may be selected from an anti-CD19 antibody, an anti-CD20 antibody, an anti-CD22 antibody, an anti-EGFR antibody, an anti-EGFRvIII antibody, an anti-Her2 antibody, an anti-CS1 antibody, an anti-BCMA antibody, an anti-CEA antibody, an anti-CLL1 antibody and an anti-CD33 antibody.

The methods may comprise administering one or more chimeric antigen receptor effector cells to a subject in need thereof and then administering one or CAR-EC switches to a subject in need thereof. The amount or dose of CAR-EC switch may affect the magnitude of the chimeric antigen receptor effector cells toward the target cells, therefore the amount or dose of the CAR-EC switch may be titrated for a desired effect. For example, tumors may be targeted by titration of CAR-EC switch to achieve suitable therapeutic index. The response may be titrated "on" to avoid CRS (cytokine release syndrome) and TLS (tumor lysis syndrome) events, providing for personalized therapy. Furthermore, administration of a switch can be terminated in case of an adverse event, control of CAR-EC cell activity, titration of off-target reactivity, abrogation of tumor lysis syndrome (TLS), or attenuation of cytokine release syndrome (CRS). The amount or dose may start at one level for a specified time period and then the amount or dose may be increased or decreased to a second level for a second specified time period. For example, the initial amount or dose of the CAR-EC switch may be the lowest dose necessary to eliminate the tumor. The amount or dose of the CAR-EC switch may then be increased to a larger dose in order to eliminate any remaining tumor cells. The methods may comprise terminating the administration of the CAR-EC switch once the tumor cells are eliminated. The methods may comprise re-administering the CAR-EC switch if the tumor cells re-occur in the patient or if the patient relapses.

The methods may comprise titrating the CAR-EC switch for a desired effect. Titrating the CAR-EC switch may enable antigen density discrimination. For example, the fatal on-target, off-tumor reactivity for Her2 targeted CAR-T cells to low levels of Her2 expression in the lung has tempered the application of CAR-T cells to solid tumors in the clinic. The use of a Fab-based switch that is expected to have a half-life of approximately 10h in human allows a more rapid decrease in activity than long-live IgG-based molecules. The methods described herein may comprise titrating a switch to an optimal level wherein the switch activity may be affected by the density of Her2, thereby discriminating or distinguishing Her2 (and switch activity) on cancer cells from Her2 on healthy tissue. In the clinic this may be used to titrate therapy to an appropriate therapeutic index. Additionally, it may be possible in patients to decouple infusion of sCAR-T cells from activation by administering the switch only after adoptively transferred sCAR-T cells have cleared a tissue (e.g., the lungs in the case of Her2), thus mitigating potential toxicities to the tissue. For example, studies have shown that transferred cytotoxic T cells immediately accumulate in the lung, but the accumulation clears over 72 hours. One advantage of sCAR-T cells is that they can be transferred and the switch dose can be delayed until the sCAR-T cells have cleared the lung, during which time, the sCAR-T cells are inert. Once cleared, switch may be administered to activate the sCAR-T upon binding of the switch to the CAR and the target antigen. One skilled in the art would readily understand how this concept would apply to other antigens besides Her2 that are expressed on cells at varying densities.

The methods may comprise administering one or more chimeric antigen receptor effector cells. The methods may comprise administering one or more T cells. The one or more effector cells may be selected from T cell is selected from a naive T cell, a memory stem cell T cell, a central memory T cell, an effector memory T cell, a helper T cell, a CD4+ T cell, a CD8+ T cell, a CD8/CD4+ T cell, an $\alpha\beta$ T cell, a $\gamma\delta$ T cell, a cytotoxic T cell, a natural killer T cell, a natural killer cell, a macrophage.

The CAR-EC switch may have a therapeutic effect that is at least partially dependent on bringing an effector cell in proximity of a target cell. The therapeutic effect on the intended indication of the CAR-EC switch may be at least partially due to the CAR-EC switch recruiting an effector cell to the target cell. The therapeutic effect on the intended indication of the CAR-EC switch may be predominantly due to the CAR-EC switch recruiting an effector cell to the target cell. The therapeutic effect of the CAR-EC switch may be at least partially dependent on stimulating an immune response in the CAR-EC cell.

Administering the CAR-EC switch may not have any therapeutic effect without further administering an effector cell. The CAR-EC switch may not have a significant, desirable and/or intended therapeutic effect without further administering an effector cell. The CAR-EC switch may not have any therapeutic effect towards an intended indication of the CAR-EC platform without further administering an effector cell. A portion or component of the CAR-EC switch (e.g., CAR-BP or targeting moiety) may not have a therapeutic effect towards the intended indication of the CAR-EC switch without being conjugated to a second portion or component of the CAR-EC switch (e.g., CAR-BP or targeting moiety). The dose of a portion or component of the CAR-EC switch (e.g., CAR-BP or targeting moiety) when administered as part of the CAR-EC platform to provide a therapeutic effect may not have a therapeutic effect when the portion or component of the CAR-EC switch is administered alone at that dose. The portion or component of the CAR-EC switch may not be intended to have any therapeutic effect besides recruiting the T cell to the target cell. Administering the portion or component of the CAR-EC switch alone may have a therapeutic effect on the target cell, wherein the therapeutic effect is negligible relative to the therapeutic effect of administering the CAR-EC switch and the CAR-EC cell. Administering the portion or component of the CAR-EC switch may have a therapeutic effect on the target cell, wherein the therapeutic effect is less than the therapeutic effect of administering the CAR-EC switch and the CAR-EC cell.

Disclosed herein are uses of CAR-EC switches disclosed herein to treat a disease or condition in a subject in need thereof. Further disclosed herein are uses of CAR-EC switches disclosed herein in the manufacture of a medicament for the treatment of a disease.

Disclosed herein is use of a switch comprising a peptidic antigen that binds a CAR (CAR-BP) on an effector cell; and a targeting polypeptide that binds an antigen on a target to treat a disease or condition in a subject in need thereof. Further disclosed herein is use of a switch comprising a peptidic antigen (CAR-BP) that binds a CAR on an effector cell, wherein the CAR-BP; and a targeting polypeptide that binds an antigen on a target in the manufacture of a medicament for the treatment of a disease.

Disclosed herein is use of a CAR-EC switch comprising a CAR-BP, wherein the CAR-BP comprises a low immunogenicity peptide (e.g., FLAG) or derivative thereof and a targeting polypeptide, wherein the targeting polypeptide comprises an anti-CD19 antibody or fragment thereof; and an effector cell comprising a CAR, wherein the CAR comprises an anti-low immunogenicity peptide antibody, wherein the anti-CD19 antibody or fragment thereof binds CD19 on a B cell to treat a multiple myeloma. Notably, no previously reported antibody-based control system has reported targeting of CD19 in vivo. As reported herein, sCAR-T cell platforms were able to eliminate Nalm-$6^{Luc/GFP}$ in vivo with comparable efficacy to conventional CART-19. Efficacy was reliant on optimal target cell engagement. More specifically, differences in the in vitro lytic activity of switch/hinge designs which were generally less than 10 fold in $EC_{50}$ were decisive for in vivo tumor elimination.

Disclosed herein is use of a CAR-EC switch comprising a CAR-BP, wherein the CAR-BP comprises a yeast transcription factor GCN4 or derivative thereof and a targeting polypeptide, wherein the targeting polypeptide comprises an anti-CD19 antibody or fragment thereof, and an effector cell comprising a CAR, wherein the CAR comprises an anti-GCN4 antibody, wherein the anti-CD19 antibody or fragment thereof binds CD19 on a lymphoblast, lymphocyte or B cell, to treat an acute lymphoblastic leukemia, a chronic lymphocytic leukemia or a B-cell lymphoma.

The disease or condition may be a cell proliferative disorder. The cell proliferative disorder may be selected from a solid tumor, a lymphoma, a leukemia and a liposarcoma. The cell proliferative disorder may be acute, chronic, recurrent, refractory, accelerated, in remission, stage I, stage II, stage III, stage IV, juvenile or adult. The cell proliferative disorder may be selected from myelogenous leukemia, lymphoblastic leukemia, myeloid leukemia, an acute myeloid leukemia, myelomonocytic leukemia, neutrophilic leukemia, myelodysplastic syndrome, B-cell lymphoma, burkitt lymphoma, large cell lymphoma, mixed cell lymphoma, follicular lymphoma, mantle cell lymphoma, hodgkin lymphoma, recurrent small lymphocytic lymphoma, hairy cell leukemia, multiple myeloma, basophilic leukemia, eosinophilic leukemia, megakaryoblastic leukemia, monoblastic leukemia, monocytic leukemia, erythroleukemia, erythroid leukemia and hepatocellular carcinoma. The cell proliferative disorder may comprise a hematological malignancy. The hematological malignancy may comprise a B cell malignancy. The cell proliferative disorder may comprise a chronic lymphocytic leukemia. The cell proliferative disorder may comprise an acute lymphoblastic leukemia. The cell proliferative disorder may comprise a CD19-positive Burkitt's lymphoma.

The disease or condition may be a cancer, a pathogenic infection, autoimmune disease, inflammatory disease, or genetic disorder.

In some instances, the one or more diseases comprise a cancer. The cancer may comprise a recurrent and/or refractory cancer. Examples of cancers include, but are not limited to, sarcomas, carcinomas, lymphomas or leukemias.

The cancer may comprise a neuroendocrine cancer. The cancer may comprise a pancreatic cancer. The cancer may comprise an exocrine pancreatic cancer. The cancer may comprise a thyroid cancer. The thyroid cancer may comprise a medullary thyroid cancer. The cancer may comprise a prostate cancer.

The cancer may comprise an epithelial cancer. The cancer may comprise a breast cancer. The cancer may comprise an endometrial cancer. The cancer may comprise an ovarian cancer. The ovarian cancer may comprise a stromal ovarian cancer. The cancer may comprise a cervical cancer.

The cancer may comprise a skin cancer. The skin cancer may comprise a neo-angiogenic skin cancer. The skin cancer may comprise a melanoma.

The cancer may comprise a kidney cancer.

The cancer may comprise a lung cancer. The lung cancer may comprise a small cell lung cancer. The lung cancer may comprise a non-small cell lung cancer.

The cancer may comprise a colorectal cancer. The cancer may comprise a gastric cancer. The cancer may comprise a colon cancer.

The cancer may comprise a brain cancer. The brain cancer may comprise a brain tumor. The cancer may comprise a glioblastoma. The cancer may comprise an astrocytoma.

The cancer may comprise a blood cancer. The blood cancer may comprise a leukemia. The leukemia may comprise a myeloid leukemia. The cancer may comprise a lymphoma. The lymphoma may comprise a non-Hodgkin's lymphoma.

The cancer may comprise a sarcoma. The sarcoma may comprise an Ewing's sarcoma.

Sarcomas are cancers of the bone, cartilage, fat, muscle, blood vessels, or other connective or supportive tissue.

Sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g., alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some instances, the cancer is a skin cancer, such as a basal cell carcinoma, squamous, melanoma, nonmelanoma, or actinic (solar) keratosis.

In some instances, the cancer is a lung cancer. Lung cancer may start in the airways that branch off the trachea to supply the lungs (bronchi) or the small air sacs of the lung (the alveoli). Lung cancers include non-small cell lung carcinoma (NSCLC), small cell lung carcinoma, and mesotheliomia. Examples of NSCLC include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

Alternatively, the cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. In some instances, the cancer is a meningioma.

The leukemia may be an acute lymphocytic leukemia, acute myelocytic leukemia, chronic lymphocytic leukemia, or chronic myelocytic leukemia. Additional types of leukemias include hairy cell leukemia, chronic myelomonocytic leukemia, and juvenile myelomonocytic leukemia.

Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenström macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

The cancer may comprise a solid tumor. The cancer may comprise a sarcoma. The cancer may be selected from a group consisting of a bladder cancer, a breast cancer, a colon cancer, a rectal cancer, an endometrial cancer, a kidney cancer, a lung cancer, melanoma, a myeloma, a thyroid cancer, a pancreatic cancer, a glioma, a malignant glioma of the brain, a glioblastoma, an ovarian cancer, and a prostate cancer. The cancer may have non-uniform antigen expression. The cancer may have modulated antigen expression. The antigen may be a surface antigen. The cancer may not comprise a myeloma. The cancer may not comprise a melanoma. The cancer may not comprise a colon cancer. The cancer may be acute lymphoblastic leukemia (ALL). The cancer may be relapsed ALL. The cancer may be refractory ALL. The cancer may be relapsed, refractory ALL. The cancer may be chronic lymphocytic leukemia (CLL). The cancer may be relapsed CLL. The cancer may be refractory CLL. The cancer may be relapsed, refractory CLL.

The cancer may comprise a breast cancer. The breast cancer may be triple positive breast cancer (estrogen receptor, progesterone receptor and Her2 positive). The breast cancer may be triple negative breast cancer (estrogen receptor, progesterone receptor and Her2 negative). The breast cancer may be estrogen receptor positive. The breast cancer may be estrogen receptor negative. The breast cancer may be progesterone receptor positive. The breast cancer may be progesterone receptor negative. The breast cancer may comprise a Her2 negative breast cancer. The breast cancer may comprise a low-expressing Her2 breast cancer. The breast cancer may comprise a Her2 positive breast cancer. Cell lines expressing Her2 have been well-characterized for antigen density, reflecting clinical immunohistochemistry characterization which classifies malignancies as 0 (<20,000 Her2 antigens per cell), 1+(100,000 Her2 antigens per cell), 2+(500,000 Her2 antigens per cell), and 3+(>2,000,000 Her2 antigens per cell). The present invention provides for methods of treating breast cancers of these classifications. The breast cancer may comprise a breast cancer classified as Her2 0. The breast cancer may comprise a breast cancer classified as Her2 1+. The breast cancer may comprise a breast cancer classified as Her2 2+. The breast cancer may comprise a breast cancer classified as a Her2 3+.

The disease or condition may be a pathogenic infection. Pathogenic infections may be caused by one or more pathogens. In some instances, the pathogen is a bacterium, fungi, virus, or protozoan.

Exemplary pathogens include but are not limited to: *Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio*, or *Yersinia*. In some cases, the disease or condition caused by the pathogen is tuberculosis and the heterogeneous sample comprises foreign molecules derived from the bacterium *Mycobacterium tuberculosis* and molecules derived from the subject. In some instances, the disease or condition is caused by a bacterium is tuberculosis, pneumonia, which may be caused by bacteria such as *Streptococcus* and *Pseudomonas*, a foodborne illness, which may be caused by bacteria such as *Shigella, Campylobacter* and *Salmonella*, and an infection such as tetanus, typhoid fever, diphtheria, syphilis and leprosy. The disease or condition may be bacterial vaginosis, a disease of the vagina caused by an imbalance of naturally occurring bacterial flora. Alternatively, the disease or condition is a bacterial meningitis, a bacterial inflammation of the meninges (e.g., the protective membranes covering the brain and spinal cord). Other diseases or conditions caused by bacteria include, but are not limited to, bacterial pneumonia, a urinary tract infection, bacterial gastroenteritis, and bacterial skin infection. Examples of bacterial skin infections include, but are not limited to, impetigo which may be caused by *Staphylococcus aureus* or *Streptococcus pyogenes*; erysipelas which may be caused by a *Streptococcus* bacterial infection of the deep epidermis with lymphatic spread; and cellulitis which may be caused by normal skin flora or by exogenous bacteria.

The pathogen may be a fungus, such as, *Candida, Aspergillus, Cryptococcus, Histoplasma, Pneumocystis*, and *Stachybotrys*. Examples of diseases or conditions caused by a fungus include, but are not limited to, jock itch, yeast infection, ringworm, and athlete's foot.

The pathogen may be a virus. Examples of viruses include, but are not limited to, adenovirus, coxsackievirus, Epstein-Barr virus, Hepatitis virus (e.g., Hepatitis A, B, and C), herpes simplex virus (type 1 and 2), cytomegalovirus, herpes virus, HIV, influenza virus, measles virus, mumps virus, papillomavirus, parainfluenza virus, poliovirus, respiratory syncytial virus, rubella virus, and varicella-zoster virus. Examples of diseases or conditions caused by viruses include, but are not limited to, cold, flu, hepatitis, AIDS, chicken pox, rubella, mumps, measles, warts, and poliomyelitis.

The pathogen may be a protozoan, such as *Acanthamoeba* (e.g., *A. astronyxis, A. castellanii, A. culbertsoni, A. hatchetti, A. polyphaga, A. rhysodes, A. healyi, A. divionensis*), *Brachiola* (e.g., *B connori, B. vesicularum*), *Cryptosporidium* (e.g., *C. parvum*), *Cyclospora* (e.g., *C. cayetanensis*), *Encephalitozoon* (e.g., *E. cuniculi, E. hellem, E. intestinalis*), *Entamoeba* (e.g., *E. histolytica*), *Enterocytozoon* (e.g., *E. bieneusi*), *Giardia* (e.g., *G. lamblia*), *Isospora* (e.g, *I. belli*), *Microsporidium* (e.g., *M. africanum, M. ceylonensis*), *Naegleria* (e.g., *N. fowleri*), *Nosema* (e.g., *N. algerae, N. ocularum*), *Pleistophora, Trachipleistophora* (e.g., *T. anthropophthera, T. hominis*), and *Vittaforma* (e.g., *V. corneae*).

The disease or condition may be an autoimmune disease or autoimmune related disease. An autoimmune disorder may be a malfunction of the body's immune system that causes the body to attack its own tissues. Examples of autoimmune diseases and autoimmune related diseases include, but are not limited to, Addison's disease, alopecia areata, ankylosing spondylitis, antiphospholipid syndrome (APS), autoimmune aplastic anemia, autoimmune hemolytic anemia, autoimmune hepatitis, autoimmune myocarditis, Behcet's disease, celiac sprue, Crohn's disease, dermatomyositis, eosinophilic fasciitis, erythema nodosum, giant cell arteritis (temporal arteritis), Goodpasture's syndrome, Graves' disease, Hashimoto's disease, idiopathic thrombocytopenic purpura (ITP), IgA nephropathy, juvenile arthritis, diabetes, juvenile diabetes, Kawasaki syndrome, Lambert-Eaton syndrome, lupus (SLE), mixed connective tissue disease (MCTD), multiple sclerosis, myasthenia gravis, pemphigus, polyarteritis nodosa, type I, II, & III autoimmune polyglandular syndromes, polymyalgia rheumatica, polymyositis, psoriasis, psoriatic arthritis, Reiter's syndrome, relapsing polychondritis, rheumatoid arthritis, sarcoidosis, scleroderma, Sjogren's syndrome, sperm & testicular autoimmunity, stiff person syndrome, Takayasu's arteritis, temporal arteritis/giant cell arteritis, ulcerative colitis, uveitis, vasculitis, vitiligo, and Wegener's granulomatosis.

The disease or condition may be an inflammatory disease. Examples of inflammatory diseases include, but are not limited to, alveolitis, amyloidosis, angiitis, ankylosing spondylitis, avascular necrosis, Basedow's disease, Bell's palsy, bursitis, carpal tunnel syndrome, celiac disease, cholangitis, chondromalacia patella, chronic active hepatitis, chronic fatigue syndrome, Cogan's syndrome, congenital hip dysplasia, costochondritis, Crohn's Disease, cystic fibrosis, De Quervain's tendinitis, diabetes associated arthritis, diffuse idiopathic skeletal hyperostosis, discoid lupus, Ehlers-Danlos syndrome, familial mediterranean fever, fascitis, fibrositis/fibromyalgia, frozen shoulder, ganglion cysts, giant cell arteritis, gout, Graves' Disease, HIV-associated rheumatic disease syndromes, hyperparathyroid associated arthritis, infectious arthritis, inflammatory bowel syndrome/irritable bowel syndrome, juvenile rheumatoid arthritis, lyme disease, Marfan's Syndrome, Mikulicz's Disease, mixed connective tissue disease, multiple sclerosis, myofascial pain syndrome, osteoarthritis, osteomalacia, osteoporosis and corticosteroid-induced osteoporosis, Paget's Disease, palindromic rheumatism, Parkinson's Disease, Plummer's Disease, polymyalgia rheumatica, polymyositis, pseudogout, psoriatic arthritis, Raynaud's Phenomenon/Syndrome, Reiter's Syndrome, rheumatic fever, rheumatoid arthritis, sarcoidosis, sciatica (lumbar radiculopathy), scleroderma, scurvy, sickle cell arthritis, Sjogren's Syndrome, spinal stenosis, spondyloisthesis, Still's Disease, systemic lupus erythematosis, Takayasu's (Pulseless) Disease, Tendinitis, tennis elbow/golf elbow, thyroid associated arthritis, trigger finger, ulcerative colitis, Wegener's Granulomatosis, and Whipple's Disease.

Methods of treatment disclosed herein may comprise off-target activity as measured by cytokine levels. The method may reduce the off-target activity, as measured by cytokine levels, when compared to other CAR-EC therapies. The method may reduce the off-target activity as measured by interferon gamma levels. Other off-target activities that may be reduced include toxic lymphophenia, fatal cytolysis of solid tumor targets and chronic hypogammaglobulinemia for hematological targets. Methods of treatment and compositions disclosed herein may be used to treat a cancer comprising CD19-mediated B cell aplasia. The methods and compositions may minimize the CD19-mediated B cell aplasia. The method may avoid long-term B-cell aplasia.

The CAR-EC platforms, methods and compositions disclosed herein may be used to treat a heterogeneous tumor or a heterogeneous blood cell malignancy in a subject in need thereof. The "pan-B cell" marker CD20 is the most prevalently targeted antigen for B cell neoplasms and the FDA-approved antibody rituximab is a vital component in the treatment of many leukemias and lymphomas. However, resistance mechanisms related to modulation of CD20 antigen expression occurs in a significant number of patients. It is clear that targeting with either CD19 or CD20 antigen alone is insufficient for a curative therapy. The methods disclosed herein provide for construction and administration of two or more switches with different specificities (e.g., an anti-CD19 antibody CAR-EC switch and an anti-CD20 antibody CAR-EC switch). The methods disclosed herein provide for construction and administration of two or more switches with different specificities (e.g., an anti-CD19 antibody CAR-EC switch and an anti-CD22 antibody CAR-EC switch). This methodology may offer a significant advantage against the propensity for relapse in the clinic while avoiding persistent loss of B cells. A heterogeneous tumor or heterogeneous blood cell malignancy may also be treated with an anti-CD19 antibody CAR-EC switch and an anti-CD22 antibody CAR-EC switch. One or more CAR-EC switches may be administered sequentially or simultaneously. A second switch targeting a second cell surface molecule on the target cell may be administered after down regulation of a first cell surface molecule on the target cell that is targeted by a first switch.

The CAR-EC switch may be administered with one or more additional therapeutic agents. The one or more additional therapeutic agents may be selected from a group consisting of an immunotherapy, a chemotherapy and a steroid. The one or more additional therapeutic agents may be a chemotherapy drug. The chemotherapy drug may be an alkylating agent, an antimetabolite, an anthracycline, a topoisomerase inhibitor, a mitotic inhibitor, a corticosteroid or a differentiating agent. The chemotherapy drug may be selected from actinomycin-D, bleomycin, altretamine, bortezomib, busulfan, carboplatin, capecitabine, carmustine, chlorambucil, cisplatin, cladribine, clofarabine, cyclophosphamide, cytarabine, dacarbazine, daunorubicin, docetaxel, doxorubicin, epirubicin, etoposide, estramustine, floxuridine, fludarabine, fluorouracil, gemcitbine (Gemzar), hydroxyurea, idarubicin, ifosfamide, irinotecan (Camptosar), ixabepilone, L-asparaginase, lomustine, mechlorethamine, melphalan, 6-mercaptopurine, methotrexate, mitomycin-C, paclitaxel (Taxol), pemetrexed, pentostatin, streptozocin, temozolomide, teniposide, thioguanine, thiotepa, topotecan (Hycamtin), vincristine, vinblastine, vinorelbine, retinoids, tretinoin (ATRA or Atralin®), bexarotene (Targretin®) and arsenic trioxide (Arsenox®). The chemotherapy may be administered as a pill to swallow, as an injection into the muscle or fat tissue, intravenously, topically or directly into a body cavity.

The one or more additional therapeutic agents may comprise an angiogenesis inhibitor. The angiogenesis inhibitor may be selected from bevacizumab, itraconazole, carboxyamidotriazole, TNP-470, CM101, IFN alpha, IL-12, platelet factor 4, suramin, SU5416, thrombospondin, a VEGFR antagonist, an angiostatic steroid with heparin, CAR-ECilage-derived angiogenesis inhibitory factor, matrix metalloprotease inhibitors, angiostatin, endostatin, sorafenib, sunitinib, pazopanib, everolimus, 2-methoxyestradiol, tecogalan, tetrathiomolybdate, thalidomide, prolactin, $\alpha v\beta_3$ inhibitor, linomide, tasquinimod, soluble VEGFR-1, soluble NRP-1, angiopoietin 2, vasostatin, calreticulin, TIMP, CDAI, Meth-1, Meth-2, interferon-alpha, interferon-beta, interferon-gamma, CXCL10, IL-4, IL-12, IL-18, prothrombin, antithrombin III fragment, prolactin, VEGI, SPARC, osteopontin, maspin, canstatin, proliferin-related protein and restin.

The one or more additional therapeutic agents may comprise a hormone therapy. The hormone therapy may be selected from an anti-estrogen (e.g., fulvestrant (Faslodex®), tamoxifen, toremifene (Fareston®)); an aromatase inhibitor (e.g., anastrozole (Arimidex®), exemestane (Aromasin®), letrozole (Femara®)); a progestin (e.g., megestrol acetate (Megace®)); an estrogen; an anti-androgen (e.g., bicalutamide (Casodex®), flutamide (Eulexin®), nilutamide (Nilandron®)); a gonadotropin-releasing hormone (GnRH) or luteinizing hormone-releasing hormone (LHRH) agonist or analog (e.g., leuprolide (Lupron®), goserelin (Zoladex®)).

The one or more additional therapeutic agents may comprise a steroid. The steroid may be a corticosteroid. The steroid may be cortisol or a derivative thereof. The steroid may be selected from prednisone, methylprednisolone (Solumedrol®) or dexamethasone.

The CAR-EC switch may be administered with one or more additional therapies. The one or more additional therapies may comprise laser therapy. The one or more additional therapies may comprise radiation therapy. The one or more additional therapies may comprise surgery.

Disclosed herein are platforms, kits and methods for treating a disease or condition in a subject. The subject may be a healthy subject. The subject may be suffering from a disease or condition. The subject may be suffering from more than one disease or condition. The subject may be suffering from chronic lymphocytic leukemia. The subject may be suffering from acute lymphoblastic leukemia. The subject may be an animal. The subject may be a mammal. The mammal may be a human, a chimpanzee, a gorilla, a monkey, a bovine, a horse, a donkey, a mule, a dog, a cat, a pig, a rabbit, a goat, a sheep, a rat, a hamster, a guinea pig or a mouse. The subject may be a bird or a chicken. The subject may be a human. The subject may be a child. The child may be suffering from acute lymphoblastic leukemia. The subject may be less than 6 months old. The subject may be about 1 year old, about 2 years old, about 3 years old, about 4 years old, about 5 years old, about 6 years old, about 7 years old, about 8 years old, about 9 years old, about 10 years old, about 11 years old, about 12 years old, about 13 years old, about 14 years old, about 15 years old, about 18 years old, about 20 years old, about 25 years old, about 30 years old, about 35 years old, about 40 years old, about 45 years old, about 50 years old, about 55 years old, about 60 years old, about 65 years old, about 70 years old, about 75 years old, about 80 years old, about 85 years old, about 90 years old, about 95 years old, about 100 years old or about 105 years old.

VII. Method of Clearing Effector Cells

Further disclosed herein are methods of clearing CAR-EC cells in a subject, comprising administering a CAR-EC off switch. The CAR-EC off switch may comprise an antibody or antibody fragment that targets a cell surface marker on the effector cell. The CAR-EC off switch may comprise a peptide that is bound by the CAR of the CAR-EC. The CAR-EC off switch may comprise a CAR-BP that is bound by the CAR of the CAR-EC.

The antibody, antibody fragment or peptide of the CAR-EC off switch may be conjugated to a drug or a toxin. The drug or toxin may be selected from maytasine (e.g., DM1, DM4), monomethylauristatin E, monomethylauristatin F, Ki-4.dgA, dolastatin 10, calicheamicin, SN-38, duocarmycin, irinotecan, ricin, saporin, gelonin, poke weed antiviral protein, *Pseudomonas aeruginosa* exotoxin A or diphtheria toxin. The toxin may comprise a poison, a bacterial toxin (e.g., bacterial toxins causing tetanus, diphtheria), a plant toxin or animal toxin. The toxin may be a snake venom. The toxin may comprise vinblastine. The toxin may comprise auristatin. The toxin may be contained in a liposome membrane-coated vesicle. Wherein the toxin is contained in a liposome membrane-coated vesicle, the antibody is attached to the vesicle.

The cell surface marker may be a viral protein or fragment thereof. Alternatively or additionally, the effector cell expresses a viral protein or fragment thereof that is not a cell surface marker. The effector cell expressing a viral protein or fragment thereof may be targeted with a drug. Wherein the effector cell comprises a viral protein or fragment thereof, the drug may be selected from a group comprising abacavir, acyclovir, acyclovir, adefovir, amantadine, amprenavir, ampligen, arbidol, atazanavir, atripla, balavir, boceprevirertet, cidofovir, combivir, darunavir, delavirdine, didanosine, docosanol, edoxudine, efavirenz, emtricitabine, enfuvirtide, entecavir, an entry inhibitor, famciclovir, a fixed dose combination antiretroviral drug, fomivirsen, fosamprenavir, foscarnet, fosfonet, a fusion inhibitor, ganciclovir, ibacitabine, imunovir, idoxuridine, imiquimod, indinavir, inosine, integrase inhibitor, interferon type III, interferon type II, interferon type I, interferon, lamivudine, lopinavir, loviride, maraviroc, moroxydine, methisazone, nelfinavir, nevirapine, nexavir, nucleoside analogue, oseltamivir, peginterferon alfa-2a, penciclovir, peramivir, pleconaril, podophyllotoxin, protease inhibiro, raltegravir, a reverse transcriptase inhibitor, ribavirin, rimantadine, ritonavir, pyramidine, saquinavir, sofosbuvir, stavudine, a synergistic enhancer retroviral durg, tea tree oil, telaprevir, tenofovir, tenofovir disoproxil, tipranavir, trifluridine, trizivir, tromantadine, truvada, valaciclovir, vicriviroc, vidarabine, viramidine, zacitabine, zanamivir or zidovudine. The drug may be ganciclovir. The drug may be acyclovir.

VIII. Pharmaceutical Compositions

Disclosed herein is a pharmaceutical composition comprising one or more of the CAR-EC switches disclosed herein. The compositions may further comprise one or more pharmaceutically acceptable salts, excipients or vehicles. Pharmaceutically acceptable salts, excipients, or vehicles for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with serum albumin are exemplary appropriate carriers. The pharmaceutical compositions may include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also may be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers may be conventional buffers such as acetate, borate, citrate, phosphate, bicarbonate, or Tris-HCl. Acetate buffer may be about pH 4-5.5, and Tris buffer may be about pH 7-8.5. Additional pharmaceutical agents are set forth in Remington's Pharmaceutical Sciences, 18th Edition, A. R. Gennaro, ed., Mack Publishing Company, 1990.

The composition may be in liquid form or in a lyophilized or freeze-dried form and may include one or more lyoprotectants, excipients, surfactants, high molecular weight structural additives and/or bulking agents (see, for example, U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g., polysorbate 20, polysorbate 80); poloxamers (e.g., poloxamer 188); poly(ethylene glycol) phenyl ethers (e.g., Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; and the MONAQUAT™. series (Mona Industries, Inc., Paterson, N.J.), polyethyl glycol, polypropyl glycol, and copolymers of ethylene and propylene glycol (e.g., Pluronics, PF68 etc). Exemplary amounts of surfactant that may be present in the pre-lyophilized formulation are from about 0.001-0.5%. High molecular weight structural additives (e.g., fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e.g., mannitol, glycine) may be included.

Compositions may be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically will be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980.

Pharmaceutical compositions described herein may be formulated for controlled or sustained delivery in a manner that provides local concentration of the product (e.g., bolus, depot effect) and/or increased stability or half-life in a particular local environment. The compositions may comprise the formulation of CAR-EC switches, polypeptides, nucleic acids, or vectors disclosed herein with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then may be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., antibodies comprising an ultralong CDR3). See, for example, the description of controlled release porous polymeric microparticles for the delivery of pharmaceutical compositions in WO 93/15722. Suitable materials for this purpose include polylactides (see, e.g., U.S. Pat. No. 3,773,919), polymers of poly-(a-hydroxycarboxylic acids), such as poly-D-(−)-3-hydroxybutyric acid (EP 133,988A), copolymers of L-glutamic acid and gamma ethyl-L-glutamate (Sidman et al., Biopolymers, 22: 547-556 (1983)), poly(2-hydroxyethyl-methacrylate) (Langer et al., J. Biomed. Mater. Res., 15: 167-277 (1981), and Langer, Chem. Tech., 12: 98-105 (1982)), ethylene vinyl acetate, or poly-D(−)-3-hydroxybutyric acid. Other biodegradable polymers include poly(lactones), poly(acetals), poly(orthoesters), and poly(orthocarbonates). Sustained-release compositions also may include liposomes, which may be prepared by any of several methods known in the art (see, e.g., Eppstein et al., Proc. Natl. Acad. Sci. USA, 82: 3688-92 (1985)). The carrier itself, or its degradation products, should be nontoxic in the target tissue and should not further aggravate the condition. This may be determined by routine screening in animal models of the target disorder or, if such models are unavailable, in normal animals. Microencapsulation of recombinant proteins for sustained release has been performed successfully with human growth hormone (rhGH), interferon-(rhIFN−), interleukin-2, and MN rgp120. Johnson et al., Nat. Med., 2:795-799 (1996); Yasuda, Biomed. Ther., 27:1221-1223 (1993); Hora et al., Bio/Technology. 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010. The sustained-release formulations of these proteins were developed using poly-lactic-coglycolic acid (PLGA) polymer due to its biocompatibility and wide range of biodegradable properties. The degradation products of PLGA, lactic and glycolic acids may be cleared quickly within the human body. Moreover, the degradability of this polymer may be depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41. Additional examples of sustained release compositions include, for example, EP 58,481A, U.S. Pat. No. 3,887,699, EP 158,277A, Canadian Patent No. 1176565, U. Sidman et al., Biopolymers 22, 547 [1983], R. Langer et al., Chem. Tech. 12, 98 [1982], Sinha et al., J. Control. Release 90, 261 [2003], Zhu et al., Nat. Biotechnol. 18, 24 [2000], and Dai et al., Colloids Surf B Biointerfaces 41, 117 [2005].

Bioadhesive polymers are also contemplated for use in or with compositions of the present disclosure. Bioadhesives are synthetic and naturally occurring materials able to adhere to biological substrates for extended time periods. For example, Carbopol and polycarbophil are both synthetic cross-linked derivatives of poly(acrylic acid). Bioadhesive delivery systems based on naturally occurring substances include for example hyaluronic acid, also known as hyaluronan. Hyaluronic acid is a naturally occurring mucopolysaccharide consisting of residues of D-glucuronic and N-acetyl-D-glucosamine. Hyaluronic acid is found in the extracellular tissue matrix of vertebrates, including in connective tissues, as well as in synovial fluid and in the vitreous and aqueous humor of the eye. Esterified derivatives of hyaluronic acid have been used to produce microspheres for use in delivery that are biocompatible and biodegradable (see, for example, Cortivo et al., Biomaterials (1991) 12:727-730; EP 517,565; WO 96/29998; Illum et al., J. Controlled Rel. (1994) 29:133-141).

Both biodegradable and non-biodegradable polymeric matrices may be used to deliver compositions of the present disclosure, and such polymeric matrices may comprise natural or synthetic polymers. Biodegradable matrices are preferred. The period of time over which release occurs is based on selection of the polymer. Typically, release over a period ranging from between a few hours and three to twelve months is most desirable. Exemplary synthetic polymers which may be used to form the biodegradable delivery system include: polymers of lactic acid and glycolic acid, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyanhydrides, polyurethanes and co-polymers thereof, poly(butic acid), poly(valeric acid), alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), polyvinyl acetate, poly vinyl chloride, polystyrene and polyvinylpyrrolidone. Exemplary natural polymers include alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The polymer optionally is in the form of a hydrogel (see, for example, WO 04/009664, WO 05/087201, Sawhney, et al., Macromolecules, 1993, 26, 581-587) that can absorb up to about 90% of its weight in water and further, optionally is cross-linked with multi-valent ions or other polymers.

Delivery systems also include non-polymer systems that are lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the product is contained in a form within a matrix such as those described in U.S. Pat. Nos. 4,452,775, 4,675,189 and 5,736,152 and (b) diffusional systems in which a product permeates at a controlled rate from a polymer such as described in U.S. Pat. Nos. 3,854,480, 5,133,974 and 5,407,686. Liposomes containing the product may be prepared by methods known methods, such as for example (DE 3,218,121; Epstein et al., Proc. Natl. Acad. Sci. USA, 82: 3688-3692 (1985); Hwang et al., Proc. Natl. Acad. Sci. USA, 77: 4030-4034 (1980); EP 52,322; EP 36,676; EP 88,046; EP 143,949; EP 142,641; JP 83-118008; U.S. Pat. Nos. 4,485,045 and 4,544,545; and EP 102,324).

Alternatively or additionally, the compositions may be administered locally via implantation into the affected area of a membrane, sponge, or other appropriate material on to which a CAR-EC switch disclosed herein has been absorbed or encapsulated. Where an implantation device is used, the device may be implanted into any suitable tissue or organ, and delivery of a CAR-EC switch, nucleic acid, or vector disclosed herein may be directly through the device via bolus, or via continuous administration, or via catheter using continuous infusion.

A pharmaceutical composition comprising a CAR-EC switch disclosed herein may be formulated for inhalation, such as for example, as a dry powder. Inhalation solutions also may be formulated in a liquefied propellant for aerosol delivery. In yet another formulation, solutions may be nebulized. Additional pharmaceutical composition for pulmonary administration include, those described, for example, in WO 94/20069, which discloses pulmonary delivery of chemically modified proteins. For pulmonary delivery, the particle size should be suitable for delivery to the distal lung. For example, the particle size may be from 1 μm to 5 μm; however, larger particles may be used, for example, if each particle is fairly porous.

Certain formulations containing CAR-EC switches disclosed herein may be administered orally. Formulations administered in this fashion may be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents may be included to facilitate absorption of a selective binding agent. Diluents, flavorings, low melting point waxes, vegetable oils, lubricants, suspending agents, tablet disintegrating agents, and binders also may be employed.

Another preparation may involve an effective quantity of a CAR-EC switch disclosed herein in a mixture with non-toxic excipients which are suitable for the manufacture of tablets. By dissolving the tablets in sterile water, or another appropriate vehicle, solutions may be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Suitable and/or preferred pharmaceutical formulations may be determined in view of the present disclosure and general knowledge of formulation technology, depending upon the intended route of administration, delivery format, and desired dosage. Regardless of the manner of administration, an effective dose may be calculated according to patient body weight, body surface area, or organ size. Further refinement of the calculations for determining the appropriate dosage for treatment involving each of the formulations described herein are routinely made in the art and is within the ambit of tasks routinely performed in the art. Appropriate dosages may be ascertained through use of appropriate dose-response data.

IX. CAR-EC Switch Production Methods

Disclosed herein are methods of producing CAR-EC switches comprising expressing one or more polypeptides from one or more vectors comprising one or more polynucleotide having one or more sequences that encode a chimeric antigen receptor-effector cell switch or a portion thereof, wherein the chimeric antigen receptor-effector cell switch comprises a peptidic antigen (CAR-BP) and a targeting polypeptide. The targeting moiety may comprise a targeting polypeptide. In general, the methods comprise fusing or grafting a polynucleotide encoding the CAR-BP to a polynucleotide encoding the targeting polypeptide. Fusing or grafting may be carried out by any standard cloning method known to one skilled in the art. Fusing or grafting the polynucleotides encoding the CAR-BP and targeting polypeptide may comprise enzymatic digestion of the polynucleotides, ligation of the polynucleotides and/or amplification of the polynucleotides.

The peptidic antigen may be fused to an N terminus of the targeting polypeptide. The peptidic antigen may be fused to a C terminus of the targeting polypeptide. The peptidic antigen may be grafted within the targeting polypeptide. The targeting polypeptide may comprise a targeting antibody or antibody fragment. The peptidic antigen may be fused to an N terminus of the targeting antibody or antibody fragment.

The peptidic antigen may be fused to a C terminus of the targeting antibody or antibody fragment.

As used herein, the term "fused" may refer to adjoining a terminus of the CAR-BP with a terminus of the targeting polypeptide. The CAR-BP may be fused to the terminus of the targeting polypeptide without replacing or removing any amino acids of the targeting polypeptide. Fusing the CAR-BP to the terminus of the targeting polypeptide may comprise removing or replacing amino acids at the terminus of the targeting polypeptide. Removing or replacing amino acids at the terminus of the targeting polypeptide may comprise removing or replacing about 1 to about 20 amino acids at the terminus of the targeting polypeptide. The CAR-BP may be fused to the terminus of the targeting polypeptide via a linker. The linker may be fused to the CAR-BP to produce a CAR-BP-linker intermediate. The linker may be fused to a CAR-BP N terminus to produce the CAR-BP-linker intermediate. The linker may be fused to a CAR-BP C terminus to produce the CAR-BP-linker intermediate. The CAR-BP-linker intermediate may be fused to the targeting polypeptide. The CAR-BP-linker intermediate may be fused to the N terminus of the targeting polypeptide. The CAR-BP-linker intermediate may be fused to the C terminus of the targeting polypeptide. A first CAR-BP linker intermediate may be fused to the N terminus of the targeting polypeptide and a second CAR-BP linker intermediate may be fused to the C terminus of the targeting polypeptide. The CAR-BP of the first CAR-BP linker intermediate may be the same or similar to the CAR-BP of the second CAR-BP linker intermediate. The CAR-BP of the first CAR-BP linker intermediate may be different from the CAR-BP of the second CAR-BP linker intermediate.

As used herein, light chain grafts on the N-terminus may be referred to as LCNT. Light chain grafts on the C-terminus may be referred to as LCCT. Light chain grafts in the C1 domain may be referred to as LCC1. Heavy chain grafts on the N-terminus may be referred to as HCNT. Heavy chain grafts on the C-terminus may be referred to as HCCT. Heavy chain grafts in the C1 domain may be referred to as HCC1. Switches expressed with N-terminal grafts on the light and heavy chain may be referred to as NTBV. Switches expressed with C-terminal grafts on the light and heavy chain may be referred to as CTBV. Switches expressed with grafts in the C1 domain of the light and heavy chain may be referred to as C1BV.

As used herein, the term "grafted" may refer to inserting a CAR-BP within a targeting polypeptide (e.g., between two amino acids of the targeting polypeptide). The CAR-BP may be grafted within the targeting polypeptide without replacing or removing any amino acids of the targeting polypeptide. Grafting the CAR-BP within the targeting polypeptide may comprise removing or replacing amino acids within the targeting polypeptide. Removing or replacing amino acids within the targeting polypeptide may comprise removing or replacing about 1 to about 20 amino acids within the targeting polypeptide. The CAR-BP may be grafted within the targeting polypeptide via one linker. The CAR-BP may be grafted within the targeting polypeptide via two linkers. The linker may be fused to the CAR-BP N terminus to produce a CAR-BP-linker intermediate. The linker may be fused to the CAR-BP C terminus to produce a CAR-BP-linker intermediate. A first linker may be fused to the CAR-BP N terminus and a second linker may be fused to the CAR-BP C terminus to produce a CAR-BP-linker intermediate. The CAR-BP linker intermediate may be grafted with in the targeting polypeptide. A first CAR-BP linker intermediate may be grafted within the targeting polypeptide and a second CAR-BP linker intermediate may be grafted within the targeting polypeptide. The first CAR-BP linker intermediate may be grafted within a first domain of the targeting polypeptide and a second CAR-BP linker intermediate may be grafted within a second domain of the targeting polypeptide. The first domain of the targeting polypeptide may be the same as the second domain of the targeting polypeptide. The first domain of the targeting polypeptide may be different from the second domain of the targeting polypeptide. The CAR-BP of the first CAR-BP linker intermediate may be the same or similar to the CAR-BP of the second CAR-BP linker intermediate. The CAR-BP of the first CAR-BP linker intermediate may be different from the CAR-BP of the second CAR-BP linker intermediate. Unless otherwise specified, the terms "graft" and "insert", as used herein, are used interchangeably.

The targeting moiety may comprise an antibody or antibody fragment. The antibody or antibody fragment may comprise a heavy chain and a light chain or fragments thereof. The methods may comprise expressing a heavy chain wherein the peptidic antigen is fused to a terminus of the heavy chain. The methods may comprise expressing a heavy chain wherein the peptidic antigen is grafted within the heavy chain. The methods may comprise expressing a light chain wherein the peptidic antigen is fused to a terminus of the light chain. The methods may comprise expressing a light chain wherein the peptidic antigen is grafted within the light chain.

The methods may further comprise cloning one or more polynucleotides encoding the targeting polypeptide and/or the peptidic antigen into an expression vector. The methods may further comprise ligation of the one or more polynucleotides encoding the targeting polypeptide and/or peptidic antigen into an expression vector. The expression vector may be a prokaryotic expression vector. The expression vector may be a eukaryotic expression vector. The expression vector may be a mammalian expression vector. The expression vector may be a viral expression vector. The expression vector may be a pFUSE vector. The methods may further comprise validating the cloning of the one or more polynucleotides encoding the targeting polypeptide and/or peptidic antigen into the expression vector comprising sequencing the expression vector, running gel electrophoresis of the vector and/or viewing the targeting polypeptide and/or peptidic antigen on an SDS page gel.

The methods may further comprise amplifying a polynucleotide encoding the targeting polypeptide and/or peptidic antigen and cloning the targeting polypeptide and/or peptidic antigen into the expression vector. Amplifying the polynucleotide encoding the targeting polypeptide and/or the peptidic antigen may comprise synthesizing oligonucleotides at least partially complementary to the gene. The oligonucleotides may be sufficiently complementary to the gene to anneal to the polynucleotide. The oligonucleotides may comprise linker sequences. The linker sequences may be selected from SEQ ID NOs: 45-50, $(GGGGS)_n$, $(GGGS)_n$, $(GGS)_n$, $(G_mS)_n$, $(X_mS)_n$, and GG. wherein n is at least 1, m is at least 1, and X is any amino acid.

The methods may further comprise transfecting or infecting a cell with the expression vector. The methods may further comprise expressing the targeting polypeptide and/or peptidic antigen in the cell. The methods may further comprise expressing the targeting polypeptide and/or peptidic antigen in a cell free system. The methods may further comprise producing a virus comprising the expression vector. The methods may further comprise propagating the virus. The methods may further comprise infecting a cell with the virus comprising the expression vector. The methods may further comprise propagating the cell.

The switch may be expressed as two vectors, one of the heavy chain of the antibody and one for the light chain of the antibody. The two vectors may be co-transfected into an expression cell. The expression cell may be selected from a prokaryotic cell and a eukaryotic cell. The expression cell may be selected from a HEK cell and a CHO cell. Expression may be carried out in HEK cells over 7 or more days with routine harvesting of media to collect and isolate the antibody switch of interest. Expression may be carried out in less than 7 days. The switch may also be expressed from CHO cells in analogous fashion using the same plasmids. The media may or may not be harvested at intervals or may be harvested at the end of the expression. Harvesting at intervals may be preferable to preventing proteolytic degradation of the switch.

The switch may be expressed in *E. coli*. The switch may be expressed in *E. coli* from a vector, such as the pBAD vector, by way of non-limiting example. The pBAD vector may harbor both the light chain and the heavy chain of the antibody. This may require transformation of *E. coli* with only one plasmid. This may be advantageous as expression in *E. coli* is generally less expensive and faster than expression in mammalian cells (e.g., HEK cells). To express the switch in *E. coli*, careful attention must be paid to the genotype of the strain used. Preferable genotypes include, but are not limited to, those with the ompT gene (an outer membrane protein protease VII which may proteolyze the expressed protein) disrupted. This includes BL21 (*E. coli* B F-dcm ompT hsdS(rB− mB−) gal [ma1B+]K-12(2\S)), OverExpress(tm)C41(DE3) (Lucigen) (F-ompT gal dcm hsdSB(rB− mB−)(DE3)), and others. The non-preferable strains for expression include DH10B (F-endA1 recA1 galE15 galK16 nupG rpsL ΔlacX74 Φ180lacZAM15 araD139 Å(ara,leu)7697 mcrA Δ(mrr-hsdRMS-mcrBC) λ−), DH5alpha (F-endA1 glnV44 thi-1 recA1 relA1 gyrA96 deoR nupG Φ80dlacZΔM15 Å(lacZYA-argF)U169, hsdR17 (rK− mK+), λ−) or other strains which do not include the ompT knockout. Strains such as DH10B and DH5alpha may be made preferable by disruption of the ompT gene. To express the LCNT1 switch from *E. coli*, the pBAD plasmid may be used (TSY-3-53_pBAD_aCD19(FMC63)-GCN4-LCNT1, (SEQ ID NO. 81)). Even more preferable is the LCNT1 switch sequence which has been codon optimized for expression in *E. coli* (TSY-3-97_pBAD_aCD19 (FMC63)_LCNT1(opt), (SEQ ID NO. 82)).

Disclosed herein are methods of grafting the antibody or antibody fragment, the peptidic antigen or the targeting peptide to produce a CAR-EC switch. The method may comprise grafting the CAR-BP to the antibody or antibody fragment. The method may comprise grafting the CAR-BP to an N terminus, C terminus or internal site of the antibody or antibody fragment. The CAR-BP may be grafted to a CL domain of the antibody or antibody fragment. The CAR-BP may be grafted to a loop of the CL domain of the antibody or antibody fragment. The method may comprise grafting the antibody or antibody fragment to the CAR-BP. The method may comprise grafting the antibody or antibody fragment to an N terminus, C terminus or internal site of the CAR-BP. The method may comprise grafting the CAR-BP to the targeting peptide. The method may comprise grafting the CAR-BP to an N terminus, C terminus or internal site of the targeting peptide. The method may comprise grafting the targeting peptide to the CAR-BP. The method may comprise grafting the targeting peptide to an N terminus, C terminus or internal site of the CAR-BP.

The CAR-BP, targeting peptide, antibody or antibody fragment may comprise one or more linkers, wherein the linker is located at the N terminus and/or C terminus of the CAR-BP, targeting peptide, antibody or antibody fragment. The method may comprise grafting the antibody or antibody fragment, the CAR-BP or the targeting peptide through the linker. The linker may comprise $(GSSSS)_n$. The linker may comprise a sequence selected from SEQ ID NOS: 45-50 and $(GGGGS)_n$, $(GGGS)_n$, $(GGS)_n$, $(G_mS)_n$, and $(X_mS)_n$, wherein n is at least 1, m is at least 1, and X is any amino acid. The linker may comprise a sequence that is at least about 50% homologous to a sequence selected from SEQ ID NOS: 45-50 and $(GGGGS)_n$, $(GGGS)_n$, $(GGS)_n$, $(G_mS)_n$, and $(X_mS)_n$, wherein n is at least 1, m is at least 1, and X is any amino acid. The linker may comprise a sequence selected from SEQ ID NOS: 68-71. The linker may comprise a sequence that is at least about 50% homologous to a sequence selected from SEQ ID NOS: 68-71.

Grafting may comprise producing a CAR-EC switch encoding nucleic acid. Producing the CAR-EC switch encoding nucleic acid may comprise one or more polymerase chain reactions. Producing the CAR-EC switch encoding nucleic acid may comprise one or more nucleic acid enzymatic digestions. The enzymatic digestion may be site specific. Producing the CAR-EC switch encoding nucleic acid may comprise one or more ligations. The methods of producing the CAR-EC switch may comprise incorporating the CAR-EC switch encoding nucleic acid into a CAR-EC switch vector. The vector may be an expression vector. The expression vector may comprise a constitutive promoter, an inducible promoter and/or a conditional promoter. The CAR-EC switch encoding nucleic acid or CAR-EC switch vector may be expressed in a cell and the resulting CAR-EC switch isolated and purified. The cell may be a prokaryotic cell. The cell may be an *E. coli*. The cell may be a eukaryotic cell. The cell may be a mammalian cell. The CAR-EC switch encoding nucleic acid or CAR-EC switch vector may be expressed in a cell-free system. Alternatively or additionally the CAR-EC switch may be synthesized from free amino acids.

Purification of CAR-EC Switches and Portions Thereof

Disclosed herein are methods of purifying CAR-EC switches disclosed herein, comprising separating the CAR-EC switches disclosed herein from components of a CAR-EC switch production system (e.g., cellular debris, free amino acids). Purifying the CAR-EC switch may comprise use of one or more concentrator columns, electrophoresis, filtration, centrifugation, chromatography or a combination thereof. Chromatography may comprise size-exclusion chromatography. Additional chromatography methods include, but are not limited to, hydrophobic interaction chromatography, ion exchange chromatography, affinity chromatography, metal binding, immunoaffinity chromatography, and high performance liquid chromatography or high pressure liquid chromatography. Electrophoresis may comprise denaturing electrophoresis or non-denaturing electrophoresis.

The CAR-EC switches may comprise one or more peptide tags. The methods of purifying CAR-EC switches may comprise binding one or more peptide tags of the CAR-EC switches to a capturing agent. The capturing agent may be selected from an antibody, a column, a bead and a combination thereof. The one or more tags may be cleaved by one or more proteases. Examples of tags include, but are not limited to, polyhistidine, FLAG® tag, HA, c-myc, V5, chitin binding protein (CBP), maltose binding protein (MBP), and glutathione-S-transferase (GST). The peptide tag may be the CAR-BP. The peptide tag may be HTP. The peptide tag may be yeast transcription factor GCN4.

The methods may further comprise lyophilization or ultracentrifugation of the CAR-BPs, targeting polypeptides and/or the CAR-EC switches.

The purity of the CAR-BPs, targeting polypeptides and/or the CAR-EC switches may be equal to or greater than 50%, 55%, 60%, 65%, 70%, 75%, 80%, 85%, 90%, 91%, 92%, 93%, 94%, 95%, 96%, 97%, 98%, 99% or more. The purity of the CAR-BPs, targeting polypeptides and/or the CAR-EC switches may be equal to or greater than 85%. The purity of the CAR-BPs, targeting polypeptides and/or the CAR-EC switches may be equal to or greater than 90%. The purity of the CAR-BPs, targeting polypeptides and/or the CAR-EC switches may be equal to or greater than 95%. The purity of the CAR-BPs, targeting polypeptides and/or the CAR-EC switches may be equal to or greater than 97%.

The methods of producing CAR-EC switches disclosed herein may comprise producing CAR-EC switches that are structurally homogeneous. The method of producing the CAR-EC switch from a polynucleotide may result in one or more CAR-EC switches that have the same or similar form, features, binding affinities (e.g., for the CAR or the target), geometry and/or size. The homogeneity of the CAR-EC switches may be equal to or greater than 50%, 55%, 60%, 65%, 70%, 75%, 80%, 85%, 90%, 91%, 92%, 93%, 94%, 95%, 96%, 97%, 98%, 99% or more. The homogeneity of the CAR-EC switches may be equal to or greater than 85%. The homogeneity CAR-EC switches may be equal to or greater than 90%. The homogeneity of the CAR-EC switches may be equal to or greater than 95%. The homogeneity of the CAR-EC switches may be equal to or greater than 97%. The homogeneity may be a structural homogeneity. The homogeneity may be a structural homogeneity prior to administering the cell to a subject. The homogeneity may be a structural homogeneity prior to modifications to the CAR-EC switch by cellular activities (methylation, acetylation, glycosylation, etc.). These high percentages of homogeneity may provide a more predictable effect of the CAR-EC switch. These high percentages of homogeneity may provide for less off-target effects of the CAR-EC switch, when combined with a CAR-EC to treat a condition in a subject.

X. Methods of Optimization

Disclosed herein are methods of optimizing a chimeric antigen receptor switch for maximum safety and efficacy in a subject. Further disclosed herein are methods of optimizing treatment of a condition in a subject comprising optimizing a chimeric antigen receptor switch. Also, disclosed herein are methods of optimizing a switchable chimeric antigen receptor platform. Also, disclosed herein are methods of optimizing a switchable chimeric antigen receptor platform for maximum safety and efficacy in a subject. Further disclosed herein are methods of optimizing treatment of a condition in a subject comprising optimizing a switchable chimeric antigen receptor platform.

Optimizing CAR-EC Activation

Disclosed herein are methods of producing an optimal switchable chimeric antigen receptor platform, comprising: incorporating a first chimeric antigen receptor binding peptide to a first site of a targeting moiety that binds a first cell surface molecule on a first target cell to produce a first switch; incorporating a second chimeric antigen receptor binding peptide to a second site of a second targeting moiety that binds a second cell surface molecule on a second target cell to produce a second switch; contacting the first target cell with the first switch and a first chimeric antigen receptor effector cell expressing a first chimeric antigen receptor; contacting the second target cell with the second switch and a second chimeric antigen receptor effector cell expressing a second chimeric antigen receptor; and comparing a first cytotoxic effect of the first switch and the first chimeric antigen receptor effector cell on the first target cell to a second cytotoxic effect of the second switch and the second chimeric antigen receptor effector cell on the second target cell; and selecting the first switch and first chimeric antigen receptor effector cell or the second switch and the second chimeric antigen receptor effector cell as the optimal switchable chimeric antigen receptor platform based on comparing the first cytotoxic effect to the second cytotoxic effect.

Further disclosed herein are methods of producing an optimal switchable chimeric antigen receptor platform, comprising: incorporating a first chimeric antigen receptor binding peptide to a first site of a targeting moiety that binds a first cell surface molecule on a first target cell to produce a first switch; incorporating a second chimeric antigen receptor binding peptide to a second site of a second targeting moiety that binds a second cell surface molecule on a second target cell to produce a second switch; contacting the first target cell with the first switch and a first chimeric antigen receptor effector cell expressing a first chimeric antigen receptor; contacting the second target cell with the second switch and a second chimeric antigen receptor effector cell expressing a second chimeric antigen receptor; and comparing a first effect of the first switch and the first chimeric antigen receptor effector cell on the first chimeric antigen receptor effector cell to a second effect of the second switch and the second chimeric antigen receptor effector cell on the second chimeric antigen receptor effector cell; and selecting the first switch and first chimeric antigen receptor effector cell or the second switch and the second chimeric antigen receptor effector cell as the optimal switchable chimeric antigen receptor platform based on comparing the first cytotoxic effect to the second cytotoxic effect.

The first chimeric antigen receptor binding peptide and the second chimeric antigen receptor binding peptide may be the same. The first targeting moiety and the second targeting moiety may be the same. The first site and the second site may be the same. The first site and the second site may be different. The methods may further comprise incorporating one or more additional chimeric antigen receptor binding peptides to the first and/or second targeting moiety to produce a first multivalent switch and/or a second multivalent switch.

The first chimeric antigen receptor and the second chimeric antigen receptor may be the same. The first chimeric antigen receptor and the second chimeric antigen receptor may be different. The first chimeric antigen receptor and the second chimeric antigen receptor may differ by a domain selected from an extracellular domain, a transmembrane domain, an intracellular domain and a hinge domain. A first hinge domain of the first chimeric antigen receptor and a second hinge domain of the second chimeric antigen receptor may differ by a feature selected from flexibility, length, amino acid sequence and combinations thereof.

Contacting the first target cell and/or contacting the second target cell may occur in vitro. Contacting the first target cell and/or contacting the second target cell may occur in vivo. By way of non-limiting example, contacting the first target cell and/or contacting the second target cell may occur in an in vivo model, such as a mouse. The in vivo model may have a condition or disease. The condition or disease may be a tumor or a cancer. Comparing the first cytotoxic effect to the second cytotoxic effect may comprise comparing a feature selected from viability of target cells, expression/production of activation markers (e.g., production of cytokines) by the first CAR-EC and/or second CAR-EC, viability of off-target cells, tumor burden, and health of an in vivo model. The method may further comprise comparing the first cytotoxic effect and or the second cytotoxic effect to that of a canonical CAR cytotoxic effect, wherein the canonical CAR is a non-switchable CAR (e.g., not controlled by a CAR switch).

The first target cell and the second target cell may express the same cell surface molecule. The first target cell and the second target cell may express different levels of the same cell surface molecule, resulting in different cell surface molecule (e.g., antigen) densities. The method may comprise comparing the first cytotoxic effect on the first target cell to the first cytotoxic effect on the second target cell. The method may comprise comparing the first cytotoxic effect on the first target cell to the second cytotoxic effect on the second target cell. The method may comprise comparing the first cytotoxic effect on the first target cell to the second cytotoxic effect on the first target cell.

The methods of optimizing may comprise modulating the distance and geometry of the immunological synapse, chimeric receptor binding affinity for the switch, the valency and location of the peptidic antigen(s) on the switch, and the density of chimeric receptors on the CAR-EC surface. The optimizing may result in activating the CAR-EC to an activation level that results in a desired CAR-EC fate or phenotype. Demonstrated herein are methods of PNE-grafting to create switches with a range of geometries, lengths, and valences which can be used to systematically optimize the sCAR immunological synapse (see, e.g., Example 29).

Optimizing the Immunological Synapse-Length and Geometry

The methods disclosed herein comprise developing sCAR-T cell systems with switch-mediated control over the immunological synapse formed by the switch between the sCAR and target cell, wherein the immunological synapse may be defined as the junction between the CAR-EC and the target cell.

The methods may comprise modulating the length of the immunological synapse or the distance between the CAR-EC and the target cell. The methods may comprise modulating the length or size of the switch. The methods may comprise modulating the length or size of the CAR extracellular domain. Modulating the length or size of the CAR extracellular domain may comprise modulating the length of the CAR hinge.

The methods may comprise modulating the length of the immunological synapse by modulating the location of the peptidic antigen(s) on the switch. In some cases, the methods comprise designing switches with the CAR-BP placed distal to an antigen binding domain of the targeting moiety. In some cases, the methods comprise designing switches with the CAR-BP placed distal to an antigen binding domain of the targeting antibody or antibody fragment. Distal may be the C terminus of the targeting antibody or antibody fragment. Distal may be the constant region of the targeting antibody or antibody fragment. In some cases, the methods comprise designing switches with the CAR-BP placed proximal to the antigen binding domain of the targeting moiety. Proximal may be the N terminus of the targeting antibody or antibody fragment. Proximal may be the variable region of the targeting antibody or antibody fragment. In some cases, the methods comprise designing a switch such that the CAR-BP is located at the C-terminus of the targeting moiety (e.g Fab) to enable sufficient length to display the CAR-BP to the sCAR-T while avoiding steric hindrance from a relatively large cell surface molecule. Thus, modulating the length of the switch and/or CAR extracellular domain may afford varying levels of sCAR-T cell activation. In some cases, switches with the CAR-BP proximal to the antigen binding domain may stimulate less CAR-EC activation than switches with the CAR-BP distal to the antigen binding domain. In other cases, switches with the CAR-BP distal to the antigen binding domain may stimulate less CAR-EC activation than switches with the CAR-BP proximal to the antigen binding domain. This underscores the necessity to empirically design switches with defined structures and valencies enabled by site specific fusing/grafting methodologies described herein. This is a significant advantage compared with previous reports that use non-specific conjugation to create switches which produce heterogeneous mixtures of conjugates. These reports do not provide methods of optimizing the sCAR immunological synapse for any antigen.

As shown in Examples 10-14, in some embodiments, CD19 targeting switches with the PNE grafted at the N-terminus of the (heavy chain, light chain or both), proximal to the antigen binding interface of the FMC63 Fab, may be superior to switches with the PNE grafted at C-terminus. Although the epitope of anti-CD19 antibody FMC63 and corresponding structure of the CD19 antigen are not known, this may be due to a decreased distance between target cell and sCAR-T cell. In the physiological immunological synapse formed by the native T cell receptor (TCR), the distance between the T cell and antigen presenting cell is approximately 150 Å. This distance is critical to sterically exclude inhibitory phosphatases such as CD45 and CD148 from the synapse which act to dephosphorylate signaling molecules and down regulate T cell activation. Without being limited by conjecture, it is likely that the longer synapse contributed by the C-terminal switches (65 Å longer than the N-terminal switches by length of Fab) is unable to sterically exclude these inhibitory molecules, resulting in less productive sCAR signaling. The increase in sCAR-T cell activity observed when the sCAR hinge was shortened from 45 amino acids to 12 amino acids supports this notion. In addition, similar switch SAR was demonstrated for the FMC63 antibody in a parallel work which used site-specific conjugation of the Fab with FITC in order to redirect the activity anti-FITC CAR-T cells. With this method, FITC conjugation sites near the antigen binding interface afforded better activity than sites distal from the binding interface (data not shown). This further confirms that the impact of switch size on the immunological synapse is an important factor in sCAR-T cell activity and not an artifact of the PNE-grafting methodology. Thus, the methods disclosed herein may comprise modulating the distance of the immunological synapse by modulating the length of the switch and/or CAR extracellular domain such that the distance of the immunological synapse is not greater than about 150 Å, about 175 Å, or about 200 Å.

In some cases, the methods comprise modulating the length of the CAR hinge. The methods may comprise activating a first CAR-EC comprising a first CAR with a first hinge and activating a second CAR-EC comprising a second CAR with a second hinge and comparing an activity of the first CAR-EC to that of the second CAR-EC. The activity, by way of non-limiting example, may be selected from cytokine release, expression of a phenotypic marker, proliferation, senescence, and migration/trafficking. The first CAR hinge may be a long hinge and the second CAR hinge may be a short hinge. In some cases, the switch may provide greater sCAR-T activity when paired with a CAR that has a long hinge versus a short hinge. In some cases, the switch may provide lesser sCAR-T activity when paired with a CAR that has a long hinge versus a short hinge. The long hinge may be a flexible hinge. The long hinge may be a rigid or structured hinge. The long hinge may have a length of about 20 to about 200 amino acids, about 20 to about 100 amino acids, about 30 to about 100 amino acids, about 40 to about 100 amino acids, or about 45 to about 100 amino acids. The long hinge may comprise a portion of a CD8 protein. The portion of the CD8 protein may be between about 4 amino acids and about 100 amino acids. The portion of the CD8 protein may be about 45 amino acids. The short hinge may be a flexible hinge. The short hinge may be a rigid or structured hinge. The short hinge may have a length of about 1 to about 20 amino acids, about 5 to about 20 amino acids, or about 10 to about 20 amino acids. The short hinge may comprise a portion of an immunoglobulin. The immunoglobulin may be an IgG. The immunoglobulin may be an IgG4. The IgG4 may be mutated (referred to herein as IgG4m). The portion of the immunoglobulin may be between about 1 amino acid and about 20 amino acids. The portion of the immunoglobulin may be about 12 amino acids.

The methods of optimizing may further comprise accounting for the size and structure of the cell surface molecule (e.g., antigen) on the target cell. In some embodiments, switches developed from an OFA antibody scaffold to target CD20 exhibited a SAR trend which was similar to the FMC63 antibody when paired with sCAR-T cells harboring the long, CD8-based hinge. Interestingly, when the sCAR hinge was shortened to 12 amino acids the SAR trend for OFA switches was reversed and C-terminally grafted switches afforded better activity than N-terminally grafted switches. While the structure of CD20 antibody is also unknown, the OFA antibody is reported to bind a small, membrane proximal loop of the multi-pass transmembrane CD20 antigen. Thus, without being limited by conjecture, in this case, it is likely that the distance of the synapse created by the N-terminally grafted OFA switches with the short-dimeric sCAR is too short to enable efficient binding of the switch to the sCAR and CD20 simultaneously. Alternatively, without being limited by conjecture, the large adjacent loop domain of the CD20 antigen may create a steric hindrance for the short-dimeric sCAR, which prefers a longer switch length in order to bind. A similar effect was observed which supports this theory in parallel work with site-specific FITC conjugation on the anti-CD22 antibody m971 (data not shown). In this case, the m971 antibody has a membrane proximal epitope on CD22 and several large modular domains which may sterically preclude binding. Correspondingly, the m971 switches were optimal with FITC placed at sites distal from the antigen binding interface (data not shown). Thus, in some embodiments, the distance of the immunological synapse is a key parameter to consider when designing switches and highlights the requirement for empirical design as described herein.

The methods disclosed herein may comprise varying the geometry of the immunological synapse. The geometry may be defined or referred to herein as the orientation of the bio-orthogonal immunological synapse The methods disclosed herein comprise optimizing geometry of the switch. The methods disclosed herein comprise optimizing geometry of the switch to be compatible with a CAR. The CAR may be a universal CAR. The first site and/or second site may be selected from an N terminus of the antibody or antibody fragment, a C terminus of the antibody or antibody fragment, and an internal site of the antibody or antibody fragment. The first site and/or second site may be selected from a light chain of the antibody or antibody fragment and a heavy chain of the antibody or antibody fragment. The first site and/or second site may be selected from a variable region of the antibody or antibody fragment and a constant region of the antibody or antibody fragment. The first site and/or second site may be selected from a VL domain, a CL domain, a VH domain, a CH1 domain, a CH2 domain, a CH3 domain, and a hinge domain of the antibody or antibody fragment. Incorporating the first/second chimeric antigen receptor binding peptide may comprise a method selected from fusing, grafting, conjugating, linking, and combinations thereof.

Optimizing the geometry of the switch may further comprise incorporating one or more linkers in the switch. Optimizing the geometry of the switch may further comprise comparing two or more linkers. The two or more linkers may differ by a feature selected from flexibility, length, amino acid sequence, and combinations thereof. The method may comprise incorporating a first linker to the first site, wherein the first linker links the first chimeric antigen receptor binding peptide to the first targeting moiety. The method may further comprise incorporating a second linker to the second site wherein the second linker links the second chimeric antigen receptor binding peptide to the second targeting moiety. The first linker and the second linker may be the same. The first linker and the second linker may be different. The first linker and the second linker may differ by a feature selected from flexibility, length, amino acid sequence, and combinations thereof. The first and/or second linker may have a sequence selected from SEQ ID NOS: 45-50, $(GGGGS)_n$, $(GGGS)_n$, $(GGS)_n$, $(G_mS)_n$, $(X_mS)_n$, and GG, wherein n is at least 1, m is at least 1, and X is any amino acid. The first and/or second linker may have a sequence that is at least about 50%, about 60%, about 70%, about 80% or about 90% homologous to a sequence selected from SEQ ID NOS: 45-50 and $(GGGGS)_n$, $(GGGS)_n$, $(GGS)_n$, $(G_mS)_n$, and $(X_mS)_n$, wherein n is at least 1, m is at least 1, and X is any amino acid.

Optimizing CAR-EC Phenotype, Activation, Fate and Progeny

CAR-T cell expansion and trafficking in humans has been shown to be predictive of clinical responses in clinical trials. The methods disclosed herein may comprise optimizing CAR-EC phenotype, activation, fate and progeny. Optimizing CAR-EC activation may comprise optimizing the switch dose. The methods may comprise administering a first dose of a switch to a subject and a second dose of the switch to the subject and comparing CAR-EC cytokine release, CAR-EC expansion/fate, CAR-EC trafficking to disease sites, CAR-EC proliferation, and any combination thereof. The method may further comprise continuing administering the first dose or the second dose in the subject or administering a third dose to the subject, after the comparing. For example, as presented herein, it was shown that switch dose may be used to control CAR-EC cytokine release in the Nalm-6$^{Luc/GFP}$ xenograft model. Because the Nalm-6 tumor lacks CD80 and CD86 co-receptors, it is difficult to treat and has become a standard for CAR-T therapy adjudication. In vivo expansion and trafficking of sCAR-T cells to sites of disease was demonstrated to be reliant on switch dosing. Importantly, serum levels of human cytokines IL-2, TNFα, and IFNγ were tightly controlled by LCNT Fab switch dose (see FIG. 33B). A key finding of these studies was that sCAR-T cells treated with lower doses of switch (0.05 mg/kg) could provide complete clearance of Nalm-$6^{Luc/GFP}$ at a slower rate and with lower levels of cytokine release (see FIG. 33C). This indicates that low dose switch treatment may be an effective method of mitigating CRS and TLS in the treatment of patients with high tumor burdens. When tumors relapsed at day 30, mice were retreated with a higher dose of 0.5 mg/kg to ensure clearance (see FIG. 33D. Due to the lower tumor burden at this stage, excessive cytokine release would not be expected. Thus, the methods may comprise administering a first dose of switch before a relapse in the subject and a second dose after the relapse. The second dose may be higher than the first dose. The method may also comprise terminating the dosing of the first or the second switch due to the occurrence of an adverse effect. The adverse effect may be cellular aplasia. The cellular aplasia may be B cell aplasia. The adverse effect may be cytokine storm.

The methods may comprise administering a first dose of a switch to a subject and a second dose of the switch to the subject and comparing CAR-EC phenotype after the first dose to CAR-EC phenotype after the second dose. Also demonstrated herein was the sCAR-T cell phenotype dependence on switch dose. This experiment again demonstrated an advantage to low dose (0.05 mg/kg) switch treatment in its ability to produce a larger central memory compartment compared with high dose (2.5 mg/kg) treatment which produced more effector memory T (TEMRA) cells at day 21 (15 days after the start of treatment). Central and stem cell memory CAR-T cells have a more naïve phenotype and provide prolonged persistence compared with relatively short-lived TEMRA cells. In the sCAR-T cell system persistence is critical to enable re-dosing strategies in the case of relapse. Persistence of sCAR-T cells may also be promoted through rest phases in which switch dosing is withheld to prevent exhaustion related to persistent T cell signaling (see FIG. 33E). Thus, the methods may further comprise comparing TEMRA cell quantity in the subject before administering the first/second switch to the subject to after administering the first/second switch to the subject. The methods may additionally or alternatively comprise comparing other populations of interest shown to correlate with good prognosis in CAR-T cell therapy before administering the first/second switch to the subject to after administering the first/second switch to the subject.

The methods may comprise optimizing the switch or sCAR-T platform to control CAR-EC fate. The methods may comprise optimizing the switch or sCAR-T platform to optimally activate the CAR-EC, thereby optimizing CAR-EC fate. For example, optimally activating the CAR-EC may cause it to become an effector memory T cell, as opposed to partially activating or over-activating, which can lead to death, senescence or anergy of the CAR-EC. The methods may comprise activating a CAR with a first switch and activating the CAR with a second switch and comparing CAR-EC fate after the first switch to CAR-EC fate after the second switch. The methods may comprise administering a first switch to a subject and a second switch to the subject and comparing CAR-EC fate after the first switch to CAR-EC fate after the second switch. The methods may comprise administering a first dose of a switch to a subject and a second dose of the switch to the subject and comparing CAR-EC fate after the first dose to CAR-EC fate after the second dose.

Optimizing Switch Valency

In various embodiments, using methods of optimizing sCAR-T configurations, sCAR-T systems disclosed herein show similar in vitro T cell activation, functional cytokine release and cell-killing sensitivity and specificity, and in vivo tumor elimination with comparable efficacy as conventional CARs. The examples disclosed herein demonstrate that in some embodiments, the methods of optimization may be highly dependent on switch and CAR hinge design, and less dependent on the targeting modality. Disclosed herein is the development of binary sCAR-T cells which function on multiple inputs (e.g., multiple orthogonal pairs) that enable precise control over sCAR-T cell function.

Methods of optimizing the CAR-EC platform or CAR-EC switch may comprise incorporating more than one peptidic antigen in to the switch to produce a multivalent switch. In some cases, a bivalent switch may be preferable to a monovalent switch. In some cases, the monovalent switch may be preferable to the bivalent switch. The methods of optimizing may comprise comparing a first effect of a CAR-EC on a target cell wherein the first CAR-BP is a first distance from the second CAR-BP to a second effect of the CAR-EC on the target cell wherein the first CAR-BP is a second distance from the second CAR-BP. The first or second distance may be between about 5 Å and about 100 Å. The first or second distance may be between about 8 Å and about 80 Å. The first or second distance may be between about 10 Å and about 50 Å. The first or second distance may be between about 10 Å and about 50 Å. The first or second distance may be between about 10 Å and about 40 Å. The first or second distance may be between about 10 Å and about 30 Å. The first or second distance may be about 12 Å. The first or second distance may be about 24 Å.

Optimizing the CAR and CAR-EC

The methods of optimizing may comprise optimizing CAR density on the membranes of the CAR-ECs. Optimizing CAR density on the membranes of the CAR-ECs may comprise modulating the expression of the CAR. This can be done, for example, by engineering cells that express a CAR under a high or low expression promoter. Alternatively, or additionally, CARs may be designed to multimerize on the CAR-EC membrane, creating "rafts" of CARs that stimulate a greater effect (e.g., cytotoxic effect) in the CAR-EC than a single CAR, or even two CARs, alone. This may be achieved, by way of non-limiting example, by incorporating a cysteine residue into the first chimeric antigen receptor and/or the second chimeric antigen receptor in order to multimerize the first chimeric antigen receptor and/or the second chimeric antigen receptor through a disulfide bond.

The first/second CAR-ECs may be derived from a T cell (e.g., genetically modified T cell or differentiated from a T cell). The CAR-EC may be a T cell. The CAR-EC may be a cell of a T cell lineage. The CAR-EC may be a mature T cell. The CAR-EC may be a precursor T cell. The CAR-EC may be a cytotoxic T cell. The CAR-EC may be a naive T cell. The CAR-EC may be a memory stem cell T cell ($T_{MSC}$). The CAR-EC may be a central memory T cell ($T_{CM}$). The CAR-EC may be an effector T cell (TE). The CAR-EC may be a CD4+ T cell. The CAR-EC may be a CD8+ T cell. The CAR-EC may be a CD4+ and CD8+ cell. The CAR-EC may be an alpha-beta T cell. The CAR-EC may be a gamma-beta T cell. The CAR-EC may be a natural killer T cell. The CAR-EC may be a helper T cell. The CAR-EC may be a neutrophil. The neutrophil may be a CD34+ neutrophil. The neutrophil may be engineered or genetically modified to have greater cytoxic capacity than a naturally-occurring neutrophil.

The methods may further comprise consideration for switch compatibility with the cell surface molecule and the CAR. The methods may comprise testing compensatory mutations in switches and CARs in the development of a single, universal sCAR.

Further disclosed herein are optimized chimeric antigen receptor-effector cell platforms, comprising: a chimeric antigen receptor-effector cell switch comprising a chimeric antigen receptor binding peptide and a targeting moiety; and a chimeric antigen receptor-effector cell that expresses a chimeric antigen receptor, wherein the chimeric antigen receptor-effector cell platform is produced/derived by methods of producing an optimal switchable chimeric antigen receptor platform disclosed herein.

XI. Models for Testing CAR-ECs & Switches

Figure 5:
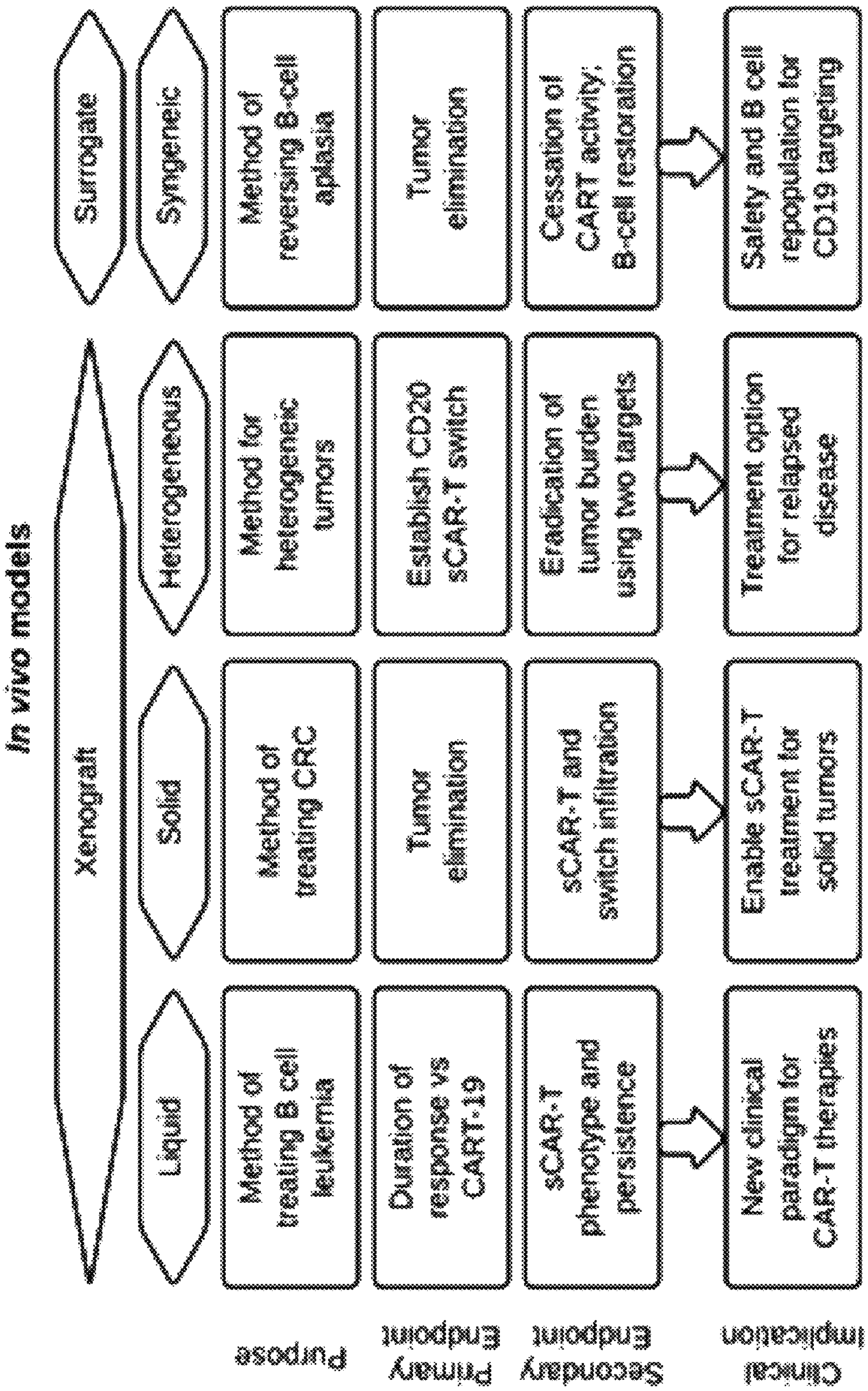
FIG. 5 shows xenograft and surrogate models in liquid and solid tumors in immunodeficient and immunocompetent mice that allow optimization of sCAR-T cell efficacy.

Although xenograft models in immunodeficient mice allow optimization of sCAR-T cell efficacy, in some cases, such models may not be optimal to assess safety (exemplary surrogate models shown in FIG. 5). Disclosed herein are model systems for evaluating the efficacy and/or safety of CAR-ECs and corresponding CAR switches. The model system may be selected from an in vitro model, an in vivo model, and combinations thereof. The model system may be a non-human in vivo model. The model system may be a rodent model. The model system may be a murine model. The model system may be a simian model. The model system may be a syngeneic model. The model system may comprise an immunocompetent animal. The immunocompetent animal may be an immunocompetent mouse. For example, immunocompetent mice have endogenous lymphocytes (i.e. $T_{reg}$ cells), as compared to immunodeficient (e.g., NSG) mice, that may affect CAR-EC activity, thus providing a clinically relevant host. The in vivo model may be a surrogate model that allows off-targeted cells to repopulate after cessation of the switch. The model system may comprise a murine surrogate CAR-EC cell. The murine surrogate CAR-EC cell may be produced by cloning a sequence encoding an anti-CAR-BP scFv into a viral vector for transduction into murine lymphocytes or splenocytes. The sequence may also comprise sequences encoding murine-derived signaling domains. The murine-derived signaling domains may be selected from CD28, a CD3 domain (e.g., zeta), and combinations thereof.

The model system may comprise a model system switch. The model system switch may comprise an antibody that targets a non-human antigen on a non-human target cell. The antibody that targets a non-human antigen on a non-human target cell may be an anti-rodent antibody. The antibody that targets a non-human antigen on a non-human target cell may be an anti-mouse antibody. The anti-mouse antibody may be selected from an anti-mouse CD19 antibody, an anti-mouse CLL1 antibody, an anti-mouse CD33 antibody, an anti-mouse BCMA antibody, an anti-mouse CD22 antibody, and an anti-mouse Her2 antibody. The anti-mouse antibody may be a rat anti-mouse CD19 clone 1D3. The anti-mouse CD19 antibody may have a sequence selected from SEQ ID NOS: 193-203. The model system switch may comprise a CAR-BP. The CAR-BP may be a synthetic (non-naturally occurring) peptide. The CAR-BP may be a non-human peptide. The CAR-BP may have low immunogenicity in a human subject. The CAR-BP may be the yeast transcription factor GCN4.

In vitro cytotoxicity may be tested in the in vitro model. The in vitro model may comprise a cell line. The cell line may be a mammalian cell line. The cell line may be a cancer cell line. The cancer cell line may be a B cell lymphoma cell line. The B cell lymphoma cell line may be CD19 positive. The B cell lymphoma cell line may be a Myc5-CD19 cell line.

Model CAR-ECs and switches may be administered with dosing schedules based on xenograft studies. Two or more different CAR-ECs and switches may be compared in these model systems. For example, efficacy and/safety of a Fab switch may be compared to a similar IgG switch.

XII. Libraries

Disclosed herein are libraries of CAR-EC switches. The libraries of CAR-EC switches may comprise a first switch comprising a first targeting moiety and a universal CAR-BP and a second switch comprising a second targeting moiety and the universal CAR-BP. The libraries of CAR-EC switches may be used with a universal CAR that binds the CAR-BP. The first/second switch may be any CAR-EC switch disclosed herein. The first targeting moiety and the second targeting moeity may be different. The first targeting moiety and the second targeting moeity may be the same.

Further disclosed herein are pluralities of libraries of CAR-EC switches, comprising a first library comprising a plurality of switches, wherein each switch of the plurality of switches comprises a first universal CAR-BP; and a second library comprising a plurality of switches, wherein each switch of the plurality of switches comprises a second universal CAR-BP. The first universal CAR-BP may interact with a first universal CAR and the second universal CAR-BP may interact with a second universal CAR. The first universal CAR and second universal CAR may differ by a characteristic selected from amino acid sequence, size, length (e.g., extracellular domain length, hinge length), hinge flexibility, and multimerization potential (e.g. ability to multimerize when expressed on the CAR-EC). A switch from the first library of switches may be administered to a subject at a different dose than that of a switch from the second library of switches. A switch from the first library of switches may comprise a first targeting moiety and a switch from the second library of switches may comprise a second targeting moiety. The first targeting moiety and the second targeting moiety may be the same. The first targeting moiety and the second targeting moiety may be different.

The universal CAR-BP may be connected to a first site on the first targeting moiety of the first switch and the universal CAR-BP may be connected to a second site on the second targeting moeity. The first site and the second site may be the same. The first site and the second site may be different. The first and/or second switch may further comprise a first/second linker. The first linker may be connected to a first site on the first targeting moiety of the first switch and the second linker may be connected to a second site on the second targeting moeity. The first site and the second site may be the same. The first site and the second site may be different.

The first/second targeting moiety may be an antibody or antibody fragment. The antibody fragment may be a Fab. The antibody or antibody fragment may be an anti-CD19 antibody or anti-CD19 antibody fragment. The antibody or antibody fragment may be an anti-CD20 antibody or anti-CD20 antibody fragment. The antibody or antibody fragment may be an anti-CD22 antibody or anti-CD22 antibody fragment. The antibody or antibody fragment may be an anti-CD33 antibody or anti-CD33 antibody fragment. The antibody or antibody fragment may be an anti-CD123 antibody or anti-CD123 antibody fragment. The antibody or antibody fragment may be an anti-CLL1 antibody or anti-CLL1 antibody fragment. The antibody or antibody fragment may be an anti-CEA antibody or anti-CEA antibody fragment. The antibody or antibody fragment may be an anti-Her2 antibody or anti-Her2 antibody fragment. The antibody or antibody fragment may be an anti-BCMA antibody or anti-BCMA antibody fragment. The antibody or antibody fragment may be an anti-CS1 antibody or anti-CS1 antibody fragment. The targeting moiety may be a T cell receptor. The targeting moiety may be a soluble T cell receptor. The soluble T cell receptor may bind an MHC-restricted NY-ESO-1 peptide.

EXAMPLES

The following illustrative examples are representative of embodiments of the software applications, systems, and methods described herein and are not meant to be limiting in any way.

Example 1—Production and Evaluation of a Switchable CAR-T Platforms

Switch Production

The solubility, stability, affinity, and potential for cross reactive epitopes in the human proteome of developed antibodies were considered in choosing a CAR-EC switch peptidic antigen. Based on these criteria, a linear amino acid epitope from the yeast transcription factor GCN4 (7P14P) was chosen. Single chain antibodies with affinities varying from 2.6 nM to 5.2 pM enable optimization of the CAR-EC through binding kinetics. Additionally, these antibodies are among the highest affinity anti-peptide single chain antibodies for linear epitopes. The dissociation constant (Kd) for the chosen GCN4 epitope (7P14P) having a sequence of NYHLENEVARLKKL (SEQ ID NO. 3) and GCN4 binding scFv (52SR4) is 5.2 pM.

Figure 6:
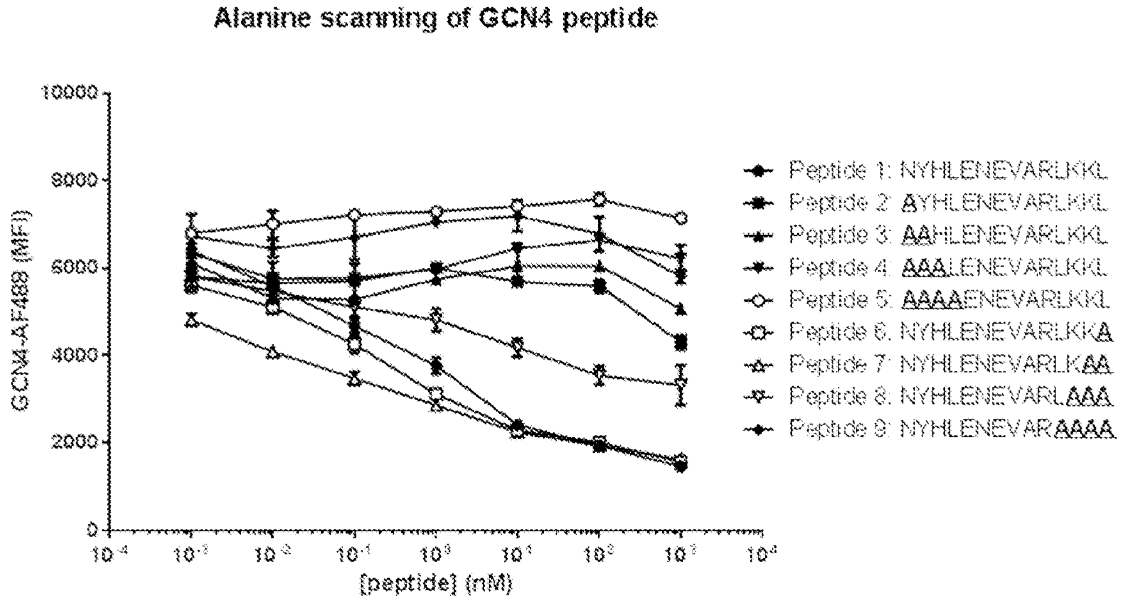
FIG. 6 shows alanine scanning of the GCN4 peptide. Alanine residues were systematically introduced into the N- and C-terminals of the GCN4 peptide (SEQ ID: 75-82). Cells harboring the anti-GCN4 scFv were incubated with 1 nM of GCN4 peptide labelled with Alexa Fluor® 488 (AF488) and increasing concentrations of un-labelled mutated GCN4 peptides. Un-labelled peptide binding efficiency was indirectly shown by measuring the mean fluorescence intensity (MFI) staining with the labelled peptide.

GCN4 peptide epitope alanine scanning: To determine the residues of the GCN4 epitope NYHLENEVARLKKL (SEQ ID NO. 3) that are important, residues from the N-terminus and from the C-terminus were replaced with alanines. Peptides (SEQ ID NOS: 75-82) were synthesized by solid phase peptide synthesis. Flow cytometry was used to assess binding to the CAR-T cell harboring the GCN4 CAR (SEQ ID NO. 74) using a fluorophore labeled GCN4 epitope (SEQ ID NO. 3 labeled with HyLyte488 dye). Cells were incubated with a saturating concentration of the GCN4 epitope (1 nM) and increasing concentrations of each mutated GCN4 peptide (10 pM-1 μM) for 30 minutes in PBS at 4° C. Cells were then washed twice with cold PBS to remove the free labelled peptide before being analyzed using the BD Accuri flow cytometer. The mean fluorescence intensity (MFI) of the AF488 labelled GCN4 peptide was plotted against the concentration of mutated peptide to show that the first 4 residues of the GCN4 polypeptide sequence were important for binding to the anti-GCN4 scFv (FIG. 6).

A small hydrophilic target peptide (HTP), based on the commonly used FLAG® tag, was developed. FLAG® has low antigenicity, is highly soluble, and has been fused to numerous proteins with little impact on protein folding or stability. In modifying FLAG to HTP, a proline residue was incorporated after the terminal lysine in an effort to increase proteolytic stability. Antibodies to this epitope are developed by traditional mouse immunization and subsequent humanization or by phage panning of a human library. Binding kinetics of evolved scFv's are fully characterized and peptide-CAR-ECs are created and tested for off-target specificity as described.

CAR Construction

The CARs were constructed as follows:

LV-EF1a-GCN4-BBZ (SEQ ID: 1) was designed to target the 7P14P epitope of the yeast transcription factor GCN4 (sequence RMKQLEPKVEELLPKNYHLENEVARLKKLVGER (SEQ ID NO. 2) where the underlined amino acids have been shown to bind to the c11L32Ser scFv in the 1P4B crystal structure from PDB. The scFv was constructed from the 52SR4 (high affinity mutant with similar sequence to c11L32Ser) antibody scFv from reference: Zahnd, C., Spinelli, S., Luginbuhl, B., Amstutz, P., Cambillau, C., and Pluckthun, A. (2004) Directed in vitro evolution and crystallographic analysis of a peptide-binding single chain antibody fragment (scFv) with low picomolar affinity, *The Journal of Biological Chemistry* 279, 18870-18877.

Example 2. Evaluation of a Switchable CAR-T Platform in a Xenograft Model

To evaluate efficacy, mouse xenograft models are used to compare these switchable platforms to previously developed by CAR-T switch platforms. Towards this end, RS4;11, NALM-6, Raji or other CD19 positive cell lines are used to establish tumor models in non-obese diabetic-severe combined immunodeficiency (NOD-SCID-$_{\gamma}^{-/-}$, NSG) mice. CAR-Ts are delivered by intravenous administration. Dose-range finding is carried out for the peptide anti-CD19 switch, and is compared to a wild type CD19 Fab control. Efficacy is judged based on tumor burden and overall survival. Mice are monitored with weekly blood draws to monitor proliferation of CAR-ECs in peripheral blood. Detailed immunophenotypic characterization of CAR-ECs focus on effector, memory, senescent (terminally differentiated), or anergized phenotypes are defined according to standard phenotypic parameters using multi-channel flow cytometry.

Primary patient-derived ALL or CLL samples are obtained and for generating xenograft models in NSG mice. Primary samples are characterized for CD19 expression by flow cytometry. Leukemia is established in mice for 2-3 weeks prior to administration of therapy. Efficacy versus CAR-T-19 is judged by monitoring CD19$^{+}$ ALL blast counts in peripheral blood. In the event that leukemia is not controlled or eliminated, proliferated blasts are immunophenotyped (specifically looking for loss of CD19 antigen expression, vida infra for further study). Persistence of CAR-ECs is also monitored (although the latter is not expected to differ substantially from RS4;11-based xenografts).

Example 3. Production of Anti-CD19-Fab/IgG-GCN4 Switches with Varying Positions of Peptide Peptide CAR-EC switches were created by fusing 14 amino acids of the GCN4 yeast transcription factor peptide sequence 7P14P (defined in Zahnd et al. (2004). Directed in vitro evolution and crystallographic analysis of a peptide-binding single chain antibody fragment (scFv) with low picomolar affinity, The Journal of Biological Chemistry 279, 18870-18877). The 14 amino acids were chosen based on those defined in crystal structure 1P4B of GCN4 peptide 7P14P with scFv c11L32Ser. The switches were constructed by either fusing the GCN4 peptide sequence to the C-terminus of the heavy chain of the Fab antibody or by fusing the GCN4 peptide sequence in the CL loop of the light chain of the Fab or IgG antibody. All expressions were carried out in CHO or HEK cells.

Figure 8A:
FIG. 8A-B shows the structure and molecular weight of a switch peptide.
Figure 8B:
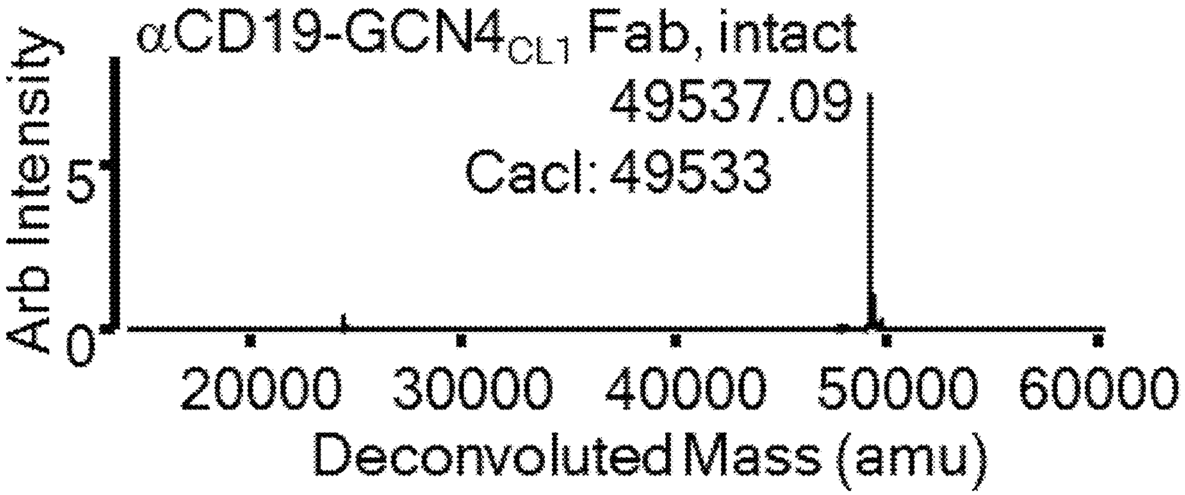

To create a grafted GCN4 peptide based anti-CD19 CAR-T switch (SEQ ID NO: 30), the peptide NYHLENEVARLKKL (SEQ ID NO: 3), suggested to be the minimal binding epitope according to the crystal structure (PDB: 1P4B) (see FIG. 8A) from the yeast transcription factor GCN4 peptide (7P14P) RMKQLEPKVEELLPKNYHLENEVARLKKLVGER (SEQ ID NO: 2), was grafted to the mouse anti-human CD19 Fab clone FMC63. The graft was carried out by replacing K63 (as counted from the N terminus of the constant region, which would be K169 when counting from the N terminus of the mature protein) of the light chain with the sequence GGGGSNYHLENEVARLKKLGGGGS (SEQ ID NO. 4), i.e., the GCN4 epitope flanked by GGGGS linkers (SEQ ID NO: 40). The mass spec of anti-CD19 Fab LCC1 is provided in FIG. 8B. Alternatively, the peptide is grafted to the heavy chain (SEQ ID NO: 29).

Figure 13A:
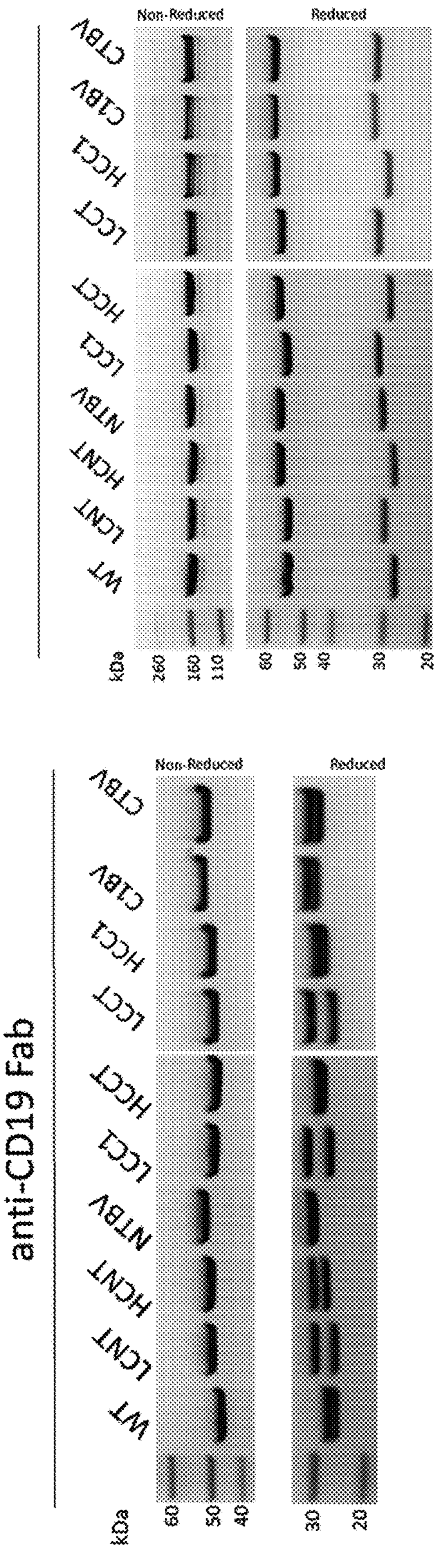
FIG. 13A-B shows biochemical assessment of switches.

Cloning: Mammalian expression vector of CD19 IgG or Fab heavy/light chains was generated by ligation of amplified CD19 IgG or Fab heavy/light chain to pFuse-hIgG1-Fc backbone vector (InvivoGen, CA) with (IgG) or without (Fab) Fc fragment. A polynucleotide encoding GCN4 (NYHLENEVARLKKL (SEQ ID NO: 3)) was synthesized with oligonucleotides and grafted into the CD19 IgG or Fab at select positions (HCl 5135, hinge C223, CL1 K169) or fused to the C and N termini of the CD19 IgG or Fab. The resulting mammalian expression vectors were confirmed by DNA sequencing. Switches were expressed through transient transfection of FreeStyle HEK 293 cells with vector pairs of light and heavy chain sequences, according to the manufacturer's protocol. The light heavy/chain pairs are shown below in Table 1. Proteins were purified by Protein G chromatography and then they were analyzed by SDS-PAGE gels. FIG. 13A shows SDS gel images of the following switches shown in Table 1.

TABLE 1

Anti-CD19 Fab and IgG Switch peptide chain pairs

| Name | Format | Light chain SEQ ID | Heavy chain SEQ ID |
|---|---|---|---|
| WT | Fab | 27 | 29 |
| LCNT | Fab | 36 | 29 |
| HCNT | Fab | 27 | 88 |
| NTBV | Fab | 36 | 88 |
| LCC1 | Fab | 30 | 29 |
| HCCT | Fab | 27 | 34 |
| LCCT | Fab | 97 | 29 |
| HCC1 | Fab | 27 | 32 |
| C1BV | Fab | 30 | 32 |
| CTBV | Fab | 97 | 32 |
| WT | IgG | 27 | 28 |
| LCNT | IgG | 36 | 28 |
| HCNT | IgG | 27 | 259 |
| NTBV | IgG | 36 | 259 |
| LCC1 | IgG | 31 | 28 |
| HCCT | IgG | 33 | 35 |
| LCCT | IgG | 97 | 28 |
| HCC1 | IgG | 27 | 33 |
| C1BV | IgG | 31 | 33 |
| CTBV | IgG | 97 | 35 |

Example 4. Cytotoxicity of Anti-CD19 Fab LCC1, Anti-CD19 IgG LCC1 and Anti-CD19 Fab-HCCT CAR-EC Switches The cytotoxic activity of the anti-CD19 Fab LCC1 switch was assessed with human PBMCs transduced with LV-EF1a-GCN4(52SR4) (SEQ ID: 1) to create CAR-T-GCN4 at E:T ratios of 10:1 and 24 hour incubation. Activity was assessed against NALM-6 ($CD19^+$), RS4;11 ($CD19^+$), or RPMI-8226 ($CD19^-$) (Table 2). The activity of the IgG (FcNull) switch was assessed against RS4;11 ($CD19^+$), or K562 ($CD19^-$) (Table 2). The activity of the C-terminal switch was assessed against RS4;11 ($CD19^+$), or K562 ($CD19^-$) (Table 4).

TABLE 2

Cytotoxicity of the anti-CD19 Fab LCC1 switch (SEQ ID: 30 & 29).

| Concentration (pM) | % Cytotoxicity NALM-6 (CD19 positive) | RS4; 11 (CD19 positive) | RPMI-8226 (CD19 negative) |
|---|---|---|---|
| 10 | 86.74405 | 104.0488 | 15.20283 |
| 1 | 82.23607 | 90.00308 | 8.149928 |
| 0.1 | 77.28449 | 84.11992 | 3.819127 |
| 0.01 | 47.15363 | 45.37116 | 2.656606 |
| 0.001 | −5.794394 | −2.258805 | −4.993927 |
| 0.0001 | −7.191706 | −8.02902 | −7.662813 |
| 0.00001 | −4.779683 | −2.792706 | −1.318068 |

TABLE 3

Cytotoxicity of anti-CD19 IgG LCC1 switch (SEQ ID: 31 & 28).

| Concentration (pM) | % Cytotoxicity RS4; 11 (CD19 positive) | K562 (CD19 negative) |
|---|---|---|
| 1 | 53.56274 | 6.218475 |
| 0.1 | 48.75237 | 1.844815 |
| 0.01 | 38.21278 | −2.777584 |
| 0.001 | 12.10702 | −2.964143 |
| 0.0001 | 0.1621473 | −6.301391 |
| 0.00001 | −0.9188344 | −4.891867 |

TABLE 4

Cytotoxicity of anti-CD19 Fab HCCT switch (SEQ ID: 27 & 32).

| Concentration (nM) | % Cytotoxicity RS4; 11 (CD19 positive) | K562 (CD19 negative) |
|---|---|---|
| 10 | 92.10811 | 1.44819 |
| 1 | 76.75676 | −3.445695 |
| 0.1 | 66.59459 | −2.197255 |
| 0.01 | 60.97298 | −1.348315 |
| 0.001 | 8.216215 | −2.147315 |
| 0.0001 | −2.162161 | −3.046195 |
| 0.00001 | 1.945946 | −0.299624 |

Figure 11A:
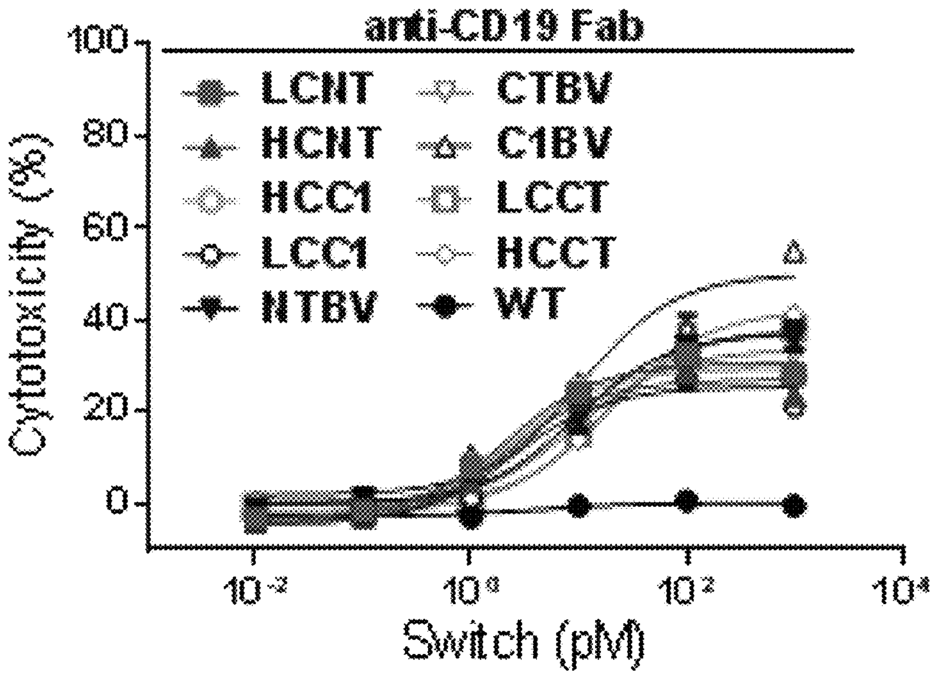
FIG. 11A shows cytotoxicity of sCAR-T cells against $CD19^+$ RS4;11 cells with titration of anti-CD19 Fab switch designs.

Example 5. Cytotoxicity of Various Anti-CD19 Switches with Peptide Grafted/Fused to Varying and Multiple Regions of an Anti-CD19 Antibody or Antibody Fragment The cytotoxic activities of various anti-CD19-GCN4 CAR-EC switches grafted/fused to different regions of anti-CD19 FMC63 antibodies or antibody fragments were assessed with human PBMCs transduced with the LV-EF1a-GCN4(52SR4) (SEQ ID: 1) to create the anti-GCN4 sCAR-T cell (SEQ ID: 180), these cells were incubated with RS4;11 (CD19 positive) target cells, at an E:T ratio of 10:1, for 24 hours (FIG. 11A). The anti-CD19 Fab switches used in this example are listed in Table 1, and are as follows: anti-CD19 Fab with no grafted peptide (WT; SEQ ID: 27 & 29), anti-CD19 Fab with the peptide grafted on the N-terminus of the light chain (LCNT; SEQ ID: 36 & 29), anti-CD19 Fab with the peptide grafted on the N-terminus of the heavy chain (HCNT; SEQ ID: 27 & 88), anti-CD19 Fab with the peptide grafted on the C-terminus of the light chain (LCCT; SEQ ID: 97 & 29), anti-CD19 Fab with the peptide grafted on the N-terminus of the heavy chain (HCCT; SEQ ID: 27 & 34), anti-CD19 Fab with the peptide grafted on the C1 domain of the light chain (LCC1; SEQ ID: 30 & 29), anti-CD19 Fab with the peptide grafted on the C1 domain of the heavy chain (HCC1; SEQ ID: 27 & 32), anti-CD19 Fab with the peptide grafted on the N-terminus of the light chain and heavy chain (NTBV; SEQ ID: 36 & 88), anti-CD19 Fab with the peptide grafted on the C-terminus of the light chain and heavy chain (CTBV; SEQ ID: 97 & 34), anti-CD19 Fab with the peptide grafted on the C1 domain of the light chain and heavy chain (C1BV; SEQ ID: 30 & 32).

Figure 24A:
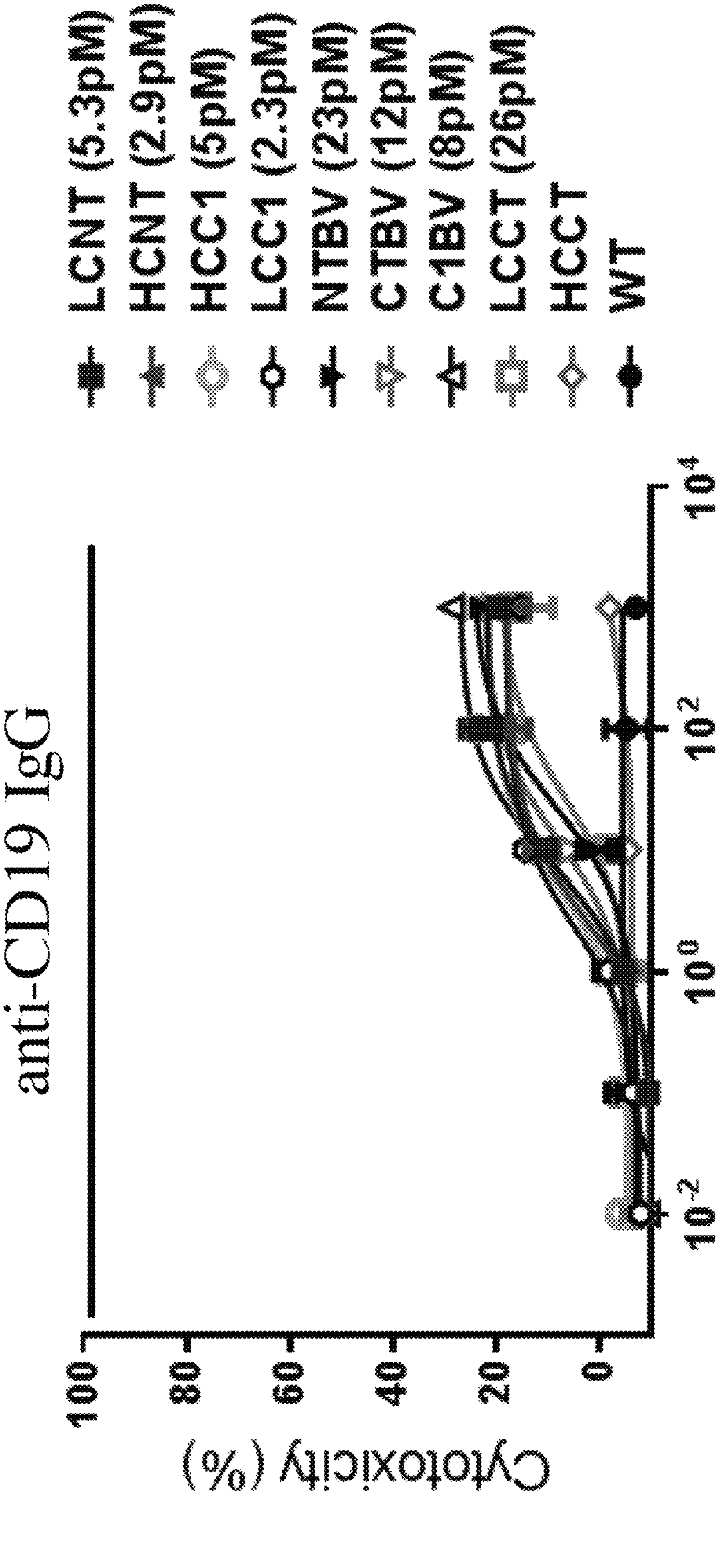
FIG. 24A-B shows in vitro sCART cell activity, wherein sCAR-T cells that were cultured with RS4;11 (A) or K562 (B) cells along with a serial dilution of the IgG anti-CD19 switches for 20-24h before the supernatants were assayed to detect LDH release as a proxy for target cell lysis.

The cytotoxic activities of various anti-CD19-GCN4 CAR-EC switches grafted/fused to different regions of anti-CD19 FMC63 antibodies or antibody fragments were assessed with human PBMCs transduced with the LV-EF1a-GCN4(52SR4) (SEQ ID: 1) to create the anti-GCN4 sCAR-T cell (SEQ ID: 180), these cells were incubated with RS4;11 (CD19 positive) target cells, at an E:T ratio of 10:1, for 24 hours (FIG. 24A). The anti-CD19 IgG switches used in this example are listed in Table 1, and are as follows: anti-CD19 IgG with no grafted peptide (WT; SEQ ID: 27 & 28), anti-CD19 IgG with the peptide grafted on the N-terminus of the light chain (LCNT; SEQ ID: 36 & 28), anti-CD19 IgG with the peptide grafted on the N-terminus of the heavy chain (HCNT; SEQ ID: 27 & 259), anti-CD19 IgG with the peptide grafted on the C-terminus of the light chain (LCCT; SEQ ID:97 & 28), anti-CD19 IgG with the peptide grafted on the N-terminus of the heavy chain (HCCT; SEQ ID: 33 & 35), anti-CD19 IgG with the peptide grafted on the C1 domain of the light chain (LCC1; SEQ ID: 31 & 28), anti-CD19 IgG with the peptide grafted on the C1 domain of the heavy chain (HCC1; SEQ ID: 27 & 33), anti-CD19 IgG with the peptide grafted on the N-terminus of the light chain and heavy chain (NTBV; SEQ ID: 36 & 259), anti-CD19 IgG with the peptide grafted on the C-terminus of the light chain and heavy chain (CTBV; SEQ ID: 97 & 35), anti-CD19 IgG with the peptide grafted on the C1 domain of the light chain and heavy chain (C1BV; SEQ ID: 31 & 33).

Figure 9:
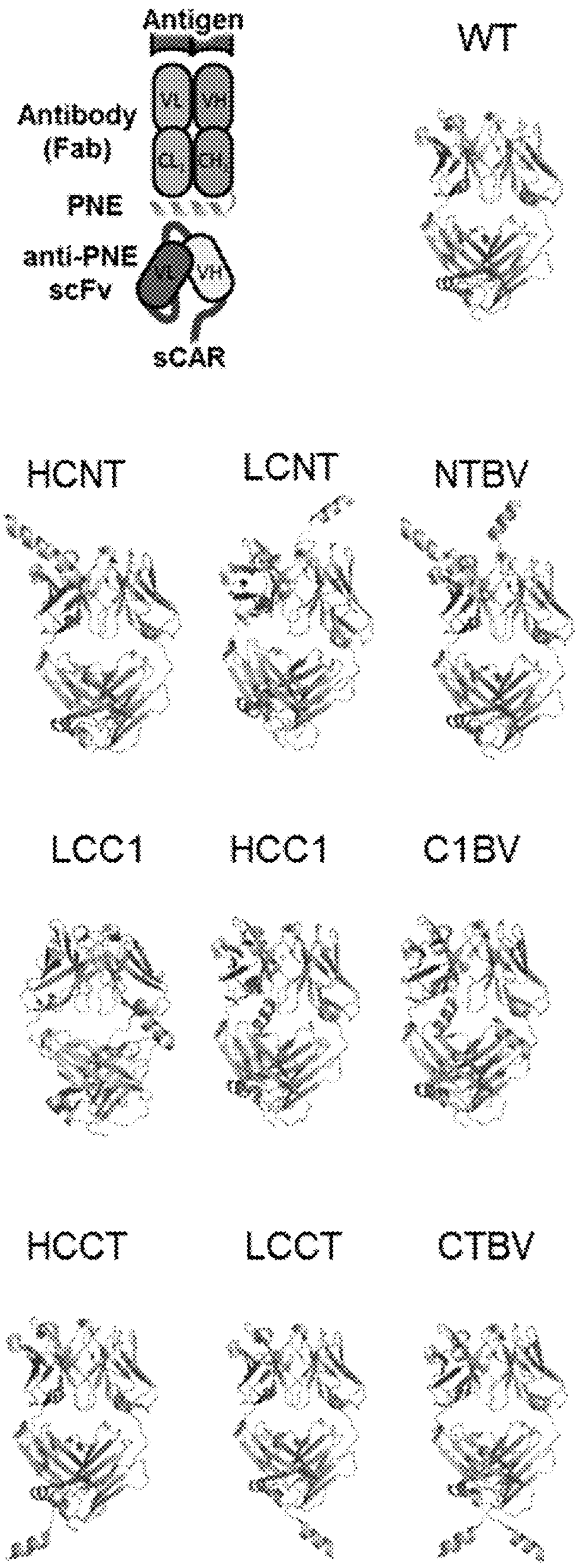
FIG. 9 shows relative orientations of non-limiting examples of switches including a cartoon depicting the immunological synapse between the sCAR, switch, and antigen (top row, left). Switches described in the text shown in Fab format (top row right and down) are isosteric in IgG format. The cartoons are oriented such that the antigen binding interface is at top.

FIG. 9 depicts certain non-limiting examples of the grafting positions of some of the switches described in this example. All formats were expressed in the Fab or IgG format. The N-terminus grafting is shown as grafted to the light chain, however N-terminal grafting is not restricted to the light chain or Fab and may also be grafted to the heavy chain as well as the IgG format. The C-term position on the Fab is isosteric with the hinge IgG. In this context all Fab constructs are monovalent and all IgG constructs are bivalent.

Example 6. Anti-CD19 sCAR-T Cell and Switch Structural Activity Relationship (SAR)

General LDH Release Cytotoxicity Assay Method sCAR-T cells were co-cultured (96-well plate round bottom; 20-24h; 37° C.; 5% $CO_2$) with RS4;11 ($CD19^+$) or K562 ($CD19^-$) cells at a ratio of 10 sCAR-T cells to 1 RS4;11/K562 cell (110,000 cells in total) in 100 uL of RPMI-1640 supplemented with 5% heat inactivated fetal calf serum (Thermo), 1% penicillin-streptomycin (Gibco), 1% L-Glutamine (Gibco), 1 mM sodium pyruvate (Gibco) and 1% non-essential amino acids (Gibco). After 24 hours, each plate was centrifuged at 400×g for 5 minutes at 4° C. To measure target cell lysis, the intracellular protein lactate dehydrogenase (LDH) was measured in the cytotoxicity assay supernatants from the co-cultured cells using the CytoTox 96® Non-Radioactive Cytotoxicity Assay kit (Promega). To measure the effector responses of the sCART cells in vitro, cytokine levels were measured in the cytotoxicity assay supernatants using the Cytometric Bead Array (CBA) Human Th1/Th2 Cytokine Kit II (BD). To measure the activation state of the sCART cells in vitro, the cells from the cytotoxicity assay were washed in PBS containing 1% BSA and 1 mM EDTA, stained with anti-CD25 (BC96; PE; BioLegend), anti-CD69 (FN50; PerCP; BioLegend) and anti CD3ζ (APC; OKT3; BioLegend), and analyzed using the BD Accuri flow cytometer; $CD3^+CD25^+CD69^+$ were classified as activated T cells.

General Flow Cytometry Based Cytotoxicity Assay

The flow cytometry based cytotoxicity assay were performed in RPMI-1640 media supplemented with 5% heat inactivated FBS, 1% Pen/Strep, 1% glutamine, and 1% Sodium pyruvate. Target cells (2×104 cells) were pre-labeled with CellVue Claret Far Red Fluorescent Cell linker (Sigma-Aldrich) and co-cultured with 1×105 sCAR-T cells. Variable concentration of switch was added to assess in vitro activity. This assay was conducted in a volume of 100 ul in 96-well U bottom plate for 24 hours, after which the cells were stained with 7-AAD viability dye (1:100; BD Biosciences) in FACs staining buffer (PBS with 2 mM EDTA and 1% FCS) and acquired on BD Accuri C6 flow cytometer. The viability was calculated as following formula:

% viability=[(no switch viable target cells-experimental viable target cells)/no switch viable target cells]*100

Hinge Development

The length of the CAR determines the distance between the CART cell and target cell. In the case of a canonical CAR this distance is fixed however with the switchable CART cell system this can be modified to provide optimal cell-cell contact conditions for cytotoxicity. Introducing a switch to the immunological increases the distance between target and effector cells, in some scenarios this added length may be beneficial or detrimental to cytotoxicity.

Hinge Development

Figure 10A:
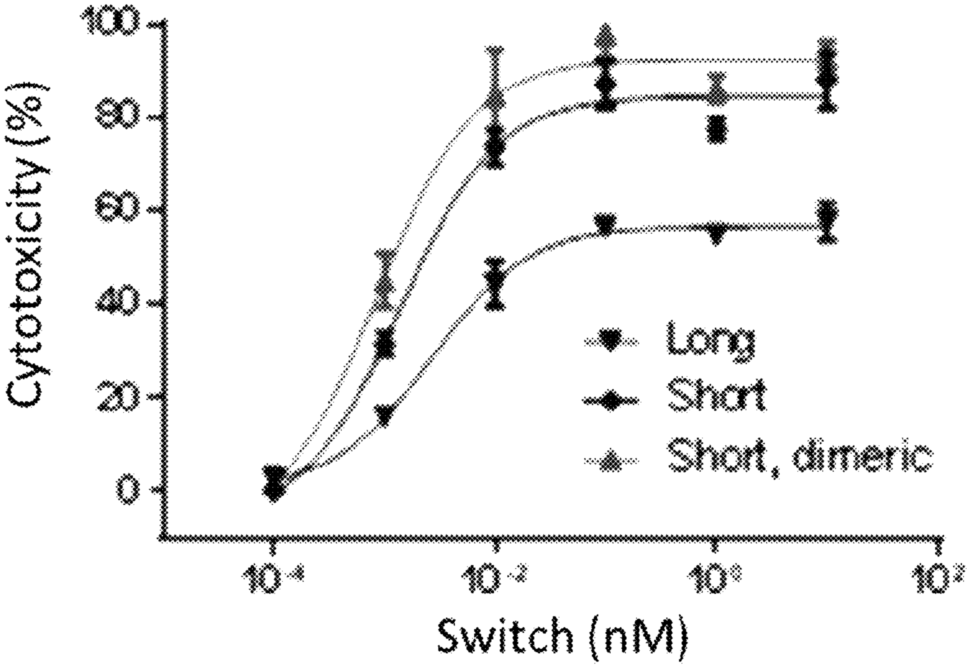
FIG. 10A-B shows results of shortening the hinge, and incorporating a dimerization motif between the scFv and the membrane of the CAR.
Figure 10B:
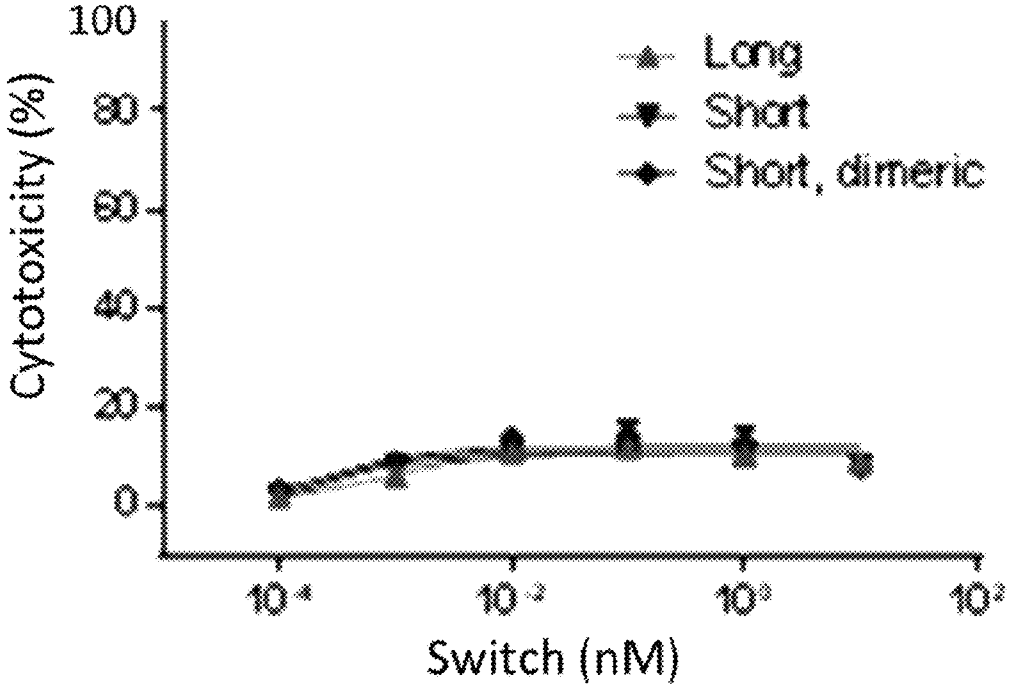
Figure 10C:
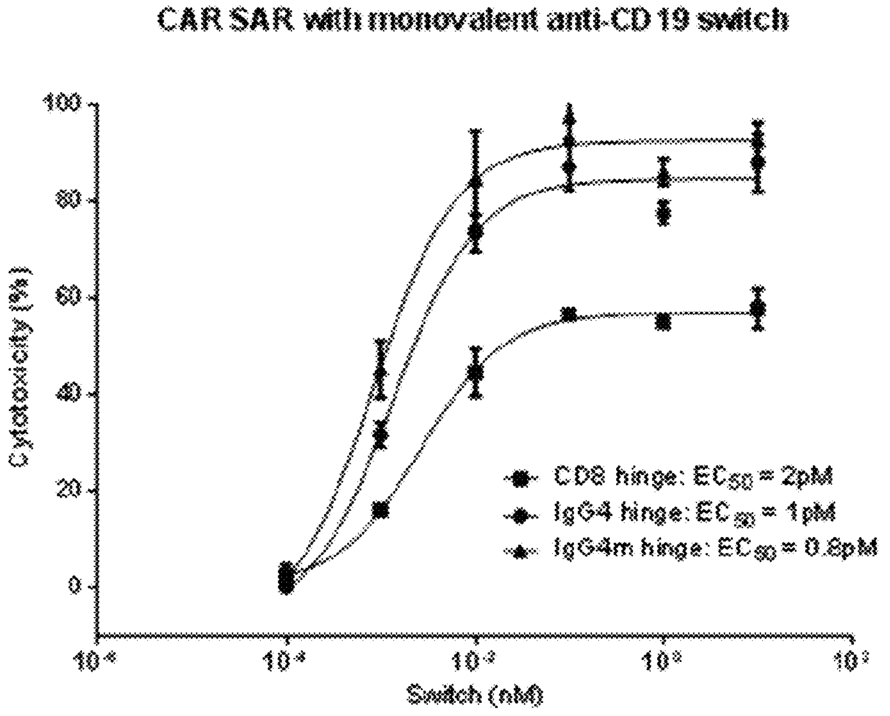
FIG. 10C shows potency is increased for all grafted switches used with the short hinge CAR.
Figure 10D:
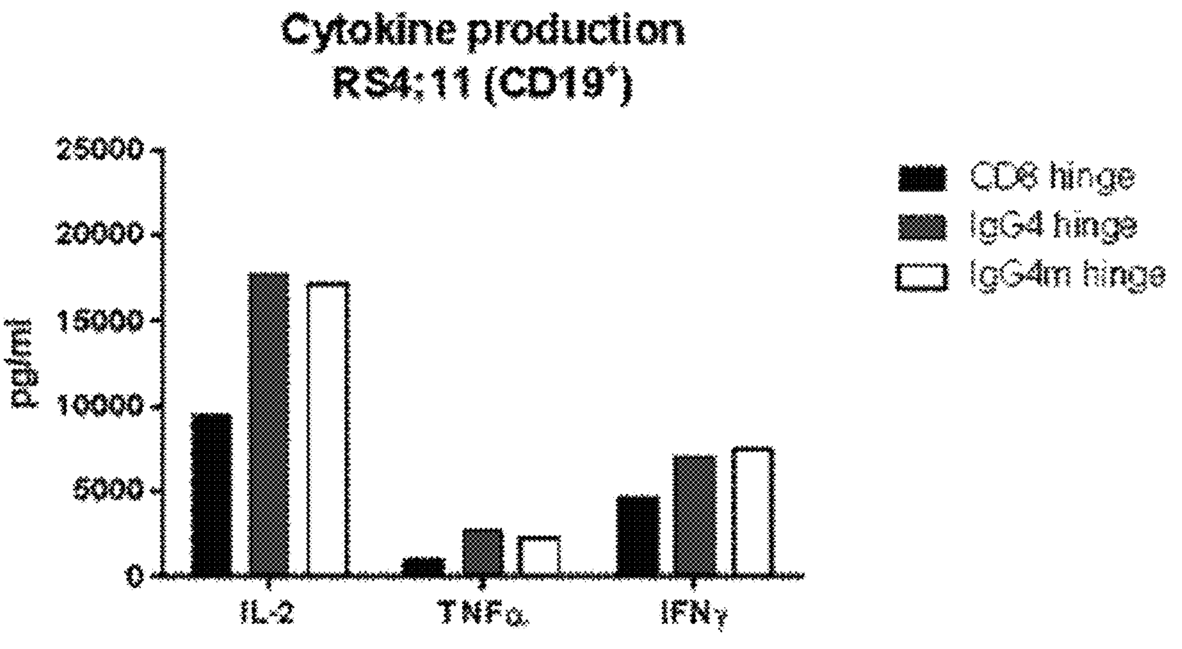
FIG. 10D shows that cytokine production by sCAR-T cells is enhanced with the IgG4 or IgG4m hinges, compared with the CD8 hinge.
Figure 27A:
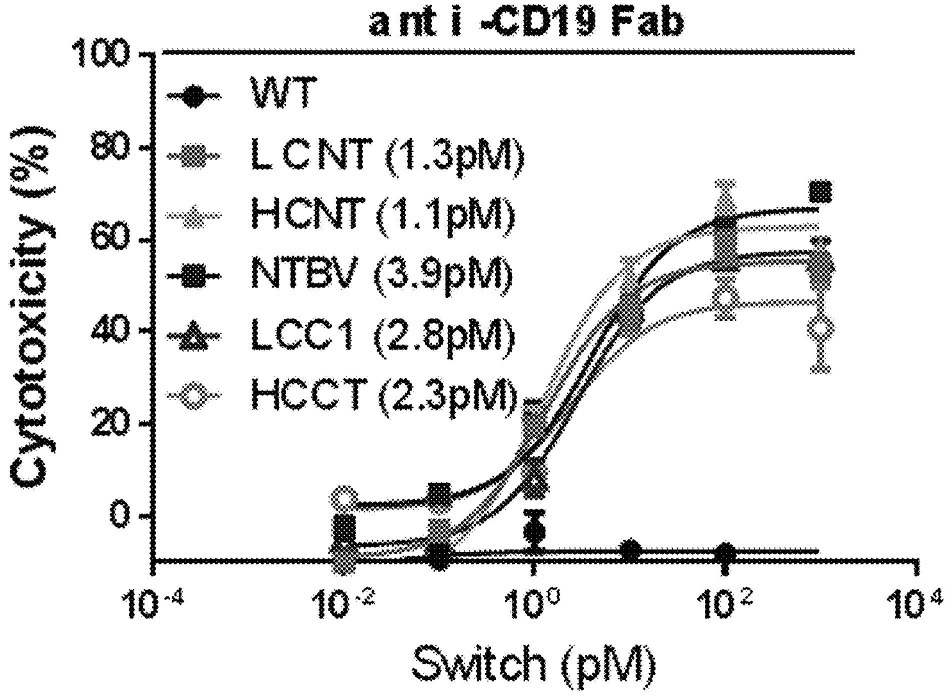
FIG. 27A-B shows cytotoxicity assay.
Figure 27B:
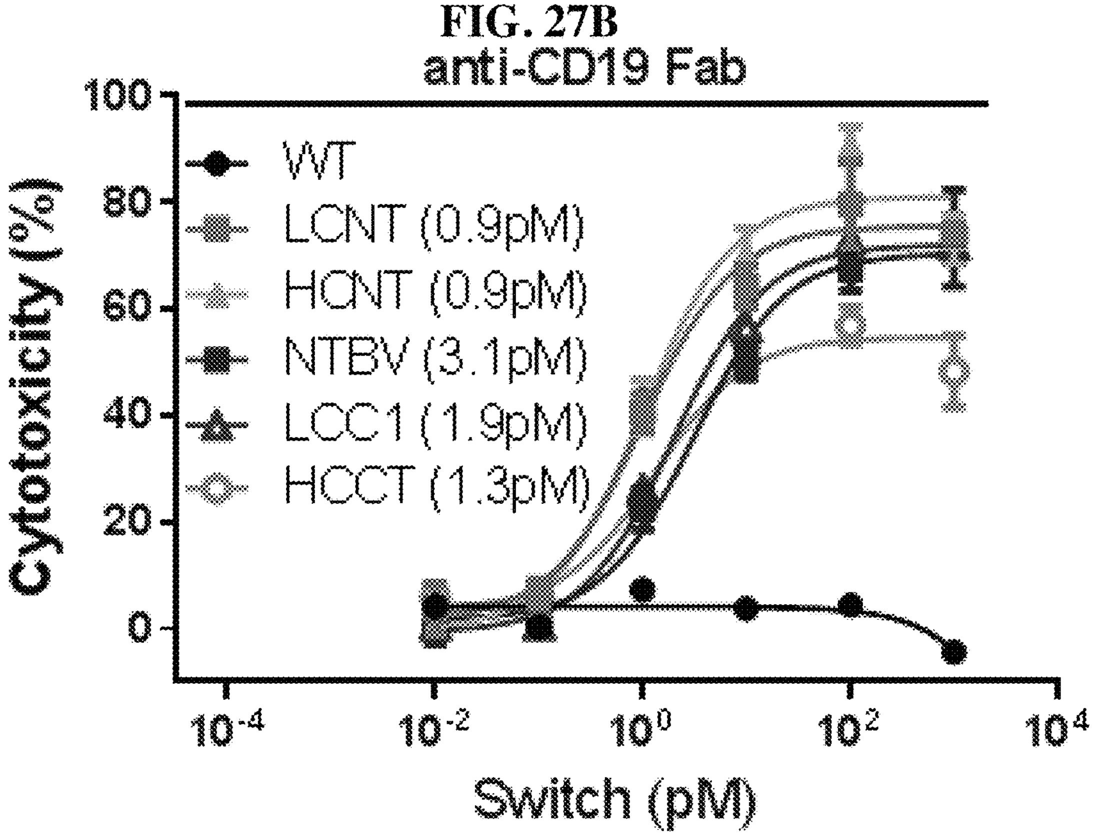

The GCN4 CAR design was therefore modified to contain the CD8 hinge region (used in CART-19), which has an extracellular CAR domain of approximately 80 Å, and an IgG4 hinge with an extracellular CAR domain of approximately 15-30 Å. An additional construct was developed where a mutation was introduced into the IgG4 hinge that allows for spontaneous disulphide bridge formation between receptor molecules (IgG4m). These three CAR designs were compared using a monovalent anti-CD19 LCNT switch (SEQ ID: 36 & 29) against the RS4;11 ($CD19^+$) cell line. Briefly, activated PBMC were transduced with lentivirus (SEQ ID: 1) containing the anti-PNE CAR construct (SEQ ID: 180) with the CD8 (SEQ ID: 68), IgG4 (SEQ ID: 70) and IgG4m (SEQ ID: 71) hinge domains. These cells were cultured for 12 days before in vitro activity with the anti-CD19 Fab LCNT switch (SEQ ID: 29 & 36) was determined. FIG. 10A shows the switch activity as assessed by analyzing the levels of LDH (see, General LDH release cytotoxicity assay [0323]). FIG. 27B shows switch activity as assessed by measuring proinflammatory cytokines released into the culture supernatants, and as shown in FIG. 10A, potency for cytotoxicity increases with shorter hinge anti-peptide CARs (LDH, E:T 10:1, 24 hr). No non-specific lysis of K562 cells was observed (FIG. 10B). Further, CARs with IgG4 hinge domains have lower $EC_{50}$ values in cytotoxicity LDH assays (FIG. 10C).

Switch Structural Activity Relationship (SAR)

The location of peptide engraftment onto the Fab switches determines the relative orientation of CART cell to target cell which greatly influences cytotoxicity. The position of the epitope that each switch binds to, be it membrane distal (far from the membrane) or membrane proximal (close to the membrane), occupies a space in the extracellular matrix that may be optimal or suboptimal for sCART cell killing. With the switchable CART cell system the peptide can be engrafted into different domains of the Fab switch to alter the overall orientation of the immunological synapse.

Figure 11B:
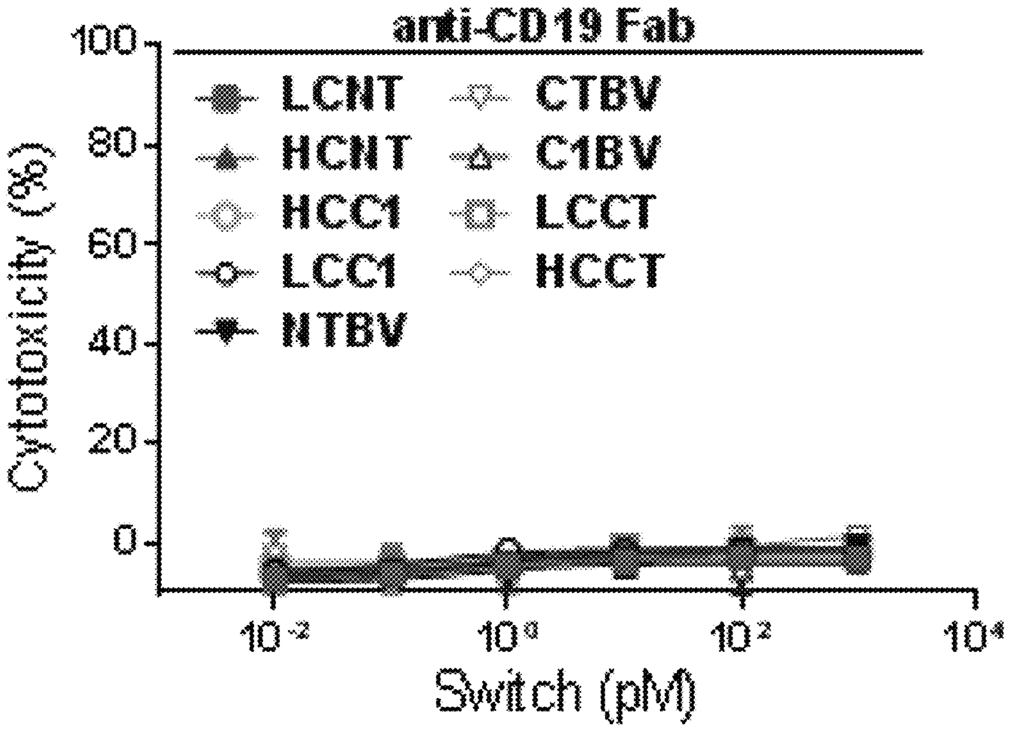
FIG. 11B shows cytotoxicity of sCAR-T cells against $CD19^-$ K562 cells with titration of the anti-CD19 Fab switch designs.
Figure 11C:
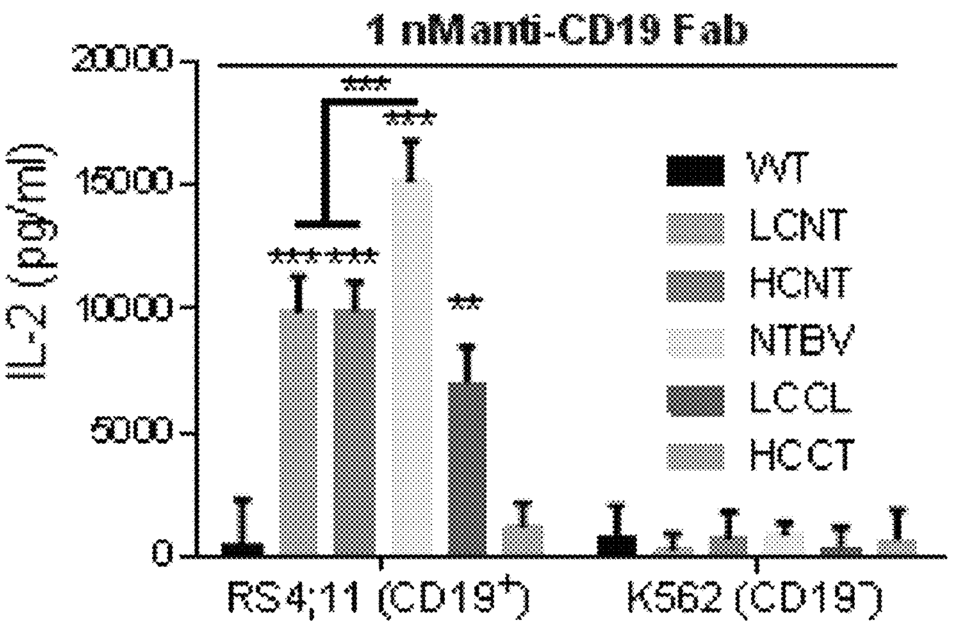
FIG. 11C shows IL-2 released from sCAR-T cells cultured with RS4;11 or K562 and 1 nM anti-CD19 Fab switches. Gray asterisk denote significance compared to WT switch and black asterisks denote significance between switches. All assays were performed with E:T=10:1 and 24 h incubation. Cytotoxicity was assessed by LDH release. Data are represented as mean±SD. Values listed next to switches show $EC_{50}$ of cytotoxicity. Significance was calculated using the student's t-test where =p<0.01 and *=p<0.001.
Figure 12A:
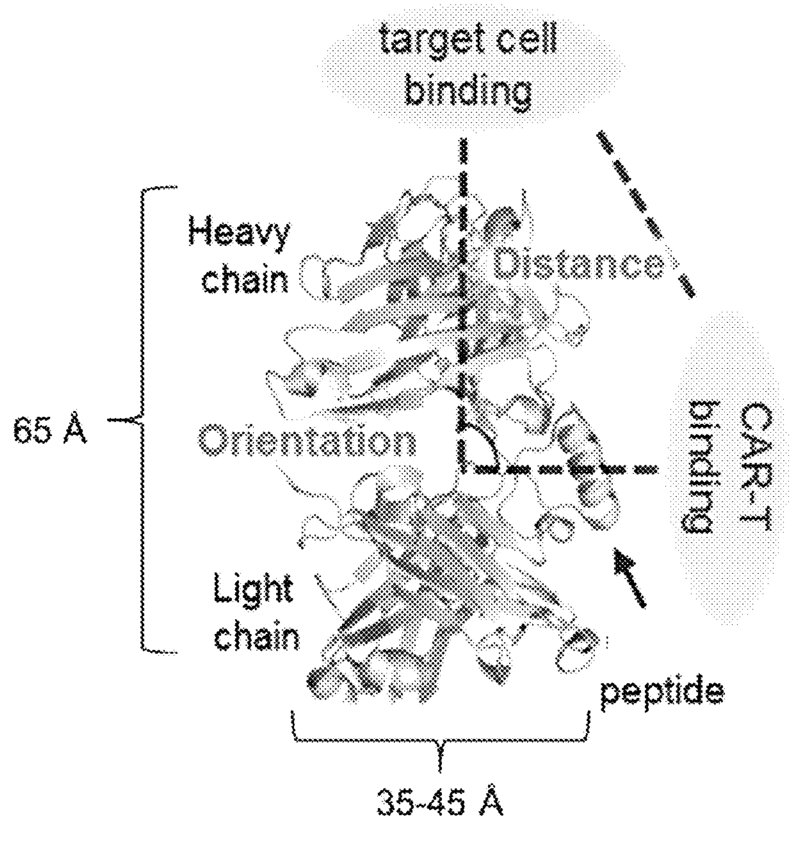
FIG. 12A-B exemplifies distance and orientation considerations as they pertain to the peptide grafting position on the Fab.
Figure 12B:
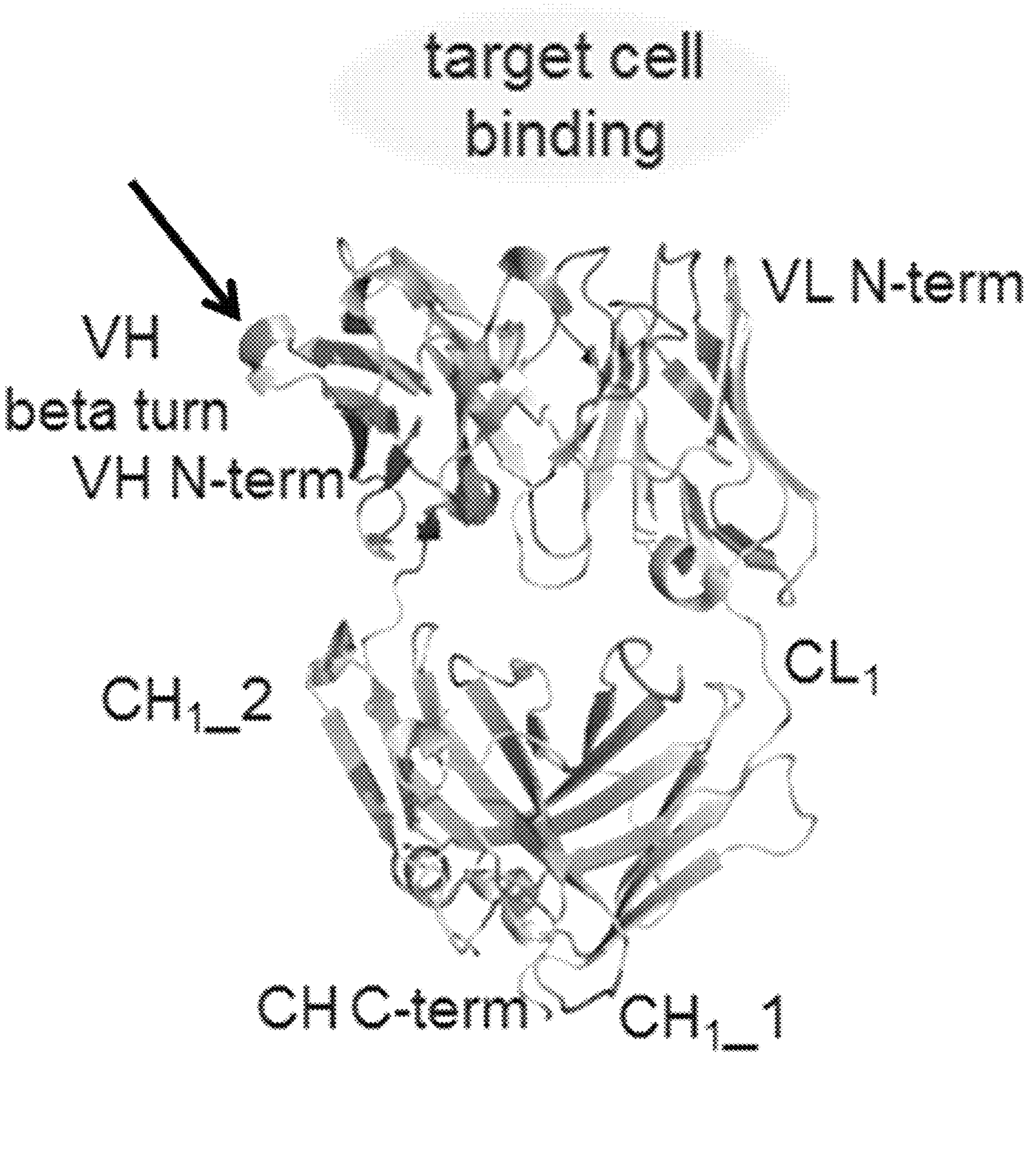

An example of switch SAR is demonstrated with an anti-CD19 switch derived from the anti-CD19 antibody Fmc63. GCN4 peptide was engrafted N-terminally, or C-terminally on each of the heavy and light chain of the Fmc63 anti-CD19 Fab molecule, or to the constant region of the light chain (CL1)(SEQ ID NOS: 30, 34, 36, 88, 97). Monovalent and bivalent combinations of these switches were expressed in mammalian protein expression systems (HEK293 or CHO cells) and purified using protein-G columns. Switches were used in cytotoxicity assays at a dose titration within the range of 10 nM to 0.0001 nM. The activity of each switch combination was tested in vitro in the General cytotoxicity assays where LDH release, cytokine production and sCART cell activation were compared (FIGS. 11A-11C). In terms of LDH release, N-terminal engraftment positions on both the light (LCNT) and heavy chains (HCNT) showed the highest levels of cytotoxicity against $CD19^+$ RS4;11 cells which correlated with elevated levels of IFNγ and IL-2 along with increased T cell activation (see FIGS. 11A-11B). Switch positions in the CL1 loop and C-terminal positions had lower cytotoxicity levels (FIG. 11A) which correlated with reduced cytokine production and sCART cell activation (FIG. 11C).

A second example of a switch SAR is demonstrated with an anti CD22 switch.

CD22 is a 135-kDa glycoprotein that is expressed in most B cell lineage and is therefore an option for the targeting of malignant B cells in non-Hodgkin's lymphomas (NHL), follicular lymphoma (FL), diffuse large B-cell lymphoma (DLBCL), and systemic lupus erythematosus. Several CD22 targeting antibodies have been published in the literature. Several of these were expressed in switch format and empirically tested in combination with the sCAR-T cells. Previously we have found that the epitope location of the antibody has a significant impact on the activity of the switchable CAR-T cell (Rodgers et al., PNAS 2016, 113: E459-68, Ma et al., PNAS 2016, 113:E450-8).

The first set of anti CD22 switches in this example were derived from the anti-CD22 antibody clone hLL2 (SEQ ID NOS: 186 and 187), which binds the membrane distal domain of CD22 with high affinity (KD=~0.7 nM). hLL2 switches with N-terminal (SEQ ID NO: 188) or C-terminal (SEQ ID NO: 189) grafts of GCN4 (SEQ ID NO: 3) on the light chain were designed. hLL2 switches with N-terminal (SEQ ID NO: 190) or C-terminal (SEQ ID NO: 191) grafts of GCN4 (SEQ ID NO: 3) on the heavy chain were designed. . Switches were expressed in mammalian protein expression systems (HEK293 or CHO cells), purified using protein-G columns, and their ability to induce cytotoxicity of Raji cells (CD22+) was tested using the general flow cytometry based cytotoxicity assay described herein.

Figure 28A:
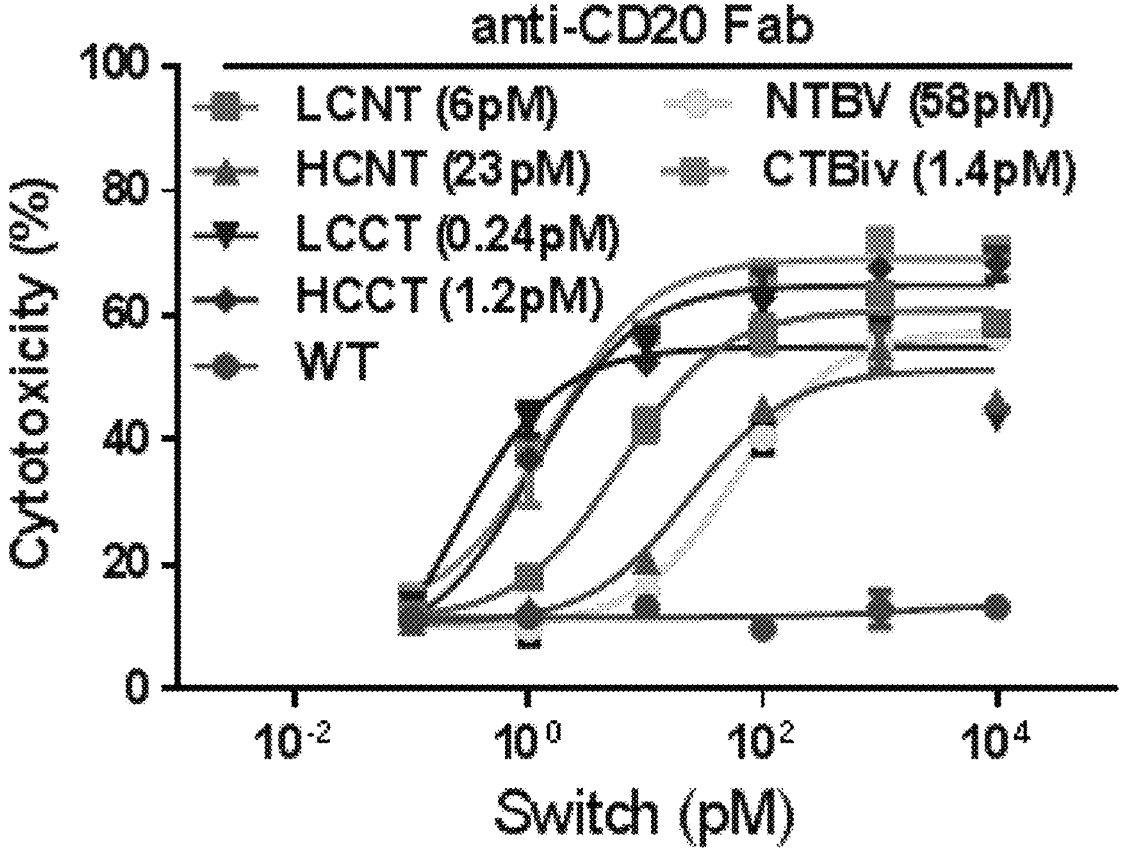
FIGS. 28A-28L.
Figure 28B:
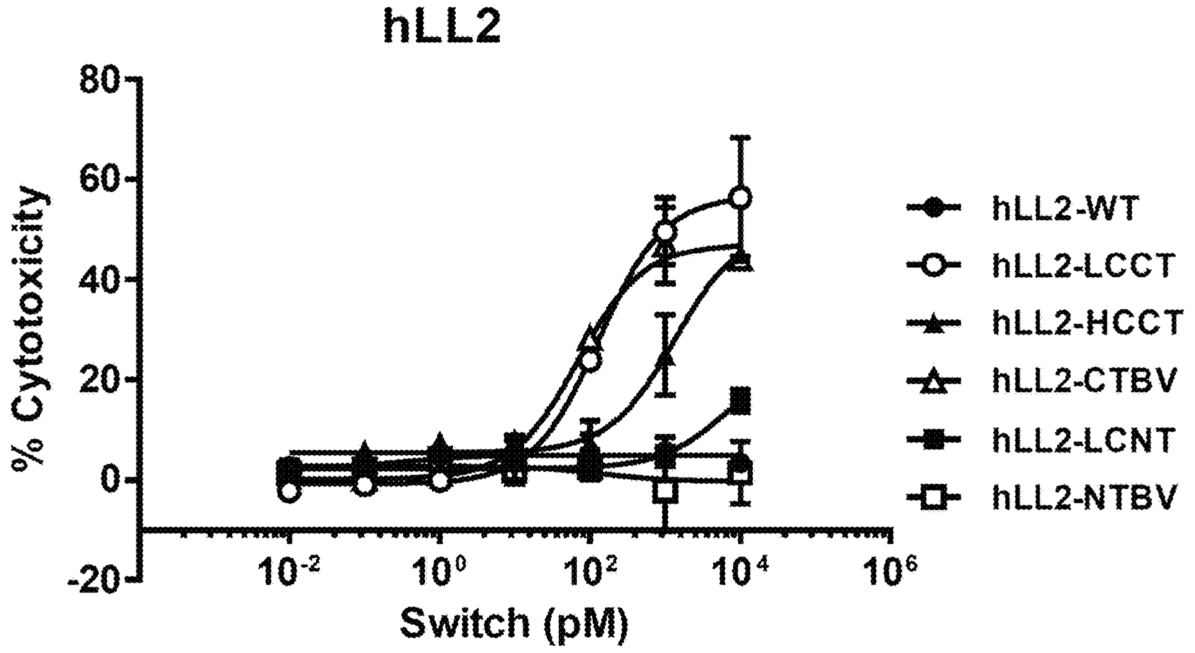

Switches were tested using a dose titration within the range of 10 nM to 0.00001 nM. FIG. 28*b* and Tables 5 and 6 show flow cytometry based cytotoxicity assay whereby sCAR-T cells (SEQ ID NO: 74) were cultured with Raji cells (CD22+) and the anti-CD22 (clone hLL2) WT (SEQ ID NO: 186 and 187), LCCT (SEQ ID NO: 189 and 187), HCCT (SEQ ID NO: 186 & 191), CTBV (SEQ ID NO: 189 & 191), LCNT (SEQ ID NO: 188 and 187) and NTBV (SEQ ID NO: 188 & 190) Fab switches. These data show that hLL2 based anti-CD22 switches with the GCN4 peptide (SEQ ID NO: 3) engrafted at the C-terminus of the FAB switch have optimal activity.

TABLE 5

| EC50 from FIG. 28B | | | | | | |
|---|---|---|---|---|---|---|
| | WT | LCCT | HCCT | CTBV | LCNT | NTBV |
| EC50 (pM) | N/A | 131.9 | 1343 | 69.11 | 6557 | 135.1 |

TABLE 6

| Raw data of cytotoxicity from FIG. 28B | | | | | | |
|---|---|---|---|---|---|---|
| Conc. (pM) | hLL2-WT | hLL2-LCCT | hLL2-HCCT | hLL2-LCNT | hLL2-CTBV | hLL2-NTBV |
| 0.01 | 2.81 | −2.13 | 1.30 | 2.50 | 1.34 | 1.52 |
| 0.1 | 2.64 | −0.84 | 6.05 | 2.21 | 0.18 | 2.19 |
| 1 | 4.59 | −0.01 | 7.67 | 0.33 | 1.38 | 4.20 |
| 10 | 5.12 | 4.80 | 8.27 | 3.91 | 4.10 | 2.07 |
| 100 | 5.40 | 23.84 | 7.35 | 3.09 | 28.19 | 2.52 |
| 1000 | 5.72 | 49.64 | 24.96 | 5.19 | 46.91 | −2.07 |
| 10000 | 3.46 | 56.47 | 45.11 | 15.81 | 44.17 | 1.50 |

A third example of a switch SAR is demonstrated with an second set of anti CD22 switches, which were derived from the anti-CD22 antibody clone m971 (SEQ ID NOS: 106, 107). M971 binds the membrane proximal domain of CD22 with low affinity (KD=~25 nM). m971 switches with N-terminal (SEQ ID NO: 109) or C-terminal (SEQ ID NO: 111) grafts of GCN4 peptide (SEQ ID NO: 3) on the light chain were designed. m971 switches with N-terminal (SEQ ID NO: 108) or C-terminal (SEQ ID NO: 110) grafts of GCN4 peptide (SEQ ID NO: 3) on the heavy chain were also designed. Switches were expressed in mammalian protein expression systems (HEK293 or CHO cells), purified using protein-G columns, and their ability to induce cytotoxicity of Raji cells (CD22+) was tested using the general flow cytometry based cytotoxicity assay described herein.

Figure 28C:
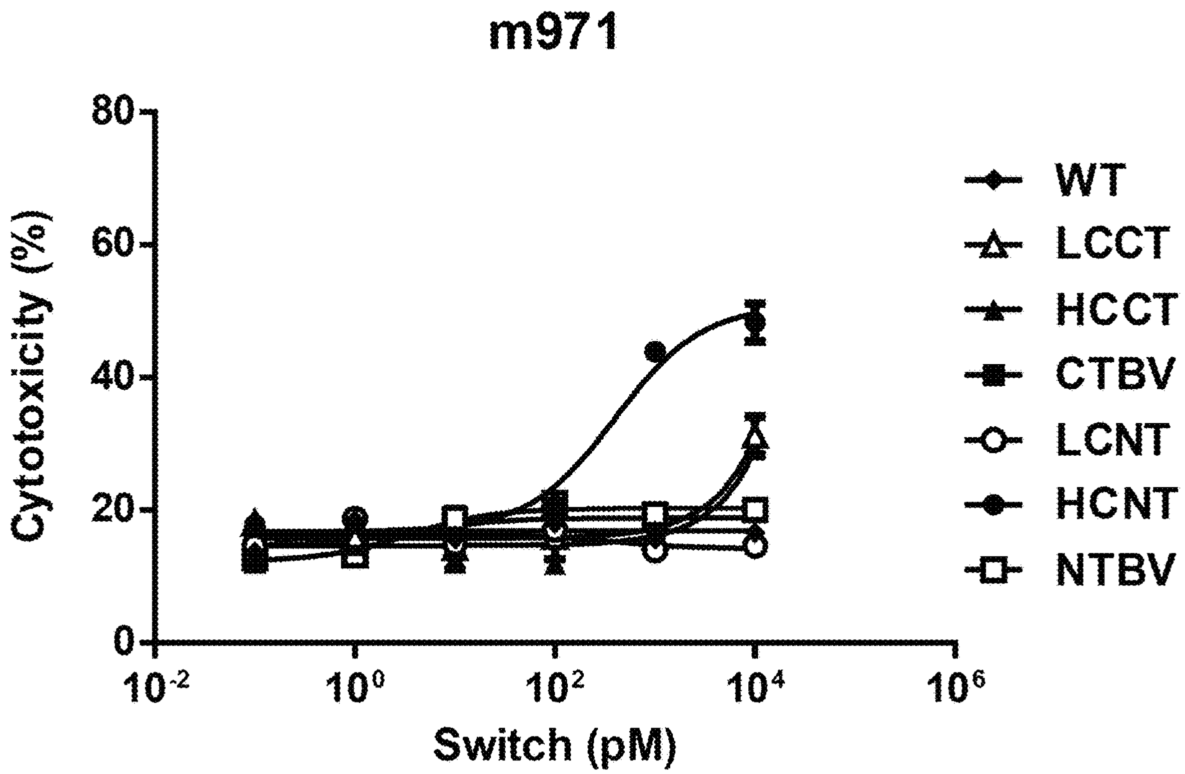

FIG. 28C and Tables [xx and xx] show results from the cytotoxicity assay, whereby sCAR-T cells (SEQ ID NO: 74) were cultured with Raji cells (CD22+) and the anti-CD22 (clone m971) WT (SEQ ID NOS: 106, 107), LCCT (SEQ ID NOS: 106, 111), HCCT (SEQ ID NOS: 107,110), CTBV (SEQ ID NOS: 110, 111), LCNT (SEQ ID NOS: 106, 109), HCNT (SEQ ID NOS: 107, 108) or NTBV (SEQ ID NOS: 108, 109) Fab switches. These data show that m971 based anti-CD22 switches with the GCN4 peptide (SEQ ID NO: 3) engrafted at the C-terminus of the FAB switch have optimal activity.

TABLE 7

| EC50 from FIG. 28C | | | | | | | |
|---|---|---|---|---|---|---|---|
| | WT | LCCT | HCCT | CTBV | LCNT | HCNT | NTBV |
| EC50 (pM) | N/A | N/A | N/A | 3.846 | 395.6 | 398.0 | 3.505 |

TABLE 8

Raw data of cytotoxicity from FIG. 28C

| Conc. (pM) | WT | LCCT | HCCT | LCNT | HCNT | CTBV | NTBV |
|---|---|---|---|---|---|---|---|
| 0.1 | 13.60544 | 17.18721 | 18.36735 | 14.62585 | 17.68708 | 14.96599 | 12.92517 |
| 1 | 18.36735 | 15.1464 | 15.64626 | 18.70748 | 19.04762 | 14.96599 | 13.26531 |
| 10 | 15.64626 | 13.44572 | 12.92517 | 14.96599 | 15.9864 | 18.36735 | 18.70749 |
| 100 | 18.02721 | 15.1464 | 11.90477 | 17.0068 | 20.7483 | 16.66667 | 21.08844 |
| 1000 | 15.64626 | 15.1464 | 15.9864 | 13.94558 | 43.87755 | 18.70748 | 19.38776 |
| 10000 | 16.66667 | 30.45252 | 29.2517 | 14.62585 | 48.29932 | 20.40816 | 20.06803 |

Figure 28D:
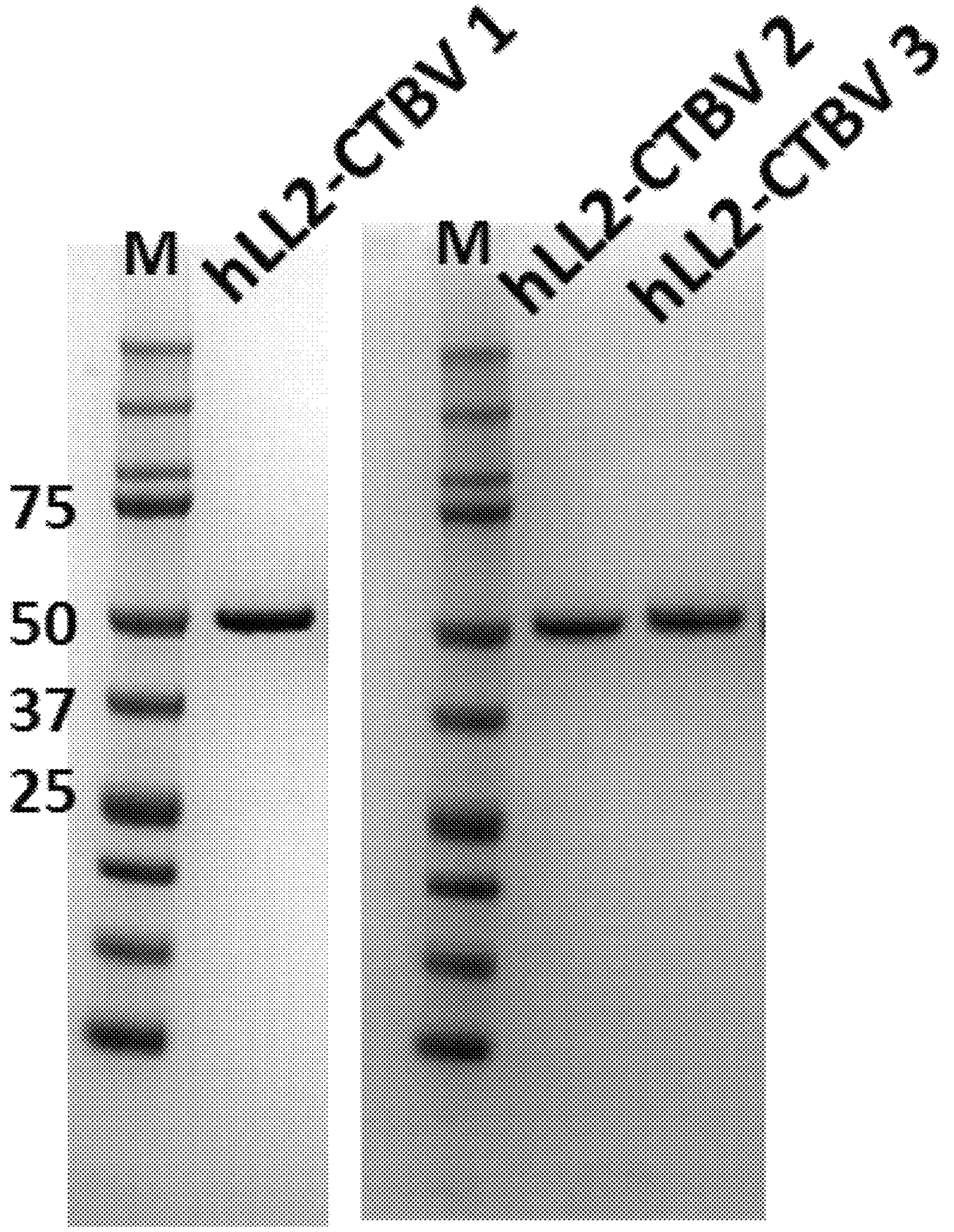

We tested whether we could increase activity by further increasing the distance between sCAR-T and target cells. This can be achieved by adding a linker, e.g., by extra GGGGS linkers between the peptide (SEQ ID: 3) and the anti-CD22 switch. To test this, hLL2 derived anti-CD22 switches were created with 1 GGGGS linker (CTBV1; SEQ ID: 189 & 191), 2 GGGGS linker (CTBV2; SEQ ID: 192 & 194) or 3 GGGGS linker (CTBV3; SEQ ID: 193 & 195). FIG. 28D shows SDS gel images of these constructs, which are labeled "hLL2-CTBV 1" for anti-CD22 (clone hLL2)-Fab CTBV1 (SEQ ID: 189 & 191), "hLL2-CTBV 2" for CTBV2 (SEQ ID: 192 & 194), and "hLL2-CTBV 3" for CTBV3 (SEQ ID: 193 & 195). M represents protein marker.

Figure 28E:
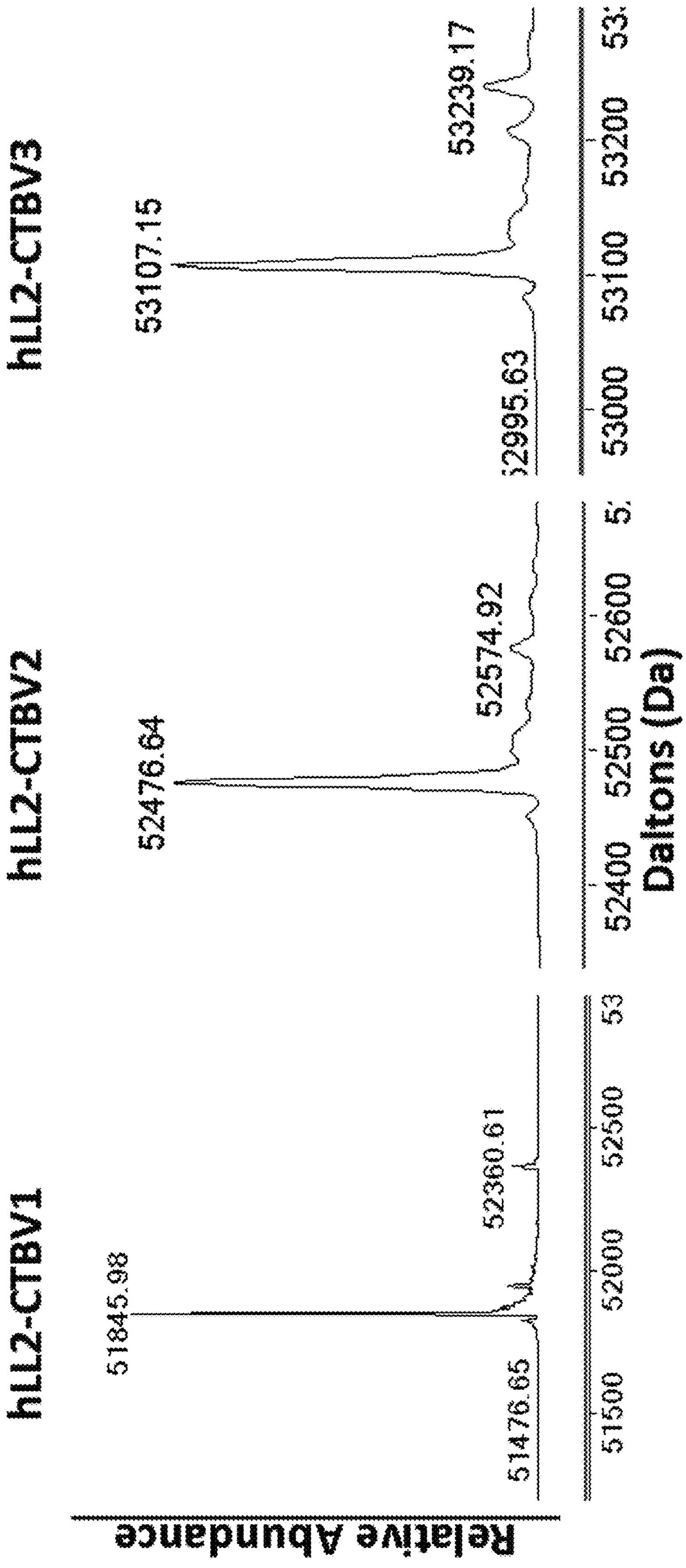

The molecular weights of hLL2 Fab with GCN4 tag was determined by Q-TOF LC/MS (FIG. 28E and Table 9. FIG. 28E shows spectrometry of these anti-CD22 (clone hLL2)-Fab-CTBVs and Table 9 shows the difference in expected and observed masses, listed as Da error, which is attributable to an N-terminal glutamine to pyroglutamate conversion.

TABLE 9

Data from FIG. 28E: Q-TOF LC/MS determined molecular weights of hLL2 Fab with GCN4 tag determined by.

| hLL2-Fab | Expected | Observed | Da error |
|---|---|---|---|
| CTBV1 | 51861.87 | 51845.98 | −15.89 |
| CTBV2 | 52492.44 | 52476.64 | −15.80 |
| CTBV3 | 53123.02 | 53107.15 | −15.87 |

Figure 28F:
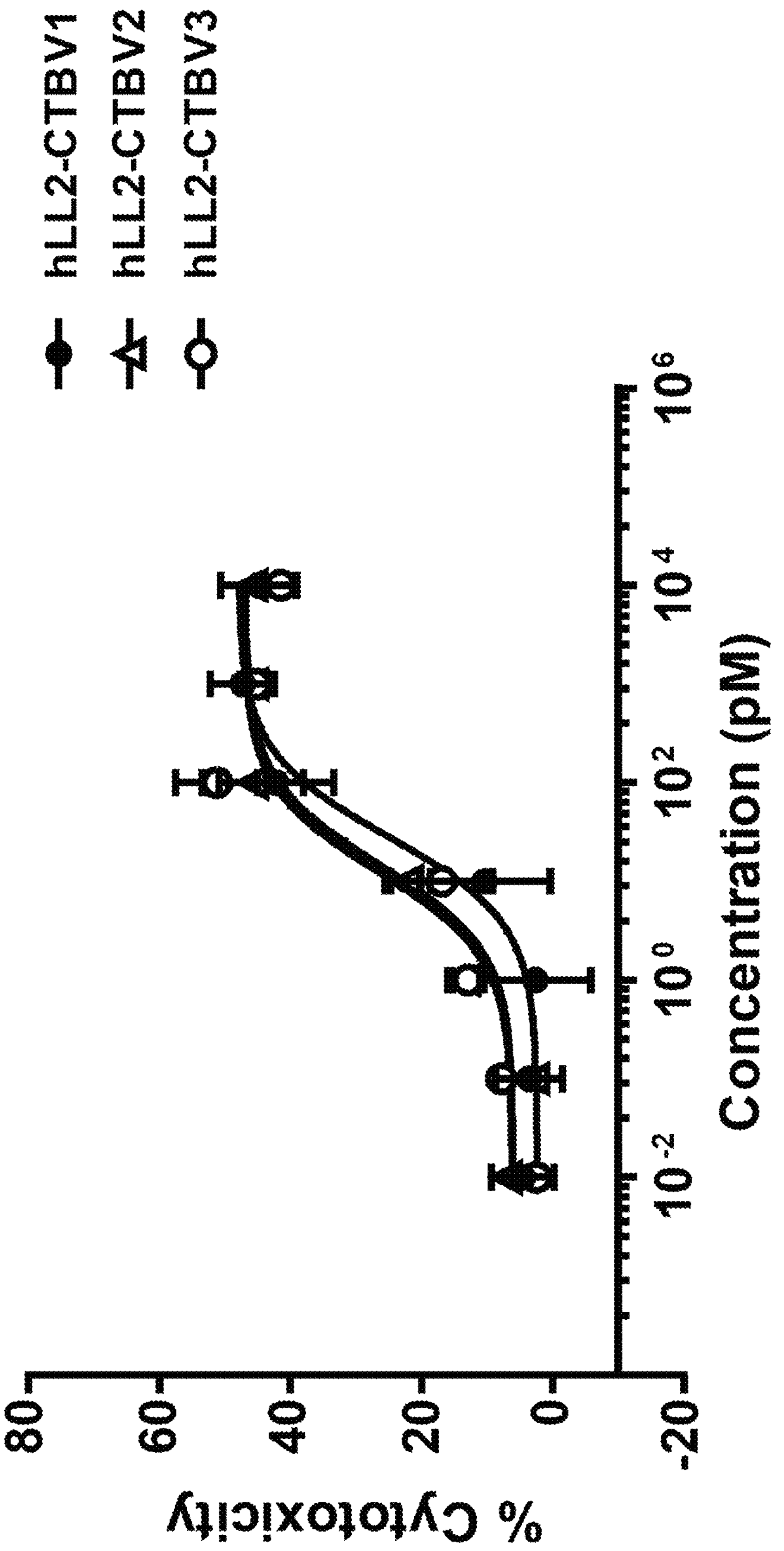

We tested the ability of these hLL2-CTBV switches to induce cytotoxicity of sCAR-T cells using a flow cytometry based cytotoxicity assay, as discussed above, whereby sCAR-T cells (SEQ ID: 74) were cultured with Raji cells (CD22+) and either one of the anti-CD22 CTBV1, CTBV2 and CTBV3 switches. As shown in FIG. 28F and Tables [XX and XX], cytotoxicity of sCAR-T cells with short-dimeric hinge against Raji cells (CD22+) was not significantly different between the groups treated with the CTBV1 (SEQ ID: 189 & 191), CTBV2 (SEQ ID: 192 & 194) or CTBV3 (SEQ ID: 193 & 195) switches. Importantly, these data demonstrate that, although activity was not improved significantly by the extension of the linker, the linkers separating the peptide from the FAB can be manipulated without loosing activity. The raw data used to generate FIG. 28F is shown below in Table 10, and EC50 values calculated from this data are shown in Table 11.

TABLE 10

Raw data of FIG. 28F cytotoxicity by anti-CD22 CTBV1, CTBV2 and CTBV3 switches.

| Conc. (pM) | hLL2-CTBV1 | hLL2-CTBV2 | hLL2-CTBV3 |
|---|---|---|---|
| 0.01 | 4.60 | 7.08 | 2.54 |
| 0.1 | 3.60 | 2.90 | 7.90 |
| 1 | 2.68 | 13.37 | 12.95 |
| 10 | 10.39 | 22.10 | 16.99 |
| 100 | 42.20 | 45.81 | 51.27 |
| 1000 | 47.38 | 45.77 | 45.27 |
| 10000 | 44.85 | 45.99 | 41.54 |

TABLE 11

EC50 values from FIG. 28F showing cytotoxicity induced by anti-CD22 CTBV1, CTBV2 and CTBV3 switches.

| | hLL2-CTBV1 | hLL2-CTBV2 | hLL2-CTBV3 |
|---|---|---|---|
| EC50 (pM) | 28.77 | 12.65 | 14.89 |

Example 7. Use of IgG Based Switches to Improve Anti-CD22 Switch Efficacy

We tested whether the efficacy of anti-CD22 switches against Raji cells may be improved by using IgG based switches, which would provide higher affinities than the FAB based switches. Increasing the affinity of the switch to the target cell, through use of a IgG vs Fab, may increase activity of the sCAR-T cells. An IgG format will also increase the valency of the molecule to 2 in the case of LCCT and HCCT, or 4 in the case of CTBV.

Figure 28G:
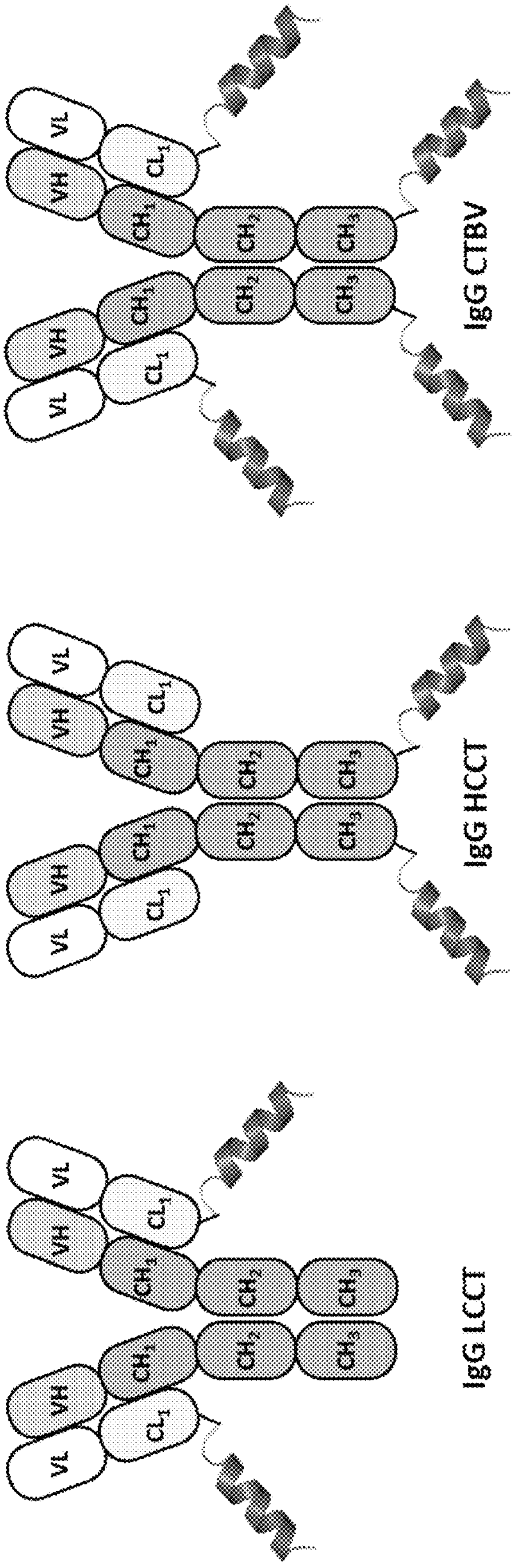
Figure 28H:
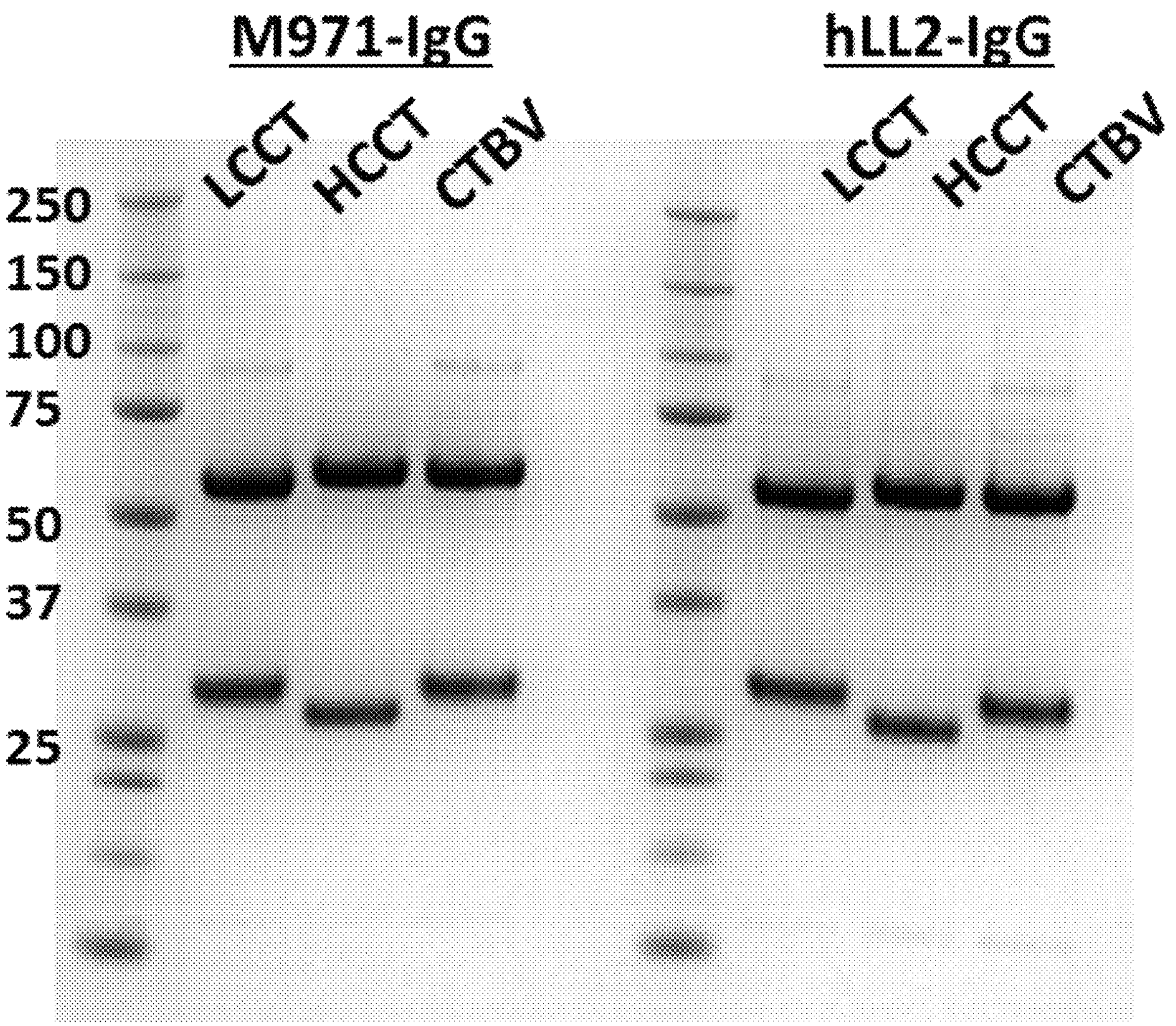

Anti-CD22-IgG switches were generated for both the m971 and hLL2 clones, each of which demonstrated in vitro activity in the FAB format. The GCN4 peptide was engrafted onto the LCCT (SEQ ID NOS: 189, 196) or the IgG HCCT (SEQ ID NOS: 186, 197) of the hLL2 clone (FIG. 28G), and the GCN4 peptide was also engrafted onto the LCCT (SEQ ID NOS: 111, 198) or the IgG HCCT (SEQ ID NOS: 107, 199) of the m971 clone (FIG. 28G). FIG. 28H shows SDS gel images of these constructs after expression and purification as described in the above examples.

Figure 28I:
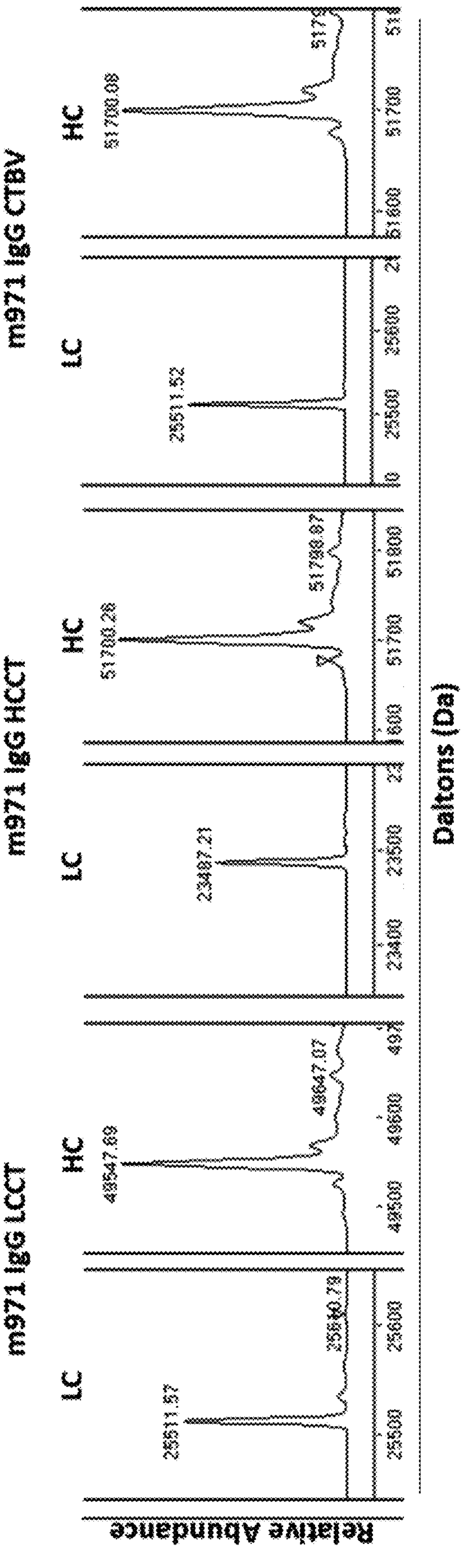

FIG. 28I and Table 12 show the molecular weights of anti-CD22-IgG (clone m971)-LCCT, HCCT, and CTBV, as determined by Q-TOF LC/MS. Samples were treated with PNGase F for deglycosylation and 10 mM DTT for reduction. Da error in heavy chain of LCCT caused by cleavage of lysine at C-terminus of heavy chain. Da erroring heavy chains of HCCT and CTBV came from the N-terminal glutamine to pyroglutamate conversion.

TABLE 12

| Data from FIG. 28I: Q-TOF LC/MS-determined molecular weights of m971-IgG switches with GCN4 tag. | | | | | | |
|---|---|---|---|---|---|---|
| m971- | expected | | observed | | Da error | |
| IgG | LC | HC | LC | HC | LC | HC |
| LCCT | 25514.39 | 49697.93 | 25511.57 | 49547.69 | −2.82 | −150.24 |
| HCCT | 23490.13 | 51722.19 | 23487.21 | 51700.26 | −2.92 | −21.93 |
| CTBV | 25514.39 | 51722.19 | 25511.52 | 51700.08 | −2.87 | −22.11 |

Figure 28J:
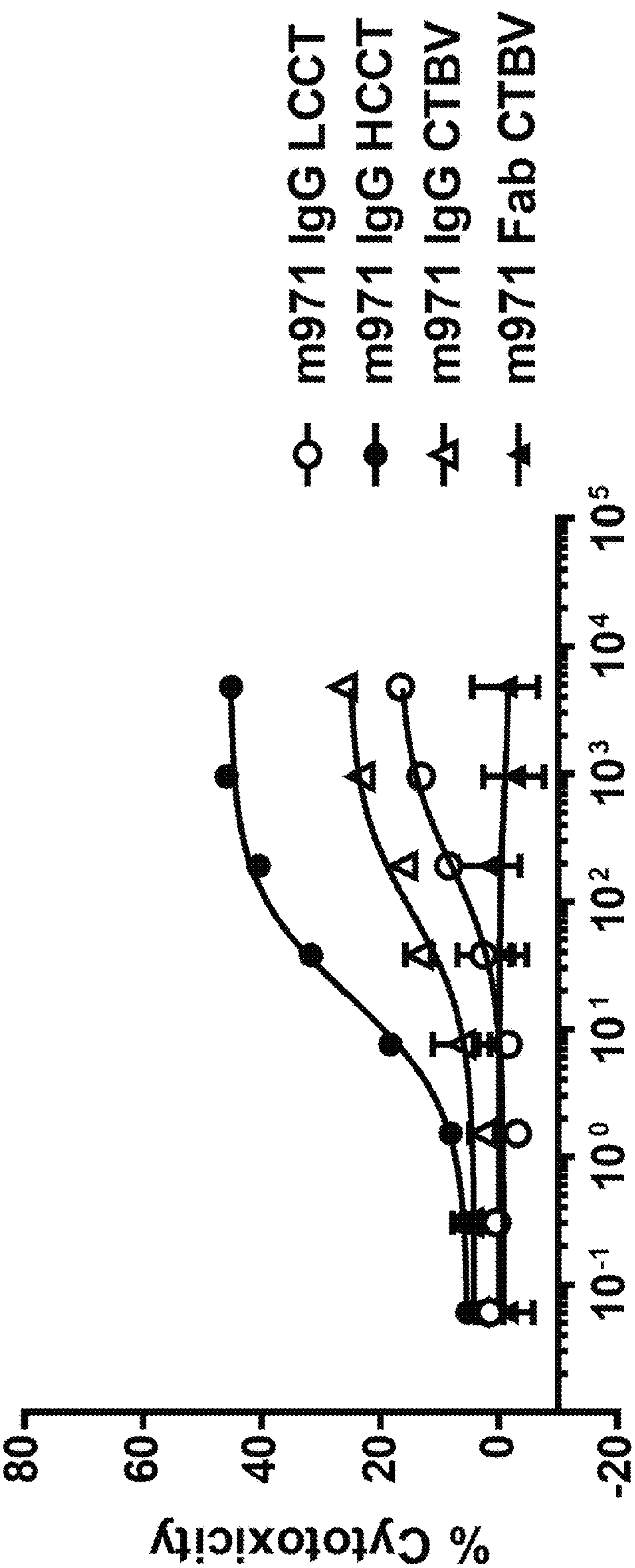
Figure 28K:
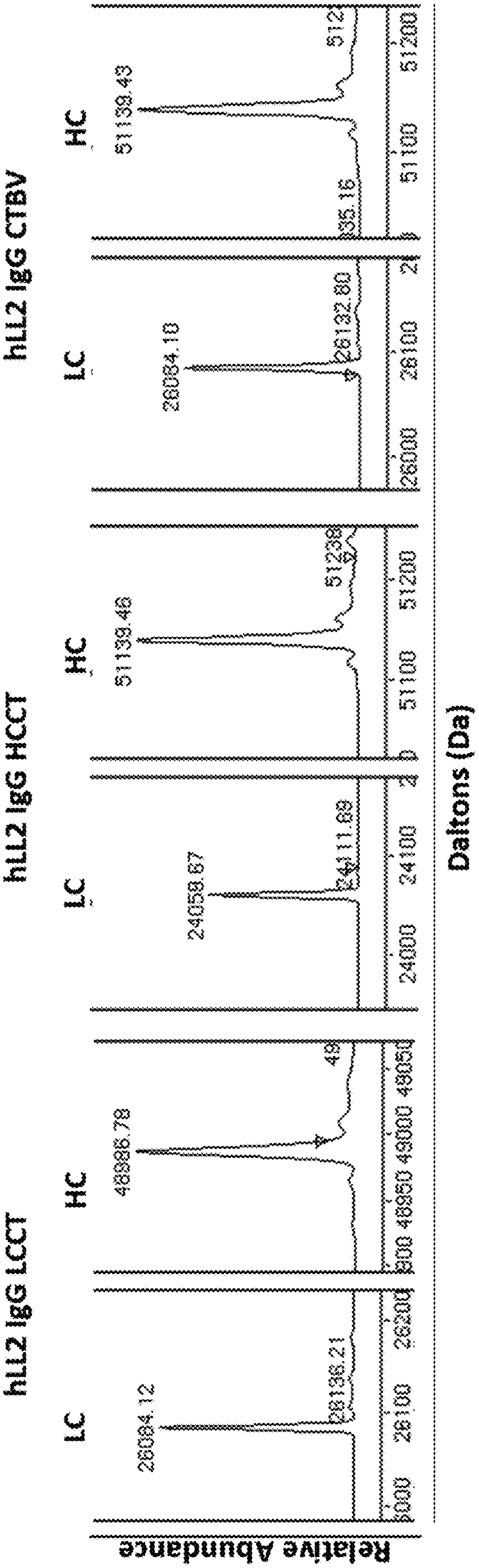

FIG. 28K and Table 13 show the molecular weights of anti-CD22-IgG (clone hLL2)-LCCT, HCCT, and CTBV, as determined by Q-TOF LC/MS. Samples were treated with PNGase F for deglycosylation and 10 mM DTT for reduction. Da error in heavy chain of LCCT caused by cleavage of lysine at C-terminus of heavy chain. Da erroring heavy chains of HCCT and CTBV came from the N-terminal glutamine to pyroglutamate conversion.

TABLE 13

| Data from FIG. 28K: Q-TOF LC/MS-determined molecular weights of hLL2-IgG switches with GCN4 tag. | | | | | | |
|---|---|---|---|---|---|---|
| hLL2- | expected | | observed | | difference | |
| IgG | LC | HC | LC | HC | LC | HC |
| LCCT | 26087.03 | 49137.32 | 26084.12 | 48986.78 | −2.91 | −150.54 |
| HCCT | 24062.77 | 51161.58 | 24059.67 | 51139.46 | −3.1 | −22.12 |
| CTBV | 26087.03 | 51161.58 | 26084.1 | 51139.43 | −2.93 | −22.15 |

Figure 28L:
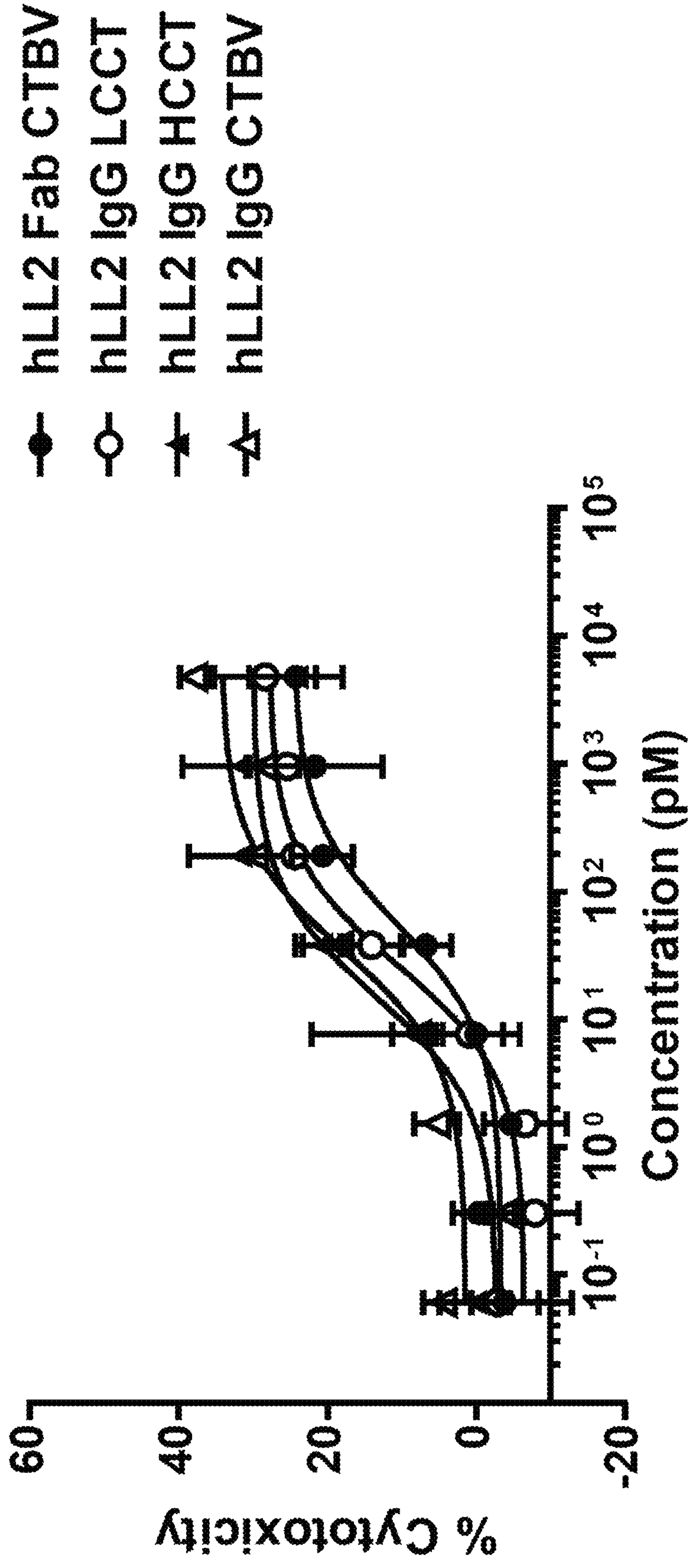

The activity of each of these m971-IgG and hLL2-IgG switches, as compared to respective bivalent m971-FAB and hLL2-FAB switches, was assessed in a flow cytometry based cytotoxicity assay, as described above. sCAR-T cells (SEQ ID: 74) were cultured with Raji cells (CD22+) and with various concentrations of the switches, which concentrations are indicated on the x axis of the figure (FIG. 28J and FIG. 28L). The raw data used to generate FIG. 28J is shown below in Table 15, and EC50 values calculated from this data are shown in Table 14; the raw data used to generate FIG. 28L is shown below in Table 17, and EC50 values calculated from this data are shown in Table 16.

As shown in FIG. 28J and FIG. 28L, for both the m971-FAB and hLL2-FAB switches, the highest efficacy was observed with the HCCT switches. Thus, in these examples, use of IgG-based switches led to increased efficacy for cytotoxicity.

TABLE 14

| m971-IgG switch EC50 values from FIG. 28J for inducing cytotoxicity | | | | |
|---|---|---|---|---|
| | m971 IgG LCCT | m971 IgG HCCT | m971 IgG CTBV | m971 Fab CTBV |
| EC50 (pM) | 194.2 | 18.13 | 83.15 | 777.5 |

TABLE 15

| Raw data of FIG. 28J m971-IgG cytotoxicity | | | | |
|---|---|---|---|---|
| Conc. (pM) | m971 IgG LCCT | m971 IgG HCCT | m971 IgG CTBV | m971 Fab CTBV |
| 0.06 | 1.51 | 5.33 | 3.93 | −1.20 |
| 0.30 | 0.42 | 5.65 | 4.93 | 2.20 |

TABLE 15-continued

| Raw data of FIG. 28J m971-IgG cytotoxicity | | | | |
|---|---|---|---|---|
| Conc. (pM) | m971 IgG LCCT | m971 IgG HCCT | m971 IgG CTBV | m971 Fab CTBV |
| 1.52 | −3.01 | 8.14 | 2.68 | −2.05 |
| 7.62 | −1.47 | 18.32 | 6.31 | 0.47 |
| 38.10 | 2.52 | 31.68 | 13.48 | −1.00 |
| 190.48 | 8.43 | 40.50 | 16.16 | 1.78 |
| 952.40 | 13.12 | 45.89 | 23.27 | −2.47 |
| 4762.00 | 16.64 | 45.16 | 26.32 | −1.02 |

TABLE 16

| hLL2-IgG switch EC50 values from FIG. 28L for inducing cytotoxicity | | | | |
|---|---|---|---|---|
| | hLL2 Fab CTBV | hLL2 IgG LCCT | hLL2 IgG HCCT | hLL2 IgG CTBV |
| EC50 (pM) | 55.55 | 26.93 | 15.32 | 34.69 |

TABLE 17

| Raw data of FIG. 28L hLL2-IgG cytotoxicity | | | | |
|---|---|---|---|---|
| Conc. (pM) | hLL2 Fab CTBV | hLL2 IgG LCCT | hLL2 IgG HCCT | hLL2 IgG CTBV |
| 0.06 | −3.84 | −2.80 | 0.25 | 4.45 |
| 0.30 | −0.28 | −7.88 | −1.05 | −3.82 |
| 1.52 | −4.59 | −6.59 | −4.45 | 5.34 |
| 7.62 | 0.02 | 0.95 | 8.18 | 7.92 |
| 38.10 | 6.77 | 14.07 | 20.88 | 18.33 |
| 190.48 | 20.72 | 24.40 | 31.78 | 29.82 |
| 952.40 | 21.70 | 25.43 | 31.70 | 28.61 |
| 4762.00 | 24.28 | 28.46 | 24.14 | 38.05 |

Figure 14:
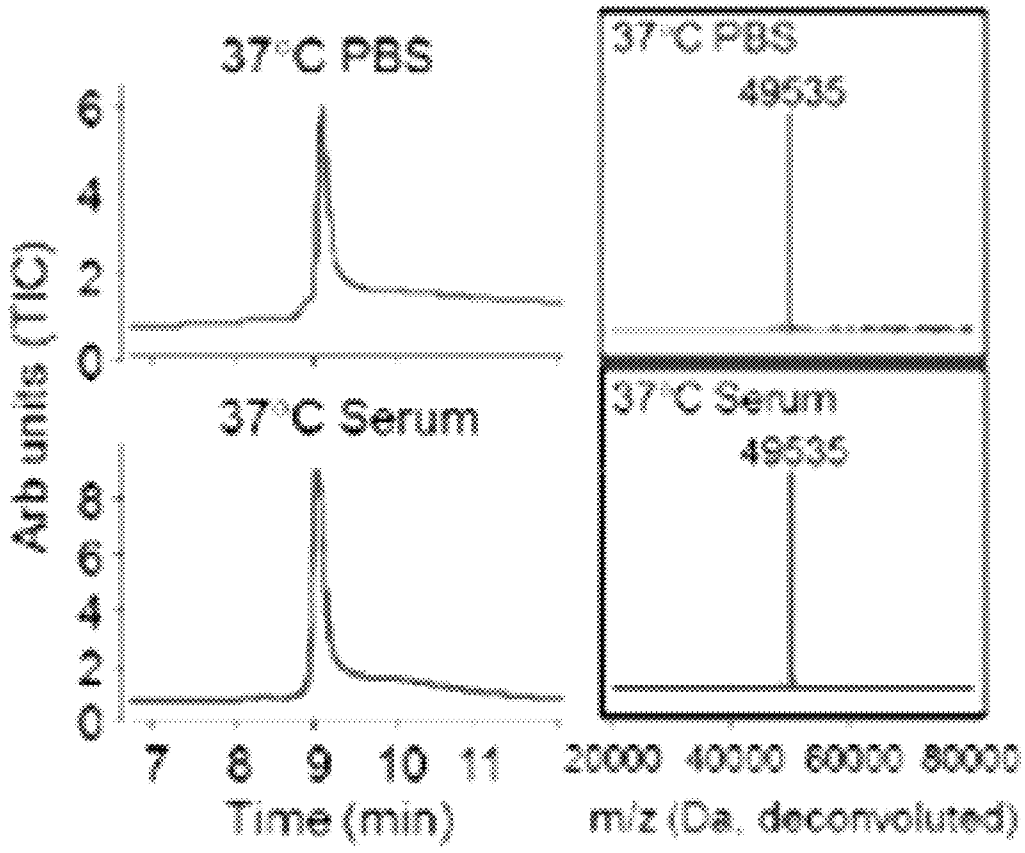
FIG. 14 shows a liquid chromatography and mass spectrometry analysis of a peptide switch indicating no proteolysis occurs in mouse serum.
Figure 15:
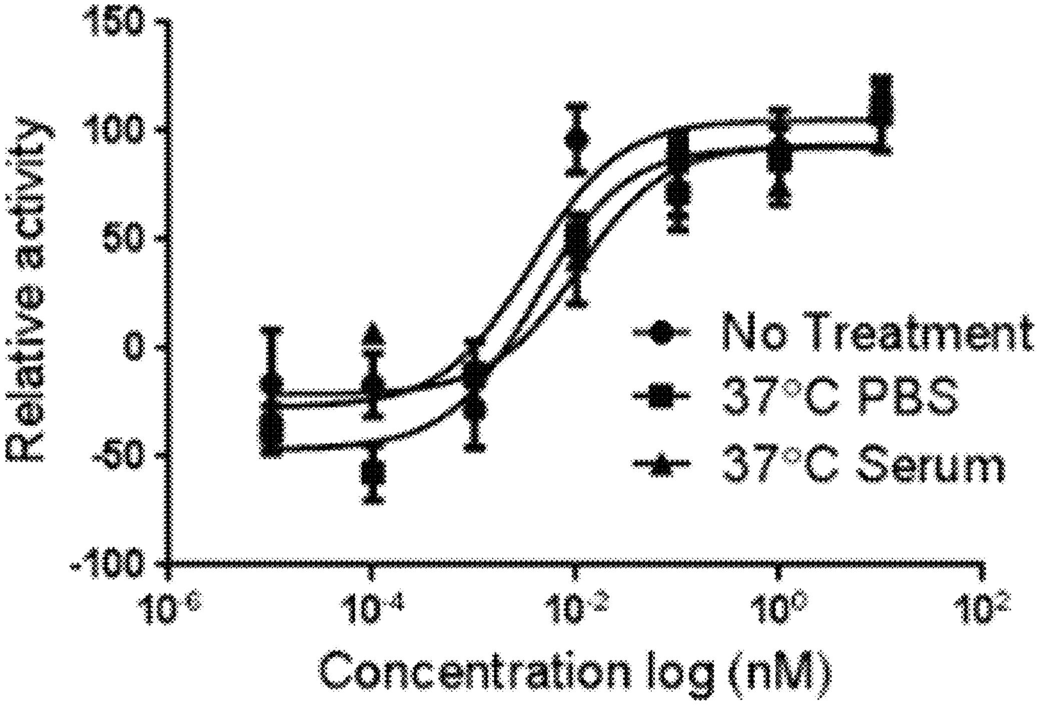
FIG. 15 shows the activity of a peptide-based switch incubated in mouse serum for 2 hours at 37 degrees celcius vs 37 degrees celcius in PBS. No treatment was incubated 2 hours at 4 degrees in PBS. This indicates there is no appreciable loss of activity in mouse serum.

Example 8. Optimization of CAR Platform-Modulating the Immunological Synapse with Compensatory Modifications of Switch Peptide Position and CAR Hinge Length To understand the relationship between peptide grafting positions and switchable CAR T (sCART) cell activity, several switch designs were generated with varied peptide engraftment positions. The expression of these were confirmed by protein gel (FIG. 13A) and QTOF mass spectrometry (Table 18) and switches showed good serum stability (FIGS. 14-15).

TABLE 18

| FMC63 | Protein mass (Da) | | Error | |
|---|---|---|---|---|
| Protein | Expected | Found | ppm | Da |
| WT | 47321.99 | 47323.03 | −21.98 | 1.04 |
| LCNT | 49346.25 | 49346.93 | −13.78 | 0.68 |
| HCNT | 50312.44 | 50314.54 | −41.74 | 2.10 |
| NTBV | 52336.70 | 52339.41 | −51.78 | 2.71 |
| LCC1 | 49533.36 | 49534.46 | −22.21 | 1.10 |
| HCC1 | 49517.41 | 49518.86 | −29.28 | 1.45 |
| C1BV | 51728.78 | 51730.26 | −28.61 | 1.48 |
| LCCT | 49160.00 | 49161.32 | −26.85 | 1.32 |
| HCCT | 49346.25 | 49347.13 | −17.83 | 0.88 |
| CTBV | 51184.26 | 51185.83 | −30.67 | 1.57 |

Switches with GCN4 peptide at different grafting positions (FIG. 9) on the anti-CD19 antibody FMC63 were used in a LDH release cytotoxicity assay and cytokine production was also measured. These data indicate a clear structure activity relationship between the different peptide grafting positions (Table 19). None of the switches had off-target effects when tested against the $CD19^-$ K562 cell line. The optimal peptide engraftment position for in vitro killing of RS4;11 ($CD19^+$) cells was at the N-terminal of the switch. Furthermore, the N-terminal bivalent construct had a low $EC_{50}$ of cytotoxicity and enhanced cytokine production indicating that bivalent switches may have enhanced activity.

TABLE 19

| Potency on CD19-positive cells | | |
|---|---|---|
| Switch | Valency | $EC_{50}$ (nM) |
| WT | N/A | N/A |
| LCNT | Mono | 0.0011 |
| HCNT | Mono | 0.0027 |
| NTBV | Bi | 0.0047 |
| LCC1 | Mono | 0.0104 |
| HCCT | Mono | 0.0263 |

Figure 16:
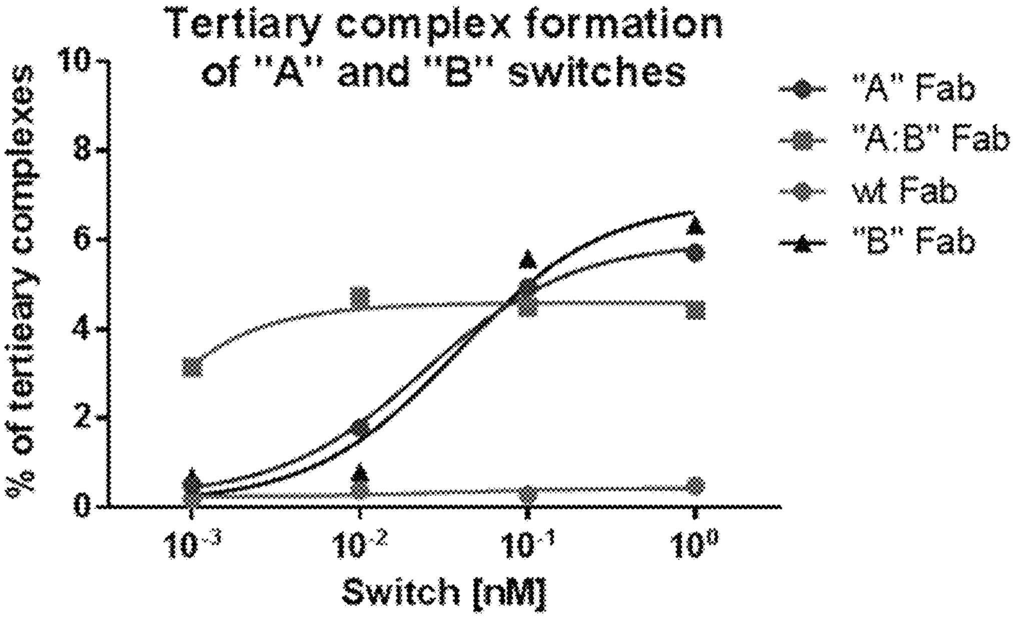
FIG. 16 shows ternary complex formation of "A" and "B" monovalent switches and A+B bivalent switches with target and CAR-T cells by flow cytometry. Fusion/grafting locations: A=LCC1 (SEQ ID: 29 & 30), B=HCCT (SEQ ID: 27 & 34), A:B=LCC1:HCCT (SEQ ID: 30 & 34).

To assess ternary complex formation, flow cytometry (FACS) was used to measure the number of double positive cell doublets that formed with increasing concentration of the switch. sCAR-T cells and RS4;11 cells were labeled with different cell stains (CFSE, FITC) and Cellvue Claret(APC)) prior to assay to enable read-out. FITC/APC double positive cell doublets were used as a surrogate read-out for the number of synapses between CAR-T cells and target cells. More synapses correlate with more double positives. In this assay the E:T was 10:1 making the theoretical maximum ternary complex percentage approximately 10%. An increased number of double positives were found with increasing concentrations of the switch. The bivalent switch A+B1 had a more potent EC50 of complex formation compared with the monovalent switches A or B1 (FIG. 16). However, the bivalent switch had a lower maximum ternary complex formation which is hypothesized to relate to the concepts of auto-inhibition.

Anti-CD19 CAR Hinge Optimization

Figure 17:
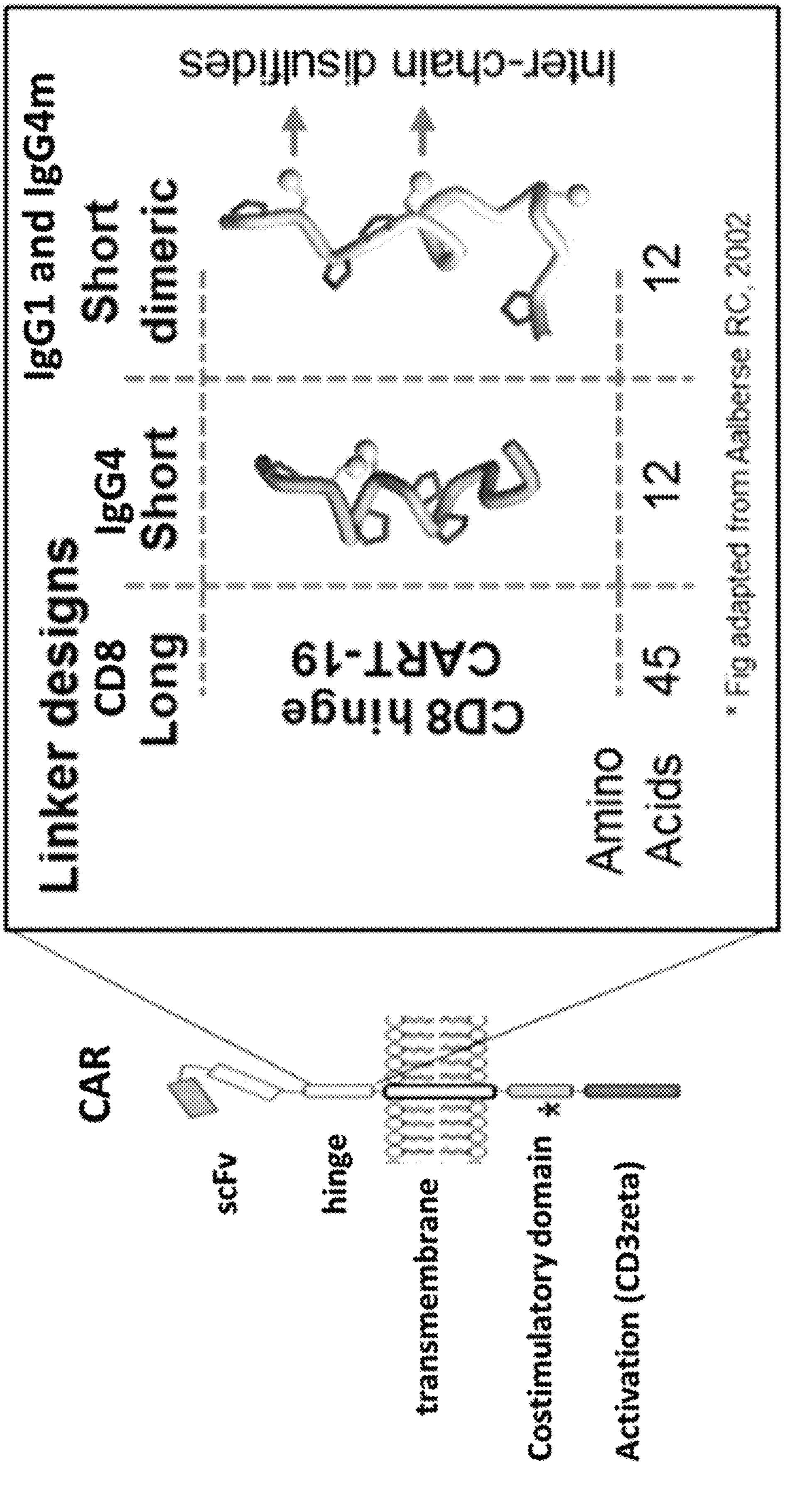
FIG. 17 exemplifies CAR hinges, with varying lengths, derived from CD8 (SEQ ID: 68), IgG4 (SEQ ID: 70), or IgG4m (SEQ ID: 71).

The addition of the switch to the sCART cell system means that there is a greater distance between the surface of the effector and target cell when compared to a conventional CART19 cell. It is possible that this has an effect on sCART cell activity. To test this, switchable and conventional anti-CD19 CAR-T platforms were compared with long and short CAR hinges. To reduce the length of the sCAR and immunological synapse, the CD8 hinge, which was initially selected due to its inclusion in the CART19 construct, was replaced with a shorter hinge derived from IgG4 (FIG. 17). Furthermore, as the bivalent switch generated enhanced cytokine responses the IgG4 hinge was mutated (IgG4m) so to form intra-chain disulphide bridges; thus enhancing sCAR dimerization. The max kill (highest cytotoxicity %) and $EC_{50}$ was improved by the inclusion of the IgG4 and IgG4m hinges indicating that the shorter immunological synapse created by the shorter sCAR and N-terminal switches improves cytotoxicity (see FIGS. 10A-C and Table 20).

TABLE 20

| Potency on CD19-positive cells | | |
|---|---|---|
| Switch | Valency | $EC_{50}$ (nM) |
| WT | N/A | N/A |
| A | Mono | 0.0020 |
| A1 | Mono | 0.0008 |
| A + A1 | Bi | 0.0028 |
| B1 | Mono | 0.0014 |
| C1 | Mono | 0.0011 |

Testing CAR Hinge Variants with Anti-CD19 Switch Variants In Vivo

The different sCAR designs were tested in a xenograft model harboring luciferized NALM-6 (CD19+, CD80−, CD86−) cells. 1 mg/kg monovalent switch “A” was administered along with sCAR cells. The short-dimeric sCAR with a switch “A” was most comparable to conventional anti-CD19 CART in tumor regression. Optimized hinge improved response. Short hinge CARs have faster clearance. Short, dimeric hinge CARs have improved persistence. Tumor burden was visualized with IVIS imaging. Experiments are repeated with a humanized scFv and bivalent switches.

Example 9. Anti-CD19 Fab Switch Tumor Penetration and Residence, In Vivo

Figure 18:
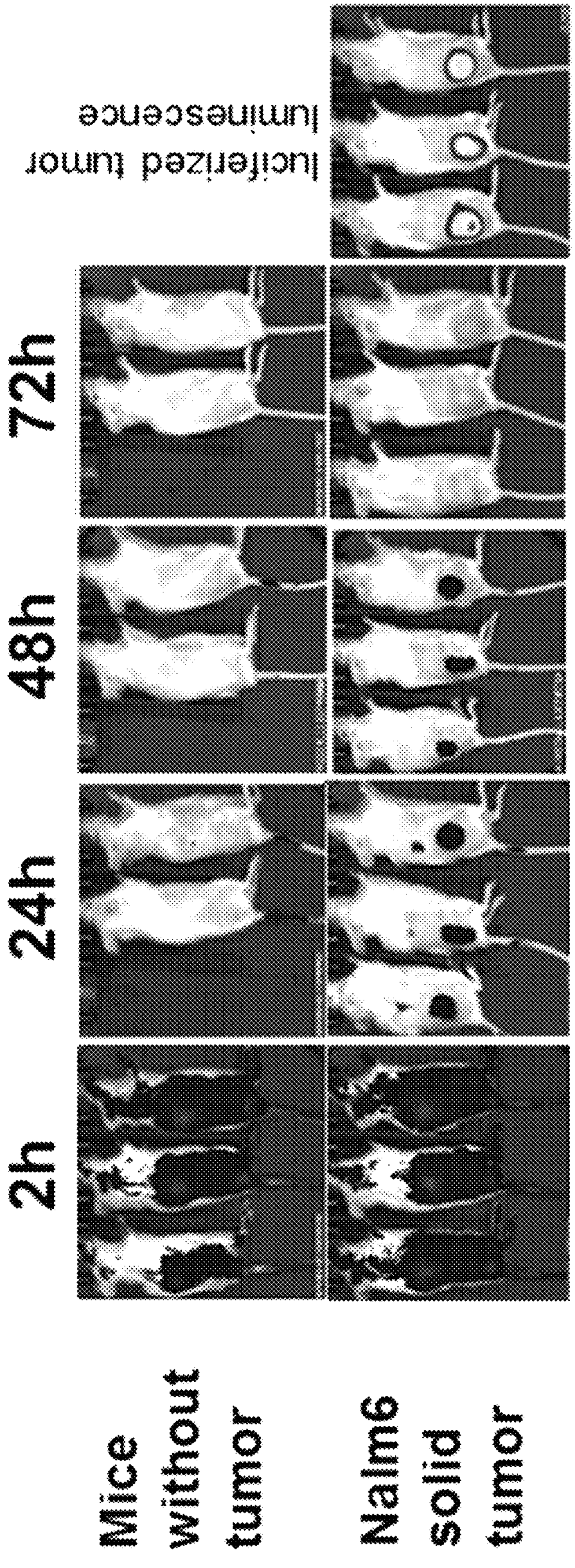
FIG. 18 shows localization of anti-CD19 switch "B" labeled infrared 750 (IR) fluorophore (using the Thermo Fisher Scientific SAIVI kit) with tumor burden in NSG mice harboring subcutaneous NALM-6 CD19+ tumors, 48 h after dosing, using luciferized tumor luminescence and switch dosed 1 mg/kg I.V.
Figure 19:
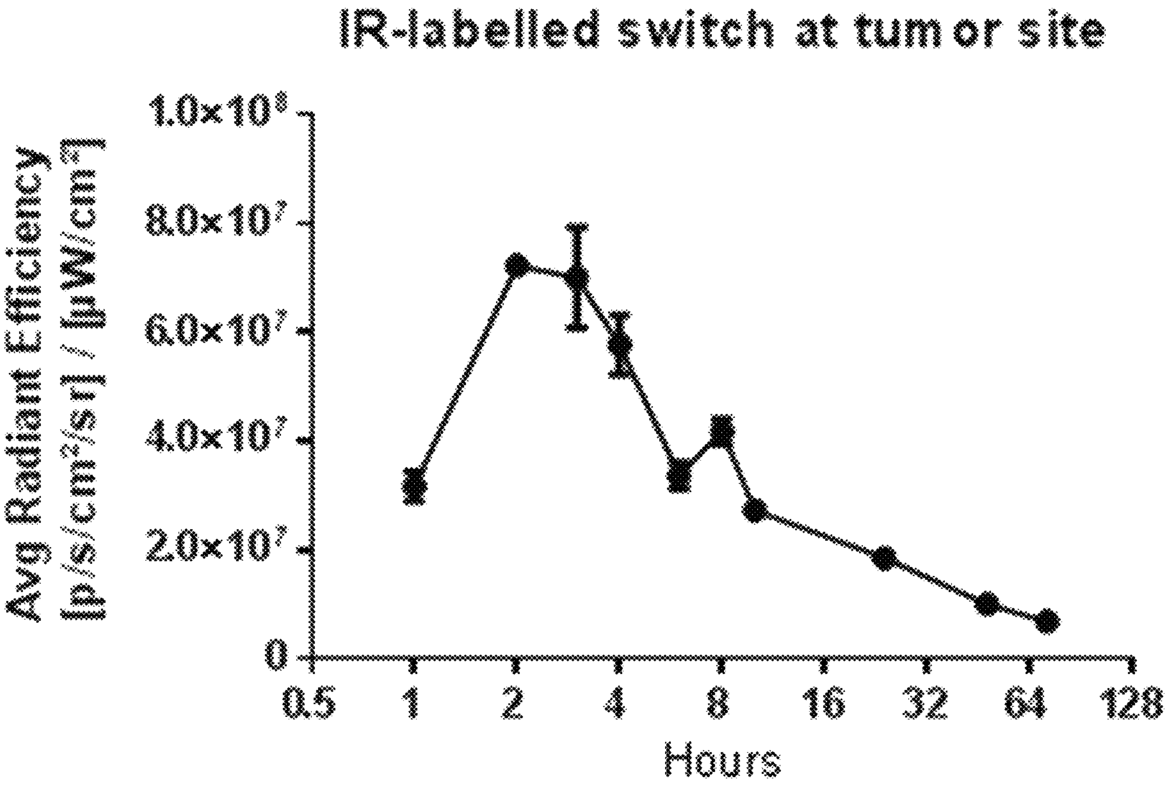
FIG. 19 shows time-dependent localization of the IR-labeled switch at tumor site.

Fab switches were able to penetrate tumors, in vivo, as demonstrated by labelling the anti-CD19 Fab switch molecules with a near-infrared dye (Alexa Fluor 700), which were detected using an IVIS machine. FIG. 18 shows localization of switches with tumor burden (NALM-6-luc subcutaneous tumor). Tumor residence kinetics are shown in FIG. 19, with residence peaking at 2 hr. These data show that the Fab switches have a good half-life in solid tumors and.

Example 10. Development of an Orthogonal Anti-CD19 sCAR-T Cell

Figure 20A:
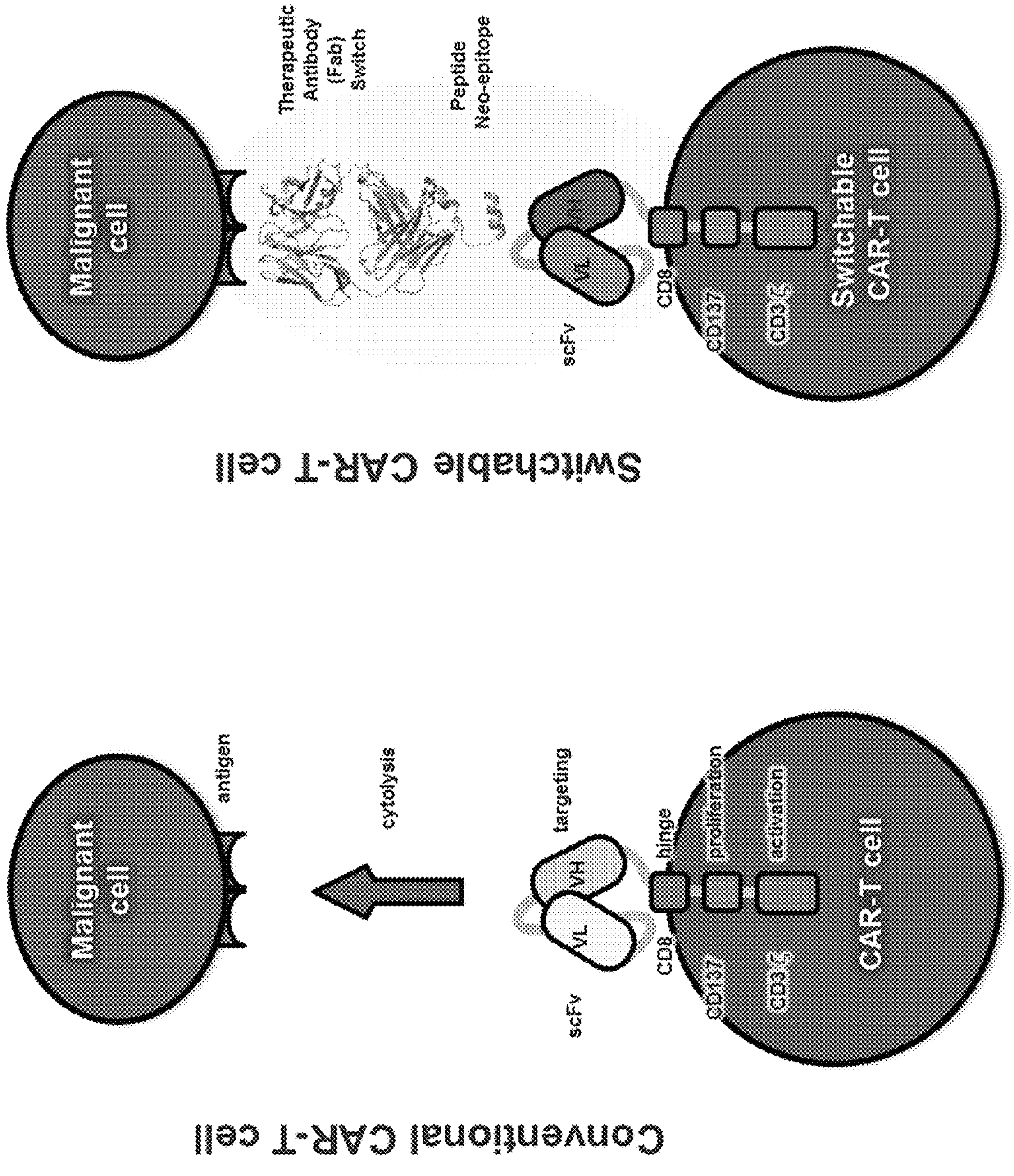
FIG. 20A-B shows a schematic of direct versus switchable CAR-T cells.
Figure 20B:
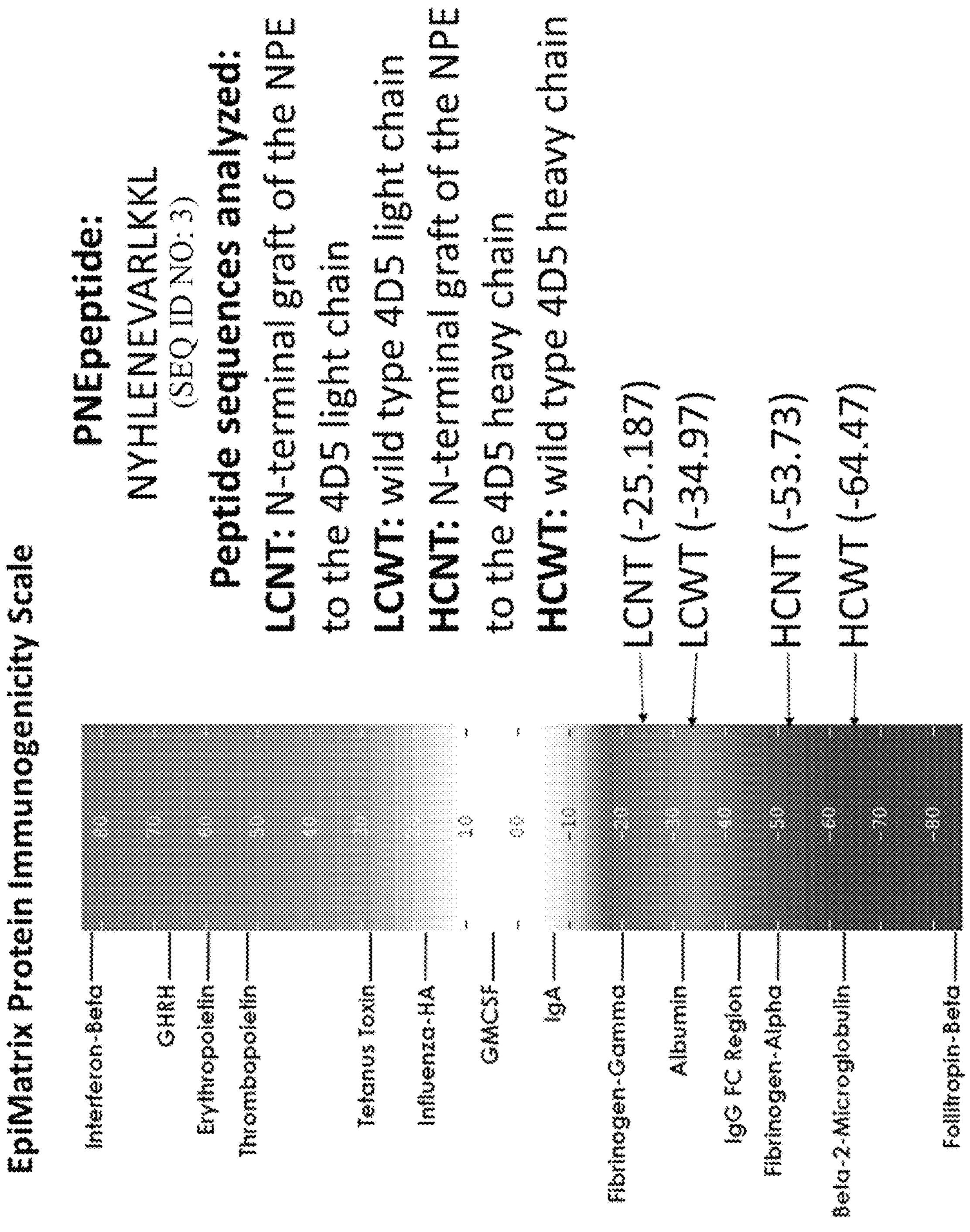
Figure 21A:
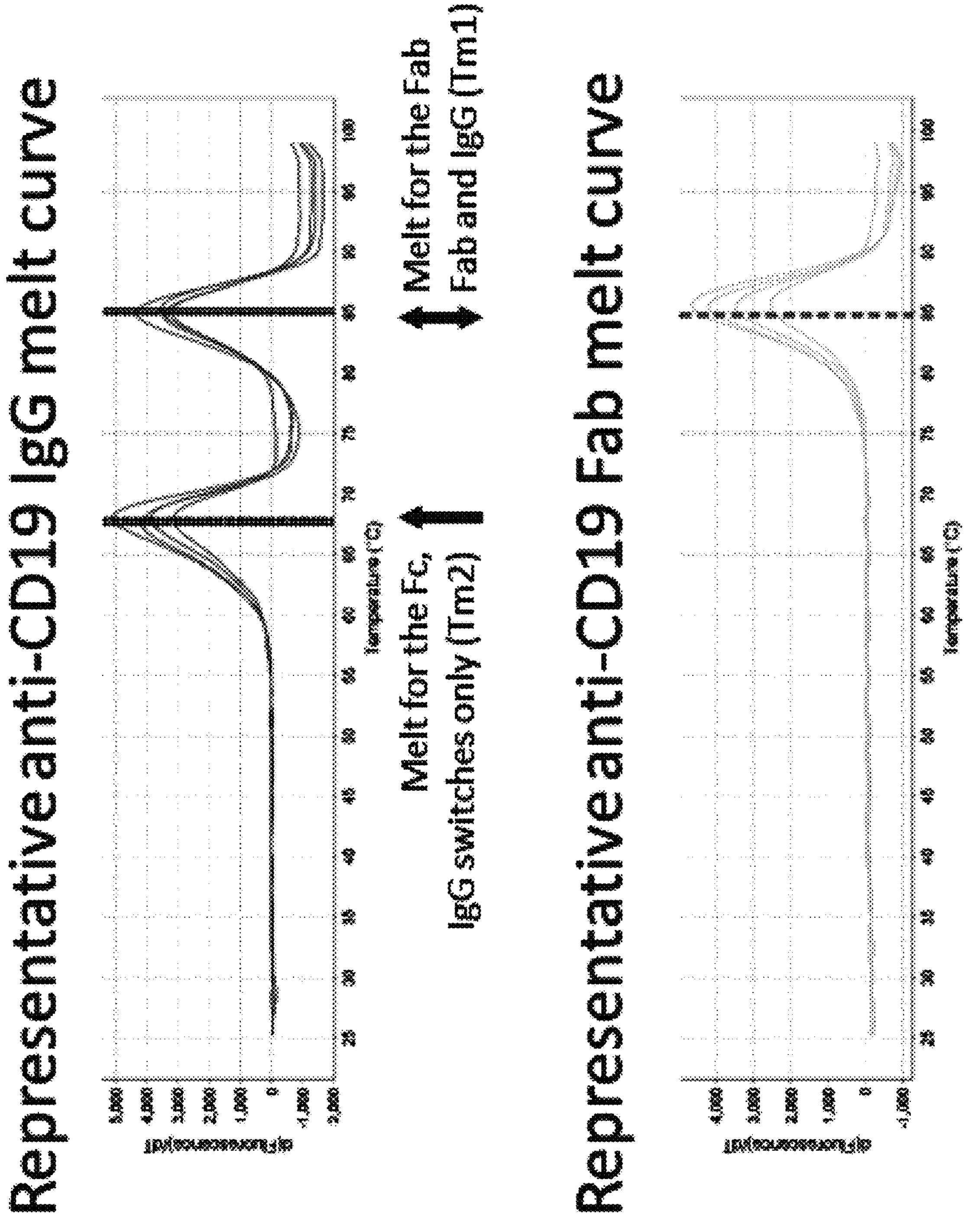
FIG. 21A-C show thermal stability and antigen binding of switches.

A 14 amino acid peptide neo-epitope (PNE) sequence was the target of the sCAR. This sequence has no instance in the human proteome and thereby provides an exclusive orthogonal interaction between the sCAR-T cell and switch. As the PNE is derived from a protein naturally found in yeast, the risk of immunogenicity was assessed in silico (EpiVax, RI) which predicted the PNE to have a low risk of immunogenicity in humans (FIG. 20B). To generate switches, the PNE was grafted at defined sites in the anti-CD19 antibody FMC63. The antigen binding region of the antibody switch relative to the scFV on the T cell surface was systematically varied with respect to valency and orientation (FIG. 9 & FIG. 20A). Four fusions of the PNE were generated by linking the PNE to the N- or C-terminus (NT, CT, respectively) of the heavy and/or light chains (HC, LC, respectively) of the antigen binding fragment (Fab) with short peptide linkers. The GGGGS linker was suitable in all positions except for fusion to the N-terminus of the heavy chain (HCNT) which gave increased yields with a rigid, helical linker sequence. In addition, the PNE was grafted directly into loops of the constant region 1 (C1) of the heavy and light chains. These constructs provided distinct binding orientation of the sCAR relative to the target antigen which in some embodiments is preferable for binding to certain antibody epitopes on target antigens. Furthermore, the PNE was engrafted into both the heavy and light chains to create bivalent switches, thus doubling the number of sCAR's that engage with each antigen. PNE-grafted switches were efficiently expressed in transient transfections using HEK cells with yields 50%-100% compared to yields of the wild type FMC63 antibody. Engraftment of the PNE to the Fab at all sites had minimal impact on protein stability and antigen binding as determined by thermal melt assay (FIG. 21A and Table 21) and flow cytometry (FIGS. 21B, 21C), respectively.

TABLE 21

| Switch | Sample | $T_m$ 1 (Fab) | St. Error | $T_m$ 2 (Fc) | St. Error |
|---|---|---|---|---|---|
| Fab | WT | 84.77 | 0.19 | — | — |
| | LCNT | 83.98 | 0.15 | — | — |
| | HCNT | 83.86 | 0.22 | — | — |
| | NTBV | 82.68 | 0.16 | — | — |
| | LCC1 | 76.75 | 0.25 | — | — |
| | HCCT | 84.33 | 0.19 | — | — |
| | LCCT | 73.95 | 0.08 | — | — |
| | CTBV | 73.29 | 0.1 | — | — |
| | HCC1 | 82.98 | 0.19 | — | — |
| | C1BV | 75.25 | 0.12 | — | — |
| IgG | WT | 85 | 0.09 | 67.78 | 0.09 |
| | LCNT | 84.26 | 0.09 | 65.85 | 0.18 |
| | HCNT | 84.45 | 0.09 | 67.87 | 0 |
| | NTBV | 83.34 | 0.23 | 67.87 | 0 |
| | LCC1 | 77.13 | 0 | 67.97 | 0.09 |
| | HCCT | 85.1 | 0.19 | 67.5 | 0 |
| | LCCT | 73.42 | 0 | 70.92 | 2.89 |
| | CTBV | 73.51 | 0.19 | 67.68 | 0.21 |
| | HCC1 | 83.6 | 0.21 | 57.58 | 0.21 |
| | C1BV | 72.21 | 0.06 | 68.23 | 0 |

Figure 21B:
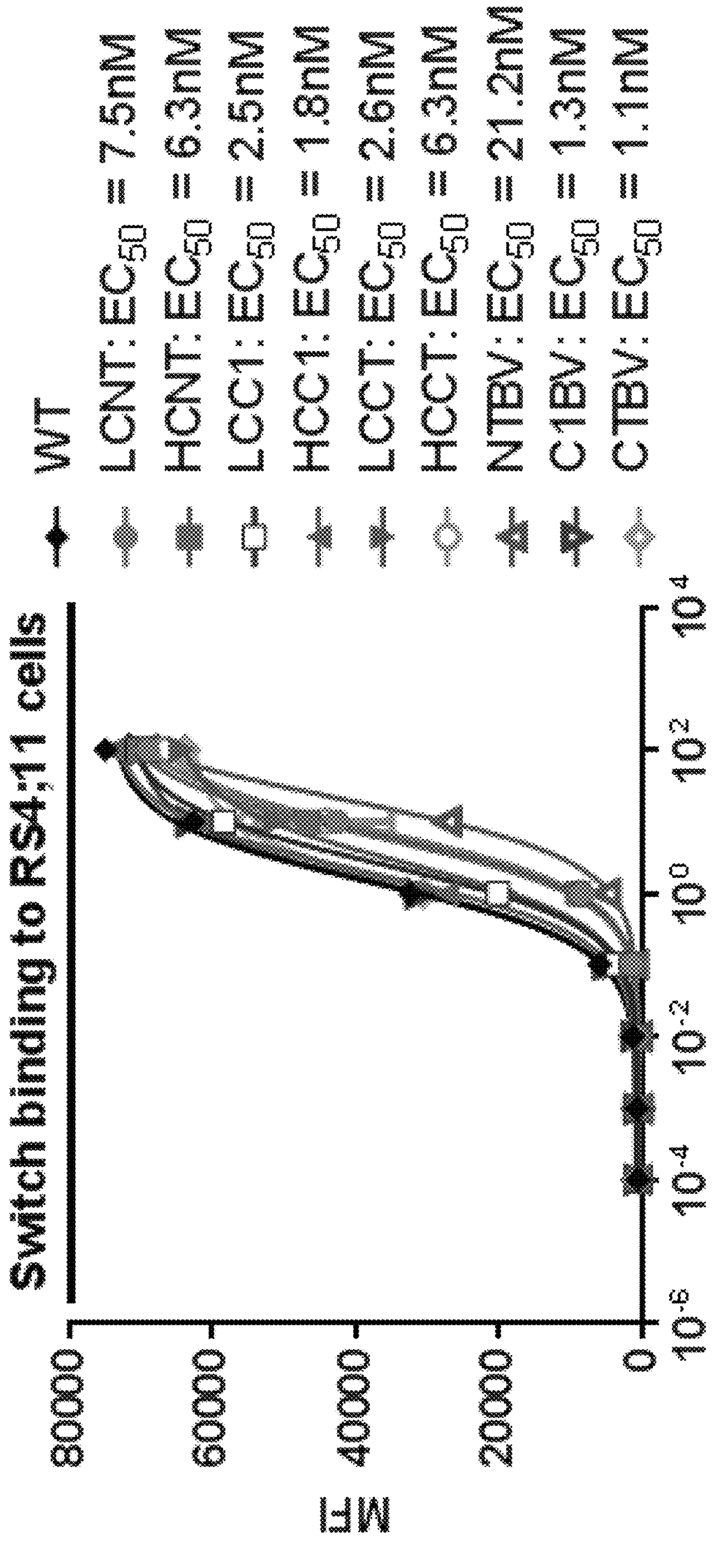
Figure 21C:
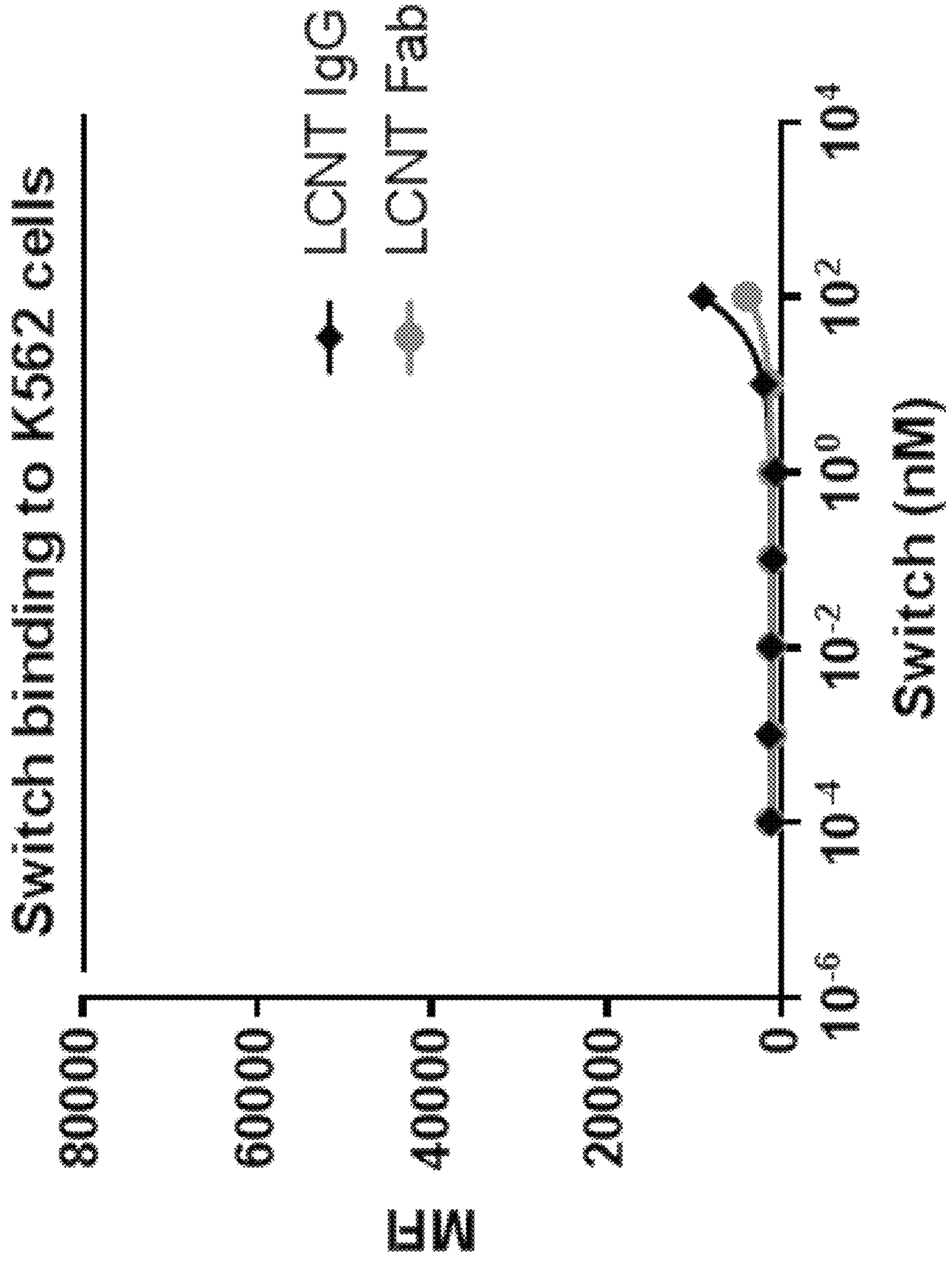
Figure 22A:
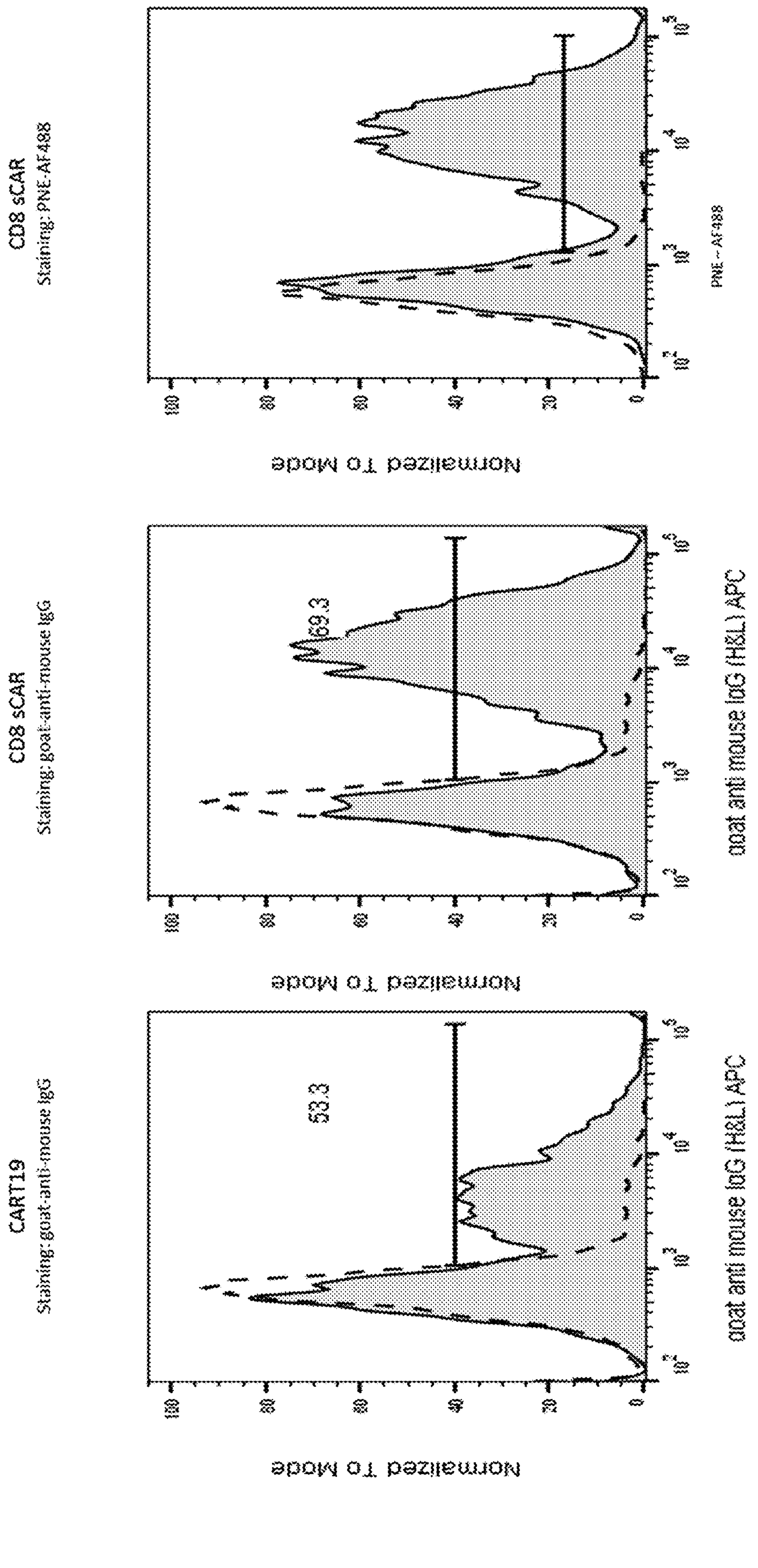
FIG. 22A-C show expression of CAR and binding to switch.
Figure 22B:
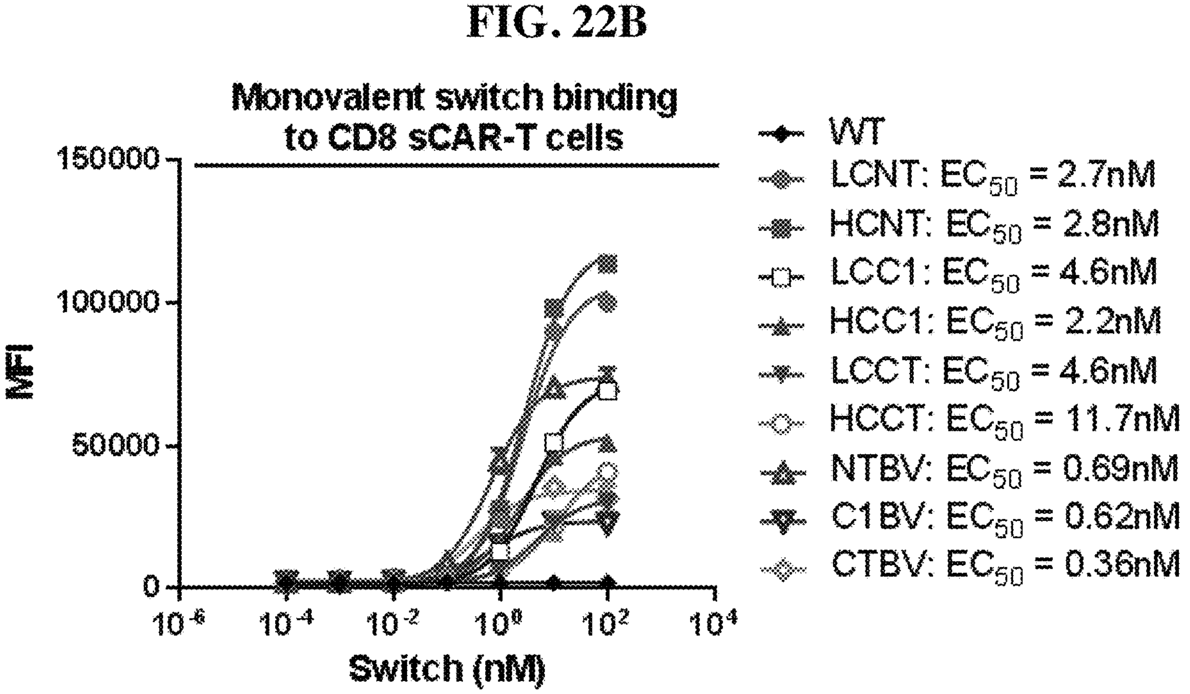
Figure 22C:
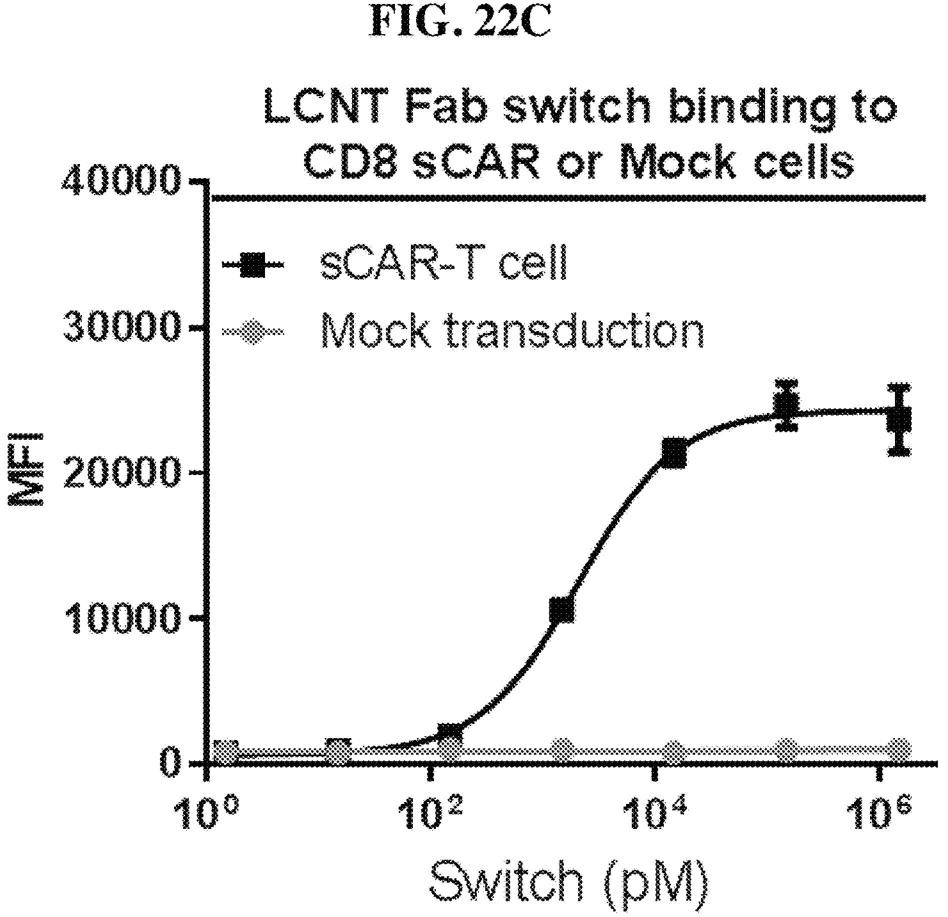

An sCAR-T cell that recognizes the switch was created using the high affinity scFv (52SR4; $K_d$=5.2 pM) specific for the PNE, incorporated into a second generation CAR harboring human CD8 hinge, CD8 transmembrane, 4-1BB costimulatory, and CD3 activation domains (SEQ ID NO: 1). Lentiviral transduction of this construct into freshly isolated human PBMCs demonstrated efficient surface expression with transduction efficiencies of 50-70% (FIG. 22A). The switches bound to $CD19^+$ RS4;11 ($EC_{50}$±S.D.=5.6 nM±6.3) cells but not $CD19^-$ K562 cells (FIGS. 21B and 21C). The switches also bound to sCAR-T cells and not to un-transduced T cells (FIGS. 22B, 22C), demonstrating that the sCAR-T cell-switch interaction is highly specific.

Example 11. PNE Grafting Position Controls sCAR-T Cell Potency In Vitro

Figure 23A:
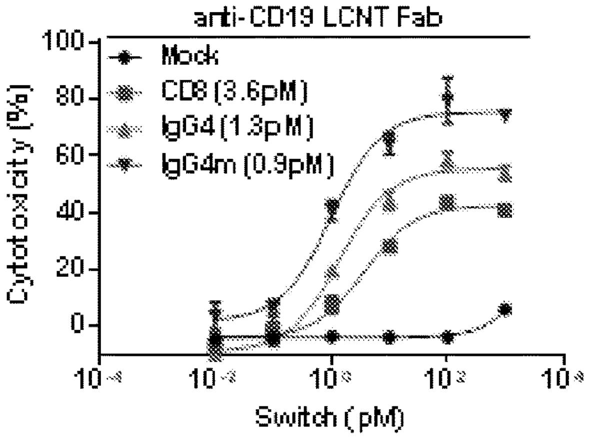
FIG. 23A-E shows activity of sCAR hinge designs.
Figure 23B:
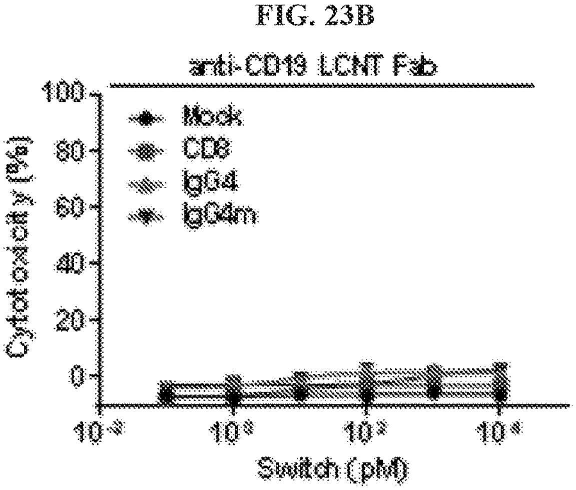
Figure 23C:
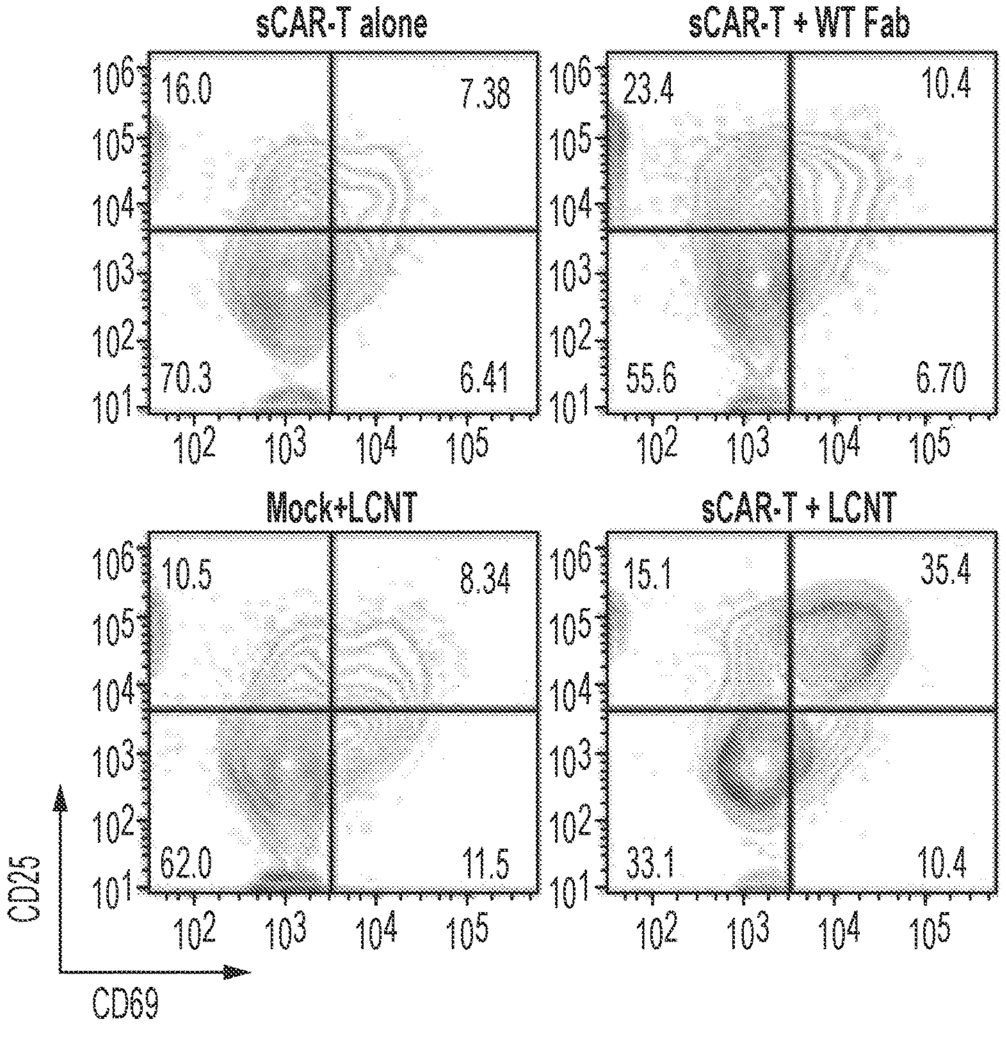
Figure 23D:
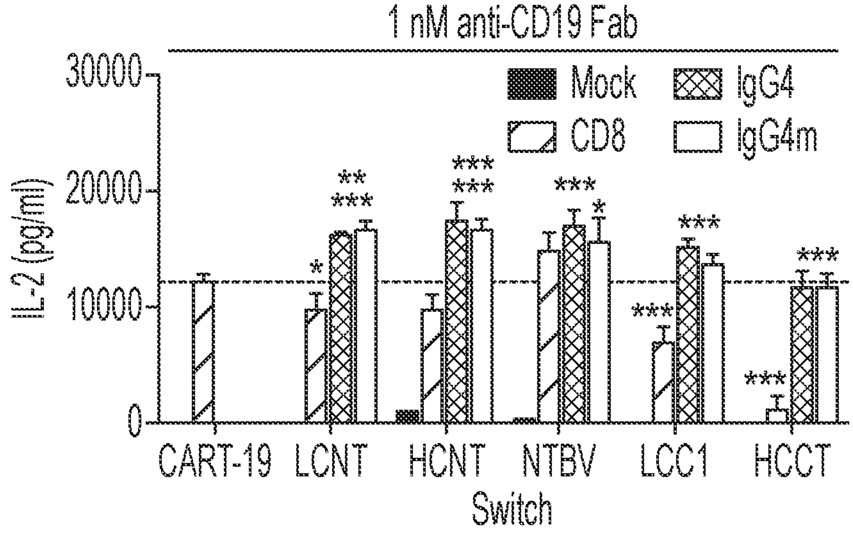
Figure 23E:
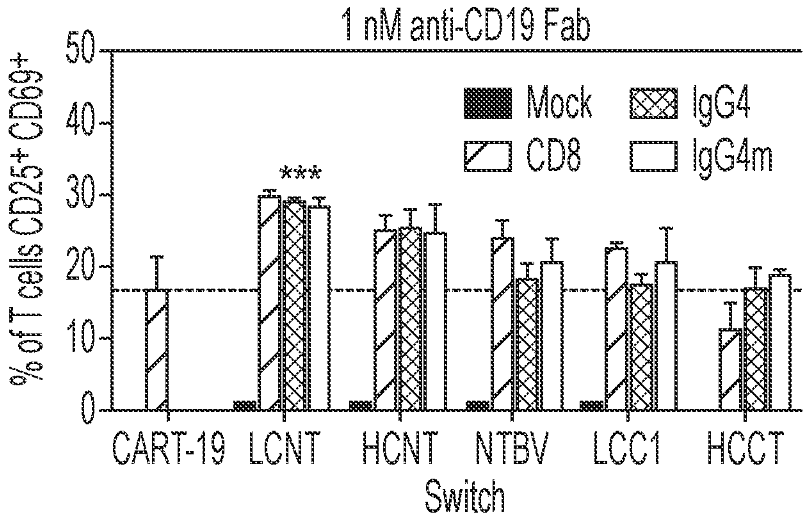
Figure 24B:
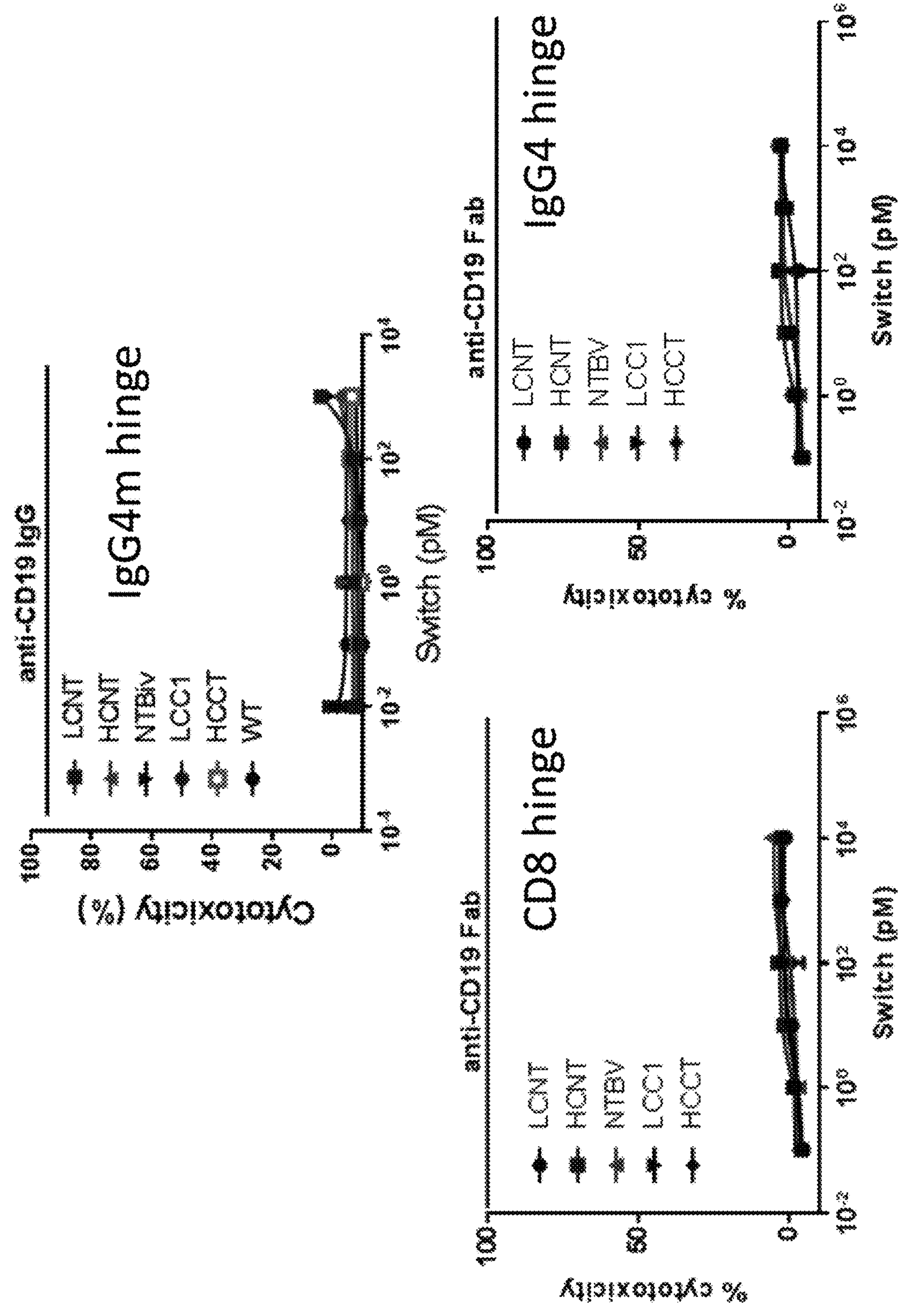

The optimal switch design for CD19 was determined empirically. The effect of switch design on activity was determined by assaying the potential of each switch to induce target cell cytotoxicity, T cell activation, and cytokine production. All switches elicited dose-dependent lysis of RS4;11 cells in the presence of sCAR-T cells at picomolar (pM) concentrations (FIG. 23 A, D and FIG. 24A-B). There was a clear structure activity relationship (SAR) between cytotoxicity and the location of the PNE in the antibody: Switches with both PNE engrafted proximal to the antigen binding site of the Fab (LCNT, HCNT, NTBV) were more potent than switches with the PNE at the center (LCC1, HCC1, C1BV) or C-terminus (LCCT, HCCT, CTBV) of the Fab region (FIG. 11A and Table 22). No significant lysis of $CD19^-$ K562 cells was observed for any Fab or IgG switch design, even at concentrations $10^3$ fold higher than the $EC_{50}$ (FIG. 11B). In addition, wild type anti-CD19 Fab and IgG lacking the PNE peptide did not induce significant cytotoxicity, demonstrating the strict requirement for PNE-mediated immunological synapse formation.

TABLE 22

| Chain | Position | Location | $EC_{50}$(pM) |
|---|---|---|---|
| LC | NT | proximal | 2.1 ± 1.3 |
| HC | NT | proximal | 2.1 ± 1.6 |
| BV | NT | proximal | 9.3 ± 1.8 |
| LC | C1 | central | 2.5 ± 2.4 |
| HC | C1 | central | 2.4 ± 1.9 |
| BV | C1 | central | 10.3 ± 3.6 |
| LC | CT | distal | 14.8 ± 1.1 |
| HC | CT | distal | 20 ± 0.9 |
| BV | CT | distal | 9.3 ± 2.2 |

Consistent with the cytotoxicity results, all switches induced robust multi-cytokine release (IL-2, IFNγ, TNFα; FIG. 11C) with the N-terminally grafted switches providing greater cytokine levels than the constant region or C-terminally positioned switches. Notably, the bivalent NTBV switch induced the greatest cytokine production against RS4;11 cells, indicating a benefit to the recruitment of two sCAR with one switch. Again, no switch stimulated cytokine release against $CD19^-$ K562 cells in the presence of the sCAR-T cells confirming that switch binding alone was not responsible for sCAR-T cell activation (FIG. 11C). In addition, markers of T cell activation ($CD25^+$, $CD69^+$) were upregulated by the sCAR-T cells in response to RS4;11 cells only in the presence of switch and $CD19^+$ cells. These results demonstrate that sCAR-T cell effector function in terms of activation, cytokine production, and target cell killing is dependent on the presence of both a target antigen and switch.

Figure 13B:
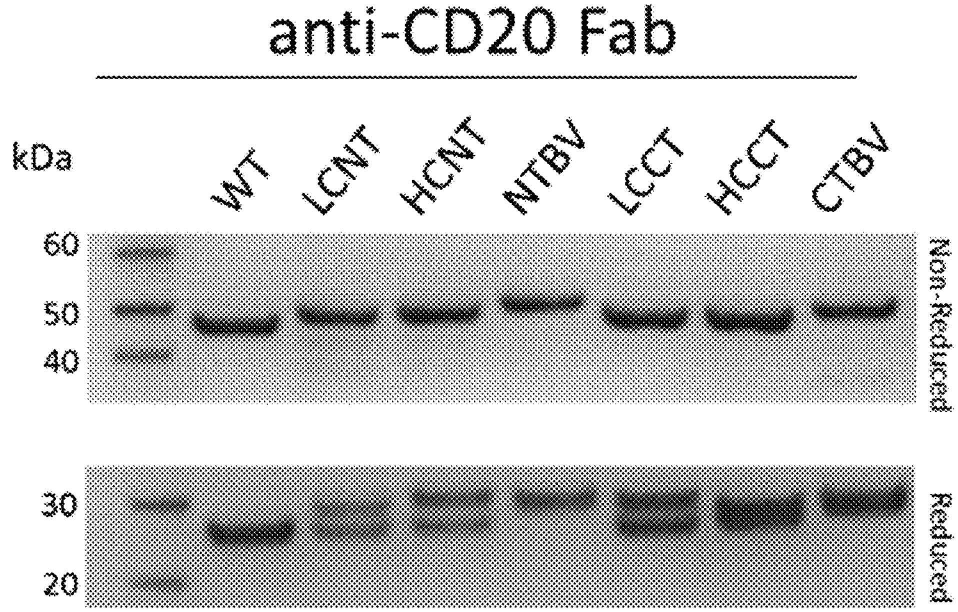
Figure 25A:
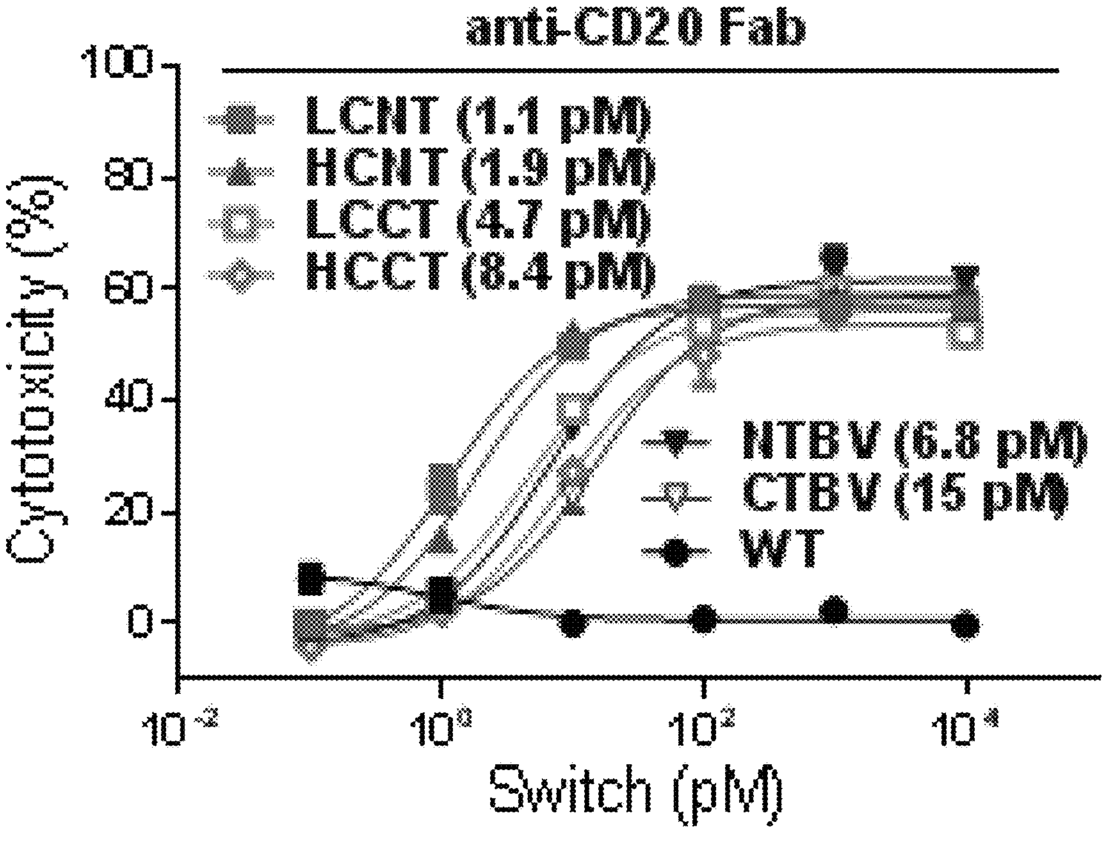
FIG. 25A-B shows activity of sCAR-T cells with anti-CD20 switch.
Figure 25B:
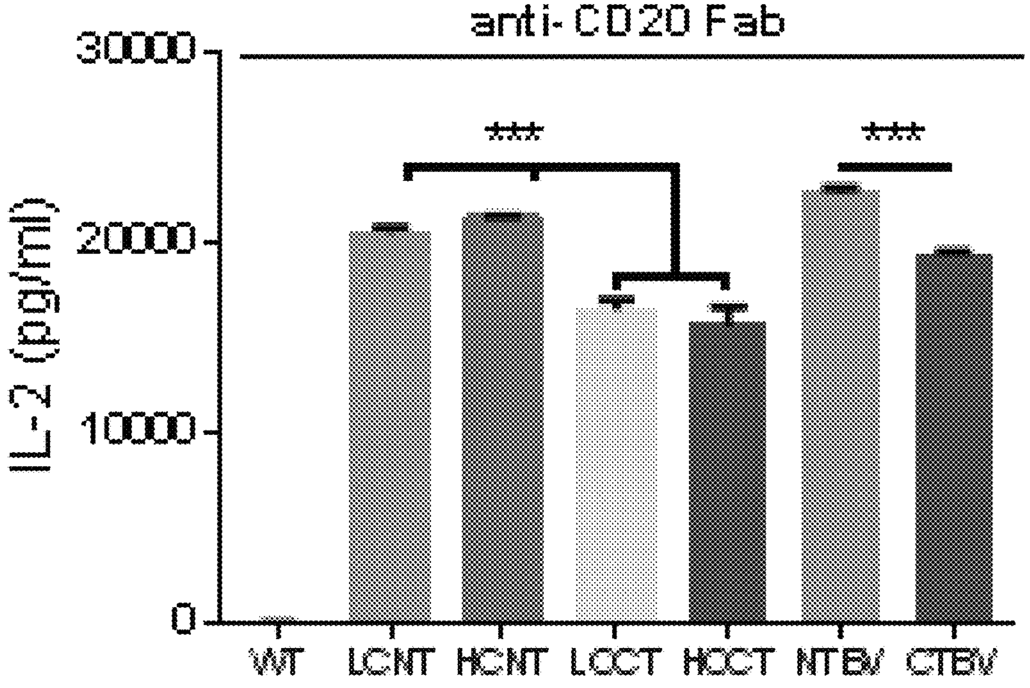

A similar panel of switches was constructed to target CD20 expressing cancers based on the anti-CD20 antibody Ofatumumab (OFA) (FIG. 13B, Table 23). Along with CD19, CD20 is an important pan-B cell antigen, and it is widely targeted therapeutically by monoclonal antibodies in clinical usage. Consistent with the SAR trend for FMC63, N-terminally grafted switches were found to be more potently cytotoxic than C-terminally grafted switches against $CD20^+$ Raji cells (FIG. 25A). In addition, N-terminally grafted switches stimulated higher levels of cytokine release at 1 nM (FIG. 25B).

TABLE 23

| OFA | Protein mass (Da) | | Error | |
|---|---|---|---|---|
| Protein | Expected | Found | ppm | Da |
| WT | 47447.42 | 47448.52 | −29.51 | 1.4 |
| LCNT | 49471.38 | 49473.84 | −49.73 | 2.46 |
| HCNT | 50437.57 | 50439.74 | −43.02 | 2.17 |
| NTBV | 52461.83 | 52465.00 | −60.42 | 3.17 |
| LCCT | 49471.38 | 49472.77 | −28.10 | 1.39 |
| HCCT | 49471.38 | 49473.05 | −33.76 | 1.67 |
| CTBV | 51495.64 | 51497.13 | −28.93 | 1.49 |

Example 12. Optimization of the Anti-CD19 sCAR Platform Design

In some embodiments, increased activity of switches observed when the PNE is grafted proximal to the antigen binding domain results from the decreased overall distance between the sCAR-T cell and target cell. To test whether this same notion applies to the design of the sCAR itself, the hinge region which connects the scFv to the transmembrane domain was modified by replacing the 45 amino acid CD8 hinge (labeled as "long") with a 12 amino acid hinge derived from IgG4 ("short", FIG. 22A). This substitution increased the potency of cytotoxicity against RS4;11 cells with the LCNT switch by 2.8 fold (FIG. 23A) while not causing lysis of K562 cells (FIG. 23B & FIG. 24A).

Figure 7A:
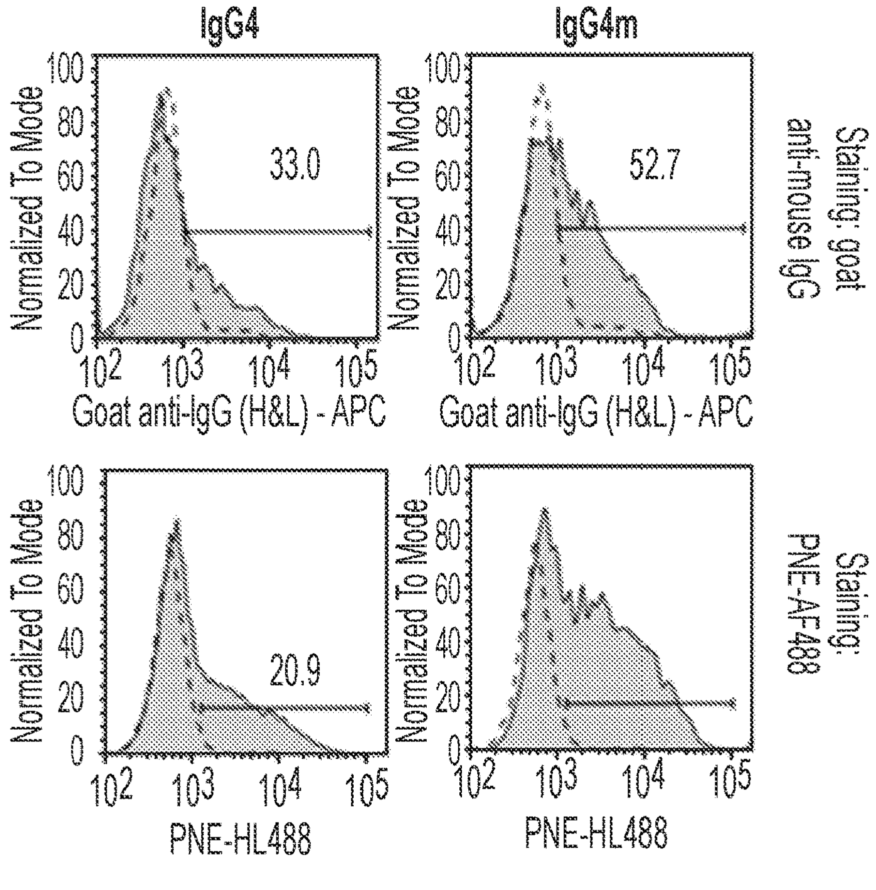
FIG. 7A-B shows sCAR hinge modifications.
Figure 7B:
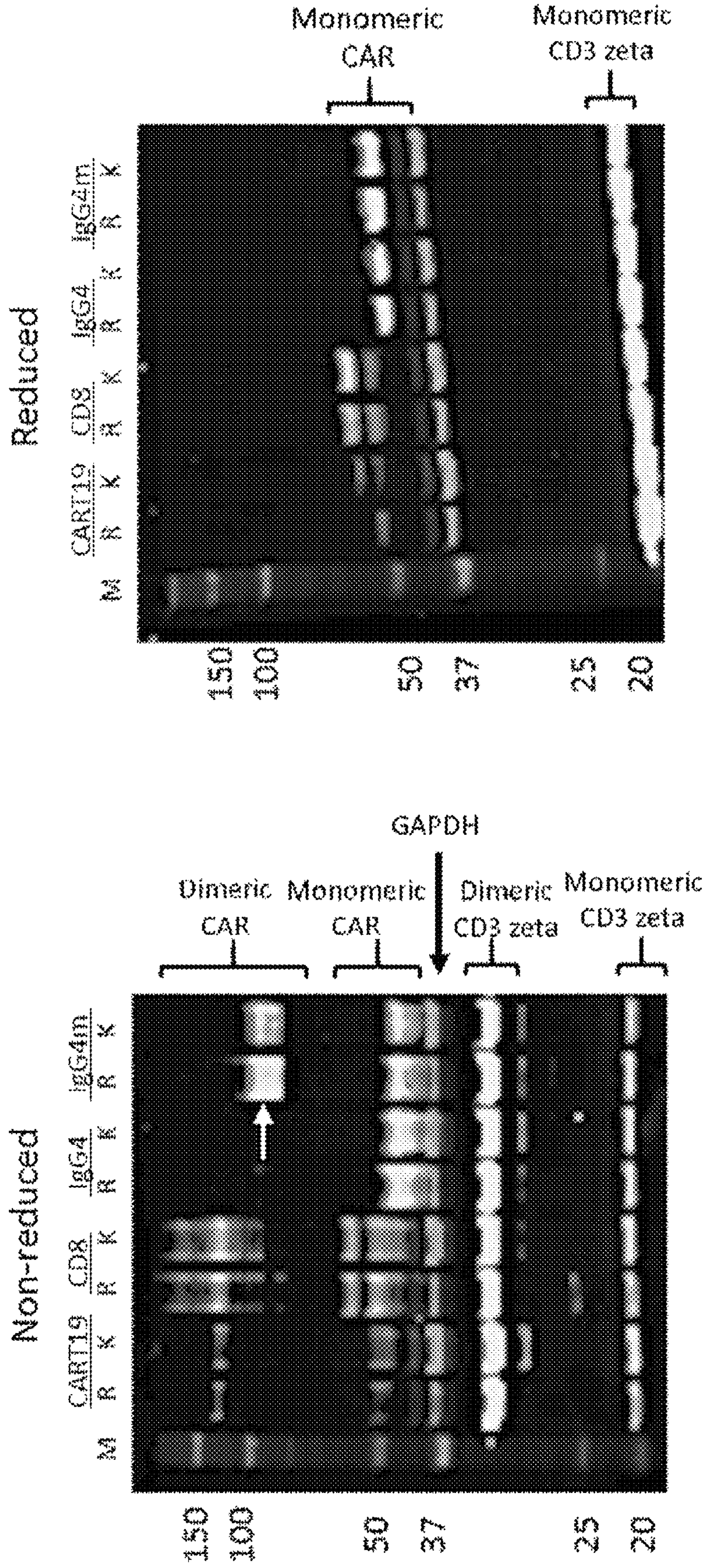

In some embodiments, the increased cytokine induction of the NTBV switch indicates a favorable effect of bivalency on sCAR activation, through the simultaneous recruitment of two sCARs by one switch. To investigate the effect of sCAR valence on activity, a second IgG4-based hinge was designed with a serine to proline mutation (S228P mutation relevant to the IgG molecule) which facilitates inter-chain disulfide formation ("short-dimeric", FIG. 7A). Analysis of hinge designs by western blot showed the long CD8-based hinge in the sCAR and CART-19 constructs formed spontaneous disulfide-mediated dimers in the absence of CAR stimulation (FIG. 7B). Dimer formation of the IgG4-based hinge designs only occurred with the S228P mutation in the short-dimeric hinge and not in the short IgG4-based hinge lacking this mutation. Correspondingly, cytotoxicity of the short-dimeric sCAR against RS4;11 cells with the LCNT Fab switch was further improved to $EC_{50}$=0.9 pM, and maximum target cell lysis increased by >80%, compared with the original CD8-based long hinge (FIG. 23A).

Specificity of sCAR-T cell activation is essential to switch-based control. Therefore, to confirm the improved activity of the short-dimeric sCAR did not sacrifice specificity, off-target cytotoxicity, upregulation of activation markers, and cytokine release were interrogated. The short-dimeric sCAR was unable to cause significant lysis of K562 cells with up to 10 nM of any switch (FIG. 23B & FIG. 24B) and did not produce cytokines in the presence of any switch and K562 cells (FIG. 23F). The short-dimeric sCAR-T cells also did not exhibit significant upregulation of activation markers compared with non-transduced (mock) cells in the absence of PNE-grafted switch and target antigen, confirming that the short-dimeric sCAR did not cause antigen-independent activation (FIG. 23C). Finally, the activity of sCAR-T cells on RS4;11 cells could be fully inhibited by the addition of an excess of soluble, synthetic PNE peptide, demonstrating the requirement for switch-mediated target cell cross-linking for activity (FIG. 26A-H).

The additive effect of switch and hinge design on activity and compared sCAR activation was determined with conventional CART-19. Each switch design was combinatorially tested in dose titration with each hinge design and assayed for cytotoxicity, cytokine release, and upregulation of activation markers in the presence of RS4;11 cells. Cytotoxicity increased as the PNE grafting position moved from C-terminus to N-terminus and as the hinge design was shortened and made dimeric (FIGS. 27A, 27B). Correspondingly, the cytokine release at 1 nM switch on RS4;11 cells was greatest with the N-terminally grafted switches (HCNT, LCNT, NTBV) with the short or short-dimeric hinges (FIG. 23D). The level of cytokine production with these optimal switch/hinge combinations was significantly greater than conventional CART-19 (which was not treated with a switch) and represented a 14-fold improvement in IL-2 secretion over the least effective combination of long hinge with the HCCT switch. The upregulation of activation makers in the presence of 1 nM switch and RS4;11 cells exhibited a similar trend in switch SAR; however, sCAR hinge design had little impact on activation markers (FIG. 23E). The potential of 1 nM LCNT switch to upregulate activation markers on sCAR-T cells was found to be significantly greater than the activation of conventional CART-19 (without switch) on RS4;11 cells.

To test whether the increased potency of the short-dimeric hinge design could extend to another antigen, the cytotoxicity of anti-CD20 switches on $CD20^+$ Raji cells was assayed. The potency of cytotoxicity was increased for all switches (FIG. 28A). Unexpectedly, however, the trend in cytotoxicity as a function of switch design was opposite what was observed for anti-CD20 switches with the long hinge sCAR design (FIG. 25B). For the short-dimeric hinge design, C-terminally grafted switches were 10-100-fold more potent than N-terminally grafted switches. Collectively, this indicates that the activity of sCAR-T cells could be significantly enhanced through hinge design, but requires empirical switch design to attain optimal efficacy.

Example 13. Switch and Hinge Design Effects on Tumor Clearance In Vivo

Figure 29A:
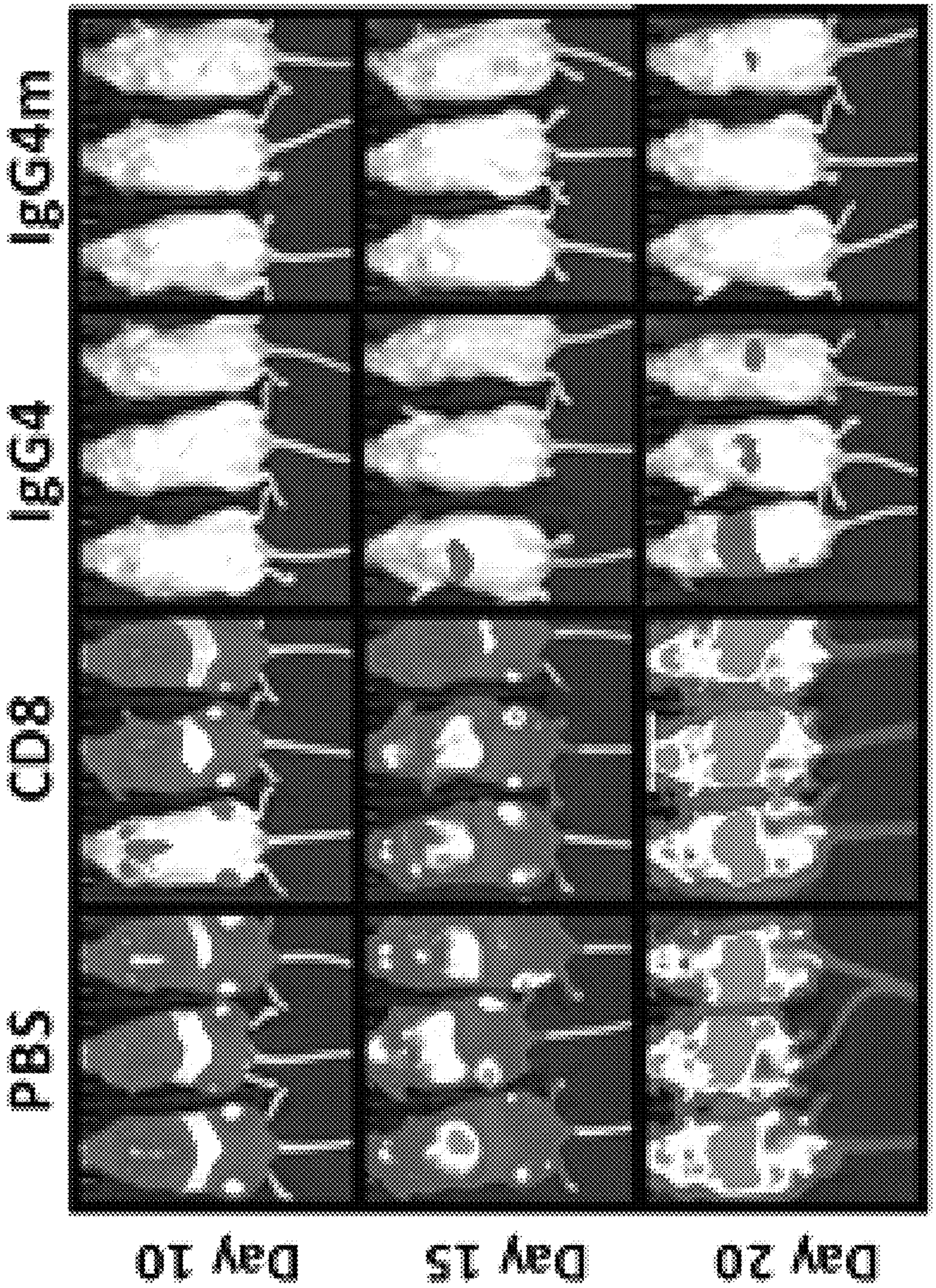
FIG. 29A-F shows in vivo activity of switch and hinge designs in Nalm-6$^{GFP/Luc}$ xenograft model. NSG mice were inoculated with CD19$^+$ Nalm-6$^{GFP/Luc}$ cells. Six days later, 40×10$^6$ sCAR-T cells were delivered IV and switch dosing commenced every other day at 0.5 mg/kg for 10 days. Tumor burden was followed by luminescence after injection of luciferin and imaged on an in vivo imaging system (IVIS; PerkinElmer, Waltham, Mass., USA).
Figure 29B:
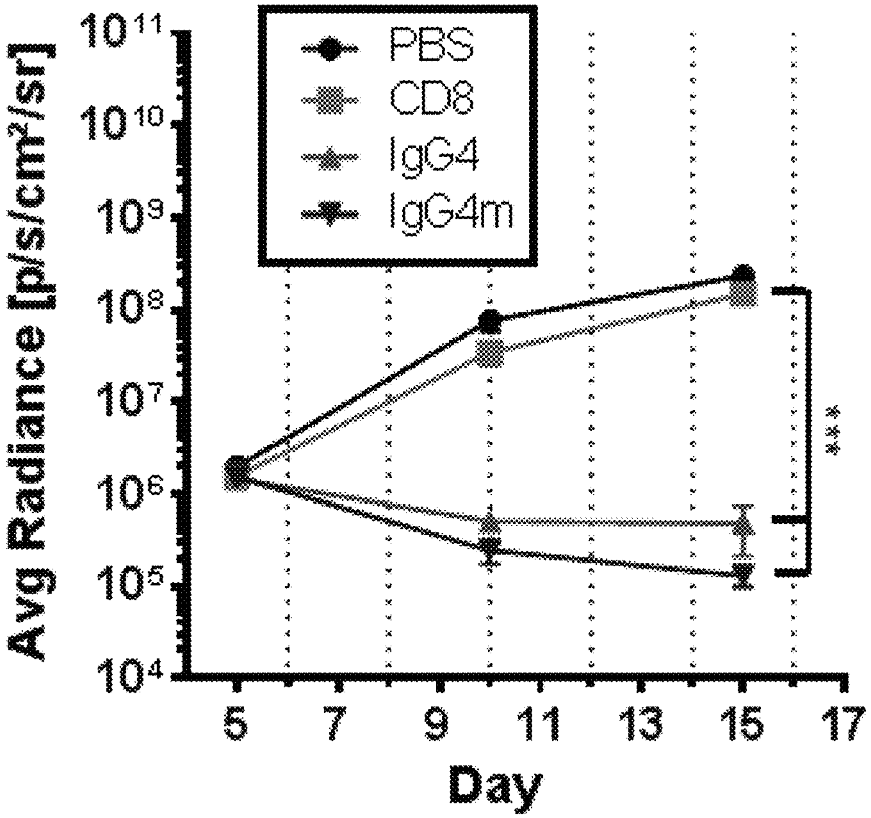
Figure 29C:
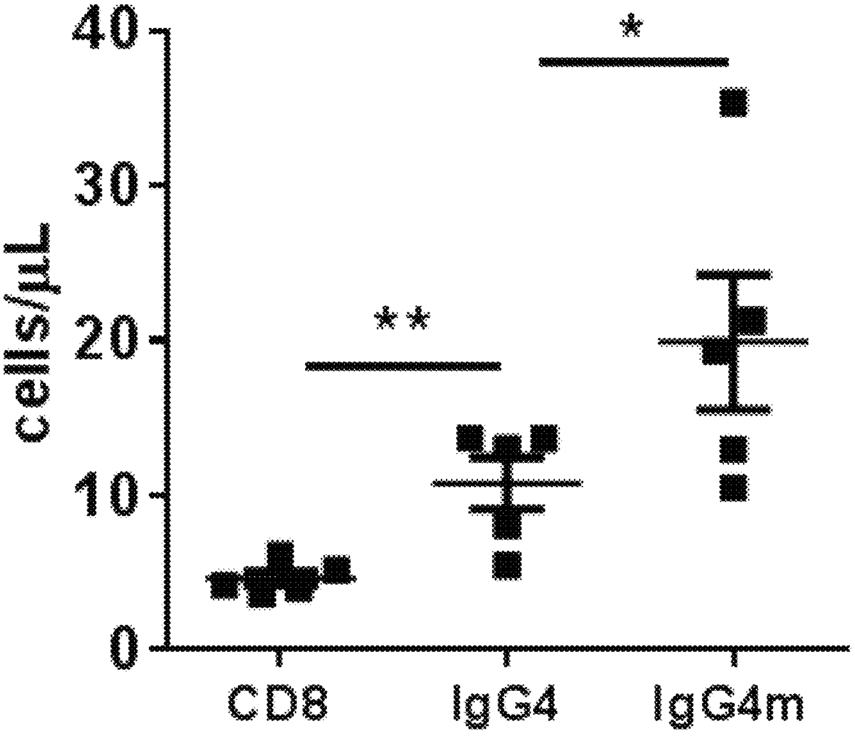

Activity of the switchable CAR-T cell platform in vivo was evaluated via tumor regression in a Nalm-$6^{Luc/GFP}$ leukemia xenograft model in immunodeficient NOD scid gamma (NSG) mice. These mice without treatment succumb to disease within 21 days. The impact of CAR hinge design on in vivo efficacy was determined using mice inoculated with Nalm-$6^{Luc/GFP}$, followed by I.V. injection of long, short, or short-dimeric sCAR-T cells 6 days later. The LCNT Fab was dosed I.V. (0.5 mg/kg) every other day for 10 days and tumor regression was followed by in vivo imaging (IVIS) of the luciferase signal from Nalm-$6^{Luc/GFP}$ cells (FIG. 29A). Both short (IgG4), and short-dimeric (IgG4m) sCAR-T cells provided a significant decrease in tumor burden; whereas long hinge sCAR-T cells (CD8) had minimal impact on disease compared with untreated control (FIG. 29B). Increased T cells counts in the peripheral blood at day 17 corresponded with reduction of tumor burden and revealed that the short-dimeric sCAR-T cells provided significantly greater T cell expansion compared with the short or long hinge designs (FIG. 29C). Based on this result, the short-dimeric sCAR construct was chosen for further in vivo studies.

Figure 29D:
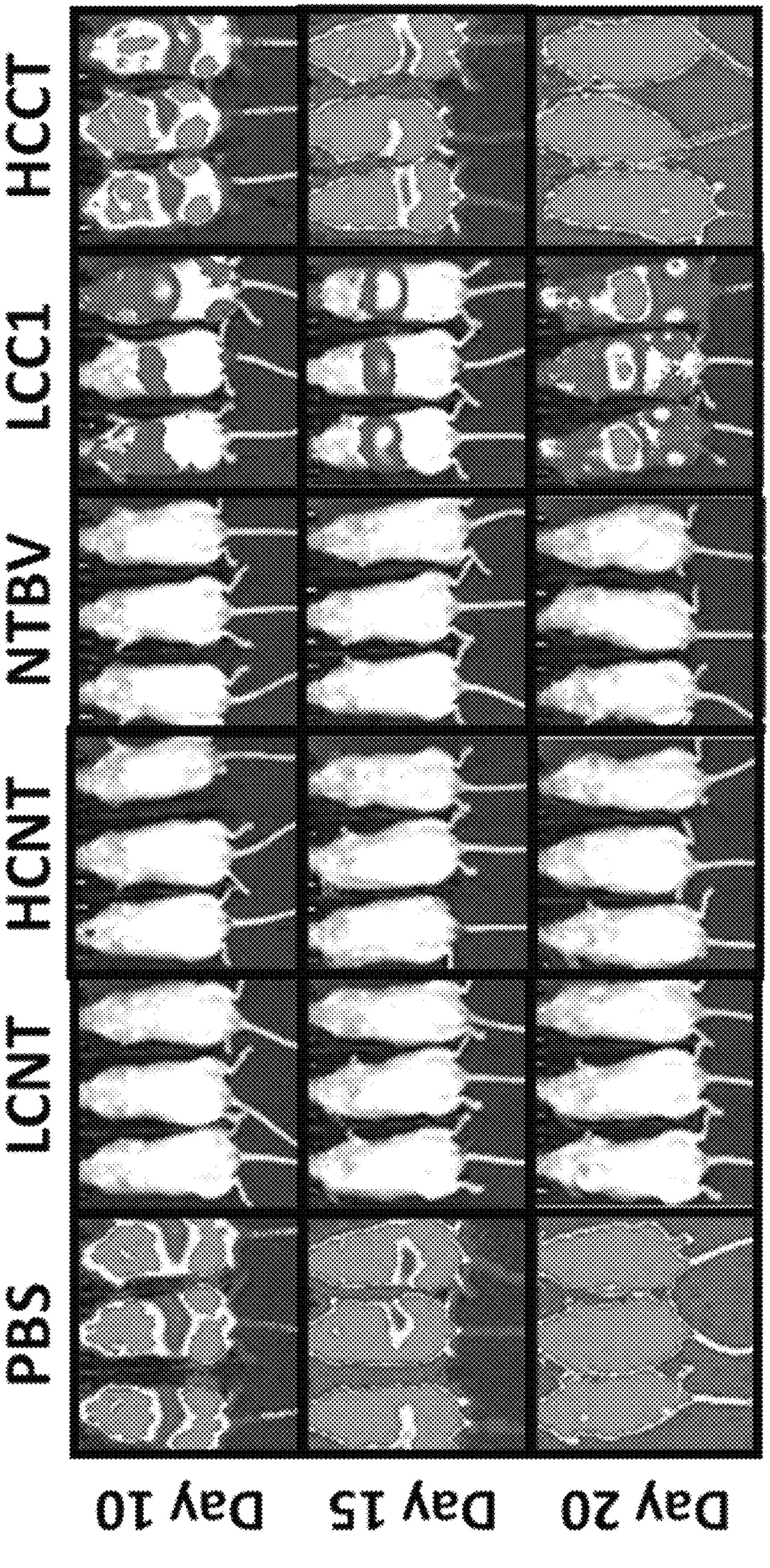
Figure 29E:
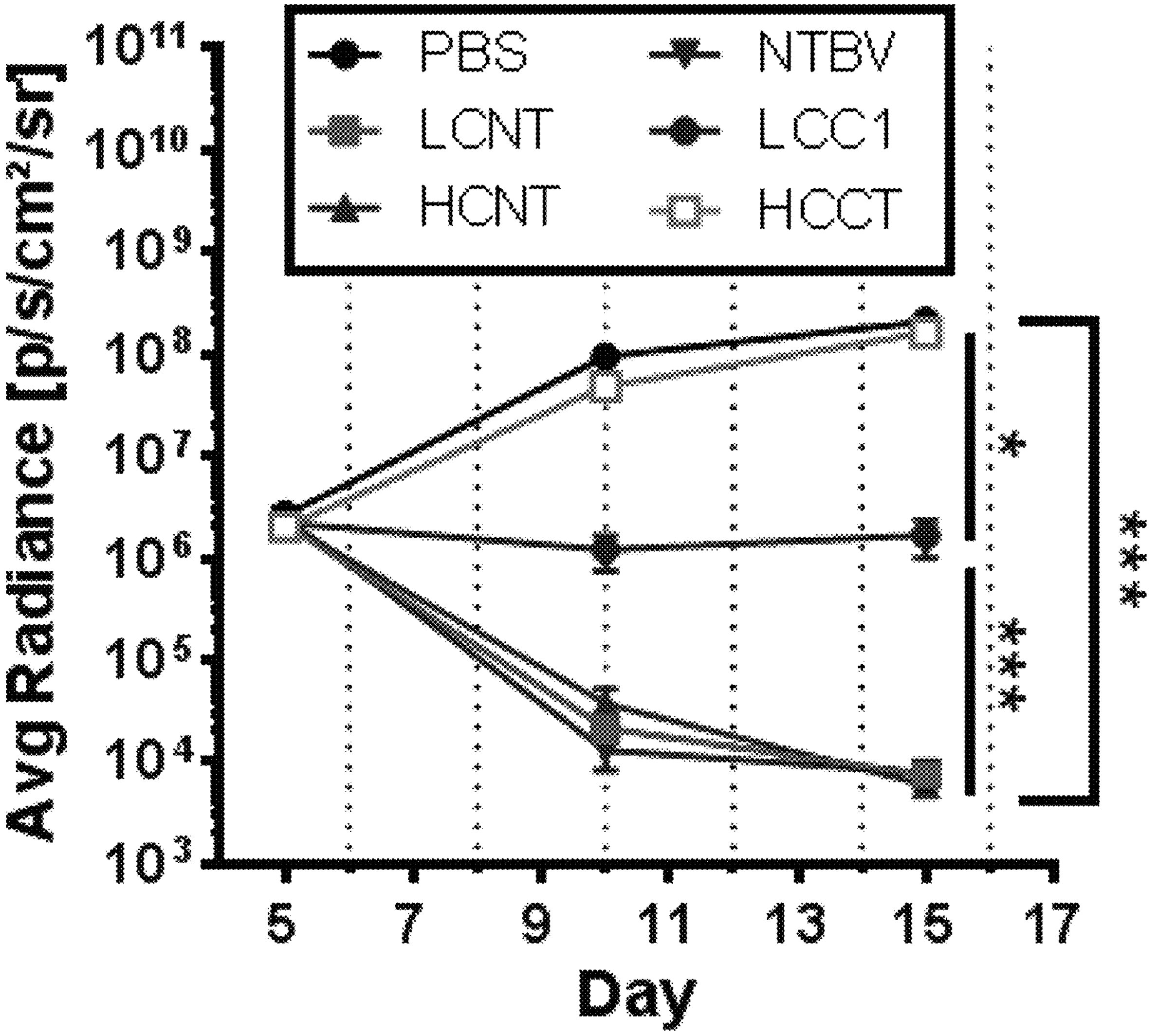
Figure 29F:
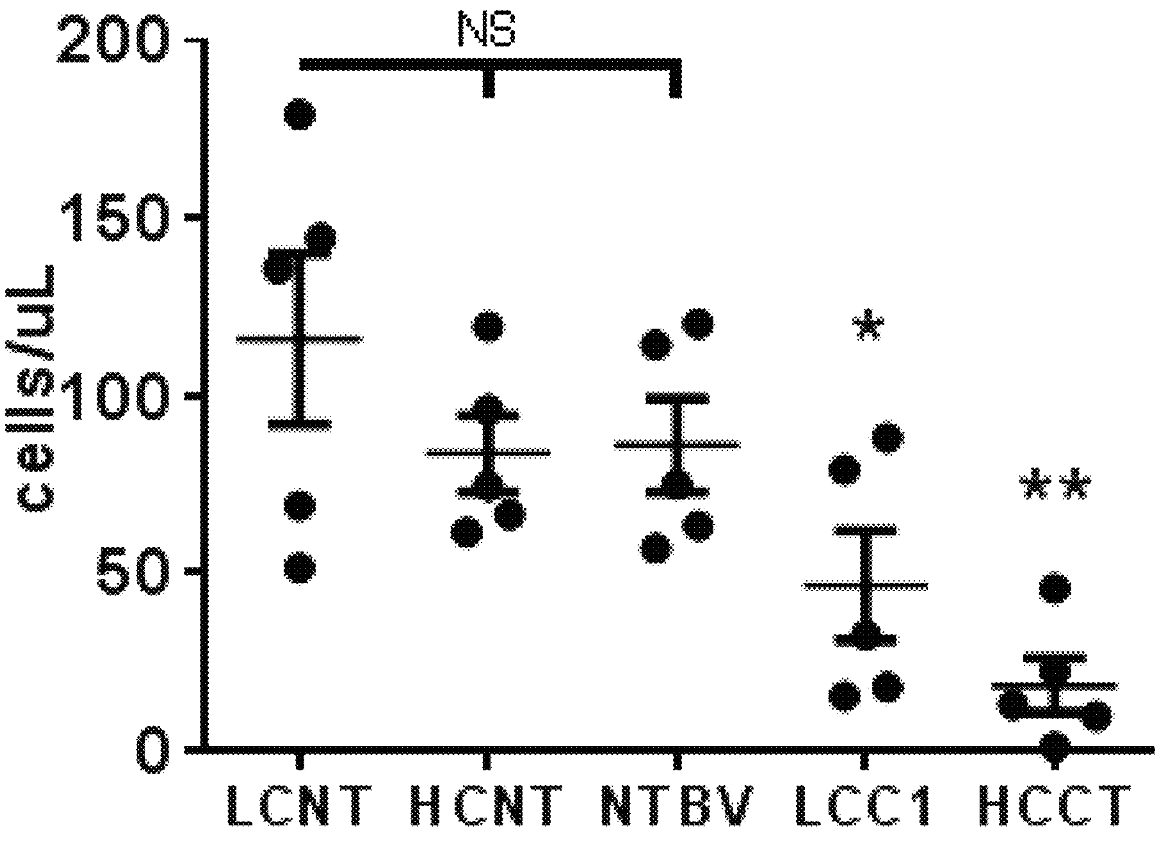

The effect of switch grafting position on the control of tumor burden was determined. As with the previous model, short-dimeric CAR-T cells were injected 6 days after tumor inoculation and mice were treated every other day (starting at day 6) with 0.5 mg/kg LCNT, HCNT, NTBV, LCC1, or HCCT Fab switches (FIG. 29D). Corresponding with the in vitro data, N-terminally grafted switches (LCNT, HCNT, and NTBV) provided the greatest reduction in tumor burden, while switches with the PNE grafted at the middle (LCC1) or C-terminus (HCCT) provided little control (FIG. 29E). T cell counts at day 17 again correlated with reduction of tumor burden and indicated the LCNT Fab switch provided the greatest T cell expansion (FIG. 29F). To determine if the LCNT switch was efficacious in IgG format the Nalm-$6^{Luc/GFP}$ model was repeated with 0.5 mg/kg LCNT IgG switch delivered I V. every 5 days for 15 days (3 doses) to compensate for the longer pharmacokinetic half-life of IgG compared with Fab. Surprisingly, the LCNT IgG switch was unable to significantly control tumor burden compared with 0.5 mg/kg LCNT Fab switch and CART-19. Increased LCNT IgG switch dosage to 1 mg/kg every day for 10 d resulted was similarly unable to control tumor growth, indicating switch dosing was not responsible for the lack of activity with the IgG format. From this data it was apparent that the combination of the LCNT Fab switch with the short-dimeric sCAR offered the most optimal therapy in vivo and thus was used in further studies of the sCAR platform.

Figure 30A:
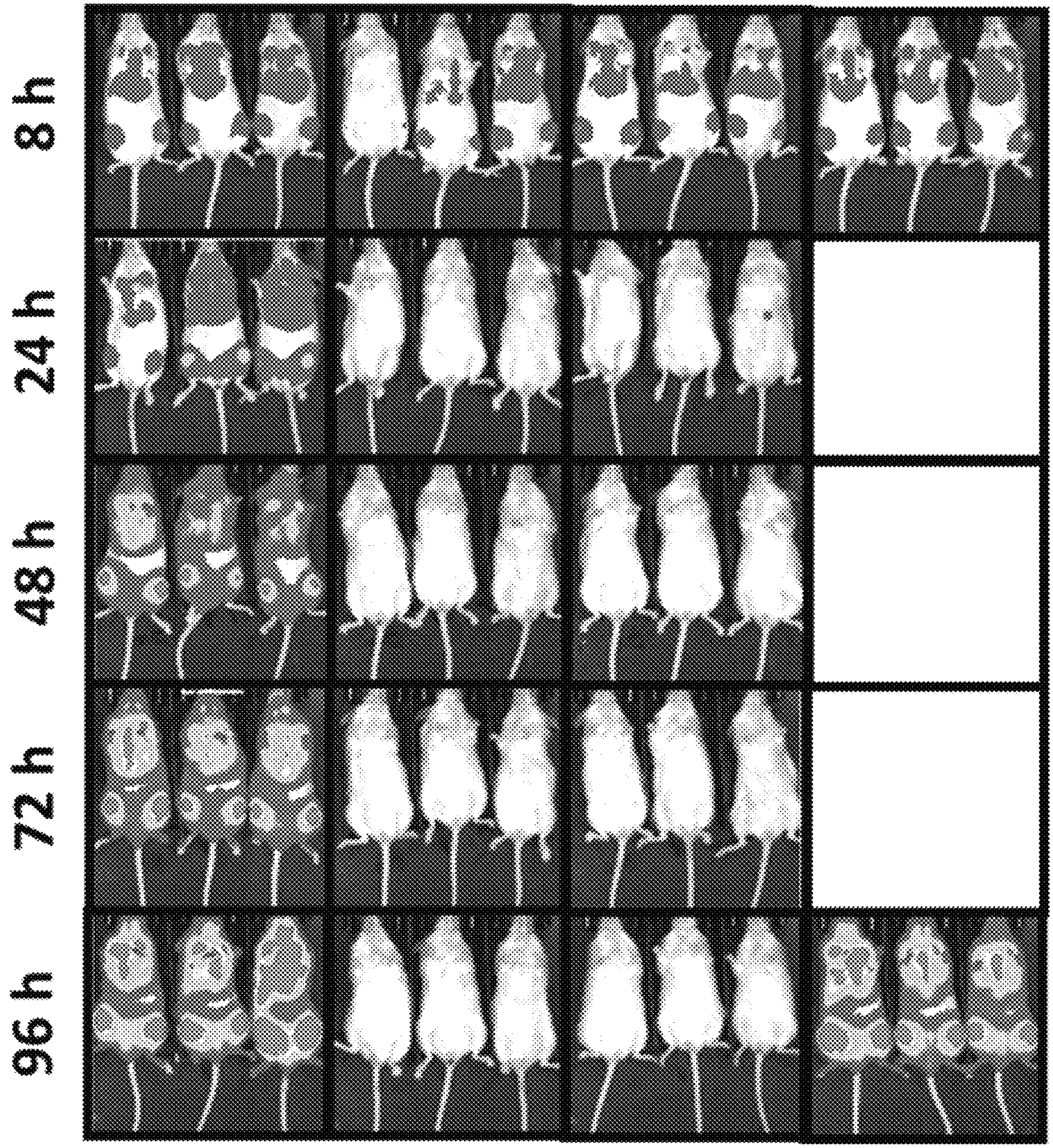
FIG. 30A-D shows sCAR-T cell expansion and localization during tumor clearance. NSG mice were inoculated with Nalm-6$^{GFP/Luc}$ as described in FIG. 28.
Figure 30B:
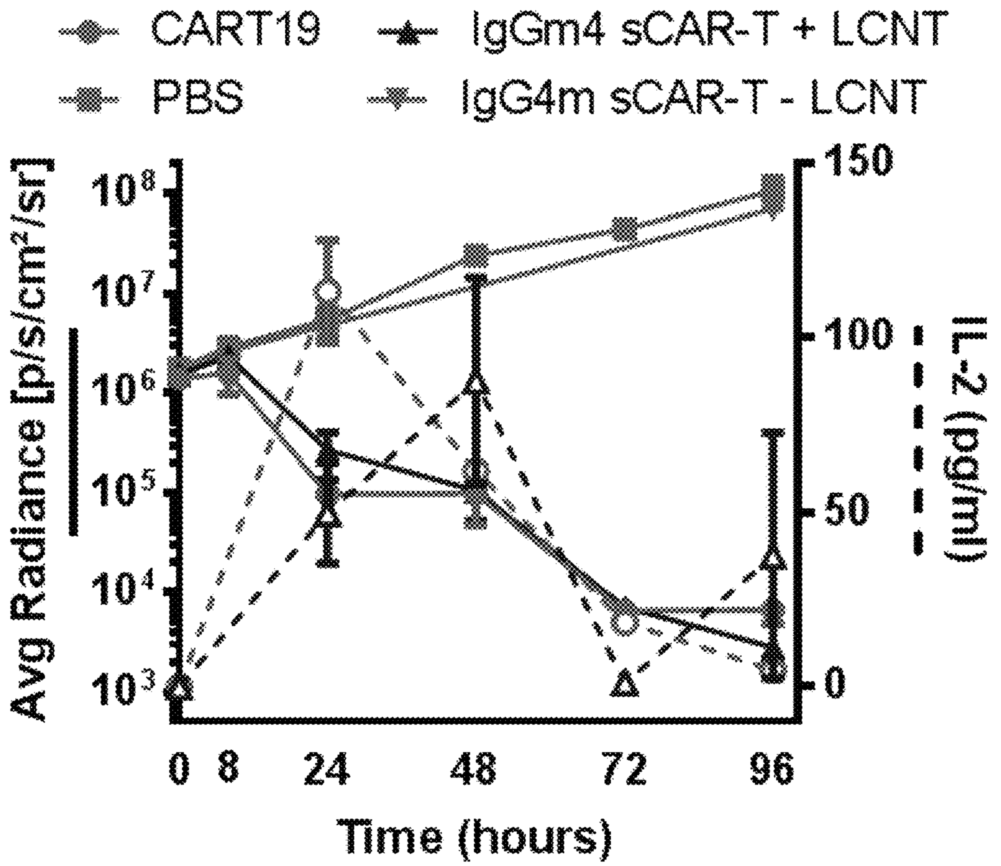

Clearance of Nalm-$6^{Luc/GFP}$ with the short-dimeric sCAR-T cell and LCNT Fab in the above model was observed to rapidly occur during the first 96 hours of treatment. To determine the proliferation and localization of sCAR-T cell cytotoxicity during this time interval, mice were sorted into 5 cohorts per treatment regimen and analyzed at 8, 24, 48, 72, and 96 h after treatment with short-dimeric sCAR-T cells+LCNT Fab switch or with conventional CART-19 and no switch. Using daily 0.5 mg/kg LCNT Fab, tumor reduction was first observed at the 24 h time point and continue to shrink to the limit of luminescence detection within 96 hours of treatment (FIG. 30A). The rate of clearance during this time was insignificantly different from CART-19 (FIG. 30B). Human IL-2 in peripheral blood peaked at similar levels at 24 h for CART-19 and at 48 h for sCAR-T cells and decreased as tumor was cleared (FIG. 30B). As expected, sCAR-T cells not treated with switch had no effect on disease progression in this model, confirming requirement for switch dosing.

Figure 30C:
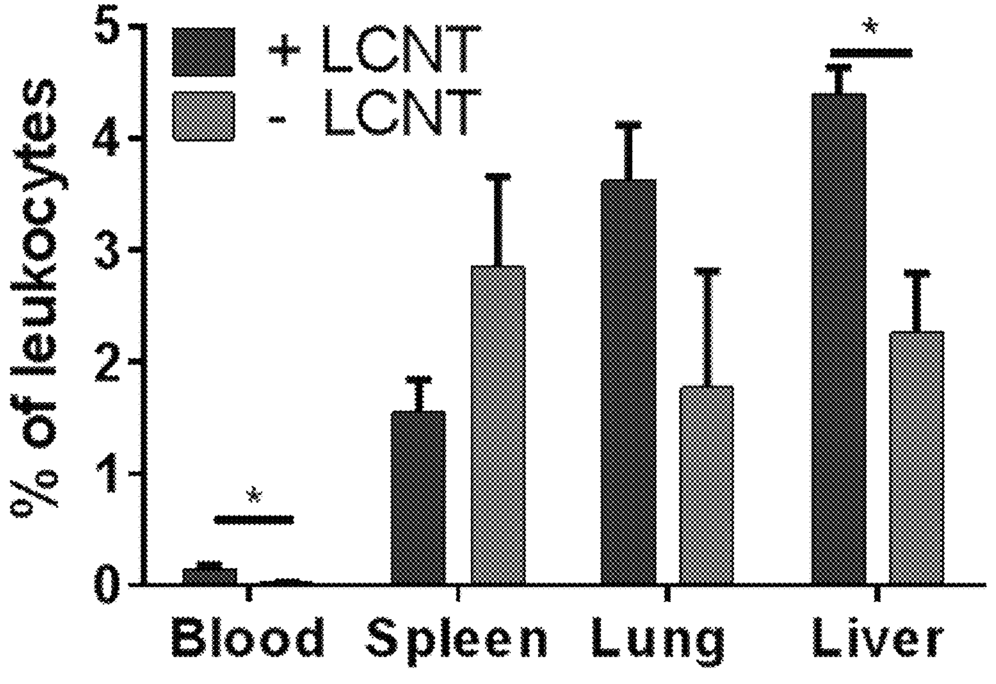
Figure 30D:
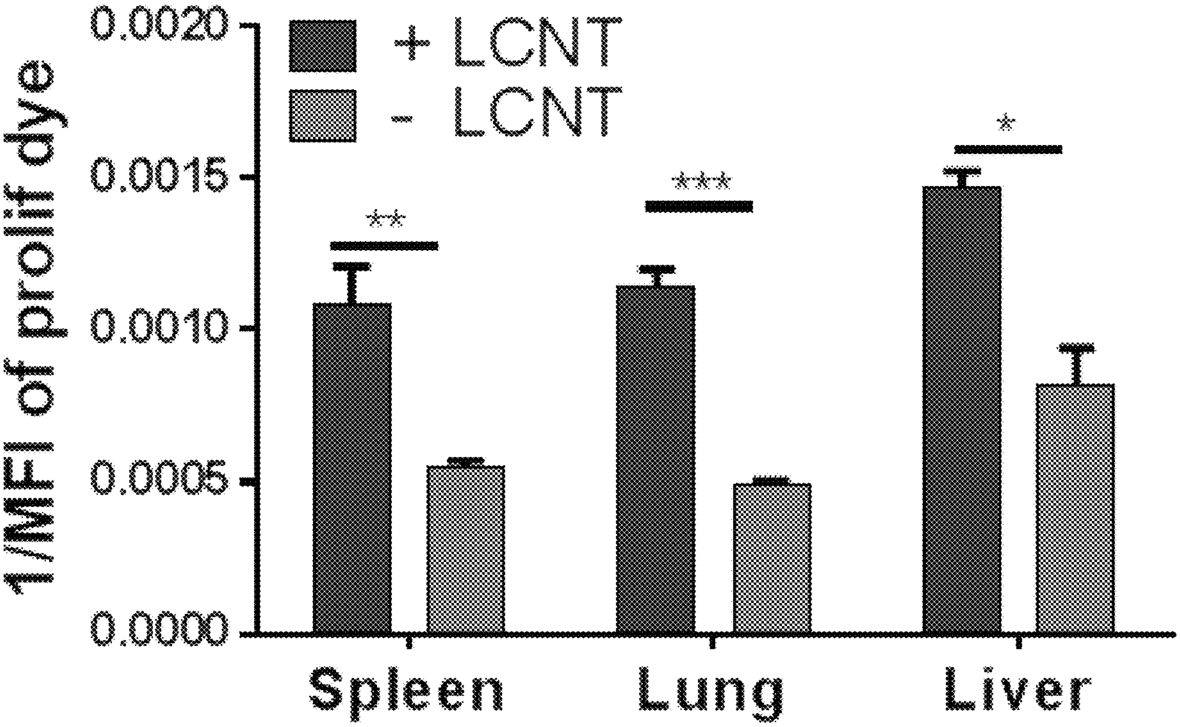
Figure 32A:
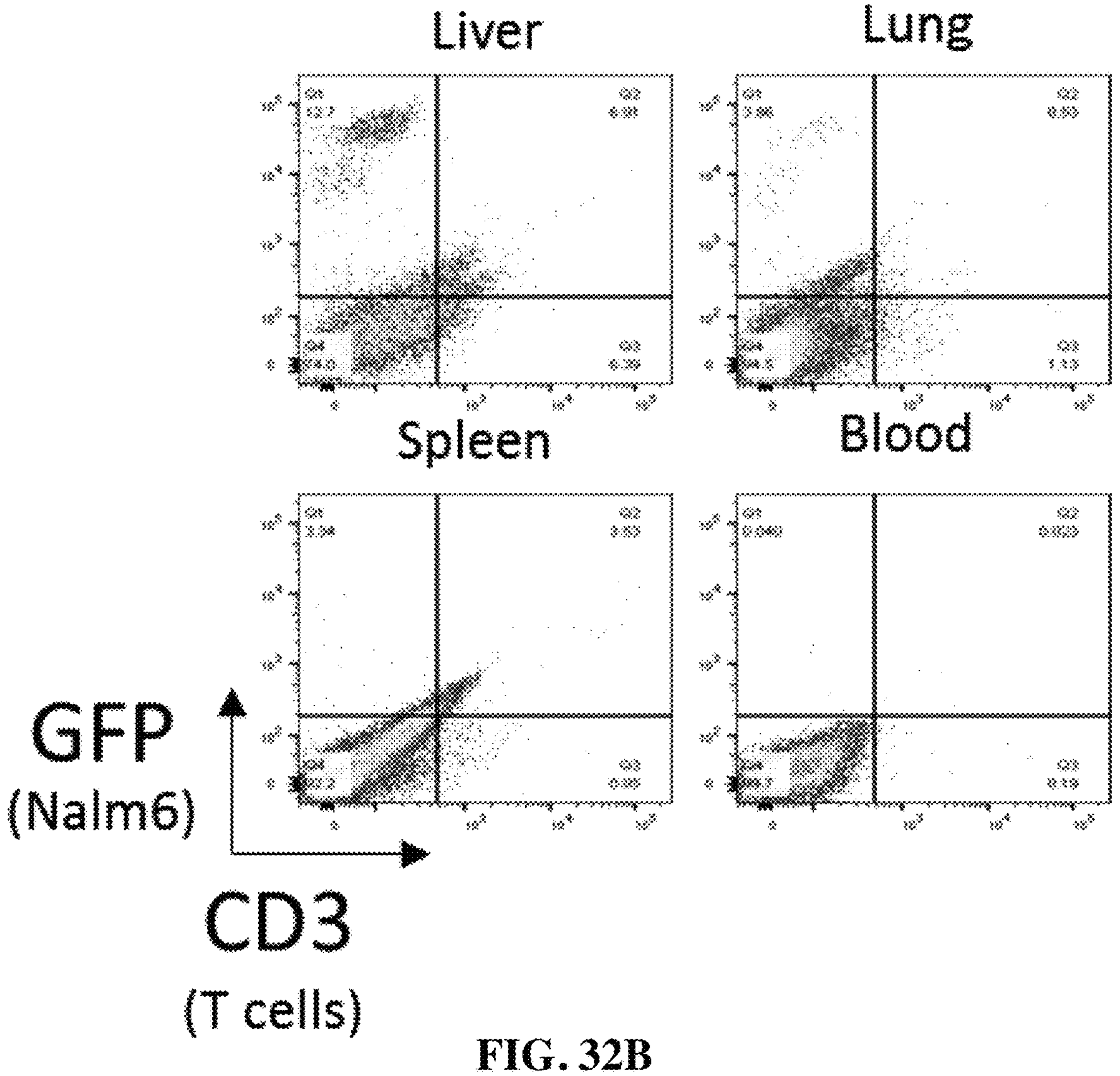
FIG. 32A-D shows in vivo kinetics of LCNT Fab clearance of tumor compared to CART19.
Figure 32B:
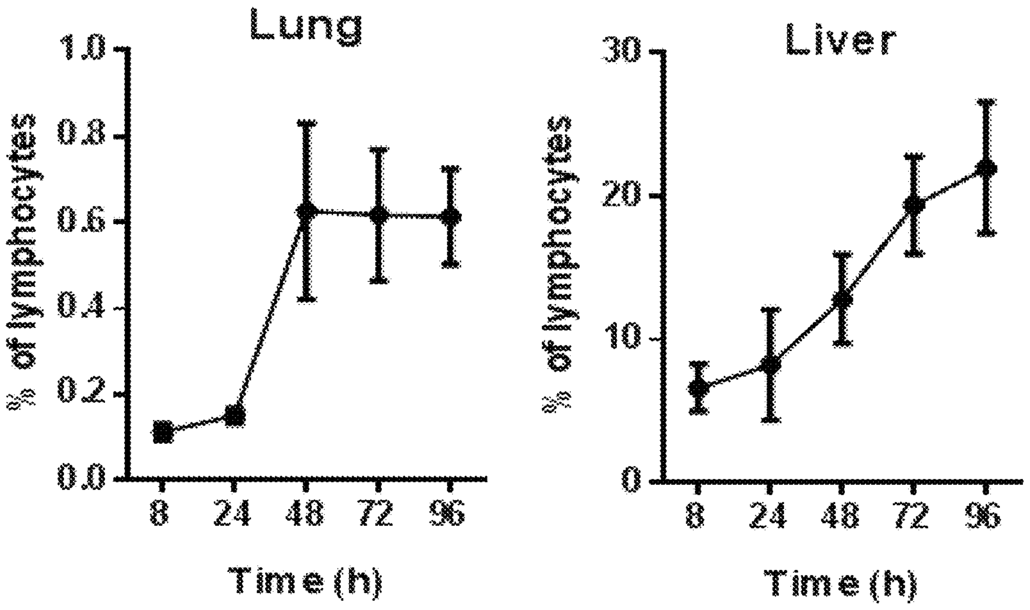
Figure 32C:
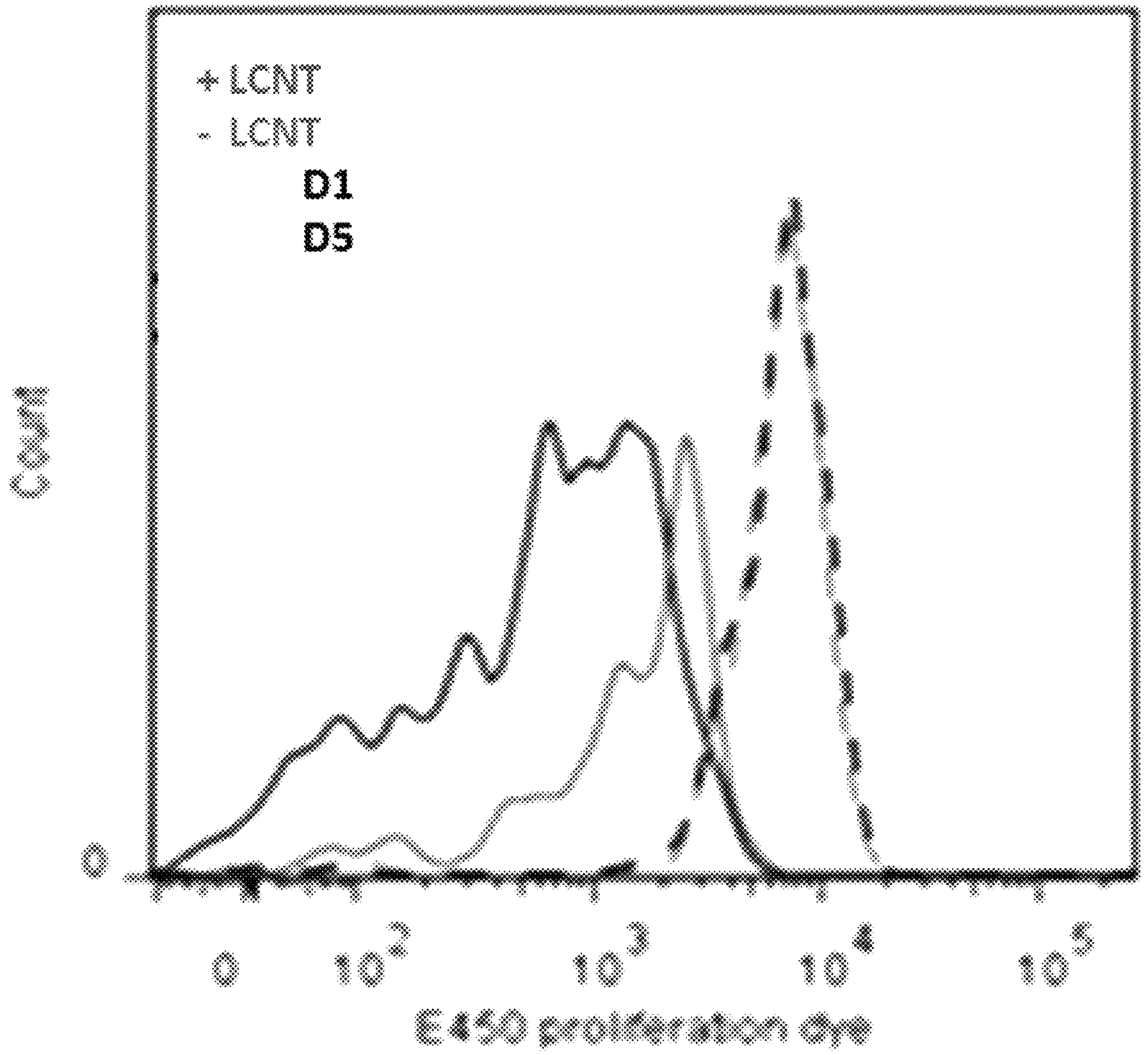
Figure 32D:
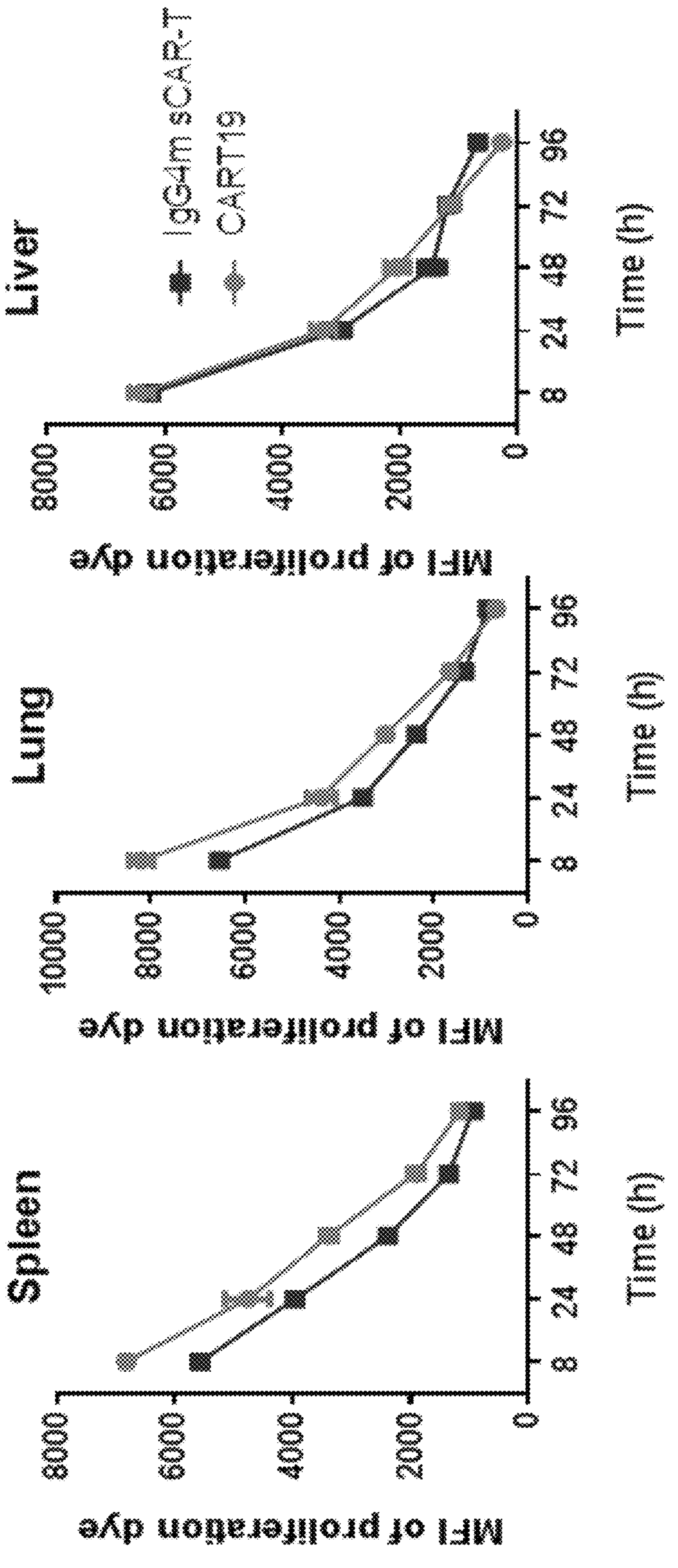

To further understand the effect of switch treatment on T cell trafficking, short-dimeric sCAR-T cells were tracked in the spleen, lungs, liver, and peripheral blood by flow cytometry over the first 96 h. During this time interval Nalm-$6^{Luc/GFP}$ cells were only detectable in the lung and liver (FIG. 32B). Correspondingly, significantly increased numbers of sCAR-T cells were found in the lung and liver at 96 h in mice dosed with LCNT Fab switch compared mice not treated with switch (FIG. 30C). Switch dosing did not increase sCAR-T recruitment to the spleen where tumor burden was not detectable. In the organs assessed, sCAR-T cells had proliferated significantly more (by dye dilution) in the mice treated with LCNT Fab switch compared to no switch treatment, again demonstrating the requirement for the switch for sCAR-T cell expansion (FIG. 30D & FIG. 32D). The magnitude of sCAR-T cell proliferation dosed with LCNT Fab switch was comparable to that of CART-19 in both liver and lung. Together, these results indicate the short-dimeric sCAR-T cells with the LCNT Fab switch can expand and eliminate tumor burden comparably to conventional CART-19.

Example 14. Dose-Dependent Control of sCAR-T Cell Activity In Vivo

Figure 33A:
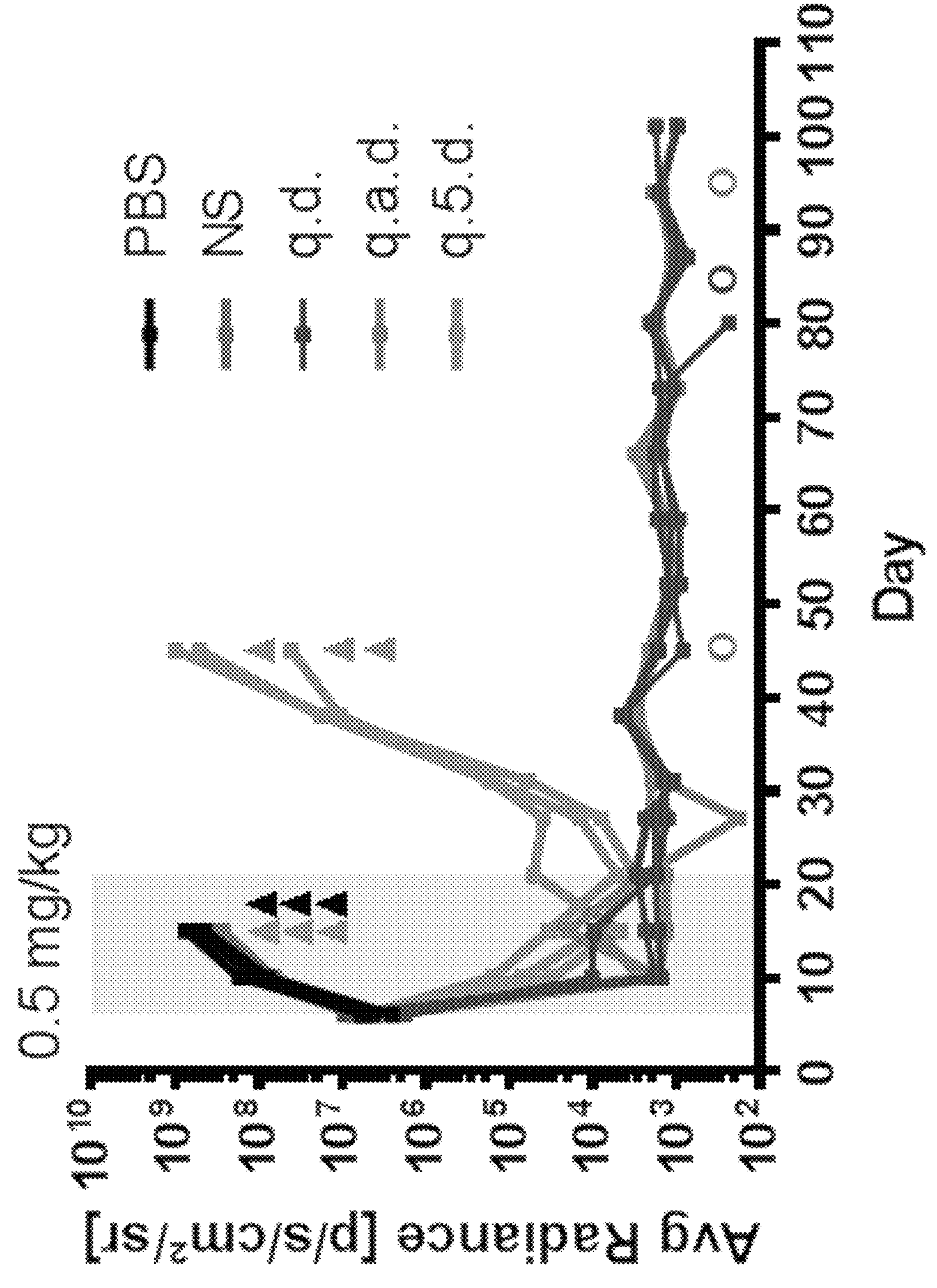
FIG. 33A-E shows the influence of switch dosing regimen on sCAR-T cell activation and efficacy. NSG mice were inoculated with $Nalm6^{GFP/Luc}$ and six days later engrafted with short-dimeric sCAR-T cells as described in FIG. 29.
Figure 33B:
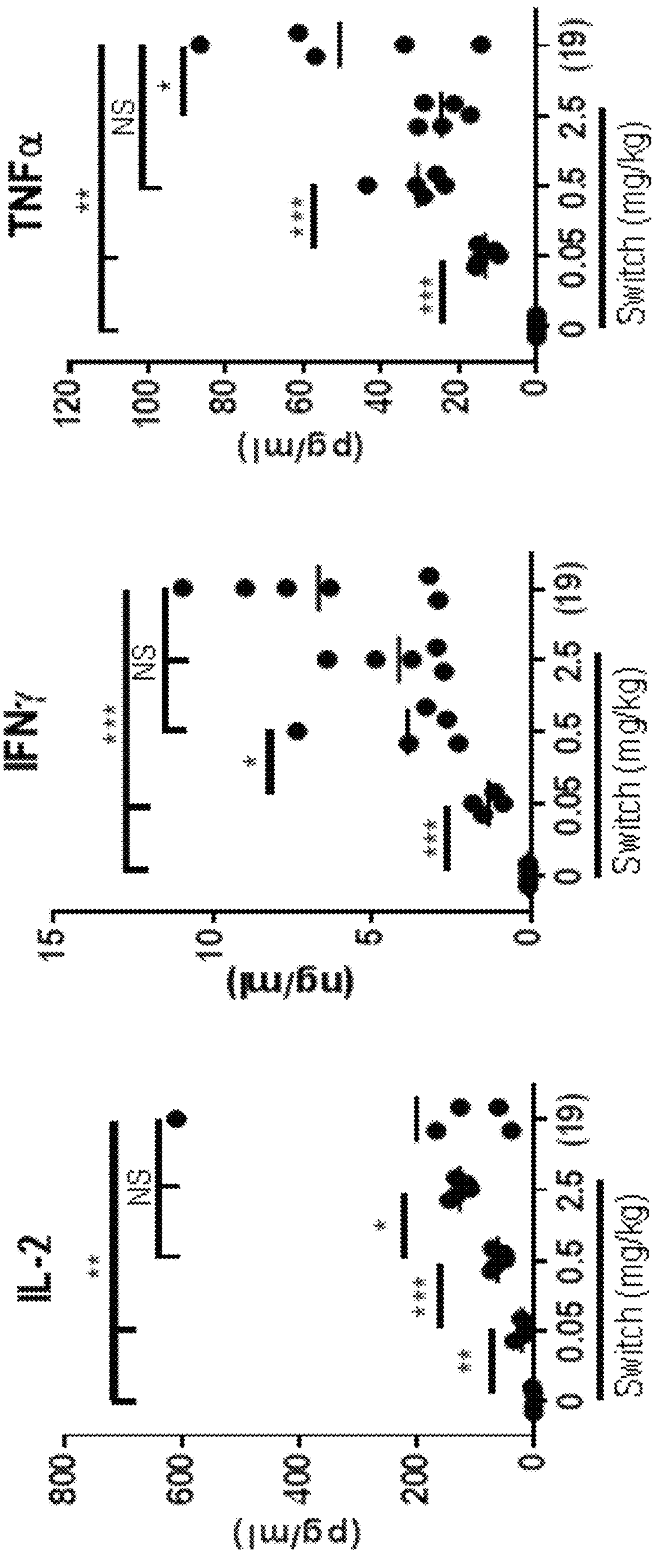

To determine the minimal dosing regimen required for a sustained response with short-dimeric sCAR-T cells, every day, every other day, or every fifth day dosing of 0.5 mg/kg LCNT Fab switch was tested for 15 days in the Nalm-$6^{Luc/GFP}$ model. Every day and every other day dosing yielded comparable rates of tumor regression which was sustained for >100 days after dosing had stopped (FIG. 33A and FIG. 32A). Mice that died between days 40 and 100 (open circles) had no evidence of disease; expiration in these cases was attributed to xenogeneic graft versus host disease caused by human T cells in the NSG mouse. Dosing every fifth day (3 total dosages) greatly decreased and stabilized disease burden at a low level, but did not completely clear disease by luciferase signal (FIG. 33A). Residual disease in this group relapsed when dosing was discontinued indicating the activity of the sCAR-T cells towards Nalm-$6^{Luc/GFP}$ had been turned "off" in the absence of the switch even though sCAR-T cells were still detectable in blood up to 64 days after injection (FIG. 32B).

Figure 33C:
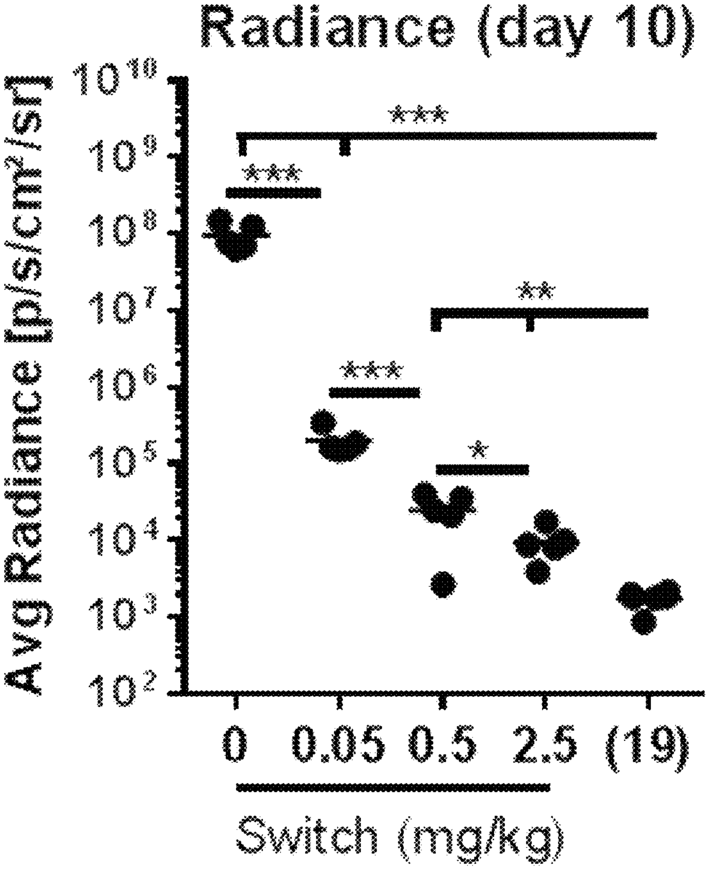

Control of cytokine release in vivo is important to prevent CRS in clinical translational. Therefore, switch dosage was correlated with short-dimeric sCAR-T cell cytokine release in the Nalm-$6^{Luc/GFP}$ model. Mice dosed everyday with 0.05, 0.5, or 2.5 mg/kg LCNT Fab switch every day showed a dose-dependent increase in serum IL-2, INFγ, and TNFα at 24 h (FIG. 33B) which correlated with dose dependent reductions in tumor burden by day 10 (FIG. 33C). Cytokine production in the 0.5 and 2.5 mg/kg groups was not significantly different from CART-19 at 24 h for all cytokines, except for serum TNFα which was decreased in the 2.5 mg/kg group compared with CART-19. However, all cytokines in the 0.05 mg/kg group were significantly lower than CART-19.

Figure 33D:
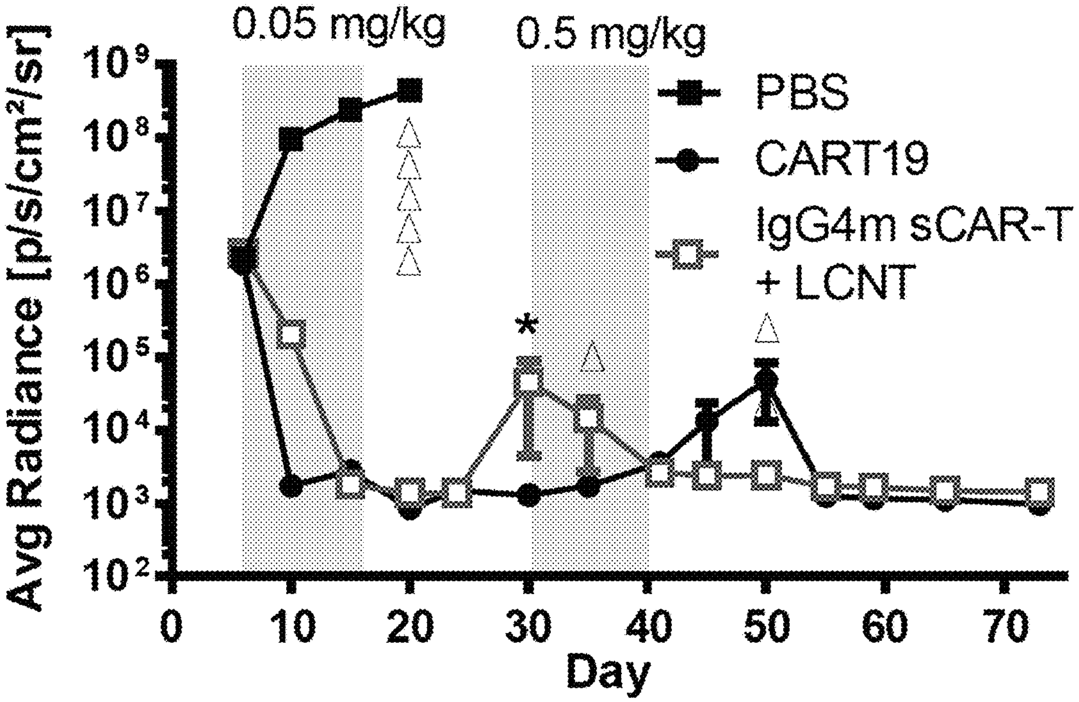

To determine if treatment with the lower dose of 0.05 mg/kg could be efficacious, despite lower levels of cytokine production, dosing of LCNT Fab switch was carried out every day for 10 d in the Nalm-$6^{Luc/GFP}$ model and tumor burden followed by IVIS. At this low dosage, tumor clearance was correspondingly slower compared with CART-19 and previous models, but still reached the limit of detection by day 16, final day of dosing (FIG. 33D & FIG. 32D). Fifteen days after the final dose, at day 30, tumor burden rose significantly higher than the CART-19 control and therefore mice were retreated with 0.5 mg/kg LCNT Fab switch for 10 days. This treatment paradigm effectively decreased tumor signal to equivalent levels as CART-19 within 5 days. Mice remained tumor-free for >35 days after the final dose of the second dosing period. Thus sCAR-T cells can control cytokine release while still providing efficacy which is an effective strategy to avoiding CRS in patients receiving therapy.

Figure 33E:
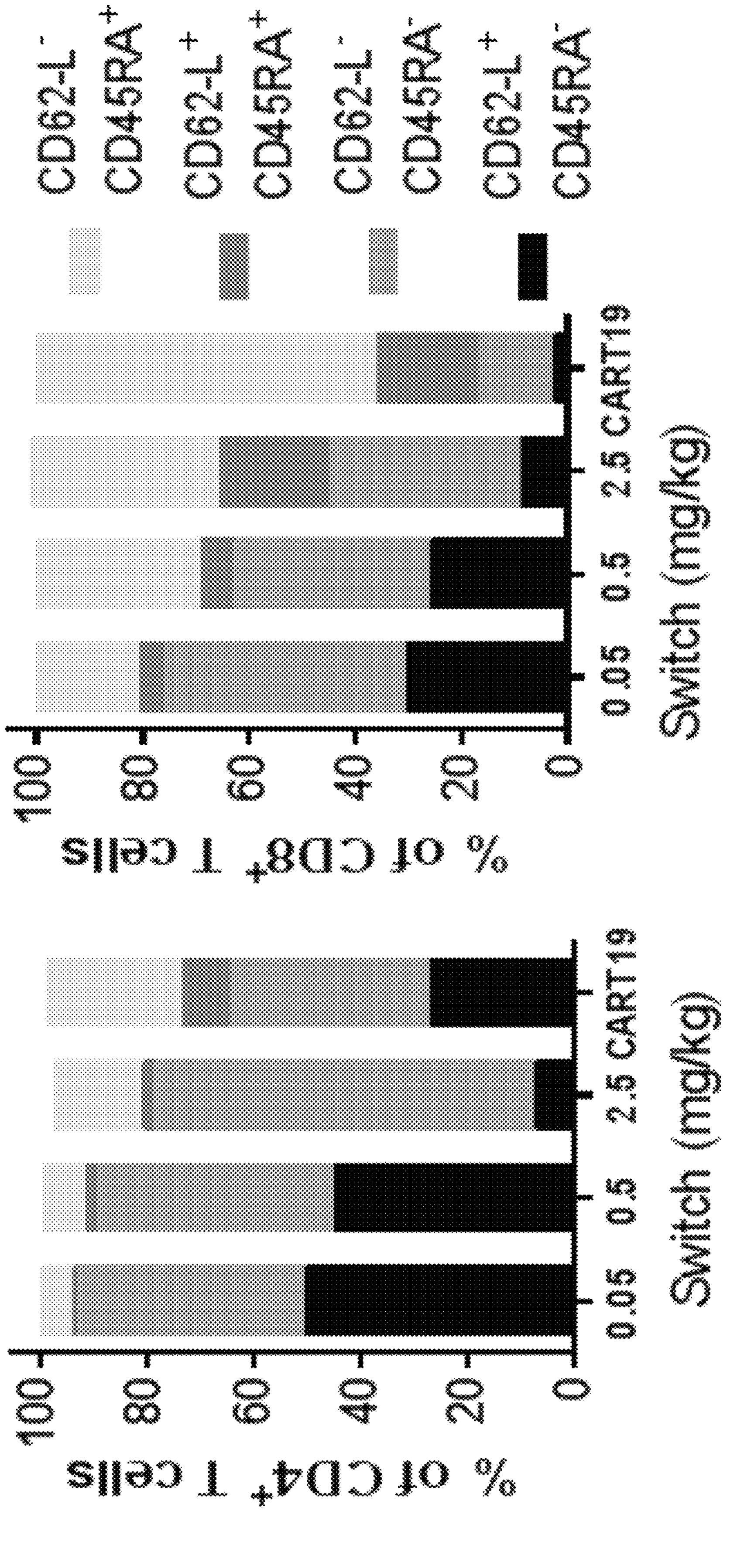

Persistent memory phenotypes have been correlated with efficacy in CAR-T cell therapy clinical trials. To understand whether switch dosage could influence sCAR-T cell phenotype, mice in the Nalm-$6^{Luc/GFP}$ model were dosed with 0.05, 0.5, or 2.5 mg/kg LCNT Fab switch and analyzed the expression of CD45RA and CD62L on CD4+ and CD8+ T cells in peripheral blood after 20 days (5 days after the final dose). The 2.5 mg/kg group demonstrated significant expansion of the $CD45RA^{+}CD62L^{-}$ effector memory RA (TEMRA) compartment in both $CD4^{+}$ and $CD8^{+}$ T cells compared with the lower dose groups (FIG. 33E). Conversely, the lower dose groups of 0.05 and 0.5 mg/kg had significantly larger populations of $CD45RA^{-}CD62L^{+}$ central memory cells compared with 2.5 mg/kg group which may be a result of decreased stimulation during the dosing period. Central memory CAR-T cells are favorable for their persistence and indicate a benefit to low dose treatment of sCAR-T cells during the initial stages of tumor clearance. Collectively these results demonstrate that the efficacy, tissue-tracking, cytokine release, and phenotype of sCAR-T cells is fully dose titratable and can be tuned to provide efficacy comparable to the corresponding conventional CART-19, but with lower levels of cytokines and increased expansion of central memory subsets.

Example 15. Dual Targeting of CD19 and CD20 In Vivo

Ten percent of all ALL patients treated with CART19 T-cells relapse due to the expansion of CD19− tumor cells, which cannot be targeted by conventional CAR-T cells because their antigen specificity is fixed against the CD19 antigen. Switchable CAR-T cells can target such tumors by utilizing two or more switches with different antigen specificities capable of targeting the tumor cells.

Figure 34A:
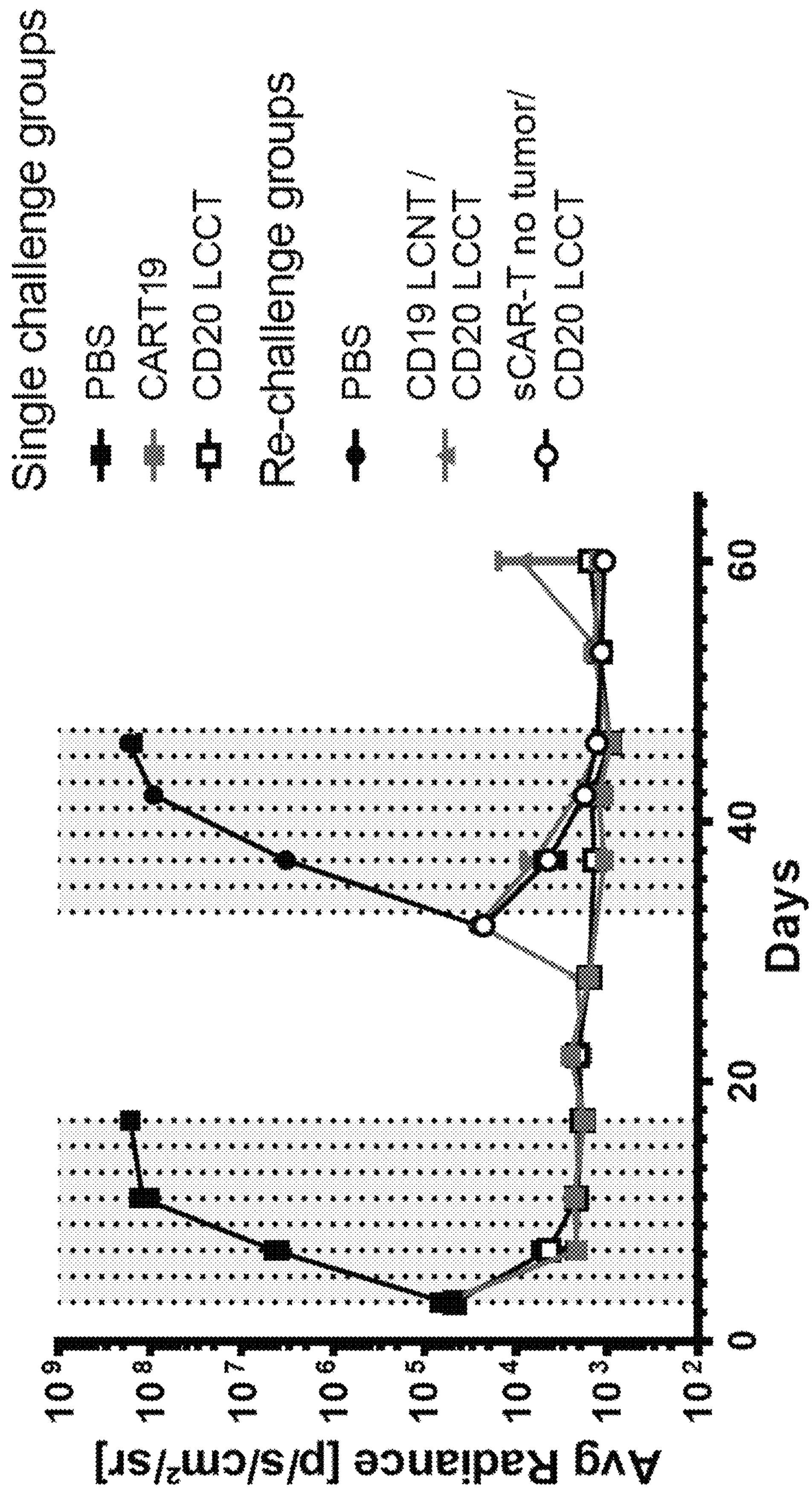
FIGS. 34A-B show antigen re-challenge models.

In one experiment, illustrated in FIG. 34A, NSG mice were injected (i.v.) with $5\times10^5$ RAJI-Luc cells ($CD19^+$ $CD20^+$) (RAJI-Luc cells are luciferase-expressing Raji cells) on day 0. On day 3, $40\times10^6$ sCAR-T cells were infused intravenously. Mice that received the sCAR-T cells were dosed 8 times (q.a.d.) with the Fmc63 anti-CD19 LCNT switch or OFA anti-CD20 LCCT switch from day 3-17. 13 days after the initial round of switch dosing, day 30, the mice originally treated with the Fmc63 anti-CD19 LCNT switch were re-challenged with RAJI-Luc cells ($CD19^+CD20^+$) and, following the 3 day engraftment period, were retreated with the OFA anti-CD20 LCCT switch. An additional group was incorporated into this study to show that sCAR-T cells were still active even after 30 days in the mice with no additional stimuli: these mice received sCAR-T cells on day 3 and were challenged, for the first time, with Raji cells on day 30 and dosed with the OFA anti-CD20 LCCT switch from day 33-47. This data show that sCAR-T cells can be reactivated in vivo to target a different cancer associated antigen using a second switch.

Figure 34B:
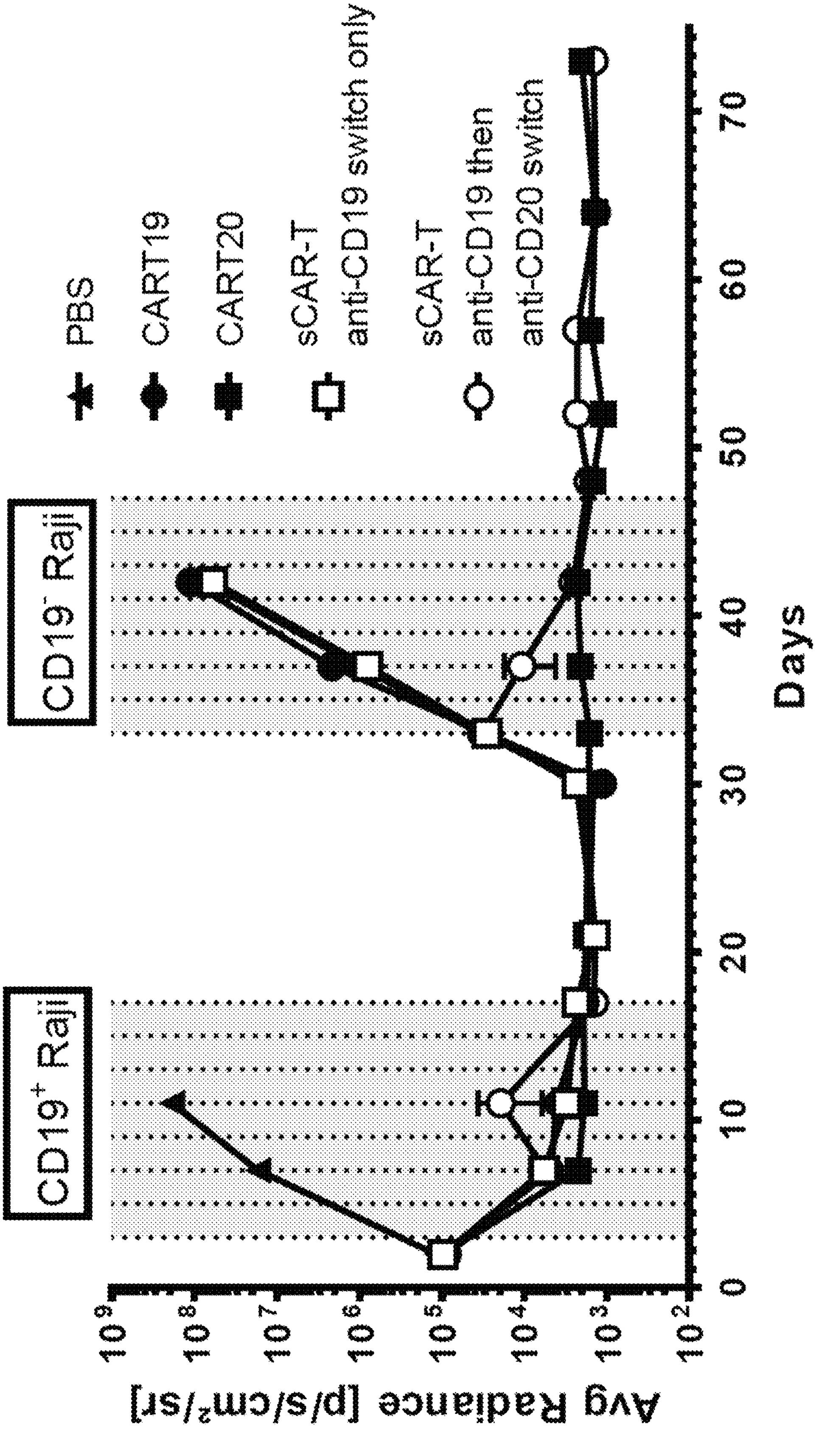

In a similar experiment, illustrated in FIG. 34B, we tested whether the use of a second switch can eliminate tumors that lack the CD19 antigen. Similar to the prior experiment, NSG mice were injected (i.v.) with $5\times10^5$ RAJI-Luc cells (CD19+ CD20+). Three days later $40\times10^6$ CART19 (SEQ ID NO: 181), CART20 (SEQ ID NO: 182; this construct used the 4-1BB and CD3 co-stimulatory domains as used with CART19) or sCAR-T (SEQ ID NO: 74) cells were injected (i.v.). The sCAR-T cell treated groups received anti-CD19 switch (LCNT graft; SEQ ID NOS: 9 and 36) q.a.d. from day 3 to day 18 (indicated by dotted lines in shaded area in FIG. 43B). The CD19+CD20+ Raji cell tumor was cleared in all groups. On day 30, the mice were re-challenged with RAJI-Luc cells (CD19-CD20+) (note, unlike the data shown in FIG. 34A, these RAJI-Luc cells are CD19 negative). Three days later, one of the sCAR-T cell groups was re-dosed with an anti-CD20 switch (CTBV graft; SEQ ID NOS: 138 and 139) q.a.d. from day 33 to day 48 (indicated by dotted lines in shaded area in FIG. 34B). The CD19-CD20+ Raji cell tumor was cleared in the groups treated with CART20 or the sCAR-T cells with the anti-CD20 switch; however, CART19 was not able to clear the rechallenged CD19-negative tumor. These data highlight one major benefit of the switchable CAR-T system, i.e., the ability of the switchable CAR-T cells to be re-directed in vivo to target different antigen specificities; thus, demonstrating a potential utility of sCAR-T cells in targeting multiple cancer associated antigens. Further, these data demonstrate the potential to treat antigen escape mutants such as, e.g., the CD19-negative tumor cells that are commonly expanded in ALL relapse patients.

Example 16. Evaluation of a Switchable CAR-T Platform in a Heterogeneous Cancer Model A first switch containing an anti-CD19 targeting antibody and a second switch containing the anti-CD20 targeting antibody rituximab are used sequentially or simultaneously to target different antigens in the same patient using a single adoptively transferred CAR-T in an effort to combat ALL relapse attributed to a CD19 escape variant during CAR-T-19 therapy.

An anti-CD20 switch is created in analogous fashion to the anti-CD19 switch using the optimal characteristics determined in Example 3. A CAR-T-20 based on rituximab is constructed for comparison. Efficacy is tested in vitro against CD20-positive IM-9 and Daudi cells lines. To create a heterogeneous B-cell lymphoblast, the chronic myelogenous leukemia-derived K562 cell line (which is negative for CD20 and CD19) is stably transduced with the CD19 antigen using a lentiviral vector. Single cell clones are obtained via flow-sorting to obtain a population with homogenous CD19 expression. This cell line is then be transduced with CD20 and sorted by high ($CD20^{hi}$) or low ($CD20^{low}$) level of antigen expression. The activation and cytotoxicity of the switchable CAR-T on mixtures of $CD19^+$ $CD20^-$ and $CD19^+CD20^{hi}$ or $CD19^+CD20^{low}$ are assessed in vitro using the CD19 and CD20 switches (simultaneous or sequential administration). The method provides an opportunity to study the lowest percentage of $CD20^{hi}$ or $CD20^{low}$ cells in a population that are necessary to stimulate the CAR-T with the rituximab switch. This may be more physiologically relevant than a homogeneous population. This system is then tested in a xenograft mouse model. A mixture of $CD19^+CD20^-$ and $CD19^+CD20^+$ is used to establish the xenograft. Alternatively, primary patient derived ALL samples are used for this experiment if found to be heterogeneous for CD19 or CD20 expression in our initial xenograft study. Switchable CAR-ECs with the anti-CD20 switch are administered to eliminate the $CD19^+CD20^+$ population and allow outgrowth of $CD19^+CD20^-$ cells. To demonstrate the feasibility of retargeting the same CAR-T, the anti-CD19 switch is subsequently dosed and growth of remaining xenograft monitored. Tumors are evaluated for antigen expression in cohorts of sacrificed mice or in primary blasts. Simultaneous targeting is also assessed. Treatment is compared with CAR-T-19, CAR-T-20, or both simultaneously.

Example 17. sCAR-T Surrogate Mouse Model

B cell aplasia is a significant side effect reported in clinical trials with CART19 therapy. With the switch platform, switch dosing may be discontinued after sCAR-T cells have had the opportunity to target CD19+ tumors, thus, allowing the B cell pool to reconstitute.

A murine surrogate model was developed in immunocompetent mice to test the ability of a sCART system to alleviate the long-term B cell aplasia associated with canonical CART-19 therapy. The surrogate model was established using the murine Myc5 ($CD19^+$) cell line in which various peptide engrafted anti-murine CD19 switches were designed and expressed.

To create the switches, the antibody fragment (Fab) from the hamster anti-mouse CD19 (1D3) antibody clone was expressed with the GCN4 peptide grafted with a linker to the N-terminus of the light chain (LCNT; SEQ ID NOS: 54 & 58) or to the N-terminus of the heavy chain (HCNT; SEQ ID NOS: 53 & 60) or to the C-terminus of the light chain (LCCT; SEQ ID NOS: 54 & 57). Alternately, switch constructs were expressed in which each of the light and heavy chains were grafted at their N-terminus with the GCN4 peptide (NTBV; SEQ ID NOS: 58 & 60).

Figure 35:
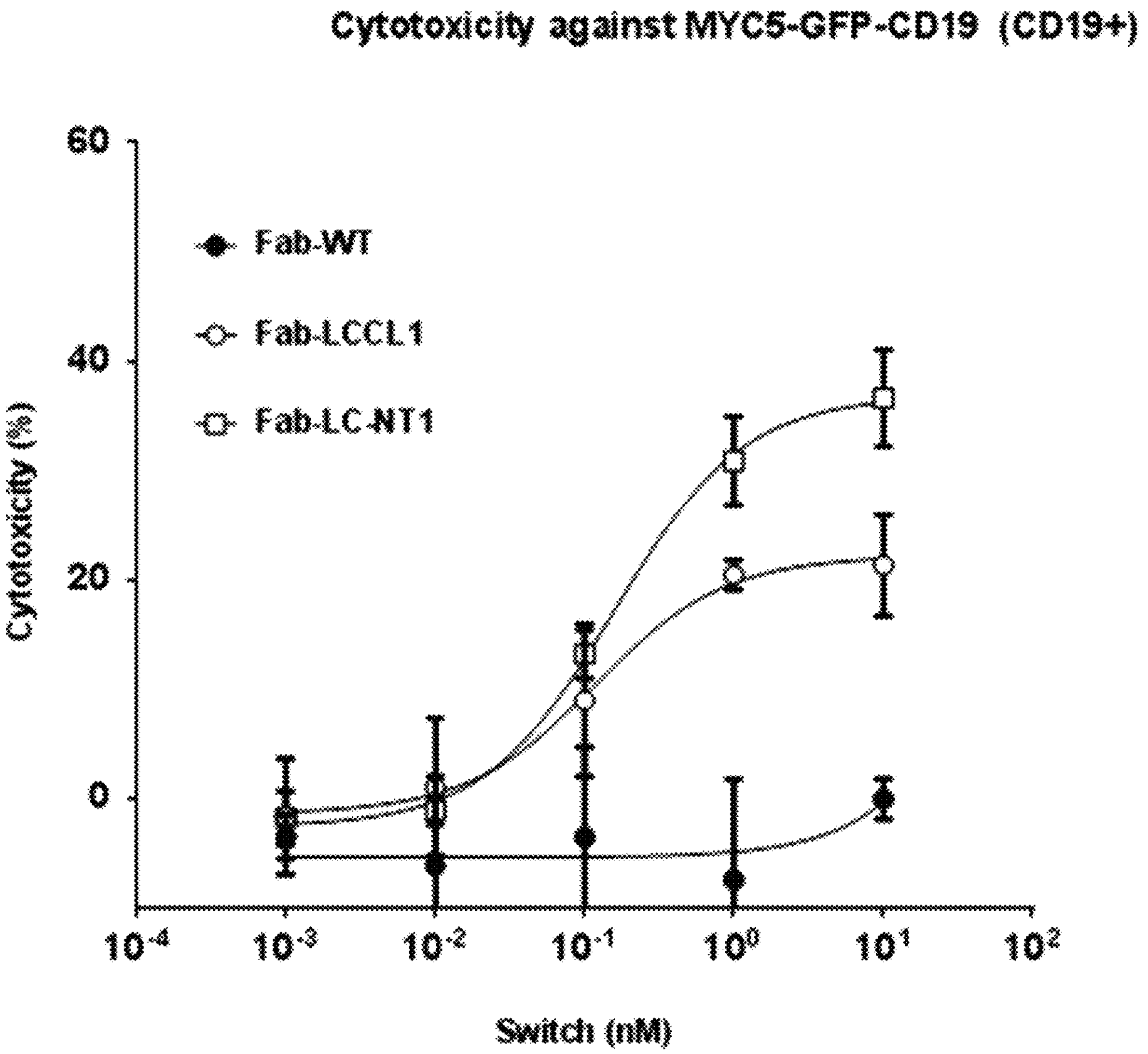
FIG. 35 shows murine surrogate anti-CD19 switch activity. Peptide based CAR-T cells are also efficacious in murine platform, using retrovirus in murine B6 cells and a CD28 costimulatory domain with hamster anti-mouse CD19 antibody and murine Myc5-CD19 target cells. Potency increases as graft moves towards N-terminus. (Fusion/grafting locations: A=LCNT1 (light chain N terminus version 1) and B=CL1 (constant region light chain 1).
Figure 36A:
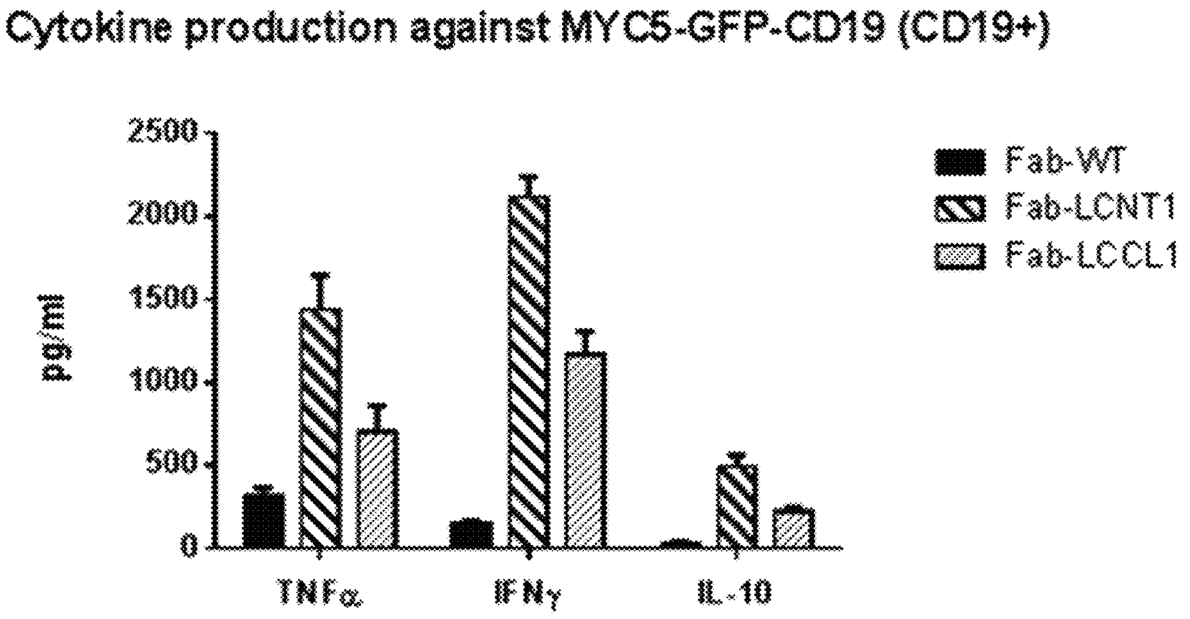
FIG. 36A-B shows cytokine production in a murine surrogate model by sCAR T-cells treated with switches.

To create the murine surrogate sCAR-T cell, we used a Moloney murine leukemia-based retroviral vector (MSGV, murine stem cell virus-based splice-gag vector) for transduction into murine splenocytes as previously described Kochenderfer, J. N., et al., Blood, 116(19): p. 3875-86 (2010), incorporated herein by reference in its entirety. The original murine construct, 1D3 CART19, was created as previously described, id, with the rat anti-mouse CD19 clone 1D3 scFv, murine CD28 hinge, transmembrane and cytoplasmic domain, and murine CD3 molecule where the first and third ITAMs (immunoreceptor tyrosine-based activation motif) were inactivated (referred to as CD3ζ(1-3)) (SEQ ID NO: 200). The sCAR construct was developed with the same design using the anti-GCN4 scFv in place of the 1D3 scFv (SEQ ID NO: 201). These switches were shown to be active against murine Myc5-CD19$^+$ target cells, in vitro, as demonstrated by LDH release cytotoxicity assay and cytokine responses (FIG. 35 and FIG. 36A). Potency increased as graft moved towards N-terminus as in human system.

This cell line is subsequently used to establish B cell lymphoma in wild type C57BL/6 mice. sCAR-T cells and switches are administered with dosing schedules based on xenograft studies. Of particular interest in this model is to compare Fab, and IgG based switches on the rate of Myc5-CD19 elimination and B cell ablation. As with xenografts studies, sCAR-T proliferation is monitored and immunophenotypic characterization is carried out ex vivo. The primary goals of this study are to demonstrate elimination of disease and repopulation of B cells on cessation of switch administration. Both the surrogate CART-19 and the surrogate sCAR-T cells eliminate disease, but only the switchable platform enables repopulation of B cells. Long-term persistence of sCAR-T cells after dosing has stopped is checked by re-dosing switch after a rest period and assessing B cell re-depletion. This is important to developing sCAR-T cells that can be reactivated to in the case of disease relapse. Other factors studied in this system are the effect of Tregs, macrophages, and myeloid cells on the switchable CAR-T cells; the ability of the switchable CAR-T cells to differentiate into memory subsets including effector memory, central memory, and stem cell memory; the natural ability for T cells to home to the lymph nodes, thymus, spleen or peripheral organs; and the effect of the switchable CAR-T cells on the immune system, including depletion of B cells.

Human signaling moieties included in CAR-T cells have been demonstrated to be function in murine T cells. To further explore the potency of sCAR-T cells in the surrogate system, additional CAR constructs containing human elements were created and transfected into and expressed by murine T cells.

An anti-GCN4 52SR4 sCAR construct was made using the 52SR4 scFv, human IgG4m hinge domain, murine CD8 transmembrane domain, murine 4-1BB costimulatory domain, and a mutated murine CD3zeta (SEQ ID NO: 202). An anti-GCN4 52SR4 sCAR construct was made using the 52SR4 scFv, human IgG4m hinge domain, murine CD8 transmembrane domain, murine 4-1BB costimulatory domain, and a intact murine CD3zeta (SEQ ID NO: 203). An anti-GCN4 52SR4 sCAR construct was made using the 52SR4 scFv, murine CD8 hinge domain, murine CD8 transmembrane domain, murine 4-1BB costimulatory domain, and a mutated murine CD3zeta (SEQ ID NO: 204). An anti-GCN4 52SR4 sCAR construct was made using the 52SR4 scFv, murine CD8 hinge domain, murine CD8 transmembrane domain, murine 4-1BB costimulatory domain, and a intact murine CD3zeta (SEQ ID NO: 205). An anti-CD19 1D3 sCAR construct was made using the 52SR4 scFv, human IgG4m hinge domain, murine CD8 transmembrane domain, murine 4-1BB costimulatory domain, and a mutated murine CD3zeta (SEQ ID NO: 206). An anti-CD19 1D3 sCAR construct was made using the 52SR4 scFv, human IgG4m hinge domain, murine CD8 transmembrane domain, murine 4-1BB costimulatory domain, and a intact murine CD3zeta (SEQ ID NO: 207). An anti-CD19 1D3 sCAR construct was made using the 52SR4 scFv, murine CD8 hinge domain, murine CD8 transmembrane domain, murine 4-1BB costimulatory domain, and a mutated murine CD3zeta (SEQ ID NO: 208). An anti-CD19 1D3 sCAR construct was made using the 52SR4 scFv, murine CD8 hinge domain, murine CD8 transmembrane domain, murine 4-1BB costimulatory domain, and a intact murine CD3zeta (SEQ ID NO: 209). An anti-GCN4 52SR4 sCAR construct was made using the 52SR4 scFv, human IgG4m hinge domain, murine CD28 transmembrane domain, murine CD28 costimulatory domain, and a mutated murine CD3zeta (SEQ ID NO: 210). An anti-GCN4 52SR4 sCAR construct was made using the 52SR4 scFv in the opposite orientation (HC then LC) than (SEQ ID NO: 210), human IgG4m hinge domain, murine CD28 transmembrane domain, murine CD28 costimulatory domain, and a mutated murine CD3zeta (SEQ ID NO: 211). An anti-GCN4 52SR4 sCAR construct was made using the 52SR4 scFv, human IgG4m hinge domain, human CD8 transmembrane domain, human 4-1BB costimulatory domain, and a human CD3zeta (SEQ ID NO: 212). An anti-CD19 1D3 sCAR construct was made using the 52SR4 scFv, human IgG4m hinge domain, human CD8 transmembrane domain, human 4-1BB costimulatory domain, and a human CD3zeta (SEQ ID NO: 213).

Example 19. Anti-CD19 sCAR-T In Vitro Model with Mouse Surrogate CARTs

Activated mouse splenocytes were transduced with gammaretrovirus containing GCN4-mCAR construct (SEQ ID NO: 203). FIG. 35 and FIG. 36 show in vitro cytotoxicity of mouse surrogate CARTs. FIG. 35 shows cytotoxicity of transduced mouse GCN4-mCAR T cells against CD19+ tumor line MYC5-GFP-CD19 with various 1D3-derived switches with wild-type heavy and light chains (Fab-LCWT) or bearing GCN4-peptide insertions in the light chain N-terminus (Fab-LCNT1) or in the constant region of the light chain (Fab-LCCL1). FIG. 36 shows cytokines released during the cytotoxicity co-culture of the transduced mouse GCN4-mCAR T cells.

The in vitro model is ideal for evaluating CAR-T cell activity that would otherwise be greatly affected by other immune cells in vivo and therefore cannot be accurately assessed in the xenograft models.

To further explore the geometry of the ternary complex formed by the switch between the effector and target cells, anti-CD19 switches were created with shorter linkers between the FAB and GCN4 peptide. As the N-terminal grafted switches provided the best activity in vitro, it may be possible to further increase this by shortening the linker. For these switches the GGGGS linker (SEQ ID NO: 40) was replaced with a GG linker. A switch was created containing a peptide and short linker on the N terminus (SEQ ID NO: 215) and on the heavy terminus (SEQ ID NO: 216) of the anti-CD19 1D3 switch. LCNT (SEQ ID NOS: 215, 54), HCNT (SEQ ID NOS: 216, 53) and NTBV (SEQ ID NOS: 215, 216) constructs were made.

Figure 36B:
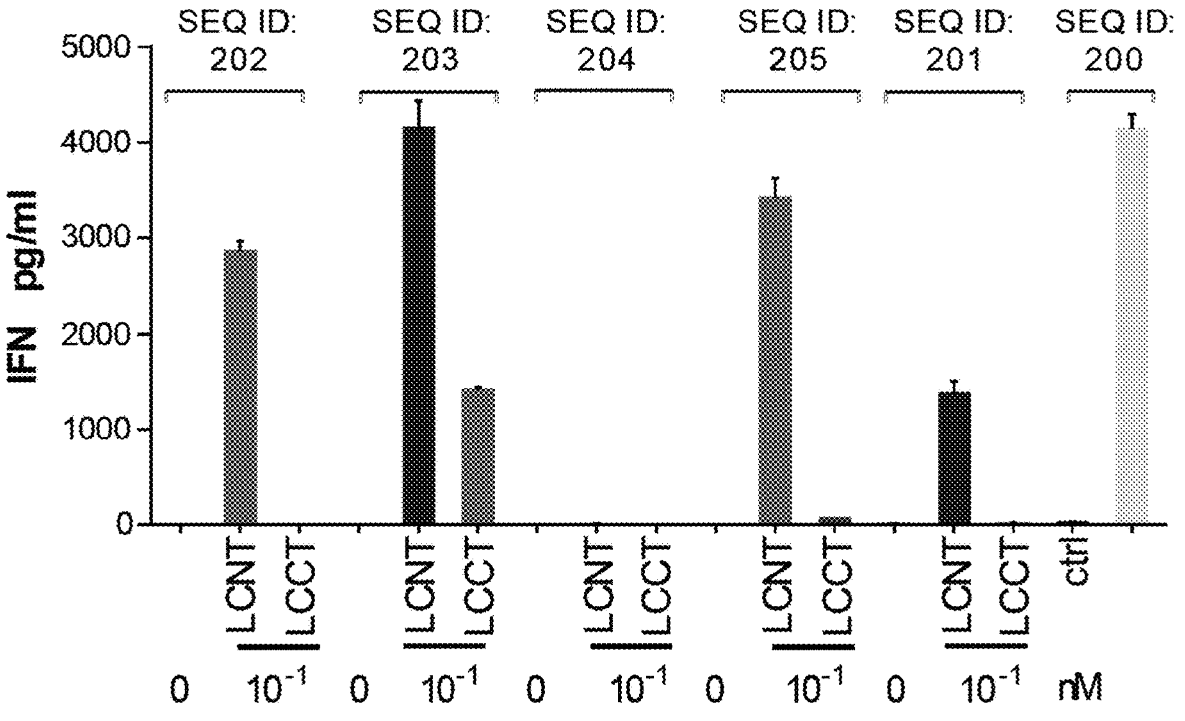

FIG. 36B shows activity data for several of these constructs, as assessed by an in vitro cytotoxicity assay, in which IFNγ production (measured by CBA assay) was the read out.

Cytokine levels produced were higher in the presence of LCNT (SEQ ID NOS: 54, 58) switch than in the presence of LCCT (SEQ ID NOS: 54, 57) switch. Cytokine levels were also higher for SEQ ID NO: 202, SEQ ID NO: 203 and SEQ ID NO: 205 in comparison with SEQ ID NO: 201. SEQ ID NO: 202 CAR-T cells secrete the same amount of IFNγ as SEQ ID NO: 200 cells. The same trends were also observed for IL-2 and TNFα cytokine production (data not shown).

General Method for Cytotoxicity Assay with Murine T Cells

Cytotoxicity assays were performed in R5 medium (RPMI 1640 (Gibco, #A10491)+10% FBS+1% Penicillin-streptomycin, 0.1% 2-Mercaptoethanol) at a 10 effectors:1 target ratio. LCNT switch dilutions are prepared in a standard 96-well plate in R5. Switches are diluted to 500 nM in 200 μl R5 then filter sterilized. Serial 10-fold dilutions are made transferring 10 ul of switch into 90 μl R5. Target cells (MYC5-GFP-CD19, mCD19+) are collected and re-suspended in R5 at a density of $4\times10^5$ cells/ml. Target cells are then added to all wells of a U-bottom 96-well plate except medium-only and CAR-T cells-only controls. CAR-T cells are collected and re-suspended in R5 at a density of $4\times10^6$ cells/ml. CAR-T cells (effector cells) (50 μl) are added to all wells except medium-only control, maximum kill, and spontaneous kill wells. Switch dilutions (2 μl) are added to cytotoxicity wells. Plate is incubated at 37° C., 5% $CO_2$ for 6h. LDH release assays are performed using the Promega CytoTox 96® Non-Radioactive Cytotoxicity Assay (Promega). Forty five minutes before the end of incubation, 10× lysis solution is added to maximum kill wells containing only target cells (1× final). Wells are mixed well to lyse cells and plate is returned to the incubator for 45 minutes. After 45 minutes incubation, plate is centrifuged at 400×g for 5 minutes to pellet cells. Supernatants (30 μl) are transferred to a 96-flat bottom well plate and 30 μl of CytoTox 96® Reagent is added and plate is incubated in the dark at room temperature for 30 minutes. Stop Solution (30 μl) is added and absorbance is measured at 490 nm on a plate reader. Cytotoxicity is calculated using the following formula: 100×((Sample OD490−medium OD490−target cells only OD490−effector cells only OD490)/(maximum kill OD490−spontaneous kill OD490)).

Example 20. Cloning, Expression and Purification of Anti-BCMA-IgG-LCC1

Cloning: Mammalian expression vector of CD19 IgG heavy chain was generated by in-frame ligation of amplified anti-BCMA IgG heavy chain (VH and CH1) to pFuse-hIgG1-Fc backbone vector (InvivoGen, CA). A gene encoding antibody BCMA light chain was amplified and cloned into the pFuse vector without hIgG1 Fc fragment. A gene encoding GCN4 (NYHLENEVARLKKL=SEQ ID NO: 3) with GGGGS (SEQ ID NO: 40) linker at both ends was synthesized as oligonucleotides. Subsequently, anti-BCMA-IgG LCC1 fusion proteins were created by grafting GCN4 with linker sequences at both ends into the CL region of the anti-BCMA light chain. The resulting mammalian expression vectors were confirmed by DNA sequencing.

Expression and Purification: anti-BCMA-IgG LCC1 was expressed through transient transfection of FreeStyle HEK 293 cells with expression vectors of BCMA-IgG heavy chain and GCN4-BCMA LCC1 light chain, according to the manufacturer's protocol. Briefly, 28 mL FreeStyle HEK 293 cells containing $3\times10^7$ cells were seeded in a 125 mL shaking flask. 15 μg light chain plasmid and 15 μg heavy chain plasmid diluted in 1 mL Opti-MEM medium were added in 1 mL Opti-MEM containing 60 μL 293fectin (Invitrogen, Inc.). After the plasmids were incubated with 293fectin for 30 min, the lipoplex mixture was added to the cell suspension. Cells were then shaken at 125 rpm in a 5% $CO_2$ environment at 37° C. Culture medium containing secreted proteins was harvested at 48 and 96 hours after transfection. anti-BCMA-IgG LCC1 was purified by Protein G chromatography (Thermo Fisher Scientific, IL).

Figure 37:
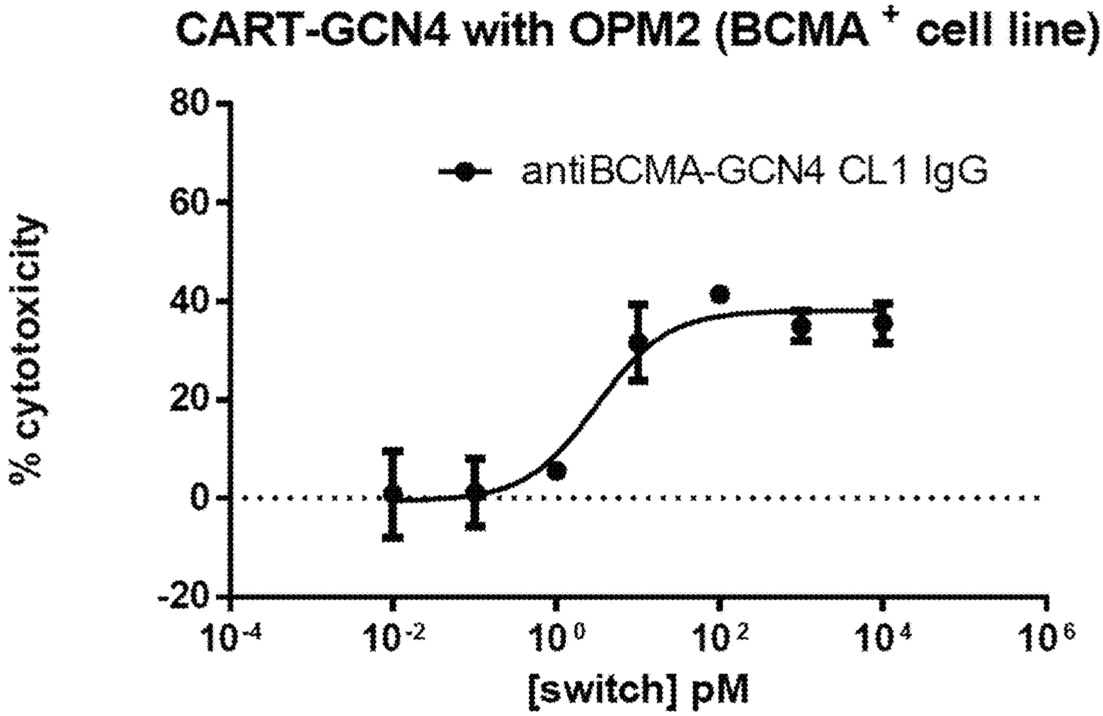
FIG. 37 shows cytotoxicity of an anti-GCN4 CAR T-cell and CAR T-cell switch (anti-BCMA antibody-GCN4 peptide grafted into the light chain constant domain) against BCMA-positive cells (OPM2).

Example 21. Cytotoxicity of Anti-BCMA-IgG LCC1 CAR-EC Switch with GCN4 Grafted to the Light Chain of an Anti-BCMA Antibody or Antibody Fragment The cytotoxic activity of the anti-BCMA-IgG LCC1 CAR-EC switch was assessed with the human PBMCs transduced with LV-EF1a-GCN4(52SR4) to create CAR-T-GCN4 at E:T ratios of 10:1 and 24 hour incubation. Transduction efficiency of PBMCs was approximately 50%. Activities were assessed against OPM2 ($BCMA^+$), by quantifying lactate dehydrogenase due to cytolysis of target cells (FIG. 37, Table 24).

TABLE 24

Cytotoxicity of anti-BCMA-IgG LCC1 CAR-EC switch and anti-GCN4 CAR-T cell

| anti-BCMA-IgG LCC1 switch concentration [pM] | % cytotoxicity |
|---|---|
| 10000.000 | 35.52758 |
| 1000.000 | 35.06853 |
| 100.000 | 41.44725 |
| 10.000 | 31.59707 |
| 1.000 | 5.575391 |
| 0.100 | 1.13803 |
| 0.010 | 0.812881 |

Example 22. Anti-CLL1 Switches

Despite current therapeutic advances, Acute Myeloid Leukemia (AML) survival rate after 5 years is below 50%, being the second most common leukemia in children. AML is a highly immune-phenotypically heterogeneous disease. Relapse is frequent in AML patients. A common event in relapsed disease, as it happens for B-cell leukemia and CD19, is the down regulation or loss of antigen expression. Therefore, conventional CAR-T treatment of AML patients will be highly susceptible to immune scape of different immune-phenotypical variants.

The switchable CAR-T (sCAR-T) approach not only will be able to overcome the immune escaping process targeting multiple antigens, but also a personalized medicine can be performed, selectively targeting specific antigens according to the immune-phenotype of each AML patient in a dose-controllable format and reducing therefore the side effects linked to each off-tumor on-target antigen which will likely cause severe chronic myelosuppression and different types of cytopenia in patients. (i.e. CD33 or CD123 are expressed in myeloid and hematopoietic precursors).

Initially, we targeted CLL1 antigen for AML, with in vitro and in vivo efficacy data supporting CLL1 as a valid target for AML. To expand the antigenic targets for AML, CD33 (hP67.6 antibody) and CD123 (26292 and 32716 antibodies) will be included in our switchable CAR-T platform.

Figure 38A:
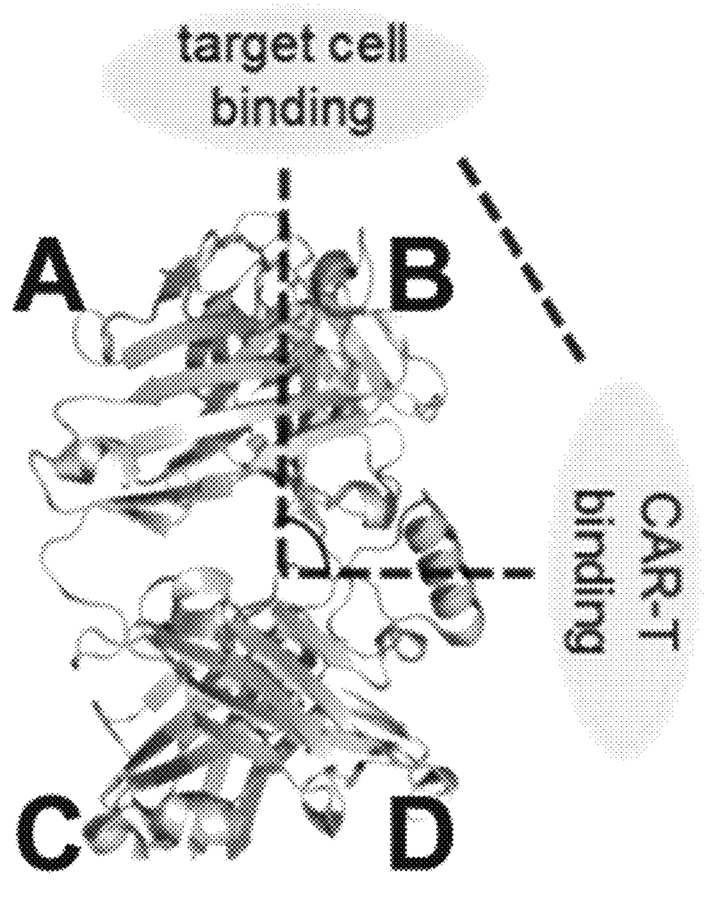
FIG. 38A-D shows an anti-CLL1 switch and its activity.
Figure 38B:
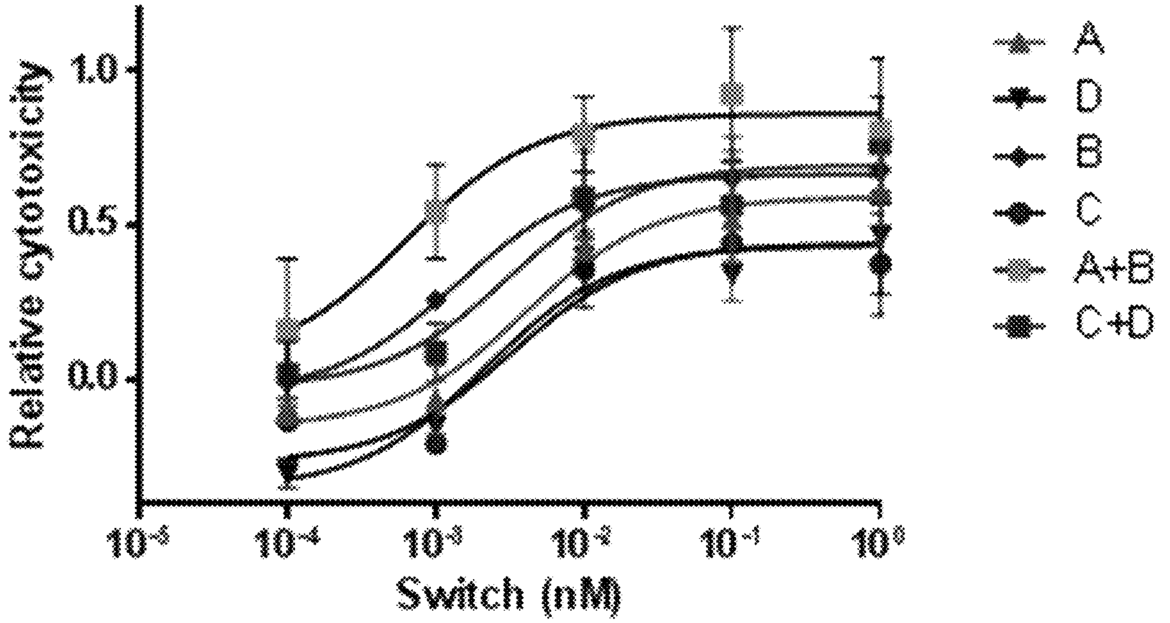
Figure 38C:
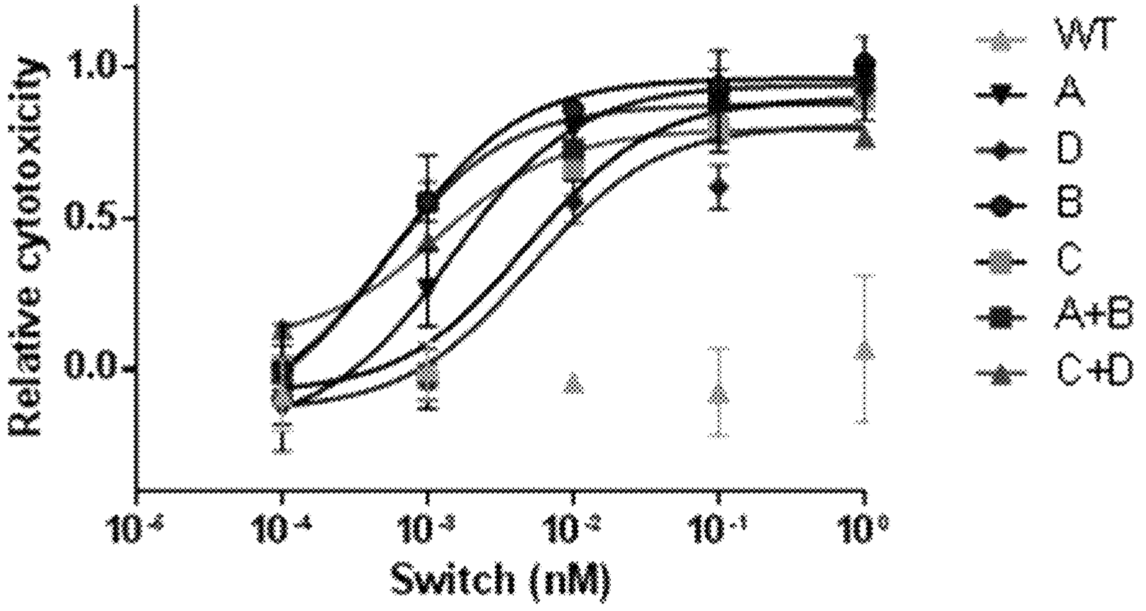

By utilizing the "universal" anti-peptide sCART cell, multiple switches targeting multiple cancer associated antigens can be rapidly developed. An example of this is the generation of peptide engrafted switches against the AML associated antigen CLL1. A series of 6 plasmids were designed into which commercially synthesized gene-blocks encoding scFv sequences were inserted by gibson phase assembly to generate: Light chain wild type, light chain N-terminal, light chain C-terminal, heavy chain wild type, heavy chain N-terminal and heavy chain C-terminal plasmid constructs. These constructs were expressed in HEK cells to generate: light chain N-terminal, light chain C-terminal, heavy chain N-terminal, heavy chain C-terminal and N- or C-terminal bivalent switches. The 6 anti-CLL1 switches were then used in cytotoxicity assays with the long, short and short-dimeric sCART cells to give a spread of data that could be used to predict the optimal immunological synapse required to kill U937 ($CLL1^+$) cells (FIG. 38A-C, Tables 25 and 26).

TABLE 25

| Potency on CLL1+ cells, Long Hinge CAR | | |
|---|---|---|
| Switch | Valency | $EC_{50}$ (nM) |
| C | Mono | 0.0033 |
| D | Mono | 0.0022 |
| C + D | Bi | 0.0031 |
| A | Mono | 0.0041 |
| B | Mono | 0.0013 |
| A + B | Bi | 0.0006 |

TABLE 26

| Potency on CLL1+ cells, Short Hinge CAR | | |
|---|---|---|
| Switch | Valency | $EC_{50}$ (nM) |
| C | Mono | 0.0049 |
| D | Mono | 0.0051 |
| C + D | Bi | 0.0012 |
| A | Mono | 0.0015 |
| B | Mono | 0.0006 |
| A + B | Bi | 0.0005 |

Example 23. Anti-CLL1 sCAR-T Cell and Switch Structural Activity Relationship (SAR)

Figure 38D:
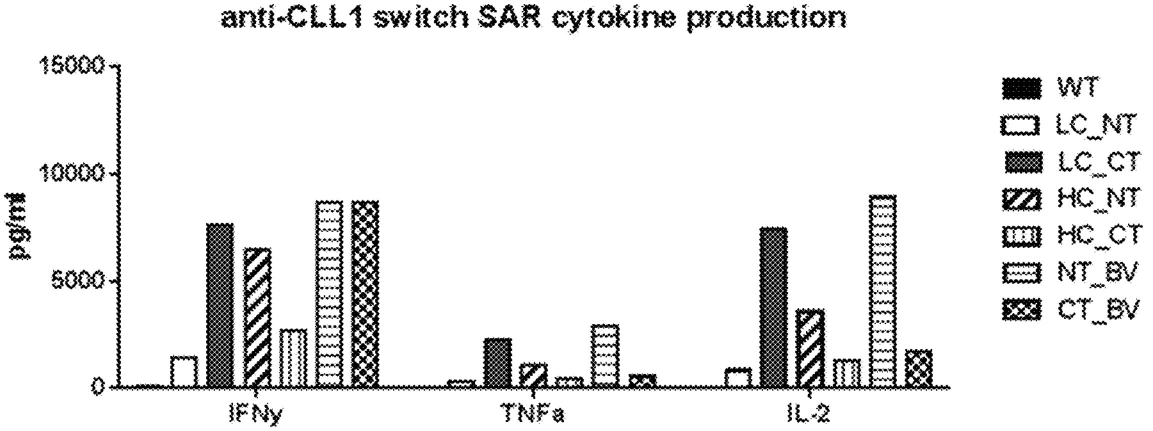

Another example (see Example 7) of switch SAR was shown with the anti-CLL1 switch derived from the anti-CLL1 antibody clone. In this example 6 generic pFuze plasmids which were wild type (without peptide) or had the GCN4 peptide positioned at the N-terminal or C-terminal of the heavy and light chains were developed. Using synthesized gene blocks containing the anti-CLL1 Fab sequence and the Gibson assembly method of cloning 6 switch constructs that could be expressed in mammalian cells to produce 7 different switches were rapidly generated: wild type, light chain N-terminal (LCNT), light chain C-terminal (LCCT), heavy chain N-terminal (HCNT), heavy chain C-terminal (HCCT), N-terminal bivalent (LCNT & HCNT; NTBv) and C-terminal bivalent (LCCT & HCCT; NTBv). Using these switches in combination with the three different CAR constructs (long, short and short dimeric) in cytotoxicity assays with the $CLL1^+$U937 cell line it was determined that N-terminal bivalent switches with the short-dimeric CAR was the most optimal for immunological synapse for the in vitro killing of U937 cells (FIG. 38D). This process is repeated for other target antigens and is one of the major advantages of the switchable system.

Example 24. Treatment of CLL1+ Solid AML Tumors with Switchable CAR-T Cells

Figure 38E:
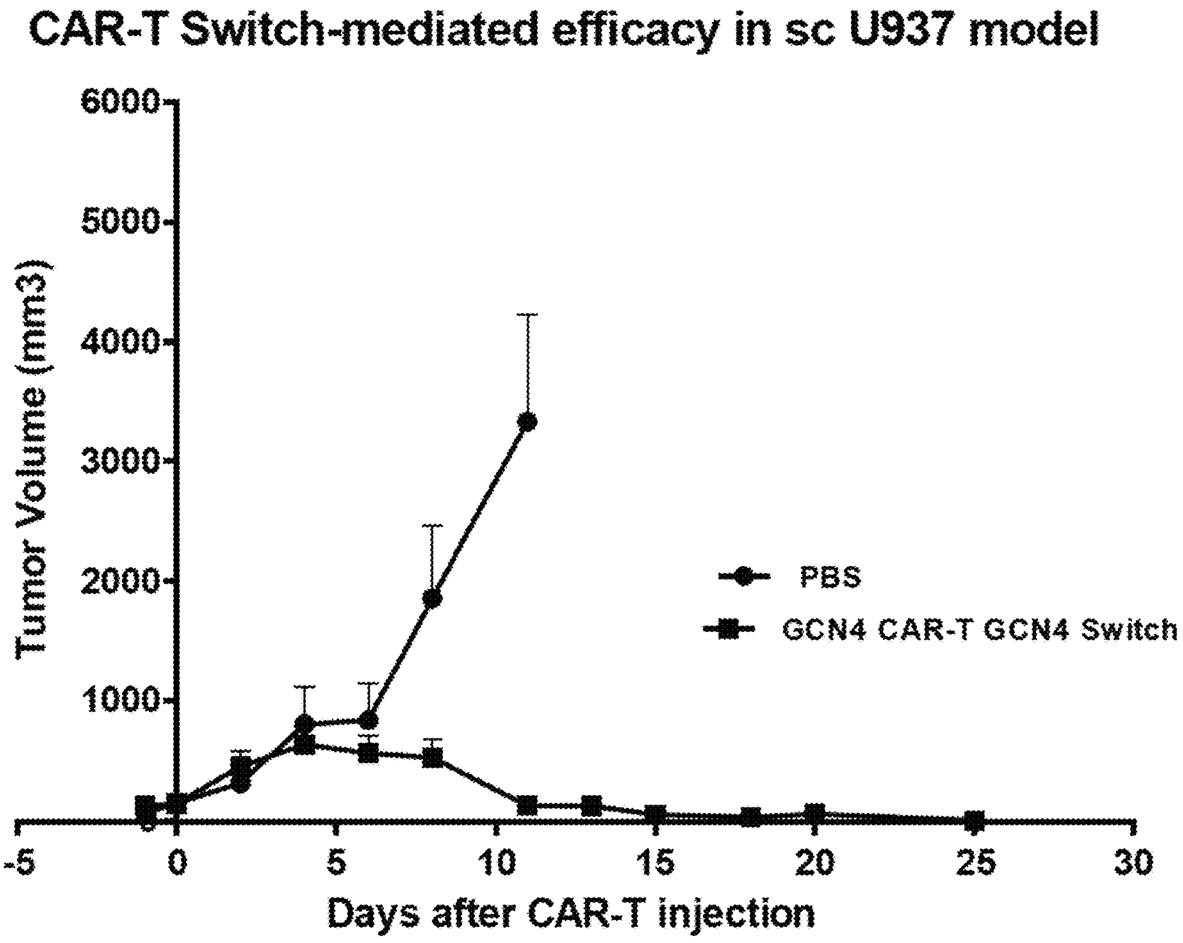
FIG. 38E shows in vivo cytotoxicity of sCAR-T cells against CLL1+U937 cells with the NTBV anti-CLL1 Fab switch in a sub-cutaneous AML model.

To test whether an anti-CLL1 switch could treat tumors, in vivo, 6-8-week old female NSG mice were injected with $2\times10^6$ U937 (CLL1+) AML cells subcutaneously in the right flank. Seven days after tumor implantation, mice received $30\times10^6$ sCAR-T cells or PBS via intra venous injection. Mice were dosed intravenously with PBS or anti-CLL1 NTBV (SEQ ID: 102 & 103) 1 mg/Kg q.d. from day 0-10. Tumors were measured twice weekly using calipers. Tumor volume was calculated based on width×length×height. FIG. 38E shows in vivo cytotoxicity of sCAR-T cells against CLL1+U937 cells with the NTBV anti-CLL1 Fab switch, as determined by tumor mean size in ($mm^3$), and Table X shows the raw data from FIG. 38E.

Example 25. Treatment of CD33+ Solid AML Tumors with Switchable CAR-T Cells

Rational:

To target $CD33^+$ tumor cells, GCN4 engrafted switches were generated using the VL and VH sequences from Mylotarg (SEQ ID: 231 & 232), a cytotoxic antibiotic linked to a recombinant monoclonal antibody directed against the CD33 antigen used in clinic; described in Vol. 7, 1490-1496, June 2001, Clinical Cancer Research and in U.S. Pat. No. 5,773,001; each of which is incorporated herein by reference in its entirety. This antibody clone has also been validated in preclinical in vitro and in vivo assays for conventional CAR-T generation described in Kenderian, et al; Leukemia; August; 29(8):1637-47 (2015), incorporated herein by reference in its entirety.

Experiment:

The cloning, expression, and purification of GCN4 peptide-engrafted switches in hP67.6 was performed as described in Example 3 for CD19 switches. Extra engraftment positions were used in order to optimize the anti-CD33 hP67.6 clone. For this purpose, flexible or rigid linkers composed by a linker listed in SEQ ID NOS: 45-50 and $(GGGGS)_n$, $(GGGS)_n$, $(GGS)_n$, $(G_mS)_n$, and $(X_mS)n$ (wherein n is at least 1, m is at least 1, and X is any amino acid) were used to engraft GCN4 peptide (SEQ ID NO: 3) at N-terminal or C-terminal or in internal loops of the Anti-CD33 hP67.6 clone light or heavy chain. (SEQ Light Chain of anti-CD33 hP67.6 Fab, Heavy Chain of anti-CD33 hP67.6 Fab). Several switch designs were generated for both clones with varied peptide engraftment positions. In one instance the peptide was engrafted on the N-terminus of the light chain of anti-CD33 hP67.6 using 1 of linker (SEQ ID NO: 40) to make (SEQ ID NO: 217). In one instance the peptide was engrafted on the N-terminus of the light chain of anti-CD33 hP67.6 using 2 of linker (SEQ ID NO: 40) to make (SEQ ID NO: 218). In one instance the peptide was engrafted on the N-terminus of the light chain of anti-CD33 hP67.6 using 3 of linker (SEQ ID NO: 40) to make (SEQ ID NO: 219). In one instance the peptide was engrafted on the N-terminus of the heavy chain of anti-CD33 hP67.6 using 1 of linker (SEQ ID NO: 45) to make (SEQ ID NO: 220). In one instance the peptide was engrafted on the N-terminus of the heavy chain of anti-CD33 hP67.6 using 2 of linker (SEQ ID NO: 47) to make (SEQ ID NO: 221). In one instance the peptide was engrafted on the C-terminus of the light chain of anti-CD33 hP67.6 using 1 of linker (SEQ ID NO: 40) to make (SEQ ID NO: 222). In one instance the peptide was engrafted on the C-terminus of the light chain of anti-CD33 hP67.6 using 2 of linker (SEQ ID NO: 40) to make (SEQ ID NO: 223). In one instance the peptide was engrafted on the C-terminus of the light chain of anti-CD33 hP67.6 using 3 of linker (SEQ ID NO: 40) to make (SEQ ID NO: 224). In one instance the peptide was engrafted on the C-terminus of the heavy chain of anti-CD33 hP67.6 using 1 of linker (SEQ ID NO: 40) to make (SEQ ID NO: 225). In one instance the peptide was engrafted on the C-terminus of the heavy chain of anti-CD33 hP67.6 using 2 of linker (SEQ ID NO: 40) to make (SEQ ID NO: 226). In one instance the peptide was engrafted on the C-terminus of the heavy chain of anti-CD33 hP67.6 using 3 of linker (SEQ ID NO: 40) to make (SEQ ID NO: 227). In one instance the peptide was engrafted in the CH1 loop of the heavy chain of anti-CD33 hP67.6 with no linker (SEQ ID NO: 228). In one instance the peptide was engrafted in the CH1 loop of the heavy chain of anti-CD33 hP67.6 with 1 linker (SEQ ID NO: 40) on either side of the peptide to make (SEQ ID NO: 229), in this construct the GCN4 peptide (SEQ ID NO: 3) was engrafted with linkers at both sites replacing S70 and G71 of the heavy chain. In one instance the peptide was engrafted in the CH1 loop of the light chain of anti-CD33 hP67.6 with 1 linker (SEQ ID NO: 40) on either side of the peptide to make (SEQ ID NO: 230). Any of these constructs could be used to express mono-valent or bivalent switches by combining an engrafted chain with a corresponding WT 'ungrafted' chain. See FIG. 38F for gel images of these switches and Table 27 for high resolution anti-CD33 (clone hP67.6) Fab switch masses obtained on an Agilent Qadruple Time-of-Flight (QTOF) mass spectrometer attached to an Agilent liquid chromatography stack. Masses were deconvoluted from charge envelopes using Agilent Qualitative Analysis software with Bioconfirm plugin. In general accuracy was ±2 Da.

TABLE 27

QTOF analysis of the anti-CD33 (clone hP67.6) Fab switches in FIG. 16F.

| Protein | Expected Mass | Observed Mass | ppm | Da |
|---|---|---|---|---|
| 1 | 47188.7 | 47189.5 | −16.9532 | 0.8 |
| 2 | 50179.15 | 50180.72 | −31.2879 | 1.57 |
| 3 | 49212.96 | 49213.93 | −19.7102 | 0.97 |
| 4 | 49212.96 | 49214.49 | −31.0894 | 1.53 |
| 5 | 49212.96 | 49213.41 | −9.14393 | 0.45 |
| 6 | 52203.41 | 52205.82 | −46.1656 | 2.41 |
| 7 | 51237.22 | 51237.65 | −8.39234 | 0.43 |
| 8 | 49384.12 | 49385.37 | −25.3118 | 1.25 |
| 9 | 49528.25 | 49529.32 | −21.6038 | 1.07 |
| 10 | 49843.53 | 49844.71 | −23.6741 | 1.18 |
| 11 | 50380.32 | 50382.36 | −40.492 | 2.04 |
| 12 | 49400.08 | 49401.3 | −24.6963 | 1.22 |
| 13 | 49528.25 | 49529.55 | −26.2476 | 1.3 |
| 14 | 49843.54 | 49844.76 | −24.4766 | 1.22 |
| 15 | 49528.25 | 49530.25 | −40.381 | 2 |
| 16 | 49843.54 | 49845.8 | −45.3419 | 2.26 |
| 17 | 47188.7 | 47190.64 | −41.1115 | 1.94 |
| 18 | 50792.7 | 50794.7 | −39.3757 | 2 |
| 19 | 51595.5 | X | | |
| 20 | 51867.8 | 51869.4 | −30.8477 | 1.6 |
| 21 | 52498.37 | 52499.8 | −27.2389 | 1.43 |
| 22 | 52719.87 | 52723.39 | −66.768 | 3.52 |
| 23 | 53035.16 | 53038.68 | −66.3711 | 3.52 |

Monovalent and bivalent combinations of these switches were expressed and tested in cytotoxicity assays at a dose titration within the range of 0.4 nM to 0.0001 nM. Results of this experiment are shown in FIG. 38G and Table 28. Additionally, FIG. 38H and Table 29 shows measurement of indicated cytokines in supernatant from each sCAR-T/switch combination in cytotoxicity assay in MOLM14 cell line using BD Cytometric Bead Array (CBA) Human Th1/Th2 II Kit according to manufacturer's protocol. Data shown are an average of duplicate samples, and error bars represent SD. Only the NT switches plus the BvCT and By CH1CL1 as references are depicted. cytokine secretion was measured.

In terms of EC50, maximum killing, and cytokine release, N-terminal engraftment positions on both the light (LCNT; SEQ ID NO: 232 with SEQ ID NO: 217, 218 or 219) and heavy chains (HCNT; SEQ ID NO: 231 with SEQ ID NO: 220 or 221) showed the highest levels of cytotoxicity against CD33+ MOLM14 cells. Positions in the C-terminal or internal sites (ie. CL1, CH1 loop; SEQ ID NO: 222, 223, 224, 225, 226, 227, 228, 229 or 230) had lower cytotoxicity. Furthermore, all bivalent constructs had a low EC50 of cytotoxicity compared to their monovalent counterparts, indicating that bivalent switches may have enhanced activity, among them the NTBV (SEQ ID NOS: 217 & 220) HCNT (SEQ ID NOS: 231 & 220; N-terminal fusion to the heavy chain using rigid linker design SEQ ID NO: 45) and [CD33 (hP67.6) LCNT (N-terminal fusion to the light chain using flexible linker GGGGS) SEQ ID NOS: 217 & 232] showed the best profile.

TABLE 28

Table of data presented in FIG. 38G.

| pM | HCNT | | LCNT | | NTBV | | HCCT | | LCCT | | CTBV | | HCC1 | |
|---|---|---|---|---|---|---|---|---|---|---|---|---|---|---|
| 400 | 69.4 | 70.2 | 59.5 | 60.9 | 69.3 | 69.5 | 44.2 | 46.3 | 48.3 | 49.7 | 56.9 | 58.3 | 47.5 | 46.7 |
| 80 | 65 | 64.4 | 66 | 66.5 | 69.7 | 69.2 | 44.3 | 42.9 | 49.4 | 48.3 | 51.4 | 49.4 | 57.3 | 55.6 |
| 16 | 47.8 | 45.5 | 58.7 | 59.2 | 55.4 | 57.1 | 20 | 13.4 | 26 | 26.3 | 48.2 | 51.5 | 40.2 | 40.2 |
| 3.2 | 10.3 | 8.3 | 36.9 | 35.9 | 23.6 | 28.4 | 0.6 | 1.3 | 1 | 2.9 | 17.2 | 16.4 | 7 | 4.4 |
| 0.64 | 1.5 | 0.5 | 5.9 | 4.6 | 0.9 | 0.8 | −0.3 | −0.2 | −0.1 | −0.3 | 2.6 | 1 | 0.5 | 0.5 |
| 0.1 | 0 | 0 | 0 | 0 | 0 | 0 | 0 | 0 | 0 | 0 | 0 | 0 | 0 | 0 |

| pM | HCCH1.2 | | HCCT2 | | HCCT3 | | HCNT2 | | LCC1 | | LCCT2 | | LCCT3 | |
|---|---|---|---|---|---|---|---|---|---|---|---|---|---|---|
| 400 | 50.6 | 50.8 | 44.3 | 43.7 | 45.1 | 43.8 | 69.2 | 64.7 | 62.5 | 62.7 | 46.2 | 45.3 | 46.4 | 47.4 |
| 80 | 58.9 | 60.9 | 52.6 | 49.5 | 49.8 | 46.9 | 64.1 | 66.6 | 65.8 | 66.1 | 54.9 | 54.2 | 53.3 | 54.6 |
| 16 | 49.9 | 51.3 | 30.3 | 29.7 | 28.5 | 26 | 51.5 | 50.5 | 50.8 | 52.5 | 40.9 | 40.8 | 44.4 | 44.5 |
| 3.2 | 24.8 | 23.6 | 2.3 | 2.7 | 2 | 2.1 | 19.9 | 16.7 | 16 | 15.5 | 4.5 | 5.3 | 11.9 | 8.4 |
| 0.64 | 3.1 | 0.9 | 0.2 | −0.1 | 0.5 | −0.6 | 0.7 | 0.9 | 1.6 | 0.1 | 0.8 | 0.3 | 1 | 0.6 |
| 0.1 | 0 | 0 | 0 | 0 | 0 | 0 | 0 | 0 | 0 | 0 | 0 | 0 | 0 | 0 |

TABLE 28-continued

Table of data presented in FIG. 38G.

| pM | LCNT2 | | LCNT3 | | C1BV | | CTBV1 | | CTBV3 | | NTBV2 | | NTBV3 | |
|---|---|---|---|---|---|---|---|---|---|---|---|---|---|---|
| 400 | 58.4 | 57.7 | 55.4 | 57.5 | 61.7 | 64.7 | 51.9 | 51.4 | 49.3 | 49.4 | 62.9 | 64.6 | 67.1 | 66 |
| 80 | 69 | 65.3 | 62.1 | 63.5 | 58.7 | 61.9 | 54.8 | 55.6 | 55.1 | 55.3 | 70.4 | 67.8 | 65.1 | 67.4 |
| 16 | 60.3 | 57.5 | 54.3 | 54 | 37.6 | 36.7 | 23.5 | 28.5 | 28.2 | 26.9 | 55.3 | 54 | 56.9 | 58.7 |
| 3.2 | 33.1 | 30.4 | 31.8 | 31.4 | 2.4 | 4.9 | 4 | 2.7 | 3.4 | 2.8 | 20.9 | 19.7 | 25.3 | 26.7 |
| 0.64 | 2.4 | 2.6 | 3.8 | 1.4 | −0.8 | 0.7 | −0.1 | 1.4 | −0.2 | 0.6 | 2 | 2.1 | 2.8 | 2.8 |
| 0.1 | 0 | 0 | 0 | 0 | 0 | 0 | 0 | 0 | 0 | 0 | 0 | 0 | 0 | 0 |

TABLE 29

Figure 38F:
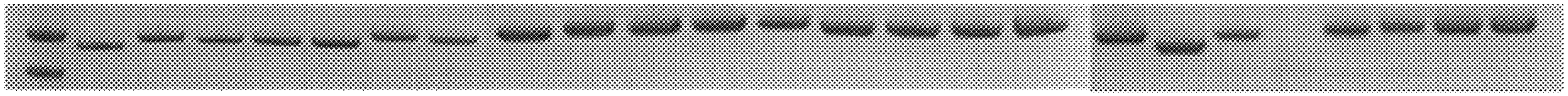
FIG. 38F shows SDS page analysis of multiple anti-CD33 (hP67.6) switches that were expressed.
Figure 38G:
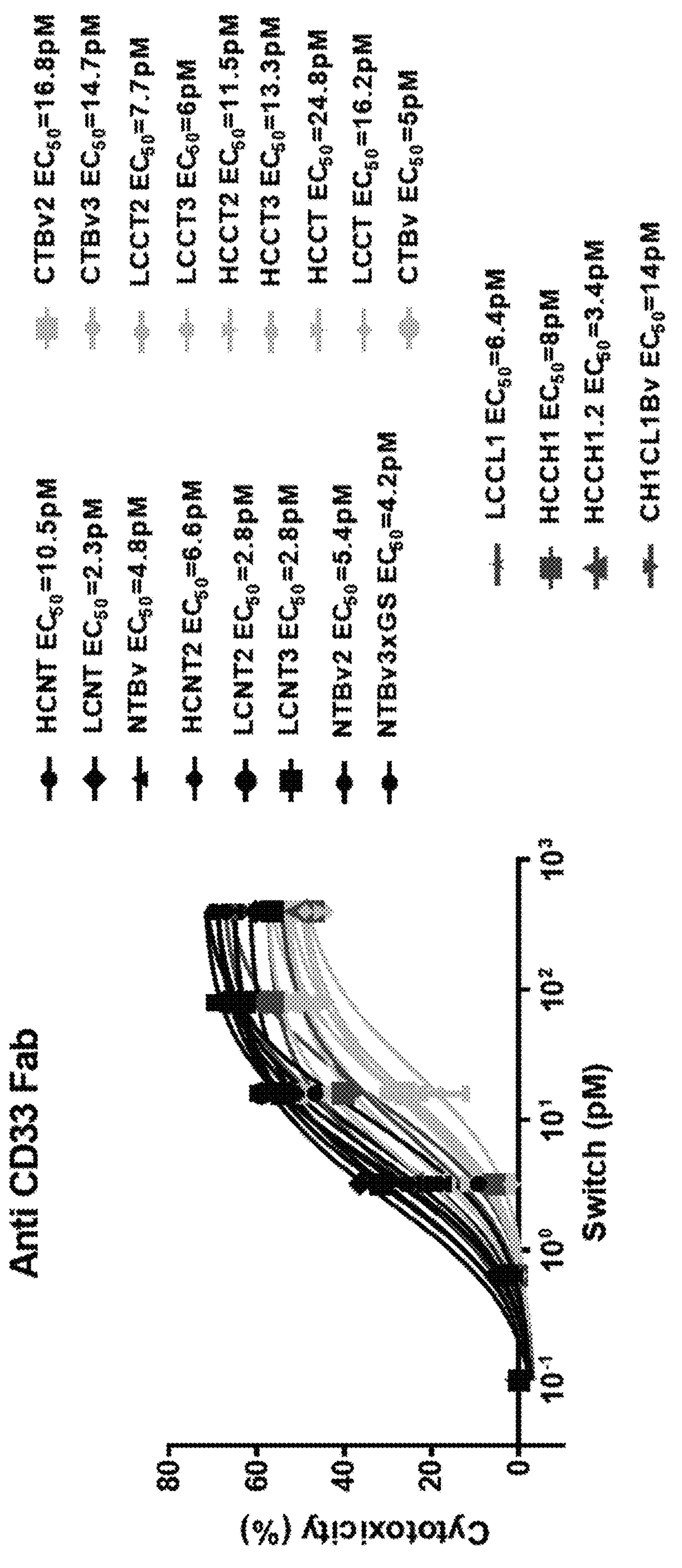
FIG. 38G shows cytotoxicity assay data for monovalent and bivalent combinations of various anti-CD33 (hP67.6) switches tested as a dose titration within the range of 0.4 nM to 0.0001 nM. in CD33+ MOLM14 cells.
Figure 38H:
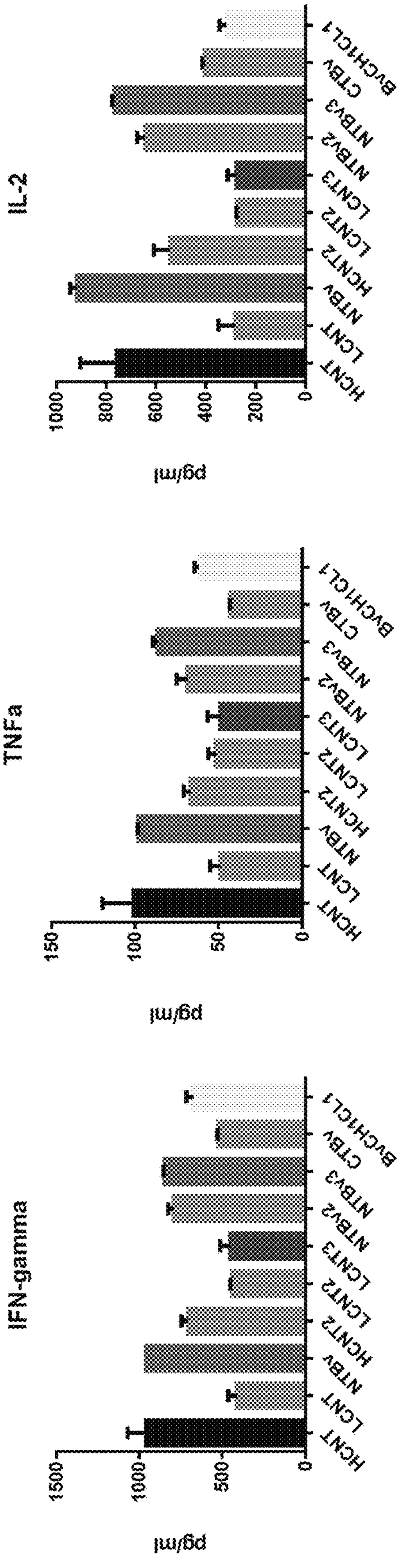
FIG. 38H shows measurement of indicated cytokines in supernatant from each sCAR-T/switch combination in cytotoxicity assay in MOLM14 cell lineby CBA. Data shown are an average of duplicate samples, and error bars represent SD. Only the NT switches plus the BvCT and By CH1CL1 as references are depicted.

Table of data presented in FIG. 38H.

| | HCNT | | LCNT | | NTBv | | CTBv | | HCNT2 | |
|---|---|---|---|---|---|---|---|---|---|---|
| IFNg | 1037.59 | 876.36 | 448.47 | 374.76 | 957.81 | 958.26 | 526.49 | 520.07 | 733.49 | 678.54 |
| TNFa | 114.13 | 87.74 | 53.4 | 44.84 | 98.48 | 97.95 | 43.06 | 42.54 | 69.7 | 63.85 |
| Il-2 | 861.13 | 653 | 328.62 | 234 | 936.57 | 898.28 | 410.48 | 397.66 | 589.59 | 495.39 |
| | LCNT2 | | LCNT3 | | BvCH1CL1 | | NTBv2 | | NTBv3 | |
| IFNg | 448.43 | 436.29 | 494.2 | 406.99 | 703.22 | 641.9 | 817.31 | 769.19 | 852.49 | 843.46 |
| TNFa | 48.69 | 54.82 | 54.25 | 43.69 | 63.66 | 60.22 | 73.22 | 64.02 | 84.81 | 88.51 |
| Il-2 | 273.1 | 276.22 | 301.05 | 250.79 | 335.69 | 296.06 | 666.7 | 621.66 | 760.22 | 774.07 |

Example 26. Treatment of $CD123^+$ Solid AML Tumors with Switchable CAR-T Cells CD123 has been described previously as a marker for AML (Jordan et al. Leukemia (2000) 14, 1777-1784 and Testa et al. Biomarker Research (2014), 2:4). Moreover, recently single chain Fragment Variable (scFv) targeting CD123 have been used in the design of conventional CAR-T cells. (Gill et al. Blood 2014) volume 123, number 15, and WO2014130635). Two anti-CD123 Fab clones were used to design CAR-T: Clone 32716 (SEQ ID NOS: 233 & 234) and Clone 26292 (SEQ ID NOS: 235 & 236). Anti CD123 32716 (SEQ ID NOS: 233 & 234) clone had increased cytokine release compared to Anti-C123 clone 26292 (SEQ ID NOS: 235 & 236) and showed in vivo efficacy in previous reports. However, complete myeloablation was observed due to the expression of CD123 in myeloid and hematopoietic precursors what makes CD123 conventional CAR-T highly toxic for clinic use.

As suggested previously, our sCAR-T platform can overcome this problem due to our ability of switch titration, targeting and activation of our switchable CAR-Ts through different switch dosing regimen. Several switch designs were generated for both clones (as described for CD19 switches) with varied peptide engraftment positions.

Figure 38I:
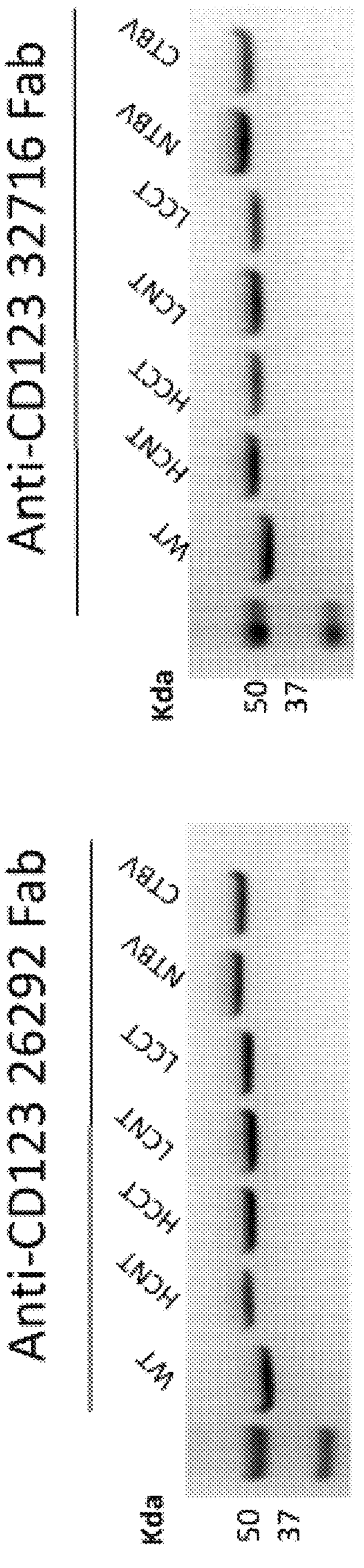
FIG. 38I shows SDS gel images of anti-CD123 Fab-GCN4 (clones 26292 and 32716) in non-reducing conditions.

In one instance the peptide was engrafted on the N-terminus of the light chain of anti-CD123 26292 using 1 of linker (SEQ ID NO: 40) to make (SEQ ID NO: 237). In one instance the peptide was engrafted on the N-terminus of the light chain of anti-CD123 32716 using 1 of linker (SEQ ID NO: 40) to make (SEQ ID NO: 238). In one instance the peptide was engrafted on the N-terminus of the light chain of anti-CD123 32716 using 3 of linker (SEQ ID NO: 40) to make (SEQ ID NO: 239). In one instance the peptide was engrafted on the N-terminus of the light chain of anti-CD123 32716 using 2 of linker (SEQ ID NO: 40) to make (SEQ ID NO: 240). In one instance the peptide was engrafted on the N-terminus of the heavy chain of anti-CD123 26292 using 1 of linker (SEQ ID NO: 45) to make (SEQ ID NO: 241). In one instance the peptide was engrafted on the N-terminus of the heavy chain of anti-CD123 32716 using 1 of linker (SEQ ID NO: 45) to make (SEQ ID NO: 242). In one instance the peptide was engrafted on the N-terminus of the heavy chain of anti-CD123 32716 using 2 of linker (SEQ ID NO: 47) to make (SEQ ID NO: 243). In one instance the peptide was engrafted on the C-terminus of the light chain of anti-CD123 26292 using 1 of linker (SEQ ID NO: 40) to make (SEQ ID NO: 244). In one instance the peptide was engrafted on the C-terminus of the light chain of anti-CD123 32716 using 1 of linker (SEQ ID NO: 40) to make (SEQ ID NO: 245). In one instance the peptide was engrafted on the C-terminus of the light chain of anti-CD123 32716 using 2 of linker (SEQ ID NO: 40) to make (SEQ ID NO: 246). In one instance the peptide was engrafted on the C-terminus of the light chain of anti-CD123 32716 using 3 of linker (SEQ ID NO: 40) to make (SEQ ID NO: 247). In one instance the peptide was engrafted on the C-terminus of the heavy chain of anti-CD123 26292 using 1 of linker (SEQ ID NO: 40) to make (SEQ ID NO: 248). In one instance the peptide was engrafted on the C-terminus of the heavy chain of anti-CD123 32716 using 1 of linker (SEQ ID NO: 40) to make (SEQ ID NO: 249). In one instance the peptide was engrafted on the C-terminus of the heavy chain of anti-CD123 32716 using 2 of linker (SEQ ID NO: 40) to make (SEQ ID NO: 250). In one instance the peptide was engrafted on the C-terminus of the heavy chain of anti-CD123 32716 using 3 of linker (SEQ ID NO: 40) to make (SEQ ID NO: 251). In one instance the peptide was engrafted on the CH1 loop of the heavy chain of anti-CD123 32716 using no linkers to make (SEQ ID NO: 252). In one instance the peptide was engrafted on the CH1 loop of the heavy chain of anti-CD123 32716 using 1 of linker (SEQ ID NO: 40) either side of the peptide to make (SEQ ID NO: 253); in this construct the GCN4 peptide (SEQ ID:3) was engrafted with linkers at both sites replacing S74 and G75 of the heavy chain. In one instance the peptide was engrafted on the CH1 loop of the light chain of anti-CD123 32716 using 1 of linker (SEQ ID NO: 40) either side of the peptide to make (SEQ ID NO: 254). These switches were expressed and several are demonstrated by SDS-Page (FIG. 38I) and switch masses are shown in Table 30, as determined by high resolution QTOF mass spectrometry.

TABLE 30

QTOF analysis of the anti-CD123 Fab-GCN4 switches in FIG. 38F.

| Protein | Expected Mass | Observed Mass | ppm | Da |
|---|---|---|---|---|
| 26292 WT | 46955.44 | 46939.3 | 343.7301 | −16.14 |
| 26292 HCNT | 49945.89 | 49947.61 | −34.4373 | 1.72 |
| 26292 HCCT | 48979.7 | 48963.21 | 336.670 | −16.49 |
| 26292 LCNT | 48979.7 | 48963.81 | 324.4201 | −15.89 |
| 26292 LCCT | 48979.7 | 48962.96 | 341.7742 | −16.74 |
| 26292 NTBV | 51970.15 | 51972.21 | −39.6381 | 2.06 |
| 26292 CTBV | 51003.96 | 50987.07 | 331.1508 | −16.89 |
| 32716 WT | 47423.98 | 47406.89 | 360.3662 | −17.09 |
| 32716 HCNT | 50414.43 | 50415.35 | −18.2487 | 0.92 |
| 32716 HCCT | 49448.24 | 49431.02 | 348.2429 | −17.22 |
| 32716 LCNT | 49448.25 | 49431.82 | 332.2666 | −16.43 |
| 32716 LCCT | 49448.25 | 49431.17 | 345.4116 | −17.08 |
| 32716 NTBV | 52438.7 | 52440.43 | −32.9909 | 1.73 |
| 32716 CTBV | 51472.51 | 51455.49 | 330.6619 | −17.02 |

Figure 38J:
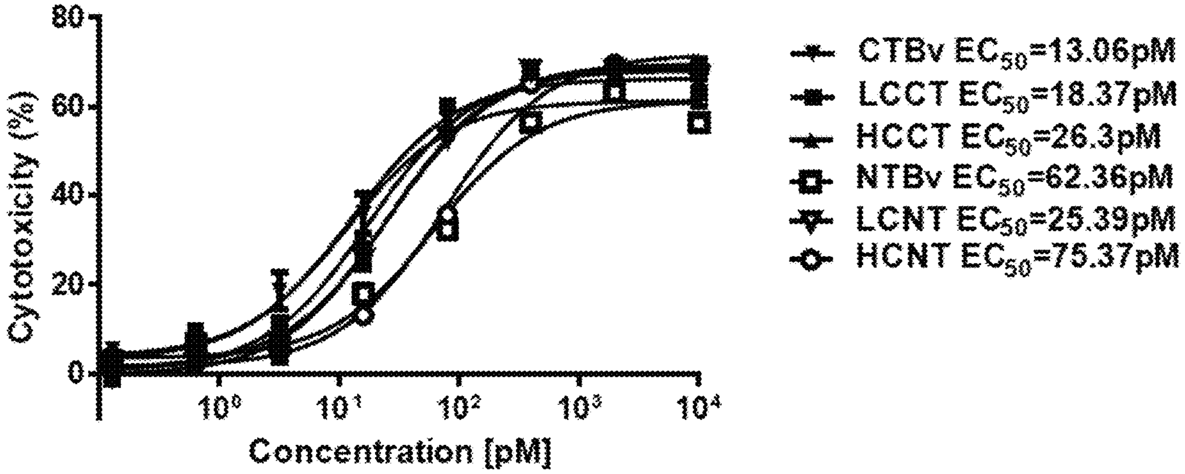
FIG. 38J shows cytotoxicity of sCAR-T cells against CD 123+ MOLM14 cells with titration of anti-CD 123 26292 Fab switch designs.
Figure 38K:
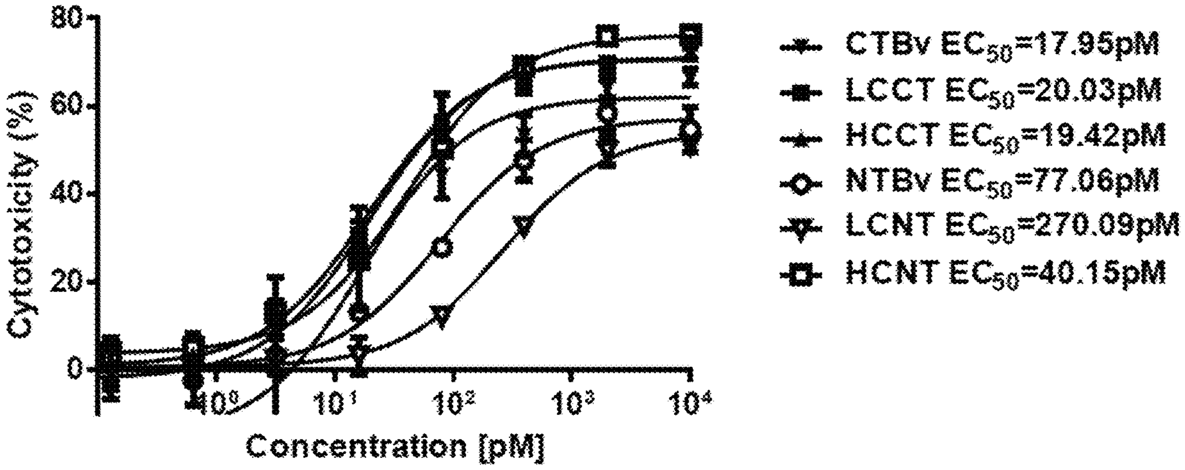
FIG. 38K shows cytotoxicity of sCAR-T cells against CD 123+ MOLM14 cells with titration of anti-CD 123 32716 Fab switch designs.

Activity was confirmed by flow cytometry based cytotoxicity assay (FIG. 38J & FIG. 38K). FIG. 38J and Table 31. Shows cytotoxicity of sCAR-T cells against CD 123+ MOLM14 cells with titration of anti-CD 123 26292 Fab switch designs. FIG. 38K and Table 32. Shows cytotoxicity of sCAR-T cells against CD 123+ MOLM14 cells with titration of anti-CD 123 32738 Fab switch designs.

Example 2Z Soluble TCR (sTCR) Switch Targeting

NY-ESO-1 is a cancer-testis antigen: expression is restricted to the testes and no other normal tissue. NY-ESO-1 expression is found in a surprisingly large range of tumors and may be particularly useful in targeting melanoma and multiple myeloma.

An NY-ESO-1 switch was produced by fusion of the GCN4 epitope to the C-terminal of the TCR β chain. This construct was expressed and purified in high yields from *E. coli*. The switch is tested for its ability to recruit sCAR-T cells using in vitro cytotoxicity assays against A375 (melanoma). Additional constructs are tested with grafting positions identified by structure-based design to assess the geometric constraints of TCR targeting in the context of sCAR-T cells. Notably, all sTCRs bind with the same relative orientation. Therefore, one optimal switch design works equally for any sTCR.

sTCR switches were expressed as follows:

TCR chains were expressed separately as inclusion bodies in the *E. coli* strain BL21-DE3(pLysS) by induction in mid-log phase with 0.5 mM IPTG. Inclusion bodies were isolated by sonication, followed by successive wash and centrifugation steps using 0.5% Triton X-100. Finally, the inclusion bodies were dissolved in 6 M guanidine, 10 mM dithiothreitol (DTT), 10 mM ethylenediaminetetra-acetate (EDTA), buffered with 50 mM Tris pH 8.1 and stored at ±80° C. Soluble TCR was refolded by rapid dilution of a mixture of the dissolved a- and b-chain inclusion bodies into 5 M urea, 0.4 M L-arginine, 100 mM Tris pH 8.1, 3.7 mM cystamine, 6.6 mM b-mercapoethylamine (4° C.) to a final concentration of 60 mg/l.

sTCR switches were purified as follows:

The refold mixture was dialysed for 24 h against 10 volumes of demineralized water, then against 10 volumes of

TABLE 31

Percent of cytotoxicity in target cells (data in FIG. 38J) (duplicate for each switch).

| pM | LCCT | | HCCT | | CTBv | | LCNT | | HCNT | | NTBv | |
|---|---|---|---|---|---|---|---|---|---|---|---|---|
| 10000 | 61 | 65.3 | 64.2 | 67.9 | 61.6 | 60.7 | 66.9 | 67.2 | 66.8 | 70 | 55.3 | 57.4 |
| 2000 | 65.9 | 68.8 | 67.2 | 67.3 | 69 | 68.2 | 66.9 | 69.9 | 69.4 | 69.6 | 64.2 | 62.1 |
| 400 | 68.9 | 67.5 | 66.5 | 68.7 | 66.9 | 68.6 | 67.6 | 69.1 | 65.5 | 64.9 | 57.5 | 55.5 |
| 80 | 59.5 | 60.9 | 53.2 | 55.3 | 55 | 59.2 | 52.7 | 54 | 35.6 | 35.8 | 31.4 | 33.2 |
| 16 | 25.8 | 30.4 | 26.4 | 24 | 32.9 | 39.1 | 24.2 | 27.5 | 11.9 | 14.3 | 16.5 | 19.3 |
| 3.2 | 10.4 | 12.6 | 9 | 3.8 | 15.6 | 21.6 | 4.5 | 9.7 | 4.7 | 5.3 | 9.8 | 4.1 |
| 0.64 | 3.5 | 5.1 | 2.6 | 9.5 | 10.2 | 6.9 | 0.7 | 4.1 | 1.3 | 7.8 | 7.4 | 6.4 |
| 0.128 | 2.4 | −1 | 1.6 | 2.9 | 6.4 | 4.6 | −0.8 | 0.4 | −1.1 | 4 | 2 | 3.4 |
| 0.01 | 0 | 0 | 0 | 0 | 0 | 0 | 0 | 0 | 0 | 0 | 0 | 0 |

TABLE 32

Percent of cytotoxicity in target cells (data in FIG. 38K) (duplicate for each switch).

| pM | LCCT | | HCCT | | CTBv | | LCNT | | HCNT | | NTBv | |
|---|---|---|---|---|---|---|---|---|---|---|---|---|
| 10000 | 73 | 75.5 | 71 | 73.6 | 65.1 | 67.8 | 52 | 50.6 | 77.1 | 74.9 | 58.3 | 51 |
| 2000 | 68.6 | 68.1 | 66.7 | 70.2 | 61.9 | 66.1 | 52.1 | 47.5 | 74.9 | 76.6 | 60.9 | 55.7 |
| 400 | 64.7 | 66.8 | 64 | 68.8 | 50 | 56.5 | 33.7 | 31.3 | 69.5 | 68.3 | 50.9 | 44.5 |
| 80 | 57.2 | 55.3 | 54.7 | 61.3 | 40.5 | 48.1 | 13.1 | 11.2 | 51.3 | 49.3 | 27 | 28.5 |
| 16 | 32.5 | 26.5 | 28.3 | 35.4 | 16.4 | 29.1 | 6.2 | 0.3 | 25.9 | 24 | 13.7 | 12.6 |
| 3.2 | 12.7 | 10.5 | 8.2 | 13.8 | −9.8 | 15.9 | 2 | 2.6 | 14.9 | 11.1 | 6.4 | 0.2 |
| 0.64 | −2.1 | −2.3 | 2.5 | 4.6 | −39.7 | −4.6 | 0.5 | −0.2 | 7.3 | 2.9 | 1.6 | −6.4 |
| 0.128 | −0.9 | −5.6 | −1.8 | 5.9 | −33.3 | −16.2 | 1.1 | 2.6 | 6.2 | 1.7 | 2.2 | 3.1 |
| 0.01 | 0 | 0 | 0 | 0 | 0 | 0 | 0 | 0 | 0 | 0 | 0 | 0 |

10 mM Tris pH 8.1 at 4° C. The refolded protein was then filtered and loaded onto a POROS 50HQ column (Applied Biosystems). The column was washed with 10 mM Tris pH 8.1 prior to elution with a 0±500 mM NaCl gradient in the same buffer. Fractions were analysed by Coomassie-stained sodium docecyl sulphate (SDS)±10% NuPAGE (Novagen, WI), and TCR-containing fractions were pooled and further purified by gel filtration on a Superdex 75PG 26/60 column (Amersham Biosciences, Uppsala, Sweden) pre-equilibrated in phosphate-buffered saline. Fractions comprising the main peak were pooled and analysed further. The ®nal Puri®ed 1G4 dsTCR was analysed by Coomassie-stained SDS±10% NuPAGE under reducing and non-reducing conditions, and an aliquot of protein was buffer exchanged into HBSE (HEPES pH 7.4, 150 mM NaCl, 3 mM EDTA) and concentrated prior to activity determination by BIAcore SPR.

Alternatively, TCR zipper chains were overexpressed in *E. coli* and purified as follows. GFG020, GFG021, JMB002, GFG089, and GFG092, the pGMT7 expression plasmids encoding the JM22a-Jun, JM22b-Fos, JM22b-Fosbt, F5a-Jun, and F5b-Fos proteins, respectively, were transformed separately into *E. coli* strain BL21pLysS ~DE3!, and single colonies were grown at 37 C in TYP ~ampicillin 100 μg/mL medium to OD600 of 0.4 before inducing protein expression with 0.5 mM IPTG. Cells were harvested 3 h postinduction by centrifugation for 30 min at 4000 rpm in a Beckman J-6B. Cell pellets were resuspended in a buffer containing 50 mM Tris-HCl, 25%~w/v sucrose, 1 mM EDTA, 0.1% w/v sodium azide, 10 mM DTT, pH 8.0. After an overnight freeze-thaw step, resuspended cells were sonicated in 1 min bursts for a total of around 10 min in a Milsonix XL2020 sonicator using a standard 12 mm diameter probe. Inclusion body pellets were recovered by centrifugation for 30 min at 13,000 rpm in a Beckman J2-21 centrifuge. Three detergent washes were then carried out to remove cell debris and membrane components. Each time the inclusion body pellet was homogenized in a Triton buffer ~50 mM Tris-HCl, 0.5% Triton X-100, 200 mM NaCl, 10 mM EDTA, 0.1%~w/v sodium azide, 2 mM DTT, pH 8.0 before being pelleted by centrifugation for 15 min at 13,000 rpm in a Beckman J2-21. Detergent and salt were then removed by a similar wash in the following buffer: 50 mM Tris-HCl, 1 mM EDTA, 0.1%~w/v sodium azide, 2 mM DTT, pH 8.0. Finally, the inclusion bodies were solubilized in denaturant for 3-4 h at 48 C. JM22a-Jun, JM22b-Fos, JM22b-Fosbt, and F5a-Jun pellets were dissolved separately in a urea solution ~50 mM MES, 8 M urea, 10 mM EDTA, 2 mM DTT, pH 6.5, whereas F5b-Fos pellets were dissolved in a guanidine solution containing 50 mM MES, 6 M guanidine, 10 mM EDTA, 2 mM DTT, pH 6.5. Insoluble material was then pelleted by centrifugation for 30 min at 13,000 rpm in a Beckman J2-21, and the supernatant was divided into 1 mL aliquots and frozen at 270 8 C. Solubilized, purified inclusion bodies were quantitated using a Bradford dye-binding assay (Biorad, Richmond, Calif.). For each chain a yield of around 100 mg of purified inclusion body was obtained from 1 L of culture. From SDS-PAGE analysis, the purity of each inclusion body was estimated to be around 90%.

Example 28. Expression of TCR Chains

TCR chains were expressed separately according to the following protocol:

1. Pick colony for 50 ml starter culture o/n at 37 with Amp
2. Seed large culture at 0.07 OD(600). Induce at 0.4 OD(600) with 0.5 mM IPTG (0.5-1.0 L 2×YT+Amp)
3. Spin down at 6 k for 20' at 4 C
4. Freeze 0/N at −80 C
5. Resuspend with 25 ml to 50 ml of buffer (50 mM Tris-HCL [8.0], 25% w/v sucrose, 1 mM EDTA, 0.1% w/v NaN3, 10 mM DTT)+0.5 mg/ml of lysozyme+1 pellet of protease inhibitors (crushed)/tube. Keep on ice.
6. Sonicate 20s on, 30s off for 15 minutes total experimental time. Keep on ice.
7. Pellet (13 k/15') and wash 3× with detergent/salt buffer (50 mM Tris-HCL [8.0], 0.5% Triton X-100, 200 mM NaCl, 10 mM EDTA, 0.1% w/v NaN3, 2 mM DTT).
8. Pellet (13 k/15') and wash 2x with (50 mM Tris-HCL [8.0], 1 mM EDTA, 0.1% w/v NaN3, 2 mM DTT).
9. Dissolve inclusion bodies in (6M guanidine, 10 mM DTT, 10 mM EDTA, 50 mM Tris [8.1] stored at −80 C To analyze protein in the lysed cells collect 100 ul before spinning down the sonicated cells and 100 uL after spinning down the cells. Get the ABS280 of the post spun cells (cleared lysate) and calculate the appropriate volume for 5 ug of protein (assume 1 mg/mL=1 ABS). Load this amount of cleared lysate on the gel. Load ½ of this amount for each of the noncleared samples.

For the remainder of the protocol:

1. Solubilize pellets in 5 mL 6 M guanidine, 10 mM dithiothreitol (DTT), 10 mM ethylenediaminetetra-acetate (EDTA), buffered with 50 mM Tris pH 8.1. (This is a 100× concentration from initial culture volume). Pellets are incubated at 48 degrees for 3-4 hours to solubilize. Alternatively, pellets are shaken at 37° C. for 4 hrs.
2. Spin to remove insoluble proteins.
3. Use supernatant to obtain protein concentration with BCA assay. Note the tolerance for guanidine in BCA (or Bradford) assay is 4M so dilute the analyte to 4M (confirm this with your assay kit). You'll likely need an additional at least 3, 10x dilutions to get in the measurable range. These should all be in 4M guanidine (water may cause crashing out of protein).
4. Load 1-2 ug of all samples on gel for analysis.
5. For test refolding, combine 300 ug of each alpha and beta protein/guanidine solution and dilute to 10 mL with 5 M urea, 0.4 M L-arginine, 100 mM Tris pH 8.1, 3.7 mM cystamine (note not cysteamine, do not need the un-induced control expressions for these refolding steps), 6.6 mM b-mercapoethylamine (4° C.) to a (final concentration of 60 mg/1). If we do not have cystamine and mecaptoethylamine in the lab use 2 mM DTT instead. Aliquot and freeze remaining unused guanidine/protein solutions.
6. Add this solution to 10 KDa MWCO snakeskin tubing or a 12 mL pierce dialysis cassette.
7. Dialyze in 100 mL of water for 6-8 hours at 4 degrees (or overnight)
8. Change buffer to 10 mM Tris pH 8.1 at 4 degrees, dialyze overnight.
9. Protein should be refolded. Remove dialyzed solution, spin to clear
10. Run gel, native and denaturing. To assess. If sufficient soluble, refolded protein can proceed with His column or anion exchange to clean up and return to frozen aliquots to scale up refolding. Note scale up will require Pierce dialysis snakeskin tubing 10 kDa MWCO.

1G4c113 TCR alpha and beta chains were expressed and refolded as described. Following the refolding samples were purified by loading onto MonoQ with 20 mM Tris (pH 8.1) and 50 mM NaCl. The refolded 1G4c113 TCR was eluted by a gradient to 20 mM Tris (pH 8.1) and 1M NaCl. Pre column and the eluted protein are shown on a Coomassie stained 10% Tris-Glycine gel. Left Panel. Native, refolded 1G4c113 TCR with GCN4-CTerm peptide grafted to the beta chain.

Right panel, reduced 1G4c113 TCR alpha chain and 1G4c113-TCR beta chain with grafted GCN4-Cterm. See FIG. 39 for expressed and purified 1G4c113 TCR with peptide graft.

Figure 39:
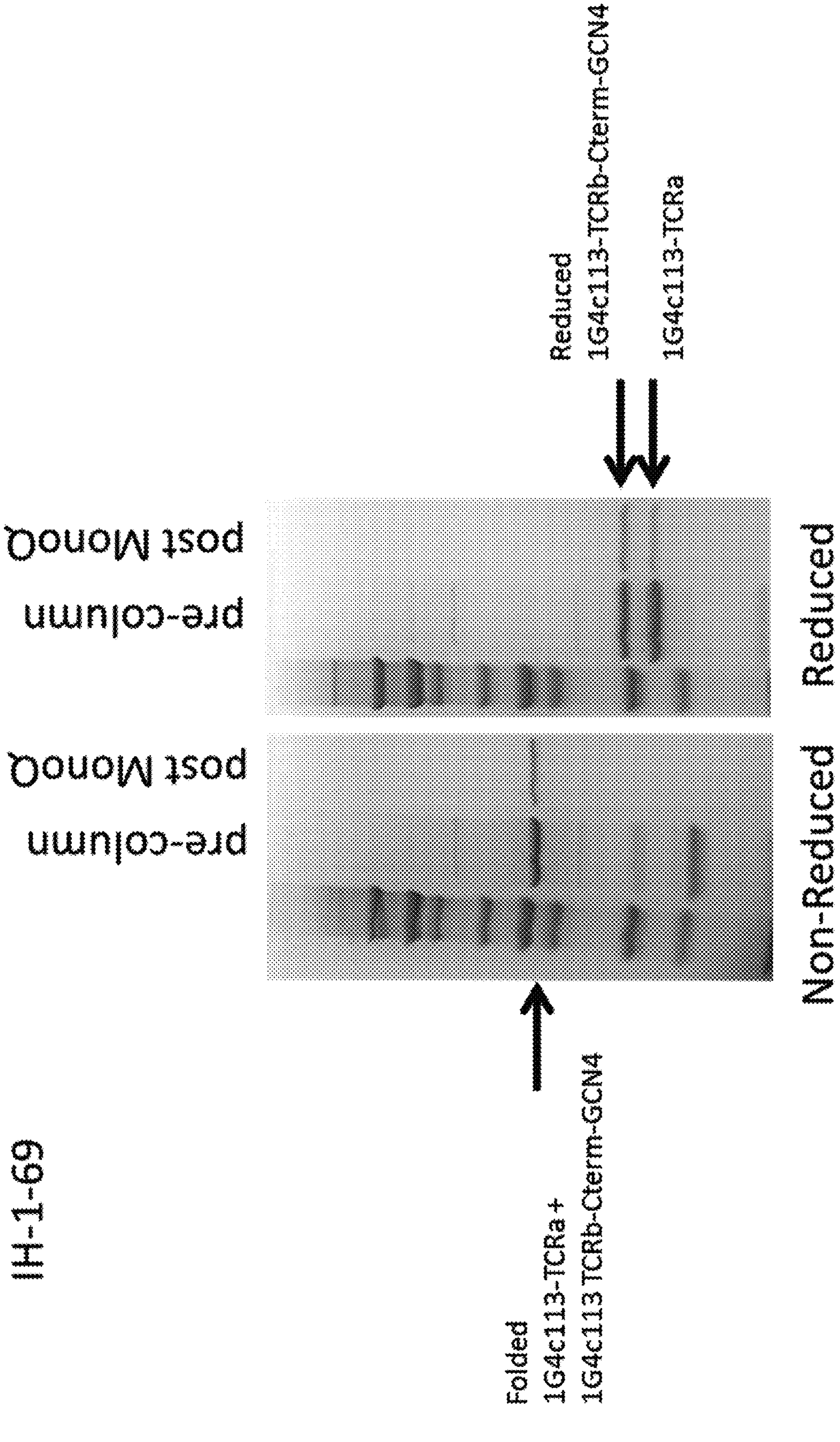
FIG. 39 shows expression and purification of 1G4c113 TCR with peptide graft. 1G4c113 TCR alpha and beta chains were expressed and refolded as described. Following the refolding samples were purified by loading onto MonoQ with 20 mM Tris (pH 8.1) and 50 mM NaCl. The refolded 1G4c113 TCR was eluted by a gradient to 20 mM Tris (pH 8.1) and 1M NaCl. Pre column and the eluted protein are shown on a Coomassie stained 10% Tris-Glycine gel. Left Panel. Native, refolded 1G4c113 TCR with GCN4-CTerm peptide grafted to the beta chain. Right panel, reduced 1G4c113 TCR alpha chain and 1G4c113-TCR beta chain with grafted GCN4-Cterm.
Figure 40A:
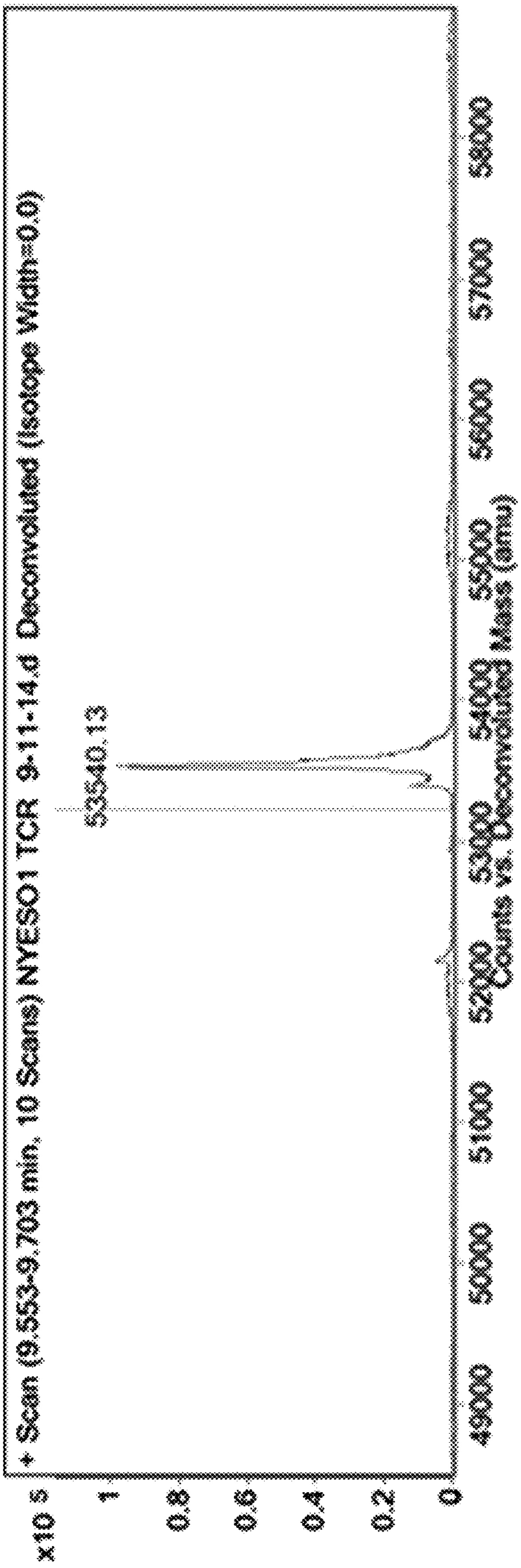
FIG. 40A-C shows mass spectrometry of purified 1G4c113 TCR with peptide graft. Samples from the post-MonoQ elutions were identified via mass spectrometry.
Figure 40B:
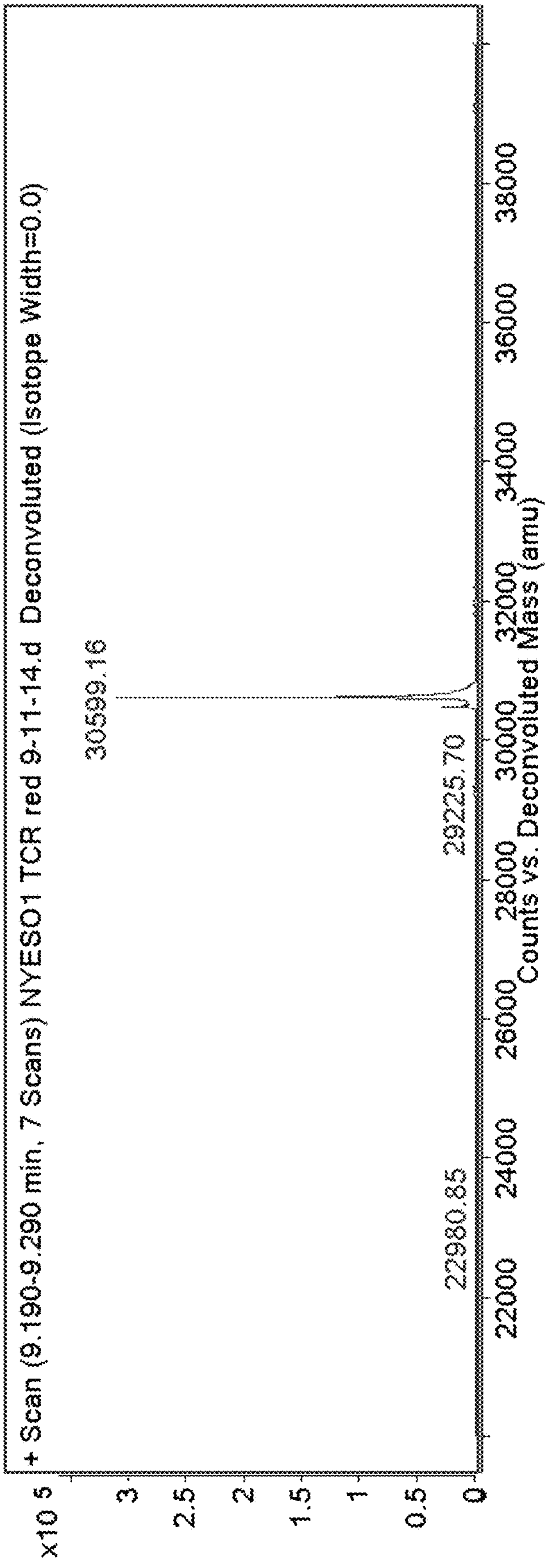
Figure 40C:
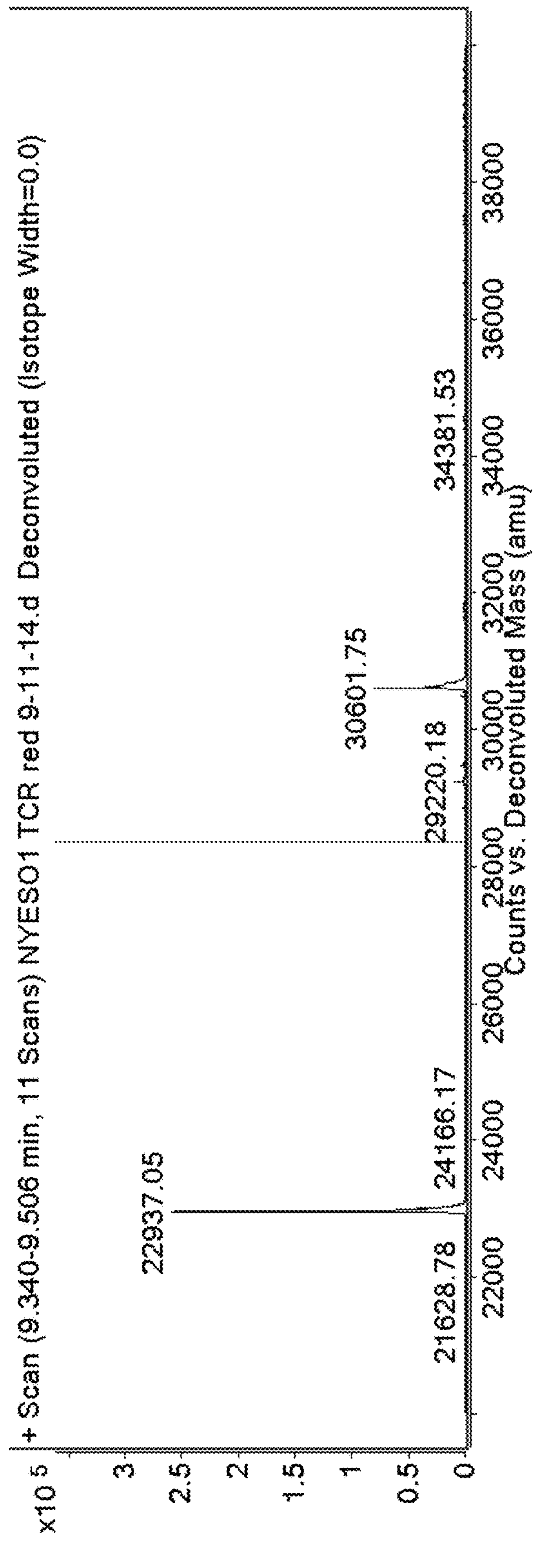

Samples from the post-MonoQ elutions as shown in FIG. 39 were identified via mass spectrometry. FIG. 40A shows non-reduced and FIGS. 40B-C show reduced peaks correlating to the non-reduced 1G4c113-TCR with GCN4-Cterm peptide graft. Table 33 shows summary of mass spectrometry data as shown in FIG. 40A-C.

TABLE 33

| Protein | Theoretic | Found | Dif. (d) | p.p.m. |
|---|---|---|---|---|
| NYESO1(1G4c113)-TCRa/TCRb-GCN4-Cterm | 53528.71 | 53540.13 | 11.42 | −213.343 |
| NYESO1(1G4c113)-TCRa | 22937.59 | 22937.05 | −0.54 | 23.54214 |
| NYESO1(1G4c113)-TCRb-GCN4-Cterm | 30601.12 | 30599.13 | −1.99 | 65.0303 |

Example 29. Soluble Based TCR (sTCR) Switches

Figure 41B:
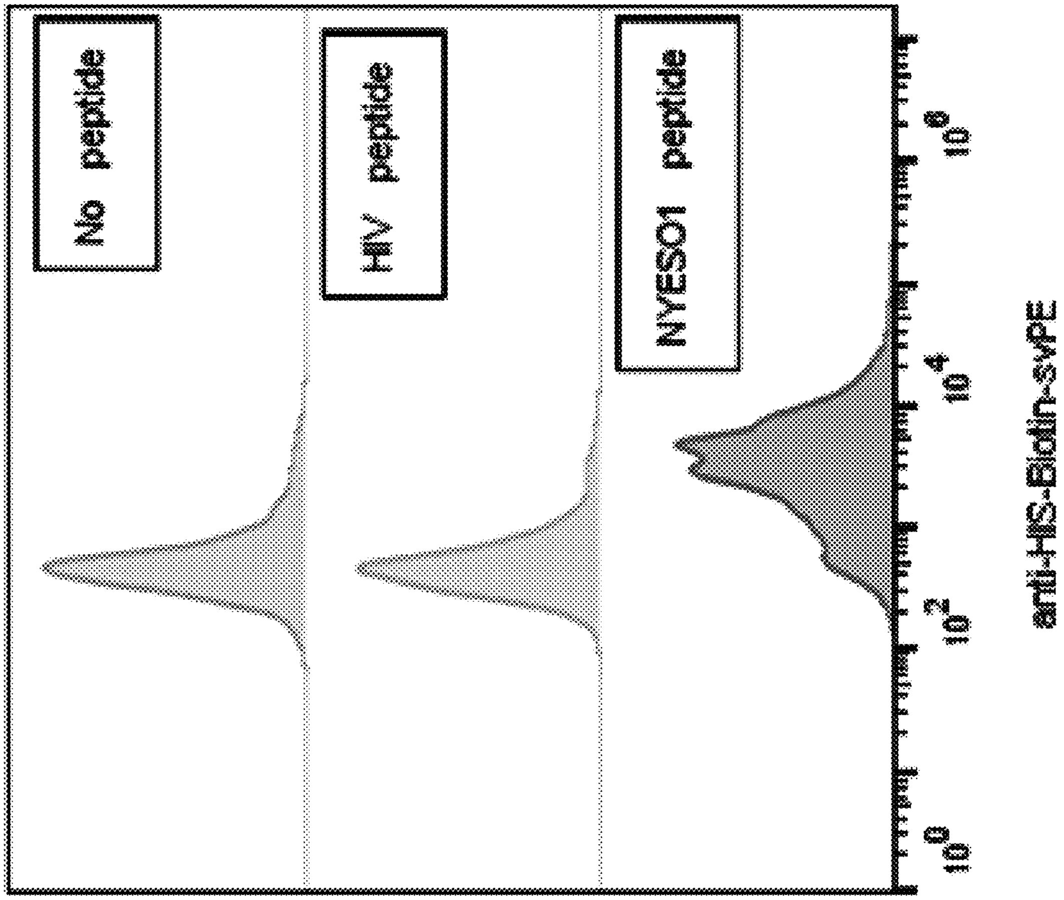
FIG. 41A-F shows data from the soluble based TCR (sTCR) switch.
Figure 41A:
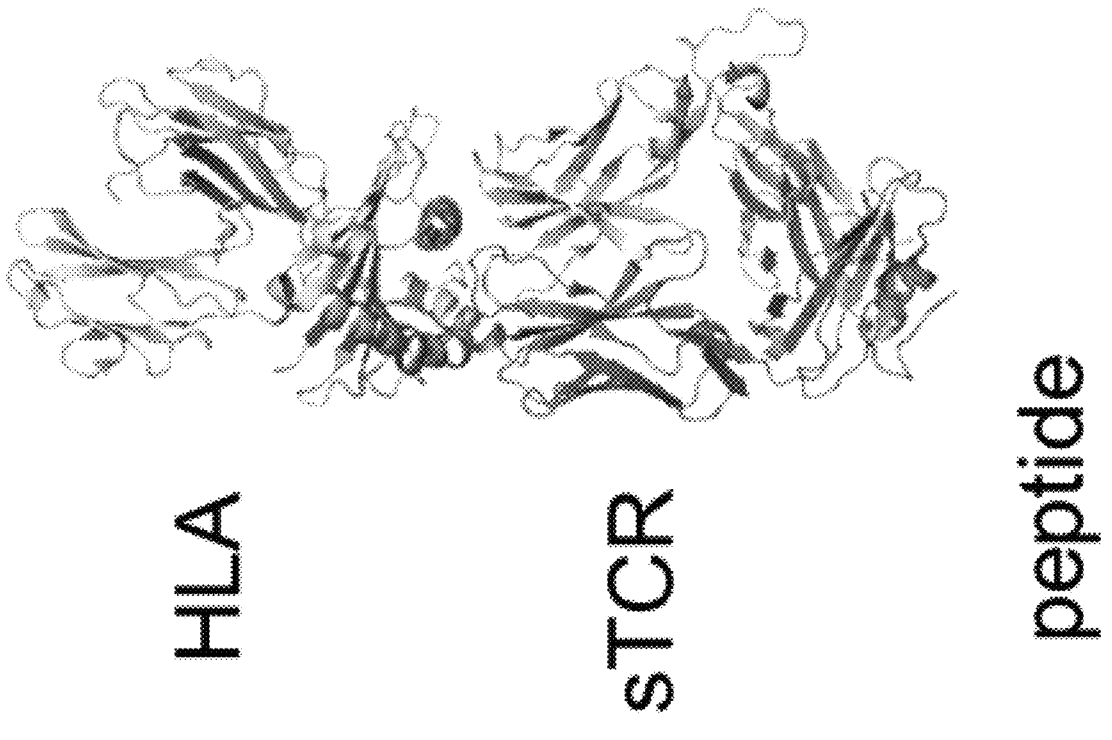

A schematic depiction of the soluble based TCR (sTCR) interacting with a peptide presenting HLA molecule. In some embodiments, the sTCR is engrafted with a peptide that could be recognized by a sCAR T cell (FIG. 41A).

A sTCR specific for HLA molecules expressing the cancer associated NY-ESO-1 peptide was expressed with a C-terminal GCN4 peptide and a His-tag. The ability of this NY-ESO-1 sTCR switch to bind to T2 cells expressing HLA molecules loaded with the NY-ESO-1 peptide was determined by flow cytometry. $10^5$ T2 cells were loaded with 10 nM of either the NY-ESO-1 or a HIV peptide for 2 hours at 37° C. in 200 μl of DMEM medium with no serum protein added. The cells were then washed with cold PBS two times before being incubated with 1 nM of the NY-ESO-1 sTCR for 30 minutes at 4° C. in 100 μL of FACS buffer (PBS, 1% FCS, 2 mM EDTA). The cells were then washed with cold PBS two times before being incubated with a Biotin-conjugated anti-HIS antibody (Sigma; 5 μg/ml) for 30 minutes at 4° C. in 100 μL of FACS buffer. The cells were then washed with cold PBS two times before being incubated with a streptavidin conjugated phycoerythrin (svPE; Biolegend; 1:200 dilution) for 30 minutes at 4° C. in 100 μL of FACS buffer. Cells were then washed a final two times and the cells were analyzed using a BD Accuri C6 flow cytometer. The sTCR bound to the T2 cells loaded with the NY-ESO-1 peptide but not the HIV peptide (FIG. 41B).

Figure 41C:
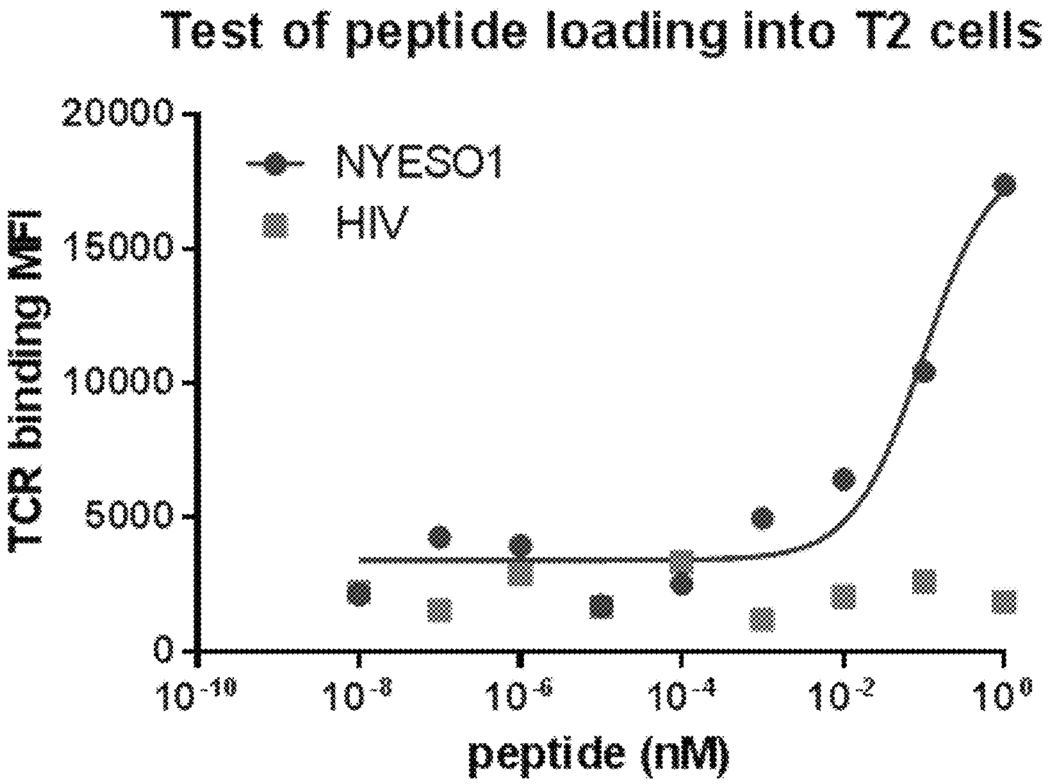

$10^5$ T2 cells were loaded with $10^0$-$10^{\prime}$ nM of the NY-ESO-1 or HIV peptide for 2 hours at 37° C. in 200 μl of DMEM medium with no serum protein added. The cells were then labelled with the NY-ESO-1 specific sTCR as described above. The data are presented as MFI of the switch binding against the concentration of the peptide used to load the cells. These data indicated that 1 nM of peptide loaded onto the T2 HLA molecules was sufficient for the sTCR to bind to the T2 cells, therefore 1 nM of the NY-ESO-1 peptide was used for subsequent experiments (FIG. 41C).

Figure 41D:
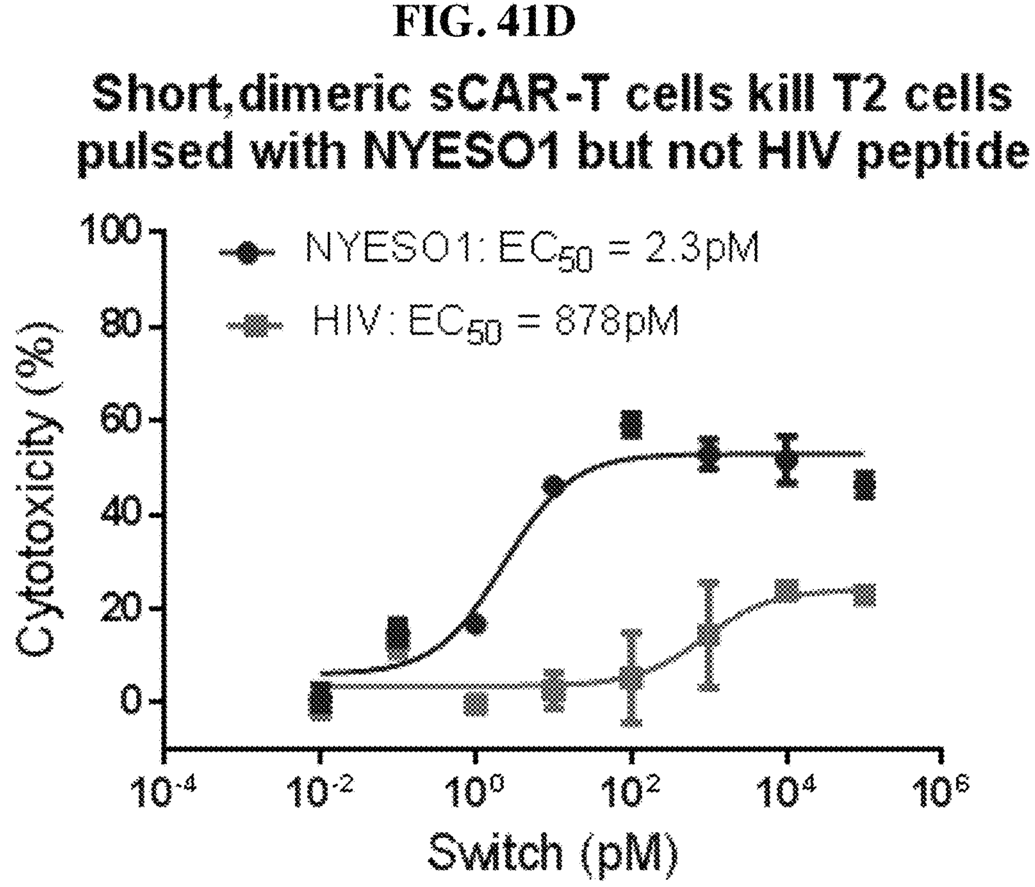
Figure 41E:
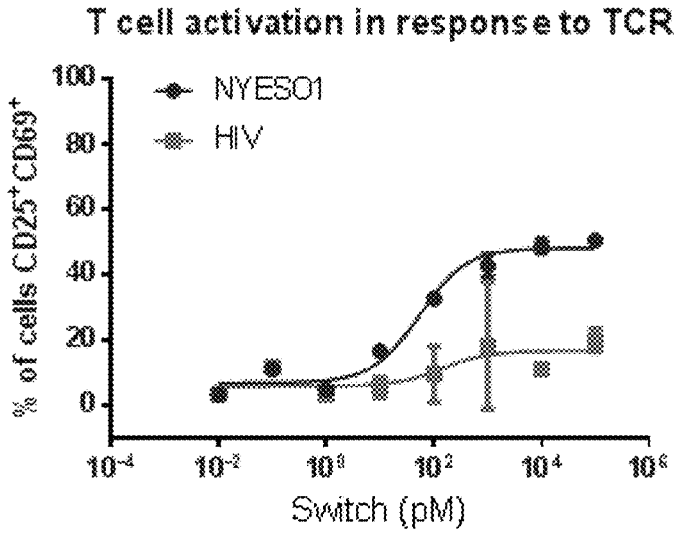
Figure 41F:
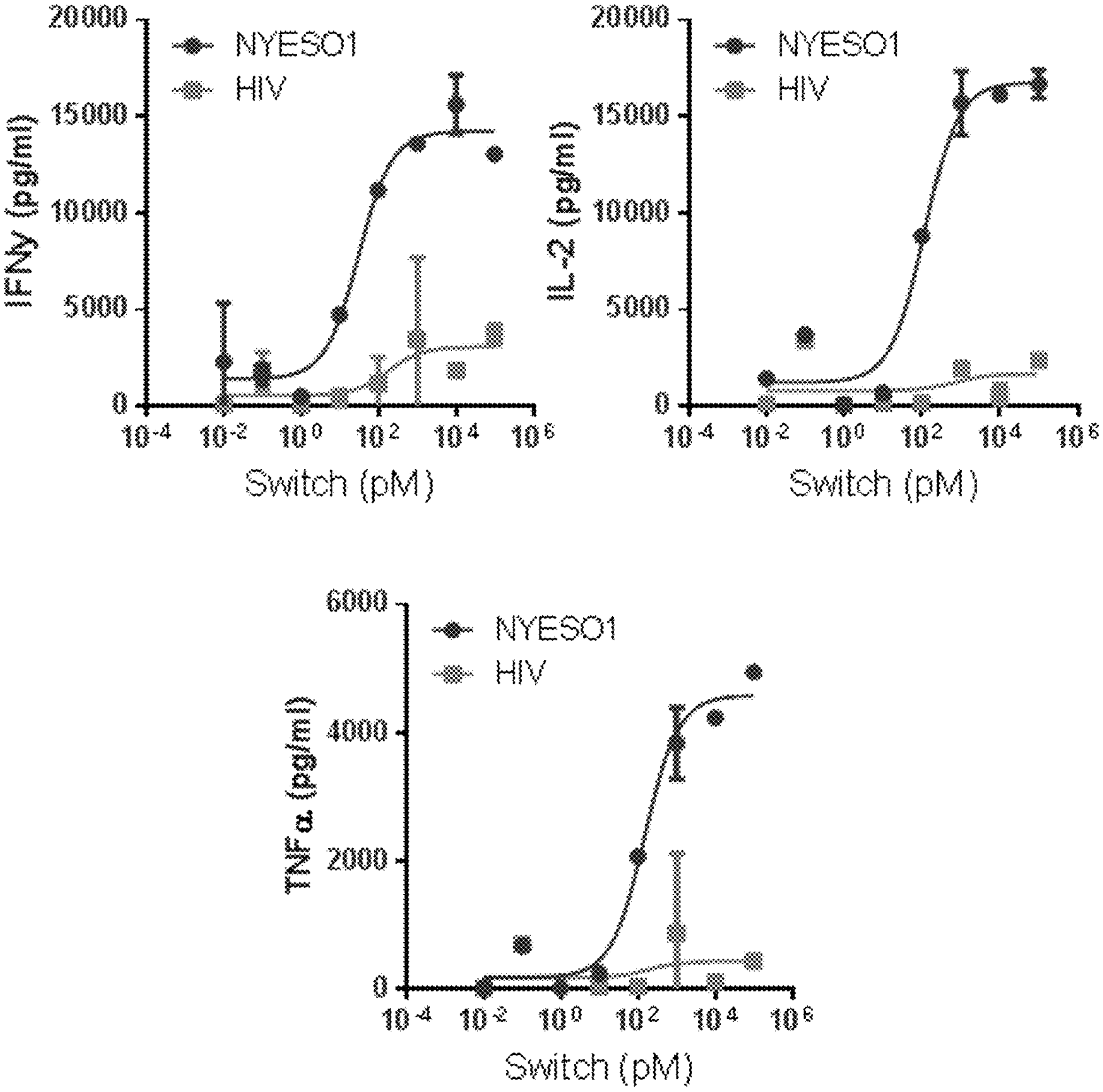

Short-dimeric sCAR-T cells (also known as IgG4m sCAR-T)can kill T2 cells pulsed with NY-ESO-1 peptide but not HIV peptide. In this experiment, the short-dimeric sCAR-T cells were cultured with T2 cells that had been pulsed with 1 nM of the NY-ESO-1 or HIV peptide as described above. This assay was conducted at an effector: target cell ratio of 10:1. A serial dilution (100,000-0.01 pM) of the sTCR GCN4 switch was added to the cells. The cells were incubated for 20-24 hours, after which the supernatants were assayed to detect LDH release as a proxy for target cell lysis. EC50 values are shown in parentheses. This data show that only T2 cells that had been pulsed with the NY-ESO-1 peptide were susceptible to killing mediated by the short-dimeric sCAR-T cells (FIG. 41D).

sTCR switches activate T cells in in vitro cytotoxicity assays. The cells from the assay described above were stained with PE-conjugated anti-human CD25 and PerCP-conjugated anti-human-CD69 for 30 minutes in FACs buffer at 4° C. These cells were then washed twice and acquired using an Accuri C6 (BD). The $CD25^{+}CD69^{+}$ T cells were considered as being activated and the proportion of these cells is plotted against the concentration of switch used in the original assay. This data shows how at sTCR switch concentrations of >1 pM the T cells become activated and express the T cell activation markers CD25 and CD69 (FIG. 41E).

sTCR switches can induce pro-inflammatory cytokine production from short-dimeric sCAR-T cells. Cytokine levels were measured in the supernatants from the assay described above by cytometric bead array (CBA, BD) as per the manufacturer's instructions. These data show how at sTCR switch concentrations of >10 pM the T cells become express the pro-inflammatory cytokines IFNγ, IL-2 and TNFα (FIG. 41F).

Collectively this data shows that soluble TCR based switches can direct sCAR-T cells to kill target cells presenting the target HLA:peptide complex and sTCR switches can activate sCAR-T cells to produce pro-inflammatory cytokines.

Example 30. Off-switch: Peptide-Based CAR-T Disruption

Figure 26A:
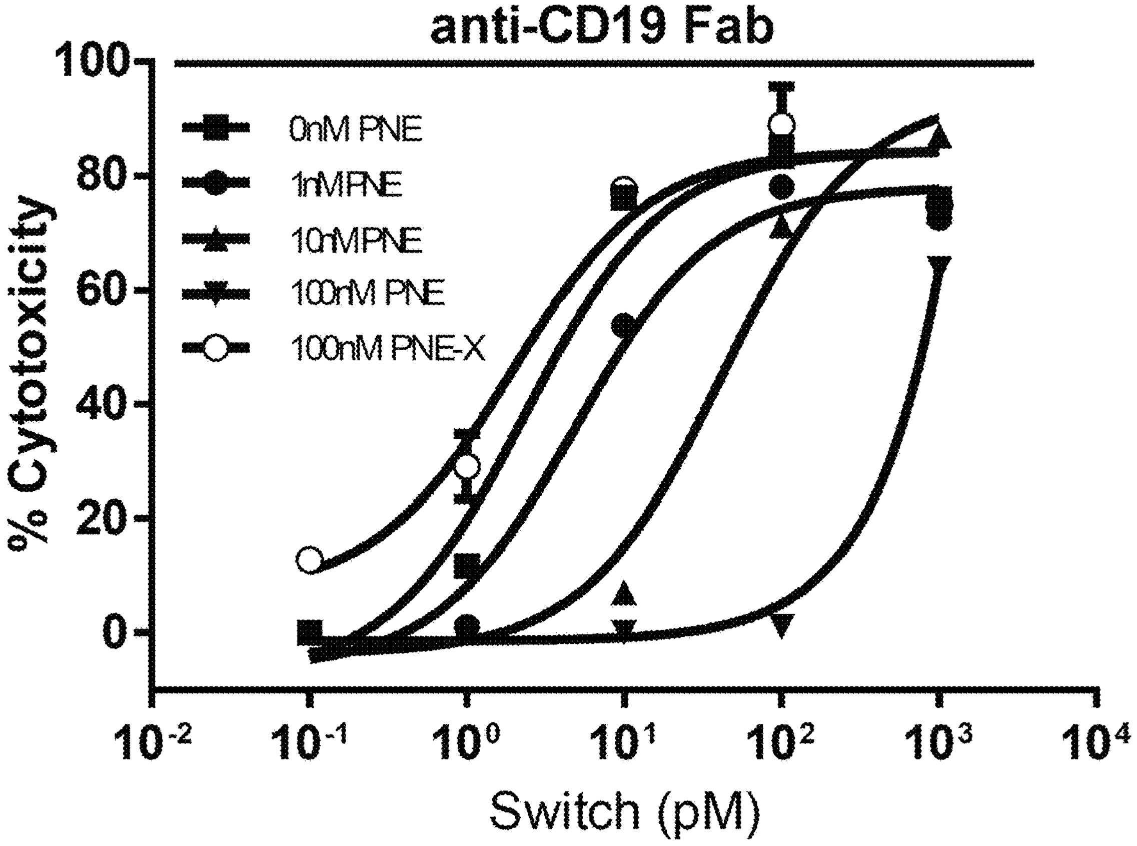
FIG. 26A-F shows sCAR modifications enhance activity and activity can be controlled using free PNE.
Figure 26B:
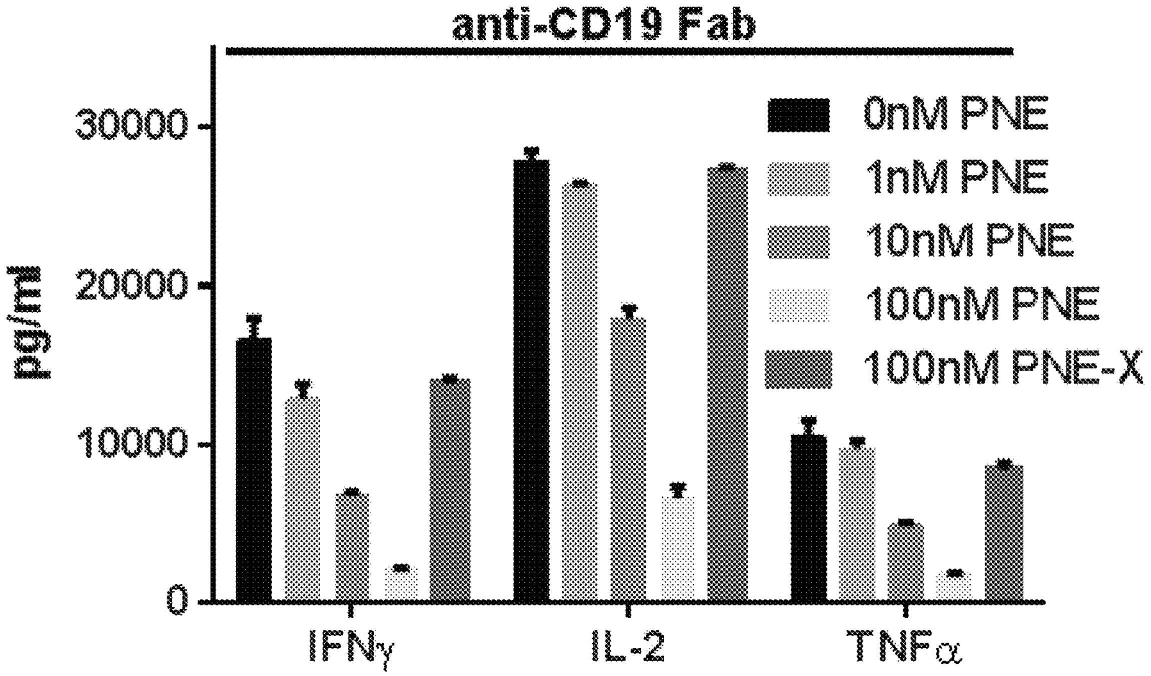
Figure 26C:
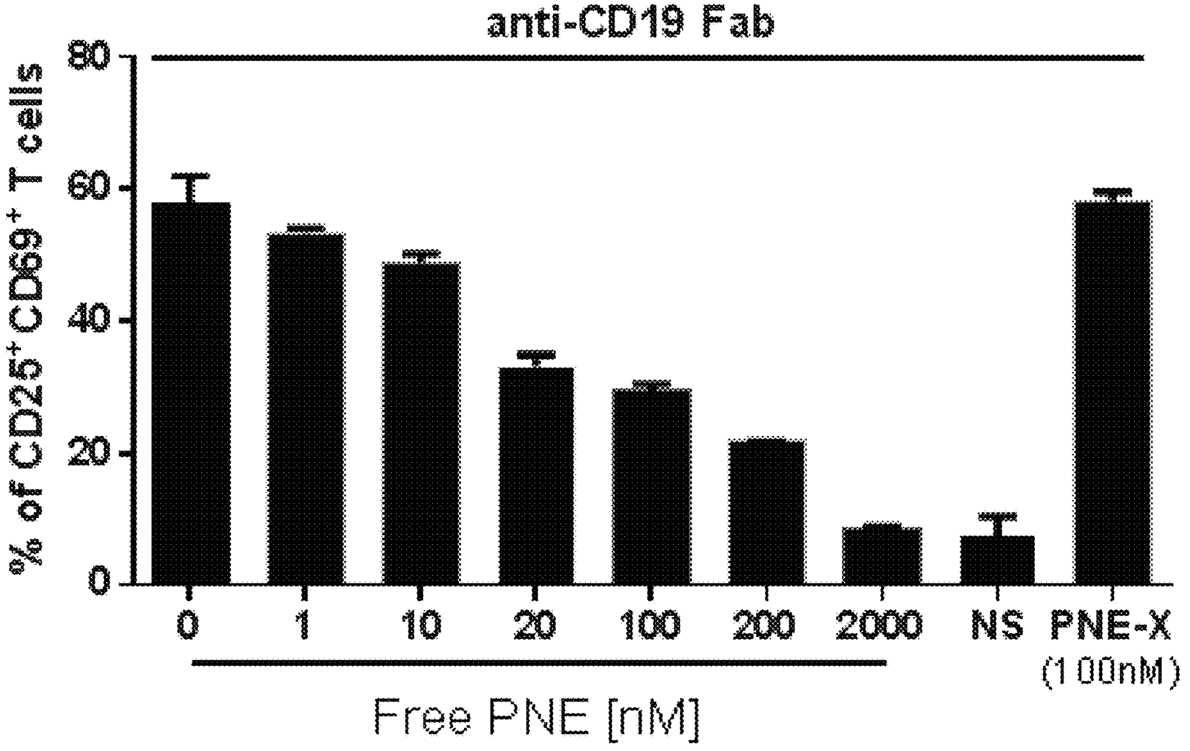
Figure 26D:
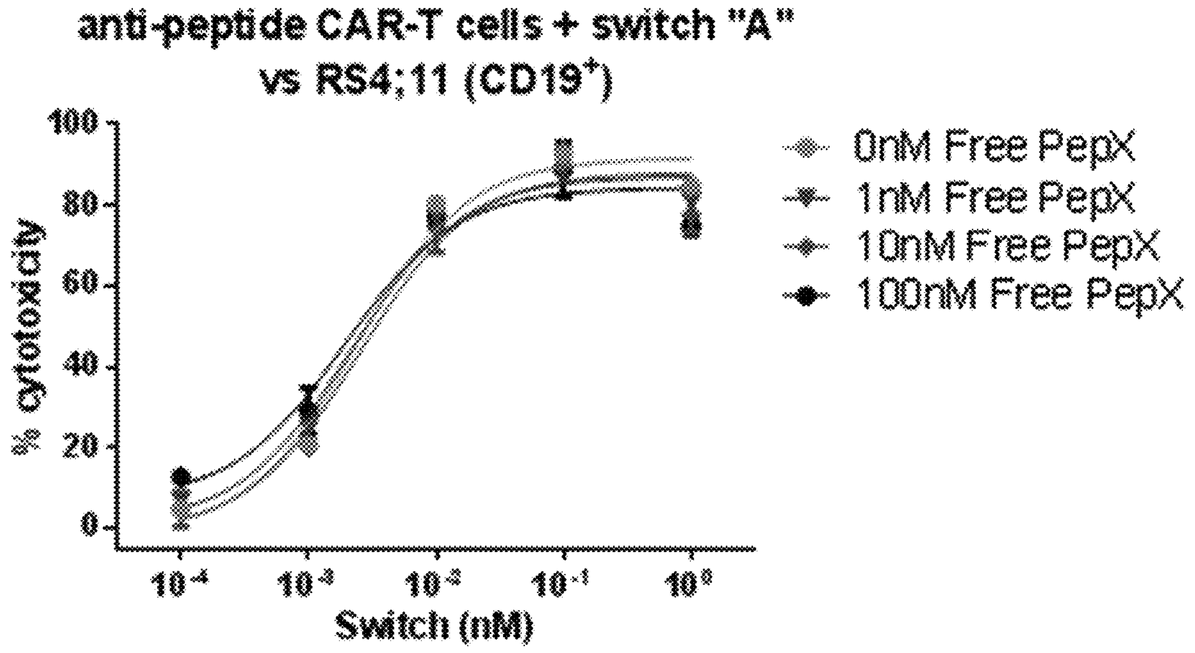
Figure 26E:
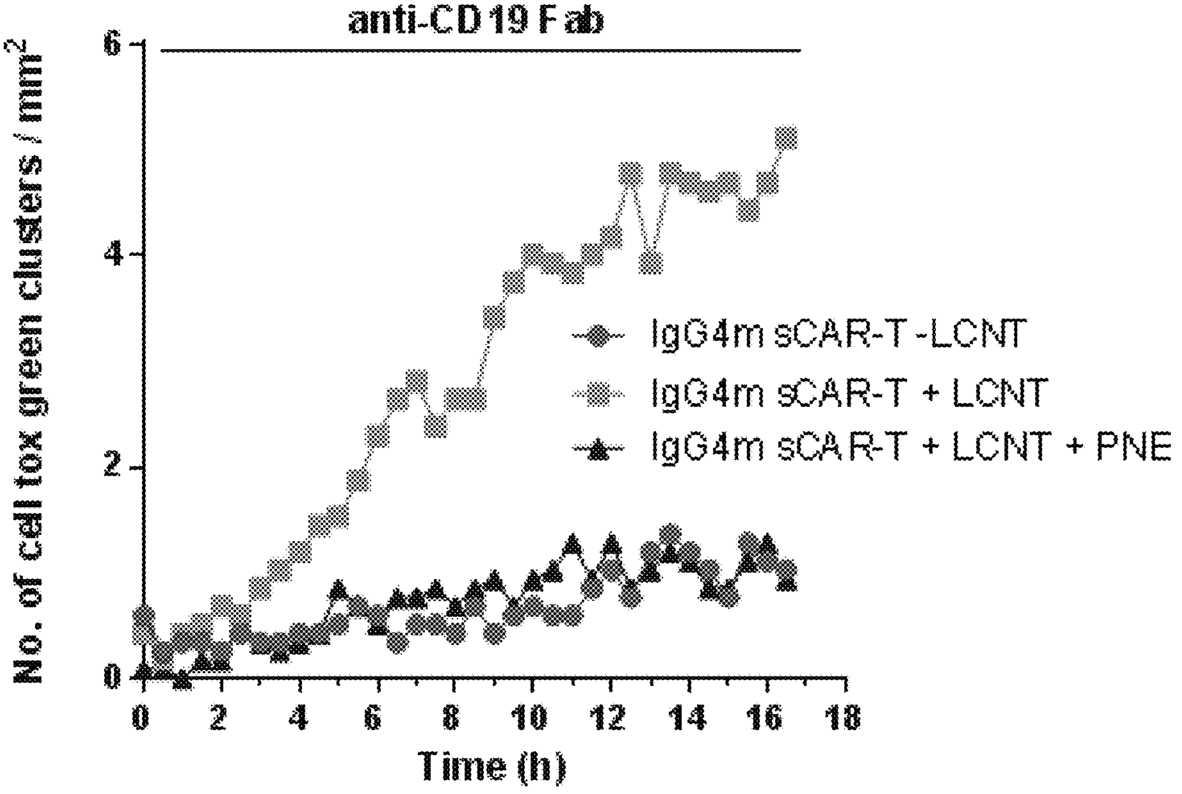
Figure 26F:
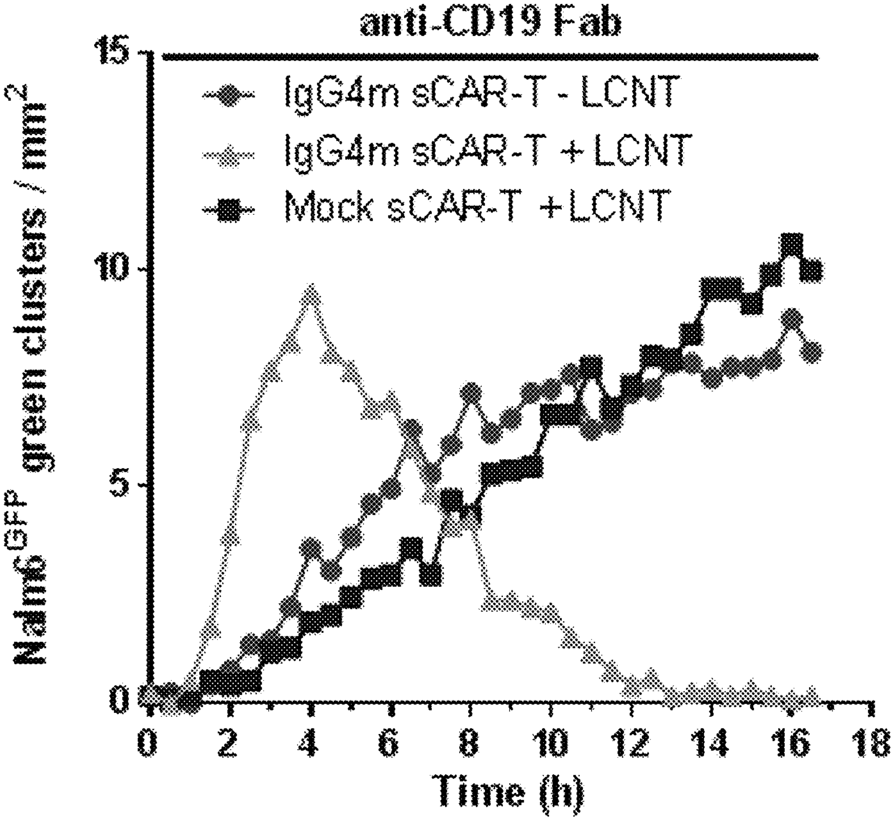

One of the great advantages of the sCART cell system is that the activity can be controlled. This can be achieved by either dose escalation of the switches or by stopping switch dosing. In the event that the cessation of switch dosing is not an acute enough response to halt sCART cell activity, immunological synapses are disrupted by the administration of free peptide. To demonstrate this, FIGS. 26A-F shows increasing the concentration of free peptide blocks sCART cell activation and activity in vitro. FIG. 26D shows that only the cognate free peptide epitope inhibited cytotoxicity, and alanine mutated free peptides (PepX) had no effect).

Example 31. Titrated Treatment of Solid Tumors with Switchable CAR T Cells

Figure 42A:
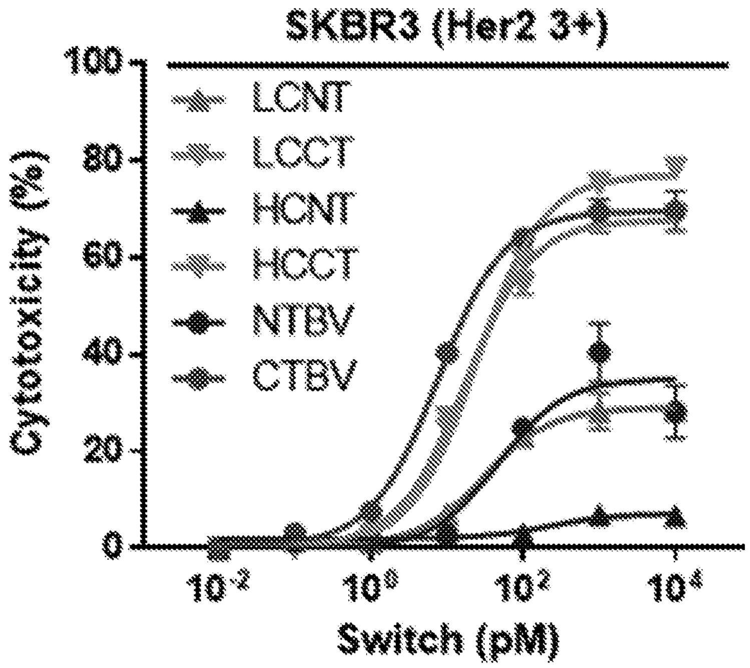
FIG. 42A-F shows data from treating solid tumors with sCAR-T cells and Herceptin-based CTBV switch.
Figure 42B:
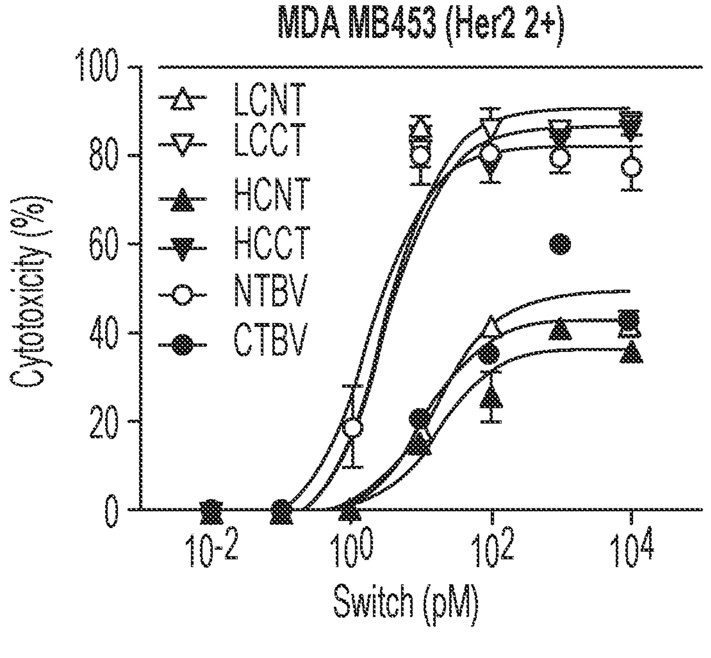
Figure 42C:
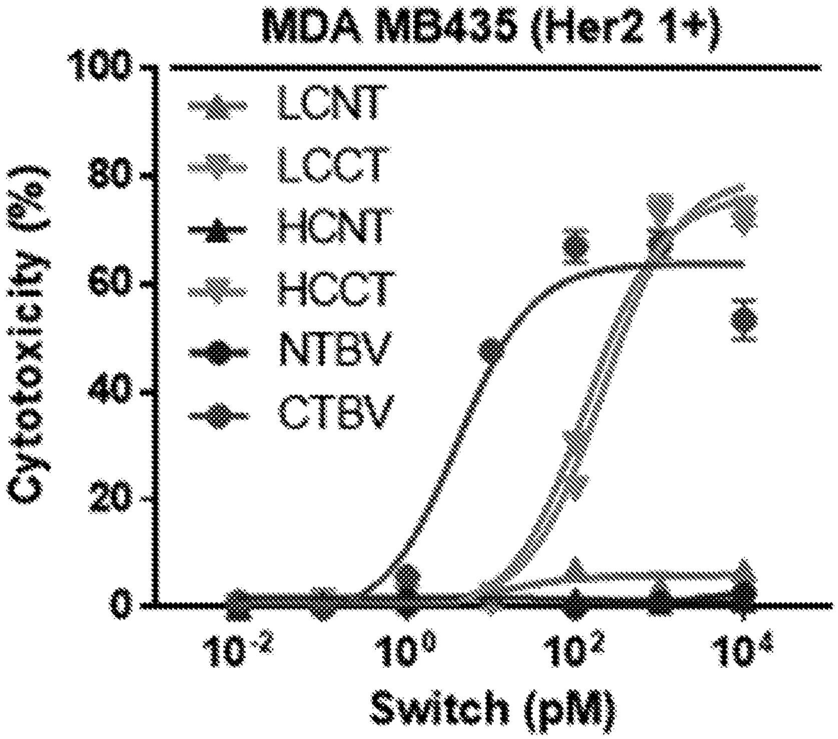
Figure 42D:
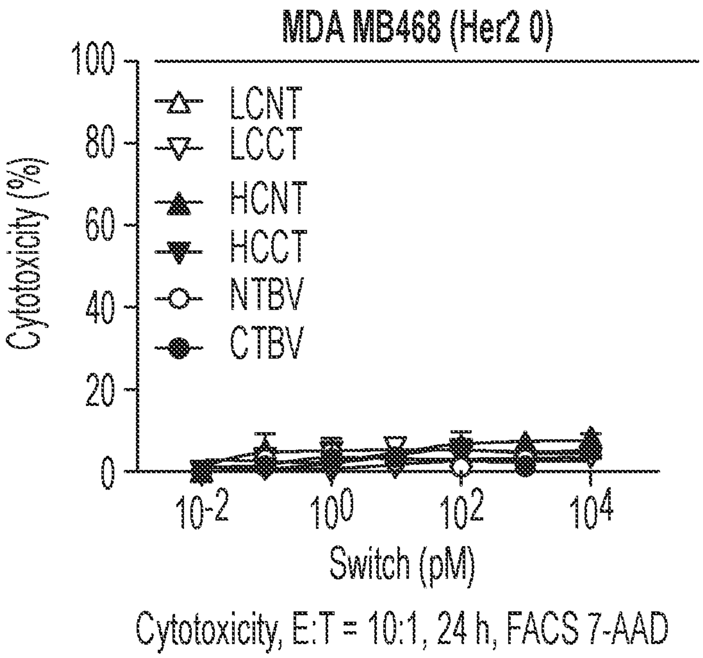
Figure 42C:
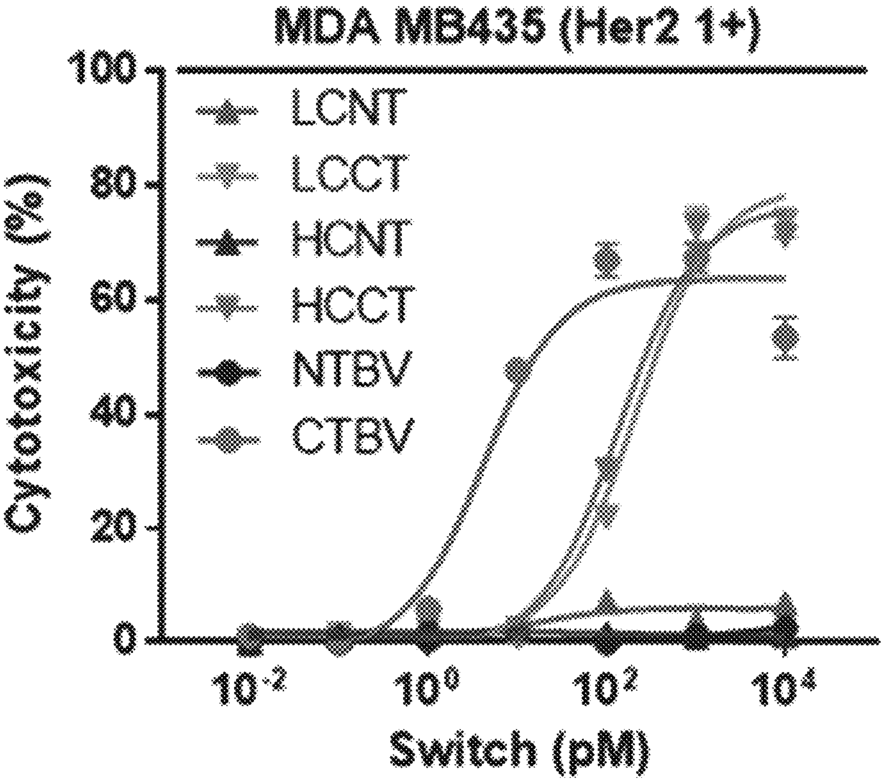
Figure 42D:
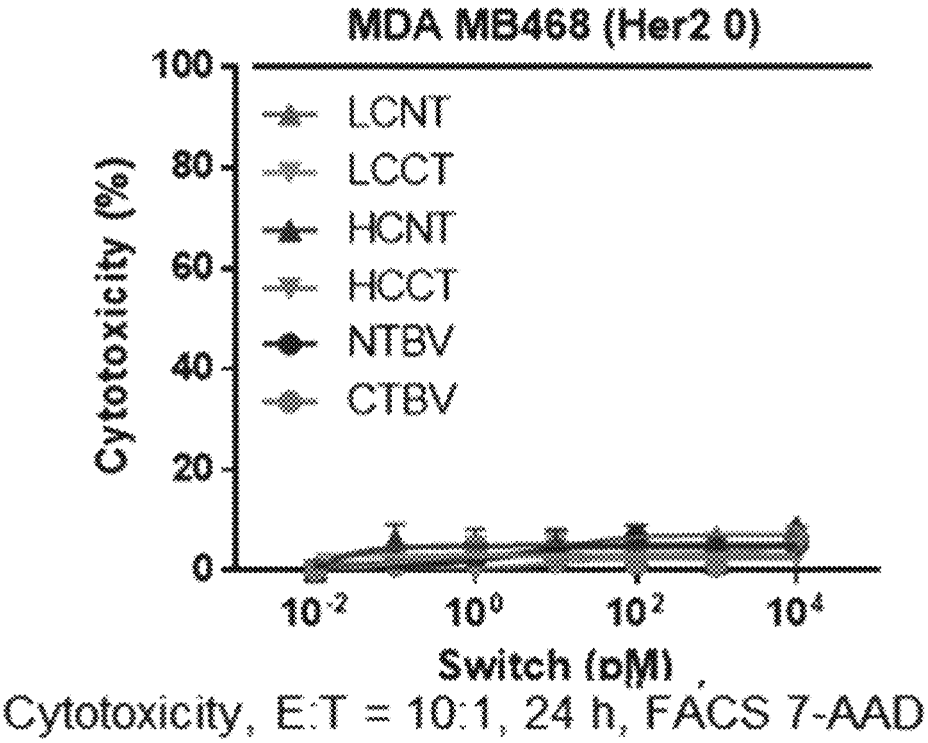

FIGS. 42A-D show in vitro activity of sCAR-T cells with anti-HER2 switch. FIG. 42A shows cytotoxicity of sCAR-T cells against Her2 3+ SKBR3 cells with titrations of anti-HER2 Fab switch designs. FIG. 42B shows cytotoxicity of sCAR-T cells against Her2 2+ MDA MB453 cells with titrations of anti-HER2 Fab switch designs. FIG. 42C shows cytotoxicity of sCAR-T cells against Her2 1+MB435 cells with titrations of anti-HER2 Fab switch designs. FIG. 42D shows cytotoxicity of sCAR-T cells against $Her2^{-}$MB468 cells with titrations of anti-HER2 Fab switch designs. In the experiments shown in FIG. 42A&B, sCAR-T cells were cultured with target cells at a ratio of 10:1, LDH levels were measured in the supernatant following 24h incubation with the anti-HER2 switch. Percent cytotoxicity was calculated by: % cytotoxicity=[(absorbance experimental−absorbance spontaneous average)/(absorbance maximum killing average−absorbance spontaneous average)]×100. This data show that sCAR-T cells have activity against HER2 3+, 2+ and 1+ but not $HER2^-$ cells.

Figure 42E:
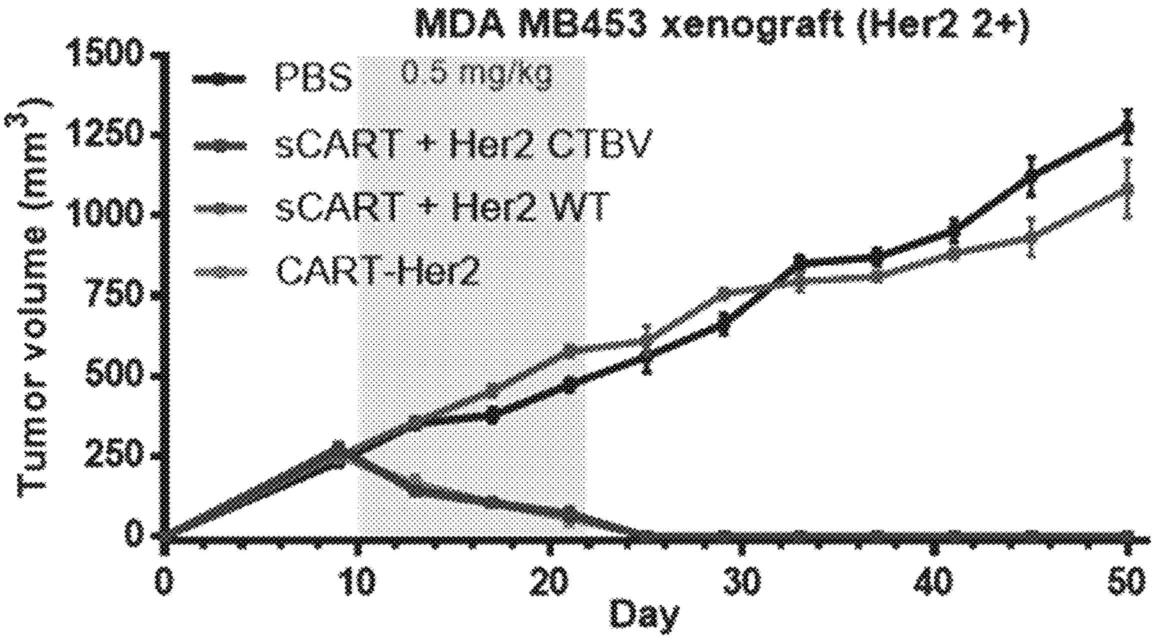
Figure 42F:
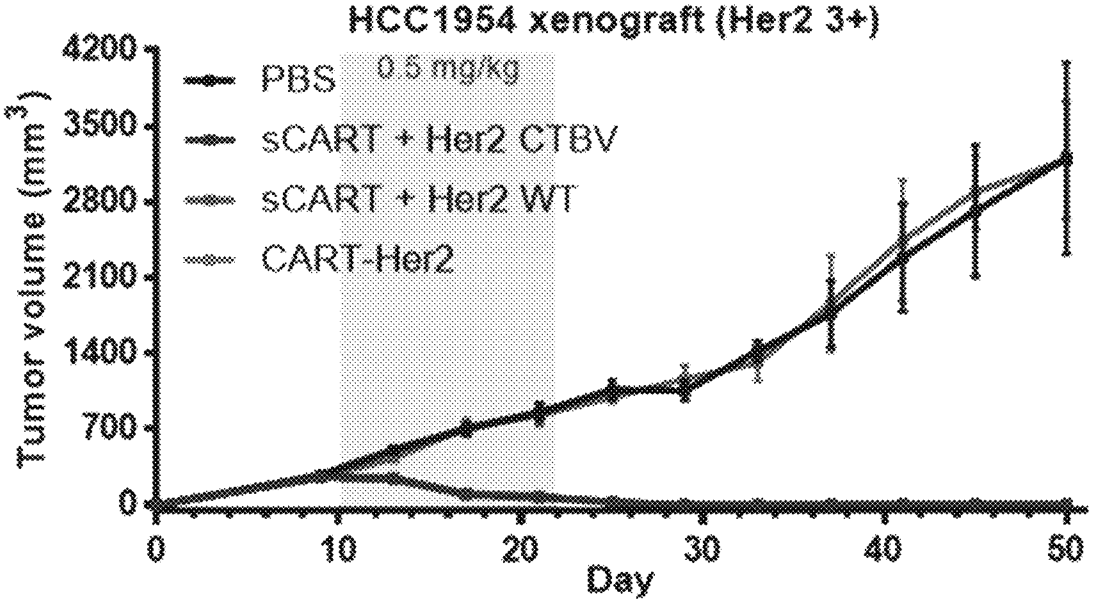

FIGS. 42E-F show in vivo activity of sCAR-T cells with anti-HER2 switch. FIG. 42E shows in vivo cytotoxicity of sCAR-T cells against Her2 2+MDA MB453 cells with the CTBV anti-HER2 Fab switch. FIG. 42F shows in vivo cytotoxicity of sCAR-T cells against Her2 3+HCC1954 cells with the CTBV anti-HER2 Fab switch. The experiments shown in FIG. 42E&F were conducted with 6 to 8-week-old female NSG mice. $5\times10^6$ of HCC1954 (HER2 3+) or MDA MB453 (HER2 2+) the human breast cancer cell lines in 50% Matrigel (BD Bioscience) were subcutaneously implanted into the right flank of mice. Ten days after tumor implantation, mice received $30\times10^6$ sCAR-T cells or the direct HER2 CAR-T cells (both with a transduction efficiency of 45-55%) via intra venous injection. Mice were dosed intravenously with PBS, WT anti-HER2 (no peptide engraft) or the CTBV anti-HER2 q.a.d. from day 10-24 as indicated by the grey shaded area of the data. Tumors were measured twice weekly using calipers. Tumor volume was calculated based on width×length×height.

Example 32. Design Optimization of Multiple sCAR T Cells Targeting Breast Cancers The standard of care for patients with Her2 positive cancer, trastuzumab, is not approved in patients with low levels of Her2 expression (Her2 1+), which occurs in ~35% of breast cancer patients and represents a major unmet medical need. This example demonstrates that optimal sCAR-T cell-switch combinations potently lysed Her2 positive tumors, including Her2 1+ tumors, both in vitro and in vivo with efficacy that is comparable to the conventional anti-Her2 CAR-T cells. Activity of these switches depended strongly on the orientation of the bio-orthogonal immunological synapse, which was determined by location of the tag incorporation in the switch.

To develop switches that redirect the activity of sCAR-T cells to Her2 expressing cancer cells, anti-Her2 (4D5 Fab) switches conjugated to GCN4 peptide at defined sites in the variable or constant regions of antibody antigen binding fragment (Fab). These tag positions were chosen to provide switches that formed the ternary complex between the sCAR-T cell, switch, and the target cell with a diverse range of distance and orientation, thus allowing the empirical optimization of immunological synapse.

Figure 43A:
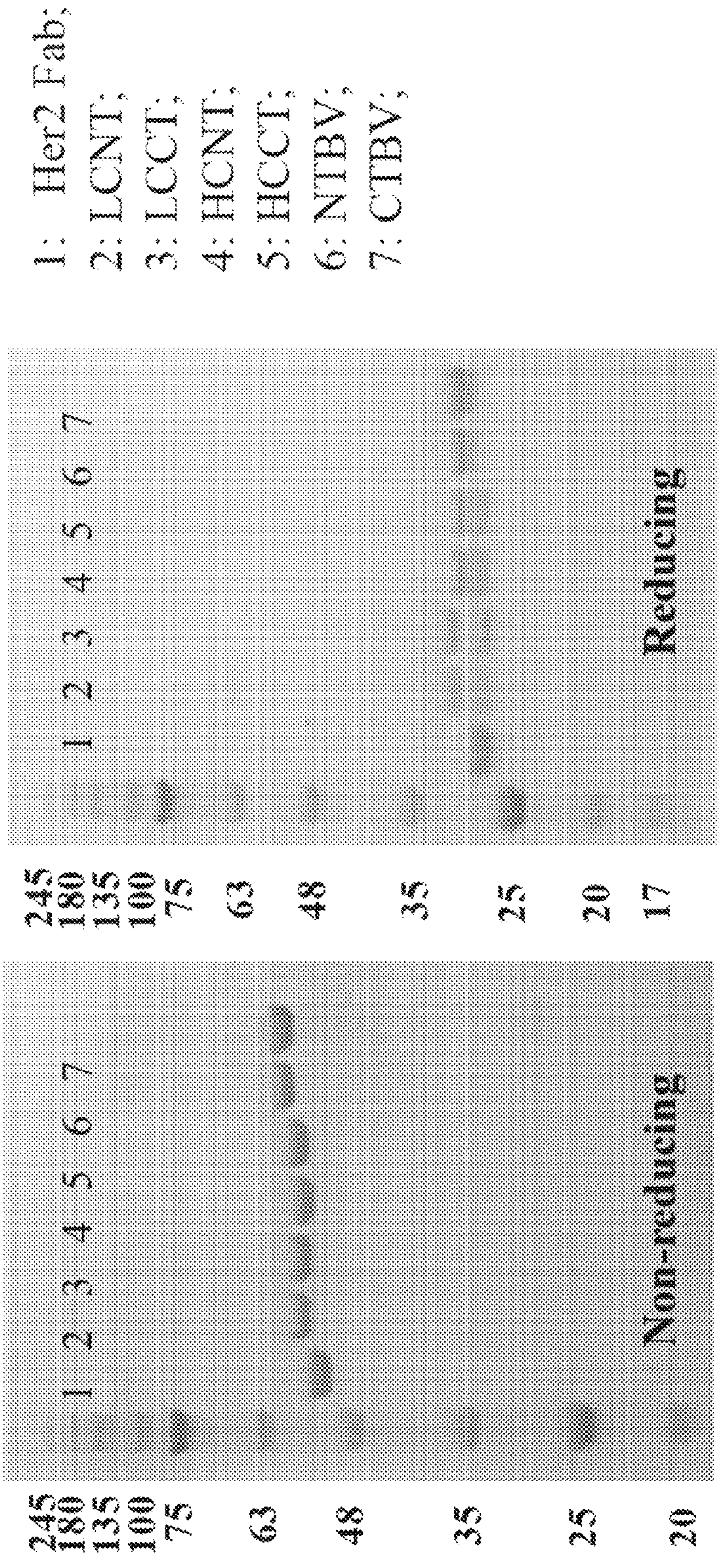
FIG. 43A-B shows production of GCN4-based anti-Her2 Fab switches.
Figure 43B:
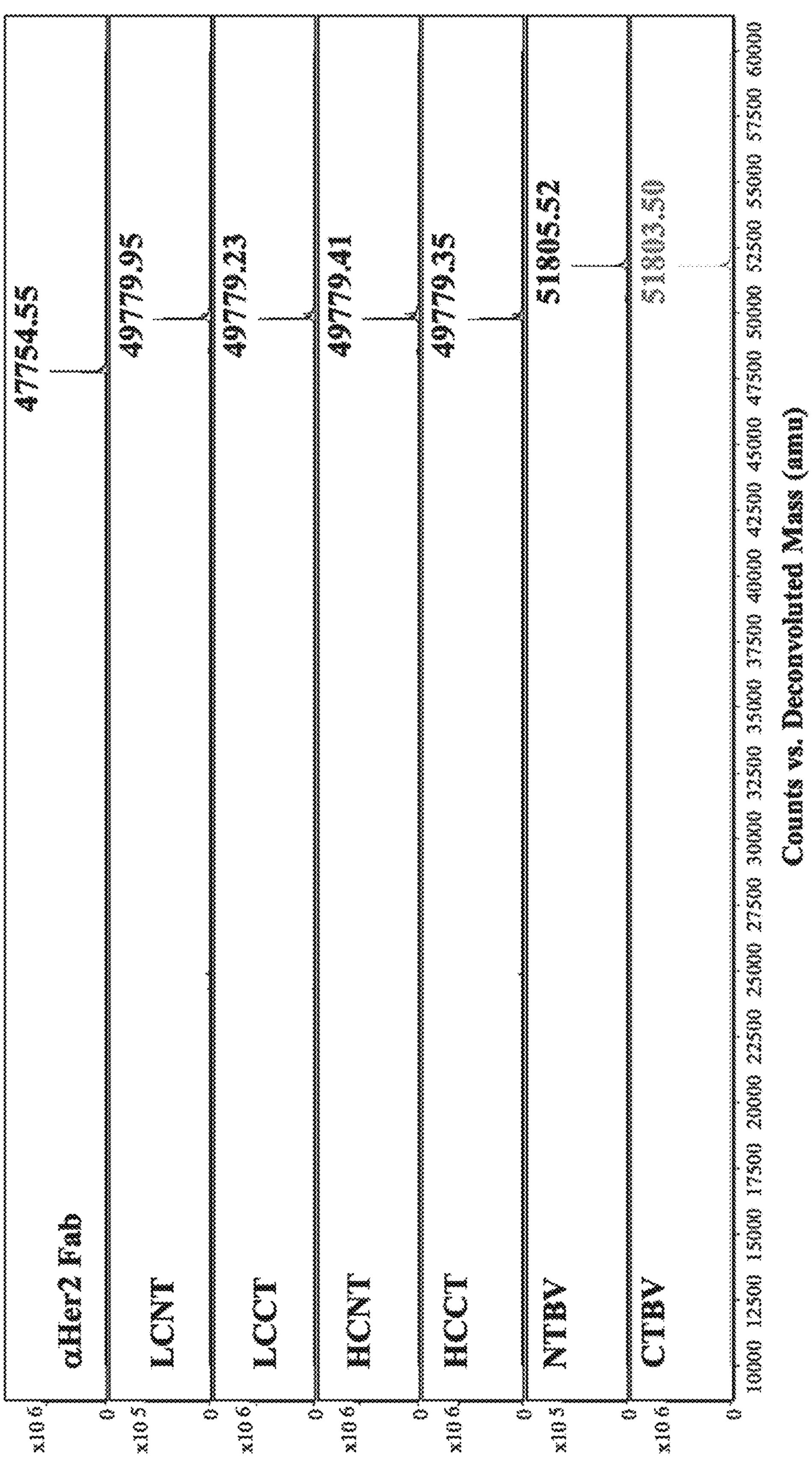
Figure 44A:
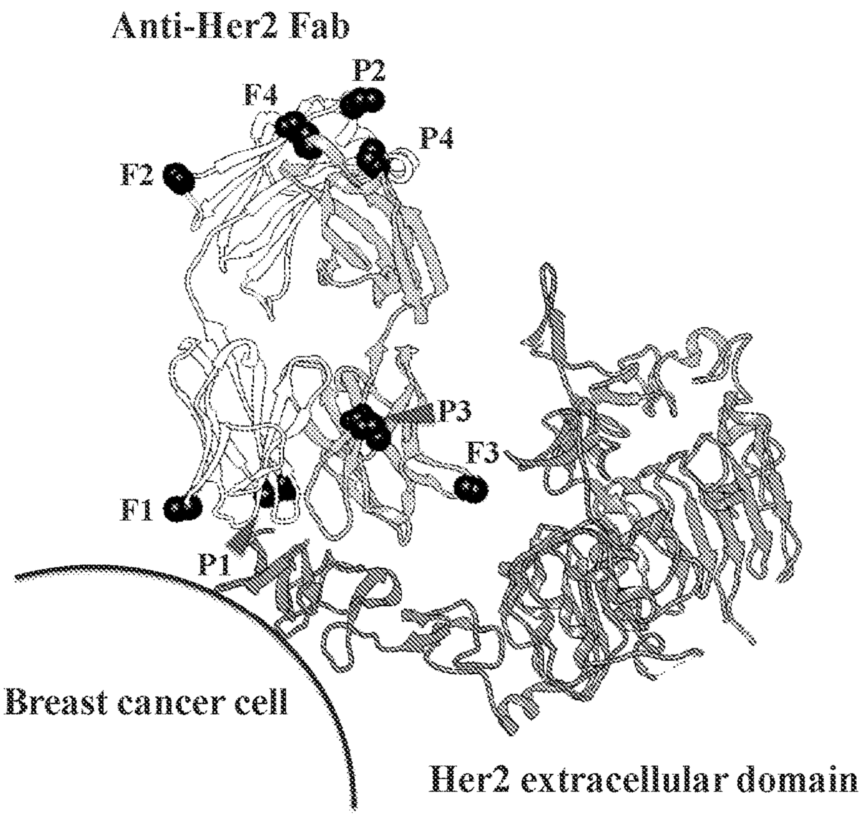
FIG. 44A-D shows construction and testing of various PNE (GCN4) anti-Her2 Fab switches and different short and long hinged anti-GCN4 CAR-T cells.

To develop GCN4 switches, we grafted the GCN4 peptide sequence to the N- or C-terminus of the 4D5 Fab heavy chain or light chains to create the light chain N-terminus (LCNT), light chain C-terminus (LCCT), heavy chain N-terminus (HCNT) or heavy chain C-terminus (HCCT) engrafted switches. A GGGGS peptide linker was used to separate the peptide tag from the Fab. To create bivalent switches, the GCN4 peptide was grafted onto either the N- or C-terminus of the heavy and light chain to create NTBV or CTBV respectively (FIG. 44A). Mass spectrometric analysis of anti-Her2-GCN4 fusions obtained on an Agilent Quadruple Time-of-Flight (QTOF) mass spectrometer. Deconvoluted masses were obtained using Agilent Qualitative Analysis software (FIG. 43B, Table 34).

TABLE 34

QTOF-MS characterization of different anti-Her2 Fab and the GCN4 fusions

| Constructs | Non-reducing condition (−DTT) Expected/Observed Mass | Reducing condition (+DTT) Expected/Observed Mass |
|---|---|---|
| Wild type | 47762/47755 | 23457/23454 (light chain)<br>24305/24302 (heavy chain) |
| LCNT | 49786/49780 | 25481/25479 (LC-NT light chain)<br>24305/24302 (heavy chain) |
| LCCT | 49786/49779 | 25481/25479 (LC-CT light chain)<br>24305/24302 (heavy chain) |
| HCNT | 49787/49779 | 23457/23454 (light chain)<br>26330/26327 (HC-NT heavy chain) |
| HCCT | 49787/49779 | 23457/23454 (light chain)<br>26330/26327 (HC-CT heavy chain) |
| NTBV | 51811/51806 | 25481/25479 (LC-NT light chain)<br>26330/26327 (HC-NT heavy chain) |
| CTBV | 51811/51804 | 25481/25478 (LC-NT light chain)<br>26330/26326 (HC-NT heavy chain) |

Figure 44B:
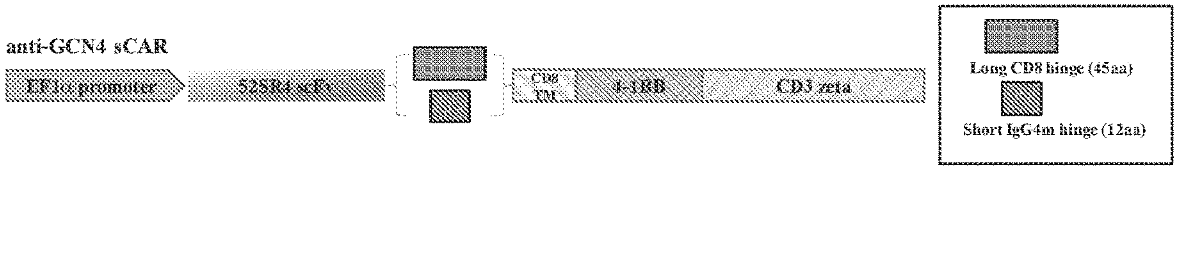
Figure 44B:
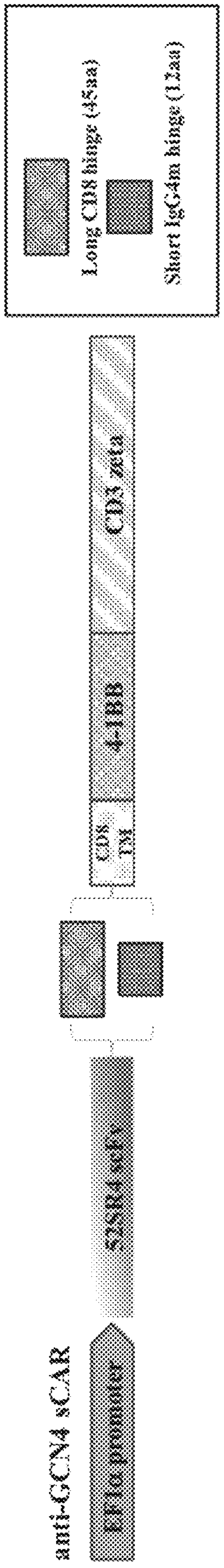
Figure 45:
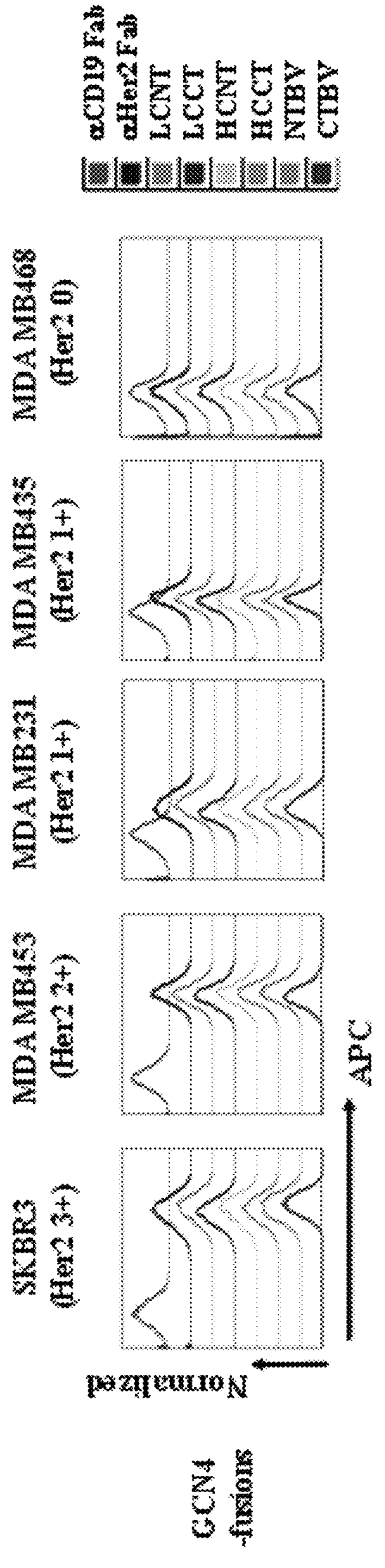
FIG. 45 shows flow cytometry analysis of GCN4-based switches and wild type 4D5 Fab bound to breast cancer cells with a range of Her2 expression levels. Bound switches were detected with an Alexa Fluor647 conjugated anti-human IgG (H+L) secondary antibody.

GCN4-based switches bound Her2 expressing cancer cells to a similar extent as wild type 4D5 Fab (Table 35, FIG. 45) and did not bind to MDA MB468 cancer cells lacking Her2 expression. Replacing the long 45 amino acid CD8 hinge CAR region with a shorter 12 amino acid hinge derived from a dimeric mutant of the IgG4 hinge (IgG4m) improved anti-GCN4 sCAR-T cell activity in the context of targeting CD19 and CD20, putatively by reducing the overall distance between the sCAR-T cell and target cell (FIG. 44B). However, it is unknown if the increased activity of the IgG4m hinge can be extended to the Her2 antigen.

TABLE 35

Comparison of binding activity of different GCN4 tagged anti-Her2 fusions on breast cancer cells

| Cell | Her2 | MFI[a]/Relative Binding Index[b] | | | | | | | |
|---|---|---|---|---|---|---|---|---|---|
| line | Level | anti-CD19 Fab | anti-Her2 Fab | LCNT | LLCT | HCNT | HCCT | NTBV | CTBV |
| SKBR3 | Her2 3+ | 151 | 14306/95 | 18068/120 | 14977/99 | 17535/116 | 17381/115 | 19253/128 | 22931/152 |
| MDA MB453 | Her2 2+ | 147 | 8081/55 | 7342/50 | 7041/48 | 7309/50 | 7947/54 | 8195/56 | 6910/47 |
| MDA MB231 | Her2 1+ | 87 | 424/5 | 475/5 | 334/4 | 414/5 | 418/5 | 458/5 | 406/5 |
| MDA MB435 | Her2 1+ | 94 | 245/3 | 213/2 | 188/2 | 191/2 | 206/2 | 210/2 | 216/2 |

TABLE 35-continued

Comparison of binding activity of different GCN4 tagged anti-Her2 fusions on breast cancer cells

| Cell line | Her2 Level | MFI[a]/Relative Binding Index[b] | | | | | | | |
|---|---|---|---|---|---|---|---|---|---|
| | | anti-CD19 Fab | anti-Her2 Fab | LCNT | LLCT | HCNT | HCCT | NTBV | CTBV |
| MDA MB468 | Her2 0 | 80 | 86/1 | 84/1 | 89/1 | 84/1 | 90/1 | 92/1 | 86/1 |

Figure 46A:
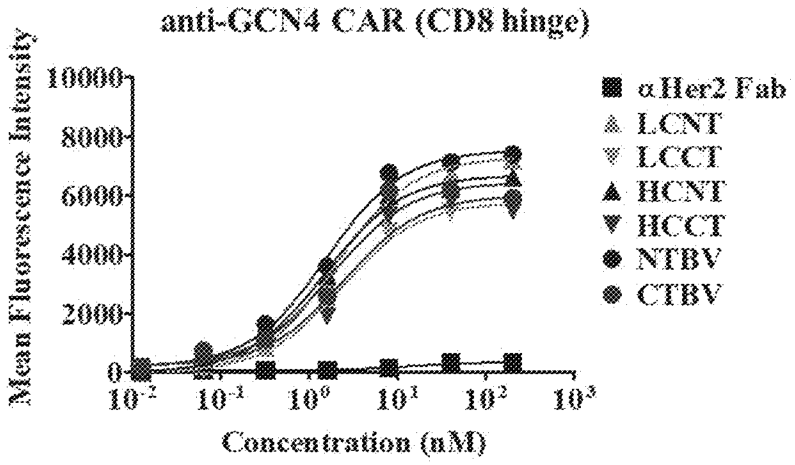
FIG. 46A-C shows binding of different GCN4 switches to GCN4 specific CAR-T cells (both CD8 and IgG4m).
Figure 46B:
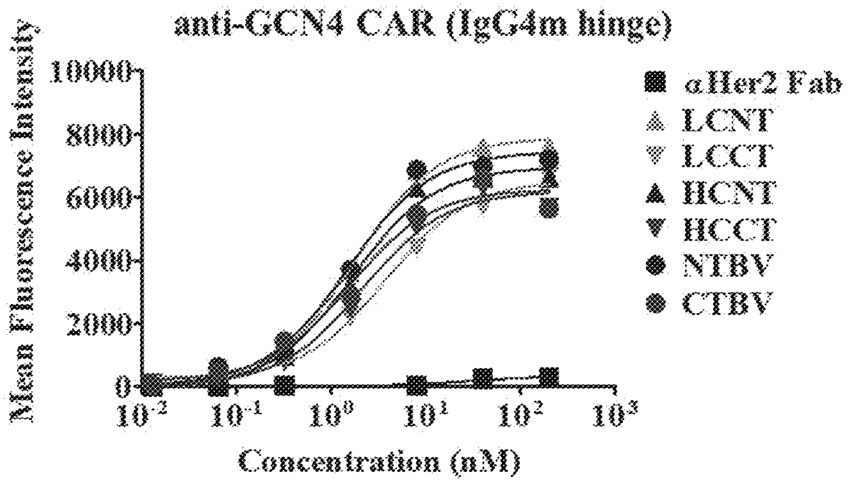
Figure 46C:
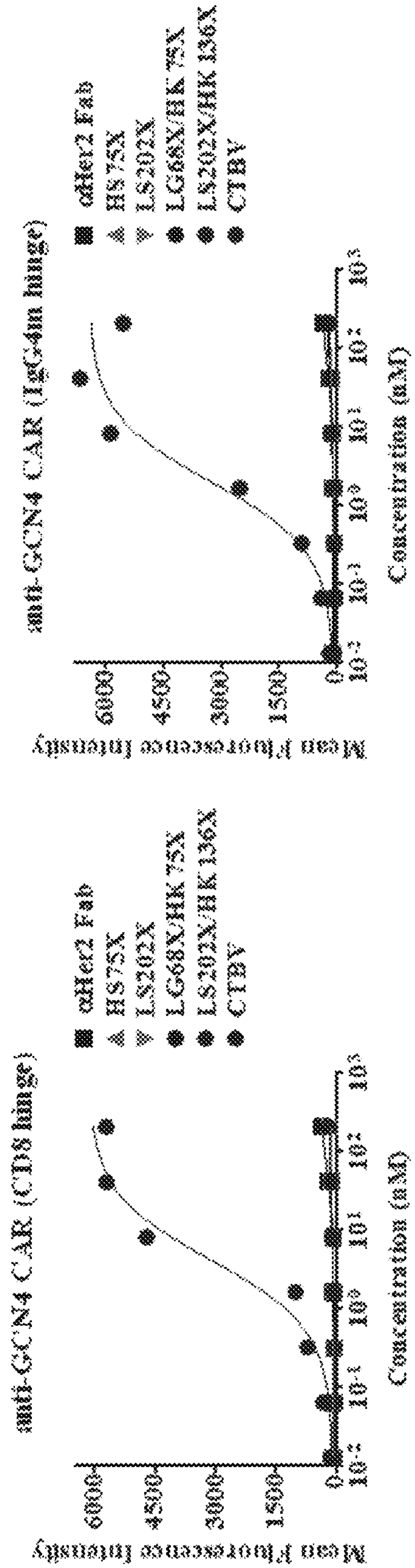

[a]MFI: mean fluorescence intensity calculated by software FlowJo X10.0.6
[b]Relative Binding index represent MFI of indicated antibody/MFI of anti-CD19 Fab Next, the capacity of sCAR-T cells with CD8 or IgG4m hinges to bind their corresponding anti-Her2 switches was tested. The GCN4 switches were used to stain anti-GCN4 sCAR-T cells, and detected with an APC-labeled anti-human kappa-chain antibody specific for the constant region at the Fab. As shown in FIGS. 46A and 46B, all the switches bound to their corresponding sCAR-T cells with similar $EC_{50}$ (1.4 to 3.8 nM for GCN4-based sCAR-T cells). The wild type 4D5 Fab failed to bind any sCAR-T cells, demonstrating the specificity of the sCAR to their specific tags. Together with the target cell binding assay, we confirmed that PNE grafted fusions reserved the binding specificity to the target cells as well as the tag recognition of 4D5-based switch by the sCAR-T cells.

Figure 44C:
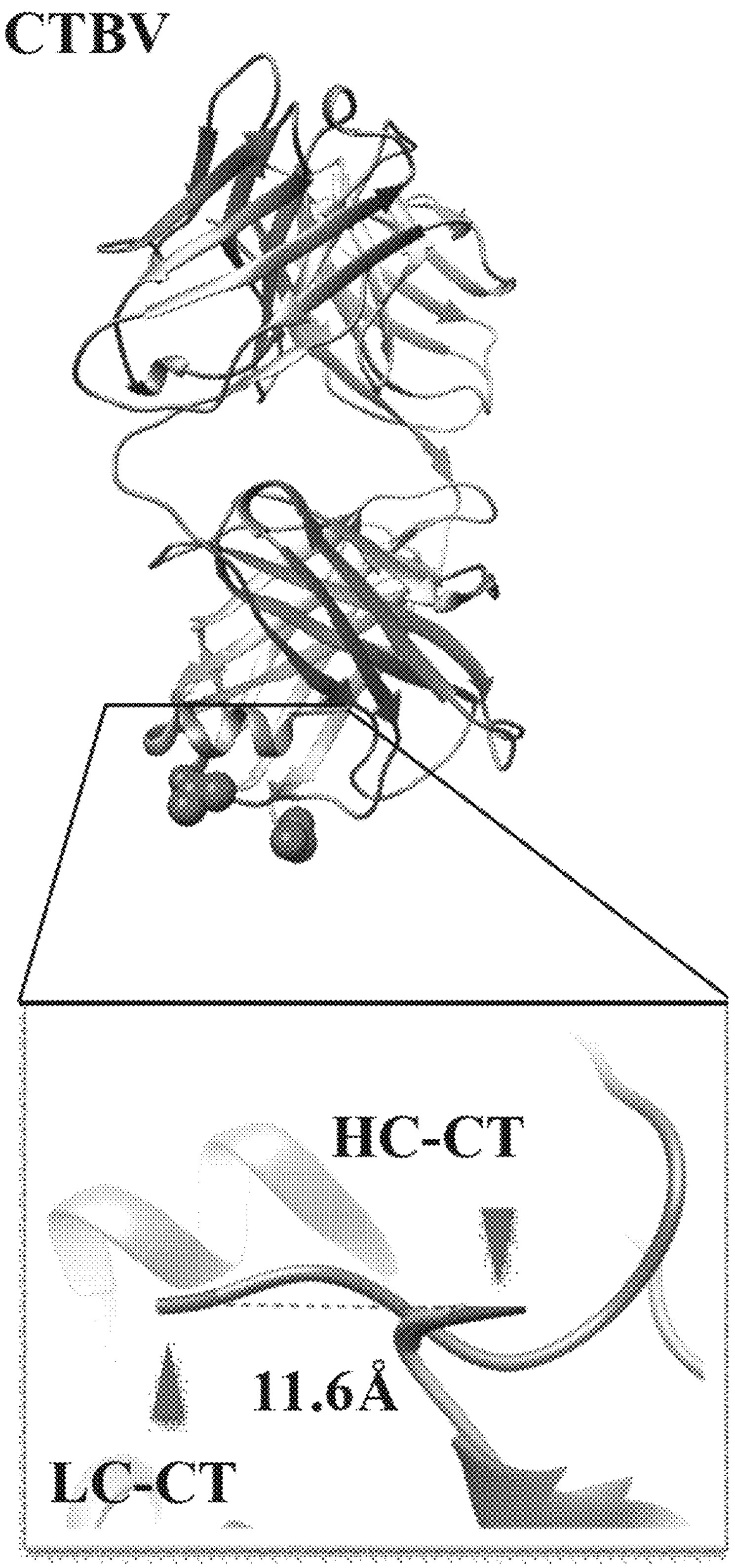
Figure 44D:
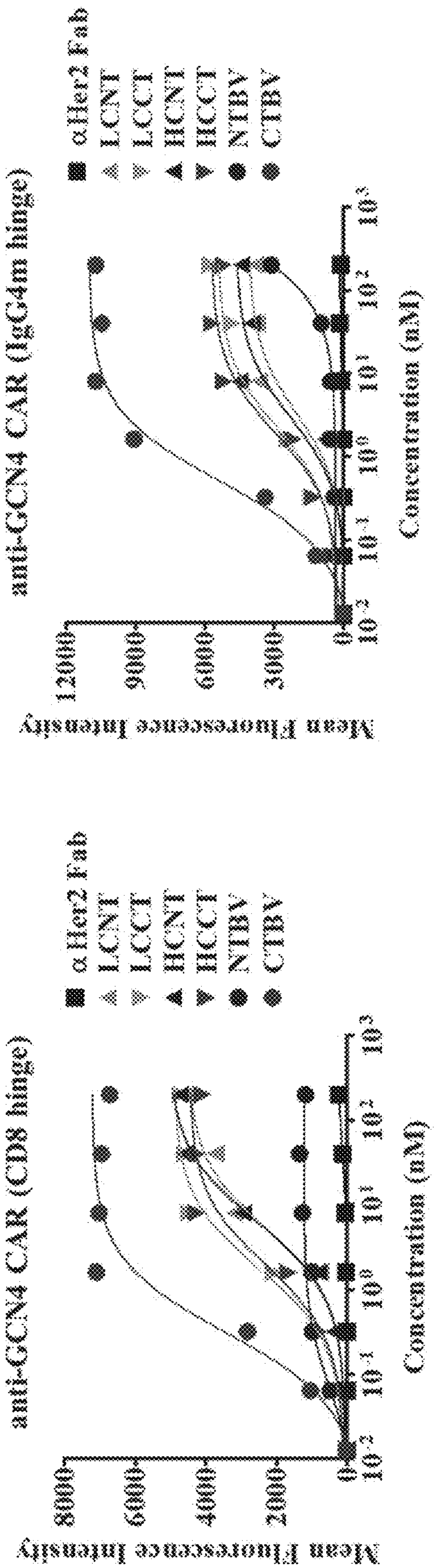

As shown in FIG. 44C and Table 36, switches with the GCN4 distal to the antigen binding interface formed ternary complex more effectively than switches where the tags were proximal to the antigen binding interface. Conversely, switches with the GCN4 tag placed distal from the antigen binding domain allow for efficient ternary complex formation as they display the tag for efficient sCAR binding. Bivalent switches were observed to form more efficient ternary complexes compared with their monovalent counterparts, presumably due to increased avidity, with the greatest complex formation observed for the distal, bivalent switch (CTBV) (FIG. 44C).

TABLE 36

Comparison of crosslinking ability between anti-GCN4 CAR-T cells and Her2 ECD by different GCN4 tagged anti-Her2 fusions. $EC_{50}$ (nM)/Maximal binding (MFI × 100)

| | Anti GCN4 CAR-EC with CD8 hinge | Anti-GCN4 CAR-EC with IgG4m hinge |
|---|---|---|
| Anti-Her2 Fab | N.D./2.9 ± 0.5 | N.D./1.6 ± 1.0 |
| LCNT | 5.1 ± 0.2/45.3 ± 1.6 | 3.3 ± 0.2/41.2 ± 3.5 |
| LCCT | 1.8 ± 0.1/49.2 ± 3.5 | 2.2 ± 0.2/54.6 ± 4.4 |
| HCNT | 6.3 ± 0.4/50.6 ± 2.4 | 2.9 ± 0.2/46.6 ± 2.1 |
| HCCT | 1.9 ± 0.2/44.7 ± 3.1 | 1.9 ± 0.1/57.4 ± 1.2 |
| NTBV | N.D./12.2 ± 1.1 | N.D./31.4 ± 0.3 |
| CTBV | 0.3 ± 0.0/72.1 ± 3.1 | 0.5 ± 0.1/110.1 ± 2.5 |

Abbreviations: $EC_{50}$, half-maximal binding concentration; N.D., not determined.
Data shown are a mean of duplicate samples ± SD.

Influence of Hinge Design on sCAR-T Cell Activity.

To test if the results of ternary complex assay correlated with sCAR-T activity, we combinatorially tested sCAR-T cell activation with representative monovalent (HCNT and LCCT GCN4) and bivalent (NTBV and CTBV GCN4) switches at 100 pM against each Her2 expressing cancer cell.

Figure 47:
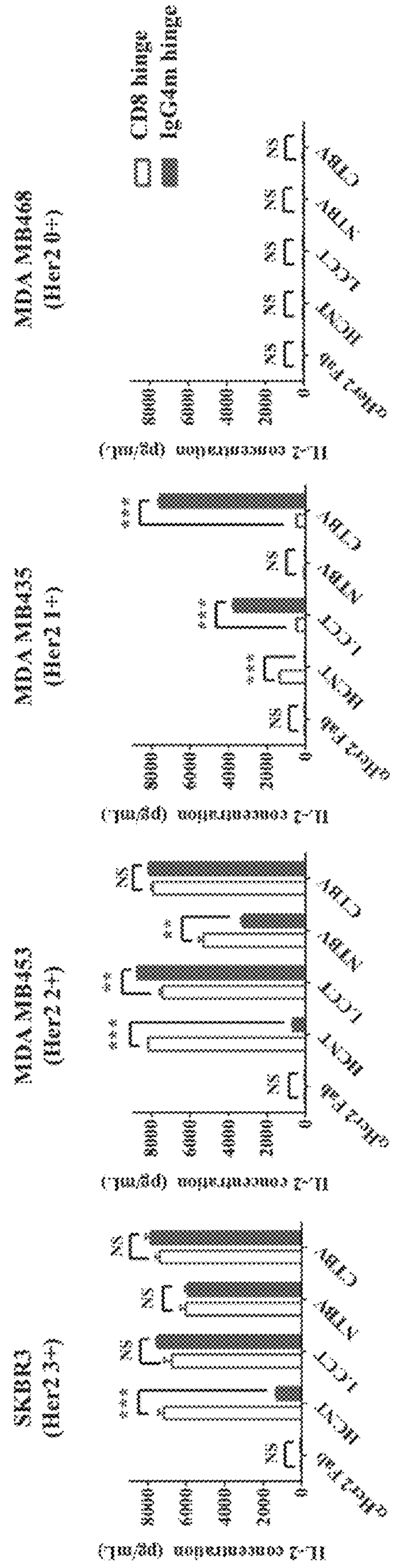
FIG. 47 shows GCN4 switch-mediated redirection of various anti-GCN4 sCAR-T cells with different hinge lengths against different Her2 expressing cancer cells, as evaluated by flow cytometry with staining for CD69 and CD25. *=$p<0.005$, =$p<0.05$ and NS=$p>0.05$ were calculated using the Student's t-test, and a p value <0.05 was considered significant.
Figure 48A:
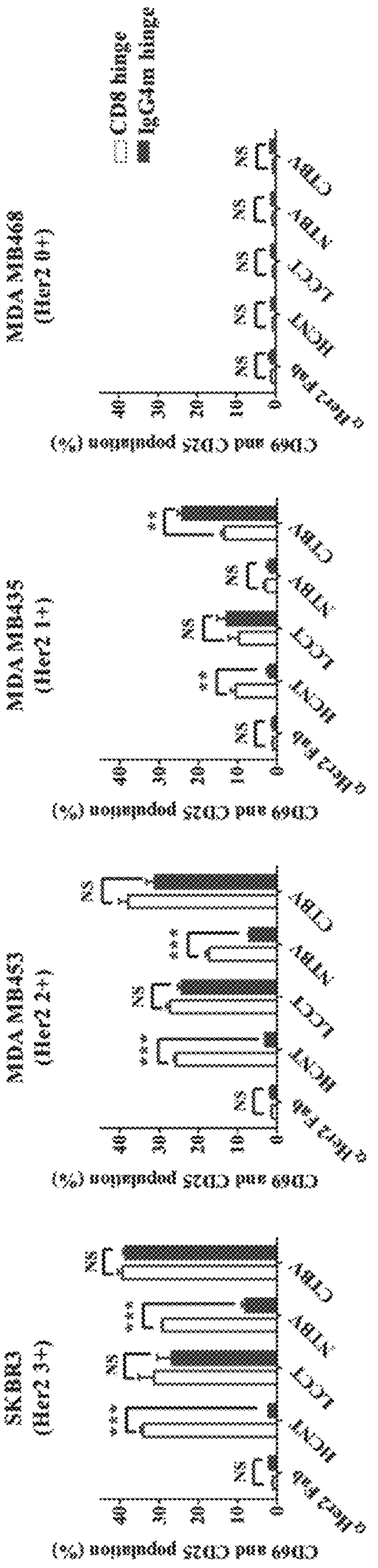
FIG. 48A-C shows sCAR-T activation by combinations of various switches and hinge length anti-GCN4 sCAR-T cells against different Her2 expressing cancer cells.
Figure 48B:
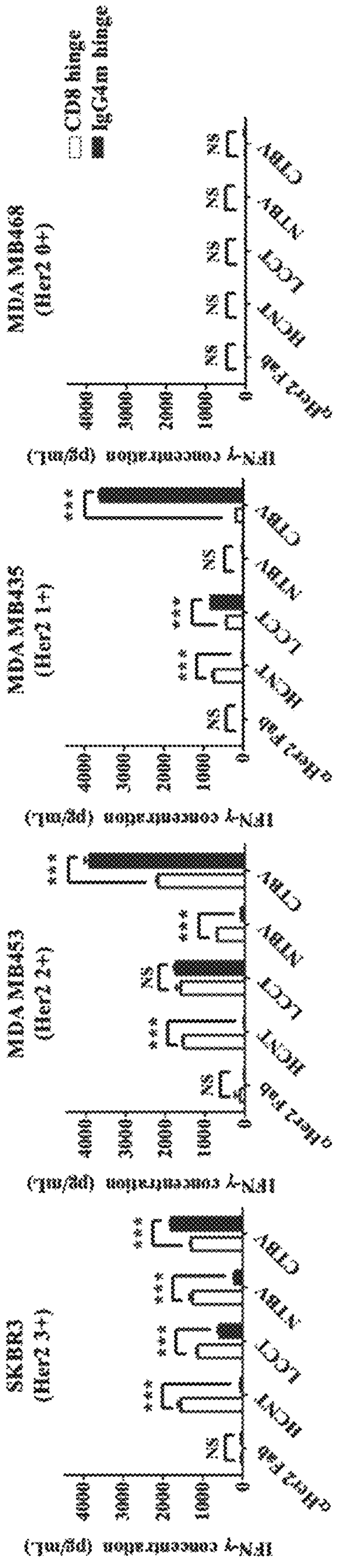
Figure 48C:
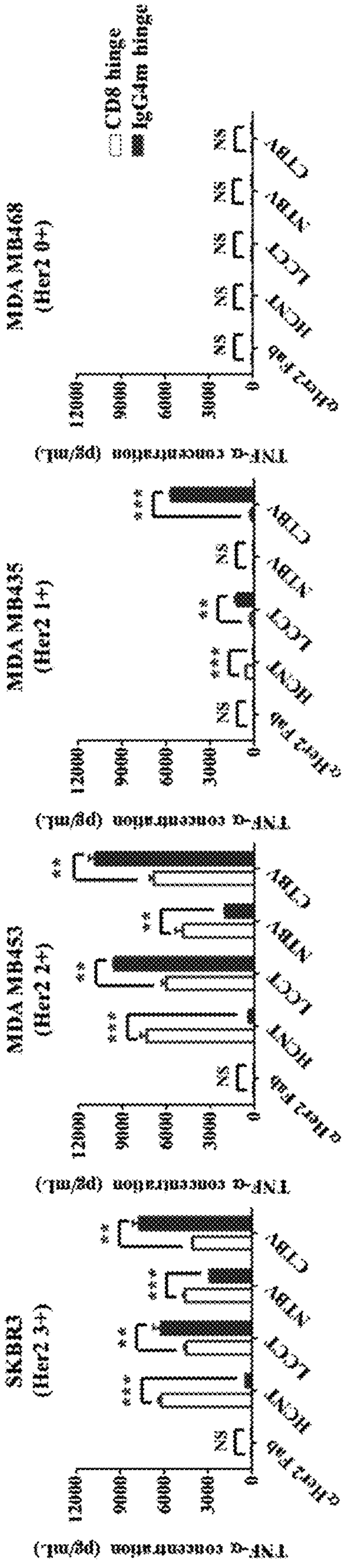

For GCN4-based switches, the same hinge was not optimal for all representative switches tested (FIG. 47, FIGS. 48 A-C). The anti-GCN4 sCAR harboring the CD8 hinge showed the greatest T cell activation and cytokine release when redirected by the switches grafted with GCN4 on the N-terminal (HCNT), but when GCN4 was grafted on the C-terminal (LCCT), the IgG4m hinge-based anti-GCN4 sCAR was optimal. Conversely, the IgG4m hinge-based anti-GCN4 sCAR had superior activation and cytokine release with C-terminal grafted switches. This suggested that the compensatory design of the sCAR hinge and switch labeling sites was required to find the optimal distance and orientation for sCAR-T cell cytotoxicity for the GCN4-based sCAR-T cells.

Figure 49:
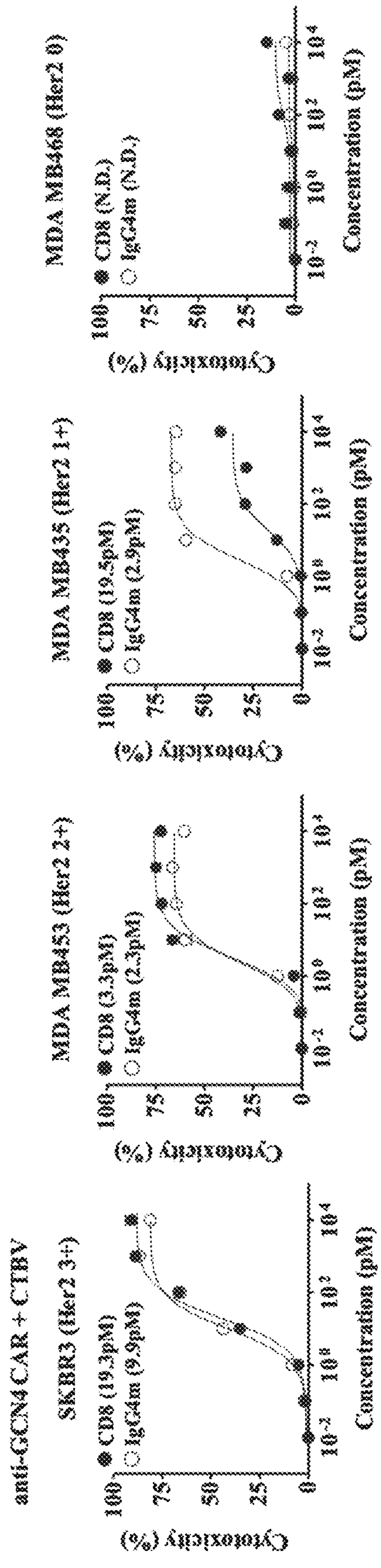
FIG. 49 shows in vitro cytotoxicity of GCN4-specific sCAR-T cells harboring the CD8 or IgG4m hinges and bivalent switches. sCAR-T cells were incubated with SKBR3 (Her2 3+), MDA MB453 (Her2 2+), MDA MB435 (Her2 1+) or MDA MB468 (Her2 0) cancer cells at an E: T=10:1 ratio with serial dilution of GCN4 switch CTBV. Cytotoxicity was assayed after 24h by measuring the amount of lactate dehydrogenase (LDH) released into cultured media. The EC50 values (mean±SD) were determined and listed in parenthesis in the figure legend inserts.
Figure 50A:
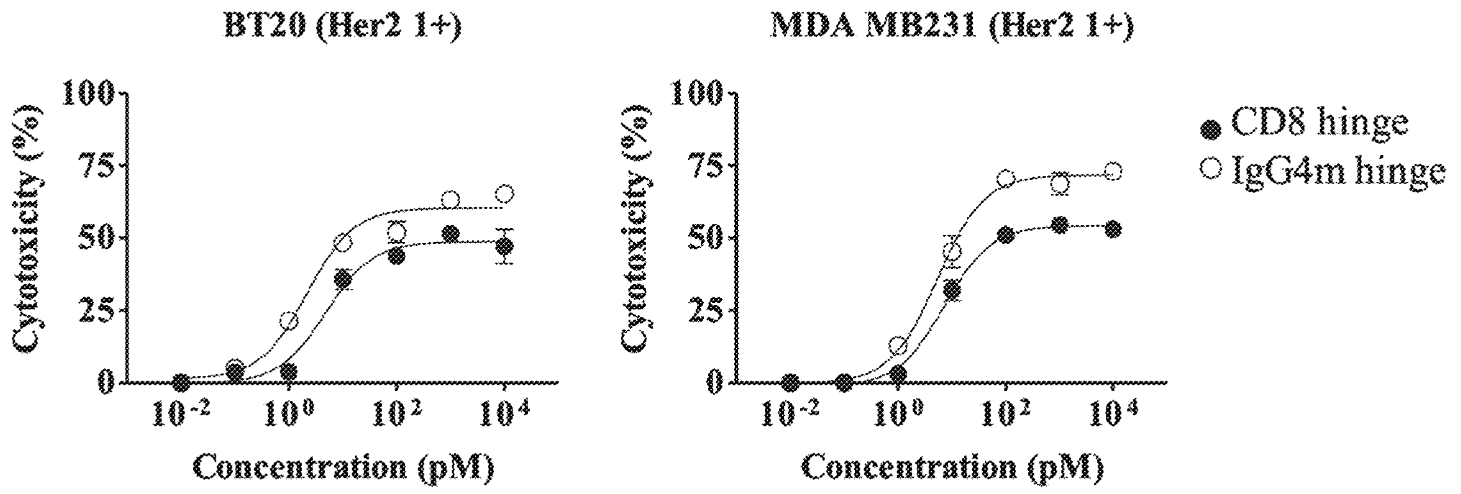
FIG. 50A-B shows in vitro cytotoxicity.
Figure 50B:
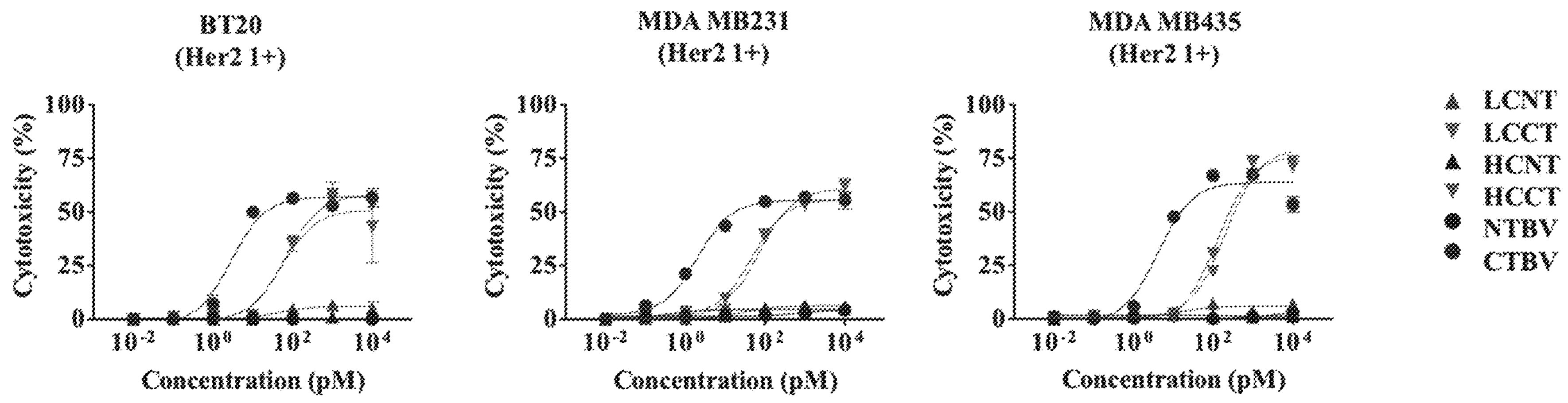

To further understand the differences observed for CD8 and IgG4m hinge designs for GCN4 sCARs, in vitro cytotoxicity was measured against a panel of breast cancer cells with different Her2 antigen densities. The CTBV GCN4 switch was used to redirect anti-GCN4 sCAR-T cells. This switch provided the greatest ternary complex formation and sCAR-T cell activation against Her2-positive cells. In agreement with this result, anti-GCN4 sCAR-T cells afforded greater potency of cytotoxicity harboring the IgG4m hinge compared with the CD8 hinge (FIG. 49). Differences in the $EC_{50}$ of cytotoxicity for different hinges were nominal against cells with high levels of Her2 expression (SKBR3, Her2 3+; MDA MB453, Her2 2+); however, the effect of hinge design afforded a marked difference on cells at low levels of Her2 expression (MDA MB435, Her2 1+). These findings were reproducible on Her2 1+ cancer cells BT20 and MDA MB231 (FIG. 50), providing further confirmation of the correlation with antigen density. This may be due to the limited number of immunological synapses that may be formed by the low antigen density cells which increases the relative contribution of each synapse, thus placing a greater emphasis on optimal complex formation.

Novel PNE FLAG-Based Switchable CAR Strategy

Figure 51:
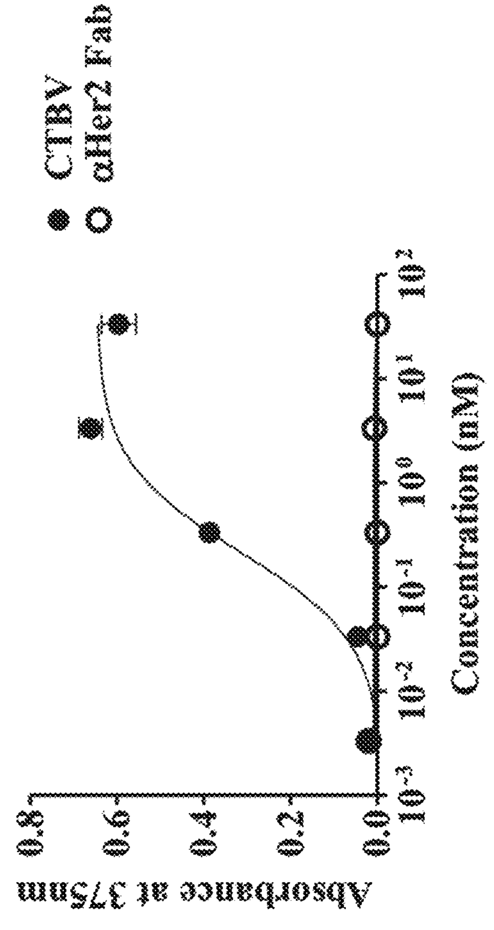
FIG. 51 shows evaluation of the binding of the anti-FLAG antibody (5B3 monoclonal antibody) to an anti-Her2-FLAG switch and wild type anti-Her2 Fab (without the FLAG tag) by ELISA.

To understand the generalizability of the switchable approach, another sCAR system based on the 9 amino acid FLAG sequence (SDYKDDDK; SEQ ID NO: 258) was developed. This short, hydrophilic PNE is reported to be non-immunogenic, and consequently is an ideal target for the sCAR. To create an anti-FLAG scFv, we immunized BALB/c mice with the FLAG peptide grafted to a prototypical Fab to obtain high affinity (apparent affinity of $2.2\times10^{-10}$ M, (FIG. 51) monoclonal antibody (clone: 5B3) from hybridoma screens. The heavy and light chain variable regions were subcloned subcloned in scFv format in the second generation CAR vector harboring the CD8 or IgG4m hinge as described above.

Figure 52A:
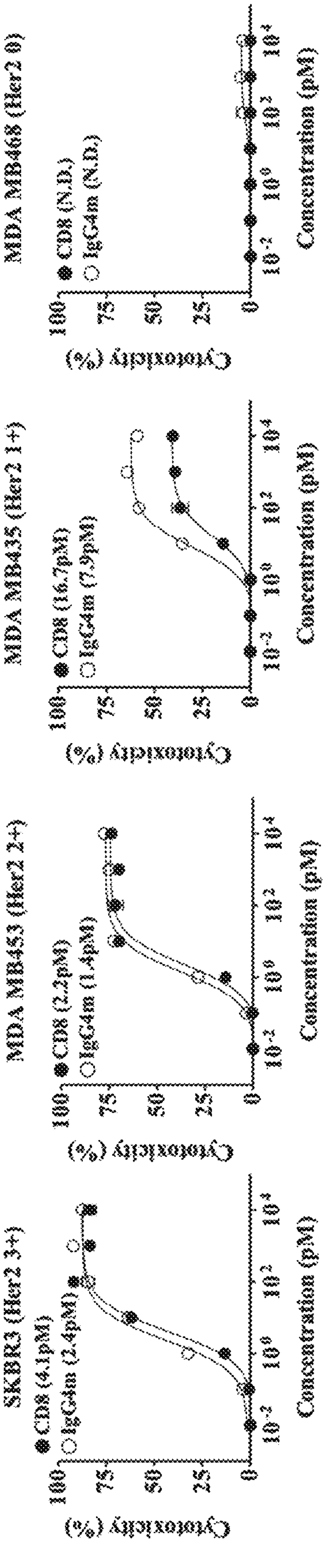
FIG. 52A-B shows FLAG-based switchable CAR-T cells by combination of CTBV and different hinge length sCAR-T cells against different Her2 expressing cancer cells.
Figure 52B:
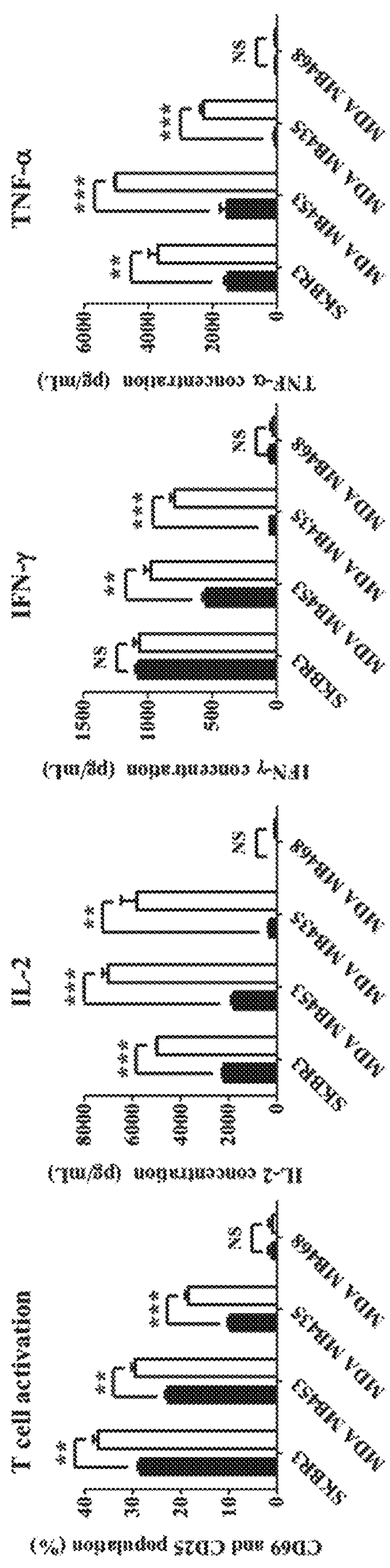

Based on the switch design optimization for GCN4 switches, a bivalent FLAG switch was made by fusing the FLAG peptide to the C-terminus of both heavy and light chains (CTBV) of anti-Her2 Fab. A (GGGGS)2 linker was used to link the FLAG peptide to the Fab which corresponded to the linker used in the immunization strategy to develop the 5B3 scFv. Following expression from *E. coli*, FLAG switches were purified to >95%, and homogeneity was confirmed by SDS-PAGE and MS analysis. To test the activity of the CTBV Flag switch with the CD8 or IgG4m-based sCAR-T cell, the functional activities of this switch with these CARs against Her2 positive cancer cells was compared. Corresponding with the GCN4 CTBV switch, the FLAG CTBV switch demonstrated enhanced activity with FLAG sCAR-T harboring IgG4m hinge compared to the CD8 hinge (FIG. 52A). This correlated with significantly greater T cell activation and cytokine release (IL-2, IFN-γ and TNF-α) with the IgG4m-based hinge FLAG sCAR-T cells, especially on Her2 1+ cells. (FIG. 52B).

Figure 53:
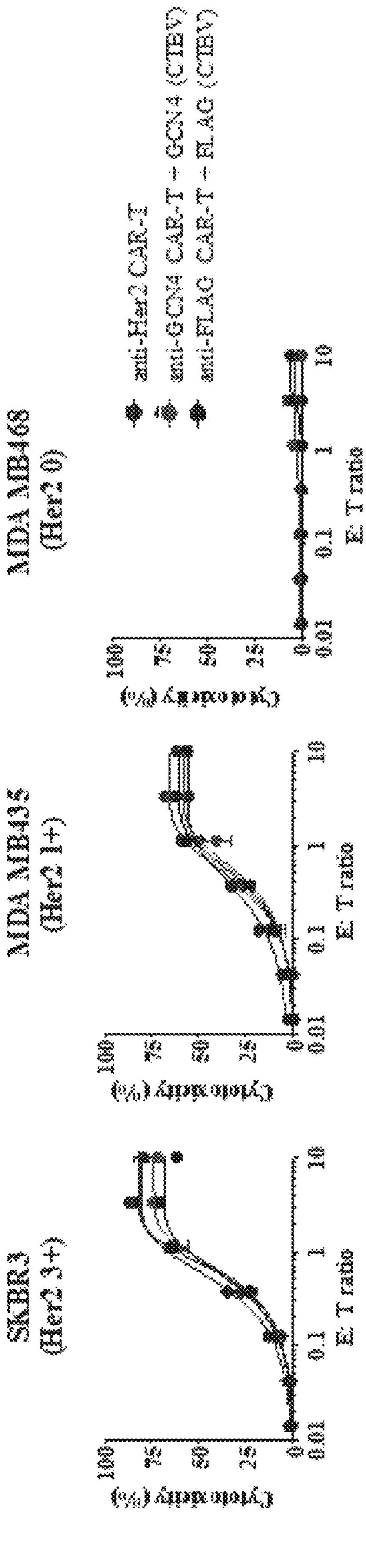
FIG. 53 shows in vitro comparison of anti-Her2 CAR-T cells with optimized anti-GCN4 and anti-FLAG sCAR-T cells. The anti-Her2 CAR-T or sCAR-T cells were co-cultured with Her2 expressing cancer cells at indicated E: T ratios with 50 pM of the corresponding bivalent switches, and target cell lysis was determined by LDH release.
Figure 54:
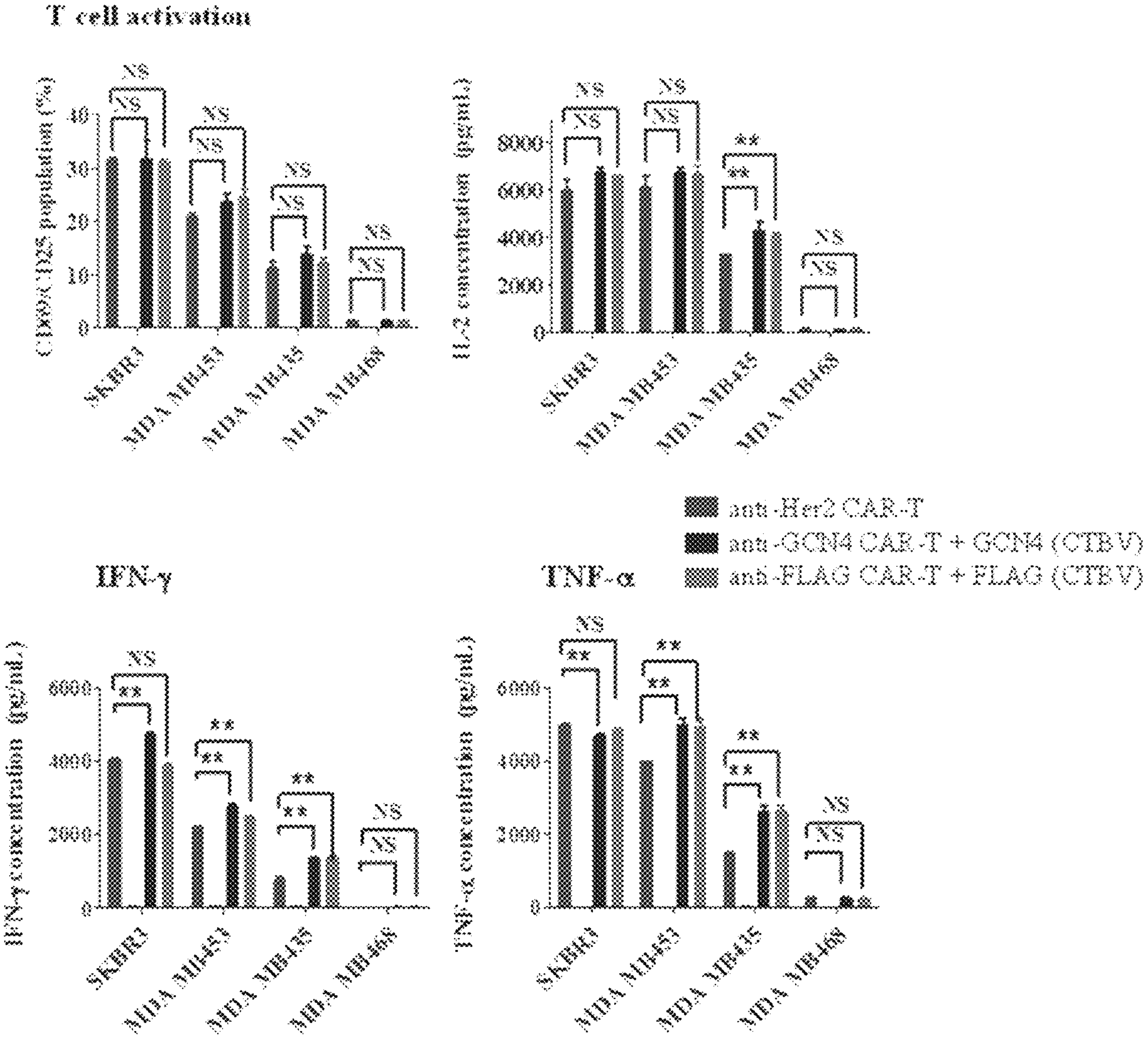
FIG. 54 shows in vitro comparison of anti-Her2 CAR-T cells with optimized anti-GCN4 and anti-FLAG sCAR-T cells. T cell activation was evaluated by CD69/CD25 staining and the cytokine release (IL-2, IFN-γ and TNF-α) in media was measured by ELISA. Error bars represent SD. *=$p<0.005$, =$p<0.05$ and NS=$p>0.05$ were calculated using the Student's t-test.

To compare the activity of the optimal switch/sCAR pair with conventional anti-Her2 CAR, in vitro cytotoxicity assays were carried out at a range of E: T ratios against the representative Her2 3+, 2+, 1+ and 0 cancer cells. The optimal sCAR-T combinations: GCN4 (CTBV with IgG4m hinge CAR) and FLAG (CTBV with IgG4m hinge CAR) were selected. For sCAR-T cells, 50 pM of each switch was used. As shown in FIG. 53 sCAR-T cells lysed Her2 cancer cells with comparable efficacy to the conventional CAR-Her2 across all E: T ratios. Both sCAR-T cells and conventional CAR-T cells showed good selectivity for Her2 cells with little lysis on Her2 negative MDA MB468 cells. Furthermore, T cell activation and cytokines at the E: T ratio of 5:1 demonstrated that the optimized sCAR-T cells afforded comparable induction of T cell function to the conventional anti-Her2 CAR-T cells (FIG. 54).

Comparison of Conventional CAR-T with SCAR-T Strategies.

Figure 55A:
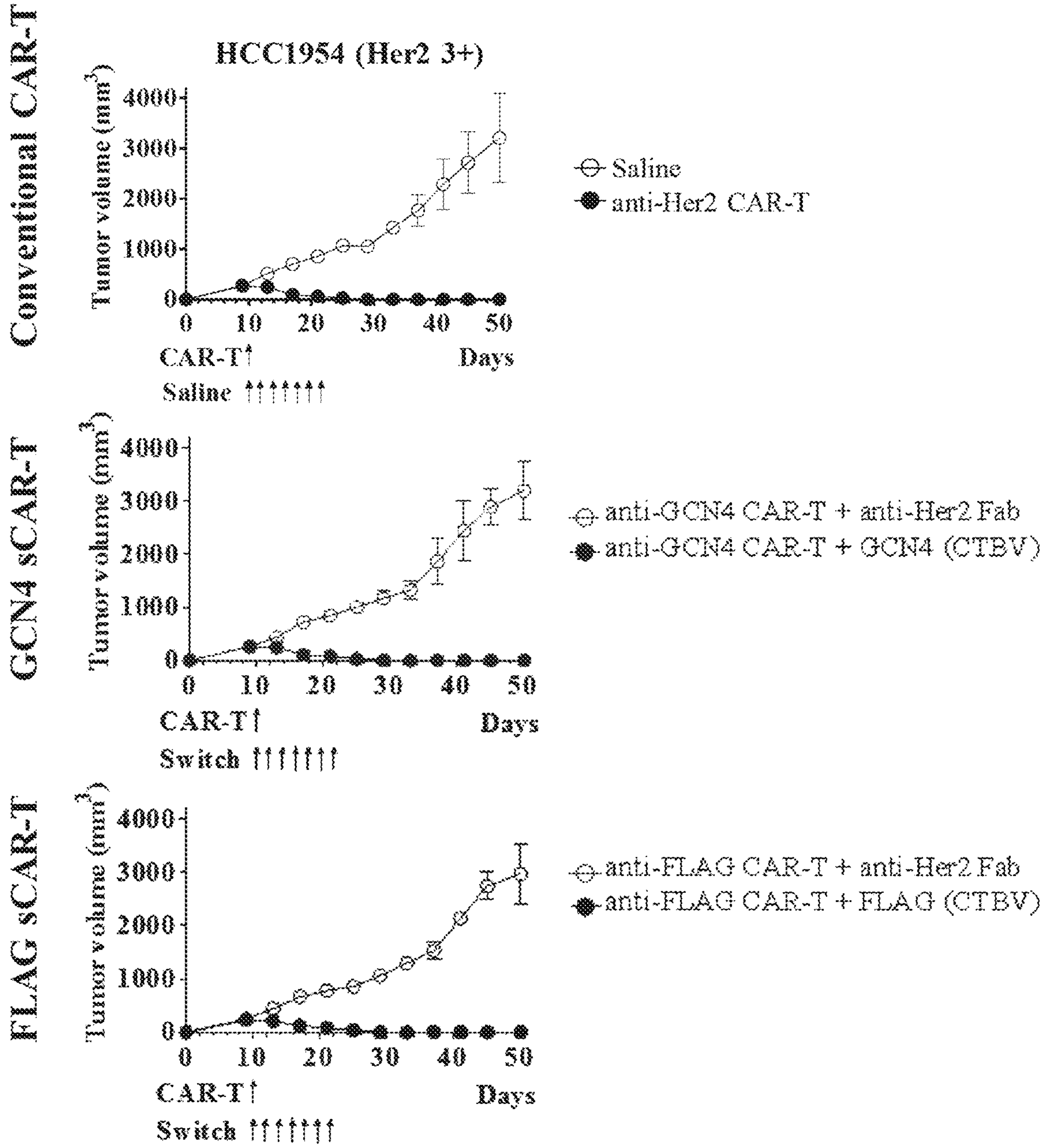
FIG. 55A-C shows in vivo antitumor efficacy of conventional anti-Her2 CAR-T and sCAR-T cell approaches in xenograft models.
Figure 55B:
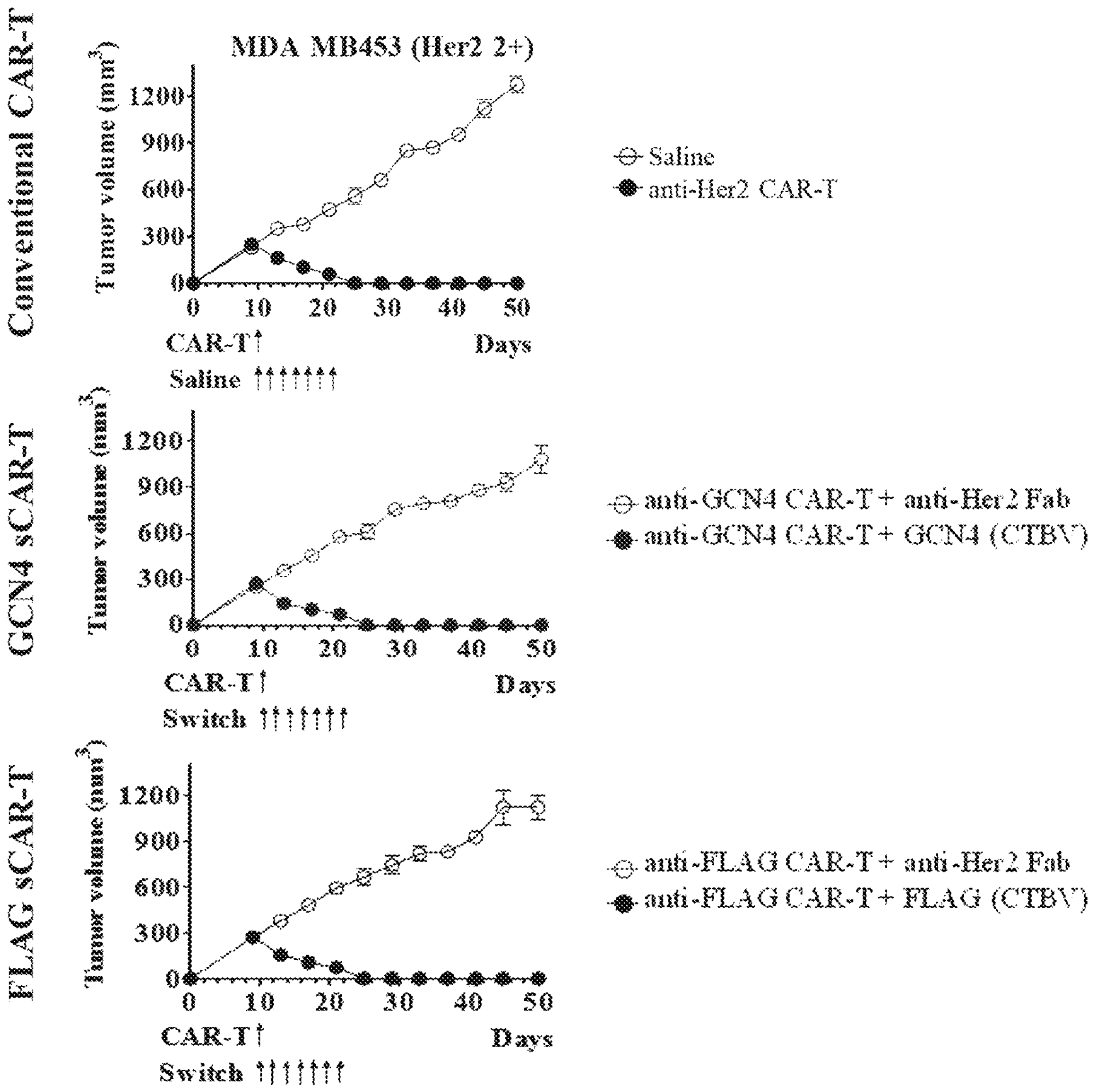

To compare the in vivo antitumor ability of each optimized sCAR-T, their in vivo efficacies were evaluated in mouse xenograft models using Her2 3+ (HCC1954) and Her2 2+ (MDA MB453) breast tumors. Tumor cells were s.c. inoculated in the right flank of NSG mice and solid tumors grown until palpable (~300 $mm^3$). On day 10, mice were infused i.v. with $30\times10^6$ anti-GCN4 or anti-FLAG sCAR-T cells, followed by i.v. injection of the corresponding switches every other day at 0.5 mg/kg for 14 days based on our earlier publications. To confirm the requirement for switch-mediated sCAR-T cell-target cell crosslinking for activity, each sCAR-T cell was dosed with wild type 4D5 Fab in control group. Tumor growth was monitored for 50 days. As shown in FIG. 55A and FIG. 55B, both conventional and sCAR-T cells showed comparable tumor regression kinetics and completely eliminated both Her2 3+ and 2+ tumors by day 25. The treatment of sCAR-T cells with wild type 4D5 Fab had no effect on tumor growth. No relapse events were observed during the course of the study.

Figure 55C:
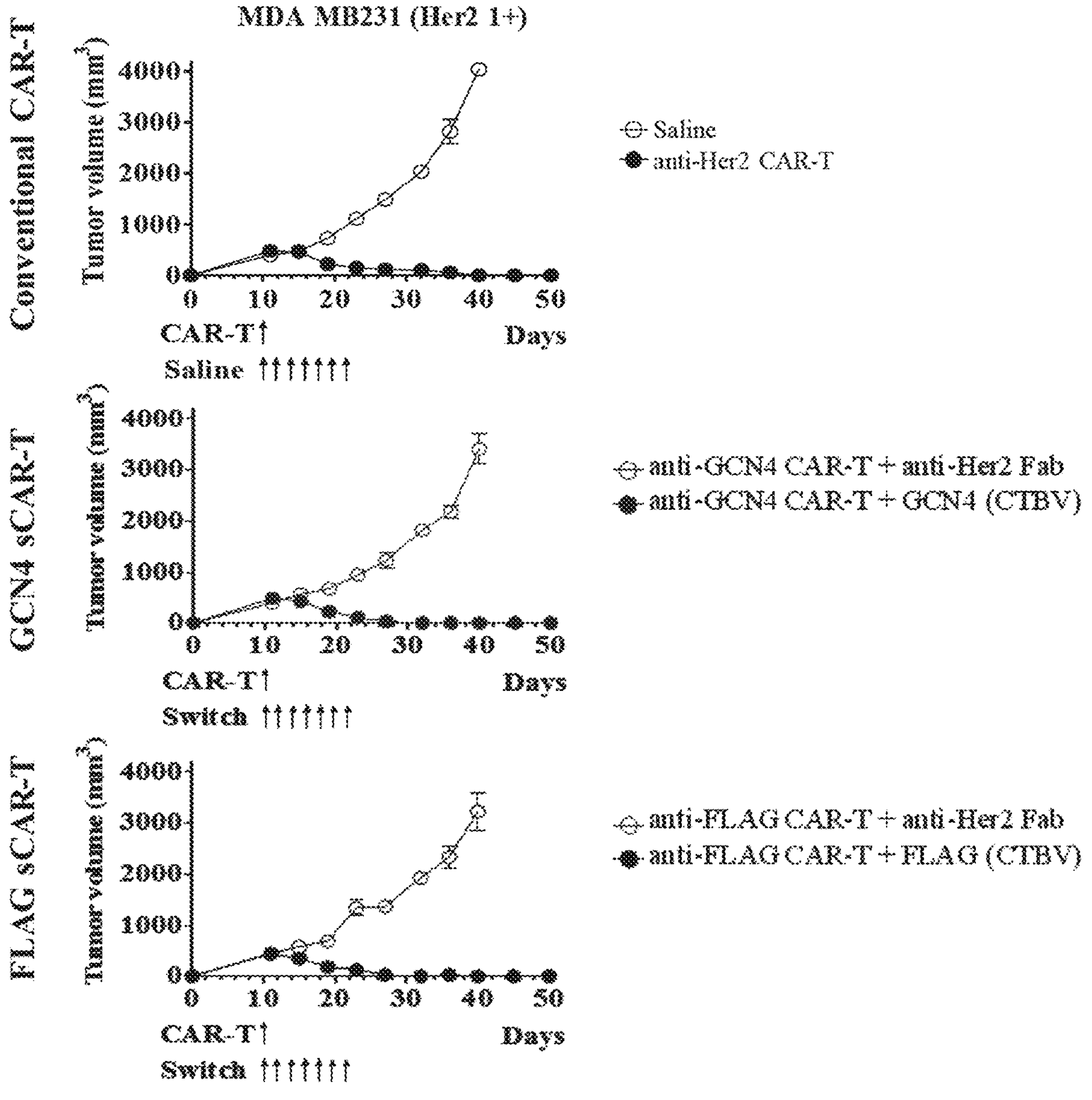

To test activity in a more stringent model, a Her2 1+ orthotopic xenograft model using MDA MB231 cells was selected. In this model, MDA MB231 (Her2 1+) cells are implanted into the right fourth mammary fat pad of female NSG mice to generate tumors. Treatment with the same dosing and schedule as the Her2 3+/2+ models above was begun ten days after tumor inoculation. As shown in FIG. 55C, sCAR-T cells induced complete eradication of Her2 1+ tumors by day 30, and no tumor relapse occurred during the 50 days of observation. The kinetics of tumor removal were comparable to conventional anti-Her2 CAR-T cells. Collectively, these in vivo findings confirmed the methodology of optimization of sCAR-T platforms. Further, this study demonstrated sCAR-T cells constructed from multiple targeting modalities and can specifically target and destroy Her2 expressing tumors with comparable efficacy to conventional CAR-T.

Example 33. Humanization of sCAR-T Cells

To reduce immunogenicity in human patients, it is important for murine antibody constructs to be humanized. Humanization of murine antibodies involves the engraftment of the murine CDR regions onto the amino acid framework of a human antibody.

In this example, the CDRs of the murine anti-GCN4 scFv (52SR4) were engrafted onto a human framework (4D5). Several other mutations were made in the framework regions of both the heavy and light chains. The potency of the humanized sCAR-T cell constructs was tested in an in vitro LDH release cytotoxicity assay. The humanized CAR-T cells were co-cultured with RS4;11 ($CD19^+$) cells at an effector:target ratio of 10:1. The murine FMC63 anti-CD19 switch (LCNT graft; SEQ ID NOS: 36 & 9) was added at concentrations ranging from 1000-0.1 pM. After a 24-hour incubation at 37° C., LDH levels were measured in the supernatant and the percentage cytotoxicity was calculated. In this example (FIG. 56 and Table 37), the parent antibody FMC63 anti-CD19 switch (LCNT graft; SEQ ID NO: 36 & 9), LS H6 (SEQ ID NO: 183), L6 H6 (SEQ ID NO: 257), LS H4b (SEQ ID NO: 256), LS H6b (SEQ ID NO: 185), L6b H4 (SEQ ID NO: 255) and L5b H4b (SEQ ID NO: 256) switches were used. Importantly, these data demonstrate that single modifications can be made to the scFv construct without a loss in in vitro activity.

TABLE 37

Figure 56:
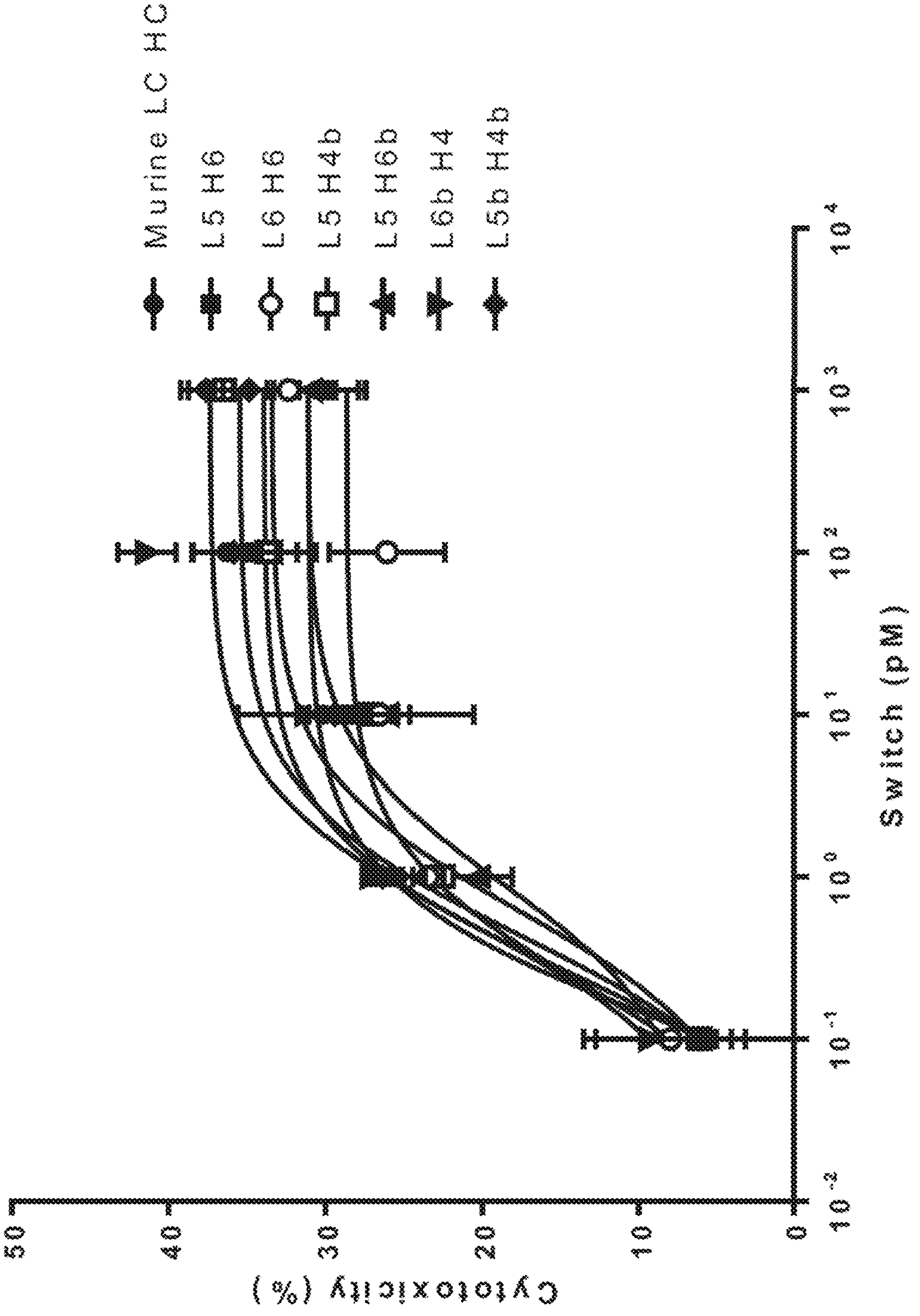
FIG. 56 shows in vitro LDH release cytotoxicity assay results using various sCAR-T cells made with sCARs incorporating humanized murine anti-GCN4 scFv (52SR4). The switch peptide comprised a LCNT graft of the GCN4 peptide to the murine FMC63 anti-CD19 FAB.

Raw data of cytotoxicity from FIG. 56

| Switch [pM] | Murine LCHC | | L5 H6 | | L6 H6 | | L5 H4b | | L5 H6b | | L6b H4 | | L5b H4b | |
|---|---|---|---|---|---|---|---|---|---|---|---|---|---|---|
| 1000 | 36.84 | 38.41 | 28.44 | 31.13 | 28.86 | 35.79 | 34.51 | 38.4 | 31.52 | 30.31 | 37.25 | 36.67 | 36.04 | 33.74 |
| 100 | 34.76 | 37.86 | 31.73 | 37.29 | 23.48 | 28.7 | 33.82 | 33.59 | 34.63 | 32.28 | 40.03 | 42.69 | 35.68 | 36.06 |
| 10 | 29.48 | 30.81 | 22.72 | 33.36 | 25.94 | 27.16 | 25.91 | 28.37 | 27.08 | 25.02 | 31.43 | 31.03 | 31.1 | 27.68 |
| 1 | 26.58 | 24.16 | 25.38 | 27.01 | 22.76 | 24.15 | 22.79 | 22.15 | 21.71 | 18.7 | 26.85 | 27.25 | 26.95 | 25.8 |
| 0.1 | 5.74 | 6.67 | 11.21 | −0.17 | 11.34 | 4.6 | 5.86 | 6.41 | 8.21 | 8.73 | 8.9 | 9.66 | 4.68 | 7.54 |
| 0 | 0 | 0 | 0 | 0 | 0 | 0 | 0 | 0 | 0 | 0 | 0 | 0 | 0 | 0 |

Example 34. Methods of Making and Using CAR T Cell Switches

Mice and Cell Lines

Female NOD scid gamma (NSG) mice, 9-11 weeks of age, were purchased from Jackson Laboratories and maintained in a vivarium on a 12 hr light cycle access to food and water ad libitum. RS4;11 and K562 cells were purchased from ATCC and cultured in RPMI supplemented with 10% heat inactivated FCS (Thermo), 0.1 mM MEM non-essential amino acids, 2 mM L-glutamine, 1 mM MEM sodium pyruvate and 1% penicillin/streptomycin (all from Life Technologies); Nalm-$6^{Luc/GFP}$ cells were also cultured in complete RPMI media. CAR-T cells were cultured in Aim-V media supplemented with 5% penicillin/streptomycin (both from Life Technologies) and 5% heat inactivated human serum (Valley Biomedical Inc.).

Switch Binding and Cytotoxicity Assays

CAR-T or target cells were incubated with 1 pM to 1.5 04 of switch in FACS buffer (PBS, 1% FCS, 2 mM EDTA) for 30 minutes at 4° C. before being washed twice and then incubated with the PE-conjugated goat-anti-human kappa antibody (1:100). Cells were washed two times and analyzed using the Accuri flow cytometer (BD). CAR-T cell activity was determined using the CytoTox 96® Non-Radioactive Cytotoxicity Assay (Promega). CAR-T cells were incubated with target cells in the presence of switch for 20-24 hours at 37° C. in complete RPMI with 5% FCS. At the end of the assay, 30 μL of cell free supernatant was added to 30 μL of the LDH assay reagent in a 96-well plate and incubated for 30 minutes at room temperature in the dark; 30 μL of stop solution was added before the plate was read at OD495. To calculate cytotoxicity, 45 minutes before the end of the assay, target cells alone were lysed using the 10× lysis solution (Promega): this OD495 value was subtracted from that of target cells alone, reflecting spontaneous lysis, and used as 100% cytotoxicity. Cytokines were analyzed in the cytotoxicity assay supernatants using the Human Th1/Th2 Cytokine Bead Array kit II (CBA; BD). Cells from the cytotoxicity assay were stained with anti-human CD3ζ (APC), anti-human CD25 (PE) and anti-human CD69 (PerCP), all from BioLegend, and analyzed by flow cytometry to determine the proportion of T cells that were activated ($CD25^+CD69^+$).

Xenograft Mouse Models

NSG mice were inoculated with $5\times10^5$Nalm-$6^{GFP/Luc}$ i.v. (day 0). On day 6, $4\times10^7$ CAR-T cells (50-70% CAR ) were infused i.v.; unless otherwise stated switches were added 6 hours later. Body weight was monitored and mice were sacrificed upon losing more that 15% of body weight or 10% body weight loss with the development of hind limb paralysis. Tumor burden was measured by IVIS and was quantified as radiance in the region of interest (ROI) which was generally the area of 1 mouse. Mouse blood was drawn at 24 hours and every 10 days after T cell infusion (maximum of 5 times) and cytokine concentrations were determined by CBA. T cells were analyzed in the blood of these mice at the stated time points by flow cytometry using: anti-CD3ζ (APC or PerCP), anti-CD4 (PerCP or PE/Cy7), anti-CD8 (PE), CD45RA (PE) or CD62-L (APC) (all from BioLegend), and were enumerated using the count bright beads (BD). T cells were defined as $CD3^+$ and either $CD4^+$ or $CD8^+$. Cells were analyzed using the Accuri or LSR-II flow cytometers (BD).

Statistical Analysis

Statistical significance and $EC_{50}$ values were calculated using GraphPad software. Unless otherwise stated, in vitro data were analyzed using the one-tailed student's t-test and in vivo data were analyzed by one-way ANOVA with Tukey's post-test. Data acquired from in vitro assays using experimental replicates are presented ±standard deviation and data acquired in vitro or in vivo using biological replicates are presented ±standard error of the mean. *= p<0.5, =p<0.01 and *=p<0.001.

Switch Cloning and Expression

Gene fragments encoding the Fmc63 (anti-CD19) or Ofatumumab (OFA, antiCD20) heavy or light chains, with or without the peptide neo-epitope (PNE) engraftment shown in FIG. 37, were synthesized (IDT) and subcloned into the pFUSE vector (InvivoGen, CA). Switches were expressed by transient transfection in the FreeStyle 293 Expression System (Thermo Fisher Scientific, CA). Heavy chain Fab constructs were expressed in vectors in which the Fc region was removed and a stop codon included after the first cysteine of the hinge region. Full length IgG heavy chain constructs were expressed in vectors harboring the IgG1 sequence with the following mutations: E233P/L234V/L235A/AG236+A327G/A330S/P331S to reduce the ADCC and CDC effector capacity of the Fc region. Expression was carried out as follows: Briefly, HEK293F cells were transfected at a density of $1\times10^6$ cells/ml with a 1:2 plasmid DNA to 293fectin ratio. Small scale expressions (30-50 ml) had a 1:1 ratio of heavy chain to light chain, whereas larger scale expressions (>100 ml) required a 3:2 ratio of heavy chain to light chain. Expression medium containing the secreted proteins was harvested 72 hours post-transfection by centrifugation at 400×g. Fab or IgG switches were purified by Protein G or Protein A (GE Healthcare Life Sciences, CA) respectively. Switches were eluted with 0.1 M glycine pH 2.8 and neutralized by the addition of 10% v/v 1M Tris-HCl pH 8. Switches were then buffer exchanged into phosphate buffered saline with PD10 desalting columns (GE Healthcare Life Sciences, CA) for subsequent assays. Switch integrity was confirmed by SDS page (Life Tech) and QTOF analysis (Agilent).

Lentivirus Generation and Transduction of Human PBMC

To create the sCAR lentiviral construct, the 52SR4 scFv specific for GCN4(7P14P) was subcloned into a lentiviral vector behind an EF1a promoter and CD8 leader sequence and in front of CD8 hinge, CD8 transmembrane, CD137(4-1BB) costimulatory, and CD3ζ domains. Conventional CART-19 was constructed in similar fashion using the scFv from anti-CD19 antibody FMC63. For the short and short, dimeric constructs of the sCAR the 45 amino acid CD8 hinge region was replaced with peptide sequences from IgG4 or IgG4m (below). For virus production, HEK293FT cells (ATCC) were sub-cultured in DMEM supplemented with 10% heat inactivated FCS, 0.1 mM MEM non-essential amino acids, 6 mM L-glutamine, 1 mM MEM sodium pyruvate, 1% penicillin/streptomycin and 1 mg/ml Geneticin (all from Life Technologies). $5\times10^6$ HEK293FT cells were transferred to a biocoat (Corning) 90 mm petri dish in antibiotic free media and transfected with pMDL (6 μg), pRev (6 μg), pMDG (2 μg) and the CAR containing lentiviral vector (7.5 μg) using the Lipofectamin-2000 transfection reagent as per manufacturers instruction (Life Technologies). Cells were incubated with the DNA-lipofectamine complexes for 6 hours before the media was replaced and the cells cultured for 48 hours, at which point lentivirus containing supernatant was removed, clarified of cell debris by centrifugation (3000RPM at 4° C.) and stored at −80° C. PBMC were isolated from healthy donor blood using Ficoll-Plaque PLUS and were rested for 1 hour before the non-adherent fraction were activated with anti-CD3/CD28 human T cell activation and expansion beads (Life Technologies; 3;1 bead to PBMC ratio) and IL-2 (300 IU/ml) for 24 hours. Activated PBMC were then transduced with lentivirus containing serum mixed with protamine sulphate (Sigma; 10 μg/ml) by spinfection (1000×g for 90 minutes). Following spinfection, cells were incubated for 24 hours with the virus before the media was replaced with AimV. Between 50-70% of the PBMC expressed the CAR by day 12, and cells were maintained at a concentration of 0.5-$2\times10^6$/ml at all times. CAR expression on CART19 cells was detected using the AF647-conjugated goat-anti-mouse IgG (H&L; Life Technologies) and CAR expression on sCAR-T cells was detected using the same antibody or an soluble AF488-conjugated synthetic PNE peptide (Anaspec).

Western Blot

CAR-T cells were incubated with RS4;11 or K562 cells with the LCNT switch for 30 minutes before being washed and lysed in ice cold RIPA buffer (supplemented with protease and phosphatase inhibitors; Sigma) for 15 minutes on ice, this was followed by a 15 minute centrifuge (12, 000×g at 4° C.). Reduced or non-reduced whole cell lysates (15 μg) were boiled in SDS for 10 minutes and then resolved on a 4-12% Bis-Tris pre-cast gel (Life Technologies). Proteins were transferred onto a nitrocellulose membrane using the iBlot system (Life Technologies), which were then incubated in Odyssey blocking buffer (LiCor) for 1 hour at room temperature followed by incubation with anti-CD3ζ (BD; 1 mg/ml) or anti-GAPDH over night at 4° C. The membrane was then washed using PBS (0.01% Tween-20; Sigma) and incubated with the IRDye-688-conjugated donkey anti-mouse or IRDye-800-conjugated donkey-anti-rabbit antibodies (LiCor) for 1 hour at room temperature before being washed several times and imaged using the LiCor scanner. Live cell imaging Live cell imaging was performed using the IncuCyte ZOOM® microscope (Essen BioScience). Basic cytotoxicity assays were set up using CAR-T cells with RS4;11 or Nalm6$^{GFP/Luc}$ cells in flat bottomed 96-well plates and were imaged every 30 minutes at 10× magnification for 16-24 hours. The Nalm6$^{GFP/Luc}$ cells were used for clustering analysis and the RS4;11 cells were used to detect cytotoxicity using the Cell Tox Green® (Promega) which was added at a 1:4000 dilution. T cells were labelled with the CellVue Claret® Far Red fluorescence stain (Sigma; Red). Images were analyzed using software provided by the manufacturer and using the following settings for cluster formation: Top-hat (500 pm and 2.0 GCU) with edge sensitivity of −59 and filters of 500 $\mu m^2$ area, 5.0 mean intensity and 5E4 integrated intensity; and for Cell Tox Green® staining: Top-hat (400 pm and 2.0 GCU) with edge sensitivity of −38 and filters of 2000 $\mu m^2$ area, 70.0 mean intensity and 2E5 integrated intensity.

Mass Spectrometry

Mass spectrometry of samples was acquired on an Agilent 6520 Accurate-Mass Quadrupole-Time-of-Flight (Q-TOF) mass spectrometer equipped with an electrospray (ESI) ionization source and liquid chromatography stack (Agilent). Ionization settings were: capillary voltage 3500 kV; positive mode; fragmentor voltage 200 V; drying nebulizer gas, 350° C. Instrument was configured to standard 2 GHz, extended dynamic range and deconvolution was performed by Agilent MassHunter Qualitative Analysis software using the maximum entropy setting. To separate antibodies a 2.1×150 mm, C8 reverse phase, wide pore (5 pm, 300 Å, Phenomenex) column was used. The gradient was: water (A)/acetonitrile (B) (0.1% formic acid) gradient (2% B for 3 min, followed by a 2-95% B gradient over 15 min, and 95% B for 7 min). Results from mass spectrometry can be found tabulated in FIG. 32B.

Example 35. Design of an Orthogonal sCAR-T Cell

A 14 amino acid PNE sequence from the yeast transcription factor GCN4 (SEQ ID: 2) was chosen as the target of the sCAR. This sequence does not occur in the human proteome and thereby provides an orthogonal interaction between the sCAR-T cell and switch. Moreover, high affinity antibodies against this peptide have been previously developed by directed evolution (19-21). To determine the risk of immunogenicity associated with engraftment of this non-human sequence into an antibody fragment (Fab) to create a switch, we performed an in silico immunogenicity analysis of the PNE linked to the N-terminus of the light or heavy chains of a model, therapeutically approved antibody (Herceptin) (SEQ ID: 11 & 12) (FIG. 20B). This analysis predicted the PNE graft to have a low probability of inducing an antibody response in the context of a prototypical antibody and supported its use in generating switches. To generate switch molecules specific for the CD19 antigen, the PNE was introduced at defined sites in the anti-CD19 antibody FMC63 (SEQ ID: 8 & 9) (22). This antibody clone is used in the most widely studied conventional CART-19 construct in clinical trials and thus provides a direct comparison for the sCAR-T cell system (23). By varying the stoichiometry and site of PNE engraftment in FMC63, we could systematically vary the valency and orientation of the antigen binding region of the antibody switch relative to the scFv on the T cell surface (FIG. 9 & FIG. 20A). Two fusions of the PNE were generated by linking the PNE to the N-terminus (NT; SEQ ID: 36) or C-terminus (CT; SEQ ID: 97) of the light chains (LC) of the antigen binding fragment (Fab) with short peptide linkers (SEQ ID: 40). Two fusions of the PNE were generated by linking the PNE to the N-terminus (NT; SEQ ID: 87) or C-terminus (CT; SEQ ID: 34) of the heavy chains (HC) of the antigen binding fragment (Fab) with short peptide linkers (SEQ ID: 40 for HCCT and SEQ ID: 45 for HCNT). We found that a GGGGS linker (SEQ ID: 40) was suitable in all positions except for fusion to the N-terminus of the heavy chain (HCNT; SEQ ID 87), which afforded increased yields with a putative helical forming EAAAK sequence (24) (SEQ ID: 45). In addition, we inserted the PNE directly into loops of the constant region 1 (C1) in the center of the heavy (HCC1; SEQ ID: 32) and light (LCC1; SEQ ID: 30) chains using a strategy similar to one we had previously developed for direct peptide-antibody loop fusions (25-27). These C1 constructs provide yet another distinct binding orientation of the sCAR relative to the target antigen, which could be preferable for certain antibody epitopes on target antigens. Finally, the PNE was engrafted into both the heavy and light chains to create the bivalent switches NTBV (SEQ ID: 36 & 87), CTBV (SEQ ID: 97 & 34) and C1BV (SEQ ID: 32 & 30). The PNE-engrafted switch molecules were efficiently expressed in Fab and IgG format using transient transfections in HEK cells with yields 50-100% that of wild type FMC63 antibody (FIG. 13A & Table 18). Engraftment of the PNE at all sites in the Fab had minimal impact on protein stability and antigen binding as determined by thermal melt assays (FIG. 21A & Table 21) and flow cytometry based binding to $CD19^+$ RS4;11 ($EC_{50}$=5.6 nM±6.3, FIG. 21B), respectively.

To create a sCAR-T cell that recognizes the switch, a sCAR was developed using the 52SR4 antibody, which selectively binds the PNE with high affinity ($K_d$=5.2 pM, (21)). The 52SR4 scFv was incorporated into a second generation CAR construct harboring the human CD8 hinge, CD8 transmembrane, 4-1BB costimulatory, and CD3 activation domains. This design is identical to the second generation CAR used by June and coworkers in CART-19 (28). Lentiviral transduction of this construct into freshly isolated human PBMCs demonstrated efficient surface expression with transduction efficiencies of 50-75%, which were comparable to the FMC63-based CART-19 (29) (FIG. 22A). Switches bound to sCAR-T cells and not to untransduced T cells (FIG. 22B), demonstrating that the sCAR-T cell-switch interaction is highly specific.

Site and Valency of PNE Engraftment Affects sCAR-T Cell Potency In Vitro

To empirically determine the optimal switch design for CD19, we tested the potency of each switch in vitro. All switches elicited dose-dependent lysis of CD19+RS4;11 cells in the presence of sCAR-T cells at picomolar (pM) concentrations (FIG. 11A & Table 22 & FIG. 24A). There was a clear structure activity relationship between cytotoxicity and the location of the PNE in the antibody. Switches with the PNE engrafted proximal to the antigen binding site (LCNT, HCNT, NTBV) were generally more potent than switches with the PNE engrafted at the C1 (LCC1, HCC1, C1BV) or C-terminus (LCCT, HCCT, CTBV) of the Fab region. No significant lysis of $CD19^-$K562 cells was observed for any Fab or IgG switch design, even at concentrations $10^3$ fold higher than the $EC_{50}$ (FIG. 11B & FIG. 24B). In addition, wild type anti-CD19 Fab and IgG lacking the PNE peptide did not induce significant cytotoxicity, demonstrating a strict requirement for PNE-mediated immunological synapse formation. We chose to further pursue switches in the Fab format rather than IgG because the Fab has a shorter pharmacokinetic half-life, which we predicted would enable greater temporal control over the response in vivo.

Figure 24C:
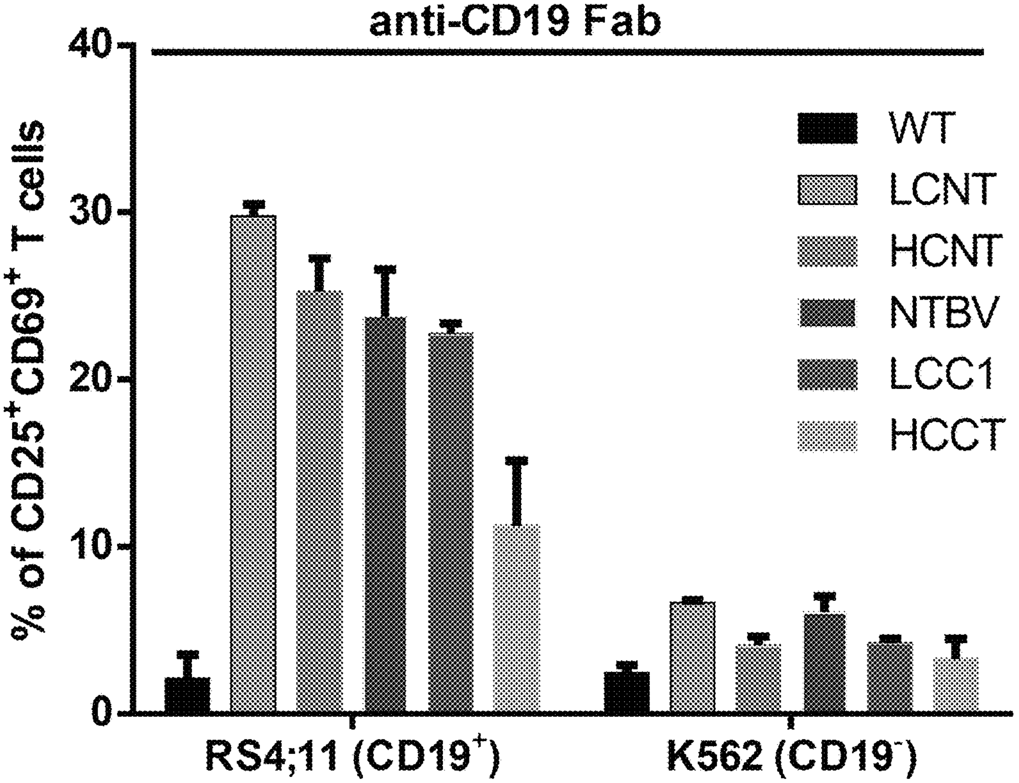
FIG. 24C shows the proportion of T cells that are activated following a 24-hour cytotoxicity assay whereby sCAR-T cells are incubated with the specific switches listed in the figure key, T cell activation is measured by flow cytometry and defined as being CD25 positive and CD69 positive.

Consistent with the cytotoxicity results, all switches induced robust IL-2 release (FIG. 11C) with the N-terminal PNE switches providing greater IL-2 responses than the constant region or C-terminal PNE switch molecules. Notably, the bivalent N-terminal NTBV (SEQ ID: 36 & 87) switch induced the greatest IL-2 production against RS4;11 cells, indicating a potential benefit of engagement of 2 sCARs with 1 switch. Again, addition of the switches stimulated no cytokine release in the presence of sCAR-T cells and $CD19^-$ K562 cells, confirming that switch binding to the sCAR-T cell alone is not sufficient for activation (FIG. 11C). Consistent with the cytokine release data, markers of T cell activation ($CD25^+$, $CD69^+$) on sCAR-T cells were only upregulated by the switches in the presence of $CD19^+$ RS4;11 cells and not $CD19^-$ K562 cells (FIG. 24C). These results clearly demonstrate that sCAR-T cell effector function, as measured by activation, cytokine production, and target cell killing, is dependent on the presence of both a target antigen and switch.

To determine whether the same sCAR-T cell could be used to target other antigens relevant to B cell malignancies, a similar panel of switches was constructed to bind CD20-expressing cancers based on the anti-CD20 antibody Ofatumumab (OFA) (FIG. 13B & Table 23) (30). Along with CD19, CD20 is an important pan-B cell marker and the most widely targeted B cell antigen in the clinic. To develop the anti-CD20 switch, the OFA antibody was chosen because it binds a membrane proximal epitope (31) which might lead to enhanced activity due to the close association of the T cell and cancer cell. Switches were generated in a fashion similar to the CD19 switches. Consistent with the trend for FMC63, N-terminal PNE switches were found to be more cytotoxic than C-terminal PNE switches ($EC_{50}$=1.1-6.8 pM vs 4.7-15 pM, respectively) against $CD20^+$ Raji cells (FIG. 25A). In addition, anti-CD20 N-terminal PNE switches stimulated higher levels of cytokine release than C-terminus PNE switches (FIG. 25B).

Optimization of the sCAR Design Improves Activity In Vitro

We hypothesized that the increased activity of switches with the PNE engrafted proximal to the antigen binding domain was the result of a decreased overall distance between the sCAR-T cell and target cell (32). To determine whether the distance could be further shortened to increase activity we modified the hinge region of the sCAR itself (also referred to as the spacer domain), which connects the anti-PNE scFv to the transmembrane domain of the sCAR. The initial sCAR design used a 45 amino acid CD8-based hinge identical to that of conventional CART-19. To test a shorter hinge, this region of the sCAR was replaced with a 12 amino acid sequence derived from the hinge of IgG4 (FIG. 7A). As expected, the IgG4-hinge-based sCAR-T cells had increased cytotoxicity in the presence of the LCNT switch against RS4;11 cells compared with CD98-hinge based sCAR-T cells (FIG. 10A) while retaining antigen specificity for $CD19^+$ cells (FIG. 10B).

We also hypothesized that the increased cytokine induction observed with the bivalent NTBV switch reflected an effect of increased valency on sCAR-T cell activation. To test whether this notion could be translated to the IgG4 sCAR design, a serine to proline mutation (S228P relative to the IgG4 molecule (33)) was incorporated in the IgG4 hinge to enhance inter-chain sCAR disulfide formation (IgG4m, FIG. 7A). Consistent with previous reports, western blot analysis confirmed that the sCAR and CART-19 CD8-based hinges formed spontaneous disulfide dimers in the absence of CAR stimulation (FIG. 7B) (34). Dimers also formed for the IgG4m-based sCAR hinge containing the S228P mutation, but not for the IgG4 hinge lacking this mutation. As expected, the maximum cell lysis and $EC_{50}$ of cytotoxicity of the IgG4m sCAR against RS4;11 cells with the LCNT switch were increased compared with the IgG4 sCAR lacking the S228P mutation (FIG. 10A). This result is consistent with Riddell and coworkers in which the same IgG4m hinge design increased the activity of anti-ROR1 conventional CAR-T cell compared with other hinge designs in their study (35, 36). However, no corresponding monomeric IgG4 hinge was compared in that study. Thus, our result supports that the S228P mutation in the IgG4 hinge confers increased sCAR-T cell activation through dimerization of the sCAR.

We next determined the additive effect of switch and hinge design on sCAR activity, and compared this with conventional CART-19. Each switch design was empirically tested in combination with each hinge design in dose response for cytotoxicity, cytokine release, and upregulation of activation markers in the presence of RS4;11 cells. As expected, the observed trend was that cytotoxicity increased as the PNE engraftment site moved from the C-to N-terminus: and as the hinge design was shortened from the 45 amino acid CD8 design to the 12 amino acid IgG4 design; this was further increased with the IgG4m design (FIG. 10F). Correspondingly, IL-2 release with 1 nM switch was greater with the N-terminal PNE switches (HCNT, LCNT, NTBV) and the IgG4 and IgG4m hinges than with the C-terminal PNE switches (HCCT, LCCT, NTCT) and CD8 hinge (FIG. 23D). The bivalent NTBV switch increased IL-2 production from CD8 sCAR-T cells by 50% but did not have a significant impact on sCAR-T cells harboring the IgG4 or IgG4m hinges. We expect this may be due to steric clashes with the shorter IgG4 and IgG4m hinges which prevent binding of 2 sCARs to 2 N-terminal PNEs on the same switch molecule. The trend in switch design on the upregulation of T cell activation markers was similar to that observed for cytotoxicity and cytokine production with the greatest activation observed in response to the LCNT switch (FIG. 23E). Collectively, the LCNT switch with the IgG4m sCAR-T cell demonstrated the greatest cytotoxicity compared with other switch/hinge designs and afforded cytokine release and upregulation of T cell activation markers that were significantly greater against $CD19^+$ RS4;11 cells.

Specificity of sCAR-T cell activation is a critical design consideration for switch-based control. Therefore, to confirm that the improved activity of the IgG4m sCAR did not sacrifice specificity, we repeated the assays above on $CD19^-$ K562 cells. The IgG4m sCAR did not cause significant lysis of K562 cells with up to 10 nM of any switch molecule (FIG. 23B, FIG. 26A, FIG. 26B), nor did the IgG4m sCAR produce IL-2 in the presence of K562 cells and any of the switches (FIG. 26C). Furthermore, the IgG4m sCAR-T cells did not exhibit significant upregulation of activation markers compared with non-transduced (mock) cells in the absence of the PNE-engrafted switch and target antigen (FIG. 23C). Together, these data confirmed that the improved activity of the IgG4m sCAR did not result in antigen-independent activation. Finally, the activity of sCAR-T cells on RS4;11 cells could be fully inhibited by the addition of an excess of soluble, synthetic PNE peptide, further demonstrating the requirement of a switch for activity (FIGS. 26A, 26B, 26C, 26D and 26E).

To test whether the improved IgG4m hinge design extends to our anti-CD20 OFA switches, we tested the anti-CD20 switches with IgG4m sCAR-T cells on $CD20^+$ Raji cells. As expected, cytotoxicity was increased with the IgG4m sCAR for all CD20 switches compared with CD8 sCAR-T cells (FIG. 28A). Unexpectedly, however, the trend in anti-CD20 switch design with the IgG4m sCAR was opposite to what was observed with the CD8 sCAR (FIG. 1G). In this case the C-terminal PNE switches were 10-100-fold more potent than the N-terminal PNE switches. We hypothesized that this is due to the membrane proximal epitope of the OFA on CD20 which may require additional distance between the PNE and antigen binding interface of the Fab when the hinge region of the sCAR is short in order to alleviate steric clashes at the immunological synapse. Collectively the above studies demonstrate that the activity of sCAR-T cells can be significantly enhanced through both sCAR hinge and switch design and underscore the advantages of being able to optimized each.

Switch and Hinge Design Effects on Tumor Clearance In Vivo

To investigate the activity of sCAR-T cells in vivo, we evaluated tumor regression in a xenograft model of B cell leukemia using luciferized human B-ALL Nalm-6 cells in immunodeficient NOD.Cg-Prkdc$^{scid}$ Il2rg$^{tm1Wjl}$/SzJ (NSG) mice. In this model, mice without treatment succumb to disease within 21 days. First, to understand the impact of CAR hinge design on in vivo efficacy, mice were inoculated with Nalm-6, followed by I.V. injection of CD8, IgG4, or IgG4m sCAR-T cells 6 days later (FIG. 32A & 32B). Based on our in vitro results we chose the anti-CD19 LCNT switch to test in this model. This switch was dosed I.V. (0.5 mg/kg) every other day for 10 days and tumor regression was followed by in vivo imaging (IVIS) of the luciferase signal from Nalm-6 cells (FIG. 29A). In line with the in vitro data, both IgG4 and IgG4m sCAR-T cells afforded a significant decrease in tumor burden; whereas CD8 sCAR-T cells had minimal impact on disease compared with untreated controls (FIG. 29B). Increased T cell counts in the peripheral blood at day 17 corresponded with reduced tumor burden and revealed that the IgG4m sCAR-T cells provided significantly greater T cell expansion compared with the IgG4 or CD8 hinge designs (FIG. 29C). Based on this result, the IgG4m sCAR construct was chosen for further in vivo analysis.

Next, we determined the effect of switch graft position and valency on in vivo efficacy. As with the previous model, IgG4m CAR-T cells were injected 6 days after tumor inoculation and mice were treated every other day (starting at day 6) with the LCNT, HCNT, NTBV, LCC1, or HCCT switches (0.5 mg/kg, FIG. 29D). Analogous to the in vitro data, the N-terminally grafted switches (LCNT, HCNT, and NTBV) afforded the greatest reduction in tumor burden, while switches with the PNE at the middle (LCC1) or C-terminus (HCCT) provided little control (FIG. 29E). T cell counts at day 20 correlated with reduction of tumor burden and indicated the LCNT switch provided the greatest T cell expansion (FIG. 29F). In agreement with our in vitro data, the combination of the LCNT switch with the IgG4m sCAR resulted in the greatest efficacy in vivo and thus was used in subsequent studies to explore the effect of switch dosing regimen.

Clearance of Nalm-6 with the IgG4m sCAR-T cell and the LCNT switch in the above model was observed to occur rapidly during the first 96 hours of treatment. To further investigate IgG4m sCAR T cell proliferation and localization during this time interval, Nalm-6 engrafted NSG mice were sorted into 4 groups that received IgG4m sCAR-T cells (with or without the LCNT switch), conventional CART-19 (with no switch) or no cells. Each group was divided into 5 cohorts per treatment regimen, which were analyzed at 8, 24, 48, 72, and 96 hours after T cell infusion. Daily dosing of the LCNT switch (0.5 mg/kg) reduced tumor burden within the 24 hours and continued to shrink the tumor to the limit of luminescence detection (approximately $10^3$-$10^4$ p/s/cm$^2$/sr) within 96 hours with daily treatment (FIG. 30A). The rate of clearance during this time was not significantly different from CART-19 (FIG. 30B). Human IL-2 in peripheral blood peaked at similar levels at 24 hours for CART-19 and at 48 hours for sCAR-T cells and decreased as tumor was cleared (FIG. 30B). As expected, IgG4m sCAR-T cells had no effect on disease progression in this model in the absence of switch, confirming requirement of switch dosing for in vivo anti-tumor effect. We also tracked IgG4m sCAR-T cells and tumor in the spleen, lungs, liver, and peripheral blood by flow cytometry over the 96 hours. During this time, Nalm-6 cells were only detectable in the lung and liver (FIG. 32A & 32B). Correspondingly, significantly increased numbers of sCAR-T cells were found in the lung and liver at 96 hours in mice dosed with the LCNT switch compared mice not treated with switch (FIG. 30C). Switch dosing did not increase sCAR-T cell recruitment to the spleen where tumor burden was not detectable. In the organs assessed, sCAR-T cells had proliferated significantly more in the mice treated with LCNT switch (by dye dilution experiments) compared to no switch treatment, again demonstrating the requirement for the switch for sCAR-T cell expansion (FIG. 30D & 32C). The magnitude of sCAR-T cell proliferation when dosed with the LCNT switch was comparable to that of CART-19 in both the liver and lung (FIG. 32D). Together, these results indicate that the IgG4m sCAR-T cells dosed with the LCNT switch can expand and eliminate tumor burden with comparable efficacy to conventional CART-19.

Dose-Dependent Control of sCAR-T Cell Activity In Vivo

Figure 31A:
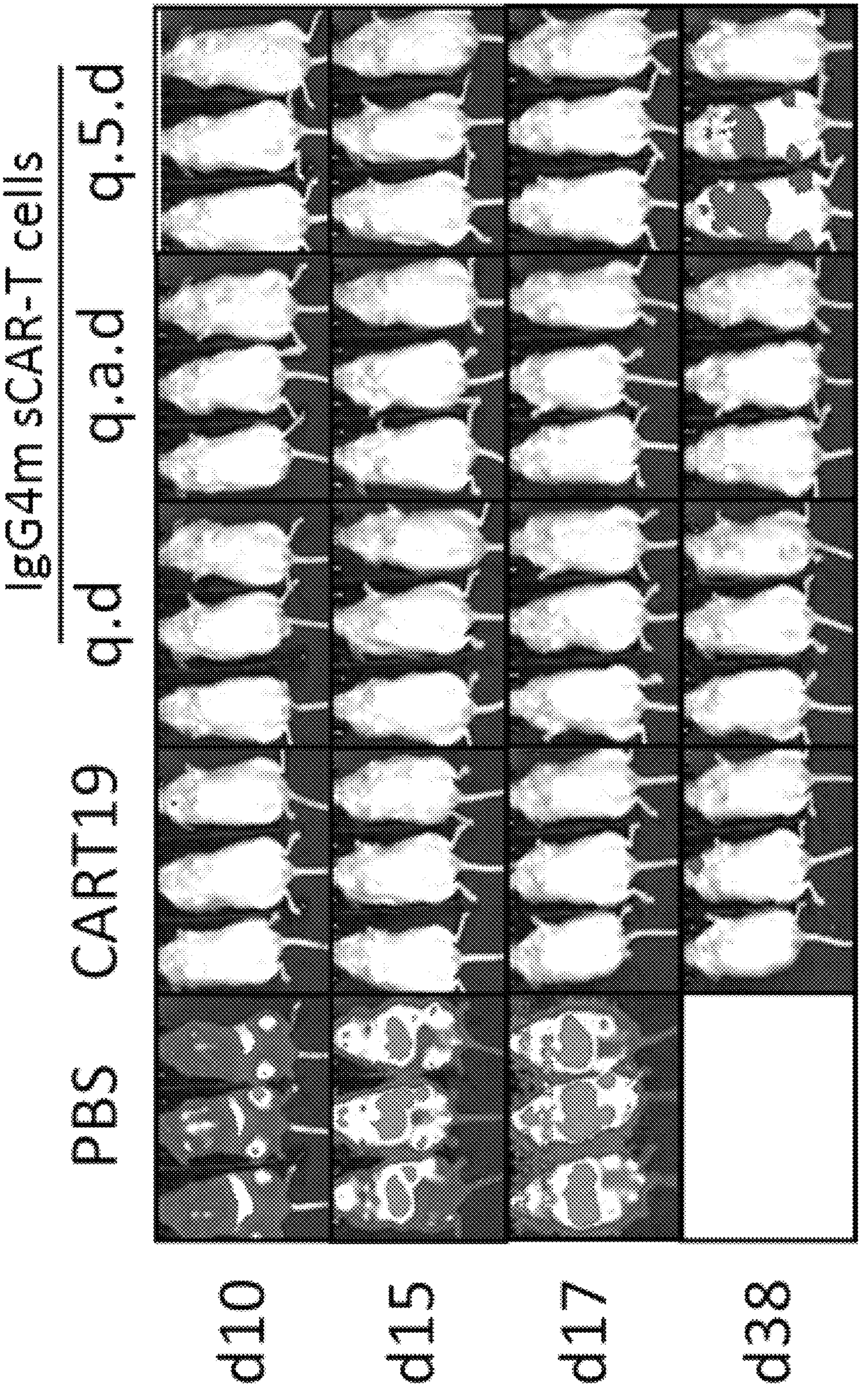
FIG. 31A-C shows T cell analysis in the peripheral blood.
Figure 31B:
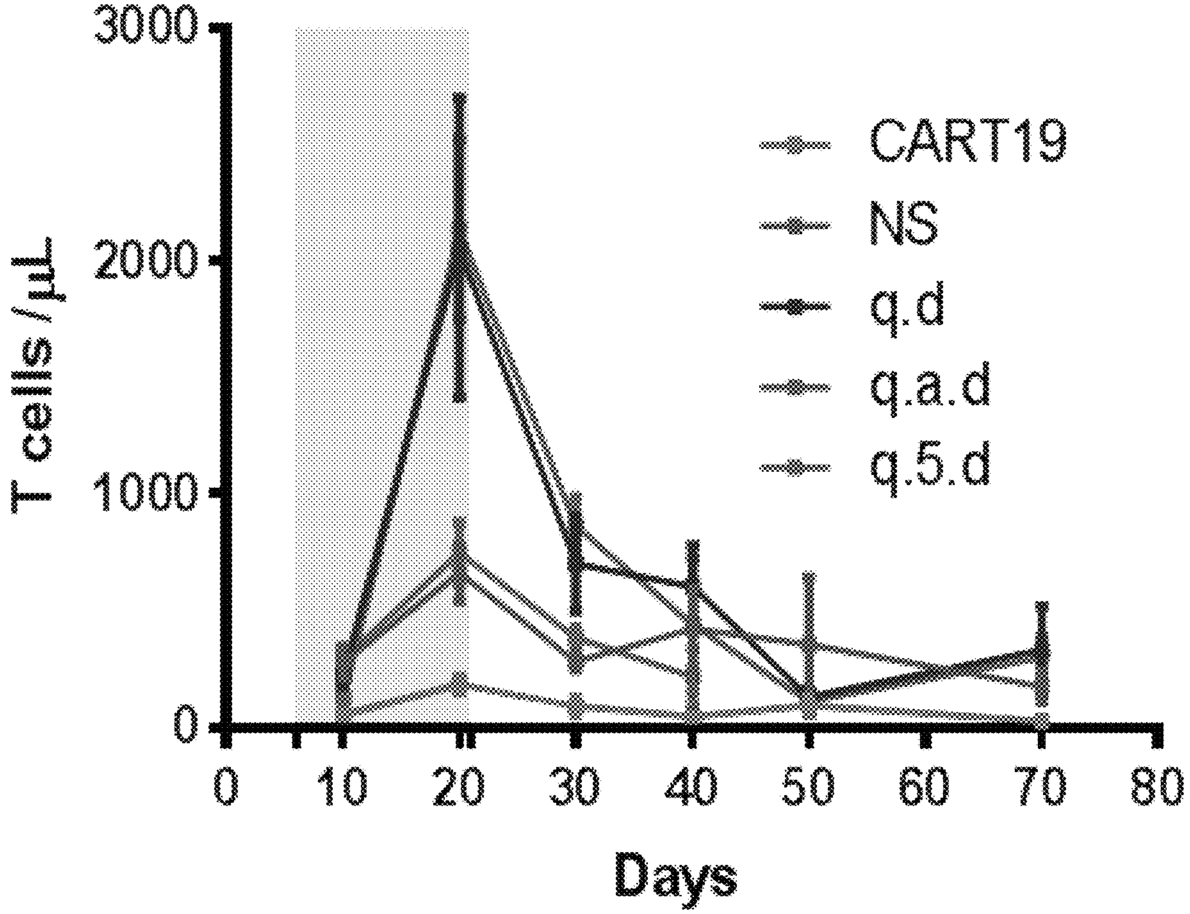
Figure 31C:
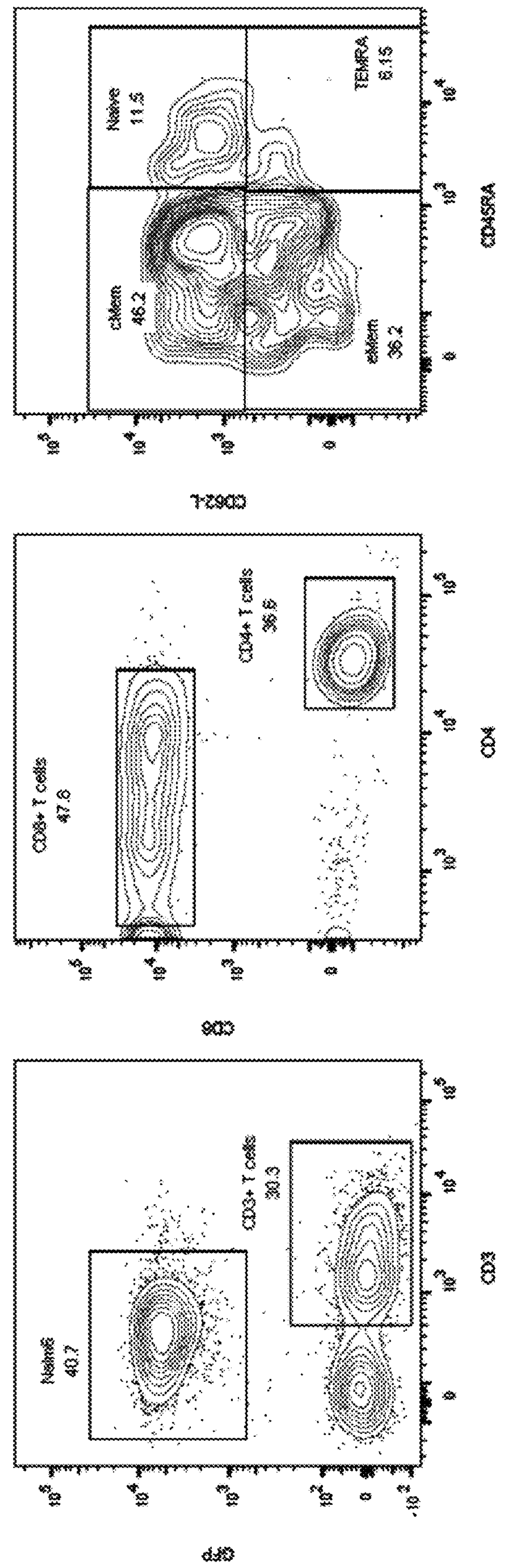

To determine the minimal dose frequency required for a sustained response with the IgG4m sCAR-T cells, we tested every day, every other day, or every fifth day dosing of the LCNT switch (0.5 mg/kg) for 15 days in the Nalm-6 model. Every day and every other day dosing yielded comparable rates of tumor regression which was sustained for >100 days after dosing was discontinued (FIG. 33A). Mice that died between days 40 and 100 (open circles) had no evidence of disease; expiration in these cases was attributed to xenogeneic graft versus host disease caused by human T cells in the NSG mouse as previously described (37). Dosing every fifth day (3 total dosages) greatly decreased and stabilized disease burden at a low level, but did not completely clear disease based on luciferase signal. This corresponds with the expected short half-life for the Fab-based switch in the mouse. Residual disease in this group relapsed when dosing was discontinued indicating that the activity of the sCAR-T cells towards the Nalm-6 cells had been turned "off" in the absence of the switch; nevertheless sCAR-T cells were still detectable in blood up to 64 days after injection (FIG. 31B).

Control of cytokine production in vivo is important to prevent CRS in patients receiving CAR-T cell therapy. To investigate the potential of switch-regulated IgG4m sCAR-T cells to achieve reduced cytokine release in vivo, we correlated switch dosage with cytokine release by the IgG4m sCAR-T cells in the Nalm-6 model. Mice dosed everyday with 0.05, 0.5, or 2.5 mg/kg of the LCNT switch showed a dose-dependent increase in serum IL-2, IFNγ, and TNFα at 24 hours (FIG. 33B) that correlated with dose dependent reductions in tumor burden by day 10 (FIG. 33C). Cytokine production in the 0.5 and 2.5 mg/kg groups was not significantly different from CART-19 at 24 hours for all cytokines, except for serum TNFα which was decreased in the 2.5 mg/kg group compared with CART-19. However, all cytokines in the 0.05 mg/kg group were significantly lower than CART-19.

To determine if treatment with the lower dose of 0.05 mg/kg could be efficacious, despite lower levels of cytokine production, dosing of the LCNT switch was carried out every day for 10 days in the Nalm-6 model. At this low dose, tumor clearance was correspondingly slower compared to the conventional CART-19 previous models, but still reached the limit of detection by the final day of dosing (day 16; FIG. 33D). The Nalm-6 tumor relapsed at in the 0.05 mg/kg treatment group at day 30 (fifteen days after the final dose) at which time the luciferase signal was significantly higher than for CART-19 treatment. These mice were retreated with a higher dose of the LCNT switch (0.5 mg/kg) for an additional 10 days. This retreatment regimen effectively decreased tumor signal to equivalent levels as CART-19 within 5 days and the mice remained tumor-free for >35 days after the final dose of the second treatment period. Thus IgG4m sCAR-T cells in combination with an escalating switch dose regimen can control cytokine release while still providing efficacy comparable to conventional CART-19. This titration approach to reducing tumor burden with a reduced initial dose of switch followed by increasing sCAR T cell activity by escalating the switch dose may be an effective strategy for avoiding CRS in the clinic.

Persistent memory phenotypes have been correlated with complete remissions in CAR-T cell therapy clinical trials for leukemia (38). To understand whether the switch dose can influence IgG4m sCAR-T cell populations, we dosed NSG mice bearing the Nalm-6 tumor xenograft with 0.05, 0.5, or 2.5 mg/kg LCNT switch and analyzed the expression of CD45RA and CD62-L on $CD4^+$ and $CD8^+$ T cells in peripheral blood after 21 days (5 days after the final dose). The 2.5 mg/kg group demonstrated significant expansion of the $CD45RA^+CD62L^-$ terminal effector memory expressing CD45RA (TEMRA) compartment in both $CD4^+$ and $CD8^+$ T cells compared with the lower dose groups (FIG. 33E). Conventional CART-19 exhibited the greatest increase in TEMRA population consistent with strong activation through the direct CAR design. Conversely, the lower dose groups that received 0.05 and 0.5 mg/kg of switch had significantly larger populations of $CD45RA^-CD62L^+$ central memory cells compared with 2.5 mg/kg group, which we hypothesize is a result of lower levels of stimulation during the initial dosing period. Thus this result may indicate a potential benefit derived from low dose treatment of sCAR-T cells during the initial stages of tumor clearance. Collectively these results demonstrate that switch dose can control the activity, tissue-localization, cytokine release, and phenotype of sCAR-T cells in the Nalm-6 xenograft model with efficacy comparable to the corresponding conventional CART-19.

Discussion

We have demonstrated that protein engineering can be used to create antibody-based switches that redirect the activity of bio-orthogonal anti-PNE sCAR-T cells to tumors. Moreover, we show this methodology allows one to systematically optimize the activity of the sCAR by varying the geometry and valency of the switch molecule. Similar approaches have been described using antibodies that are non-specifically or enzymatically labeled with small molecule haptens to redirect the activity anti-hapten CARs (16, 17). However these systems do not easily allow for optimization of the immunological synapse between the CAR-T cell, antibody and target cell. The importance of the spatial orientation between the T cell and target cell demonstrated in our studies is in agreement with several recent studies using conventional CAR, which showed that variation in the epitope location of different targeting scFv's require compensatory CAR hinge designs for good CAR-T cell activity (35, 36, 39, 40).

In the context of CD19 targeting, switches with the PNE engrafted at the N-terminus (HCNT, LCNT, NTBV), proximal to the antigen binding interface of the FMC63, were found to be superior to switches with the PNE grafted at the C-terminus (HCCT, LCCT, CTBV). Although the epitope of FMC63 and corresponding structure of the CD19 antigen are not known (41), we hypothesized that this trend was due to a decreased distance between target cell and sCAR-T cell. In the case of the immunological synapse formed by the native T cell receptor (TCR), the distance between the T cell and antigen presenting cell is reported to be approximately 130-150 Å (42, 43). This distance is important to sterically exclude inhibitory phosphatases such as CD45 and CD148 from the synapse, which act to dephosphorylate signaling molecules and down regulate T cell activation (44). It is likely that the longer synapse resulting from the C-terminal switches (approximately 70 Å longer than the N-terminal switches) is unable to sterically exclude these inhibitory molecules, resulting in less productive sCAR signaling. The increase in sCAR-T cell activity observed when the sCAR hinge was shortened from 45 amino acids to 12 amino acids supports this hypothesis. A similar relationship was observed in the accompanying publication which reports a sCAR-T cell specific for FITC and a FMC63-based switch molecule that is site-specifically modified with FITC (45). FITC conjugation sites near the antigen binding interface afforded better activity than sites distal to the binding interface. Moreover, we have shown, in that study, that non-specific conjugation of switches with FITC did not provide sufficient in vivo activity to clear Nalm-6 tumor (45). Collectively, these studies underscore the importance of switch structure on optimizing immunological synapse geometry, which directly impacts sCAR-T cell activity.

Switches based on the OFA antibody scaffold that target CD20 exhibited a trend similar to the FMC63 antibody when paired with sCAR-T cells harboring the CD8-based hinge. Interestingly, when the sCAR hinge was shortened to the 12 amino acid IgG4m hinge the trend for OFA switches was reversed and C-terminal PNE switches afforded better activity than N-terminal switches. While the structure of CD20 antibody is also unknown, the OFA antibody is reported to bind a small, membrane proximal loop of the multi-pass transmembrane CD20 antigen (31). In this case, it is likely that the distance created by the N-terminal OFA switches with the IgG4m sCAR is too short to enable efficient synapse formation between the sCAR and CD20. Alternatively, the large adjacent loop domain of the CD20 antigen may create a steric hindrance for binding of the IgG4m sCAR. We observed a similar effect supporting this hypothesis in our work with site-specific FITC conjugation on the anti-CD22 antibody m971 (45). In this case, the m971 antibody has a membrane proximal epitope on CD22 (39) and several large modular domains that may sterically preclude binding. Correspondingly, the m971 switches were optimal with FITC placed at sites distal from the antigen binding interface. Thus the geometry of the immunological synapse is a key parameter to consider when designing switches and highlights the requirement for precise control over switch structure which cannot be accomplished with previously reported platforms.

A central tenant of the sCAR-T cells described here is the orthogonality of PNE-engrafted switches in that they only interact with the target cell and sCAR and no other immune receptors or cell types. Recently, Campana and coworkers reported a CD16 (Fc receptor)-based CAR-T cell for use in combination with therapeutic monoclonal antibodies (46). However, CD16 indiscriminately binds to therapeutic and naturally occurring antibodies, which yields the potential for any endogenous antibody to activate the CD16-CAR. This lack of orthogonality has the potential to cause off-target effects. Thus, in the development of orthogonal switches, Fab's may be desirable because their lack of an Fc domain removes the possibility of an Fc receptor-mediated off target binding. In addition, the smaller size and shorter half-life of Fab molecules (approximately 12-20 hours for Fab (47) vs 10 days for IgG (48)) is also expected to provide better tumor penetration and greater temporal control over sCAR-T cell activation in clinical translation. We expect this will correlate with a dosage of every other day or twice a week dosing in the clinic.

To assess the efficacy of the sCAR-T cell approach in vivo, we chose the Nalm-6 xenograft model. Because the Nalm-6 tumor lacks CD80 and CD86 co-receptors, it is difficult to treat and has become a standard for CAR-T therapy adjudication (49). Our sCAR-T cell platform was able to eliminate Nalm-6 with comparable efficacy to conventional CART-19 T cells. Interestingly, differences in the in vitro lytic activity of switch/hinge designs that were generally less than 10 fold by EC50, were highly amplified for in vivo tumor elimination, reinforcing the need for careful in vitro design to provide robust in vivo activity. In addition to eliminating the tumor, in vivo expansion and trafficking of sCAR-T cells to sites of disease was demonstrated to be reliant on switch dosing. CAR-T cell expansion and trafficking in human trials have been shown to be predictive of clinical responses (50). Importantly, serum levels of human cytokines IL-2, TNFα, and IFNγ were tightly controlled by LCNT switch dose. The exception was TNFα which was not increased in the 2.5 mg/kg group compared with the 0.5 mg/kg group suggesting a potential maximum induction of this cytokine with 0.5 mg/kg LCNT; however it is also possible that TNFα in the 2.5 mg/kg group peaked earlier than 24 hours which was not captured in this experiment.

A key finding of this study was that sCAR-T cells treated with lower levels of LCNT switch (0.05 mg/kg) provided complete clearance of Nalm-6 at a slower rate and with lower levels of cytokine release. This suggests that low dose switch treatment could be an effective method of mitigating CRS and TLS in the treatment of patients with high tumor burdens. When tumor relapsed at day 30, mice were retreated with a higher dose of 0.5 mg/kg to ensure clearance. Due to the lower tumor burden at this stage, excessive cytokine release would not be expected. The titration of sCAR-T cell "on" activity to prevent CRS and TLS in the clinic would be a significant paradigm shift from proposed use of kill switches which can only turn "off" the CAR-T cell response in the case of an adverse event (14).

Another key finding of the dose titration study was the impact of switch dose on sCAR-T cell phenotype. This experiment demonstrated a potential advantage to low dose (0.05 mg/kg) switch treatment in its ability to maintain a larger CD62-L$^+$ central memory compartment compared with high dose (2.5 mg/kg) treatment which produced more TEMRA cells at day 21 (15 days after T cell infusion). The formation of central memory CAR-T cells has been shown to provide prolonged persistence in clinical trials, where persistence has been correlated with sustained remissions for ALL and CLL patients (51, 52). In the sCAR-T cell system, clinical persistence will also be critical to enable re-dosing strategies in the case of relapse. Thus, the ability to affect CAR-T cell phenotype through dosing paradigms may be advantageous in the clinic. We are currently exploring the impact of sCAR-T cell phenotype on persistence in surrogate, syngeneic mouse models.

Towards translating sCAR-T cells to the clinic we have initiated humanization and in silico prediction of T cell epitopes for the murine 52SR4-based sCAR and FMC63-based switch to reduce the risk of development of human anti-mouse (HAMA) antibodies. We expect this will be important to ensure orthogonality of the sCAR-T cell/switch interaction is not compromised by a HAMA response and to prevent immunological clearance of sCAR-T cells. Although the PNE sequence does not occur in the human proteome, it cannot be excluded that antigenic mimicry could lead to off-target activation. Towards understanding this risk we have initiated tissue cross-reactivity studies with the 52SR4 scFv.

In summary, sCAR-T cells represent a promising new paradigm in cell therapy that have the potential for improved safety and versatility compared to current T cell therapies. We are currently testing sCAR-T cells in solid tumor models where the ability to titrate therapy to minimize organ toxicity due to shared antigen expression and bystander cellular toxicity may be critical (53). In addition, this added control over sCAR-T cell activity may allow engineered cells to be turned off after tumor elimination to allow healthy B cells to repopulate in leukemia and lymphoma patients who are in remission. Indeed, in the accompanying publication we show that switch discontinuation can lead to the restoration of the peripheral blood B cells in a surrogate mouse model using anti-FITC CAR-T cells and FITC labeled anti-murine CD19 switches (45). Finally, we are also evaluating the ability of sCAR-T cells to target more than one antigen in vivo by co-delivery of CD19 and CD20 switches, which may be an effective method to prevent relapse due to antigen-loss escape mutations in patients (11), and may provide improved efficacy in the treatment of cancers with heterogeneous antigen expression. Furthermore, the development of a single, universal sCAR-T cell is expected to obviate the development of a new CAR for each target and off-set the cost of cell therapy by standardizing vector design, cell manufacture, and treatment protocols across multiple indications.

TABLE 38

Chimeric Antigen Receptor-Nucleotide Sequence

| SEQ ID NO | SEQUENCE |
|---|---|
| 1 | CAGGTGGCACTTTTCGGGGAAATGTGCGCGGAACCCCTATTTGTTTATTTTTCTAAATACA<br>TTCAAATATGTATCCGCTCATGAGACAATAACCCTGATAAATGCTTCAATAATATTGAAA<br>AAGGAAGAGTATGAGTATTCAACATTTCCGTGTCGCCCTTATTCCCTTTTTTGCGGCATTT<br>TGCCTTCCTGTTTTTGCTCACCCAGAAACGCTGGTGAAAGTAAAAGATGCTGAAGATCAG<br>TTGGGTGCACGAGTGGGTTACATCGAACTGGATCTCAACAGCGGTAAGATCCTTGAGAGT<br>TTTCGCCCCGAAGAACGTTTTCCAATGATGAGCACTTTTAAAGTTCTGCTATGTGGCGCG<br>GTATTATCCCGTATTGACGCCGGGCAAGAGCAACTCGGTCGCCGCATACACTATTCTCAG<br>AATGACTTGGTTGAGTACTCACCAGTCACAGAAAAGCATCTTACGGATGGCATGACAGTA<br>AGAGAATTATGCAGTGCTGCCATAACCATGAGTGATAACACTGCGGCCAACTTACTTCTG<br>ACAACGATCGGAGGACCGAAGGAGCTAACCGCTTTTTTGCACAACATGGGGGATCATGT<br>AACTCGCCTTGATCGTTGGGAACCGGAGCTGAATGAAGCCATACCAAACGACGAGCGTG<br>ACACCACGATGCCTGTAGCAATGGCAACAACGTTGCGCAAACTATTAACTGGCGAACTA<br>CTTACTCTAGCTTCCCGGCAACAATTAATAGACTGGATGGAGGCGGATAAAGTTGCAGGA<br>CCACTTCTGCGCTCGGCCCTTCCGGCTGGCTGGTTTATTGCTGATAAATCTGGAGCCGGTG<br>AGCGTGGGTCTCGCGGTATCATTGCAGCACTGGGGCCAGATGGTAAGCCCTCCCGTATCG<br>TAGTTATCTACACGACGGGGAGTCAGGCAACTATGGATGAACGAAATAGACAGATCGCT<br>GAGATAGGTGCCTCACTGATTAAGCATTGGTAACTGTCAGACCAAGTTTACTCATATATA<br>CTTTAGATTGATTTAAAACTTCATTTTTAATTTAAAAGGATCTAGGTGAAGATCCTTTTTG<br>ATAATCTCATGACCAAAATCCCTTAACGTGAGTTTTCGTTCCACTGAGCGTCAGACCCCG<br>TAGAAAAGATCAAAGGATCTTCTTGAGATCCTTTTTTTCTGCGCGTAATCTGCTGCTTGCA<br>AACAAAAAAACCACCGCTACCAGCGGTGGTTTGTTTGCCGGATCAAGAGCTACCAACTCT<br>TTTTCCGAAGGTAACTGGCTTCAGCAGAGCGCAGATACCAAATACTGTCCTTCTAGTGTA<br>GCCGTAGTTAGGCCACCACTTCAAGAACTCTGTAGCACCGCCTACATACCTCGCTCTGCT<br>AATCCTGTTACCAGTGGCTGCTGCCAGTGGCGATAAGTCGTGTCTTACCGGGTTGGACTC<br>AAGACGATAGTTACCGGATAAGGCGCAGCGGTCGGGCTGAACGGGGGGTTCGTGCACAC<br>AGCCCAGCTTGGAGCGAACGACCTACACCGAACTGAGATACCTACAGCGTGAGCTATGA<br>GAAAGCGCCACGCTTCCCGAAGGGAGAAAGGCGGACAGGTATCCGGTAAGCGGCAGGG<br>TCGGAACAGGAGAGCGCACGAGGGAGCTTCCAGGGGGAAACGCCTGGTATCTTTATAGT<br>CCTGTCGGGTTTCGCCACCTCTGACTTGAGCGTCGATTTTTGTGATGCTCGTCAGGGGGGC<br>GGAGCCTATGGAAAAACGCCAGCAACGCGGCCTTTTTACGGTTCCTGGCCTTTTGCTGGC<br>CTTTTGCTCACATGTTCTTTCCTGCGTTATCCCCTGATTCTGTGGATAACCGTATTACCGCC<br>TTTGAGTGAGCTGATACCGCTCGCCGCAGCCGAACGACCGAGCGCAGCGAGTCAGTGAG<br>CGAGGAAGCGGAAGAGCGCCCAATACGCAAACCGCCTCTCCCCGCGCGTTGGCCGATTC<br>ATTAATGCAGCTGGCACGACAGGTTTCCCGACTGGAAAGCGGGCAGTGAGCGCAACGCA<br>ATTAATGTGAGTTAGCTCACTCATTAGGCACCCCAGGCTTTACACTTTATGCTTCCGGCTC<br>GTATGTTGTGTGGAATTGTGAGCGGATAACAATTTCACACAGGAAACAGCTATGACCATG<br>ATTACGCCAAGCGCGCAATTAACCCTCACTAAAGGGAACAAAAGCTGGAGCTGCAAGCT<br>TAATGTAGTCTTATGCAATACTCTTGTAGTCTTGCAACATGGTAACGATGAGTTAGCAAC<br>ATGCCTTACAAGGAGAGAAAAAGCACCGTGCATGCCGATTGGTGGAAGTAAGGTGGTAC<br>GATCGTGCCTTATTAGGAAGGCAACAGACGGGTCTGACATGGATTGGACGAACCACTGA<br>ATTGCCGCATTGCAGAGATATTGTATTTAAGTGCCTAGCTCGATACAATAAACGGGTCTC<br>TCTGGTTAGACCAGATCTGAGCCTGGGAGCTCTCTGGCTAACTAGGGAACCCACTGCTTA<br>AGCCTCAATAAAGCTTGCCTTGAGTGCTTCAAGTAGTGTGTGCCCGTCTGTTGTGTGACTC<br>TGGTAACTAGAGATCCCTCAGACCCTTTTAGTCAGTGTGGAAAATCTCTAGCAGTGGCGC<br>CCGAACAGGGACCTGAAAGCGAAAGGGAAACCAGAGCTCTCTCGACGCAGGACTCGGCT<br>TGCTGAAGCGCGCACGGCAAGAGGCGAGGGGCGGCGACTGGTGAGTACGCCAAAAATTT<br>TGACTAGCGGAGGCTAGAAGGAGAGAGATGGGTGCGAGAGCGTCAGTATTAAGCGGGG<br>GAGAATTAGATCGCGATGGGAAAAAATTCGGTTAAGGCCAGGGGGAAAGAAAAAATAT<br>AAATTAAAACATATAGTATGGGCAAGCAGGGAGCTAGAACGATTCGCAGTTAATCCTGG<br>CCTGTTAGAAACATCAGAAGGCTGTAGACAAATACTGGGACAGCTACAACCATCCCTTC<br>AGACAGGATCAGAAGAACTTAGATCATTATATAATACAGTAGCAACCCTCTATTGTGTGC<br>ATCAAAGGATAGAGATAAAAGACACCAAGGAAGCTTTAGACAAGATAGAGGAAGAGCA<br>AAACAAAAGTAAGACCACCGCACAGCAAGCGGCCGCTGATCTTCAGACCTGGAGGAGGA<br>GATATGAGGGACAATTGGAGAAGTGAATTATATAAATATAAAGTAGTAAAAATTGAACC<br>ATTAGGAGTAGCACCCACCAAGGCAAAGAGAAGAGTGGTGCAGAGAGAAAAAAGAGCA<br>GTGGGAATAGGAGCTTTGTTCCTTGGGTTCTTGGGAGCAGCAGGAAGCACTATGGGCGCA<br>GCCTCAATGACGCTGACGGTACAGGCCAGACAATTATTGTCTGGTATAGTGCAGCAGCA<br>GAACAATTTGCTGAGGGCTATTGAGGCGCAACAGCATCTGTTGCAACTCACAGTCTGGGG<br>CATCAAGCAGCTCCAGGCAAGAATCCTGGCTGTGGAAAGATACCTAAAGGATCAACAGC<br>TCCTGGGGATTTGGGGTTGCTCTGGAAAACTCATTTGCACCACTGCTGTGCCTTGGAATG<br>CTAGTTGGAGTAATAAATCTCTGGAACAGATTGGAATCACACGACCTGGATGGAGTGGG<br>ACAGAGAAATTAACAATTACACAAGCTTAATACACTCCTTAATTGAAGAATCGCAAAAC<br>CAGCAAGAAAAGAATGAACAAGAATTATTGGAATTAGATAAATGGGCAAGTTTGTGGAA<br>TTGGTTTAACATAACAAATTGGCTGTGGTATATAAAATTATTCATAATGATAGTAGGAGG<br>CTTGGTAGGTTTAAGAATAGTTTTTGCTGTACTTTCTATAGTGAATAGAGTTAGGCAGGG<br>ATATTCACCATTATCGTTTCAGACCCACCTCCCAACCCCGAGGGGACCCGACAGGCCCGA<br>AGGAATAGAAGAAGAAGGTGGAGAGAGAGACAGAGACAGATCCATTCGATTAGTGAAC<br>GGATCTCGACGGTTAACTTTTAAAAGAAAAGGGGGGATTGGGGGGTACAGTGCAGGGGA<br>AAGAATAGTAGACATAATAGCAACAGACATACAAACTAAAGAATTACAAAAACAAATTA<br>CAAAAATTCAAAATTTTATCGAGCTTTGCAAAGATGGATAAAGTTTTAAACAGAGAGGA<br>ATCTTTGCAGCTAATGGACCTTCTAGGTCTTGAAAGGAGTGCCTCGTGAGGCTCCGGTGC<br>CCGTCAGTGGGCAGAGCGCACATCGCCCACAGTCCCCGAGAAGTTGGGGGGAGGGGTCG<br>GCAATTGAACCGGTGCCTAGAGAAGGTGGCGCGGGGTAAACTGGGAAAGTGATGTCGTG<br>TACTGGCTCCGCCTTTTTCCCGAGGGTGGGGGAGAACCGTATATAAGTGCAGTAGTCGCC<br>GTGAACGTTCTTTTTCGCAACGGGTTTGCCGCCAGAACACAGGTAAGTGCCGTGTGTGGT |

TABLE 38-continued

Chimeric Antigen Receptor-Nucleotide Sequence

| SEQ ID NO | SEQUENCE |
|---|---|
| | TCCCGCGGGCCTGGCCTCTTTACGGGTTATGGCCCTTGCGTGCCTTGAATTACTTCCACCT<br>GGCTGCAGTACGTGATTCTTGATCCCGAGCTTCGGGTTGGAAGTGGGTGGGAGAGTTCGA<br>GGCCTTGCGCTTAAGGAGCCCCTTCGCCTCGTGCTTGAGTTGAGGCCTGGCCTGGGCGCT<br>GGGGCCGCCGCGTGCGAATCTGGTGGCACCTTCGCGCCTGTCTCGCTGCTTTCGATAAGT<br>CTCTAGCCATTTAAAATTTTTGATGACCTGCTGCGACGCTTTTTTTCTGGCAAGATAGTCT<br>TGTAAATGCGGGCCAAGATCTGCACACTGGTATTTCGGTTTTTGGGGCCGCGGGCGGCGA<br>CGGGGCCCGTGCGTCCCAGCGCACATGTTCGGCGAGGCGGGGCCTGCGAGCGCGGCCAC<br>CGAGAATCGGACGGGGGTAGTCTCAAGCTGGCCGGCCTGCTCTGGTGCCTGGCCTCGCGC<br>CGCCGTGTATCGCCCCGCCCTGGGCGGCAAGGCTGGCCCGGTCGGCACCAGTTGCGTGA<br>GCGGAAAGATGGCCGCTTCCCGGCCCTGCTGCAGGGAGCTCAAAATGGAGGACGCGGCG<br>CTCGGGAGAGCGGGCGGGTGAGTCACCCACACAAAGGAAAAGGGCCTTTCCGTCCTCAG<br>CCGTCGCTTCATGTGACTCCACGGAGTACCGGGCGCCGTCCAGGCACCTCGATTAGTTCT<br>CGAGCTTTTGGAGTACGTCGTCTTTAGGTTGGGGGGAGGGGTTTTATGCGATGGAGTTTC<br>CCCACACTGAGTGGGTGGAGACTGAAGTTAGGCCAGCTTGGCACTTGATGTAATTCTCCT<br>TGGAATTTGCCCTTTTTGAGTTTGGATCTTGGTTCATTCTCAAGCCTCAGACAGTGGTTCA<br>AAGTTTTTTTCTTCCATTTCAGGTGTCGTGAGGAATTCGGTACCGCGGCCGCCCGGGGATC<br>CATGGCCTTACCAGTGACCGCCTTGCTCCTGCCGCTGGCCTTGCTGCTCCACGCCGCCAG<br>GCCGGACGCCGTTGTGACCCAGGAATCCGCTCTGACCTCTTCTCCAGGCGAAACCGTGAC<br>TCTGACTTGCCGTAGTAGCACCGGGGCTGTGACCACATCTAACTATGCCAGTTGGGTCCA<br>GGAAAAACCGGATCACCTGTTTACTGGCCTGATTGGCGGCACCAACAATCGCGCACCGG<br>GTGTGCCCGCTCGTTTCAGCGGTTCCCTGATTGGGGACAAGGCAGCACTGACTATCACCG<br>GCGCCCAGACCGAAGATGAGGCGATCTATTTTTGCGTCCTGTGGTACAGCGACCATTGGG<br>TGTTCGGGGGAGGCACCAAACTGACAGTGCTGGGCGGAGGAGGAGGTTCAGGAGGAGG<br>AGGTAGCGGGGGAGGCGGTTCCGGGGGAGGCGGTTCTGATGTGCAGCTGCAAGAATCCG<br>GGCCAGGACTGGTTGCGCCTTCTCAGAGTCTGTCAATTACATGTACTGTTAGTGGCTTTCT<br>GCTGACCGACTATGGTGTGAACTGGGTTCGTCAGAGCCCAGGCAAGGGTCTGGAGTGGC<br>TGGGAGTGATTTGGGGGGATGGAATCACAGACTACAATAGCGCACTGAAATCTCGGCTG<br>AGTGTTACCAAAGATAACAGCAAGTCCCAGGTCTTCCTGAAGATGAACAGCCTGCAAAG<br>CGGCGACTCCGCTCGCTATTACTGCGTTACCGGACTGTTTGATTATTGGGGGCAGGGGAC<br>AACTCTGACTGTTTCCTCCACCACGACGCCAGCGCCGCGACCACCAACACCGGCGCCCAC<br>CATCGCGTCGCAGCCCCTGTCCCTGCGCCCAGAGGCGTGCCGGCCAGCGGCGGGGGGCG<br>CAGTGCACACGAGGGGGCTGGACTTCGCCTGTGATATCTACATCTGGGCGCCCTTGGCCG<br>GGACTTGTGGGGTCCTTCTCCTGTCACTGGTTATCACCCTTTACTGCAAACGGGGCAGAA<br>AGAAACTCCTGTATATATTCAAACAACCATTTATGAGACCAGTACAAACTACTCAAGAGG<br>AAGATGGCTGTAGCTGCCGATTTCCAGAAGAAGAAGAAGGAGGATGTGAACTGAGAGTG<br>AAGTTCAGCAGGAGCGCAGACGCCCCCGCGTACAAGCAGGGCCAGAACCAGCTCTATAA<br>CGAGCTCAATCTAGGACGAAGAGAGGAGTACGATGTTTTGGACAAGAGACGTGGCCGGG<br>ACCCTGAGATGGGGGGAAAGCCGAGAAGGAAGAACCCTCAGGAAGGCCTGTACAATGA<br>ACTGCAGAAAGATAAGATGGCGGAGGCCTACAGTGAGATTGGGATGAAAGGCGAGCGC<br>CGGAGGGGCAAGGGGCACGATGGCCTTTACCAGGGTCTCAGTACAGCCACCAAGGACAC<br>CTACGACGCCCTTCACATGCAGGCCCTGCCCCCTCGCTAAGTCGACAATCAACCTCTGGA<br>TTACAAAATTTGTGAAAGATTGACTGGTATTCTTAACTATGTTGCTCCTTTTACGCTATGT<br>GGATACGCTGCTTTAATGCCTTTGTATCATGCTATTGCTTCCCGTATGGCTTTCATTTTCTC<br>CTCCTTGTATAAATCCTGGTTGCTGTCTCTTTATGAGGAGTTGTGGCCCGTTGTCAGGCAA<br>CGTGGCGTGGTGTGCACTGTGTTTGCTGACGCAACCCCCACTGGTTGGGGCATTGCCACC<br>ACCTGTCAGCTCCTTTCCGGGACTTTCGCTTTCCCCCTCCCTATTGCCACGGCGGAACTCA<br>TCGCCGCCTGCCTTGCCCGCTGCTGGACAGGGGCTCGGCTGTTGGGCACTGACAATTCCG<br>TGGTGTTGTCGGGGAAGCTGACGTCCTTTCCATGGCTGCTCGCCTGTGTTGCCACCTGGAT<br>TCTGCGCGGGACGTCCTTCTGCTACGTCCCTTCGGCCCTCAATCCAGCGGACCTTCCTTCC<br>CGCGGCCTGCTGCCGGCTCTGCGGCCTCTTCCGCGTCTTCGCCTTCGCCCTCAGACGAGTC<br>GGATCTCCCTTTGGGCCGCCTCCCCGCCTGGAATTCGAGCTCGGTACCTTTAAGACCAAT<br>GACTTACAAGGCAGCTGTAGATCTTAGCCACTTTTTAAAAGAAAAGGGGGGACTGGAAG<br>GGCTAATTCACTCCCAACGAAGACAAGATCTGCTTTTTGCTTGTACTGGGTCTCTCTGGTT<br>AGACCAGATCTGAGCCTGGGAGCTCTCTGGCTAACTAGGGAACCCACTGCTTAAGCCTCA<br>ATAAAGCTTGCCTTGAGTGCTTCAAGTAGTGTGTGCCCGTCTGTTGTGTGACTCTGGTAAC<br>TAGAGATCCCTCAGACCCTTTTAGTCAGTGTGGAAAATCTCTAGCAGTAGTAGTTCATGT<br>CATCTTATTATTCAGTATTTATAACTTGCAAAGAAATGAATATCAGAGAGTGAGAGGAAC<br>TTGTTTATTGCAGCTTATAATGGTTACAAATAAAGCAATAGCATCACAAATTTCACAAAT<br>AAAGCATTTTTTTCACTGCATTCTAGTTGTGGTTTGTCCAAACTCATCAATGTATCTTATC<br>ATGTCTGGCTCTAGCTATCCCGCCCCTAACTCCGCCCAGTTCCGCCCATTCTCCGCCCCAT<br>GGCTGACTAATTTTTTTTATTTATGCAGAGGCCGAGGCCGCCTCGGCCTCTGAGCTATTCC<br>AGAAGTAGTGAGGAGGCTTTTTTGGAGGCCTAGGCTTTTGCGTCGAGACGTACCCAATTC<br>GCCCTATAGTGAGTCGTATTACGCGCGCTCACTGGCCGTCGTTTTACAACGTCGTGACTG<br>GGAAAACCCTGGCGTTACCCAACTTAATCGCCTTGCAGCACATCCCCCTTTCGCCAGCTG<br>GCGTAATAGCGAAGAGGCCCGCACCGATCGCCCTTCCCAACAGTTGCGCAGCCTGAATG<br>GCGAATGGCGCGACGCGCCCTGTAGCGGCGCATTAAGCGCGGCGGGTGTGGTGGTTACG<br>CGCAGCGTGACCGCTACACTTGCCAGCGCCCTAGCGCCCGCTCCTTTCGCTTTCTTCCCTT<br>CCTTTCTCGCCACGTTCGCCGGCTTTCCCCGTCAAGCTCTAAATCGGGGGCTCCCTTTAGG<br>GTTCCGATTTAGTGCTTTACGGCACCTCGACCCCAAAAAACTTGATTAGGGTGATGGTTC<br>ACGTAGTGGGCCATCGCCCTGATAGACGGTTTTTCGCCCTTTGACGTTGGAGTCCACGTT<br>CTTTAATAGTGGACTCTTGTTCCAAACTGGAACAACACTCAACCCTATCTCGGTCTATTCT<br>TTTGATTTATAAGGGATTTTGCCGATTTCGGCCTATTGGTTAAAAAATGAGCTGATTTAAC<br>AAAAATTTAACGCGAATTTTAACAAAATATTAACGTTTACAATTTCC |

TABLE 39

CAR Binding Region-Nucleotide & Amino Acid Sequences

| SEQ ID NO | SEQUENCE |
|---|---|
| 2 | RMKQLEPKVEELLPKNYHLENEVARLKKLVGER |
| 3 | NYHLENEVARLKKL |
| 4 | GGGGSNYHLENEVARLKKLGGGGS |

TABLE 39-continued

CAR Binding Region-Nucleotide & Amino Acid Sequences

| SEQ ID NO | SEQUENCE |
|---|---|
| 5 | GGGGSDYKDDDDK |
| 6 | GGGGSDYKDDDDKP |
| 7 | DYKDDDDK |

TABLE 40

CAR-T switch targeting polypeptides-Nucleotide Sequence

| SEQ ID NO | SEQUENCE |
|---|---|
| 8 | GACATCCAGATGACACAGACTACATCCTCCCTGTCTGCCTCTCTGGGAGACAGAGTCACC<br>ATCAGTTGCAGGGCAAGTCAGGACATTAGTAAATATTTAAATTGGTATCAGCAGAAACC<br>AGATGGAACTGTTAAACTCCTGATCTACCATACATCAAGATTACACTCAGGAGTCCCATC<br>AAGGTTCAGTGGCAGTGGGTCTGGAACAGATTATTCTCTCACCATTAGCAACCTGGAGCA<br>AGAAGATATTGCCACTTACTTTTGCCAACAGGGTAATACGCTTCCGTACACGTTCGGAGG<br>GGGGACCAAGCTTGAGATCAAACGAACTGTGGCTGCACCATCTGTCTTCATCTTCCCGCC<br>ATCTGATGAGCAGTTGAAATCTGGAACTGCCTCTGTCGTGTGCCTGCTGAATAACTTCTAT<br>CCCAGAGAGGCCAAAGTACAGTGGAAGGTGGATAACGCCCTCCAATCGGGTAACTCCCA<br>GGAGAGTGTCACAGAGCAGGACAGCAAGGACAGCACCTACAGCCTCAGCAGCACCCTGA<br>CGCTGAGCAAAGCAGACTACGAGAAACACAAAGTCTACGCCTGCGAAGTCACCCATCAG<br>GGCCTGTCCTCGCCCGTCACAAAGAGCTTCAACAGGGGAGAGTGT |
| 9 | GAGGTGAAACTGCAGGAGTCAGGACCTGGCCTGGTGGCGCCCTCACAGAGCCTGTCCGT<br>CACATGCACTGTCTCAGGGGTCTCATTACCCGACTATGGTGTAAGCTGGATTCGCCAGCC<br>TCCACGAAAGGGTCTGGAGTGGCTGGGAGTAATATGGGGTAGTGAAACCACATACTATA<br>ATTCAGCTCTCAAATCCAGACTGACCATCATCAAGGACAACTCCAAGAGCCAAGTTTTCT<br>TAAAAATGAACAGTCTGCAAACTGATGACACAGCCATTTACTACTGTGCCAAACATTATT<br>ACTACGGTGGTAGCTATGCTATGGACTACTGGGGCCAAGGAACCTCAGTCACCGTCTCCT<br>CAGCCTCCACCAAGGGCCCATCGGTCTTCCCCCTGGCACCCTCCTCCAAGAGCACCTCTG<br>GGGGCACAGCGGCCCTGGGCTGCCTGGTCAAGGACTACTTCCCCGAACCGGTGACGGTG<br>TCGTGGAACTCAGGCGCCCTGACCAGCGGCGTGCACACCTTCCCGGCTGTCCTACAGTCC<br>TCAGGACTCTACTCCCTCAGCAGCGTGGTGACTGTGCCCTCTAGCAGCTTGGGCACCCAG<br>ACCTACATCTGCAACGTGAATCACAAGCCCAGCAACACCAAGGTGGACAAGAAAGTTGA<br>GCCCAAATCTTGT |
| 10 | GAGGTGAAACTGCAGGAGTCAGGACCTGGCCTGGTGGCGCCCTCACAGAGCCTGTCCGT<br>CACATGCACTGTCTCAGGGGTCTCATTACCCGACTATGGTGTAAGCTGGATTCGCCAGCC<br>TCCACGAAAGGGTCTGGAGTGGCTGGGAGTAATATGGGGTAGTGAAACCACATACTATA<br>ATTCAGCTCTCAAATCCAGACTGACCATCATCAAGGACAACTCCAAGAGCCAAGTTTTCT<br>TAAAAATGAACAGTCTGCAAACTGATGACACAGCCATTTACTACTGTGCCAAACATTATT<br>ACTACGGTGGTAGCTATGCTATGGACTACTGGGGCCAAGGAACCTCAGTCACCGTCTCCT<br>CAGCCTCCACCAAGGGCCCATCGGTCTTCCCCCTGGCACCCTCCTCCAAGAGCACCTCTG<br>GGGGCACAGCGGCCCTGGGCTGCCTGGTCAAGGACTACTTCCCCGAACCGGTGACGGTG<br>TCGTGGAACTCAGGCGCCCTGACCAGCGGCGTGCACACCTTCCCGGCTGTCCTACAGTCC<br>TCAGGACTCTACTCCCTCAGCAGCGTGGTGACTGTGCCCTCTAGCAGCTTGGGCACCCAG<br>ACCTACATCTGCAACGTGAATCACAAGCCCAGCAACACCAAGGTGGACAAGAAAGTTGA<br>GCCCAAATCTTGTGACAAAACTCACACATGCCCACCGTGCCCAGCACCTCCAGTCGCCGG<br>ACCGTCAGTCTTCCTCTTCCCTCCAAAACCCAAGGACACCCTCATGATCTCCCGGACCCCT<br>GAGGTCACATGCGTGGTGGTGGACGTGAGCCACGAAGACCCTGAGGTCAAGTTCAACTG<br>GTACGTGGACGGCGTGGAGGTGCATAATGCCAAGACAAAGCCGCGGGAGGAGCAGTAC<br>AACAGCACGTACCGTGTGGTCAGCGTCCTCACCGTCCTGCACCAGGACTGGCTGAATGGC<br>AAGGAGTACAAGTGCAAGGTCTCCAACAAAGGCCTCCCAAGCTCCATCGAGAAAACCAT<br>CTCCAAAGCCAAAGGGCAGCCCCGAGAACCACAGGTGTACACCCTGCCTCCATCCCGGG<br>ATGAGCTGACCAAGAACCAGGTCAGCCTGACCTGCCTGGTCAAAGGCTTCTATCCCAGCG<br>ACATCGCCGTGGAGTGGGAGAGCAATGGGCAGCCGGAGAACAACTACAAGACCACGCCT<br>CCCGTGCTGGACTCCGACGGCTCCTTCTTCCTCTACAGCAAGCTCACCGTGGACAAGAGC<br>AGGTGGCAGCAGGGGAACGTCTTCTCATGCTCCGTGATGCATGAGGCTCTGCACAACCAC<br>TACACGCAGAAGAGCCTCTCCCTGTCTCCGGGTAAA |
| 11 | ATGAAAAAGAATATCGCATTTCTTCTTGCTAGCATGTTCGTTTTTTCTATTGCTACAAACG<br>CATACGCTGACATCCAGATGACCCAGTCTCCATCCTCCCTGTCTGCATCTGTAGGAGACA<br>GAGTCACCATCACTTGCCGGGCAAGTCAGGATGTGAATACCGCGGTCGCATGGTATCAG<br>CAGAAACCAGGGAAAGCCCCTAAGCTCCTGATCTATTCTGCATCCTTCTTGTATAGTGGG<br>GTCCCATCAAGGTTCAGTGGCAGTAGATCTGGGACAGATTTCACTCTCACCATCAGCAGT<br>CTGCAACCTGAAGATTTTGCAACTTACTACTGTCAACAGCATTACACTACCCCTCCGACG<br>TTCGGCCAAGGTACCAAGCTTGAGATCAAACGAACTGTGGCTGCACCATCTGTCTTCATC<br>TTCCCGCCATCTGATGAGCAGTTGAAATCTGGAACTGCCTCTGTCGTGTGCCTGCTGAAT<br>AACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCA |

TABLE 40-continued

CAR-T switch targeting polypeptides-Nucleotide Sequence

| SEQ ID NO | SEQUENCE |
| --- | --- |
| | GCACCCTGACGCTGAGCAAAGCAGACTACGAGAAACACAAAGTCTACGCCTGCGAAGTC<br>ACCCATCAGGGCCTGTCCTCGCCCGTCACAAAGAGCTTCAACAGGGGAGAGTGT |
| 12 | ATGAAAAAGAATATCGCATTTCTTCTTGCATCTATGTTCGTTTTTTCTATTGCTACAAACG<br>CGTACGCTGAGGTGCAGCTGGTGGAGTCTGGAGGAGGCTTGGTCCAGCCTGGGGGGTCC<br>CTGAGACTCTCCTGTGCAGCCTCTGGGTTCAATATTAAGGACACTTACATCCACTGGGTC<br>CGCCAGGCTCCAGGGAAGGGGCTGGAGTGGGTCGCACGTATTTATCCTACCAATGGTTAC<br>ACACGCTACGCAGACTCCGTGAAGGGCCGATTCACCATCTCCGCAGACACTTCCAAGAA<br>CACGGCGTATCTTCAAATGAACAGCCTGAGAGCCGAGGACACGGCCGTGTATTACTGTTC<br>GAGATGGGGCGGTGACGGCTTCTATGCCATGGACTACTGGGGCCAAGGAACCCTGGTCA<br>CCGTCTCCTCAGCCTCCACCAAGGGCCCATCGGTCTTCCCCCTGGCACCCTCCTCCAAGA<br>GCACCTCTGGGGGCACAGCGGCCCTGGGCTGCCTGGTCAAGGACTACTTCCCCGAACCG<br>GTGACGGTGTCGTGGAACTCAGGCGCCCTGACCAGCGGCGTGCACACCTTCCCGGCTGTC<br>CTACAGTCCTCAGGACTCTACTCCCTCAGCAGCGTGGTGACTGTGCCCTCTAGCAGCTTG<br>GGCACCCAGACCTACATCTGCAACGTGAATCACAAGCCCAGCAACACCAAGGTGGACAA<br>GAAAGTTGAGCCCAAATCTTGTGACAAAACTCACACA |
| 13 | ATGAAAAAGAATATCGCATTTCTTCTTGCTAGCATGTTCGTTTTTTCTATTGCTACAAACG<br>CATACGCTCAGATTGTGCTGAGCCAGAGCCCGGCGATTCTGAGCGCGAGCCCGGGCGAA<br>AAAGTGACCATGACCTGCCGCGCGAGCAGCAGCGTGAGCTATATTCATTGGTTTCAGCAG<br>AAACCGGGCAGCAGCCCGAAACCGTGGATTTATGCGACCAGCAACCTGGCGAGCGGCGT<br>GCCGGTGCGCTTTAGCGGCAGCGGCAGCGGCACCAGCTATAGCCTGACCATTAGCCGCG<br>TGGAAGCGGAAGATGCGGCGACCTATTATTGCCAGCAGTGGACCAGCAACCCGCCGACC<br>TTTGGCGGCGGCACCAAGCTTGAGATCAAACGAACTGTGGCTGCACCATCTGTCTTCATC<br>TTCCCGCCATCTGATGAGCAGTTGAAATCTGGAACTGCCTCTGTCGTGTGCCTGCTGAAT<br>AACTTCTATCCCAGAGAGGCCAAAGTACAGTGGAAGGTGGATAACGCCCTCCAATCGGG<br>TAACTCCCAGGAGAGTGTCACAGAGCAGGACAGCAAGGACAGCACCTACAGCCTCAGCA<br>GCACCCTGACGCTGAGCAAAGCAGACTACGAGAAACACAAAGTCTACGCCTGCGAAGTC<br>ACCCATCAGGGCCTGTCCTCGCCCGTCACAAAGAGCTTCAACAGGGGAGAGTGT |
| 14 | ATGAAAAAGAATATCGCATTTCTTCTTGCATCTATGTTCGTTTTTTCTATTGCTACAAACG<br>CGTACGCTCAGGTGCAGCTGCAGCAGCCGGGCGCGGAACTGGTGAAACCGGGCGCGAGC<br>GTGAAAATGAGCTGCAAAGCGAGCGGCTATACCTTTACCAGCTATAACATGCATTGGGTG<br>AAACAGACCCCGGGCCGCGGCCTGGAATGGATTGGCGCGATTTATCCGGGCAACGGCGA<br>TACCAGCTATAACCAGAAATTTAAAGGCAAAGCGACCCTGACCGCGGATAAAAGCAGCA<br>GCACCGCGTATATGCAGCTGAGCAGCCTGACCAGCGAAGATAGCGCGGTGTATTATTGC<br>GCGCGCAGCACCTATTATGGCGGCGATTGGTATTTTAACGTGTGGGGCGCGGGCACCACC<br>GTGACCGTGAGCGCGGCGAGCACCAAGGGCCCATCGGTCTTCCCCCTGGCACCCTCCTCC<br>AAGAGCACCTCTGGGGGCACAGCGGCCCTGGGCTGCCTGGTCAAGGACTACTTCCCCGA<br>ACCGGTGACGGTGTCGTGGAACTCAGGCGCCCTGACCAGCGGCGTGCACACCTTCCCGG<br>CTGTCCTACAGTCCTCAGGACTCTACTCCCTCAGCAGCGTGGTGACTGTGCCCTCTAGCA<br>GCTTGGGCACCCAGACCTACATCTGCAACGTGAATCACAAGCCCAGCAACACCAAGGTG<br>GACAAGAAAGTTGAGCCCAAATCTTGTGACAAAACTCACACA |
| 15 | ATGAGGGTCCCCGCTCAGCTCCTGGGGCTCCTGCTGCTCTGGCTCCCAGGTGCACGATGT<br>GACATCCTGCTGACCCAGTCCCCCGTGATCCTGTCCGTGTCCCCTGGCGAGCGGGTGTCC<br>TTCTCCTGCCGGGCCTCCCAGTCCATCGGCACCAACATCCACTGGTATCAGCAGCGGACC<br>AACGGCTCCCCTCGGCTGCTGATCAAGTACGCCTCCGAGTCTATCTCCGGCATCCCTTCCC<br>GGTTCTCCGGCTCCGGCTCTGGCACCGACTTCACCCTGTCCATCAACTCCGTGGAGTCCG<br>AGGATATCGCCGACTACTACTGCCAGCAGAACAACAACTGGCCTACCACCTTCGGCGCTG<br>GAACCAAGCTGGAGCTGAAGCGTACGGTGGCTGCACCATCTGTCTTCATCTTCCCGCCAT<br>CTGATGAGCAGTTGAAATCTGGAACTGCCTCTGTTGTGTGCCTGCTGAATAACTTCTATCC<br>CAGAGAGGCCAAAGTACAGTGGAAGGTGGATAACGCCCTCCAATCGGGTAACTCCCAGG<br>AGAGTGTCACAGAGCAGGACAGCAAGGACAGCACCTACAGCCTCAGCAGCACCCTGACG<br>CTGAGCAAAGCAGACTACGAGAAACACAAAGTCTACGCCTGCGAAGTCACCCATCAGGG<br>CCTGAGCTCGCCCGTCACAAAGAGCTTCAACAGGGGAGAGTGTTGATGA |
| 16 | ATGGGTTGGAGCCTCATCTTGCTCTTCCTTGTCGCTGTTGCTACGCGTGTCCACTCCCAGG<br>TGCAGCTGAAGCAGTCCGGCCCTGGCCTGGTGCAGCCTTCCCAGTCCCTGTCCATCACCT<br>GCACCGTGTCCGGCTTCTCCCTGACCAACTACGGCGTGCACTGGGTGCGCCAGTCCCCCG<br>GCAAGGGCCTGGAGTGGCTGGGCGTGATCTGGTCCGGCGGCAACACCGACTACAACACC<br>CCTTTCACCTCCCGGCTGTCCATCAACAAGGACAACTCCAAGTCCCAGGTGTTCTTCAAG<br>ATGAACTCCCTGCAGTCCAACGACACCGCCATCTACTACTGCGCCAGAGCCCTGACCTAC<br>TATGACTACGAGTTCGCCTACTGGGGCCAGGGCACCCTGGTGACCGTGTCCGCCGCTAGC<br>ACCAAGGGCCCATCGGTCTTCCCCCTGGCACCCTCCTCCAAGAGCACCTCTGGGGGCACA<br>GCGGCCCTGGGCTGCCTGGTCAAGGACTACTTCCCCGAACCGGTGACGGTGTCGTGGAAC<br>TCAGGCGCCCTGACCAGCGGCGTGCACACCTTCCCGGCTGTCCTACAGTCCTCAGGACTC<br>TACTCCCTCAGCAGCGTGGTGACCGTGCCCTCCAGCAGCTTGGGCACCCAGACCTACATC<br>TGCAACGTGAATCACAAGCCCAGCAACACCAAGGTGGACAAGAAAGTTGAGCCCAAATC<br>TTGTGACAAAACTCACACATGCCCACCGTGCCCA |
| 17 | GAGAACGTGCTCACCCAATCCCCCGCCATTATGTCCGCCTCCCCAGGCGAAAAGGTGACA<br>ATGACCTGCAGGGCCAGCTCCAACGTGATCAGCTCTTACGTGCACTGGTACCAGCAACGG<br>TCCGGCGCCTCCCCTAAGCTGTGGATCTATAGCACAAGCAACCTGGCTTCCGGCGTGCCT<br>GCACGGTTCAGCGGAAGCGGAAGCGGAACAAGTTACTCCCTCACCATTTCTAGCGTTGA |

TABLE 40-continued

| CAR-T switch targeting polypeptides-Nucleotide Sequence | |
|---|---|
| SEQ ID NO | SEQUENCE |
| | AGCCGAGGATGCCGCTACATACTATTGTCAACAGTACAGCGGATACCCCCTGACCTTCGG<br>AGCCGGCACAAAACTGGAGCTCAAGAGAGCAGCTGCAGCTCCCAGCGTGTTCATTTTTCC<br>TCCCTCCGACGAACAACTGAAAAGCGGAACAGCCTCTGTCGTTTGCCTGTTGAACAATTT<br>CTACCCTAGGGAGGCCAAGGTCCAGTGGAAAGTGGATAACGCTCTGCAAAGCGGAAATT<br>CTCAGGAAAGCGTTACCGAACAGGATTCTAAGGACTCTACATACTCTCTGTCTAGCACAC<br>TCACGCTGAGCAAAGCAGACTACGAGAAACACAAAGTCTACGCCTGCGAAGTCACCCAT<br>CAGGGCCTGTCCTCGCCCGTCACAAAGAGCTTCAACAGGGGAGAGTGT |
| 18 | GACATCCAGCTGCAGGAGAGCGGCCCCGGCCTGGTGAAGCCCAGCCAGAGCCTGAGCCT<br>GACCTGCAGCGTGACCGGCTACAGCATCACCAGCGCCTATTACTGGAACTGGATCCGGC<br>AGTTCCCCGGCAACAAGCTGGAGTGGATGGGCTACATCAGCTACGACGGCCGGAACAAC<br>TACAACCCAAGCCTGAAGAACCGGATCAGCATCACCCGGGACACCAGCAAGAACCAGTT<br>TTTCCTGAAGCTGAACAGCGTGACCACAGAGGACACCGCCACCTATTACTGCGCCAAGG<br>AGGGAGACTACGACGTGGGCAACTACTACGCCATGGACTACTGGGGCCAGGGCACCAGC<br>GTGACCGTGTCTAGCGCCCGGACCAAGGGCCCCAGCGTGTTCCCCCTGGCCCCCAGCTCT<br>AAGAGCACCAGCGGCGGAACCGCCGCTCTGGGCTGCCTGGTGAAGGACTACTTCCCCGA<br>GCCCGTGACCGTGAGCTGGAACAGCGGCGCCCTGACCAGCGGCGTGCACACCTTCCCCG<br>CCGTGCTGCAGAGCTCTGGCCTGTACAGCCTGAGCAGCGTGGTTACCGTGCCCAGTTCTT<br>CCCTGGGCACCCAGACCTACATCTGCAACGTGAACCACAAGCCCAGCAACACCAAGGTG<br>GACAAGAAAGTGGAGCCCAAGAGCTGC |
| 19 | GATATTCAGATGACCCAGAGCCCGAGCAGCCTGAGCGCGAGCGTGGGCGATCGCGTGAC<br>CATTACCTGCCGCGCGAGCGAAAGCGTGGATAACTATGGCATTAGCTTTATGAACTGGTT<br>TCAGCAGAAACCGGGCAAAGCGCCGAAACTGCTGATTTATGCGGCGAGCAACCAGGGCA<br>GCGGCGTGCCGAGCCGCTTTAGCGGCAGCGGCAGCGGCACCGATTTTACCCTGAACATTA<br>GCAGCCTGCAGCCGGATGATTTTGCGACCTATTATTGCCAGCAGAGCAAAGAAGTGCCGT<br>GGACCTTTGGCCAGGGCACCAAAGTGGAAATTAAACGAACTGTGGCTGCACCATCTGTCT<br>TCATCTTCCCGCCATCTGATGAGCAGTTGAAATCTGGAACTGCCTCTGTTGTGTGCCTGCT<br>GAATAACTTCTATCCCAGAGAGGCCAAAGTACAGTGGAAGGTGGATAACGCCCTCCAAT<br>CGGGTAACTCCCAGGAGAGTGTCACAGAGCAGGACAGCAAGGACAGCACCTACAGCCTC<br>AGCAGCACCCTGACGCTGAGCAAAGCAGACTACGAGAAACACAAAGTCTACGCCTGCGA<br>AGTCACCCATCAGGGCCTGAGCTCGCCCGTCACAAAGAGCTTCAACAGGGGAGAGTGT |
| 20 | CAGGTGCAGCTGGTGCAGAGCGGCGCGGAAGTGAAAAAACCGGGCAGCAGCGTGAAAG<br>TGAGCTGCAAAGCGAGCGGCTATACCTTTACCGATTATAACATGCATTGGGTGCGCCAGG<br>CGCCGGGCCAGGGCCTGGAATGGATTGGCTATATTTATCCGTATAACGGCGGCACCGGCT<br>ATAACCAGAAATTTAAAAGCAAAGCGACCATTACCGCGGATGAAAGCACCAACACCGCG<br>TATATGGAACTGAGCAGCCTGCGCAGCGAAGATACCGCGGTGTATTATTGCGCGCGCGG<br>CCGCCCGGCGATGGATTATTGGGGCCAGGGCACCCTGGTGACCGTGAGCAGCGCCTCCA<br>CCAAGGGCCCATCGGTCTTCCCCCTGGCACCCTCCTCCTAGAGCACCTCTGGGGGCACAG<br>CGGCCCTGGGCTGCCTGGTCAAGGACTACTTCCCCGAACCGGTGACGGTGTCGTGGAACT<br>CAGGCGCCCTGACCAGCGGCGTGCACACCTTCCCGGCTGTCCTACAGTCCTCAGGACTCT<br>ACTCCCTCAGCAGCGTGGTGACCGTGCCCTCCAGCAGCTTGGGCACCCAGACCTACATCT<br>GCAACGTGAATCACAAGCCCAGCAACACCAAGGTCGACAAGAAAGTTGAGCCCAAATCT<br>TGTGGTGGCGGTCACCATCACCATCATCACCACCAC |

TABLE 41

| CAR-T switch targeting polypeptides-Amino Acid Sequence | |
|---|---|
| SEQ ID NO | SEQUENCE |
| 21 | DIQMTQSPSSLSASVGDRVTITCKASQDVGIAVAWYQQKPGKVPKLLIYWASTRHTGVPDRFSG<br>SGSGTDFTLTISSLQPEDVATYYCQQYSSYPYTFGQGTKLEIK |
| 22 | EVQLVESGGGLVQPGGSLRLSCAASGFDFSRYWMSWVRQAPGKGLEWIGEINPDSSTINYAPS<br>LKDKFIISRDNAKNSLYLQMNSLRAEDTAVYYCARPDGNYWYFDVWGQGTLVTVSSASTKGP<br>SVFPLAPSSKSTSGGTAALGCLVKDYFPEPVTVSWNSGALTSGVHTFPAVLQSSGLYSLSSVVT<br>VPSSSLGTQTYICNVNHKPSNTKVDKKVEPKSC |
| 23 | DIQMTQSPSSMSVSVGDRVTITCHSSQDINSNIGWLQQKPGKSFKGLIYHGTNLDDGVPSRFSGS<br>GSGTDYTLTISSLQPEDFATYYCVQYAQFPWTFGGGTKLEIKRTVAAPSVFIFPPSDEQLKSGTA<br>SVVCLLNNFYPREAKVQWKVDNALQSGNSQESVTEQDSKDSTYSLSSTLTLSKADYEKHKVY<br>ACEVTHQGLSSPVTKSFNRGEC |
| 24 | QLQESGPGLVKPSQTLSLTCTVSGYSISSDFAWNWIRQPPGKGLEWMGYISYSGNTRYQPSLKS<br>RITISRDTSKNQFFLKLNSVTAADTATYYCVTAGRGFPYWGQGTLVTVSSASTKGPSVFPLAPSS<br>KSTSGGTAALGCLVKDYFPEPVTVSWNSGALTSGVHTFPAVLQSSGLYSLSSVVTVPSSSLGTQ<br>TYICNVNHKPSNTKVDKKVEPKSC |

TABLE 41-continued

CAR-T switch targeting polypeptides-Amino Acid Sequence

| SEQ ID NO | SEQUENCE |
|---|---|
| 25 | DIQMTQSPSSLSASVGDRVTITCRANQGISNNLNWYQQKPGKAPKPLIYYTSNLQSGVPSRFSGS GSGTDYTLTISSLQPEDFATYYCQQFTSLPYTFGQGTKLEIKRTVAAPSVFIFPPSDEQLKSGTAS VVCLLNNFYPREAKVQWKVDNALQSGNSQESVTEQDSKDSTYSLSSTLTLSKADYEKHKVYA CEVTHQGLSSPVTKSFNRGEC |
| 26 | EVQLVESGGGLVQPGGSLRLSCAASGFTFSNFDMAWVRQAPGKGLVWVSSITTGGGDTYYAD SVKGRFTISRDNAKSTLYLQMDSLRSEDTAVYYCVRHGYYDGYHLFDYWGQGTLVTVSSAST KGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKVEPKSC |
| 27 | DIQMTQTTSSLSASLGDRVTISCRASQDISKYLNWYQQKPDGTVKLLIYHTSRLHSGVPSRFSGS GSGTDYSLTISNLEQEDIATYFCQQGNTLPYTFGGGTKLEIKRTVAAPSVFIFPPSDEQLKSGTAS VVCLLNNFYPREAKVQWKVDNALQSGNSQESVTEQDSKDSTYSLSSTLTLSKADYEKHKVYA CEVTHQGLSSPVTKSFNRGEC |
| 28 | EVKLQESGPGLVAPSQSLSVTCTVSGVSLPDYGVSWIRQPPRKGLEWLGVIWGSETTYYNSALK SRLTIIKDNSKSQVFLKMNSLQTDDTAIYYCAKHYYYGGSYAMDYWGQGTSVTVSSASTKGPS VFPLAPSSKSTSGGTAALGCLVKDYFPEPVTVSWNSGALTSGVHTFPAVLQSSGLYSLSSVVTV PSSSLGTQTYICNVNHKPSNTKVDKKVEPKSCDKTHTCPPCPAPPVAGPSVFLFPPKPKDTLMIS RTPEVTCVVVDVSHEDPEVKFNWYVDGVEVHNAKTKPREEQYNSTYRVVSVLTVLHQDWLN GKEYKCKVSNKGLPSSIEKTISKAKGQPREPQVYTLPPSRDELTKNQVSLTCLVKGFYPSDIAVE WESNGQPENNYKTTPPVLDSDGSFFLYSKLTVDKSRWQQGNVFSCSVMHEALHNHYTQKSLS LSPGK |
| 29 | EVKLQESGPGLVAPSQSLSVTCTVSGVSLPDYGVSWIRQPPRKGLEWLGVIWGSETTYYNSALK SRLTIIKDNSKSQVFLKMNSLQTDDTAIYYCAKHYYYGGSYAMDYWGQGTSVTVSSASTKGPS VFPLAPSSKSTSGGTAALGCLVKDYFPEPVTVSWNSGALTSGVHTFPAVLQSSGLYSLSSVVTV PSSSLGTQTYICNVNHKPSNTKVDKKVEPKSC |

TABLE 42

CAR-T switches-Amino Acid Sequence

| SEQ ID NO | SEQUENCE |
|---|---|
| 30 | DIQMTQTTSSLSASLGDRVTISCRASQDISKYLNWYQQKPDGTVKLLIYHTSRLHSGVPSRFSGSG SGTDYSLTISNLEQEDIATYFCQQGNTLPYTFGGGTKLEIKRTVAAPSVFIFPPSDEQLKSGTASVV CLLNNFYPREAKVQWKVDNALQSGNSQESVTEQDS**GGGGSNYHLENEVARLKKLGGGGS**DS TYSLSSTLTLSKADYEKHKVYACEVTHQGLSSPVTKSFNRGEC |
| 31 | DIQMTQTTSSLSASLGDRVTISCRASQDISKYLNWYQQKPDGTVKLLIYHTSRLHSGVPSRFSGSG SGTDYSLTISNLEQEDIATYFCQQGNTLPYTFGGGTKLEIKRTVAAPSVFIFPPSDEQLKSGTASVV CLLNNFYPREAKVQWKVDNALQSGNSQESVTEQDS**GGGGSNYHLENEVARLKKLGGGGS**DS TYSLSSTLTLSKADYEKHKVYACEVTHQGLSSPVTKSFNRGEC |
| 32 | EVKLQESGPGLVAPSQSLSVTCTVSGVSLPDYGVSWIRQPPRKGLEWLGVIWGSETTYYNSALK SRLTIIKDNSKSQVFLKMNSLQTDDTAIYYCAKHYYYGGSYAMDYWGQGTSVTVSSASTKGPS VFPLAPSS**NYHLENEVARLKKL**SGGTAALGCLVKDYFPEPVTVSWNSGALTSGVHTFPAVLQS SGLYSLSSVVTVPSSSLGTQTYICNVNHKPSNTKVDKKVEPKSC |
| 33 | EVKLQESGPGLVAPSQSLSVTCTVSGVSLPDYGVSWIRQPPRKGLEWLGVIWGSETTYYNSALK SRLTIIKDNSKSQVFLKMNSLQTDDTAIYYCAKHYYYGGSYAMDYWGQGTSVTVSSASTKGPS VFPLAPSS**NYHLENEVARLKKL**SGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPPVAGPSVFLF PPKPKDTLMISRTPEVTCVVVDVSHEDPEVKFNWYVDGVEVHNAKTKPREEQYNSTYRVVSVL TVLHQDWLNGKEYKCKVSNKGLPSSIEKTISKAKGQPREPQVYTLPPSRDELTKNQVSLTCLVK GFYPSDIAVEWESNGQPENNYKTTPPVLDSDGSFFLYSKLTVDKSRWQQGNVFSCSVMHEALHN HYTQKSLSLSPGK |
| 34 | EVKLQESGPGLVAPSQSLSVTCTVSGVSLPDYGVSWIRQPPRKGLEWLGVIWGSETTYYNSALK SRLTIIKDNSKSQVFLKMNSLQTDDTAIYYCAKHYYYGGSYAMDYWGQGTSVTVSSASTKGPS VFPLAPSSKSTSGGTAALGCLVKDYFPEPVTVSWNSGALTSGVHTFPAVLQSSGLYSLSSVVTVP SSSLGTQTYICNVNHKPSNTKVDKKVEPKSC**GGGGSNYHLENEVARLKKL** |
| 35 | EVKLQESGPGLVAPSQSLSVTCTVSGVSLPDYGVSWIRQPPRKGLEWLGVIWGSETTYYNSALK SRLTIIKDNSKSQVFLKMNSLQTDDTAIYYCAKHYYYGGSYAMDYWGQGTSVTVSSASTKGPS VFPLAPSSKSTSGGTAALGCLVKDYFPEPVTVSWNSGALTSGVHTFPAVLQSSGLYSLSSVVTVP SSSLGTQTYICNVNHKPSNTKVDKKVEPKSC**GGGGSNYHLENEVARLKKLGGS**DKTHTCPPCP APPVAGPSVFLFPPKPKDTLMISRTPEVTCVVVDVSHEDPEVKFNWYVDGVEVHNAKTKPREEQ YNSTYRVVSVLTVLHQDWLNGKEYKCKVSNKGLPSSIEKTISKAKGQPREPQVYTLPPSRDELT |

TABLE 42-continued

CAR-T switches-Amino Acid Sequence

| SEQ ID NO | SEQUENCE |
|---|---|
| | KNQVSLTCLVKGFYPSDIAVEWESNGQPENNYKTTPPVLDSDGSFFLYSKLTVDKSRWQQGNVF<br>SCSVMHEALHNHYTQKSLSLSPGK |
| 36 | **NYHLENEVARLKKLGGGGS**DIQMTQTTSSLSASLGDRVTISCRASQDISKYLNWYQQKPDGTV<br>KLLIYHTSRLHSGVPSRFSGSGSGTDYSLTISNLEQEDIATYFCQQGNTLPYTFGGGTKLEIKRTVA<br>APSVFIFPPSDEQLKSGTASVVCLLNNFYPREAKVQWKVDNALQSGNSQESVTEQDSKDSTYSLS<br>STLTLSKADYEKHKVYACEVTHQGLSSPVTKSFNRGEC |
| 37 | DIQMTQSPSSLSASVGDRVTITCRANQGISNNLNWYQQKPGKAPKPLIYYTSNLQSGVPSRFSGS<br>GSGTDYTLTISSLQPEDFATYYCQQFTSLPYTFGQGTKLEIKRTVAAPSVFIFPPSDEQLKSGTASV<br>VCLLNNFYPREAKVQWKVDNALQSGNSQESVTEQDS**GGGGSNYHLENEVARLKKLGGGGS**D<br>STYSLSSTLTLSKADYEKHKVYACEVTHQGLSSPVTKSFNRGEC |
| 38 | EVQLVESGGGLVQPGGSLRLSCAASGFTFSNFDMAWVRQAPGKGLVWVSSITTGGGDTYYADS<br>VKGRFTISRDNAKSTLYLQMDSLRSEDTAVYYCVRHGYYDGYHLFDYWGQGTLVTVSSASTKG<br>PSVFPLAPSSKSTSGGTAALGCLVKDYFPEPVTVSWNSGALTSGVHTFPAVLQSSGLYSLSSVVT<br>VPSSSLGTQTYICNVNHKPSNTKVDKKVEPKSCDKTHTCPPCPAPPVAGPSVFLFPPKPKDTLMIS<br>RTPEVTCVVVDVSHEDPEVKFNWYVDGVEVHNAKTKPREEQYNSTYRVVSVLTVLHQDWLNG<br>KEYKCKVSNKGLPSSIEKTISKAKGQPREPQVYTLPPSRDELTKNQVSLTCLVKGFYPSDIAVEW<br>ESNGQPENNYKTTPPVLDSDGSFFLYSKLTVDKSRWQQGNVFSCSVMHEALHNHYTQKSLSLSP<br>GK |

TABLE 43 pBAD vector with CAR-T targeting moiety-Nucleotide Sequence

| SEQ ID NO | SEQUENCE |
|---|---|
| 39 | AAGAAACCAATTGTCCATATTGCATCAGACATTGCCGTCACTGCGTCTTTTACTGGCTCTTCT<br>CGCTAACCAAACCGGTAACCCTGATTATTTGCACGGAGTCACACTTTGCTATGCCATAGCAT<br>TTTTATCCATAAGATTAGCGGATCCTACCTGACGCTTTTTATCGCAACTCTCTACTGTTTCTCC<br>ATACCCGTTTTTTTGGGCTAGAAATAATTTTGTTTAACTTTAAGAAGGAGAATACATCAACT<br>AGTACGCAAGTTCACGTAAAAAGGGTATCTAGAGGTTGAGGTGATTTTATGAAAAAGAATA<br>TCGCATTTCTTCTTGCTAGCATGTTCGTTTTTTCTATTGCTACAAACGCATACGCTGACATCC<br>AGATGACACAGACTACATCCTCCCTGTCTGCCTCTCTGGGAGACAGAGTCACCATCAGTTGC<br>AGGGCAAGTCAGGACATTAGTAAATATTTAAATTGGTATCAGCAGAAACCAGATGGAACTG<br>TTAAACTCCTGATCTACCATACATCAAGATTACACTCAGGAGTCCCATCAAGGTTCAGTGGC<br>AGTGGGTCTGGAACAGATTATTCTCTCACCATTAGCAACCTGGAGCAAGAAGATATTGCCAC<br>TTACTTTTGCCAACAGGGTAATACGCTTCCGTACACGTTCGGAGGGGGGACCAAGCTTGAGA<br>TCAAACGAACTGTGGCTGCACCATCTGTCTTCATCTTCCCGCCATCTGATGAGCAGTTGAAA<br>TCTGGAACTGCCTCTGTCGTGTGCCTGCTGAATAACTTCTATCCCAGAGAGGCCAAAGTACA<br>GTGGAAGGTGGATAACGCCCTCCAATCGGGTAACTCCCAGGAGAGTGTCACAGAGCAGGAC<br>AGCAAGGACAGCACCTACAGCCTCAGCAGCACCCTGACGCTGAGCAAAGCAGACTACGAGA<br>AACACAAAGTCTACGCCTGCGAAGTCACCCATCAGGGCCTGTCCTCGCCCGTCACAAAGAG<br>CTTCAACAGGGGAGAGTGTTAAGCTGGGGATCCTCTAGAGGTTGAGGTGATTTTATGAAAA<br>AGAATATCGCATTTCTTCTTGCATCTATGTTCGTTTTTTCTATTGCTACAAACGCGTACGCTG<br>AGGTGAAACTGCAGGAGTCAGGACCTGGCCTGGTGGCGCCCTCACAGAGCCTGTCCGTCAC<br>ATGCACTGTCTCAGGGGTCTCATTACCCGACTATGGTGTAAGCTGGATTCGCCAGCCTCCAC<br>GAAAGGGTCTGGAGTGGCTGGGAGTAATATGGGGTAGTGAAACCACATACTATAATTCAGC<br>TCTCAAATCCAGACTGACCATCATCAAGGACAACTCCAAGAGCCAAGTTTTCTTAAAAATGA<br>ACAGTCTGCAAACTGATGACACAGCCATTTACTACTGTGCCAAACATTATTACTACGGTGGT<br>AGCTATGCTATGGACTACTGGGGCCAAGGAACCTCAGTCACCGTCTCCTCAGCCTCCACCAA<br>GGGCCCATCGGTCTTCCCCCTGGCACCCTCCTCCAAGAGCACCTCTGGGGGCACAGCGGCCC<br>TGGGCTGCCTGGTCAAGGACTACTTCCCCGAACCGGTGACGGTGTCGTGGAACTCAGGCGCC<br>CTGACCAGCGGCGTGCACACCTTCCCGGCTGTCCTACAGTCCTCAGGACTCTACTCCCTCAG<br>CAGCGTGGTGACTGTGCCCTCTAGCAGCTTGGGCACCCAGACCTACATCTGCAACGTGAATC<br>ACAAGCCCAGCAACACCAAGGTGGACAAGAAAGTTGAGCCCAAATCTTGTGACAAAACTCA<br>CACATAATAAGTCGACCGATGCCCTTGAGAGCCTTCAACCCAGTCAGCTCCTTCCGGTGGGC<br>GCGGGGCATGACTATCGTCGCCGCACTTATGACTGTCTTCTTTATCATGCAACTCGTAGGAC<br>AGGTGCCAAACGGTCTCCAGCTTGGCTGTTTTGGCGGATGAGAGAAGATTTTCAGCCTGATA<br>CAGATTAAATCAGAACGCAGAAGCGGTCTGATAAAACAGAATTTGCCTGGCGGCAGTAGCG<br>CGGTGGTCCCACCTGACCCCATGCCGAACTCAGAAGTGAAACGCCGTAGCGCCGATGGTAG<br>TGTGGGGTCTCCCCATGCGAGAGTAGGGAACTGCCAGGCATCAAATAAAACGAAAGGCTCA<br>GTCGAAAGACTGGGCCTTTCGTTTTATCTGTTGTTTGTCGGTGAACGCTCTCCTGAGTAGGAC<br>AAATCCGCCGGGAGCGGATTTGAACGTTGCGAAGCAACGGCCCGGAGGGTGGCGGGCAGG<br>ACGCCCGCCATAAACTGCCAGGCATCAAATTAAGCAGAAGGCCATCCTGACGGATGGCCTT<br>TTTGCGTTTCTACAAACTCTTTTTGTTTATTTTTCTAAATACATTCAAATATGTATCCGCTCAT<br>GAGACAATAACCCTGATAAATGCTTCAATAATATTGAAAAAGGAAGAGTATGAGTATTCAA<br>CATTTCCGTGTCGCCCTTATTCCCTTTTTTGCGGCATTTTGCCTTCCTGTTTTTGCTCACCCAG |

TABLE 43-continued

| pBAD vector with CAR-T targeting moiety-Nucleotide Sequence | |
|---|---|
| SEQ ID NO | SEQUENCE |
| | AAACGCTGGTGAAAGTAAAAGATGCTGAAGATCAGTTGGGTGCACGAGTGGGTTACATCGA<br>ACTGGATCTCAACAGCGGTAAGATCCTTGAGAGTTTTCGCCCCGAAGAACGTTTTCCAATGA<br>TGAGCACTTTTAAAGTTCTGCTATGTGGCGCGGTATTATCCCGTGTTGACGCCGGGCAAGAG<br>CAACTCGGTCGCCGCATACACTATTCTCAGAATGACTTGGTTGAGTACTCACCAGTCACAGA<br>AAAGCATCTTACGGATGGCATGACAGTAAGAGAATTATGCAGTGCTGCCATAACCATGAGT<br>GATAACACTGCGGCCAACTTACTTCTGACAACGATCGGAGGACCGAAGGAGCTAACCGCTT<br>TTTTGCACAACATGGGGGATCATGTAACTCGCCTTGATCGTTGGGAACCGGAGCTGAATGAA<br>GCCATACCAAACGACGAGCGTGACACCACGATGCCTGTAGCAATGGCAACAACGTTGCGCA<br>AACTATTAACTGGCGAACTACTTACTCTAGCTTCCCGGCAACAATTAATAGACTGGATGGAG<br>GCGGATAAAGTTGCAGGACCACTTCTGCGCTCGGCCCTTCCGGCTGGCTGGTTTATTGCTGA<br>TAAATCTGGAGCCGGTGAGCGTGGGTCTCGCGGTATCATTGCAGCACTGGGGCCAGATGGT<br>AAGCCCTCCCGTATCGTAGTTATCTACACGACGGGGAGTCAGGCAACTATGGATGAACGAA<br>ATAGACAGATCGCTGAGATAGGTGCCTCACTGATTAAGCATTGGTAACTGTCAGACCAAGTT<br>TACTCATATATACTTTAGATTGATTTAAAACTTCATTTTTAATTTAAAAGGATCTAGGTGAAG<br>ATCCTTTTTGATAATCTCATGACCAAAATCCCTTAACGTGAGTTTTCGTTCCACTGAGCGTCA<br>GACCCCGTAGAAAAGATCAAAGGATCTTCTTGAGATCCTTTTTTTCTGCGCGTAATCTGCTGC<br>TTGCAAACAAAAAAACCACCGCTACCAGCGGTGGTTTGTTTGCCGGATCAAGAGCTACCAA<br>CTCTTTTTCCGAAGGTAACTGGCTTCAGCAGAGCGCAGATACCAAATACTGTCCTTCTAGTG<br>TAGCCGTAGTTAGGCCACCACTTCAAGAACTCTGTAGCACCGCCTACATACCTCGCTCTGCT<br>AATCCTGTTACCAGTGGCTGCTGCCAGTGGCGATAAGTCGTGTCTTACCGGGTTGGACTCAA<br>GACGATAGTTACCGGATAAGGCGCAGCGGTCGGGCTGAACGGGGGGTTCGTGCACACAGCC<br>CAGCTTGGAGCGAACGACCTACACCGAACTGAGATACCTACAGCGTGAGCTATGAGAAAGC<br>GCCACGCTTCCCGAAGGGAGAAAGGCGGACAGGTATCCGGTAAGCGGCAGGGTCGGAACA<br>GGAGAGCGCACGAGGGAGCTTCCAGGGGGAAACGCCTGGTATCTTTATAGTCCTGTCGGGT<br>TTCGCCACCTCTGACTTGAGCGTCGATTTTTGTGATGCTCGTCAGGGGGGCGGAGCCTATGG<br>AAAAACGCCAGCAACGCGGCCTTTTTACGGTTCCTGGCCTTTTGCTGGCCTTTTGCTCACATG<br>TTCTTTCCTGCGTTATCCCCTGATTCTGTGGATAACCGTATTACCGCCTTTGAGTGAGCTGAT<br>ACCGCTCGCCGCAGCCGAACGACCGAGCGCAGCGAGTCAGTGAGCGAGGAAGCGGAAGAG<br>CGCCTGATGCGGTATTTTCTCCTTACGCATCTGTGCGGTATTTCACACCGCATATGGTGCACT<br>CTCAGTACAATCTGCTCTGATGCCGCATAGTTAAGCCAGTATACACTCCGCTATCGCTACGT<br>GACTGGGTCATGGCTGCGCCCCGACACCCGCCAACACCCGCTGACGCGCCCTGACGGGCTTG<br>TCTGCTCCCGGCATCCGCTTACAGACAAGCTGTGACCGTCTCCGGGAGCTGCATGTGTCAGA<br>GGTTTTCACCGTCATCACCGAAACGCGCGAGGCAGCAGATCAATTCGCGCGCGAAGGCGAA<br>GCGGCATGCATAATGTGCCTGTCAAATGGACGAAGCAGGGATTCTGCAAACCCTATGCTACT<br>CCGTCAAGCCGTCAATTGTCTGATTCGTTACCAATTATGACAACTTGACGGCTACATCATTCA<br>CTTTTTCTTCACAACCGGCACGGAACTCGCTCGGGCTGGCCCCGGTGCATTTTTTAAATACCC<br>GCGAGAAATAGAGTTGATCGTCAAAACCAACATTGCGACCGACGGTGGCGATAGGCATCCG<br>GGTGGTGCTCAAAAGCAGCTTCGCCTGGCTGATACGTTGGTCCTCGCGCCAGCTTAAGACGC<br>TAATCCCTAACTGCTGGCGGAAAAGATGTGACAGACGCGACGGCGACAAGCAAACATGCTG<br>TGCGACGCTGGCGATATCAAAATTGCTGTCTGCCAGGTGATCGCTGATGTACTGACAAGCCT<br>CGCGTACCCGATTATCCATCGGTGGATGGAGCGACTCGTTAATCGCTTCCATGCGCCGCAGT<br>AACAATTGCTCAAGCAGATTTATCGCCAGCAGCTCCGAATAGCGCCCTTCCCCTTGCCCGGC<br>GTTAATGATTTGCCCAAACAGGTCGCTGAAATGCGGCTGGTGCGCTTCATCCGGGCGAAAGA<br>ACCCCGTATTGGCAAATATTGACGGCCAGTTAAGCCATTCATGCCAGTAGGCGCGCGGACG<br>AAAGTAAACCCACTGGTGATACCATTCGCGAGCCTCCGGATGACGACCGTAGTGATGAATCT<br>CTCCTGGCGGGAACAGCAAAATATCACCCGGTCGGCAAACAAATTCTCGTCCCTGATTTTTC<br>ACCACCCCCTGACCGCGAATGGTGAGATTGAGAATATAACCTTTCATTCCCAGCGGTCGGTC<br>GATAAAAAAATCGAGATAACCGTTGGCCTCAATCGGCGTTAAACCCGCCACCAGATGGGCA<br>TTAAACGAGTATCCCGGCAGCAGGGGATCATTTTGCGCTTCAGCCATACTTTTCATACTCCC<br>GCCATTCAGAG |

TABLE 44

| Linker-Amino Acid Sequence | |
|---|---|
| SEQ ID NO | SEQUENCE |
| 40 | GGGGS |
| 41 | GGGS |
| 45 | LVGEAAAKEAAAKA |
| 46 | AEAAAKEAAAKA |
| 47 | EAAAKEAAAKEAAAKA |
| 48 | EGKSSGSGSESKST |
| 49 | GSAGSAAGSGEF |
| 50 | APAPAPAPAPAP |

TABLE 45 direct GCN4-CAR with mouse signaling domains-Nucleotide Sequence

| SEQ ID NO | SEQUENCE |
|---|---|
| 51 | tcgagaagcttgccaccatgggtgtccctacccagctcctgggactgctcctgctgtggatcaccgacgccatctgcGACGCCGTTGTGACCCAGGAATC<br>CGCTCTGACCTCTTCTCCAGGCGAAACCGTGACTCTGACTTGCCGTAGTAGCACCGGGGCTGTGACCACATCTAACTATGCCAGTTGGGTCCAGGAAAAA<br>CCGGATCACCTGTTTACTGGCCTGATTGGCGGCACCAACAATCGCGCACCGGGTGTGCCCGCTCGTTTCAGCGGTTCCCTGATTGGGGACAAGGCAGCAC<br>TGACTATCACCGGCGCCCAGACCGAAGATGAGGCGATCTATTTTTGCGTCCTGTGGTACAGCGACCATTGGGTGTTCGGGGGAGGCACCAAACTGACAGT<br>GCTGGGCGGAGGAGGAGGTTCAGGAGGAGGAGGTAGCGGGGGAGGCGGTTCCGGGGGAGGCGGTTCTGATGTGCAGCTGCAAGAATCCGGGCCAGGACTG<br>GTTGCGCCTTCTCAGAGTCTGTCAATTACATGTACTGTTAGTGGCTTTCTGCTGACCGACTATGGTGTGAACTGGGTTCGTCAGAGCCCAGGCAAGGGTC<br>TGGAGTGGCTGGGAGTGATTTGGGGGGATGGAATCACAGACTACAATAGCGCACTGAAATCTCGGCTGAGTGTTACCAAAGATAACAGCAAGTCCCAGGT<br>CTTCCTGAAGATGAACAGCCTGCAAAGCGGCGACTCCGCTCGCTATTACTGCGTTACCGGACTGTTTGATTATTGGGGGCAGGGGACAACTCTGACTGTT<br>TCCTCCatcgagttcatgtaccccctccctacctggacaacgagagaagcaacggcaccatcatccacatcaaagaaaagcacctgtgccacacccaga<br>gcagccccaagctgttctgggccctggtggtggtggccggcgtgctgttctgttacggcctgctggtcacagtggccctgtgcgtgatctggaccaacag<br>cagaagaaacagaggcggccagagcgactacatgaacatgacccccagaaggccaggcctgaccagaaagccctaccagccctacgcccctgccagagac<br>ttcgccgcctacagacccagagccaagttcagcagatccgccgagacagccgccaacctgcaggatcccaaccagctgttcaacgagctgaacctgggca<br>gacgggaggaattcgacgtgctggaaaagaagagagccagggaccccgagatgggcggcaagcagcagagaagaagaaaccctcaggaaggcgtctacaa<br>cgccctgcagaaagacaagatggccgaggcctacagcgagatcggcaccaagggcgagagaagaaggggcaagggccacgatggcctgttccagggcctg<br>tccaccgccaccaaggacaccttcgacgccctgcacatgcagaccctggcccccagatgagtcgacggtaccgcggcccgggatccgataaaataaaag<br>attttatttagtctccagaaaaaggggggaatgaaagaccccacctgtaggtttggcaagctagcttaagtaacgccattttgcaaggcatggaaaatac<br>ataactgagaatagagaagttcagatcaaggttaggaacagagagacagcagaatatgggccaaacaggatatctgtggtaagcagttcctgccccggct<br>cagggccaagaacagatggtccccagatgcggtcccgccctcagcagtttctagagaaccatcagatgtttccagggtgccccaaggacctgaaatgac<br>cctgtgccttatttgaactaaccaatcagttcgcttctcgcttctgttcgcgcgcttctgctccccgagctcaataaaagagcccacaacccctcactcg<br>gcgcgccagtcctccgatagactgcgtcgcccgggtacccgtgtatccaataaaccctcttgcagttgcatccgacttgtggtctcgctgttccttggga<br>gggtctcctctgagtgattgactacccgtcagcgggggtctttcatgggtaacagtttcttgaagttggagaacaacattctgagggtaggagtcgaata<br>ttaagtaatcctgactcaattagccactgttttgaatccacatactccaatactcctgaaatccatcgatggagttcattatggacagcgcagaaagagc<br>tggggagaattgtgaaattgttatccgctcacaattccacacaacatacgagccggaagcataaagtgtaaagcctggggtgcctaatgagtgagctaac<br>tcacattaattgcgttgcgctcactgcccgctttccagtcgggaaacctgtcgtgccagctgcattaatgaatcggccaacgcgcggggagaggcggttt<br>gcgtattgggcgctcttccgcttcctcgctcactgactcgctgcgctcggtcgttcggctgcggcgagcggtatcagctcactcaaaggcggtaatacgg<br>ttatccacagaatcaggggataacgcaggaaagaacatgtgagcaaaaggccagcaaaaggccaggaaccgtaaaaaggccgcgttgctggcgtttttcc<br>ataggctccgcccccctgacgagcatcacaaaaatcgacgctcaagtcagaggtggcgaaacccgacaggactataaagataccaggcgtttccccctgg<br>aagctccctcgtgcgctctcctgttccgaccctgccgcttaccggatacctgtccgcctttctcccttcgggaagcgtggcgctttctcatagctcacgc<br>tgtaggtatctcagttcggtgtaggtcgttcgctccaagctgggctgtgtgcacgaaccccccgttcagcccgaccgctgcgccttatccggtaactatc<br>gtcttgagtccaacccggtaagacacgacttatcgccactggcagcagccactggtaacaggattagcagagcgaggtatgtaggcggtgctacagagtt<br>cttgaagtggtggcctaactacggctacactagaaggacagtatttggtatctgcgctctgctgaagccagttaccttcggaaaaagagttggtagctct<br>tgatccggcaaacaaaccaccgctggtagcggtggtttttttgtttgcaagcagcagattacgcgcagaaaaaaaggatctcaagaagatcctttgatct<br>tttctacggggtctgacgctcagtggaacgaaaactcacgttaagggattttggtcatgagattatcaaaaaggatcttcacctagatccttttaaatta<br>aaaatgaagttttaaatcaatctaaagtatatatgagtaaacttggtctgacagttaccaatgcttaatcagtgaggcacctatctcagcgatctgtcta<br>tttcgttcatccatagttgcctgactccccgtcgtgtagataactacgatacgggagggcttaccatctggccccagtgctgcaatgataccgcgagacc<br>cacgctcaccggctccagatttatcagcaataaaccagccagccggaagggccgagcgcagaagtggtcctgcaactttatccgcctccatccagtctat<br>taattgttgccgggaagctagagtaagtagttcgccagttaatagtttgcgcaacgttgttgccattgctacaggcatcgtggtgtcacgctcgtcgttt<br>ggtatggcttcattcagctccggttcccaacgatcaaggcgagttacatgatcccccatgttgtgcaaaaaagcggttagctccttcggtcctccgatcg<br>ttgtcagaagtaagttggccgcagtgttatcactcatggttatggcagcactgcataattctcttactgtcatgccatccgtaagatgcttttctgtgac<br>tggtgagtactcaaccaagtcattctgagaatagtgtatgcggcgaccgagttgctcttgcccggcgtcaatacgggataataccgcgccacatagcaga<br>actttaaaagtgctcatcattggaaaacgttcttcggggcgaaaactctcaaggatcttaccgctgttgagatccagttcgatgtaacccactcgtgcac<br>ccaactgatcttcagcatcttttactttcaccagcgtttctgggtgagcaaaaacaggaaggcaaaatgccgcaaaaaagggaataagggcgacacggaa<br>atgttgaatactcatactcttcctttttcaatattattgaagcatttatcagggttattgtctcatgagcggatacatatttgaatgtatttagaaaaat<br>aaacaaataggggttccgcgcacatttccccgaaaagtgccacctgacgtctaagaaaccattattatcatgacattaacctataaaaataggcgtatca<br>cgaggccctttcgtctcgcgcgtttcggtgatgacggtgaaaacctctgacacatgcagctcccggagacggtcacagcttgtctgtaagcggatgccgg<br>gagcagacaagcccgtcagggcgcgtcagcgggtgttggcgggtgtcggggctggcttaactatgcggcatcagagcagattgtactgagagtgcaccat<br>atgcggtgtgaaataccgcacagatgcgtaaggagaaaataccgcatcaggcgccattcgccattcaggctgcgcaactgttgggaagggcgatcggtgc<br>gggcctcttcgctattacgccagctggcgaaaggggggatgtgctgcaaggcgattaagttgggtaacgccagggttttcccagtcacgacgttgtaaaac<br>gacggccagtgccacgctctcccttatgcgactcctgcattaggaagcagcccagtagtaggttgaggccgttgagcaccgccgccgcaaggaatggtgc<br>atgcaaggagatggcgcccaacagtcccccggccacggggcctgccaccatacccacgccgaaacaagcgctcatgagcccgaagtggcgagcccgatct<br>tccccatcggtgatgtcggcgatataggcgccagcaaccgcacctgtggcgccggtgatgccggccacgatgcgtccggcgtagaggcgatttaaagaca<br>ggatatcagtggtccaggctctagttttgactcaacaatatcaccagctgaagcctatagagtacgagccatagataaaataaaagattttatttagtct<br>ccagaaaaaggggggaatgaaagaccccacctgtaggtttggcaagctagcttaagtaacgccattttgcaaggcatggaaaatacataactgagaatag<br>agaagttcagatcaaggttaggaacagagagacagcagaatatgggccaaacaggatatctgtggtaagcagttcctgccccggctcagggccaagaaca<br>gatggtccccagatgcggtcccgccctcagcagtttctagagaaccatcagatgtttccagggtgccccaaggacctgaaatgaccctgtgccttattt<br>gaactaaccaatcagttcgcttctcgcttctgttcgcgcgcttctgctccccgagctcaataaaagagcccacaacccctcactcggcgcgccagtcctc<br>cgatagactgcgtcgcccgggtacccgtattcccaataaagcctcttgctgtttgcatccgaatcgtggactcgctgatccttgggagggtctcctcaga<br>ttgattgactgcccacctcgggggtctttcatttggaggttccaccgagatttggagacccctgcctagggaccaccgacccccccgccgggaggtaagc<br>tggccagcggtcgtttcgtgtctgtctctgtctttgtgcgtgtttgtgccggcatctaatgtttgcgcctgcgtctgtactagttagctaactagctctg<br>tatctggcggacccgtggtggaactgacgagttcggaacacccggccgcaaccctgggagacgtcccagggacttcgggggccgtttttgtggcccgacc<br>tgagtccaaaaatcccgatcgttttggactctttggtgcacccccccttagaggagggatatgtggttctggtaggagacgagaacctaaaacagttcccg<br>cctccgtctgaatttttgctttcggtttgggaccgaagccgcgccgcgcgtcttgtctgctgcagcatcgttctgtgttgtctctgtctgactgtgtttc<br>tgtatttgtctgagaatatgggcccgggctagcctgttaccactcccttaagtttgaccttaggtcactggaaagatgtcgagcggatcgctcacaacca<br>gtcggtagatgtcaagaagagacgttgggttaccttctgctctgcagaatggccaacctttaacgtcggatggccgcgagacggcacctttaaccgagac<br>ctcatcacccaggttaagatcaaggtcttttcacctggcccgcatggacacccagaccaggtcccctacatcgtgacctgggaagccttggcttttgacc<br>cccctccctgggtcaagccctttgtacaccctaagcctccgcctcctcttcctccatccgccccgtctctcccccttgaacctcctcgttcgaccccgcc<br>tcgatcctccctttatccagccctcactccttctctaggcgcccccatatggccatatgagatcttatatggggcacccccgccccttgtaaacttccct<br>gaccctgacatgacaagagttactaacagcccctctctccaagctcacttacaggctctctacttagtccagcacgaagtctggagacctctggcggcag<br>cctaccaagaacaactggaccgaccggtggtacctcacccttaccgagtcggcgacacagtgtgggtccgccgacaccagactaagaacctagaacctcg<br>ctggaaaggaccttacacagtcctgctgaccaccccccaccgccctcaaagtagacggcatcgcagcttggatacacgccgcccacgtgaaggctgccgac<br>cccgggggtggaccatcctctagactgc |

TABLE 46 anti-mouse CD19 switch antibody chains-Nucleotide Sequence

| SEQ ID NO | SEQUENCE |
|---|---|
| 52 | ggatctgcgatcgctccggtgcccgtcagtgggcagagcgcacatcgcccacagtccccgagaagttggggggaggggtcggcaattgaacgggtgccta<br>gagaaggtggcgcggggtaaactgggaaagtgatgtcgtgtactggctccgcctttttcccgagggtgggggagaaccgtatataagtgcagtagtcgcc<br>gtgaacgttctttttcgcaacgggtttgccgccagaacacagctgaagcttcgaggggctcgcatctctccttcacgcgcccgccgccctacctgaggcc<br>gccatccacgccggttgagtcgcgttctgccgcctcccgcctgtggtgcctcctgaactgcgtccgccgtctaggtaagtttaaagctcaggtcgagacc<br>gggcctttgtccggcgctcccttggagcctacctagactcagccggctctccacgctttgcctgaccctgcttgctcaactctacgtctttgtttcgttt<br>tctgttctgcgccgttacagatccaagctgtgaccggcgcctacctgagatcaccggcgaaggagggccaccatgtacaggatgcaactcctgtcttgca<br>ttgcactaagtcttgcacttgtcacgaattcgGACATTCAGCTGACCCAGTCTCCAGCTTCCCTGTCTACATCTCTGGGAGAAACTGTCACCATCCAATG<br>TCAAGCAAGTGAGGACATTTACAGTGGTTTAGCGTGGTATCAGCAGAAGCCAGGGAAATCTCCTCAGCTCCTGATCTATGGTGCAAGTGACTTACAAGAC<br>GGCGTCCCATCACGATTCAGTGGCAGTGGATCTGGCACACAGTATTCTCTCAAGATCACCAGCATGCAAACTGAAGATGAAGGGGTTTATTTCTGTCAAC<br>AGGGTTTAACGTATCCTCGGACGTTCGGTGGCGGCACCAAGCTGGAAATCaaacgaactgtggctgcaccatctgtcttcatcttcccgccatctgatga<br>gcagttgaaatctggaactgcctctgtcgtgtgcctgctgaataacttctatcccagagaggccaaagtacagtggaaggtggataacgccctccaatcg<br>ggtaactcccaggagagtgtcacagagcaggacagcGGCGGAGGCGGGAGCaattatcatcttgaaaatgaggtcgctcgtctcaagaaactcGGTGGCG<br>GAGGCAGCgacagcacctacagcctcagcagcaccctgacgcttagcaaagcagactacgagaaacacaaagtctacgcctgcgaagtcacccatcaggg<br>cctgtcctcgcccgtcacaaagagcttcaacaggggagagtgttgataagtgctagctggccagacatgataagatacattgatgagtttggacaaacca<br>caactagaatgcagtgaaaaaaatgctttatttgtgaaatttgtgatgctattgctttatttgtaaccattataagctgcaataaacaagttaacaacaa<br>caattgcattcattttatgtttcaggttcagggggaggtgtgggaggttttttaaagcaagtaaaacctctacaaatgtggtatggaattaattctaaaa<br>tacagcatagcaaaactttaacctccaaatcaagcctctacttgaatccttttctgagggatgaataaggcataggcatcaggggctgttgccaatgtgc<br>attagctgtttgcagcctcaccttctttcatggagtttaagatatagtgtattttcccaaggtttgaactagctcttcatttctttatgttttaaatgca<br>ctgacctcccacattccctttttagtaaaatattcagaaataatttaaatacatcattgcaatgaaaataaatgtttttttattaggcagaatccagatgc<br>tcaaggcccttcataatatcccccagtttagtagttggacttagggaacaaaggaacctttaatagaaattggacagcaagaaagcgagcttctagctta<br>tcctcagtcctgctcctctgccacaaagtgcacgcagttgccggccgggtcgcgcagggcgaactcccgcccccacggctgctcgccgatctcggtcatg<br>gccggcccggaggcgtcccggaagttcgtggacacgacctccgaccactcggcgtacagctcgtccaggccgcgcacccacacccaggccagggtgttgt<br>ccggcaccacctggtcctggaccgcgctgatgaacagggtcacgtcgtcccggaccacaccggcgaagtcgtcctccacgaagtcccgggagaacccgag<br>ccggtcggtccagaactcgaccgctccggcgacgtcgcgcgcggtgagcaccggaacggcactggtcaacttggccatgatggctcctcctgtcaggaga<br>ggaaagagaagaaggttagtacaattgctatagtgagttgtattatactatgcagatatactatgccaatgattaattgtcaaactagggctgcagggtt<br>catagtgccacttttcctgcactgccccatctcctgcccaccctttcccaggcatagacagtcagtgacttaccaaactcacaggagggagaaggcagaa<br>gcttgagacagacccgcgggaccgccgaactgcgaggggacgtggctagggcggcttcttttatggtgcgccggccctcggaggcagggcgctcggggag<br>gcctagcggccaatctgcggtggcaggaggcggggccgaaggccgtgcctgaccaatccggagcacataggagtctcagccccccgccccaaagcaaggg<br>gaagtcacgcgcctgtagcgccagcgtgttgtgaaatgggggcttgggggggttggggccctgactagtcaaaacaaactcccattgacgtcaatggggt<br>ggagacttggaaatccccgtgagtcaaaccgctatccacgcccattgatgtactgccaaaaccgcatcatcatggtaatagcgatgactaatacgtagat<br>gtactgccaagtaggaaagtcccataaggtcatgtactgggcataatgccaggcgggccatttaccgtcattgacgtcaatagggggcgtacttggcata<br>tgatacacttgatgtactgccaagtgggcagtttaccgtaaatactccacccattgacgtcaatggaaagtccctattggcgttactatgggaacatacg<br>tcattattgacgtcaatgggcgggggtcgttgggcggtcagccaggcgggccatttaccgtaagttatgtaacgcctgcaggttaattaagaacatgtga<br>gcaaaaggccagcaaaaggccaggaaccgtaaaaaggccgcgttgctggcgtttttccataggctccgcccccctgacgagcatcacaaaaatcgacgct<br>caagtcagaggtggcgaaacccgacaggactataaagataccaggcgtttccccctggaagctccctcgtgcgctctcctgttccgaccctgccgcttac<br>cggatacctgtccgcctttctcccttcgggaagcgtggcgctttctcatagctcacgctgtaggtatctcagttcggtgtaggtcgttcgctccaagctg<br>ggctgtgtgcacgaaccccccgttcagcccgaccgctgcgccttatccggtaactatcgtcttgagtccaacccggtaagacacgacttatcgccactgg<br>cagcagccactggtaacaggattagcagagcgaggtatgtaggcggtgctacagagttcttgaagtggtggcctaactacggctacactagaagaacagt<br>atttggtatctgcgctctgctgaagccagttaccttcggaaaaagagttggtagctcttgatccggcaaacaaaccaccgctggtagcggtggtttttt<br>gtttgcaagcagcagattacgcgcagaaaaaaaggatctcaagaagatcctttgatcttttctacggggtctgacgctcagtggaacgaaaactcacgtt<br>aagggattttggtcatggctagttaattaacatttaaatcagcggccgcaataaaatatctttattttcattacatctgtgtgttggttttttgtgtgaa<br>tcgtaactaacatacgctctccatcaaaacaaaacgaaacaaaacaaactagcaaaataggctgtccccagtgcaagtgcaggtgccagaacatttctct<br>atcgaa |
| 53 | ggatctgcgatcgctccggtgcccgtcagtgggcagagcgcacatcgcccacagtccccgagaagttggggggaggggtcggcaattgaacgggtgccta<br>gagaaggtggcgcggggtaaactgggaaagtgatgtcgtgtactggctccgcctttttcccgagggtgggggagaaccgtatataagtgcagtagtcgcc<br>gtgaacgttctttttcgcaacgggtttgccgccagaacacagctgaagcttcgaggggctcgcatctctccttcacgcgcccgccgccctacctgaggcc<br>gccatccacgccggttgagtcgcgttctgccgcctcccgcctgtggtgcctcctgaactgcgtccgccgtctaggtaagtttaaagctcaggtcgagacc<br>gggcctttgtccggcgctcccttggagcctacctagactcagccggctctccacgctttgcctgaccctgcttgctcaactctacgtctttgtttcgttt<br>tctgttctgcgccgttacagatccaagctgtgaccggcgcctacctgagatcaccggcgaaggagggccaccatgtacaggatgcaactcctgtcttgca<br>ttgcactaagtcttgcacttgtcacgaattcgGACATTCAGCTGACCCAGTCTCCAGCTTCCCTGTCTACATCTCTGGGAGAAACTGTCACCATCCAATG<br>TCAAGCAAGTGAGGACATTTACAGTGGTTTAGCGTGGTATCAGCAGAAGCCAGGGAAATCTCCTCAGCTCCTGATCTATGGTGCAAGTGACTTACAAGAC<br>GGCGTCCCATCACGATTCAGTGGCAGTGGATCTGGCACACAGTATTCTCTCAAGATCACCAGCATGCAAACTGAAGATGAAGGGGTTTATTTCTGTCAAC<br>AGGGTTTAACGTATCCTCGGACGTTCGGTGGCGGCACCAAGCTgGAaATCaaacgaactgtggctgcaccatctgtcttcatcttcccgccatctgatga<br>gcagttgaaatctggaactgcctctgtcgtgtgcctgctgaataacttctatcccagagaggccaaagtacagtggaaggtggataacgccctccaatcg<br>ggtaactcccaggagagtgtcacagagcaggacagcaaggacagcacctacagcctcagcagcaccctgacgctgagcaaagcagactacgagaaacaca<br>aagtctacgcctgcgaagtcacccatcagggcctgtcctcgcccgtcacaaagagcttcaacaggggagagtgttgataagtgctagctggccagacatg<br>ataagatacattgatgagtttggacaaaccacaactagaatgcagtgaaaaaaatgctttatttgtgaaatttgtgatgctattgctttatttgtaacca<br>ttataagctgcaataaacaagttaacaacaacaattgcattcattttatgtttcaggttcagggggaggtgtgggaggttttttaaagcaagtaaaacct<br>ctacaaatgtggtatggaattaattctaaaatacagcatagcaaaactttaacctccaaatcaagcctctacttgaatccttttctgagggatgaataag<br>gcataggcatcaggggctgttgccaatgtgcattagctgtttgcagcctcaccttctttcatggagtttaagatatagtgtattttcccaaggtttgaac<br>tagctcttcatttctttatgttttaaatgcactgacctcccacattccctttttagtaaaatattcagaaataatttaaatacatcattgcaatgaaaat<br>aaatgtttttttattaggcagaatccagatgctcaaggcccttcataatatcccccagtttagtagttggacttagggaacaaaggaacctttaatagaaa<br>ttggacagcaagaaagcgagcttctagcttatcctcagtcctgctcctctgccacaaagtgcacgcagttgccggccgggtcgcgcagggcgaactcccg<br>cccccacggctgctcgccgatctcggtcatggccggcccggaggcgtcccggaagttcgtggacacgacctccgaccactcggcgtacagctcgtccagg<br>ccgcgcacccacacccaggccagggtgttgtccggcaccacctggtcctggaccgcgctgatgaacagggtcacgtcgtcccggaccacaccggcgaagt<br>cgtcctccacgaagtcccgggagaacccgagccggtcggtccagaactcgaccgctccggcgacgtcgcgcgcggtgagcaccggaacggcactggtcaa<br>cttggccatgatggctcctcctgtcaggagaggaaagagaagaaggttagtacaattgctatagtgagttgtattatactatgcagatatactatgccaa<br>tgattaattgtcaaactagggctgcagggttcatagtgccacttttcctgcactgccccatctcctgcccaccctttcccaggcatagacagtcagtgac<br>ttaccaaactcacaggagggagaaggcagaagcttgagacagacccgcgggaccgccgaactgcgaggggacgtggctagggcggcttcttttatggtgc<br>gccggccctcggaggcagggcgctcggggaggcctagcggccaatctgcggtggcaggaggcggggccgaaggccgtgcctgaccaatccggagcacata<br>ggagtctcagccccccgccccaaagcaaggggaagtcacgcgcctgtagcgccagcgtgttgtgaaatgggggcttgggggggttggggccctgactagt<br>caaaacaaactcccattgacgtcaatggggtggagacttggaaatccccgtgagtcaaaccgctatccacgcccattgatgtactgccaaaaccgcatca<br>tcatggtaatagcgatgactaatacgtagatgtactgccaagtaggaaagtcccataaggtcatgtactgggcataatgccaggcgggccatttaccgtc |

TABLE 46-continued anti-mouse CD19 switch antibody chains-Nucleotide Sequence

| SEQ ID NO | SEQUENCE |
|---|---|
| | attgacgtcaatagggggcgtacttggcatatgatacacttgatgtactgccaagtgggcagtttaccgtaaatactccacccattgacgtcaatggaaa<br>gtccctattggcgttactatgggaacatacgtcattattgacgtcaatgggcgggggtcgttgggcggtcagccaggcgggccatttaccgtaagttatg<br>taacgcctgcaggttaattaagaacatgtgagcaaaaggccagcaaaaggccaggaaccgtaaaaaggccgcgttgctggcgtttttccataggctccgc<br>ccccctgacgagcatcacaaaaatcgacgctcaagtcagaggtggcgaaacccgacaggactataaagataccaggcgtttccccctggaagctccctcg<br>tgcgctctcctgttccgaccctgccgcttaccggatacctgtccgcctttctcccttcgggaagcgtggcgctttctcatagctcacgctgtaggtatct<br>cagttcggtgtaggtcgttcgctccaagctgggctgtgtgcacgaaccccccgttcagcccgaccgctgcgccttatccggtaactatcgtcttgagtcc<br>aacccggtaagacacgacttatcgccactggcagcagccactggtaacaggattagcagagcgaggtatgtaggcggtgctacagagttcttgaagtggt<br>ggcctaactacggctacactagaagaacagtatttggtatctgcgctctgctgaagccagttaccttcggaaaaagagttggtagctcttgatccggcaa<br>acaaaccaccgctggtagcggtggtttttttgtttgcaagcagcagattacgcgcagaaaaaaaggatctcaagaagatcctttgatcttttctacgggg<br>tctgacgctcagtggaacgaaaactcacgttaagggattttggtcatggctagttaattaacatttaaatcagcggccgcaataaaatatctttattttc<br>attacatctgtgtgttggttttttgtgtgaatcgtaactaacatacgctctccatcaaaacaaaacgaaacaaaacaaactagcaaaataggctgtcccc<br>agtgcaagtgcaggtgccagaacatttctctatcgaa |
| 54 | ggatctgcgatcgctccggtgcccgtcagtgggcagagcgcacatcgcccacagtccccgagaagttggggggaggggtcggcaattgaacgggtgccta<br>gagaaggtggcgcggggtaaactgggaaagtgatgtcgtgtactggctccgcctttttcccgagggtgggggagaaccgtatataagtgcagtagtcgcc<br>gtgaacgttctttttcgcaacgggtttgccgccagaacacagctgaagcttcgaggggctcgcatctctccttcacgcgcccgccgccctacctgaggcc<br>gccatccacgccggttgagtcgcgttctgccgcctcccgcctgtggtgcctcctgaactgcgtccgccgtctaggtaagtttaaagctcaggtcgagacc<br>gggcctttgtccggcgctcccttggagcctacctagactcagccggctctccacgctttgcctgaccctgcttgctcaactctacgtctttgtttcgttt<br>tctgttctgcgccgttacagatccaagctgtgaccggcgcctacctgagatcaccggcgaaggagggccaccatgtacaggatgcaactcctgtcttgca<br>ttgcactaagtcttgcacttgtcacgaattcgCAAGTGCAGCTGGTGCAGTCTGGGGCTGAGCTTGTGAGACCTGGGACCTCTGTGAAGTTATCTTGCAA<br>AGTTTCTGGCGATACCATTACATTTTACTACATGCACTTTGTGAAGCAAAGGCCTGGACAGGGTCTGGAATGGATAGGAAGGATTGATCCTGAGGATGAA<br>AGTACTAAATATTCTGAGAAGTTCAAAAACAAGGCGACACTCACTGCAGATACATCTTCCAACACAGCCTACCTGAAGCTCAGCAGCCTGACCTCTGAGG<br>ACACTGCAACCTATTTTTGTATCTACGGAGGATACTACTTTGATTACTGGGGcCCAGGAACCATGGTCACCGTGTCCTCAgcctccaccaagggcccatc<br>ggtcttccccctggcaccctcctccaagagcacctctgggggcacagcggccctgggctgcctggtcaaggactacttccccgaaccggtgacggtgtcg<br>tggaactcaggcgccctgaccagcggcgtgcacaccttcccggctgtcctacagtcctcaggactctactccctcagcagcgtggtgactgtgccctcta<br>gcagcttgggcacccagacctacatctgcaacgtgaatcacaagcccagcaacaccaaggtggacaagaaagttgagcccaaatcttgttgataagtgct<br>agctggccagacatgataagatacattgatgagtttggacaaaccacaactagaatgcagtgaaaaaaatgctttatttgtgaaatttgtgatgctattg<br>ctttatttgtaaccattataagctgcaataaacaagttaacaacaacaattgcattcattttatgtttcaggttcagggggaggtgtgggaggttttttta<br>aagcaagtaaaacctctacaaatgtggtatggaattaattctaaaatacagcatagcaaaactttaacctccaaatcaagcctctacttgaatcctttttc<br>tgagggatgaataaggcataggcatcaggggctgttgccaatgtgcattagctgtttgcagcctcaccttctttcatggagtttaagatatagtgtattt<br>tcccaaggtttgaactagctcttcatttctttatgtttaaatgcactgacctcccacattcccttttttagtaaaatattcagaaataatttaaatacat<br>cattgcaatgaaaataaatgtttttttattaggcagaatccagatgctcaaggcccttcataatatcccccagtttagtagttggacttagggaacaaagg<br>aacctttaatagaaattggacagcaagaaagcgagcttctagcttatcctcagtcctgctcctctgccacaaagtgcacgcagttgccggccgggtcgcg<br>cagggcgaactcccgcccccacggctgctcgccgatctcggtcatggccggcccggaggcgtcccggaagttcgtggacacgacctccgaccactcggcg<br>tacagctcgtccaggccgcgcacccacacccaggccagggtgttgtccggcaccacctggtcctggaccgcgctgatgaacagggtcacgtcgtcccgga<br>ccacaccggcgaagtcgtcctccacgaagtcccgggagaacccgagccggtcggtccagaactcgaccgctccggcgacgtcgcgcgcggtgagcaccgg<br>aacggcactggtcaacttggccatgatggctcctcctgtcaggagaggaaagagaagaaggttagtacaattgctatagtgagttgtattatactatgca<br>gatatactatgccaatgattaattgtcaaactagggctgcagggttcatagtgccacttttcctgcactgccccatctcctgcccaccctttcccaggca<br>tagacagtcagtgacttaccaaactcacaggagggagaaggcagaagcttgagacagacccgcgggaccgccgaactgcgaggggacgtggctagggcgg<br>cttcttttatggtgcgccggccctcggaggcagggcgctcggggaggcctagcggccaatctgcggtggcaggaggcggggccgaaggccgtgcctgacc<br>aatccggagcacataggagtctcagccccccgccccaaagcaaggggaagtcacgcgcctgtagcgccagcgtgttgtgaaatgggggcttgggggggtt<br>ggggccctgactagtcaaaacaaactcccattgacgtcaatggggtggagacttggaaatccccgtgagtcaaaccgctatccacgcccattgatgtact<br>gccaaaaccgcatcatcatggtaatagcgatgactaatacgtagatgtactgccaagtaggaaagtcccataaggtcatgtactgggcataatgccaggc<br>gggccatttaccgtcattgacgtcaatagggggcgtacttggcatatgatacacttgatgtactgccaagtgggcagtttaccgtaaatactccacccat<br>tgacgtcaatggaaagtccctattggcgttactatgggaacatacgtcattattgacgtcaatgggcgggggtcgttgggcggtcagccaggcgggccat<br>ttaccgtaagttatgtaacgcctgcaggttaattaagaacatgtgagcaaaaggccagcaaaaggccaggaaccgtaaaaaggccgcgttgctggcgttt<br>ttccataggctccgcccccctgacgagcatcacaaaaatcgacgctcaagtcagaggtggcgaaacccgacaggactataaagataccaggcgtttcccc<br>ctggaagctccctcgtgcgctctcctgttccgaccctgccgcttaccggatacctgtccgcctttctcccttcgggaagcgtggcgctttctcatagctc<br>acgctgtaggtatctcagttcggtgtaggtcgttcgctccaagctgggctgtgtgcacgaaccccccgttcagcccgaccgctgcgccttatccggtaac<br>tatcgtcttgagtccaacccggtaagacacgacttatcgccactggcagcagccactggtaacaggattagcagagcgaggtatgtaggcggtgctacag<br>agttcttgaagtggtggcctaactacggctacactagaagaacagtatttggtatctgcgctctgctgaagccagttaccttcggaaaaagagttggtag<br>ctcttgatccggcaaacaaaccaccgctggtagcggtggtttttttgtttgcaagcagcagattacgcgcagaaaaaaaggatctcaagaagatcctttg<br>atcttttctacggggtctgacgctcagtggaacgaaaactcacgttaagggattttggtcatggctagttaattaacatttaaatcagcggccgcaataa<br>aatatctttattttcattacatctgtgtgttggttttttgtgtgaatcgtaactaacatacgctctccatcaaaacaaaacgaaacaaaacaaactagca<br>aaataggctgtccccagtgcaagtgcaggtgccagaacatttctctatcgaa |
| 55 | ggatctgcgatcgctccggtgcccgtcagtgggcagagcgcacatcgcccacagtccccgagaagttggggggaggggtcggcaattgaacgggtgccta<br>gagaaggtggcgcggggtaaactgggaaagtgatgtcgtgtactggctccgcctttttcccgagggtgggggagaaccgtatataagtgcagtagtcgcc<br>gtgaacgttctttttcgcaacgggtttgccgccagaacacagctgaagcttcgaggggctcgcatctctccttcacgcgcccgccgccctacctgaggcc<br>gccatccacgccggttgagtcgcgttctgccgcctcccgcctgtggtgcctcctgaactgcgtccgccgtctaggtaagtttaaagctcaggtcgagacc<br>gggcctttgtccggcgctcccttggagcctacctagactcagccggctctccacgctttgcctgaccctgcttgctcaactctacgtctttgtttcgttt<br>tctgttctgcgccgttacagatccaagctgtgaccggcgcctacctgagatcaccggcgaaggagggccaccatgtacaggatgcaactcctgtcttgca<br>ttgcactaagtcttgcacttgtcacgaattcgaactaccacctggagaatgaagtcgccagactgaagaaactgctggttggcgaggccgcagctaagga<br>agccgcagctaaagccCAAGTGCAGCTGGTGCAGTCTGGGGCTGAGCTTGTGAGACCTGGGACCTCTGTGAAGTTATCTTGCAAAGTTTCTGGCGATACC<br>ATTACATTTTACTACATGCACTTTGTGAAGCAAAGGCCTGGACAGGGTCTGGAATGGATAGGAAGGATTGATCCTGAGGATGAAAGTACTAAATATTCTG<br>AGAAGTTCAAAAACAAGGCGACACTCACTGCAGATACATCTTCCAACACAGCCTACCTGAAGCTCAGCAGCCTGACCTCTGAGGACACTGCAACCTATTT<br>TTGTATCTACGGAGGATACTACTTTGATTACTGGGGCCCAGGAACCATGGTCACCGTGTCCTCAgcctccaccaagggcccatcggtcttccccctggca<br>ccctcctccaagagcacctctgggggcacagcggccctgggctgcctggtcaaggactacttccccgaaccggtgacggtgtcgtggaactcaggcgccc<br>tgaccagcggcgtgcacaccttcccggctgtcctacagtcctcaggactctactccctcagcagcgtggtgactgtgccctctagcagcttgggcaccca<br>gacctacatctgcaacgtgaatcacaagcccagcaacaccaaggtggacaagaaagttgagcccaaatcttgttgataagtgctagctggccagacatga<br>taagatacattgatgagtttggacaaaccacaactagaatgcagtgaaaaaaatgctttatttgtgaaatttgtgatgctattgctttatttgtaaccat<br>tataagctgcaataaacaagttaacaacaacaattgcattcattttatgtttcaggttcagggggaggtgtgggaggttttttaaagcaagtaaaacctc<br>tacaaatgtggtatggaattaattctaaaatacagcatagcaaaactttaacctccaaatcaagcctctacttgaatcctttttctgagggatgaataagg<br>cataggcatcaggggctgttgccaatgtgcattagctgtttgcagcctcaccttctttcatggagtttaagatatagtgtattttcccaaggtttgaact |

TABLE 46-continued anti-mouse CD19 switch antibody chains-Nucleotide Sequence

| SEQ ID NO | SEQUENCE |
|---|---|
| | agctcttcatttctttatgttttaaatgcactgacctcccacattcccatttagtaaaatattcagaaataatttaaatacatcattgcaatgaaaataa<br>atgtttttattaggcagaatccagatgctcaaggcccttcataatatcccccagtttagtagttggacttagggaacaaaggaacctttaatagaaatt<br>ggacagcaagaaagcgagcttctagcttatcctcagtcctgctcctctgccacaaagtgcacgcagttgccggccgggtcgcgcagggcgaactcccgcc<br>cccacggctgctcgccgatctcggtcatggccggcccggaggcgtcccggaagttcgtggacacgacctccgaccactcggcgtacagctcgtccaggcc<br>gcgcacccacacccaggccagggtgttgtccggcaccacctggtcctggaccgcgctgatgaacagggtcacgtcgtcccggaccacaccggcgaagtcg<br>tcctccacgaagtcccgggagaacccgagccggtcggtccagaactcgaccgctccggcgacgtcgcgcgcggtgagcaccggaacggcactggtcaact<br>tggccatgatggctcctcctgtcaggagaggaaagagaagaaggttagtacaattgctatagtgagttgtattatactatgcagatatactatgccaatg<br>attaattgtcaaactagggctgcagggttcatagtgccacttttcctgcactgccccatctcctgcccaccctttcccaggcatagacagtcagtgactt<br>accaaactcacaggagggagaaggcagaagcttgagacagacccgcgggaccgccgaactgcgaggggacgtggctagggcggcttcttttatggtgcgc<br>cggccctcggaggcagggcgctcggggaggcctagcggccaatctgcggtggcaggaggcggggccgaaggccgtgcctgaccaatccggagcacatagg<br>agtctcagcccccgccccaaagcaaggggaagtcacgcgcctgtagcgccagcgtgttgtgaaatgggggcttgggggggttggggccctgactagtca<br>aaacaaactcccattgacgtcaatggggtggagacttggaaatccccgtgagtcaaaccgctatccacgcccattgatgtactgccaaaaccgcatcatc<br>atggtaatagcgatgactaatacgtagatgtactgccaagtaggaaagtcccataaggtcatgtactgggcataatgccaggcgggccatttaccgtcat<br>tgacgtcaatagggggcgtacttggcatatgatacacttgatgtactgccaagtgggcagtttaccgtaaatactccacccattgacgtcaatggaaagt<br>ccctattggcgttactatgggaacatacgtcattattgacgtcaatgggcgggggtcgttgggcggtcagccaggcgggccatttaccgtaagttatgta<br>acgcctgcaggttaattaagaacatgtgagcaaaaggccagcaaaaggccaggaaccgtaaaaaggccgcgttgctggcgtttttccataggctccgccc<br>ccctgacgagcatcacaaaaatcgacgctcaagtcagaggtggcgaaacccgacaggactataaagataccaggcgtttccccctggaagctccctcgtg<br>cgctctcctgttccgaccctgccgcttaccggatacctgtccgcctttctcccttcgggaagcgtggcgctttctcatagctcacgctgtaggtatctca<br>gttcggtgtaggtcgttcgctccaagctgggctgtgtgcacgaaccccccgttcagcccgaccgctgcgccttatccggtaactatcgtcttgagtccaa<br>cccggtaagacacgacttatcgccactggcagcagccactggtaacaggattagcagagcgaggtatgtaggcggtgctacagagttcttgaagtggtgg<br>cctaactacggctacactagaagaacagtatttggtatctgcgctctgctgaagccagttaccttcggaaaaagagttggtagctcttgatccggcaaac<br>aaaccaccgctggtagcggtggtttttttgtttgcaagcagcagattacgcgcagaaaaaaaggatctcaagaagatcctttgatcttttctacggggtc<br>tgacgctcagtggaacgaaaactcacgttaagggattttggtcatggctagttaattaacatttaaatcagcggccgcaataaaatatctttattttcat<br>tacatctgtgtgttggtttttgtgtgaatcgtaactaacatacgctctccatcaaaacaaaacgaaacaaaacaaactagcaaaataggctgtccccag<br>tgcaagtgcaggtgccagaacatttctctatcgaa |
| 56 | ggatctgcgatcgctccggtgcccgtcagtgggcagagcgcacatcgcccacagtccccgagaagttggggggaggggtcggcaattgaacgggtgccta<br>gagaaggtggcgcggggtaaactgggaaagtgatgtcgtgtactggctccgcctttttcccgagggtgggggagaaccgtatataagtgcagtagtcgcc<br>gtgaacgttctttttcgcaacgggtttgccgccagaacacagctgaagcttcgaggggctcgcatctctccttcacgcgcccgccgccctacctgaggcc<br>gccatccacgccggttgagtcgcgttctgccgcctcccgcctgtggtgcctcctgaactgcgtccgccgtctaggtaagtttaaagctcaggtcgagacc<br>gggcctttgtccggcgctcccttggagcctacctagactcagccggctctccacgctttgcctgaccctgcttgctcaactctacgtctttgtttcgttt<br>tctgttctgcgccgttacagatccaagctgtgaccggcgcctacctgagatcaccggcgaaggagggccaccatgtacaggatgcaactcctgtcttgca<br>ttgcactaagtcttgcacttgtcacgaattcgCAAGTGCAGCTGGTGCAGTCTGGGGCTGAGCTTGTGAGACCTGGGACCTCTGTGAAGTTATCTTGCAA<br>AGTTTCTGGCGATACCATTACATTTTACTACATGCACTTTGTGAAGCAAAGGCCTGGACAGGGTCTGGAATGGATAGGAAGGATTGATCCTGAGGATGAA<br>AGTACTAAATATTCTGAGAAGTTCAAAAACAAGGCGACACTCACTGCAGATACATCTTCCAACACAGCCTACCTGAAGCTCAGCAGCCTGACCTCTGAGG<br>ACACTGCAACCTATTTTTGTATCTACGGAGGATACTACTTTGATTACTGGGGCCCAGGAACCATGGTCACCGTGTCCTCAgcctccaccaagggcccatc<br>ggtcttccccctggcaccctcctccaagagcacctctgggggcacagcggccctgggctgcctggtcaaggactacttccccgaaccggtgacggtgtcg<br>tggaactcaggcgccctgaccagcggcgtgcacaccttcccggctgtcctacagtcctcaggactctactccctcagcagcgtggtgactgtgccctcta<br>gcagcttgggcacccagacctacatctgcaacgtgaatcacaagcccagcaacaccaaggtggacaagaaagttgagcccaaatcttgtggcgggggagg<br>ctcaaactaccacctggagaatgaagtcgccagactgaagaaactgtgataagtgctagctggccagacatgataagatacattgatgagtttggacaaa<br>ccacaactagaatgcagtgaaaaaaatgctttatttgtgaaatttgtgatgctattgctttatttgtaaccattataagctgcaataaacaagttaacaa<br>caacaattgcattcattttatgtttcaggttcagggggaggtgtgggaggttttttaaagcaagtaaaacctctacaaatgtggtatggaattaattcta<br>aaatacagcatagcaaaactttaacctccaaatcaagcctctacttgaatccttttctgagggatgaataaggcataggcatcaggggctgttgccaatg<br>tgcattagctgtttgcagcctcaccttctttcatggagtttaagatatagtgtattttcccaaggtttgaactagctcttcatttctttatgttttaaat<br>gcactgacctcccacattccctttttagtaaaatattcagaaataatttaaatacatcattgcaatgaaaataaatgtttttattaggcagaatccaga<br>tgctcaaggcccttcataatatcccccagtttagtagttggacttagggaacaaaggaacctttaatagaaattggacagcaagaaagcgagcttctagc<br>ttatcctcagtcctgctcctctgccacaaagtgcacgcagttgccggccgggtcgcgcagggcgaactcccgcccccacggctgctcgccgatctcggtc<br>atggccggcccggaggcgtcccggaagttcgtggacacgacctccgaccactcggcgtacagctcgtccaggccgcgcacccacacccaggccagggtgt<br>tgtccggcaccacctggtcctggaccgcgctgatgaacagggtcacgtcgtcccggaccacaccggcgaagtcgtcctccacgaagtcccgggagaaccc<br>gagccggtcggtccagaactcgaccgctccggcgacgtcgcgcgcggtgagcaccggaacggcactggtcaacttggccatgatggctcctcctgtcagg<br>agaggaaagagaagaaggttagtacaattgctatagtgagttgtattatactatgcagatatactatgccaatgattaattgtcaaactagggctgcagg<br>gttcatagtgccacttttcctgcactgccccatctcctgcccaccctttcccaggcatagacagtcagtgacttaccaaactcacaggagggagaaggca<br>gaagcttgagacagacccgcgggaccgccgaactgcgaggggacgtggctagggcggcttcttttatggtgcgccggccctcggaggcagggcgctcggg<br>gaggcctagcggccaatctgcggtggcaggaggcggggccgaaggccgtgcctgaccaatccggagcacataggagtctcagcccccgccccaaagcaa<br>ggggaagtcacgcgcctgtagcgccagcgtgttgtgaaatgggggcttgggggggttggggccctgactagtcaaaacaaactcccattgacgtcaatgg<br>ggtggagacttggaaatccccgtgagtcaaaccgctatccacgcccattgatgtactgccaaaaccgcatcatcatggtaatagcgatgactaatacgta<br>gatgtactgccaagtaggaaagtcccataaggtcatgtactgggcataatgccaggcgggccatttaccgtcattgacgtcaatagggggcgtacttggc<br>atatgatacacttgatgtactgccaagtgggcagtttaccgtaaatactccacccattgacgtcaatggaaagtccctattggcgttactatgggaacat<br>acgtcattattgacgtcaatgggcgggggtcgttgggcggtcagccaggcgggccatttaccgtaagttatgtaacgcctgcaggttaattaagaacatg<br>tgagcaaaaggccagcaaaaggccaggaaccgtaaaaaggccgcgttgctggcgtttttccataggctccgcccccctgacgagcatcacaaaaatcgac<br>gctcaagtcagaggtggcgaaacccgacaggactataaagataccaggcgtttccccctggaagctccctcgtgcgctctcctgttccgaccctgccgct<br>taccggatacctgtccgcctttctcccttcgggaagcgtggcgctttctcatagctcacgctgtaggtatctcagttcggtgtaggtcgttcgctccaag<br>ctgggctgtgtgcacgaaccccccgttcagcccgaccgctgcgccttatccggtaactatcgtcttgagtccaacccggtaagacacgacttatcgccac<br>tggcagcagccactggtaacaggattagcagagcgaggtatgtaggcggtgctacagagttcttgaagtggtggcctaactacggctacactagaagaac<br>agtatttggtatctgcgctctgctgaagccagttaccttcggaaaaagagttggtagctcttgatccggcaaacaaaccaccgctggtagcggtggtttt<br>tttgtttgcaagcagcagattacgcgcagaaaaaaaggatctcaagaagatcctttgatcttttctacggggtctgacgctcagtggaacgaaaactcac<br>gttaagggattttggtcatggctagttaattaacatttaaatcagcggccgcaataaaatatctttattttcattacatctgtgtgttggtttttttgtgt<br>gaatcgtaactaacatacgctctccatcaaaacaaaacgaaacaaaacaaactagcaaaataggctgtccccagtgcaagtgcaggtgccagaacatttc<br>tctatcgaa |
| 57 | ggatctgcgatcgctccggtgcccgtcagtgggcagagcgcacatcgcccacagtccccgagaagttggggggaggggtcggcaattgaacgggtgccta<br>gagaaggtggcgcggggtaaactgggaaagtgatgtcgtgtactggctccgcctttttcccgagggtgggggagaaccgtatataagtgcagtagtcgcc<br>gtgaacgttctttttcgcaacgggtttgccgccagaacacagctgaagcttcgaggggctcgcatctctccttcacgcgcccgccgccctacctgaggcc<br>gccatccacgccggttgagtcgcgttctgccgcctcccgcctgtggtgcctcctgaactgcgtccgccgtctaggtaagtttaaagctcaggtcgagacc |

TABLE 46-continued anti-mouse CD19 switch antibody chains-Nucleotide Sequence

| SEQ ID NO | SEQUENCE |
|---|---|
| | gggcctttgtccggcgctcccttggagcctacctagactcagccggctctccacgctttgcctgaccctgcttgctcaactctacgtctttgtttcgttt<br>tctgttctgcgccgttacagatccaagctgtgaccggcgcctacctgagatcaccggcgaaggagggccaccatgtacaggatgcaactcctgtcttgca<br>ttgcactaagtcttgcacttgtcacgaattcgGACATTCAGCTGACCCAGTCTCCAGCTTCCCTGTCTACATCTCTGGGAGAAACTGTCACCATCCAATG<br>TCAAGCAAGTGAGGACATTTACAGTGGTTTAGCGTGGTATCAGCAGAAGCCAGGGAAATCTCCTCAGCTCCTGATCTATGGTGCAAGTGACTTACAAGAC<br>GGCGTCCCATCACGATTCAGTGGCAGTGGATCTGGCACACAGTATTCTCTCAAGATCACCAGCATGCAAACTGAAGATGAAGGGGTTTATTTCTGTCAAC<br>AGGGTTTAACGTATCCTCGGACGTTCGGTGGCGGCACCAAGCTgGAaATCaaacgaactgtggctgcaccatctgtcttcatcttcccgccatctgatga<br>gcagttgaaatctggaactgcctctgtcgtgtgcctgctgaataacttctatcccagagaggccaaagtacagtggaaggtggataacgccctccaatcg<br>ggtaactcccaggagagtgtcacagagcaggacagcaaggacagcacctacagcctcagcagcaccctgacgctgagcaaagcagactacgagaaacaca<br>aagtctacgcctgcgaagtcacccatcagggcctgtcctcgcccgtcacaaagagcttcaacaggggagagtgtggcgggggaggctcaaactaccacct<br>ggagaatgaagtcgccagactgaagaaactgtgataagtgctagctggccagacatgataagatacattgatgagtttggacaaaccacaactagaatgc<br>agtgaaaaaaatgctttatttgtgaaatttgtgatgctattgctttatttgtaaccattataagctgcaataaacaagttaacaacaacaattgcattca<br>ttttatgtttcaggttcagggggaggtgtgggaggttttttaaagcaagtaaaacctctacaaatgtggtatggaattaattctaaaatacagcatagca<br>aaactttaacctccaaatcaagcctctacttgaatccttttctgagggatgaataaggcataggcatcaggggctgttgccaatgtgcattagctgtttg<br>cagcctcaccttctttcatggagtttaagatatagtgtattttcccaaggtttgaactagctcttcatttctttatgttttaaatgcactgacctcccac<br>attccctttttagtaaaatattcagaaataatttaaatacatcattgcaatgaaaataaatgtttttttattaggcagaatccagatgctcaaggcccttc<br>ataatatcccccagtttagtagttggacttagggaacaaaggaacctttaatagaaattggacagcaagaaagcgagcttctagcttatcctcagtcctg<br>ctcctctgccacaaagtgcacgcagttgccggccgggtcgcgcagggcgaactcccgcccccacggctgctcgccgatctcggtcatggccggcccggag<br>gcgtcccggaagttcgtggacacgacctccgaccactcggcgtacagctcgtccaggccgcgcacccacacccaggccagggtgttgtccggcaccacct<br>ggtcctggaccgcgctgatgaacagggtcacgtcgtcccggaccacaccggcgaagtcgtcctccacgaagtcccgggagaacccgagccggtcggtcca<br>gaactcgaccgctccggcgacgtcgcgcgcggtgagcaccggaacggcactggtcaacttggccatgatggctcctcctgtcaggagaggaaagagaaga<br>aggttagtacaattgctatagtgagttgtattatactatgcagatatactatgccaatgattaattgtcaaactagggctgcagggttcatagtgccact<br>tttcctgcactgccccatctcctgcccaccctttcccaggcatagacagtcagtgacttaccaaactcacaggagggagaaggcagaagcttgagacaga<br>cccgcgggaccgccgaactgcgaggggacgtggctagggcggcttcttttatggtgcgccggccctcggaggcagggcgctcggggaggcctagcggcca<br>atctgcggtggcaggaggcggggccgaaggccgtgcctgaccaatccggagcacataggagtctcagccccccgccccaaagcaaggggaagtcacgcgc<br>ctgtagcgccagcgtgttgtgaaatgggggcttgggggggttggggccctgactagtcaaaacaaactcccattgacgtcaatggggtggagacttggaa<br>atccccgtgagtcaaaccgctatccacgcccattgatgtactgccaaaaccgcatcatcatggtaatagcgatgactaatacgtagatgtactgccaagt<br>aggaaagtcccataaggtcatgtactgggcataatgccaggcgggccatttaccgtcattgacgtcaatagggggcgtacttggcatatgatacacttga<br>tgtactgccaagtgggcagtttaccgtaaatactccacccattgacgtcaatggaaagtccctattggcgttactatgggaacatacgtcattattgacg<br>tcaatgggcgggggtcgttgggcggtcagccaggcgggccatttaccgtaagttatgtaacgcctgcaggttaattaagaacatgtgagcaaaaggccag<br>caaaaggccaggaaccgtaaaaaggccgcgttgctggcgtttttccataggctccgcccccctgacgagcatcacaaaaatcgacgctcaagtcagaggt<br>ggcgaaacccgacaggactataaagataccaggcgtttccccctggaagctccctcgtgcgctctcctgttccgaccctgccgcttaccggatacctgtc<br>cgcctttctcccttcgggaagcgtggcgctttctcatagctcacgctgtaggtatctcagttcggtgtaggtcgttcgctccaagctgggctgtgtgcac<br>gaaccccccgttcagcccgaccgctgcgccttatccggtaactatcgtcttgagtccaacccggtaagacacgacttatcgccactggcagcagccactg<br>gtaacaggattagcagagcgaggtatgtaggcggtgctacagagttcttgaagtggtggcctaactacggctacactagaagaacagtatttggtatctg<br>cgctctgctgaagccagttaccttcggaaaaagagttggtagctcttgatccggcaaacaaaccaccgctggtagcggtggtttttttgtttgcaagcag<br>cagattacgcgcagaaaaaaaggatctcaagaagatcctttgatcttttctacggggtctgacgctcagtggaacgaaaactcacgttaagggattttgg<br>tcatggctagttaattaacatttaaatcagcggccgcaataaaatatctttattttcattacatctgtgtgttggttttttgtgtgaatcgtaactaaca<br>tacgctctccatcaaaacaaaacgaaacaaaacaaactagcaaaataggctgtccccagtgcaagtgcaggtgccagaacatttctctatcgaa |
| 58 | ggatctgcgatcgctccggtgcccgtcagtgggcagagcgcacatcgcccacagtccccgagaagttggggggaggggtcggcaattgaacgggtgccta<br>gagaaggtggcgcggggtaaactgggaaagtgatgtcgtgtactggctccgcctttttcccgagggtgggggagaaccgtatataagtgcagtagtcgcc<br>gtgaacgttctttttcgcaacgggtttgccgccagaacacagctgaagcttcgaggggctcgcatctctccttcacgcgcccgccgccctacctgaggcc<br>gccatccacgccggttgagtcgcgttctgccgcctcccgcctgtggtgcctcctgaactgcgtccgccgtctaggtaagtttaaagctcaggtcgagacc<br>gggcctttgtccggcgctcccttggagcctacctagactcagccggctctccacgctttgcctgaccctgcttgctcaactctacgtctttgtttcgttt<br>tctgttctgcgccgttacagatccaagctgtgaccggcgcctacctgagatcaccggcgaaggagggccaccatgtacaggatgcaactcctgtcttgca<br>ttgcactaagtcttgcacttgtcacgaattcgaactaccacctggagaatgaagtcgccagactgaagaaactgggcgggggaggctcaGACATTCAGCT<br>GACCCAGTCTCCAGCTTCCCTGTCTACATCTCTGGGAGAAACTGTCACCATCCAATGTCAAGCAAGTGAGGACATTTACAGTGGTTTAGCGTGGTATCAG<br>CAGAAGCCAGGGAAATCTCCTCAGCTCCTGATCTATGGTGCAAGTGACTTACAAGACGGCGTCCCATCACGATTCAGTGGCAGTGGATCTGGCACACAGT<br>ATTCTCTCAAGATCACCAGCATGCAAACTGAAGATGAAGGGGTTTATTTCTGTCAACAGGGTTTAACGTATCCTCGGACGTTCGGTGGCGGCACCAAGCT<br>TGAGATCaaacgaactgtggctgcaccatctgtcttcatcttcccgccatctgatgagcagttgaaatctggaactgcctctgtcgtgtgcctgctgaat<br>aacttctatcccagagaggccaaagtacagtggaaggtggataacgccctccaatcgggtaactcccaggagagtgtcacagagcaggacagcaaggaca<br>gcacctacagcctcagcagcaccctgacgctgagcaaagcagactacgagaaacacaaagtctacgcctgcgaagtcacccatcagggcctgtcctcgcc<br>cgtcacaaagagcttcaacaggggagagtgttgataagtgctagctggccagacatgataagatacattgatgagtttggacaaaccacaactagaatgc<br>agtgaaaaaaatgctttatttgtgaaatttgtgatgctattgctttatttgtaaccattataagctgcaataaacaagttaacaacaacaattgcattca<br>ttttatgtttcaggttcagggggaggtgtgggaggttttttaaagcaagtaaaacctctacaaatgtggtatggaattaattctaaaatacagcatagca<br>aaactttaacctccaaatcaagcctctacttgaatccttttctgagggatgaataaggcataggcatcaggggctgttgccaatgtgcattagctgtttg<br>cagcctcaccttctttcatggagtttaagatatagtgtattttcccaaggtttgaactagctcttcatttctttatgttttaaatgcactgacctcccac<br>attccctttttagtaaaatattcagaaataatttaaatacatcattgcaatgaaaataaatgtttttttattaggcagaatccagatgctcaaggcccttc<br>ataatatcccccagtttagtagttggacttagggaacaaaggaacctttaatagaaattggacagcaagaaagcgagcttctagcttatcctcagtcctg<br>ctcctctgccacaaagtgcacgcagttgccggccgggtcgcgcagggcgaactcccgcccccacggctgctcgccgatctcggtcatggccggcccggag<br>gcgtcccggaagttcgtggacacgacctccgaccactcggcgtacagctcgtccaggccgcgcacccacacccaggccagggtgttgtccggcaccacct<br>ggtcctggaccgcgctgatgaacagggtcacgtcgtcccggaccacaccggcgaagtcgtcctccacgaagtcccgggagaacccgagccggtcggtcca<br>gaactcgaccgctccggcgacgtcgcgcgcggtgagcaccggaacggcactggtcaacttggccatgatggctcctcctgtcaggagaggaaagagaaga<br>aggttagtacaattgctatagtgagttgtattatactatgcagatatactatgccaatgattaattgtcaaactagggctgcagggttcatagtgccact<br>tttcctgcactgccccatctcctgcccaccctttcccaggcatagacagtcagtgacttaccaaactcacaggagggagaaggcagaagcttgagacaga<br>cccgcgggaccgccgaactgcgaggggacgtggctagggcggcttcttttatggtgcgccggccctcggaggcagggcgctcggggaggcctagcggcca<br>atctgcggtggcaggaggcggggccgaaggccgtgcctgaccaatccggagcacataggagtctcagccccccgccccaaagcaaggggaagtcacgcgc<br>ctgtagcgccagcgtgttgtgaaatgggggcttgggggggttggggccctgactagtcaaaacaaactcccattgacgtcaatggggtggagacttggaa<br>atccccgtgagtcaaaccgctatccacgcccattgatgtactgccaaaaccgcatcatcatggtaatagcgatgactaatacgtagatgtactgccaagt<br>aggaaagtcccataaggtcatgtactgggcataatgccaggcgggccatttaccgtcattgacgtcaatagggggcgtacttggcatatgatacacttga<br>tgtactgccaagtgggcagtttaccgtaaatactccacccattgacgtcaatggaaagtccctattggcgttactatgggaacatacgtcattattgacg<br>tcaatgggcgggggtcgttgggcggtcagccaggcgggccatttaccgtaagttatgtaacgcctgcaggttaattaagaacatgtgagcaaaaggccag<br>caaaaggccaggaaccgtaaaaaggccgcgttgctggcgtttttccataggctccgcccccctgacgagcatcacaaaaatcgacgctcaagtcagaggt<br>ggcgaaacccgacaggactataaagataccaggcgtttccccctggaagctccctcgtgcgctctcctgttccgaccctgccgcttaccggatacctgtc |

TABLE 46-continued

| anti-mouse CD19 switch antibody chains-Nucleotide Sequence | |
|---|---|
| SEQ ID NO | SEQUENCE |
| | cgcctttctcccttcgggaagcgtggcgctttctcatagctcacgctgtaggtatctcagttcggtgtaggtcgttcgctccaagctgggctgtgtgcac<br>gaaccccccgttcagcccgaccgctgcgccttatccggtaactatcgtcttgagtccaacccggtaagacacgacttatcgccactggcagcagccactg<br>gtaacaggattagcagagcgaggtatgtaggcggtgctacagagttcttgaagtggtggcctaactacggctacactagaagaacagtatttggtatctg<br>cgctctgctgaagccagttaccttcggaaaaagagttggtagctcttgatccggcaaacaaaccaccgctggtagcggtggtttttttgtttgcaagcag<br>cagattacgcgcagaaaaaaaggatctcaagaagatcctttgatcttttctacggggtctgacgctcagtggaacgaaaactcacgttaagggattttgg<br>tcatggctagttaattaacatttaaatcagcggccgcaataaaatatctttattttcattacatctgtgtgttggttttttgtgtgaatcgtaactaaca<br>tacgctctccatcaaaacaaaacgaaacaaaacaaactagcaaaataggctgtccccagtgcaagtgcaggtgccagaacatttctctatcgaa |
| 59 | ggatctgcgatcgctccggtgcccgtcagtgggcagagcgcacatcgcccacagtccccgagaagttggggggaggggtcggcaattgaacgggtgccta<br>gagaaggtggcgcggggtaaactgggaaagtgatgtcgtgtactggctccgcctttttcccgagggtgggggagaaccgtatataagtgcagtagtcgcc<br>gtgaacgttctttttcgcaacgggtttgccgccagaacacagctgaagcttcgaggggctcgcatctctccttcacgcgcccgccgccctacctgaggcc<br>gccatccacgccggttgagtcgcgttctgccgcctcccgcctgtggtgcctcctgaactgcgtccgccgtctaggtaagtttaaagctcaggtcgagacc<br>gggcctttgtccggcgctcccttggagcctacctagactcagccggctctccacgctttgcctgaccctgcttgctcaactctacgtctttgtttcgttt<br>tctgttctgcgccgttacagatccaagctgtgaccggcgcctacctgagatcaccggcgaaggagggccaccatgtacaggatgcaactcctgtcttgca<br>ttgcactaagtcttgcacttgtcacgaattcgaactaccacctggagaatgaagtcgccagactgaagaaactgggcgggggaggctcaggggggaggcgg<br>gtcaGACATTCAGCTGACCCAGTCTCCAGCTTCCCTGTCTACATCTCTGGGAGAAACTGTCACCATCCAATGTCAAGCAAGTGAGGACATTTACAGTGGT<br>TTAGCGTGGTATCAGCAGAAGCCAGGGAAATCTCCTCAGCTCCTGATCTATGGTGCAAGTGACTTACAAGACGGCGTCCCATCACGATTCAGTGGCAGTG<br>GATCTGGCACACAGTATTCTCTCAAGATCACCAGCATGCAAACTGAAGATGAAGGGGTTTATTTCTGTCAACAGGGTTTAACGTATCCTCGGACGTTCGG<br>TGGCGGCACCAAGCTTGAGATCaaacgaactgtggctgcaccatctgtcttcatcttcccgccatctgatgagcagttgaaatctggaactgcctctgtc<br>gtgtgcctgctgaataacttctatcccagagaggccaaagtacagtggaaggtggataacgccctccaatcgggtaactcccaggagagtgtcacagagc<br>aggacagcaaggacagcacctacagcctcagcagcaccctgacgctgagcaaagcagactacgagaaacacaaagtctacgcctgcgaagtcacccatca<br>gggcctgtcctcgcccgtcacaaagagcttcaacaggggagagtgttgataagtgctagctggccagacatgataagatacattgatgagtttggacaaa<br>ccacaactagaatgcagtgaaaaaaatgctttatttgtgaaatttgtgatgctattgctttatttgtaaccattataagctgcaataaacaagttaacaa<br>caacaattgcattcattttatgtttcaggttcaggggggaggtgtgggaggttttttaaagcaagtaaaacctctacaaatgtggtatggaattaattcta<br>aaatacagcatagcaaaactttaacctccaaatcaagcctctacttgaatccttttctgagggatgaataaggcataggcatcaggggctgttgccaatg<br>tgcattagctgtttgcagcctcaccttctttcatggagtttaagatatagtgtattttcccaaggtttgaactagctcttcatttctttatgttttaaat<br>gcactgacctcccacattccctttttagtaaaatattcagaaataatttaaatacatcattgcaatgaaaataaatgttttttattaggcagaatccaga<br>tgctcaaggcccttcataatatcccccagtttagtagttggacttagggaacaaaggaacctttaatagaaattggacagcaagaaagcgagcttctagc<br>ttatcctcagtcctgctcctctgccacaaagtgcacgcagttgccggccgggtcgcgcagggcgaactcccgcccccacggctgctcgccgatctcggtc<br>atggccggcccggaggcgtcccggaagttcgtggacacgacctccgaccactcggcgtacagctcgtccaggccgcgcacccacacccaggccagggtgt<br>tgtccggcaccacctggtcctggaccgcgctgatgaacagggtcacgtcgtcccggaccacaccggcgaagtcgtcctccacgaagtcccgggagaaccc<br>gagccggtcggtccagaactcgaccgctccggcgacgtcgcgcgcggtgagcaccggaacggcactggtcaacttggccatgatggctcctcctgtcagg<br>agaggaaagagaagaaggttagtacaattgctatagtgagttgtattatactatgcagatatactatgccaatgattaattgtcaaactagggctgcagg<br>gttcatagtgccacttttcctgcactgccccatctcctgcccaccctttcccaggcatagacagtcagtgacttaccaaactcacaggagggagaaggca<br>gaagcttgagacagacccgcgggaccgccgaactgcgaggggacgtggctagggcggcttcttttatggtgcgccggccctcggaggcagggcgctcggg<br>gaggcctagcggccaatctgcggtggcaggaggcggggccgaaggccgtgcctgaccaatccggagcacataggagtctcagccccccgccccaaagcaa<br>ggggaagtcacgcgcctgtagcgccagcgtgttgtgaaatgggggcttgggggggttggggccctgactagtcaaaacaaactcccattgacgtcaatgg<br>ggtggagacttggaaatccccgtgagtcaaaccgctatccacgcccattgatgtactgccaaaaccgcatcatcatggtaatagcgatgactaatacgta<br>gatgtactgccaagtaggaaagtcccataaggtcatgtactgggcataatgccaggcgggccatttaccgtcattgacgtcaataggggcgtacttggc<br>atatgatacacttgatgtactgccaagtgggcagtttaccgtaaatactccacccattgacgtcaatggaaagtccctattggcgttactatgggaacat<br>acgtcattattgacgtcaatgggcgggggtcgttgggcggtcagccaggcgggccatttaccgtaagttatgtaacgcctgcaggttaattaagaacatg<br>tgagcaaaaggccagcaaaaggccaggaaccgtaaaaaggccgcgttgctggcgtttttccataggctccgcccccctgacgagcatcacaaaaatcgac<br>gctcaagtcagaggtggcgaaacccgacaggactataaagataccaggcgtttccccctggaagctccctcgtgcgctctcctgttccgaccctgccgct<br>taccggatacctgtccgcctttctcccttcgggaagcgtggcgctttctcatagctcacgctgtaggtatctcagttcggtgtaggtcgttcgctccaag<br>ctgggctgtgtgcacgaaccccccgttcagcccgaccgctgcgccttatccggtaactatcgtcttgagtccaacccggtaagacacgacttatcgccac<br>tggcagcagccactggtaacaggattagcagagcgaggtatgtaggcggtgctacagagttcttgaagtggtggcctaactacggctacactagaagaac<br>agtatttggtatctgcgctctgctgaagccagttaccttcggaaaaagagttggtagctcttgatccggcaaacaaaccaccgctggtagcggtggtttt<br>tttgtttgcaagcagcagattacgcgcagaaaaaaaggatctcaagaagatcctttgatcttttctacggggtctgacgctcagtggaacgaaaactcac<br>gttaagggattttggtcatggctagttaattaacatttaaatcagcggccgcaataaaatatctttattttcattacatctgtgtgttggttttttgtgt<br>gaatcgtaactaacatacgctctccatcaaaacaaaacgaaacaaaacaaactagcaaaataggctgtccccagtgcaagtgcaggtgccagaacatttc<br>tctatcgaa |
| 60 | ggatctgcgatcgctccggtgcccgtcagtgggcagagcgcacatcgcccacagtccccgagaagttggggggaggggtcggcaattgaacgggtgccta<br>gagaaggtggcgcggggtaaactgggaaagtgatgtcgtgtactggctccgcctttttcccgagggtgggggagaaccgtatataagtgcagtagtcgcc<br>gtgaacgttctttttcgcaacgggtttgccgccagaacacagctgaagcttcgaggggctcgcatctctccttcacgcgcccgccgccctacctgaggcc<br>gccatccacgccggttgagtcgcgttctgccgcctcccgcctgtggtgcctcctgaactgcgtccgccgtctaggtaagtttaaagctcaggtcgagacc<br>gggcctttgtccggcgctcccttggagcctacctagactcagccggctctccacgctttgcctgaccctgcttgctcaactctacgtctttgtttcgttt<br>tctgttctgcgccgttacagatccaagctgtgaccggcgcctacctgagatcaccggcgaaggagggccaccatgtacaggatgcaactcctgtcttgca<br>ttgcactaagtcttgcacttgtcacgaattcgaactaccacctggagaatgaagtcgccagactgaagaaactgggcgggggaggctcaggggggaggcgg<br>gtcaGACATTCAGCTGACCCAGTCTCCAGCTTCCCTGTCTACATCTCTGGGAGAAACTGTCACCATCCAATGTCAAGCAAGTGAGGACATTTACAGTGGT<br>TTAGCGTGGTATCAGCAGAAGCCAGGGAAATCTCCTCAGCTCCTGATCTATGGTGCAAGTGACTTACAAGACGGCGTCCCATCACGATTCAGTGGCAGTG<br>GATCTGGCACACAGTATTCTCTCAAGATCACCAGCATGCAAACTGAAGATGAAGGGGTTTATTTCTGTCAACAGGGTTTAACGTATCCTCGGACGTTCGG<br>TGGCGGCACCAAGCTTGAGATCaaacgaactgtggctgcaccatctgtcttcatcttcccgccatctgatgagcagttgaaatctggaactgcctctgtc<br>gtgtgcctgctgaataacttctatcccagagaggccaaagtacagtggaaggtggataacgccctccaatcgggtaactcccaggagagtgtcacagagc<br>aggacagcaaggacagcacctacagcctcagcagcaccctgacgctgagcaaagcagactacgagaaacacaaagtctacgcctgcgaagtcacccatca<br>gggcctgtcctcgcccgtcacaaagagcttcaacaggggagagtgttgataagtgctagctggccagacatgataagatacattgatgagtttggacaaa<br>ccacaactagaatgcagtgaaaaaaatgctttatttgtgaaatttgtgatgctattgctttatttgtaaccattataagctgcaataaacaagttaacaa<br>caacaattgcattcattttatgtttcaggttcaggggggaggtgtgggaggttttttaaagcaagtaaaacctctacaaatgtggtatggaattaattcta<br>aaatacagcatagcaaaactttaacctccaaatcaagcctctacttgaatccttttctgagggatgaataaggcataggcatcaggggctgttgccaatg<br>tgcattagctgtttgcagcctcaccttctttcatggagtttaagatatagtgtattttcccaaggtttgaactagctcttcatttctttatgttttaaat<br>gcactgacctcccacattccctttttagtaaaatattcagaaataatttaaatacatcattgcaatgaaaataaatgttttttattaggcagaatccaga<br>tgctcaaggcccttcataatatcccccagtttagtagttggacttagggaacaaaggaacctttaatagaaattggacagcaagaaagcgagcttctagc<br>ttatcctcagtcctgctcctctgccacaaagtgcacgcagttgccggccgggtcgcgcagggcgaactcccgcccccacggctgctcgccgatctcggtc<br>atggccggcccggaggcgtcccggaagttcgtggacacgacctccgaccactcggcgtacagctcgtccaggccgcgcacccacacccaggccagggtgt |

TABLE 46-continued anti-mouse CD19 switch antibody chains-Nucleotide Sequence

| SEQ ID NO | SEQUENCE |
|---|---|
| | tgtccggcaccacctggtcctggaccgcgctgatgaacagggtcacgtcgtcccggaccacaccggcgaagtcgtcctccacgaagtcccgggagaaccc |
| | gagccggtcggtccagaactcgaccgctccggcgacgtcgcgcgcggtgagcaccggaacggcactggtcaacttggccatgatggctcctcctgtcagg |
| | agaggaaagagaagaaggttagtacaattgctatagtgagttgtattatactatgcagatatactatgccaatgattaattgtcaaactagggctgcagg |
| | gttcatagtgccacttttcctgcactgccccatctcctgcccaccctttcccaggcatagacagtcagtgacttaccaaactcacaggagggagaaggca |
| | gaagcttgagacagacccgcgggaccgccgaactgcgaggggacgtggctagggcggcttcttttatggtgcgccggccctcggaggcagggcgctcggg |
| | gaggcctagcggccaatctgcggtggcaggaggcggggccgaaggccgtgcctgaccaatccggagcacataggagtctcagccccccgccccaaagcaa |
| | ggggaagtcacgcgcctgtagcgccagcgtgttgtgaaatgggggcttgggggggttggggccctgactagtcaaaacaaactcccattgacgtcaatgg |
| | ggtggagacttggaaatccccgtgagtcaaaccgctatccacgcccattgatgtactgccaaaaccgcatcatcatggtaatagcgatgactaatacgta |
| | gatgtactgccaagtaggaaagtcccataaggtcatgtactgggcataatgccaggcgggccatttaccgtcattgacgtcaataggggggcgtacttggc |
| | atatgatacacttgatgtactgccaagtgggcagtttaccgtaaatactccacccattgacgtcaatggaaagtccctattggcgttactatgggaacat |
| | acgtcattattgacgtcaatgggcgggggtcgttgggcggtcagccaggcgggccatttaccgtaagttatgtaacgcctgcaggttaattaagaacatg |
| | tgagcaaaaggccagcaaaaggccaggaaccgtaaaaaggccgcgttgctggcgtttttccataggctccgcccccctgacgagcatcacaaaaatcgac |
| | gctcaagtcagaggtggcgaaacccgacaggactataaagataccaggcgtttccccctggaagctccctcgtgcgctctcctgttccgaccctgccgct |
| | taccggatacctgtccgcctttctcccttcgggaagcgtggcgctttctcatagctcacgctgtaggtatctcagttcggtgtaggtcgttcgctccaag |
| | ctgggctgtgtgcacgaaccccccgttcagcccgaccgctgcgccttatccggtaactatcgtcttgagtccaacccggtaagacacgacttatcgccac |
| | tggcagcagccactggtaacaggattagcagagcgaggtatgtaggcggtgctacagagttcttgaagtggtggcctaactacggctacactagaagaac |
| | agtatttggtatctgcgctctgctgaagccagttaccttcggaaaaagagttggtagctcttgatccggcaaacaaaccaccgctggtagcggtggtttt |
| | tttgtttgcaagcagcagattacgcgcagaaaaaaaggatctcaagaagatcctttgatcttttctacggggtctgacgctcagtggaacgaaaactcac |
| | gttaagggattttggtcatggctagttaattaacatttaaatcagcggccgcaataaaatatctttattttcattacatctgtgtgttggtttttttgtgt |
| | gaatcgtaactaacatacgctctccatcaaaacaaaacgaaacaaaacaaactagcaaaataggctgtccccagtgcaagtgcaggtgccagaacatttc |
| | tctatcgaa |
| 61 | ggatctgcgatcgctccggtgcccgtcagtgggcagagcgcacatcgcccacagtccccgagaagttggggggaggggtcggcaattgaacgggtgccta |
| | gagaaggtggcgcggggtaaactgggaaagtgatgtcgtgtactggctccgcctttttcccgagggtgggggagaaccgtatataagtgcagtagtcgcc |
| | gtgaacgttctttttcgcaacgggtttgccgccagaacacagctgaagcttcgaggggctcgcatctctccttcacgcgcccgccgccctacctgaggcc |
| | gccatccacgccggttgagtcgcgttctgccgcctcccgcctgtggtgcctcctgaactgcgtccgccgtctaggtaagtttaaagctcaggtcgagacc |
| | gggcctttgtccggcgctcccttggagcctacctagactcagccggctctccacgctttgcctgaccctgcttgctcaactctacgtctttgtttcgttt |
| | tctgttctgcgccgttacagatccaagctgtgaccggcgcctacctgagatcaccggcgaaggagggccaccatgtacaggatgcaactcctgtcttgca |
| | ttgcactaagtcttgcacttgtcacgaattcgaactaccacctggagaatgaagtcgccagactgaagaaactgggcgggggaggctcagggggaggcgg |
| | gtcaCAAGTGCAGCTGGTGCAGTCTGGGGCTGAGCTTGTGAGACCTGGGACCTCTGTGAAGTTATCTTGCAAAGTTTCTGGCGATACCATTACATTTTAC |
| | TACATGCACTTTGTGAAGCAAAGGCCTGGACAGGGTCTGGAATGGATAGGAAGGATTGATCCTGAGGATGAAAGTACTAAATATTCTGAGAAGTTCAAAA |
| | ACAAGGCGACACTCACTGCAGATACATCTTCCAACACAGCCTACCTGAAGCTCAGCAGCCTGACCTCTGAGGACACTGCAACCTATTTTTGTATCTACGG |
| | AGGATACTACTTTGATTACTGGGGACCAGGAACCATGGTCACCGTGTCCTCAgcctccaccaagggcccatcggtcttccccctggcaccctcctccaag |
| | agcacctctgggggcacagcggccctgggctgcctggtcaaggactacttccccgaaccggtgacggtgtcgtggaactcaggcgccctgaccagcggcg |
| | tgcacaccttcccggctgtcctacagtcctcaggactctactccctcagcagcgtggtgactgtgccctctagcagcttgggcacccagacctacatctg |
| | caacgtgaatcacaagcccagcaacaccaaggtggacaagaaagttgagcccaaatcttgttgataagtgctagctggccagacatgataagatacattg |
| | atgagtttggacaaaccacaactagaatgcagtgaaaaaaatgctttatttgtgaaatttgtgatgctattgctttatttgtaaccattataagctgcaa |
| | taaacaagttaacaacaacaattgcattcattttatgtttcaggttcagggggaggtgtgggaggttttttaaagcaagtaaaacctctacaaatgtggt |
| | atggaattaattctaaaatacagcatagcaaaactttaacctccaaatcaagcctctacttgaatccttttctgagggatgaataaggcataggcatcag |
| | gggctgttgccaatgtgcattagctgtttgcagcctcaccttctttcatggagtttaagatatagtgtattttcccaaggtttgaactagctcttcattt |
| | ctttatgttttaaatgcactgacctcccacattccctttttagtaaaatattcagaaataatttaaatacatcattgcaatgaaaataaatgtttttat |
| | taggcagaatccagatgctcaaggcccttcataatatcccccagtttagtagttggacttagggaacaaaggaacctttaatagaaattggacagcaaga |
| | aagcgagcttctagcttatcctcagtcctgctcctctgccacaaagtgcacgcagttgccggccgggtcgcgcagggcgaactcccgcccccacggctgc |
| | tcgccgatctcggtcatggccggcccggaggcgtcccggaagttcgtggacacgacctccgaccactcggcgtacagctcgtccaggccgcgcacccaca |
| | cccaggccagggtgttgtccggcaccacctggtcctggaccgcgctgatgaacagggtcacgtcgtcccggaccacaccggcgaagtcgtcctccacgaa |
| | gtcccgggagaacccgagccggtcggtccagaactcgaccgctccggcgacgtcgcgcgcggtgagcaccggaacggcactggtcaacttggccatgatg |
| | gctcctcctgtcaggagaggaaagagaagaaggttagtacaattgctatagtgagttgtattatactatgcagatatactatgccaatgattaattgtca |
| | aactagggctgcagggttcatagtgccacttttcctgcactgccccatctcctgcccaccctttcccaggcatagacagtcagtgacttaccaaactcac |
| | aggagggagaaggcagaagcttgagacagacccgcgggaccgccgaactgcgaggggacgtggctagggcggcttcttttatggtgcgccggccctcgga |
| | ggcagggcgctcggggaggcctagcggccaatctgcggtggcaggaggcggggccgaaggccgtgcctgaccaatccggagcacataggagtctcagccc |
| | cccgccccaaagcaaggggaagtcacgcgcctgtagcgccagcgtgttgtgaaatgggggcttgggggggttggggccctgactagtcaaaacaaactcc |
| | cattgacgtcaatggggtggagacttggaaatccccgtgagtcaaaccgctatccacgcccattgatgtactgccaaaaccgcatcatcatggtaatagc |
| | gatgactaatacgtagatgtactgccaagtaggaaagtcccataaggtcatgtactgggcataatgccaggcgggccatttaccgtcattgacgtcaata |
| | gggggcgtacttggcatatgatacacttgatgtactgccaagtgggcagtttaccgtaaatactccacccattgacgtcaatggaaagtccctattggcg |
| | ttactatgggaacatacgtcattattgacgtcaatgggcgggggtcgttgggcggtcagccaggcgggccatttaccgtaagttatgtaacgcctgcagg |
| | ttaattaagaacatgtgagcaaaaggccagcaaaaggccaggaaccgtaaaaaggccgcgttgctggcgtttttccataggctccgcccccctgacgagc |
| | atcacaaaaatcgacgctcaagtcagaggtggcgaaacccgacaggactataaagataccaggcgtttccccctggaagctccctcgtgcgctctcctgt |
| | tccgaccctgccgcttaccggatacctgtccgcctttctcccttcgggaagcgtggcgctttctcatagctcacgctgtaggtatctcagttcggtgtag |
| | gtcgttcgctccaagctgggctgtgtgcacgaaccccccgttcagcccgaccgctgcgccttatccggtaactatcgtcttgagtccaacccggtaagac |
| | acgacttatcgccactggcagcagccactggtaacaggattagcagagcgaggtatgtaggcggtgctacagagttcttgaagtggtggcctaactacgg |
| | ctacactagaagaacagtatttggtatctgcgctctgctgaagccagttaccttcggaaaaagagttggtagctcttgatccggcaaacaaaccaccgct |
| | ggtagcggtggtttttttgtttgcaagcagcagattacgcgcagaaaaaaaggatctcaagaagatcctttgatcttttctacggggtctgacgctcagt |
| | ggaacgaaaactcacgttaagggattttggtcatggctagttaattaacatttaaatcagcggccgcaataaaatatctttattttcattacatctgtgt |
| | gttggtttttttgtgtgaatcgtaactaacatacgctctccatcaaaacaaaacgaaacaaaacaaactagcaaaataggctgtccccagtgcaagtgcag |
| | gtgccagaacatttctctatcgaa |

TABLE 47

| Soluble T cell receptors-Nucleotide Sequence | |
|---|---|
| SEQ ID NO | SEQUENCE |
| 62 | atccggatatagttcctcctttcagcaaaaaacccctcaagacccgtttagaggccccaaggggttatgctagttattgctcagcggtggcagcagccaa<br>ctcagcttcctttcgggctttgttagcagccggatctcagtggtggtggtggtggtgctcgagTTAGTCAGCACGACCCCACGCTTCTGCACTGACAATT<br>TGCGTAACCGGTTTTGCACGGTCCTGGGTCCATTCATCATTTTCGCTCAGGCCGTAGAATTGAACCTGACAGCGAAAATGGTTACGCGGGTCCTGCCAGA<br>AGGTGGCAGACACGCGCAGACGGGAACTCAGGGCATAACGGCTGTCATTCAGCGCCGGTTGTTCTTTCAGCGGCTGCGGATCGGTACACACACCCGAGTG<br>GACTTCTTTGCCGTTCACCCACCATGACAGTTCGACATGGTCCGGATAAAAGCCGGTGGCCAGGCACACCAGCGTCGCTTTCTGGGTATGGGAGATTTCA<br>GCTTCACTCGGTTCGAAAACTGCCACTTCCGGCGGAAAGACATTTTTCAGATCTTCCAGAACCGTCAGACGAGAACCTTCGCCGAAAAACAGTTCACCGG<br>TGTTGCCCAGGTAAGAGCTTGCGCAGAAATAAACAGACGTTTGGCTCGGTGCTGCGCTCAGCAGACGCAGCGGAAAGTCTTCAATGGTCGAACGTGAAAC<br>ATTGTAACCGTTCGGCACTTCGCCTTGATCCGTGGTCTGGATGGCGACCGAATAGTGAATCAGACGCAGACCCATACCCGGGTCCTGACGGTACCATGAC<br>ATATATTCATGGTTCATATCTTGGGCACATTGCAGCGTCATGGATTGGCCCGTTTTCAGGACTTGGAATTTCGGCGTTTGGGTCACACCAGCGTTCATat<br>gtatatctccttcttaaagttaaacaaaattatttctagaggggaattgttatccgctcacaattcccctatagtgagtcgtattaatttcgcgggatcg<br>agatctcgatcctctacgccggacgcatcgtggccggcatcaccggcgccacaggtgcggttgctggcgcctatatcgccgacatcaccgatggggaaga<br>tcgggctcgccacttcgggctcatgagcgcttgtttcggcgtgggtatggtggcaggccccgtggccgggggactgttgggcgccatctccttgcatgca<br>ccattccttgcggcggcggtgctcaacggcctcaacctactactgggctgcttcctaatgcaggagtcgcataagggagagcgtcgagatcccggacacc<br>atcgaatggcgcaaaacctttcgcggtatggcatgatagcgcccggaagagagtcaattcagggtggtgaatgtgaaaccagtaacgttatacgatgtcg<br>cagagtatgccggtgtctcttatcagaccgtttcccgcgtggtgaaccaggccagccacgtttctgcgaaaacgcgggaaaaagtggaagcggcgatggc<br>ggagctgaattacattcccaaccgcgtggcacaacaactggcgggcaaacagtcgttgctgattggcgttgccacctccagtctggccctgcacgcgccg<br>tcgcaaattgtcgcggcgattaaatctcgcgccgatcaactgggtgccagcgtggtggtgtcgatggtagaacgaagcggcgtcgaagcctgtaaagcgg<br>cggtgcacaatcttctcgcgcaacgcgtcagtgggctgatcattaactatccgctggatgaccaggatgccattgctgtggaagctgcctgcactaatgt<br>tccggcgttatttcttgatgtctctgaccagacacccatcaacagtattattttctcccatgaagacggtacgcgactgggcgtggagcatctggtcgca<br>ttgggtcaccagcaaatcgcgctgttagcgggcccattaagttctgtctcggcgcgtctgcgtctggctggctggcataaatatctcactcgcaatcaaa<br>ttcagccgatagcggaacgggaaggcgactggagtgccatgtccggttttcaacaaaccatgcaaatgctgaatgagggcatcgttcccactgcgatgct<br>ggttgccaacgatcagatggcgctgggcgcaatgcgcgccattaccgagtccgggctgcgcgttggtgcggatatctcggtagtgggatacgacgatacc<br>gaagacagctcatgttatatcccgccgttaaccaccatcaaacaggattttcgcctgctggggcaaaccagcgtggaccgcttgctgcaactctctcagg<br>gccaggcggtgaagggcaatcagctgttgcccgtctcactggtgaaaagaaaaaccaccctggcgcccaatacgcaaaccgcctctccccgcgcgttggc<br>cgattcattaatgcagctggcacgacaggtttcccgactggaaagcgggcagtgagcgcaacgcaattaatgtaagttagctcactcattaggcaccggg<br>atctcgaccgatgcccttgagagccttcaacccagtcagctccttccggtgggcgcggggcatgactatcgtcgccgcacttatgactgtcttctttatc<br>atgcaactcgtaggacaggtgccggcagcgctctgggtcattttcggcgaggaccgctttcgctggagcgcgacgatgatcggcctgtcgcttgcggtat<br>tcggaatcttgcacgccctcgctcaagccttcgtcactggtcccgccaccaaacgtttcggcgagaagcaggccattatcgccggcatggcggccccacg<br>ggtgcgcatgatcgtgctcctgtcgttgaggacccggctaggctggcggggttgccttactggttagcagaatgaatcaccgatacgcgagcgaacgtga<br>agcgactgctgctgcaaaacgtctgcgacctgagcaacaacatgaatggtcttcggtttccgtgtttcgtaaagtctggaaacgcggaagtcagcgccct<br>gcaccattatgttccggatctgcatcgcaggatgctgctggctaccctgtggaacacctacatctgtattaacgaagcgctggcattgaccctgagtgat<br>ttttctctggtcccgccgcatccataccgccagttgtttaccctcacaacgttccagtaaccgggcatgttcatcatcagtaacccgtatcgtgagcatc<br>ctctctcgtttcatcggtatcattacccccatgaacagaaatcccccttacacggaggcatcagtgaccaaacaggaaaaaaccgcccttaacatggccc<br>gctttatcagaagccagacattaacgcttctggagaaactcaacgagctggacgcggatgaacaggcagacatctgtgaatcgcttcacgaccacgctga<br>tgagctttaccgcagctgcctcgcgcgtttcggtgatgacggtgaaaacctctgacacatgcagctcccggagacggtcacagcttgtctgtaagcggat<br>gccgggagcagacaagcccgtcagggcgcgtcagcgggtgttggcgggtgtcggggcgcagccatgacccagtcacgtagcgatagcggagtgtatactg<br>gcttaactatgcggcatcagagcagattgtactgagagtgcaccatatatgcggtgtgaaataccgcacagatgcgtaaggagaaaataccgcatcaggc<br>gctcttccgcttcctcgctcactgactcgctgcgctcggtcgttcggctgcggcgagcggtatcagctcactcaaaggcggtaatacggttatccacaga<br>atcaggggataacgcaggaaagaacatgtgagcaaaaggccagcaaaaggccaggaaccgtaaaaaggccgcgttgctggcgtttttccataggctccgc<br>ccccctgacgagcatcacaaaaatcgacgctcaagtcagaggtggcgaaacccgacaggactataaagataccaggcgtttccccctggaagctccctcg<br>tgcgctctcctgttccgaccctgccgcttaccggatacctgtccgcctttctcccttcgggaagcgtggcgctttctcatagctcacgctgtaggtatct<br>cagttcggtgtaggtcgttcgctccaagctgggctgtgtgcacgaaccccccgttcagcccgaccgctgcgccttatccggtaactatcgtcttgagtcc<br>aacccggtaagacacgacttatcgccactggcagcagccactggtaacaggattagcagagcgaggtatgtaggcggtgctacagagttcttgaagtggt<br>ggcctaactacggctacactagaaggacagtatttggtatctgcgctctgctgaagccagttaccttcggaaaaagagttggtagctcttgatccggcaa<br>acaaaccaccgctggtagcggtggtttttttgtttgcaagcagcagattacgcgcagaaaaaaaggatctcaagaagatcctttgatcttttctacgggg<br>tctgacgctcagtggaacgaaaactcacgttaagggattttggtcatgagattatcaaaaaggatcttcacctagatccttttaaattaaaaatgaagtt<br>ttaaatcaatctaaagtatatatgagtaaacttggtctgacagttaccaatgcttaatcagtgaggcacctatctcagcgatctgtctatttcgttcatc<br>catagttgcctgactccccgtcgtgtagataactacgatacgggagggcttaccatctggccccagtgctgcaatgataccgcgagacccacgctcaccg<br>gctccagatttatcagcaataaaccagccagccggaagggccgagcgcagaagtggtcctgcaactttatccgcctccatccagtctattaattgttgcc<br>gggaagctagagtaagtagttcgccagttaatagtttgcgcaacgttgttgccattgctgcaggcatcgtggtgtcacgctcgtcgtttggtatggcttc<br>attcagctccggttcccaacgatcaaggcgagttacatgatcccccatgttgtgcaaaaaagcggttagctccttcggtcctccgatcgttgtcagaagt<br>aagttggccgcagtgttatcactcatggttatggcagcactgcataattctcttactgtcatgccatccgtaagatgcttttctgtgactggtgagtact<br>caaccaagtcattctgagaatagtgtatgcggcgaccgagttgctcttgcccggcgtcaatacgggataataccgcgccacatagcagaactttaaaagt<br>gctcatcattggaaaacgttcttcggggcgaaaactctcaaggatcttaccgctgttgagatccagttcgatgtaacccactcgtgcacccaactgatct<br>tcagcatcttttactttcaccagcgtttctgggtgagcaaaaacaggaaggcaaaatgccgcaaaaaagggaataagggcgacacggaaatgttgaatac<br>tcatactcttcctttttcaatattattgaagcatttatcagggttattgtctcatgagcggatacatatttgaatgtatttagaaaaataaacaaatagg<br>ggttccgcgcacatttccccgaaaagtgccacctgaaattgtaaacgttaatattttgttaaaattcgcgttaaatttttgttaaatcagctcattttt<br>aaccaataggccgaaatcggcaaaatcccttataaatcaaaagaatagaccgagatagggttgagtgttgttccagtttggaacaagagtccactattaa<br>agaacgtggactccaacgtcaaagggcgaaaaaccgtctatcagggcgatggcccactacgtgaaccatcaccctaatcaagttttttggggtcgaggtg<br>ccgtaaagcactaaatcggaaccctaaagggagcccccgatttagagcttgacggggaaagccggcgaacgtggcgagaaaggaagggaagaaagcgaaa<br>ggagcgggcgctagggcgctggcaagtgtagcggtcacgctgcgcgtaaccaccacacccgccgcgcttaatgcgccgctacagggcgcgtcccattcgc<br>ca |
| 63 | atccggatatagttcctcctttcagcaaaaaacccctcaagacccgtttagaggccccaaggggttatgctagttattgctcagcggtggcagcagccaa<br>ctcagcttcctttcgggctttgttagcagccggatctcagtggtggtggtggtggtgctcgagTTAGTCAGCACGACCCCACGCTTCTGCACTGACAATT<br>TGCGTAACCGGTTTTGCACGGTCCTGGGTCCATTCATCATTTTCGCTCAGGCCGTAGAATTGAACCTGACAGCGAAAATGGTTACGCGGGTCCTGCCAGA<br>AGGTGGCAGACACGCGCAGACGGGAACTCAGGGCATAACGGCTGTCATTCAGCGCCGGTTGTTCTTTCAGCGGCTGCGGATCGGTACACACACCCGAGTG<br>GACTTCTTTGCCGTTCACCCACCATGACAGTTCGACATGGTCCGGATAAAAGCCGGTGGCCAGGCACACCAGCGTCGCTTTCTGGGTATGGGAGATTTCA<br>GCTTCACTCGGTTCGAAAACTGCCACTTCCGGCGGAAAGACATTTTTCAGATCTTCCAGAACCGTCAGACGAGAACCTTCGCCGAAAAACAGTTCACCGG<br>TGTTGCCCAGGTAAGAGCTTGCGCAGAAATAAACAGACGTTTGGCTCGGTGCTGCGCTCAGCAGACGCAGCGGAAAGTCTTCAATGGTCGAACGTGAAAC<br>ATTGTAACCGTTCGGCACTTCGCCTTGATCCGTGGTCTGGATGGCGACCGAATAGTGAATCAGACGCAGACCCATACCCGGGTCCTGACGGTACCATGAC<br>ATATATTCATGGTTCATATCTTGGGCACATTGCAGCGTCATGGATTGGCCCGTTTTCAGGACTTGGAATTTCGGCGTTTGGGTCACACCAGCGTTGCTAC<br>CGCCACCGCCCAGTTTTTTCAGGCGCGCAACTTCATTTTCCAGGTGGTAGTTCATatgtatatctccttcttaaagttaaacaaaattatttctagaggg<br>gaattgttatccgctcacaattcccctatagtgagtcgtattaatttcgcgggatcgagatctcgatcctctacgccggacgcatcgtggccggcatcac |

TABLE 47-continued

Soluble T cell receptors-Nucleotide Sequence

| SEQ ID NO | SEQUENCE |
|---|---|
| | cggcgccacaggtgcggttgctggcgcctatatcgccgacatcaccgatggggaagatcgggctcgccacttcgggctcatgagcgcttgtttcggcgtg ggtatggtggcaggccccgtggccgggggactgttgggcgccatctccttgcatgcaccattccttgcggcggcggtgctcaacggcctcaacctactac tgggctgcttcctaatgcaggagtcgcataagggagagcgtcgagatcccggacaccatcgaatggcgcaaaacctttcgcggtatggcatgatagcgcc cggaagagagtcaattcagggtggtgaatgtgaaaccagtaacgttatacgatgtcgcagagtatgccggtgtctcttatcagaccgtttcccgcgtggt gaaccaggccagccacgtttctgcgaaaacgcgggaaaaagtggaagcggcgatggcggagctgaattacattcccaaccgcgtggcacaacaactggcg ggcaaacagtcgttgctgattggcgttgccacctccagtctggccctgcacgcgccgtcgcaaattgtcgcggcgattaaatctcgcgccgatcaactgg gtgccagcgtggtggtgtcgatggtagaacgaagcggcgtcgaagcctgtaaagcggcggtgcacaatcttctcgcgcaacgcgtcagtgggctgatcat taactatccgctggatgaccaggatgccattgctgtggaagctgcctgcactaatgttccggcgttatttcttgatgtctctgaccagacacccatcaac agtattattttctcccatgaagacggtacgcgactgggcgtggagcatctggtcgcattgggtcaccagcaaatcgcgctgttagcgggcccattaagtt ctgtctcggcgcgtctgcgtctggctggctggcataaatatctcactcgcaatcaaattcagccgatagcggaacgggaaggcgactggagtgccatgtc cggttttcaacaaaccatgcaaatgctgaatgagggcatcgttcccactgcgatgctggttgccaacgatcagatggcgctgggcgcaatgcgcgccatt accgagtccgggctgcgcgttggtgcggatatctcggtagtgggatacgacgataccgaagacagctcatgttatatcccgccgttaaccaccatcaaac aggattttcgcctgctggggcaaaccagcgtggaccgcttgctgcaactctctcagggccaggcggtgaagggcaatcagctgttgcccgtctcactggt gaaaagaaaaaccaccctggcgcccaatacgcaaaccgcctctccccgcgcgttggccgattcattaatgcagctggcacgacaggtttcccgactggaa agcgggcagtgagcgcaacgcaattaatgtaagttagctcactcattaggcaccgggatctcgaccgatgcccttgagagccttcaacccagtcagctcc ttccggtgggcgcggggcatgactatcgtcgccgcacttatgactgtcttctttatcatgcaactcgtaggacaggtgccggcagcgctctgggtcattt tcggcgaggaccgctttcgctggagcgcgacgatgatcggcctgtcgcttgcggtattcggaatcttgcacgccctcgctcaagccttcgtcactggtcc cgccaccaaacgtttcggcgagaagcaggccattatcgccggcatggcggccccacgggtgcgcatgatcgtgctcctgtcgttgaggacccggctaggc tggcggggttgccttactggttagcagaatgaatcaccgatacgcgagcgaacgtgaagcgactgctgctgcaaaacgtctgcgacctgagcaacaacat gaatggtcttcggtttccgtgtttcgtaaagtctggaaacgcggaagtcagcgccctgcaccattatgttccggatctgcatcgcaggatgctgctggct accctgtggaacacctacatctgtattaacgaagcgctggcattgaccctgagtgattttttctctggtcccgccgcatccataccgccagttgtttaccc tcacaacgttccagtaaccgggcatgttcatcatcagtaacccgtatcgtgagcatcctctctcgtttcatcggtatcattacccccatgaacagaaatc ccccttacacggaggcatcagtgaccaaacaggaaaaaaccgcccttaacatggcccgctttatcagaagccagacattaacgcttctggagaaactcaa cgagctggacgcggatgaacaggcagacatctgtgaatcgcttcacgaccacgctgatgagctttaccgcagctgcctcgcgcgtttcggtgatgacggt gaaaacctctgacacatgcagctcccggagacggtcacagcttgtctgtaagcggatgccgggagcagacaagcccgtcagggcgcgtcagcgggtgttg gcgggtgtcggggcgcagccatgacccagtcacgtagcgatagcggagtgtatactggcttaactatgcggcatcagagcagattgtactgagagtgcac catatatgcggtgtgaaataccgcacagatgcgtaaggagaaaataccgcatcaggcgctcttccgcttcctcgctcactgactcgctgcgctcggtcgt tcggctgcggcgagcggtatcagctcactcaaaggcggtaatacggttatccacagaatcaggggataacgcaggaaagaacatgtgagcaaaaggccag caaaaggccaggaaccgtaaaaaggccgcgttgctggcgtttttccataggctccgcccccctgacgagcatcacaaaaatcgacgctcaagtcagaggt ggcgaaacccgacaggactataaagataccaggcgtttccccctggaagctccctcgtgcgctctcctgttccgaccctgccgcttaccggatacctgtc cgcctttctcccttcgggaagcgtggcgctttctcatagctcacgctgtaggtatctcagttcggtgtaggtcgttcgctccaagctgggctgtgtgcac gaaccccccgttcagcccgaccgctgcgccttatccggtaactatcgtcttgagtccaacccggtaagacacgacttatcgccactggcagcagccactg gtaacaggattagcagagcgaggtatgtaggcggtgctacagagttcttgaagtggtggcctaactacggctacactagaaggacagtatttggtatctg cgctctgctgaagccagttaccttcggaaaaagagttggtagctcttgatccggcaaacaaaccaccgctggtagcggtggtttttttgtttgcaagcag cagattacgcgcagaaaaaaaggatctcaagaagatcctttgatcttttctacggggtctgacgctcagtggaacgaaaactcacgttaagggattttgg tcatgagattatcaaaaaggatcttcacctagatccttttaaattaaaaatgaagttttaaatcaatctaaagtatatatgagtaaacttggtctgacag ttaccaatgcttaatcagtgaggcacctatctcagcgatctgtctatttcgttcatccatagttgcctgactccccgtcgtgtagataactacgatacgg gagggcttaccatctggccccagtgctgcaatgataccgcgagacccacgctcaccggctccagatttatcagcaataaaccagccagccggaagggccg agcgcagaagtggtcctgcaactttatccgcctccatccagtctattaattgttgccgggaagctagagtaagtagttcgccagttaatagtttgcgcaa cgttgttgccattgctgcaggcatcgtggtgtcacgctcgtcgtttggtatggcttcattcagctccggttcccaacgatcaaggcgagttacatgatcc cccatgttgtgcaaaaaagcggttagctccttcggtcctccgatcgttgtcagaagtaagttggccgcagtgttatcactcatggttatggcagcactgc ataattctcttactgtcatgccatccgtaagatgcttttctgtgactggtgagtactcaaccaagtcattctgagaatagtgtatgcggcgaccgagttg ctcttgcccggcgtcaatacgggataataccgcgccacatagcagaactttaaaagtgctcatcattggaaaacgttcttcggggcgaaaactctcaagg atcttaccgctgttgagatccagttcgatgtaacccactcgtgcacccaactgatcttcagcatcttttactttcaccagcgtttctgggtgagcaaaaa caggaaggcaaaatgccgcaaaaaagggaataagggcgacacggaaatgttgaatactcatactcttcctttttcaatattattgaagcatttatcaggg ttattgtctcatgagcggatacatatttgaatgtatttagaaaaataaacaaataggggttccgcgcacatttccccgaaaagtgccacctgaaattgta aacgttaatattttgttaaaattcgcgttaaatttttgttaaatcagctcattttttaaccaataggccgaaatcggcaaaatcccttataaatcaaaag aatagaccgagatagggttgagtgttgttccagtttggaacaagagtccactattaaagaacgtggactccaacgtcaaagggcgaaaaaccgtctatca gggcgatggcccactacgtgaaccatcaccctaatcaagttttttggggtcgaggtgccgtaaagcactaaatcggaaccctaaagggagcccccgattt agagcttgacggggaaagccggcgaacgtggcgagaaaggaagggaagaaagcgaaaggagcgggcgctagggcgctggcaagtgtagcggtcacgctgc gcgtaaccaccacacccgccgcgcttaatgcgccgctacagggcgcgtcccattcgcca |
| 64 | atccggatatagttcctcctttcagcaaaaaacccctcaagacccgtttagaggccccaaggggttatgctagttattgctcagcggtggcagcagccaa ctcagcttcctttcgggctttgttagcagccggatctcagtggtggtggtggtggtgctcgagTTAAGAGCTTTCCGGGCTCGGGAAAAACGTATCTTCC GGGATAATACTATTGTTGAATGCGTTGGCGCACGCAAAGTCAGATTTATTGCTCCAAGCAACTGCCGAGTTTGATTTGAAATCCATAGAGCGCATGTCCA GAACACATTTATCGGTAATATACACGTCGGAATCTTTGGATTGACTGACATTCGTCTGACTGTCGAAATCGGTAAACAGGCACACGCTTTTGTCCGATGA TTTGCTATCACGCAGTTGGTACACCGCCGGGTCCGGGTTCTGGATATACGGATGGACAATCAGGCTGGTACCGCGGCCAAACGTCGGGATATAGGTACCA TCCAGCAGCGGACGCACCGCACACAGGTACGTAGCGGAGTCACCCGGCTGACTTGCTGCAATATACAGGGTGGAACTACCAGAGCTTTTATCCAGCGATG CATTCAGGCGGCCTGAGGTTTGTTCACGCTGCCACGGCGTGATCAGCAGCAGGCTGGTCAGACCTTTGCCCGGATCTTGACGAAACCACTGCAGGTTGTA AATGGCGCTATCCGTAAAGGAGCAATTCAGCACCAGATTTTCACCTTCCGGGACCGACAGAGCAGCCGGGATTTGGGTAACTTCTTGTTTGCTACCGCCA CCGCCCAGTTTTTTCAGGCGCGCAACTTCATTTTCAGGTGGTAGTTCATatgtatatctccttcttaaagttaaacaaaattatttctagaggggaatt gttatccgctcacaattcccctatagtgagtcgtattaatttcgcgggatcgagatctcgatcctctacgccggacgcatcgtggccggcatcaccggcg ccacaggtgcggttgctggcgcctatatcgccgacatcaccgatggggaagatcgggctcgccacttcgggctcatgagcgcttgtttcggcgtgggtat ggtggcaggccccgtggccgggggactgttgggcgccatctccttgcatgcaccattccttgcggcggcggtgctcaacggcctcaacctactactgggc tgcttcctaatgcaggagtcgcataagggagagcgtcgagatcccggacaccatcgaatggcgcaaaacctttcgcggtatggcatgatagcgcccggaa gagagtcaattcagggtggtgaatgtgaaaccagtaacgttatacgatgtcgcagagtatgccggtgtctcttatcagaccgtttcccgcgtggtgaacc aggccagccacgtttctgcgaaaacgcgggaaaaagtggaagcggcgatggcggagctgaattacattcccaaccgcgtggcacaacaactggcgggcaa acagtcgttgctgattggcgttgccacctccagtctggccctgcacgcgccgtcgcaaattgtcgcggcgattaaatctcgcgccgatcaactgggtgcc agcgtggtggtgtcgatggtagaacgaagcggcgtcgaagcctgtaaagcggcggtgcacaatcttctcgcgcaacgcgtcagtgggctgatcattaact atccgctggatgaccaggatgccattgctgtggaagctgcctgcactaatgttccggcgttatttcttgatgtctctgaccagacacccatcaacagtat tattttctcccatgaagacggtacgcgactgggcgtggagcatctggtcgcattgggtcaccagcaaatcgcgctgttagcgggcccattaagttctgtc tcggcgcgtctgcgtctggctggctggcataaatatctcactcgcaatcaaattcagccgatagcggaacgggaaggcgactggagtgccatgtccggtt ttcaacaaaccatgcaaatgctgaatgagggcatcgttcccactgcgatgctggttgccaacgatcagatggcgctgggcgcaatgcgcgccattaccga gtccgggctgcgcgttggtgcggatatctcggtagtgggatacgacgataccgaagacagctcatgttatatcccgccgttaaccaccatcaaacaggat |

TABLE 47-continued

Soluble T cell receptors-Nucleotide Sequence

| SEQ ID NO | SEQUENCE |
|---|---|
| | tttcgcctgctggggcaaaccagcgtggaccgcttgctgcaactctctcagggccaggcggtgaagggcaatcagctgttgcccgtctcactggtgaaaa<br>gaaaaaccaccctggcgcccaatacgcaaaccgcctctccccgcgcgttggccgattcattaatgcagctggcacgacaggtttcccgactggaaagcgg<br>gcagtgagcgcaacgcaattaatgtaagttagctcactcattaggcaccgggatctcgaccgatgcccttgagagccttcaacccagtcagctccttccg<br>gtgggcgcggggcatgactatcgtcgccgcacttatgactgtcttctttatcatgcaactcgtaggacaggtgccggcagcgctctgggtcattttcggc<br>gaggaccgctttcgctggagcgcgacgatgatcggcctgtcgcttgcggtattcggaatcttgcacgccctcgctcaagccttcgtcactggtcccgcca<br>ccaaacgtttcggcgagaagcaggccattatcgccggcatggcggccccacgggtgcgcatgatcgtgctcctgtcgttgaggacccggctaggctggcg<br>gggttgccttactggttagcagaatgaatcaccgatacgcgagcgaacgtgaagcgactgctgctgcaaaacgtctgcgacctgagcaacaacatgaatg<br>gtcttcggtttccgtgtttcgtaaagtctggaaacgcggaagtcagcgccctgcaccattatgttccggatctgcatcgcaggatgctgctggctaccct<br>gtggaacacctacatctgtattaacgaagcgctggcattgaccctgagtgatttttctctggtcccgccgcatccataccgccagttgtttaccctcaca<br>acgttccagtaaccgggcatgttcatcatcagtaacccgtatcgtgagcatcctctctcgtttcatcggtatcattacccccatgaacagaaatcccccct<br>tacacggaggcatcagtgaccaaacaggaaaaaaccgcccttaacatggcccgctttatcagaagccagacattaacgcttctggagaaactcaacgagc<br>tggacgcggatgaacaggcagacatctgtgaatcgcttcacgaccacgctgatgagctttaccgcagctgcctcgcgcgtttcggtgatgacggtgaaaa<br>cctctgacacatgcagctcccggagacggtcacagcttgtctgtaagcggatgccgggagcagacaagcccgtcagggcgcgtcagcgggtgttggcggg<br>tgtcggggcgcagccatgacccagtcacgtagcgatagcggagtgtatactggcttaactatgcggcatcagagcagattgtactgagagtgcaccatat<br>atgcggtgtgaaataccgcacagatgcgtaaggagaaaataccgcatcaggcgctcttccgcttcctcgctcactgactcgctgcgctcggtcgttcggc<br>tgcggcgagcggtatcagctcactcaaaggcggtaatacggttatccacagaatcaggggataacgcaggaaagaacatgtgagcaaaaggccagcaaaa<br>ggccaggaaccgtaaaaaggccgcgttgctggcgtttttccataggctccgcccccctgacgagcatcacaaaaatcgacgctcaagtcagaggtggcga<br>aacccgacaggactataaagataccaggcgtttccccctggaagctccctcgtgcgctctcctgttccgaccctgccgcttaccggatacctgtccgcct<br>ttctcccttcgggaagcgtggcgctttctcatagctcacgctgtaggtatctcagttcggtgtaggtcgttcgctccaagctgggctgtgtgcacgaacc<br>ccccgttcagcccgaccgctgcgccttatccggtaactatcgtcttgagtccaacccggtaagacacgacttatcgccactggcagcagccactggtaac<br>aggattagcagagcgaggtatgtaggcggtgctacagagttcttgaagtggtggcctaactacggctacactagaaggacagtatttggtatctgcgctc<br>tgctgaagccagttaccttcggaaaaagagttggtagctcttgatccggcaaacaaaccaccgctggtagcggtggtttttttgtttgcaagcagcagat<br>tacgcgcagaaaaaaaggatctcaagaagatcctttgatcttttctacggggtctgacgctcagtggaacgaaaactcacgttaagggattttggtcatg<br>agattatcaaaaaggatcttcacctagatccttttaaattaaaaatgaagttttaaatcaatctaaagtatatatgagtaaacttggtctgacagttacc<br>aatgcttaatcagtgaggcacctatctcagcgatctgtctatttcgttcatccatagttgcctgactccccgtcgtgtagataactacgatacgggaggg<br>cttaccatctggccccagtgctgcaatgataccgcgagacccacgctcaccggctccagatttatcagcaataaaccagccagccggaagggccgagcgc<br>agaagtggtcctgcaactttatccgcctccatccagtctattaattgttgccgggaagctagagtaagtagttcgccagttaatagtttgcgcaacgttg<br>ttgccattgctgcaggcatcgtggtgtcacgctcgtcgtttggtatggcttcattcagctccggttcccaacgatcaaggcgagttacatgatcccccat<br>gttgtgcaaaaaagcggttagctccttcggtcctccgatcgttgtcagaagtaagttggccgcagtgttatcactcatggttatggcagcactgcataat<br>tctcttactgtcatgccatccgtaagatgcttttctgtgactggtgagtactcaaccaagtcattctgagaatagtgtatgcggcgaccgagttgctctt<br>gcccggcgtcaatacgggataataccgcgccacatagcagaactttaaaagtgctcatcattggaaaacgttcttcggggcgaaaactctcaaggatctt<br>accgctgttgagatccagttcgatgtaacccactcgtgcacccaactgatcttcagcatcttttactttcaccagcgtttctgggtgagcaaaaacagga<br>aggcaaaatgccgcaaaaaagggaataagggcgacacggaaatgttgaatactcatactcttcctttttcaatattattgaagcatttatcagggttatt<br>gtctcatgagcggatacatatttgaatgtatttagaaaaataaacaaataggggttccgcgcacatttccccgaaaagtgccacctgaaattgtaaacgt<br>taatattttgttaaaattcgcgttaaatttttgttaaatcagctcattttttaaccaataggccgaaatcggcaaaatcccttataaatcaaaagaatag<br>accgagatagggttgagtgttgttccagtttggaacaagagtccactattaaagaacgtggactccaacgtcaaagggcgaaaaaccgtctatcagggcg<br>atggcccactacgtgaaccatcaccctaatcaagttttttggggtcgaggtgccgtaaagcactaaatcggaaccctaaagggagcccccgatttagagc<br>ttgacggggaaagccggcgaacgtggcgagaaaggaagggaagaaagcgaaaggagcgggcgctagggcgctggcaagtgtagcggtcacgctgcgcgta<br>accaccacacccgccgcgcttaatgcgccgctacagggcgcgtcccattcgcca |
| 65 | atccggatatagttcctcctttcagcaaaaaacccctcaagacccgtttagaggccccaaggggttatgctagttattgctcagcggtggcagcagccaa<br>ctcagcttcctttcgggctttgttagcagccggatctcagtggtggtggtggtggtgctcgagTTAAGAGCTTTCCGGGCTCGGGAAAAACGTATCTTCC<br>GGGATAATACTATTGTTGAATGCGTTGGCGCACGCAAAGTCAGATTTATTGCTCCAAGCAACTGCCGAGTTTGATTTGAAATCCATAGAGCGCATGTCCA<br>GAACACATTTATCGGTAATATACACGTCGGAATCTTTGGATTGACTGACATTCGTCTGACTGTCGAAATCGGTAAACAGGCACACGCTTTTGTCCGATGA<br>TTTGCTATCACGCAGTTGGTACACCGCCGGGTCCGGGTTCTGGATATACGGATGGACAATCAGGCTGGTACCGCGGCCAAACGTCGGGATATAGGTACCA<br>TCCAGCAGCGGACGCACCGCACACAGGTACGTAGCGGAGTCACCCGGCTGACTTGCTGCAATATACAGGGTGGAACTACCAGAGCTTTTATCCAGCGATG<br>CATTCAGGCGGCCTGAGGTTTGTTCACGCTGCCACGGCGTGATCAGCAGCAGGCTGGTCAGACCTTTGCCCGGATCTTGACGAAACCACTGCAGGTTGTA<br>AATGGCGCTATCCGTAAAGGAGCAATTCAGCACCAGATTTTCACCTTCCGGGACCGACAGAGCAGCCGGGATTTGGGTAACTTCTTGTTTCATatgtata<br>tctccttcttaaagttaaacaaaattatttctagaggggaattgttatccgctcacaattcccctatagtgagtcgtattaatttcgcgggatcgagatc<br>tcgatcctctacgccggacgcatcgtggccggcatcaccggcgccacaggtgcggttgctggcgcctatatcgccgacatcaccgatggggaagatcggg<br>ctcgccacttcgggctcatgagcgcttgtttcggcgtgggtatggtggcaggccccgtggccgggggactgttgggcgccatctccttgcatgcaccatt<br>ccttgcggcggcggtgctcaacggcctcaacctactactgggctgcttcctaatgcaggagtcgcataagggagagcgtcgagatcccggacaccatcga<br>atggcgcaaaacctttcgcggtatggcatgatagcgcccggaagagagtcaattcagggtggtgaatgtgaaaccagtaacgttatacgatgtcgcagag<br>tatgccggtgtctcttatcagaccgtttcccgcgtggtgaaccaggccagccacgtttctgcgaaaacgcgggaaaaagtggaagcggcgatggcggagc<br>tgaattacattcccaaccgcgtggcacaacaactggcgggcaaacagtcgttgctgattggcgttgccacctccagtctggccctgcacgcgccgtcgca<br>aattgtcgcggcgattaaatctcgcgccgatcaactgggtgccagcgtggtggtgtcgatggtagaacgaagcggcgtcgaagcctgtaaagcggcggtg<br>cacaatcttctcgcgcaacgcgtcagtgggctgatcattaactatccgctggatgaccaggatgccattgctgtggaagctgcctgcactaatgttccgg<br>cgttatttcttgatgtctctgaccagacacccatcaacagtattattttctcccatgaagacggtacgcgactgggcgtggagcatctggtcgcattggg<br>tcaccagcaaatcgcgctgttagcgggcccattaagttctgtctcggcgcgtctgcgtctggctggctggcataaatatctcactcgcaatcaaattcag<br>ccgatagcggaacgggaaggcgactggagtgccatgtccggttttcaacaaaccatgcaaatgctgaatgagggcatcgttcccactgcgatgctggttg<br>ccaacgatcagatggcgctgggcgcaatgcgcgccattaccgagtccgggctgcgcgttggtgcggatatctcggtagtgggatacgacgataccgaaga<br>cagctcatgttatatcccgccgttaaccaccatcaaacaggattttcgcctgctggggcaaaccagcgtggaccgcttgctgcaactctctcagggccag<br>gcggtgaagggcaatcagctgttgcccgtctcactggtgaaaagaaaaaccaccctggcgcccaatacgcaaaccgcctctccccgcgcgttggccgatt<br>cattaatgcagctggcacgacaggtttcccgactggaaagcgggcagtgagcgcaacgcaattaatgtaagttagctcactcattaggcaccgggatctc<br>gaccgatgcccttgagagccttcaacccagtcagctccttccggtgggcgcggggcatgactatcgtcgccgcacttatgactgtcttctttatcatgca<br>actcgtaggacaggtgccggcagcgctctgggtcattttcggcgaggaccgctttcgctggagcgcgacgatgatcggcctgtcgcttgcggtattcgga<br>atcttgcacgccctcgctcaagccttcgtcactggtcccgccaccaaacgtttcggcgagaagcaggccattatcgccggcatggcggccccacgggtgc<br>gcatgatcgtgctcctgtcgttgaggacccggctaggctggcggggttgccttactggttagcagaatgaatcaccgatacgcgagcgaacgtgaagcga<br>ctgctgctgcaaaacgtctgcgacctgagcaacaacatgaatggtcttcggtttccgtgtttcgtaaagtctggaaacgcggaagtcagcgccctgcacc<br>attatgttccggatctgcatcgcaggatgctgctggctaccctgtggaacacctacatctgtattaacgaagcgctggcattgaccctgagtgatttttc<br>tctggtcccgccgcatccataccgccagttgtttaccctcacaacgttccagtaaccgggcatgttcatcatcagtaacccgtatcgtgagcatcctctc<br>tcgtttcatcggtatcattacccccatgaacagaaatcccccttacacggaggcatcagtgaccaaacaggaaaaaaccgcccttaacatggcccgcttt<br>atcagaagccagacattaacgcttctggagaaactcaacgagctggacgcggatgaacaggcagacatctgtgaatcgcttcacgaccacgctgatgagc<br>tttaccgcagctgcctcgcgcgtttcggtgatgacggtgaaaacctctgacacatgcagctcccggagacggtcacagcttgtctgtaagcggatgccgg |

TABLE 47-continued

Soluble T cell receptors-Nucleotide Sequence

| SEQ ID NO | SEQUENCE |
|---|---|
| | gagcagacaagcccgtcagggcgcgtcagcgggtgttggcgggtgtcggggcgcagccatgacccagtcacgtagcgatagcggagtgtatactggctta |
| | actatgcggcatcagagcagattgtactgagagtgcaccatatatgcggtgtgaaataccgcacagatgcgtaaggagaaaataccgcatcaggcgctct |
| | tccgcttcctcgctcactgactcgctgcgctcggtcgttcggctgcggcgagcggtatcagctcactcaaaggcggtaatacggttatccacagaatcag |
| | gggataacgcaggaaagaacatgtgagcaaaaggccagcaaaaggccaggaaccgtaaaaaggccgcgttgctggcgtttttccataggctccgcccccc |
| | tgacgagcatcacaaaaatcgacgctcaagtcagaggtggcgaaacccgacaggactataaagataccaggcgtttccccctggaagctccctcgtgcgc |
| | tctcctgttccgaccctgccgcttaccggatacctgtccgcctttctcccttcgggaagcgtggcgctttctcatagctcacgctgtaggtatctcagtt |
| | cggtgtaggtcgttcgctccaagctgggctgtgtgcacgaaccccccgttcagcccgaccgctgcgccttatccggtaactatcgtcttgagtccaaccc |
| | ggtaagacacgacttatcgccactggcagcagccactggtaacaggattagcagagcgaggtatgtaggcggtgctacagagttcttgaagtggtggcct |
| | aactacggctacactagaaggacagtatttggtatctgcgctctgctgaagccagttaccttcggaaaaagagttggtagctcttgatccggcaaacaaa |
| | ccaccgctggtagcggtggtttttttgtttgcaagcagcagattacgcgcagaaaaaaaggatctcaagaagatcctttgatcttttctacggggtctga |
| | cgctcagtggaacgaaaactcacgttaagggattttggtcatgagattatcaaaaaggatcttcacctagatccttttaaattaaaaatgaagttttaaa |
| | tcaatctaaagtatatatgagtaaacttggtctgacagttaccaatgcttaatcagtgaggcacctatctcagcgatctgtctatttcgttcatccatag |
| | ttgcctgactccccgtcgtgtagataactacgatacgggagggcttaccatctggccccagtgctgcaatgataccgcgagacccacgctcaccggctcc |
| | agatttatcagcaataaaccagccagccggaagggccgagcgcagaagtggtcctgcaactttatccgcctccatccagtctattaattgttgccgggaa |
| | gctagagtaagtagttcgccagttaatagtttgcgcaacgttgttgccattgctgcaggcatcgtggtgtcacgctcgtcgtttggtatggcttcattca |
| | gctccggttcccaacgatcaaggcgagttacatgatcccccatgttgtgcaaaaaagcggttagctccttcggtcctccgatcgttgtcagaagtaagtt |
| | ggccgcagtgttatcactcatggttatggcagcactgcataattctcttactgtcatgccatccgtaagatgcttttctgtgactggtgagtactcaacc |
| | aagtcattctgagaatagtgtatgcggcgaccgagttgctcttgcccggcgtcaatacgggataataccgcgccacatagcagaactttaaaagtgctca |
| | tcattggaaaacgttcttcggggcgaaaactctcaaggatcttaccgctgttgagatccagttcgatgtaacccactcgtgcacccaactgatcttcagc |
| | atcttttactttcaccagcgtttctgggtgagcaaaaacaggaaggcaaaatgccgcaaaaaagggaataagggcgacacggaaatgttgaatactcata |
| | ctcttcctttttcaatattattgaagcatttatcagggttattgtctcatgagcggatacatatttgaatgtatttagaaaaataaacaaataggggttc |
| | cgcgcacatttccccgaaaagtgccacctgaaattgtaaacgttaatattttgttaaaattcgcgttaaatttttgttaaatcagctcattttttaacca |
| | ataggccgaaatcggcaaaatcccttataaatcaaaagaatagaccgagatagggttgagtgttgttccagtttggaacaagagtccactattaaagaac |
| | gtggactccaacgtcaaagggcgaaaaaccgtctatcagggcgatggcccactacgtgaaccatcaccctaatcaagttttttggggtcgaggtgccgta |
| | aagcactaaatcggaaccctaaagggagcccccgatttagagcttgacggggaaagccggcgaacgtggcgagaaaggaagggaagaaagcgaaaggagc |
| | gggcgctagggcgctggcaagtgtagcggtcacgctgcgcgtaaccaccacacccgccgcgcttaatgcgccgctacagggcgcgtcccattcgcca |
| 66 | atccggatatagttcctcctttcagcaaaaaacccctcaagacccgtttagaggccccaaggggttatgctagttattgctcagcggtggcagcagccaa |
| | ctcagcttcctttcgggctttgttagcagccggatctcagtggtggtggtggtggtgctcgagTTAGTGATGGTGATGGTGATGGCTACCGCCACCGCCC |
| | AGTTTTTCAGGCGCGCAACTTCATTTTCCAGGTGGTAGTTGGAACCGCCACCGCCGTCAGCACGACCCCACGCTTCTGCACTGACAATTTGCGTAACCG |
| | GTTTTGCACGGTCCTGGGTCCATTCATCATTTTCGCTCAGGCCGTAGAATTGAACCTGACAGCGAAAATGGTTACGCGGGTCCTGCCAGAAGGTGGCAGA |
| | CACGCGCAGACGGGAACTCAGGGCATAACGGCTGTCATTCAGCGCCGGTTGTTCTTTCAGCGGCTGCGGATCGGTACACACACCCGAGTGGACTTCTTTG |
| | CCGTTCACCCACCATGACAGTTCGACATGGTCCGGATAAAAGCCGGTGGCCAGGCACACCAGCGTCGCTTTCTGGGTATGGGAGATTTCAGCTTCACTCG |
| | GTTCGAAAACTGCCACTTCCGGCGGAAAGACATTTTTCAGATCTTCCAGAACCGTCAGACGAGAACCTTCGCCGAAAAACAGTTCACCGGTGTTGCCCAG |
| | GTAAGAGCTTGCGCAGAAATAAACAGACGTTTGGCTCGGTGCTGCGCTCAGCAGACGCAGCGGAAAGTCTTCAATGGTCGAACGTGAAACATTGTAACCG |
| | TTCGGCACTTCGCCTTGATCCGTGGTCTGGATGGCGACCGAATAGTGAATCAGACGCAGACCCATACCCGGGTCCTGACGGTACCATGACATATATTCAT |
| | GGTTCATATCTTGGGCACATTGCAGCGTCATGGATTGGCCCGTTTTCAGGACTTGGAATTTCGGCGTTTGGGTCACACCAGCGTTCATatgtatatctcc |
| | ttcttaaagttaaacaaaattatttctagaggggaattgttatccgctcacaattcccctatagtgagtcgtattaatttcgcgggatcgagatctcgat |
| | cctctacgccggacgcatcgtggccggcatcaccggcgccacaggtgcggttgctggcgcctatatcgccgacatcaccgatggggaagatcgggctcgc |
| | cacttcgggctcatgagcgcttgtttcggcgtgggtatggtggcaggccccgtggccgggggactgttgggcgccatctccttgcatgcaccattccttg |
| | cggcggcggtgctcaacggcctcaacctactactgggctgcttcctaatgcaggagtcgcataagggagagcgtcgagatcccggacaccatcgaatggc |
| | gcaaaacctttcgcggtatggcatgatagcgcccggaagagagtcaattcagggtggtgaatgtgaaaccagtaacgttatacgatgtcgcagagtatgc |
| | cggtgtctcttatcagaccgtttcccgcgtggtgaaccaggccagccacgtttctgcgaaaacgcgggaaaaagtggaagcggcgatggcggagctgaat |
| | tacattcccaaccgcgtggcacaacaactggcgggcaaacagtcgttgctgattggcgttgccacctccagtctggccctgcacgcgccgtcgcaaattg |
| | tcgcggcgattaaatctcgcgccgatcaactgggtgccagcgtggtggtgtcgatggtagaacgaagcggcgtcgaagcctgtaaagcggcggtgcacaa |
| | tcttctcgcgcaacgcgtcagtgggctgatcattaactatccgctggatgaccaggatgccattgctgtggaagctgcctgcactaatgttccggcgtta |
| | tttcttgatgtctctgaccagacacccatcaacagtattattttctcccatgaagacggtacgcgactgggcgtggagcatctggtcgcattgggtcacc |
| | agcaaatcgcgctgttagcgggcccattaagttctgtctcggcgcgtctgcgtctggctggctggcataaatatctcactcgcaatcaaattcagccgat |
| | agcggaacgggaaggcgactggagtgccatgtccggttttcaacaaaccatgcaaatgctgaatgagggcatcgttcccactgcgatgctggttgccaac |
| | gatcagatggcgctgggcgcaatgcgcgccattaccgagtccgggctgcgcgttggtgcggatatctcggtagtgggatacgacgataccgaagacagct |
| | catgttatatcccgccgttaaccaccatcaaacaggattttcgcctgctggggcaaaccagcgtggaccgcttgctgcaactctctcagggccaggcggt |
| | gaagggcaatcagctgttgcccgtctcactggtgaaaagaaaaaccaccctggcgcccaatacgcaaaccgcctctccccgcgcgttggccgattcatta |
| | atgcagctggcacgacaggtttcccgactggaaagcgggcagtgagcgcaacgcaattaatgtgagttagctcactcattaggcaccccaggctttacac |
| | tttatgcttccggctcgtatgttgtgtggaattgtgagcggataacaatttcacacaggaaacagctatgaccatgattacggattcactggccgtcgtt |
| | ttacaacgtcgtgactgggaaaaccctggcgttacccaacttaatcgccttgcagcacatccccctttcgccagctggcgtaatagcgaagaggcccgca |
| | ccgatcgcccttcccaacagttgcgcagcctgaatggcgaatggcgctttgcctggtttccggcaccagaagcggtgccggaaagctggctggagtgcga |
| | tcttcctgaggccgatactgtcgtcgtcccctcaaactggcagatgcacggttacgatgcgcccatctacaccaacgtgacctatcccattacggtcaat |
| | ccgccgtttgttcccacggagaatccgacgggttgttactcgctcacatttaatgttgatgaaagctggctacaggaaggccagacgcgaattatttttg |
| | atggcgttaactcggcgtttcatctgtggtgcaacgggcgctgggtcggttacggccaggacagtcgtttgccgtctgaatttgacctgagcgcatttt |
| | taggacaggtgccggcagcgctctgggtcattttcggcgaggaccgctttcgctggagcgcgacgatgatcggcctgtcgcttgcggtattcggaatctt |
| | gcacgccctcgctcaagccttcgtcactggtcccgccaccaaacgtttcggcgagaagcaggccattatcgccggcatggcggccccacgggtgcgcatg |
| | atcgtgctcctgtcgttgaggacccggctaggctggcggggttgccttactggttagcagaatgaatcaccgatacgcgagcgaacgtgaagcgactgct |
| | gctgcaaaacgtctgcgacctgagcaacaacatgaatggtcttcggtttccgtgtttcgtaaagtctggaaacgcggaagtcagcgccctgcaccattat |
| | gttccggatctgcatcgcaggatgctgctggctaccctgtggaacacctacatctgtattaacgaagcgctggcattgaccctgagtgattttttctctgg |
| | tcccgccgcatccataccgccagttgtttaccctcacaacgttccagtaaccgggcatgttcatcatcagtaacccgtatcgtgagcatcctctctcgtt |
| | tcatcggtatcattacccccatgaacagaaatcccccttacacggaggcatcagtgaccaaacaggaaaaaaccgcccttaacatggcccgctttatcag |
| | aagccagacattaacgcttctggagaaactcaacgagctggacgcggatgaacaggcagacatctgtgaatcgcttcacgaccacgctgatgagctttac |
| | cgcagctgcctcgcgcgtttcggtgatgacggtgaaaacctctgacacatgcagctcccggagacggtcacagcttgtctgtaagcggatgccgggagca |
| | gacaagcccgtcagggcgcgtcagcgggtgttggcgggtgtcggggcgcagccatgacccagtcacgtagcgatagcggagtgtatactggcttaactat |
| | gcggcatcagagcagattgtactgagagtgcaccatatatgcggtgtgaaataccgcacagatgcgtaaggagaaaataccgcatcaggcgctcttccgc |
| | ttcctcgctcactgactcgctgcgctcggtcgttcggctgcggcgagcggtatcagctcactcaaaggcggtaatacggttatccacagaatcaggggat |
| | aacgcaggaaagaacatgtgagcaaaaggccagcaaaaggccaggaaccgtaaaaaggccgcgttgctggcgtttttccataggctccgcccccctgacg |
| | agcatcacaaaaatcgacgctcaagtcagaggtggcgaaacccgacaggactataaagataccaggcgtttccccctggaagctccctcgtgcgctctcc |
| | tgttccgaccctgccgcttaccggatacctgtccgcctttctcccttcgggaagcgtggcgctttctcatagctcacgctgtaggtatctcagttcggtg |
| | taggtcgttcgctccaagctgggctgtgtgcacgaaccccccgttcagcccgaccgctgcgccttatccggtaactatcgtcttgagtccaacccggtaa |
| | gacacgacttatcgccactggcagcagccactggtaacaggattagcagagcgaggtatgtaggcggtgctacagagttcttgaagtggtggcctaacta |
| | cggctacactagaaggacagtatttggtatctgcgctctgctgaagccagttaccttcggaaaaagagttggtagctcttgatccggcaaacaaaccacc |
| | gctggtagcggtggtttttttgtttgcaagcagcagattacgcgcagaaaaaaaggatctcaagaagatcctttgatcttttctacggggtctgacgctc |
| | agtggaacgaaaactcacgttaagggattttggtcatgagattatcaaaaaggatcttcacctagatccttttaaattaaaaatgaagttttaaatcaat |

TABLE 47-continued

Soluble T cell receptors-Nucleotide Sequence

| SEQ ID NO | SEQUENCE |
|---|---|
| | ctaaagtatatatgagtaaacttggtctgacagttaccaatgcttaatcagtgaggcacctatctcagcgatctgtctatttcgttcatccatagttgcc |
| | tgactccccgtcgtgtagataactacgatacgggagggcttaccatctggccccagtgctgcaatgataccgcgagacccacgctcaccggctccagatt |
| | tatcagcaataaaccagccagccggaagggccgagcgcagaagtggtcctgcaactttatccgcctccatccagtctattaattgttgccgggaagctag |
| | agtaagtagttcgccagttaatagtttgcgcaacgttgttgccattgctgcaggcatcgtggtgtcacgctcgtcgtttggtatggcttcattcagctcc |
| | ggttcccaacgatcaaggcgagttacatgatcccccatgttgtgcaaaaaagcggttagctccttcggtcctccgatcgttgtcagaagtaagttggccg |
| | cagtgttatcactcatggttatggcagcactgcataattctcttactgtcatgccatccgtaagatgcttttctgtgactggtgagtactcaaccaagtc |
| | attctgagaatagtgtatgcggcgaccgagttgctcttgcccggcgtcaatacgggataataccgcgccacatagcagaactttaaaagtgctcatcatt |
| | ggaaaacgttcttcggggcgaaaactctcaaggatcttaccgctgttgagatccagttcgatgtaacccactcgtgcacccaactgatcttcagcatctt |
| | ttactttcaccagcgtttctgggtgagcaaaaacaggaaggcaaaatgccgcaaaaaagggaataagggcgacacggaaatgttgaatactcatactctt |
| | cctttttcaatattattgaagcatttatcagggttattgtctcatgagcggatacatatttgaatgtatttagaaaaataaacaaataggggttccgcgc |
| | acatttccccgaaaagtgccacctgaaattgtaaacgttaatattttgttaaaattcgcgttaaatttttgttaaatcagctcattttttaaccaatagg |
| | ccgaaatcggcaaaatcccttataaatcaaaagaatagaccgagatagggttgagtgttgttccagtttggaacaagagtccactattaaagaacgtgga |
| | ctccaacgtcaaagggcgaaaaaccgtctatcagggcgatggcccactacgtgaaccatcaccctaatcaagttttttggggtcgaggtgccgtaaagca |
| | ctaaatcggaaccctaaagggagcccccgatttagagcttgacggggaaagccggcgaacgtggcgagaaaggaagggaagaaagcgaaaggagcgggcg |
| | ctagggcgctggcaagtgtagcggtcacgctgcgcgtaaccaccacacccgccgcgcttaatgcgccgctacagggcgcgtcccattcgcca |
| 67 | atccggatatagttcctcctttcagcaaaaaacccctcaagacccgtttagaggccccaaggggttatgctagttattgctcagcggtggcagcagccaa |
| | ctcagcttcctttcgggctttgttagcagccggatctcagtggtggtggtggtggtgctcgagTTACAGTTTTTCAGGCGCGCAACTTCATTTTCCAGG |
| | TGGTAGTTGGAACCGCCACCGCCAGAGCTTTCCGGGCTCGGGAAAAACGTATCTTCCGGGATAATACTATTGTTGAATGCGTTGGCGCACGCAAAGTCAG |
| | ATTTATTGCTCCAAGCAACTGCCGAGTTTGATTTGAAATCCATAGAGCGCATGTCCAGAACACATTTATCGGTAATATACACGTCGGAATCTTTGGATTG |
| | ACTGACATTCGTCTGACTGTCGAAATCGGTAAACAGGCACACGCTTTTGTCCGATGATTTGCTATCACGCAGTTGGTACACCGCCGGGTCCGGGTTCTGG |
| | ATATACGGATGGACAATCAGGCTGGTACCGCGGCCAAACGTCGGGATATAGGTACCATCCAGCAGCGGACGCACCGCACACAGGTACGTAGCGGAGTCAC |
| | CCGGCTGACTTGCTGCAATATACAGGGTGGAACTACCAGAGCTTTTATCCAGCGATGCATTCAGGCGGCCTGAGGTTTGTTCACGCTGCCACGGCGTGAT |
| | CAGCAGCAGGCTGGTCAGACCTTTGCCCGGATCTTGACGAAACCACTGCAGGTTGTAAATGGCGCTATCCGTAAAGGAGCAATTCAGCACCAGATTTTCA |
| | CCTTCCGGGACCGACAGAGCAGCCGGGATTTGGGTAACTTCTTGTTTCATatgtatatctccttcttaaagttaaacaaaattatttctagaggggaatt |
| | gttatccgctcacaattcccctatagtgagtcgtattaatttcgcgggatcgagatctcgatcctctacgccggacgcatcgtggccggcatcaccggcg |
| | ccacaggtgcggttgctggcgcctatatcgccgacatcaccgatggggaagatcgggctcgccacttcgggctcatgagcgcttgtttcggcgtgggtat |
| | ggtggcaggccccgtggccgggggactgttgggcgccatctccttgcatgcaccattccttgcggcggcggtgctcaacggcctcaacctactactgggc |
| | tgcttcctaatgcaggagtcgcataagggagagcgtcgagatcccggacaccatcgaatggcgcaaaacctttcgcggtatggcatgatagcgcccggaa |
| | gagagtcaattcagggtggtgaatgtgaaaccagtaacgttatacgatgtcgcagagtatgccggtgtctcttatcagaccgtttcccgcgtggtgaacc |
| | aggccagccacgtttctgcgaaaacgcgggaaaaagtggaagcggcgatggcggagctgaattacattcccaaccgcgtggcacaacaactggcgggcaa |
| | acagtcgttgctgattggcgttgccacctccagtctggccctgcacgcgccgtcgcaaattgtcgcggcgattaaatctcgcgccgatcaactgggtgcc |
| | agcgtggtggtgtcgatggtagaacgaagcggcgtcgaagcctgtaaagcggcggtgcacaatcttctcgcgcaacgcgtcagtgggctgatcattaact |
| | atccgctggatgaccaggatgccattgctgtggaagctgcctgcactaatgttccggcgttatttcttgatgtctctgaccagacacccatcaacagtat |
| | tattttctcccatgaagacggtacgcgactgggcgtggagcatctggtcgcattgggtcaccagcaaatcgcgctgttagcgggcccattaagttctgtc |
| | tcggcgcgtctgcgtctggctggctggcataaatatctcactcgcaatcaaattcagccgatagcggaacgggaaggcgactggagtgccatgtccggtt |
| | ttcaacaaaccatgcaaatgctgaatgagggcatcgttcccactgcgatgctggttgccaacgatcagatggcgctgggcgcaatgcgcgccattaccga |
| | gtccgggctgcgcgttggtgcggatatctcggtagtgggatacgacgataccgaagacagctcatgttatatcccgccgttaaccaccatcaaacaggat |
| | tttcgcctgctggggcaaaccagcgtggaccgcttgctgcaactctctcagggccaggcggtgaagggcaatcagctgttgcccgtctcactggtgaaaa |
| | gaaaaaccaccctggcgcccaatacgcaaaccgcctctccccgcgcgttggccgattcattaatgcagctggcacgacaggtttcccgactggaaagcgg |
| | gcagtgagcgcaacgcaattaatgtaagttagctcactcattaggcaccgggatctcgaccgatgcccttgagagccttcaacccagtcagctccttccg |
| | gtgggcgcggggcatgactatcgtcgccgcacttatgactgtcttctttatcatgcaactcgtaggacaggtgccggcagcgctctgggtcattttcggc |
| | gaggaccgctttcgctggagcgcgacgatgatcggcctgtcgcttgcggtattcggaatcttgcacgccctcgctcaagccttcgtcactggtcccgcca |
| | ccaaacgtttcggcgagaagcaggccattatcgccggcatggcggccccacgggtgcgcatgatcgtgctcctgtcgttgaggacccggctaggctggcg |
| | gggttgccttactggttagcagaatgaatcaccgatacgcgagcgaacgtgaagcgactgctgctgcaaaacgtctgcgacctgagcaacaacatgaatg |
| | gtcttcggtttccgtgtttcgtaaagtctggaaacgcggaagtcagcgccctgcaccattatgttccggatctgcatcgcaggatgctgctggctaccct |
| | gtggaacacctacatctgtattaacgaagcgctggcattgaccctgagtgatttttctctggtcccgccgcatccataccgccagttgtttaccctcaca |
| | acgttccagtaaccgggcatgttcatcatcagtaacccgtatcgtgagcatcctctctcgtttcatcggtatcattacccccatgaacagaaatccccct |
| | tacacggaggcatcagtgaccaaacaggaaaaaaccgcccttaacatggcccgctttatcagaagccagacattaacgcttctggagaaactcaacgagc |
| | tggacgcggatgaacaggcagacatctgtgaatcgcttcacgaccacgctgatgagctttaccgcagctgcctcgcgcgtttcggtgatgacggtgaaaa |
| | cctctgacacatgcagctcccggagacggtcacagcttgtctgtaagcggatgccgggagcagacaagcccgtcagggcgcgtcagcgggtgttggcggg |
| | tgtcggggcgcagccatgacccagtcacgtagcgatagcggagtgtatactggcttaactatgcggcatcagagcagattgtactgagagtgcaccatat |
| | atgcggtgtgaaataccgcacagatgcgtaaggagaaaataccgcatcaggcgctcttccgcttcctcgctcactgactcgctgcgctcggtcgttcggc |
| | tgcggcgagcggtatcagctcactcaaaggcggtaatacggttatccacagaatcaggggataacgcaggaaagaacatgtgagcaaaaggccagcaaaa |
| | ggccaggaaccgtaaaaaggccgcgttgctggcgtttttccataggctccgcccccctgacgagcatcacaaaaatcgacgctcaagtcagaggtggcga |
| | aacccgacaggactataaagataccaggcgtttccccctggaagctccctcgtgcgctctcctgttccgaccctgccgcttaccggatacctgtccgcct |
| | ttctcccttcgggaagcgtggcgctttctcatagctcacgctgtaggtatctcagttcggtgtaggtcgttcgctccaagctgggctgtgtgcacgaacc |
| | ccccgttcagcccgaccgctgcgccttatccggtaactatcgtcttgagtccaacccggtaagacacgacttatcgccactggcagcagccactggtaac |
| | aggattagcagagcgaggtatgtaggcggtgctacagagttcttgaagtggtggcctaactacggctacactagaaggacagtatttggtatctgcgctc |
| | tgctgaagccagttaccttcggaaaaagagttggtagctcttgatccggcaaacaaaccaccgctggtagcggtggtttttttgtttgcaagcagcagat |
| | tacgcgcagaaaaaaaggatctcaagaagatcctttgatcttttctacggggtctgacgctcagtggaacgaaaactcacgttaagggattttggtcatg |
| | agattatcaaaaaggatcttcacctagatccttttaaattaaaaatgaagttttaaatcaatctaaagtatatatgagtaaacttggtctgacagttacc |
| | aatgcttaatcagtgaggcacctatctcagcgatctgtctatttcgttcatccatagttgcctgactccccgtcgtgtagataactacgatacgggaggg |
| | cttaccatctggccccagtgctgcaatgataccgcgagacccacgctcaccggctccagatttatcagcaataaaccagccagccggaagggccgagcgc |
| | agaagtggtcctgcaactttatccgcctccatccagtctattaattgttgccgggaagctagagtaagtagttcgccagttaatagtttgcgcaacgttg |
| | ttgccattgctgcaggcatcgtggtgtcacgctcgtcgtttggtatggcttcattcagctccggttcccaacgatcaaggcgagttacatgatcccccat |
| | gttgtgcaaaaaagcggttagctccttcggtcctccgatcgttgtcagaagtaagttggccgcagtgttatcactcatggttatggcagcactgcataat |
| | tctcttactgtcatgccatccgtaagatgcttttctgtgactggtgagtactcaaccaagtcattctgagaatagtgtatgcggcgaccgagttgctctt |
| | gcccggcgtcaatacgggataataccgcgccacatagcagaactttaaaagtgctcatcattggaaaacgttcttcggggcgaaaactctcaaggatctt |
| | accgctgttgagatccagttcgatgtaacccactcgtgcacccaactgatcttcagcatcttttactttcaccagcgtttctgggtgagcaaaaacagga |
| | aggcaaaatgccgcaaaaaagggaataagggcgacacggaaatgttgaatactcatactcttcctttttcaatattattgaagcatttatcagggttatt |
| | gtctcatgagcggatacatatttgaatgtatttagaaaaataaacaaataggggttccgcgcacatttccccgaaaagtgccacctgaaattgtaaacgt |
| | taatattttgttaaaattcgcgttaaatttttgttaaatcagctcattttttaaccaataggccgaaatcggcaaaatcccttataaatcaaaagaatag |
| | accgagatagggttgagtgttgttccagtttggaacaagagtccactattaaagaacgtggactccaacgtcaaagggcgaaaaaccgtctatcagggcg |

TABLE 47-continued

| Soluble T cell receptors-Nucleotide Sequence | |
|---|---|
| SEQ ID NO | SEQUENCE |
| | atggcccactacgtgaaccatcaccctaatcaagttttttggggtcgaggtgccgtaaagcactaaatcggaaccctaaagggagcccccgatttagagc<br>ttgacggggaaagccggcgaacgtggcgagaaaggaagggaagaaagcgaaaggagcgggcgctagggcgctggcaagtgtagcggtcacgctgcgcgta<br>accaccacacccgccgcgcttaatgcgccgctacagggcgcgtcccattcgcca |

TABLE 48

| CAR Hinge-Amino Acid Sequence | |
|---|---|
| SEQ ID NO | SEQUENCE |
| 68 | TTTPAPRPPTPAPTIASQPLSLRPEACRPAAGGAVHTRGLDFACD |
| 70 | ESKYGPPCPSCP |
| 71 | ESKYGPPCPPCP |

TABLE 49

| CAR containing hinge variant-Nucleotide Sequence | |
|---|---|
| SEQ ID NO | SEQUENCE |
| 72 | atggccttaccagtgaccgccttgctcctgccgctggccttgctgctccacgccgccaggccgGACGCCGTTGTGACCCAGGAATCCGCTCTGACCTCTT<br>CTCCAGGCGAAACCGTGACTCTGACTTGCCGTAGTAGCACCGGGGCTGTGACCACATCTAACTATGCCAGTTGGGTCCAGGAAAAACCGGATCACCTGTT<br>TACTGGCCTGATTGGCGGCACCAACAATCGCGCACCGGGTGTGCCCGCTCGTTTCAGCGGTTCCCTGATTGGGGACAAGGCAGCACTGACTATCACCGGC<br>GCCCAGACCGAAGATGAGGCGATCTATTTTTGCGTCCTGTGGTACAGCGACCATTGGGTGTTCGGGGGAGGCACCAAACTGACAGTGCTGGGCGGAGGAG<br>GAGGTTCAGGAGGAGGAGGTAGCGGGGGAGGCGGTTCCGGGGGAGGCGGTTCTGATGTGCAGCTGCAAGAATCCGGGCCAGGACTGGTTGCGCCTTCTCA<br>GAGTCTGTCAATTACATGTACTGTTAGTGGCTTTCTGCTGACCGACTATGGTGTGAACTGGGTTCGTCAGAGCCCAGGCAAGGGTCTGGAGTGGCTGGGA<br>GTGATTTGGGGGGATGGAATCACAGACTACAATAGCGCACTGAAATCTCGGCTGAGTGTTACCAAAGATAACAGCAAGTCCCAGGTCTTCCTGAAGATGA<br>ACAGCCTGCAAAGCGGCGACTCCGCTCGCTATTACTGCGTTACCGGACTGTTTGATTATTGGGGGCAGGGGACAACTCTGACTGTTTCCTCCgatatcta<br>catctgggcgcccttggccgggacttgtggggtccttctcctgtcactggttatcaccctttactgcaaacggggcagaaagaaactcctgtatatattc<br>aaacaaccatttatgagaccagtacaaactactcaagaggaagatggctgtagctgccgatttccagaagaagaagaaggaggatgtgaactgagagtga<br>agttcagcaggagcgcagacgcccccgcgtacaagcagggccagaaccagctctataacgagctcaatctaggacgaagagaggagtacgatgttttgga<br>caagagacgtggccgggaccctgagatggggggaaagccgagaaggaagaaccctcaggaaggcctgtacaatgaactgcagaaagataagatggcggag<br>gcctacagtgagattgggatgaaaggcgagcgccggaggggcaaggggcacgatggcctttaccagggtctcagtacagccaccaaggacacctacgacg<br>cccttcacatgcaggccctgccccctcgc |
| 73 | atggccttaccagtgaccgccttgctcctgccgctggccttgctgctccacgccgccaggccgGACGCCGTTGTGACCCAGGAATCCGCTCTGACCTCTT<br>CTCCAGGCGAAACCGTGACTCTGACTTGCCGTAGTAGCACCGGGGCTGTGACCACATCTAACTATGCCAGTTGGGTCCAGGAAAAACCGGATCACCTGTT<br>TACTGGCCTGATTGGCGGCACCAACAATCGCGCACCGGGTGTGCCCGCTCGTTTCAGCGGTTCCCTGATTGGGGACAAGGCAGCACTGACTATCACCGGC<br>GCCCAGACCGAAGATGAGGCGATCTATTTTTGCGTCCTGTGGTACAGCGACCATTGGGTGTTCGGGGGAGGCACCAAACTGACAGTGCTGGGCGGAGGAG<br>GAGGTTCAGGAGGAGGAGGTAGCGGGGGAGGCGGTTCCGGGGGAGGCGGTTCTGATGTGCAGCTGCAAGAATCCGGGCCAGGACTGGTTGCGCCTTCTCA<br>GAGTCTGTCAATTACATGTACTGTTAGTGGCTTTCTGCTGACCGACTATGGTGTGAACTGGGTTCGTCAGAGCCCAGGCAAGGGTCTGGAGTGGCTGGGA<br>GTGATTTGGGGGGATGGAATCACAGACTACAATAGCGCACTGAAATCTCGGCTGAGTGTTACCAAAGATAACAGCAAGTCCCAGGTCTTCCTGAAGATGA<br>ACAGCCTGCAAAGCGGCGACTCCGCTCGCTATTACTGCGTTACCGGACTGTTTGATTATTGGGGGCAGGGGACAACTCTGACTGTTTCCTCCGAAAGCAA<br>GTATGGCCCaCCTTGTCCAagcTGTCCCgatatctacatctgggcgcccttggccgggacttgtggggtccttctcctgtcactggttatcaccctttac<br>tgcaaacggggcagaaagaaactcctgtatatattcaaacaaccatttatgagaccagtacaaactactcaagaggaagatggctgtagctgccgatttc<br>cagaagaagaagaaggaggatgtgaactgagagtgaagttcagcaggagcgcagacgcccccgcgtacaagcagggccagaaccagctctataacgagct<br>caatctaggacgaagagaggagtacgatgttttggacaagagacgtggccgggaccctgagatggggggaaagccgagaaggaagaaccctcaggaaggc<br>ctgtacaatgaactgcagaaagataagatggcggaggcctacagtgagattgggatgaaaggcgagcgccggaggggcaaggggcacgatggcctttacc<br>agggtctcagtacagccaccaaggacacctacgacgcccttcacatgcaggccctgccccctcgc |
| 74 | atggccttaccagtgaccgccttgctcctgccgctggccttgctgctccacgccgccaggccgGACGCCGTTGTGACCCAGGAATCCGCTCTGACCTCTT<br>CTCCAGGCGAAACCGTGACTCTGACTTGCCGTAGTAGCACCGGGGCTGTGACCACATCTAACTATGCCAGTTGGGTCCAGGAAAAACCGGATCACCTGTT<br>TACTGGCCTGATTGGCGGCACCAACAATCGCGCACCGGGTGTGCCCGCTCGTTTCAGCGGTTCCCTGATTGGGGACAAGGCAGCACTGACTATCACCGGC<br>GCCCAGACCGAAGATGAGGCGATCTATTTTTGCGTCCTGTGGTACAGCGACCATTGGGTGTTCGGGGGAGGCACCAAACTGACAGTGCTGGGCGGAGGAG<br>GAGGTTCAGGAGGAGGAGGTAGCGGGGGAGGCGGTTCCGGGGGAGGCGGTTCTGATGTGCAGCTGCAAGAATCCGGGCCAGGACTGGTTGCGCCTTCTCA<br>GAGTCTGTCAATTACATGTACTGTTAGTGGCTTTCTGCTGACCGACTATGGTGTGAACTGGGTTCGTCAGAGCCCAGGCAAGGGTCTGGAGTGGCTGGGA<br>GTGATTTGGGGGGATGGAATCACAGACTACAATAGCGCACTGAAATCTCGGCTGAGTGTTACCAAAGATAACAGCAAGTCCCAGGTCTTCCTGAAGATGA<br>ACAGCCTGCAAAGCGGCGACTCCGCTCGCTATTACTGCGTTACCGGACTGTTTGATTATTGGGGGCAGGGGACAACTCTGACTGTTTCCTCCGAAAGCAA<br>GTATGGCCCaCCTTGTCCACCTTGTCCCgatatctacatctgggcgcccttggccgggacttgtggggtccttctcctgtcactggttatcaccctttac<br>tgcaaacggggcagaaagaaactcctgtatatattcaaacaaccatttatgagaccagtacaaactactcaagaggaagatggctgtagctgccgatttc<br>cagaagaagaagaaggaggatgtgaactgagagtgaagttcagcaggagcgcagacgcccccgcgtacaagcagggccagaaccagctctataacgagct |

TABLE 49-continued

| CAR containing hinge variant-Nucleotide Sequence | |
|---|---|
| SEQ ID NO | SEQUENCE |
| | caatctaggacgaagagaggagtacgatgttttggacaagagacgtggccgggaccctgagatgggggaaagccgagaaggaagaaccctcaggaaggcctgtacaatgaactgcagaaagataagatggcggaggcctacagtgagattgggatgaaaggcgagcgccggaggggcaaggggcacgatggcctttaccagggtctcagtacagccaccaaggacacctacgacgcccttcacatgcaggccctgccccctcgc |

TABLE 50

| GCN4 epitope-Amino Acid Sequence | |
|---|---|
| SEQ ID NO | SEQUENCE |
| 75 | AYHLENEVARLKKL |
| 76 | AAHLENEVARLKKL |
| 77 | AAALENEVARLKKL |
| 78 | AAAAENEVARLKKL |
| 79 | NYHLENEVARLKKA |
| 80 | NYHLENEVARLKAA |
| 81 | NYHLENEVARLAAA |
| 82 | NYHLENEVARAAAA |
| 83 | LLPKNYHLENEVARLKKL |
| 84 | DLPQKYHLENEVARLKKL |

TABLE 51

| Switch Antibody Chains | |
|---|---|
| SEQ ID NO | SEQUENCE |
| 85 | aattatcatcttgaaaatgaggtcgctcgtctcaagaaactcGGCGGAGGCGGGAGCGGCGGAGGCGGGAGCGACATCCAGATGACACAGACTACATCCTCCCTGTCTGCCTCTCTGGGAGACAGAGTCACCATCAGTTGCAGGGCAAGTCAGGACATTAGTAAATATTTAAATTGGTATCAGCAGAAACCAGATGGAACTGTTAAACTCCTGATCTACCATACATCAAGATTACACTCAGGAGTCCCATCAAGGTTCAGTGGCAGTGGGTCTGGAACAGATTATTCTCTCACCATTAGCAACCTGGAGCAAGAAGATATTGCCACTTACTTTTGCCAACAGGGTAATACGCTTCCGTACACGTTCGGAGGGGGGACCAAGCTTGAGATCaaacgaactgtggctgcaccatctgtcttcatcttcccgccatctgatgagcagttgaaatctggaactgcctctgtcgtgtgcctgctgaataacttctatcccagagaggccaaagtacagtggaaggtggataacgccctccaatcgggtaactcccaggagagtgtcacagagcaggacagcAAGgacagcacctacagcctcagcagcaccctgacgctgagcaaagcagactacgagaaacacaaagtctacgcctgcgaagtcacccatcagggcctgtcctcgcccgtcacaaagagcttcaacaggggagagtgt |
| 86 | aattatcatcttgaaaatgaggtcgctcgtctcaagaaactcGGCGGAGGCGGGAGCGAGGTGAAACTGCAGGAGTCAGGACCTGGCCTGGTGGCGCCCTCACAGAGCCTGTCCGTCACATGCACTGTCTCAGGGGTCTCATTACCCGACTATGGTGTAAGCTGGATTCGCCAGCCTCCACGAAAGGGTCTGGAGTGGCTGGGAGTAATATGGGGTAGTGAAACCACATACTATAATTCAGCTCTCAAATCCAGACTGACCATCATCAAGGACAACTCCAAGAGCCAAGTTTTCTTAAAAATGAACAGTCTGCAAACTGATGACACAGCCATTTACTACTGTGCCAAACATTATTACTACGGTGGTAGCTATGCTATGGACTACTGGGGCCAAGGAACCTCAGTCACCGTCTCCTCAgcctccaccaagggcccatcggtcttccccctggcaccctcctccaagagcacctctgggggcacagcggccctgggctgcctggtcaaggactacttccccgaaccggtgacggtgtcgtggaactcaggcgccctgaccagcggcgtgcacaccttcccggctgtcctacagtcctcaggactctactccctcagcagcgtggtgactgtgccctctagcagcttgggcacccagacctacatctgcaacgtgaatcacaagcccagcaacaccaaggtggacaagaaagttgagcccaaatcttgt |
| 87 | aattatcatcttgaaaatgaggtcgctcgtctcaagaaactcGGCGGAGGCGGGAGCGGCGGAGGCGGGAGCGAGGTGAAACTGCAGGAGTCAGGACCTGGCCTGGTGGCGCCCTCACAGAGCCTGTCCGTCACATGCACTGTCTCAGGGGTCTCATTACCCGACTATGGTGTAAGCTGGATTCGCCAGCCTCCACGAAAGGGTCTGGAGTGGCTGGGAGTAATATGGGGTAGTGAAACCACATACTATAATTCAGCTCTCAAATCCAGACTGACCATCATCAAGGACAACTCCAAGAGCCAAGTTTTCTTAAAAATGAACAGTCTGCAAACTGATGACACAGCCATTTACTACTGTGCCAAACATTATTACTACGGTGGTAGCTATGCTATGGACTACTGGGGCCAAGGAACCTCAGTCACCGTCTCCTCAgcctccaccaagggcccatcggtcttccccctggcaccctcctccaagagcacctctgggggcacagcggccctgggctgcctggtcaaggactacttccccgaaccggtgacggtgtcgtggaactcaggcgccctgaccagcggcgtgcacaccttcccggctgtcctacagtcctcaggactctactccctcagcagcgtggtgactgtgccctctagcagcttgggcacccagacctacatctgcaacgtgaatcacaagcccagcaacaccaaggtggacaagaaagttgagcccaaatcttgt |
| 88 | aattatcatcttgaaaatgaggtcgctcgtctcaagaaactcctggttggcgaggccgcagctaaggaagccgcagctaaagccGAGGTGAAACTGCAGGAGTCAGGACCTGGCCTGGTGGCGCCCTCACAGAGCCTGTCCGTCACATGCACTGTCTCAGGGGTCTCATTACCCGACTATGGTGTAAGCTGGATTCGCCAGCCTCCACGAAAGGGTCTGGAGTGGCTGGGAGTAATATGGGGTAGTGAAACCACATACTATAATTCAGCTCTCAAATCCAGACTGACCATCATCAAGGACAACTCCAAGAGCCAAGTTTTCTTAAAAATGAACAGTCTGCAAACTGATGACACAGCCATTTACTACTGTGCCAAACATTATTACTACGGTGGTAGCTATGCTATGGACTACTGGGGCCAAGGAACCTCAGTCACCGTCTCCTCAgcctccaccaagggcccatcggtcttccccctggcaccctcctccaagagcacctctgggggcacagcggccctgggctgcctggtcaaggactacttccccgaaccggtgacggtgtcgtggaactcaggcgccctgaccagcggcgtgcacaccttcccggctgtcctacagtcctcaggactctactccctcagcagcgtggtgactgtgccctctagcagcttgggcacccagacctacatctgcaacgtgaatcacaagcccagcaacaccaaggtggacaagaaagttgagcccaaatcttgt |
| 89 | aattatcatcttgaaaatgaggtcgctcgtctcaagaaactcgccgaggccgccgcaaaggaagctgctgccaaggctGAGGTGAAACTGCAGGAGTCAGGACCTGGCCTGGTGGCGCCCTCACAGAGCCTGTCCGTCACATGCACTGTCTCAGGGGTCTCATTACCCGACTATGGTGTAAGCTGGATTCGCCAGCCTCCACGAAAGGGTCTGGAGTGGCTGGGAGTAATATGGGGTAGTGAAACCACATACTATAATTCAGCTCTCAAATCCAGACTGACCATCATCAAGGACAACTCCAAGAGCCAAGTTTTCTTAAAAATGAACAGTCTGCAAACTGATGACACAGCCATTTACTACTGTGCCAAACATTATTACTACGGTGGTAGCTATGCTATGGACTACTGGGGCCAAGGAACCTCAGTCACCGTCTCCTCAgcctccaccaagggcccatcggtcttccccctggcaccctcctccaagagcacctctggggg |

TABLE 51-continued

| SEQ ID NO | Switch Antibody Chains<br>SEQUENCE |
|---|---|
| | cacagcggccctgggctgcctggtcaaggactacttccccgaaccggtgacggtgtcgtggaactcaggcgccctgaccagcggcgtgcacaccttcccg<br>gctgtcctacagtcctcaggactctactccctcagcagcgtggtgactgtgccctctagcagcttgggcacccagacctacatctgcaacgtgaatcaca<br>agcccagcaacaccaaggtggacaagaaagttgagcccaaatcttgt |
| 90 | GAGGTGAAACTGCAGGAGTCAGGACCTGGCCTGGTGGCGCCCTCACAGAGCCTGTCCGTCACATGCACTGTCTCAGGGGTCTCATTACCCGACTATGGTG<br>TAAGCTGGATTCGCCAGCCTCCACGAAAGGGTCTGGAGTGGCTGGGAGTAATATGGGGTAGTGAAACCACATACTATAATTCAGCTCTCAAATCCAGACT<br>GACCATCATCAAGGACAACTCCAAGAGCCAAGTTTTCTTAAAAATGAACAGTCTGCAAACTGATGACACAGCCATTTACTACTGTGCCAAACATTATTAC<br>TACGGTGGTAGCTATGCTATGGACTACTGGGGCCAAGGAACCTCAGTCACCGTCTCCTCAgcctccaccaagggcccatcggtcttccccctggcaccct<br>cctccaagagcacctctgggggcacagcggccctgggctgcctggtcaaggactacttccccgaaccggtgacggtgtcgtggaactcaggcgccctgac<br>cagcggcgtgcacaccttcccggctgtcctacagtccGGCGGGGGAGGCTCAAACTACCACCTGGAGAATGAAGTCGCCAGACTGAAGAAACTGGGGGGA<br>GGCGGGTCActctactccctcagcagcgtggtgactgtgccctctagcagcttgggcacccagacctacatctgcaacgtgaatcacaagcccagcaaca<br>ccaaggtggacaagaaagttgagcccaaatcttgt |
| 91 | GAGGTGAAACTGCAGGAGTCAGGACCTGGCCTGGTGGCGCCCTCACAGAGCCTGTCCGTCACATGCACTGTCTCAGGGGTCTCATTACCCGACTATGGTG<br>TAAGCTGGATTCGCCAGCCTCCACGAAAGGGTCTGGAGTGGCTGGGAGTAATATGGGGTAGTGAAACCACATACTATAATTCAGCTCTCAAATCCAGACT<br>GACCATCATCAAGGACAACTCCGGCGGAGGCGGGAGCaactatcacctggaaaacgaagtggcaaggctgaaaaaactgggcgggggcggaagtAAGAGC<br>CAAGTTTTCTTAAAAATGAACAGTCTGCAAACTGATGACACAGCCATTTACTACTGTGCCAAACATTATTACTACGGTGGTAGCTATGCTATGGACTACT<br>GGGGCCAAGGAACCTCAGTCACCGTCTCCTCAgcctccaccaagggcccatcggtcttccccctggcaccctcctccaagagcacctctgggggcacagc<br>ggccctgggctgcctggtcaaggactacttccccgaaccggtgacggtgtcgtggaactcaggcgccctgaccagcggcgtgcacaccttcccggctgtc<br>ctacagtcctcaggactctactccctcagcagcgtggtgactgtgccctctagcagcttgggcacccagacctacatctgcaacgtgaatcacaagccca<br>gcaacaccaaggtggacaagaaagttgagcccaaatcttgt |
| 92 | GAGGTGAAACTGCAGGAGTCAGGACCTGGCCTGGTGGCGCCCTCACAGAGCCTGTCCGTCACATGCACTGTCTCAGGGGTCTCATTACCCGACTATGGTG<br>TAAGCTGGATTCGCCAGCCTCCACGAAAGGGTCTGGAGTGGCTGGGAGTAATATGGGGTAGTGAAACCACATACTATAATTCAGCTCTCAAATCCAGACT<br>GACCATCATCAAGGACAACGGCGGAGGCGGGAGCaactatcacctggaaaacgaagtggcaaggctgaaaaaactgggcgggggcggaagtAGCCAAGTT<br>TTCTTAAAAATGAACAGTCTGCAAACTGATGACACAGCCATTTACTACTGTGCCAAACATTATTACTACGGTGGTAGCTATGCTATGGACTACTGGGGCC<br>AAGGAACCTCAGTCACCGTCTCCTCAgcctccaccaagggcccatcggtcttccccctggcaccctcctccaagagcacctctgggggcacagcggccct<br>gggctgcctggtcaaggactacttccccgaaccggtgacggtgtcgtggaactcaggcgccctgaccagcggcgtgcacaccttcccggctgtcctacag<br>tcctcaggactctactccctcagcagcgtggtgactgtgccctctagcagcttgggcacccagacctacatctgcaacgtgaatcacaagcccagcaaca<br>ccaaggtggacaagaaagttgagcccaaatcttgt |
| 93 | aactatcacctggaaaacgaagtggcaaggctgaaaaaactgGAGGCCGCCGCAAAGGAAGCAGCCGCCAAAGAGGCTGCCGCGAAAGCGGACATCCAGA<br>TGACACAGACTACATCCTCCCTGTCTGCCTCTCTGGGAGACAGAGTCACCATCAGTTGCAGGGCAAGTCAGGACATTAGTAAATATTTAAATTGGTATCA<br>GCAGAAACCAGATGGAACTGTTAAACTCCTGATCTACCATACATCAAGATTACACTCAGGAGTCCCATCAAGGTTCAGTGGCAGTGGGTCTGGAACAGAT<br>TATTCTCTCACCATTAGCAACCTGGAGCAAGAAGATATTGCCACTTACTTTTGCCAACAGGGTAATACGCTTCCGTACACGTTCGGAGGGGGGACCAAGC<br>TTGAGATCaaacgaactgtggctgcaccatctgtcttcatcttcccgccatctgatgagcagttgaaatctggaactgcctctgtcgtgtgcctgctgaa<br>taacttctatcccagagaggccaaagtacagtggaaggtggataacgccctccaatcgggtaactcccaggagagtgtcacagagcaggacagcAAGgac<br>agcacctacagcctcagcagcaccctgacgctgagcaaagcagactacgagaaacacaaagtctacgcctgcgaagtcacccatcagggcctgtcctcgc<br>ccgtcacaaagagcttcaacaggggagagtgt |
| 94 | aactatcacctggaaaacgaagtggcaaggctgaaaaaactgGGTTCCGCCGGTTCCGCAGCCGGCTCCGGAGAATTCGACATCCAGATGACACAGACTA<br>CATCCTCCCTGTCTGCCTCTCTGGGAGACAGAGTCACCATCAGTTGCAGGGCAAGTCAGGACATTAGTAAATATTTAAATTGGTATCAGCAGAAACCAGA<br>TGGAACTGTTAAACTCCTGATCTACCATACATCAAGATTACACTCAGGAGTCCCATCAAGGTTCAGTGGCAGTGGGTCTGGAACAGATTATTCTCTCACC<br>ATTAGCAACCTGGAGCAAGAAGATATTGCCACTTACTTTTGCCAACAGGGTAATACGCTTCCGTACACGTTCGGAGGGGGGACCAAGCTTGAGATCaaac<br>gaactgtggctgcaccatctgtcttcatcttcccgccatctgatgagcagttgaaatctggaactgcctctgtcgtgtgcctgctgaataacttctatcc<br>cagagaggccaaagtacagtggaaggtggataacgccctccaatcgggtaactcccaggagagtgtcacagagcaggacagcAAGgacagcacctacagc<br>ctcagcagcaccctgacgctgagcaaagcagactacgagaaacacaaagtctacgcctgcgaagtcacccatcagggcctgtcctcgcccgtcacaaaga<br>gcttcaacaggggagagtgt |
| 95 | aattatcatcttgaaaatgaggtcgctcgtctcaagaaactcGAGGCCGCCGCAAAGGAAGCAGCCGCCAAAGAGGCTGCCGCGAAAGCGGAGGTGAAAC<br>TGCAGGAGTCAGGACCTGGCCTGGTGGCGCCCTCACAGAGCCTGTCCGTCACATGCACTGTCTCAGGGGTCTCATTACCCGACTATGGTGTAAGCTGGAT<br>TCGCCAGCCTCCACGAAAGGGTCTGGAGTGGCTGGGAGTAATATGGGGTAGTGAAACCACATACTATAATTCAGCTCTCAAATCCAGACTGACCATCATC<br>AAGGACAACTCCAAGAGCCAAGTTTTCTTAAAAATGAACAGTCTGCAAACTGATGACACAGCCATTTACTACTGTGCCAAACATTATTACTACGGTGGTA<br>GCTATGCTATGGACTACTGGGGCCAAGGAACCTCAGTCACCGTCTCCTCAgcctccaccaagggcccatcggtcttccccctggcaccctcctccaagag<br>cacctctgggggcacagcggccctgggctgcctggtcaaggactacttccccgaaccggtgacggtgtcgtggaactcaggcgccctgaccagcggcgtg<br>cacaccttcccggctgtcctacagtcctcaggactctactccctcagcagcgtggtgactgtgccctctagcagcttgggcacccagacctacatctgca<br>acgtgaatcacaagcccagcaacaccaaggtggacaagaaagttgagcccaaatcttgt |
| 96 | aattatcatcttgaaaatgaggtcgctcgtctcaagaaactcGGTTCCGCCGGTTCCGCAGCCGGCTCCGGAGAATTCGAGGTGAAACTGCAGGAGTCAG<br>GACCTGGCCTGGTGGCGCCCTCACAGAGCCTGTCCGTCACATGCACTGTCTCAGGGGTCTCATTACCCGACTATGGTGTAAGCTGGATTCGCCAGCCTCC<br>ACGAAAGGGTCTGGAGTGGCTGGGAGTAATATGGGGTAGTGAAACCACATACTATAATTCAGCTCTCAAATCCAGACTGACCATCATCAAGGACAACTCC<br>AAGAGCCAAGTTTTCTTAAAAATGAACAGTCTGCAAACTGATGACACAGCCATTTACTACTGTGCCAAACATTATTACTACGGTGGTAGCTATGCTATGG<br>ACTACTGGGGCCAAGGAACCTCAGTCACCGTCTCCTCAgcctccaccaagggcccatcggtcttccccctggcaccctcctccaagagcacctctggggg<br>cacagcggccctgggctgcctggtcaaggactacttccccgaaccggtgacggtgtcgtggaactcaggcgccctgaccagcggcgtgcacaccttcccg<br>gctgtcctacagtcctcaggactctactccctcagcagcgtggtgactgtgccctctagcagcttgggcacccagacctacatctgcaacgtgaatcaca<br>agcccagcaacaccaaggtggacaagaaagttgagcccaaatcttgt |
| 97 | GACATCCAGATGACACAGACTACATCCTCCCTGTCTGCCTCTCTGGGAGACAGAGTCACCATCAGTTGCAGGGCAAGTCAGGACATTAGTAAATATTTAA<br>ATTGGTATCAGCAGAAACCAGATGGAACTGTTAAACTCCTGATCTACCATACATCAAGATTACACTCAGGAGTCCCATCAAGGTTCAGTGGCAGTGGGTC<br>TGGAACAGATTATTCTCTCACCATTAGCAACCTGGAGCAAGAAGATATTGCCACTTACTTTTGCCAACAGGGTAATACGCTTCCGTACACGTTCGGAGGG<br>GGGACCAAGCTTGAGATCaaacgaactgtggctgcaccatctgtcttcatcttcccgccatctgatgagcagttgaaatctggaactgcctctgtcgtgt<br>gcctgctgaataacttctatcccagagaggccaaagtacagtggaaggtggataacgccctccaatcgggtaactcccaggagagtgtcacagagcagga<br>cagcAAGgacagcacctacagcctcagcagcaccctgacgctgagcaaagcagactacgagaaacacaaagtctacgcctgcgaagtcacccatcagggc<br>ctgtcctcgcccgtcacaaagagcttcaacaggggagagtgtGGCGGAGGCGGGAGCaattatcatcttgaaaatgaggtcgctcgtctcaagaaactc |

TABLE 51-continued

| Switch Antibody Chains | |
|---|---|
| SEQ ID NO | SEQUENCE |
| 98 | CTGCTGCCGAAAaattatcatcttgaaaatgaggtcgctcgtctcaagaaactcGGCGGAGGCGGGAGCGACATCCAGATGACACAGACTACATCCTCCC<br>TGTCTGCCTCTCTGGGAGACAGAGTCACCATCAGTTGCAGGGCAAGTCAGGACATTAGTAAATATTTAAATTGGTATCAGCAGAAACCAGATGGAACTGT<br>TAAACTCCTGATCTACCATACATCAAGATTACACTCAGGAGTCCCATCAAGGTTCAGTGGCAGTGGGTCTGGAACAGATTATTCTCTCACCATTAGCAAC<br>CTGGAGCAAGAAGATATTGCCACTTACTTTTGCCAACAGGGTAATACGCTTCCGTACACGTTCGGAGGGGGGACCAAGCTTGAGATCaaacgaactgtgg<br>ctgcaccatctgtcttcatcttcccgccatctgatgagcagttgaaatctggaactgcctctgtcgtgtgcctgctgaataacttctatcccagagaggc<br>caaagtacagtggaaggtggataacgccctccaatcgggtaactcccaggagagtgtcacagagcaggacagcAAGgacagcacctacagcctcagcagc<br>accctgacgctgagcaaagcagactacgagaaacacaaagtctacgcctgcgaagtcacccatcagggcctgtcctcgcccgtcacaaagagcttcaaca<br>ggggagagtgt |
| 99 | GACCTCCCCAAGCAGtatcatcttgaaaatgaggtcgctcgtctcaagaaactcGGCGGAGGCGGGAGCGACATCCAGATGACACAGACTACATCCTCCC<br>TGTCTGCCTCTCTGGGAGACAGAGTCACCATCAGTTGCAGGGCAAGTCAGGACATTAGTAAATATTTAAATTGGTATCAGCAGAAACCAGATGGAACTGT<br>TAAACTCCTGATCTACCATACATCAAGATTACACTCAGGAGTCCCATCAAGGTTCAGTGGCAGTGGGTCTGGAACAGATTATTCTCTCACCATTAGCAAC<br>CTGGAGCAAGAAGATATTGCCACTTACTTTTGCCAACAGGGTAATACGCTTCCGTACACGTTCGGAGGGGGGACCAAGCTTGAGATCaaacgaactgtgg<br>ctgcaccatctgtcttcatcttcccgccatctgatgagcagttgaaatctggaactgcctctgtcgtgtgcctgctgaataacttctatcccagagaggc<br>caaagtacagtggaaggtggataacgccctccaatcgggtaactcccaggagagtgtcacagagcaggacagcAAGgacagcacctacagcctcagcagc<br>accctgacgctgagcaaagcagactacgagaaacacaaagtctacgcctgcgaagtcacccatcagggcctgtcctcgcccgtcacaaagagcttcaaca<br>ggggagagtgt |
| 100 | aagaaaccaattgtccatattgcatcagacattgccgtcactgcgtcttttactggctcttctcgctaaccaaaccggtaaccctgattatttgcacgga<br>gtcacactttgctatgccatagcatttttatccataagattagcggatcctacctgacgctttttatcgcaactctctactgtttctccatacccgtttt<br>tttgggctagaaataattttgtttaactttaagaaggagaatacatcaactagtacgcaagttcacgtaaaaagggtatctagaggttgaggtgattta<br>tgaaaaagaatatcgcatttcttcttgctagcatgttcgtttttctattgctacaaacgcatacgctAACTACCATCTGGAAAACGAAGTTGCGCGCCT<br>GAAAAAACTGGGTGGCGGTGGCAGCGACATCCAGATGACACAGACTACATCCTCCCTGTCTGCCTCTCTGGGAGACAGAGTCACCATCAGTTGCAGGGCA<br>AGTCAGGACATTAGTAAATATTTAAATTGGTATCAGCAGAAACCAGATGGAACTGTTAAACTCCTGATCTACCATACATCAAGATTACACTCAGGAGTCC<br>CATCAAGGTTCAGTGGCAGTGGGTCTGGAACAGATTATTCTCTCACCATTAGCAACCTGGAGCAAGAAGATATTGCCACTTACTTTTGCCAACAGGGTAA<br>TACGCTTCCGTACACGTTCGGAGGGGGGACCAAGCTGGAGATCaaacgaactgtggctgcaccatctgtcttcatcttcccgccatctgatgagcagttg<br>aaatctggaactgcctctgtcgtgtgcctgctgaataacttctatcccagagaggccaaagtacagtggaaggtggataacgccctccaatcgggtaact<br>cccaggagagtgtcacagagcaggacagcaaggacagcacctacagcctcagcagcaccctgacgctgagcaaagcagactacgagaaacacaaagtcta<br>cgcctgcgaagtcacccatcagggcctgtcctcgcccgtcacaaagagcttcaacaggggagagtgttaagctggggatcctctagaggttgaggtgatt<br>ttatgaaaaagaatatcgcatttcttcttgcatctatgttcgtttttctattgctacaaacgcgtacgctGAGGTGAAACTGCAGGAGTCAGGACCTGG<br>CCTGGTGGCGCCCTCACAGAGCCTGTCCGTCACATGCACTGTCTCAGGGGTATCATTACCCGACTATGGTGTAAGCTGGATTCGCCAGCCTCCACGAAAG<br>GGTCTGGAGTGGCTGGGAGTAATATGGGGTAGTGAAACCACATACTATAATTCAGCTCTCAAATCCAGACTGACCATCATCAAGGACAACTCCAAGAGCC<br>AAGTTTTCTTAAAAATGAACAGTCTGCAAACTGATGACACAGCCATTTACTACTGTGCCAAACATTATTACTACGGTGGTAGCTATGCTATGGACTACTG<br>GGGCCAAGGAACCTCAGTCACCGTCTCCTCAgcctccaccaagggcccatcggtcttccccctggcaccctcctccaagagcacctctgggggcacagcg<br>gccctgggctgcctggtcaaggactacttccccgaaccggtgacggtgtcgtggaactcaggcgccctgaccagcggcgtgcacaccttcccggctgtcc<br>tacagtcctcaggactctactccctcagcagcgtggtgactgtgccctctagcagcttgggcacccagacctacatctgcaacgtgaatcacaagcccag<br>caacaccaaggtggacaagaaagttgagcccaaatcttgtgacaaaactcacacataataagtcgaccgatgcccttgagagccttcaacccagtcagct<br>ccttccggtgggcgcggggcatgactatcgtcgccgcacttatgactgtcttctttatcatgcaactcgtaggacaggtgccaaacggtctccagcttgg<br>ctgttttggcggatgagagaagattttcagcctgatacagattaaatcagaacgcagaagcggtctgataaaacagaatttgcctggcggcagtagcgcg<br>gtggtcccacctgaccccatgccgaactcagaagtgaaacgccgtagcgccgatggtagtgtggggtctccccatgcgagagtagggaactgccaggcat<br>caaataaaacgaaaggctcagtcgaaagactgggcctttcgttttatctgttgtttgtcggtgaacgctctcctgagtaggacaaatccgccgggagcgg<br>atttgaacgttgcgaagcaacggcccggagggtggcgggcaggacgcccgccataaactgccaggcatcaaattaagcagaaggccatcctgacggatgg<br>cctttttgcgtttctacaaactctttttgtttatttttctaaatacattcaaatatgtatccgctcatgagacaataaccctgataaatgcttcaataat<br>attgaaaaaggaagagtatgagtattcaacatttccgtgtcgcccttattcccttttttgcggcattttgccttcctgtttttgctcacccagaaacgct<br>ggtgaaagtaaaagatgctgaagatcagttgggtgcacgagtgggttacatcgaactggatctcaacagcggtaagatccttgagagttttcgccccgaa<br>gaacgttttccaatgatgagcacttttaaagttctgctatgtggcgcggtattatcccgtgttgacgccgggcaagagcaactcggtcgccgcatacact<br>attctcagaatgacttggttgagtactcaccagtcacagaaaagcatcttacggatggcatgacagtaagagaattatgcagtgctgccataaccatgag<br>tgataacactgcggccaacttacttctgacaacgatcggaggaccgaaggagctaaccgcttttttgcacaacatgggggatcatgtaactcgccttgat<br>cgttgggaaccggagctgaatgaagccataccaaacgacgagcgtgacaccacgatgcctgtagcaatggcaacaacgttgcgcaaactattaactggcg<br>aactacttactctagcttcccggcaacaattaatagactggatggaggcggataaagttgcaggaccacttctgcgctcggcccttccggctggctggtt<br>tattgctgataaatctggagccggtgagcgtgggtctcgcggtatcattgcagcactggggccagatggtaagccctcccgtatcgtagttatctacacg<br>acggggagtcaggcaactatggatgaacgaaatagacagatcgctgagataggtgcctcactgattaagcattggtaactgtcagaccaagtttactcat<br>atatactttagattgatttaaaacttcatttttaatttaaaaggatctaggtgaagatcctttttgataatctcatgaccaaaatcccttaacgtgagtt<br>ttcgttccactgagcgtcagaccccgtagaaaagatcaaaggatcttcttgagatcctttttttctgcgcgtaatctgctgcttgcaaacaaaaaaacca<br>ccgctaccagcggtggtttgtttgccggatcaagagctaccaactctttttccgaaggtaactggcttcagcagagcgcagataccaaatactgtccttc<br>tagtgtagccgtagttaggccaccacttcaagaactctgtagcaccgcctacatacctcgctctgctaatcctgttaccagtggctgctgccagtggcga<br>taagtcgtgtcttaccgggttggactcaagacgatagttaccggataaggcgcagcggtcgggctgaacggggggttcgtgcacacagcccagcttggag<br>cgaacgacctacaccgaactgagatacctacagcgtgagctatgagaaagcgccacgcttcccgaagggagaaaggcggacaggtatccggtaagcggca<br>gggtcggaacaggagagcgcacgagggagcttccagggggaaacgcctggtatctttatagtcctgtcgggtttcgccacctctgacttgagcgtcgatt<br>tttgtgatgctcgtcaggggggcggagcctatggaaaaacgccagcaacgcggcctttttacggttcctggccttttgctggccttttgctcacatgttc<br>tttcctgcgttatcccctgattctgtggataaccgtattaccgcctttgagtgagctgataccgctcgccgcagccgaacgaccgagcgcagcgagtcag<br>tgagcgaggaagcggaagagcgcctgatgcggtattttctccttacgcatctgtgcggtatttcacaccgcatatggtgcactctcagtacaatctgctc<br>tgatgccgcatagttaagccagtatacactccgctatcgctacgtgactgggtcatggctgcgccccgacacccgccaacacccgctgacgcgccctgac<br>gggcttgtctgctcccggcatccgcttacagacaagctgtgaccgtctccgggagctgcatgtgtcagaggttttcaccgtcatcaccgaaacgcgcgag<br>gcagcagatcaattcgcgcgcgaaggcgaagcggcatgcataatgtgcctgtcaaatggacgaagcagggattctgcaaaccctatgctactccgtcaag<br>ccgtcaattgtctgattcgttaccaattatgacaacttgacggctacatcattcacttttttcttcacaaccggcacggaactcgctcgggctggccccgg<br>tgcatttttaaatacccgcgagaaatagagttgatcgtcaaaaccaacattgcgaccgacggtggcgataggcatccgggtggtgctcaaaagcagctt<br>cgcctggctgatacgttggtcctcgcgccagcttaagacgctaatccctaactgctggcggaaaagatgtgacagacgcgacggcgacaagcaaacatgc<br>tgtgcgacgctggcgatatcaaaattgctgtctgccaggtgatcgctgatgtactgacaagcctcgcgtacccgattatccatcggtggatggagcgact<br>cgttaatcgcttccatgcgccgcagtaacaattgctcaagcagatttatcgccagcagctccgaatagcgcccttccccttgcccggcgttaatgatttg<br>cccaaacaggtcgctgaaatgcggctggtgcgcttcatccgggcgaaagaaccccgtattggcaaatattgacggccagttaagccattcatgccagtag<br>gcgcgcggacgaaagtaaacccactggtgataccattcgcgagcctccggatgacgaccgtagtgatgaatctctcctggcgggaacagcaaaatatcac<br>ccggtcggcaaacaaattctcgtccctgatttttcaccaccccctgaccgcgaatggtgagattgagaatataacctttcattcccagcggtcggtcgat |

TABLE 51-continued

Switch Antibody Chains

| SEQ ID NO | SEQUENCE |
|---|---|
| | aaaaaaatcgagataaccgttggcctcaatcggcgttaaacccgccaccagatgggcattaaacgagtatcccggcagcaggggatcattttgcgcttca<br>gccatacttttcatactcccgccattcagag |
| 101 | aagaaaccaattgtccatattgcatcagacattgccgtcactgcgtcttttactggctcttctcgctaaccaaaccggtaaccctgattatttgcacgga<br>gtcacactttgctatgccatagcatttttatccataagattagcggatcctacctgacgctttttatcgcaactctctactgtttctccatacccgtttt<br>tttgggctagaaataattttgtttaactttaagaaggagaatacatcaactagtacgcaagttcacgtaaaaagggtatctagaggttgaggtgattta<br>tgaaaaagaatatcgcatttcttcttgctagcatgttcgtttttctattgctacaaacgcatacgctAACTACCATCTGGAAAACGAAGTTGCGCGCCT<br>GAAAAAACTGGGTGGCGGTGGCAGCGATATTCAGATGACGCAGACCACCTCATCTCTCAGCGCGTCCTTAGGTGATCGCGTAACAATTTCCTGTCGTGCC<br>TCTCAGGATATTAGCAAGTACCTGAATTGGTATCAGCAGAAGCCTGATGGGACCGTTAAACTTCTCATTTATCACACTAGTCGTCTGCATTCGGGCGTTC<br>CATCCCGGTTCTCCGGTTCTGGTTCGGGCACTGACTACTCGTTAACCATCTCGAATCTGGAACAGGAGGATATTGCAACCTATTTTTGTCAGCAAGGTAA<br>TACGCTGCCGTACACGTTCGGCGGAGGTACGaagcttGAAATCAAACGCACCGTCGCGGCGCCGAGCGTGTTTATCTTCCCGCCGAGTGATGAACAGCTC<br>AAAAGCGGTACTGCCAGCGTTGTTTGCTTACTCAACAATTTTTATCCACGGGAGGCCAAAGTTCAATGGAAAGTTGACAACGCACTGCAGAGCGGTAACA<br>GTCAAGAATCTGTCACGGAGCAAGACTCGAAAGACAGCACCTACAGCTTATCCAGCACCCTGACGCTTTCGAAAGCGGACTACGAAAAGCACAAAGTTTA<br>TGCATGTGAAGTGACCCATCAGGGCCTTTCCTCACCGGTGACCAAATCATTTAACCGTGGCGAGTGCtaagctggggatcctctagaggttgaggtgatt<br>ttatgaaaaagaatatcgcatttcttcttgcatctatgttcgtttttctattgctacaaacgcgtacgctGAGGTTAAGTTGCAGGAGTCAGGCCCGGG<br>TTTAGTGGCACCTTCTCAGTCCTTGTCAGTGACATGCACGGTTAGCGGCGTGAGCTTGCCGGACTATGGCGTGAGCTGGATCCGCCAGCCCCCGCGCAAA<br>GGTCTGGAGTGGTTGGGCGTTATTTGGGGCTCCGAAACCACCTACTACAACAGCGCGTTGAAAAGTCGTCTGACGATCATTAAAGATAACTCGAAATCGC<br>AGGTTTTTCTGAAGATGAACTCCCTGCAGACCGATGATACAGCGATCTATTATTGCGCGAAACATTACTATTATGGCGGTAGTTACGCGATGGACTACTG<br>GGGTCAGGGAACGAGCGTAACCGTGTCATCGGCcAGCACTAAGGGCCCGAGCGTATTCCCGTTGGCTCCATCTTCTAAAAGTACCAGCGGGGGTACCGCG<br>GCGCTGGGCTGTTTAGTGAAAGACTATTTTCCTGAGCCCGTGACGGTTTCGTGGAACAGCGGTGCGCTGACCTCTGGTGTTCATACTTTTCCGGCCGTCT<br>TGCAGAGCTCTGGTTTATACAGCCTCTCAAGTGTGGTGACGGTACCTTCTAGCTCACTGGGTACTCAGACATATATTTGTAACGTTAACCACAAGCCGAG<br>CAACACCAAAGTCGATAAAAAAGTGGAACCTAAAAGCTGCGATAAAACCCATACGtaataagtcgaccgatgcccttgagagccttcaacccagtcagct<br>ccttccggtgggcgcggggcatgactatcgtcgccgcacttatgactgtcttctttatcatgcaactcgtaggacaggtgccaaacggtctccagcttgg<br>ctgttttggcggatgagagaagattttcagcctgatacagattaaatcagaacgcagaagcggtctgataaaacagaatttgcctggcggcagtagcgcg<br>gtggtcccacctgaccccatgccgaactcagaagtgaaacgccgtagcgccgatggtagtgtggggtctccccatgcgagagtagggaactgccaggcat<br>caaataaaacgaaaggctcagtcgaaagactgggcctttcgttttatctgttgtttgtcggtgaacgctctcctgagtaggacaaatccgccgggagcgg<br>atttgaacgttgcgaagcaacggcccggagggtggcgggcaggacgcccgccataaactgccaggcatcaaattaagcagaaggccatcctgacggatgg<br>cctttttgcgtttctacaaactcttttgtttatttttctaaatacattcaaatatgtatccgctcatgagacaataaccctgataaatgcttcaataat<br>attgaaaaaggaagagtatgagtattcaacatttccgtgtcgcccttattcccttttttgcggcattttgccttcctgtttttgctcacccagaaacgct<br>ggtgaaagtaaaagatgctgaagatcagttgggtgcacgagtgggttacatcgaactggatctcaacagcggtaagatccttgagagttttcgccccgaa<br>gaacgttttccaatgatgagcacttttaaagttctgctatgtggcgcggtattatcccgtgttgacgccgggcaagagcaactcggtcgccgcatacact<br>attctcagaatgacttggttgagtactcaccagtcacagaaaagcatcttacggatggcatgacagtaagagaattatgcagtgctgccataaccatgag<br>tgataacactgcggccaacttacttctgacaacgatcggaggaccgaaggagctaaccgcttttttgcacaacatgggggatcatgtaactcgccttgat<br>cgttgggaaccggagctgaatgaagccataccaaacgacgagcgtgacaccacgatgcctgtagcaatggcaacaacgttgcgcaaactattaactggcg<br>aactacttactctagcttcccggcaacaattaatagactggatggaggcggataaagttgcaggaccacttctgcgctcggcccttccggctggctggtt<br>tattgctgataaatctggagccggtgagcgtgggtctcgcggtatcattgcagcactggggccagatggtaagccctcccgtatcgtagttatctacacg<br>acggggagtcaggcaactatggatgaacgaaatagacagatcgctgagataggtgcctcactgattaagcattggtaactgtcagaccaagtttactcat<br>atatactttagattgatttaaaacttcatttttaatttaaaaggatctaggtgaagatcctttttgataatctcatgaccaaaatcccttaacgtgagtt<br>ttcgttccactgagcgtcagaccccgtagaaaagatcaaaggatcttcttgagatcctttttttctgcgcgtaatctgctgcttgcaaacaaaaaaacca<br>ccgctaccagcggtggtttgtttgccggatcaagagctaccaactctttttccgaaggtaactggcttcagcagagcgcagataccaaatactgtccttc<br>tagtgtagccgtagttaggccaccacttcaagaactctgtagcaccgcctacatacctcgctctgctaatcctgttaccagtggctgctgccagtggcga<br>taagtcgtgtcttaccgggttggactcaagacgatagttaccggataaggcgcagcggtcgggctgaacggggggttcgtgcacacagcccagcttggag<br>cgaacgacctacaccgaactgagatacctacagcgtgagctatgagaaagcgccacgcttcccgaagggagaaaggcggacaggtatccggtaagcggca<br>gggtcggaacaggagagcgcacgagggagcttccagggggaaacgcctggtatctttatagtcctgtcgggtttcgccacctctgacttgagcgtcgatt<br>tttgtgatgctcgtcaggggggcggagcctatggaaaaacgccagcaacgcggcctttttacggttcctggccttttgctggccttttgctcacatgttc<br>tttcctgcgttatcccctgattctgtggataaccgtattaccgcctttgagtgagctgataccgctcgccgcagccgaacgaccgagcgcagcgagtcag<br>tgagcgaggaagcggaagagcgcctgatgcggtattttctccttacgcatctgtgcggtatttcacaccgcatatggtgcactctcagtacaatctgctc<br>tgatgccgcatagttaagccagtatacactccgctatcgctacgtgactgggtcatggctgcgccccgacacccgccaacacccgctgacgcgccctgac<br>gggcttgtctgctcccggcatccgcttacagacaagctgtgaccgtctccgggagctgcatgtgtcagaggttttcaccgtcatcaccgaaacgcgcgag<br>gcagcagatcaattcgcgcgcgaaggcgaagcggcatgcataatgtgcctgtcaaatggacgaagcagggattctgcaaaccctatgctactccgtcaag<br>ccgtcaattgtctgattcgttaccaattatgacaacttgacggctacatcattcactttttcttcacaaccggcacggaactcgctcgggctggccccgg<br>tgcatttttaaatacccgcgagaaatagagttgatcgtcaaaaccaacattgcgaccgacggtggcgataggcatccgggtggtgctcaaaagcagctt<br>cgcctggctgatacgttggtcctcgcgccagcttaagacgctaatccctaactgctggcggaaaagatgtgacagacgcgacggcgacaagcaaacatgc<br>tgtgcgacgctggcgatatcaaaattgctgtctgccaggtgatcgctgatgtactgacaagcctcgcgtacccgattatccatcggtggatggagcgact<br>cgttaatcgcttccatgcgccgcagtaacaattgctcaagcagatttatcgccagcagctccgaatagcgcccttccccttgcccggcgttaatgatttg<br>cccaaacaggtcgctgaaatgcggctggtgcgcttcatccgggcgaaagaaccccgtattggcaaatattgacggccagttaagccattcatgccagtag<br>gcgcgcggacgaaagtaaacccactggtgataccattcgcgagcctccggatgacgaccgtagtgatgaatctctcctggcgggaacagcaaaatatcac<br>ccggtcggcaaacaaattctcgtccctgatttttcaccaccccctgaccgcgaatggtgagattgagaatataacctttcattcccagcggtcggtcgat<br>aaaaaaatcgagataaccgttggcctcaatcggcgttaaacccgccaccagatgggcattaaacgagtatcccggcagcaggggatcattttgcgcttca<br>gccatacttttcatactcccgccattcagag |
| 102 | aattatcatcttgaaaatgaggtcgctcgtctcaagaaactcctggttggcgaggccgcagctaaggaagccgcagctaaagccGATATCCAGCTGCAGG<br>AGTCCGGACCAGGTCTGGTGAAGCCCAGCCAGTCCCTGTCTCTGACCTGCAGCGTCACTGGCTATTCCATCACCAGTGCATACTATTGGAACTGGATCAG<br>ACAGTTCCCTGGAAACAAACTGGAGTGGATGGGGTACATCTCTTACGACGGTAGAAACAACTACAACCCCAGCCTCAAAAACAGGATTAGCATTACCCGC<br>GACACTAGTAAGAACCAGTTTTTCCTGAAGCTCAACAGTGTGACAACTGAGGACACTGCTACTTATTATTGTGCCAAGGAGGGCGACTATGATGTCGGCA<br>ATTATTACGCTATGGACTATTGGGGTCAGGGGACTAGCGTGACCGTCAGTTCTGCCAGGACCAAAGGACCGTCCGTCTTTCCTCTGGCCCCTTCCTCTAA<br>GTCCACAAGCGGTGGGACCGCAGCACTGGGATGCCTGGTGAAGGATTACTTCCCTGAGCCGGTGACCGTGTCCTGGAACTCCGGAGCTCTCACCTCCGGT<br>GTCCATACCTTTCCTGCCGTCCTGCAGTCCTCCGGCCTGTACAGCCTCTCTAGCGTCGTGACTGTGCCCTCCAGCTCCCTGGGCACCCAAACTTATATCT<br>GCAATGTTAACCACAAGCCTTCTAATACCAAGGTCGACAAGAAAGTGGAGCCGAAGAGCTGT |
| 103 | aactatcacctggaaaacgaagtggcaaggctgaaaaaactgggcgggggcggaagtGAAAACGTGCTCACCCAGAGTCCCGCCATCATGAGCGCCAGTC<br>CCGGCGAGAAGGTGACCATGACCTGTAGGGCCTCTTCCAATGTGATCTCTAGCTACGTGCATTGGTACCAGCAGCGTAGTGGGGCCAGCCCTAAGCTCTG<br>GATTTACTCCACCTCCAACCTGGCCTCCGGGGTCCCCGCCCGTTTCTCTGGCAGTGGCTCTGGTACCTCTTACTCCCTGACTATCAGCAGCGTCGAGGCC<br>GAGGATGCCGCTACATACTACTGTCAGCAGTACAGTGGATACCCTCTGACCTTCGGGGCTGGCACCAAGCTGGAGCTGAAGCGCGCTGCCGCCGCCCCCA |

TABLE 51-continued

Switch Antibody Chains

| SEQ ID NO | SEQUENCE |
|---|---|
| | GTGTCTTCATTTTCCCCCCTTCCGATGAGCAGCTGAAGAGCGGTACAGCCTCTGTTGTTTGTCTGCTGAACAACTTCTATCCACGCGAGGCCAAGGTGCA GTGGAAAGTTGATAACGCGCTGCAGAGTGGCAACTCCCAGGAGTCTGTGACAGAGCAGGACAGTAAAGACAGCACATATTCCCTGTCTAGCACACTGACT CTGTCCAAGGCTGACTATGAGAAGCACAAGGTGTACGCTTGCGAGGTCACCCACCAGGGACTGAGTTCTCCTGTGACCAAGTCCTTCAATCGCGGCGAGT GT |
| 104 | GATATCCAGCTGCAGGAGTCCGGACCAGGTCTGGTGAAGCCCAGCCAGTCCCTGTCTCTGACCTGCAGCGTCACTGGCTATTCCATCACCAGTGCATACT ATTGGAACTGGATCAGACAGTTCCCTGGAAACAAACTGGAGTGGATGGGGTACATCTCTTACGACGGTAGAAACAACTACAACCCCAGCCTCAAAAACAG GATTAGCATTACCCGCGACACTAGTAAGAACCAGTTTTTCCTGAAGCTCAACAGTGTGACAACTGAGGACACTGCTACTTATTATTGTGCCAAGGAGGGC GACTATGATGTCGGCAATTATTACGCTATGGACTATTGGGGTCAGGGGACTAGCGTGACCGTCAGTTCTGCCAGGACCAAAGGACCGTCCGTCTTTCCTC TGGCCCCTTCCTCTAAGTCCACAAGCGGTGGGACCGCAGCACTGGGATGCCTGGTGAAGGATTACTTCCCTGAGCCGGTGACCGTGTCCTGGAACTCCGG AGCTCTCACCTCCGGTGTCCATACCTTTCCTGCCGTCCTGCAGTCCTCCGGCCTGTACAGCCTCTCTAGCGTCGTGACTGTGCCCTCCAGCTCCCTGGGC ACCCAAACTTATATCTGCAATGTTAACCACAAGCCTTCTAATACCAAGGTCGACAAGAAAGTGGAGCCGAAGAGCTGTGGCGGAGGCGGGAGCaattatc atcttgaaaatgaggtcgctcgtctcaagaaactc |
| 105 | GAAAACGTGCTCACCCAGAGTCCCGCCATCATGAGCGCCAGTCCCGGCGAGAAGGTGACCATGACCTGTAGGGCCTCTTCCAATGTGATCTCTAGCTACG TGCATTGGTACCAGCAGCGTAGTGGGGCCAGCCCTAAGCTCTGGATTTACTCCACCTCCAACCTGGCCTCCGGGGTCCCCGCCCGTTTCTCTGGCAGTGG CTCTGGTACCTCTTACTCCCTGACTATCAGCAGCGTCGAGGCCGAGGATGCCGCTACATACTACTGTCAGCAGTACAGTGGATACCCTCTGACCTTCGGG GCTGGCACCAAGCTGGAGCTGAAGCGCGCTGCCGCCGCCCCCAGTGTCTTCATTTTCCCCCCTTCCGATGAGCAGCTGAAGAGCGGTACAGCCTCTGTTG TTTGTCTGCTGAACAACTTCTATCCACGCGAGGCCAAGGTGCAGTGGAAAGTTGATAACGCGCTGCAGAGTGGCAACTCCCAGGAGTCTGTGACAGAGCA GGACAGTAAAGACAGCACATATTCCCTGTCTAGCACACTGACTCTGTCCAAGGCTGACTATGAGAAGCACAAGGTGTACGCTTGCGAGGTCACCCACCAG GGACTGAGTTCTCCTGTGACCAAGTCCTTCAATCGCGGCGAGTGTGGCGGAGGCGGGAGCaattatcatcttgaaaatgaggtcgctcgtctcaagaaac tc |
| 106 | caggtacagctgcagcagtcaggtccaggactggtgaagccctcgcagaccctctcactcacctgtgccatctccggggacagtgtctctagcaacagtg ctgcttggaactggatcaggcagtccccatcgagaggccttgagtggctgggaaggacatactacaggtccaagtggtataatgattatgcagtatctgt gaaaagtcgaataaccatcaacccagacacatccaagaaccagttctccctgcagctgaactctgtgactcccgaggacacggctgtgtattactgtgca agagaagtgactggggatctcgaggatgcttttgatatctggggccaagggacaatggtcaccgtctcctcagcctccaccaagggcccatcggtcttcc ccctggcaccctcctccaagagcacctctgggggcacagcggccctgggctgcctggtcaaggactacttccccgaaccggtgacggtgtcgtggaactc aggcgccctgaccagcggcgtgcacaccttcccggctgtcctacagtcctcaggactctactccctcagcagcgtggtgactgtgccctctagcagcttg ggcacccagacctacatctgcaacgtgaatcacaagcccagcaacaccaaggtggacaagaaagttgagcccaaatcttgt |
| 107 | gacatccagatgacccagtctccatcgtccctgtctgcatctgtaggagacagagtcaccatcacttgccgggcaagccagaccatttggagctacttaa attggtatcagcagagaccagggaaagcccctaacctcctgatctatgctgcatccagtttgcaaagtggggtcccatcaaggttcagtggcaggggatc tgggacagatttcactctcaccatcagcagtctgcaagctgaagattttgcaacttactactgtcaacagagttacagtatccctcagacttttggccag gggaccaagctggagatcaaacgaactgtggctgcaccatctgtcttcatcttcccgccatctgatgagcagttgaaatctggaactgcctctgtcgtgt gcctgctgaataacttctatcccagagaggccaaagtacagtggaaggtggataacgccctccaatcgggtaactcccaggagagtgtcacagagcagga cagcaaggacagcacctacagcctcagcagcaccctgacgctgagcaaagcagactacgagaaacacaaagtctacgcctgcgaagtcacccatcagggc ctgtcctcgcccgtcacaaagagcttcaacaggggagagtgt |
| 108 | aattatcatcttgaaaatgaggtcgctcgtctcaagaaactcctggttggcgaggccgcagctaaggaagccgcagctaaagcccaggtacagctgcagc agtcaggtccaggactggtgaagccctcgcagaccctctcactcacctgtgccatctccggggacagtgtctctagcaacagtgctgcttggaactggat caggcagtccccatcgagaggccttgagtggctgggaaggacatactacaggtccaagtggtataatgattatgcagtatctgtgaaaagtcgaataacc atcaacccagacacatccaagaaccagttctccctgcagctgaactctgtgactcccgaggacacggctgtgtattactgtgcaagagaagtgactgggg atctcgaggatgcttttgatatctggggccaagggacaatggtcaccgtctcctcagcctccaccaagggcccatcggtcttccccctggcaccctcctc caagagcacctctgggggcacagcggccctgggctgcctggtcaaggactacttccccgaaccggtgacggtgtcgtggaactcaggcgccctgaccagc ggcgtgcacaccttcccggctgtcctacagtcctcaggactctactccctcagcagcgtggtgactgtgccctctagcagcttgggcacccagacctaca tctgcaacgtgaatcacaagcccagcaacaccaaggtggacaagaaagttgagcccaaatcttgt |
| 109 | aactatcacctggaaaacgaagtggcaaggctgaaaaaactgggcgggggcggaagtgacatccagatgacccagtctccatcgtccctgtctgcatctg taggagacagagtcaccatcacttgccgggcaagccagaccatttggagctacttaaattggtatcagcagagaccagggaaagcccctaacctcctgat ctatgctgcatccagtttgcaaagtggggtcccatcaaggttcagtggcaggggatctgggacagatttcactctcaccatcagcagtctgcaagctgaa gattttgcaacttactactgtcaacagagttacagtatccctcagacttttggccaggggaccaagctggagatcaaacgaactgtggctgcaccatctg tcttcatcttcccgccatctgatgagcagttgaaatctggaactgcctctgtcgtgtgcctgctgaataacttctatcccagagaggccaaagtacagtg gaaggtggataacgccctccaatcgggtaactcccaggagagtgtcacagagcaggacagcaaggacagcacctacagcctcagcagcaccctgacgctg agcaaagcagactacgagaaacacaaagtctacgcctgcgaagtcacccatcagggcctgtcctcgcccgtcacaaagagcttcaacaggggagagtgt |
| 110 | caggtacagctgcagcagtcaggtccaggactggtgaagccctcgcagaccctctcactcacctgtgccatctccggggacagtgtctctagcaacagtg ctgcttggaactggatcaggcagtccccatcgagaggccttgagtggctgggaaggacatactacaggtccaagtggtataatgattatgcagtatctgt gaaaagtcgaataaccatcaacccagacacatccaagaaccagttctccctgcagctgaactctgtgactcccgaggacacggctgtgtattactgtgca agagaagtgactggggatctcgaggatgcttttgatatctggggccaagggacaatggtcaccgtctcctcagcctccaccaagggcccatcggtcttcc ccctggcaccctcctccaagagcacctctgggggcacagcggccctgggctgcctggtcaaggactacttccccgaaccggtgacggtgtcgtggaactc aggcgccctgaccagcggcgtgcacaccttcccggctgtcctacagtcctcaggactctactccctcagcagcgtggtgactgtgccctctagcagcttg ggcacccagacctacatctgcaacgtgaatcacaagcccagcaacaccaaggtggacaagaaagttgagcccaaatcttgtGGCGGAGGCGGGAGCaatt atcatcttgaaaatgaggtcgctcgtctcaagaaactc |
| 111 | gacatccagatgacccagtctccatcgtccctgtctgcatctgtaggagacagagtcaccatcacttgccgggcaagccagaccatttggagctacttaa attggtatcagcagagaccagggaaagcccctaacctcctgatctatgctgcatccagtttgcaaagtggggtcccatcaaggttcagtggcaggggatc tgggacagatttcactctcaccatcagcagtctgcaagctgaagattttgcaacttactactgtcaacagagttacagtatccctcagacttttggccag gggaccaagctggagatcaaacgaactgtggctgcaccatctgtcttcatcttcccgccatctgatgagcagttgaaatctggaactgcctctgtcgtgt gcctgctgaataacttctatcccagagaggccaaagtacagtggaaggtggataacgccctccaatcgggtaactcccaggagagtgtcacagagcagga cagcaaggacagcacctacagcctcagcagcaccctgacgctgagcaaagcagactacgagaaacacaaagtctacgcctgcgaagtcacccatcagggc ctgtcctcgcccgtcacaaagagcttcaacaggggagagtgtGGCGGAGGCGGGAGCaattatcatcttgaaaatgaggtcgctcgtctcaagaaactc |

TABLE 51-continued

Switch Antibody Chains

| SEQ ID NO | SEQUENCE |
|---|---|
| 112 | GAGGTGCAACTCGTTCAGAGCGGGGGCGGCGTCGTCAGGCCTGGCGGCTCCCTCCGTCTGCCTTGTGCTGCCTCCGGCTTTACCTTCGACGATTACGGAATGTCCTGGGTTCGCCAGGCTCCTGGCAAGGGTCTGGAGTGGGTCTCTGGCATCAACTGGAATGGCGGCAGCACCGGTTATGCTGACAGTGTGAAGGGGAGGTTCACAATTAGCCGGGACAATGCCAAGAACAGCCTGTACCTGCAGATGAACTCCCTGCGTGCTGAGGACACCGCTCTGTATCACTGCGCGAGAGGCGGTGACGACGCCTTTGACATTTGGGGCCAGGGTACCATGGTTACAGTGAGCTCTGCTAGCACCAAGGGCCCGAGCGTCTTCCCTCTGGCCCCCAGCTCTAAATCTACTTCCGGGGGCACCGCCGCCCTCGGGTGCCTGGTGAAGGACTATTTCCCTGAGCCTGTGACAGTGAGCTGGAACTCCGGAGCATTGACTTCTGGTGTGCACACTTTCCCCGCTGTGCTGCAGTCCTCTGGACTGTATTCCCTGTCCTCCGTGGTGACTGTCCCAAGCTCCTCTCTGGGGACACAGACATACATCTGTAATGTGAACCACAAACCGTCCAACACTAAGGTGGACAAGAAAGTGGAACCAAAGTCTTGT |
| 113 | CGGATCGTTATGACACAGTCCCCGGGCACCCTGAGCGTCAGCCCCGGAGAGACCGCTACACTCTCCTGCAGGGCCTCCCAGTCTTTTAGCAACATGCTCGCGTGGTACCAACAGAAGAGCGGACAACCACCTCGCCTGCTCATTTATGGCGTTTCTACCCGGGCAGCTGGGGTGCCTGCGCGGTTCTCTGGCTCCGGGTCCGGAACTGAGTTTACTCTGACAATTAGCAACCTCCAATCCGAGGACTTTGCTGTCTACTACTGTCAACAATACGGAGACTGGCCGCGCTACACCTTTGGCCAAGGGACTAAAGTGGAAAGAAAGCGTACAGTTGCCGCTCCTAGCGTCTTCATCTTCCCCCCCTCTGATGAGCAGTTGAAGTCCGGAACCGCCTCCGTGGTGTGTCTGCTGAACAACTTCTACCCCCGCGAGGCTAAGGTGCAGTGGAAGGTCGATAACGCCTTGCAATCTGGGAACTCTCAGGAAAGCGTGACAGAGCAGGACTCCAAAGACAGCACCTATAGCCTGAGCTCTACTCTGACCCTGAGCAAGGCTGACTACGAGAAACATAAGGTTTACGCATGCGAGGTGACCCACCAGGGACTGAGTAGTCCTGTCACCAAGAGTTTCAATCGTGGCGAATGT |
| 114 | aattatcatcttgaaaatgaggtcgctcgtctcaagaaactcctggttggcgaggccgcagctaaggaagccgcagctaaagccGAGGTGCAACTCGTTCAGAGCGGGGGCGGCGTCGTCAGGCCTGGCGGCTCCCTCCGTCTGCCTTGTGCTGCCTCCGGCTTTACCTTCGACGATTACGGAATGTCCTGGGTTCGCCAGGCTCCTGGCAAGGGTCTGGAGTGGGTCTCTGGCATCAACTGGAATGGCGGCAGCACCGGTTATGCTGACAGTGTGAAGGGGAGGTTCACAATTAGCCGGGACAATGCCAAGAACAGCCTGTACCTGCAGATGAACTCCCTGCGTGCTGAGGACACCGCTCTGTATCACTGCGCGAGAGGCGGTGACGACGCCTTTGACATTTGGGGCCAGGGTACCATGGTTACAGTGAGCTCTGCTAGCACCAAGGGCCCGAGCGTCTTCCCTCTGGCCCCCAGCTCTAAATCTACTTCCGGGGGCACCGCCGCCCTCGGGTGCCTGGTGAAGGACTATTTCCCTGAGCCTGTGACAGTGAGCTGGAACTCCGGAGCATTGACTTCTGGTGTGCACACTTTCCCCGCTGTGCTGCAGTCCTCTGGACTGTATTCCCTGTCCTCCGTGGTGACTGTCCCAAGCTCCTCTCTGGGGACACAGACATACATCTGTAATGTGAACCACAAACCGTCCAACACTAAGGTGGACAAGAAAGTGGAACCAAAGTCTTGT |
| 115 | aactatcacctggaaaacgaagtggcaaggctgaaaaaactgggcgggggcggaagtCGGATCGTTATGACACAGTCCCCGGGCACCCTGAGCGTCAGCCCCGGAGAGACCGCTACACTCTCCTGCAGGGCCTCCCAGTCTTTTAGCAACATGCTCGCGTGGTACCAACAGAAGAGCGGACAACCACCTCGCCTGCTCATTTATGGCGTTTCTACCCGGGCAGCTGGGGTGCCTGCGCGGTTCTCTGGCTCCGGGTCCGGAACTGAGTTTACTCTGACAATTAGCAACCTCCAATCCGAGGACTTTGCTGTCTACTACTGTCAACAATACGGAGACTGGCCGCGCTACACCTTTGGCCAAGGGACTAAAGTGGAAAGAAAGCGTACAGTTGCCGCTCCTAGCGTCTTCATCTTCCCCCCCTCTGATGAGCAGTTGAAGTCCGGAACCGCCTCCGTGGTGTGTCTGCTGAACAACTTCTACCCCCGCGAGGCTAAGGTGCAGTGGAAGGTCGATAACGCCTTGCAATCTGGGAACTCTCAGGAAAGCGTGACAGAGCAGGACTCCAAAGACAGCACCTATAGCCTGAGCTCTACTCTGACCCTGAGCAAGGCTGACTACGAGAAACATAAGGTTTACGCATGCGAGGTGACCCACCAGGGACTGAGTAGTCCTGTCACCAAGAGTTTCAATCGTGGCGAATGT |
| 116 | GAGGTGCAACTCGTTCAGAGCGGGGGCGGCGTCGTCAGGCCTGGCGGCTCCCTCCGTCTGCCTTGTGCTGCCTCCGGCTTTACCTTCGACGATTACGGAATGTCCTGGGTTCGCCAGGCTCCTGGCAAGGGTCTGGAGTGGGTCTCTGGCATCAACTGGAATGGCGGCAGCACCGGTTATGCTGACAGTGTGAAGGGGAGGTTCACAATTAGCCGGGACAATGCCAAGAACAGCCTGTACCTGCAGATGAACTCCCTGCGTGCTGAGGACACCGCTCTGTATCACTGCGCGAGAGGCGGTGACGACGCCTTTGACATTTGGGGCCAGGGTACCATGGTTACAGTGAGCTCTGCTAGCACCAAGGGCCCGAGCGTCTTCCCTCTGGCCCCCAGCTCTAAATCTACTTCCGGGGGCACCGCCGCCCTCGGGTGCCTGGTGAAGGACTATTTCCCTGAGCCTGTGACAGTGAGCTGGAACTCCGGAGCATTGACTTCTGGTGTGCACACTTTCCCCGCTGTGCTGCAGTCCTCTGGACTGTATTCCCTGTCCTCCGTGGTGACTGTCCCAAGCTCCTCTCTGGGGACACAGACATACATCTGTAATGTGAACCACAAACCGTCCAACACTAAGGTGGACAAGAAAGTGGAACCAAAGTCTTGT |
| 117 | CGGATCGTTATGACACAGTCCCCGGGCACCCTGAGCGTCAGCCCCGGAGAGACCGCTACACTCTCCTGCAGGGCCTCCCAGTCTTTTAGCAACATGCTCGCGTGGTACCAACAGAAGAGCGGACAACCACCTCGCCTGCTCATTTATGGCGTTTCTACCCGGGCAGCTGGGGTGCCTGCGCGGTTCTCTGGCTCCGGGTCCGGAACTGAGTTTACTCTGACAATTAGCAACCTCCAATCCGAGGACTTTGCTGTCTACTACTGTCAACAATACGGAGACTGGCCGCGCTACACCTTTGGCCAAGGGACTAAAGTGGAAAGAAAGCGTACAGTTGCCGCTCCTAGCGTCTTCATCTTCCCCCCCTCTGATGAGCAGTTGAAGTCCGGAACCGCCTCCGTGGTGTGTCTGCTGAACAACTTCTACCCCCGCGAGGCTAAGGTGCAGTGGAAGGTCGATAACGCCTTGCAATCTGGGAACTCTCAGGAAAGCGTGACAGAGCAGGACTCCAAAGACAGCACCTATAGCCTGAGCTCTACTCTGACCCTGAGCAAGGCTGACTACGAGAAACATAAGGTTTACGCATGCGAGGTGACCCACCAGGGACTGAGTAGTCCTGTCACCAAGAGTTTCAATCGTGGCGAATGTGGCGGAGGCGGGAGCaattatcatcttgaaaatgaggtcgctcgtctcaagaaactc |
| 118 | GAAGTGCAACTGCAGCAGTCCGGGACTGTGCTGGCCCGTCCCGGAGCAAGCGTCAAGATGAGCTGTAAGGCGTCTGGGTACAGGTTCACCAATTACTGGATCCACTGGGTGAAACAAAGGCCAGGTCAGGGTCTGGAATGGATTGGTGGCATCAACCCAGGAAATAACTATACCACTTACAAACGTAACCTGAAAGGCAAGGCCACCCTGACTGCCGTTACAAGCGCCAGCACTGCTTATATGGATCTGAGCAGTCTCACCTCCGAGGATTCCGCTGTGTACTACTGCACACGCGAAGGCTACGGTAACTATGGCGCCTGGTTCGCCTACTGGGGCCAGGGCACCTTGGTTACCGTGTCCTCTGCGTCCACCAAGGGACCAAGCGTGTTTCCCCTCGCCCCAAGCAGCAAGAGCACTTCTGGCGGCACTGCGGCTTTGGGCTGCCTGGTCAAAGATTACTTTCCCGAGCCCGTTACCGTGAGCTGGAACTCCGGAGCTCTGACCTCCGGCGTTCATACCTTTCCGGCGGTGCTGCAGTCCTCTGGCCTGTATTCTCTGTCCTCTGTCGTCACCGTTCCTTCCTCCTCCCTCGGAACCCAAACCTACATCTGTAACGTGAACCACAAACCCTCTAACACAAAGGTTGACAAGAAGGTTGAGCCAAAATCCTGT |
| 119 | GATGTGGTCGTGACCCAGACTCCACTGTCTCTGCCTGTGAGTTTCGGTGACCAAGTCAGCATTTCTTGCAGAAGTTCTCAATCCCTGGCTAACTCTTACGGTAACACCTTTCTGTCTTGGTATCTGGACAAACCTGGCGAGAGCCCTCAGCTGCTGATCTACGGCATCAGCAACCGGTTCAGCGGTGTCCCCGACCGCTTCACCGGTTCTGGCTCCGGCACTGACTTCACACTGAAGATCTCTACTATCAAACCAGAAGACTTGGGCATGTACTATTGTTTGGAAGGCACCCACCAGCCATATACTTTCGGTGGCGGCACAAAGCTGGAGATCAAACGCACCGTCGCCGCCCCTTCCGTGTTCATCTTTCCTCCTTCCGACGAACAGCTGAAGAGTGGCACAGCATCTGTGGTCTGCCTGCTGAACAATTTCTACCCTAGAGAGGCCAAGGTCCAGTGGAAGGTGGACAATGCACTCCAGTCCGGGAACTCTCAGGAGAGTGTGACAGAGCAGGATTCTAAGGATTCCACTTACTCCCTGAGCTCTACATTGACTCTGTCCAAAGCCGACTACGAAAAGCATAAGGTTTACGCGTGTGAAGTGACCCACCAGGGCCTGTCCAGCCCTGTGACCAAGAGTTTTAACCGGGGGGAGTGC |
| 120 | aattatcatcttgaaaatgaggtcgctcgtctcaagaaactcctggttggcgaggccgcagctaaggaagccgcagctaaagccGAAGTGCAACTGCAGCAGTCCGGGACTGTGCTGGCCCGTCCCGGAGCAAGCGTCAAGATGAGCTGTAAGGCGTCTGGGTACAGGTTCACCAATTACTGGATCCACTGGGTGAAACAAAGGCCAGGTCAGGGTCTGGAATGGATTGGTGGCATCAACCCAGGAAATAACTATACCACTTACAAACGTAACCTGAAAGGCAAGGCCACCCTGACTGCCGTTACAAGCGCCAGCACTGCTTATATGGATCTGAGCAGTCTCACCTCCGAGGATTCCGCTGTGTACTACTGCACACGCGAAGGCTACGGTAACTATGGCGCCTGGTTCGCCTACTGGGGCCAGGGCACCTTGGTTACCGTGTCCTCTGCGTCCACCAAGGGACCAAGCGTGTTTCCCCTCGCCCCAAGCAGCAAGAGCAC |

TABLE 51-continued

| Switch Antibody Chains | |
|---|---|
| SEQ ID NO | SEQUENCE |
| | TTCTGGCGGCACTGCGGCTTTGGGCTGCCTGGTCAAAGATTACTTTCCCGAGCCCGTTACCGTGAGCTGGAACTCCGGAGCTCTGACCTCCGGCGTTCATACCTTTCCGGCGGTGCTGCAGTCCTCTGGCCTGTATTCTCTGTCCTCTGTCGTCACCGTTCCTTCCTCCTCCCTCGGAACCCAAACCTACATCTGTAACGTGAACCACAAACCCTCTAACACAAAGGTTGACAAGAAGGTTGAGCCAAAATCCTGT |
| 121 | aactatcacctggaaaacgaagtggcaaggctgaaaaaactgggcgggggcggaagtGATGTGGTCGTGACCCAGACTCCACTGTCTCTGCCTGTGAGTTTCGGTGACCAAGTCAGCATTTCTTGCAGAAGTTCTCAATCCCTGGCTAACTCTTACGGTAACACCTTTCTGTCTTGGTATCTGGACAAACCTGGCGAGAGCCCTCAGCTGCTGATCTACGGCATCAGCAACCGGTTCAGCGGTGTCCCCGACCGCTTCACCGGTTCTGGCTCCGGCACTGACTTCACACTGAAGATCTCTACTATCAAACCAGAAGACTTGGGCATGTACTATTGTTTGGAAGGCACCCACCAGCCATATACTTTCGGTGGCGGCACAAAGCTGGAGATCAAACGCACCGTCGCCGCCCCTTCCGTGTTCATCTTTCCTCCTTCCGACGAACAGCTGAAGAGTGGCACAGCATCTGTGGTCTGCCTGCTGAACAATTTCTACCCTAGAGAGGCCAAGGTCCAGTGGAAGGTGGACAATGCACTCCAGTCCGGGAACTCTCAGGAGAGTGTGACAGAGCAGGATTCTAAGGATTCCACTTACTCCCTGAGCTCTACATTGACTCTGTCCAAAGCCGACTACGAAAAGCATAAGGTTTACGCGTGTGAAGTGACCCACCAGGGCCTGTCCAGCCCTGTGACCAAGAGTTTTAACCGGGGGGAGTGC |
| 122 | GAAGTGCAACTGCAGCAGTCCGGGACTGTGCTGGCCCGTCCCGGAGCAAGCGTCAAGATGAGCTGTAAGGCGTCTGGGTACAGGTTCACCAATTACTGGATCCACTGGGTGAAACAAAGGCCAGGTCAGGGTCTGGAATGGATTGGTGGCATCAACCCAGGAAATAACTATACCACTTACAAACGTAACCTGAAAGGCAAGGCCACCCTGACTGCCGTTACAAGCGCCAGCACTGCTTATATGGATCTGAGCAGTCTCACCTCCGAGGATTCCGCTGTGTACTACTGCACACGCGAAGGCTACGGTAACTATGGCGCCTGGTTCGCCTACTGGGGCCAGGGCACCTTGGTTACCGTGTCCTCTGCGTCCACCAAGGGACCAAGCGTGTTTCCCCTCGCCCCAAGCAGCAAGAGCACTTCTGGCGGCACTGCGGCTTTGGGCTGCCTGGTCAAAGATTACTTTCCCGAGCCCGTTACCGTGAGCTGGAACTCCGGAGCTCTGACCTCCGGCGTTCATACCTTTCCGGCGGTGCTGCAGTCCTCTGGCCTGTATTCTCTGTCCTCTGTCGTCACCGTTCCTTCCTCCTCCCTCGGAACCCAAACCTACATCTGTAACGTGAACCACAAACCCTCTAACACAAAGGTTGACAAGAAGGTTGAGCCAAAATCCTGTGGCGGAGGCGGGAGCaattatcatcttgaaaatgaggtcgctcgtctcaagaaactctaa |
| 123 | GATGTGGTCGTGACCCAGACTCCACTGTCTCTGCCTGTGAGTTTCGGTGACCAAGTCAGCATTTCTTGCAGAAGTTCTCAATCCCTGGCTAACTCTTACGGTAACACCTTTCTGTCTTGGTATCTGGACAAACCTGGCGAGAGCCCTCAGCTGCTGATCTACGGCATCAGCAACCGGTTCAGCGGTGTCCCCGACCGCTTCACCGGTTCTGGCTCCGGCACTGACTTCACACTGAAGATCTCTACTATCAAACCAGAAGACTTGGGCATGTACTATTGTTTGGAAGGCACCCACCAGCCATATACTTTCGGTGGCGGCACAAAGCTGGAGATCAAACGCACCGTCGCCGCCCCTTCCGTGTTCATCTTTCCTCCTTCCGACGAACAGCTGAAGAGTGGCACAGCATCTGTGGTCTGCCTGCTGAACAATTTCTACCCTAGAGAGGCCAAGGTCCAGTGGAAGGTGGACAATGCACTCCAGTCCGGGAACTCTCAGGAGAGTGTGACAGAGCAGGATTCTAAGGATTCCACTTACTCCCTGAGCTCTACATTGACTCTGTCCAAAGCCGACTACGAAAAGCATAAGGTTTACGCGTGTGAAGTGACCCACCAGGGCCTGTCCAGCCCTGTGACCAAGAGTTTTAACCGGGGGGAGTGCGGCGGAGGCGGGAGCaattatcatcttgaaaatgaggtcgctcgtctcaagaaactc |
| 124 | aattatcatcttgaaaatgaggtcgctcgtctcaagaaactcctggttggcgaggccgcagctaaggaagccgcagctaaagcccaggtgcagctgcagcagccgggcgcggaactggtgaaaccgggcgcgagcgtgaaaatgagctgcaaagcgagcggctatacctttaccagctataacatgcattgggtgaaacagaccccgggccgcggcctggaatggattggcgcgatttatccgggcaacggcgataccagctataaccagaaatttaaaggcaaagcgaccctgaccgcggataaaagcagcagcaccgcgtatatgcagctgagcagcctgaccagcgaagatagcgcggtgtattattgcgcgcgcagcacctattatggcggcgattggtattttaacgtgtggggcgcgggcaccaccgtgaccgtgagcgcggcgagcaccaagggcccatcggtcttccccctggcaccctcctccaagagcacctctgggggcacagcggccctgggctgcctggtcaaggactacttccccgaaccggtgacggtgtcgtggaactcaggcgccctgaccagcggcgtgcacaccttcccggctgtcctacagtcctcaggactctactccctcagcagcgtggtgactgtgccctctagcagcttgggcacccagacctacatctgcaacgtgaatcacaagcccagcaacaccaaggtggacaagaaagttgagcccaaatcttgt |
| 125 | aactatcacctggaaaacgaagtggcaaggctgaaaaaactgggcgggggcggaagtcagattgtgctgagccagagcccggcgattctgagcgcgagcccgggcgaaaaagtgaccatgacctgccgcgcgagcagcagcgtgagctatattcattggtttcagcagaaaccgggcagcagcccgaaaccgtggatttatgcgaccagcaacctggcgagcggcgtgccggtgcgctttagcggcagcggcagcggcaccagctatagcctgaccattagccgcgtggaagcggaagatgcggcgacctattattgccagcagtggaccagcaacccgccgacctttggcggcggcaccaagcttgagatcaaacgaactgtggctgcaccatctgtcttcatcttcccgccatctgatgagcagttgaaatctggaactgcctctgtcgtgtgcctgctgaataacttctatcccagagaggccaaagtacagtggaaggtggataacgccctccaatcgggtaactcccaggagagtgtcacagagcaggacagcaaggacagcacctacagcctcagcagcaccctgacgctgagcaaagcagactacgagaaacacaaagtctacgcctgcgaagtcacccatcagggcctgtcctcgcccgtcacaaagagcttcaacaggggagagtgt |
| 126 | caggtgcagctgcagcagccgggcgcggaactggtgaaaccgggcgcgagcgtgaaaatgagctgcaaagcgagcggctatacctttaccagctataacatgcattgggtgaaacagaccccgggccgcggcctggaatggattggcgcgatttatccgggcaacggcgataccagctataaccagaaatttaaaggcaaagcgaccctgaccgcggataaaagcagcagcaccgcgtatatgcagctgagcagcctgaccagcgaagatagcgcggtgtattattgcgcgcgcagcacctattatggcggcgattggtattttaacgtgtggggcgcgggcaccaccgtgaccgtgagcgcggcgagcaccaagggcccatcggtcttccccctggcaccctcctccaagagcacctctgggggcacagcggccctgggctgcctggtcaaggactacttccccgaaccggtgacggtgtcgtggaactcaggcgccctgaccagcggcgtgcacaccttcccggctgtcctacagtcctcaggactctactccctcagcagcgtggtgactgtgccctctagcagcttgggcacccagacctacatctgcaacgtgaatcacaagcccagcaacaccaaggtggacaagaaagttgagcccaaatcttgtGGCGGAGGCGGGAGCaattatcatcttgaaaatgaggtcgctcgtctcaagaaactc |
| 127 | cagattgtgctgagccagagcccggcgattctgagcgcgagcccgggcgaaaaagtgaccatgacctgccgcgcgagcagcagcgtgagctatattcattggtttcagcagaaaccgggcagcagcccgaaaccgtggatttatgcgaccagcaacctggcgagcggcgtgccggtgcgctttagcggcagcggcagcggcaccagctatagcctgaccattagccgcgtggaagcggaagatgcggcgacctattattgccagcagtggaccagcaacccgccgacctttggcggcggcaccaagcttgagatcaaacgaactgtggctgcaccatctgtcttcatcttcccgccatctgatgagcagttgaaatctggaactgcctctgtcgtgtgcctgctgaataacttctatcccagagaggccaaagtacagtggaaggtggataacgccctccaatcgggtaactcccaggagagtgtcacagagcaggacagcaaggacagcacctacagcctcagcagcaccctgacgctgagcaaagcagactacgagaaacacaaagtctacgcctgcgaagtcacccatcagggcctgtcctcgcccgtcacaaagagcttcaacaggggagagtgtGGCGGAGGCGGGAGCaattatcatcttgaaaatgaggtcgctcgtctcaagaaactc |
| 128 | CAAGTGCAGCTCGTGCAGAGTGGCGCAGAGGTGAAGAAACCTGGCTCAAGTGTTAAGGTGTCCTGTAAGGCTAGTGGCTACGCTTTTTCTTACAGTTGGATCAACTGGGTTCGCCAAGCCCCCGGGCAGGGATTGGAATGGATGGGCAGGATCTTTCCAGGCGATGGAGACACTGACTATAACGGCAAGTTTAAGGGCAGGGTGACAATCACGGCGGACAAAAGCACAAGCACTGCCTACATGGAGCTGAGCTCACTGCGGTCAGAGGACACGGCTGTATATTACTGCGCCAGGAACGTGTTCGATGGCTACTGGCTGGTGTATTGGGGGCAGGGCACGCTTGTGACTGTTAGCAGCGCAAGTACTAAGGGTCCATCAGTGTTCCCACTGGCTCCATCCTCTAAGTCAACGTCTGGCGGTACAGCAGCTCTTGGCTGTCTCGTTAAGGACTATTTTCCGGAGCCTGTGACCGTCAGTTGGAATTCTGGCGCACTGACGTCAGGAGTGCATACTTTTCCTGCCGTCCTGCAGAGTTCCGGACTGTACAGCCTTTCCTCCGTCGTGACTGTTCCATCCAGCAGCCTGGGAACCCAGACCTATATTTGTAACGTGAACCACAAGCCCTCAAACACCAAGGTTGACAAGAAGGTGGAGCCTAAGAGTTGT |

TABLE 51-continued

Switch Antibody Chains

| SEQ ID NO | SEQUENCE |
| --- | --- |
| 129 | GATATAGTAATGACACAAACGCCTCTGTCTCTTCCTGTCACGCCCGGCGAACCAGCCTCCATATCCTGCAGATCATCTAAAAGTCTTCTCCACTCCAACGGAATTACGTATTTGTACTGGTATTTGCAGAAGCCTGGGCAGTCTCCCCAACTGCTGATTTATCAGATGTCTAACTTGGTAAGCGGGGTGCCCGATAGGTTTTCAGGGTCCGGAAGCGGCACAGATTTCACGCTGAAGATCAGCAGAGTGGAAGCCGAGGACGTGGGCGTGTATTATTGCGCGCAGAATTTGGAGCTCCCATATACCTTCGGAGGTGGGACCAAGGTAGAAATCAAGCGAACTGTCAGGACTGTCGCTGCCCCGAGCGTTTTCATCTTCCCCCCGTCTGACGAACAGCTTAAAAGCGGCACTGCAAGCGTGGTGTGCCTGCTTAACAATTTCTATCCCAGAGAAGCGAAGGTTCAGTGGAAGGTGGATAACGCCCTGCAATCTGGCAATAGCCAGGAGTCCGTTACAGAACAAGATTCAAAAGACTCAACGTACTCTCTGTCCTCCACACTGACCCTGAGCAAAGCTGATTACGAAAAACATAAGGTTTACGCCTGCGAGGTCACACACCAGGGGCTTTCTAGTCCGGTGACTAAATCTTTTAACCGCGGGGAATGT |
| 130 | aattatcatcttgaaaatgaggtcgctcgtctcaagaaactcctggttggcgaggccgcagctaaggaagccgcagctaaagccCAAGTGCAGCTCGTGCAGAGTGGCGCAGAGGTGAAGAAACCTGGCTCAAGTGTTAAGGTGTCCTGTAAGGCTAGTGGCTACGCTTTTTCTTACAGTTGGATCAACTGGGTTCGCCAAGCCCCCGGGCAGGGATTGGAATGGATGGGCAGGATCTTTCCAGGCGATGGAGACACTGACTATAACGGCAAGTTTAAGGGCAGGGTGACAATCACGGCGGACAAAAGCACAAGCACTGCCTACATGGAGCTGAGCTCACTGCGGTCAGAGGACACGGCTGTATATTACTGCGCCAGGAACGTGTTCGATGGCTACTGGCTGGTGTATTGGGGGCAGGGCACGCTTGTGACTGTTAGCAGCGCAAGTACTAAGGGTCCATCAGTGTTCCCACTGGCTCCATCCTCTAAGTCAACGTCTGGCGGTACAGCAGCTCTTGGCTGTCTCGTTAAGGACTATTTTCCGGAGCCTGTGACCGTCAGTTGGAATTCTGGCGCACTGACGTCAGGAGTGCATACTTTTCCTGCCGTCCTGCAGAGTTCCGGACTGTACAGCCTTTCCTCCGTCGTGACTGTTCCATCCAGCAGCCTGGGAACCCAGACCTATATTTGTAACGTGAACCACAAGCCCTCAAACACCAAGGTTGACAAGAAGGTGGAGCCTAAGAGTTGT |
| 131 | aactatcacctggaaaacgaagtggcaaggctgaaaaaactgggcgggggcggaagtGATATAGTAATGACACAAACGCCTCTGTCTCTTCCTGTCACGCCCGGCGAACCAGCCTCCATATCCTGCAGATCATCTAAAAGTCTTCTCCACTCCAACGGAATTACGTATTTGTACTGGTATTTGCAGAAGCCTGGGCAGTCTCCCCAACTGCTGATTTATCAGATGTCTAACTTGGTAAGCGGGGTGCCCGATAGGTTTTCAGGGTCCGGAAGCGGCACAGATTTCACGCTGAAGATCAGCAGAGTGGAAGCCGAGGACGTGGGCGTGTATTATTGCGCGCAGAATTTGGAGCTCCCATATACCTTCGGAGGTGGGACCAAGGTAGAAATCAAGCGAACTGTCAGGACTGTCGCTGCCCCGAGCGTTTTCATCTTCCCCCCGTCTGACGAACAGCTTAAAAGCGGCACTGCAAGCGTGGTGTGCCTGCTTAACAATTTCTATCCCAGAGAAGCGAAGGTTCAGTGGAAGGTGGATAACGCCCTGCAATCTGGCAATAGCCAGGAGTCCGTTACAGAACAAGATTCAAAAGACTCAACGTACTCTCTGTCCTCCACACTGACCCTGAGCAAAGCTGATTACGAAAAACATAAGGTTTACGCCTGCGAGGTCACACACCAGGGGCTTTCTAGTCCGGTGACTAAATCTTTTAACCGCGGGGAATGT |
| 132 | CAAGTGCAGCTCGTGCAGAGTGGCGCAGAGGTGAAGAAACCTGGCTCAAGTGTTAAGGTGTCCTGTAAGGCTAGTGGCTACGCTTTTTCTTACAGTTGGATCAACTGGGTTCGCCAAGCCCCCGGGCAGGGATTGGAATGGATGGGCAGGATCTTTCCAGGCGATGGAGACACTGACTATAACGGCAAGTTTAAGGGCAGGGTGACAATCACGGCGGACAAAAGCACAAGCACTGCCTACATGGAGCTGAGCTCACTGCGGTCAGAGGACACGGCTGTATATTACTGCGCCAGGAACGTGTTCGATGGCTACTGGCTGGTGTATTGGGGGCAGGGCACGCTTGTGACTGTTAGCAGCGCAAGTACTAAGGGTCCATCAGTGTTCCCACTGGCTCCATCCTCTAAGTCAACGTCTGGCGGTACAGCAGCTCTTGGCTGTCTCGTTAAGGACTATTTTCCGGAGCCTGTGACCGTCAGTTGGAATTCTGGCGCACTGACGTCAGGAGTGCATACTTTTCCTGCCGTCCTGCAGAGTTCCGGACTGTACAGCCTTTCCTCCGTCGTGACTGTTCCATCCAGCAGCCTGGGAACCCAGACCTATATTTGTAACGTGAACCACAAGCCCTCAAACACCAAGGTTGACAAGAAGGTGGAGCCTAAGAGTTGTGGCGGAGGCGGGAGCaattatcatcttgaaaatgaggtcgctcgtctcaagaaactc |
| 133 | GATATAGTAATGACACAAACGCCTCTGTCTCTTCCTGTCACGCCCGGCGAACCAGCCTCCATATCCTGCAGATCATCTAAAAGTCTTCTCCACTCCAACGGAATTACGTATTTGTACTGGTATTTGCAGAAGCCTGGGCAGTCTCCCCAACTGCTGATTTATCAGATGTCTAACTTGGTAAGCGGGGTGCCCGATAGGTTTTCAGGGTCCGGAAGCGGCACAGATTTCACGCTGAAGATCAGCAGAGTGGAAGCCGAGGACGTGGGCGTGTATTATTGCGCGCAGAATTTGGAGCTCCCATATACCTTCGGAGGTGGGACCAAGGTAGAAATCAAGCGAACTGTCAGGACTGTCGCTGCCCCGAGCGTTTTCATCTTCCCCCCGTCTGACGAACAGCTTAAAAGCGGCACTGCAAGCGTGGTGTGCCTGCTTAACAATTTCTATCCCAGAGAAGCGAAGGTTCAGTGGAAGGTGGATAACGCCCTGCAATCTGGCAATAGCCAGGAGTCCGTTACAGAACAAGATTCAAAAGACTCAACGTACTCTCTGTCCTCCACACTGACCCTGAGCAAAGCTGATTACGAAAAACATAAGGTTTACGCCTGCGAGGTCACACACCAGGGGCTTTCTAGTCCGGTGACTAAATCTTTTAACCGCGGGGAATGTGGCGGAGGCGGGAGCaattatcatcttgaaaatgaggtcgctcgtctcaagaaactc |
| 134 | GAGGTGCAGCTGGTCGAGTCAGGCGGAGGCCTGGTTCAGCCAGGGAGATCCCTCAGGCTTTCCTGCGCCGCCTCCGGTTTTACCTTCAACGACTACGCTATGCACTGGGTTCGCCAGGCTCCCGGAAAGGGACTTGAATGGGTGAGCACTATCAGCTGGAATTCTGGAAGCATTGGGTATGCCGACTCCGTCAAGGGCCGCTTTACTATTTCTCGGGATAATGCGAAGAAGTCTCTGTACCTGCAGATGAACAGTCTTCGGGCAGAAGACACGGCTCTTTACTATTGCGCAAAAGACATCCAGTACGGAAACTATTATTACGGAATGGATGTGTGGGGTCAGGGCACCACTGTGACAGTAAGCAGTGCTAGTACAAAGGGACCTTCTGTGTTTCCACTTGCTCCTAGCTCCAAATCCACGTCCGGGGGCACTGCCGCTCTGGGCTGCCTCGTTAAAGATTACTTCCCAGAGCCTGTCACTGTGTCCTGGAATTCCGGCGCCCTTACGTCAGGGGTACACACATTTCCCGCGGTACTCCAGTCAAGCGGCTTGTACAGCCTGTCCTCCGTAGTGACAGTGCCTTCCTCTTCTCTCGGCACTCAAACTTACATCTGCAATGTCAATCACAAACCGAGTAACACTAAGGTTGACAAGAAAGTTGAACCTAAGAGCTGT |
| 135 | GAAATCGTCCTGACGCAGTCACCTGCAACCCTGAGTCTCAGCCCTGGTGAGCGGGCCACCCTGAGCTGCAGGGCCAGCCAGAGTGTATCTTCTTACCTGGCTTGGTATCAGCAGAAACCAGGACAGGCCCCAAGACTGCTGATCTACGACGCTTCCAATAGAGCCACGGGCATCCCTGCCCGATTTTCCGGATCAGGGTCCGGTACAGATTTCACGCTGACCATCAGCTCCCTCGAGCCCGAAGATTTTGCTGTGTATTATTGCCAGCAGCGGTCCAATTGGCCCATTACCTTCGGTCAGGGGACCAGGCTGGAGATTAAACGGACCGTGGCTGCTCCCTCAGTTTTCATCTTTCCCCCATCTGATGAGCAGCTGAAGTCCGGGACCGCAAGCGTCGTGTGCCTCCTTAACAATTTTTACCCACGAGAAGCTAAGGTTCAGTGGAAGGTGGATAATGCTCTCCAGTCCGGTAATTCTCAGGAATCAGTGACCGAACAGGATAGCAAAGATTCTACCTATAGCTTGTCATCAACTCTGACCCTCTCCAAAGCCGACTACGAGAAACACAAAGTCTACGCATGCGAGGTGACTCACCAAGGTCTGAGTTCACCCGTTACTAAAAGCTTTAACAGAGGAGAATGT |
| 136 | aattatcatcttgaaaatgaggtcgctcgtctcaagaaactcctggttggcgaggccgcagctaaggaagccgcagctaaagccGAGGTGCAGCTGGTCGAGTCAGGCGGAGGCCTGGTTCAGCCAGGGAGATCCCTCAGGCTTTCCTGCGCCGCCTCCGGTTTTACCTTCAACGACTACGCTATGCACTGGGTTCGCCAGGCTCCCGGAAAGGGACTTGAATGGGTGAGCACTATCAGCTGGAATTCTGGAAGCATTGGGTATGCCGACTCCGTCAAGGGCCGCTTTACTATTTCTCGGGATAATGCGAAGAAGTCTCTGTACCTGCAGATGAACAGTCTTCGGGCAGAAGACACGGCTCTTTACTATTGCGCAAAAGACATCCAGTACGGAAACTATTATTACGGAATGGATGTGTGGGGTCAGGGCACCACTGTGACAGTAAGCAGTGCTAGTACAAAGGGACCTTCTGTGTTTCCACTTGCTCCTAGCTCCAAATCCACGTCCGGGGGCACTGCCGCTCTGGGCTGCCTCGTTAAAGATTACTTCCCAGAGCCTGTCACTGTGTCCTGGAATTCCGGCGCCCTTACGTCAGGGGTACACACATTTCCCGCGGTACTCCAGTCAAGCGGCTTGTACAGCCTGTCCTCCGTAGTGACAGTGCCTTCCTCTTCTCTCGGCACTCAAACTTACATCTGCAATGTCAATCACAAACCGAGTAACACTAAGGTTGACAAGAAAGTTGAACCTAAGAGCTGT |
| 137 | aactatcacctggaaaacgaagtggcaaggctgaaaaaactgggcgggggcggaagtGAAATCGTCCTGACGCAGTCACCTGCAACCCTGAGTCTCAGCCCTGGTGAGCGGGCCACCCTGAGCTGCAGGGCCAGCCAGAGTGTATCTTCTTACCTGGCTTGGTATCAGCAGAAACCAGGACAGGCCCCAAGACTGCTGATCTACGACGCTTCCAATAGAGCCACGGGCATCCCTGCCCGATTTTCCGGATCAGGGTCCGGTACAGATTTCACGCTGACCATCAGCTCCCTCGAGCCCGAAGATTTTGCTGTGTATTATTGCCAGCAGCGGTCCAATTGGCCCATTACCTTCGGTCAGGGGACCAGGCTGGAGATTAAACGGACCGTGGCTGCTCCCTCAGTTTTCATCTTTCCCCCATCTGATGAGCAGCTGAAGTCCGGGACCGCAAGCGTCGTGTGCCTCCTTAACAATTTTTACCCACGAGAAGCTAAGGTTCAGTG |

TABLE 51-continued

| Switch Antibody Chains | |
|---|---|
| SEQ ID NO | SEQUENCE |
| | GAAGGTGGATAATGCTCTCCAGTCCGGTAATTCTCAGGAATCAGTGACCGAACAGGATAGCAAAGATTCTACCTATAGCTTGTCATCAACTCTGACCCTC<br>TCCAAAGCCGACTACGAGAAACACAAAGTCTACGCATGCGAGGTGACTCACCAAGGTCTGAGTTCACCCGTTACTAAAAGCTTTAACAGAGGAGAATGT |
| 138 | GAGGTGCAGCTGGTCGAGTCAGGCGGAGGCCTGGTTCAGCCAGGGAGATCCCTCAGGCTTTCCTGCGCCGCCTCCGGTTTTACCTTCAACGACTACGCTA<br>TGCACTGGGTTCGCCAGGCTCCCGGAAAGGGACTTGAATGGGTGAGCACTATCAGCTGGAATTCTGGAAGCATTGGGTATGCCGACTCCGTCAAGGGCCG<br>CTTTACTATTTCTCGGGATAATGCGAAGAAGTCTCTGTACCTGCAGATGAACAGTCTTCGGGCAGAAGACACGGCTCTTTACTATTGCGCAAAAGACATC<br>CAGTACGGAAACTATTATTACGGAATGGATGTGTGGGGTCAGGGCACCACTGTGACAGTAAGCAGTGCTAGTACAAAGGGACCTTCTGTGTTTCCACTTG<br>CTCCTAGCTCCAAATCCACGTCCGGGGGCACTGCCGCTCTGGGCTGCCTCGTTAAAGATTACTTCCCAGAGCCTGTCACTGTGTCCTGGAATTCCGGCGC<br>CCTTACGTCAGGGGTACACACATTTCCCGCGGTACTCCAGTCAAGCGGCTTGTACAGCCTGTCCTCCGTAGTGACAGTGCCTTCCTCTTCTCTCGGCACT<br>CAAACTTACATCTGCAATGTCAATCACAAACCGAGTAACACTAAGGTTGACAAGAAAGTTGAACCTAAGAGCTGTGGCGGAGGCGGAGCaattatcatc<br>ttgaaaatgaggtcgctcgtctcaagaaactc |
| 139 | GAAATCGTCCTGACGCAGTCACCTGCAACCCTGAGTCTCAGCCCTGGTGAGCGGGCCACCCTGAGCTGCAGGGCCAGCCAGAGTGTATCTTCTTACCTGG<br>CTTGGTATCAGCAGAAACCAGGACAGGCCCCAAGACTGCTGATCTACGACGCTTCCAATAGAGCCACGGGCATCCCTGCCCGATTTTCCGGATCAGGGTC<br>CGGTACAGATTTCACGCTGACCATCAGCTCCCTCGAGCCCGAAGATTTTGCTGTGTATTATTGCCAGCAGCGGTCCAATTGGCCCATTACCTTCGGTCAG<br>GGGACCAGGCTGGAGATTAAACGGACCGTGGCTGCTCCCTCAGTTTTCATCTTTCCCCCATCTGATGAGCAGCTGAAGTCCGGGACCGCAAGCGTCGTGT<br>GCCTCCTTAACAATTTTTACCCACGAGAAGCTAAGGTTCAGTGGAAGGTGGATAATGCTCTCCAGTCCGGTAATTCTCAGGAATCAGTGACCGAACAGGA<br>TAGCAAAGATTCTACCTATAGCTTGTCATCAACTCTGACCCTCTCCAAAGCCGACTACGAGAAACACAAAGTCTACGCATGCGAGGTGACTCACCAAGGT<br>CTGAGTTCACCCGTTACTAAAAGCTTTAACAGAGGAGAATGTGGCGGAGGCGGAGCaattatcatcttgaaaatgaggtcgctcgtctcaagaaactc |
| 140 | aattatcatcttgaaaatgaggtcgctcgtctcaagaaactcctggttggcgaggccgcagctaaggaagccgcagctaaagccgaagtgcagctggtgg<br>agtctggcggaggactggtgcagccaggggggcagcctgagactgtcttgcgccgcctccggcttcaacatcaaggacacctacatccactgggtccgcca<br>ggcaccaggcaagggactggaatgggtggcccggatctaccctaccaacggctacaccagatacgccgactccgtgaagggccggttcaccatctccgcc<br>gacacctccaagaacaccgcctacctgcagatgaattccctgagggccgaggacaccgccgtgtactactgctccagatggggaggcgacggcttctacg<br>ccatggactactggggccagggcaccctggtcacagtgtcctctgctagcaccaagggcccatcggtcttccccctggcaccctcctccaagagcacctc<br>tgggggcacagcggccctgggctgcctggtcaaggactacttccccgaaccggtgacggtgtcgtggaactcaggcgccctgaccagcggcgtgcacacc<br>ttcccggctgtcctacagtcctcaggactctactccctcagcagcgtggtgaccgtgccctccagcagcttgggcacccagacctacatctgcaacgtga<br>atcacaagcccagcaacaccaaggtggacaagaaagttgagcccaaatcttgt |
| 141 | aactatcacctggaaaacgaagtggcaaggctgaaaaaactgggcgggggcggaagtgacatccagatgacccagtcccccctcctccctgtctgcctccg<br>tgggcgacagagtgaccatcacctgtcgggcctcccaggatgtgaacaccgccgtggcctggtatcagcagaagcctggcaaggcccctaagctgctgat<br>ctactccgcctccttcctgtactccggcgtgccctcccggttctccggctccagatccggcaccgacttcaccctgaccatctccagcctgcagcctgag<br>gacttcgccacctactactgccagcagcactacaccacccctccaaccttcggccagggcaccaaggtggagatcaagcgtacggtggctgcaccatctg<br>tcttcatcttcccgccatctgatgagcagttgaaatctggaactgcctctgttgtgtgcctgctgaataacttctatcccagagaggccaaagtacagtg<br>gaaggtggataacgccctccaatcgggtaactcccaggagagtgtcacagagcaggacagcaaggacagcacctacagcctcagcagcaccctgacgctg<br>agcaaagcagactacgagaaacacaaagtctacgcctgcgaagtcacccatcagggcctgagctcgcccgtcacaaagagcttcaacaggggagagtgt |
| 142 | gaagtgcagctggtggagtctggcggaggactggtgcagccaggggggcagcctgagactgtcttgcgccgcctccggcttcaacatcaaggacacctaca<br>tccactgggtccgccaggcaccaggcaagggactggaatgggtggcccggatctaccctaccaacggctacaccagatacgccgactccgtgaagggccg<br>gttcaccatctccgccgacacctccaagaacaccgcctacctgcagatgaattccctgagggccgaggacaccgccgtgtactactgctccagatgggga<br>ggcgacggcttctacgccatggactactggggccagggcaccctggtcacagtgtcctctgctagcaccaagggcccatcggtcttccccctggcaccct<br>cctccaagagcacctctgggggcacagcggccctgggctgcctggtcaaggactacttccccgaaccggtgacggtgtcgtggaactcaggcgccctgac<br>cagcggcgtgcacaccttcccggctgtcctacagtcctcaggactctactccctcagcagcgtggtgaccgtgccctccagcagcttgggcacccagacc<br>tacatctgcaacgtgaatcacaagcccagcaacaccaaggtggacaagaaagttgagcccaaatcttgtGGCGGAGGCGGAGCaattatcatcttgaaa<br>atgaggtcgctcgtctcaagaaactc |
| 143 | gacatccagatgacccagtcccccctcctccctgtctgcctccgtgggcgacagagtgaccatcacctgtcgggcctcccaggatgtgaacaccgccgtgg<br>cctggtatcagcagaagcctggcaaggcccctaagctgctgatctactccgcctccttcctgtactccggcgtgccctcccggttctccggctccagatc<br>cggcaccgacttcaccctgaccatctccagcctgcagcctgaggacttcgccacctactactgccagcagcactacaccacccctccaaccttcggccag<br>ggcaccaaggtggagatcaagcgtacggtggctgcaccatctgtcttcatcttcccgccatctgatgagcagttgaaatctggaactgcctctgttgtgt<br>gcctgctgaataacttctatcccagagaggccaaagtacagtggaaggtggataacgccctccaatcgggtaactcccaggagagtgtcacagagcagga<br>cagcaaggacagcacctacagcctcagcagcaccctgacgctgagcaaagcagactacgagaaacacaaagtctacgcctgcgaagtcacccatcagggc<br>ctgagctcgcccgtcacaaagagcttcaacaggggagagtgtGGCGGAGGCGGAGCaattatcatcttgaaaatgaggtcgctcgtctcaagaaactc |
| 144 | GAAGTTCAGCTGGTTGAATCTGGTGGTGGTCTGGTTCAGCCGGGTGGTTCTCTGCGTCTGTCTTGCGCTGCTTCTGGTTTCACCTTCTCTAACTTCGACA<br>TGGCTTGGGTTCGTCAGGCTCCGGGTAAAGGTCTGGTTTGGGTTTCTTCTATCACCACCGGTGGTGGTGACACCTACTACGCTGACTCTGTTAAAGGTCG<br>TTTCACCATCTCTCGTGACAACGCTAAATCTACCCTGTACCTGCAGATGGACTCTCTGCGTTCTGAAGACACCGCTGTTTACTACTGCGTTCGTCACGGT<br>TACTACGACGGTTACCACCTGTTCGACTACTGGGGTCAGGGTACCCTGGTTACCGTTTCTTCTgcctccaccaagggcccatcggtcttccccctggcac<br>cctcctccaagagcacctctgggggcacagcggccctgggctgcctggtcaaggactacttccccgaaccggtgacggtgtcgtggaactcaggcgccct<br>gaccagcggcgtgcacaccttcccggctgtcctacagtcctcaggactctactccctcagcagcgtggtgactgtgccctctagcagcttgggcacccag<br>acctacatctgcaacgtgaatcacaagcccagcaacaccaaggtggacaagaaagttgagcccaaatcttgt |
| 145 | aactaccacctggagaatgaagtcgccagactgaagaaactgggcgggggaggctcaGACATCCAGATGACCCAGTCTCCGTCTTCTCTGTCTGCTTCTG<br>TTGGTGACCGTGTTACCATCACCTGCCGTGCTAACCAGGGTATCTCTAACAACCTGAACTGGTACCAGCAGAAACCGGGTAAAGCTCCGAAACCGCTGAT<br>CTACTACACCTCTAACCTGCAGTCTGGTGTTCCGTCTCGTTTCTCTGGTTCTGGTTCTGGTACCGACTACACCCTGACCATCTCTTCTCTGCAGCCGGAA<br>GACTTCGCTACCTACTACTGCCAGCAGTTCACCTCTCTGCCGTACACCTTCGGTCAGGGTACCAAACTGGAAATCAAAcgaactgtggctgcaccatctg<br>tcttcatcttcccgccatctgatgagcagttgaaatctggaactgcctctgtcgtgtgcctgctgaataacttctatcccagagaggccaaagtacagtg<br>gaaggtggataacgccctccaatcgggtaactcccaggagagtgtcacagagcaggacagcaaagacagcacctacagcctcagcagcaccctgacgctg<br>agcaaagcagactacgagaaacacaaagtctacgcctgcgaagtcacccatcagggcctgtcctcgcccgtcacaaagagcttcaacaggggagagtgt |
| 146 | aactaccacctggagaatgaagtcgccagactgaagaaactgggcgggggaggctcagggggaggcgggtcaGACATCCAGATGACCCAGTCTCCGTCTT<br>CTCTGTCTGCTTCTGTTGGTGACCGTGTTACCATCACCTGCCGTGCTAACCAGGGTATCTCTAACAACCTGAACTGGTACCAGCAGAAACCGGGTAAAGC<br>TCCGAAACCGCTGATCTACTACACCTCTAACCTGCAGTCTGGTGTTCCGTCTCGTTTCTCTGGTTCTGGTTCTGGTACCGACTACACCCTGACCATCTCT<br>TCTCTGCAGCCGGAAGACTTCGCTACCTACTACTGCCAGCAGTTCACCTCTCTGCCGTACACCTTCGGTCAGGGTACCAAACTGGAAATCAAAcgaactg |

TABLE 51-continued

Switch Antibody Chains

| SEQ ID NO | SEQUENCE |
|---|---|
| | tggctgcaccatctgtcttcatcttcccgccatctgatgagcagttgaaatctggaactgcctctgtcgtgtgcctgctgaataacttctatcccagaga<br>ggccaaagtacagtggaaggtggataacgccctccaatcgggtaactcccaggagagtgtcacagagcaggacagcaaagacagcacctacagcctcagc<br>agcaccctgacgctgagcaaagcagactacgagaaacacaaagtctacgcctgcgaagtcacccatcagggcctgtcctcgcccgtcacaaagagcttca<br>acaggggagagtgt |
| 147 | aactaccacctggagaatgaagtcgccagactgaagaaactgggcgggggaggctcaGAAGTTCAGCTGGTTGAATCTGGTGGTGGTCTGGTTCAGCCGG<br>GTGGTTCTCTGCGTCTGTCTTGCGCTGCTTCTGGTTTCACCTTCTCTAACTTCGACATGGCTTGGGTTCGTCAGGCTCCGGGTAAAGGTCTGGTTTGGGT<br>TTCTTCTATCACCACCGGTGGTGGTGACACCTACTACGCTGACTCTGTTAAAGGTCGTTTCACCATCTCTCGTGACAACGCTAAATCTACCCTGTACCTG<br>CAGATGGACTCTCTGCGTTCTGAAGACACCGCTGTTTACTACTGCGTTCGTCACGGTTACTACGACGGTTACCACCTGTTCGACTACTGGGGTCAGGGTA<br>CCCTGGTTACCGTTTCTTCTgcctccaccaagggcccatcggtcttccccctggcaccctcctccaagagcacctctgggggcacagcggccctgggctg<br>cctggtcaaggactacttccccgaaccggtgacggtgtcgtggaactcaggcgccctgaccagcggcgtgcacaccttcccggctgtcctacagtcctca<br>ggactctactccctcagcagcgtggtgactgtgccctctagcagcttgggcacccagacctacatctgcaacgtgaatcacaagcccagcaacaccaagg<br>tggacaagaaagttgagcccaaatcttgt |
| 148 | aactaccacctggagaatgaagtcgccagactgaagaaactgggcgggggaggctcagggggaggcgggtcaGAAGTTCAGCTGGTTGAATCTGGTGGTG<br>GTCTGGTTCAGCCGGGTGGTTCTCTGCGTCTGTCTTGCGCTGCTTCTGGTTTCACCTTCTCTAACTTCGACATGGCTTGGGTTCGTCAGGCTCCGGGTAA<br>AGGTCTGGTTTGGGTTTCTTCTATCACCACCGGTGGTGGTGACACCTACTACGCTGACTCTGTTAAAGGTCGTTTCACCATCTCTCGTGACAACGCTAAA<br>TCTACCCTGTACCTGCAGATGGACTCTCTGCGTTCTGAAGACACCGCTGTTTACTACTGCGTTCGTCACGGTTACTACGACGGTTACCACCTGTTCGACT<br>ACTGGGGTCAGGGTACCCTGGTTACCGTTTCTTCTgcctccaccaagggcccatcggtcttccccctggcaccctcctccaagagcacctctgggggcac<br>agcggccctgggctgcctggtcaaggactacttccccgaaccggtgacggtgtcgtggaactcaggcgccctgaccagcggcgtgcacaccttcccggct<br>gtcctacagtcctcaggactctactccctcagcagcgtggtgactgtgccctctagcagcttgggcacccagacctacatctgcaacgtgaatcacaagc<br>ccagcaacaccaaggtggacaagaaagttgagcccaaatcttgt |
| 149 | GAGATTGTCCTGACCCAGTCCCCTGCTATTATGTCTGCTTCCCCCGGCGAAAGAGTGACCATGACCTGTAGTGCCTCCAGCGGCGTCAACTACATGCACT<br>GGTATCAGCAGAAGCCAGGGACCTCTCCCCGGAGATGGATCTACGACACATCAAAGCTGGCCAGCGGAGTGCCTGCACGGTTCTCCGGATCTGGCAGTGG<br>GACTGACTATAGCCTGACCATCAGCAGCATGGAGCCAGAAGATGCCGCTACCTACTATTGCCATCAGAGGGGCTCCTACACATTTGGCGGGGGAACTAAG<br>CTGGAGATCAAACGCACAGTGGCAGCCCCCAGCGTCTTCATTTTTCCCCCTTCCGATGAACAGCTGAAGTCCGGCACTGCTTCTGTGGTCTGTCTGCTGA<br>ACAATTTCTATCCCAGAGAGGCCAAGGTGCAGTGGAAAGTGGACAACGCTCTGCAGTCCGGCAACAGCCAGGAGAGTGTGACCGAACAGGATAGTAAGGA<br>CAGCACATATTCTCTGTCTAGTACCCTGACACTGAGTAAGGCAGATTACGAGAAGCACAAAGTGTATGCCTGCGAAGTCACTCATCAGGGACTGTCAAGC<br>CCCGTGACCAAGAGCTTCAACCGGGGCGAGTGT |
| 150 | CAGGTGCAGCTGGTCCAGCCAGGGGCAGAGGTCGTCAAGCCAGGAGCATCCGTCAAACTGTCATGTAAAACAAGCGGGTATACTTTCACCAGCAATTGGA<br>TGCACTGGGTGAAGCAGGCCCCCGGACAGGGCCTGGAGTGGATCGGGGAAATTGACCCTAGTGATTCATACACTAACTACAACCAGAACTTCCAGGGAAA<br>GGCCAAACTGACCGTGGACAAAAGCACCTCCACAGCTTATATGGAGGTGAGCAGCCTGCGGTCCGACGATACTGCAGTCTACTATTGCGCCAGAGGCTCT<br>AACCCTTACTATTACGCTATGGATTACTGGGGGCAGGGAACAAGCGTGACTGTCTCTAGTGCATCAACAAAGGGACCAAGCGTGTTTCCACTGGCCCCCT<br>CAAGCAAGAGCACCTCCGGAGGGACAGCCGCTCTGGGATGTCTGGTGAAAGACTACTTCCCCGAGCCTGTGACTGTCTCTTGGAATAGTGGCGCTCTGAC<br>CTCCGGGGTGCACACATTTCCAGCAGTCCTGCAGTCCTCTGGACTGTATTCTCTGAGTTCAGTGGTCACCGTGCCCAGCTCCTCTCTGGGCACTCAGACC<br>TACATCTGCAATGTCAACCATAAGCCTAGTAACACAAAAGTGGATAAGAAAGTCGAACCAAAGAGCTGT |
| 151 | GAGATTGTCCTGACCCAGTCCCCTGCTATTATGTCTGCTTCCCCCGGCGAAAGAGTGACCATGACCTGTAGTGCCTCCAGCGGCGTCAACTACATGCACT<br>GGTATCAGCAGAAGCCAGGGACCTCTCCCCGGAGATGGATCTACGACACATCAAAGCTGGCCAGCGGAGTGCCTGCACGGTTCTCCGGATCTGGCAGTGG<br>GACTGACTATAGCCTGACCATCAGCAGCATGGAGCCAGAAGATGCCGCTACCTACTATTGCCATCAGAGGGGCTCCTACACATTTGGCGGGGGAACTAAG<br>CTGGAGATCAAACGCACAGTGGCAGCCCCCAGCGTCTTCATTTTTCCCCCTTCCGATGAACAGCTGAAGTCCGGCACTGCTTCTGTGGTCTGTCTGCTGA<br>ACAATTTCTATCCCAGAGAGGCCAAGGTGCAGTGGAAAGTGGACAACGCTCTGCAGTCCGGCAACAGCCAGGAGAGTGTGACCGAACAGGATAGTGGCGG<br>GGGAGGCTCAAACTACCACCTGGAGAATGAAGTCGCCAGACTGAAGAAACTGGGGGGAGGCGGGTCAGACAGCACATATTCTCTGTCTAGTACCCTGACA<br>CTGAGTAAGGCAGATTACGAGAAGCACAAAGTGTATGCCTGCGAAGTCACTCATCAGGGACTGTCAAGCCCCGTGACCAAGAGCTTCAACCGGGGCGAGT<br>GT |
| 152 | CAGGTGCAGCTGGTCCAGCCAGGGGCAGAGGTCGTCAAGCCAGGAGCATCCGTCAAACTGTCATGTAAAACAAGCGGGTATACTTTCACCAGCAATTGGA<br>TGCACTGGGTGAAGCAGGCCCCCGGACAGGGCCTGGAGTGGATCGGGGAAATTGACCCTAGTGATTCATACACTAACTACAACCAGAACTTCCAGGGAAA<br>GGCCAAACTGACCGTGGACAAAAGCACCTCCACAGCTTATATGGAGGTGAGCAGCCTGCGGTCCGACGATACTGCAGTCTACTATTGCGCCAGAGGCTCT<br>AACCCTTACTATTACGCTATGGATTACTGGGGGCAGGGAACAAGCGTGACTGTCTCTAGTGCATCAACAAAGGGACCAAGCGTGTTTCCACTGGCCCCCT<br>CAAGCAATTATCATCTGGAGAACGAAGTGGCCAGGCTGAAGAAACTGTCCGGAGGGACAGCCGCTCTGGGATGTCTGGTGAAAGACTACTTCCCCGAGCC<br>TGTGACTGTCTCTTGGAATAGTGGCGCTCTGACCTCCGGGGTGCACACATTTCCAGCAGTCCTGCAGTCCTCTGGACTGTATTCTCTGAGTTCAGTGGTC<br>ACCGTGCCCAGCTCCTCTCTGGGCACTCAGACCTACATCTGCAATGTCAACCATAAGCCTAGTAACACAAAAGTGGATAAGAAAGTCGAACCAAAGAGCT<br>GT |
| 153 | aactaccacctggagaatgaagtcgccagactgaagaaactgggcgggggaggctcaGAGATTGTCCTGACCCAGTCCCCTGCTATTATGTCTGCTTCCC<br>CCGGCGAAAGAGTGACCATGACCTGTAGTGCCTCCAGCGGCGTCAACTACATGCACTGGTATCAGCAGAAGCCAGGGACCTCTCCCCGGAGATGGATCTA<br>CGACACATCAAAGCTGGCCAGCGGAGTGCCTGCACGGTTCTCCGGATCTGGCAGTGGGACTGACTATAGCCTGACCATCAGCAGCATGGAGCCAGAAGAT<br>GCCGCTACCTACTATTGCCATCAGAGGGGCTCCTACACATTTGGCGGGGGAACTAAGCTGGAGATCAAACGCACAGTGGCAGCCCCCAGCGTCTTCATTT<br>TTCCCCCTTCCGATGAACAGCTGAAGTCCGGCACTGCTTCTGTGGTCTGTCTGCTGAACAATTTCTATCCCAGAGAGGCCAAGGTGCAGTGGAAAGTGGA<br>CAACGCTCTGCAGTCCGGCAACAGCCAGGAGAGTGTGACCGAACAGGATAGTAAGGACAGCACATATTCTCTGTCTAGTACCCTGACACTGAGTAAGGCA<br>GATTACGAGAAGCACAAAGTGTATGCCTGCGAAGTCACTCATCAGGGACTGTCAAGCCCCGTGACCAAGAGCTTCAACCGGGGCGAGTGT |
| 154 | aactaccacctggagaatgaagtcgccagactgaagaaactgggcgggggaggctcagggggaggcgggtcaGAGATTGTCCTGACCCAGTCCCCTGCTA<br>TTATGTCTGCTTCCCCCGGCGAAAGAGTGACCATGACCTGTAGTGCCTCCAGCGGCGTCAACTACATGCACTGGTATCAGCAGAAGCCAGGGACCTCTCC<br>CCGGAGATGGATCTACGACACATCAAAGCTGGCCAGCGGAGTGCCTGCACGGTTCTCCGGATCTGGCAGTGGGACTGACTATAGCCTGACCATCAGCAGC<br>ATGGAGCCAGAAGATGCCGCTACCTACTATTGCCATCAGAGGGGCTCCTACACATTTGGCGGGGGAACTAAGCTGGAGATCAAACGCACAGTGGCAGCCC<br>CCAGCGTCTTCATTTTTCCCCCTTCCGATGAACAGCTGAAGTCCGGCACTGCTTCTGTGGTCTGTCTGCTGAACAATTTCTATCCCAGAGAGGCCAAGGT<br>GCAGTGGAAAGTGGACAACGCTCTGCAGTCCGGCAACAGCCAGGAGAGTGTGACCGAACAGGATAGTAAGGACAGCACATATTCTCTGTCTAGTACCCTG<br>ACACTGAGTAAGGCAGATTACGAGAAGCACAAAGTGTATGCCTGCGAAGTCACTCATCAGGGACTGTCAAGCCCCGTGACCAAGAGCTTCAACCGGGGCG<br>AGTGT |

TABLE 51-continued

Switch Antibody Chains

| SEQ ID NO | SEQUENCE |
|---|---|
| 155 | aactaccacctggagaatgaagtcgccagactgaagaaactgggcgggggaggctcaCAGGTGCAGCTGGTCCAGCCAGGGGCAGAGGTCGTCAAGCCAG<br>GAGCATCCGTCAAACTGTCATGTAAAACAAGCGGGTATACTTTCACCAGCAATTGGATGCACTGGGTGAAGCAGGCCCCCGGACAGGGCCTGGAGTGGAT<br>CGGGGAAATTGACCCTAGTGATTCATACACTAACTACAACCAGAACTTCCAGGGAAAGGCCAAACTGACCGTGGACAAAAGCACCTCCACAGCTTATATG<br>GAGGTGAGCAGCCTGCGGTCCGACGATACTGCAGTCTACTATTGCGCCAGAGGCTCTAACCCTTACTATTACGCTATGGATTACTGGGGGCAGGGAACAA<br>GCGTGACTGTCTCTAGTGCATCAACAAAGGGACCAAGCGTGTTTCCACTGGCCCCCTCAAGCAAGAGCACCTCCGGAGGGACAGCCGCTCTGGGATGTCT<br>GGTGAAAGACTACTTCCCCGAGCCTGTGACTGTCTCTTGGAATAGTGGCGCTCTGACCTCCGGGGTGCACACATTTCCAGCAGTCCTGCAGTCCTCTGGA<br>CTGTATTCTCTGAGTTCAGTGGTCACCGTGCCCAGCTCCTCTCTGGGCACTCAGACCTACATCTGCAATGTCAACCATAAGCCTAGTAACACAAAAGTGG<br>ATAAGAAAGTCGAACCAAAGAGCTGT |
| 156 | aactaccacctggagaatgaagtcgccagactgaagaaactgggcgggggaggctcaggggggaggcgggtcaCAGGTGCAGCTGGTCCAGCCAGGGGCAG<br>AGGTCGTCAAGCCAGGAGCATCCGTCAAACTGTCATGTAAAACAAGCGGGTATACTTTCACCAGCAATTGGATGCACTGGGTGAAGCAGGCCCCCGGACA<br>GGGCCTGGAGTGGATCGGGGAAATTGACCCTAGTGATTCATACACTAACTACAACCAGAACTTCCAGGGAAAGGCCAAACTGACCGTGGACAAAAGCACC<br>TCCACAGCTTATATGGAGGTGAGCAGCCTGCGGTCCGACGATACTGCAGTCTACTATTGCGCCAGAGGCTCTAACCCTTACTATTACGCTATGGATTACT<br>GGGGGCAGGGAACAAGCGTGACTGTCTCTAGTGCATCAACAAAGGGACCAAGCGTGTTTCCACTGGCCCCCTCAAGCAAGAGCACCTCCGGAGGGACAGC<br>CGCTCTGGGATGTCTGGTGAAAGACTACTTCCCCGAGCCTGTGACTGTCTCTTGGAATAGTGGCGCTCTGACCTCCGGGGTGCACACATTTCCAGCAGTC<br>CTGCAGTCCTCTGGACTGTATTCTCTGAGTTCAGTGGTCACCGTGCCCAGCTCCTCTCTGGGCACTCAGACCTACATCTGCAATGTCAACCATAAGCCTA<br>GTAACACAAAAGTGGATAAGAAAGTCGAACCAAAGAGCTGT |
| 157 | caggtccaactgcaggagtcaggaggaggcttggtacagcctggggggttctctgagactctcctgtgcaacttctgggttcaccttcactgattactaca<br>tgaactgggtccgccagcctccaggaaaggcacttgagtggttgggttttattggaaacaaagctaatggttacacaacagagtacagtgcatctgtgaa<br>gggtcggttcaccatctccagagataaatcccaaagcatcctctatcttcaaatgaacaccctgagagctgaggacagtgccacttattactgtaccaga<br>gataggggctacggttctactttgactactggggccaagggaccacggtcaccgtctcctcagcctccaccaagggcccatcggtcttcccccctggcac<br>cctcctccaagagcacctctgggggcacagcggccctgggctgcctggtcaaggactacttccccgaaccggtgacggtgtcgtggaactcaggcgccct<br>gaccagcggcgtgcacaccttcccggctgtcctacagtcctcaggactctactccctcagcagcgtggtgactgtgccctctagcagcttgggcacccag<br>acctacatctgcaacgtgaatcacaagcccagcaacaccaaggtggacaagaaagttgagcccaaatcttgt |
| 158 | gacattgagctcacccagtctccagcaatcctgtctgcatctccaggggagaaggtcacaatgacttgcagggccagctcaagtgtaacttacattcact<br>ggtaccagcagaagccaggatcctcccccaaatcctggatttatgccacatccaacctggcttctggagtccctgctcgcttcagtggcagtgggtctgg<br>gacctcttactctctcacaatcagcagagtggaggctgaagatgctgccacttattactgccaacattggagtagtaaaccaccgacgttcggtggaggg<br>accaagctcgagatcaaaaaacgaactgtggctgcaccatctgtcttcatcttcccgccatctgatgagcagttgaaatctggaactgcctctgtcgtgt<br>gcctgctgaataacttctatcccagagaggccaaagtacagtggaaggtggataacgccctccaatcgggtaactcccaggagagtgtcacagagcagga<br>cagcGGCGGAGGCGGGAGCaattatcatcttgaaaatgaggtcgctcgtctcaagaaactcGGTGGCGGAGGCAGCgacagcacctacagcctcagcagc<br>accctgacgctgagcaaagcagactacgagaaacacaaagtctacgcctgcgaagtcacccatcagggcctgtcctcgcccgtcacaaagagcttcaaca<br>ggggagagtgt |
| 159 | gacattgagctcacccagtctccagcaatcctgtctgcatctccaggggagaaggtcacaatgacttgcagggccagctcaagtgtaacttacattcact<br>ggtaccagcagaagccaggatcctcccccaaatcctggatttatgccacatccaacctggcttctggagtccctgctcgcttcagtggcagtgggtctgg<br>gacctcttactctctcacaatcagcagagtggaggctgaagatgctgccacttattactgccaacattggagtagtaaaccaccgacgttcggtggaggg<br>accaagctcgagatcaaaaaacgaactgtggctgcaccatctgtcttcatcttcccgccatctgatgagcagttgaaatctggaactgcctctgtcgtgt<br>gcctgctgaataacttctatcccagagaggccaaagtacagtggaaggtggataacgccctccaatcgggtaactcccaggagagtgtcacagagcagga<br>cagcAAGgacagcacctacagcctcagcagcaccctgacgctgagcaaagcagactacgagaaacacaaagtctacgcctgcgaagtcacccatcagggc<br>ctgtcctcgcccgtcacaaagagcttcaacaggggagagtgt |
| 160 | caggtccaactgcaggagtcaggaggaggcttggtacagcctggggggttctctgagactctcctgtgcaacttctgggttcaccttcactgattactaca<br>tgaactgggtccgccagcctccaggaaaggcacttgagtggttgggttttattggaaacaaagctaatggttacacaacagagtacagtgcatctgtgaa<br>gggtcggttcaccatctccagagataaatcccaaagcatcctctatcttcaaatgaacaccctgagagctgaggacagtgccacttattactgtaccaga<br>gataggggctacggttctactttgactactggggccaagggaccacggtcaccgtctcctcagcctccaccaagggcccatcggtcttcccccctggcac<br>cctcctccaagagcacctctgggggcacagcggccctgggctgcctggtcaaggactacttccccgaaccggtgacggtgtcgtggaactcaggcgccct<br>gaccagcggcgtgcacaccttcccggctgtcctacagtcctcaggactctactccctcagcagcgtggtgactgtgccctctagcagcttgggcacccag<br>acctacatctgcaacgtgaatcacaagcccagcaacaccaaggtggacaagaaagttgagcccaaatcttgtGGCGGAGGCGGGAGCaattatcatcttg<br>aaaatgaggtcgctcgtctcaagaaactc |
| 161 | aattatcatcttgaaaatgaggtcgctcgtctcaagaaactcctggttggcgaggccgcagctaaggaagccgcagctaaagcccaggtgcagctggtgc<br>agagcggcgcggaagtgaaaaaaccgggcagcagcgtgaaagtgagctgcaaagcgagcggctatacctttaccgattataacatgcattgggtgcgcca<br>ggcgccgggccagggcctggaatggattggctatatttatccgtataacggcggcaccggctataaccagaaatttaaaagcaaagcgaccattaccgcg<br>gatgaaagcaccaacaccgcgtatatggaactgagcagcctgcgcagcgaagataccgcggtgtattattgcgcgcgcggccgcccggcgatggattatt<br>ggggccagggcaccctggtgaccgtgagcagcgcctccaccaagggcccatcggtcttcccccctggcaccctcctccaagagcacctctgggggcacagc<br>ggccctgggctgcctggtcaaggactacttccccgaaccggtgacggtgtcgtggaactcaggcgccctgaccagcggcgtgcacaccttcccggctgtc<br>ctacagtcctcaggactctactccctcagcagcgtggtgactgtgccctctagcagcttgggcacccagacctacatctgcaacgtgaatcacaagccca<br>gcaacaccaaggtggacaagaaagttgagcccaaatcttgtgacaaaactcacaca |
| 162 | aactatcacctggaaaacgaagtggcaaggctgaaaaaactgggcgggggcggaagtgatattcagatgacccagagcccgagcagcctgagcgcgagcg<br>tgggcgatcgcgtgaccattacctgccgcgcgagcgaaagcgtggataactatggcattagctttatgaactggtttcagcagaaaccgggcaaagcgcc<br>gaaactgctgatttatgcggcgagcaaccagggcagcggcgtgccgagccgctttagcggcagcggcagcggcaccgatttaccctgaacattagcagc<br>ctgcagccggatgattttgcgacctattattgccagcagagcaaagaagtgccgtggacctttggccagggcaccaaagtggaaattaaacgaactgtgg<br>ctgcaccatctgtcttcatcttcccgccatctgatgagcagttgaaatctggaactgcctctgttgtgtgcctgctgaataacttctatcccagagaggc<br>caaagtacagtggaaggtggataacgccctccaatcgggtaactcaccaggagagtgtcacagagcaggacagcaaggacagcacctacagcctcagcag<br>caccctgacgctgagcaaagcagactacgagaaacacaaagtctacgcctgcgaagtcacccatcagggcctgagctcgcccgtcacaaagagcttcaac<br>aggggagagtgt |
| 163 | caggtgcagctggtgcagagcggcgcggaagtgaaaaaaccgggcagcagcgtgaaagtgagctgcaaagcgagcggctatacctttaccgattataaca<br>tgcattgggtgcgccaggcgccgggccagggcctggaatggattggctatatttatccgtataacggcggcaccggctataaccagaaatttaaaagcaa<br>agcgaccattaccgcggatgaaagcaccaacaccgcgtatatggaactgagcagcctgcgcagcgaagataccgcggtgtattattgcgcgcgcggccgc<br>ccggcgatggattattggggccagggcaccctggtgaccgtgagcagcgcctccaccaagggcccatcggtcttcccccctggcaccctcctccaagagca |

TABLE 51-continued

| Switch Antibody Chains | |
|---|---|
| SEQ ID NO | SEQUENCE |
| | cctctgggggcacagcggccctgggctgcctggtcaaggactacttccccgaaccggtgacggtgtcgtggaactcaggcgccctgaccagcggcgtgca<br>caccttcccggctgtcctacagtcctcaggactctactccctcagcagcgtggtgactgtgccctctagcagcttgggcacccagacctacatctgcaac<br>gtgaatcacaagcccagcaacaccaaggtggacaagaaagttgagcccaaatcttgtgacaaaactcacacaGGCGGAGGCGGGAGCaattatcatcttg<br>aaaatgaggtcgctcgtctcaagaaactc |
| 164 | gatattcagatgacccagagcccgagcagcctgagcgcgagcgtgggcgatcgcgtgaccattacctgccgcgcgagcgaaagcgtggataactatggca<br>ttagctttatgaactggtttcagcagaaaccgggcaaagcgccgaaactgctgatttatgcggcgagcaaccagggcagcggcgtgccgagccgctttag<br>cggcagcggcagcggcaccgattttaccctgaacattagcagcctgcagccggatgattttgcgacctattattgccagcagagcaaagaagtgccgtgg<br>acctttggccagggcaccaaagtggaaattaaacgaactgtggctgcaccatctgtcttcatcttcccgccatctgatgagcagttgaaatctggaactg<br>cctctgttgtgtgcctgctgaataacttctatcccagagaggccaaagtacagtggaaggtggataacgccctccaatcgggtaactcccaggagagtgt<br>cacagagcaggacagcaaggacagcacctacagcctcagcagcaccctgacgctgagcaaagcagactacgagaaacacaaagtctacgcctgcgaagtc<br>acccatcagggcctgagctcgcccgtcacaaagagcttcaacaggggagagtgtGGCGGAGGCGGGAGCaattatcatcttgaaaatgaggtcgctcgtc<br>tcaagaaactc |

TABLE 52

| humanized GCN4 scFv-Amino Acid Sequence (protein sequence of a humanized scFv of the murine, phage affinity matured 52SR4 scFv specific for the GCN4 peptide epitope) | |
|---|---|
| SEQ ID NO | SEQUENCE |
| 165 | QAVVTQEPSLTVSPGGTVTLTCGSSTGAVTTSNYASWVQQKPGQAPRGLIGGTNNRAPGVPARF<br>SGSLLGGKAALTISGAQPEDEAEYYCVLWYSDHWVFGGGTKLTVLGGGGSGGGGSGGGGSQV<br>QLQESGPGLVKPSETLSLTCTVSGFLLTDYGVNWIRQPPGKGLEWIGVIWGDGITDYNPSLKSRV<br>TISKDtSKNQFSLKLSSVTAADTAVYYCVTGLFDYWGQGTLVTVSS |
| 166 | QAVVTQEPSLTVSPGGTVTLTCGSSTGAVTTSNYASWVQQKPGQAPRGLIGGTNNRAPGVPARF<br>SGSLLGGKAALTISGAQPEDEAEYYCVLWYSDHWVFGGGTKLTVLGGGGSGGGGSGGGGSQV<br>QLQESGPGLVKPSETLSITCTVSGFLLTDYGVNWVRQPPGKGLEWLGVIWGDGITDYNPSLKSRL<br>TVSKDTSKNQVSLKMSSLTAADTAVYYCVTGLFDYWGQGTLLTVSS |
| 167 | QAVVTQEPSLTVSPGGTVTLTCGSSTGAVTTSNYASWVQQKPGQAFRGLIGGTNNRAPGVPARF<br>SGSLLGGKAALTISGAQPEDEAEYYCVLWYSDHWVFGGGTKLTVLGGGGSGGGGSGGGGSQV<br>QLQESGPGLVKPSETLSLTCTVSGFLLTDYGVNWIRQPPGKGLEWIGVIWGDGITDYNPSLKSRV<br>TISKDTSKNQFSLKLSSVTAADTAVYYCVTGLFDYWGQGTLVTVSS |
| 168 | QAVVTQEPSLTVSPGGTVTLTCGSSTGAVTTSNYASWVQQKPGQAFRGLIGGTNNRAPGVPARF<br>SGSLLGGKAALTISGAQPEDEAEYYCVLWYSDHWVFGGGTKLTVLGGGGSGGGGSGGGGSQV<br>QLQESGPGLVKPSETLSITCTVSGFLLTDYGVNWVRQPPGKGLEWLGVIWGDGITDYNPSLKSRL<br>TVSKDTSKNQVSLKMSSLTAADTAVYYCVTGLFDYWGQGTLLTVSS |
| 169 | QAVVTQEPSLTVSPGGTVTLTCGSSTGAVTTSNYASWVQQKPDHLFRGLIGGTNNRAPGVPARF<br>SGSLLGGKAALTISGAQPEDEAEYYCVLWYSDHWVFGGGTKLTVLGGGGSGGGGSGGGGSQV<br>QLQESGPGLVKPSETLSLTCTVSGFLLTDYGVNWIRQPPGKGLEWIGVIWGDGITDYNPSLKSRV<br>TISKDTSKNQFSLKLSSVTAADTAVYYCVTGLFDYWGQGTLVTVSS |
| 170 | QAVVTQEPSLTVSPGGTVTLTCGSSTGAVTTSNYASWVQQKPDHLFRGLIGGTNNRAPGVPARF<br>SGSLLGGKAALTISGAQPEDEAEYYCVLWYSDHWVFGGGTKLTVLGGGGSGGGGSGGGGSQV<br>QLQESGPGLVKPSETLSITCTVSGFLLTDYGVNWVRQPPGKGLEWLGVIWGDGITDYNPSLKSRL<br>TVSKDTSKNQVSLKMSSLTAADTAVYYCVTGLFDYWGQGTLLTVSS |

TABLE 53

| humanized GCN4 scFv in CAR-Nucleotide Sequence (DNA sequence of a humanized scFv of the murine, phage affinity matured 52SR4 scFv specific for the GCN4 peptide epitope. The sequence is in the open reading frame of the CAR which includes the leader sequence) | |
|---|---|
| SEQ ID NO | SEQUENCE |
| 171 | atggccttaccagtgaccgccttgctcctgccgctggccttgctgctccacgccgccaggccgCAGGCGGTAGTCACCCA<br>GGAGCCAAGTCTCACGGTGAGCCCCGGCGGTACCGTCACACTTACATGCGGAAGCT<br>CTACCGGGGCTGTGACCACAAGCAACTACGCATCCTGGGTCCAGCAGAAACCCGGT<br>CAGGCTCCTCGGGGCCTCATTGGTGGGACAAATAACAGAGCCCCGGGTGTTCCCGC |

TABLE 53-continued humanized GCN4 scFv in CAR-Nucleotide Sequence
(DNA sequence of a humanized scFv of the murine, phage affinity matured 52SR4 scFv specific for the GCN4 peptide epitope. The sequence is in the open reading frame of the CAR which includes the leader sequence)

| SEQ ID NO | SEQUENCE |
|---|---|
| | CCGATTTTCTGGCAGTCTTCTGGGAGGAAAGGCCGCTCTGACAATATCTGGCGCAC<br>AGCCCGAAGACGAGGCCGAGTACTATTGCGTGTTGTGGTATAGCGACCACTGGGTA<br>TTCGGTGGAGGAACAAAGCTGACAGTGCTCGGCGGTGGAGGGAGTGGTGGCGGTG<br>GCAGCGGAGGGGGCGGATCACAAGTGCAATTGCAGGAGAGTGGACCTGGACTCGT<br>GAAACCATCTGAAACACTCTCCCTGACTTGTACGGTTTCAGGGTTCCTGCTGACAG<br>ACTATGGAGTAAACTGGATCAGGCAGCCACCCGGCAAGGGCTTGGAGTGGATTGG<br>CGTCATTTGGGGCGACGGAATCACCGACTATAACCCATCACTCAAATCTCGGGTGA<br>CCATTTCCAAGGATAcCAGTAAGAATCAGTTCAGCCTGAAACTTTCATCCGTGACAG<br>CTGCGGACACCGCCGTGTACTACTGTGTGACAGGACTTTTTGACTACTGGGGCCAG<br>GGGACCCTGGTGACAGTTAGCTCCaccacgacgccagcgccgcgaccaccaacaccggcgcccaccatcgcgt<br>cgcagcccctgtccctgcgcccagaggcgtgccggccagcggcggggggcgcagtgcacacgagggggctggacttcgcctgtgat<br>atctacatctgggcgcccttggccgggacttgtggggtccttctcctgtcactggttatcaccctttactgcaaacggggcagaaagaaact<br>cctgtatatattcaaacaaccatttatgagaccagtacaaactactcaagaggaagatggctgtagctgccgatttccagaagaagaagaag<br>gaggatgtgaactgagagtgaagttcagcaggagcgcagacgcccccgcgtacaagcagggccagaaccagctctataacgagctca<br>atctaggacgaagagaggagtacgatgttttggacaagagacgtggccgggaccctgagatgggggaaagccgagaaggaagaac<br>cctcaggaaggcctgtacaatgaactgcagaaagataagatggcggaggcctacagtgagattgggatgaaaggcgagcgccggagg<br>ggcaaggggcacgatggcctttaccagggtctcagtacagccaccaaggacacctacgacgcccttcacatgcaggccctgccccctc<br>gc |
| 172 | atggccttaccagtgaccgccttgctcctgccgctggccttgctgctccacgccgccaggccgCAGGCGGTAGTCACCCA<br>GGAGCCAAGTCTCACGGTGAGCCCCGGCGGTACCGTCACACTTACATGCGGAAGCT<br>CTACCGGGGCTGTGACCACAAGCAACTACGCATCCTGGGTCCAGCAGAAACCCGGT<br>CAGGCGCCCCGGGGCCTCATTGGTGGGACAAATAACAGAGCCCCGGGTGTTCCCGC<br>CCGATTTTCTGGCAGTCTTCTGGGAGGAAAGGCCGCTCTGACAATATCTGGCGCAC<br>AGCCCGAAGACGAGGCCGAGTACTATTGCGTGTTGTGGTATAGCGACCACTGGGTA<br>TTCGGTGGAGGAACAAAGCTGACAGTGCTCGGCGGTGGAGGGAGTGGTGGCGGTG<br>GCAGCGGAGGGGGCGGATCACAAGTGCAATTGCAGGAGAGTGGACCTGGACTCGT<br>GAAACCATCTGAAACACTCTCCATAACTTGTACGGTTTCAGGGTTCCTGCTGACAG<br>ACTATGGAGTAAACTGGGTTAGGCAGCCACCCGGCAAGGGCTTGGAGTGGCTGGG<br>CGTCATTTGGGGCGACGGAATCACCGACTATAACCCATCACTCAAATCTCGGCTTA<br>CCGTCTCCAAGGATACGAGTAAGAATCAGGTCAGCCTGAAAATGTCATCCCTCACA<br>GCTGCGGACACCGCCGTGTACTACTGTGTGACAGGACTTTTTGACTACTGGGGCCA<br>GGGGACCCTGCTCACAGTTAGCTCCaccacgacgccagcgccgcgaccaccaacaccggcgcccaccatcgc<br>gtcgcagcccctgtccctgcgcccagaggcgtgccggccagcggcggggggcgcagtgcacacgagggggctggacttcgcctgtg<br>atatctacatctgggcgcccttggccgggacttgtggggtccttctcctgtcactggttatcaccctttactgcaaacggggcagaaagaaa<br>ctcctgtatatattcaaacaaccatttatgagaccagtacaaactactcaagaggaagatggctgtagctgccgatttccagaagaagaaga<br>aggaggatgtgaactgagagtgaagttcagcaggagcgcagacgcccccgcgtacaagcagggccagaaccagctctataacgagct<br>caatctaggacgaagagaggagtacgatgttttggacaagagacgtggccgggaccctgagatgggggaaagccgagaaggaaga<br>accctcaggaaggcctgtacaatgaactgcagaaagataagatggcggaggcctacagtgagattgggatgaaaggcgagcgccgga<br>ggggcaaggggcacgatggcctttaccagggtctcagtacagccaccaaggacacctacgacgcccttcacatgcaggccctgccccc<br>tcgc |
| 173 | atggccttaccagtgaccgccttgctcctgccgctggccttgctgctccacgccgccaggccgCAGGCGGTAGTCACCCA<br>GGAGCCAAGTCTCACGGTGAGCCCCGGCGGTACCGTCACACTTACATGCGGAAGCT<br>CTACCGGGGCTGTGACCACAAGCAACTACGCATCCTGGGTCCAGCAGAAACCCGG<br>ACAAGCGTTCCGGGGCCTCATTGGTGGGACAAATAACAGAGCCCCGGGTGTTCCCG<br>CCCGATTTTCTGGCAGTCTTCTGGGAGGAAAGGCCGCTCTGACAATATCTGGCGCA<br>CAGCCCGAAGACGAGGCCGAGTACTATTGCGTGTTGTGGTATAGCGACCACTGGGT<br>ATTCGGTGGAGGAACAAAGCTGACAGTGCTCGGCGGTGGAGGGAGTGGTGGCGGT<br>GGCAGCGGAGGGGGCGGATCACAAGTGCAATTGCAGGAGAGTGGACCTGGACTCG<br>TGAAACCATCTGAAACACTCTCCCTCACTTGTACGGTTTCAGGGTTCCTGCTGACAG<br>ACTATGGAGTAAACTGGATTAGGCAGCCACCCGGCAAGGGCTTGGAGTGGATCGG<br>CGTCATTTGGGGCGACGGAATCACCGACTATAACCCATCACTCAAATCTCGGGTCA<br>CCATCTCCAAGGATACCAGTAAGAATCAGTTCAGCCTGAAACTGTCATCCGTCACA<br>GCTGCGGACACCGCCGTGTACTACTGTGTGACAGGACTTTTTGACTACTGGGGCCA<br>GGGGACCCTGGTAACAGTTAGCTCCaccacgacgccagcgccgcgaccaccaacaccggcgcccaccatcgc<br>gtcgcagcccctgtccctgcgcccagaggcgtgccggccagcggcggggggcgcagtgcacacgagggggctggacttcgcctgtg<br>atatctacatctgggcgcccttggccgggacttgtggggtccttctcctgtcactggttatcaccctttactgcaaacggggcagaaagaaa<br>ctcctgtatatattcaaacaaccatttatgagaccagtacaaactactcaagaggaagatggctgtagctgccgatttccagaagaagaaga<br>aggaggatgtgaactgagagtgaagttcagcaggagcgcagacgcccccgcgtacaagcagggccagaaccagctctataacgagct<br>caatctaggacgaagagaggagtacgatgttttggacaagagacgtggccgggaccctgagatgggggaaagccgagaaggaaga<br>accctcaggaaggcctgtacaatgaactgcagaaagataagatggcggaggcctacagtgagattgggatgaaaggcgagcgccgga<br>ggggcaaggggcacgatggcctttaccagggtctcagtacagccaccaaggacacctacgacgcccttcacatgcaggccctgccccc<br>tcgc |
| 174 | atggccttaccagtgaccgccttgctcctgccgctggccttgctgctccacgccgccaggccgCAGGCGGTAGTCACCCA<br>GGAGCCAAGTCTCACGGTGAGCCCCGGCGGTACCGTCACACTTACATGCGGAAGCT<br>CTACCGGGGCTGTGACCACAAGCAACTACGCATCCTGGGTCCAGCAGAAACCCGGT<br>CAGGCATTCCGGGGCCTCATTGGTGGGACAAATAACAGAGCCCCGGGTGTTCCCGC<br>CCGATTTTCTGGCAGTCTTCTGGGAGGAAAGGCCGCTCTGACAATATCTGGCGCAC<br>AGCCCGAAGACGAGGCCGAGTACTATTGCGTGTTGTGGTATAGCGACCACTGGGTA<br>TTCGGTGGAGGAACAAAGCTGACAGTGCTCGGCGGTGGAGGGAGTGGTGGCGGTG |

TABLE 53-continued humanized GCN4 scFv in CAR-Nucleotide Sequence
(DNA sequence of a humanized scFv of the murine, phage affinity matured 52SR4 scFv specific for the GCN4 peptide epitope. The sequence is in the open reading frame of the CAR which includes the leader sequence)

| SEQ ID NO | SEQUENCE |
|---|---|
| | GCAGCGGAGGGGGCGGATCACAAGTGCAATTGCAGGAGAGTGGACCTGGACTCGT<br>GAAACCATCTGAAACACTCTCCATAACTTGTACGGTTTCAGGGTTCCTGCTGACAG<br>ACTATGGAGTAAACTGGGTCAGGCAGCCACCCGGCAAGGGCTTGGAGTGGCTCGG<br>CGTCATTTGGGGCGACGGAATCACCGACTATAACCCATCACTCAAATCTCGGTTGA<br>CCGTGTCCAAGGATACCAGTAAGAATCAGGTCAGCCTGAAAATGTCATCCCTGACA<br>GCTGCGGACACCGCCGTGTACTACTGTGTGACAGGACTTTTTGACTACTGGGGCCA<br>GGGGACCCTGTTGACAGTTAGCTCCaccacgacgccagcgccgcgaccaccaacaccggcgcccaccatcgc<br>gtcgcagcccctgtccctgcgcccagaggcgtgccggccagcggcggggggcgcagtgcacacgagggggctggacttcgcctgtg<br>atatctacatctgggcgcccttggccgggacttgtggggtccttctcctgtcactggttatcaccctttactgcaaacggggcagaaagaaa<br>ctcctgtatatattcaaacaaccatttatgagaccagtacaaactactcaagaggaagatggctgtagctgccgatttccagaagaagaaga<br>aggaggatgtgaactgagagtgaagttcagcaggagcgcagacgcccccgcgtacaagcagggccagaaccagctctataacgagct<br>caatctaggacgaagagaggagtacgatgttttggacaagagacgtggccgggaccctgagatggggggaaagccgagaaggaaga<br>accctcaggaaggcctgtacaatgaactgcagaaagataagatggcggaggcctacagtgagattgggatgaaaggcgagcgccgga<br>ggggcaaggggcacgatggcctttaccagggtctcagtacagccaccaaggacacctacgacgcccttcacatgcaggccctgccccc<br>tcgc |
| 175 | atggccttaccagtgaccgccttgctcctgccgctggccttgctgctccacgccgccaggccgCAGGCGGTAGTCACCCA<br>GGAGCCAAGTCTCACGGTGAGCCCCGGCGGTACCGTCACACTTACATGCGGAAGCT<br>CTACCGGGGCTGTGACCACAAGCAACTACGCATCCTGGGTCCAGCAGAAACCCGAT<br>CACCTGTTCCGGGGCCTCATTGGTGGGACAAATAACAGAGCCCCGGGTGTTCCCGC<br>CCGATTTTCTGGCAGTCTTCTGGGAGGAAAGGCCGCTCTGACAATATCTGGCGCAC<br>AGCCCGAAGACGAGGCCGAGTACTATTGCGTGTTGTGGTATAGCGACCACTGGGTA<br>TTCGGTGGAGGAACAAAGCTGACAGTGCTCGGCGGTGGAGGGAGTGGTGGCGGTG<br>GCAGCGGAGGGGGCGGATCACAAGTGCAATTGCAGGAGAGTGGACCTGGACTCGT<br>GAAACCATCTGAAACACTCTCCCTTACTTGTACGGTTTCAGGGTTCCTGCTGACAGA<br>CTATGGAGTAAACTGGATCAGGCAGCCACCCGGCAAGGGCTTGGAGTGGATCGGC<br>GTCATTTGGGGCGACGGAATCACCGACTATAACCCATCACTCAAATCTCGGGTCAC<br>CATCTCCAAGGATACGAGTAAGAATCAGTTCAGCCTGAAACTCTCATCCGTTACAG<br>CTGCGGACACCGCCGTGTACTACTGTGTGACAGGACTTTTTGACTACTGGGGCCAG<br>GGGACCCTGGTAACAGTTAGCTCCaccacgacgccagcgccgcgaccaccaacaccggcgcccaccatcgcgt<br>cgcagcccctgtccctgcgcccagaggcgtgccggccagcggcggggggcgcagtgcacacgagggggctggacttcgcctgtgat<br>atctacatctgggcgcccttggccgggacttgtggggtccttctcctgtcactggttatcaccctttactgcaaacggggcagaaagaaact<br>cctgtatatattcaaacaaccatttatgagaccagtacaaactactcaagaggaagatggctgtagctgccgatttccagaagaagaagaag<br>gaggatgtgaactgagagtgaagttcagcaggagcgcagacgcccccgcgtacaagcagggccagaaccagctctataacgagctca<br>atctaggacgaagagaggagtacgatgttttggacaagagacgtggccgggaccctgagatggggggaaagccgagaaggaagaac<br>cctcaggaaggcctgtacaatgaactgcagaaagataagatggcggaggcctacagtgagattgggatgaaaggcgagcgccggagg<br>ggcaaggggcacgatggcctttaccagggtctcagtacagccaccaaggacacctacgacgcccttcacatgcaggccctgccccctc<br>gc |
| 176 | atggccttaccagtgaccgccttgctcctgccgctggccttgctgctccacgccgccaggccgCAGGCGGTAGTCACCCA<br>GGAGCCAAGTCTCACGGTGAGCCCCGGCGGTACCGTCACACTTACATGCGGAAGCT<br>CTACCGGGGCTGTGACCACAAGCAACTACGCATCCTGGGTCCAGCAGAAACCCGAC<br>CATCTGTTTCGGGGCCTCATTGGTGGGACAAATAACAGAGCCCCGGGTGTTCCCGC<br>CCGATTTTCTGGCAGTCTTCTGGGAGGAAAGGCCGCTCTGACAATATCTGGCGCAC<br>AGCCCGAAGACGAGGCCGAGTACTATTGCGTGTTGTGGTATAGCGACCACTGGGTA<br>TTCGGTGGAGGAACAAAGCTGACAGTGCTCGGCGGTGGAGGGAGTGGTGGCGGTG<br>GCAGCGGAGGGGGCGGATCACAAGTGCAATTGCAGGAGAGTGGACCTGGACTCGT<br>GAAACCATCTGAAACACTCTCCATTACTTGTACGGTTTCAGGGTTCCTGCTGACAGA<br>CTATGGAGTAAACTGGGTGAGGCAGCCACCCGGCAAGGGCTTGGAGTGGCTCGGC<br>GTCATTTGGGGCGACGGAATCACCGACTATAACCCATCACTCAAATCTCGGTTGAC<br>CGTGTCCAAGGATACCAGTAAGAATCAGGTGAGCCTGAAAATGTCATCCCTGACAG<br>CTGCGGACACCGCCGTGTACTACTGTGTGACAGGACTTTTTGACTACTGGGGCCAG<br>GGGACCCTGCTGACAGTTAGCTCCaccacgacgccagcgccgcgaccaccaacaccggcgcccaccatcgcgt<br>cgcagcccctgtccctgcgcccagaggcgtgccggccagcggcggggggcgcagtgcacacgagggggctggacttcgcctgtgat<br>atctacatctgggcgcccttggccgggacttgtggggtccttctcctgtcactggttatcaccctttactgcaaacggggcagaaagaaact<br>cctgtatatattcaaacaaccatttatgagaccagtacaaactactcaagaggaagatggctgtagctgccgatttccagaagaagaagaag<br>gaggatgtgaactgagagtgaagttcagcaggagcgcagacgcccccgcgtacaagcagggccagaaccagctctataacgagctca<br>atctaggacgaagagaggagtacgatgttttggacaagagacgtggccgggaccctgagatggggggaaagccgagaaggaagaac<br>cctcaggaaggcctgtacaatgaactgcagaaagataagatggcggaggcctacagtgagattgggatgaaaggcgagcgccggagg<br>ggcaaggggcacgatggcctttaccagggtctcagtacagccaccaaggacacctacgacgcccttcacatgcaggccctgccccctc<br>gc |

TABLE 54

| Additional Antibody and sCAR Amino Acid Sequences | |
|---|---|
| SEQ ID NO | SEQUENCE |
| 177 | EIVLTQSPATLSLSPGERATLSCRASQSVSSYLAWYQQKPGQAPRLLIYDASNRATGIPARFSGSGSGT DFTLTISSLEPEDFAVYYCQQRSNWPITFGQGTRLEIKRTVAAPSVFIFPPSDEQLKSGTASVVCLLNNF YPREAKVQWKVDNALQSGNSQESVTEQDSKDSTYSLSSTLTLSKADYEKHKVYACEVTHQGLSSPV TKSFNRGEC |
| 178 | EVQLVESGGGLVQPGRSLRLSCAASGFTFNDYAMHWVRQAPGKGLEWVSTISWNSGSIGYADSVKG RFTISRDNAKKSLYLQMNSLRAEDTALYYCAKDIQYGNYYYGMDVWGQGTTVTVSSASTKGPSVFP LAPSSKSTSGGTAALGCLVKDYFPEPVTVSWNSGALTSGVHTFPAVLQSSGLYSLSSVVTVPSSSLGT QTYICNVNHKPSNTKVDKKVEPKSC |
| 179 | DKTHTCPPCPAPPVAGPSVFLFPPKPKDTLMISRTPEVTCVVVDVSHEDPEVKFNWYVDGVEVHNAK TKPREEQYNSTYRVVSVLTVLHQDWLNGKEYKCKVSNKGLPSSIEKTISKAKGQPREPQVYTLPPSRD ELTKNQVSLTCLVKGFYPSDIAVEWESNGQPENNYKTTPPVLDSDGSFFLYSKLTVDKSRWQQGNVF SCSVMHEALHNHYTQKSLSLSPGK |
| 180 | MALPVTALLLPLALLLHAARPDAVVTQESALTSSPGETVTLTCRSSTGAVTTSNYASWVQEKPDHLF TGLIGGTNNRAPGVPARFSGSLIGDKAALTITGAQTEDEAIYFCVLWYSDHWVFGGGTKLTVLGGGG GSGGGGSGGGGSGGGGSDVQLQESGPGLVAPSQSLSITCTVSGFLLTDYGVNWVRQSPGKGLEWLG VIWGDGITDYNSALKSRLSVTKDNSKSQVFLKMNSLQSGDSARYYCVTGLFDYWGQGTTLTVSSTTT PAPRPPTPAPTIASQPLSLRPEACRPAAGGAVHTRGLDFACDIYIWAPLAGTCGVLLLSLVITLYCKRG RKKLLYIFKQPFMRPVQTTQEEDGCSCRFPEEEEGGCELRVKFSRSADAPAYKQGQNQLYNELNLGR REEYDVLDKRRGRDPEMGGKPRRKNPQEGLYNELQKDKMAEAYSEIGMKGERRRGKGHDGLYQG LSTATKDTYDALHMQALPPR |
| 181 | MALPVTALLLPLALLLHAARPDIQMTQTTSSLSASLGDRVTISCRASQDISKYLNWYQQKPDGTVKLL IYHTSRLHSGVPSRFSGSGSGTDYSLTISNLEQEDIATYFCQQGNTLPYTFGGGTKLEITGGGGSGGGGS GGGGSEVKLQESGPGLVAPSQSLSVTCTVSGVSLPDYGVSWIRQPPRKGLEWLGVIWGSETTYYNSA LKSRLTIIKDNSKSQVFLKMNSLQTDDTAIYYCAKHYYYGGSYAMDYWGQGTSVTVSSTTTPAPRPP TPAPTIASQPLSLRPEACRPAAGGAVHTRGLDFACDIYIWAPLAGTCGVLLLSLVITLYCKRGRKKLLY IFKQPFMRPVQTTQEEDGCSCRFPEEEEGGCELRVKFSRSADAPAYKQGQNQLYNELNLGRREEYDV LDKRRGRDPEMGGKPRRKNPQEGLYNELQKDKMAEAYSEIGMKGERRRGKGHDGLYQGLSTATKD TYDALHMQALPPR |

TABLE 55

| CAR-EC switch targeting moiety (antibodies) with GCN4 peptide-Amino Acid Sequence | | |
|---|---|---|
| Name | Light chain | Heavy Chain |
| anti-Her2 Fab wild type | DIQMTQSPSSLSASVGDRVTITCRASQDVNTAV AWYQQKPGKAPKLLIYSASFLYSGVPSRFSGSRS GTDFTLTISSLQPEDFATYYCQQHYTTPPTFGQ GTKLEIKRTVAAPSVFIFPPSDEQLKSGTASVVCL LNNFYPREAKVQWKVDNALQSGNSQESVTEQ DSKDSTYSLSSTLTLSKADYEKHKVYACEVTHQG LSSPVTKSFNRGEC (SEQ ID NO: 261) | EVQLVESGGGLVQPGGSLRLSCAASGFNIKDTYIHWVRQAP GKGLEWVARIYPTNGYTRYADSVKGRFTISADTSKNTAYLQ MNSLRAEDTAVYYCSRWGGDGFYAMDYWGQGTLVTVSS ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKKVEPKSCDKTHT (SEQ ID NO: 262) |
| anti-Her2 Fab (LCNT) | NYHLENEVARLKKLGGGGSDIQMTQSPSSLSAS VGDRVTITCRASQDVNTAVAWYQQKPGKAPK LLIYSASFLYSGVPSRFSGSRSGTDFTLTISSLQPE DFATYYCQQHYTTPPTFGQGTKLEIKRTVAAPS VFIFPPSDEQLKSGTASVVCLLNNFYPREAKVQ WKVDNALQSGNSQESVTEQDSKDSTYSLSSTLT LSKADYEKHKVYACEVTHQGLSSPVTKSFNRGE C (SEQ ID NO: 263) | EVQLVESGGGLVQPGGSLRLSCAASGFNIKDTYIHWVRQAP GKGLEWVARIYPTNGYTRYADSVKGRFTISADTSKNTAYLQ MNSLRAEDTAVYYCSRWGGDGFYAMDYWGQGTLVTVSS ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKKVEPKSCDKTHT (SEQ ID NO: 262) |
| anti-Her2 Fab (LCCT) | DIQMTQSPSSLSASVGDRVTITCRASQDVNTAV AWYQQKPGKAPKLLIYSASFLYSGVPSRFSGSRS GTDFTLTISSLQPEDFATYYCQQHYTTPPTFGQ GTKLEIKRTVAAPSVFIFPPSDEQLKSGTASVVCL LNNFYPREAKVQWKVDNALQSGNSQESVTEQ DSKDSTYSLSSTLTLSKADYEKHKVYACEVTHQG LSSPVTKSFNRGECGGGGSNYHLENEVARLKKL (SEQ ID NO: 264) | EVQLVESGGGLVQPGGSLRLSCAASGFNIKDTYIHWVRQAP GKGLEWVARIYPTNGYTRYADSVKGRFTISADTSKNTAYLQ MNSLRAEDTAVYYCSRWGGDGFYAMDYWGQGTLVTVSS ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKKVEPKSCDKTHT (SEQ ID NO: 262) |
| anti-Her2 Fab (HCNT) | DIQMTQSPSSLSASVGDRVTITCRASQDVNTAV AWYQQKPGKAPKLLIYSASFLYSGVPSRFSGSRS GTDFTLTISSLQPEDFATYYCQQHYTTPPTFGQ GTKLEIKRTVAAPSVFIFPPSDEQLKSGTASVVCL LNNFYPREAKVQWKVDNALQSGNSQESVTEQ | NYHLENEVARLKKLGGGGSEVQLVESGGGLVQPGGSLRLSC AASGFNIKDTYIHWVRQAPGKGLEWVARIYPTNGYTRYADS VKGRFTISADTSKNTAYLQMNSLRAEDTAVYYCSRWGGDG FYAMDYWGQGTLVTVSSASTKGPSVFPLAPSSKSTSGGTAA LGCLVKDYFPEPVTVSWNSGALTSGVHTFPAVLQSSGLYSLS |

TABLE 55-continued

CAR-EC switch targeting moiety (antibodies) with GCN4 peptide-Amino Acid Sequence

| Name | Light chain | Heavy Chain |
|---|---|---|
| | DSKDSTYSLSSTLTLSKADYEKHKVYACEVTHQGLSSPVTKSFNRGEC (SEQ ID NO: 261) | SVVTVPSSSLGTQTYICNVNHKPSNTKVDKKVEPKSC (SEQ ID NO: 265) |
| anti-Her2 Fab (HCCT) | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 261) | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTGGGGSNYHLENEVARLKKL (SEQ ID NO: 266) |
| anti-Her2 Fab (NTBV) | NYHLENEVARLKKLGGGGSDIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 263) | NYHLENEVARLKKLGGGGSEVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC (SEQ ID NO: 265) |
| anti-Her2 Fab (CTBV) | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSNYHLENEVARLKKL (SEQ ID NO: 264) | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTGGGGSNYHLENEVARLKKL (SEQ ID NO: 266) |

TABLE 56

CAR-EC switch targeting moiety (antibodies) with FLAG tag-Amino Acid Sequence

| Name | Light chain | Heavy Chain |
|---|---|---|
| anti-Her2 Fab wild type | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 261) | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 262) |
| anti-Her2 Fab (LCNT) | DYKDDDDKGGGGSGGGGSDIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 267) | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 262) |
| anti-Her2 Fab (LCCT) | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSGGGGSDYKDDDDK (SEQ ID NO: 268) | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 262) |
| anti-Her2 Fab (HCNT) | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 261) | DYKDDDDKGGGGSGGGGSEVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO: 269) |
| anti-Her2 Fab | DIQMTQSPSSLSASVGDRVTITCRASQDVNTAVAWYQQKPGKAPKLLIYSASFLYSGVPSRFSGSRS | EVQLVESGGGLVQPGGSLRLSCAASGFNIKDTYIHWVRQAPGKGLEWVARIYPTNGYTRYADSVKGRFTISADTSKNTAYLQ |

TABLE 56-continued

CAR-EC switch targeting moiety (antibodies) with FLAG tag-Amino Acid Sequence

| Name | Light chain | Heavy Chain |
|---|---|---|
| (HCCT) | GTDFTLTISSLQPEDFATYYCQQHYTTPPTFGQ GTKLEIKRTVAAPSVFIFPPSDEQLKSGTASVVCL LNNFYPREAKVQWKVDNALQSGNSQESVTEQ DSKDSTYSLSSTLTLSKADYEKHKVYACEVTHQG LSSPVTKSFNRGEC (SEQ ID NO: 261) | MNSLRAEDTAVYYCSRWGGDGFYAMDYWGQGTLVTVSS ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKKVEPKSCDKTHTGGGGSGGGGSDYKDDD DK (SEQ ID NO: 270) |
| anti-Her2 Fab (NTBV) | DYKDDDDKGGGGSGGGGSDIQMTQSPSSLSA SVGDRVTITCRASQDVNTAVAWYQQKPGKAP KLLIYSASFLYSGVPSRFSGSRSGTDFTLTISSLQP EDFATYYCQQHYTTPPTFGQGTKLEIKRTVAAP SVFIFPPSDEQLKSGTASVVCLLNNFYPREAKVQ WKVDNALQSGNSQESVTEQDSKDSTYSLSSTLT LSKADYEKHKVYACEVTHQGLSSPVTKSFNRGE C (SEQ ID NO: 267) | DYKDDDDKGGGGSGGGGSEVQLVESGGGLVQPGGSLRLS CAASGFNIKDTYIHWVRQAPGKGLEWVARIYPTNGYTRYA DSVKGRFTISADTSKNTAYLQMNSLRAEDTAVYYCSRWGG DGFYAMDYWGQGTLVTVSSASTKGPSVFPLAPSSKSTSGGT AALGCLVKDYFPEPVTVSWNSGALTSGVHTFPAVLQSSGLY SLSSVVTVPSSSLGTQTYICNVNHKPSNTKVDKKVEPKSCDK THT (SEQ ID NO: 269) |
| anti-Her2 Fab (CTBV) | DIQMTQSPSSLSASVGDRVTITCRASQDVNTAV AWYQQKPGKAPKLLIYSASFLYSGVPSRFSGSRS GTDFTLTISSLQPEDFATYYCQQHYTTPPTFGQ GTKLEIKRTVAAPSVFIFPPSDEQLKSGTASVVCL LNNFYPREAKVQWKVDNALQSGNSQESVTEQ DSKDSTYSLSSTLTLSKADYEKHKVYACEVTHQG LSSPVTKSFNRGECGGGGSGGGGSDYKDDDDK (SEQ ID NO: 268) | EVQLVESGGGLVQPGGSLRLSCAASGFNIKDTYIHWVRQAP GKGLEWVARIYPTNGYTRYADSVKGRFTISADTSKNTAYLQ MNSLRAEDTAVYYCSRWGGDGFYAMDYWGQGTLVTVSS ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKKVEPKSCDKTHTGGGGSGGGGSDYKDDD DK (SEQ ID NO: 270) |

TABLE 57 sCAR seequences

| Name | Sequence |
|---|---|
| CAR-Her2 (CD8 hinge) | DIQMTQSPSSLSASVGDRVTITCRASQDVNTAVAWYQQKPGKAPKLLIYSASFLYSGVPSRFSGSRSGTD FTLTISSLQPEDFATYYCQQHYTTPPTFGQGTKVEIKRTGGGGSGGGGSGGGGSEVQLVESGGGLVQPG GSLRLSCAASGFNIKDTYIHWVRQAPGKGLEWVARIYPTNGYTRYADSVKGRFTISADTSKNTAYLQMNS LRAEDTAVYYCSRWGGDGFYAMDYWGQGTLVTVSSAAATTTPAPRPPTPAPTIASQPLSLRPEACRPAA GGAVHTRGLDFACDIYIWAPLAGTCGVLLLSLVITLYCKRGRKKLLYIFKQPFMRPVQTTQEEDGCSCRFP EEEEGGCELRVKFSRSADAPAYKQGQNQLYNELNLGRREEYDVLDKRRGRDPEMGGKPRRKNPQEGLY NELQKDKMAEAYSEIGMKGERRRGKGHDGLYQGLSTATKDTYDALHMQALPPR (SEQ ID NO: 271) |
| CAR-Her2 (IgG4m hinge) | DIQMTQSPSSLSASVGDRVTITCRASQDVNTAVAWYQQKPGKAPKLLIYSASFLYSGVPSRFSGSRSGTD FTLTISSLQPEDFATYYCQQHYTTPPTFGQGTKVEIKRTGGGGSGGGGSGGGGSEVQLVESGGGLVQPG GSLRLSCAASGFNIKDTYIHWVRQAPGKGLEWVARIYPTNGYTRYADSVKGRFTISADTSKNTAYLQMNS LRAEDTAVYYCSRWGGDGFYAMDYWGQGTLVTVSSAAAESKYGPPCPPCPDIYIWAPLAGTCGVLLLSL VITLYCKRGRKKLLYIFKQPFMRPVQTTQEEDGCSCRFPEEEEGGCELRVKFSRSADAPAYKQGQNQLYN ELNLGRREEYDVLDKRRGRDPEMGGKPRRKNPQEGLYNELQKDKMAEAYSEIGMKGERRRGKGHDGL YQGLSTATKDTYDALHMQALPPR (SEQ ID NO: 272) |
| CAR-GCN4 (CD8 hinge) | DAVVTQESALTSSPGETVTLTCRSSTGAVTTSNYASWVQEKPDHLFTGLIGGTNNRAPGVPARFSGSLIG DKAALTITGAQTEDEAIYFCVLWYSDHWVFGGGTKLTVLGGGGGSGGGGSGGGGSGGGGSDVQLQES GPGLVAPSQSLSITCTVSGFLLTDYGVNWVRQSPGKGLEWLGVIWGDGITDYNSALKSRLSVTKDNSKS QVFLKMNSLQSGDSARYYCVTGLFDYWGQGTTLTVSSTTTPAPRPPTPAPTIASQPLSLRPEACRPAAGG AVHTRGLDFACDIYIWAPLAGTCGVLLLSLVITLYCKRGRKKLLYIFKQPFMRPVQTTQEEDGCSCRFPEEE EGGCELRVKFSRSADAPAYKQGQNQLYNELNLGRREEYDVLDKRRGRDPEMGGKPRRKNPQEGLYNEL QKDKMAEAYSEIGMKGERRRGKGHDGLYQGLSTATKDTYDALHMQALPPR (SEQ ID NO: 273) |
| CAR-GCN4 (IgG4m hinge) | DAVVTQESALTSSPGETVTLTCRSSTGAVTTSNYASWVQEKPDHLFTGLIGGTNNRAPGVPARFSGSLIG DKAALTITGAQTEDEAIYFCVLWYSDHWVFGGGTKLTVLGGGGGSGGGGSGGGGSGGGGSDVQLQES GPGLVAPSQSLSITCTVSGFLLTDYGVNWVRQSPGKGLEWLGVIWGDGITDYNSALKSRLSVTKDNSKS QVFLKMNSLQSGDSARYYCVTGLFDYWGQGTTLTVSSESKYGPPCPPCPDIYIWAPLAGTCGVLLLSLVIT LYCKRGRKKLLYIFKQPFMRPVQTTQEEDGCSCRFPEEEEGGCELRVKFSRSADAPAYKQGQNQLYNELN LGRREEYDVLDKRRGRDPEMGGKPRRKNPQEGLYNELQKDKMAEAYSEIGMKGERRRGKGHDGLYQG LSTATKDTYDALHMQALPPR (SEQ ID NO: 274) |
| CAR-FLAG (CD8 hinge) | DIVMTQTPLTLSVTFGQPASISCKSSQSLLDSDGQTYLNWLLQRPGQSPKRLIYLVSKLDSGVPDRFTGSG SGTDFTLKISRVEAEDLGVYYCWQGTHFPWTFGGGTKLEIKGGGGSGGGGSGGGGSEVQLQQSGAELV KPGASVKLSCTASGFNIKDYYMHWVKQRTEQGLEWIGRIDPEDGETKYAPKFQGKATITADTSSKTAYLQ LSSLTSEDTAVYYCARLKGGYWGQGTTLTVSSTTTPAPRPPTPAPTIASQPLSLRPEACRPAAGGAVHTRG LDFACDIYIWAPLAGTCGVLLLSLVITLYCKRGRKKLLYIFKQPFMRPVQTTQEEDGCSCRFPEEEEGGCEL RVKFSRSADAPAYKQGQNQLYNELNLGRREEYDVLDKRRGRDPEMGGKPRRKNPQEGLYNELQKDKM AEAYSEIGMKGERRRGKGHDGLYQGLSTATKDTYDALHMQALPPR (SEQ ID NO: 275) |

TABLE 57-continued sCAR seeequences

| Name | Sequence |
|---|---|
| CAR-FLAG (IgG4m hinge) | DIVMTQTPLTLSVTFGQPASISCKSSQSLLDSDGQTYLNWLLQRPGQSPKRLIYLVSKLDSGVPDRFTGSG<br>SGTDFTLKISRVEAEDLGVYYCWQGTHFPWTFGGGTKLEIKGGGGSGGGGSGGGGSEVQLQQSGAELV<br>KPGASVKLSCTASGFNIKDYYMHWVKQRTEQGLEWIGRIDPEDGETKYAPKFQGKATITADTSSKTAYLQ<br>LSSLTSEDTAVYYCARLKGGYWGQGTTLTVSSESKYGPPCPPCPDIYIWAPLAGTCGVLLLSLVITLYCKRG<br>RKKLLYIFKQPFMRPVQTTQEEDGCSCRFPEEEEGGCELRVKFSRSADAPAYKQGQNQLYNELNLGRREE<br>YDVLDKRRGRDPEMGGKPRRKNPQEGLYNELQKDKMAEAYSEIGMKGERRRGKGHDGLYQGLSTATK<br>DTYDALHMQALPPR (SEQ ID NO: 276) |

TABLE 58 sCAR sequences, heavy and light chain sequences, and other sequences

| SEQ ID NO | SEQUENCE |
|---|---|
| 182 | GAGGTGCAGCTGGTCGAGTCAGGCGGAGGCCTGGTTCAGCCAGGGAGATCCCTCAGGC<br>TTTCCTGCGCCGCCTCCGGTTTTACCTTCAACGACTACGCTATGCACTGGGTTCGCCAGG<br>CTCCCGGAAAGGGACTTGAATGGGTGAGCACTATCAGCTGGAATTCTGGAAGCATTGGG<br>TATGCCGACTCCGTCAAGGGCCGCTTTACTATTTCTCGGGATAATGCGAAGAAGTCTCTG<br>TACCTGCAGATGAACAGTCTTCGGGCAGAAGACACGGCTCTTTACTATTGCGCAAAAGA<br>CATCCAGTACGGAAACTATTATTACGGAATGGATGTGTGGGGTCAGGGCACCACTGTGA<br>CAGTAAGCAGTGGCGGAGGAGGAGGTTCAGGAGGAGGAGGTAGCGGGGGAGGCGGTT<br>CCGGGGGAGGCGGTTCTGAAATCGTCCTGACGCAGTCACCTGCAACCCTGAGTCTCAGC<br>CCTGGTGAGCGGGCCACCCTGAGCTGCAGGGCCAGCCAGAGTGTATCTTCTTACCTGGC<br>TTGGTATCAGCAGAAACCAGGACAGGCCCCAAGACTGCTGATCTACGACGCTTCCAATA<br>GAGCCACGGGCATCCCTGCCCGATTTTCCGGATCAGGGTCCGGTACAGATTTCACGCTG<br>ACCATCAGCTCCCTCGAGCCCGAAGATTTTGCTGTGTATTATTGCCAGCAGCGGTCCAAT<br>TGGCCCATTACCTTCGGTCAGGGGACCAGGCTGGAGATTAAAaccacgacgccagcgccgcgaccacc<br>aacaccggcgcccaccatcgcgtcgcagcccctgtccctgcgcccagaggcgtgccggccagcggcgggggggcgcagtgcacacgaggg<br>ggctggacttcgcctgtgatatctacatctgggcgcccttggccgggacttgtggggtccttctcctgtcactggttatcaccctttactgcaaacgg<br>ggcagaaagaaactcctgtatatattcaaacaaccatttatgagaccagtacaaactactcaagaggaagatggctgtagctgccgatttccagaa<br>gaagaagaaggaggatgtgaactgagagtgaagttcagcaggagcgcagacgcccccgcgtacaagcagggccagaaccagctctataacg<br>agctcaatctaggacgaagagaggagtacgatgttttggacaagagacgtggccgggaccctgagatggggggaaagccgagaaggaagaa<br>ccctcaggaaggcctgtacaatgaactgcagaaagataagatggcggaggcctacagtgagattgggatgaaaggcgagcgccggaggggc<br>aaggggcacgatggcctttaccagggtctcagtacagccaccaaggacacctacgacgcccttcacatgcaggccctgccccctcgc |
| 183 | caggctgtggtgactcaggagccctcactgactgtgtccccaggagggacagtcactctcacctgtggctccagcactggagctgtcaccacttc<br>caactatgcctcatgggtgcaggagaagcctgAccaCCTCTTCaggggggctgattggtggcacaaacaacagggctcctggggtgcctg<br>cccggttctcaggctccctccttgggggcaaagctgccctgaccatttcgggtgcgcagcctgaggatgaggctatttatttctgcgtgctctggtat<br>agtgaccattgggtgttcggcggagggaccaagctgaccgtcctaGGCGGAGGAGGAGGTTCAGGAGGAGGAGGT<br>AGCGGGGGAGGCGGTTCCGGGGGAGGCGGTTCTcaggtgcagctgcagcagtcgggcccaggactggtgaag<br>ccttcggagaccctgtccatcacctgcactgtctctggtttctccctgaccgactacggcgtaaactgggtgcggcagcccccagggaagggact<br>ggagtggctgggggtgatctggggtgacgggagcaccgactacaacccctccctcaagagtcgactgaccgtgtccaaggacaactccaagaa<br>ccaggtgtccctgaagatgagctctctgaccgccgcagacacggccgtgtattactgtgtcaccggcctgttcgactactggggccagggcaccc<br>tgctgaccgtctcctca |
| 184 | caggctgtggtgactcaggagccctcactgactgtgtccccaggagggacagtcactctcacctgtggctccagcactggagctgtcaccacttc<br>caactatgcctcatgggtgcaggagaagcctgAccaCCTCTTCaggggggctgattggtggcacaaacaacagggctcctggggtgcctg<br>cccggttctcaggctccctccttgggggcaaagctgccctgaccatttcgggtgcgcagcctgaggatgaggctatttatttctgcgtgctctggtat<br>agtgaccattgggtgttcggcggagggaccaagctgaccgtcctaGGCGGAGGAGGAGGTTCAGGAGGCGGAGGT<br>AGCGGGGGAGGCGGTTCCGGGGGAGGCGGTTCTcaggtgcagctgcagCAGtcgggcccaggactggtgaa<br>gccttcggagaccctgtccatcacctgcactgtctctggtttcCTGctgaccgactacggcgtaaactgggtgcggcagcccccagggaaggg<br>actggagtggctgggggtgatctggggtgacgggATCaccgactacaacccctccctcaagagtcgactgaccgtgtccaaggacACAtc<br>caagaaccaggtgtccctgaagatgagctctctgaccgccgcagacacggccCGGtattactgtgtcaccggcctgttcgactactggggcca<br>gggcaccACCctgaccgtctcctcaGAAAGCAAGTATGGCCCaCCTTGTCCACCTTGTCCCgatatctacatct<br>gggcgcccttggccgggacttgtggggtccttctcctgtcactggttatcaccctttactgcaaacggggcagaaagaaactcctgtatatattcaaa<br>caaccatttatgagaccagtacaaactactcaagaggaagatggctgtagctgccgatttccagaagaagaagaaggaggatgtgaactgagagt<br>gaagttcagcaggagcgcagacgcccccgcgtacaagcagggccagaaccagctctataacgagctcaatctaggacgaagagaggagtac<br>gatgttttggacaagagacgtggccgggaccctgagatggggggaaagccgagaaggaagaaccctcaggaaggcctgtacaatgaactgca<br>gaaagataagatggcggaggcctacagtgagattgggatgaaaggcgagcgccggaggggcaaggggcacgatggcctttaccagggtctc<br>agtacagccaccaaggacacctacgacgcccttcacatgcaggccctgccccctcgc |
| 185 | caggctgtggtgactcaggagccctcactgactgtgtccccaggagggacagtcactctcacctgtggctccagcactggagctgtcaccacttc<br>caactatgcctcatgggtgcaggagaagcctgAccaCCTCTTCaggggggctgattggtggcacaaacaacagggctcctggggtgcctg<br>cccggttctcaggctccctccttgggggcaaagctgccctgaccatttcgggtgcgcagcctgaggatgaggctatttatttctgcgtgctctggtat<br>agtgaccattgggtgttcggcggagggaccaagctgaccgtcctaGGCGGAGGAGGAGGTTCAGGAGGcGGAGGT<br>AGCGGGGGAGGCGGTTCCGGGGGAGGCGGTTCTcaggtgcagctgcagcagtcgggcccaggactggtgaag<br>ccttcggagaccctgtccatcacctgcactgtctctggtttctccctgaccgactacggcgtaaactgggtgcggcagcccccagggaagggact<br>ggagtggctgggggtgatctggggtgacgggagcaccgactacaacccctccctcaagagtcgactgaccgtgtccaaggacaCctccaaga<br>accaggtgtccctgaagatgagctctctgaccgccgcagacacggccgtgtattactgtgtcaccggcctgttcgactactggggccagggcacc<br>ctgctgaccgtctcctcaGAAAGCAAGTATGGCCCaCCTTGTCCACCTTGTCCCgatatctacatctgggcgccct<br>tggccgggacttgtggggtccttctcctgtcactggttatcaccctttactgcaaacggggcagaaagaaactcctgtatatattcaaacaaccattta |

TABLE 58-continued

| sCAR sequences, heavy and light chain sequences, and other sequences | |
|---|---|
| SEQ ID NO | SEQUENCE |
| | tgagaccagtacaaactactcaagaggaagatggctgtagctgccgatttccagaagaagaagaaggaggatgtgaactgagagtgaagttcag<br>caggagcgcagacgcccccgcgtacaagcagggccagaaccagctctataacgagctcaatctaggacgaagagaggagtacgatgttttgg<br>acaagagacgtggccgggaccctgagatggggggaaagccgagaaggaagaaccctcaggaaggcctgtacaatgaactgcagaaagataa<br>gatggcggaggcctacagtgagattgggatgaaaggcgagcgccggaggggcaaggggcacgatggcctttaccagggtctcagtacagcc<br>accaaggacacctacgacgcccttcacatgcaggccctgccccctcgc |
| 186 | GACATCCAGCTGACCCAGTCCCCCTCCTCCCTGTCCGCCTCCGTGGGCGACCGGGTGAC<br>CATGAGCTGCAAGTCCTCCCAGTCCGTGCTGTACTCCGCCAACCACAAGAACTACCTGG<br>CCTGGTACCAGCAGAAGCCCGGCAAGGCCCCCAAGCTGCTGATCTACTGGGCCAGCACC<br>CGCGAGAGCGGCGTGCCCTCCCGGTTCTCCGGCTCCGGCTCCGGCACCGACTTCACCTTC<br>ACCATCTCCTCCCTGCAGCCCGAGGACATCGCCACCTACTACTGCCACCAGTACCTGTCC<br>TCCTGGACCTTCGGCGGCGGCACCAAGCTGGAGATCAAGCGCacggtgGCCGCCCCCAGTG<br>TCTTCATTTTCCCCCCTTCCGATGAGCAGCTGAAGAGCGGTACAGCCTCTGTTGTTTGTC<br>TGCTGAACAACTTCTATCCACGCGAGGCCAAGGTGCAGTGGAAAGTTGATAACGCGCTG<br>CAGAGTGGCAACTCCCAGGAGTCTGTGACAGAGCAGGACAGTAAAGACAGCACATATT<br>CCCTGTCTAGCACACTGACTCTGTCCAAGGCTGACTATGAGAAGCACAAGGTGTACGCT<br>TGCGAGGTCACCCACCAGGGACTGAGTTCTCCTGTGACCAAGTCCTTCAATCGCGGCGA<br>GTGTtaa |
| 187 | CAGGTGCAGCTGGTGCAGTCCGGCGCCGAGGTGAAGAAGCCCGGCTCCTCCGTGAAGG<br>TGTCCTGCAAGGCCTCCGGCTACACCTTCACCTCCTACTGGCTGCACTGGGTGCGGCAG<br>GCCCCCGGCCAGGGCCTGGAGTGGATCGGCTACATCAACCCCCGGAACGACTACACCG<br>AGTACAACCAGAACTTCAAGGACAAGGCCACCATCACCGCCGACGAGTCCACCAACAC<br>CGCCTACATGGAGCTGTCCTCCCTGCGGTCCGAGGACACCGCCTTCTACTTCTGCGCCCG<br>GCGGGACATCACCACCTTCTACTGGGGCCAGGGCACCACTGTGACCGTGTCCTCCGCCA<br>GGACCAAAGGACCGTCCGTCTTTCCTCTGGCCCCTTCCTCTAAGTCCACAAGCGGTGGG<br>ACCGCAGCACTGGGATGCCTGGTGAAGGATTACTTCCCTGAGCCGGTGACCGTGTCCTG<br>GAACTCCGGAGCTCTCACCTCCGGTGTCCATACCTTTCCTGCCGTCCTGCAGTCCTCCGG<br>CCTGTACAGCCTCTCTAGCGTCGTGACTGTGCCCTCCAGCTCCCTGGGCACCCAAACTTA<br>TATCTGCAATGTTAACCACAAGCCTTCTAATACCAAGGTCGACAAGAAAGTGGAGCCGA<br>AGAGCTGTtaa |
| 188 | aactatcacctggaaaacgaagtggcaaggctgaaaaaactgggcgggggcggaagtGACATCCAGCTGACCCAGTCCC<br>CCTCCTCCCTGTCCGCCTCCGTGGGCGACCGGGTGACCATGAGCTGCAAGTCCTCCCAGT<br>CCGTGCTGTACTCCGCCAACCACAAGAACTACCTGGCCTGGTACCAGCAGAAGCCCGGC<br>AAGGCCCCCAAGCTGCTGATCTACTGGGCCAGCACCCGCGAGAGCGGCGTGCCCTCCCG<br>GTTCTCCGGCTCCGGCTCCGGCACCGACTTCACCTTCACCATCTCCTCCCTGCAGCCCGA<br>GGACATCGCCACCTACTACTGCCACCAGTACCTGTCCTCCTGGACCTTCGGCGGCGGCA<br>CCAAGCTGGAGATCAAGCGCacggtgGCCGCCCCCAGTGTCTTCATTTTCCCCCCTTCCGAT<br>GAGCAGCTGAAGAGCGGTACAGCCTCTGTTGTTTGTCTGCTGAACAACTTCTATCCACG<br>CGAGGCCAAGGTGCAGTGGAAAGTTGATAACGCGCTGCAGAGTGGCAACTCCCAGGAG<br>TCTGTGACAGAGCAGGACAGTAAAGACAGCACATATTCCCTGTCTAGCACACTGACTCT<br>GTCCAAGGCTGACTATGAGAAGCACAAGGTGTACGCTTGCGAGGTCACCCACCAGGGA<br>CTGAGTTCTCCTGTGACCAAGTCCTTCAATCGCGGCGAGTGTtaa |
| 189 | GACATCCAGCTGACCCAGTCCCCCTCCTCCCTGTCCGCCTCCGTGGGCGACCGGGTGAC<br>CATGAGCTGCAAGTCCTCCCAGTCCGTGCTGTACTCCGCCAACCACAAGAACTACCTGG<br>CCTGGTACCAGCAGAAGCCCGGCAAGGCCCCCAAGCTGCTGATCTACTGGGCCAGCACC<br>CGCGAGAGCGGCGTGCCCTCCCGGTTCTCCGGCTCCGGCTCCGGCACCGACTTCACCTTC<br>ACCATCTCCTCCCTGCAGCCCGAGGACATCGCCACCTACTACTGCCACCAGTACCTGTCC<br>TCCTGGACCTTCGGCGGCGGCACCAAGCTGGAGATCAAGCGCacggtgGCCGCCCCCAGTG<br>TCTTCATTTTCCCCCCTTCCGATGAGCAGCTGAAGAGCGGTACAGCCTCTGTTGTTTGTC<br>TGCTGAACAACTTCTATCCACGCGAGGCCAAGGTGCAGTGGAAAGTTGATAACGCGCTG<br>CAGAGTGGCAACTCCCAGGAGTCTGTGACAGAGCAGGACAGTAAAGACAGCACATATT<br>CCCTGTCTAGCACACTGACTCTGTCCAAGGCTGACTATGAGAAGCACAAGGTGTACGCT<br>TGCGAGGTCACCCACCAGGGACTGAGTTCTCCTGTGACCAAGTCCTTCAATCGCGGCGA<br>GTGTGGCGGAGGCGGGAGCaattatcatcttgaaaatgaggtcgctcgtctcaagaaactctaa |
| 190 | aattatcatcttgaaaatgaggtcgctcgtctcaagaaactcctggttggcgaggccgcagctaaggaagccgcagctaaagccCAGGTGC<br>AGCTGGTGCAGTCCGGCGCCGAGGTGAAGAAGCCCGGCTCCTCCGTGAAGGTGTCCTGC<br>AAGGCCTCCGGCTACACCTTCACCTCCTACTGGCTGCACTGGGTGCGGCAGGCCCCCGG<br>CCAGGGCCTGGAGTGGATCGGCTACATCAACCCCCGGAACGACTACACCGAGTACAAC<br>CAGAACTTCAAGGACAAGGCCACCATCACCGCCGACGAGTCCACCAACACCGCCTACAT<br>GGAGCTGTCCTCCCTGCGGTCCGAGGACACCGCCTTCTACTTCTGCGCCCGGCGGGACA<br>TCACCACCTTCTACTGGGGCCAGGGCACCACTGTGACCGTGTCCTCCGCCAGGACCAAA<br>GGACCGTCCGTCTTTCCTCTGGCCCCTTCCTCTAAGTCCACAAGCGGTGGGACCGCAGCA<br>CTGGGATGCCTGGTGAAGGATTACTTCCCTGAGCCGGTGACCGTGTCCTGGAACTCCGG<br>AGCTCTCACCTCCGGTGTCCATACCTTTCCTGCCGTCCTGCAGTCCTCCGGCCTGTACAG<br>CCTCTCTAGCGTCGTGACTGTGCCCTCCAGCTCCCTGGGCACCCAAACTTATATCTGCAA<br>TGTTAACCACAAGCCTTCTAATACCAAGGTCGACAAGAAAGTGGAGCCGAAGAGCTGTt<br>aa |
| 191 | CAGGTGCAGCTGGTGCAGTCCGGCGCCGAGGTGAAGAAGCCCGGCTCCTCCGTGAAGG<br>TGTCCTGCAAGGCCTCCGGCTACACCTTCACCTCCTACTGGCTGCACTGGGTGCGGCAG |

TABLE 58-continued

| SEQ ID NO | sCAR sequences, heavy and light chain sequences, and other sequences<br>SEQUENCE |
|---|---|
| | GCCCCCGGCCAGGGCCTGGAGTGGATCGGCTACATCAACCCCCGGAACGACTACACCG AGTACAACCAGAACTTCAAGGACAAGGCCACCATCACCGCCGACGAGTCCACCAACAC CGCCTACATGGAGCTGTCCTCCCTGCGGTCCGAGGACACCGCCTTCTACTTCTGCGCCCG GCGGGACATCACCACCTTCTACTGGGGCCAGGGCACCACTGTGACCGTGTCCTCCGCCA GGACCAAAGGACCGTCCGTCTTTCCTCTGGCCCCTTCCTCTAAGTCCACAAGCGGTGGG ACCGCAGCACTGGGATGCCTGGTGAAGGATTACTTCCCTGAGCCGGTGACCGTGTCCTG GAACTCCGGAGCTCTCACCTCCGGTGTCCATACCTTTCCTGCCGTCCTGCAGTCCTCCGG CCTGTACAGCCTCTCTAGCGTCGTGACTGTGCCCTCCAGCTCCCTGGGCACCCAAACTTA TATCTGCAATGTTAACCACAAGCCTTCTAATACCAAGGTCGACAAGAAAGTGGAGCCGA AGAGCTGTGGCGGAGGCGGGAGCaattatcatcttgaaaatgaggtcgctcgtctcaagaaactctaa |
| 192 | GACATCCAGCTGACCCAGTCCCCCTCCTCCCTGTCCGCCTCCGTGGGCGACCGGGTGAC CATGAGCTGCAAGTCCTCCCAGTCCGTGCTGTACTCCGCCAACCACAAGAACTACCTGG CCTGGTACCAGCAGAAGCCCGGCAAGGCCCCCAAGCTGCTGATCTACTGGGCCAGCACC CGCGAGAGCGGCGTGCCCTCCCGGTTCTCCGGCTCCGGCTCCGGCACCGACTTCACCTTC ACCATCTCCTCCCTGCAGCCCGAGGACATCGCCACCTACTACTGCCACCAGTACCTGTCC TCCTGGACCTTCGGCGGCGGCACCAAGCTGGAGATCAAGCGCacggtgGCCGCCCCCAGTG TCTTCATTTTCCCCCCTTCCGATGAGCAGCTGAAGAGCGGTACAGCCTCTGTTGTTTGTC TGCTGAACAACTTCTATCCACGCGAGGCCAAGGTGCAGTGGAAAGTTGATAACGCGCTG CAGAGTGGCAACTCCCAGGAGTCTGTGACAGAGCAGGACAGTAAAGACAGCACATATT CCCTGTCTAGCACACTGACTCTGTCCAAGGCTGACTATGAGAAGCACAAGGTGTACGCT TGCGAGGTCACCCACCAGGGACTGAGTTCTCCTGTGACCAAGTCCTTCAATCGCGGCGA GTGTGGCGGAGGCGGGAGCGGCGGAGGCGGGAGCaattatcatcttgaaaatgaggtcgctcgtctcaagaaact ctaa |
| 193 | GACATCCAGCTGACCCAGTCCCCCTCCTCCCTGTCCGCCTCCGTGGGCGACCGGGTGAC CATGAGCTGCAAGTCCTCCCAGTCCGTGCTGTACTCCGCCAACCACAAGAACTACCTGG CCTGGTACCAGCAGAAGCCCGGCAAGGCCCCCAAGCTGCTGATCTACTGGGCCAGCACC CGCGAGAGCGGCGTGCCCTCCCGGTTCTCCGGCTCCGGCTCCGGCACCGACTTCACCTTC ACCATCTCCTCCCTGCAGCCCGAGGACATCGCCACCTACTACTGCCACCAGTACCTGTCC TCCTGGACCTTCGGCGGCGGCACCAAGCTGGAGATCAAGCGCacggtgGCCGCCCCCAGTG TCTTCATTTTCCCCCCTTCCGATGAGCAGCTGAAGAGCGGTACAGCCTCTGTTGTTTGTC TGCTGAACAACTTCTATCCACGCGAGGCCAAGGTGCAGTGGAAAGTTGATAACGCGCTG CAGAGTGGCAACTCCCAGGAGTCTGTGACAGAGCAGGACAGTAAAGACAGCACATATT CCCTGTCTAGCACACTGACTCTGTCCAAGGCTGACTATGAGAAGCACAAGGTGTACGCT TGCGAGGTCACCCACCAGGGACTGAGTTCTCCTGTGACCAAGTCCTTCAATCGCGGCGA GTGTGGCGGAGGCGGGAGCGGCGGAGGCGGGAGCGGCGGAGGCGGGAGCaattatcatcttgaa aatgaggtcgctcgtctcaagaaactctaa |
| 194 | CAGGTGCAGCTGGTGCAGTCCGGCGCCGAGGTGAAGAAGCCCGGCTCCTCCGTGAAGG TGTCCTGCAAGGCCTCCGGCTACACCTTCACCTCCTACTGGCTGCACTGGGTGCGGCAG GCCCCCGGCCAGGGCCTGGAGTGGATCGGCTACATCAACCCCCGGAACGACTACACCG AGTACAACCAGAACTTCAAGGACAAGGCCACCATCACCGCCGACGAGTCCACCAACAC CGCCTACATGGAGCTGTCCTCCCTGCGGTCCGAGGACACCGCCTTCTACTTCTGCGCCCG GCGGGACATCACCACCTTCTACTGGGGCCAGGGCACCACTGTGACCGTGTCCTCCGCCA GGACCAAAGGACCGTCCGTCTTTCCTCTGGCCCCTTCCTCTAAGTCCACAAGCGGTGGG ACCGCAGCACTGGGATGCCTGGTGAAGGATTACTTCCCTGAGCCGGTGACCGTGTCCTG GAACTCCGGAGCTCTCACCTCCGGTGTCCATACCTTTCCTGCCGTCCTGCAGTCCTCCGG CCTGTACAGCCTCTCTAGCGTCGTGACTGTGCCCTCCAGCTCCCTGGGCACCCAAACTTA TATCTGCAATGTTAACCACAAGCCTTCTAATACCAAGGTCGACAAGAAAGTGGAGCCGA AGAGCTGTGGCGGAGGCGGGAGCGGCGGAGGCGGGAGCaattatcatcttgaaaatgaggtcgctcgtctca agaaactctaa |
| 195 | CAGGTGCAGCTGGTGCAGTCCGGCGCCGAGGTGAAGAAGCCCGGCTCCTCCGTGAAGG TGTCCTGCAAGGCCTCCGGCTACACCTTCACCTCCTACTGGCTGCACTGGGTGCGGCAG GCCCCCGGCCAGGGCCTGGAGTGGATCGGCTACATCAACCCCCGGAACGACTACACCG AGTACAACCAGAACTTCAAGGACAAGGCCACCATCACCGCCGACGAGTCCACCAACAC CGCCTACATGGAGCTGTCCTCCCTGCGGTCCGAGGACACCGCCTTCTACTTCTGCGCCCG GCGGGACATCACCACCTTCTACTGGGGCCAGGGCACCACTGTGACCGTGTCCTCCGCCA GGACCAAAGGACCGTCCGTCTTTCCTCTGGCCCCTTCCTCTAAGTCCACAAGCGGTGGG ACCGCAGCACTGGGATGCCTGGTGAAGGATTACTTCCCTGAGCCGGTGACCGTGTCCTG GAACTCCGGAGCTCTCACCTCCGGTGTCCATACCTTTCCTGCCGTCCTGCAGTCCTCCGG CCTGTACAGCCTCTCTAGCGTCGTGACTGTGCCCTCCAGCTCCCTGGGCACCCAAACTTA TATCTGCAATGTTAACCACAAGCCTTCTAATACCAAGGTCGACAAGAAAGTGGAGCCGA AGAGCTGTGGCGGAGGCGGGAGCGGCGGAGGCGGGAGCGGCGGAGGCGGGAGCaattatca tcttgaaaatgaggtcgctcgtctcaagaaactctaa |
| 196 | CAGGTGCAGCTGGTGCAGTCCGGCGCCGAGGTGAAGAAGCCCGGCTCCTCCGTGAAGG TGTCCTGCAAGGCCTCCGGCTACACCTTCACCTCCTACTGGCTGCACTGGGTGCGGCAG GCCCCCGGCCAGGGCCTGGAGTGGATCGGCTACATCAACCCCCGGAACGACTACACCG AGTACAACCAGAACTTCAAGGACAAGGCCACCATCACCGCCGACGAGTCCACCAACAC CGCCTACATGGAGCTGTCCTCCCTGCGGTCCGAGGACACCGCCTTCTACTTCTGCGCCCG GCGGGACATCACCACCTTCTACTGGGGCCAGGGCACCACTGTGACCGTGTCCTCCGCCA GGACCAAAGGACCGTCCGTCTTTCCTCTGGCCCCTTCCTCTAAGTCCACAAGCGGTGGG |

TABLE 58-continued sCAR sequences, heavy and light chain sequences, and other sequences

| SEQ ID NO | SEQUENCE |
|---|---|
| | ACCGCAGCACTGGGATGCCTGGTGAAGGATTACTTCCCTGAGCCGGTGACCGTGTCCTG<br>GAACTCCGGAGCTCTCACCTCCGGTGTCCATACCTTTCCTGCCGTCCTGCAGTCCTCCGG<br>CCTGTACAGCCTCTCTAGCGTCGTGACTGTGCCCTCCAGCTCCCTGGGCACCCAAACTTA<br>TATCTGCAATGTTAACCACAAGCCTTCTAATACCAAGGTCGACAAGAAAGTGGAGCCGA<br>AGAGCTGTgacaaaactcacacatgcccaccgtgcccagcacctCCaGtcGCcggaccgtcagtcttcctcttcccTccaaaaccca<br>aggacaccctcatgatctcccggacccctgaggtcacatgcgtggtggtggacgtgagccacgaagaccctgaggtcaagttcaactggtacgt<br>ggacggcgtggaggtgcataatgccaagacaaagccgcgggaggagcagtacaacagcacgtaccgtgtggtcagcgtcctcaccgtcctgc<br>accaggactggctgaatggcaaggagtacaagtgcaaggtctccaacaaagGcctcccaAGcTccatcgagaaaaccatctccaaagccaa<br>agggcagccccgagaaccacaggtgtacaccctgccTccatcccgggatgagctgaccaagaaccaggtcagcctgacctgcctggtcaaag<br>gcttctatcccagcgacatcgccgtggagtgggagagcaatgggcagccggagaacaactacaagaccacgcctcccgtgctggactccgac<br>ggctccttcttcctctacagcaagctcaccgtggacaagagcaggtggcagcaggggaacgtcttctcatgctccgtgatgcatgaggctctgcac<br>aaccactacacgcagaagagcctctccctgtctccgggtaaataa |
| 197 | CAGGTGCAGCTGGTGCAGTCCGGCGCCGAGGTGAAGAAGCCCGGCTCCTCCGTGAAGG<br>TGTCCTGCAAGGCCTCCGGCTACACCTTCACCTCCTACTGGCTGCACTGGGTGCGGCAG<br>GCCCCCGGCCAGGGCCTGGAGTGGATCGGCTACATCAACCCCCGGAACGACTACACCG<br>AGTACAACCAGAACTTCAAGGACAAGGCCACCATCACCGCCGACGAGTCCACCAACAC<br>CGCCTACATGGAGCTGTCCTCCCTGCGGTCCGAGGACACCGCCTTCTACTTCTGCGCCCG<br>GCGGGACATCACCACCTTCTACTGGGGCCAGGGCACCACTGTGACCGTGTCCTCCGCCA<br>GGACCAAAGGACCGTCCGTCTTTCCTCTGGCCCCTTCCTCTAAGTCCACAAGCGGTGGG<br>ACCGCAGCACTGGGATGCCTGGTGAAGGATTACTTCCCTGAGCCGGTGACCGTGTCCTG<br>GAACTCCGGAGCTCTCACCTCCGGTGTCCATACCTTTCCTGCCGTCCTGCAGTCCTCCGG<br>CCTGTACAGCCTCTCTAGCGTCGTGACTGTGCCCTCCAGCTCCCTGGGCACCCAAACTTA<br>TATCTGCAATGTTAACCACAAGCCTTCTAATACCAAGGTCGACAAGAAAGTGGAGCCGA<br>AGAGCTGTgacaaaactcacacatgcccaccgtgcccagcacctCCaGtcGCcggaccgtcagtcttcctcttcccTccaaaaccca<br>aggacaccctcatgatctcccggacccctgaggtcacatgcgtggtggtggacgtgagccacgaagaccctgaggtcaagttcaactggtacgt<br>ggacggcgtggaggtgcataatgccaagacaaagccgcgggaggagcagtacaacagcacgtaccgtgtggtcagcgtcctcaccgtcctgc<br>accaggactggctgaatggcaaggagtacaagtgcaaggtctccaacaaagGcctcccaAGcTccatcgagaaaaccatctccaaagccaa<br>agggcagccccgagaaccacaggtgtacaccctgccTccatcccgggatgagctgaccaagaaccaggtcagcctgacctgcctggtcaaag<br>gcttctatcccagcgacatcgccgtggagtgggagagcaatgggcagccggagaacaactacaagaccacgcctcccgtgctggactccgac<br>ggctccttcttcctctacagcaagctcaccgtggacaagagcaggtggcagcaggggaacgtcttctcatgctccgtgatgcatgaggctctgcac<br>aaccactacacgcagaagagcctctccctgtctccgggtaaaGGCGGAGGCGGGAGCaattatcatcttgaaaatgaggtcgctcgt<br>ctcaagaaactctaa |
| 198 | caggtacagctgcagcagtcaggtccaggactggtgaagccctcgcagaccctctcactcacctgtgccatctccggggacagtgtctctagcaa<br>cagtgctgcttggaactggatcaggcagtccccatcgagaggccttgagtggctgggaaggacatactacaggtccaagtggtataatgattatgc<br>agtatctgtgaaaagtcgaataaccatcaacccagacacatccaagaaccagttctccctgcagctgaactctgtgactcccgaggacacggctgt<br>gtattactgtgcaagagaagtgactggggatctcgaggatgcttttgatatctggggccaagggacaatggtcaccgtctcctcagcctccaccaa<br>gggcccatcggtcttccccctggcaccctcctccaagagcacctctgggggcacagcggccctgggctgcctggtcaaggactacttccccgaa<br>ccggtgacggtgtcgtggaactcaggcgccctgaccagcggcgtgcacaccttcccggctgtcctacagtcctcaggactctactccctcagcag<br>cgtggtgactgtgccctctagcagcttgggcacccagacctacatctgcaacgtgaatcacaagcccagcaacaccaaggtggacaagaaagtt<br>gagcccaaatcttgtgacaaaactcacacatgcccaccgtgcccagcacctCCaGtcGCcggaccgtcagtcttcctcttcccTccaaaacc<br>caaggacaccctcatgatctcccggacccctgaggtcacatgcgtggtggtggacgtgagccacgaagaccctgaggtcaagttcaactggtac<br>gtggacggcgtggaggtgcataatgccaagacaaagccgcgggaggagcagtacaacagcacgtaccgtgtggtcagcgtcctcaccgtcct<br>gcaccaggactggctgaatggcaaggagtacaagtgcaaggtctccaacaaagGcctcccaAGcTccatcgagaaaaccatctccaaagcc<br>aaagggcagccccgagaaccacaggtgtacaccctgccTccatcccgggatgagctgaccaagaaccaggtcagcctgacctgcctggtcaa<br>aggcttctatcccagcgacatcgccgtggagtgggagagcaatgggcagccggagaacaactacaagaccacgcctcccgtgctggactccg<br>acggctccttcttcctctacagcaagctcaccgtggacaagagcaggtggcagcaggggaacgtcttctcatgctccgtgatgcatgaggctctgc<br>acaaccactacacgcagaagagcctctccctgtctccgggtaaataa |
| 199 | caggtacagctgcagcagtcaggtccaggactggtgaagccctcgcagaccctctcactcacctgtgccatctccggggacagtgtctctagcaa<br>cagtgctgcttggaactggatcaggcagtccccatcgagaggccttgagtggctgggaaggacatactacaggtccaagtggtataatgattatgc<br>agtatctgtgaaaagtcgaataaccatcaacccagacacatccaagaaccagttctccctgcagctgaactctgtgactcccgaggacacggctgt<br>gtattactgtgcaagagaagtgactggggatctcgaggatgcttttgatatctggggccaagggacaatggtcaccgtctcctcagcctccaccaa<br>gggcccatcggtcttccccctggcaccctcctccaagagcacctctgggggcacagcggccctgggctgcctggtcaaggactacttccccgaa<br>ccggtgacggtgtcgtggaactcaggcgccctgaccagcggcgtgcacaccttcccggctgtcctacagtcctcaggactctactccctcagcag<br>cgtggtgactgtgccctctagcagcttgggcacccagacctacatctgcaacgtgaatcacaagcccagcaacaccaaggtggacaagaaagtt<br>gagcccaaatcttgtgacaaaactcacacatgcccaccgtgcccagcacctCCaGtcGCcggaccgtcagtcttcctcttcccTccaaaacc<br>caaggacaccctcatgatctcccggacccctgaggtcacatgcgtggtggtggacgtgagccacgaagaccctgaggtcaagttcaactggtac<br>gtggacggcgtggaggtgcataatgccaagacaaagccgcgggaggagcagtacaacagcacgtaccgtgtggtcagcgtcctcaccgtcct<br>gcaccaggactggctgaatggcaaggagtacaagtgcaaggtctccaacaaagGcctcccaAGcTccatcgagaaaaccatctccaaagcc<br>aaagggcagccccgagaaccacaggtgtacaccctgccTccatcccgggatgagctgaccaagaaccaggtcagcctgacctgcctggtcaa<br>aggcttctatcccagcgacatcgccgtggagtgggagagcaatgggcagccggagaacaactacaagaccacgcctcccgtgctggactccg<br>acggctccttcttcctctacagcaagctcaccgtggacaagagcaggtggcagcaggggaacgtcttctcatgctccgtgatgcatgaggctctgc<br>acaaccactacacgcagaagagcctctccctgtctccgggtaaaGGCGGAGGCGGGAGCaattatcatcttgaaaatgaggtcgct<br>cgtctcaagaaactctaa |
| 200 | atgggtgtccctacccagctcctgggactgctcctgctgtggatcaccgacgccatctgcgacatccagatgacccagagccctgccagcctgtct<br>accagcctgggcgagacagtgaccatccagtgtcaggccagcgaggacatctactctggcctggcttggtatcagcagaagcccggcaagagc<br>cctcagctgctgatctacggcgccagcgacctgcaggacggcgtgcctagcagattcagcggcagcggctccggaacccagtacagcctgaa<br>gatcaccagcatgcagaccgaggacgagggcgtgtacttctgccagcaaggcctgacctaccctagaaccttcggaggaggcaccaagctgg<br>aactgaagggcggaggcggaagtggaggcggaggatctggcggcggaggctctgaagtgcagctgcagcagtctggcgctgaactggtccg<br>gcctggcactagcgtgaagctgtcctgcaaggtgtccggcgacaccatcaccttctactacatgcacttcgtgaagcagaggccaggacagggc<br>ctggaatggatcggcagaatcgaccctgaggacgagagcaccaagtacagcgagaagttcaagaacaaggccaccctgaccgccgacacca |

TABLE 58-continued sCAR sequences, heavy and light chain sequences, and other sequences

| SEQ ID NO | SEQUENCE |
|---|---|
| | gcagcaacaccgcctacctgaagctgtctagcctgacctccgaggacaccgccacctacttttgcatctacggcggctactacttcgactactggg<br>gccagggcgtgatggtcaccgtgtccagcatcgagttcatgtacccccctccctacctggacaacgagagaagcaacggcaccatcatccacat<br>caaagaaaagcacctgtgccacacccagagcagccccaagctgttctgggccctggtggtggtggccggcgtgctgttctgttacggcctgctg<br>gtcacagtggccctgtgcgtgatctggaccaacagcagaagaaacagaggcggccagagcgactacatgaacatgacccccagaaggccag<br>gcctgaccagaaagccctaccagccctacgcccctgccagagacttcgccgcctacagacccagagccaagttcagcagatccgccgagaca<br>gccgccaacctgcaggatcccaaccagctgttcaacgagctgaacctgggcagacgggaggaattcgacgtgctggaaaagaagagagccag<br>ggaccccgagatgggcggcaagcagcagagaagaagaaaccctcaggaaggcgtctacaacgccctgcagaaagacaagatggccgaggc<br>ctacagcgagatcggcaccaagggcgagagaagaaggggcaagggccacgatggcctgttccagggcctgtccaccgccaccaaggacac<br>cttcgacgccctgcacatgcagaccctggcccccagatga |
| 201 | atgggtgtccctacccagctcctgggactgctcctgctgtggatcaccgacgccatctgcGACGCCGTTGTGACCCAGGAAT<br>CCGCTCTGACCTCTTCTCCAGGCGAAACCGTGACTCTGACTTGCCGTAGTAGCACCGGG<br>GCTGTGACCACATCTAACTATGCCAGTTGGGTCCAGGAAAAACCGGATCACCTGTTTAC<br>TGGCCTGATTGGCGGCACCAACAATCGCGCACCGGGTGTGCCCGCTCGTTTCAGCGGTT<br>CCCTGATTGGGGACAAGGCAGCACTGACTATCACCGGCGCCCAGACCGAAGATGAGGC<br>GATCTATTTTTGCGTCCTGTGGTACAGCGACCATTGGGTGTTCGGGGGAGGCACCAAAC<br>TGACAGTGCTGGGCGGAGGAGGAGGTTCAGGAGGAGGAGGTAGCGGGGGAGGCGGTTC<br>CGGGGGAGGCGGTTCTGATGTGCAGCTGCAAGAATCCGGGCCAGGACTGGTTGCGCCTT<br>CTCAGAGTCTGTCAATTACATGTACTGTTAGTGGCTTTCTGCTGACCGACTATGGTGTGA<br>ACTGGGTTCGTCAGAGCCCAGGCAAGGGTCTGGAGTGGCTGGGAGTGATTTGGGGGA<br>TGGAATCACAGACTACAATAGCGCACTGAAATCTCGGCTGAGTGTTACCAAAGATAACA<br>GCAAGTCCCAGGTCTTCCTGAAGATGAACAGCCTGCAAAGCGGCGACTCCGCTCGCTAT<br>TACTGCGTTACCGGACTGTTTGATTATTGGGGGCAGGGGACAACTCTGACTGTTTCCTCC<br>atcgagttcatgtacccccctccctacctggacaacgagagaagcaacggcaccatcatccacatcaaagaaaagcacctgtgccacacccaga<br>gcagccccaagctgttctgggccctggtggtggtggccggcgtgctgttctgttacggcctgctggtcacagtggccctgtgcgtgatctggacca<br>acagcagaagaaacagaggcggccagagcgactacatgaacatgacccccagaaggccaggcctgaccagaaagccctaccagccctacg<br>cccctgccagagacttcgccgcctacagacccagagccaagttcagcagatccgccgagacagccgccaacctgcaggatcccaaccagctgt<br>tcaacgagctgaacctgggcagacgggaggaattcgacgtgctggaaaagaagagagccagggaccccgagatgggcggcaagcagcaga<br>gaagaagaaaccctcaggaaggcgtctacaacgccctgcagaaagacaagatggccgaggcctacagcgagatcggcaccaagggcgaga<br>gaagaaggggcaagggccacgatggcctgttccagggcctgtccaccgccaccaaggacaccttcgacgccctgcacatgcagaccctggcc<br>cccagatga |
| 202 | atgggtgtccctacccagctcctgggactgctcctgctgtggatcaccgacgccatctgcGACGCCGTTGTGACCCAGGAAT<br>CCGCTCTGACCTCTTCTCCAGGCGAAACCGTGACTCTGACTTGCCGTAGTAGCACCGGG<br>GCTGTGACCACATCTAACTATGCCAGTTGGGTCCAGGAAAAACCGGATCACCTGTTTAC<br>TGGCCTGATTGGCGGCACCAACAATCGCGCACCGGGTGTGCCCGCTCGTTTCAGCGGTT<br>CCCTGATTGGGGACAAGGCAGCACTGACTATCACCGGCGCCCAGACCGAAGATGAGGC<br>GATCTATTTTTGCGTCCTGTGGTACAGCGACCATTGGGTGTTCGGGGGAGGCACCAAAC<br>TGACAGTGCTGGGCGGAGGAGGAGGTTCAGGAGGAGGAGGTAGCGGGGGAGGCGGTTC<br>CGGGGGAGGCGGTTCTGATGTGCAGCTGCAAGAATCCGGGCCAGGACTGGTTGCGCCTT<br>CTCAGAGTCTGTCAATTACATGTACTGTTAGTGGCTTTCTGCTGACCGACTATGGTGTGA<br>ACTGGGTTCGTCAGAGCCCAGGCAAGGGTCTGGAGTGGCTGGGAGTGATTTGGGGGA<br>TGGAATCACAGACTACAATAGCGCACTGAAATCTCGGCTGAGTGTTACCAAAGATAACA<br>GCAAGTCCCAGGTCTTCCTGAAGATGAAttcCCTGCAAAGCGGCGACTCCGCTCGCTATTA<br>CTGCGTTACCGGACTGTTTGATTATTGGGGGCAGGGGACAACTCTGACTGTTTCCTCCGA<br>AAGCAAGTATGGCCCaCCTTGTCCACCTTGTCCCATTTACATCTGGGCACCCTTGGCCGG<br>AATCTGCGTGGCCCTTCTGCTGTCCTTGATCATCACTCTCATCTGCAAATGGATCAGGAA<br>AAAATTCCCCCACATATTCAAGCAACCATTTAAGAAGACCACTGGAGCAGCTCAAGAGG<br>AAGATGCTTGTAGCTGCCGATGTCCACAGGAAGAAGAAGGAGGAGGAGGAGGCTATGA<br>GCTGagagccaagttcagcagatccgccgagacagccgccaacctgcaggatcccaaccagctgttcaacgagctgaacctgggcagacg<br>ggaggaattcgacgtgctggaaaagaagagagccagggaccccgagatgggcggcaagcagcagagaagaagaaaccctcaggaaggcg<br>tctacaacgccctgcagaaagacaagatggccgaggcctacagcgagatcggcaccaagggcgagagaagaaggggcaagggccacgatg<br>gcctgttccagggcctgtccaccgccaccaaggacaccttcgacgccctgcacatgcagaccctggcccccagatga |
| 203 | atgggtgtccctacccagctcctgggactgctcctgctgtggatcaccgacgccatctgcGACGCCGTTGTGACCCAGGAAT<br>CCGCTCTGACCTCTTCTCCAGGCGAAACCGTGACTCTGACTTGCCGTAGTAGCACCGGG<br>GCTGTGACCACATCTAACTATGCCAGTTGGGTCCAGGAAAAACCGGATCACCTGTTTAC<br>TGGCCTGATTGGCGGCACCAACAATCGCGCACCGGGTGTGCCCGCTCGTTTCAGCGGTT<br>CCCTGATTGGGGACAAGGCAGCACTGACTATCACCGGCGCCCAGACCGAAGATGAGGC<br>GATCTATTTTTGCGTCCTGTGGTACAGCGACCATTGGGTGTTCGGGGGAGGCACCAAAC<br>TGACAGTGCTGGGCGGAGGAGGAGGTTCAGGAGGAGGAGGTAGCGGGGGAGGCGGTTC<br>CGGGGGAGGCGGTTCTGATGTGCAGCTGCAAGAATCCGGGCCAGGACTGGTTGCGCCTT<br>CTCAGAGTCTGTCAATTACATGTACTGTTAGTGGCTTTCTGCTGACCGACTATGGTGTGA<br>ACTGGGTTCGTCAGAGCCCAGGCAAGGGTCTGGAGTGGCTGGGAGTGATTTGGGGGA<br>TGGAATCACAGACTACAATAGCGCACTGAAATCTCGGCTGAGTGTTACCAAAGATAACA<br>GCAAGTCCCAGGTCTTCCTGAAGATGAAttcCCTGCAAAGCGGCGACTCCGCTCGCTATTA<br>CTGCGTTACCGGACTGTTTGATTATTGGGGGCAGGGGACAACTCTGACTGTTTCCTCCGA<br>AAGCAAGTATGGCCCaCCTTGTCCACCTTGTCCCATTTACATCTGGGCACCCTTGGCCGG<br>AATCTGCGTGGCCCTTCTGCTGTCCTTGATCATCACTCTCATCTGCAAATGGATCAGGAA<br>AAAATTCCCCCACATATTCAAGCAACCATTTAAGAAGACCACTGGAGCAGCTCAAGAGG<br>AAGATGCTTGTAGCTGCCGATGTCCACAGGAAGAAGAAGGAGGAGGAGGAGGCTATGA<br>GCTGAGAGCAAAATTCAGCAGGAGTGCAGAGACTGCTGCCAACCTGCAGGACCCCAAC<br>CAGCTCTACAATGAGCTCAATCTAGGGCGAAGAGAGGAATATGACGTCTTGGAGAAGA<br>AGCGGGCTCGGGATCCAGAGATGGGAGGCAAACAGCAGAGGAGGAGGAACCCCCAGG |

TABLE 58-continued sCAR sequences, heavy and light chain sequences, and other sequences

SEQ ID NO SEQUENCE

AAGGCGTATACAATGCACTGCAGAAAGACAAGATGGCAGAAGCCTACAGTGAGATCGG
CACAAAAGGCGAGAGGCGGAGAGGCAAGGGGCACGATGGCCTTTACCAGGGTCTCAGC
ACTGCCACCAAGGACACCTATGATGCCCTGCATATGCAGACCCTGGCCCCTCGCTAA 204 atgggtgtccctacccagctcctgggactgctcctgctgtggatcaccgacgccatctgcGACGCCGTTGTGACCCAGGAAT
CCGCTCTGACCTCTTCTCCAGGCGAAACCGTGACTCTGACTTGCCGTAGTAGCACCGGG
GCTGTGACCACATCTAACTATGCCAGTTGGGTCCAGGAAAAACCGGATCACCTGTTTAC
TGGCCTGATTGGCGGCACCAACAATCGCGCACCGGGTGTGCCCGCTCGTTTCAGCGGTT
CCCTGATTGGGGACAAGGCAGCACTGACTATCACCGGCGCCCAGACCGAAGATGAGGC
GATCTATTTTTGCGTCCTGTGGTACAGCGACCATTGGGTGTTCGGGGGAGGCACCAAAC
TGACAGTGCTGGGCGGAGGAGGAGGTTCAGGAGGAGGAGGTAGCGGGGGAGGCGGTTC
CGGGGGAGGCGGTTCTGATGTGCAGCTGCAAGAATCCGGGCCAGGACTGGTTGCGCCTT
CTCAGAGTCTGTCAATTACATGTACTGTTAGTGGCTTTCTGCTGACCGACTATGGTGTGA
ACTGGGTTCGTCAGAGCCCAGGCAAGGGTCTGGAGTGGCTGGGAGTGATTTGGGGGGA
TGGAATCACAGACTACAATAGCGCACTGAAATCTCGGCTGAGTGTTACCAAAGATAACA
GCAAGTCCCAGGTCTTCCTGAAGATGAAttcCCTGCAAAGCGGCGACTCCGCTCGCTATTA
CTGCGTTACCGGACTGTTTGATTATTGGGGGCAGGGGACAACTCTGACTGTTTCCTCCAC
TACTACCAAGCCAGTGCTGCGAACTCCCTCACCTGTGCACCCTACCGGGACATCTCAGC
CCCAGAGACCAGAAGATTGTCGGCCCCGTGGCTCAGTGAAGGGGACCGGATTGGACTTC
GCCTGTGATATTTACATCTGGGCACCCTTGGCCGGAATCTGCGTGGCCCTTCTGCTGTCC
TTGATCATCACTCTCATCTGCAAATGGATCAGGAAAAAATTCCCCCACATATTCAAGCA
ACCATTTAAGAAGACCACTGGAGCAGCTCAAGAGGAAGATGCTTGTAGCTGCCGATGTC
CACAGGAAGAAGAAGGAGGAGGAGGAGGCTATGAGCTGagagccaagttcagcagatccgccgagacag
ccgccaacctgcaggatcccaaccagctgttcaacgagctgaacctgggcagacgggaggaattcgacgtgctggaaaagaagagagccagg
gaccccgagatgggcggcaagcagcagagaagaagaaaccctcaggaaggcgtctacaacgccctgcagaaagacaagatggccgaggcc
tacagcgagatcggcaccaagggcgagagaagaaggggcaagggccacgatggcctgttccagggcctgtccaccgccaccaaggacacct
tcgacgccctgcacatgcagaccctggcccccagatga 205 atgggtgtccctacccagctcctgggactgctcctgctgtggatcaccgacgccatctgcGACGCCGTTGTGACCCAGGAAT
CCGCTCTGACCTCTTCTCCAGGCGAAACCGTGACTCTGACTTGCCGTAGTAGCACCGGG
GCTGTGACCACATCTAACTATGCCAGTTGGGTCCAGGAAAAACCGGATCACCTGTTTAC
TGGCCTGATTGGCGGCACCAACAATCGCGCACCGGGTGTGCCCGCTCGTTTCAGCGGTT
CCCTGATTGGGGACAAGGCAGCACTGACTATCACCGGCGCCCAGACCGAAGATGAGGC
GATCTATTTTTGCGTCCTGTGGTACAGCGACCATTGGGTGTTCGGGGGAGGCACCAAAC
TGACAGTGCTGGGCGGAGGAGGAGGTTCAGGAGGAGGAGGTAGCGGGGGAGGCGGTTC
CGGGGGAGGCGGTTCTGATGTGCAGCTGCAAGAATCCGGGCCAGGACTGGTTGCGCCTT
CTCAGAGTCTGTCAATTACATGTACTGTTAGTGGCTTTCTGCTGACCGACTATGGTGTGA
ACTGGGTTCGTCAGAGCCCAGGCAAGGGTCTGGAGTGGCTGGGAGTGATTTGGGGGGA
TGGAATCACAGACTACAATAGCGCACTGAAATCTCGGCTGAGTGTTACCAAAGATAACA
GCAAGTCCCAGGTCTTCCTGAAGATGAAttcCCTGCAAAGCGGCGACTCCGCTCGCTATTA
CTGCGTTACCGGACTGTTTGATTATTGGGGGCAGGGGACAACTCTGACTGTTTCCTCCAC
TACTACCAAGCCAGTGCTGCGAACTCCCTCACCTGTGCACCCTACCGGGACATCTCAGC
CCCAGAGACCAGAAGATTGTCGGCCCCGTGGCTCAGTGAAGGGGACCGGATTGGACTTC
GCCTGTGATATTTACATCTGGGCACCCTTGGCCGGAATCTGCGTGGCCCTTCTGCTGTCC
TTGATCATCACTCTCATCTGCAAATGGATCAGGAAAAAATTCCCCCACATATTCAAGCA
ACCATTTAAGAAGACCACTGGAGCAGCTCAAGAGGAAGATGCTTGTAGCTGCCGATGTC
CACAGGAAGAAGAAGGAGGAGGAGGAGGCTATGAGCTGAGAGCAAAATTCAGCAGGA
GTGCAGAGACTGCTGCCAACCTGCAGGACCCCAACCAGCTCTACAATGAGCTCAATCTA
GGGCGAAGAGAGGAATATGACGTCTTGGAGAAGAAGCGGGCTCGGGATCCAGAGATGG
GAGGCAAACAGCAGAGGAGGAGGAACCCCCAGGAAGGCGTATACAATGCACTGCAGA
AAGACAAGATGGCAGAAGCCTACAGTGAGATCGGCACAAAAGGCGAGAGGCGGAGAG
GCAAGGGGCACGATGGCCTTTACCAGGGTCTCAGCACTGCCACCAAGGACACCTATGAT
GCCCTGCATATGCAGACCCTGGCCCCTCGCTAA 206 atgggtgtccctacccagctcctgggactgctcctgctgtggatcaccgacgccatctgcgacatccagatgacccagagccctgccagcctgtct
accagcctgggcgagacagtgaccatccagtgtcaggccagcgaggacatctactctggcctggcttggtatcagcagaagcccggcaagagc
cctcagctgctgatctacggcgccagcgacctgcaggacggcgtgcctagcagattcagcggcagcggctccggaacccagtacagcctgaa
gatcaccagcatgcagaccgaggacgagggcgtgtacttctgccagcaaggcctgacctaccctagaaccttcggaggaggcaccaagctgg
aactgaagggcggaggcggaagtggaggcggaggatctggcggcggaggctctgaagtgcagctgcagcagtctggcgctgaactggtccg
gcctggcactagcgtgaagctgtcctgcaaggtgtccggcgacaccatcaccttctactacatgcacttcgtgaagcagaggccaggacagggc
ctggaatggatcggcagaatcgaccctgaggacgagagcaccaagtacagcgagaagttcaagaacaaggccaccctgaccgccgacacca
gcagcaacaccgcctacctgaagctgtctagcctgacctccgaggacaccgccacctacttttgcatctacggcggctactacttcgactactggg
gccagggcgtgatggtcaccgtgtccagcGAAAGCAAGTATGGCCCaCCTTGTCCACCTTGTCCCATTTA
CATCTGGGCACCCTTGGCCGGAATCTGCGTGGCCCTTCTGCTGTCCTTGATCATCACTCT
CATCTGCAAATGGATCAGGAAAAAATTCCCCCACATATTCAAGCAACCATTTAAGAAGA
CCACTGGAGCAGCTCAAGAGGAAGATGCTTGTAGCTGCCGATGTCCACAGGAAGAAGA
AGGAGGAGGAGGAGGCTATGAGCTGagagccaagttcagcagatccgccgagacagccgccaacctgcaggatccca
accagctgttcaacgagctgaacctgggcagacgggaggaattcgacgtgctggaaaagaagagagccagggaccccgagatgggcggcaa
gcagcagagaagaagaaaccctcaggaaggcgtctacaacgccctgcagaaagacaagatggccgaggcctacagcgagatcggcaccaa
gggcgagagaagaaggggcaagggccacgatggcctgttccagggcctgtccaccgccaccaaggacaccttcgacgccctgcacatgcag
accctggcccccagatga 207 atgggtgtccctacccagctcctgggactgctcctgctgtggatcaccgacgccatctgcgacatccagatgacccagagccctgccagcctgtct
accagcctgggcgagacagtgaccatccagtgtcaggccagcgaggacatctactctggcctggcttggtatcagcagaagcccggcaagagc TABLE 58-continued

| SEQ ID NO | SEQUENCE |
|---|---|
| | cctcagctgctgatctacggcgccagcgacctgcaggacggcgtgcctagcagattcagcggcagcggctccggaacccagtacagcctgaa<br>gatcaccagcatgcagaccgaggacgagggcgtgtacttctgccagcaaggcctgacctaccctagaaccttcggaggaggcaccaagctgg<br>aactgaagggcggaggcggaagtggaggcggaggatctggcggcggaggctctgaagtgcagctgcagcagtctggcgctgaactggtccg<br>gcctggcactagcgtgaagctgtcctgcaaggtgtccggcgacaccatcaccttctactacatgcacttcgtgaagcagaggccaggacagggc<br>ctggaatggatcggcagaatcgaccctgaggacgagagcaccaagtacagcgagaagttcaagaacaaggccaccctgaccgccgacacca<br>gcagcaacaccgcctacctgaagctgtctagcctgacctccgaggacaccgccacctacttttgcatctacggcggctactacttcgactactggg<br>gccagggcgtgatggtcaccgtgtccagcGAAAGCAAGTATGGCCCaCCTTGTCCACCTTGTCCCATTTA<br>CATCTGGGCACCCTTGGCCGGAATCTGCGTGGCCCTTCTGCTGTCCTTGATCATCACTCT<br>CATCTGCAAATGGATCAGGAAAAAATTCCCCCACATATTCAAGCAACCATTTAAGAAGA<br>CCACTGGAGCAGCTCAAGAGGAAGATGCTTGTAGCTGCCGATGTCCACAGGAAGAAGA<br>AGGAGGAGGAGGAGGCTATGAGCTGAGAGCAAAATTCAGCAGGAGTGCAGAGACTGCT<br>GCCAACCTGCAGGACCCCAACCAGCTCTACAATGAGCTCAATCTAGGGCGAAGAGAGG<br>AATATGACGTCTTGGAGAAGAAGCGGGCTCGGGATCCAGAGATGGGAGGCAAACAGCA<br>GAGGAGGAGGAACCCCCAGGAAGGCGTATACAATGCACTGCAGAAAGACAAGATGGC<br>AGAAGCCTACAGTGAGATCGGCACAAAAGGCGAGAGGCGGAGAGGCAAGGGGCACGA<br>TGGCCTTTACCAGGGTCTCAGCACTGCCACCAAGGACACCTATGATGCCCTGCATATGC<br>AGACCCTGGCCCCTCGCTAA |
| 208 | atgggtgtccctacccagctcctgggactgctcctgctgtggatcaccgacgccatctgcgacatccagatgacccagagccctgccagcctgtct<br>accagcctgggcgagacagtgaccatccagtgtcaggccagcgaggacatctactctggcctggcttggtatcagcagaagcccggcaagagc<br>cctcagctgctgatctacggcgccagcgacctgcaggacggcgtgcctagcagattcagcggcagcggctccggaacccagtacagcctgaa<br>gatcaccagcatgcagaccgaggacgagggcgtgtacttctgccagcaaggcctgacctaccctagaaccttcggaggaggcaccaagctgg<br>aactgaagggcggaggcggaagtggaggcggaggatctggcggcggaggctctgaagtgcagctgcagcagtctggcgctgaactggtccg<br>gcctggcactagcgtgaagctgtcctgcaaggtgtccggcgacaccatcaccttctactacatgcacttcgtgaagcagaggccaggacagggc<br>ctggaatggatcggcagaatcgaccctgaggacgagagcaccaagtacagcgagaagttcaagaacaaggccaccctgaccgccgacacca<br>gcagcaacaccgcctacctgaagctgtctagcctgacctccgaggacaccgccacctacttttgcatctacggcggctactacttcgactactggg<br>gccagggcgtgatggtcaccgtgtccagcACTACTACCAAGCCAGTGCTGCGAACTCCCTCACCTGTGCA<br>CCCTACCGGGACATCTCAGCCCCAGAGACCAGAAGATTGTCGGCCCCGTGGCTCAGTGA<br>AGGGGACCGGATTGGACTTCGCCTGTGATATTTACATCTGGGCACCCTTGGCCGGAATC<br>TGCGTGGCCCTTCTGCTGTCCTTGATCATCACTCTCATCTGCAAATGGATCAGGAAAAAA<br>TTCCCCCACATATTCAAGCAACCATTTAAGAAGACCACTGGAGCAGCTCAAGAGGAAGA<br>TGCTTGTAGCTGCCGATGTCCACAGGAAGAAGAAGGAGGAGGAGGAGGCTATGAGCTG<br>agagccaagttcagcagatccgccgagacagccgccaacctgcaggatcccaaccagctgttcaacgagctgaacctgggcagacgggagg<br>aattcgacgtgctggaaaagaagagagccagggaccccgagatgggcggcaagcagcagagaagaagaaaccctcaggaaggcgtctaca<br>acgccctgcagaaagacaagatggccgaggcctacagcgagatcggcaccaagggcgagagaagaaggggcaagggccacgatggcctgt<br>tccagggcctgtccaccgccaccaaggacaccttcgacgccctgcacatgcagaccctggcccccagatga |
| 209 | atgggtgtccctacccagctcctgggactgctcctgctgtggatcaccgacgccatctgcgacatccagatgacccagagccctgccagcctgtct<br>accagcctgggcgagacagtgaccatccagtgtcaggccagcgaggacatctactctggcctggcttggtatcagcagaagcccggcaagagc<br>cctcagctgctgatctacggcgccagcgacctgcaggacggcgtgcctagcagattcagcggcagcggctccggaacccagtacagcctgaa<br>gatcaccagcatgcagaccgaggacgagggcgtgtacttctgccagcaaggcctgacctaccctagaaccttcggaggaggcaccaagctgg<br>aactgaagggcggaggcggaagtggaggcggaggatctggcggcggaggctctgaagtgcagctgcagcagtctggcgctgaactggtccg<br>gcctggcactagcgtgaagctgtcctgcaaggtgtccggcgacaccatcaccttctactacatgcacttcgtgaagcagaggccaggacagggc<br>ctggaatggatcggcagaatcgaccctgaggacgagagcaccaagtacagcgagaagttcaagaacaaggccaccctgaccgccgacacca<br>gcagcaacaccgcctacctgaagctgtctagcctgacctccgaggacaccgccacctacttttgcatctacggcggctactacttcgactactggg<br>gccagggcgtgatggtcaccgtgtccagcACTACTACCAAGCCAGTGCTGCGAACTCCCTCACCTGTGCA<br>CCCTACCGGGACATCTCAGCCCCAGAGACCAGAAGATTGTCGGCCCCGTGGCTCAGTGA<br>AGGGGACCGGATTGGACTTCGCCTGTGATATTTACATCTGGGCACCCTTGGCCGGAATC<br>TGCGTGGCCCTTCTGCTGTCCTTGATCATCACTCTCATCTGCAAATGGATCAGGAAAAAA<br>TTCCCCCACATATTCAAGCAACCATTTAAGAAGACCACTGGAGCAGCTCAAGAGGAAGA<br>TGCTTGTAGCTGCCGATGTCCACAGGAAGAAGAAGGAGGAGGAGGAGGCTATGAGCTG<br>AGAGCAAAATTCAGCAGGAGTGCAGAGACTGCTGCCAACCTGCAGGACCCCAACCAGC<br>TCTACAATGAGCTCAATCTAGGGCGAAGAGAGGAATATGACGTCTTGGAGAAGAAGCG<br>GGCTCGGGATCCAGAGATGGGAGGCAAACAGCAGAGGAGGAGGAACCCCCAGGAAGG<br>CGTATACAATGCACTGCAGAAAGACAAGATGGCAGAAGCCTACAGTGAGATCGGCACA<br>AAAGGCGAGAGGCGGAGAGGCAAGGGGCACGATGGCCTTTACCAGGGTCTCAGCACTG<br>CCACCAAGGACACCTATGATGCCCTGCATATGCAGACCCTGGCCCCTCGCTAA |
| 210 | atgggtgtccctacccagctcctgggactgctcctgctgtggatcaccgacgccatctgcGACGCCGTTGTGACCCAGGAAT<br>CCGCTCTGACCTCTTCTCCAGGCGAAACCGTGACTCTGACTTGCCGTAGTAGCACCGGG<br>GCTGTGACCACATCTAACTATGCCAGTTGGGTCCAGGAAAAACCGGATCACCTGTTTAC<br>TGGCCTGATTGGCGGCACCAACAATCGCGCACCGGGTGTGCCCGCTCGTTTCAGCGGTT<br>CCCTGATTGGGGACAAGGCAGCACTGACTATCACCGGCGCCCAGACCGAAGATGAGGC<br>GATCTATTTTTGCGTCCTGTGGTACAGCGACCATTGGGTGTTCGGGGGAGGCACCAAAC<br>TGACAGTGCTGGGCGGAGGAGGAGGTTCAGGAGGAGGAGGTAGCGGGGGAGGCGGTTC<br>CGGGGGAGGCGGTTCTGATGTGCAGCTGCAAGAATCCGGGCCAGGACTGGTTGCGCCTT<br>CTCAGAGTCTGTCAATTACATGTACTGTTAGTGGCTTTCTGCTGACCGACTATGGTGTGA<br>ACTGGGTTCGTCAGAGCCCAGGCAAGGGTCTGGAGTGGCTGGGAGTGATTTGGGGGGA<br>TGGAATCACAGACTACAATAGCGCACTGAAATCTCGGCTGAGTGTTACCAAAGATAACA<br>GCAAGTCCCAGGTCTTCCTGAAGATGAACAGCCTGCAAAGCGGCGACTCCGCTCGCTAT<br>TACTGCGTTACCGGACTGTTTGATTATTGGGGGCAGGGGACAACTCTGACTGTTTCCTCC<br>GAAAGCAAGTATGGCCCaCCTTGTCCACCTTGTCCCttctgggccctggtggtggtggccggcgtgctgttctgtt<br>acggcctgctggtcacagtggccctgtgcgtgatctggaccaacagcagaagaaacagaggcggccagagcgactacatgaacatgaccccc<br>agaaggccaggcctgaccagaaagccctaccagccctacgcccctgccagagacttcgccgcctacagacccagagccaagttcagcagatc |

TABLE 58-continued

| sCAR sequences, heavy and light chain sequences, and other sequences | |
|---|---|
| SEQ ID NO | SEQUENCE |
| | cgccgagacagccgccaacctgcaggatcccaaccagctgttcaacgagctgaacctgggcagacgggaggaattcgacgtgctggaaaaga<br>agagagccagggaccccgagatgggcggcaagcagcagagaagaagaaaccctcaggaaggcgtctacaacgccctgcagaaagacaag<br>atggccgaggcctacagcgagatcggcaccaagggcgagagaagaaggggcaagggccacgatggcctgttccagggcctgtccaccgcc<br>accaaggacaccttcgacgccctgcacatgcagaccctggcccccagatga |
| 211 | atgggtgtccctacccagctcctgggactgctcctgctgtggatcaccgacgccatctgcGATGTGCAGCTGCAAGAATCCG<br>GGCCAGGACTGGTTGCGCCTTCTCAGAGTCTGTCAATTACATGTACTGTTAGTGGCTTTC<br>TGCTGACCGACTATGGTGTGAACTGGGTTCGTCAGAGCCCAGGCAAGGGTCTGGAGTGG<br>CTGGGAGTGATTTGGGGGGATGGAATCACAGACTACAATAGCGCACTGAAATCTCGGCT<br>GAGTGTTACCAAAGATAACAGCAAGTCCCAGGTCTTCCTGAAGATGAACAGCCTGCAAA<br>GCGGCGACTCCGCTCGCTATTACTGCGTTACCGGACTGTTTGATTATTGGGGGCAGGGG<br>ACAACTCTGACTGTTTCCTCCGGAGGAGGAGGTTCAGGAGGAGGAGGTAGCGGGGGAG<br>GCGGTTCCGGGGGAGGCGGTTCTGACGCCGTTGTGACCCAGGAATCCGCTCTGACCTCT<br>TCTCCAGGCGAAACCGTGACTCTGACTTGCCGTAGTAGCACCGGGGCTGTGACCACATC<br>TAACTATGCCAGTTGGGTCCAGGAAAAACCGGATCACCTGTTTACTGGCCTGATTGGCG<br>GCACCAACAATCGCGCACCGGGTGTGCCCGCTCGTTTCAGCGGTTCCCTGATTGGGGAC<br>AAGGCAGCACTGACTATCACCGGCGCCCAGACCGAAGATGAGGCGATCTATTTTTGCGT<br>CCTGTGGTACAGCGACCATTGGGTGTTCGGGGGAGGCACCAAACTGACAGTGCTGGGCG<br>AAAGCAAGTATGGCCCaCCTTGTCCACCTTGTCCCttctgggccctggtggtggtggccggcgtgctgttctgtta<br>cggcctgctggtcacagtggccctgtgcgtgatctggaccaacagcagaagaaacagaggcggccagagcgactacatgaacatgacccccca<br>gaaggccaggcctgaccagaaagccctaccagccctacgcccctgccagagacttcgccgcctacagacccagagccaagttcagcagatcc<br>gccgagacagccgccaacctgcaggatcccaaccagctgttcaacgagctgaacctgggcagacgggaggaattcgacgtgctggaaaagaa<br>gagagccagggaccccgagatgggcggcaagcagcagagaagaagaaaccctcaggaaggcgtctacaacgccctgcagaaagacaagat<br>ggccgaggcctacagcgagatcggcaccaagggcgagagaagaaggggcaagggccacgatggcctgttccagggcctgtccaccgccac<br>caaggacaccttcgacgccctgcacatgcagaccctggcccccagatga |
| 212 | atgggtgtccctacccagctcctgggactgctcctgctgtggatcaccgacgccatctgcGACGCCGTTGTGACCCAGGAAT<br>CCGCTCTGACCTCTTCTCCAGGCGAAACCGTGACTCTGACTTGCCGTAGTAGCACCGGG<br>GCTGTGACCACATCTAACTATGCCAGTTGGGTCCAGGAAAAACCGGATCACCTGTTTAC<br>TGGCCTGATTGGCGGCACCAACAATCGCGCACCGGGTGTGCCCGCTCGTTTCAGCGGTT<br>CCCTGATTGGGGACAAGGCAGCACTGACTATCACCGGCGCCCAGACCGAAGATGAGGC<br>GATCTATTTTTGCGTCCTGTGGTACAGCGACCATTGGGTGTTCGGGGGAGGCACCAAAC<br>TGACAGTGCTGGGCGGAGGAGGAGGTTCAGGAGGAGGAGGTAGCGGGGGAGGCGGTTC<br>CGGGGGAGGCGGTTCTGATGTGCAGCTGCAAGAATCCGGGCCAGGACTGGTTGCGCCTT<br>CTCAGAGTCTGTCAATTACATGTACTGTTAGTGGCTTTCTGCTGACCGACTATGGTGTGA<br>ACTGGGTTCGTCAGAGCCCAGGCAAGGGTCTGGAGTGGCTGGGAGTGATTTGGGGGGA<br>TGGAATCACAGACTACAATAGCGCACTGAAATCTCGGCTGAGTGTTACCAAAGATAACA<br>GCAAGTCCCAGGTCTTCCTGAAGATGAACAGCCTGCAAAGCGGCGACTCCGCTCGCTAT<br>TACTGCGTTACCGGACTGTTTGATTATTGGGGGCAGGGGACAACTCTGACTGTTTCCTCC<br>GAAAGCAAGTATGGCCCaCCTTGTCCACCTTGTCCCgatatctacatctgggcgcccttggccgggacttgtggg<br>gtccttctcctgtcactggttatcaccctttactgcaaacggggcagaaagaaactcctgtatatattcaaacaaccatttatgagaccagtacaaact<br>actcaagaggaagatggctgtagctgccgatttccagaagaagaagaaggaggatgtgaactgagagtgaagttcagcaggagcgcagacgc<br>cccgcgtacaagcagggccagaaccagctctataacgagctcaatctaggacgaagagaggagtacgatgttttggacaagagacgtggccg<br>ggaccctgagatgggggaaagccgagaaggaagaaccctcaggaaggcctgtacaatgaactgcagaaagataagatggcggaggcctac<br>agtgagattgggatgaaaggcgagcgccggaggggcaaggggcacgatggcctttaccagggtctcagtacagccaccaaggacacctacg<br>acgcccttcacatgcaggccctgccccctcgctaa |
| 213 | atgggtgtccctacccagctcctgggactgctcctgctgtggatcaccgacgccatctgcgacatccagatgacccagagccctgccagcctgtct<br>accagcctgggcgagacagtgaccatccagtgtcaggccagcgaggacatctactctggcctggcttggtatcagcagaagcccggcaagagc<br>cctcagctgctgatctacggcgccagcgacctgcaggacggcgtgcctagcagattcagcggcagcggctccggaacccagtacagcctgaa<br>gatcaccagcatgcagaccgaggacgagggcgtgtacttctgccagcaaggcctgacctaccctagaaccttcggaggaggcaccaagctgg<br>aactgaagggcggaggcggaagtggaggcggaggatctggcggcggaggctctgaagtgcagctgcagcagtctggcgctgaactggtccg<br>gcctggcactagcgtgaagctgtcctgcaaggtgtccggcgacaccatcaccttctactacatgcacttcgtgaagcagaggccaggacagggc<br>ctggaatggatcggcagaatcgaccctgaggacgagagcaccaagtacagcgagaagttcaagaacaaggccaccctgaccgccgacacca<br>gcagcaacaccgcctacctgaagctgtctagcctgacctccgaggacaccgccacctacttttgcatctacggcggctactacttcgactactggg<br>gccagggcgtgatggtcaccgtgtccagcaccacgacgccagcgccgcgaccaccaacaccggcgcccaccatcgcgtcgcagcccctgtc<br>cctgcgcccagaggcgtgccggccagcggcggggggcgcagtgcacacgagggggctggacttcgcctgtgatatctacatctgggcgccct<br>tggccgggacttgtggggtccttctcctgtcactggttatcaccctttactgcaaacggggcagaaagaaactcctgtatatattcaaacaaccattta<br>tgagaccagtacaaactactcaagaggaagatggctgtagctgccgatttccagaagaagaagaaggaggatgtgaactgagagtgaagttcag<br>caggagcgcagacgcccccgcgtacaagcagggccagaaccagctctataacgagctcaatctaggacgaagagaggagtacgatgttttgg<br>acaagagacgtggccgggaccctgagatgggggaaagccgagaaggaagaaccctcaggaaggcctgtacaatgaactgcagaaagataa<br>gatggcggaggcctacagtgagattgggatgaaaggcgagcgccggaggggcaaggggcacgatggcctttaccagggtctcagtacagcc<br>accaaggacacctacgacgcccttcacatgcaggccctgccccctcgctaa |
| 214 | GG |
| 215 | MYRMQLLSCIALSLALVTNS**NYHLENEVARLKKLGG**DIQLTQSPASLSTSLGETVTIQCQA<br>SEDIYSGLAWYQQKPGKSPQLLIYGASDLQDGVPSRFSGSGSGTQYSLKITSMQTEDEGVYF<br>CQQGLTYPRTFGGGTKLEIKRTVAAPSVFIFPPSDEQLKSGTASVVCLLNNFYPREAKVQWK<br>VDNALQSGNSQESVTEQDSKDSTYSLSSTLTLSKADYEKHKVYACEVTHQGLSSPVTKSFN<br>RGEC. |
| 216 | MYRMQLLSCIALSLALVTNS**NYHLENEVARLKKLGG**QVQLVQSGAELVRPGTSVKLSCK<br>VSGDTITFYYMHFVKQRPGQGLEWIGRIDPEDESTKYSEKFKNKATLTADTSSNTAYLKLSS |

TABLE 58-continued sCAR sequences, heavy and light chain sequences, and other sequences

| SEQ ID NO | SEQUENCE |
|---|---|
| | LTSEDTATYFCIYGGYYFDYWGPGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC. |
| 217 | **NYHLENEVARLKKL**GGGGSDIQLTQSPSTLSASVGDRVTITCRASESLDNYGIRFLTWFQQKPGKAPKLLMYAASNQGSGVPSRFSGSGSGTEFTLTISSLQPDDFATYYCQQTKEVPWSFGQGTKVEVRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 218 | **NYHLENEVARLKKL**GGGGSGGGGSDIQLTQSPSTLSASVGDRVTITCRASESLDNYGIRFLTWFQQKPGKAPKLLMYAASNQGSGVPSRFSGSGSGTEFTLTISSLQPDDFATYYCQQTKEVPWSFGQGTKVEVRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 219 | **NYHLENEVARLKKL**GGGGSGGGGSGGGGSDIQLTQSPSTLSASVGDRVTITCRASESLDNYGIRFLTWFQQKPGKAPKLLMYAASNQGSGVPSRFSGSGSGTEFTLTISSLQPDDFATYYCQQTKEVPWSFGQGTKVEVRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 220 | **NYHLENEVARLKKLL**VGEAAAKEAAAKAEVQLVQSGAEVKKPGSSVKVSCKASGYTITDSNIHWVRQAPGQSLEWIGYIYPYNGGTDYNQKFKNRATLTVDNPTNTAYMELSSLRSEDTAFYYCVNGNPWLAYWGQGTLVTVSSARTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 221 | **NYHLENEVARLKKL**EAAAKEAAAKEAAAKAEVQLVQSGAEVKKPGSSVKVSCKASGYTITDSNIHWVRQAPGQSLEWIGYIYPYNGGTDYNQKFKNRATLTVDNPTNTAYMELSSLRSEDTAFYYCVNGNPWLAYWGQGTLVTVSSARTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| 222 | DIQLTQSPSTLSASVGDRVTITCRASESLDNYGIRFLTWFQQKPGKAPKLLMYAASNQGSGVPSRFSGSGSGTEFTLTISSLQPDDFATYYCQQTKEVPWSFGQGTKVEVRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGS**NYHLENEVARLKKL** |
| 223 | DIQLTQSPSTLSASVGDRVTITCRASESLDNYGIRFLTWFQQKPGKAPKLLMYAASNQGSGVPSRFSGSGSGTEFTLTISSLQPDDFATYYCQQTKEVPWSFGQGTKVEVRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSGGGGSNYHLENEVARLKKL |
| 224 | DIQLTQSPSTLSASVGDRVTITCRASESLDNYGIRFLTWFQQKPGKAPKLLMYAASNQGSGVPSRFSGSGSGTEFTLTISSLQPDDFATYYCQQTKEVPWSFGQGTKVEVRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSGGGGSGGGGS**NYHLENEVARLKKL** |
| 225 | EVQLVQSGAEVKKPGSSVKVSCKASGYTITDSNIHWVRQAPGQSLEWIGYIYPYNGGTDYNQKFKNRATLTVDNPTNTAYMELSSLRSEDTAFYYCVNGNPWLAYWGQGTLVTVSSARTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCGGGGS**NYHLENEVARLKKL** |
| 226 | EVQLVQSGAEVKKPGSSVKVSCKASGYTITDSNIHWVRQAPGQSLEWIGYIYPYNGGTDYNQKFKNRATLTVDNPTNTAYMELSSLRSEDTAFYYCVNGNPWLAYWGQGTLVTVSSARTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCGGGGSGGGGS**NYHLENEVARLKKL** |
| 227 | EVQLVQSGAEVKKPGSSVKVSCKASGYTITDSNIHWVRQAPGQSLEWIGYIYPYNGGTDYNQKFKNRATLTVDNPTNTAYMELSSLRSEDTAFYYCVNGNPWLAYWGQGTLVTVSSARTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCGGGGSGGGGSGGGGS**NYHLENEVARLKKL** |
| 228 | EVQLVQSGAEVKKPGSSVKVSCKASGYTITDSNIHWVRQAPGQSLEWIGYIYPYNGGTDYNQKFKNRATLTVDNPTNTAYMELSSLRSEDTAFYYCVNGNPWLAYWGQGTLVTVSSARTKGPSVFPLAPSS**NYHLENEVARLKKL**SGGTAALGCLVKDYFPEPVTVSWNSGALTSGVHTFPAVLQSSGLYSLSSVVTVPSSSLGTQTYICNVNHKPSNTKVDKKVEPKSC |
| 229 | EVQLVQSGAEVKKPGSSVKVSCKASGYTITDSNIHWVRQAPGQSLEWIGYIYPYNGGTDYNQKFKNRATLTVDNPTNTAYMELSSLRSEDTAFYYCVNGNPWLAYWGQGTLVTVSSARTKGPSVFPLAPSSKSTSGGTAALGCLVKDYFPEPVTVSWNSGALTSGVHTFPAVLQSGGGGS**NYHLENEVARLKKL**GGGGSLYSLSSVVTVPSSSLGTQTYICNVNHKPSNTKVDKKVEPKSC |
| 230 | DIQLTQSPSTLSASVGDRVTITCRASESLDNYGIRFLTWFQQKPGKAPKLLMYAASNQGSGVPSRFSGSGSGTEFTLTISSLQPDDFATYYCQQTKEVPWSFGQGTKVEV |

TABLE 58-continued sCAR sequences, heavy and light chain sequences, and other sequences

| SEQ ID NO | SEQUENCE |
|---|---|
| | RTVAAPSVFIFPPSDEQLKSGTASVVCLLNNFYPREAKVQWKVDNALQSGNSQESVTEQDS<br>GGGGS**NYHLENEVARLKKL**GGGGSDSTYSLSSTLTLSKADYEKHKVYACEVTHQGLSSPV<br>TKSFNRGEC |
| 231 | DIQLTQSPSTLSASVGDRVTITCRASESLDNYGIRFLTWFQQKPGKAPKLLMYAASNQGSGV<br>PSRFSGSGSGTEFTLTISSLQPDDFATYYCQQTKEVPWSFGQGTKVEVKRTVAAPSVFIFPPS<br>DEQLKSGTASVVCLLNNFYPREAKVQWKVDNALQSGNSQESVTEQDSKDSTYSLSSTLTLS<br>KADYEKHKVYACEVTHQGLSSPVTKSFNRGEC |
| 232 | EVQLVQSGAEVKKPGSSVKVSCKASGYTITDSNIHWVRQAPGQSLEWIGYIYPYNGGTDYN<br>QKFKNRATLTVDNPTNTAYMELSSLRSEDTAFYYCVNGNPWLAYWGQGTLVTVSSASTKG<br>PSVFPLAPSSKSTSGGTAALGCLVKDYFPEPVTVSWNSGALTSGVHTFPAVLQSSGLYSLSSV<br>VTVPSSSLGTQTYICNVNHKPSNTKVDKKVEPKSCDKTHT |
| 233 | DIVLTQSPASLAVSLGQRATISCRASESVDNYGNTFMHWYQQKPGQPPKWYRASNLESGIP<br>ARFSGSGSRTDFTLTINPVEADDVATYYCQQSNEDPPTFGAGTKLELRTVAAPSVFIFPPSDE<br>QLKSGTASVVCLLNNFYPREAKVQWKVDNALQSGNSQESVTEQDSKDSTYSLSSTLTLSKA<br>DYEKHKVYACEVTHQGLSSPVTKSFNRGEC |
| 234 | QIQLVQSGPELKKPGETVKISCKASGYIFTNYGMNWVKQAPGKSFKWMGWINTYTGESTYS<br>ADFKGRFAFSLETSASTAYLHINDLKNEDTATYFCARSGGYDPMDYWGQGTSVTVSSARTK<br>GPSVFPLAPSSKSTSGGTAALGCLVKDYFPEPVTVSWNSGALTSGVHTFPAVLQSSGLYSLSS<br>VVTVPSSSLGTQTYICNVNHKPSNTKVDKKVEPKSC |
| 235 | DVQITQSPSYLAASPGETITINCRASKSISKDLAWYQEKPGKTNKLLIYSGSTLQSGIPSRFSGS<br>GSGTDFTLTISSLEPEDFAMYYCQQHNKYPYTFGGGTKLEIRTVAAPSVFIFPPSDEQLKSGT<br>ASVVCLLNNFYPREAKVQWKVDNALQSGNSQESVTEQDSKDSTYSLSSTLTLSKADYEKHK<br>VYACEVTHQGLSSPVTKSFNRGEC |
| 236 | QVQLQQPGAELVRPGASVKLSCKASGYTFTSYWMNWVKQRPDQGLEWIGRIDPYDSETHY<br>NQKFKDKAILTVDKSSSTAYMQLSSLTSEDSAVYYCARGNWDDYWGQGTTLTVSSARTKG<br>PSVFPLAPSSKSTSGGTAALGCLVKDYFPEPVTVSWNSGALTSGVHTFPAVLQSSGLYSLSSV<br>VTVPSSSLGTQTYICNVNHKPSNTKVDKKVEPKSC |
| 237 | **NYHLENEVARLKKL**GGGGSDVQITQSPSYLAASPGETITINCRASKSISKDLAWYQEKPGK<br>TNKLLIYSGSTLQSGIPSRFSGSGSGTDFTLTISSLEPEDFAMYYCQQHNKYPYTFGGGTKLEI<br>RTVAAPSVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGEC |
| 238 | **NYHLENEVARLKKL**GGGGSDIVLTQSPASLAVSLGQRATISCRASESVDNYGNTFMHWYQ<br>QKPGQPPKLLIYRASNLESGIPARFSGSGSRTDFTLTINPVEADDVATYYCQQSNEDPPTFGA<br>GTKLELRTVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| 239 | **NYHLENEVARLKKL**GGGGSGGGGSGGGGSDIVLTQSPASLAVSLGQRATISCRASESVDN<br>YGNTFMHWYQQKPGQPPKLLIYRASNLESGIPARFSGSGSRTDFTLTINPVEADDVATYYCQ<br>QSNEDPPTFGAGTKLELRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSPVTKSFNRGEC |
| 240 | **NYHLENEVARLKKL**GGGGSGGGGSDIVLTQSPASLAVSLGQRATISCRASESVDNYGNTF<br>MHWYQQKPGQPPKLLIYRASNLESGIPARFSGSGSRTDFTLTINPVEADDVATYYCQQSNED<br>PPTFGAGTKLELRTVAAPSVFIFPPSDEQLKSGTASVVCLLNNFYPREAKVQWKVDNALQSG<br>NSQESVTEQDSKDSTYSLSSTLTLSKADYEKHKVYACEVTHQGLSSPVTKSFNRGEC |
| 241 | **NYHLENEVARLKKL**LVGEAAAKEAAAKAQVQLQQPGAELVRPGASVKLSCKASGYTFTS<br>YWMNWVKQRPDQGLEWIGRIDPYDSETHYNQKFKDKAILTVDKSSSTAYMQLSSLTSEDS<br>AVYYCARGNWDDYWGQGTTLTVSSARTKGPSVFPLAPSSKSTSGGTAALGCLVKDYFPEP<br>VTVSWNSGALTSGVHTFPAVLQSSGLYSLSSVVTVPSSSLGTQTYICNVNHKPSNTKVDKKV<br>EPKSC |
| 242 | **NYHLENEVARLKKLL**VGEAAAKEAAAKAQIQLVQSGPELKKPGETVKISCKASGYIFTNY<br>GMNWVKQAPGKSFKWMGWINTYTGESTYSADFKGRFAFSLETSASTAYLHINDLKNEDTA<br>TYFCARSGGYDPMDYWGQGTSVTVSSARTKGPSVFPLAPSSKSTSGGTAALGCLVKDYFPE<br>PVTVSWNSGALTSGVHTFPAVLQSSGLYSLSSVVTVPSSSLGTQTYICNVNHKPSNTKVDKK<br>VEPKSC |
| 243 | **NYHLENEVARLKKL**EAAAKEAAAKEAAAKAQIQLVQSGPELKKPGETVKISCKASGYIFT<br>NYGMNWVKQAPGKSFKWMGWINTYTGESTYSADFKGRFAFSLETSASTAYLHINDLKNED<br>TATYFCARSGGYDPMDYWGQGTSVTVSSARTKGPSVFPLAPSSKSTSGGTAALGCLVKDYF<br>PEPVTVSWNSGALTSGVHTFPAVLQSSGLYSLSSVVTVPSSSLGTQTYICNVNHKPSNTKVD<br>KKVEPKSC |
| 244 | DVQITQSPSYLAASPGETITINCRASKSISKDLAWYQEKPGKTNKLLIYSGSTLQSGIPSRFSGS<br>GSGTDFTLTISSLEPEDFAMYYCQQHNKYPYTFGGGTKLEIRTVAAPSVFIFPPSDEQLKSGT |

TABLE 58-continued

| SEQ ID NO | SEQUENCE |
|---|---|
| | ASVVCLLNNFYPREAKVQWKVDNALQSGNSQESVTEQDSKDSTYSLSSTLTLSKADYEKHK<br>VYACEVTHQGLSSPVTKSFNRGECGGGGS**NYHLENEVARLKKL** |
| 245 | DIVLTQSPASLAVSLGQRATISCRASESVDNYGNTFMHWYQQKPGQPPKLLIYRASNLESGIP<br>ARFSGSGSRTDFTLTINPVEADDVATYYCQQSNEDPPTFGAGTKLELRTVAAPSVFIFPPSDE<br>QLKSGTASVVCLLNNFYPREAKVQWKVDNALQSGNSQESVTEQDSKDSTYSLSSTLTLSKA<br>DYEKHKVYACEVTHQGLSSPVTKSFNRGECGGGGS**NYHLENEVARLKKL** |
| 246 | DIVLTQSPASLAVSLGQRATISCRASESVDNYGNTFMHWYQQKPGQPPKLLIYRASNLESGIP<br>ARFSGSGSRTDFTLTINPVEADDVATYYCQQSNEDPPTFGAGTKLELRTVAAPSVFIFPPSDE<br>QLKSGTASVVCLLNNFYPREAKVQWKVDNALQSGNSQESVTEQDSKDSTYSLSSTLTLSKA<br>DYEKHKVYACEVTHQGLSSPVTKSFNRGECGGGGSGGGGS**NYHLENEVARLKKL** |
| 247 | DIVLTQSPASLAVSLGQRATISCRASESVDNYGNTFMHWYQQKPGQPPKLLIYRASNLESGIP<br>ARFSGSGSRTDFTLTINPVEADDVATYYCQQSNEDPPTFGAGTKLELRTVAAPSVFIFPPSDE<br>QLKSGTASVVCLLNNFYPREAKVQWKVDNALQSGNSQESVTEQDSKDSTYSLSSTLTLSKA<br>DYEKHKVYACEVTHQGLSSPVTKSFNRGECGGGGSGGGGSGGGGS**NYHLENEVARLKKL** |
| 248 | QVQLQQPGAELVRPGASVKLSCKASGYTFTSYWMNWVKQRPDQGLEWIGRIDPYDSETHY<br>NQKFKDKAILTVDKSSSTAYMQLSSLTSEDSAVYYCARGNWDDYWGQGTTLTVSSARTKG<br>PSVFPLAPSSKSTSGGTAALGCLVKDYFPEPVTVSWNSGALTSGVHTFPAVLQSSGLYSLSSV<br>VTVPSSSLGTQTYICNVNHKPSNTKVDKKVEPKSCGGGGS**NYHLENEVARLKKL** |
| 249 | QIQLVQSGPELKKPGETVKISCKASGYIFTNYGMNWVKQAPGKSFKWMGWINTYTGESTYS<br>ADFKGRFAFSLETSASTAYLHINDLKNEDTATYFCARSGGYDPMDYWGQGTSVTVSSARTK<br>GPSVFPLAPSSKSTSGGTAALGCLVKDYFPEPVTVSWNSGALTSGVHTFPAVLQSSGLYSLSS<br>VVTVPSSSLGTQTYICNVNHKPSNTKVDKKVEPKSCGGGGS**NYHLENEVARLKKL** |
| 250 | QIQLVQSGPELKKPGETVKISCKASGYIFTNYGMNWVKQAPGKSFKWMGWINTYTGESTYS<br>ADFKGRFAFSLETSASTAYLHINDLKNEDTATYFCARSGGYDPMDYWGQGTSVTVSSARTK<br>GPSVFPLAPSSKSTSGGTAALGCLVKDYFPEPVTVSWNSGALTSGVHTFPAVLQSSGLYSLSS<br>VVTVPSSSLGTQTYICNVNHKPSNTKVDKKVEPKSCGGGGSGGGGS**NYHLENEVARLKKL** |
| 251 | QIQLVQSGPELKKPGETVKISCKASGYIFTNYGMNWVKQAPGKSFKWMGWINTYTGESTYS<br>ADFKGRFAFSLETSASTAYLHINDLKNEDTATYFCARSGGYDPMDYWGQGTSVTVSSARTK<br>GPSVFPLAPSSKSTSGGTAALGCLVKDYFPEPVTVSWNSGALTSGVHTFPAVLQSSGLYSLSS<br>VVTVPSSSLGTQTYICNVNHKPSNTKVDKKVEPKSCGGGGSGGGGSGGGGS**NYHLENEVA**<br>**RLKKL** |
| 252 | QIQLVQSGPELKKPGETVKISCKASGYIFTNYGMNWVKQAPGKSFKWMGWINTYTGESTYS<br>ADFKGRFAFSLETSASTAYLHINDLKNEDTATYFCARSGGYDPMDYWGQGTSVTVSSARTK<br>GPSVFPLAPSSN**YHLENEVARLKKL**LSGGTAALGCLVKDYFPEPVTVSWNSGALTSGVHTFP<br>AVLQSSGLYSLSSVVTVPSSSLGTQTYICNVNHKPSNTKVDKKVEPKSC |
| 253 | QIQLVQSGPELKKPGETVKISCKASGYIFTNYGMNWVKQAPGKSFKWMGWINTYTGESTYS<br>ADFKGRFAFSLETSASTAYLHINDLKNEDTATYFCARSGGYDPMDYWGQGTSVTVSSARTK<br>GPSVFPLAPSSKSTSGGTAALGCLVKDYFPEPVTVSWNSGALTSGVHTFPAVLQSGGGGS**NY**<br>**HLENEVARLKKL**GGGGSLYSLSSVVTVPSSSLGTQTYICNVNHKPSNTKVDKKVEPKSC |
| 254 | DIVLTQSPASLAVSLGQRATISCRASESVDNYGNTFMHWYQQKPGQPPKLLIYRASNLESGIP<br>ARFSGSGSRTDFTLTINPVEADDVATYYCQQSNEDPPTFGAGTKLELRTVAAPSVFIFPPSDE<br>QLKSGTASVVCLLNNFYPREAKVQWKVDNALQSGNSQESVTEQDSGGGGS**NYHLENEVA**<br>**RLKKL**GGGGSDSTYSLSSTLTLSKADYEKHKVYACEVTHQGLSSPVTKSFNRGEC |
| 255 | caggctgtggtgactcaggagccctcactgactgtgtccccaggagggacagtcactctcacctgtggctccagcactggagctgtcaccacttc<br>caactatgcctcatgggtgcaggagaagcctggccaagccTTcaggggggctgattggtggcacaaacaacagggctcctggggtgcctgccc<br>ggttctcaggctccctccttgggggcaaagctgccctgaccatttcgggtgcgcagcctgaggatgaggctatttatttctgcgtgctctggtatagt<br>gaccattgggtgttcggcggagggaccaagctgaccgtcctaGGCGGAGGAGGAGGTTCAGGAGGcGGAGGTAG<br>CGGGGGAGGCGGTTCCGGGGGAGGCGGTTCTcaggtgcagctgcagGAGtcgggcccaggactggtgaagcc<br>ttcggagaccctgtccatcacctgcactgtctctggtttcCTGctgaccgactacggcgtaaactgggtgcggcagcccccagggaagggact<br>ggagtggctgggggtgatctggggtgacgggATCaccgactacaacccctccctcaagagtcgactgaccgtgtccaaggacACAtccaa<br>gaaccaggtgtccctgaagatgagctctctgaccgccgcagacacggccCGGtattactgtgtcaccggcctgttcgactactggggccaggg<br>caccACCctgaccgtctcctcaGAAAGCAAGTATGGCCCaCCTTGTCCACCTTGTCCCgatatctacatctggg<br>cgcccttggccgggacttgtggggtccttctcctgtcactggttatcaccctttactgcaaacggggcagaaagaaactcctgtatatattcaaacaa<br>ccatttatgagaccagtacaaactactcaagaggaagatggctgtagctgccgatttccagaagaagaagaaggaggatgtgaactgagagtga<br>agttcagcaggagcgcagacgcccccgcgtacaagcagggccagaaccagctctataacgagctcaatctaggacgaagagaggagtacgat<br>gttttggacaagagacgtggccgggaccctgagatggggggaaagccgagaaggaagaaccctcaggaaggcctgtacaatgaactgcaga<br>aagataagatggcggaggcctacagtgagattgggatgaaaggcgagcgccggaggggcaaggggcacgatggcctttaccagggtctcagt<br>acagccaccaaggacacctacgacgcccttcacatgcaggccctgccccctcgc |
| 256 | caggctgtggtgactcaggagccctcactgactAGCtccccaggagggacagtcactctcacctgtggctccagcactggagctgtcaccact<br>tccaactatgcctcatgggtgcaggagaagcctgAccaCCTCTTCaggggggctgattggtggcacaaacaacagggctcctggggtgcc<br>tgcccggttctcaggctccctccttgggggcaaagctgccctgaccatttcgggtgcgcagcctgaggatgaggctatttatttctgcgtgctctggt<br>atagtgaccattgggtgttcggcggagggaccaagctgaccgtcctaGGCGGAGGAGGAGGTTCAGGAGGcGGAGG |

TABLE 58-continued

| sCAR sequences, heavy and light chain sequences, and other sequences | |
|---|---|
| SEQ ID NO | SEQUENCE |
| | TAGCGGGGGAGGCGGTTCCGGGGGAGGCGGTTCTcaggtgcagctgcagCAGtcgggcccaggactggtg<br>aagccttcggagaccctgtccatcacctgcactgtctctggtttcCTGctgaccgactacggcgtaaactgggtgcggcagcccccagggaag<br>ggactggagtggctgggggtgatctggggtgacgggATCaccgactacaacccctccctcaagagtcgactgaccgtgtccaaggacAC<br>AtccaagaaccaggtgtccctgaagatgagctctctgaccgccgcagacacggccCGGtattactgtgtcaccggcctgttcgactactgggg<br>ccagggcaccACCctgaccgtctcctcaGAAAGCAAGTATGGCCCaCCTTGTCCACCTTGTCCCgatatctac<br>atctgggcgcccttggccgggacttgtggggtccttctcctgtcactggttatcaccctttactgcaaacggggcagaaagaaactcctgtatatatt<br>caaacaaccatttatgagaccagtacaaactactcaagaggaagatggctgtagctgccgatttccagaagaagaagaaggaggatgtgaactg<br>agagtgaagttcagcaggagcgcagacgcccccgcgtacaagcagggccagaaccagctctataacgagctcaatctaggacgaagagagg<br>agtacgatgttttggacaagagacgtggccgggaccctgagatgggggaaagccgagaaggaagaaccctcaggaaggcctgtacaatgaa<br>ctgcagaaagataagatggcggaggcctacagtgagattgggatgaaaggcgagcgccggaggggcaaggggcacgatggcctttaccagg<br>gtctcagtacagccaccaaggacacctacgacgcccttcacatgcaggccctgccccctcgc |
| 257 | caggctgtggtgactcaggagccctcactgactgtgtccccaggagggacagtcactctcacctgtggctccagcactggagctgtcaccacttc<br>caactatgcctcatgggtgcaggagaagcctggccaagcccccaggggctgattggtggcacaaacaacagggctcctggggtgcctgccc<br>ggttctcaggctccctccttgggggcaaagctgccctgaccatttcgggtgcgcagcctgaggatgaggctatttatttctgcgtgctctggtatagt<br>gaccattgggtgttcggcggagggaccaagctgaccgtcctaGGCGGAGGAGGAGGTTCAGGAGGAGGAGGTA<br>GCGGGGGAGGCGGTTCCGGGGGAGGCGGTTCTcaggtgcagctgcagcagtcgggcccaggactggtgaagcc<br>ttcggagaccctgtccatcacctgcactgtctctggtttctccctgaccgactacggcgtaaactgggtgcggcagcccccagggaagggactgg<br>agtggctgggggtgatctggggtgacgggagcaccgactacaacccctccctcaagagtcgactgaccgtgtccaaggacaactccaagaacc<br>aggtgtccctgaagatgagctctctgaccgccgcagacacggccgtgtattactgtgtcaccggcctgttcgactactggggccagggcaccctg<br>ctgaccgtctcctcaGAAAGCAAGTATGGCCCaCCTTGTCCACCTTGTCCCgatatctacatctgggcgcccttgg<br>ccgggacttgtggggtccttctcctgtcactggttatcaccctttactgcaaacggggcagaaagaaactcctgtatatattcaaacaaccatttatga<br>gaccagtacaaactactcaagaggaagatggctgtagctgccgatttccagaagaagaagaaggaggatgtgaactgagagtgaagttcagca<br>ggagcgcagacgcccccgcgtacaagcagggccagaaccagctctataacgagctcaatctaggacgaagagaggagtacgatgttttggac<br>aagagacgtggccgggaccctgagatgggggaaagccgagaaggaagaaccctcaggaaggcctgtacaatgaactgcagaaagataag<br>atggcggaggcctacagtgagattgggatgaaaggcgagcgccggaggggcaaggggcacgatggcctttaccagggtctcagtacagcca<br>ccaaggacacctacgacgcccttcacatgcaggccctgccccctcgc |

TABLE 59

| Sequence Identifier Description | |
|---|---|
| SEQ ID NO. | NAME/DESCRIPTION |
| 1 | LV-EF1a-GCN4(52SR4)-BBZ |
| 2 | yeast transcription factor GCN4 (7P14P) |
| 3 | yeast transcription factor GCN4 minimal binding peptide |
| 4 | yeast transcription factor GCN4 minimal binding peptide with linkers |
| 5 | Hydrophilic target peptide (HTP) |
| 6 | Hydrophilic target peptide (HTP) P |
| 7 | FLAG ® |
| 8 | Light chain of anti-CD19 antibody |
| 9 | Heavy chain of anti-CD19 antibody Fab |
| 10 | Heavy chain of anti-CD19 IgG |
| 11 | Light chain of Trastuzumab (anti-Her2) |
| 12 | Heavy chain of Trastuzumab (anti-Her2) |
| 13 | Light Chain of Rituximab (anti-CD20) |
| 14 | Heavy Chain of Rituximab (anti-CD20) |
| 15 | Light chain of Clone C225 (anti-EGFR) |
| 16 | Heavy chain of Clone C225 (anti-EGFR) |
| 17 | Light chain of anti-CLL1 antibody |
| 18 | Heavy chain of anti-CLL1 antibody |
| 19 | Light chain of anti-CD33 antibody |
| 20 | Heavy chain of anti-CD33 antibody |
| 21 | Light chain of wildtype anti-CS1 antibody |
| 22 | Heavy chain of wildtype anti-CS1 antibody Fab |
| 23 | Light chain of anti-EGFRvIII antibody (Hu806) Fab |
| 24 | Heavy chain of anti-EGFRvIII antibody (Hu806) Fab |
| 25 | Light chain of anti-BCMA antibody (BCMA98) Fab |
| 26 | Heavy chain of anti-BCMA antibody (BCMA98) Fab |
| 27 | Light Chain of anti-CD19 antibody |
| 28 | Heavy Chain of anti-CD19 antibody IgG |
| 29 | Heavy Chain of anti-CD19 antibody Fab |
| 30 | anti-CD19 Fab CL1-GCN4 switch Light Chain |
| 31 | anti-CD19 IgG CL1-GCN4 switch Light Chain |
| 32 | anti-CD19 Fab HC1-GCN4 switch Heavy Chain |
| 33 | anti-CD19 IgG HC1-GCN4 switch Heavy Chain |
| 34 | anti-CD19 Fab C term-GCN4 switch Heavy Chain |
| 35 | anti-CD19 IgG hinge-GCN4 switch Heavy Chain |
| 36 | anti-CD19 Fab Light Chain NT1 |

TABLE 59-continued

| Sequence Identifier Description | |
|---|---|
| SEQ ID NO. | NAME/DESCRIPTION |
| 37 | anti-BCMA GCN4 CL1 light chain |
| 38 | anti-BCMA heavy chain WT IgG |
| 39 | pBAD-CD19wt |
| 40 | GGGGS linker |
| 41 | GGGS linker |
| 42 | GGS linker |
| 43 | GS linker |
| 44 | XS linker |
| 45 | rigid switch fusion/grafting linker 3 |
| 46 | rigid switch fusion/grafting linker 4 |
| 47 | rigid switch fusion/grafting linker 4a |
| 48 | flexible switch fusion/grafting linker - prophetic |
| 49 | rigid switch fusion/grafting linker 5 |
| 50 | prolyl switch fusion/grafting linker - prophetic |
| 51 | GCN4-CD28-CD3z(1-3) |
| 52 | mCD19(1D3)-LC-CL1 |
| 53 | mCD19(1D3)-LC-WT |
| 54 | mCD19(1D3)-HC-WT Fab |
| 55 | mCD19(1D3)-HC_NT3 |
| 56 | mCD19(1D3)-HC-Cterm |
| 57 | mCD19(1D3)-LC-Cterm |
| 58 | mCD19(1D3)-LC_NT1 |
| 59 | mCD19(1D3)-LC_NT2 |
| 60 | mCD19(1D3)-HC_NT1 |
| 61 | mCD19(1D3)-HC_NT2 |
| 62 | NYESO1(1G4-113)-TCRb-WT |
| 63 | NYESO1(1G4-113)-TCRb-GCN4-NT1 |
| 64 | NYESO1(1G4-113)-TCRa-GCN4-NT1 |
| 65 | NYESO1(1G4-113)-TCRa-WT |
| 66 | NYESO1(1G4-113)-TCRb-GCN4-Cterm |
| 67 | NYESO1(1G4-113)-TCRa-GCN4-Cterm |
| 68 | CD8 hinge peptide sequence |
| 69 | no hinge peptide sequence |
| 70 | IgG4 hinge peptide sequence |
| 71 | IgG4 m hinge peptide sequence |
| 72 | LV-EF1a-GCN4(52SR4)-BBZ_no hinge |
| 73 | LV-EF1a-GCN4(52SR4)-BBZ_IgG4(Pro) (CAR containing hinge) |
| 74 | LV-EF1a-GCN4(52SR4)-BBZ_IgG4(Ser) (CAR containing hinge) |
| 75 | GCN4 epitope alanine mutant 1 |
| 76 | GCN4 epitope alanine mutant 2 |
| 77 | GCN4 epitope alanine mutant 3 |
| 78 | GCN4 epitope alanine mutant 4 |
| 79 | GCN4 epitope alanine mutant 5 |
| 80 | GCN4 epitope alanine mutant 6 |
| 81 | GCN4 epitope alanine mutant 7 |
| 82 | GCN4 epitope alanine mutant 8 |
| 83 | GCN4 epitope extended 1 |
| 84 | GCN4 epitope extended 2 |
| 85 | CD19(FMC63)-LC-NT2 (N-terminal fusion using flexible GGGGSGGGGS linker) |
| 86 | CD19(FMC63)-HC-NT1 (N-terminal fusion using flexible GGGGS linker) |
| 87 | CD19(FMC63)-HC-NT2 (N-terminal fusion using flexible GGGGSGGGGS linker) |
| 88 | CD19(FMC63)-HC-NT3 (N-terminal fusion using rigid linker design 3) |
| 89 | CD19(FMC63)-HC-NT4 (N-terminal fusion using rigid linker design 4) |
| 90 | CD19(FMC63)-HC2 (grafting the GCN4 peptide to region 2 of the heavy chain constant region) |
| 91 | CD19(FMC63)-S74_1 (grafting the GCN4 peptide to the region of S74 in the heavy chain, this version places it inbeween S74 and K75 of the wild type sequence) |
| 92 | CD19(FMC63)-S74_2 (grafting the GCN4 peptide to the region of S74 in the heavy chain, this version replaces S74 and K75 of the wild type sequence with the GCN4 peptide sequence (with GGGGS linkers on either side)) |
| 93 | CD19(FMC63)-LC-NT4a (N-terminal light chain fusion using rigid linker design 4a) |
| 94 | CD19(FMC63)-LC-NT5 (N-terminal light chain fusion using flexible linker design 5) |
| 95 | CD19(FMC63)-HC-NT4a (N-terminal heavy chain fusion using rigid linker design 4a) |
| 96 | CD19(FMC63)-HC-NT5 (N-terminal heavy chain fusion using flexible linker design 5) |
| 97 | CD19(FMC63)-LC-Cterm (C-terminal fusion of GCN4 epitope to the light chain) |
| 98 | CD19(FMC63)-LC-NT1_LLPKN (Extension of the Nterminus with LLPKN of the GCN4 epitope in the light chain N-terminal fusion with a flexible linker GGGGS) |
| 99 | CD19(FMC63)-LC-NT1_DLPKQ (Extension of the Nterminus with DLPKQ of the GCN4 epitope in the light chain N-terminal fusion with a flexible linker GGGGS) |
| 100 | CD19(FMC63)-HC-WT/LC-NT1 (Entire vector sequence of the pBAD vector harboring the anti-CD19(FMC63) LC-NT1 switch (both chains)) |
| 101 | CD19(FMC63)-HC-WT/LC-NT1 (Entire vector sequence of the pBAD vector harboring the anti-CD19(FMC63) LC-NT1 switch (both chains) in which the protein sequence has been codon optimized) |
| 102 | CLL1(1075.7)-HC_NT3 (N-terminal fusion to the heavy chain using rigid linker design 3) |
| 103 | CLL1(1075.7)-LC_NT1 (N-terminal fusion to the light chain using flexible GGGGS linker) |

TABLE 59-continued

| Sequence Identifier Description | |
|---|---|
| SEQ ID NO. | NAME/DESCRIPTION |
| 104 | CLL1(1075.7)-HC_Cterm (C-terminal fusion to the heavy chain using flexible linker) |
| 105 | CLL1(1075.7)-LC_Cterm (C-terminal fusion to the light chain using flexible linker) |
| 106 | CD22(m971)-HC-WT Fab (wild type heavy chain sequence) |
| 107 | CD22(m971)-LC-WT (wild type light chain sequence) |
| 108 | CD22(m971)-HC_NT3 (N-terminal fusion to the heavy chain using rigid linker design 3) |
| 109 | CD22(m971)-LC_NT1 (N-terminal fusion to the light chain using flexible GGGGS linker) |
| 110 | CD22(m971)-HC_Cterm (C-terminal fusion to the heavy chain using flexible linker) |
| 111 | CD22(m971)-LC_Cterm (C-terminal fusion to the light chain using flexible linker) |
| 112 | CD22(m972)-HC-WT Fab (wild type heavy chain sequence) |
| 113 | CD22(m972)-LC-WT (wild type light chain sequence) |
| 114 | CD22(m972)-HC_NT3 (N-terminal fusion to the heavy chain using rigid linker design 3) |
| 115 | CD22(m972)-LC_NT1 (N-terminal fusion to the light chain using flexible GGGGS linker) |
| 116 | CD22(m972)-HC_Cterm (C-terminal fusion to the heavy chain using flexible linker) |
| 117 | CD22(m972)-LC_Cterm (C-terminal fusion to the light chain using flexible linker) |
| 118 | CD22(CMC544)-HC-WT Fab (wild type heavy chain sequence) |
| 119 | CD22(CMC544)-LC-WT (wild type light chain sequence) |
| 120 | CD22(CMC544)-HC_NT3 (N-terminal fusion to the heavy chain using rigid linker design 3) |
| 121 | CD22(CMC544)-LC_NT1 (N-terminal fusion to the light chain using flexible GGGGS linker) |
| 122 | CD22(CMC544)-HC_Cterm (C-terminal fusion to the heavy chain using flexible linker) |
| 123 | CD22(CMC544)-LC_Cterm (C-terminal fusion to the light chain using flexible linker) |
| 124 | CD20(RTX)-HC_NT3 (N-terminal fusion to the heavy chain using rigid linker design 3) |
| 125 | CD20(RTX)-LC_NT1 (N-terminal fusion to the light chain using flexible GGGGS linker) |
| 126 | CD20(RTX)-HC_Cterm (C-terminal fusion to the heavy chain using flexible linker) |
| 127 | CD20(RTX)-LC_Cterm (C-terminal fusion to the light chain using flexible linker) |
| 128 | CD20(GA101[34I])-HC-WTFab (wild type heavy chain sequence) |
| 129 | CD20(GA101[34I])-LC-WT (wild type light chain sequence) |
| 130 | CD20(GA101[34I])-HC_NT3 (N-terminal fusion to the heavy chain using rigid linker design 3) |
| 131 | CD20(GA101[341])-LC_NT1 (N-terminal fusion to the light chain using flexible GGGGS linker) |
| 132 | CD20(GA101[34I])-HC_Cterm (C-terminal fusion to the heavy chain using flexible linker) |
| 133 | CD20(GA101[34I])-LC_Cterm (C-terminal fusion to the light chain using flexible linker) |
| 134 | CD20(OFA)-HC-WT Fab (wild type heavy chain sequence) |
| 135 | CD20(OFA)-LC-WT (wild type light chain sequence) |
| 136 | CD20(OFA)-HC_NT3 (N-terminal fusion to the heavy chain using rigid linker design 3) |
| 137 | CD20(OFA)-LC_NT1 (N-terminal fusion to the light chain using flexible GGGGS linker) |
| 138 | CD20(OFA)-HC_Cterm (C-terminal fusion to the heavy chain using flexible linker) |
| 139 | CD20(OFA)-LC_Cterm (C-terminal fusion to the light chain using flexible linker) |
| 140 | Her2(trastuzumab)-HC_NT3 (N-terminal fusion to the heavy chain using rigid linker design 3) |
| 141 | Her2(trastuzumab)-LC_NT1 (N-terminal fusion to the light chain using flexible GGGGS linker) |
| 142 | Her2(trastuzumab)-HC_Cterm (C-terminal fusion to the heavy chain using flexible linker) |
| 143 | Her2(trastuzumab)-LC_Cterm (C-terminal fusion to the light chain using flexible linker) |
| 144 | BCMA(BCMA-98)-HC-WT Fab (wild type heavy chain sequence Fab) |
| 145 | BCMA(BCMA-98)-LC-NT1 (N-terminal fusion using flexible GGGGS linker) |
| 146 | BCMA(BCMA-98)-LC-NT2 (N-terminal fusion using flexible GGGGSGGGGS linker) |
| 147 | BCMA(BCMA-98)-HC-NT1 (N-terminal fusion using flexible GGGGS linker) |
| 148 | BCMA(BCMA-98)-HC-NT2 (N-terminal fusion using flexible GGGGSGGGGS linker) |
| 149 | CD19(huB4)-LC-WT (wild type light chain sequence) |
| 150 | CD19(huB4)-HC-WT Fab (wild type heavy chain sequence) |
| 151 | CD19(huB4)-LC1 (fusion to the constant region 1 of the light chain) |
| 152 | CD19(huB4)-HC1 (fusion to the constant region 1 of the heavy chain) |
| 153 | CD19(huB4)-LC-NT1 (N-terminal fusion using flexible GGGGS linker) |
| 154 | CD19(huB4)-LC-NT2 (N-terminal fusion using flexible GGGGSGGGGS linker) |
| 155 | CD19(huB4)-HC-NT1 (N-terminal fusion using flexible GGGGS linker) |
| 156 | CD19(huB4)-HC-NT2 (N-terminal fusion using flexible GGGGSGGGGS linker) |
| 157 | CEA(A5B7)-HC-WT Fab (wild type heavy chain sequence) |
| 158 | CEA(A5B7)-CL1 (fusion to the constant region 1 of the light chain) |
| 159 | CEA(A5B7)-LC-WT (wild type light chain sequence) |
| 160 | CEA(A5B7)-HC-Cterm (C-terminal fusion to the heavy chain using flexible linker) |
| 161 | CD33(hM195)-HC_NT3 (N-terminal fusion to the heavy chain using rigid linker design 3) |
| 162 | CD33(hM195)-LC_NT1 (N-terminal fusion to the light chain using flexible GGGGS linker) |
| 163 | CD33(hM195)-HC_Cterm (C-terminal fusion to the heavy chain using flexible linker) |
| 164 | CD33(hM195)-LC_Cterm (C-terminal fusion to the light chain using flexible linker) |
| 165 | h52SR4L2_h52SR4H2 |
| 166 | h52SR4L2_h52SR4H3 |
| 167 | h52SR4L3_h52SR4H2 |
| 168 | h52SR4L3_h52SR4H3 |
| 169 | h52SR4L4_h52SR4H2 |
| 170 | h52SR4L4_h52SR4H3 |
| 171 | LV-EF1a-huGCN4-BBZ_L2,H2 |
| 172 | LV-EF1a-huGCN4-BBZ_L2,H3 |
| 173 | LV-EF1a-huGCN4-BBZ_L3,H2 |
| 174 | LV-EF1a-huGCN4-BBZ_L3,H3 |
| 175 | LV-EF1a-huGCN4-BBZ_L4,H2 |
| 176 | LV-EF1a-huGCN4-BBZ_L4,H3 |
| 177 | Anti-CD20 OFA Light chain WT |
| 178 | Anti-CD20 OFA Heavy chain (Fab) WT |

TABLE 59-continued

| Sequence Identifier Description | |
|---|---|
| SEQ ID NO. | NAME/DESCRIPTION |
| 179 | IgG1 Fc region (E233P/L234V/L235A/ΔG236 + A327G/A330S/P331S) |
| 180 | sCAR (long) sequence |
| 181 | CART-19 sequence |
| 182 | CART20 BBZ |
| 183 | hu 52SR4 L5 H6 |
| 184 | hu 52SR4 L5 H4b |
| 185 | hu 52SR4 L5 H6b |
| 186 | hLL2 LC WT FAB |
| 187 | hLL2 HC WT FAB |
| 188 | hLL2 LCNT FAB |
| 189 | hLL2 LCCT FAB |
| 190 | hLL2 HCNT FAB |
| 191 | hLL2 HCCT FAB |
| 192 | hLL2 LCCT2 FAB |
| 193 | hLL2 LCCT3 FAB |
| 194 | hLL2 HCCT2 FAB |
| 195 | hLL2 HCCT3 FAB |
| 196 | hLL2 HC WT IgG |
| 197 | hLL2 HCCT IgG |
| 198 | m971 HC WT IgG |
| 199 | m971 HCCT IgG |
| 200 | 1D3 CART19 |
| 201 | murine sCAR 28Z |
| 202 | 52SR4, co-stim chimera 1 |
| 203 | 52SR4, co-stim chimera 2 |
| 204 | 52SR4, co-stim chimera 3 |
| 205 | 52SR4, co-stim chimera 4 |
| 206 | 1D3, co-stim chimera 1 |
| 207 | 1D3, co-stim chimera 2 |
| 208 | 1D3, co-stim chimera 3 |
| 209 | 1D3, co-stim chimera 4 |
| 210 | 52SR4, co-stim chimera 5 |
| 211 | 52SR4, co-stim chimera 6 |
| 212 | 52SR4, co-stim chimera 7 |
| 213 | 1D3, co-stim chimera 5 |
| 215 | 1D3 LCNT short linker |
| 216 | 1D3 HCNT short linker |
| 217 | CD33 (hP67.6) LCNT1 |
| 218 | CD33 (hP67.6) LCNT2 |
| 219 | CD33 (hP67.6) LCNT3 |
| 220 | CD33 (hP67.6) HCNT1 |
| 221 | CD33 (hP67.6) HCNT2 |
| 222 | CD33 (hP67.6) LCCT1 |
| 223 | CD33 (hP67.6) LCCT2 |
| 224 | CD33 (hP67.6) LCCT3 |
| 225 | CD33 (hP67.6) HCCT1 |
| 226 | CD33 (hP67.6) HCCT2 |
| 227 | CD33 (hP67.6) HCCT3 |
| 228 | CD33 (hP67.6) HCC1 |
| 229 | CD33 (hP67.6) HCC1 G4S |
| 230 | CD33 (hP67.6) LCC1 G4S |
| 231 | CD33 (hP67.6) LCWT |
| 232 | CD33 (hP67.6) HCWT |
| 233 | CD123 32716 LCWT |
| 234 | CD123 32716 HCWT |
| 235 | CD123 26292 LCWT |
| 236 | CD123 26292 HCWT |
| 237 | CD123 26292 LCNT1 |
| 238 | CD123 32716 LCNT1 |
| 239 | CD123 32716 LCNT3 |
| 240 | CD123 32716 LCNT2 |
| 241 | CD123 26292 HCNT1 |
| 242 | CD123 32716 HCNT1 |
| 243 | CD123 32716 HCNT2 |
| 244 | CD123 26292 LCCT1 |
| 245 | CD123 32716 LCCT1 |
| 246 | CD123 32716 LCCT2 |
| 247 | CD123 32716 LCCT3 |
| 248 | CD123 26292 HCCT1 |
| 249 | CD123 32716 HCCT1 |
| 250 | CD123 32716 HCCT2 |
| 251 | CD123 32716 HCCT3 |
| 252 | CD123 32716 HCC1 |
| 253 | CD123 32716 HCC1 G4S |
| 254 | CD123 32716 LCC1 G4S |

TABLE 59-continued

| Sequence Identifier Description | |
|---|---|
| SEQ ID NO. | NAME/DESCRIPTION |
| 255 | hu 52SR4 L6b H4 |
| 256 | hu 52SR4 L5b H4b |
| 257 | hu 52SR4 L6 H6 |

What is claimed is:

1. An optimized chimeric antigen receptor-effector cell (CAR-EC) platform, comprising:

(a) (1) a CAR-EC switch that comprises a chimeric antigen receptor binding peptide (CAR-BP) and a targeting moiety, wherein said targeting moiety is a Fab fragment specific for a membrane distal epitope of a cell surface molecule on a target cell, and wherein said CAR-BP is linked to the N-terminus of said Fab fragment with a linker, and (2) a CAR-EC that comprises a CAR, wherein said CAR comprises a transmembrane domain, an intracellular signaling domain, and an extracellular domain that binds said CAR-BP, wherein said CAR-EC is a T cell, wherein said extracellular domain comprises a hinge region and an scFv that is specific for said CAR-BP; or (b) (1) a CAR-EC switch that comprises a chimeric antigen receptor binding peptide (CAR-BP) and a targeting moiety, wherein said targeting moiety is a Fab fragment specific for a membrane proximal epitope of a cell surface molecule on a target cell, and wherein said CAR-BP is linked to the C-terminus of said Fab fragment with a linker, and (2) a CAR-EC that comprises a CAR, wherein said CAR comprises a transmembrane domain, an intracellular signaling domain, and an extracellular domain that binds said CAR-BP, wherein said CAR-EC is a T cell, wherein said extracellular domain comprises a hinge region and an scFv that is specific for said CAR-BP;

wherein the hinge region is between 1-20 amino acid residues in length; and wherein the linker is between 4-16 amino acid residues in length.

2. A method of treating relapsed cancer, comprising administering to the subject the chimeric antigen receptor switch and the chimeric antigen receptor effector cell of the optimized chimeric antigen receptor-effector cell platform of claim 1.

3. A method of treating cancer, comprising administering to a subject an optimized first chimeric antigen receptor effector cell (CAR-EC) platform of claim 1.

4. The optimized CAR-EC platform of claim 1, wherein the CAR-BP comprising a length of between about 10 and about 20 amino acids.

5. The optimized CAR-EC platform of claim 1, wherein the CAR-EC switch comprises a plurality of CAR-BPs.

6. The optimized CAR-EC platform of claim 1, wherein the CAR-BP comprises a peptide selected from a non-human peptide, a non-mammalian peptide, a synthetic non-naturally occurring peptide, a non-endogenous peptide, a non-immunogenic peptide, and a peptide that has low immunogenicity in a human subject.

7. The optimized CAR-EC platform of claim 1, wherein the targeting moiety comprises (a) a Fab fragment that binds a cell surface molecule selected from CD19, CD20, CD22, CD33, CEA, CLL1, BCMA, CS1, CD123 and Her2, or (b) a sequence selected from SEQ ID NOS: 21-38, or a portion thereof, or a homolog thereof.

8. The optimized CAR-EC platform of claim 1, wherein the targeting moiety comprises a Fab fragment specific for CD19.

9. The optimized CAR-EC platform of claim 1, wherein the CAR-BP comprises a GCN4 peptide that is at least 85% identical to SEQ ID NO: 3.

10. The optimized CAR-EC platform of claim 1 or 9, wherein the CAR-BP is attached to the N-terminus of the heavy chain, the light chain, or both the heavy and the light chains of the Fab fragment.

11. The optimized CAR-EC platform of claim 1 or 9, wherein the CAR comprises an anti-GCN4 scFv.

12. The optimized CAR-EC platform of claim 1, wherein (a) the number of CAR-BPs on the CAR-EC is between about 1 and about 8; (b) the CAR density on the CAR-EC membrane is a magnitude of about 100 to about $10^{\hat{}10}$ CAR per CAR-EC; and/or (c) the number of engagements between the CAR-EC and the target cell is about 1 to about 100.

* * * * *